(12) United States Patent
Erlanson et al.

(10) Patent No.: US 12,281,149 B2
(45) Date of Patent: Apr. 22, 2025

(54) MODULATORS OF G-PROTEIN COUPLED RECEPTORS

(71) Applicant: Carmot Therapeutics, Inc., Berkeley, CA (US)

(72) Inventors: Daniel Erlanson, San Francisco, CA (US); Raymond V. Fucini, San Bruno, CA (US); Stig Hansen, Kensington, CA (US); Jeff Iwig, Berkeley, CA (US); Shyam Krishnan, Novato, CA (US); Enrique Moya, Berkeley, CA (US); Steven Sethofer, Emeryville, CA (US)

(73) Assignee: Carmot Therapeutics, Inc., Berkeley, CA (US)

( * ) Notice: Subject to any disclaimer, the term of this patent is extended or adjusted under 35 U.S.C. 154(b) by 151 days.

(21) Appl. No.: 17/744,540

(22) Filed: May 13, 2022

(65) Prior Publication Data
US 2023/0151074 A1 May 18, 2023

Related U.S. Application Data

(60) Provisional application No. 63/188,342, filed on May 13, 2021.

(51) Int. Cl.
*C07K 14/605* (2006.01)
*A61K 38/00* (2006.01)

(52) U.S. Cl.
CPC ............ *C07K 14/605* (2013.01); *A61K 38/00* (2013.01)

(58) Field of Classification Search
None
See application file for complete search history.

(56) References Cited

U.S. PATENT DOCUMENTS

| | | |
|---|---|---|
| 8,163,757 B2 | 4/2012 | Matthews et al. |
| 8,372,837 B2 | 2/2013 | Wacker et al. |
| 8,551,946 B2 | 10/2013 | Dimarchi et al. |
| 8,975,223 B2 | 3/2015 | Vignati et al. |
| 9,062,124 B2 | 6/2015 | Dimarchi et al. |
| 9,474,780 B2 | 10/2016 | Bokvist et al. |
| 9,487,571 B2 | 11/2016 | Dimarchi et al. |
| 9,764,004 B2 | 9/2017 | Alsina-Fernandez et al. |
| 9,884,091 B2 | 2/2018 | Hölscher et al. |
| 9,884,093 B2 | 2/2018 | Alsina-Fernandez et al. |
| 11,220,534 B2 | 1/2022 | Hölscher et al. |
| 2006/0275288 A1 | 12/2006 | Grihalde et al. |
| 2010/0190750 A1 | 7/2010 | Chu et al. |
| 2012/0021979 A1 | 1/2012 | Galli et al. |
| 2012/0148586 A1 | 6/2012 | Chou et al. |
| 2013/0040884 A1 | 2/2013 | Lau et al. |
| 2015/0322130 A1 | 11/2015 | Dimarchi et al. |
| 2015/0352219 A1 | 12/2015 | Anderson et al. |
| 2016/0175400 A1 | 6/2016 | Vignati et al. |
| 2017/0095554 A1 | 4/2017 | Brimble et al. |
| 2017/0326233 A1 | 11/2017 | Demeule et al. |
| 2022/0033457 A1 | 2/2022 | Hölscher et al. |
| 2022/0135639 A1 | 5/2022 | Coffin et al. |
| 2022/0251163 A1 | 8/2022 | Zhao et al. |
| 2022/0298214 A1 | 9/2022 | Chen et al. |
| 2023/0241178 A1 | 8/2023 | Thennati et al. |

FOREIGN PATENT DOCUMENTS

| | | |
|---|---|---|
| CN | 105219802 A2 | 1/2016 |
| EP | 1883419 A2 | 2/2008 |
| EP | 2300035 B1 | 8/2015 |
| EP | 2952202 B1 | 10/2017 |
| EP | 3242887 B1 | 8/2019 |
| EP | 3548061 B1 | 9/2020 |
| GB | 2551945 A | 1/2018 |
| WO | WO-1997/010224 A1 | 3/1997 |
| WO | WO-1999/043707 A1 | 9/1999 |
| WO | WO-2000/034331 A2 | 6/2000 |

(Continued)

OTHER PUBLICATIONS

Lafferty et al. "Proglucagon-Derived Peptides as Therapeutics" Frontiers in Endocrinology 12:689678. (Year: 2021).*
American Diabetes Association's (ADA), "Standards of Medical Care in Diabetes-2022 Abridged for Primary Care Providers," *Clin Diabetes*. (2022) 40(1):10-38).
Angulo et al., "Non-alcoholic fatty liver disease," *J Gastroenterol Hepatol*. (2002) 17 suppl: S186-90.
Azimova et al., "Cardiovascular Safety Profile of Currently Available Diabetic Drugs," *Ochsner J*. (2014) 14(4):616-32.
Battelino et al., "Continuous glucose monitoring and metrics for clinical trials: an international consensus statement," *Lancet Diabetes Endocrinol*. (2023) 11:42-57.
Bonnet et al., "Structural studies in aqueous solution of new binuclear lanthanide luminescent peptide conjugates," *Chem Commun (Camb)*. (2008) 38:4552-4.

(Continued)

*Primary Examiner* — Sudhakar Katakam
*Assistant Examiner* — Zachary J Miknis
(74) *Attorney, Agent, or Firm* — Steptoe LLP; Z. Ying Li; David Caianiello

(57) ABSTRACT

This disclosure features chemical entities (e.g., a compound or a pharmaceutically acceptable salt) that modulate (e.g., agonize or partially agonize or antagonize) glucagon-like peptide-1 receptor ("GLP-1R") and/or the gastric inhibitory polypeptide receptor ("GIPR"). The chemical entities are useful, e.g., for treating a disease, disorder, or condition in which modulation (e.g., agonism, partial agonism or antagonism) of GLP-1R and/or GIPR activities is beneficial for the treatment or prevention of the underlying pathology and/or symptoms and/or progression of the disease, disorder, or condition. In some embodiments, modulation results in enhancement of (e.g., increases) existing levels (e.g., normal or below normal levels) of GLP-1R and/or GIPR activity (e.g., signaling). In some embodiments, the chemical entities described herein further modulate (e.g., attenuate, uncouple) β-arrestin signaling relative to what is observed with the native ligand. This disclosure also features compositions as well as other methods of using and making the said chemical entities.

11 Claims, 178 Drawing Sheets
Specification includes a Sequence Listing.

(56) References Cited

FOREIGN PATENT DOCUMENTS

| | | |
|---|---|---|
| WO | WO-2001/014371 A1 | 3/2001 |
| WO | WO-2001/014372 A1 | 3/2001 |
| WO | WO-2001/017568 A2 | 3/2001 |
| WO | WO-2001/062765 A2 | 8/2001 |
| WO | WO-2002/006234 A1 | 1/2002 |
| WO | WO-2004/039365 A1 | 5/2004 |
| WO | WO-2004/041266 A1 | 5/2004 |
| WO | WO-2004/048363 A1 | 6/2004 |
| WO | WO-2004/067548 A2 | 8/2004 |
| WO | WO-2004/106276 A1 | 12/2004 |
| WO | WO-2005/030740 A1 | 4/2005 |
| WO | WO-2005/058823 A1 | 6/2005 |
| WO | WO-2005/063725 A1 | 7/2005 |
| WO | WO-2005/063729 A1 | 7/2005 |
| WO | WO-2005/087710 A1 | 9/2005 |
| WO | WO-2005/095338 A1 | 10/2005 |
| WO | WO-2005/113504 A1 | 12/2005 |
| WO | WO-2006/112549 A1 | 10/2006 |
| WO | WO-2006/121860 A2 | 11/2006 |
| WO | WO-2007/013689 A1 | 2/2007 |
| WO | WO-2007/013694 A1 | 2/2007 |
| WO | WO-2007/018314 A2 | 2/2007 |
| WO | WO-2007/028135 A2 | 3/2007 |
| WO | WO-2008/001931 A2 | 1/2008 |
| WO | WO-2008/021560 A2 | 2/2008 |
| WO | WO-2008/047821 A1 | 4/2008 |
| WO | WO-2008/050821 A1 | 5/2008 |
| WO | WO-2008/093639 A1 | 8/2008 |
| WO | WO-2008/099794 A1 | 8/2008 |
| WO | WO-2008/136428 A1 | 11/2008 |
| WO | WO-2008/156757 A1 | 12/2008 |
| WO | 2009/115469 A1 | 9/2009 |
| WO | WO-2010/011439 A2 | 1/2010 |
| WO | WO-2011/044212 A1 | 4/2011 |
| WO | WO-2011/094337 A1 | 8/2011 |
| WO | WO-2011/143365 A1 | 11/2011 |
| WO | WO-2012/088379 A2 | 6/2012 |
| WO | WO-2012/158965 A2 | 11/2012 |
| WO | WO-2012/167744 A1 | 12/2012 |
| WO | WO-2013/148579 A1 | 10/2013 |
| WO | WO-2014/074218 A1 | 5/2014 |
| WO | WO-2014/165240 A1 | 10/2014 |
| WO | WO-2015/031268 A1 | 3/2015 |
| WO | WO-2016/131893 A1 | 8/2016 |
| WO | WO-2018/104718 A1 | 6/2018 |
| WO | WO-2019/183577 A1 | 9/2019 |
| WO | WO-2020/159949 A1 | 8/2020 |
| WO | WO-2022/079639 A1 | 4/2022 |
| WO | WO-2022/080986 A1 | 4/2022 |
| WO | WO-2022/121666 A1 | 6/2022 |
| WO | WO-2022/139538 A1 | 6/2022 |
| WO | WO-2022241287 A2 * | 11/2022 ............... A61P 3/10 |
| WO | WO-2023/028466 A1 | 3/2023 |
| WO | WO-2023/030444 A1 | 3/2023 |
| WO | WO-2023/089594 A1 | 5/2023 |

OTHER PUBLICATIONS

Bonnet et al., "Luminescent lanthanide-binding peptides: sensitising the excited states of Eu(iii) and Tb(iii) with a 1,8-naphthalimide-based antenna," *Organic & Biomolecular Chemistry* (2012) 10(1): 126-133.

Chitturi et al., "NASH and insulin resistance: Insulin hypersecretion and specific association with the insulin resistance syndrome," *Hepatology* (2002) 35(2):373-9.

Choi et al., "Highly efficient and fast pre-activation cyclization of the long peptide: Succinimidyl ester-amine reaction revisited," *Bioorg & Med Chem Lett.* (2015) 25(22) 5335-8.

Chopra et al., "Versatile cyclic templates for assembly of axially oriented ligands," *Bioconjug Chem.* (2009) 20(2):231-40.

Clarke et al., "Reduced awareness of hypoglycemia in adults with IDDM. A prospective study of hypoglycemic frequency and associated symptoms," *Diabetes Care.* (1995) 18(4):517-22.

Deacon et al., "Degradation of glucagon-like peptide-1 by human plasma in vitro yields an N-terminally truncated peptide that is a major endogenous metabolite in vivo," *J Clin Endocrinol Metab.* (1995) 80(3):952-7.

Demoin et al., "Monooxorhenium (V) complexes with 222-N2S2 MAMA ligands for bifunctional chelator agents: Syntheses and preliminary in vivo evaluation," *Nucl Med Biol.* (2016) 43(12):802-811.

Elduque et al., "Straightforward synthesis of cyclic and bicyclic peptides," *Org Lett.* (2013) 15(8):2038-41.

Faull et al., "Revised primary structures of rat pituitary gamma-lipotrophin and beta-endorphin," *Neuropeptides.* (1998) 32(4):339-49.

Finan et al., "Unimolecular dual incretins maximize metabolic benefits in rodents, monkeys, and humans," *Sci Transl Med.* (2013) 5(209): 1-17.

Gregory et al., "Iatrogenic hyperinsulinemia, not hyperglycemia, drives insulin resistance in Type 1 Diabetes as revealed by comparison with GCK-MODY (MODY2)," *Diabetes.* (2019) 68(8):1565-76.

Gupta et al., "Whole-virus screening to develop synbodies for the influenza virus," *Bioconjug Chem.* (2016) 27(10):2505-2512.

Guy et al., "De novo helical peptides as target sequences for a specific, fluorogenic protein labelling strategy," *Mol Biosyst.* (2010) 6(6):976-87.

Hsia et al., "An update on sodium-glucose co-transporter-2 inhibitors for the treatment of diabetes mellitus," *Curr Opin Endocrinol Diabetes Obes.* (2017). 24(1):73-9.

Khaodhiar et al., "Treating diabetes and prediabetes by focusing on obesity management," *Curr Diab Rep.* (2009) 9(5):348-54.

Kim et al., "Targeting of secretory proteins as a therapeutic strategy for treatment of nonalcoholic steatohepatitis (NASH)," *Int J Mol Sci.* (2020) 21(7): 2296.

Kitabchi et al., "Hyperglycemic crises in adult patients with diabetes," *Diabetes Care.* (2009) 32(7):1335-43.

Lisse et al., "Monofunctional stealth nanoparticle for unbiased single molecule tracking inside living cells," *Nano Lett.* (2014) 14(4):2189-95.

Lisse et al., "Supplementary information and results: Monofunctional Stealth Nanoparticle for Unbiased Single Molecule Tracking Inside Living Cells," *Nano Lett.* (2014) 14:2189-2195.

Marín-Peñalver et al., "Update on the treatment of type 2 diabetes mellitus," *World J Diabetes.* (2016) 7(17):354-95.

Moshitzky et al., "Determination of locust AKH-I by radioimmunoassay and the identification of an AKH-like factor in the locust brain," *Insect Biochem.* (1987) 17:5:765-769.

Nacheva et al., "Fluorescent properties and resonance energy transfer of 3,4-bis(2,4-difluorophenyl)-maleimide," *Organic & Biomolecular Chemistry* (2012) 10:38:7840-7846.

Sakai et al., "Self-assembly: Formation of functionalized nanowires by control of self-assembly using multiple modified amyloid peptides," *Adv. Funct. Mater.* (2013) 23:39:4881-4887.

Schauer et al., "Insulin resistance, defective insulin-mediated fatty acid suppression, and coronary artery calcification in subjects with and without type 1 diabetes: The CACTI study," *Diabetes.* (2011) 60(1):306-14.

Sieno et al., "Glucose-dependent insulinotropic polypeptide and glucagon-like peptide-1: Incretin actions beyond the pancreas," *J Diabetes Investig.* (2013) 4(2): 108-130.

Shirmardi et al., "Preclinical evaluation of a new bombesin analog for imaging of gastrin-releasing peptide receptors," *Cancer Biother Radiopharm.* (2011) 26(3):309-16.

Skelly et al., "Finding on liver biopsy to investigate abnormal liver function tests in the absence of diagnostic serology," 2001, *J. Hepatol.* (2001) 35:195-199.

Van Der Schueren et al., "Obesity in people living with type 1 diabetes," *Lancet Diabetes Endocrinol.* (2021) 9(11):776-85.

Extended Search Report in European Application No. 19772275.4, dated Apr. 7, 2022, 11 pages.

Written Opinion and Search Report in Singaporean Application No. 11202009338S, dated Mar. 15, 2022, 9 pages.

* cited by examiner

Compound 101

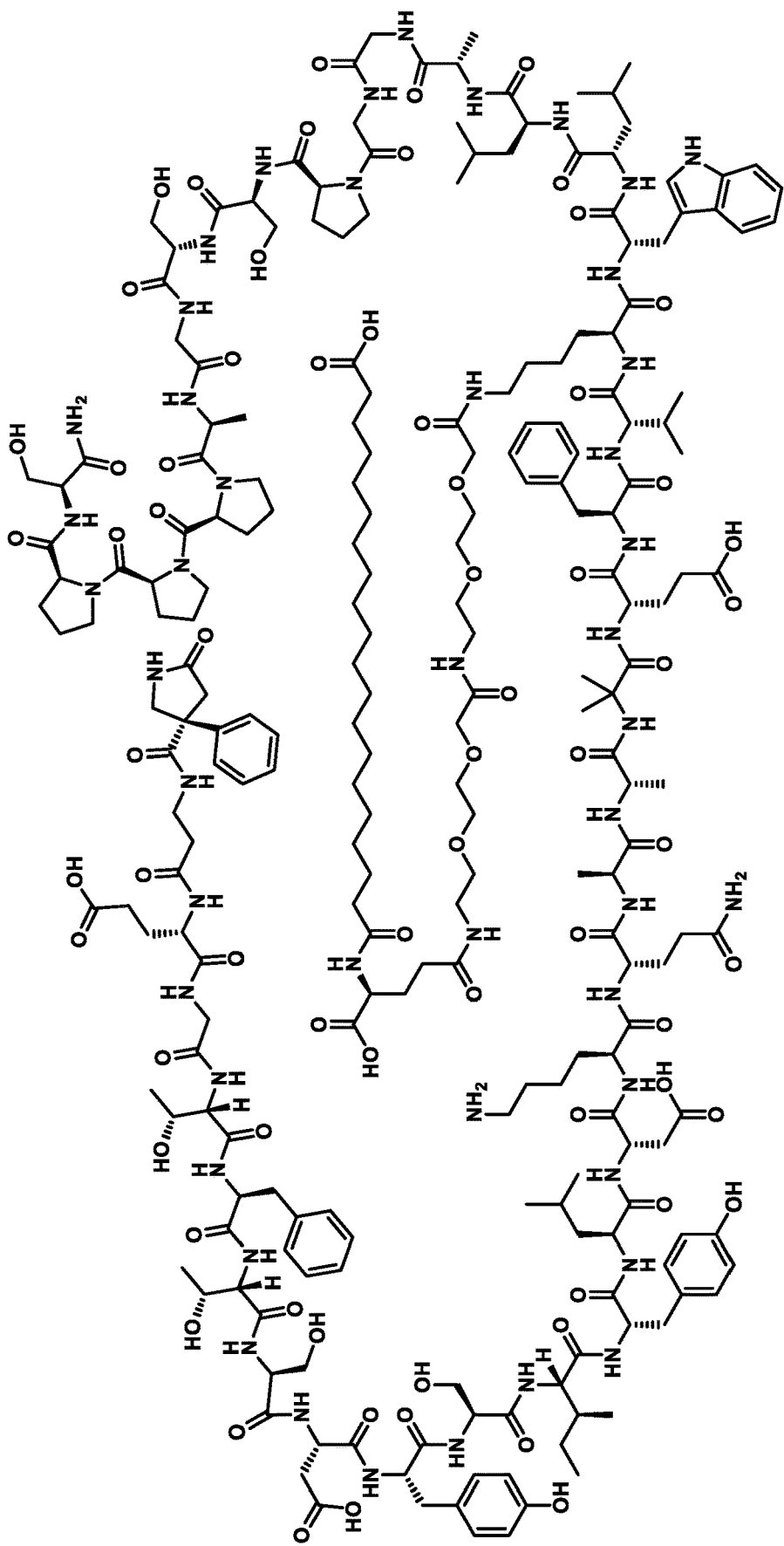
Compound 102
FIG. 1 - Cont'd

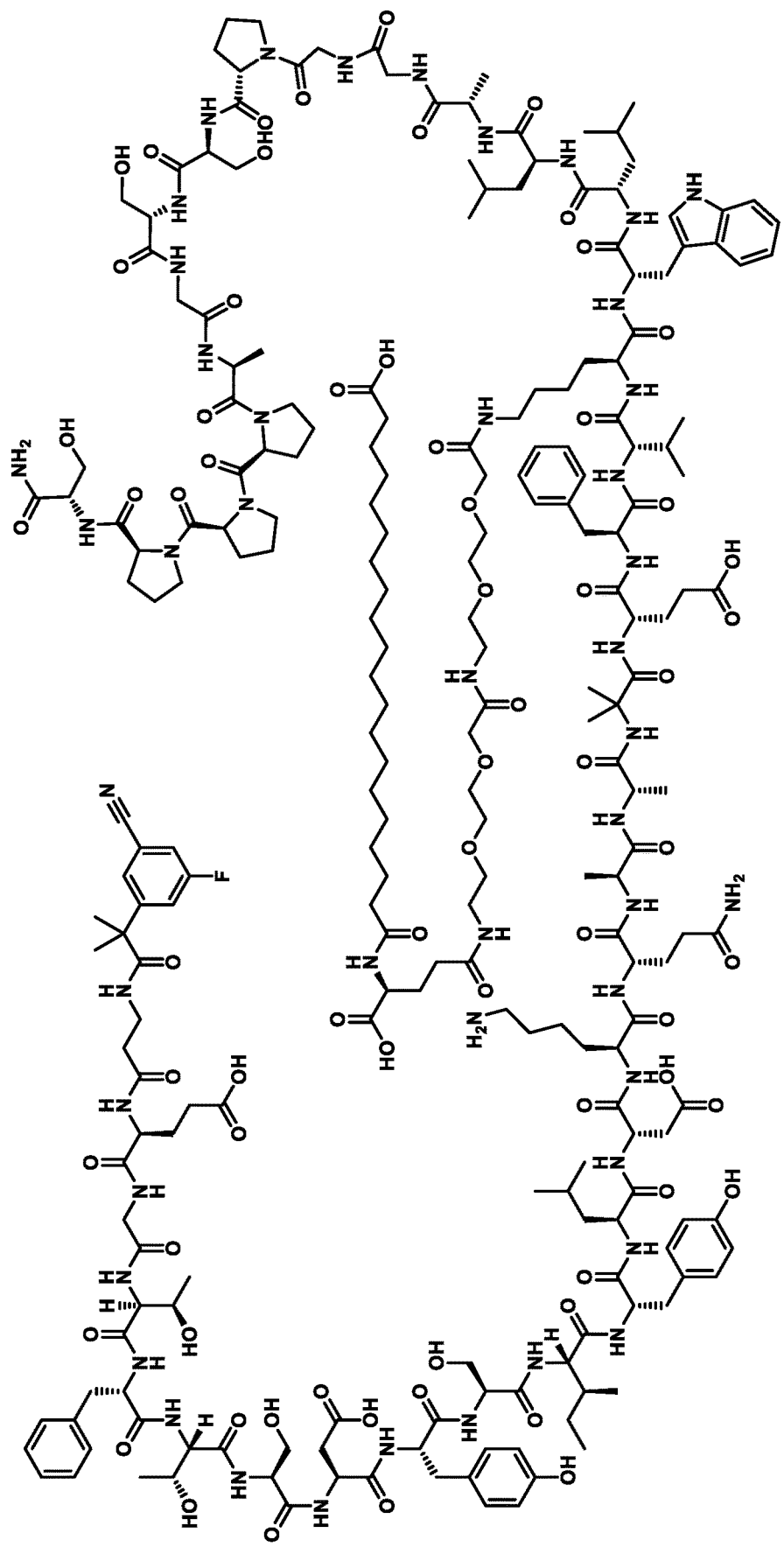
Compound 103
FIG. 1 - Cont'd

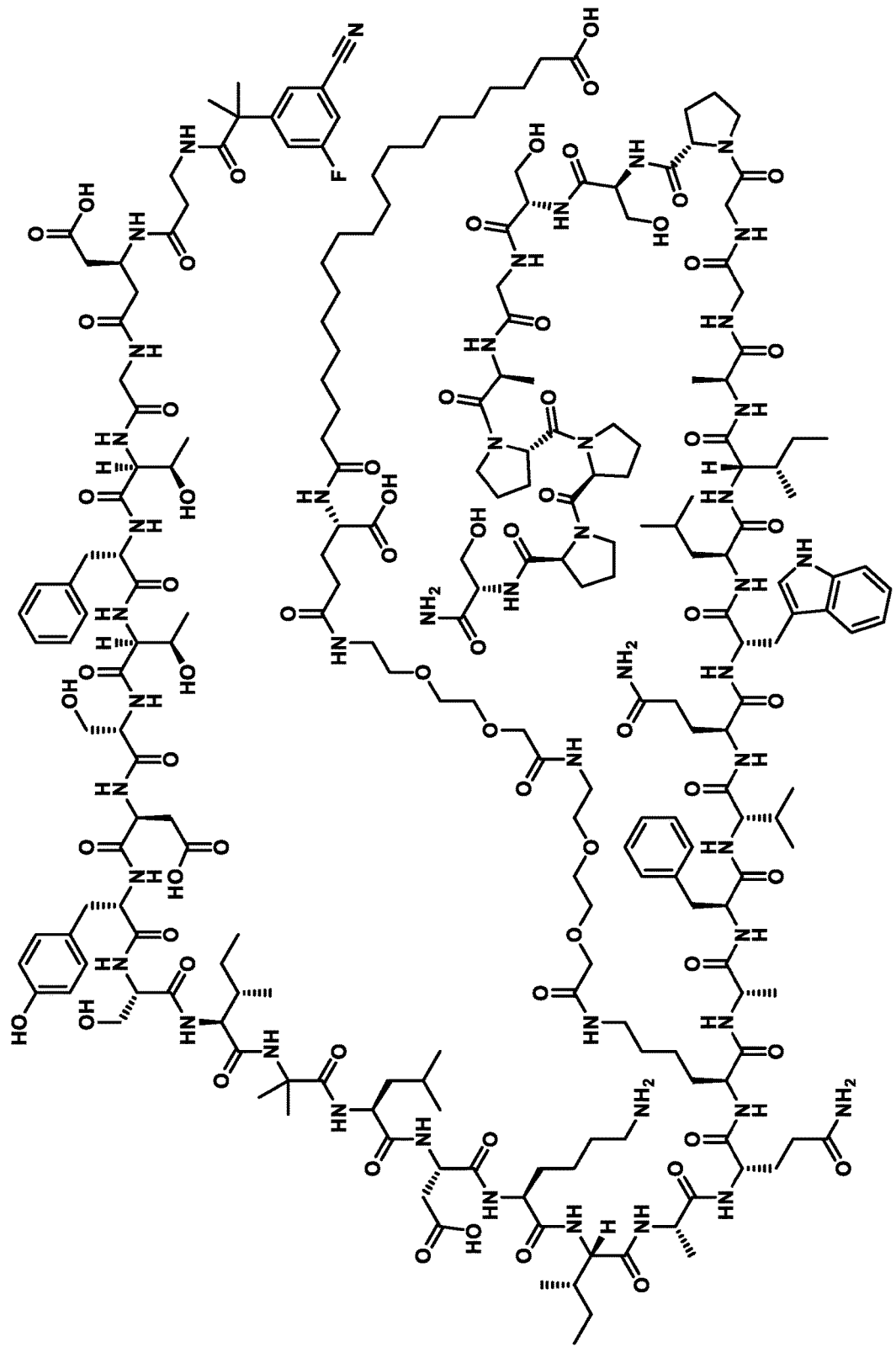
Compound 104
FIG. 1 - Cont'd

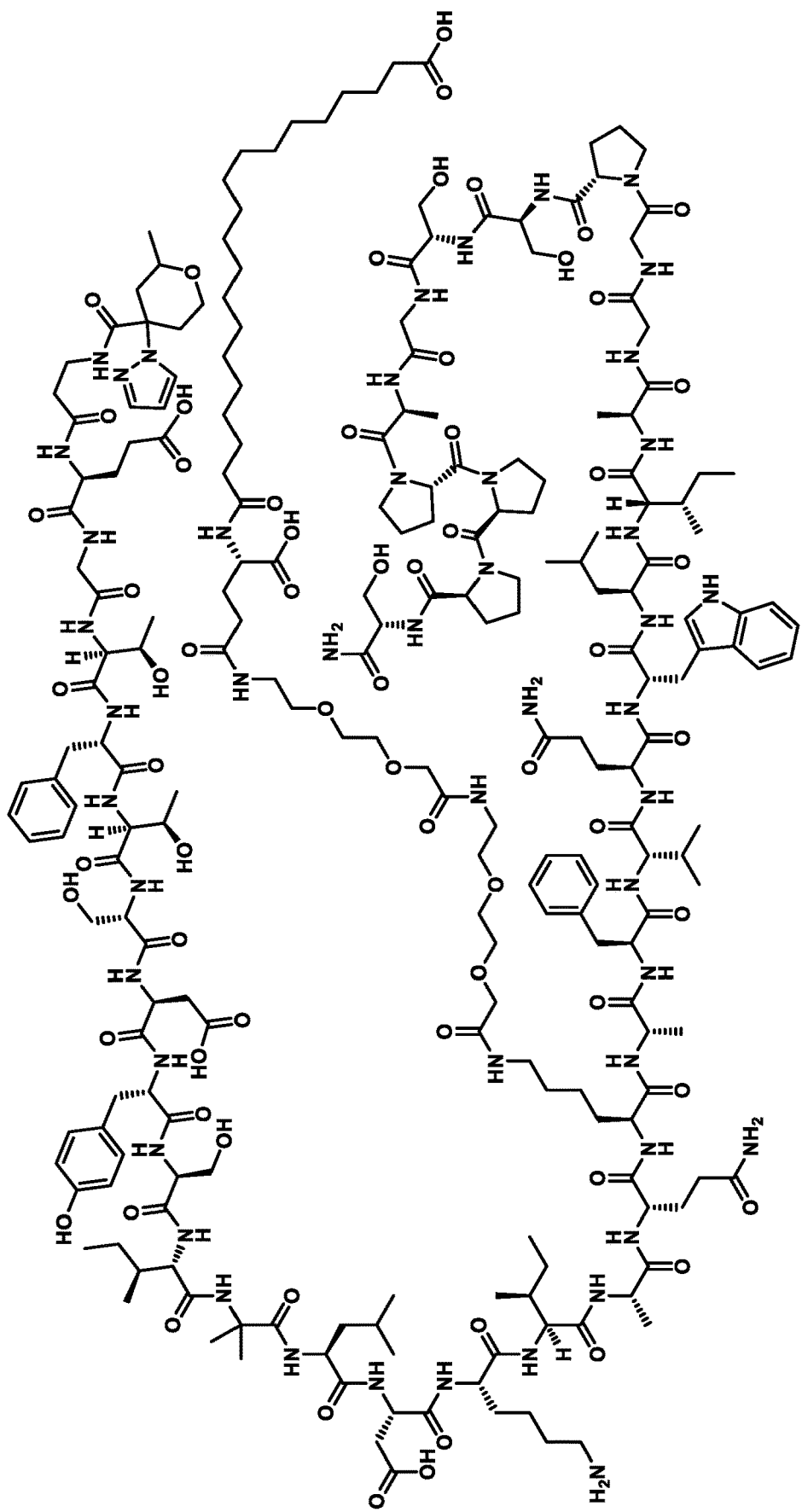
FIG. 1 - Cont'd
Compound 105

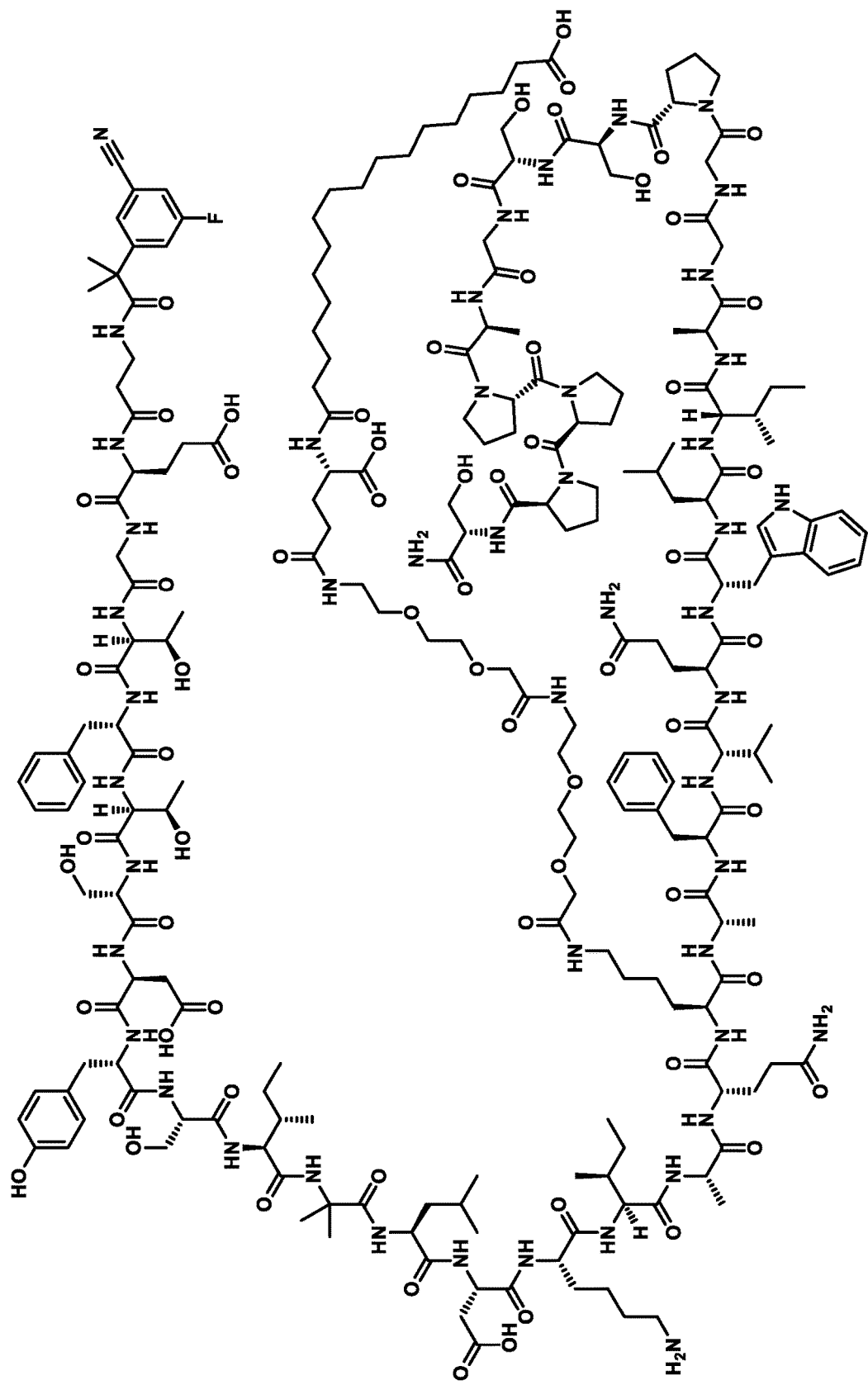
FIG. 1 - Cont'd
Compound 106

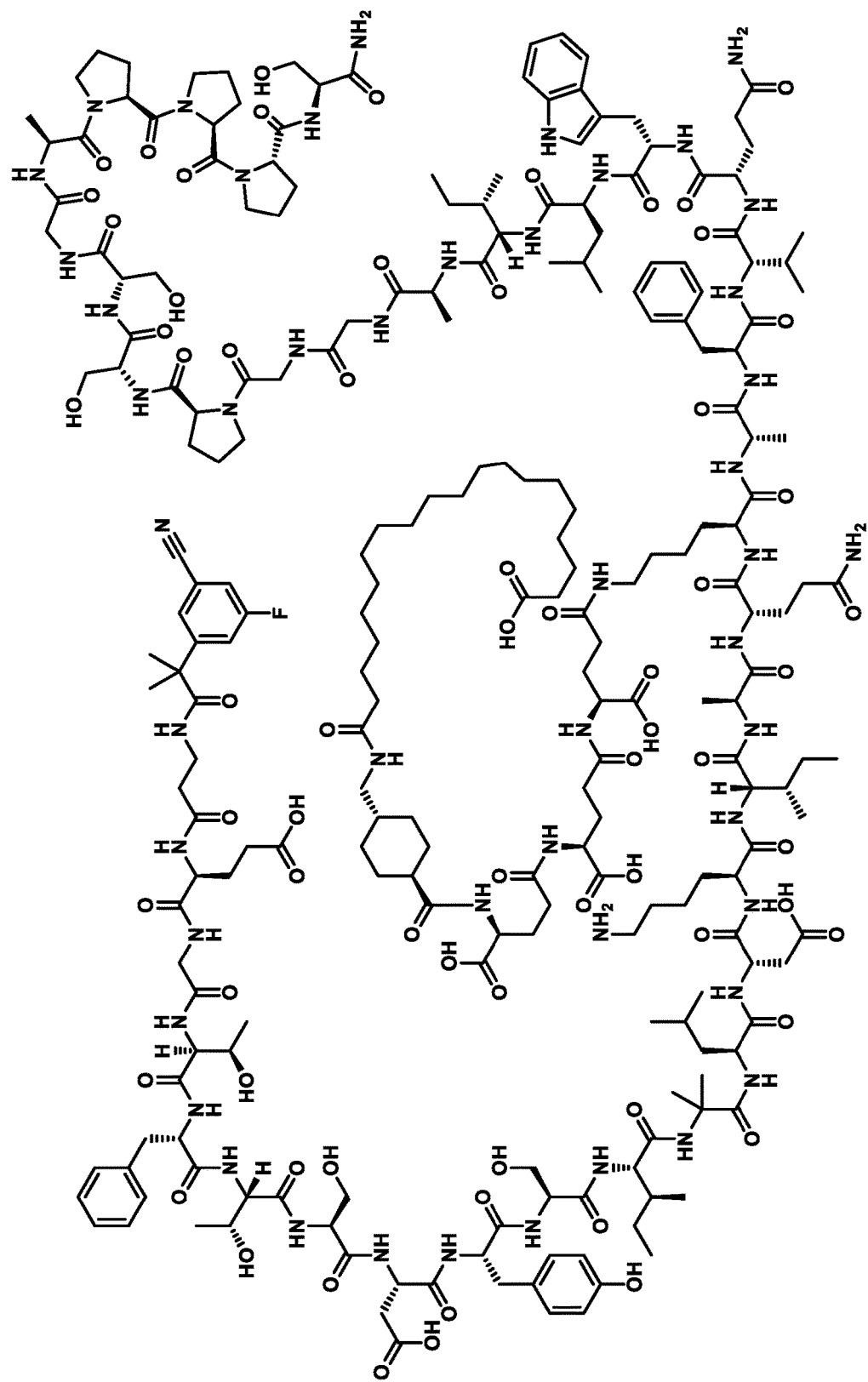
Compound 107
FIG. 1 - Cont'd

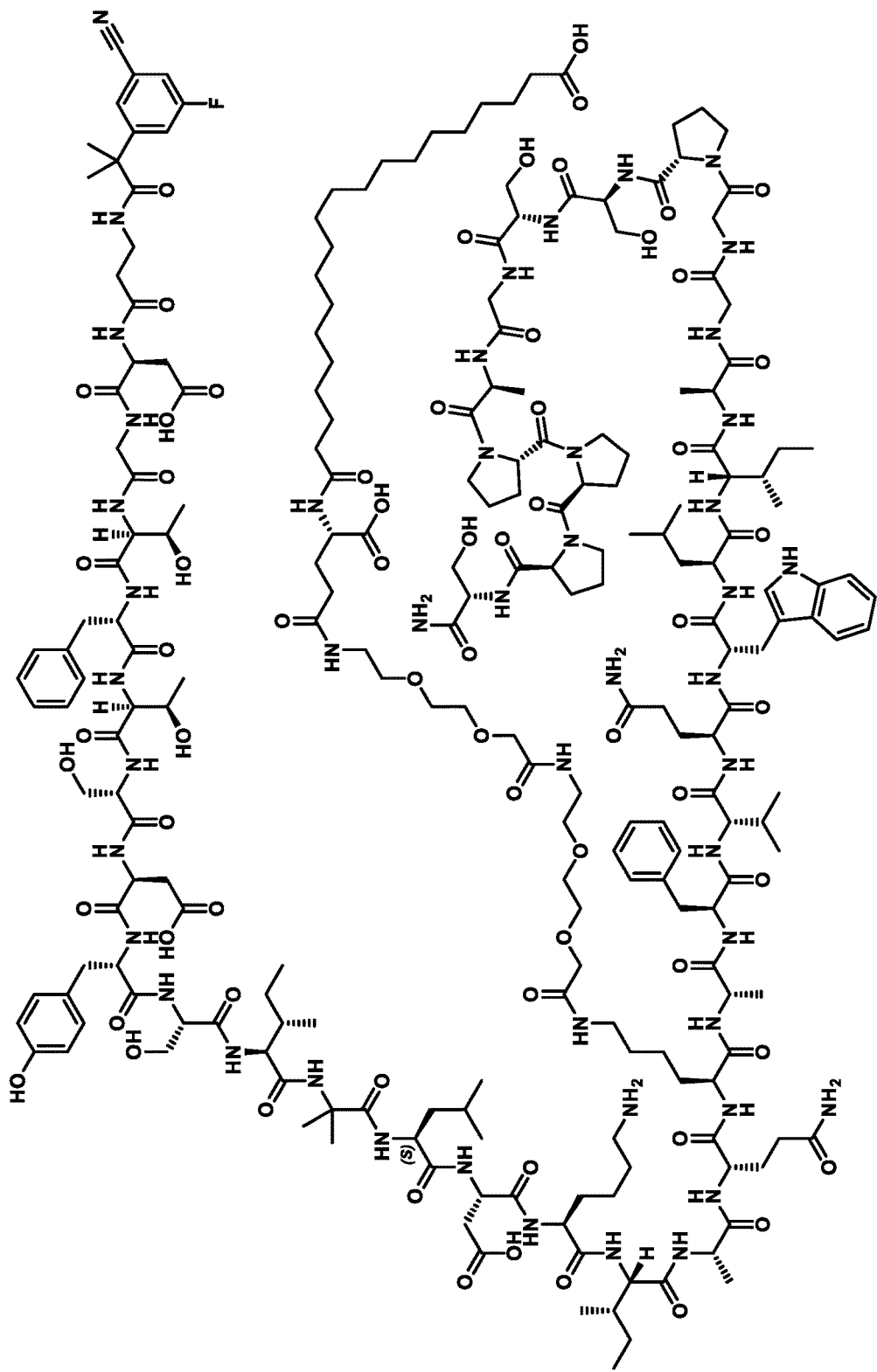
Compound 108
FIG. 1 - Cont'd

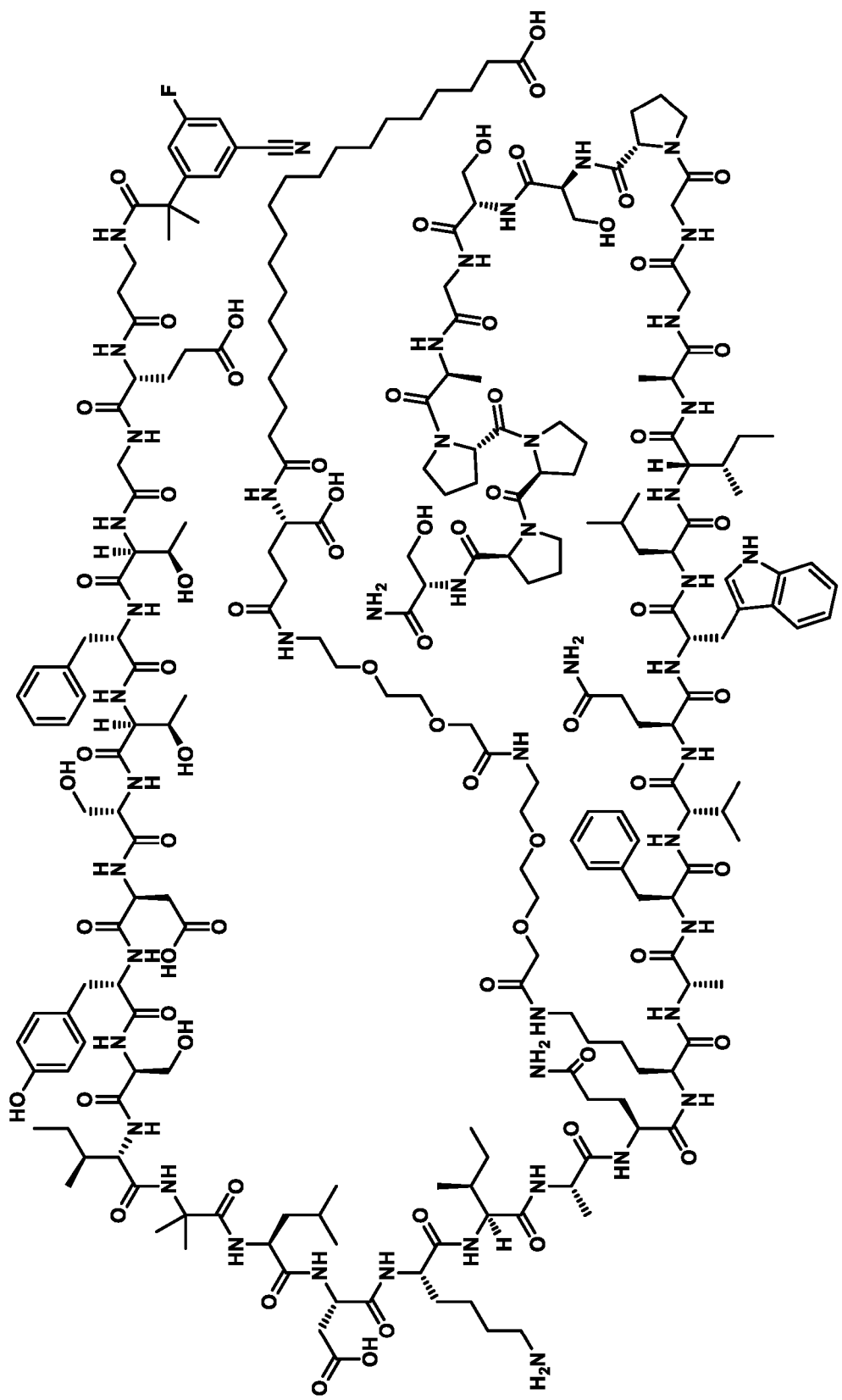
Compound 109
FIG. 1 - Cont'd

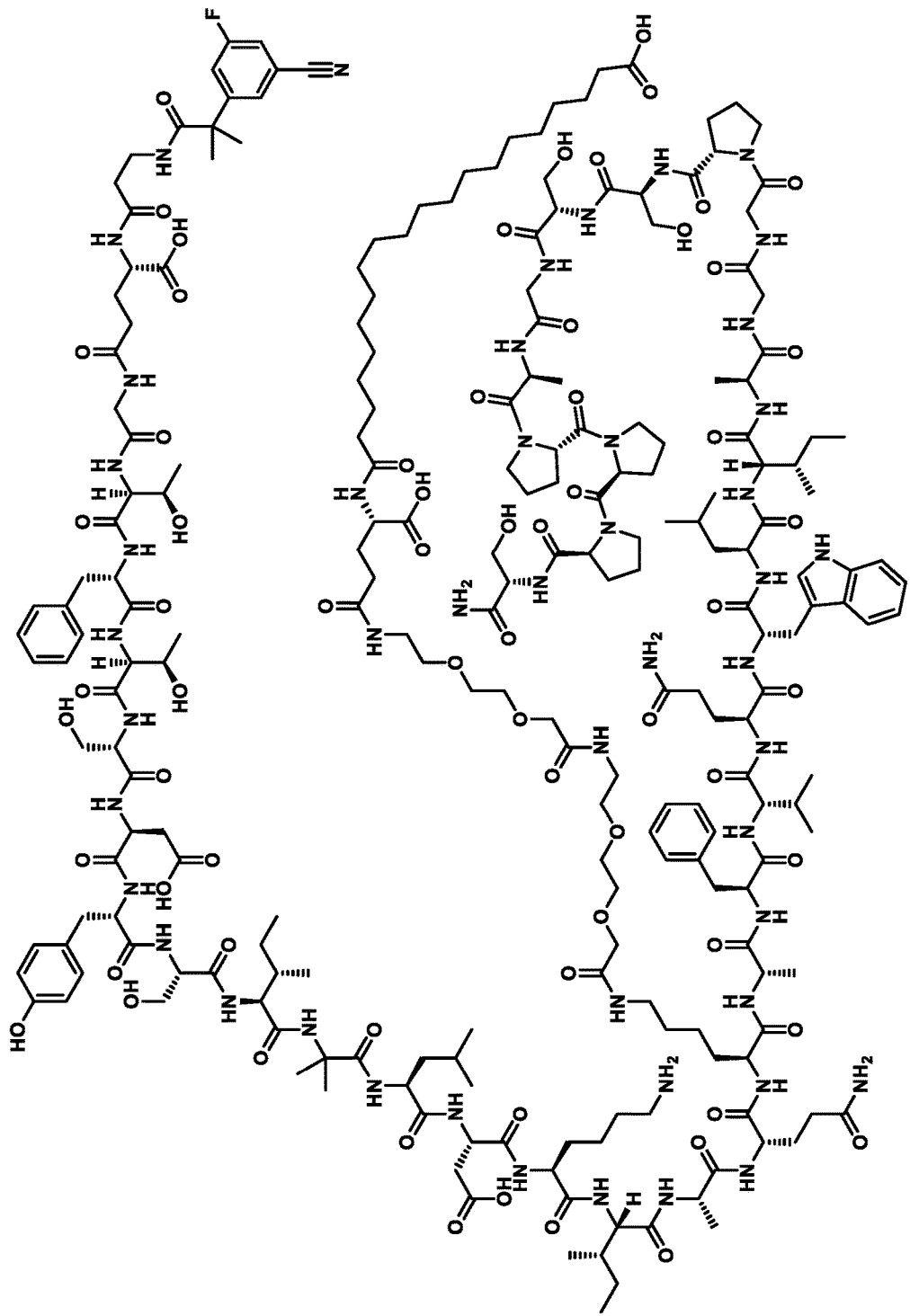
FIG. 1 - Cont'd
Compound 110

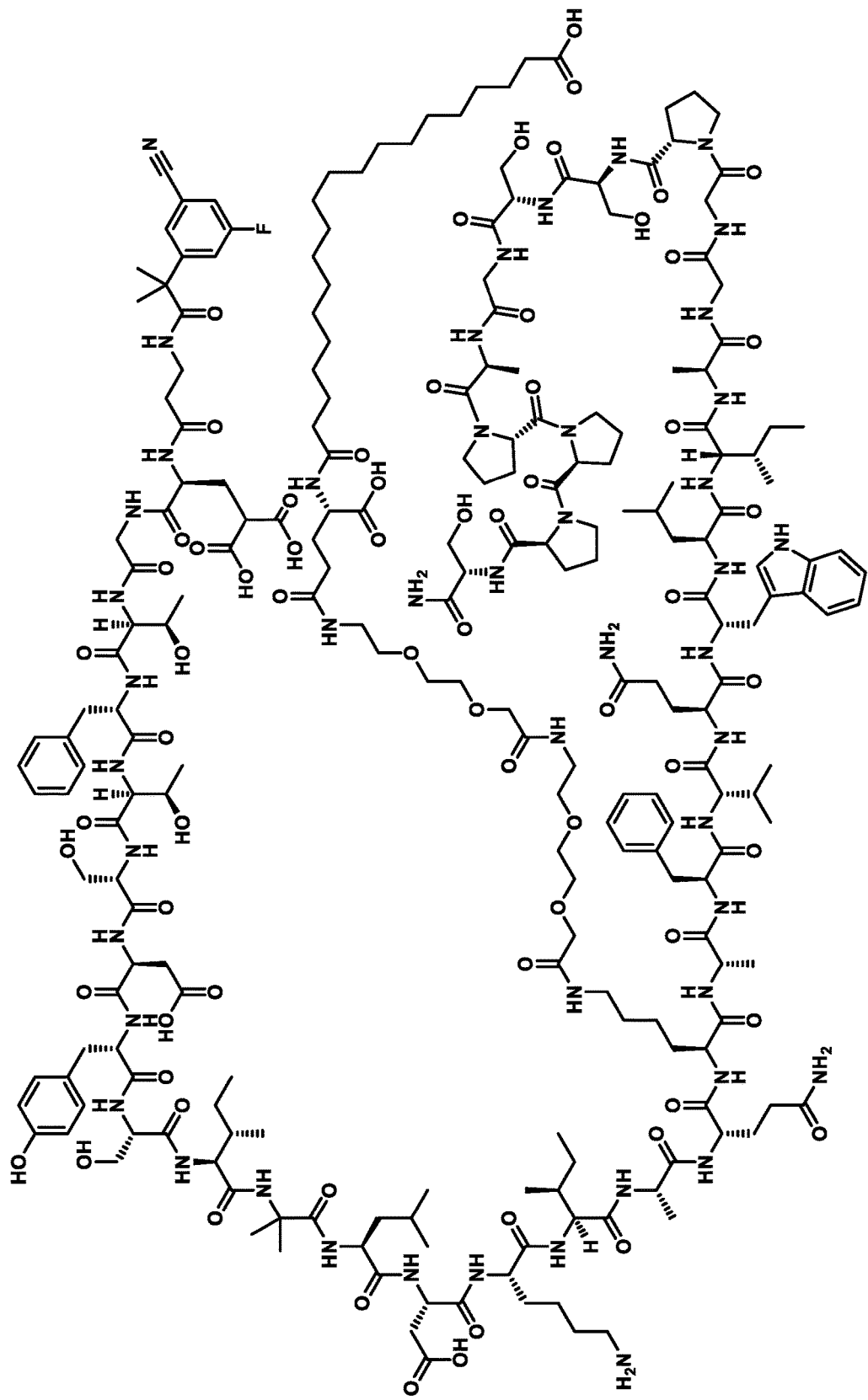
FIG. 1 - Cont'd
Compound 111

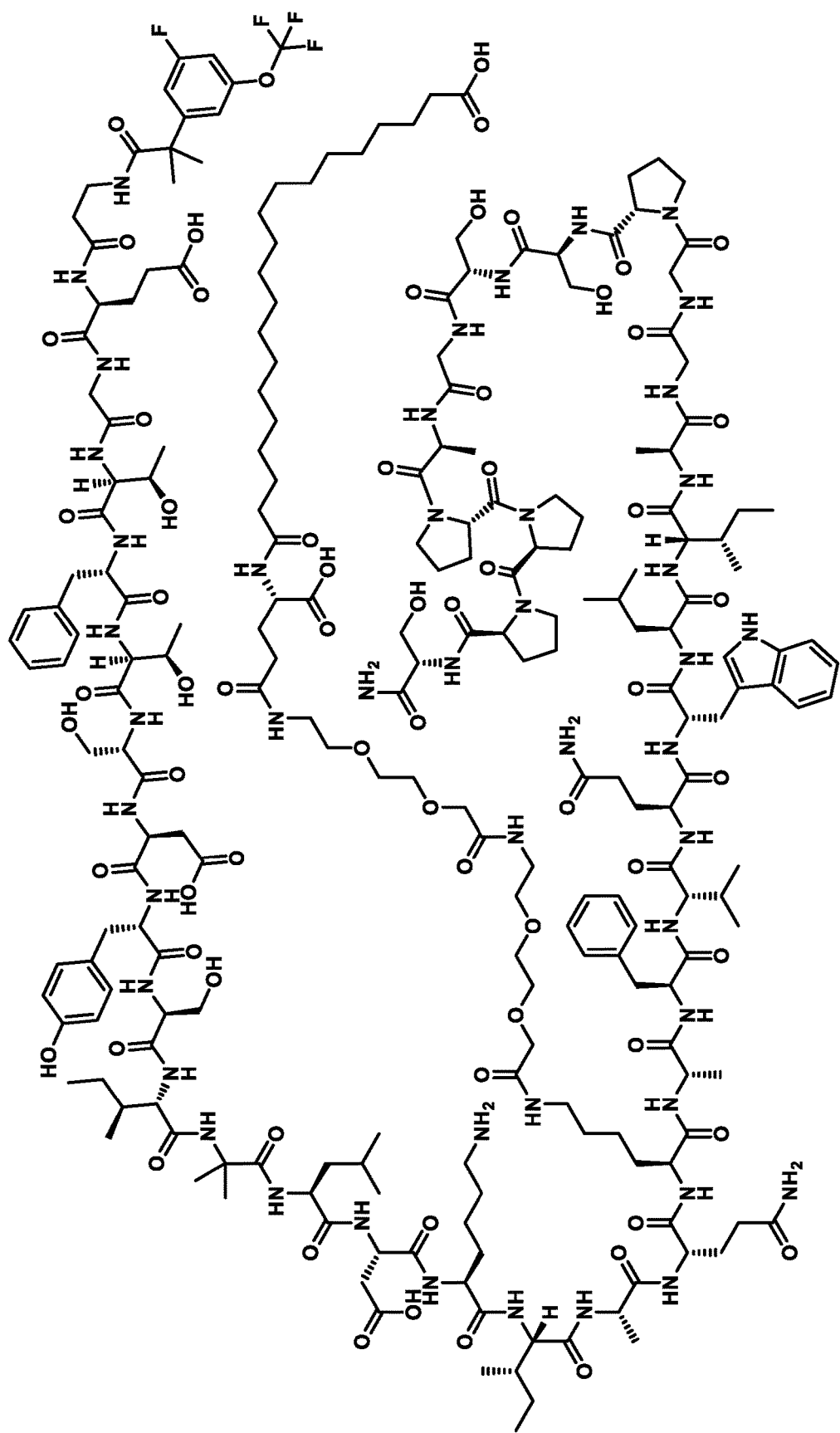
Compound 112
FIG. 1 - Cont'd

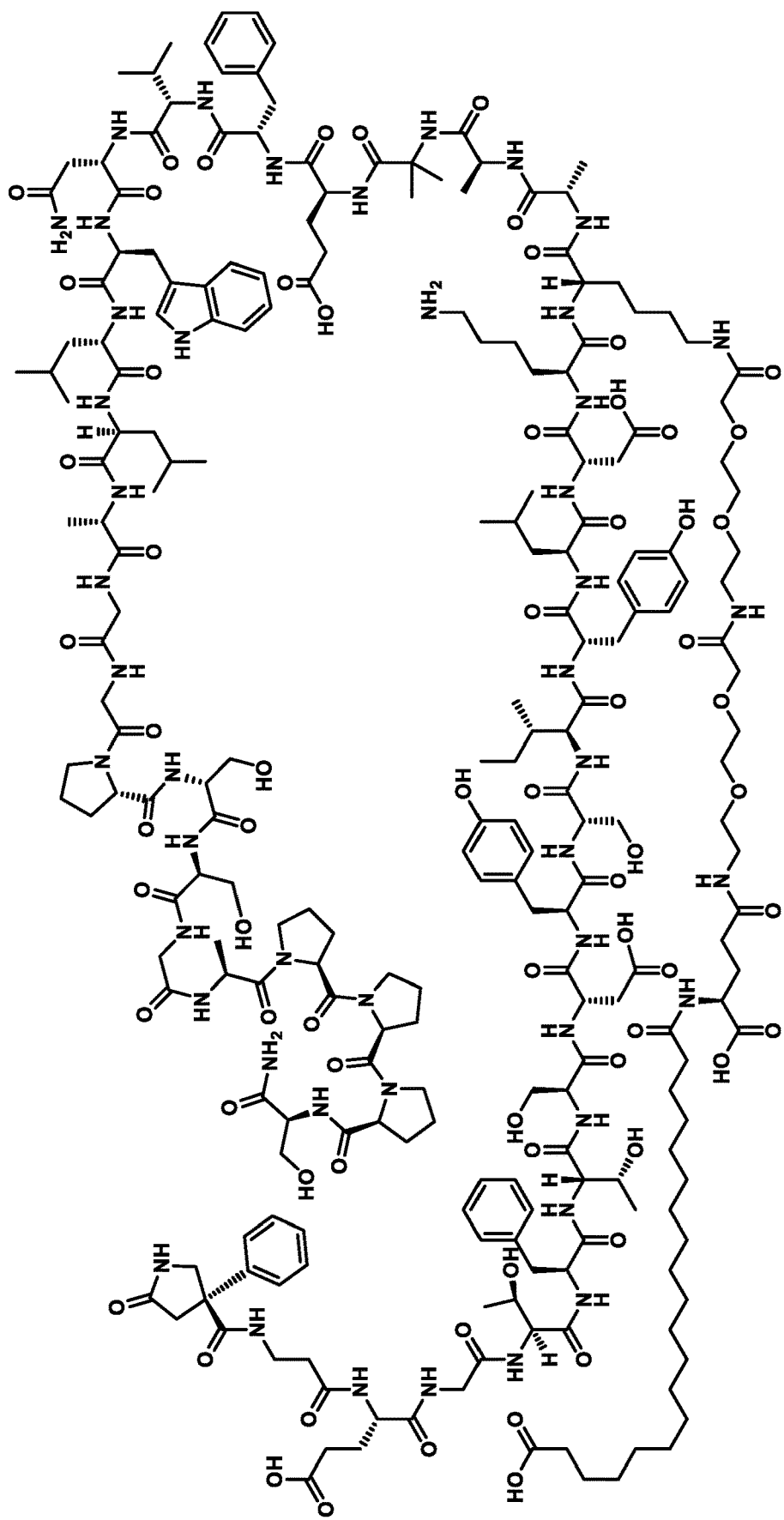
Compound 113
FIG. 1 - Cont'd

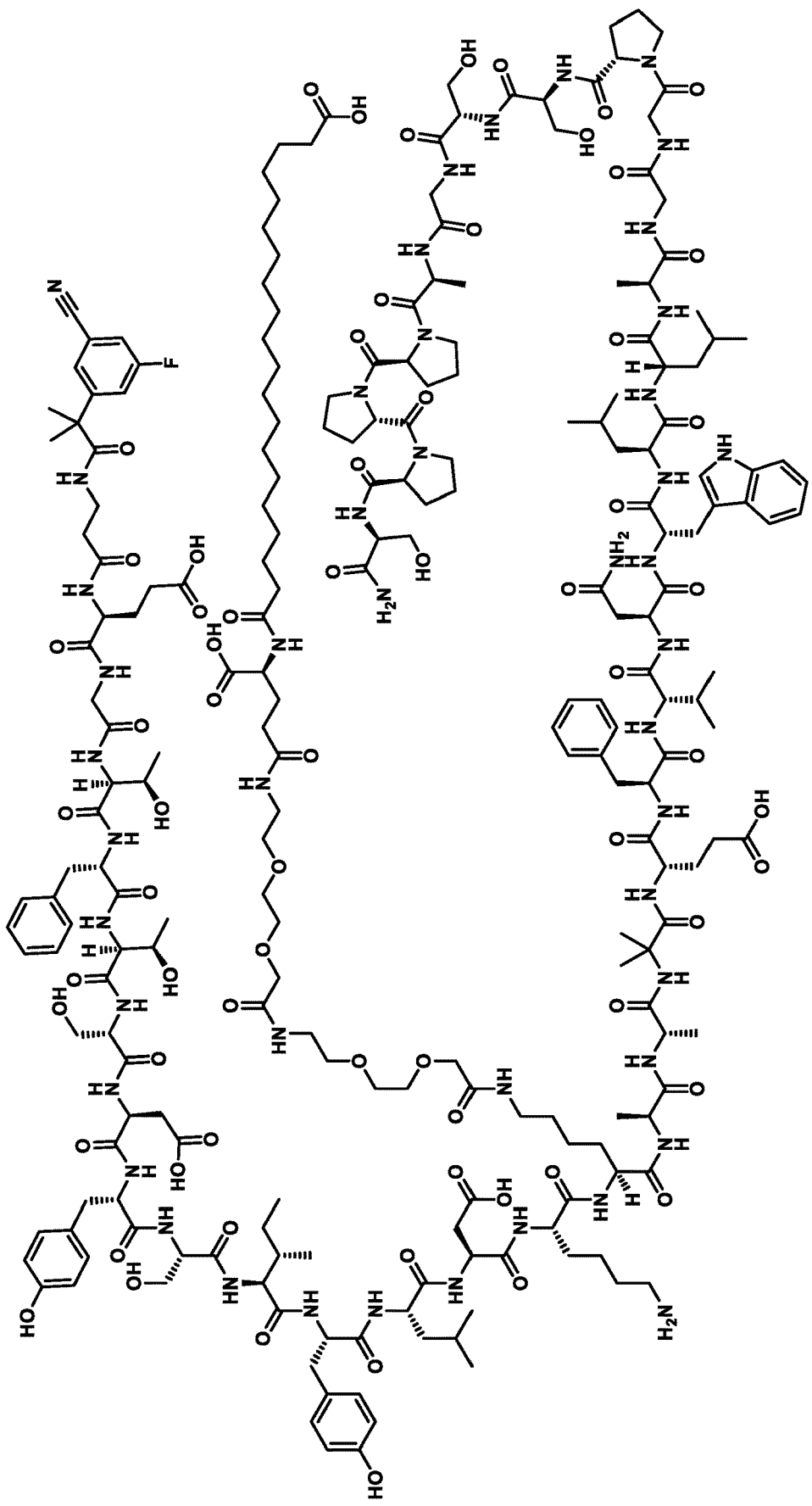
FIG. 1 - Cont'd
Compound 114

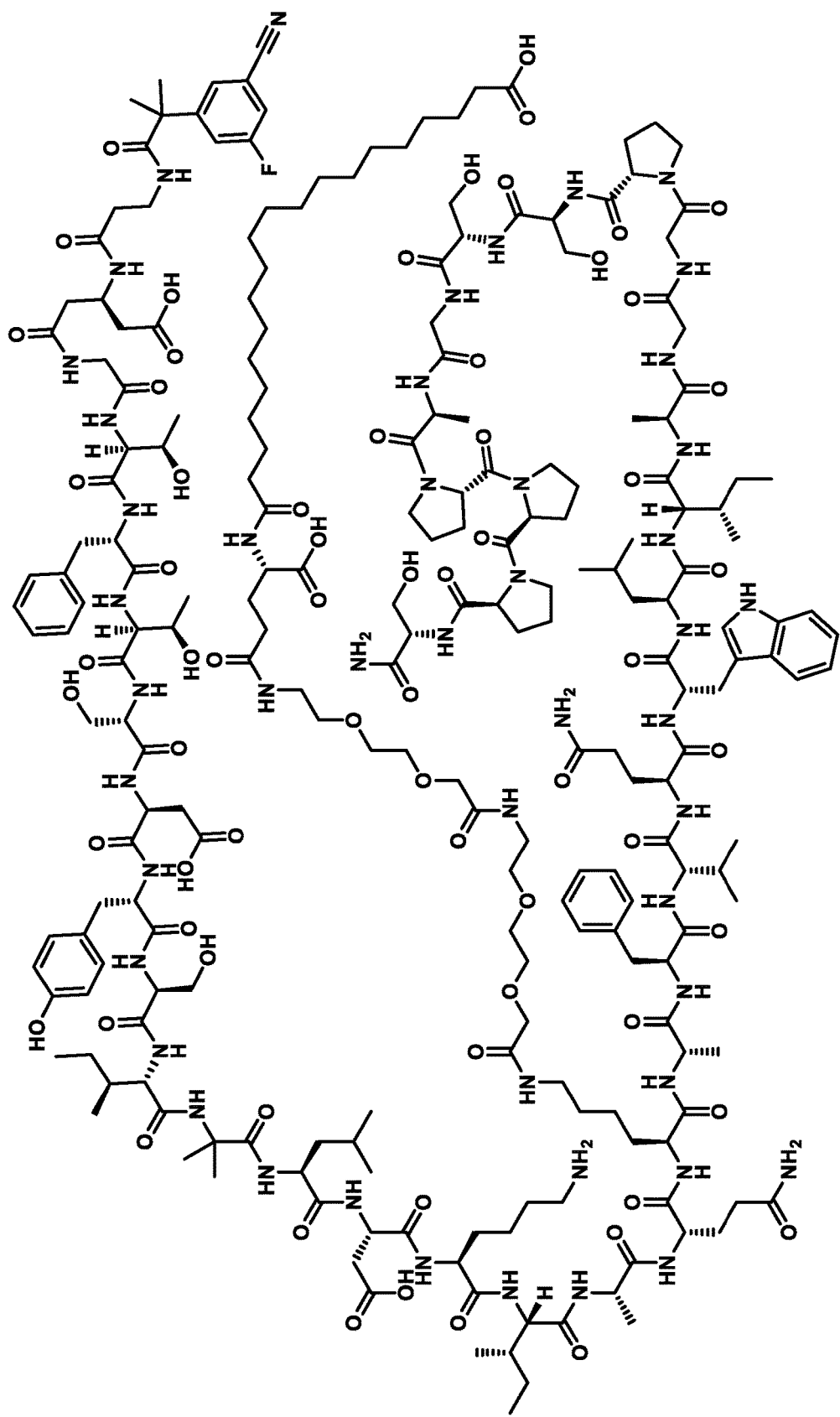
Compound 115
FIG. 1 - Cont'd

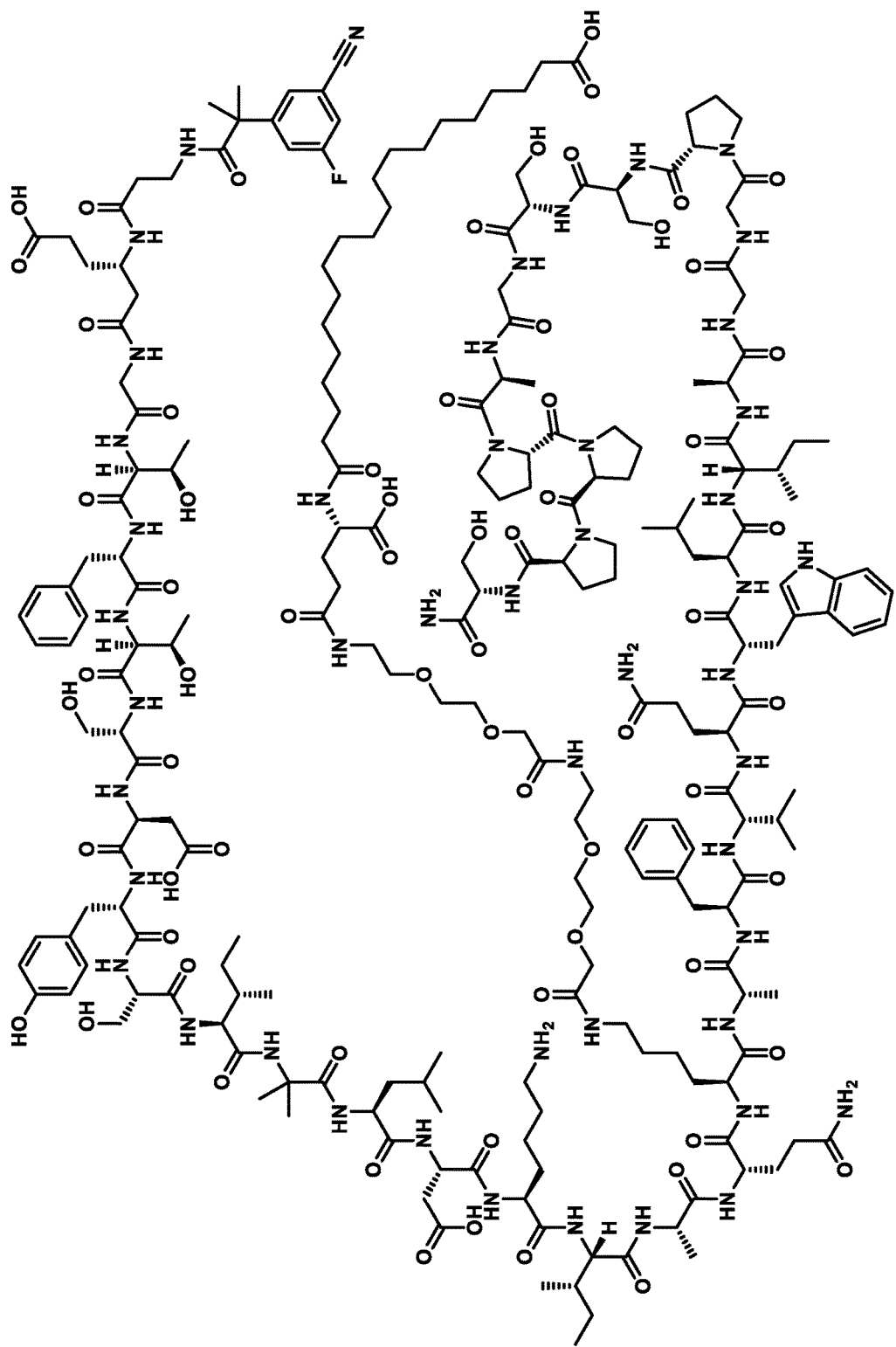
FIG. 1 - Cont'd
Compound 116

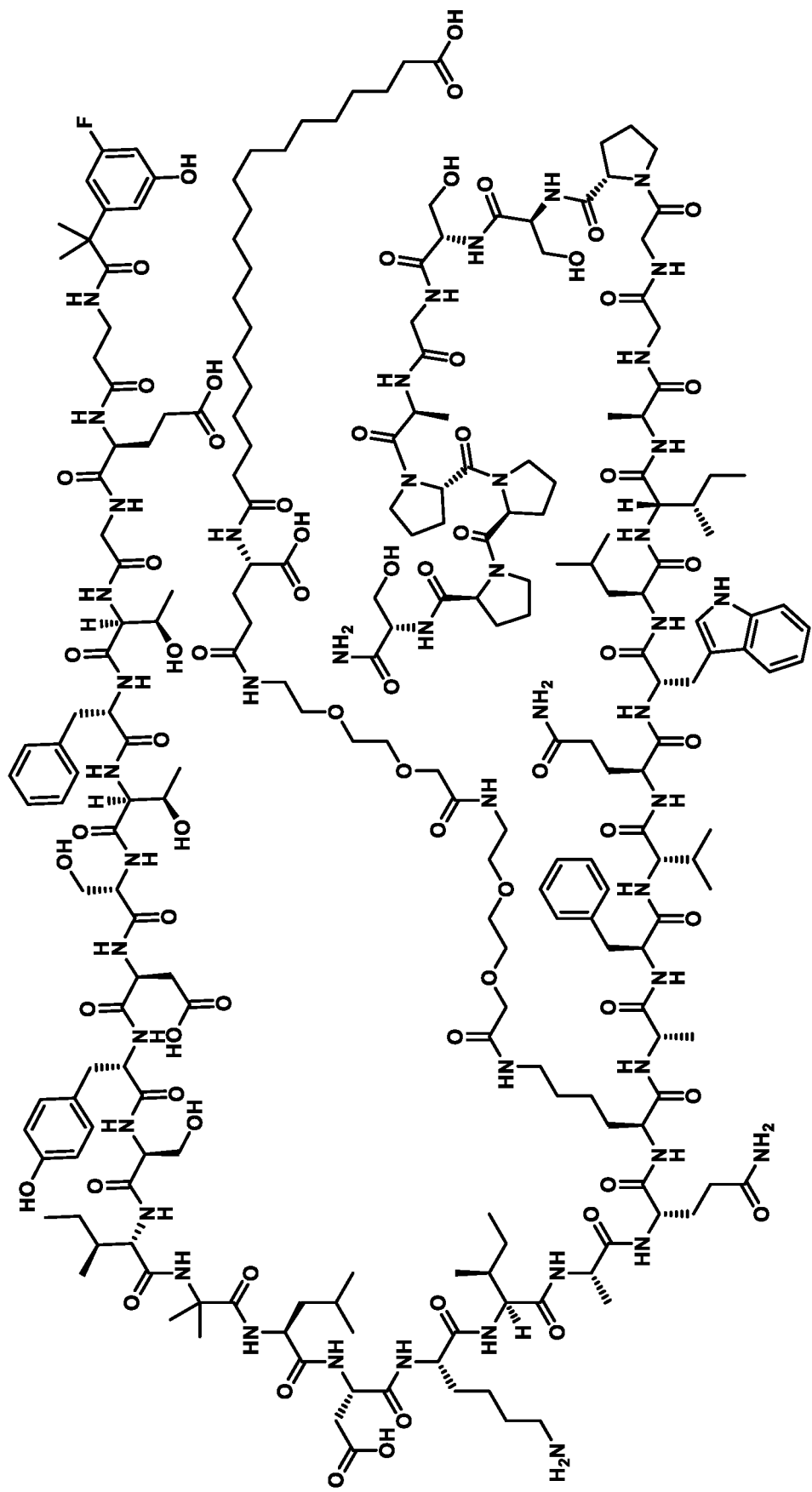
Compound 117
FIG. 1 - Cont'd

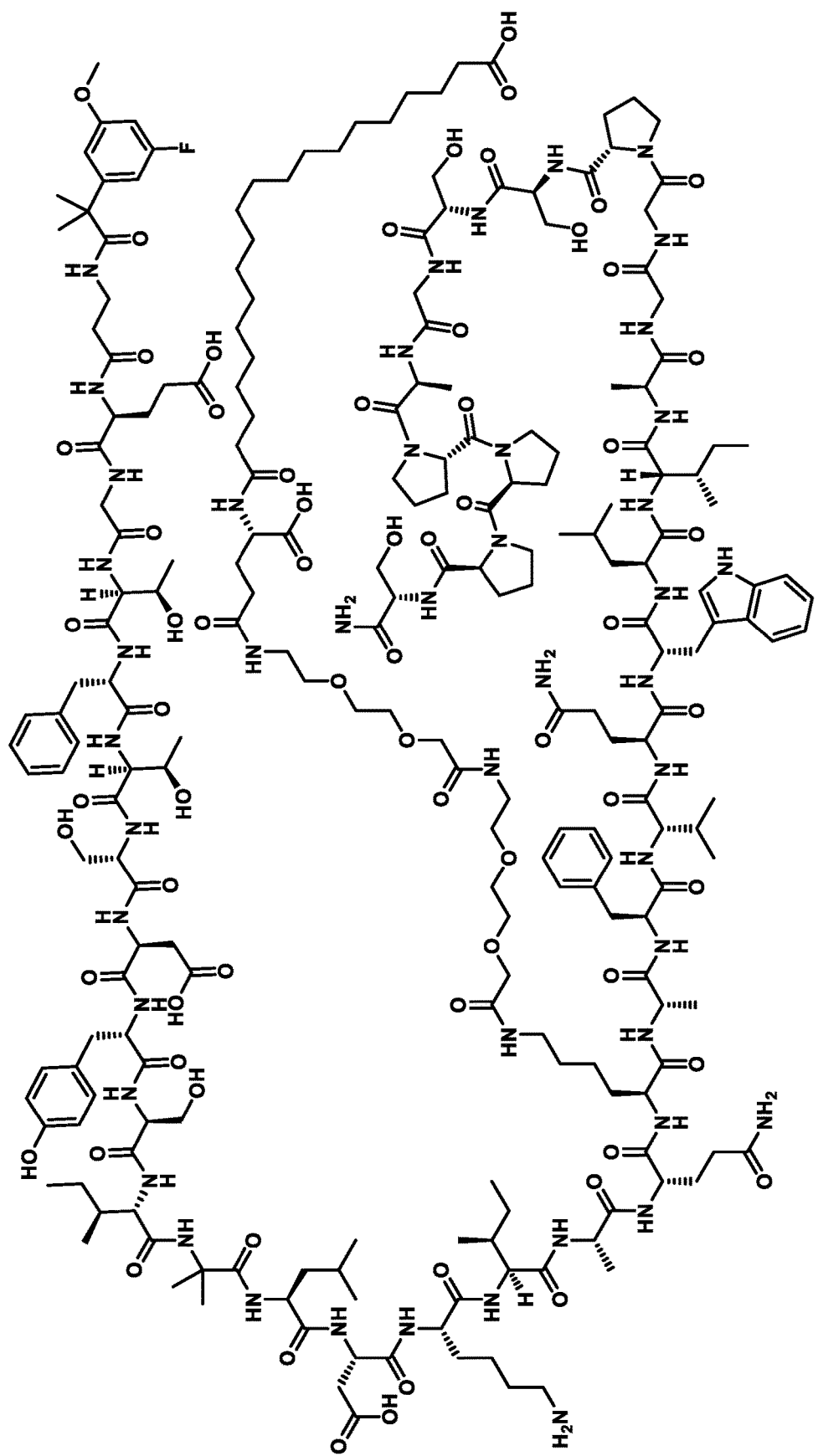
Compound 118
FIG. 1 - Cont'd

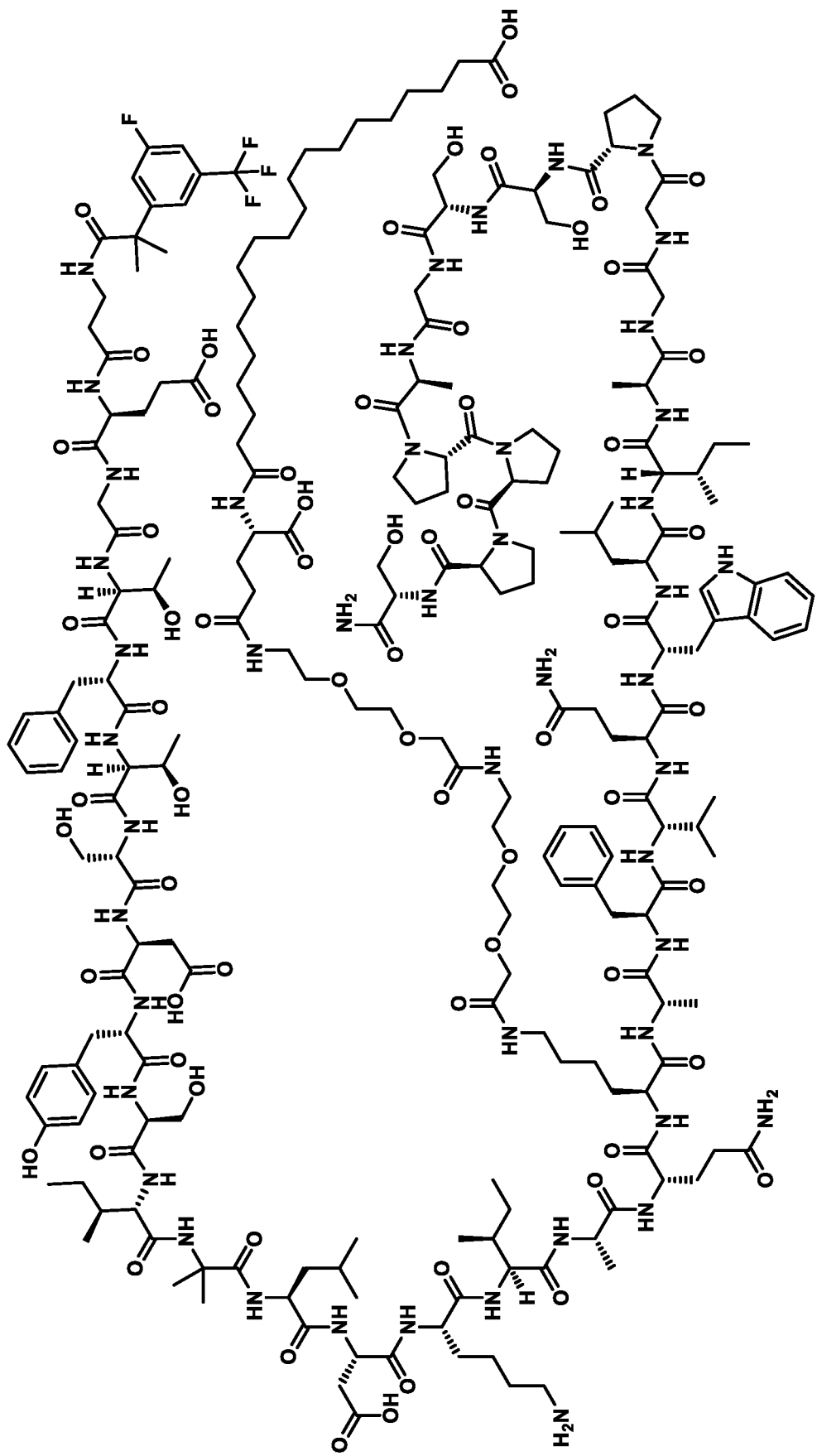
Compound 119
FIG. 1 - Cont'd

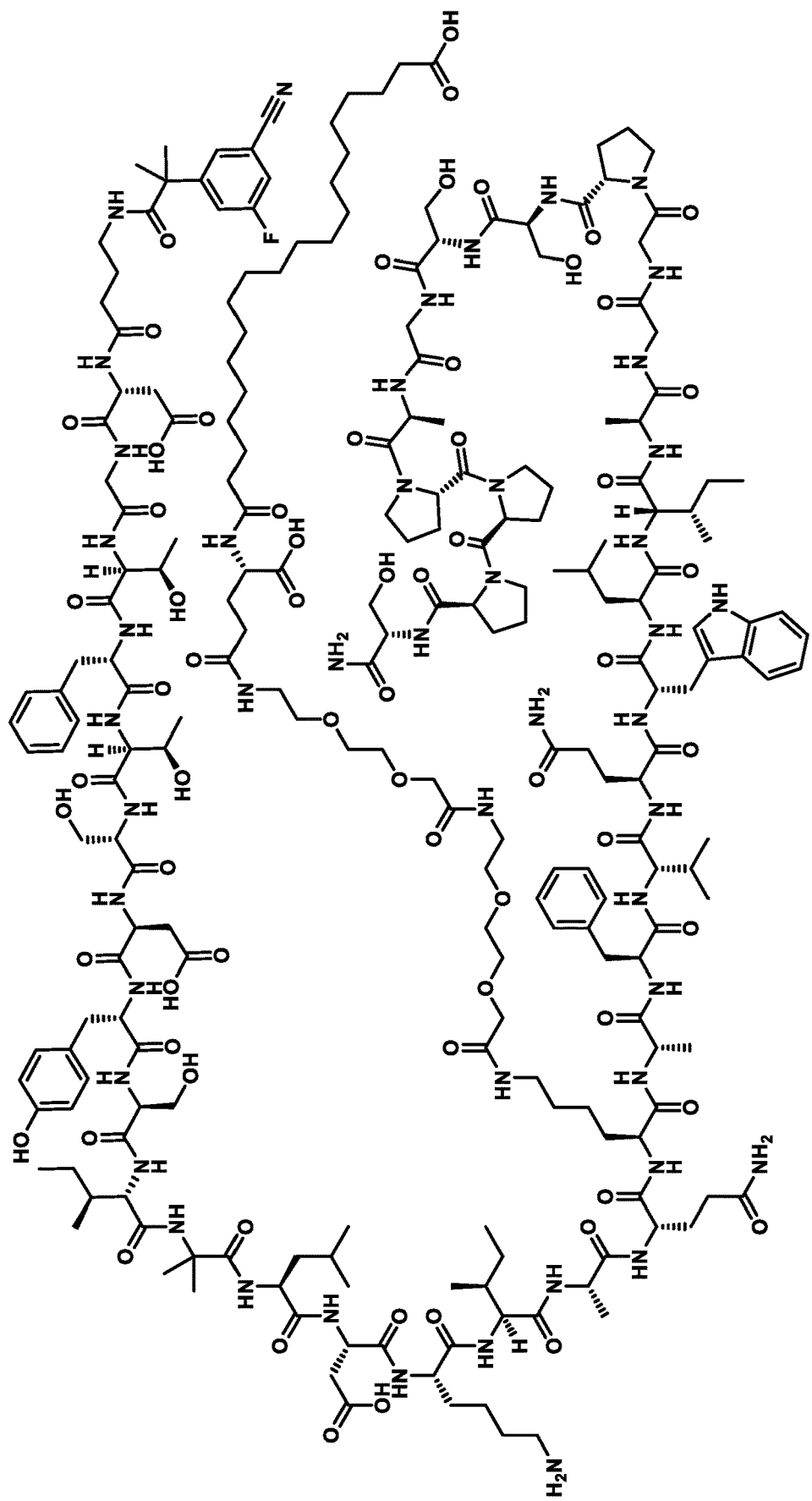
Compound 120
FIG. 1 - Cont'd

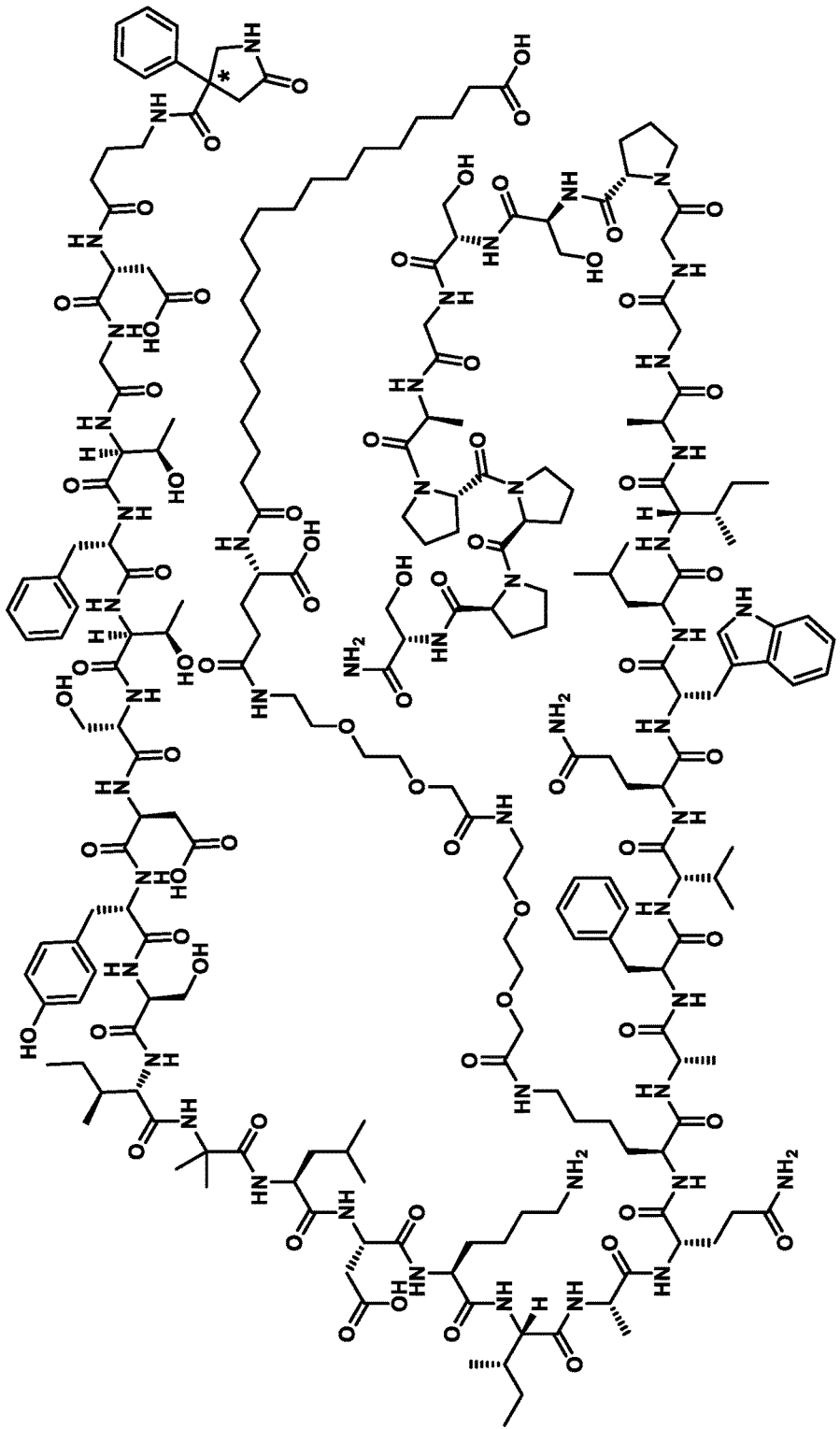
Compound 121
FIG. 1 - Cont'd

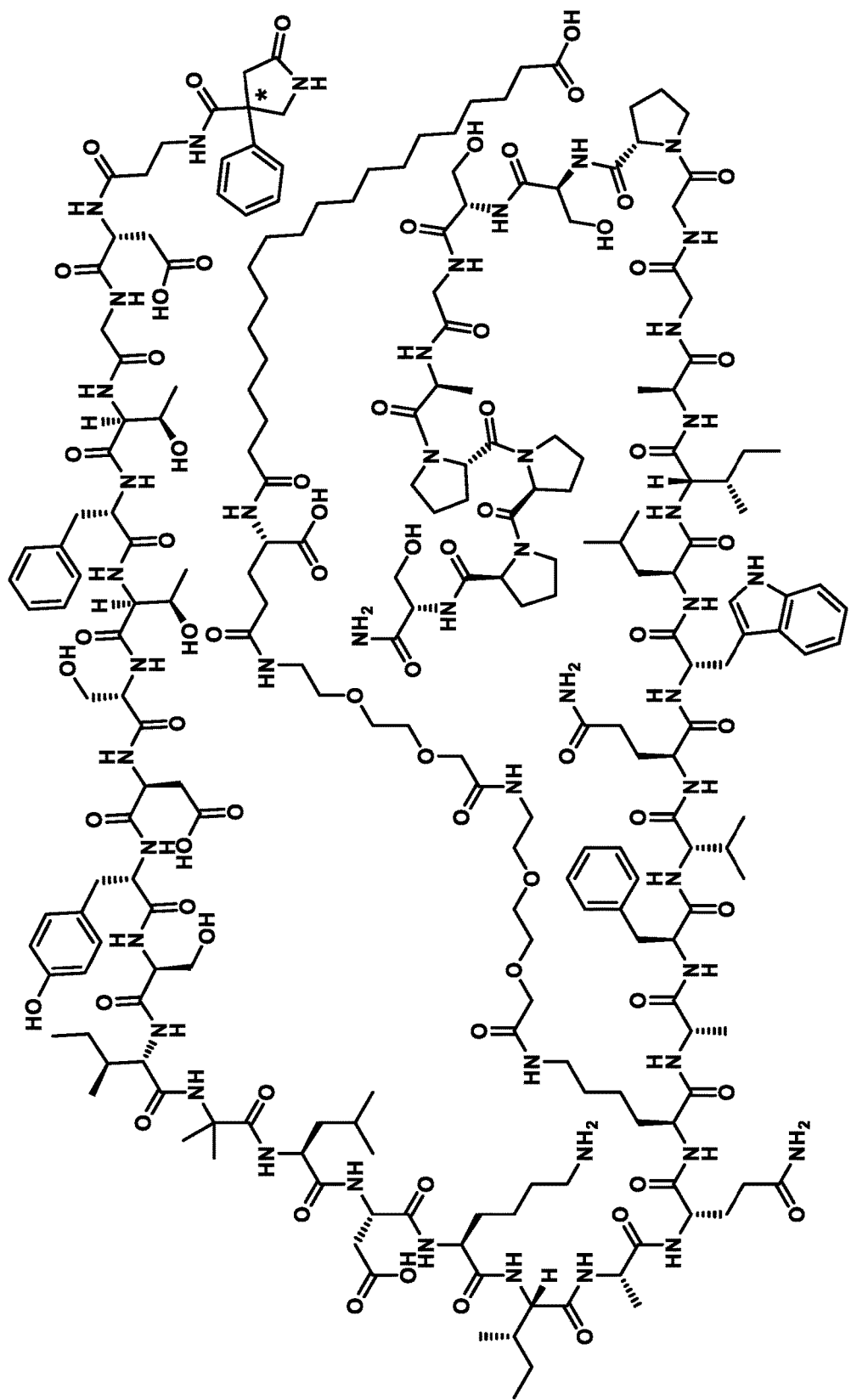
Compound 122
FIG. 1 - Cont'd

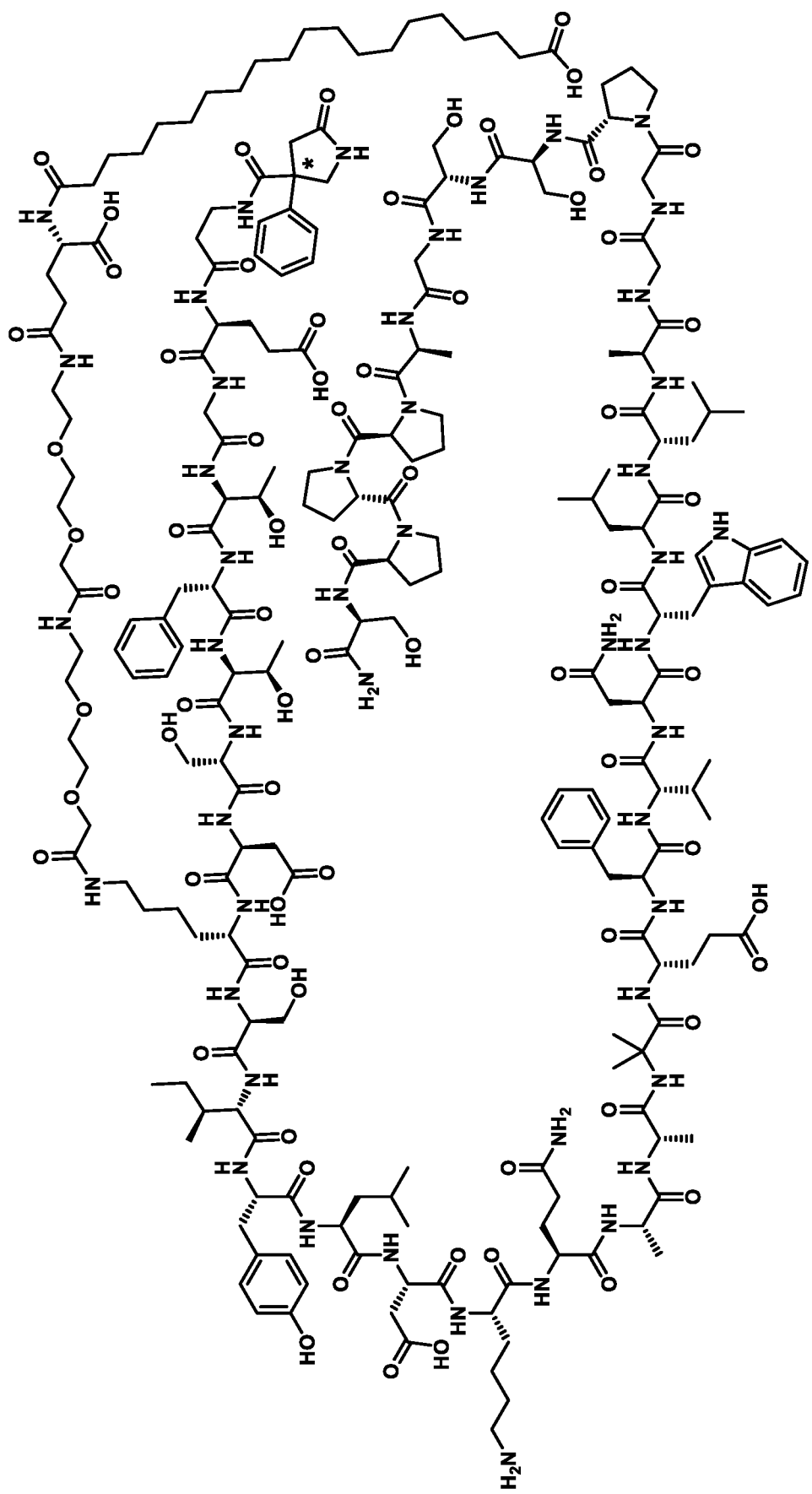
Compound 123
FIG. 1 - Cont'd

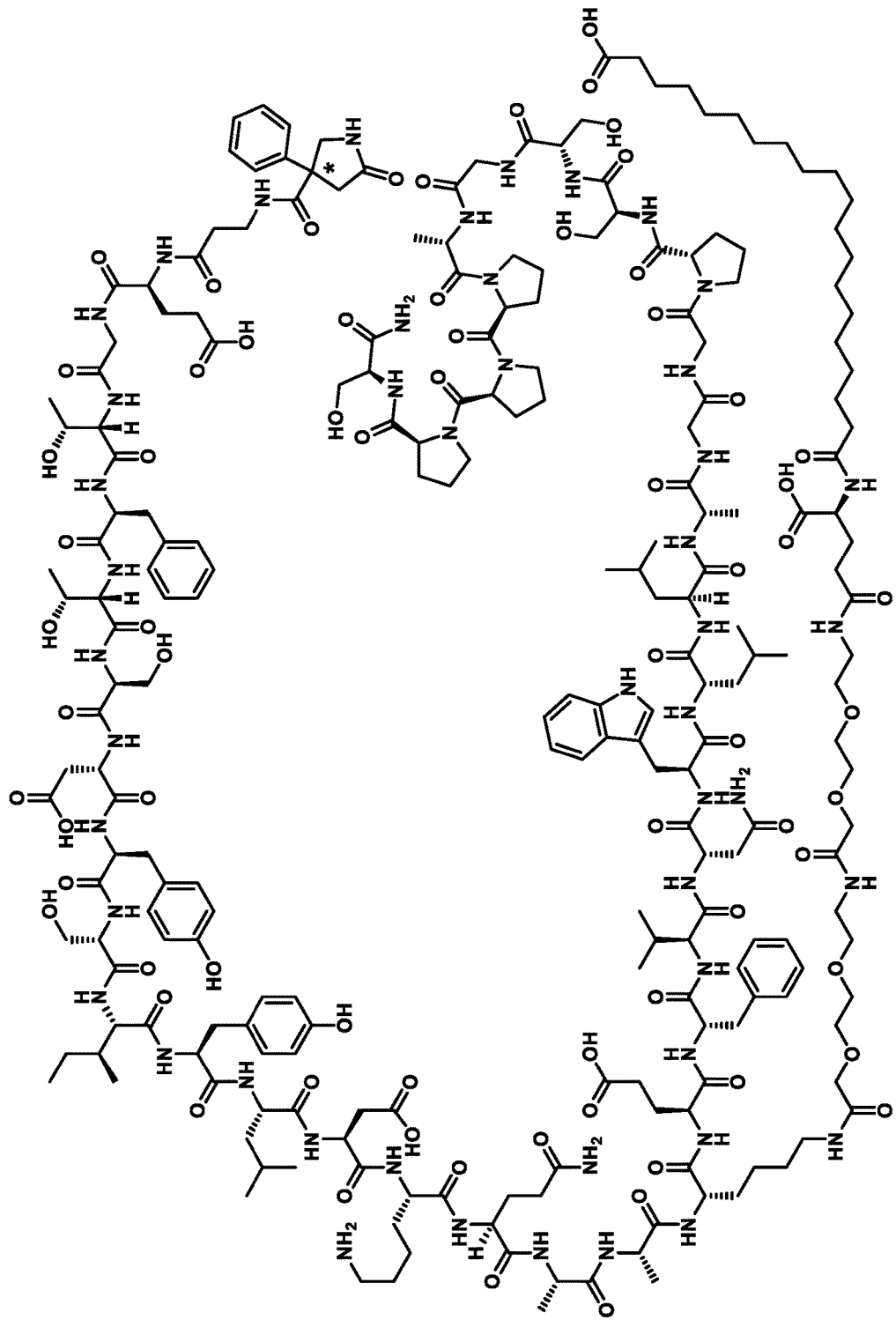
FIG. 1 - Cont'd
Compound 124

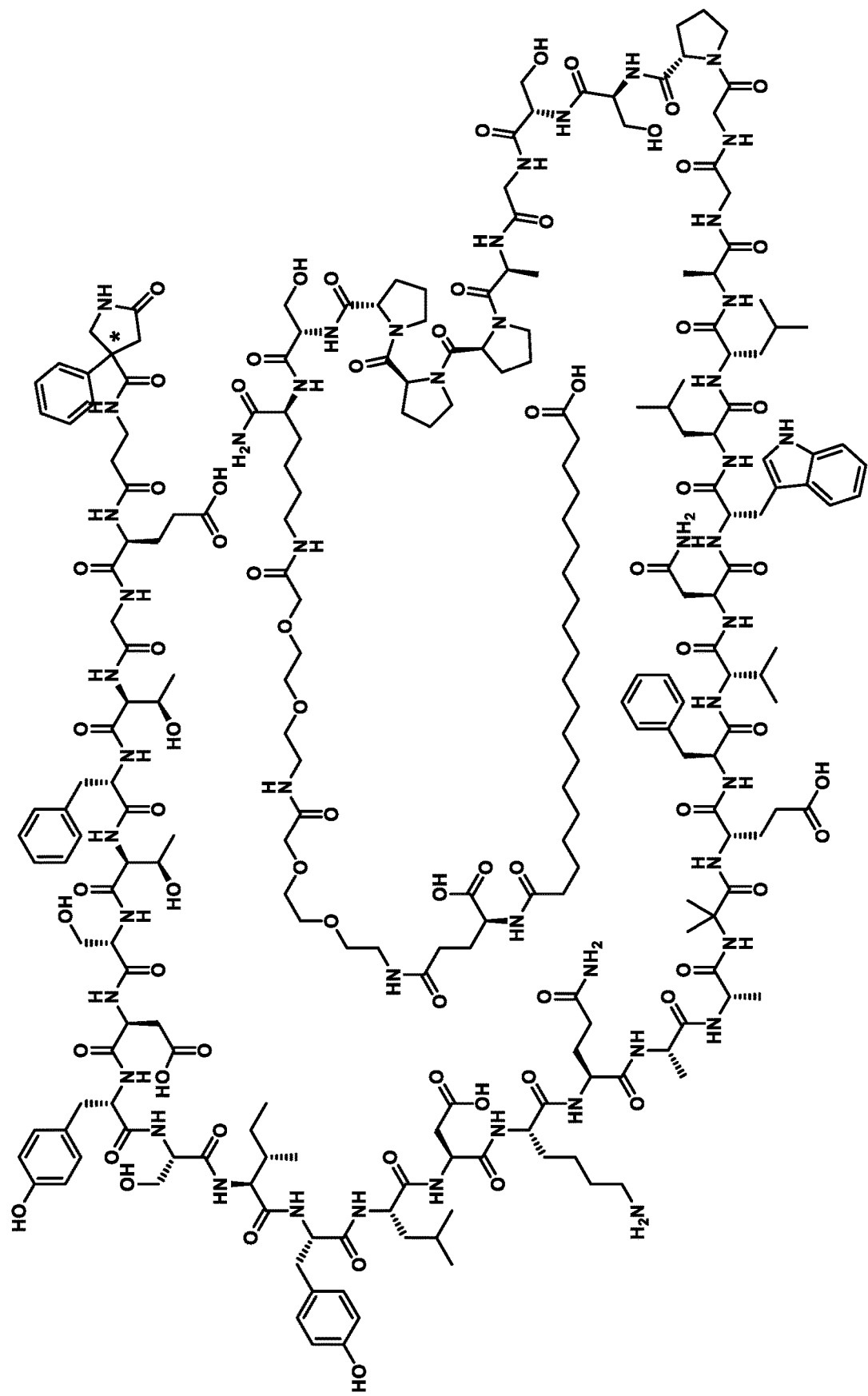
FIG. 1 - Cont'd
Compound 125

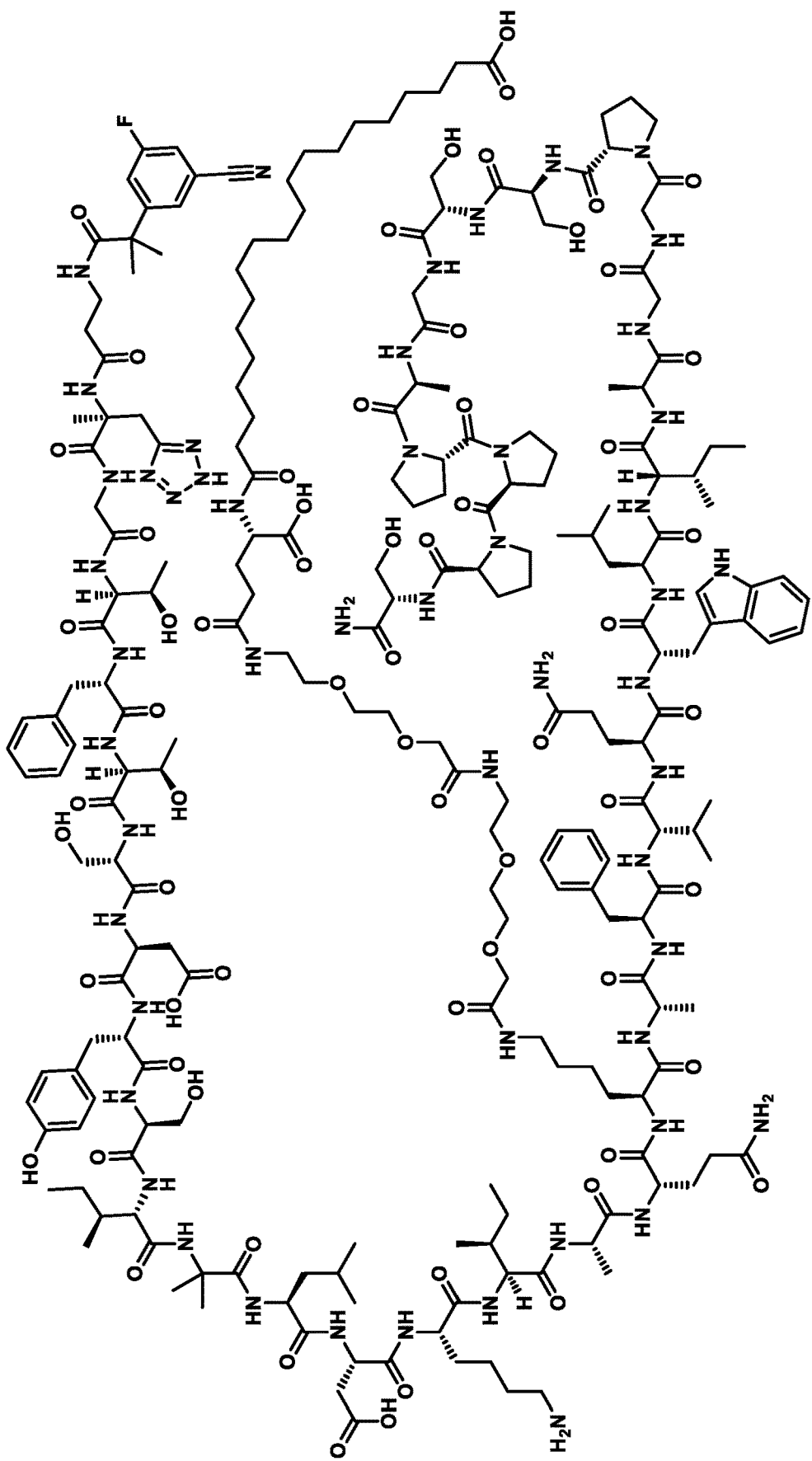
Compound 126
FIG. 1 - Cont'd

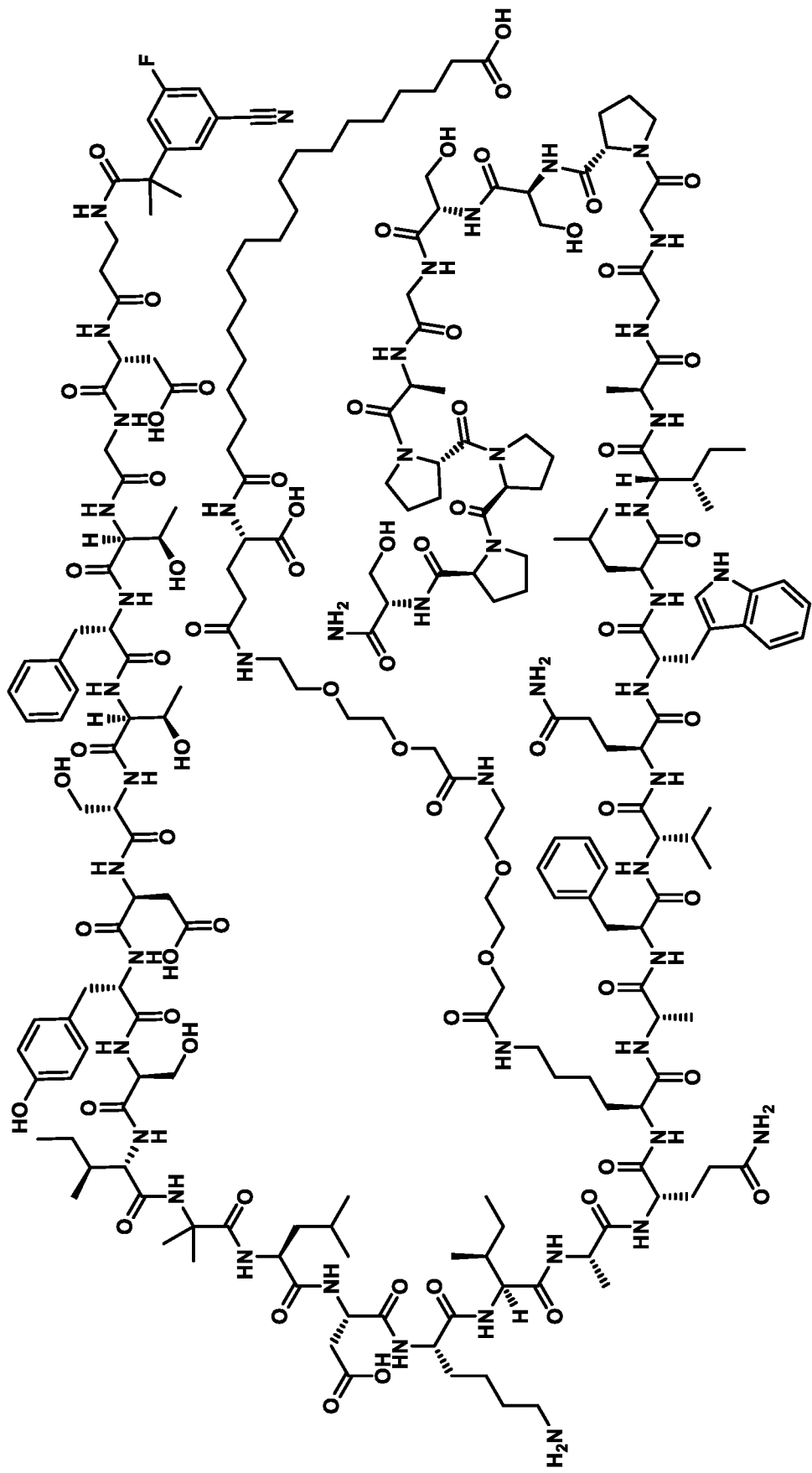
Compound 127
FIG. 1 - Cont'd

Compound 128
FIG. 1 - Cont'd

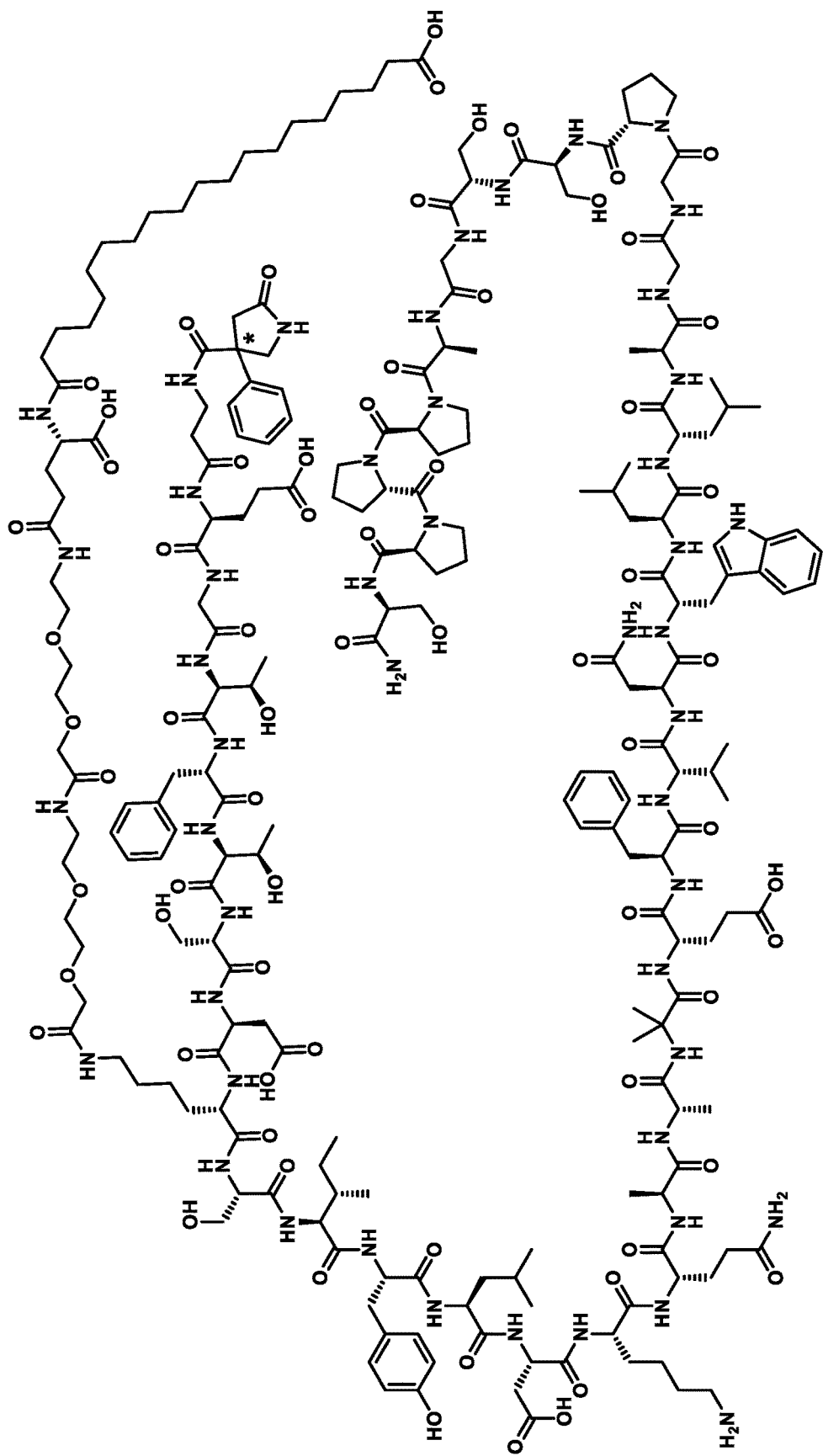
FIG. 1 - Cont'd
Compound 129

Compound 130
FIG. 1 - Cont'd

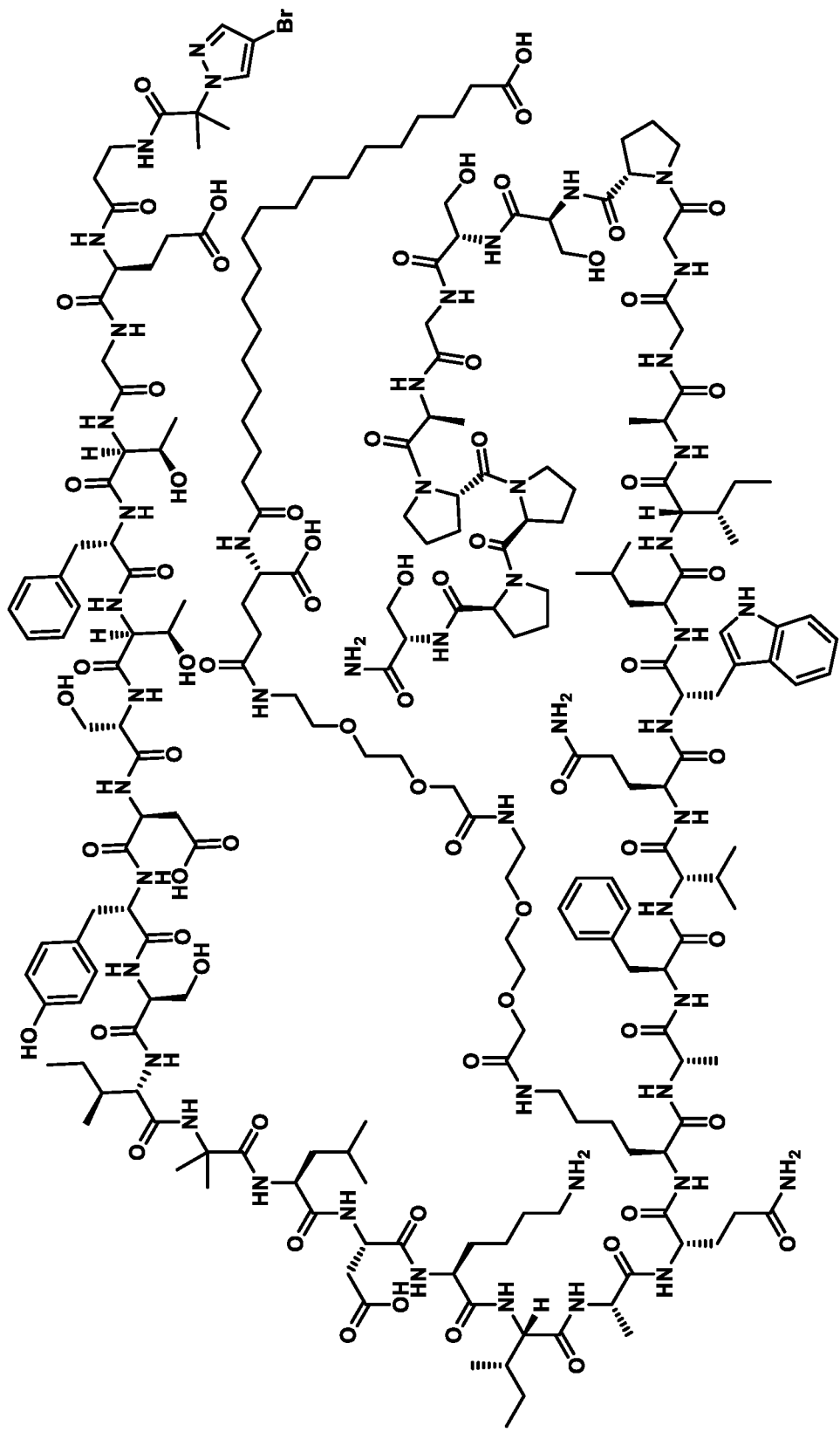
FIG. 1 - Cont'd
Compound 131

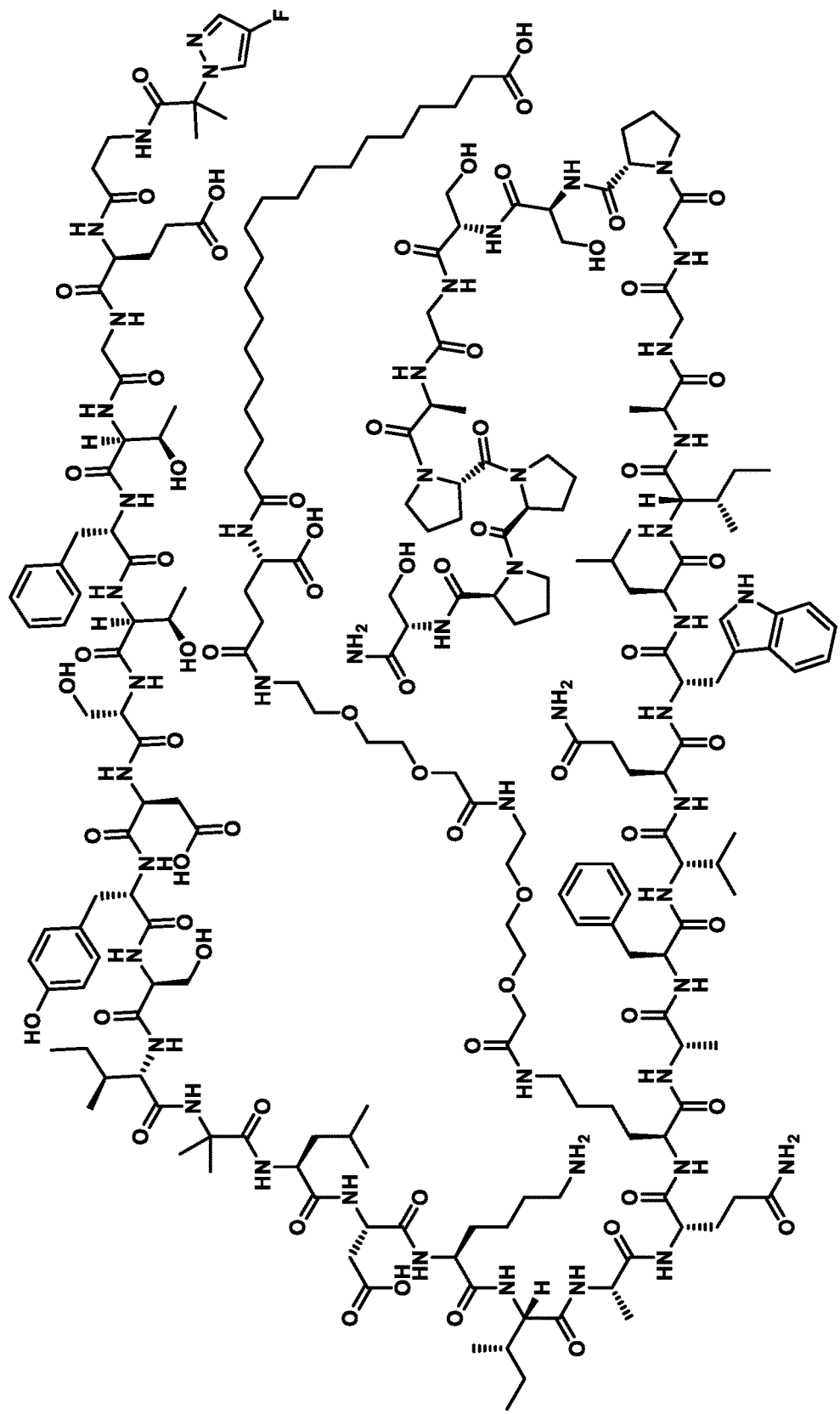
Compound 132
FIG. 1 - Cont'd

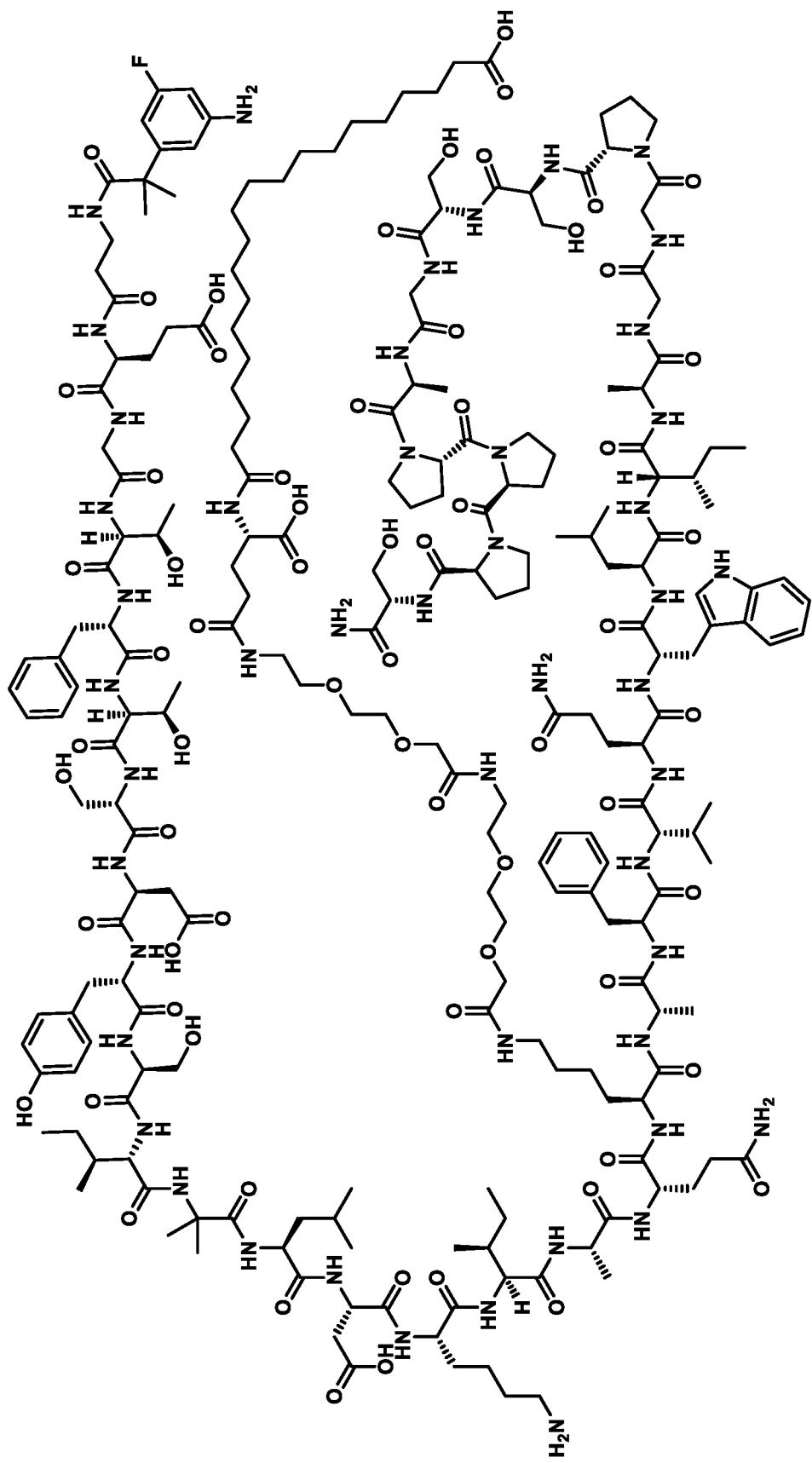
Compound 133
FIG. 1 - Cont'd

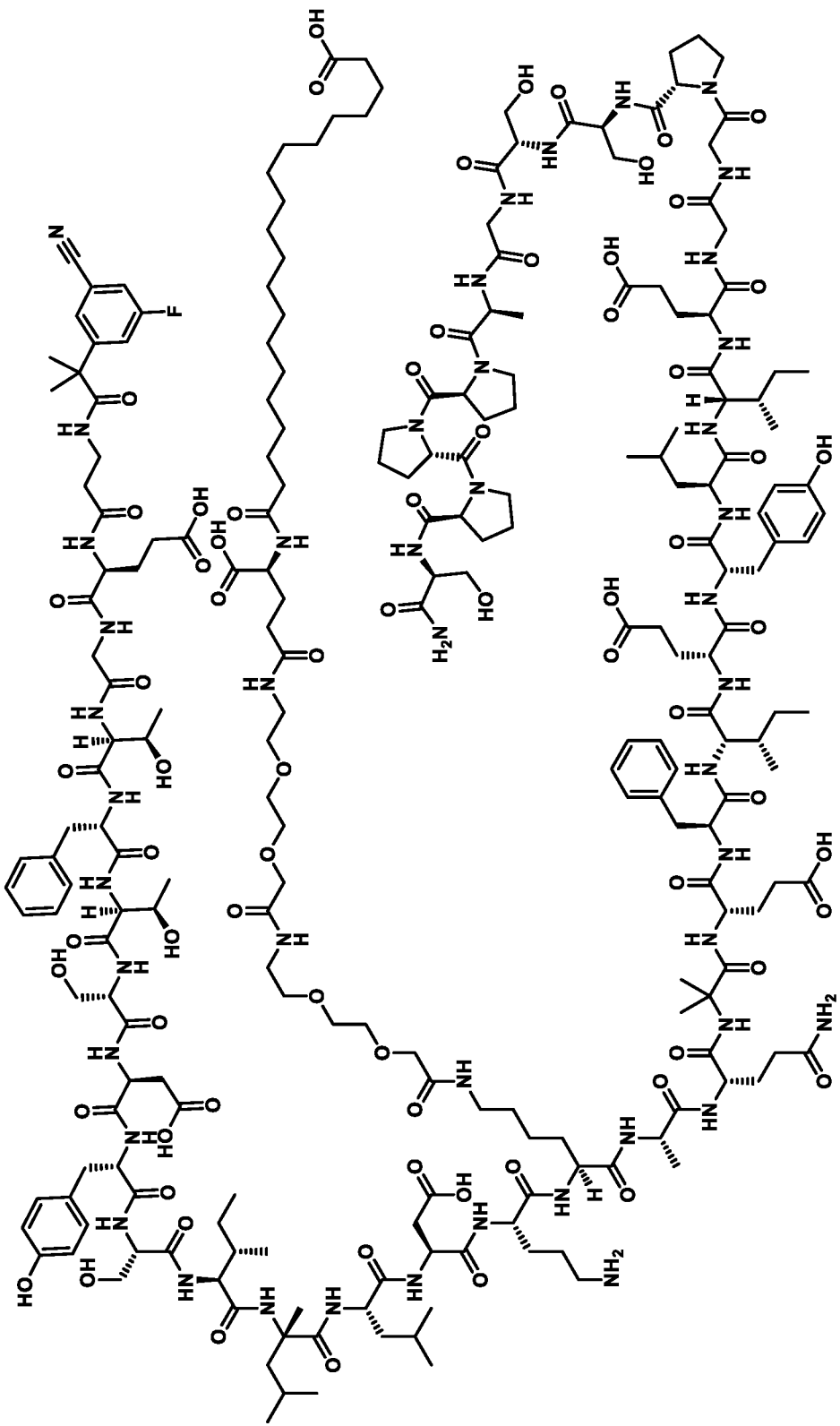
Compound 134
FIG. 1 - Cont'd

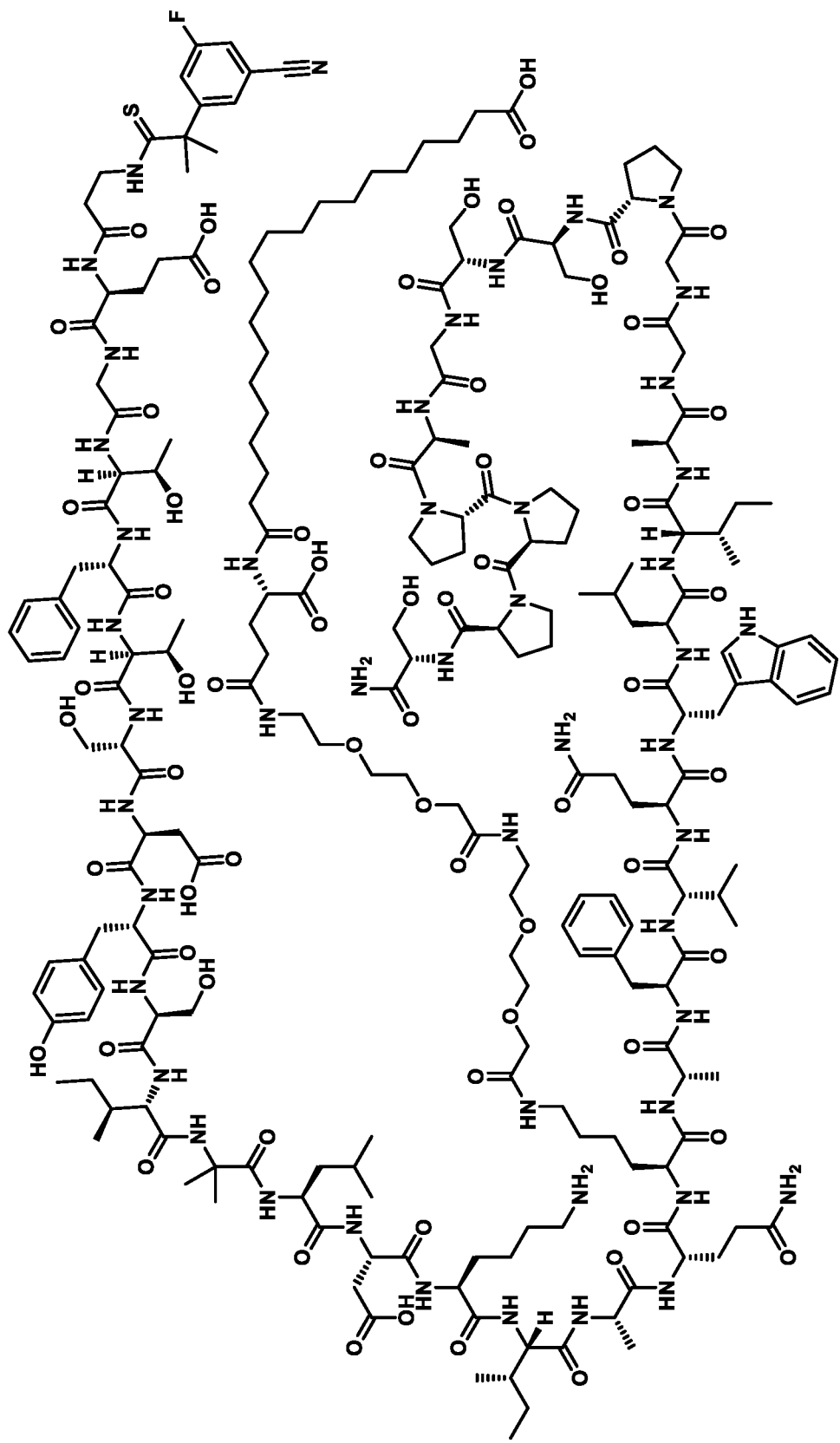
Compound 135
FIG. 1 - Cont'd

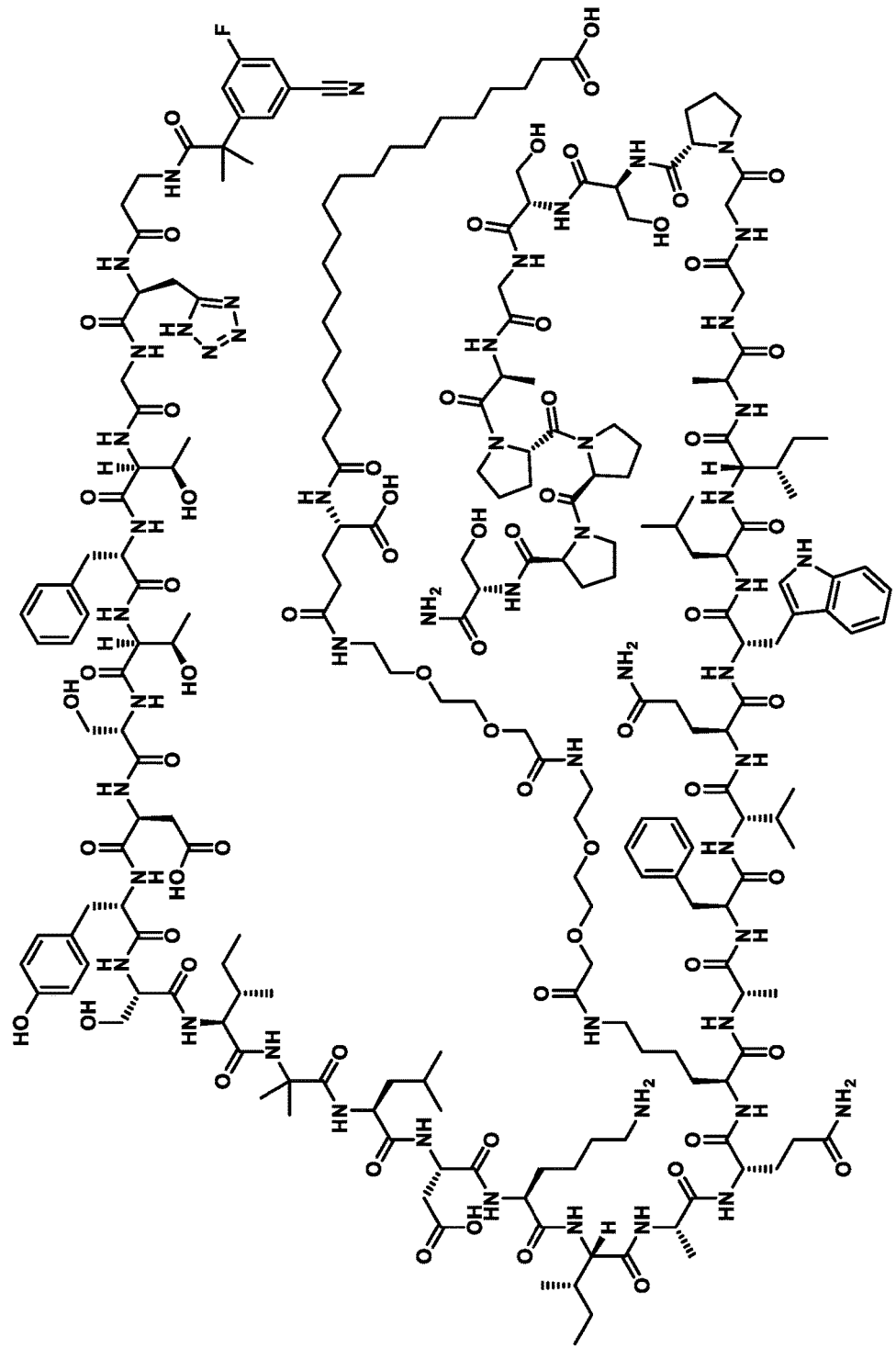
Compound 136
FIG. 1 - Cont'd

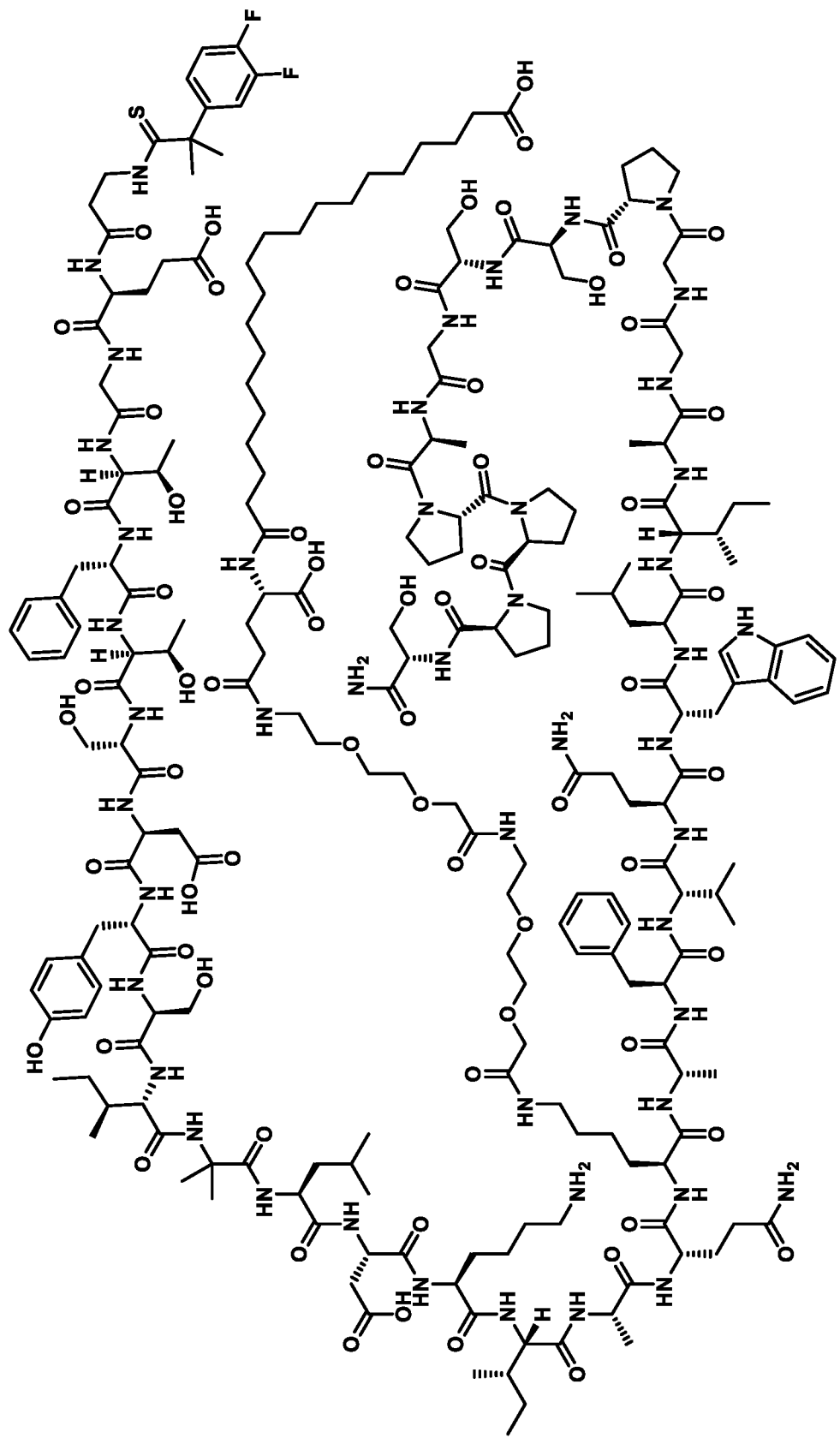
Compound 137
FIG. 1 - Cont'd

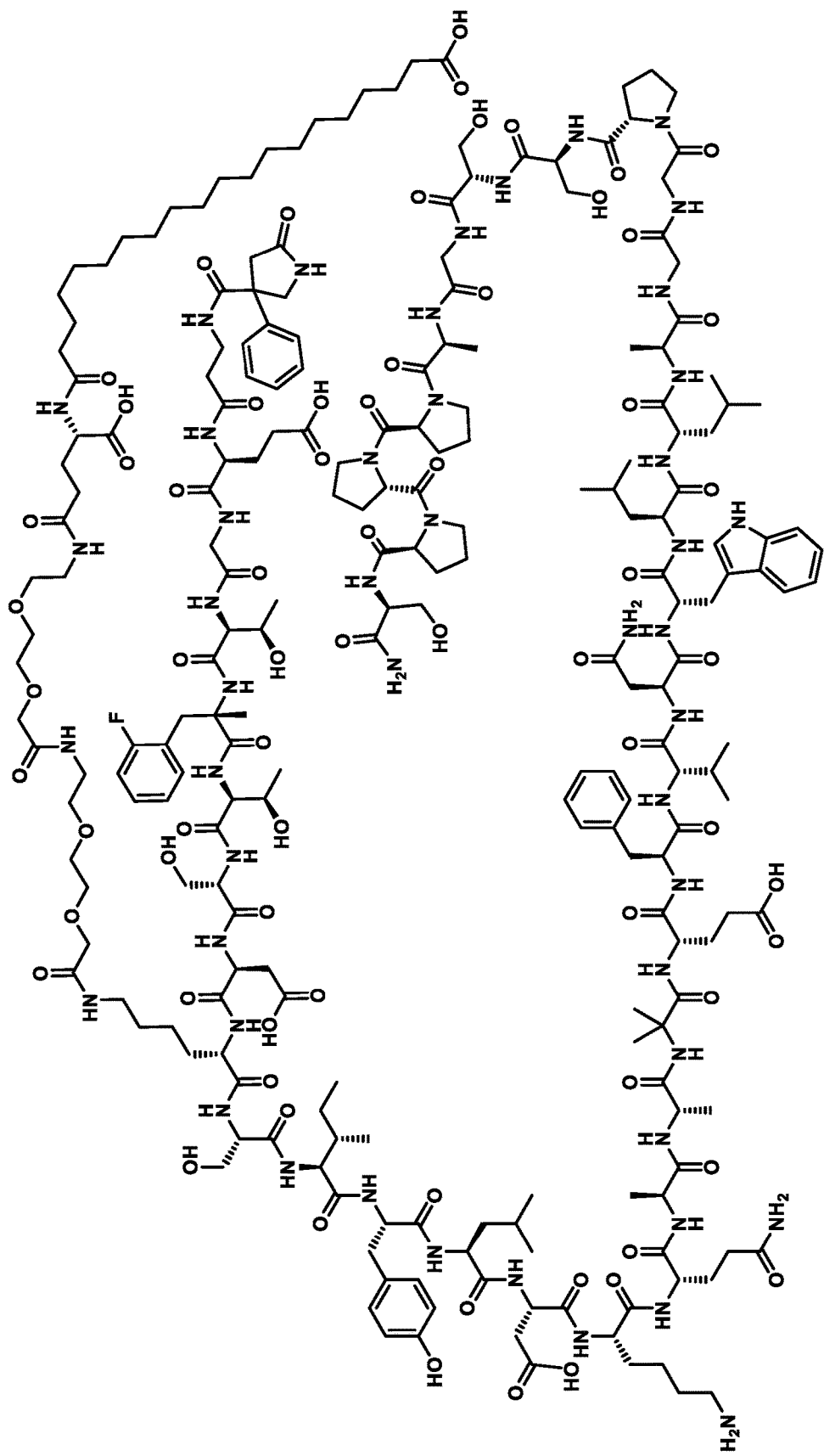
Compound 138
FIG. 1 - Cont'd

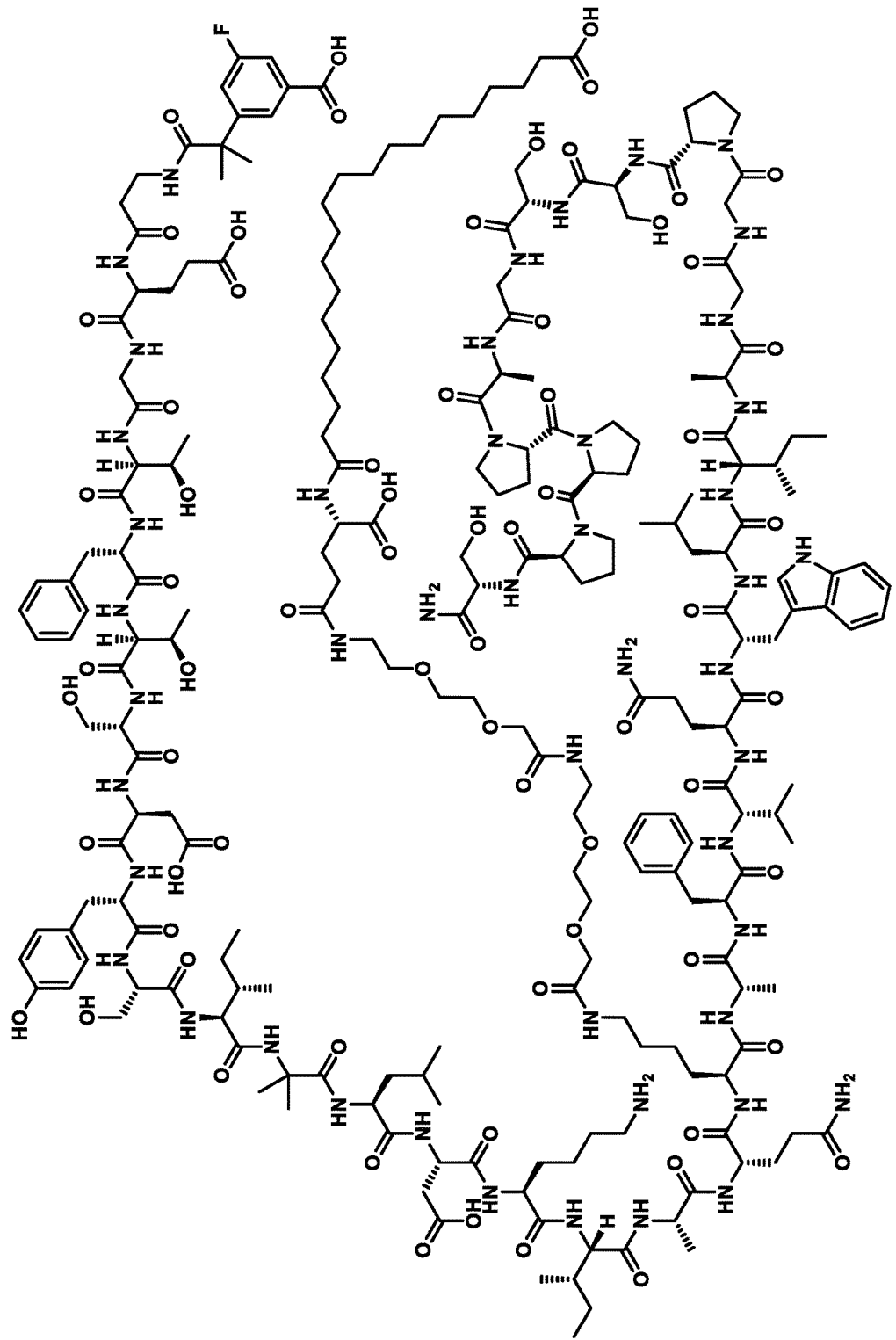
FIG. 1 - Cont'd
Compound 139

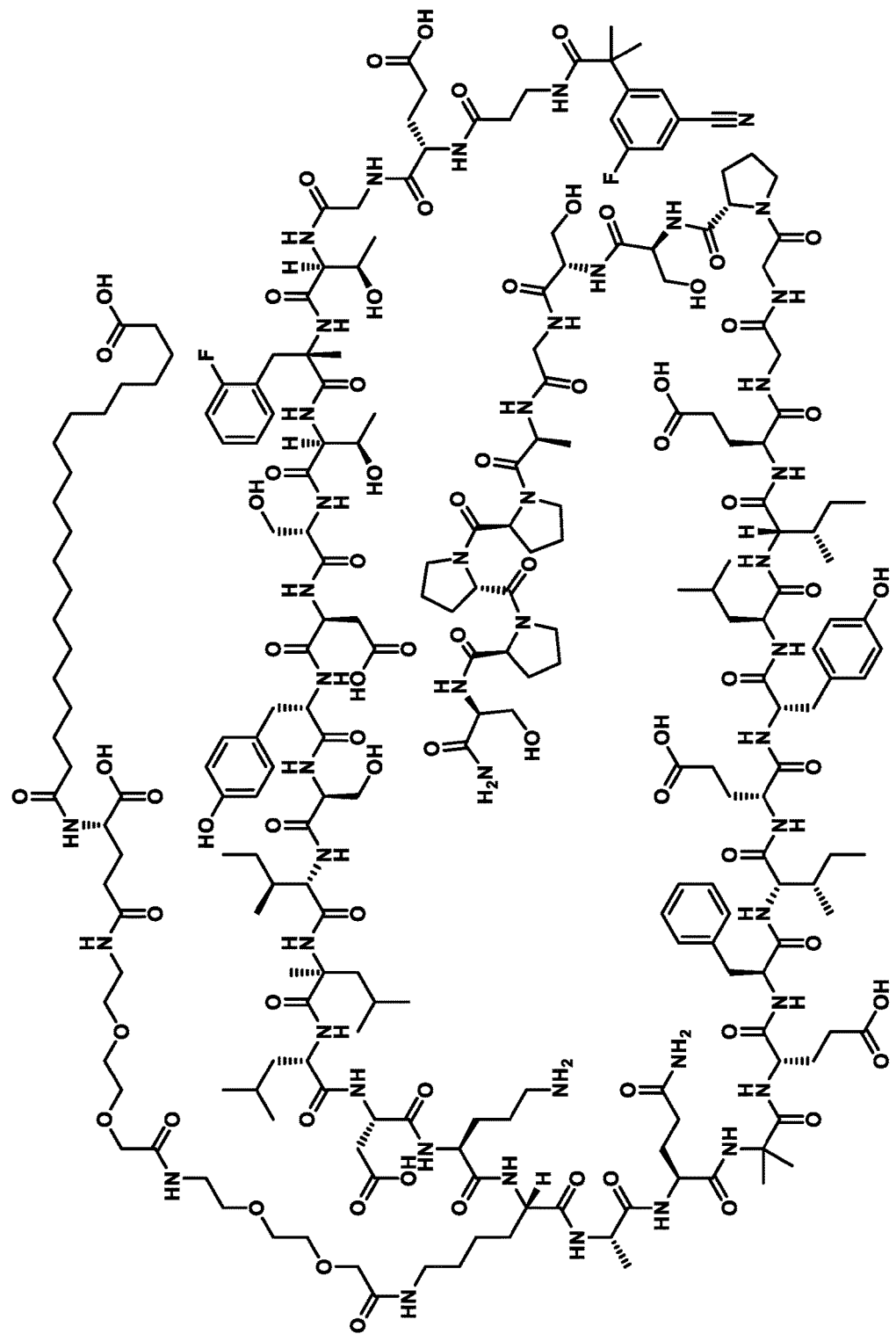
FIG. 1 - Cont'd
Compound 140

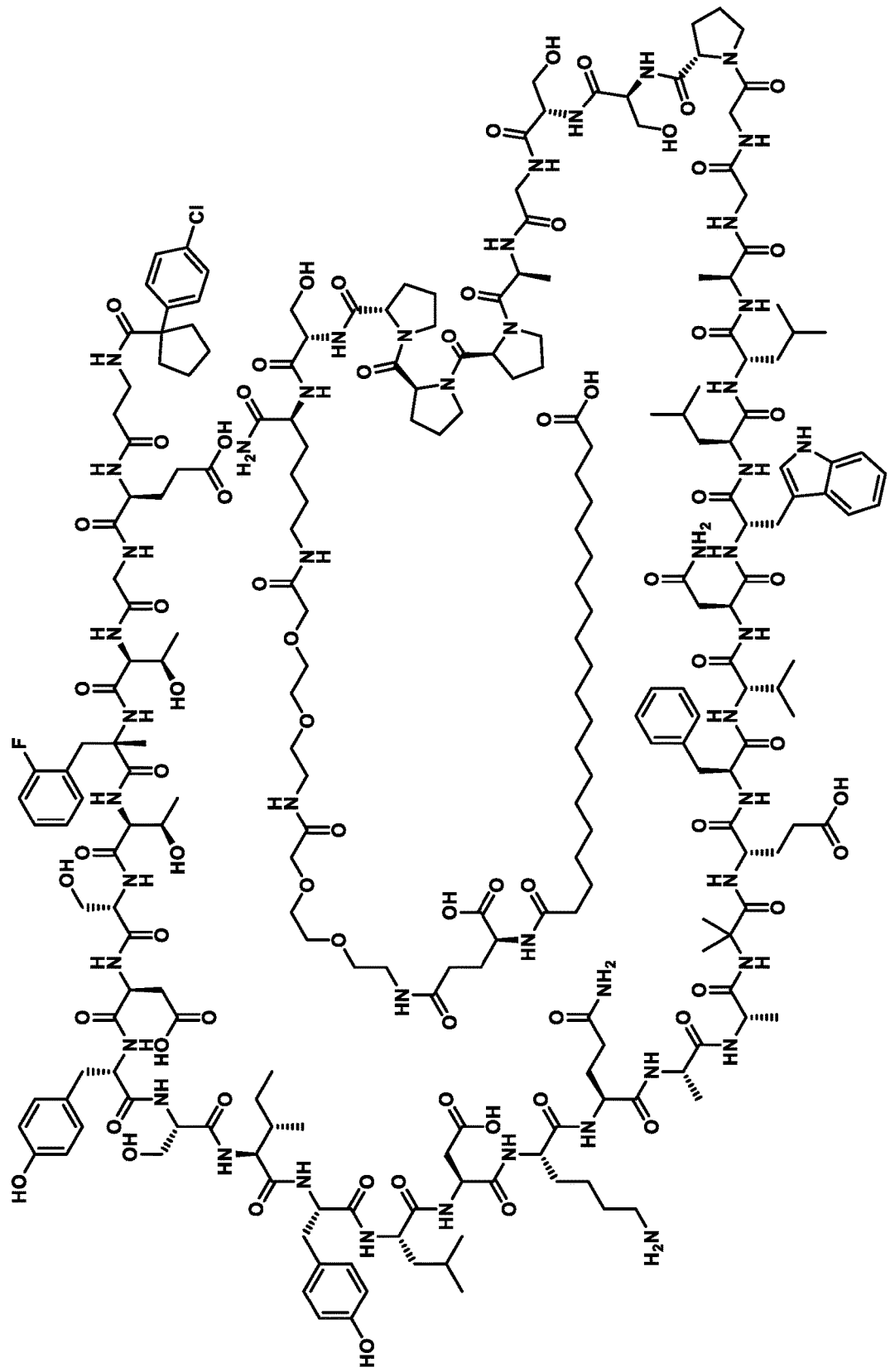
Compound 141
FIG. 1 - Cont'd

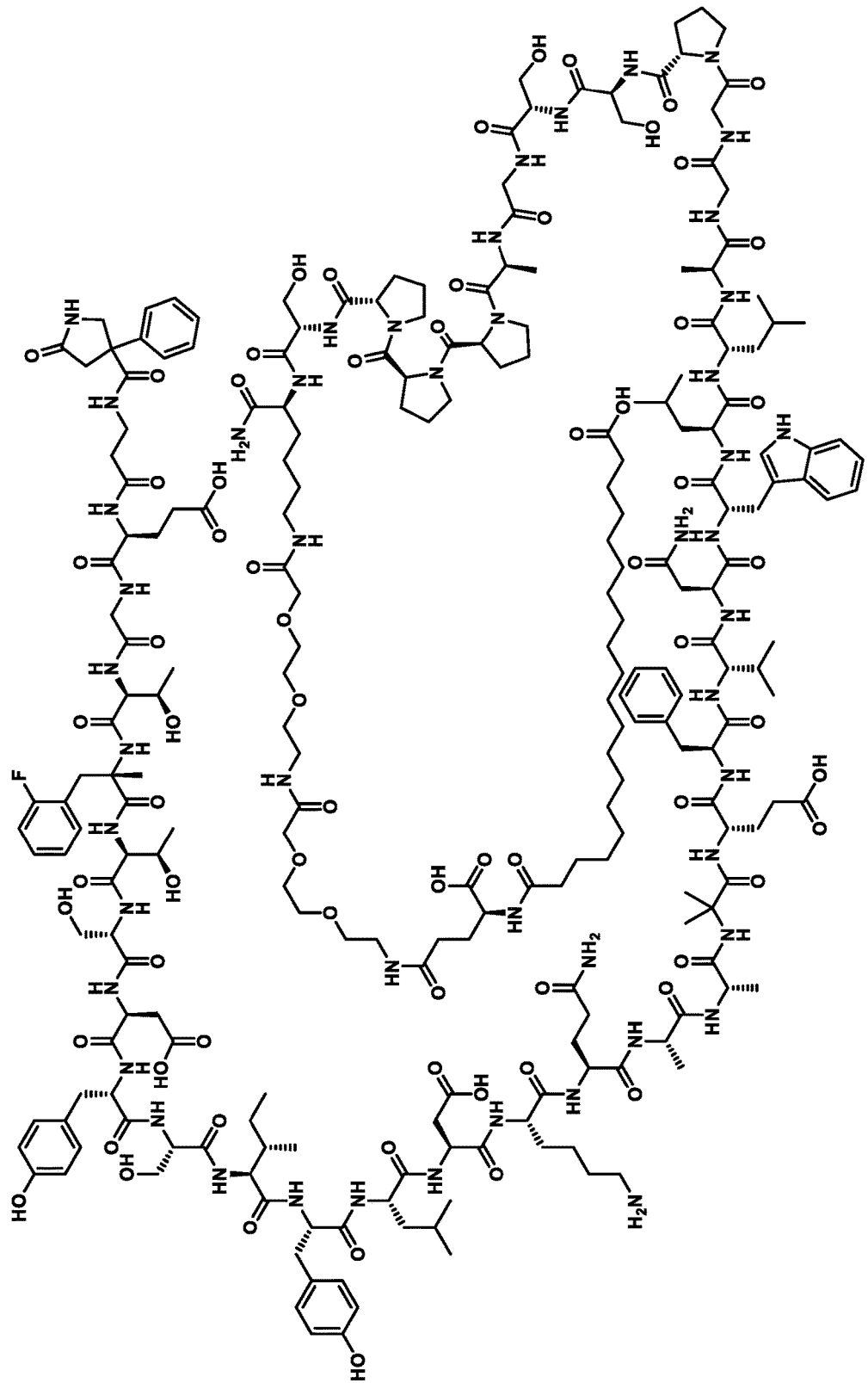
Compound 142
FIG. 1 - Cont'd

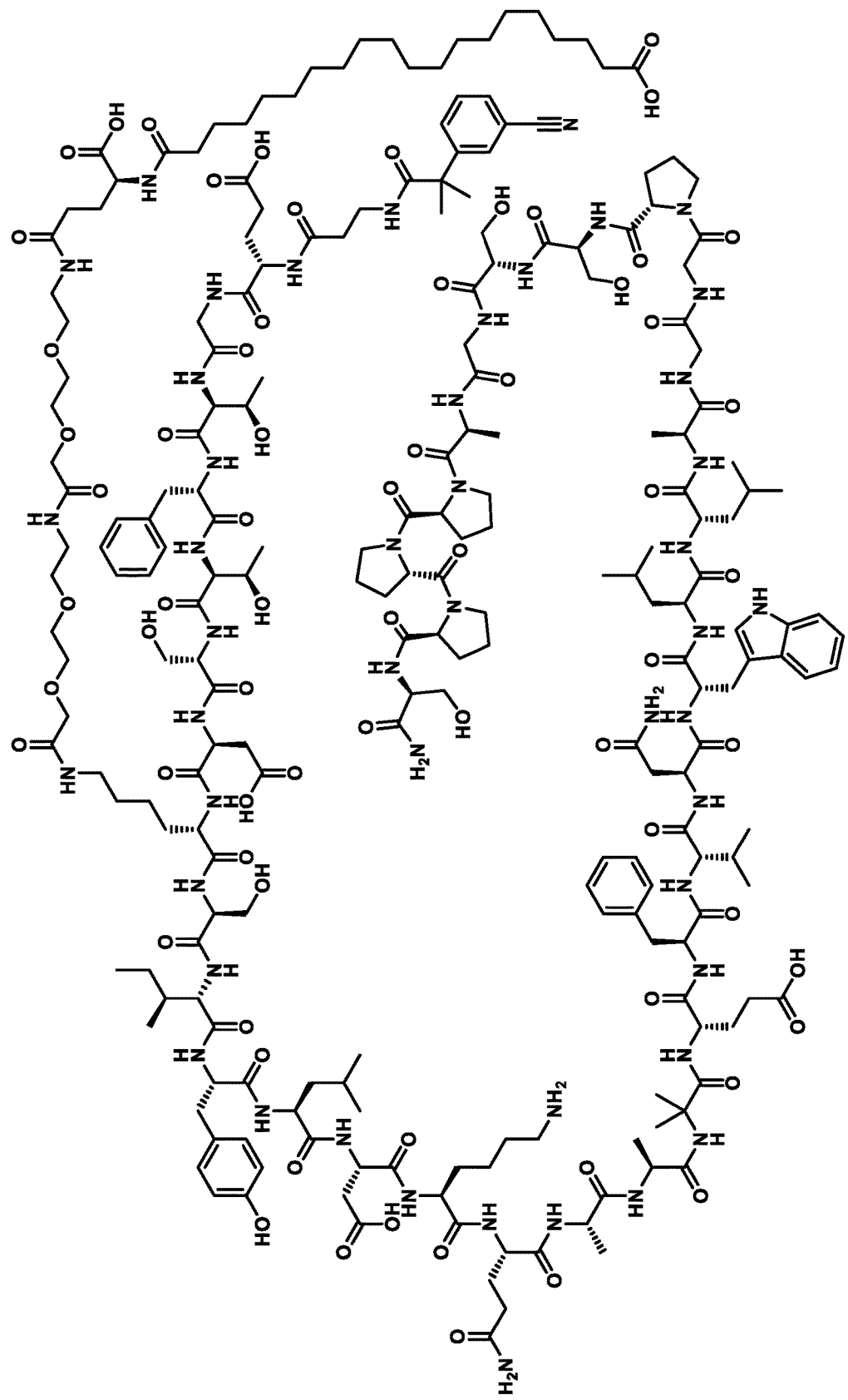
FIG. 1 - Cont'd
Compound 143

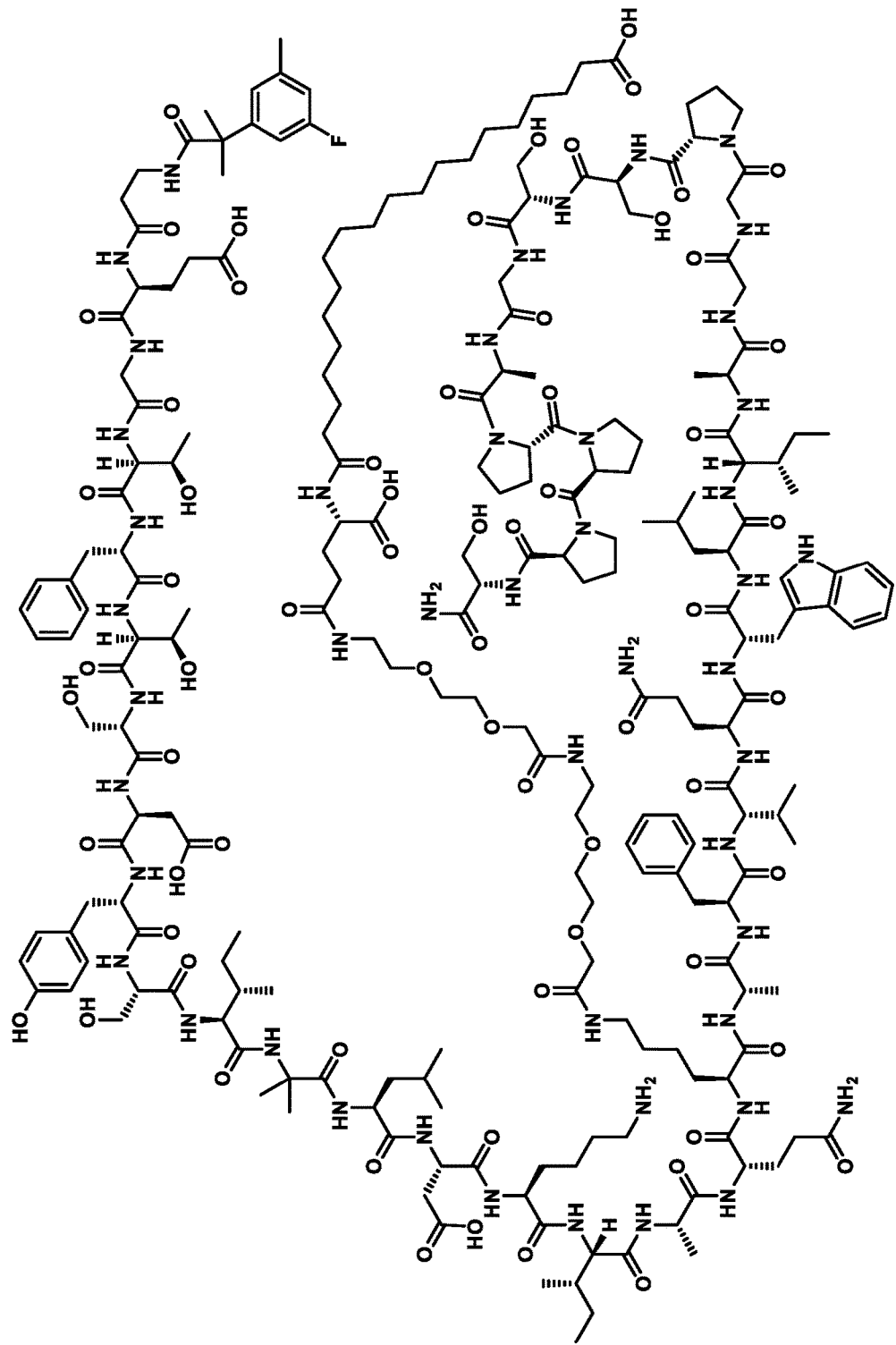
FIG. 1 - Cont'd
Compound 144

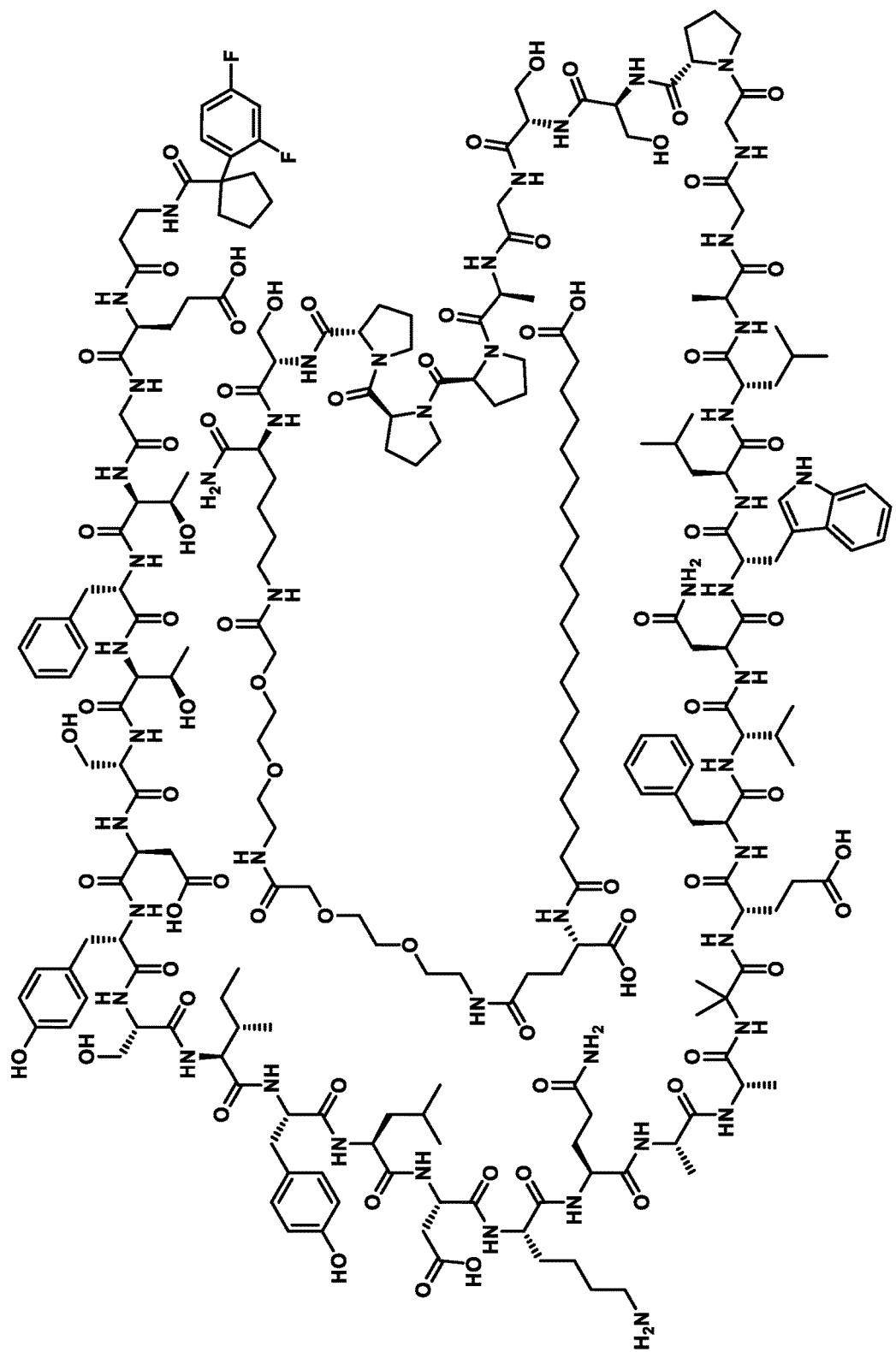
Compound 145
FIG. 1 - Cont'd

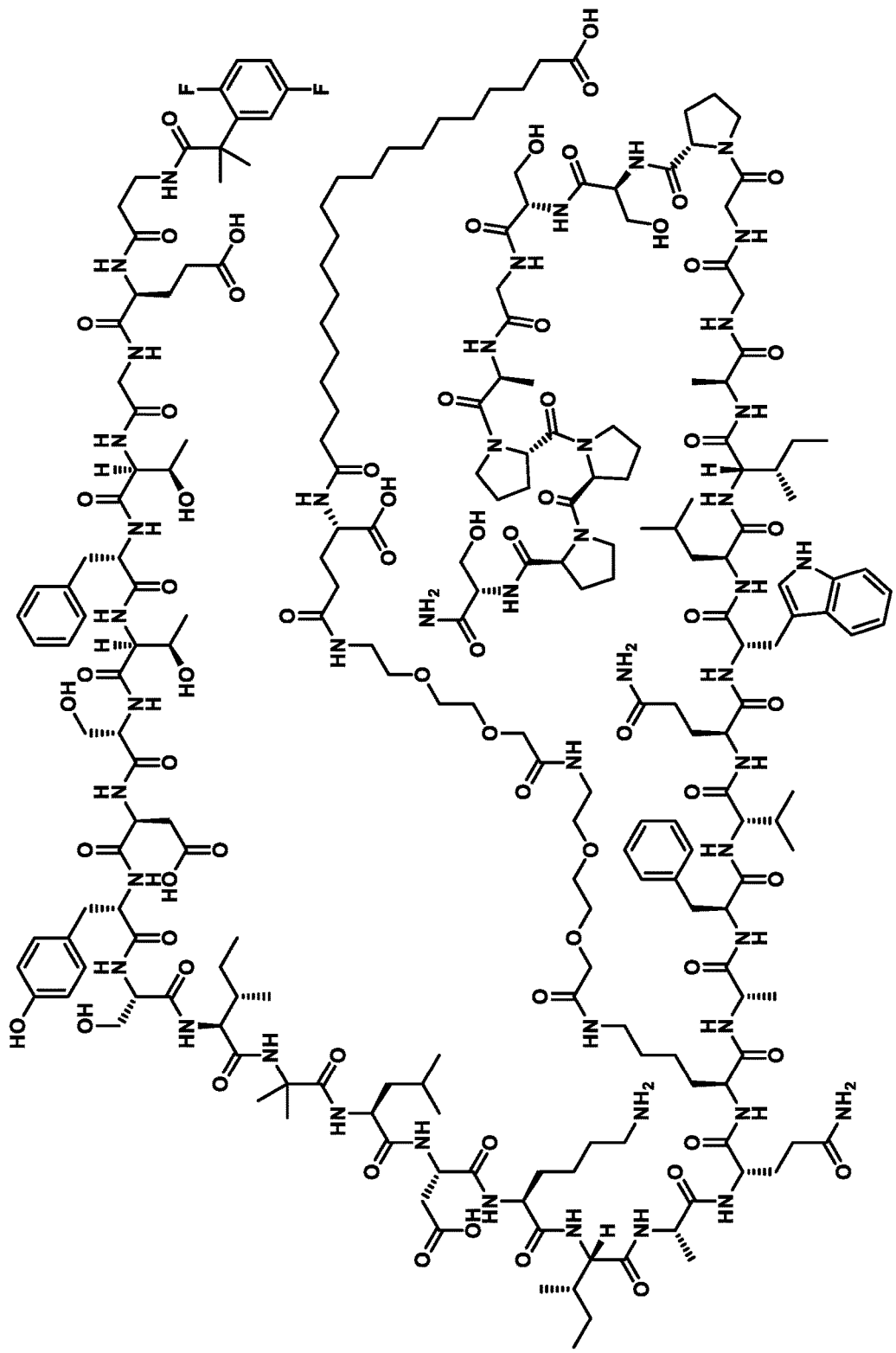
Compound 146
FIG. 1 - Cont'd

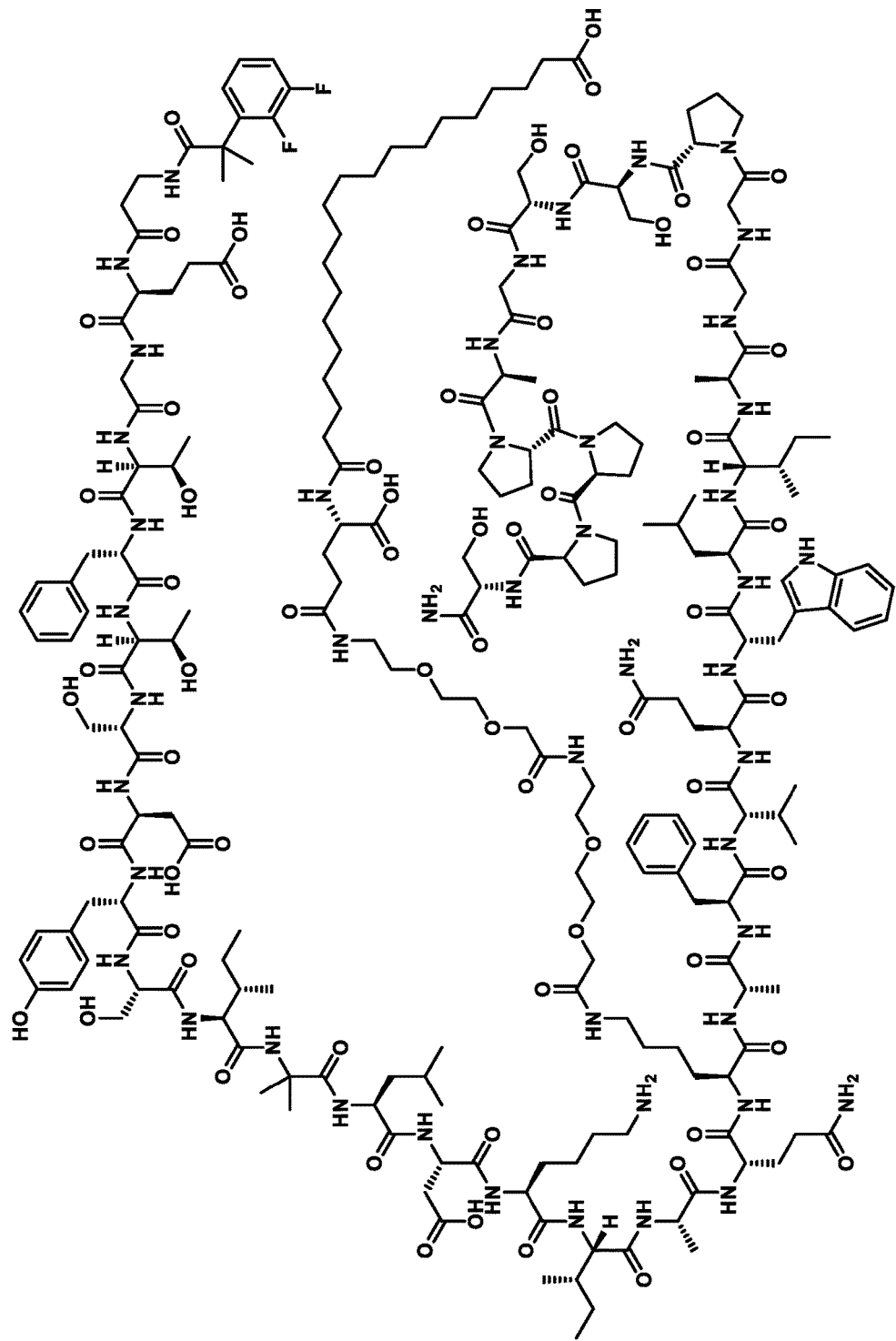
Compound 147
FIG. 1 - Cont'd

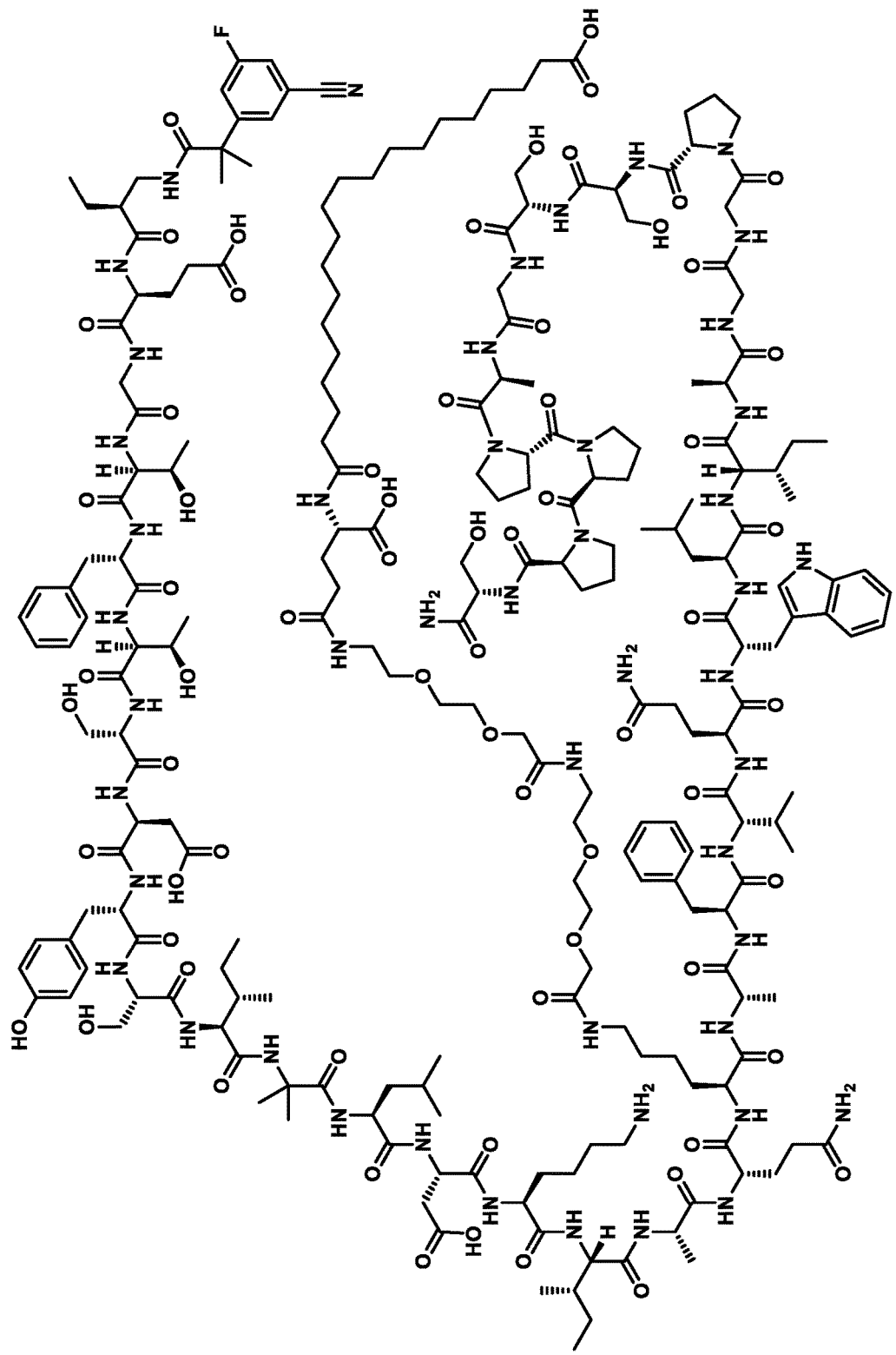
Compound 148
FIG. 1 - Cont'd

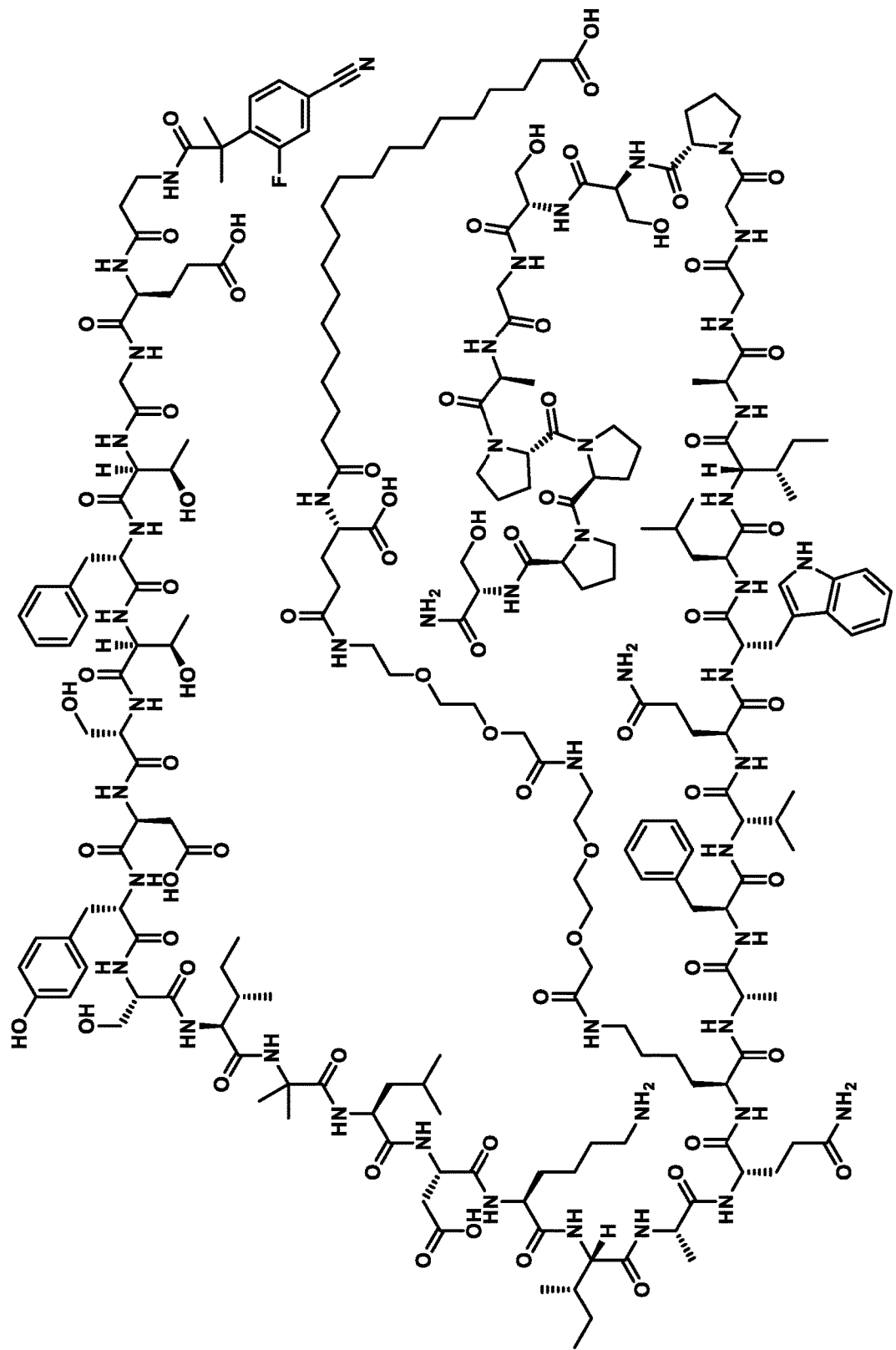
Compound 149
FIG. 1 - Cont'd

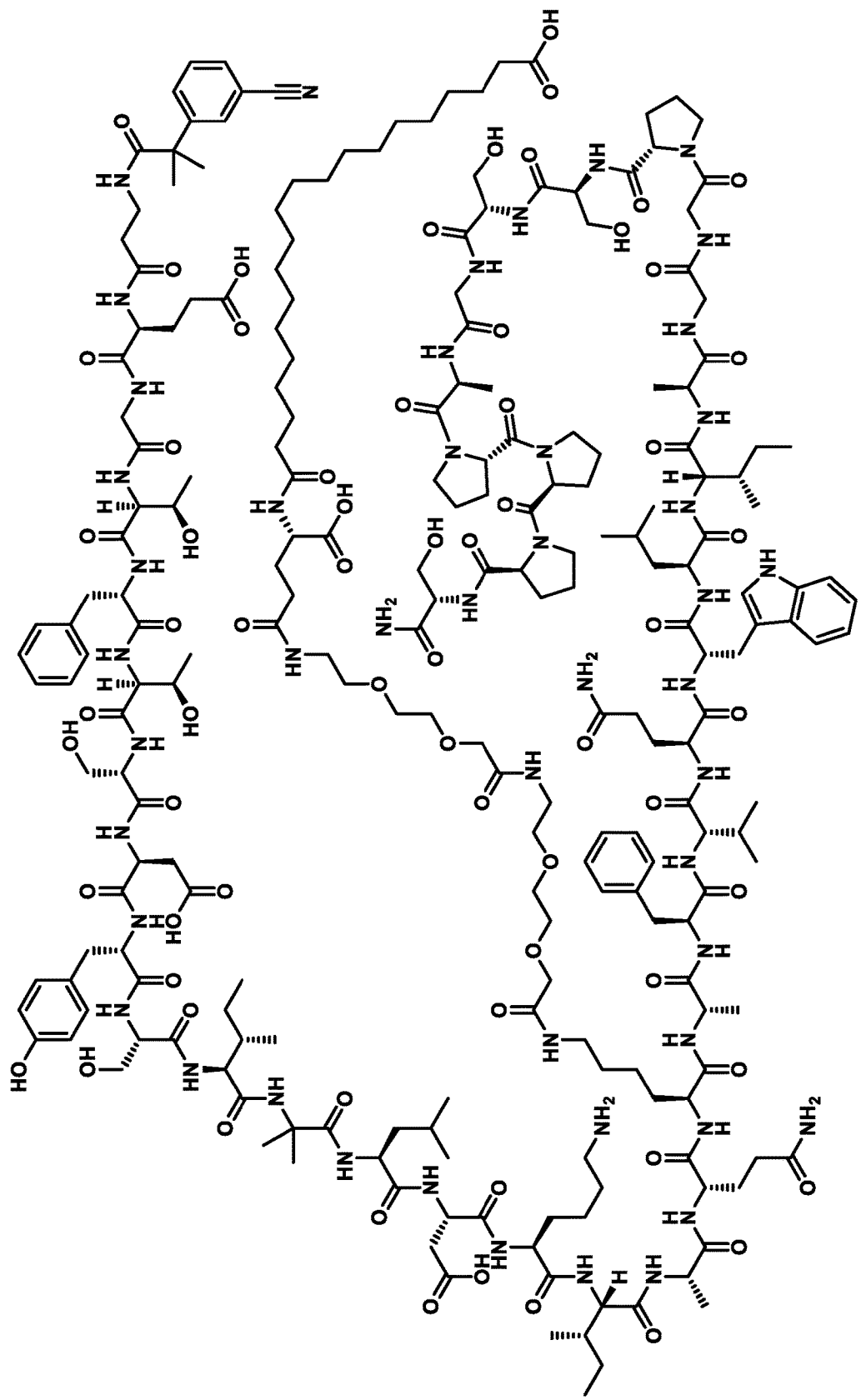
Compound 150
FIG. 1 - Cont'd

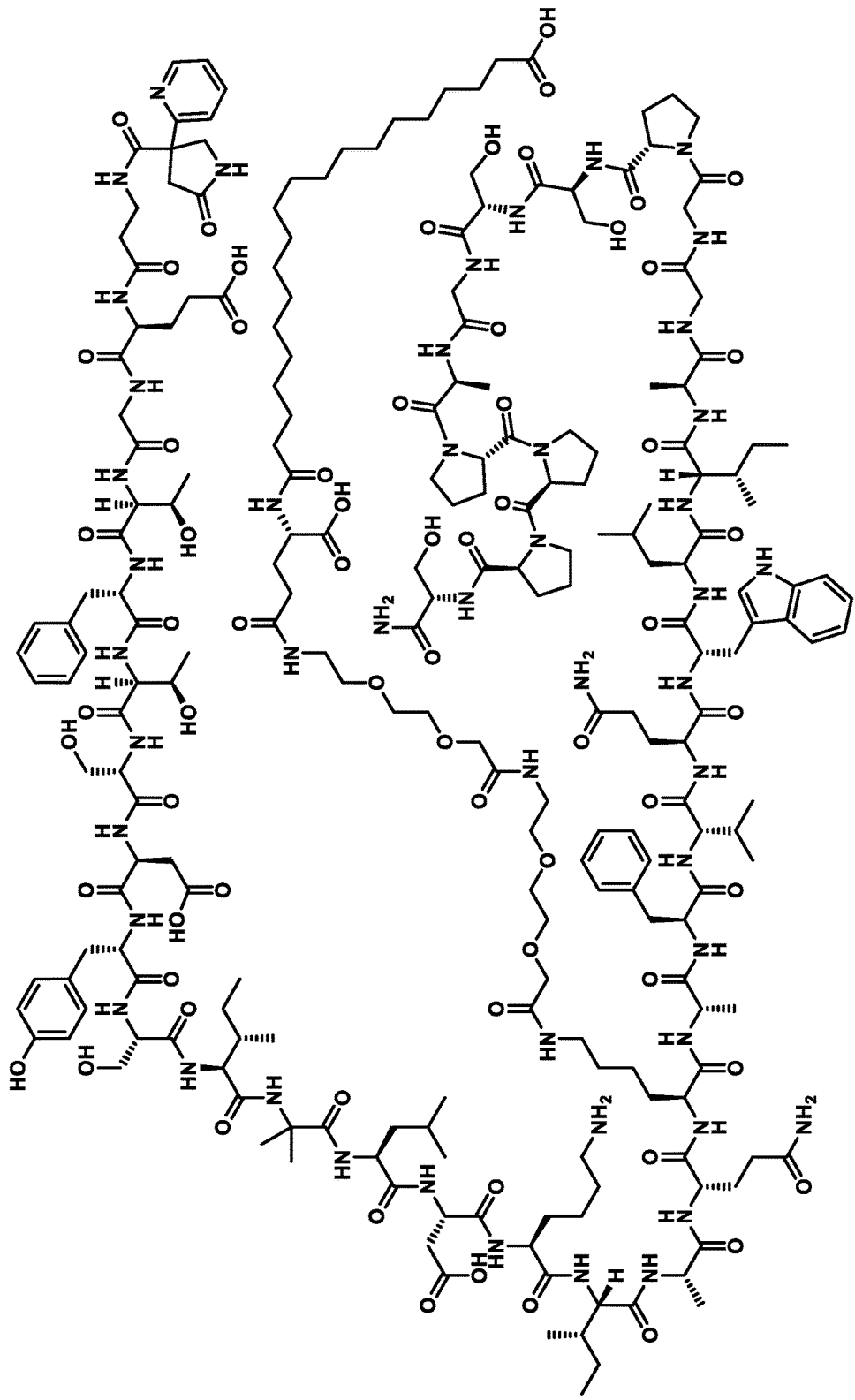
Compound 151
FIG. 1 - Cont'd

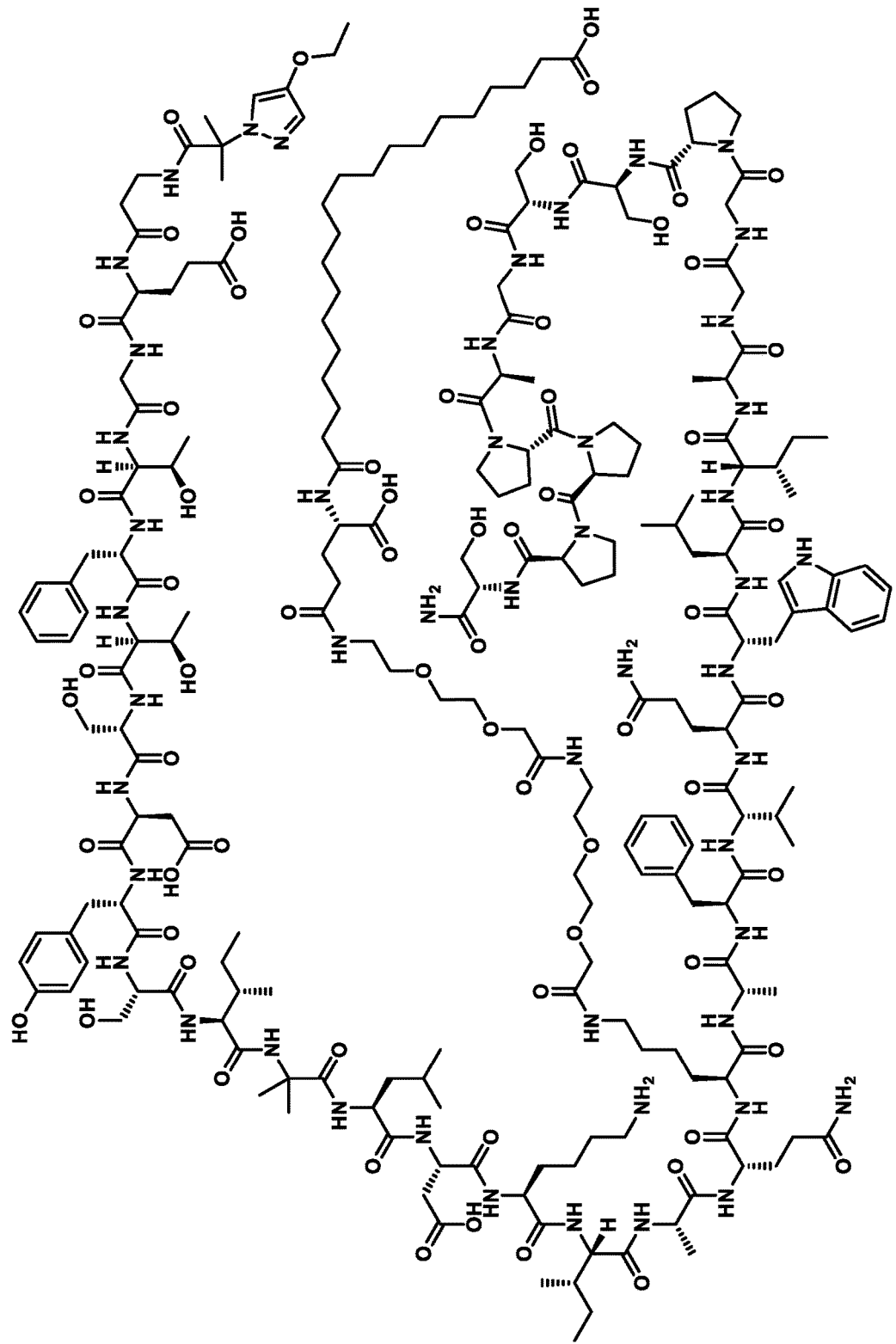
Compound 152
FIG. 1 - Cont'd

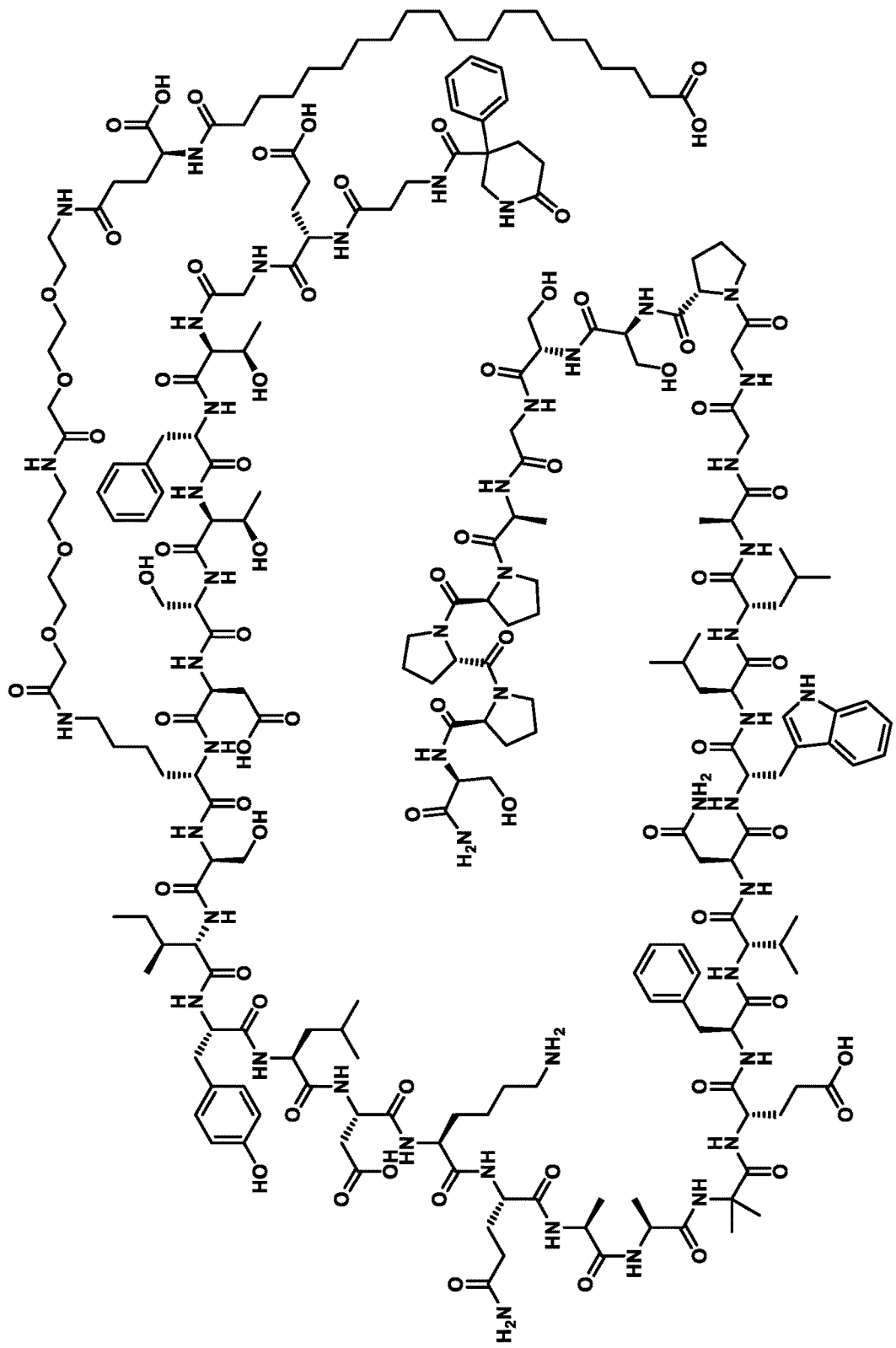
Compound 153
FIG. 1 - Cont'd

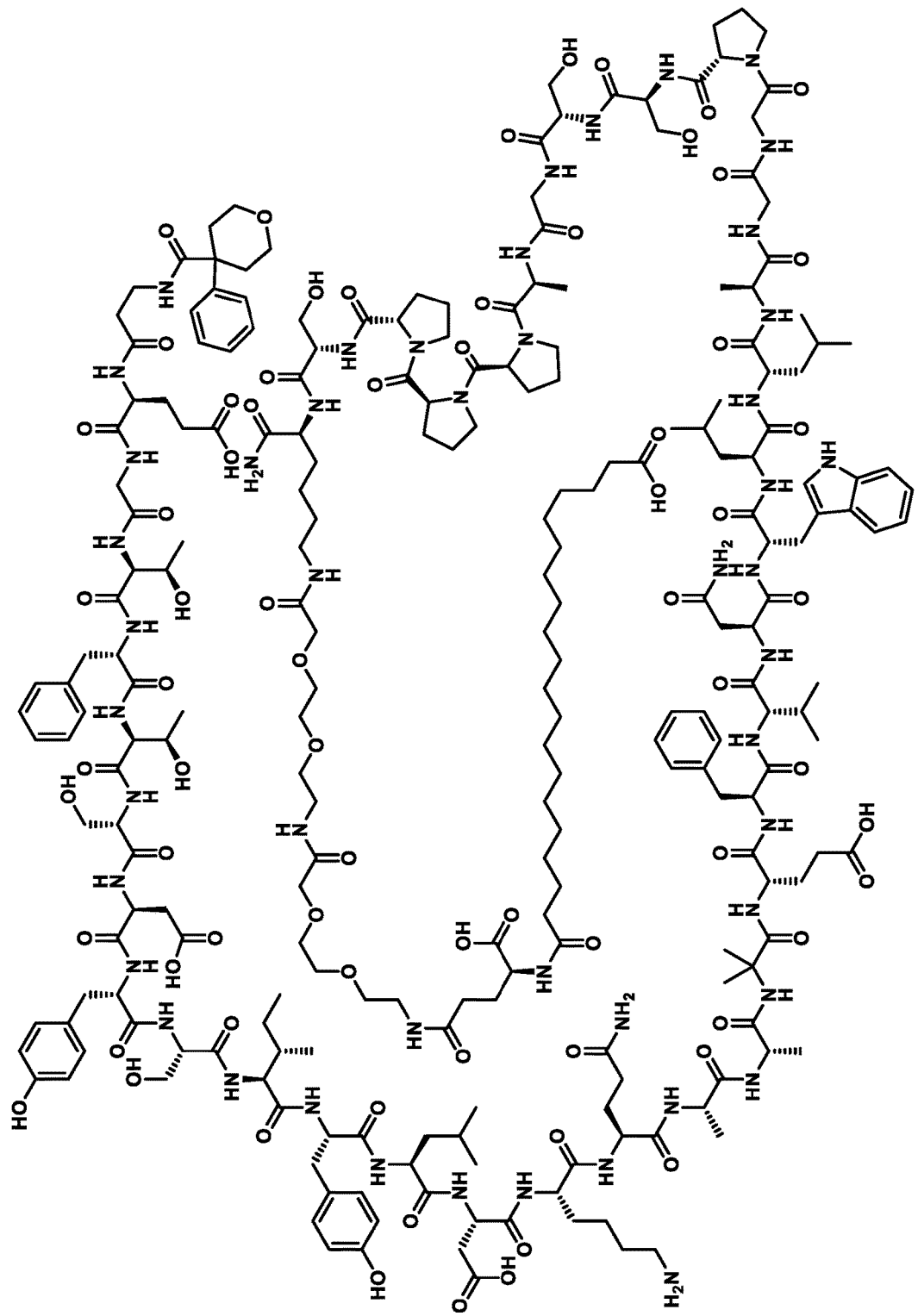
Compound 154
FIG. 1 - Cont'd

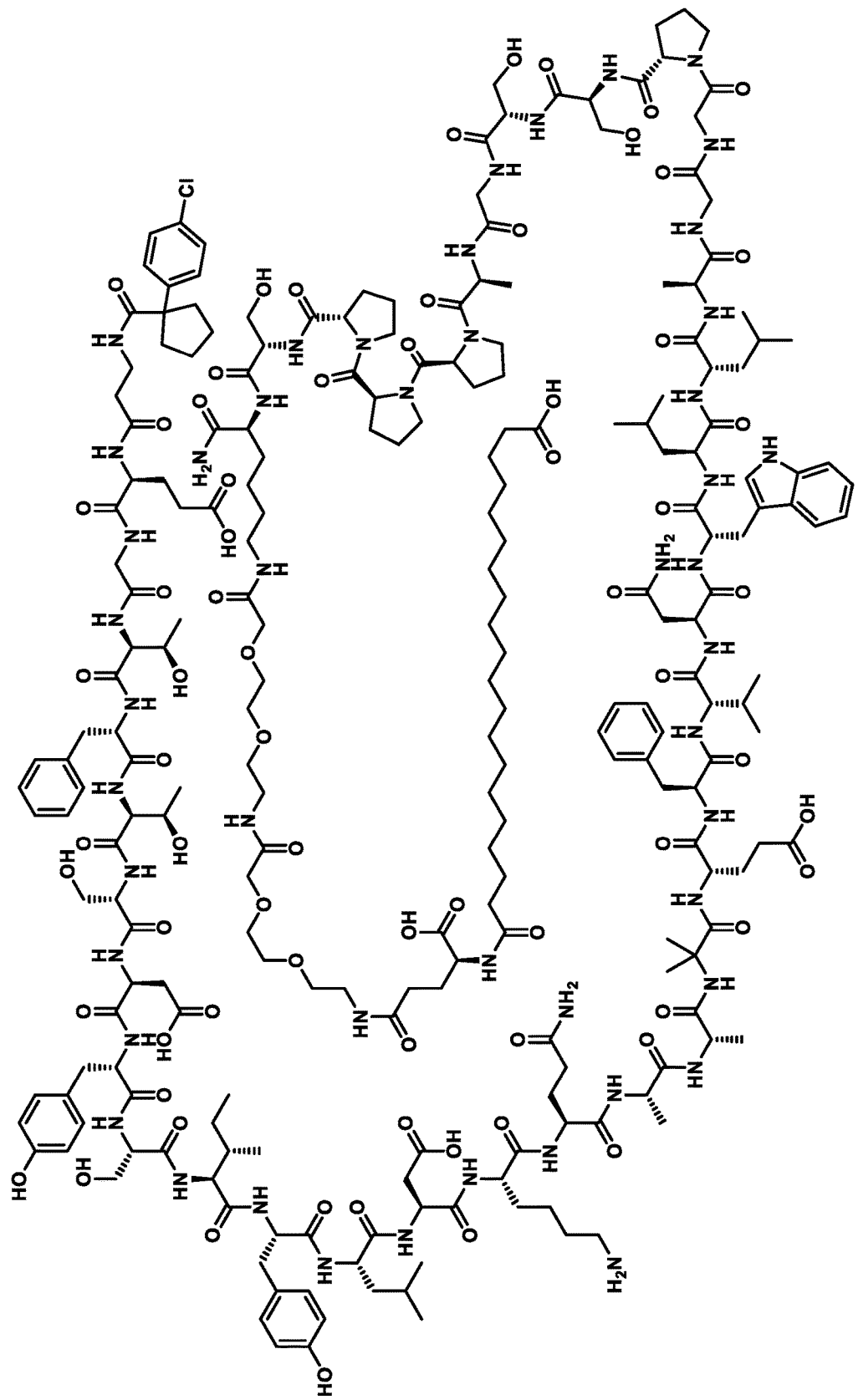
Compound 155
FIG. 1 - Cont'd

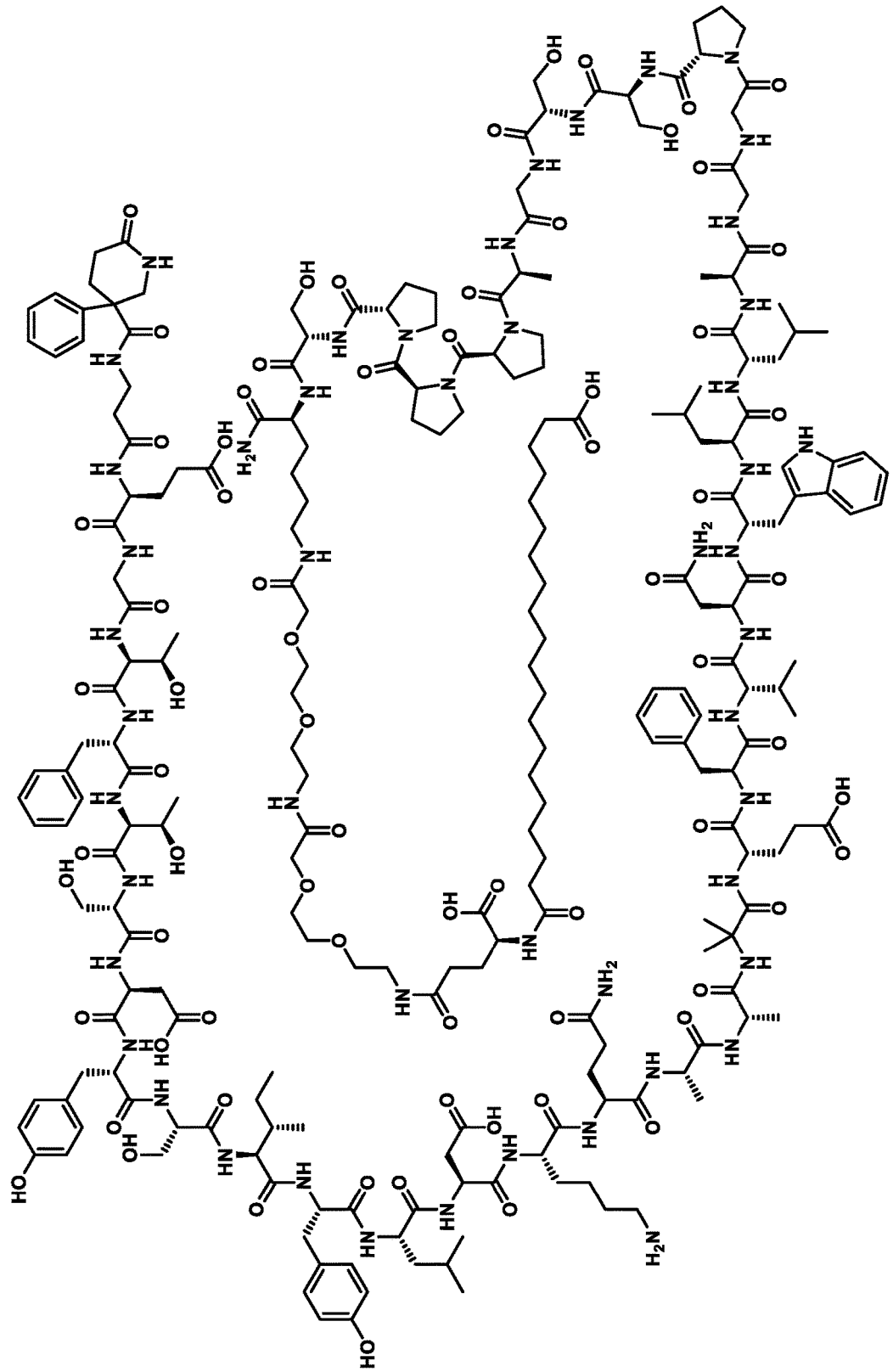
Compound 156
FIG. 1 - Cont'd

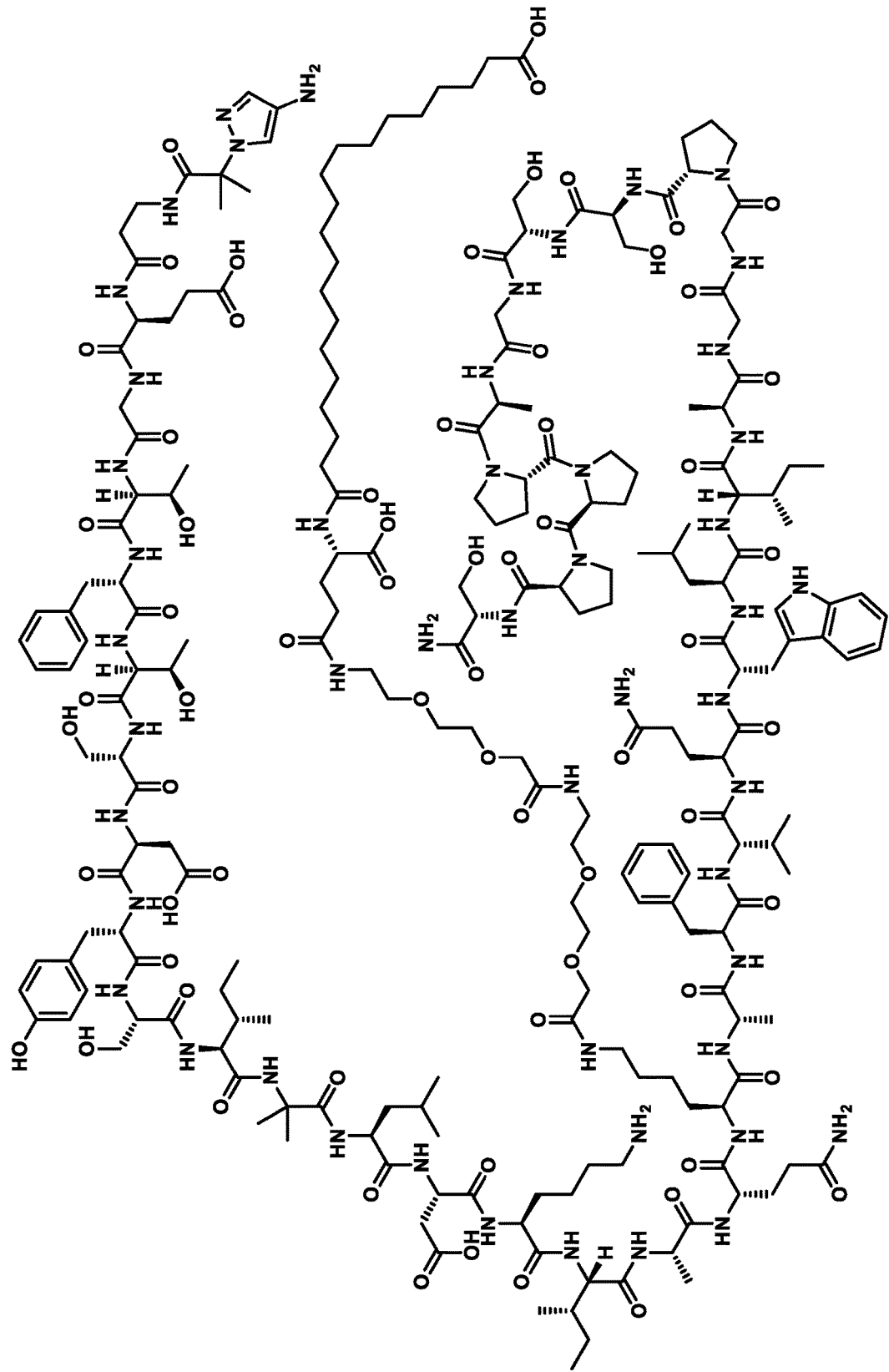
Compound 157
FIG. 1 - Cont'd

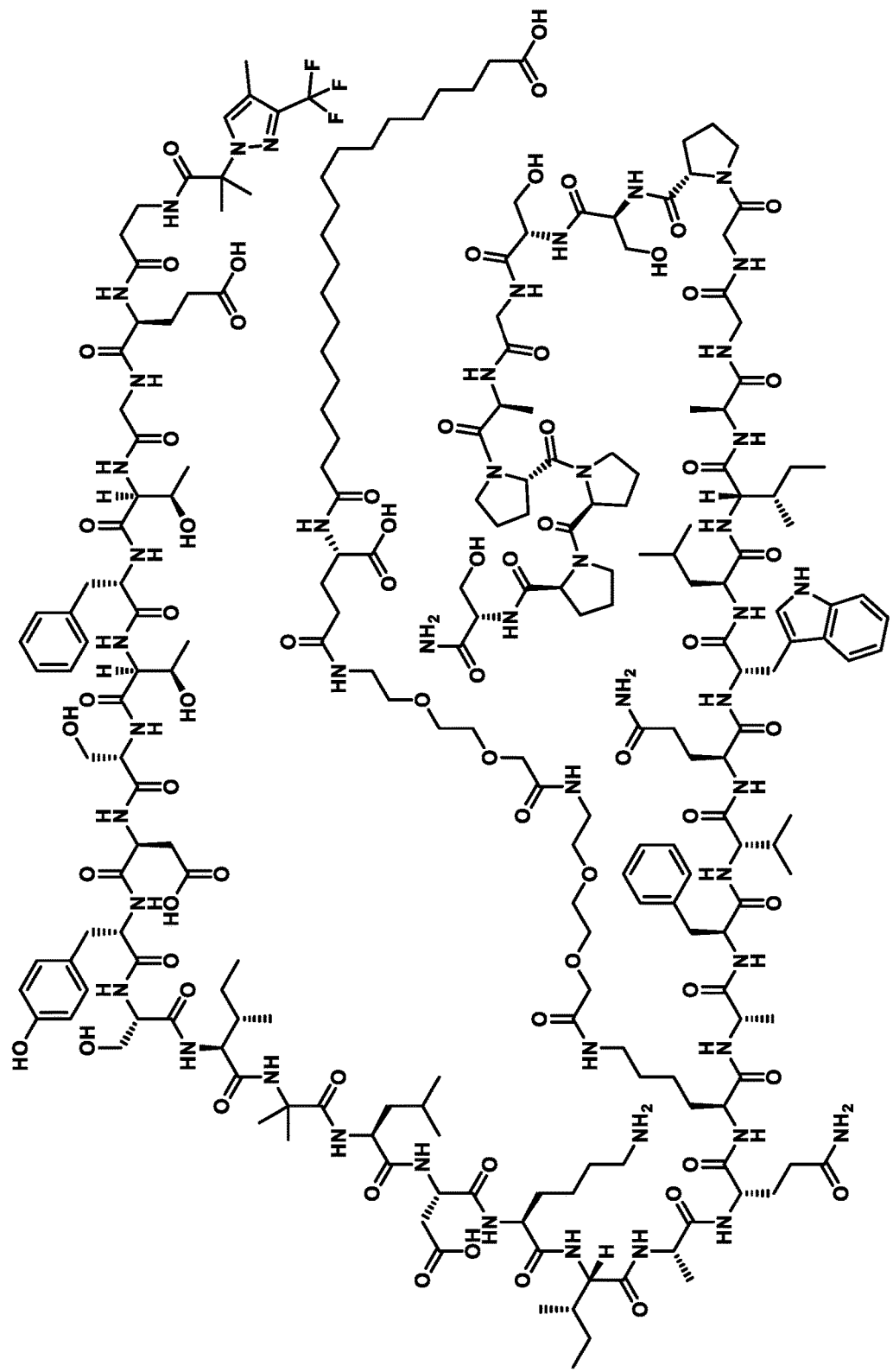
Compound 158
FIG. 1 - Cont'd

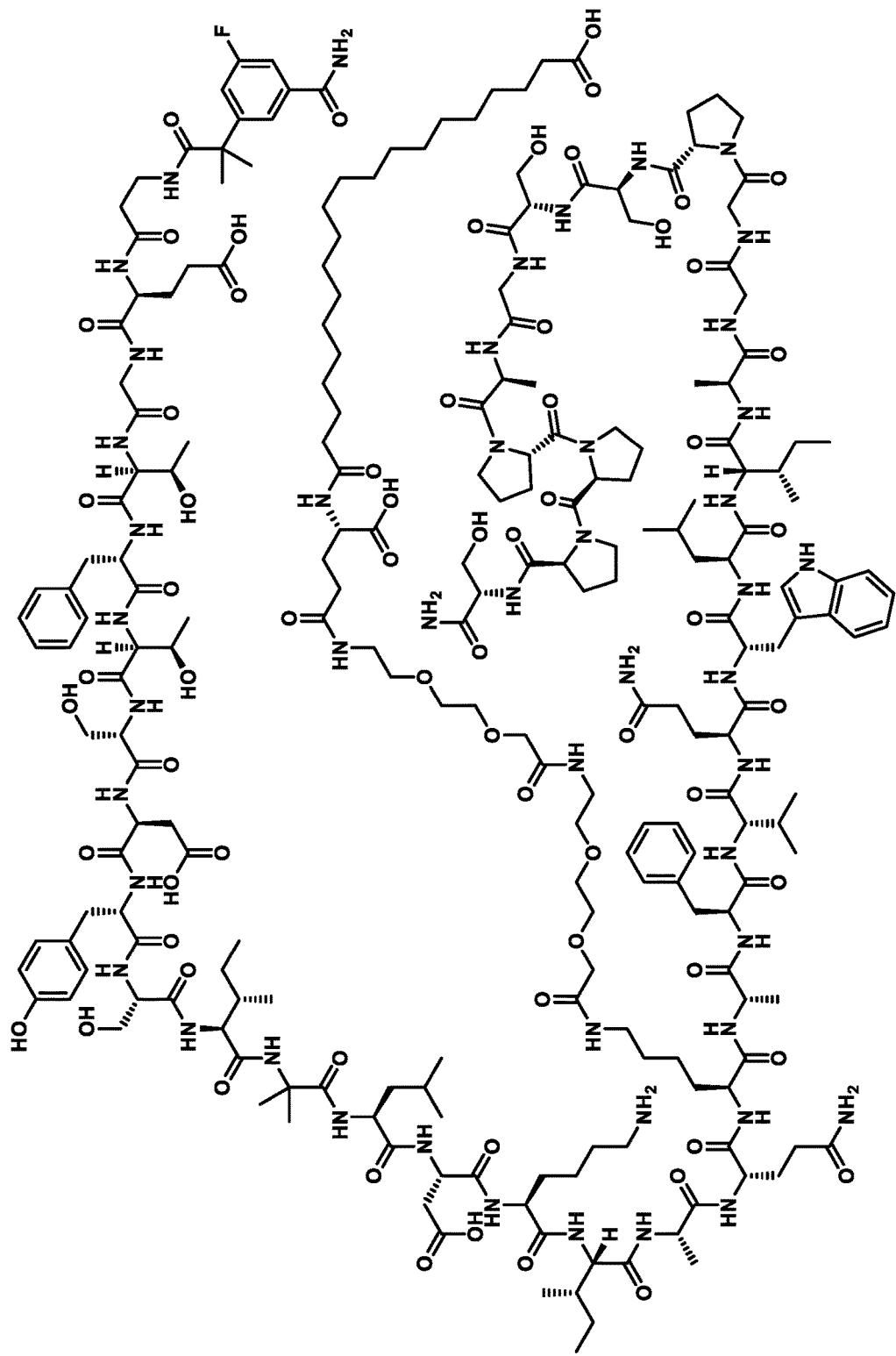
Compound 159
FIG. 1 - Cont'd

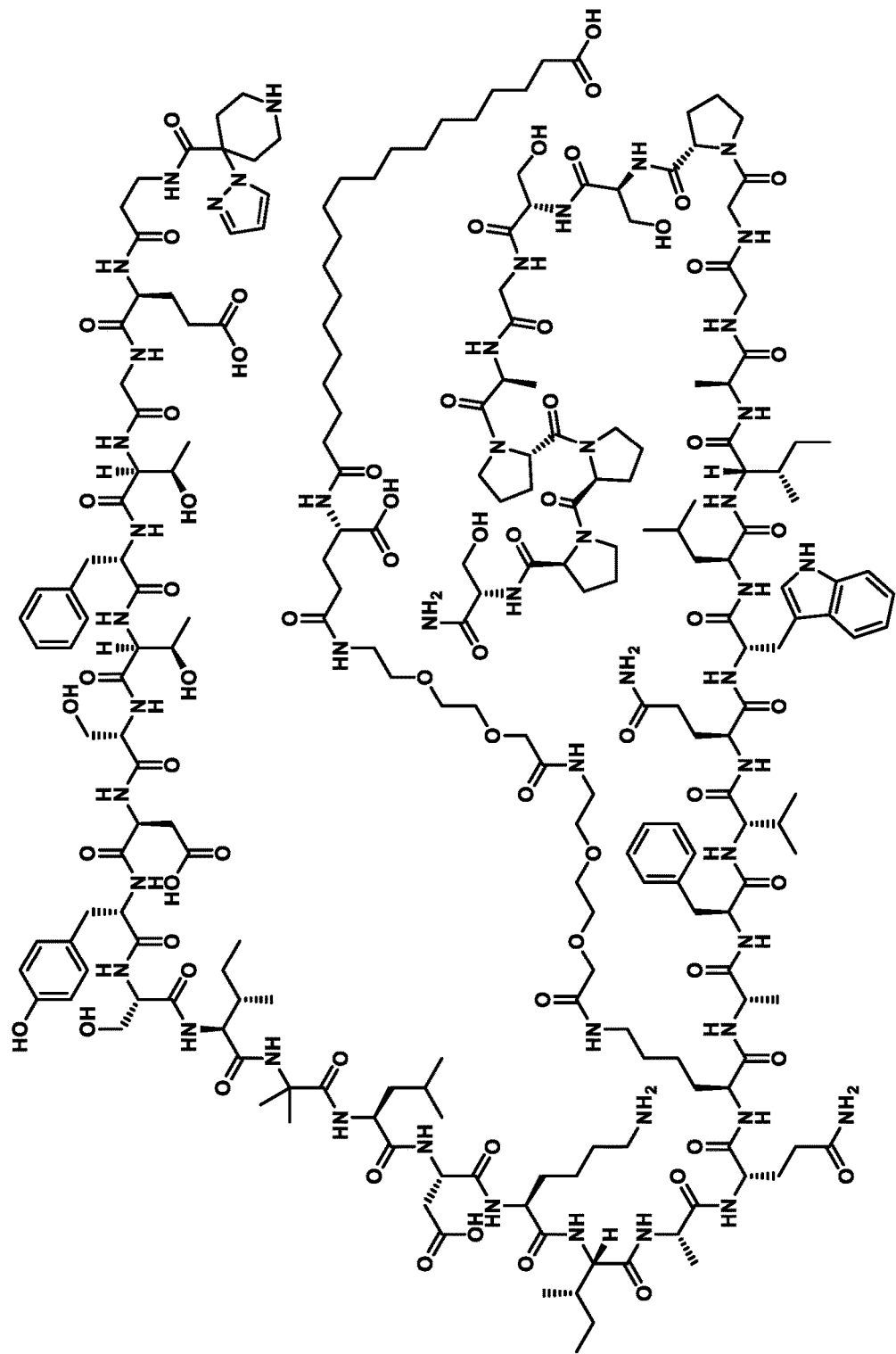
Compound 160
FIG. 1 - Cont'd

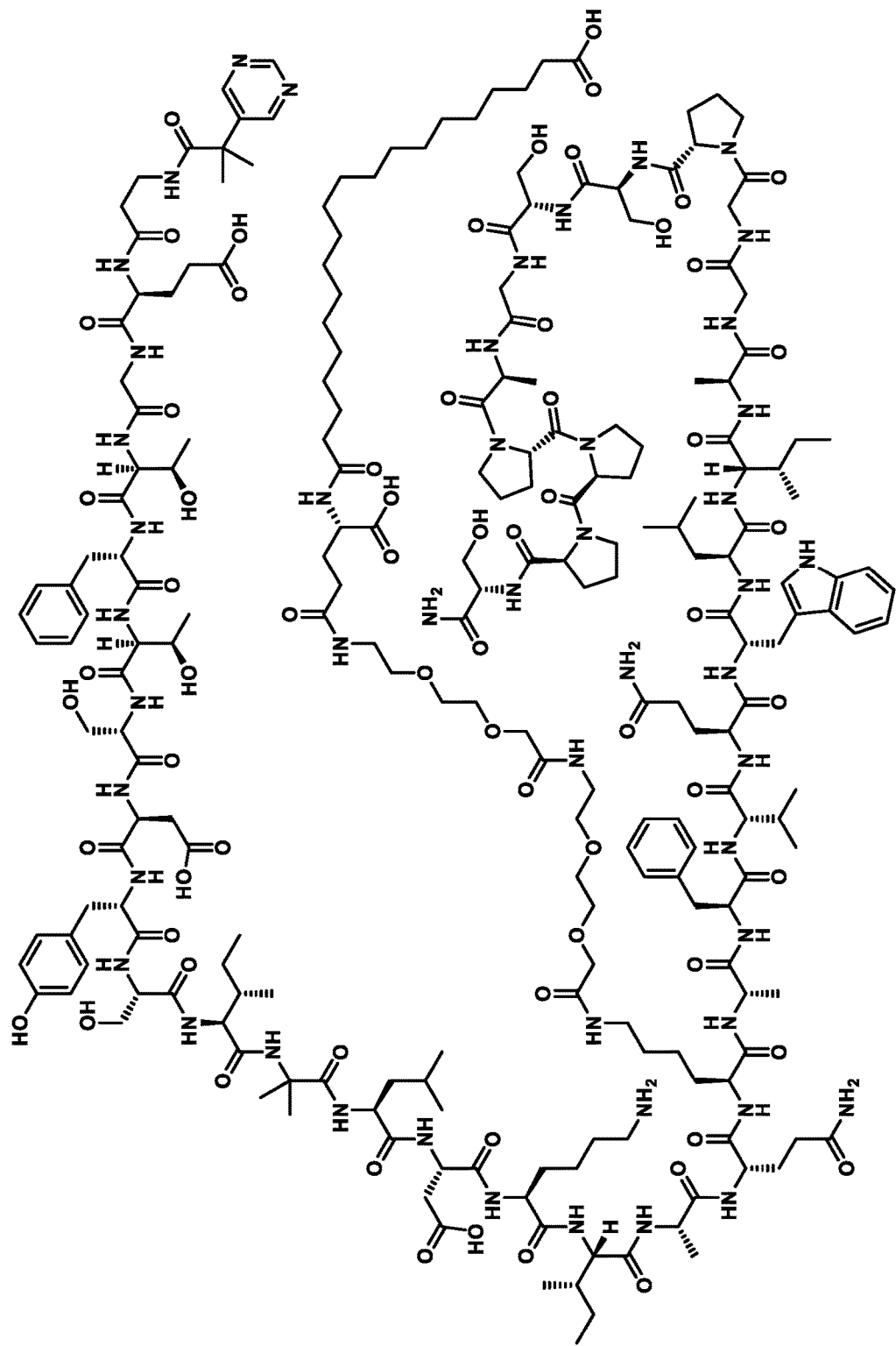
Compound 161
FIG. 1 - Cont'd

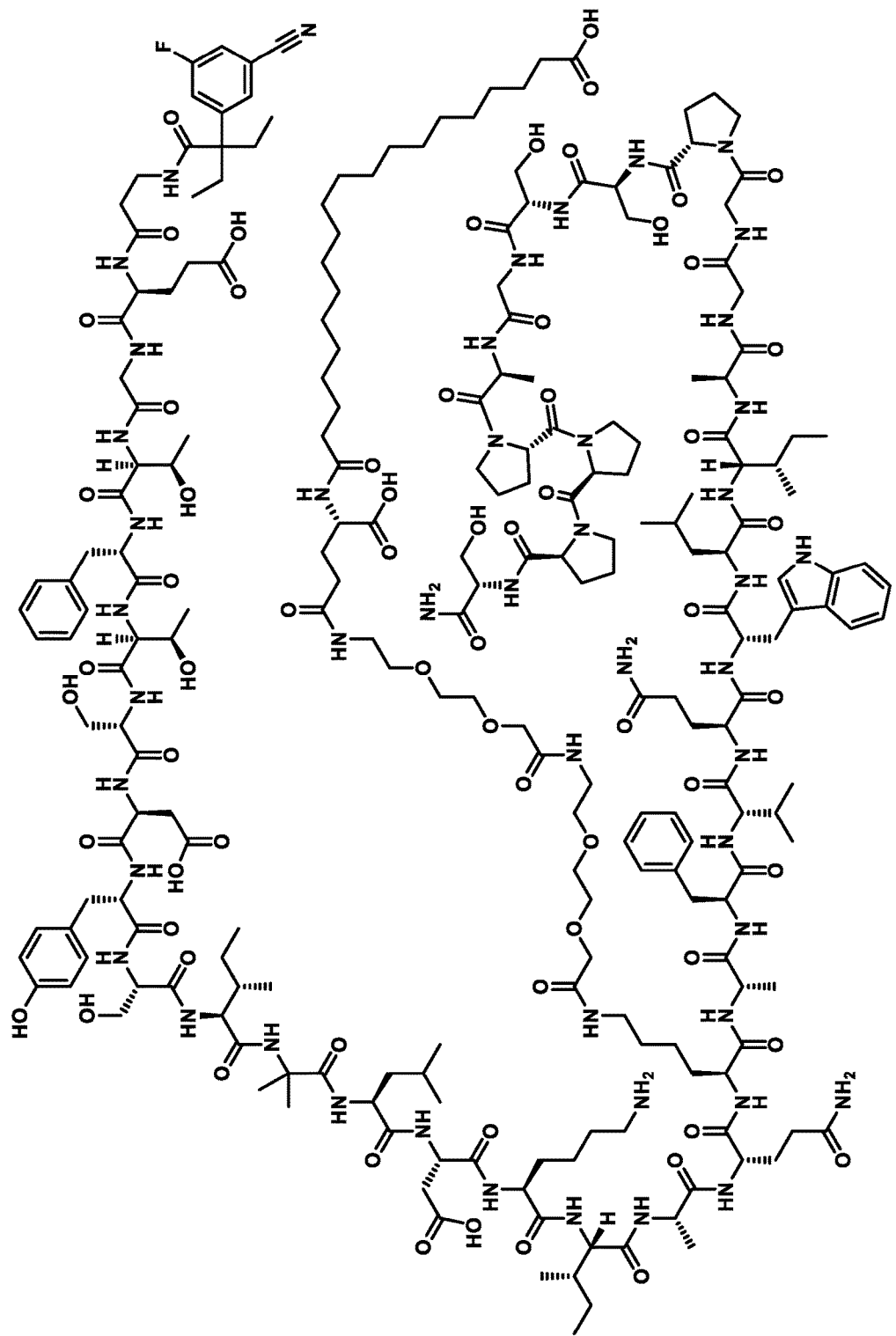
Compound 162
FIG. 1 - Cont'd

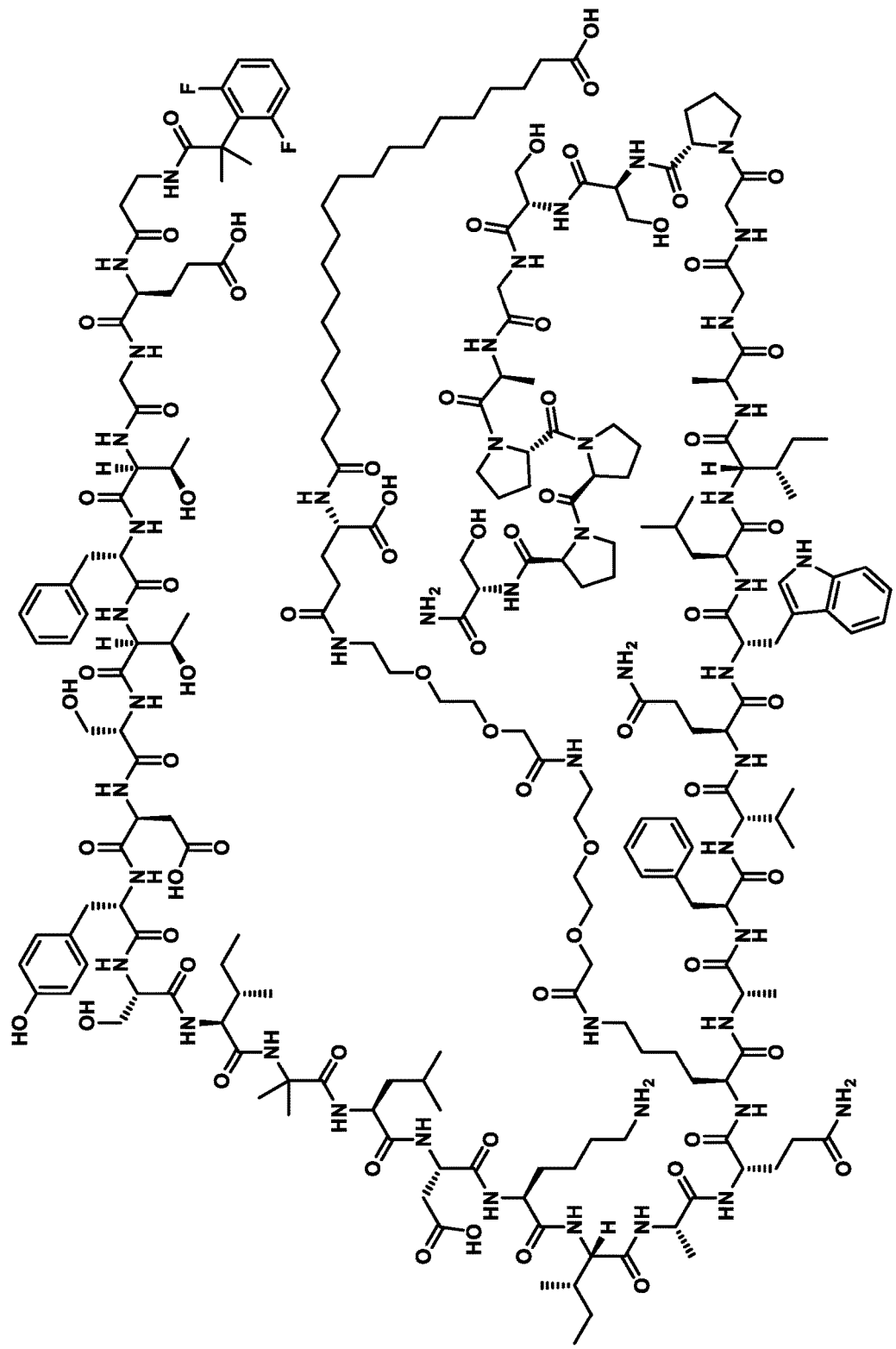
Compound 163
FIG. 1 - Cont'd

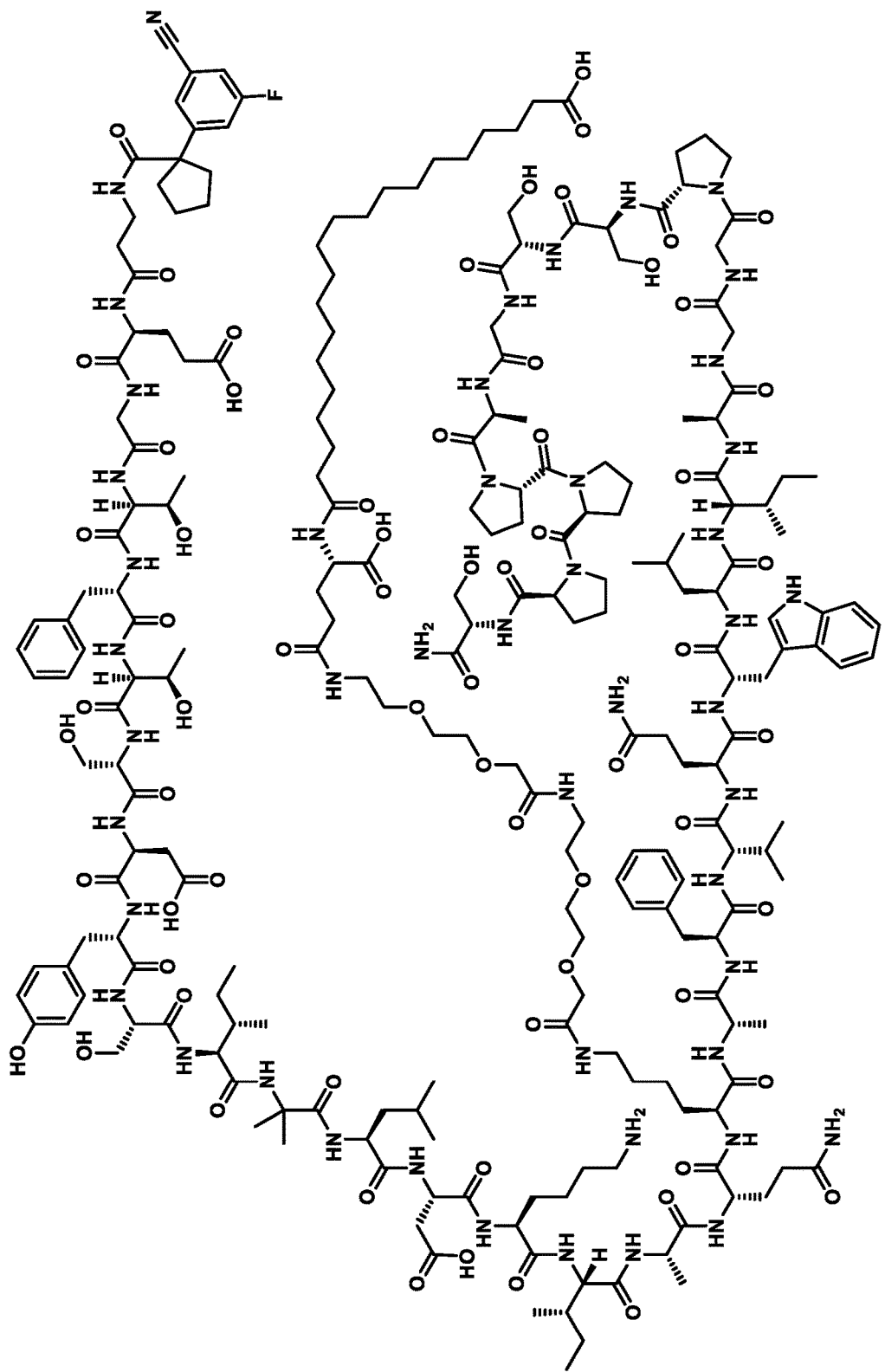
Compound 164
FIG. 1 - Cont'd

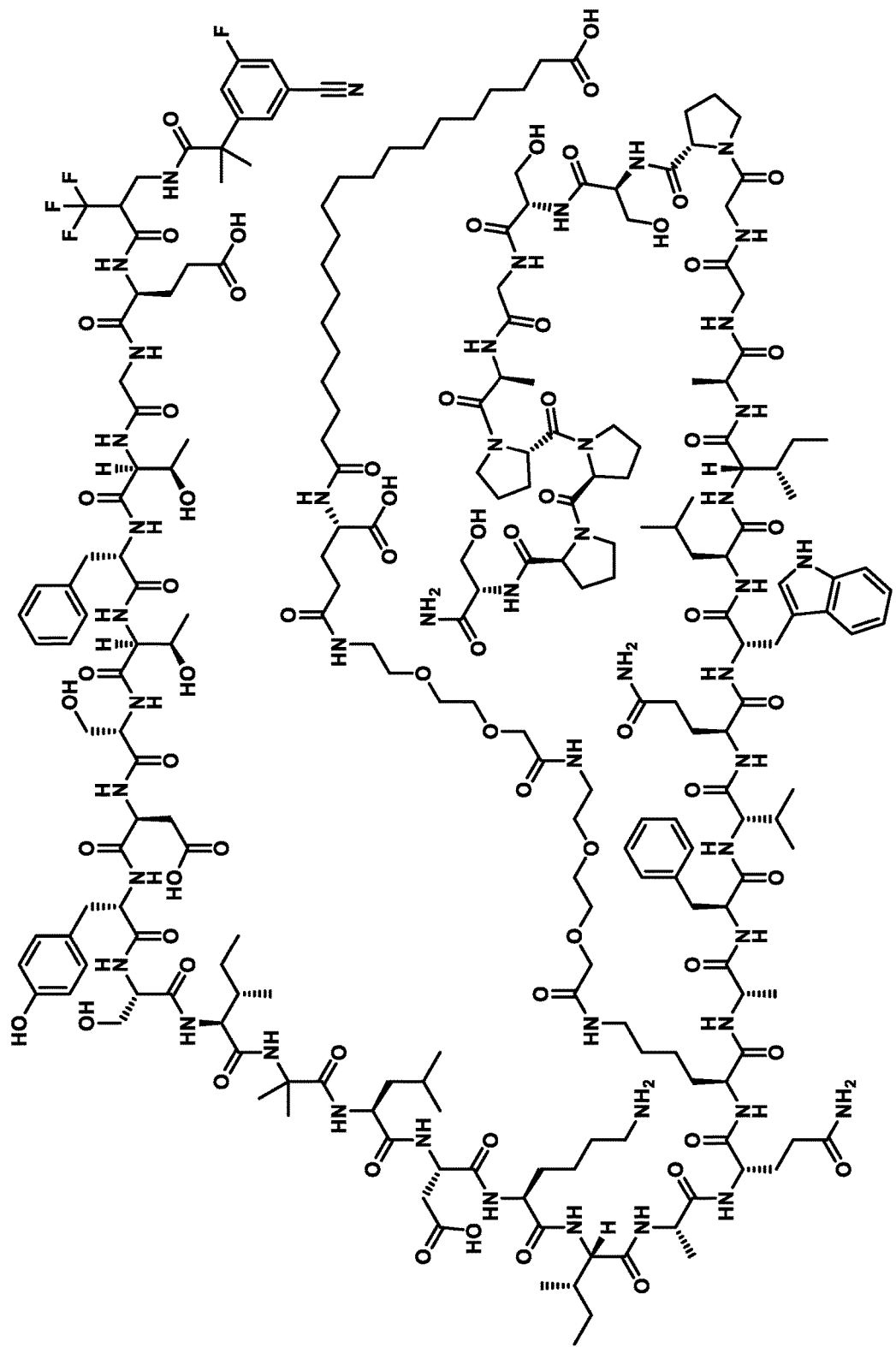
Compound 165
FIG. 1 - Cont'd

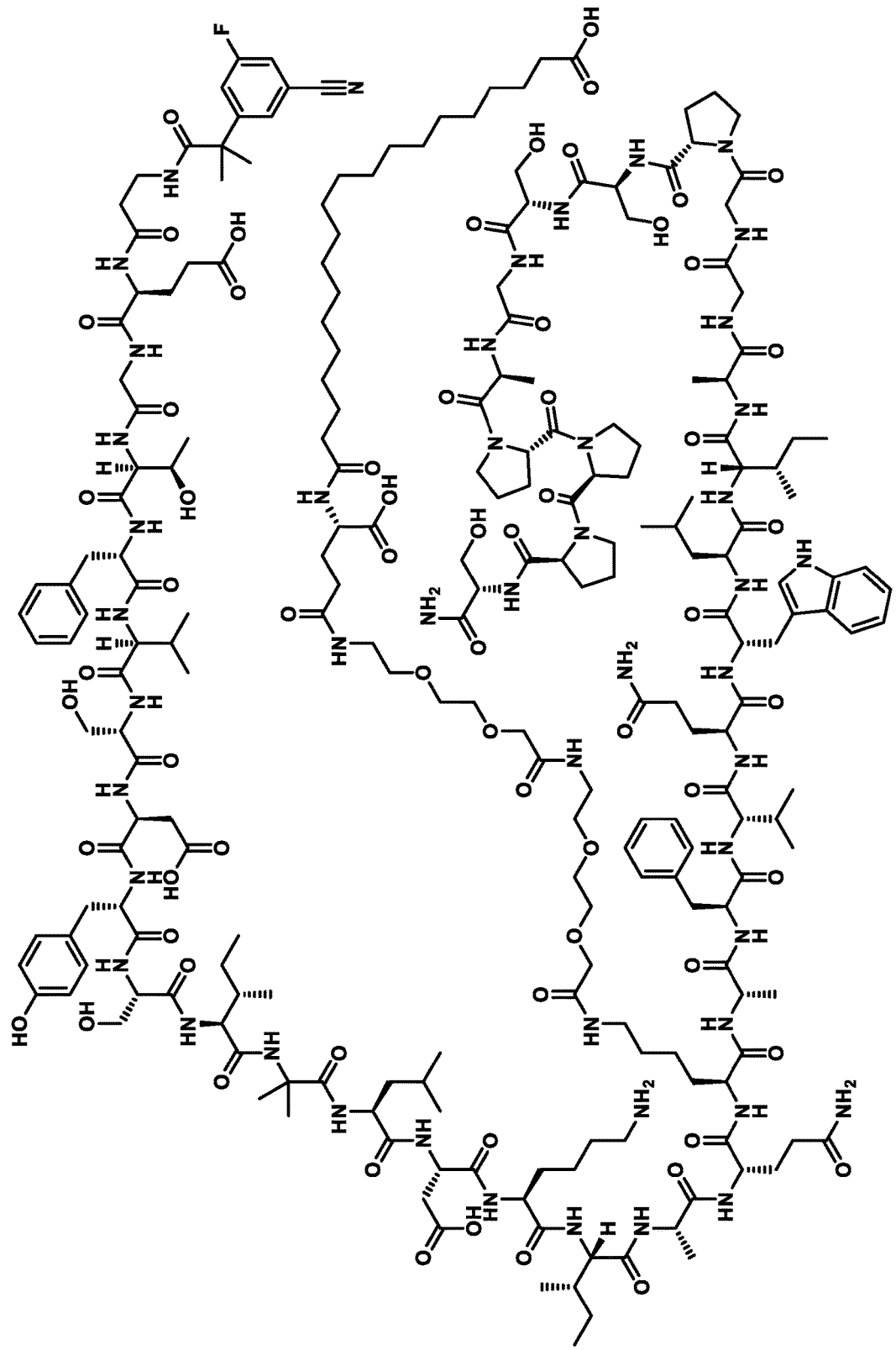
Compound 166
FIG. 1 - Cont'd

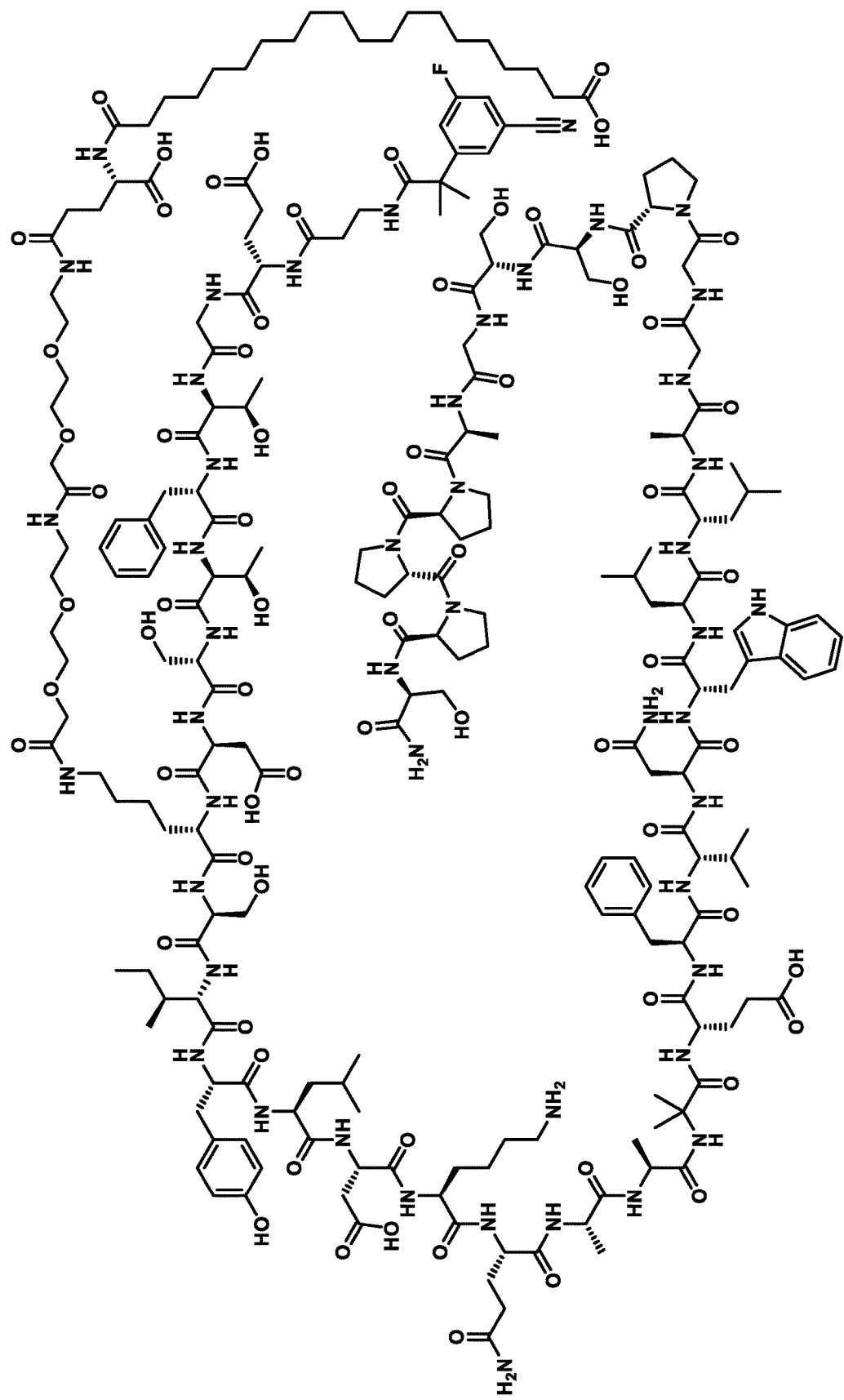
Compound 167
FIG. 1 - Cont'd

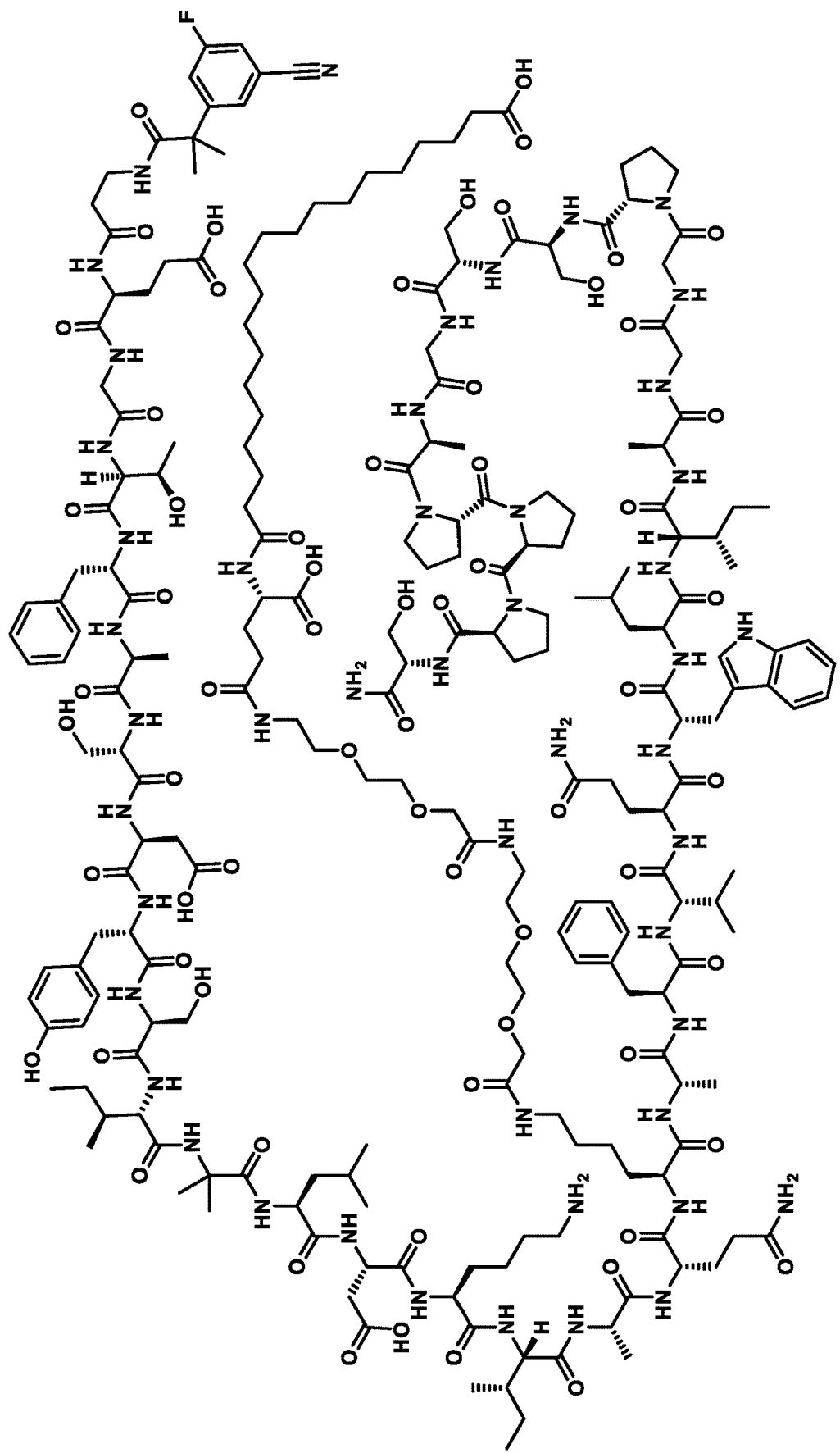
Compound 168
FIG. 1 - Cont'd

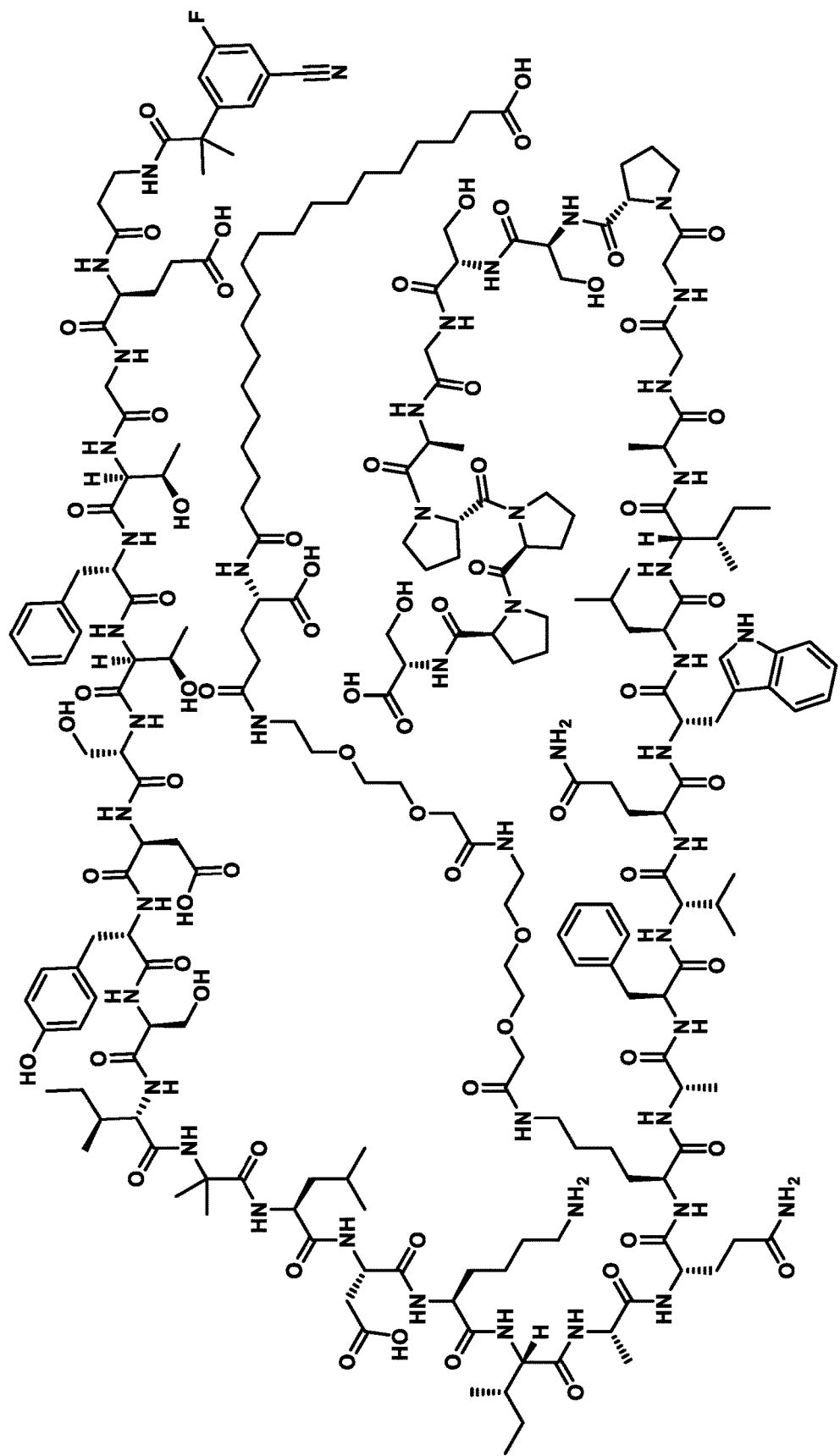
Compound 169
FIG. 1 - Cont'd

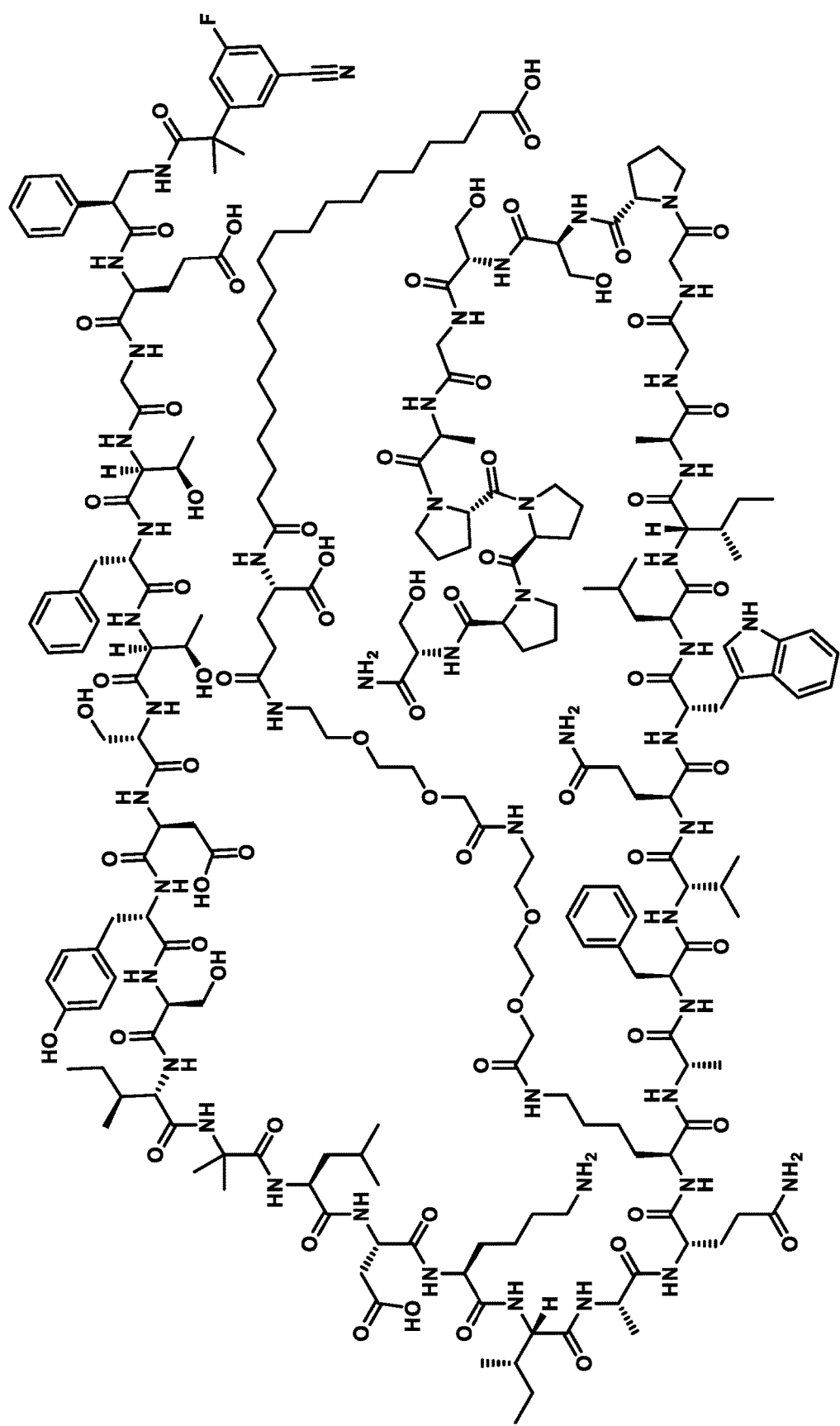
Compound 170
FIG. 1 - Cont'd

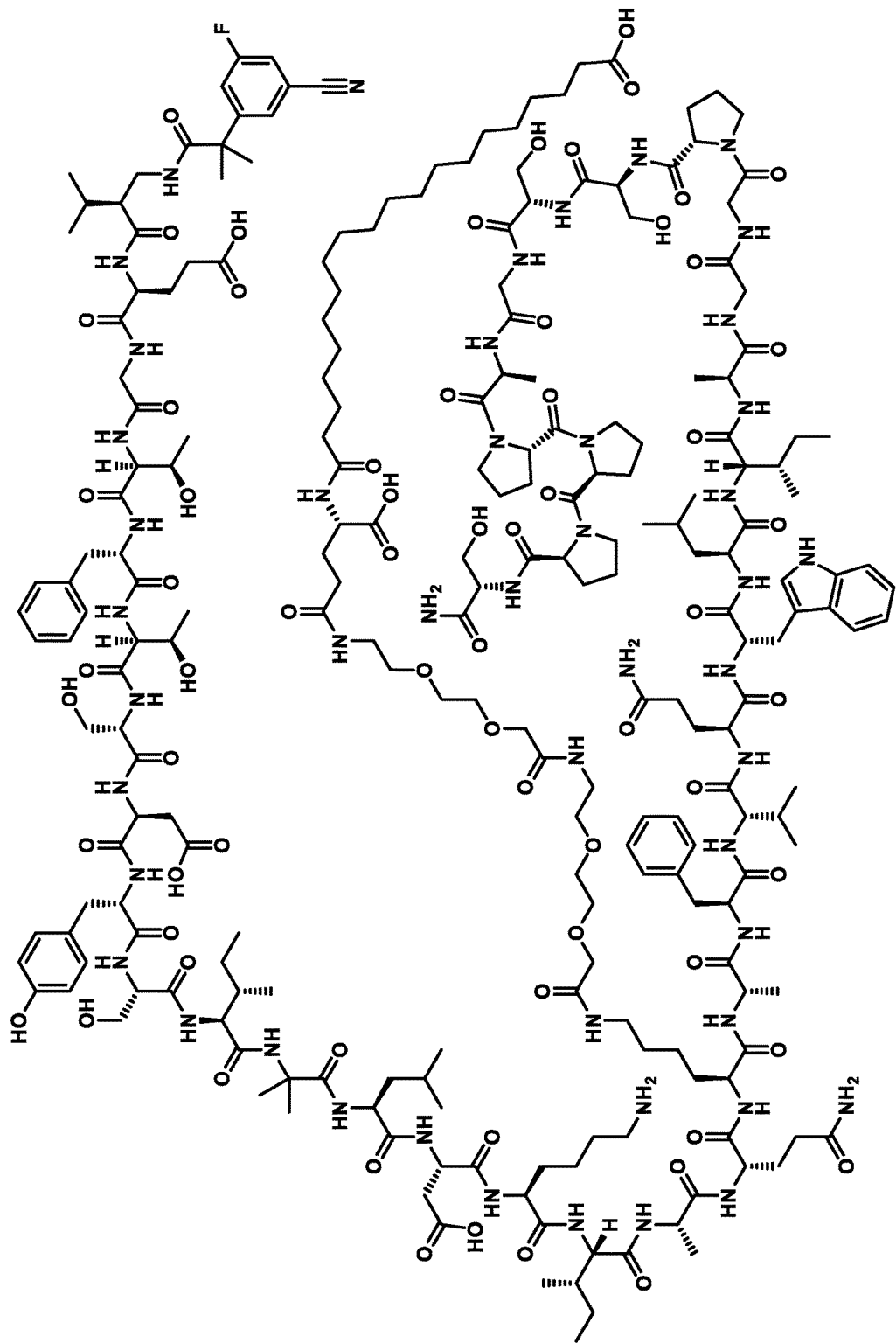
Compound 171
FIG. 1 - Cont'd

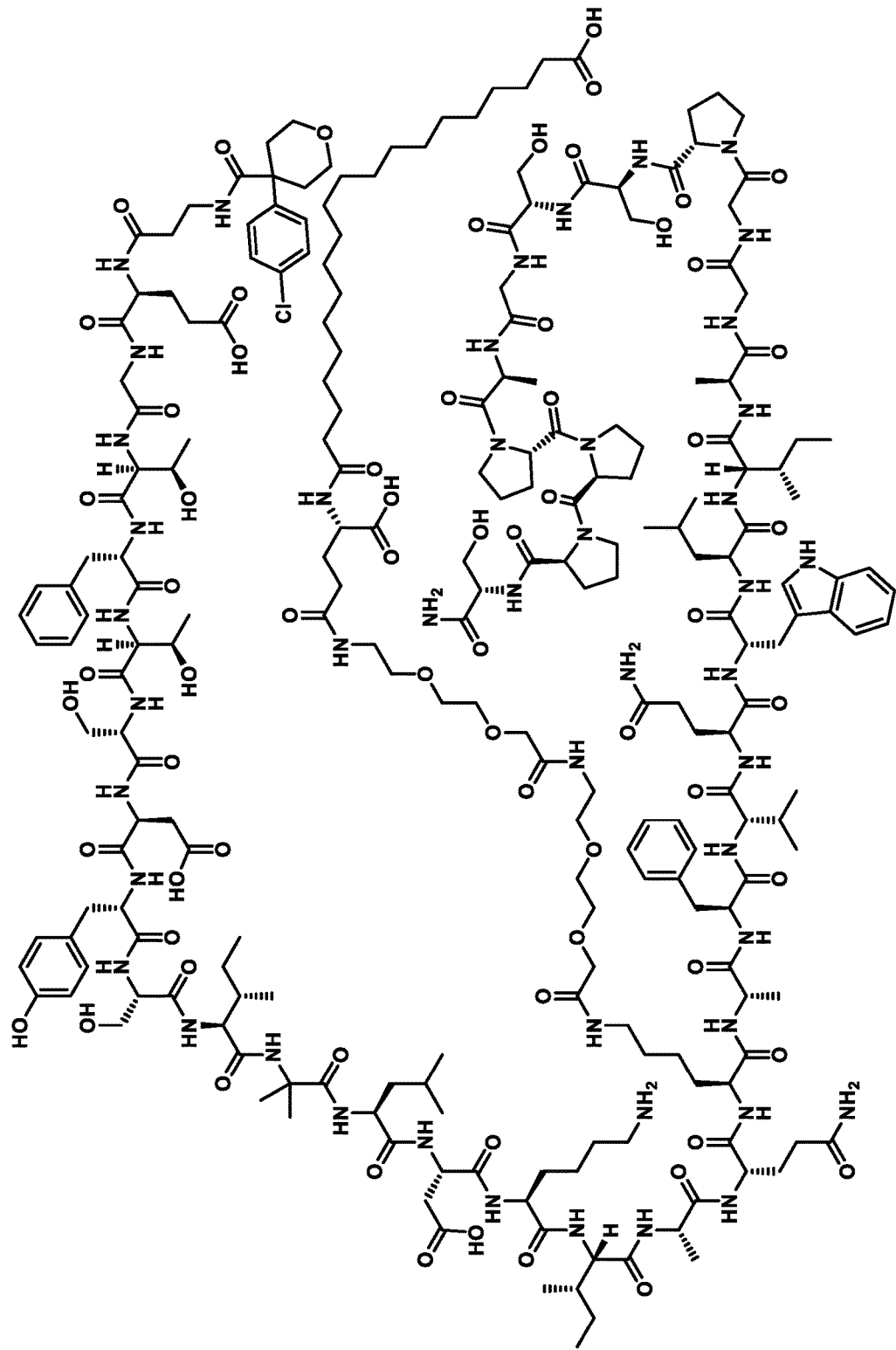
Compound 172
FIG. 1 - Cont'd

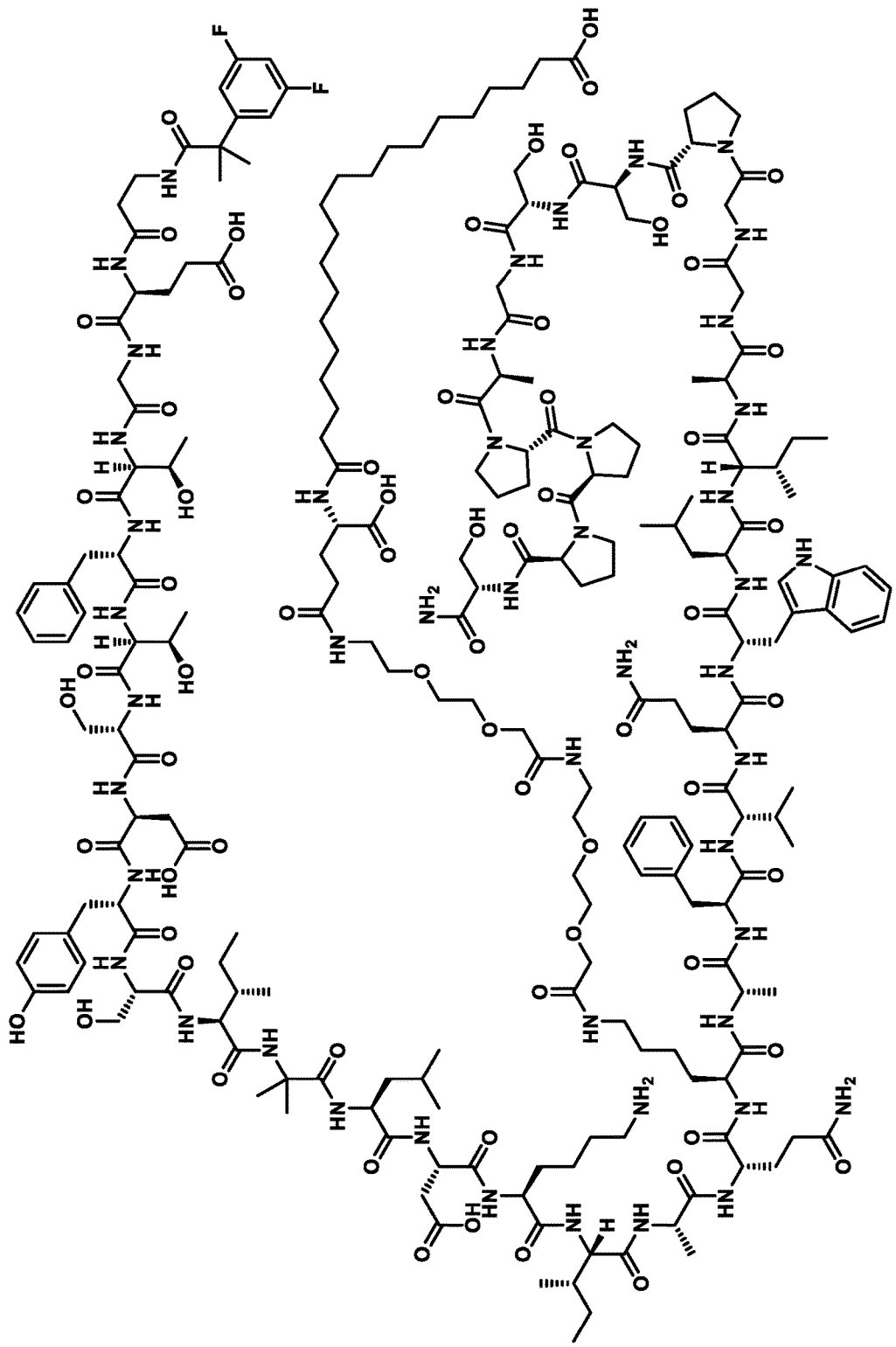
Compound 173
FIG. 1 - Cont'd

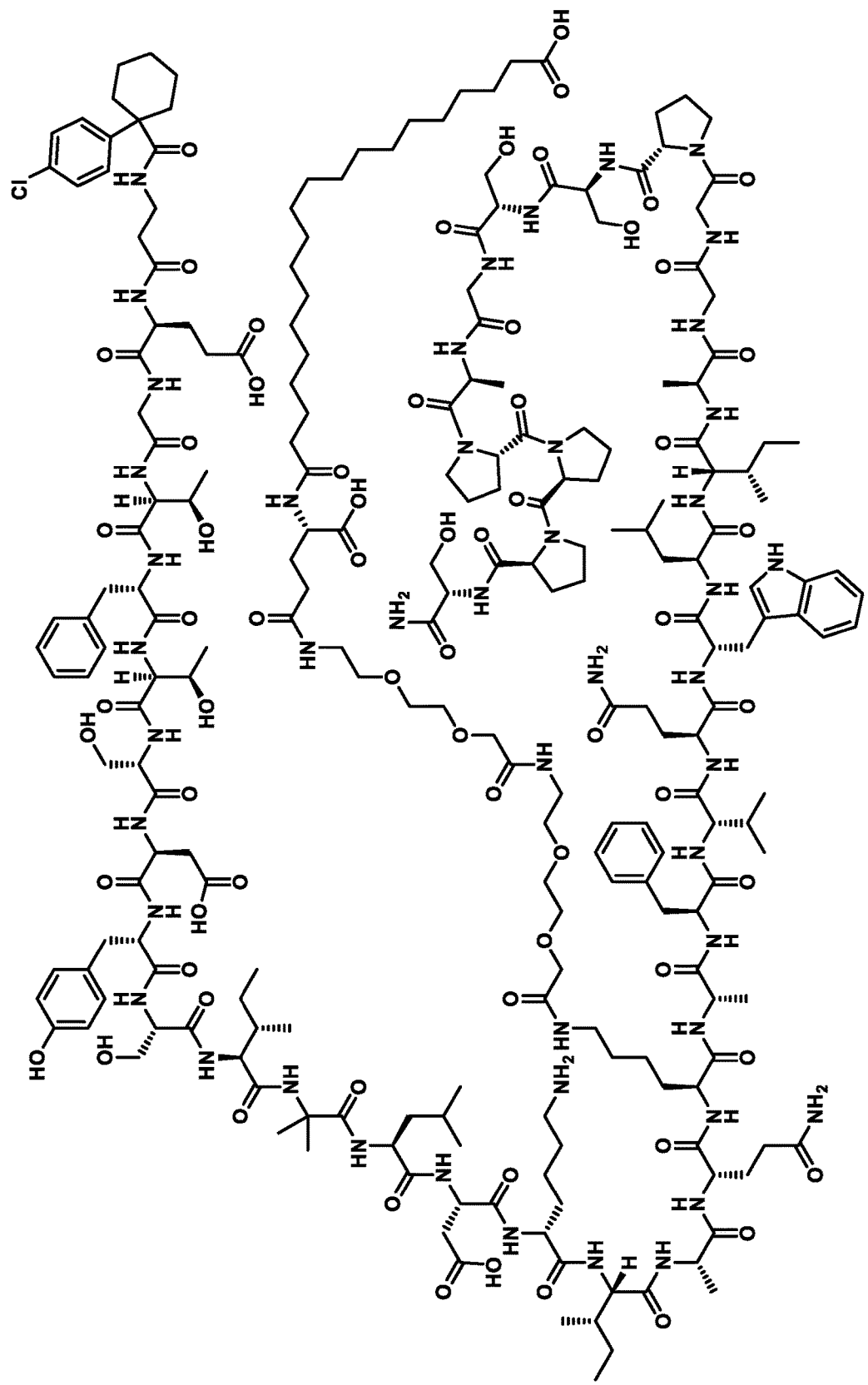
Compound 174
FIG. 1 - Cont'd

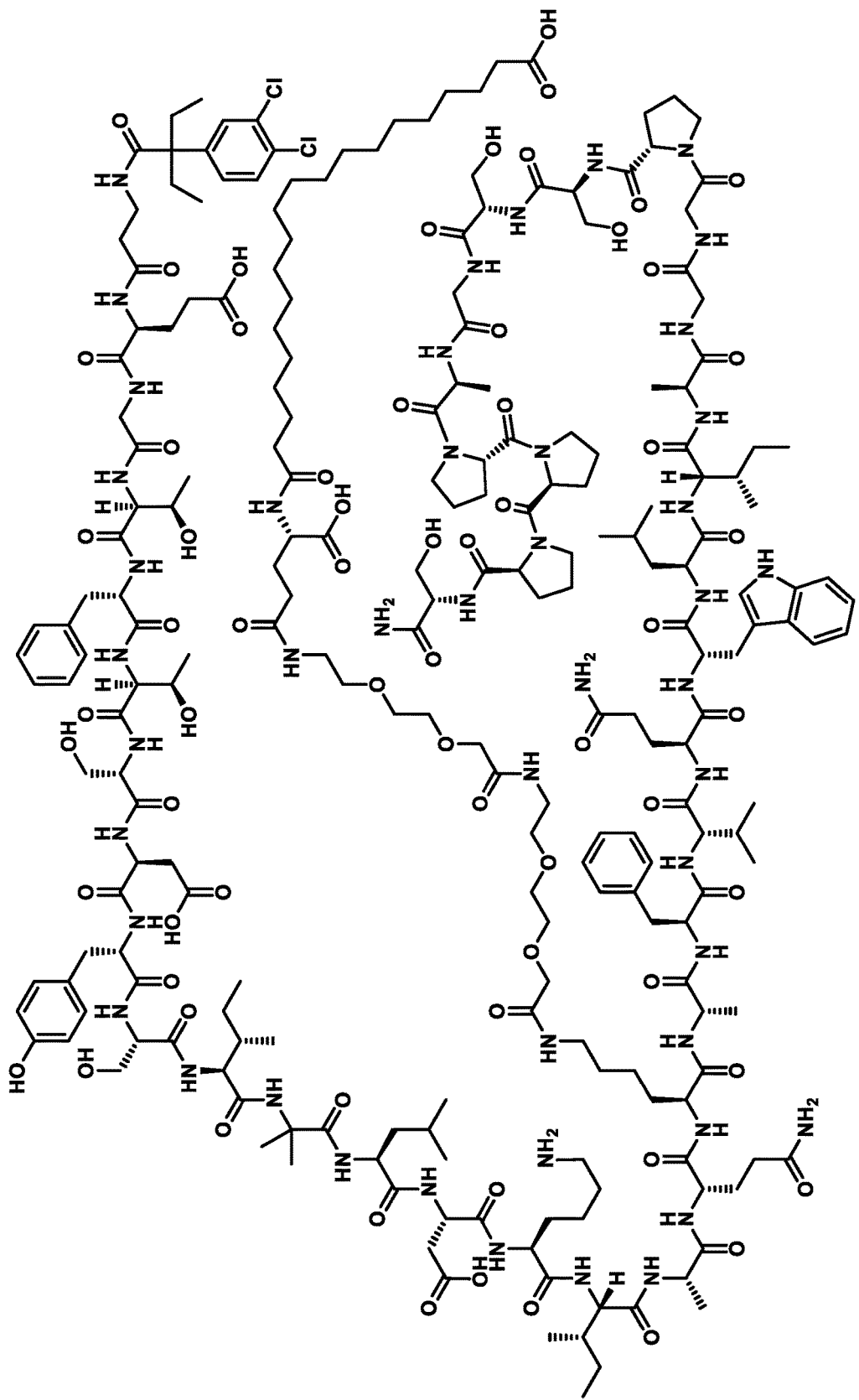
Compound 175
FIG. 1 - Cont'd

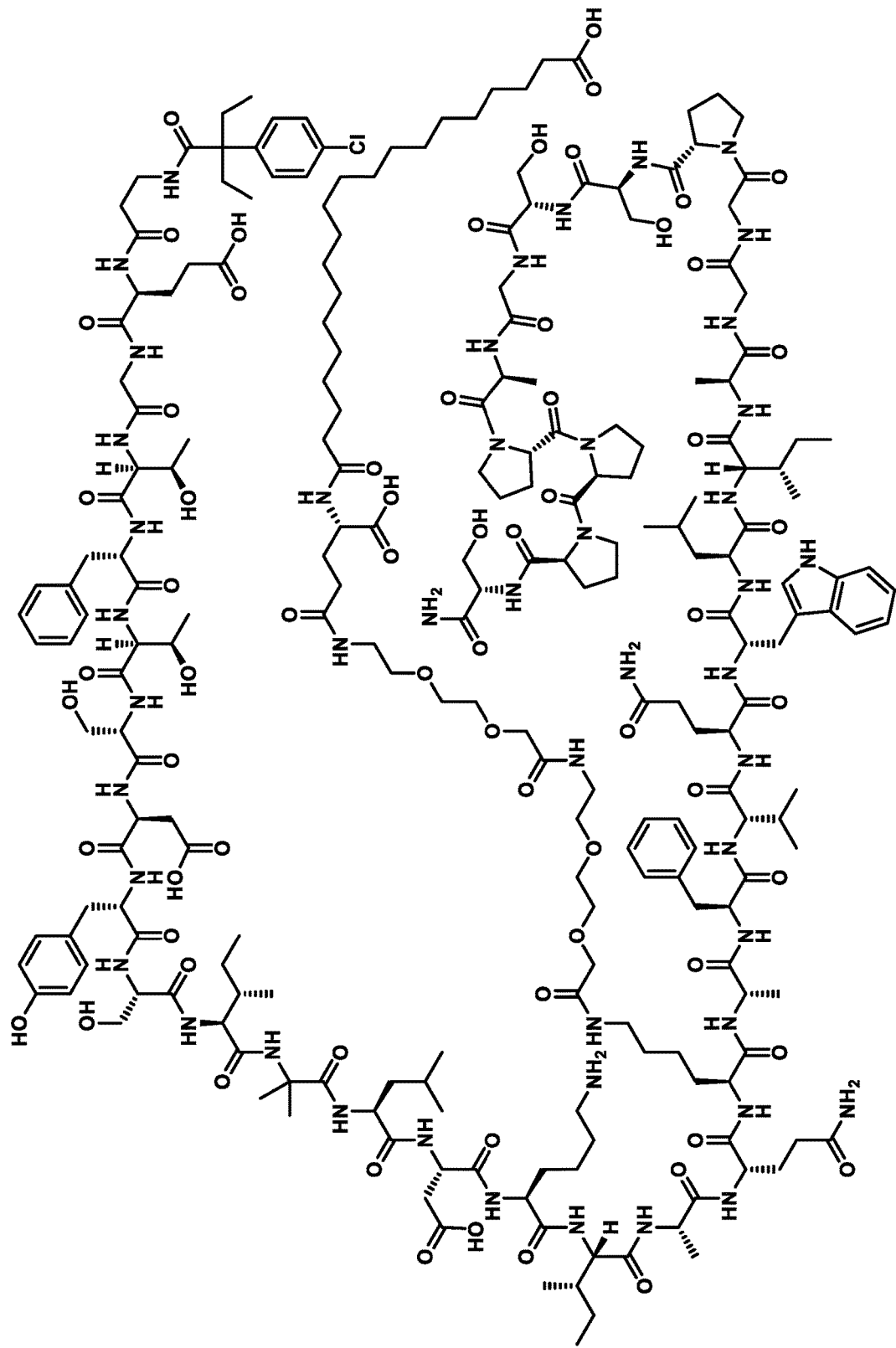
Compound 176
FIG. 1 - Cont'd

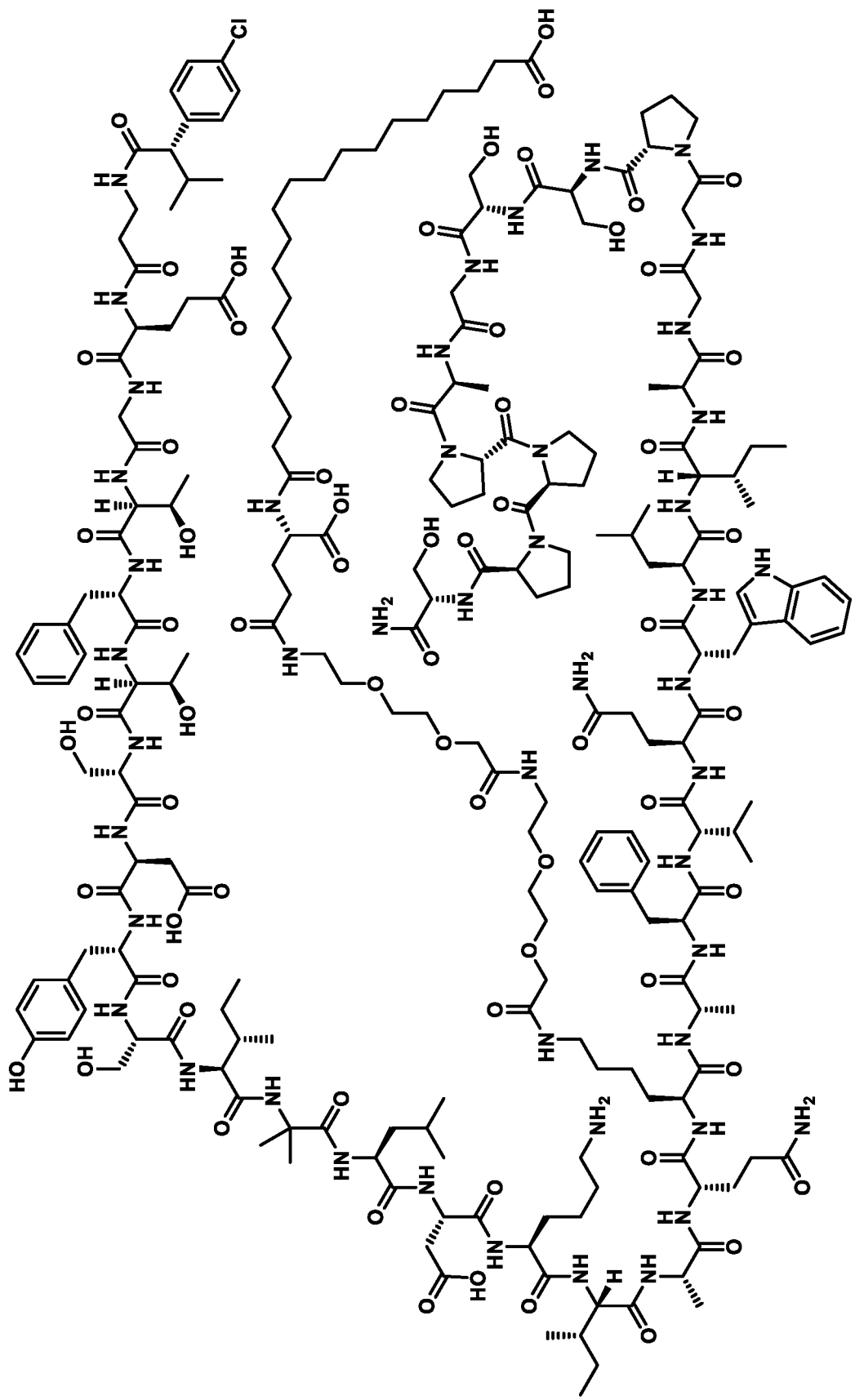
Compound 177
FIG. 1 - Cont'd

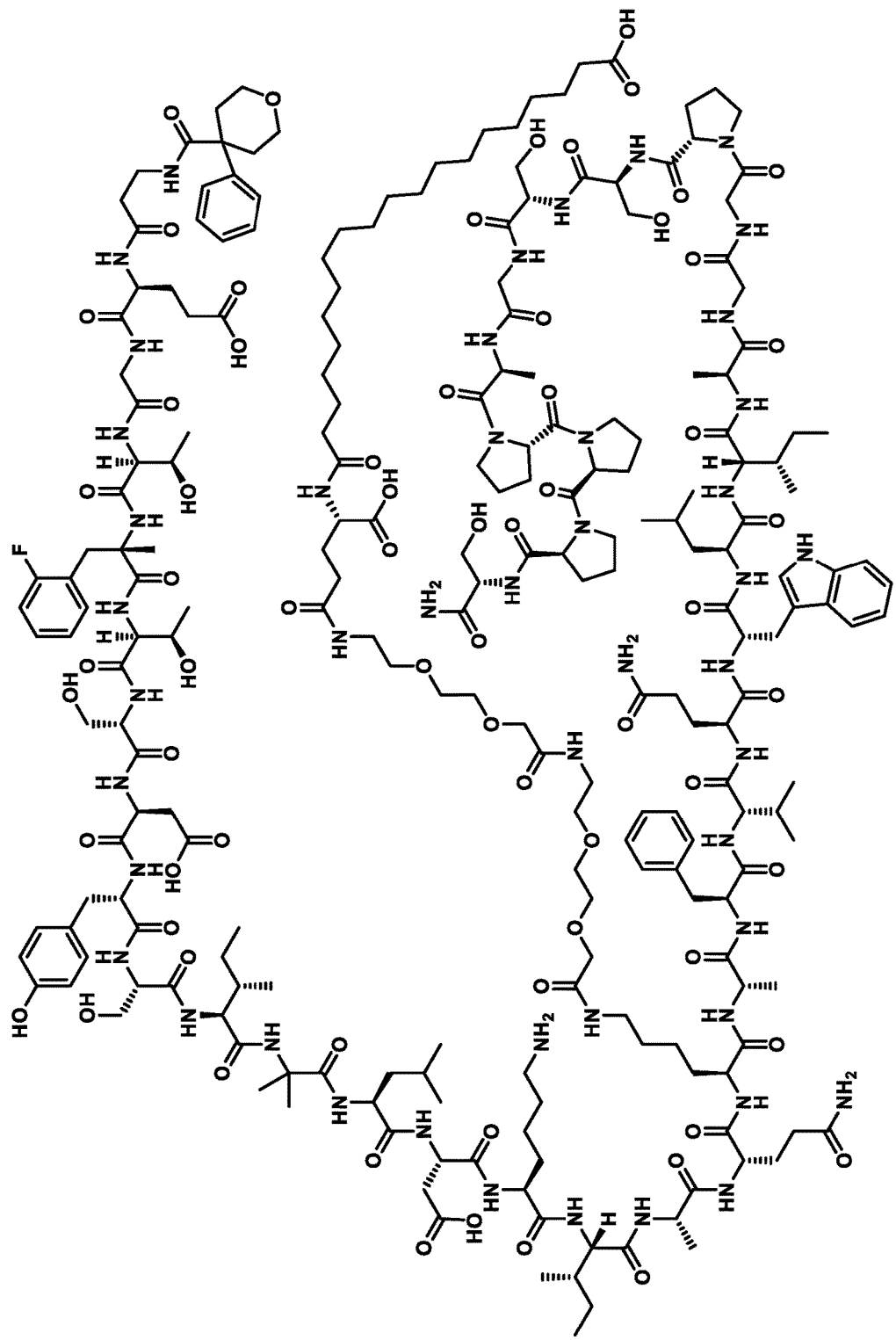
Compound 178
FIG. 1 - Cont'd

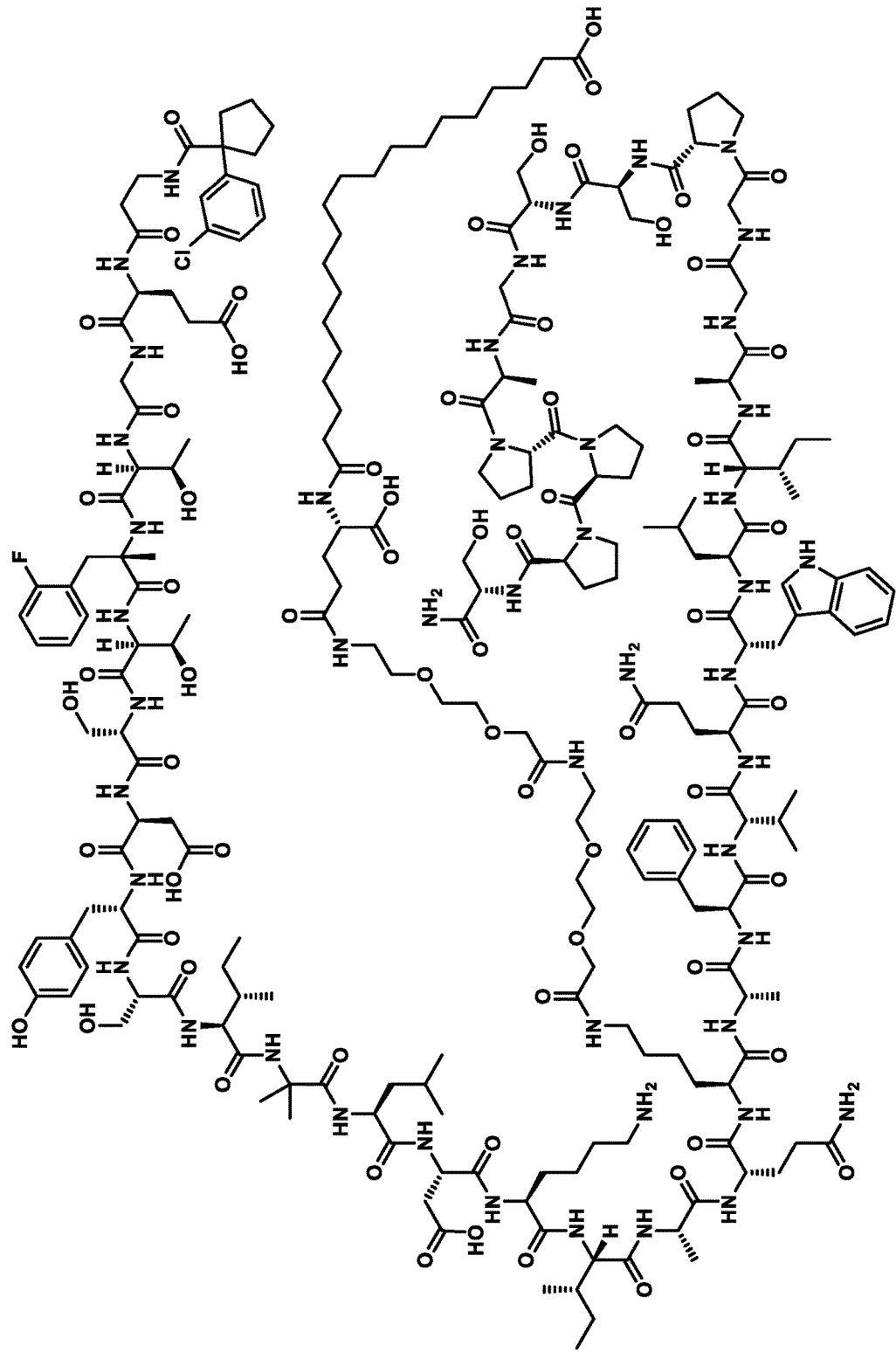
Compound 179
FIG. 1 - Cont'd

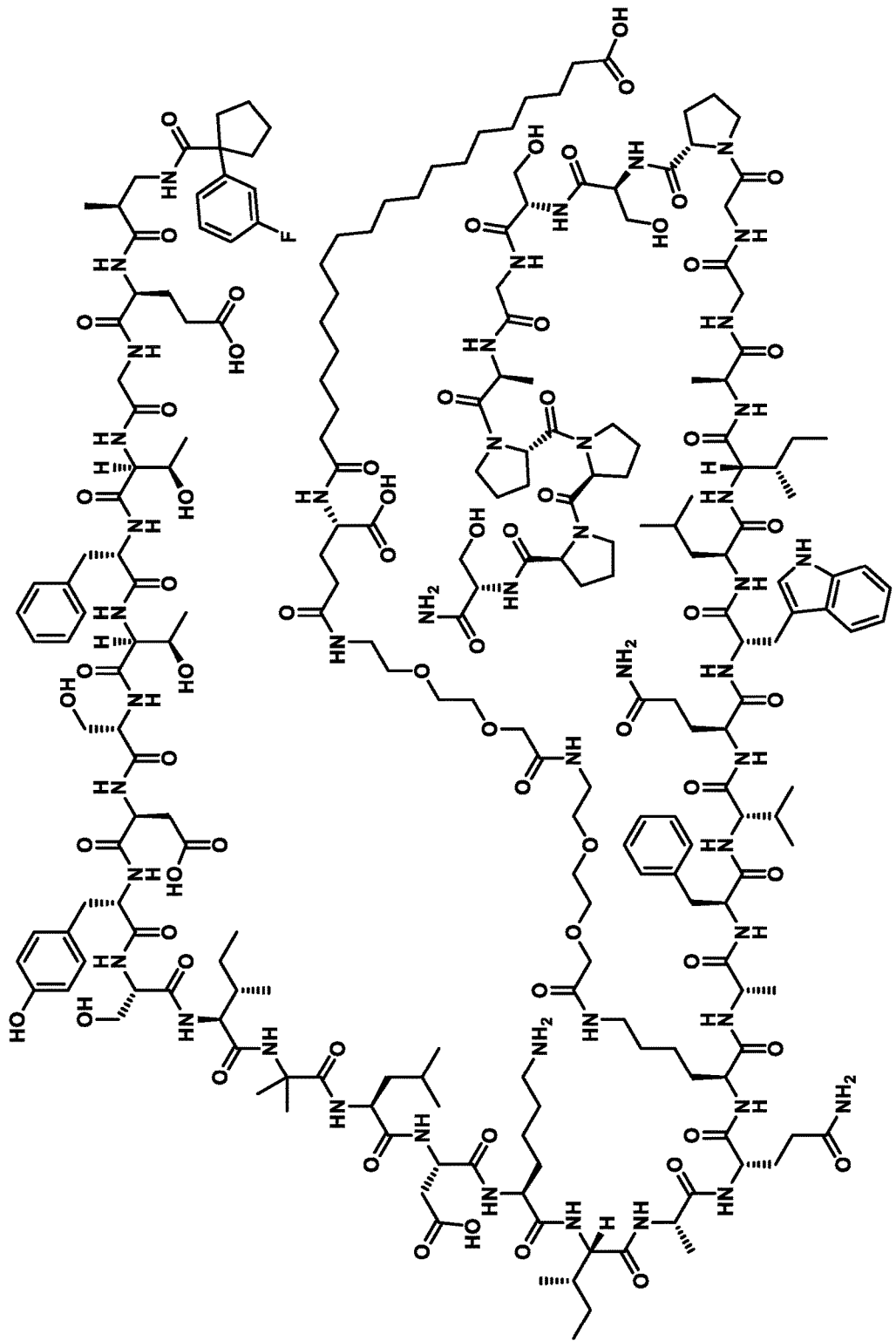
Compound 180
FIG. 1 - Cont'd

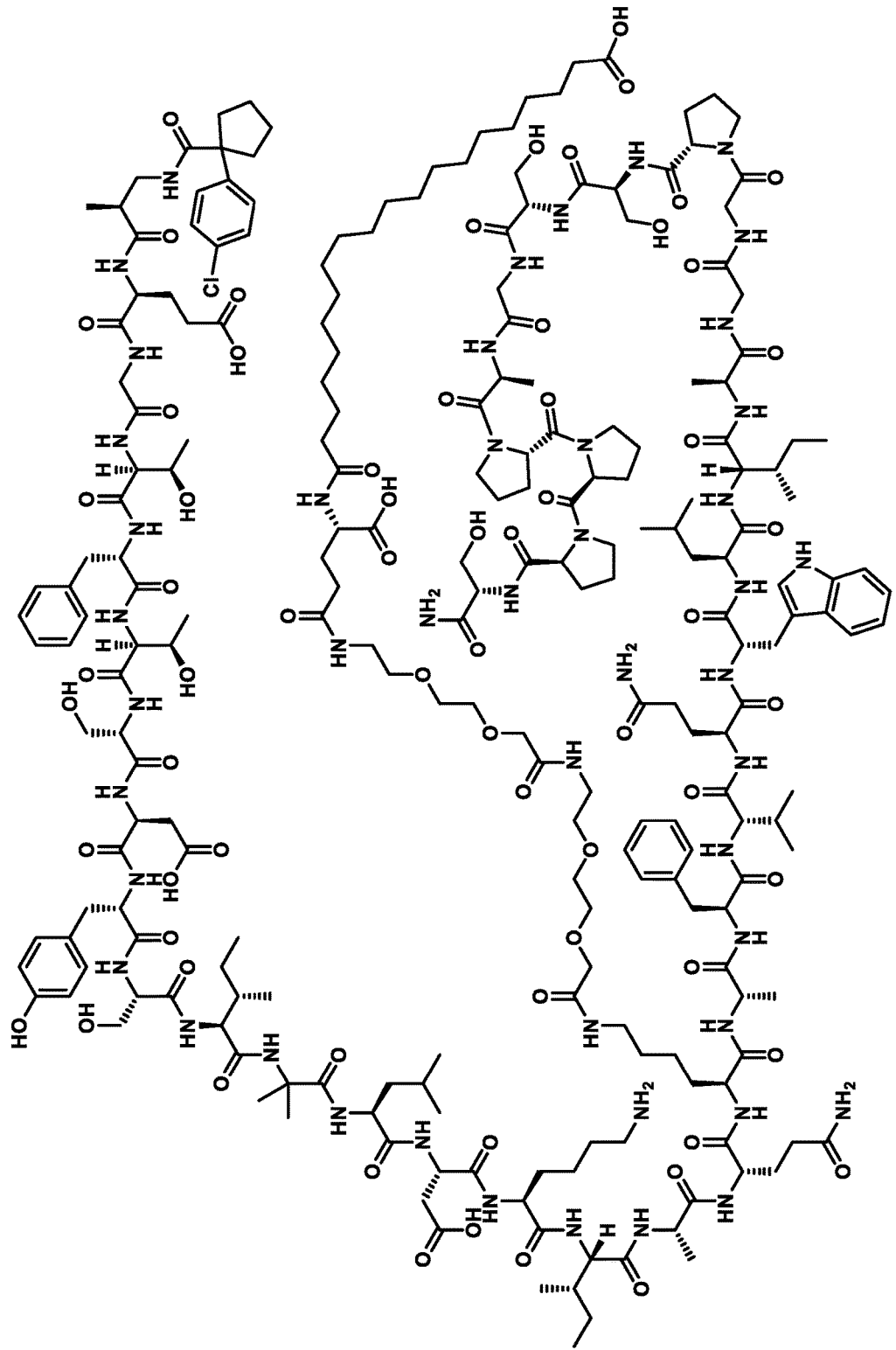
Compound 181
FIG. 1 - Cont'd

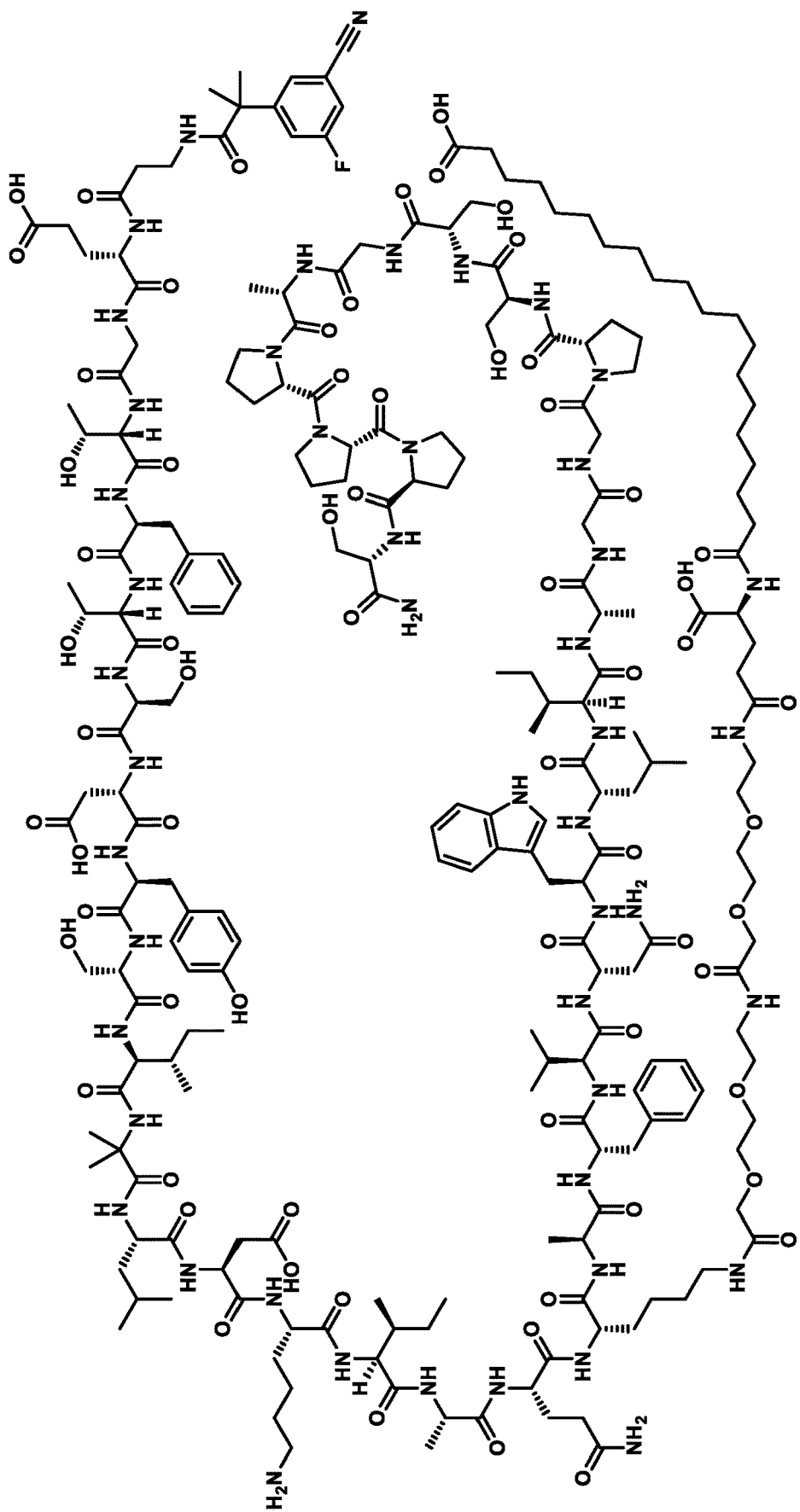
Compound 182
FIG. 1 - Cont'd

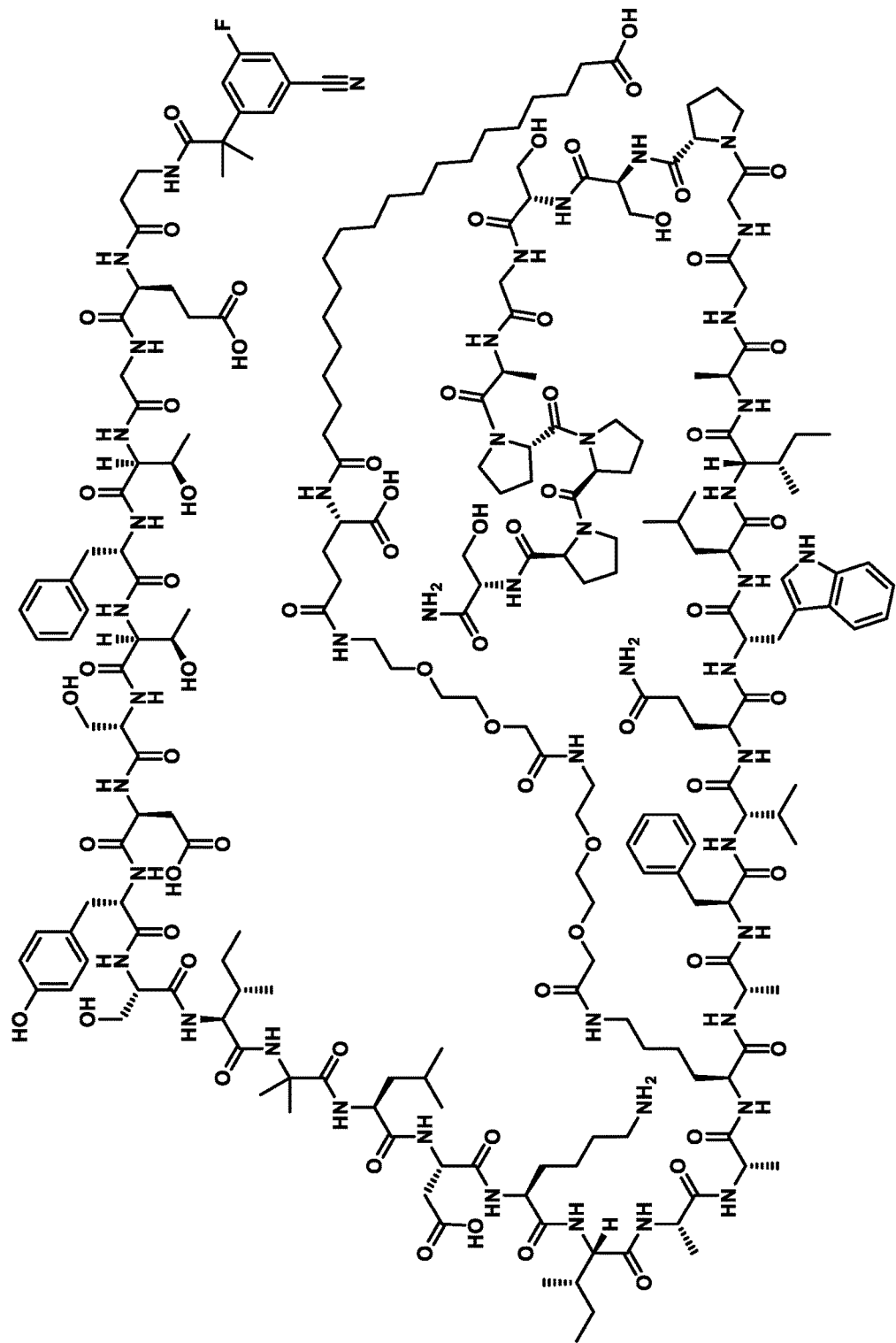
Compound 183
FIG. 1 - Cont'd

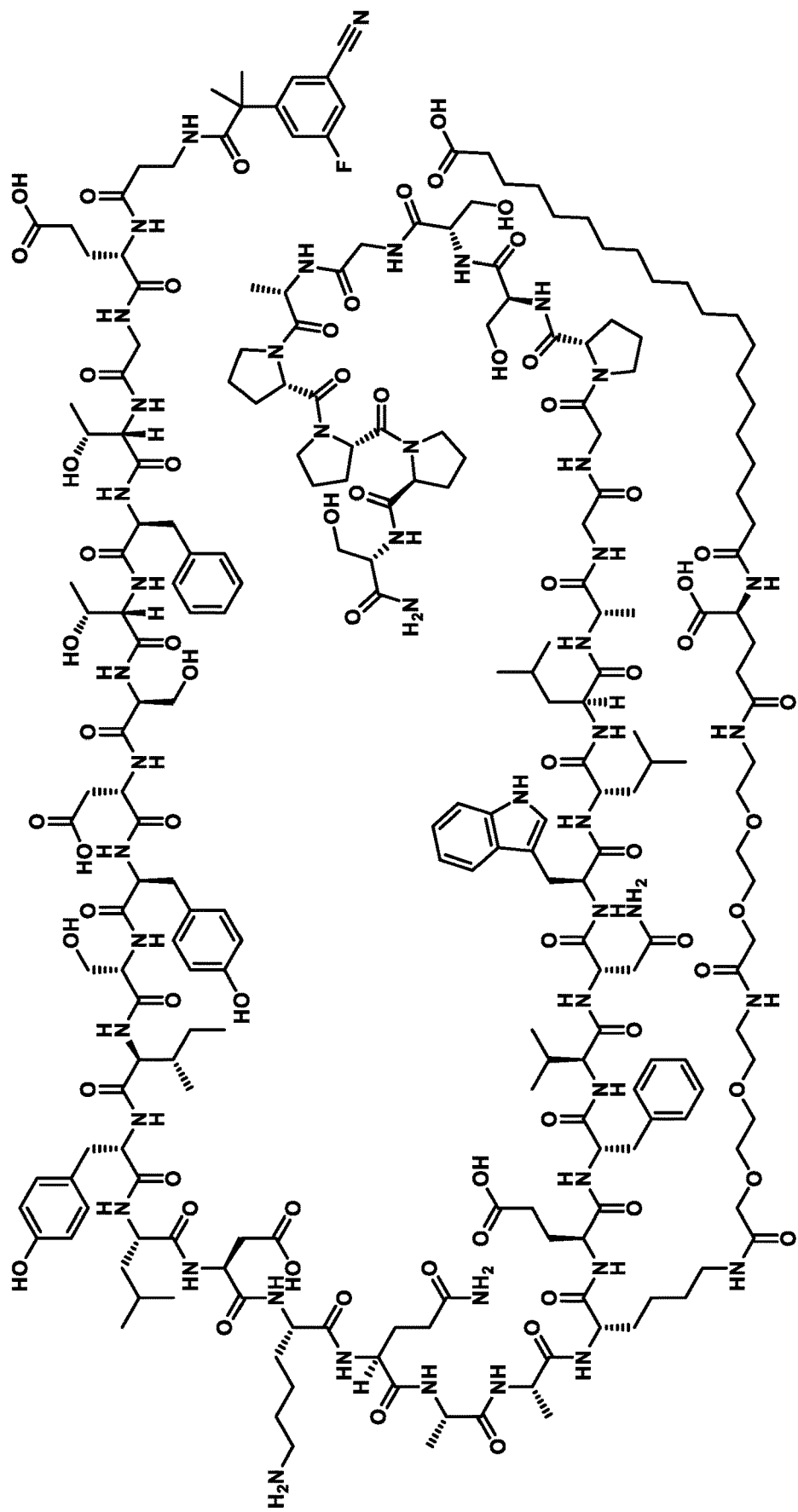
Compound 184
FIG. 1 - Cont'd

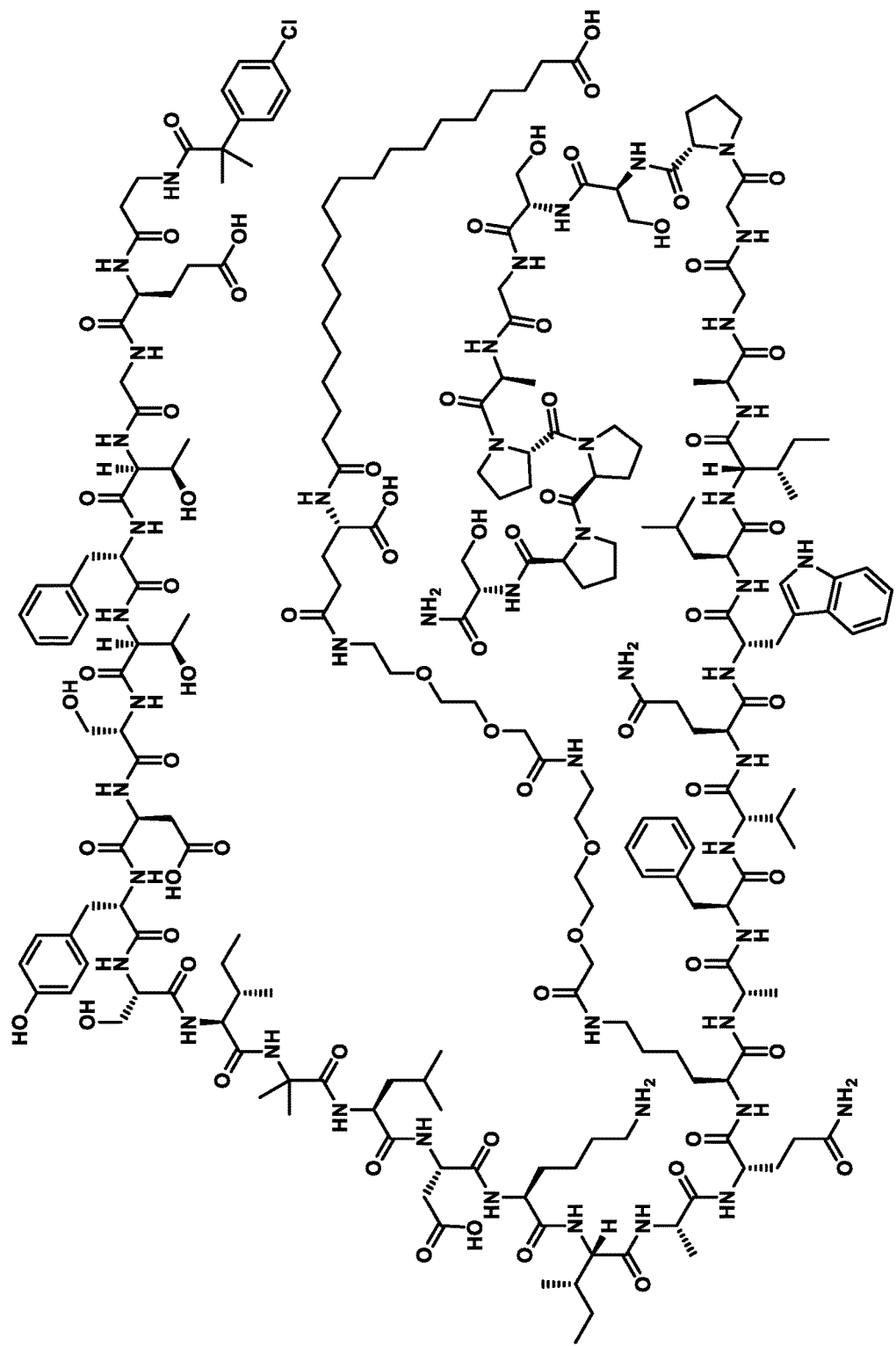
Compound 185
FIG. 1 - Cont'd

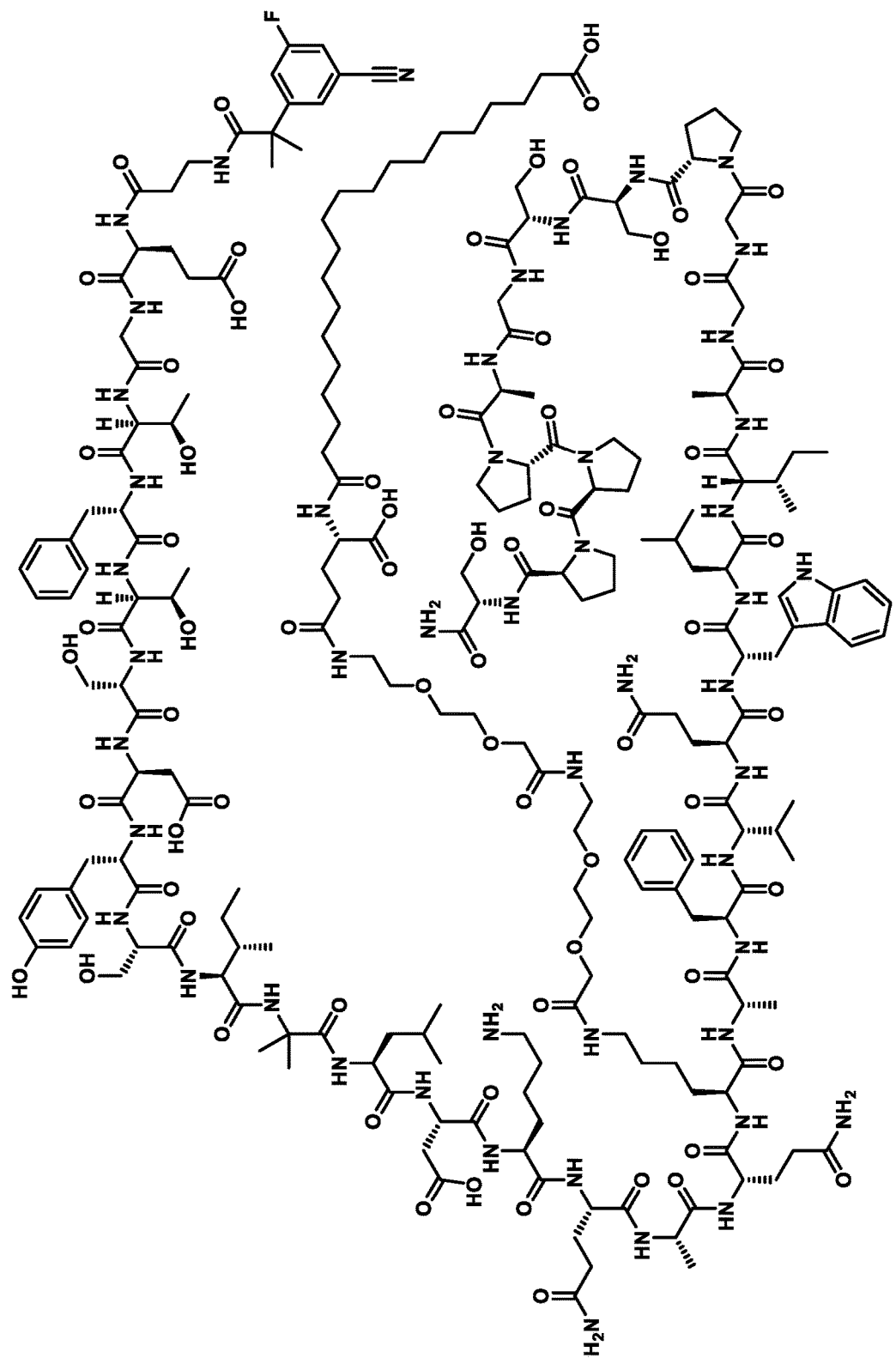
Compound 186
FIG. 1 - Cont'd

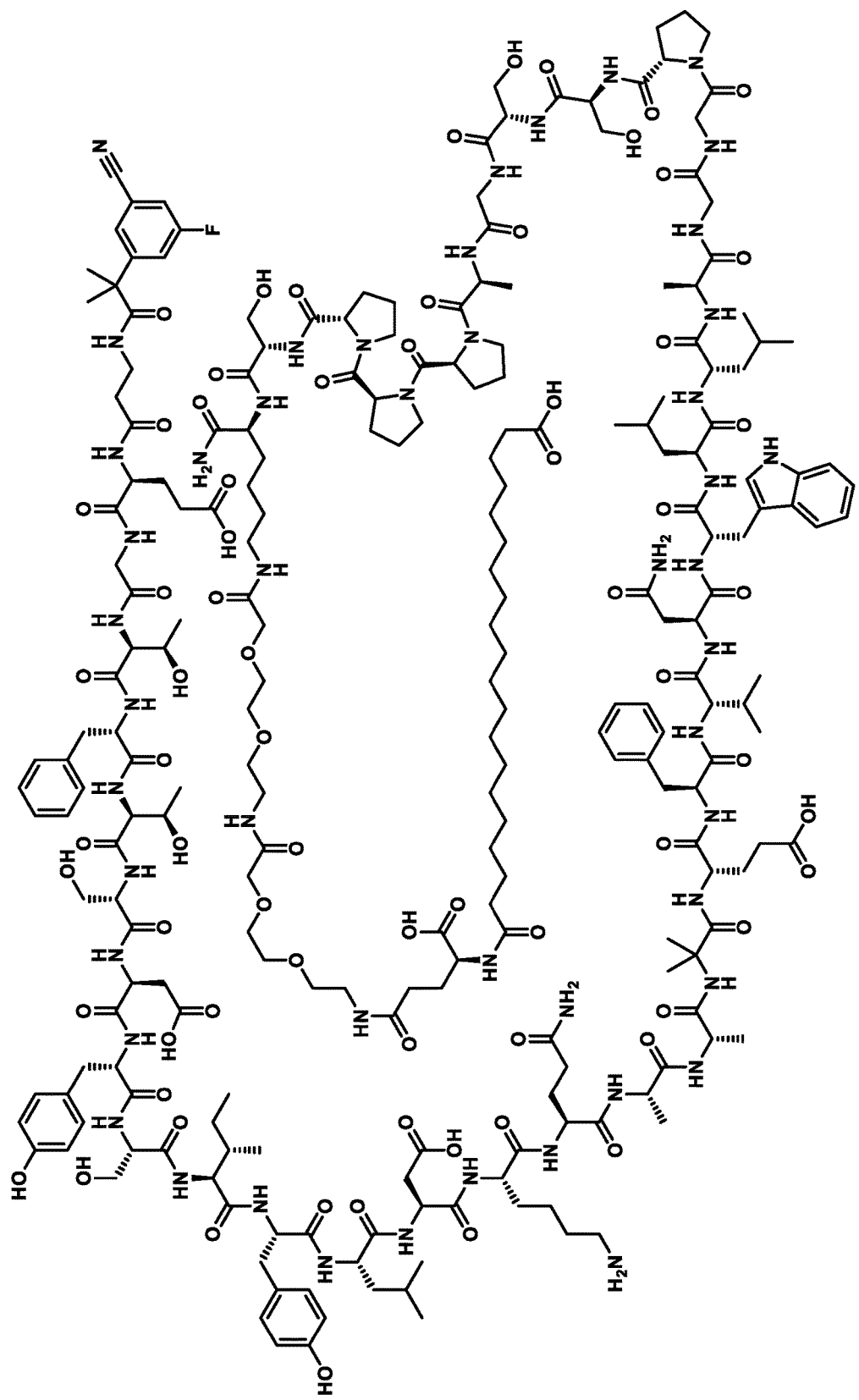
Compound 187
FIG. 1 - Cont'd

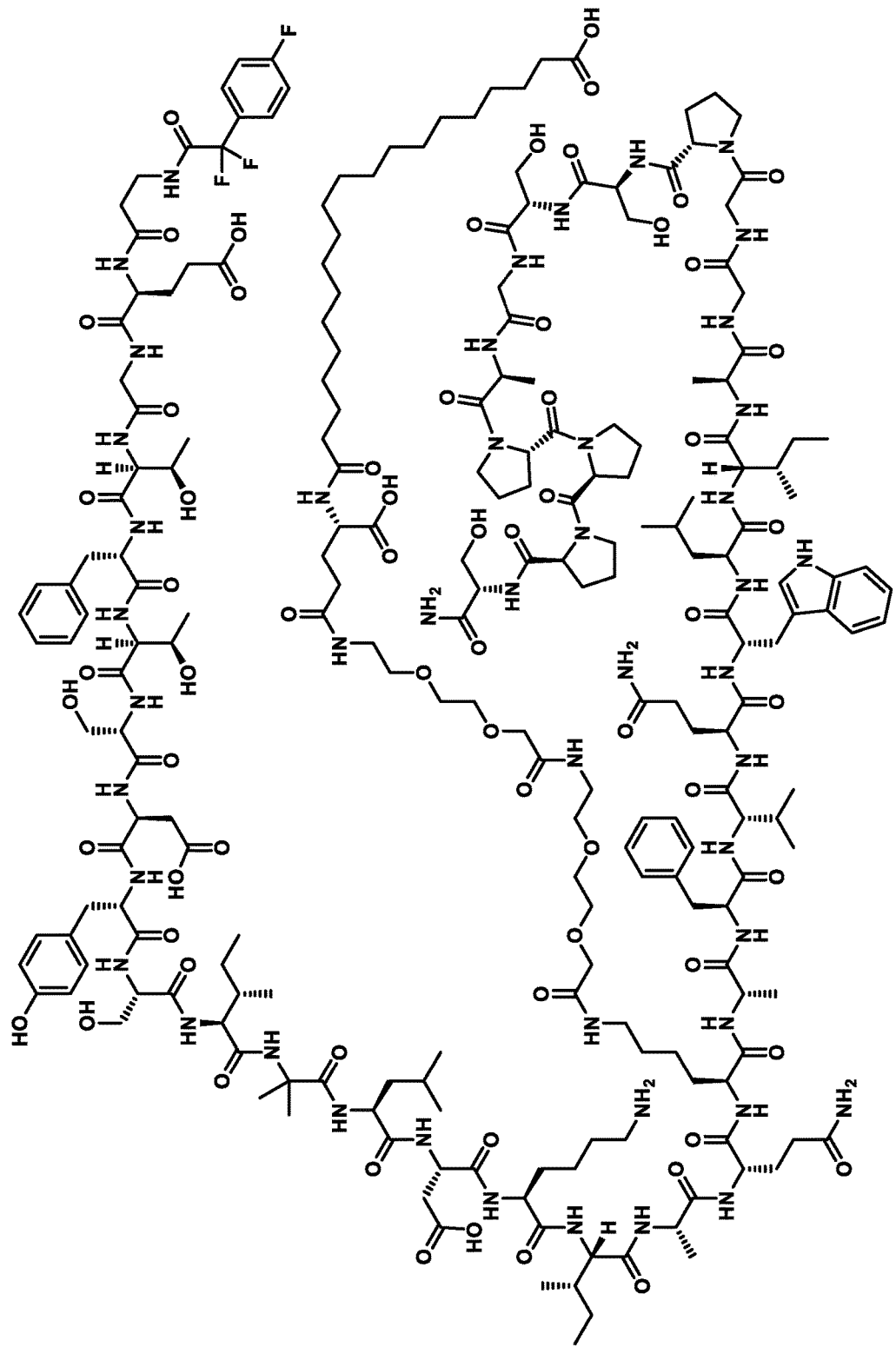
Compound 188
FIG. 1 - Cont'd

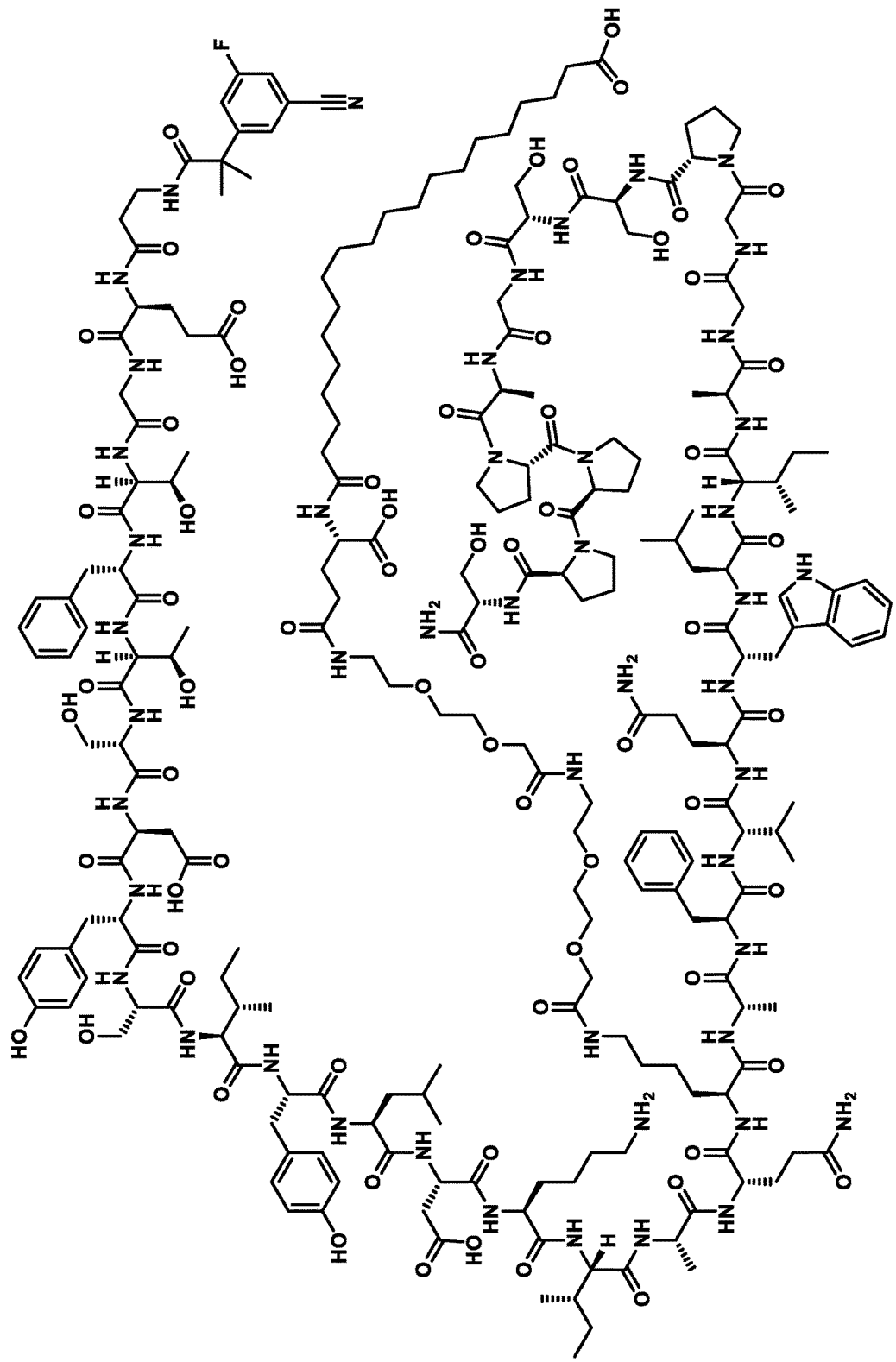
Compound 189
FIG. 1 - Cont'd

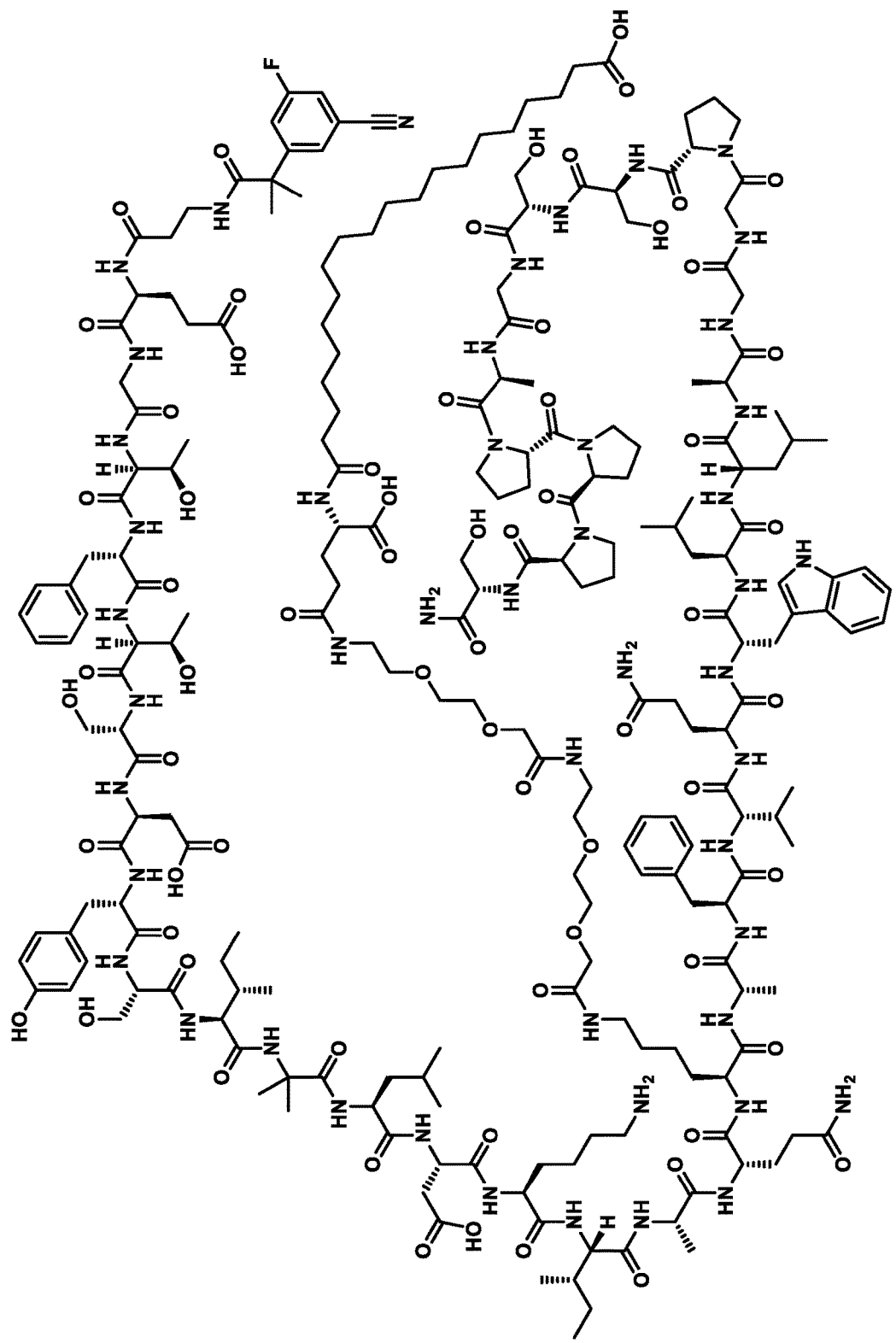
FIG. 1 - Cont'd
Compound 190

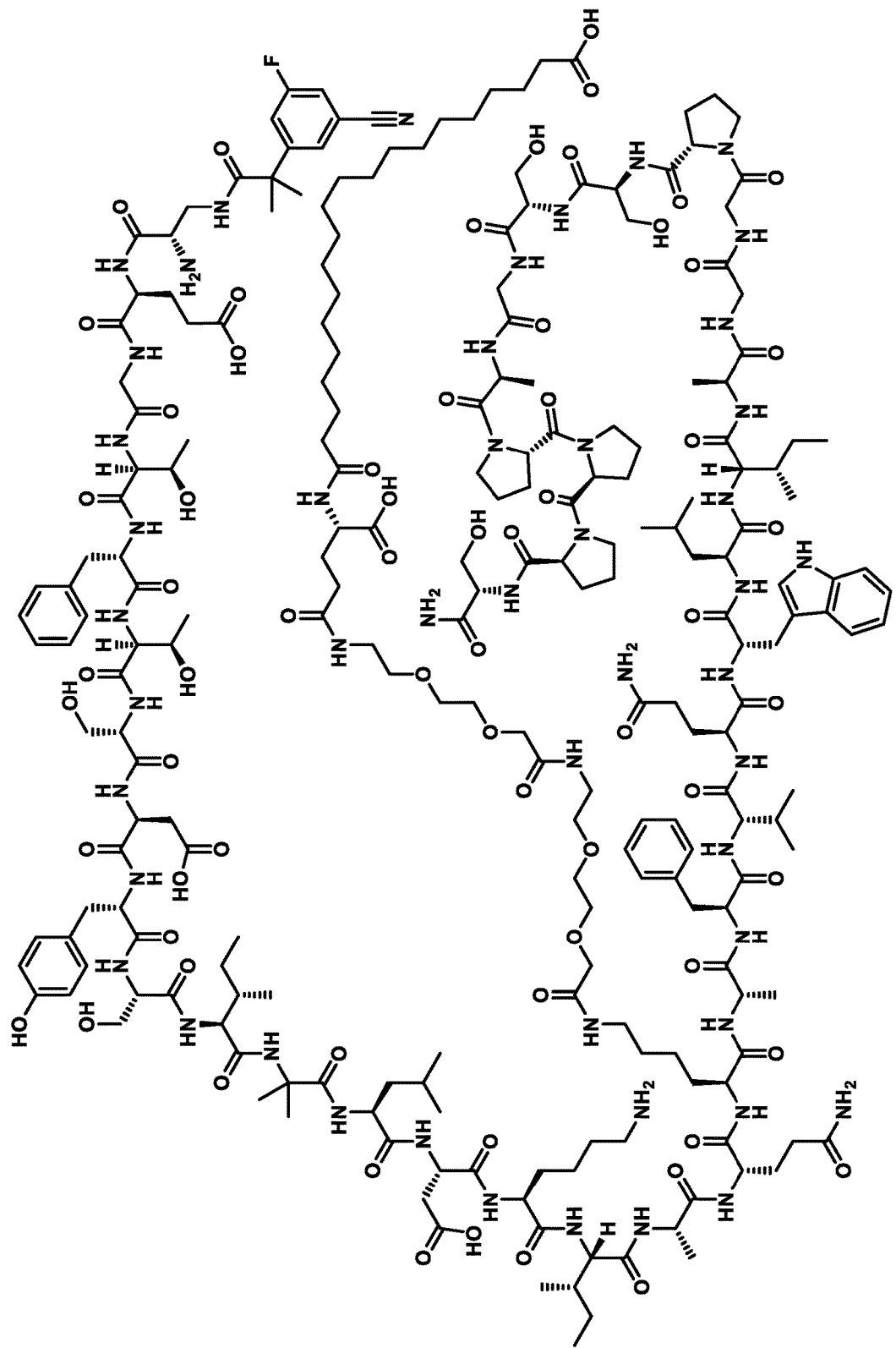
Compound 191
FIG. 1 - Cont'd

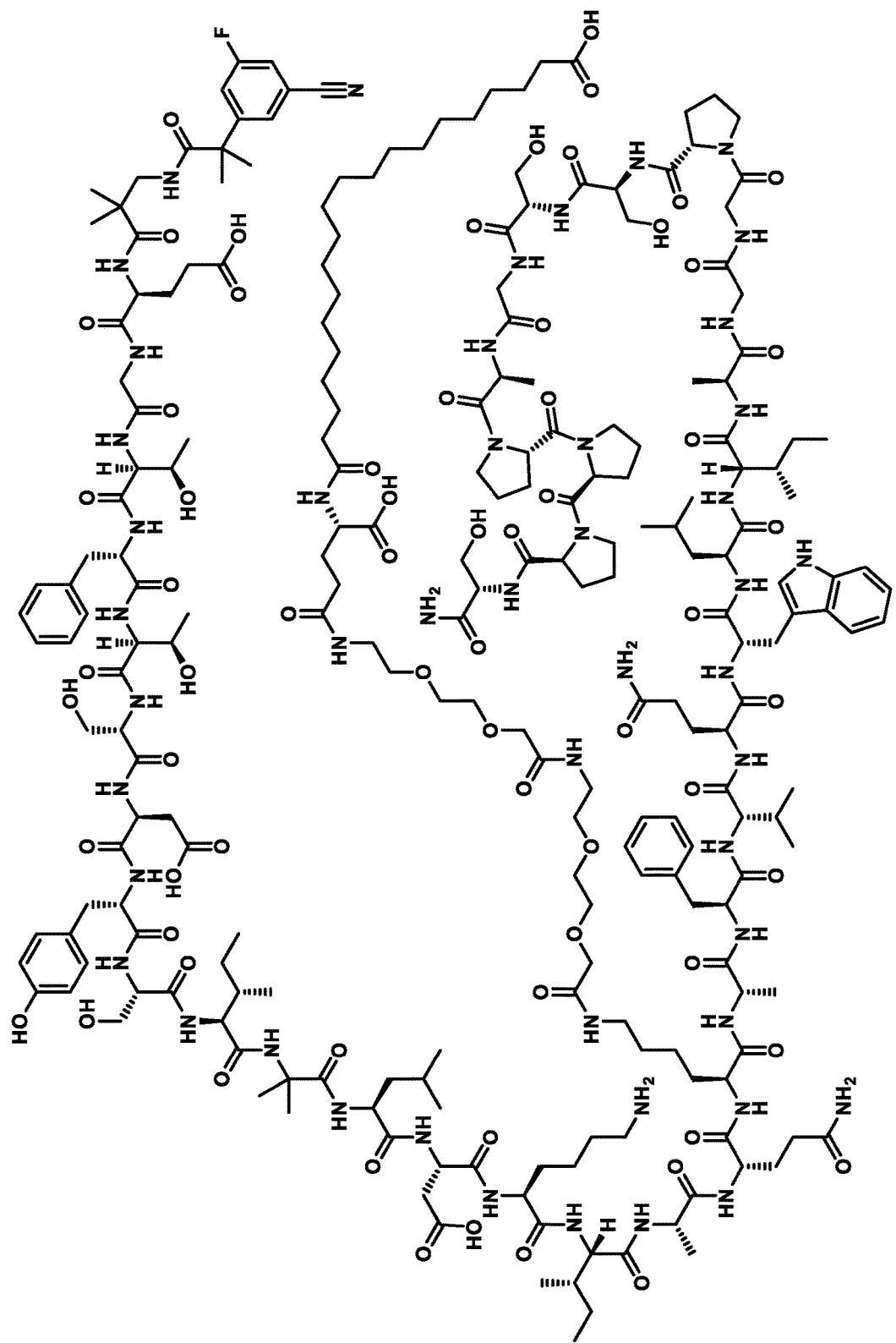
Compound 192
FIG. 1 - Cont'd

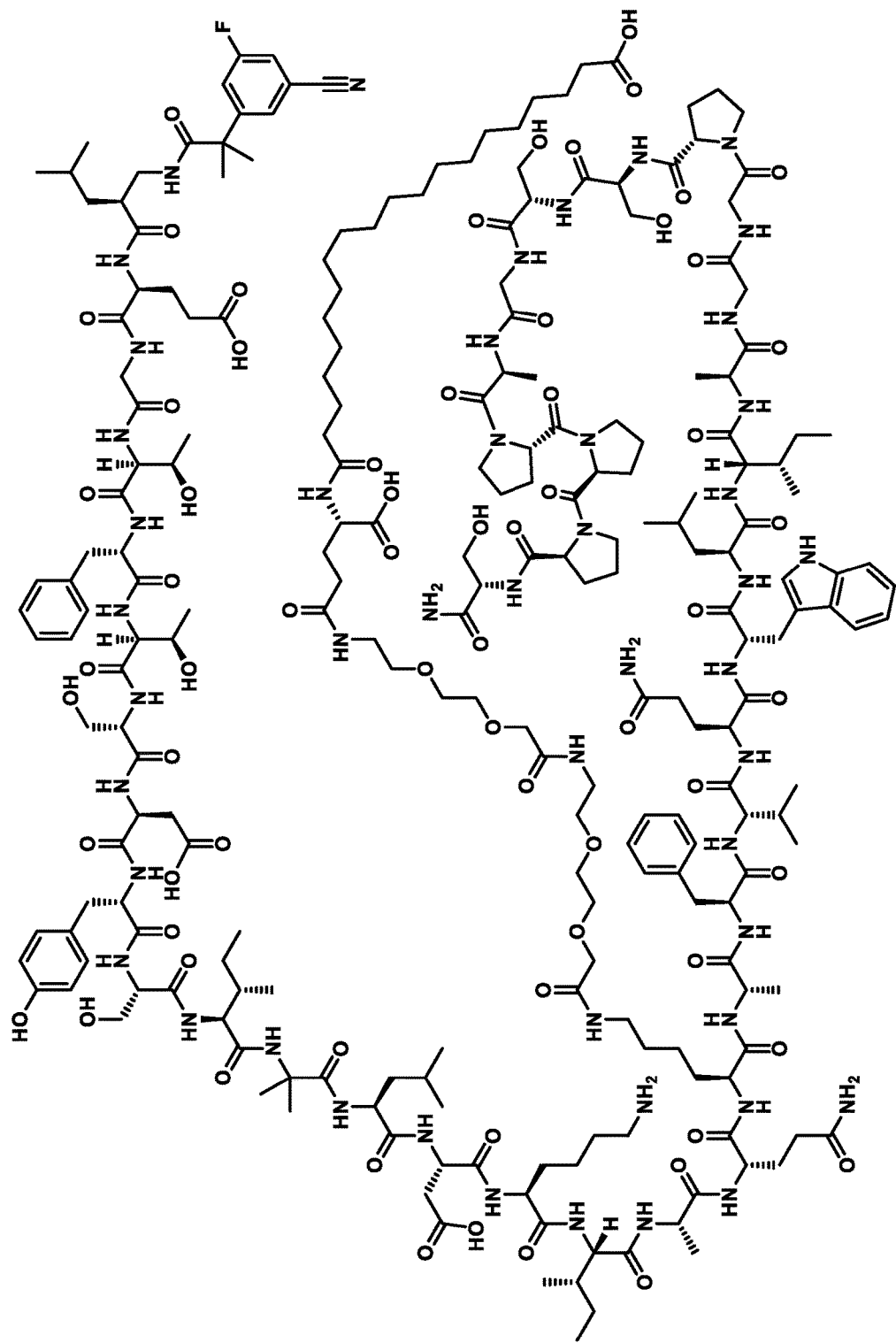
Compound 193
FIG. 1 - Cont'd

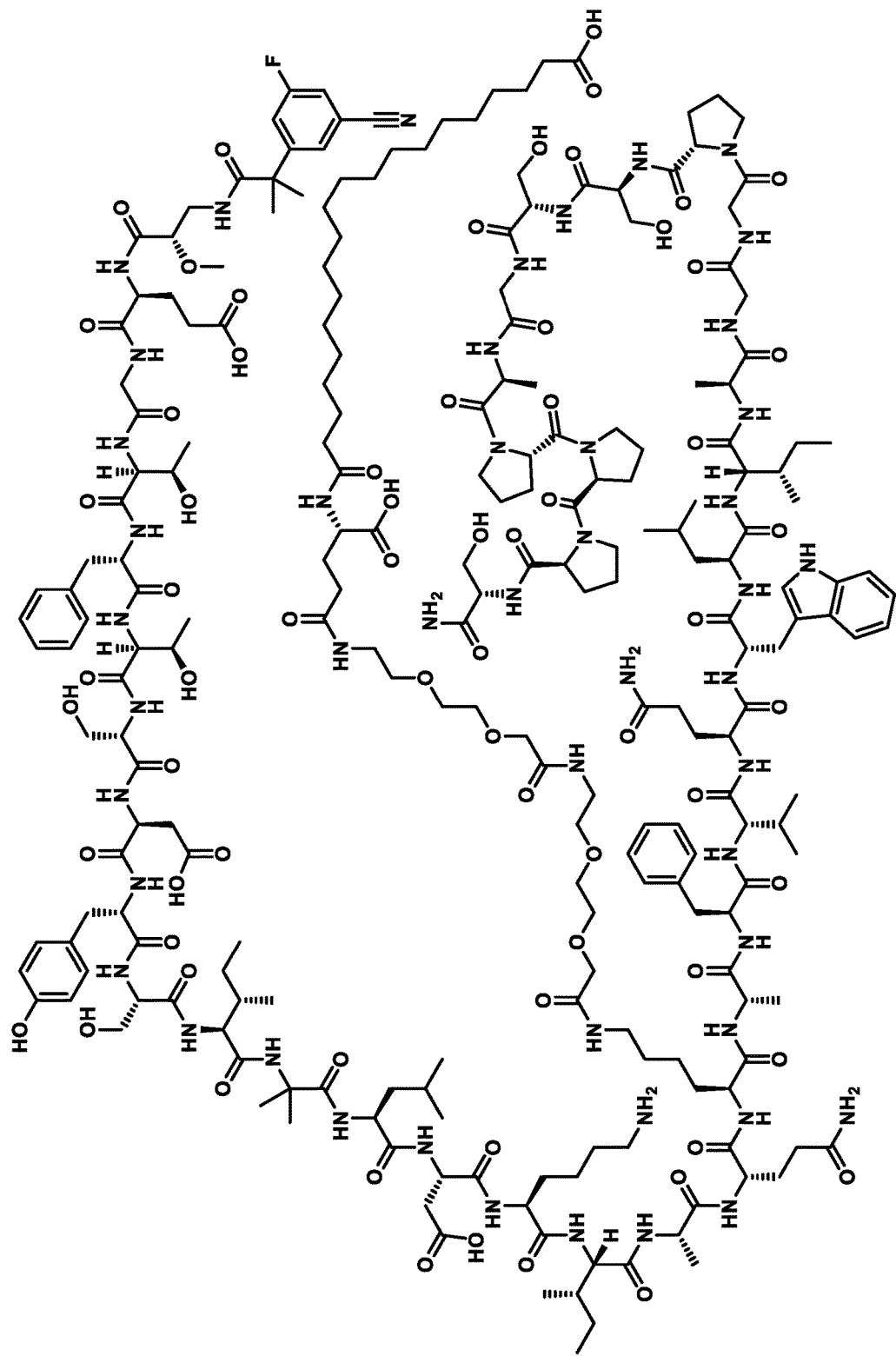
Compound 194
FIG. 1 - Cont'd

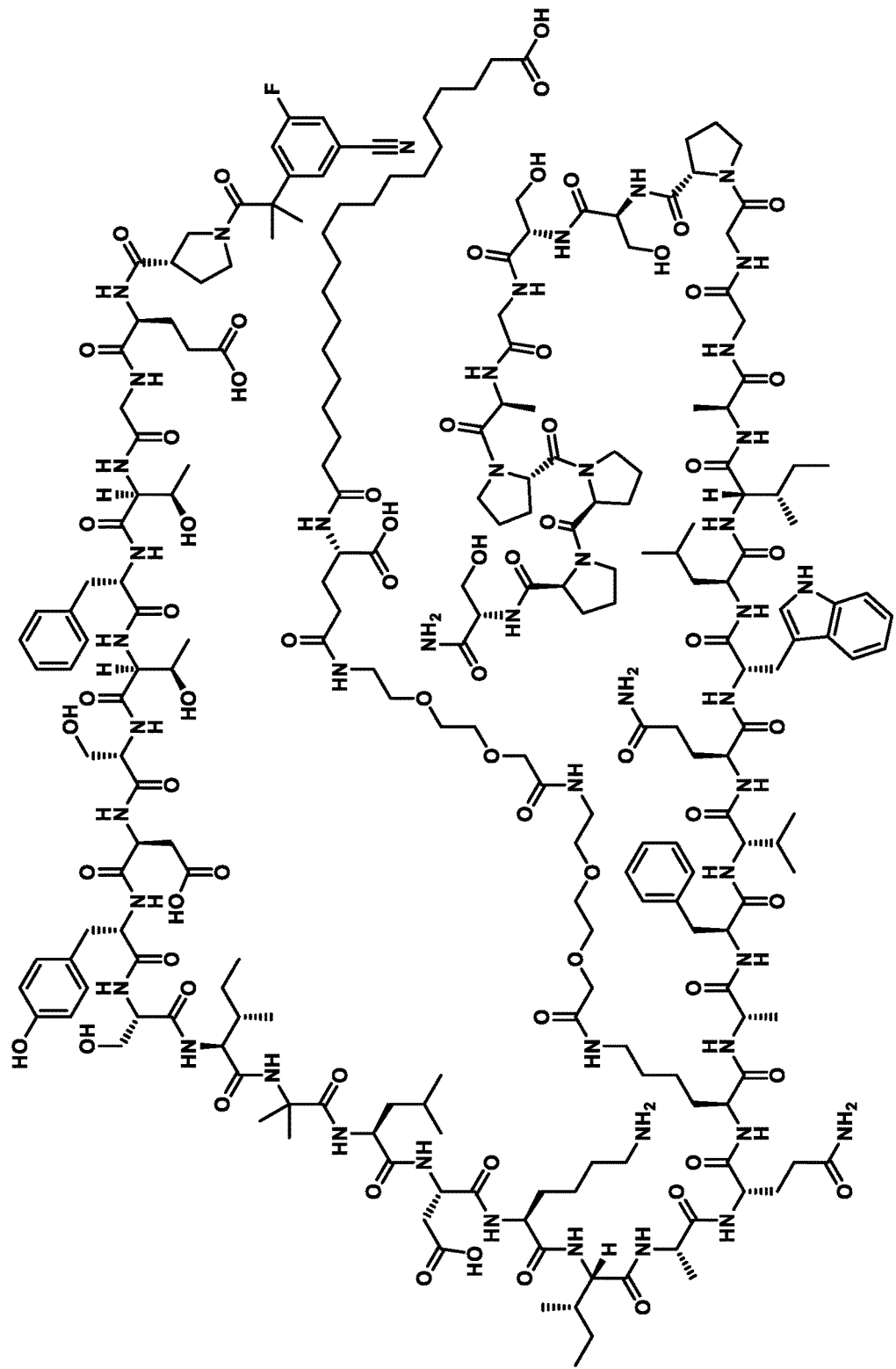
Compound 195
FIG. 1 - Cont'd

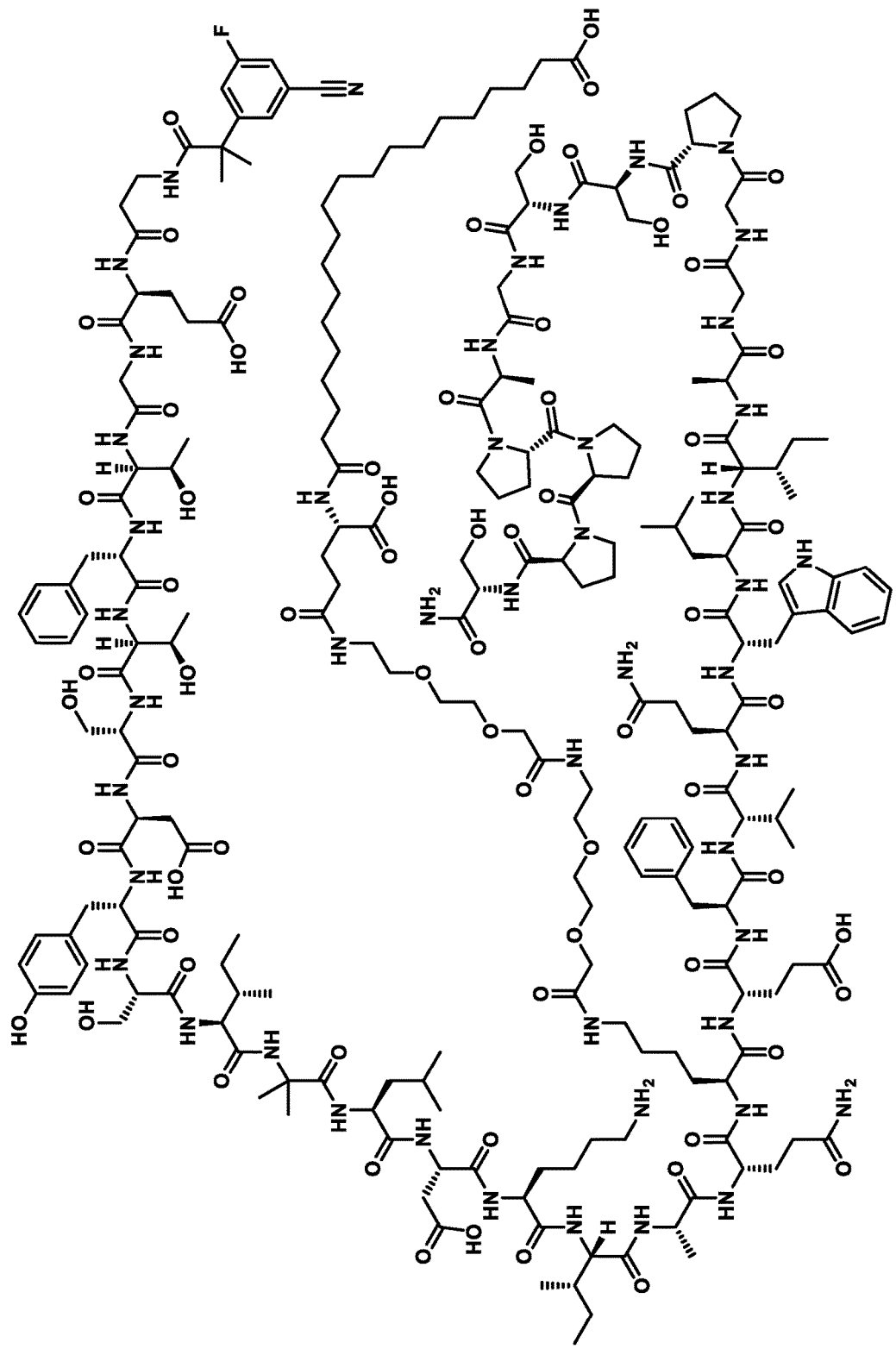
Compound 196
FIG. 1 - Cont'd

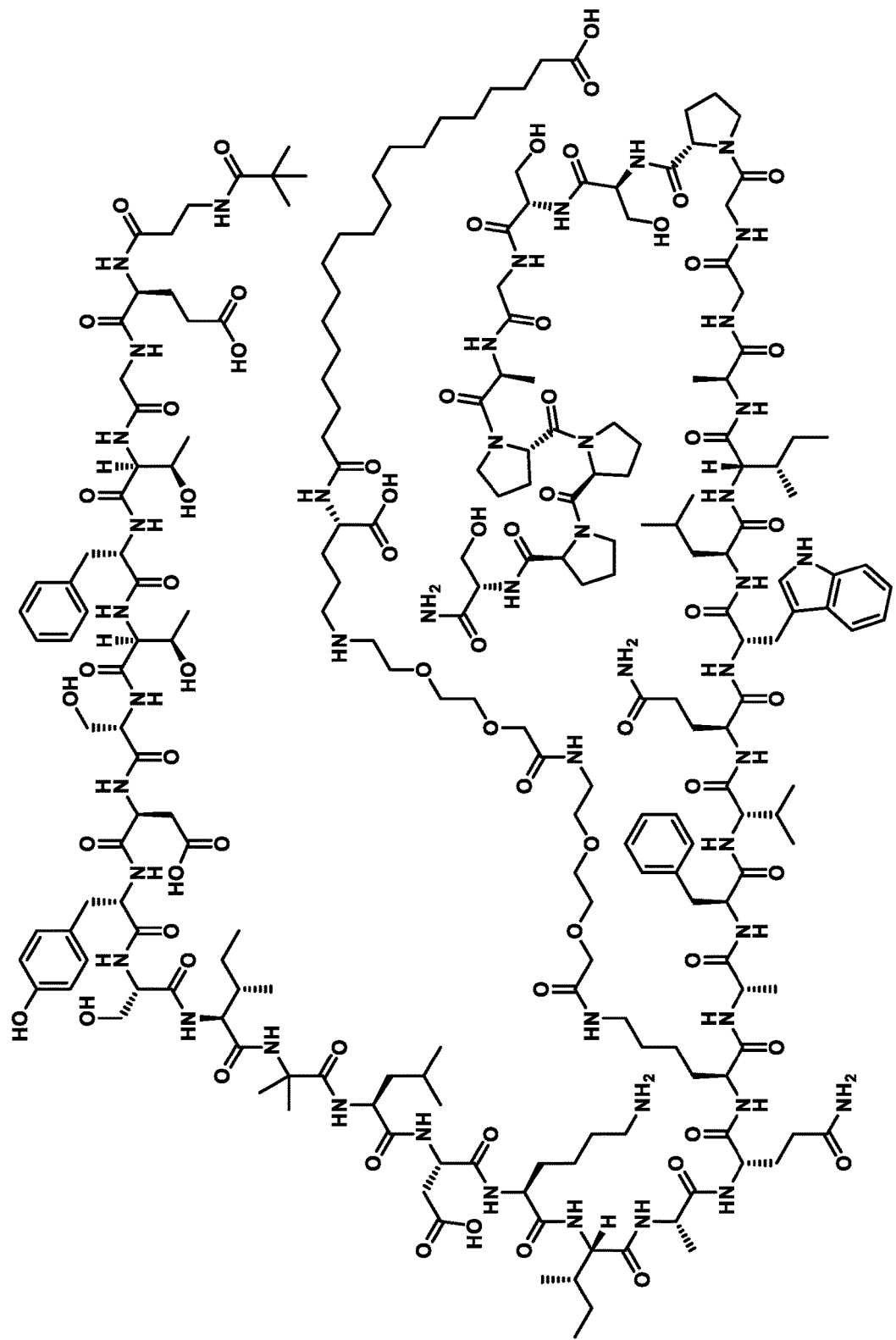
Compound 197
FIG. 1 - Cont'd

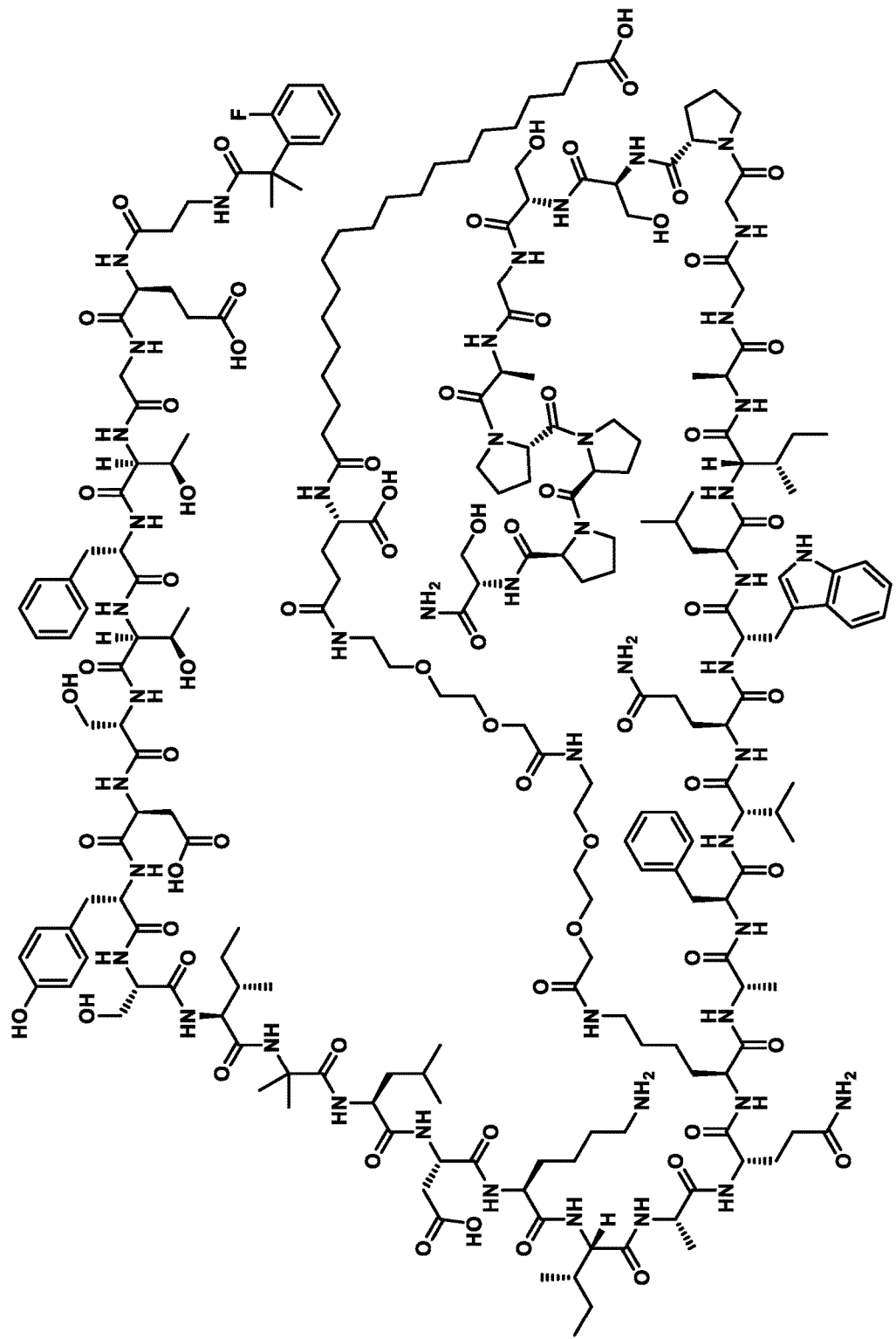
Compound 198
FIG. 1 - Cont'd

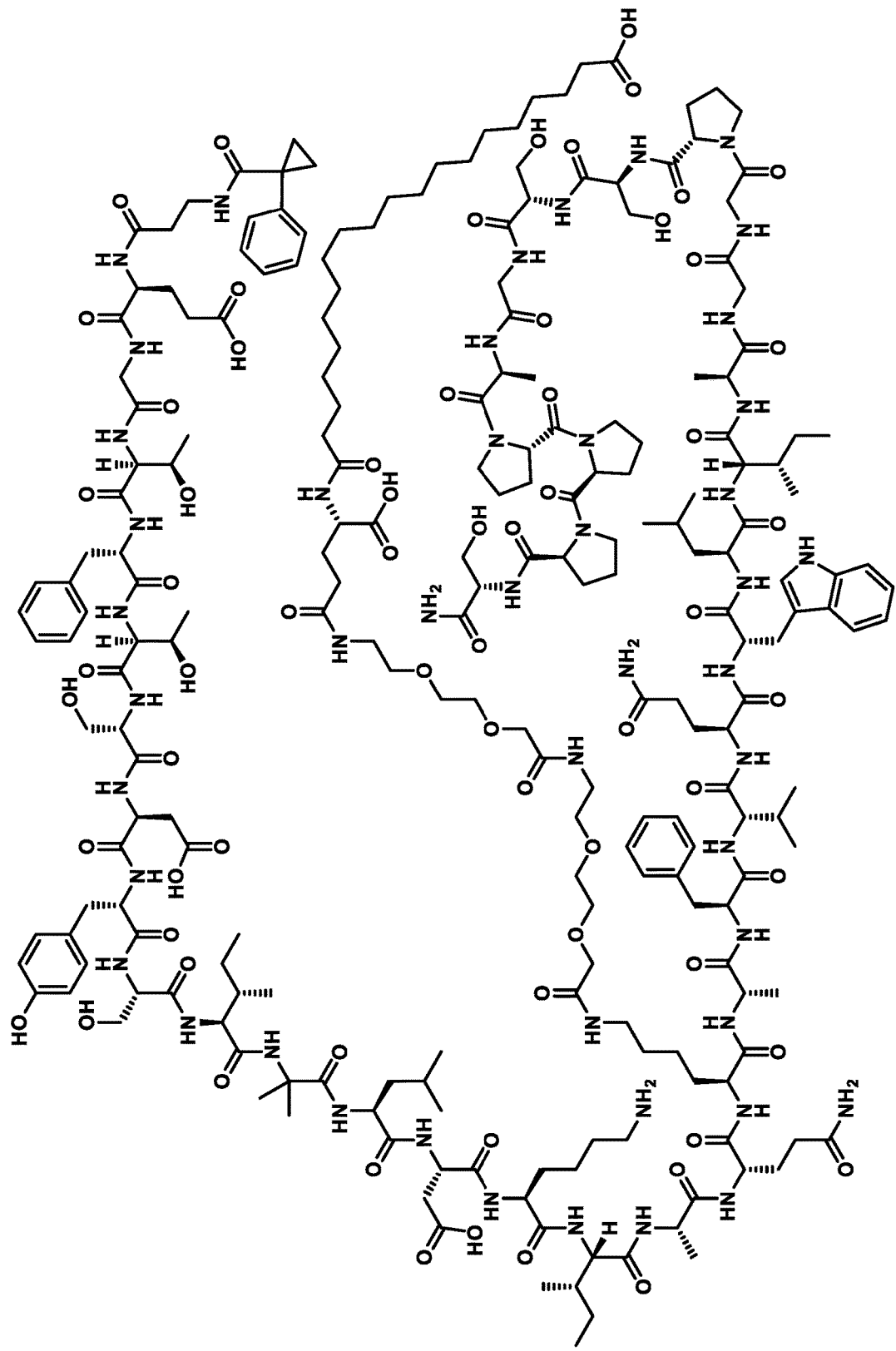
Compound 199
FIG. 1 - Cont'd

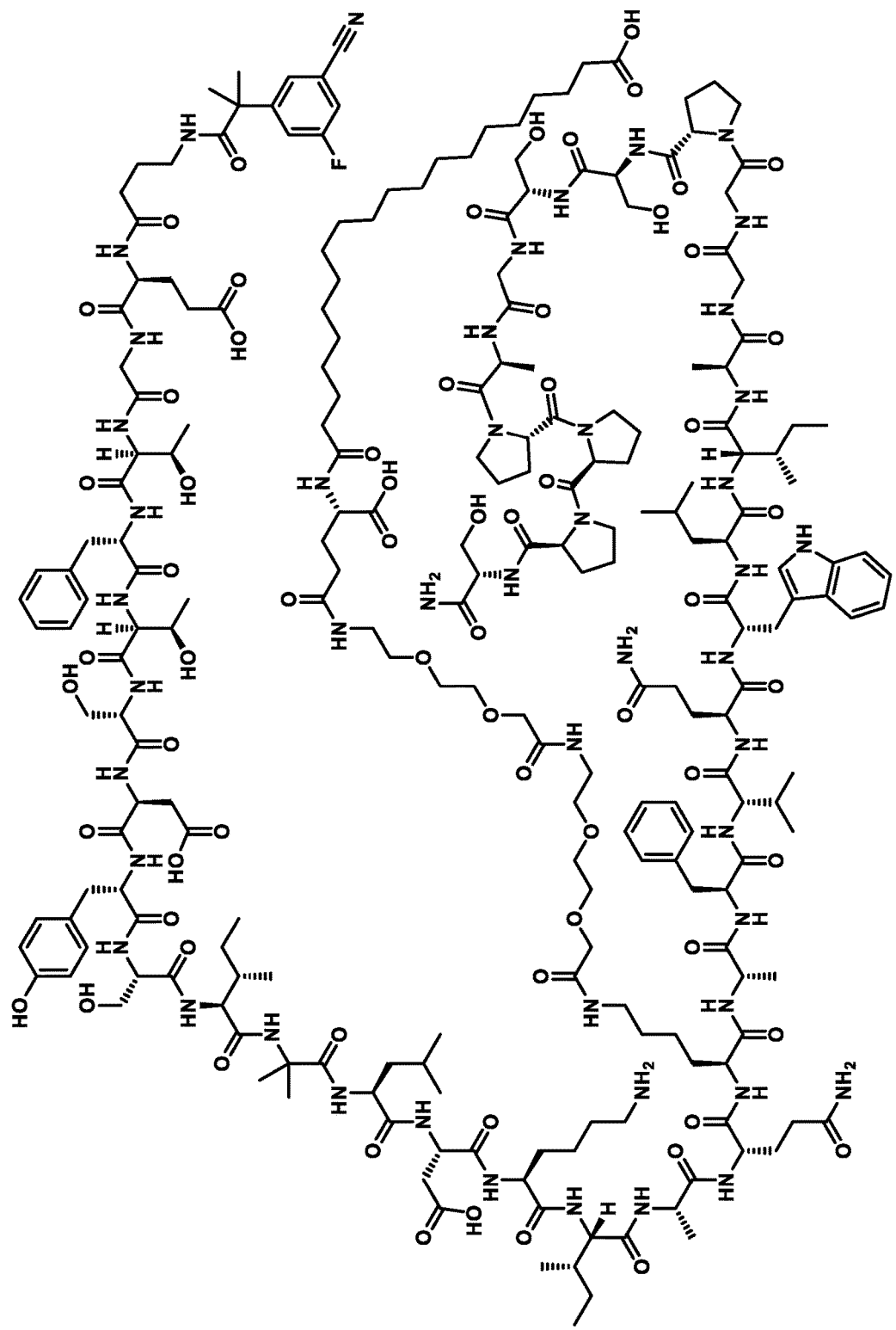
Compound 200
FIG. 1 - Cont'd

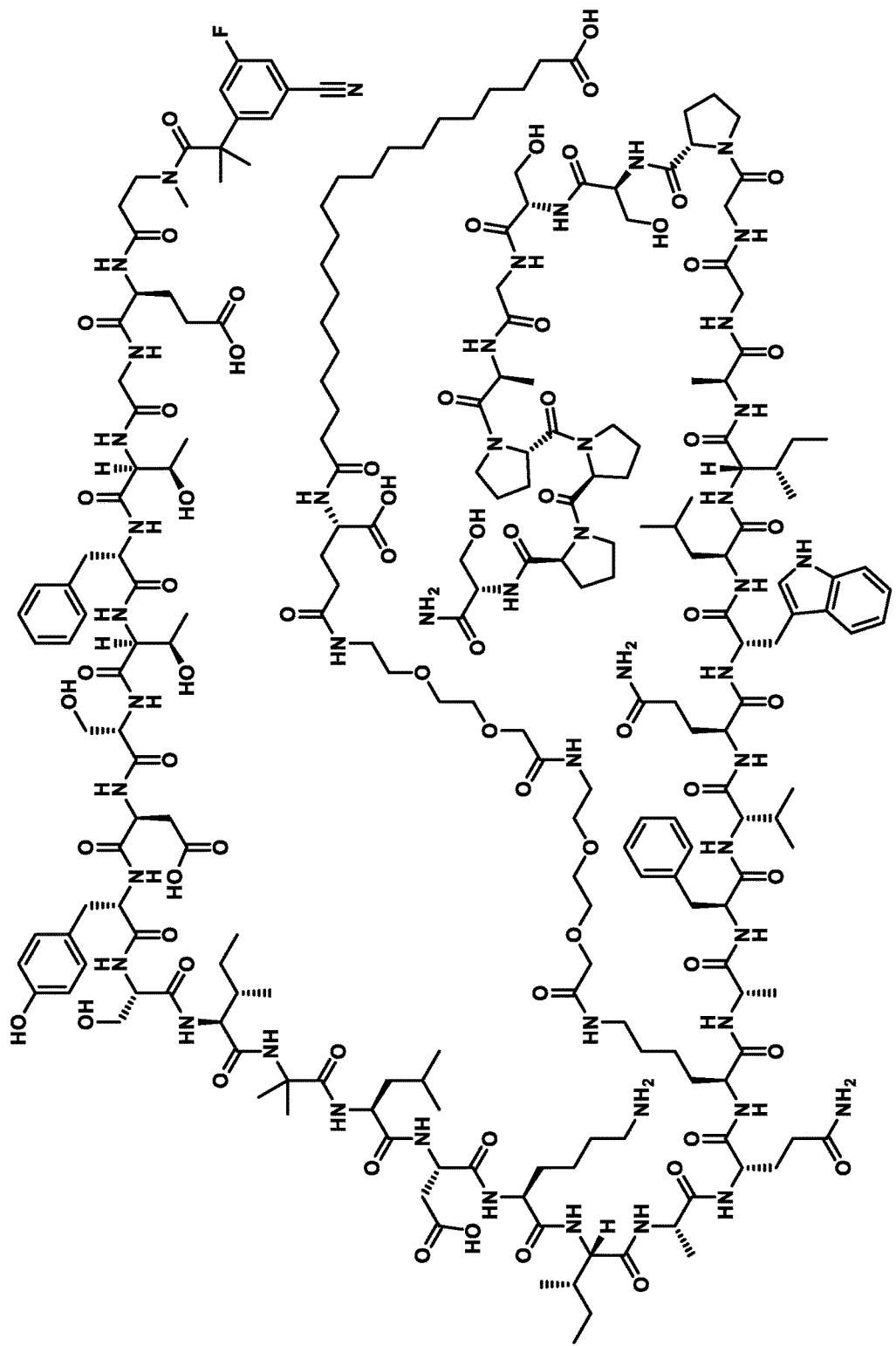
Compound 201
FIG. 1 - Cont'd

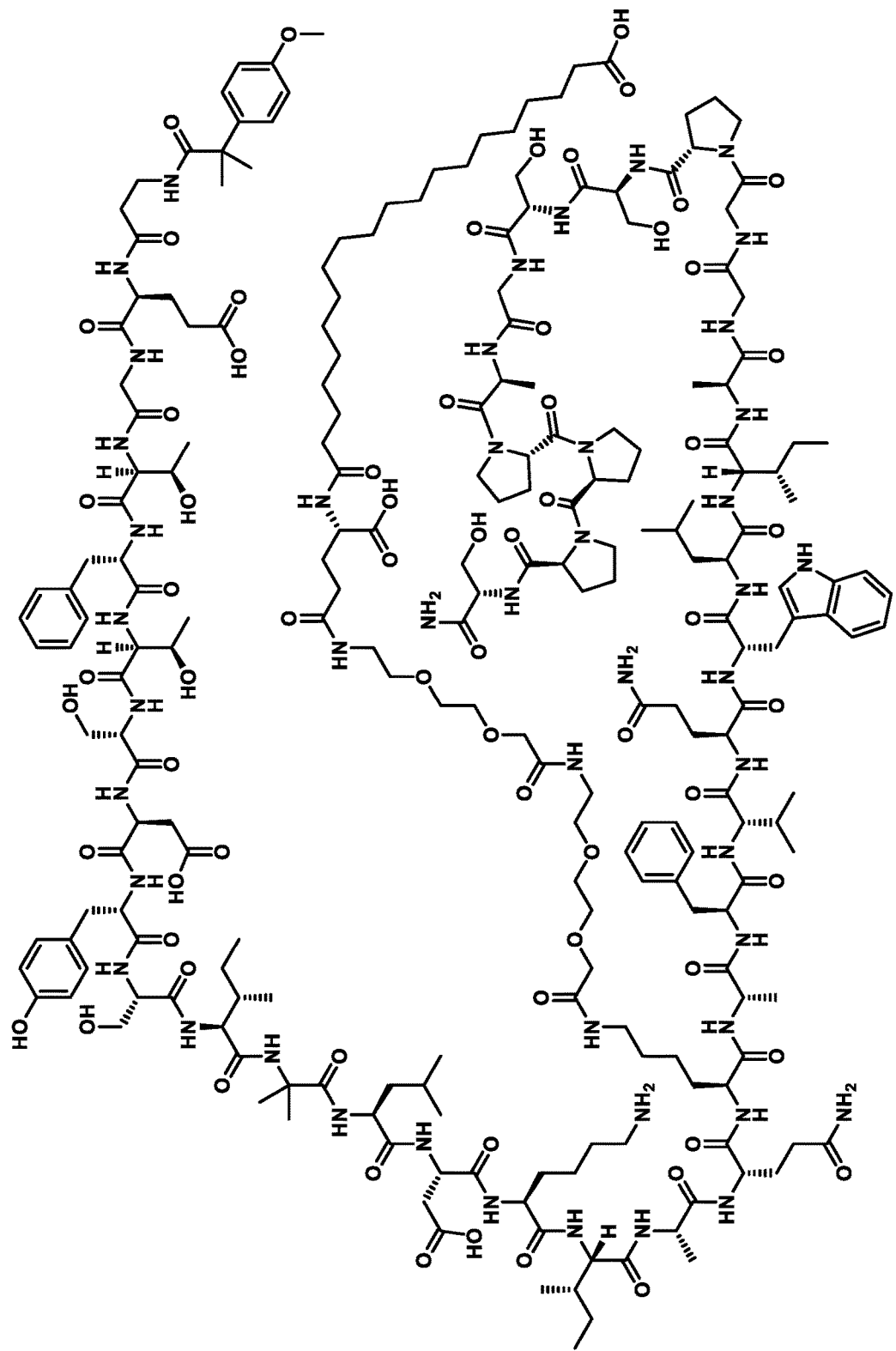
Compound 203
FIG. 1 - Cont'd

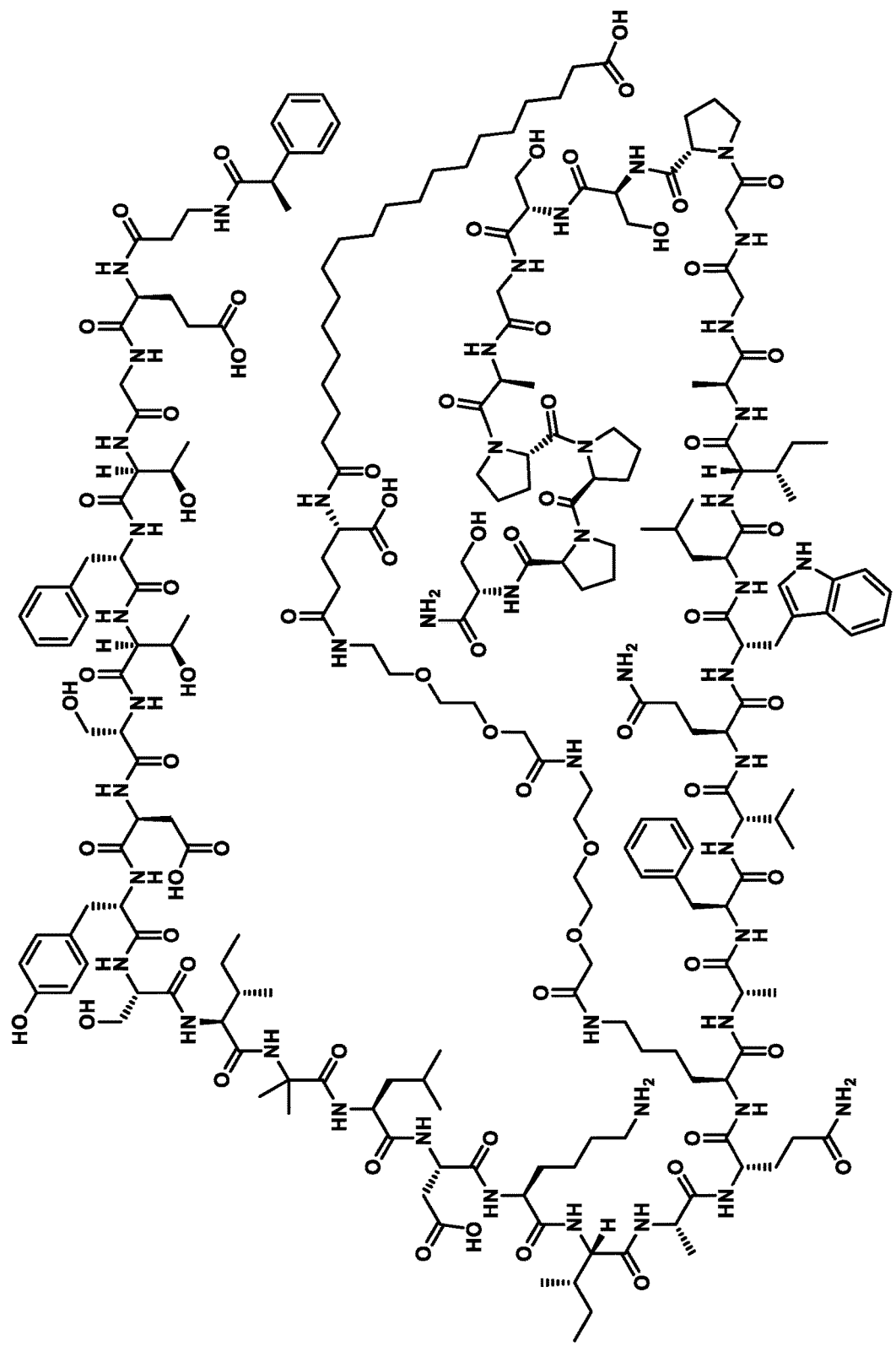
Compound 204
FIG. 1 - Cont'd

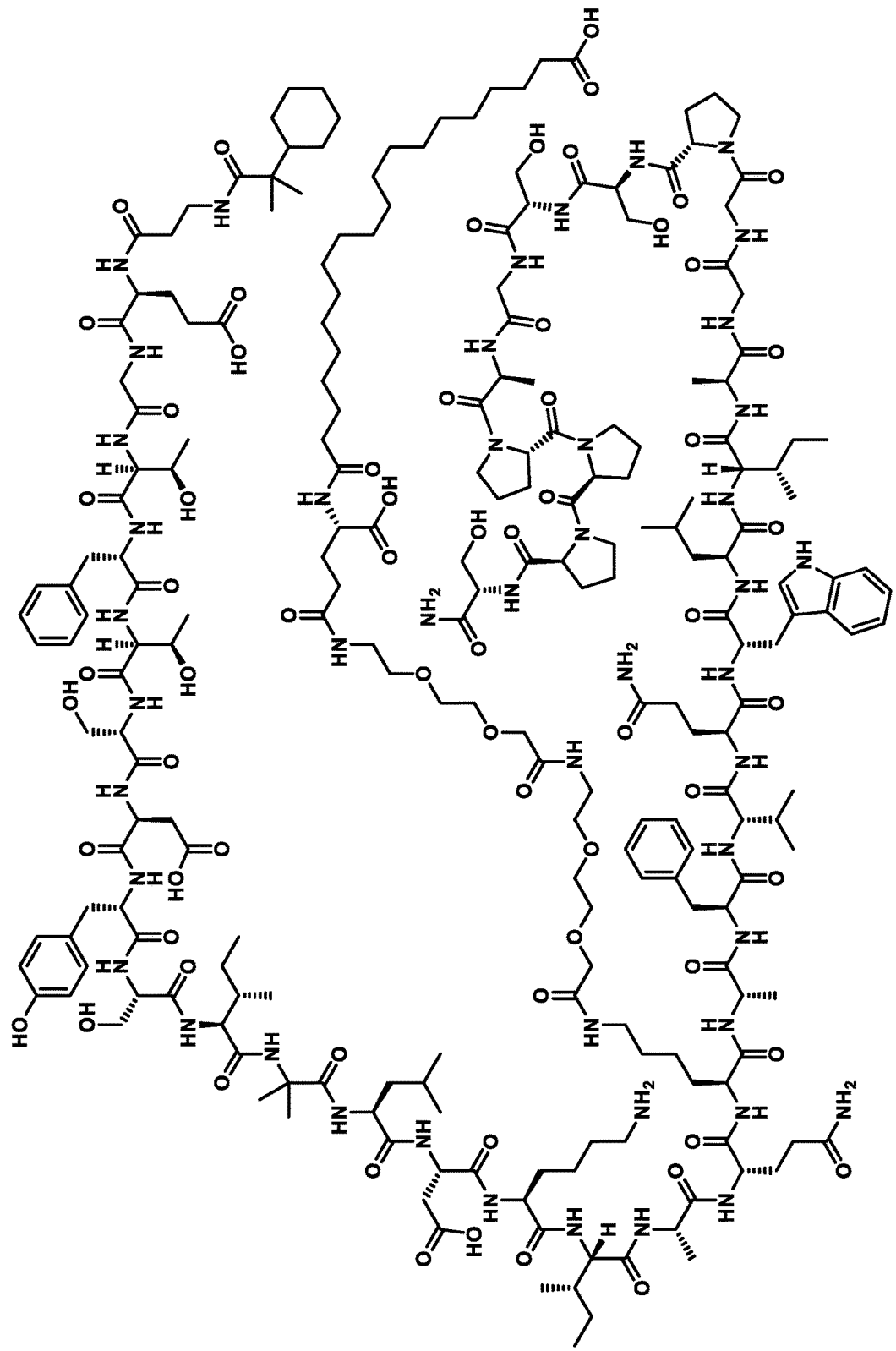
Compound 205
FIG. 1 - Cont'd

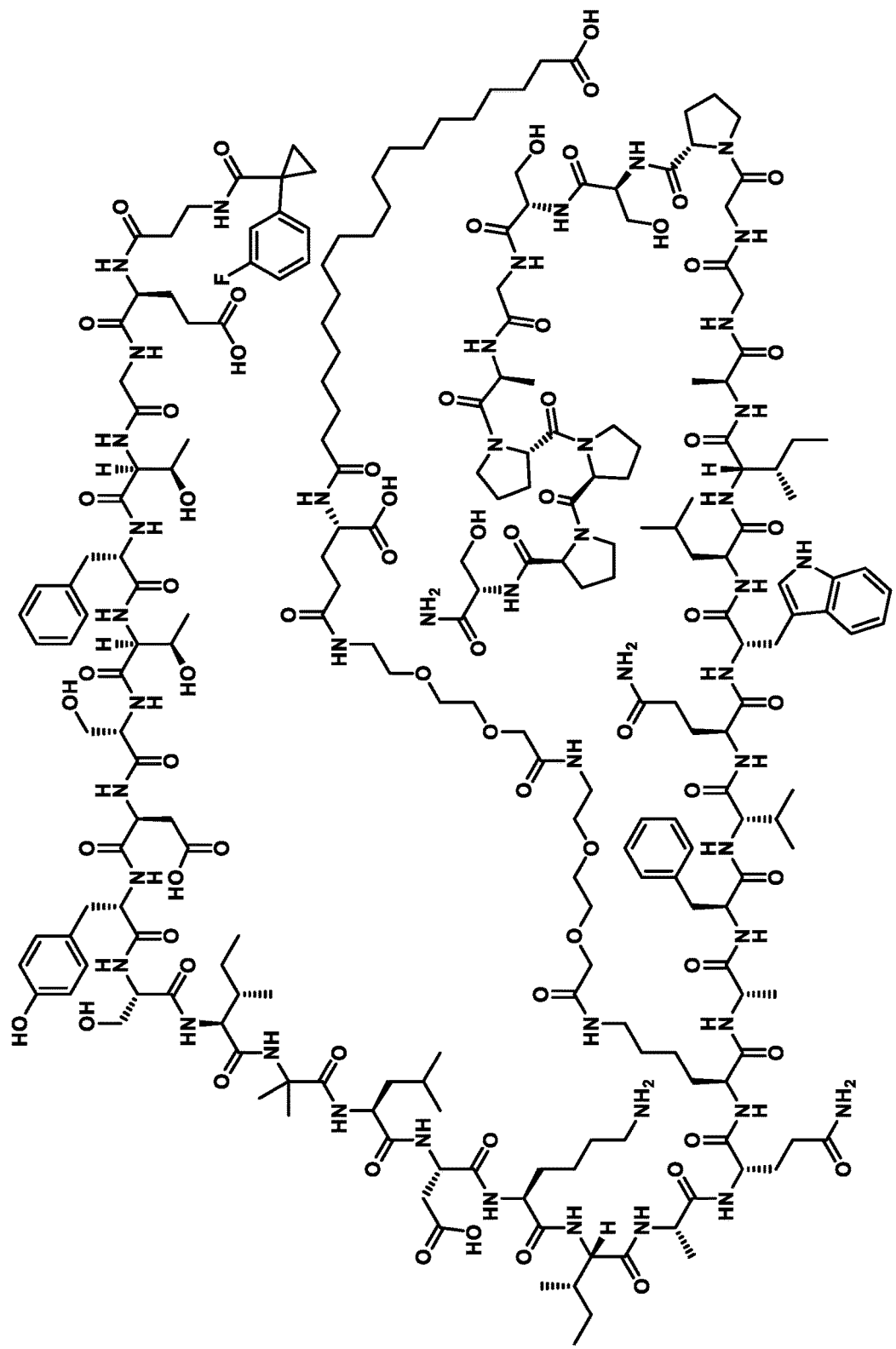
FIG. 1 - Cont'd
Compound 206

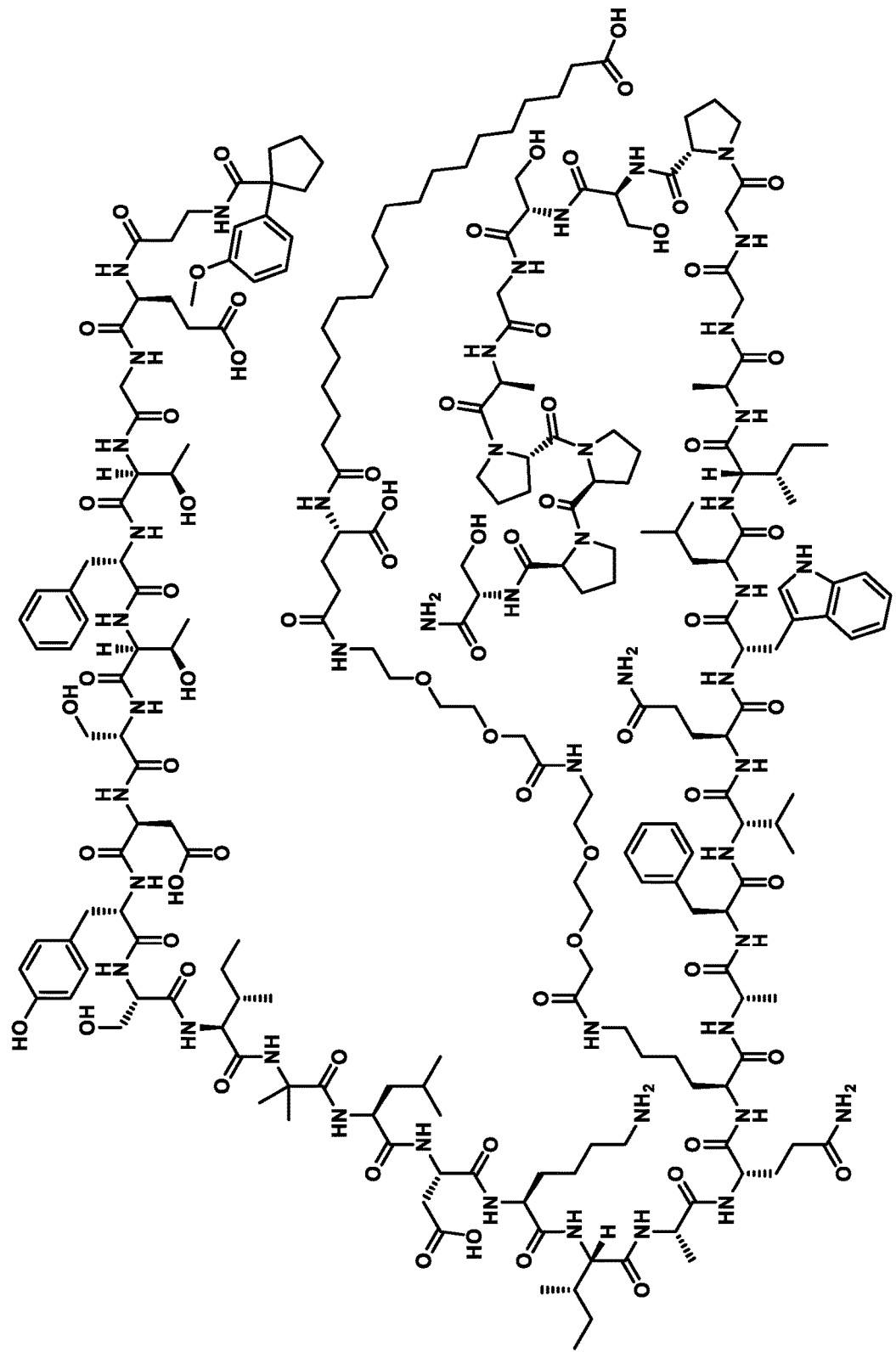
Compound 207
FIG. 1 - Cont'd

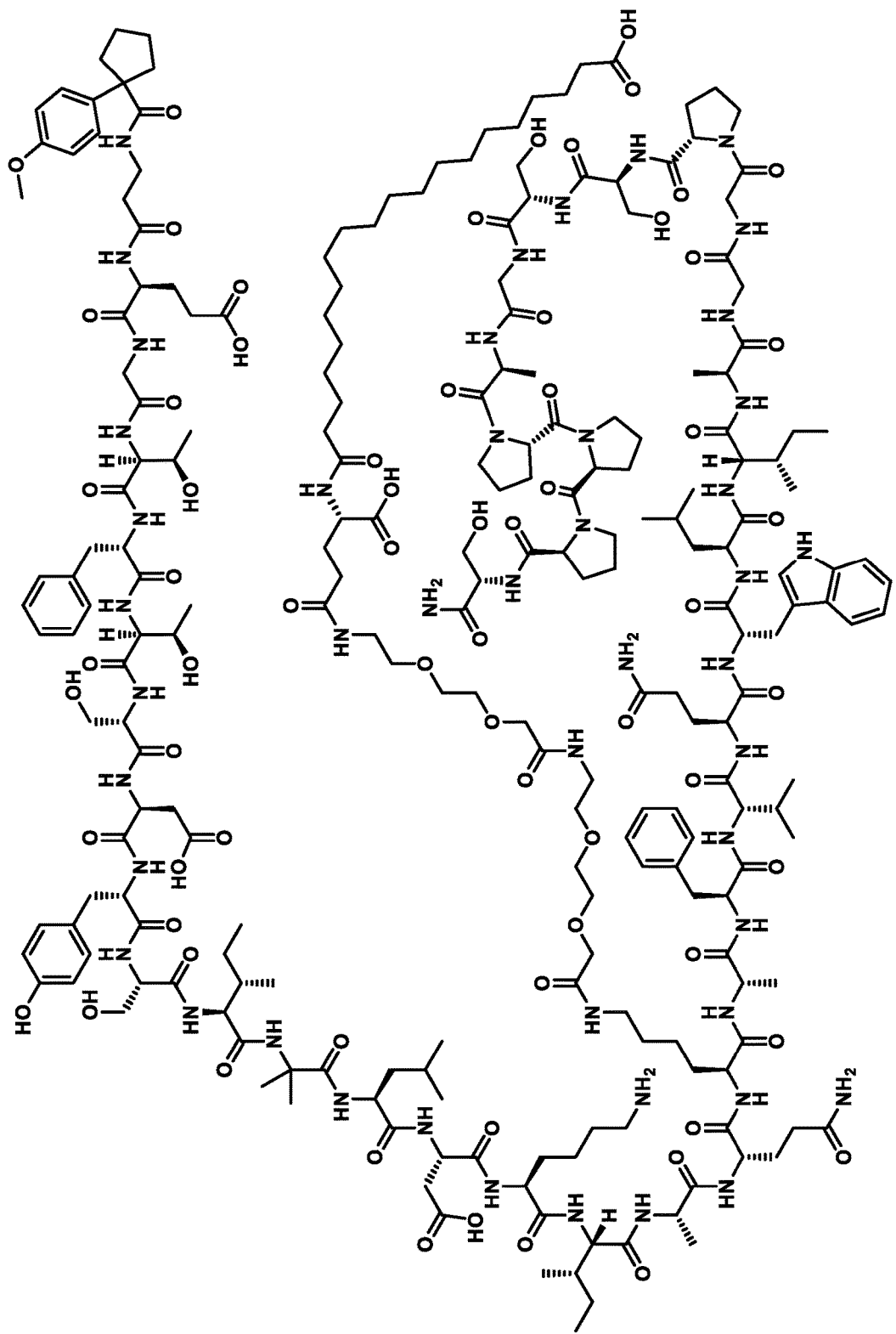
FIG. 1 - Cont'd
Compound 208

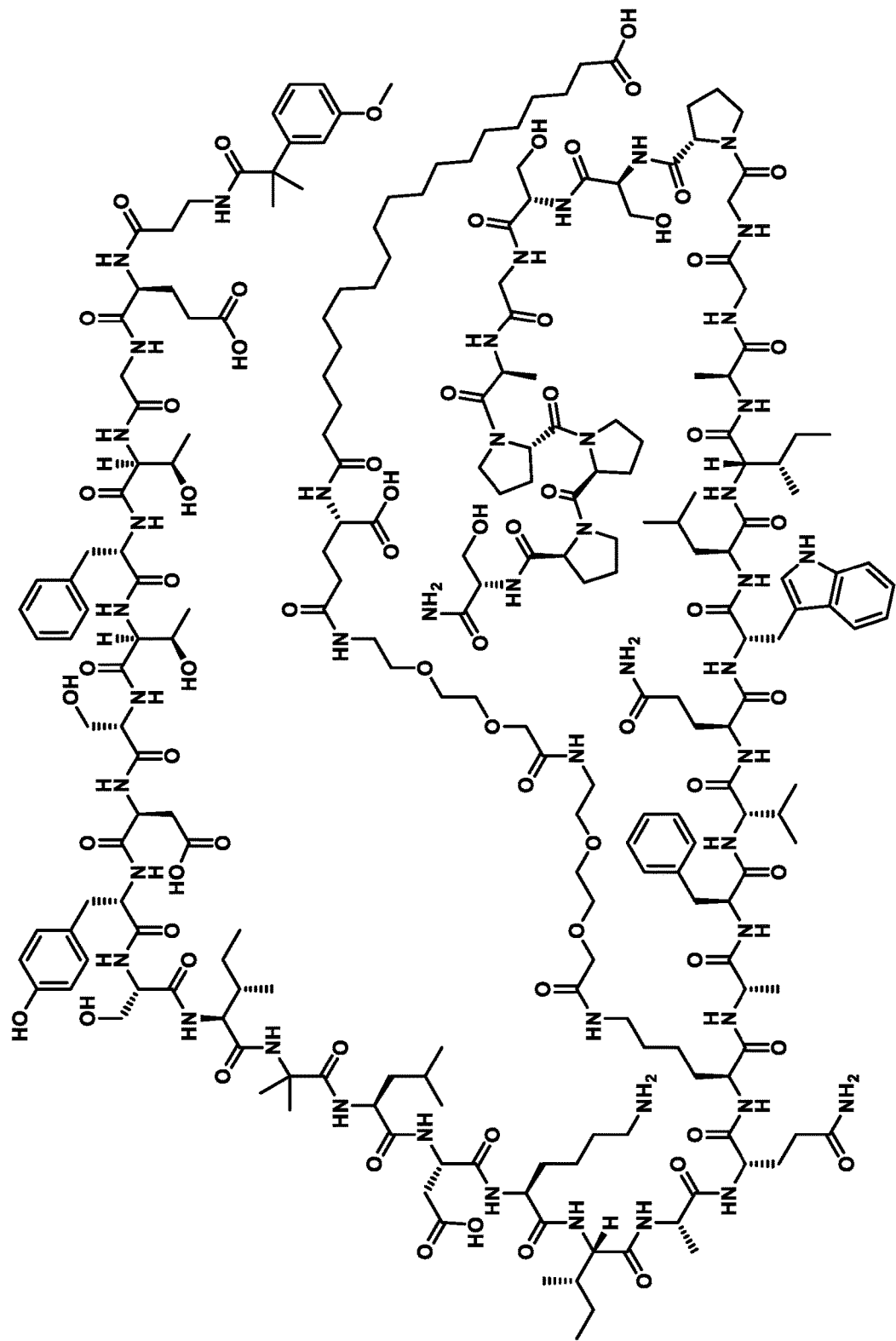
FIG. 1 - Cont'd
Compound 209

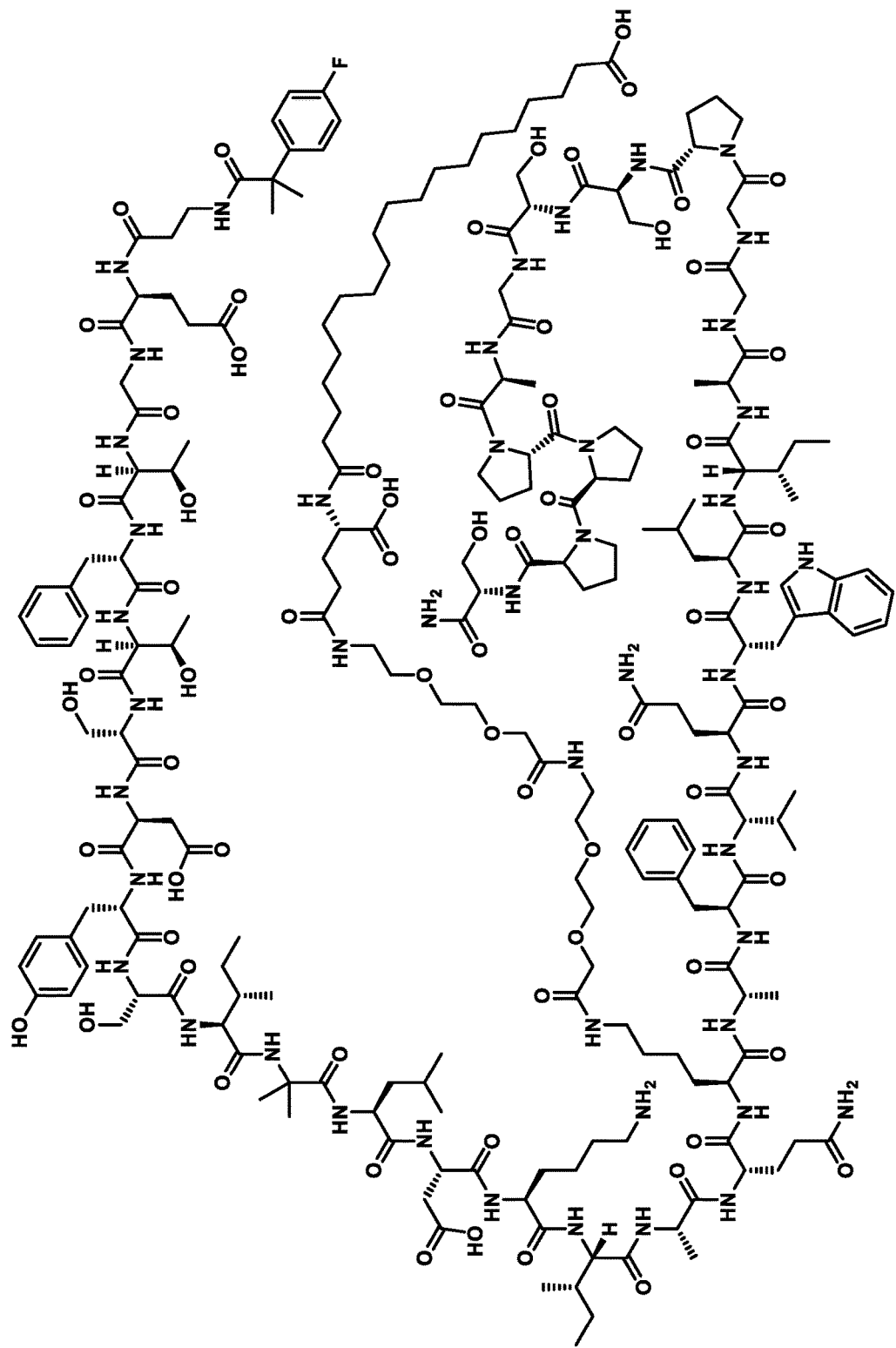
Compound 210
FIG. 1 - Cont'd

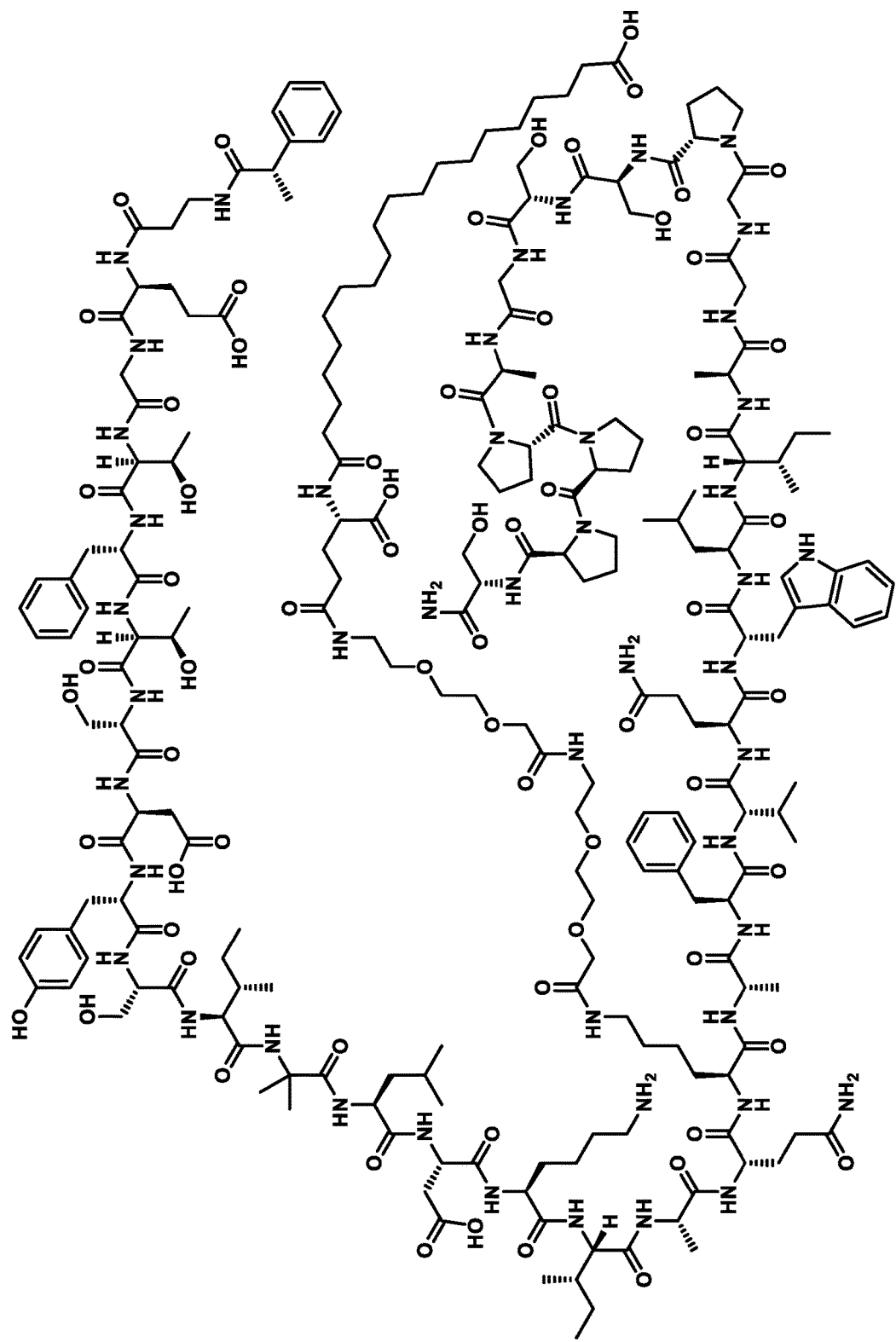
FIG. 1 - Cont'd
Compound 211

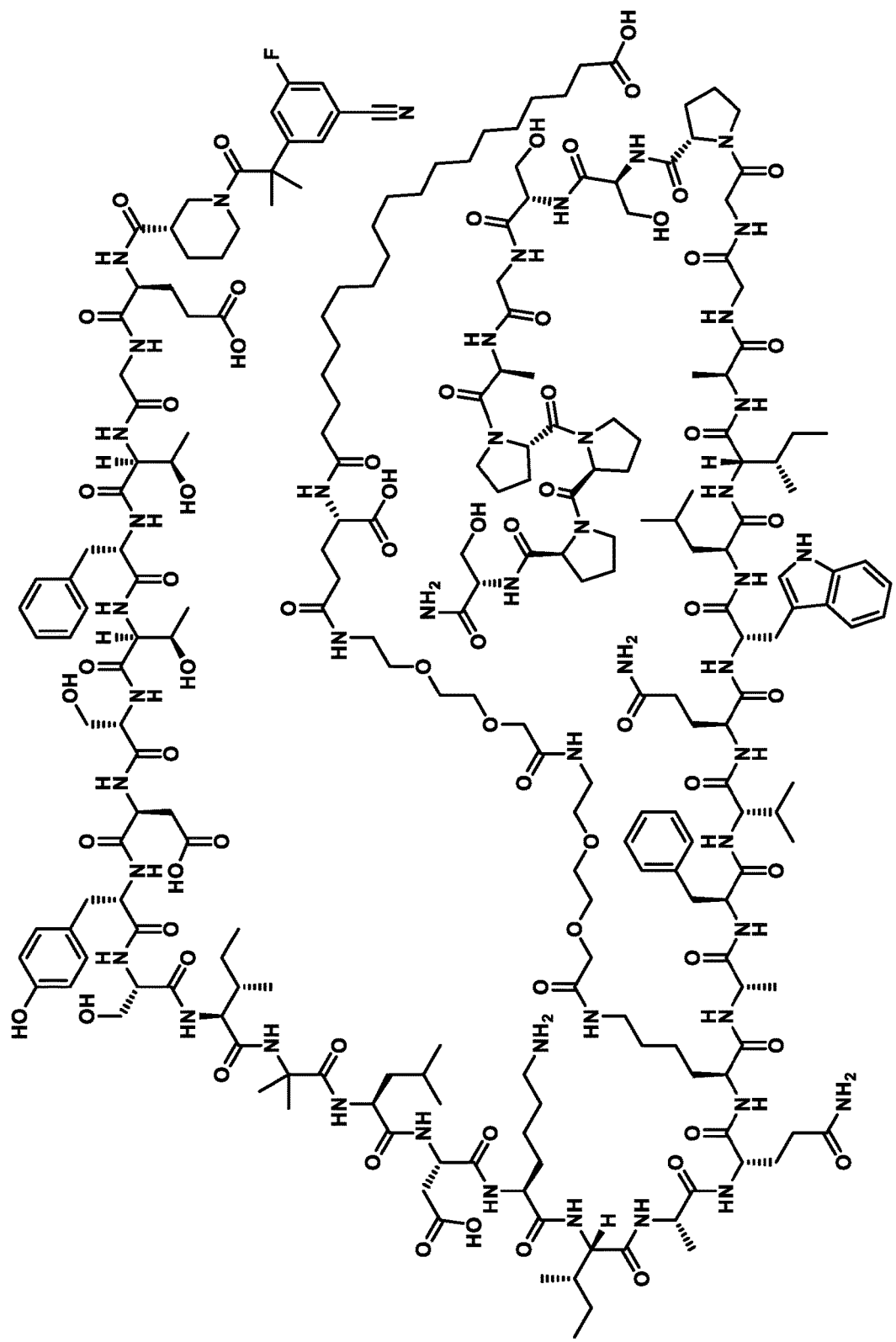
Compound 212
FIG. 1 - Cont'd

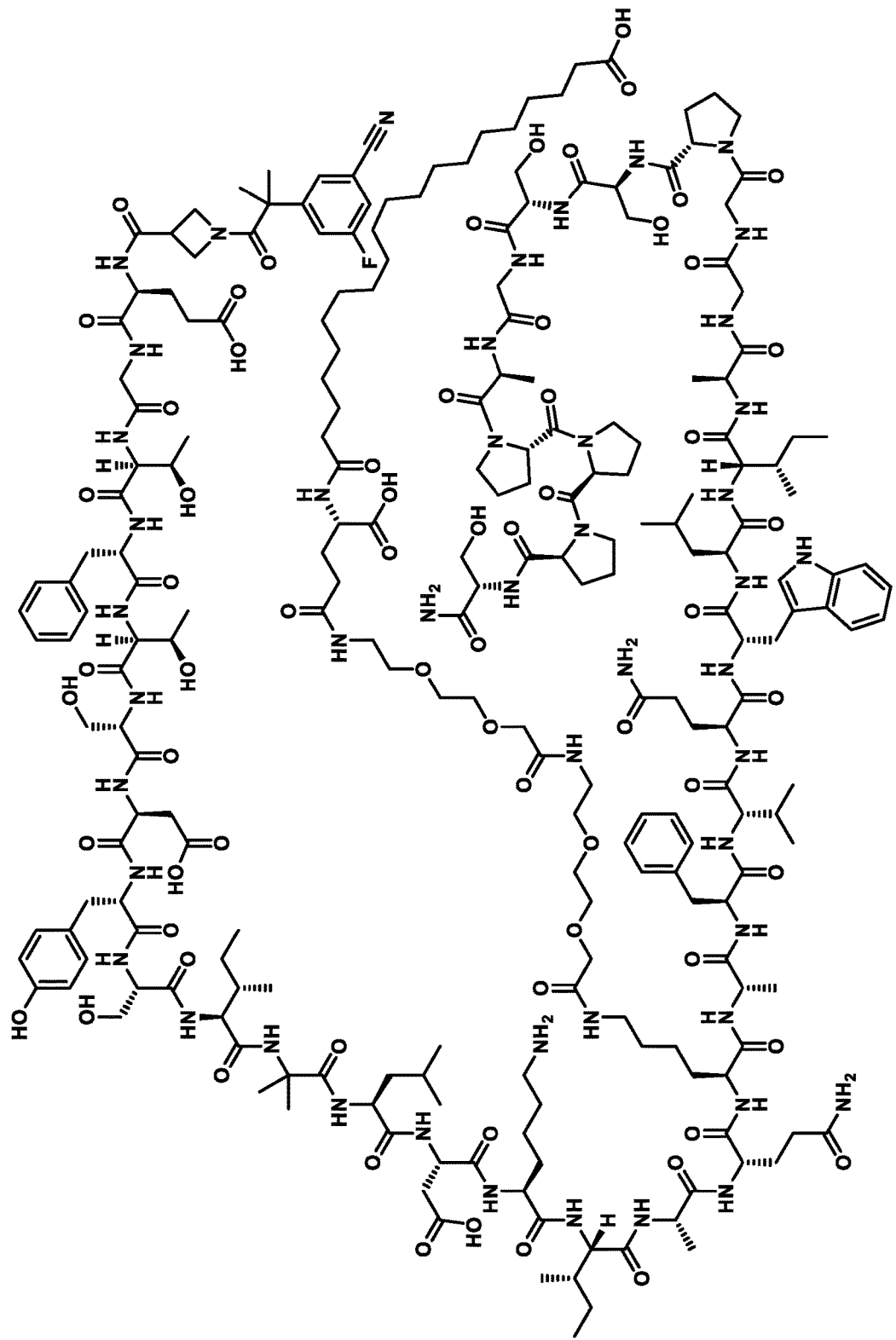
Compound 213
FIG. 1 - Cont'd

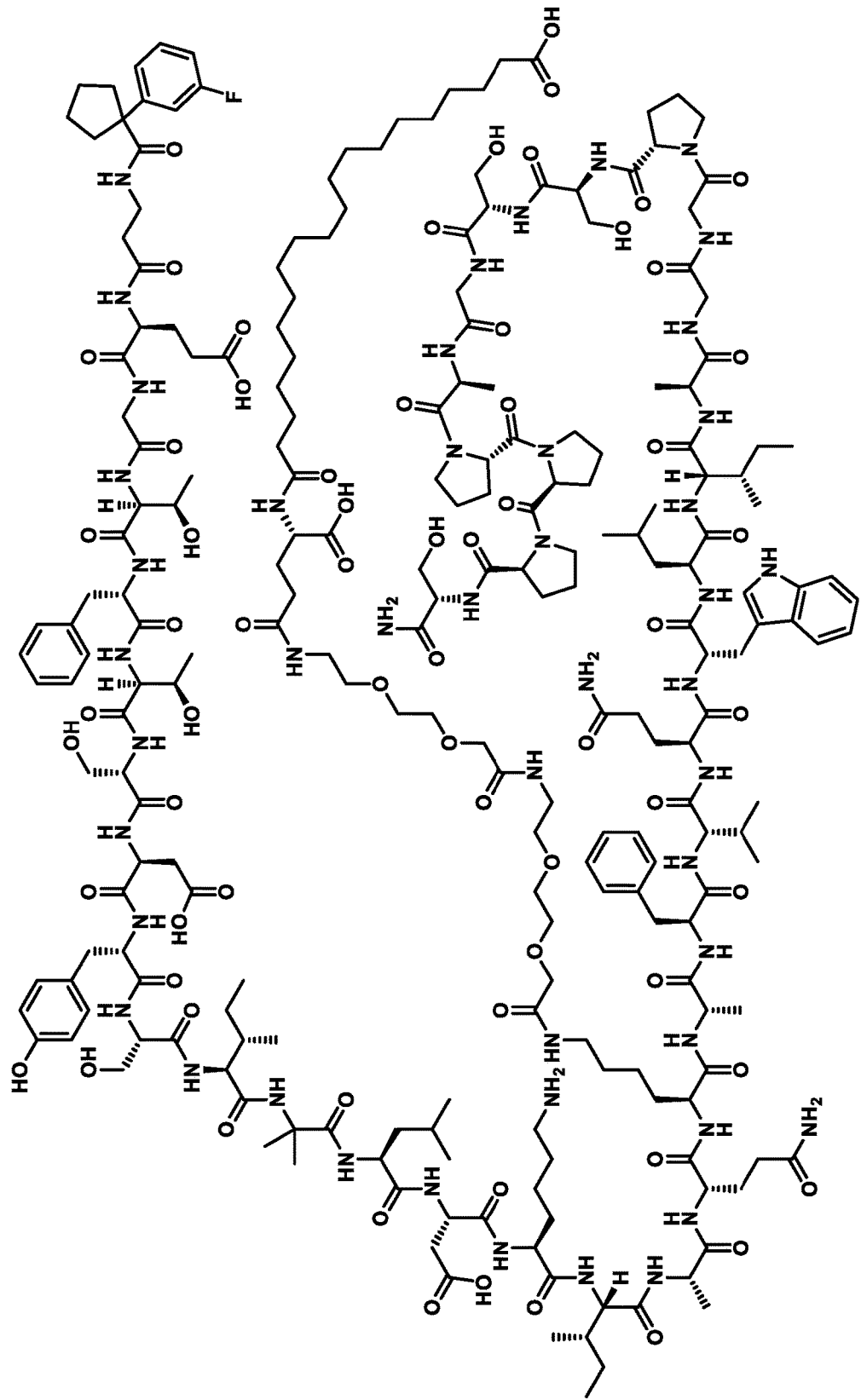
Compound 214
FIG. 1 - Cont'd

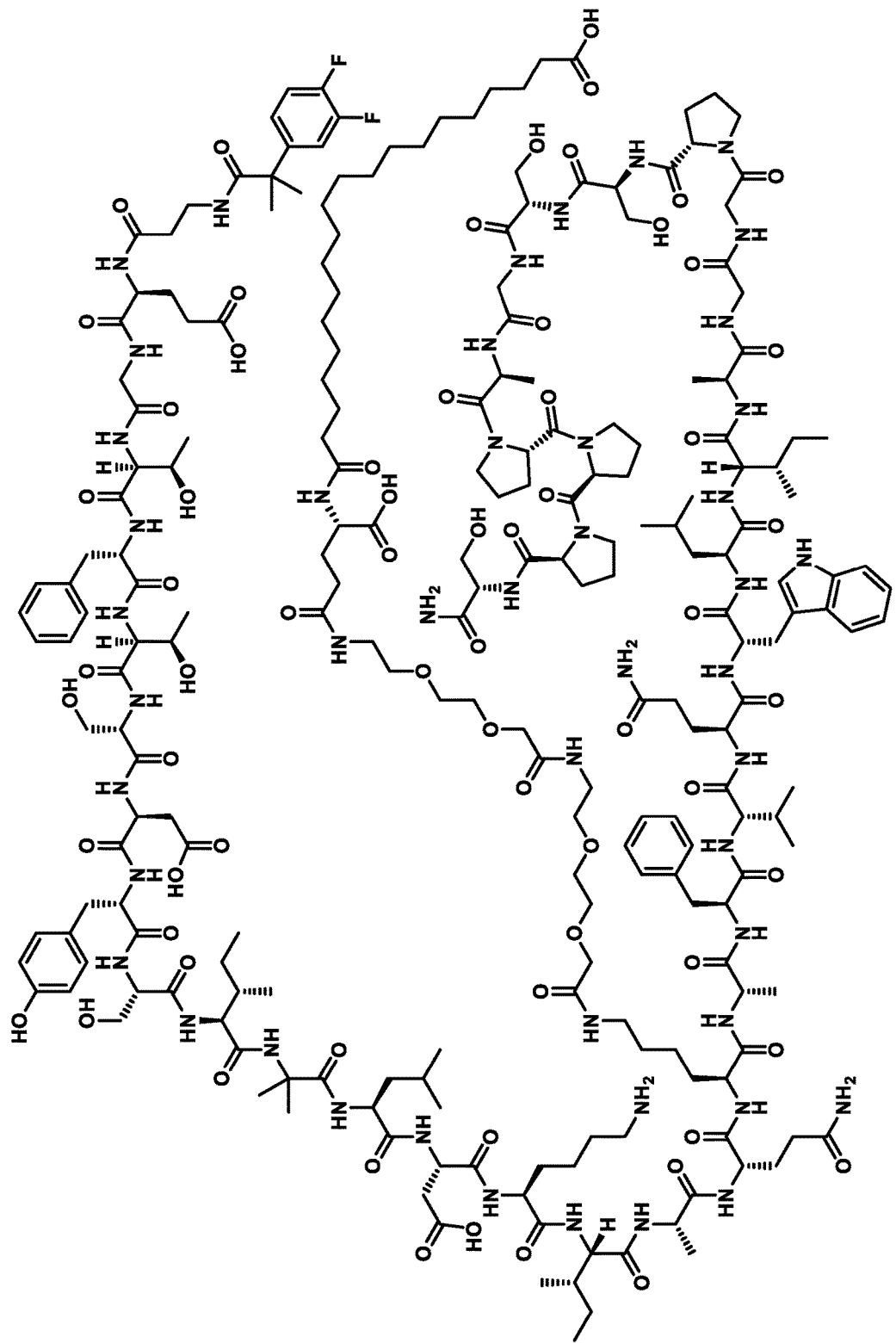
Compound 215
FIG. 1 - Cont'd

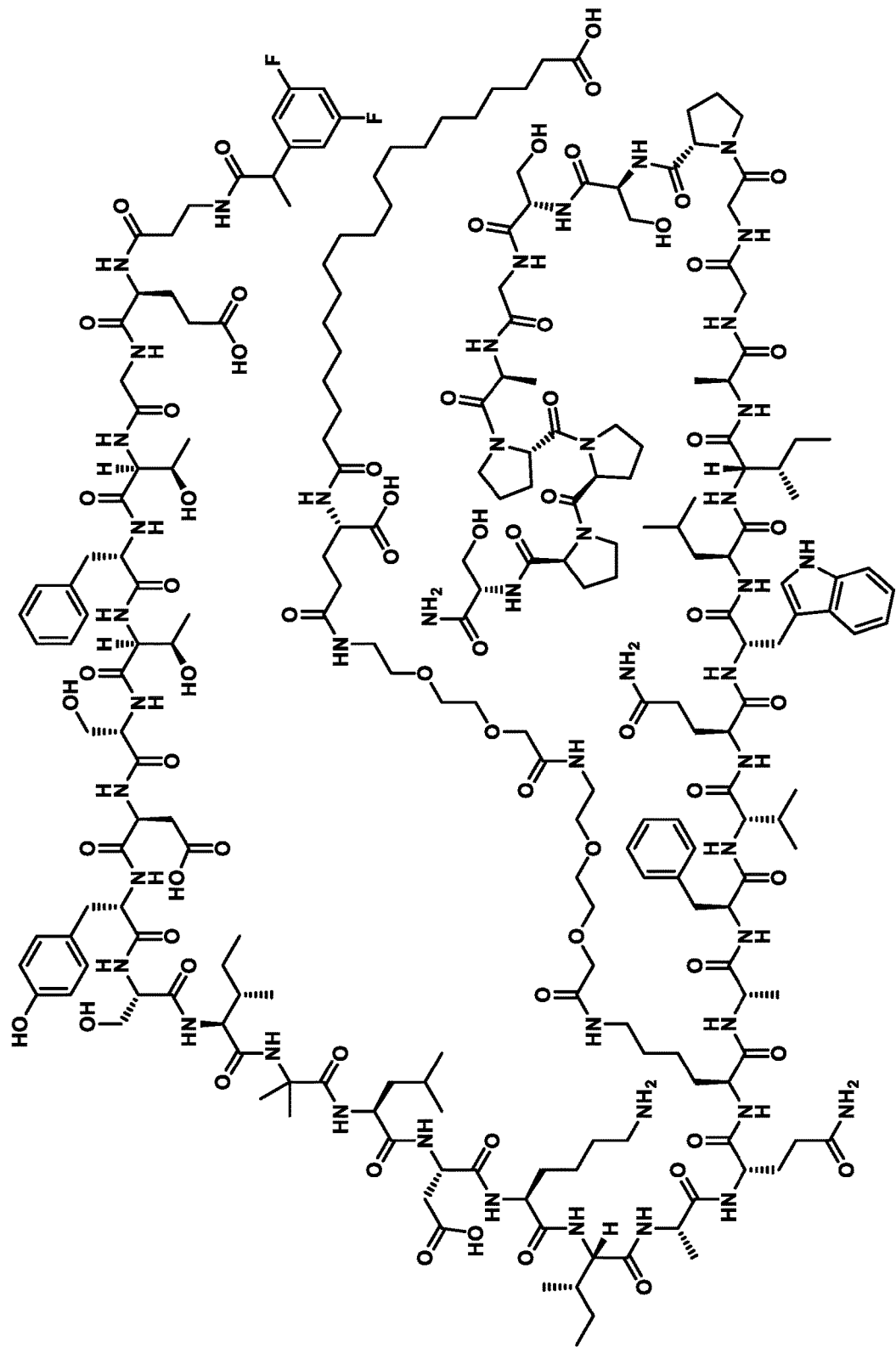
Compound 216
FIG. 1 - Cont'd

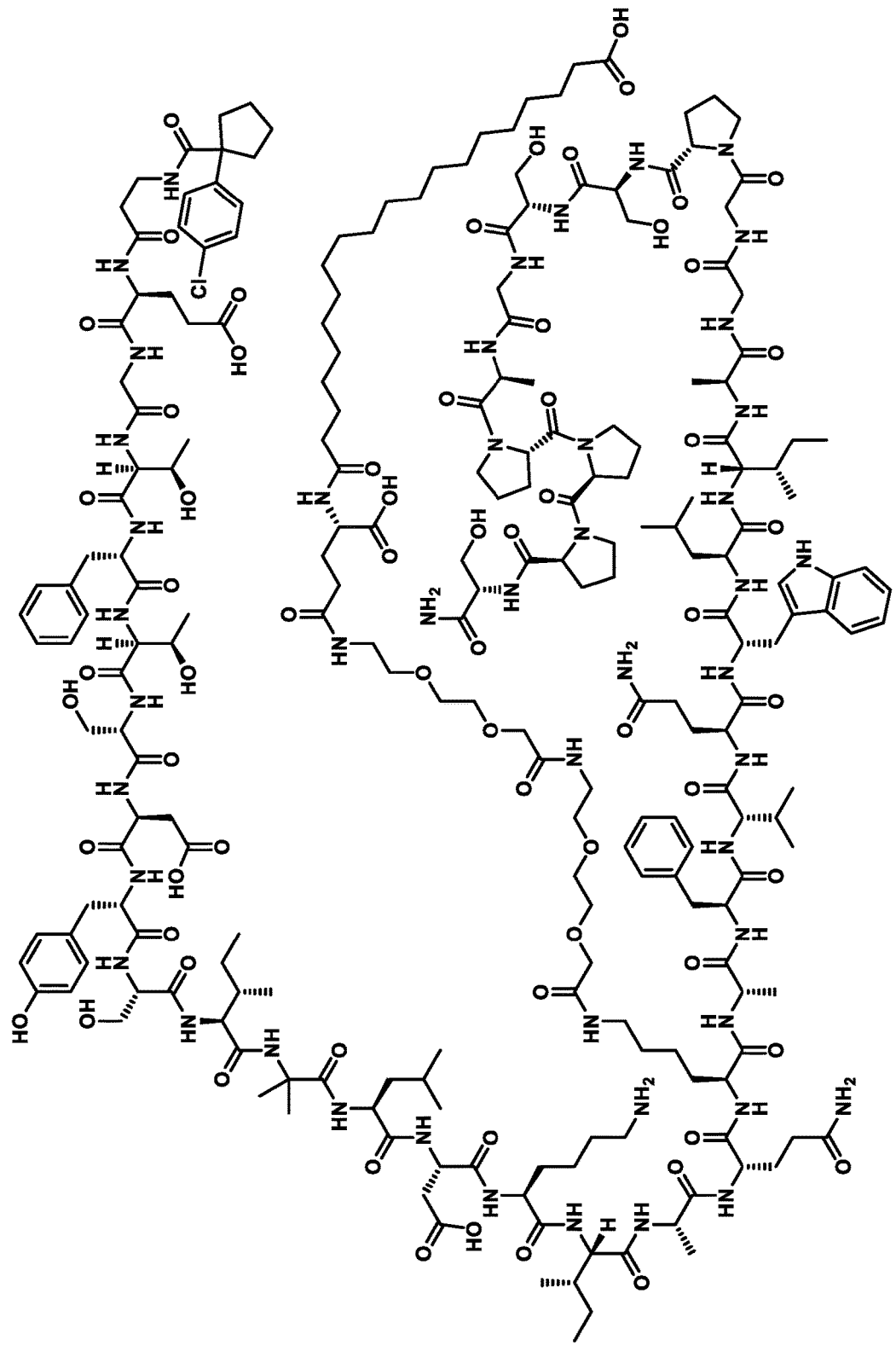
Compound 217
FIG. 1 - Cont'd

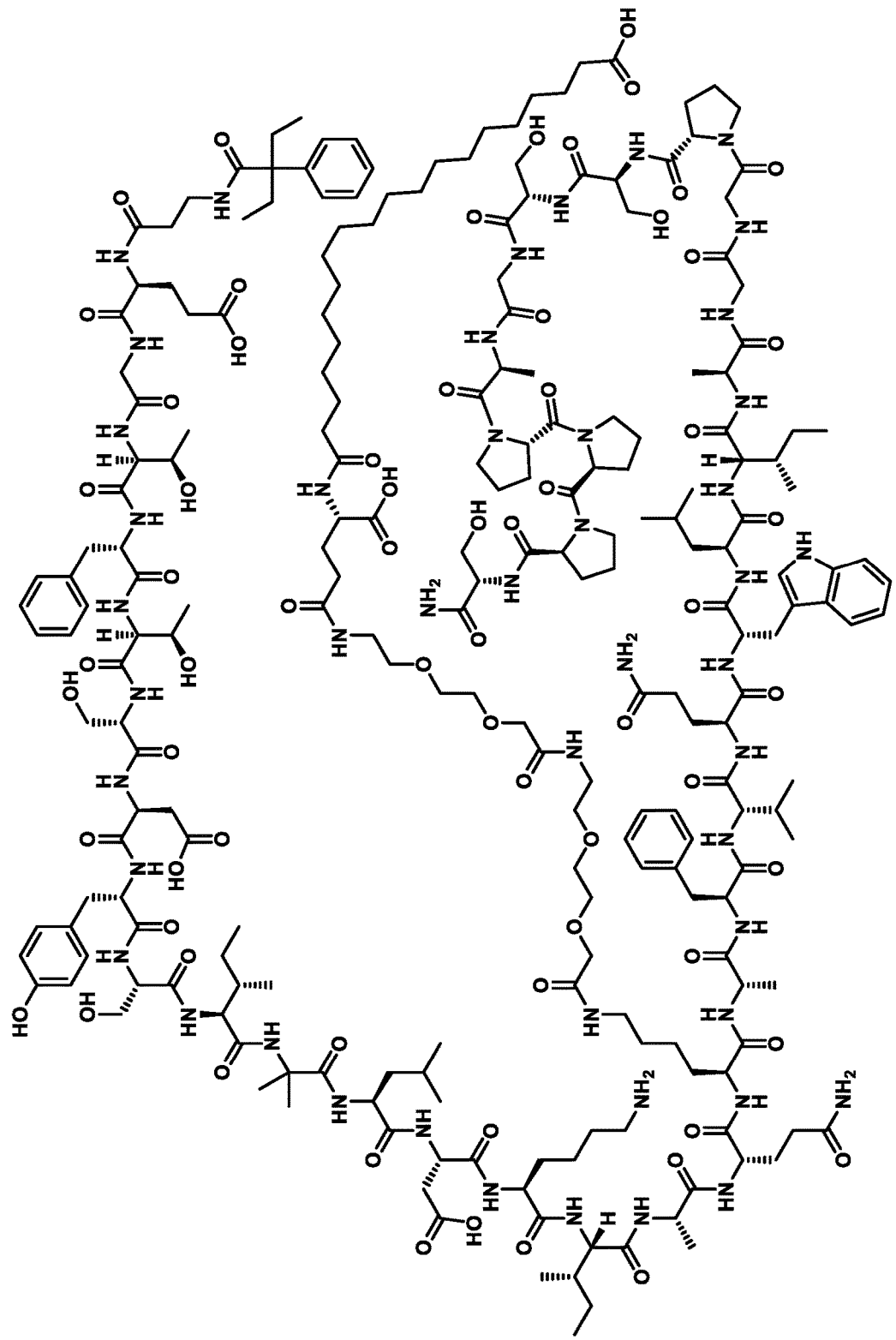
Compound 218
FIG. 1 - Cont'd

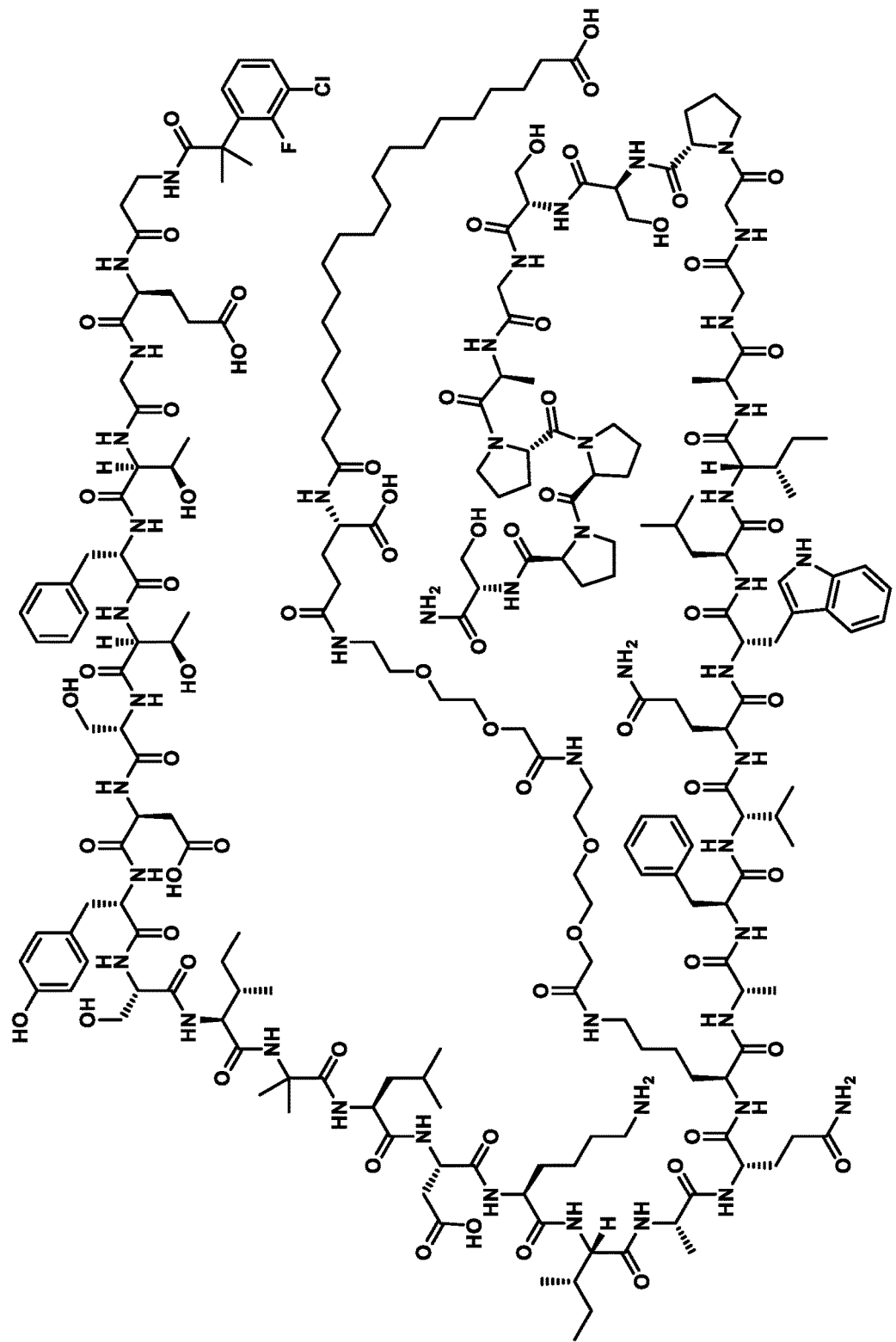
FIG. 1 - Cont'd
Compound 219

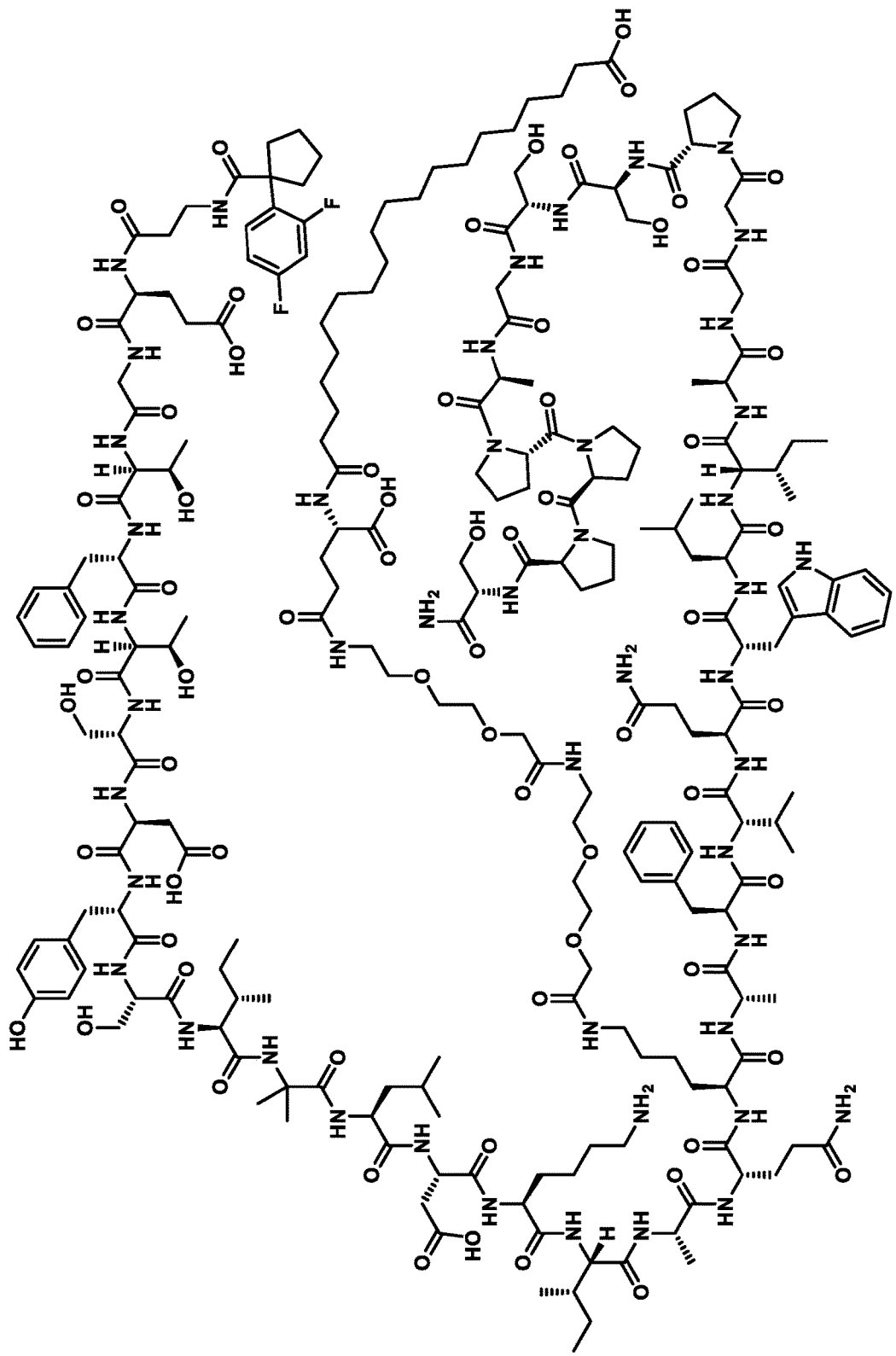
Compound 220
FIG. 1 - Cont'd

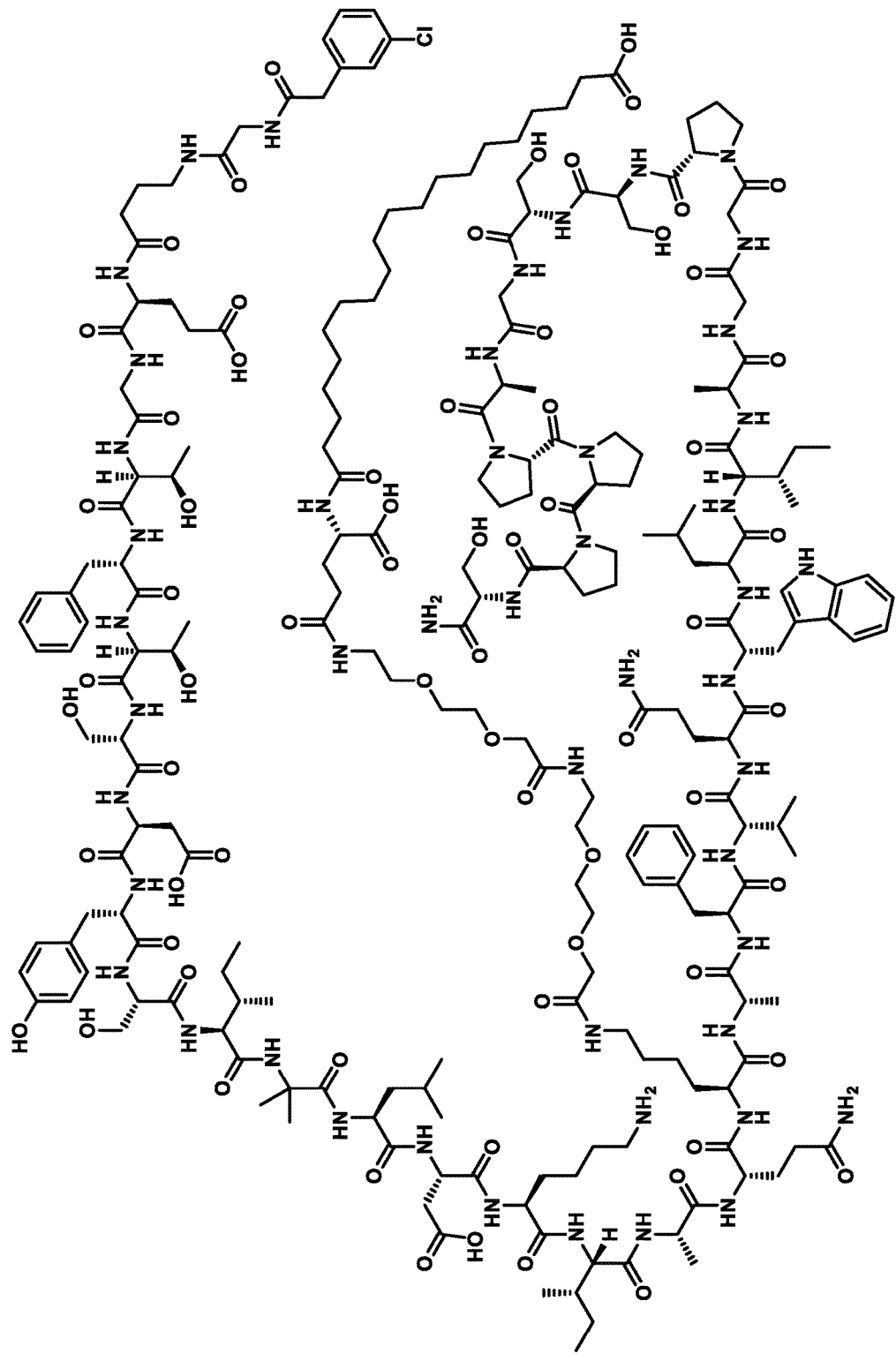
Compound 221
FIG. 1 - Cont'd

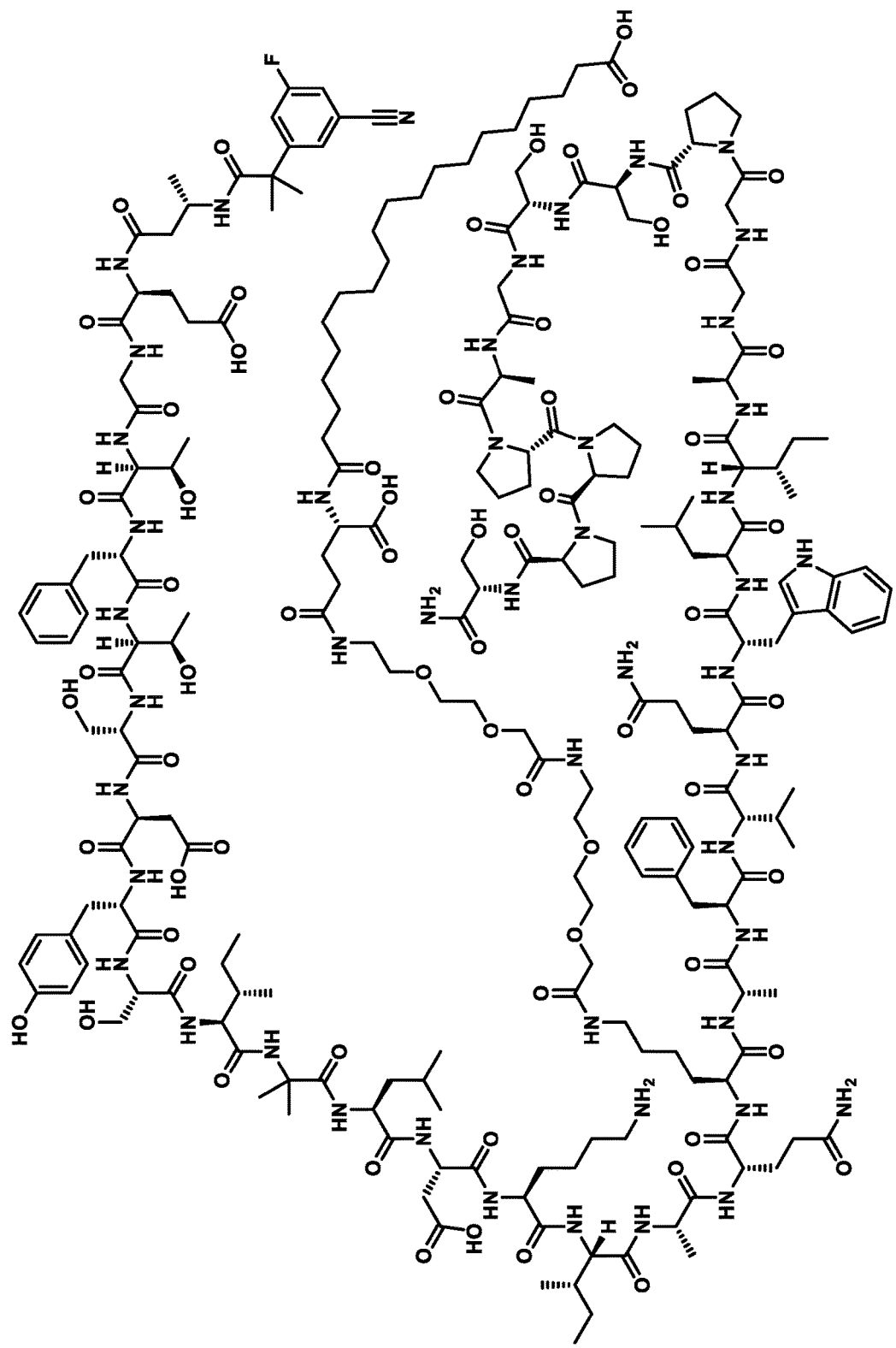
Compound 222
FIG. 1 - Cont'd

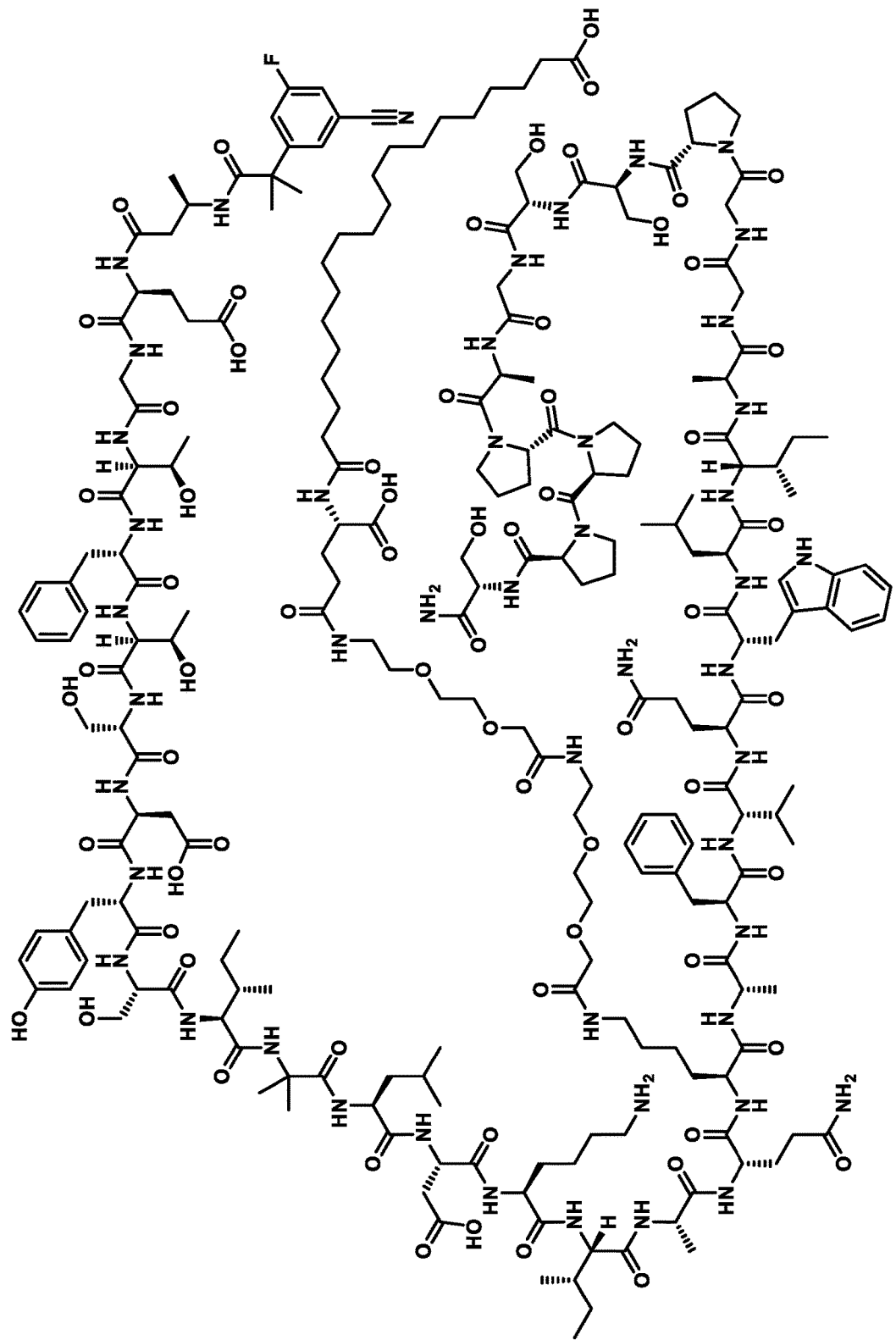
Compound 223
FIG. 1 - Cont'd

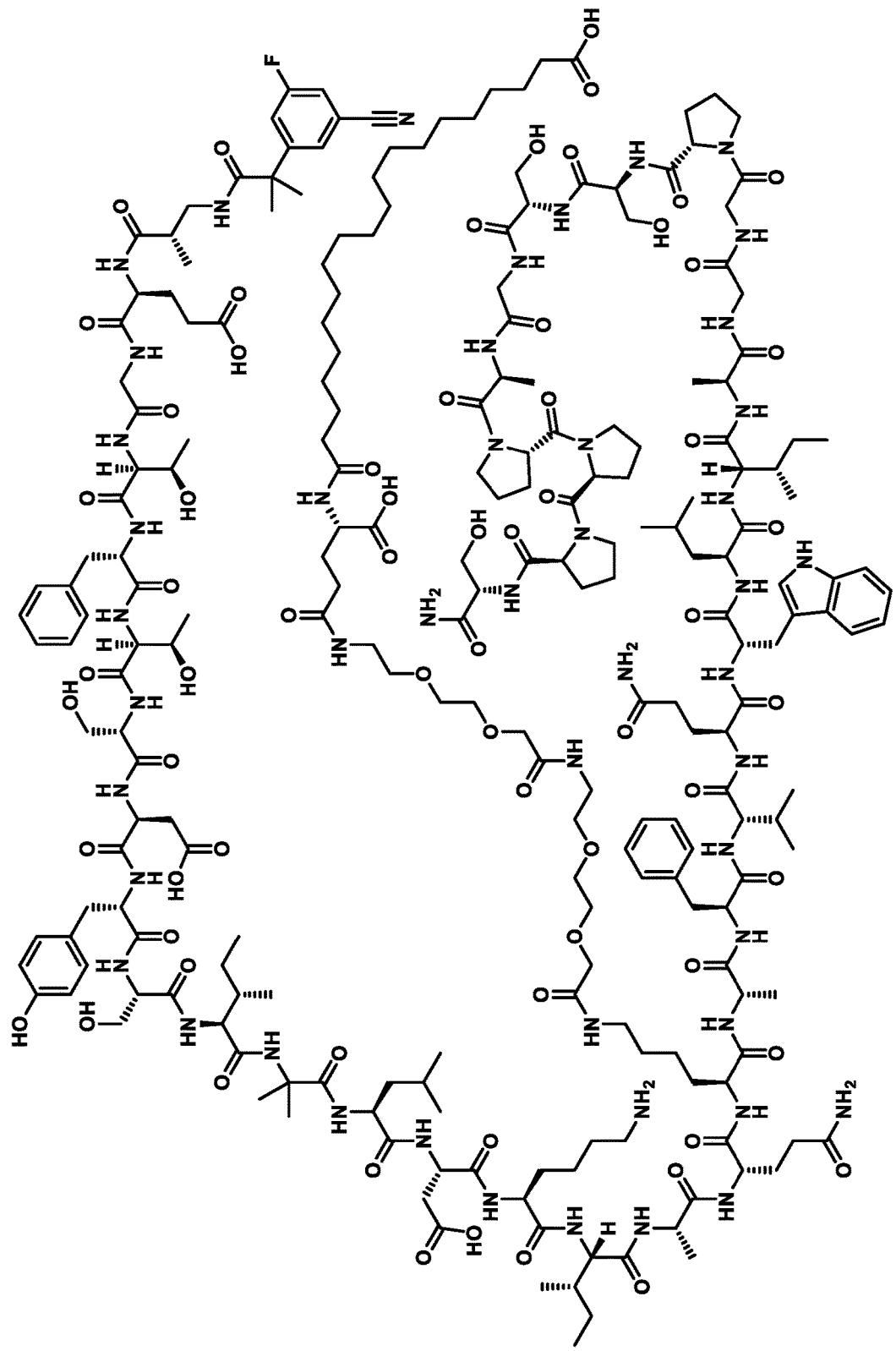
Compound 224
FIG. 1 - Cont'd

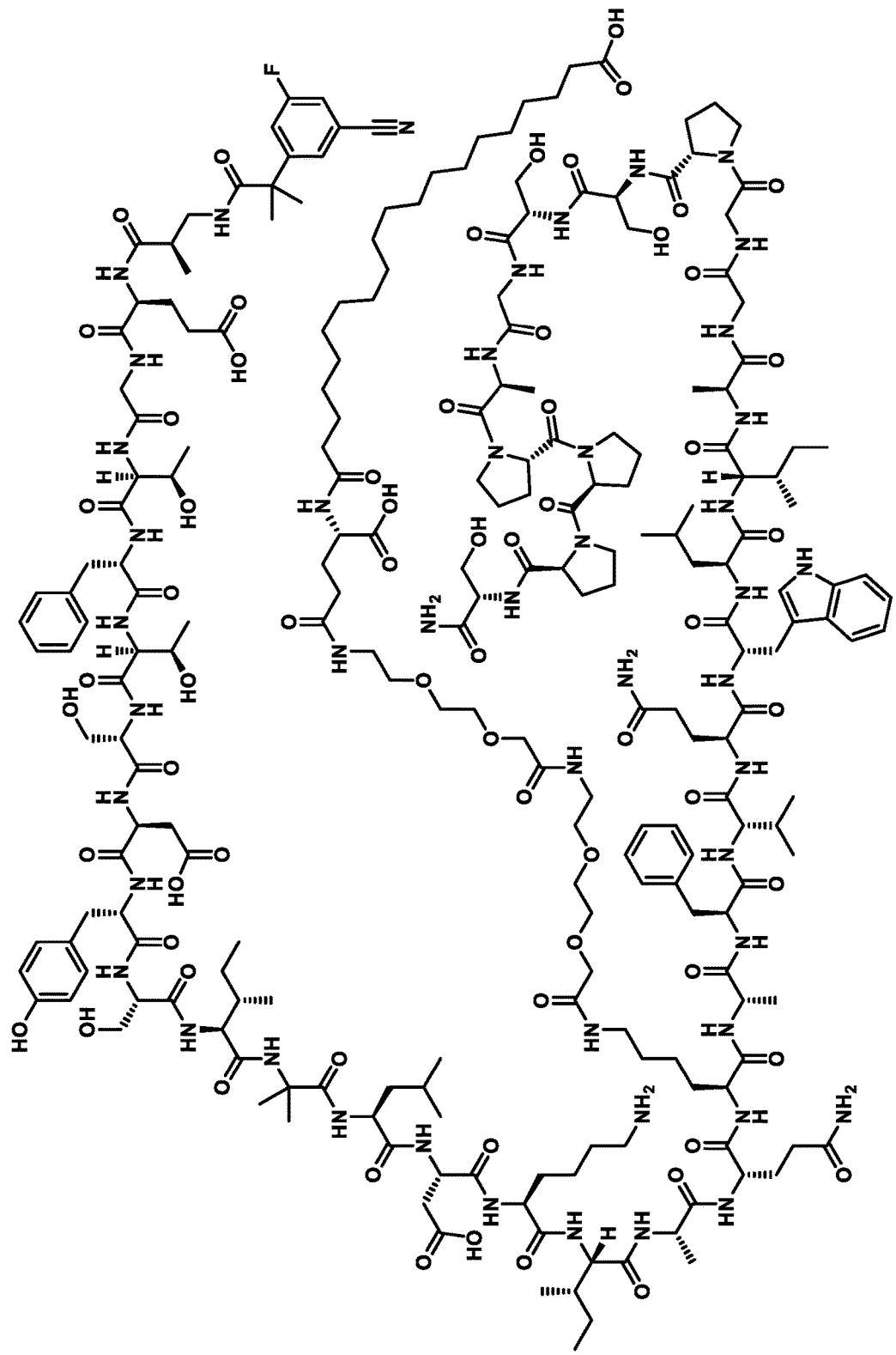
Compound 225
FIG. 1 - Cont'd

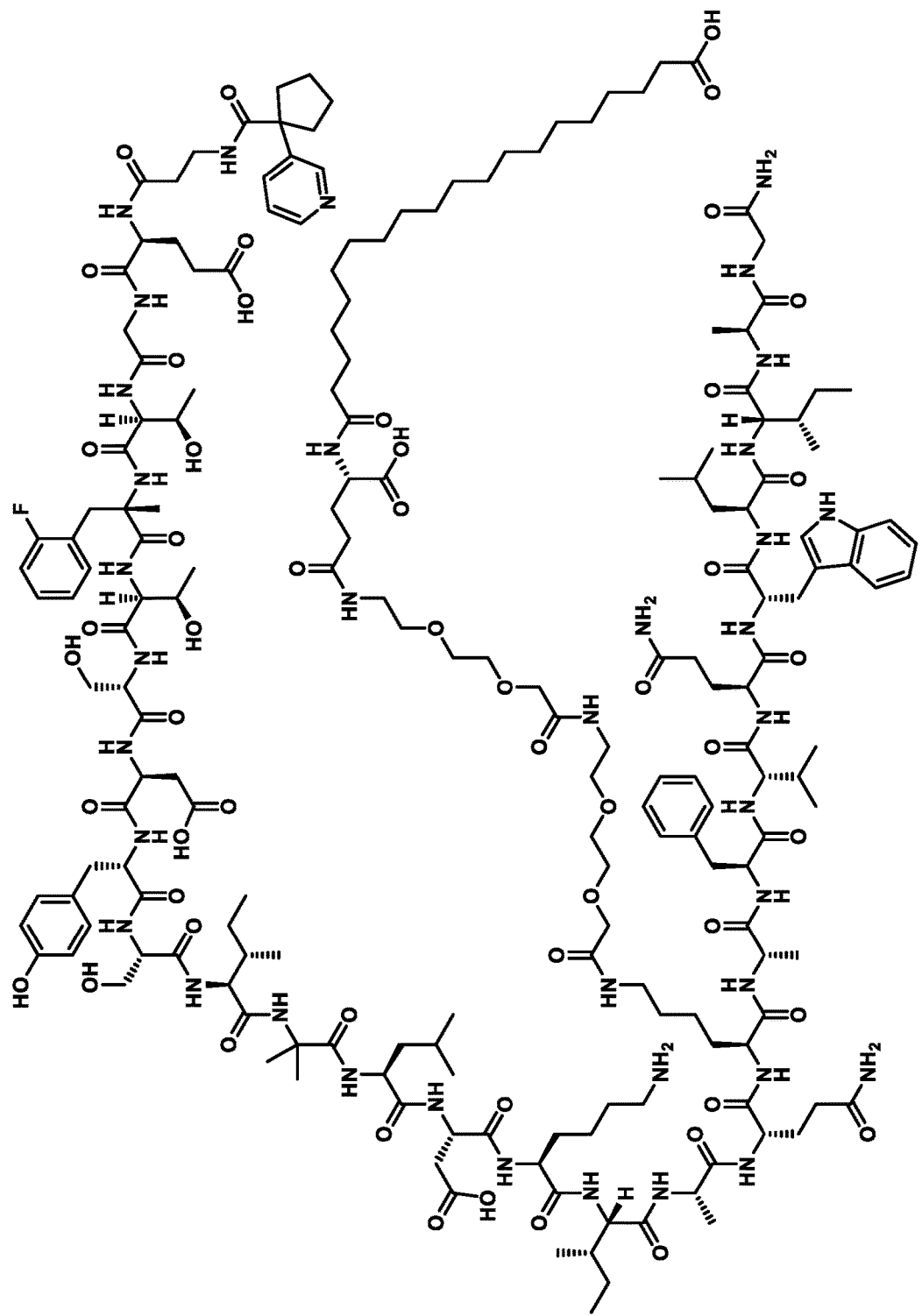
Compound 226
FIG. 1 - Cont'd

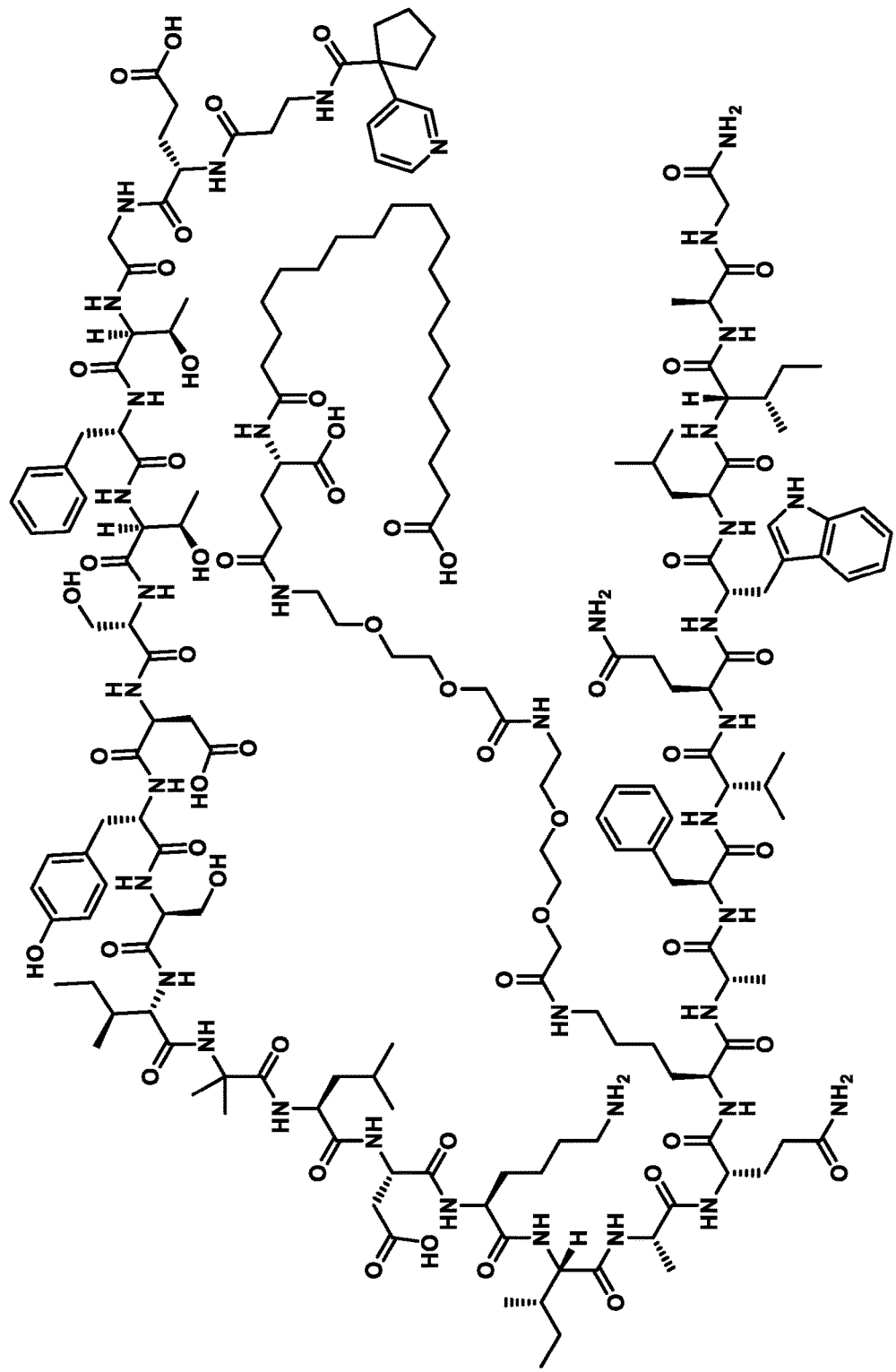
Compound 227
FIG. 1 - Cont'd

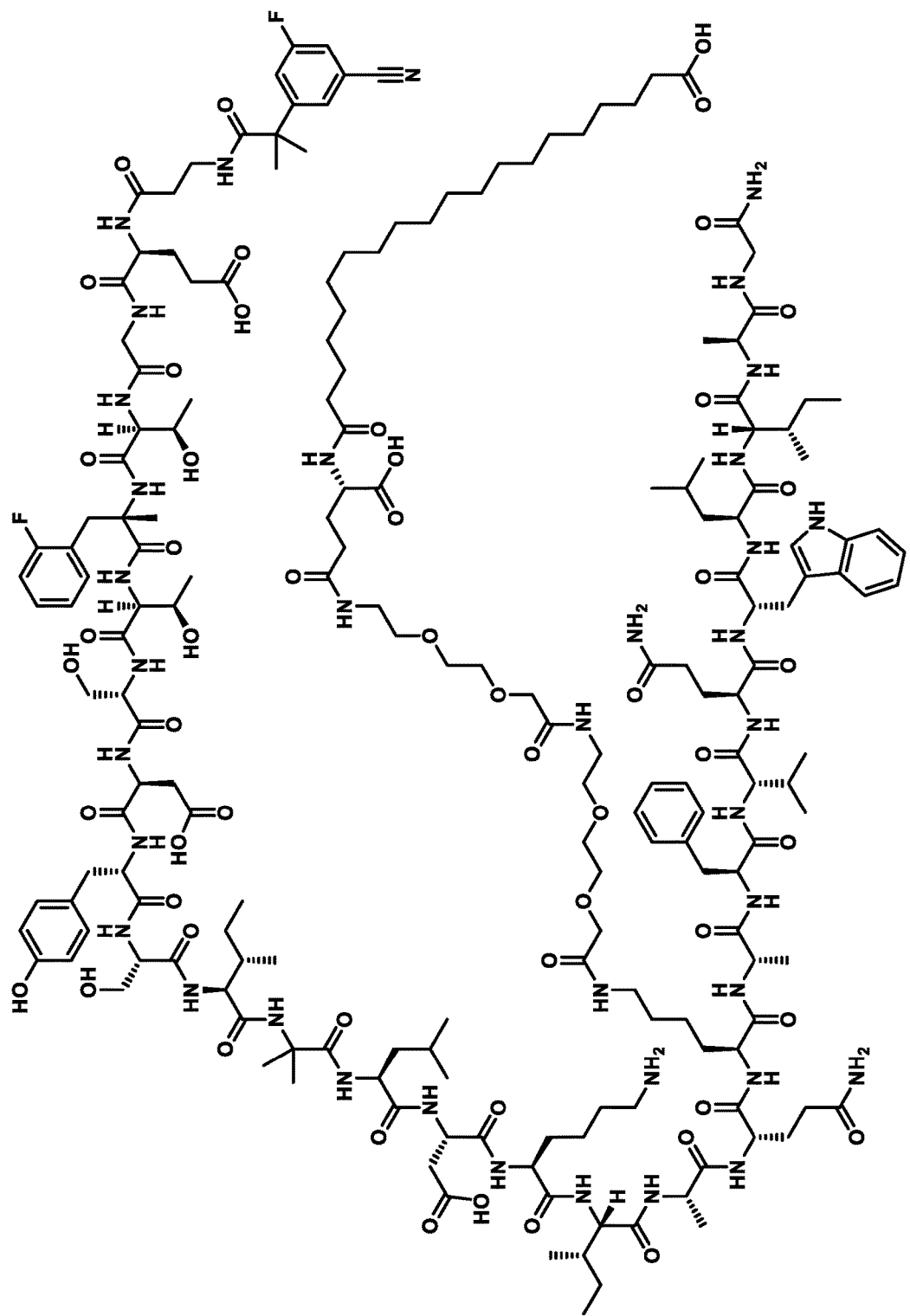
Compound 228
FIG. 1 - Cont'd

Compound 229
FIG. 1 - Cont'd

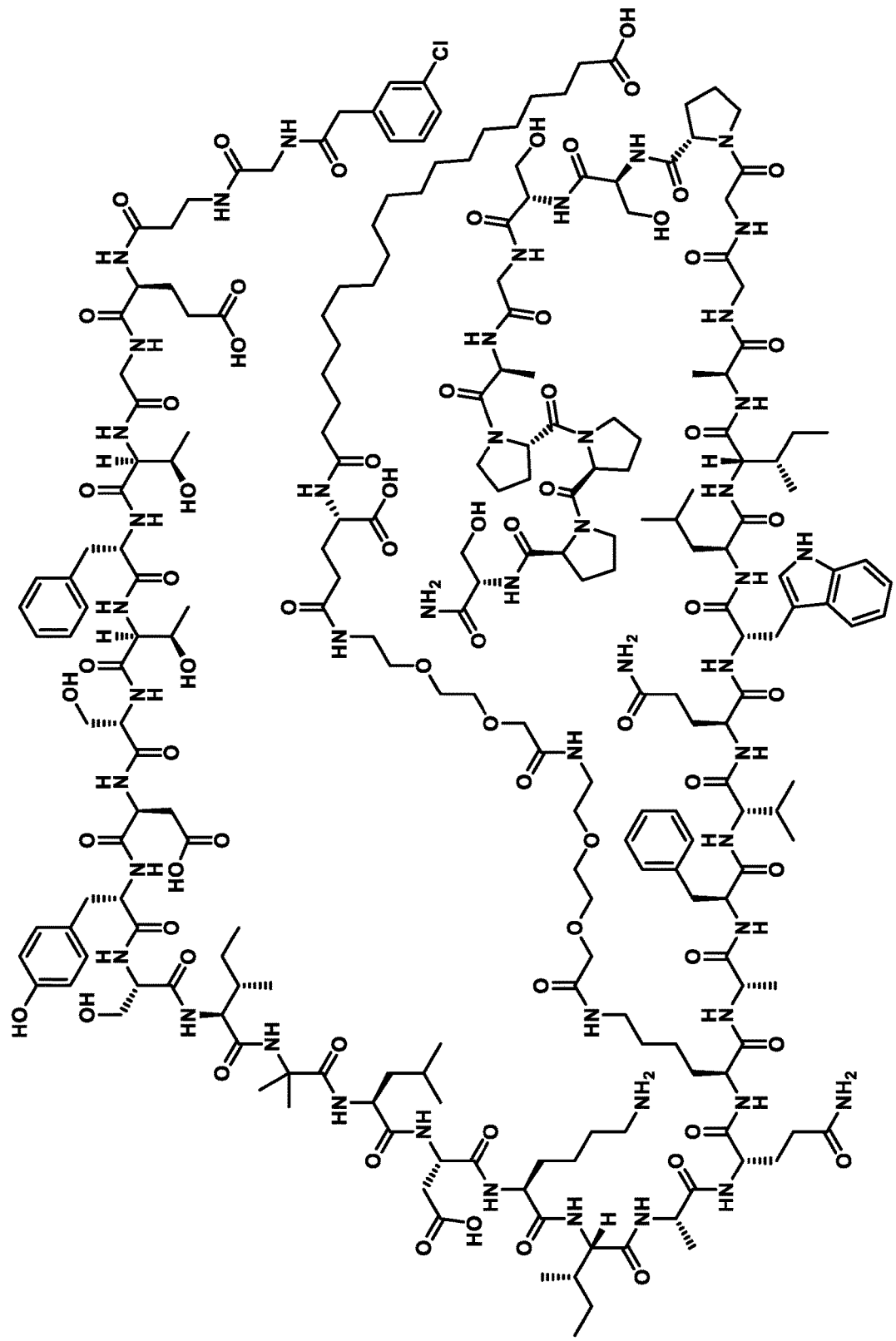
Compound 230
FIG. 1 - Cont'd

Compound 231
FIG. 1 - Cont'd

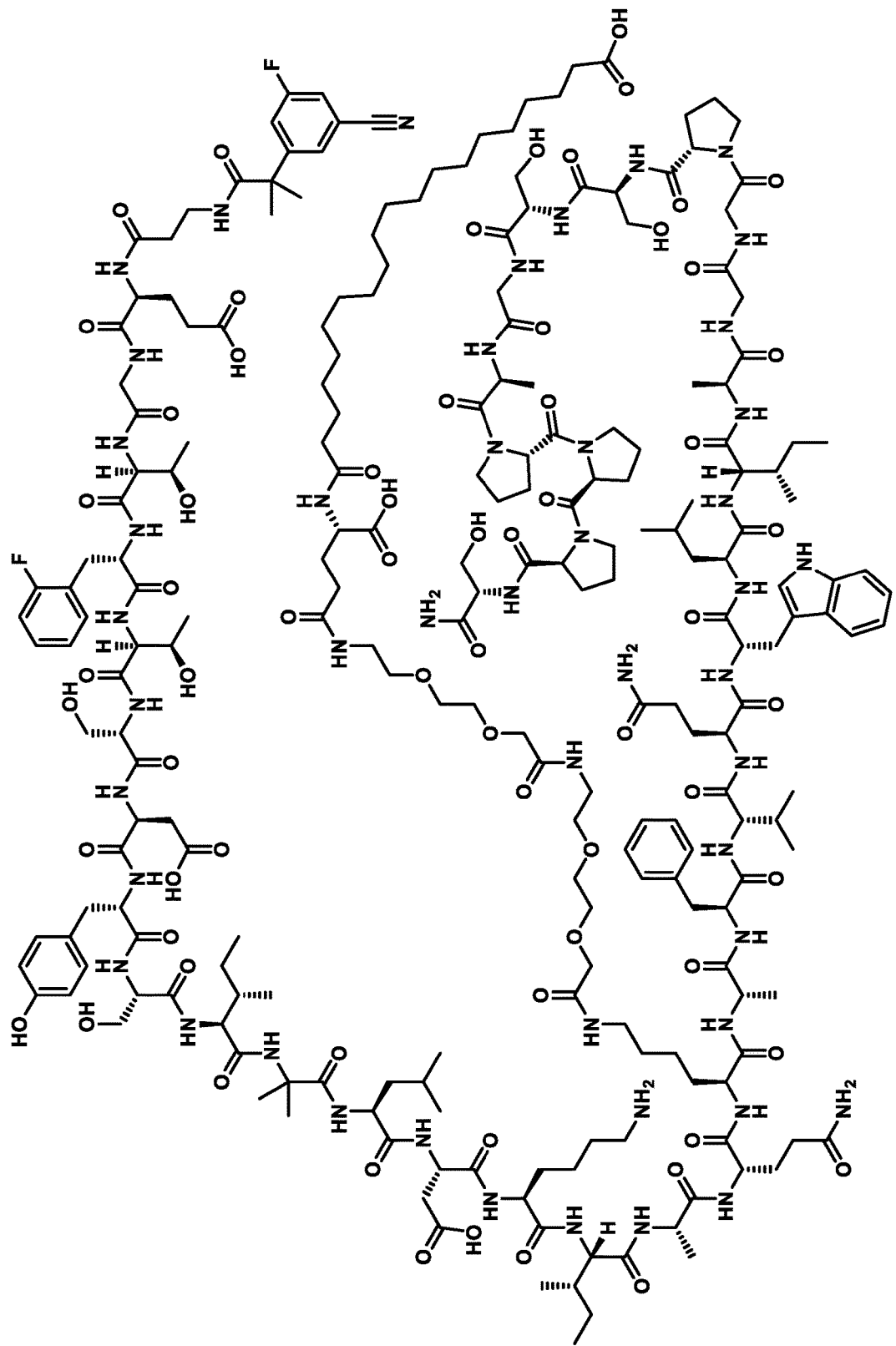
Compound 233
FIG. 1 - Cont'd

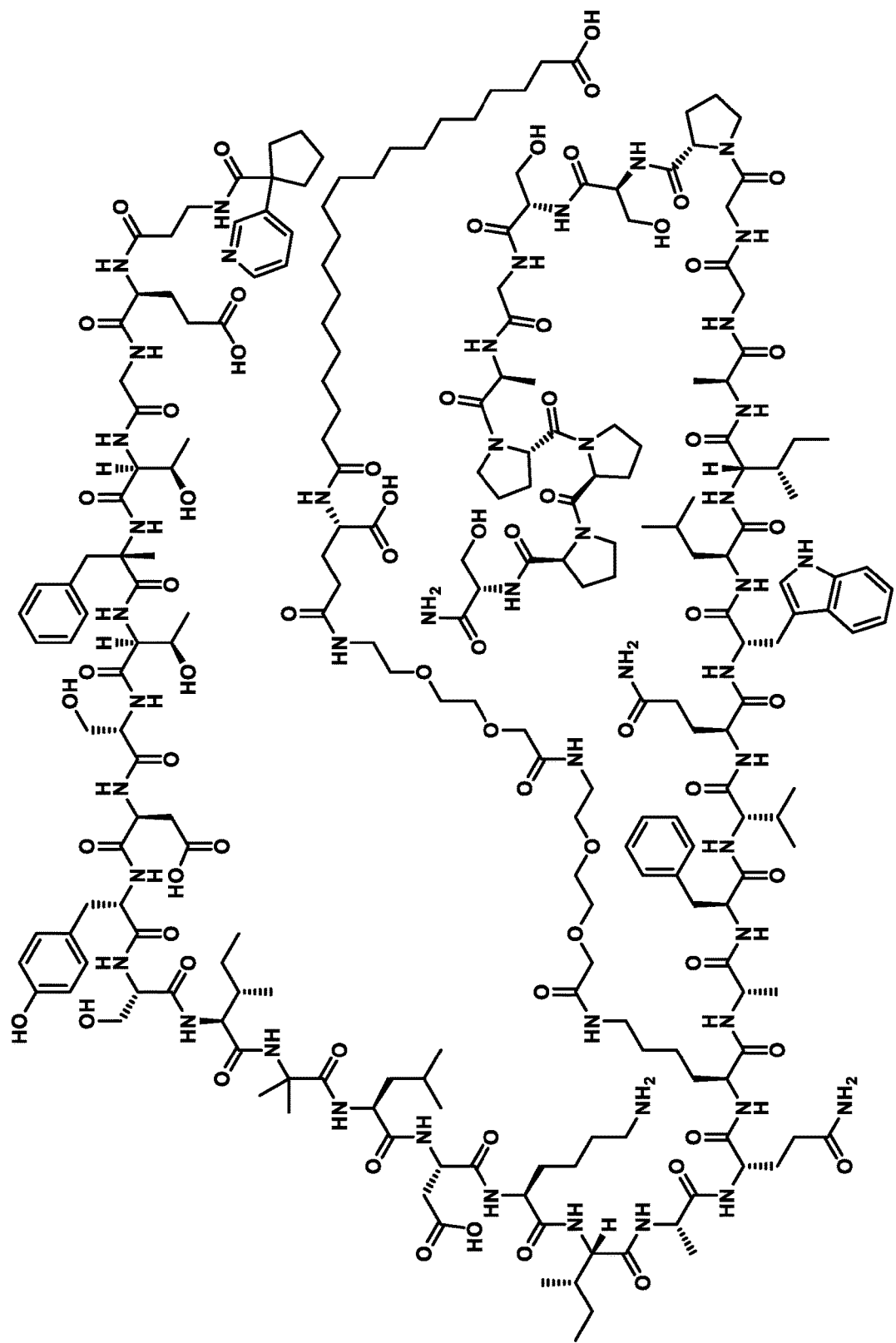
Compound 234
FIG. 1 - Cont'd

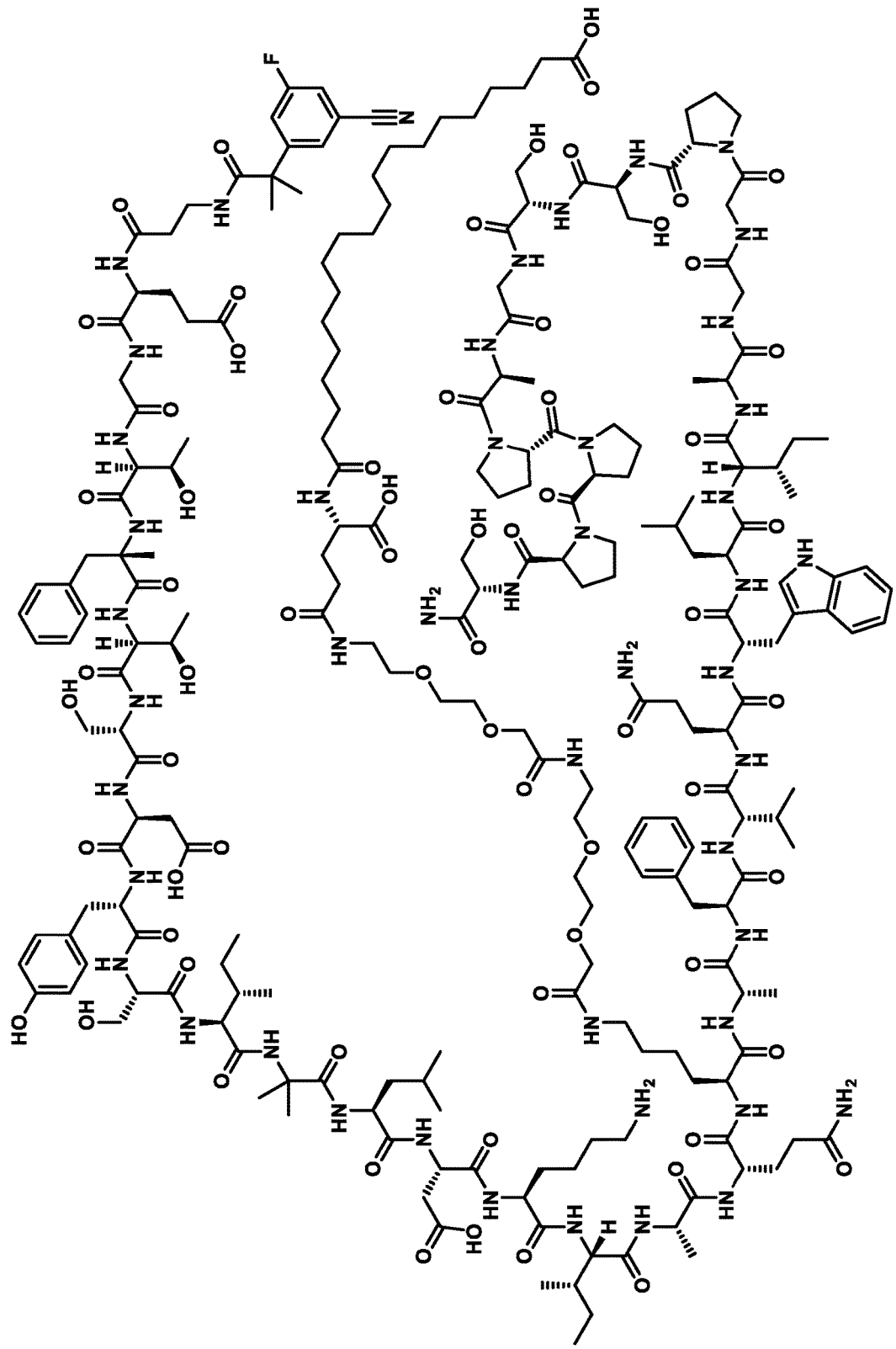
Compound 235
FIG. 1 - Cont'd

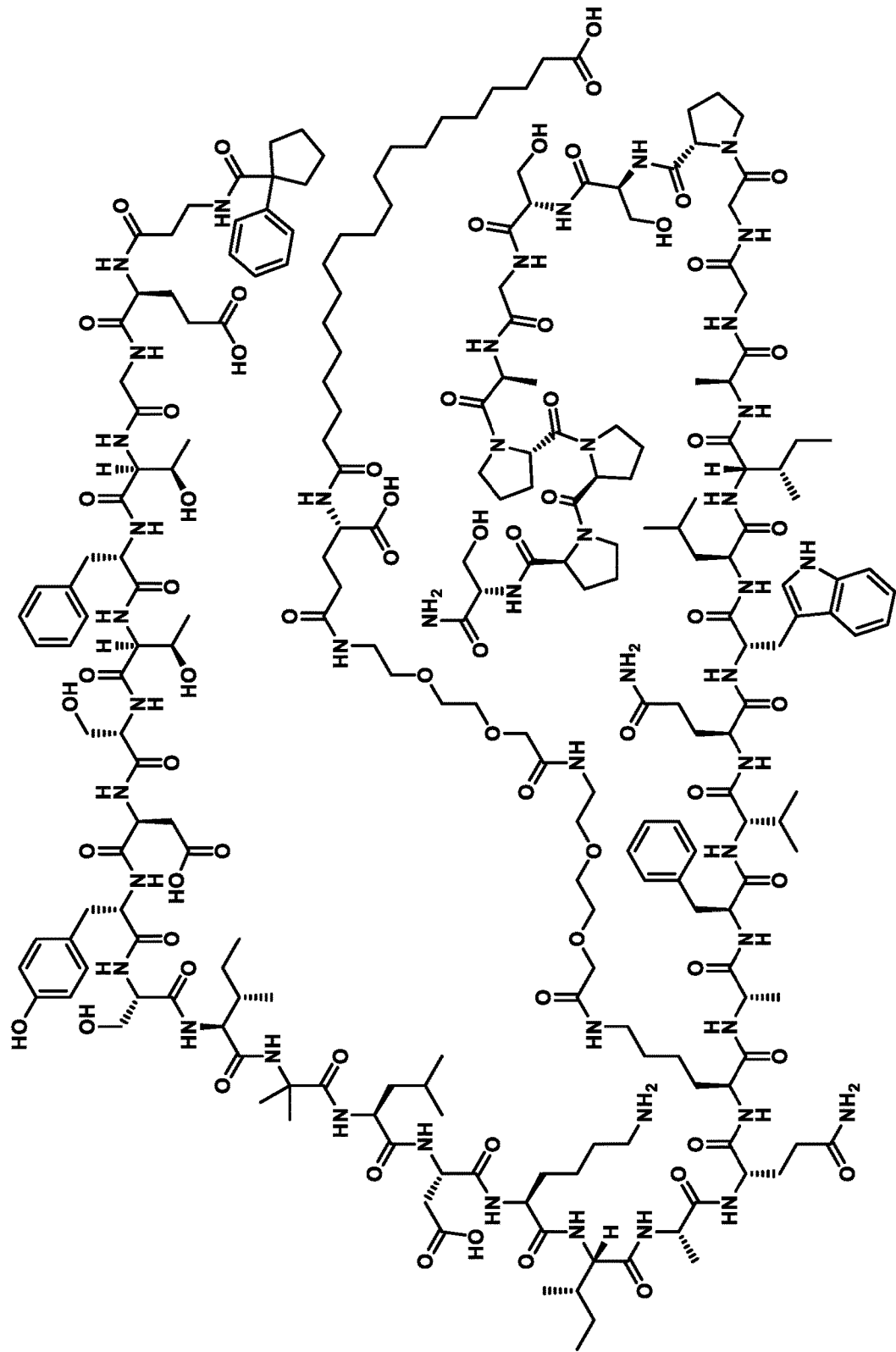
Compound 236
FIG. 1 - Cont'd

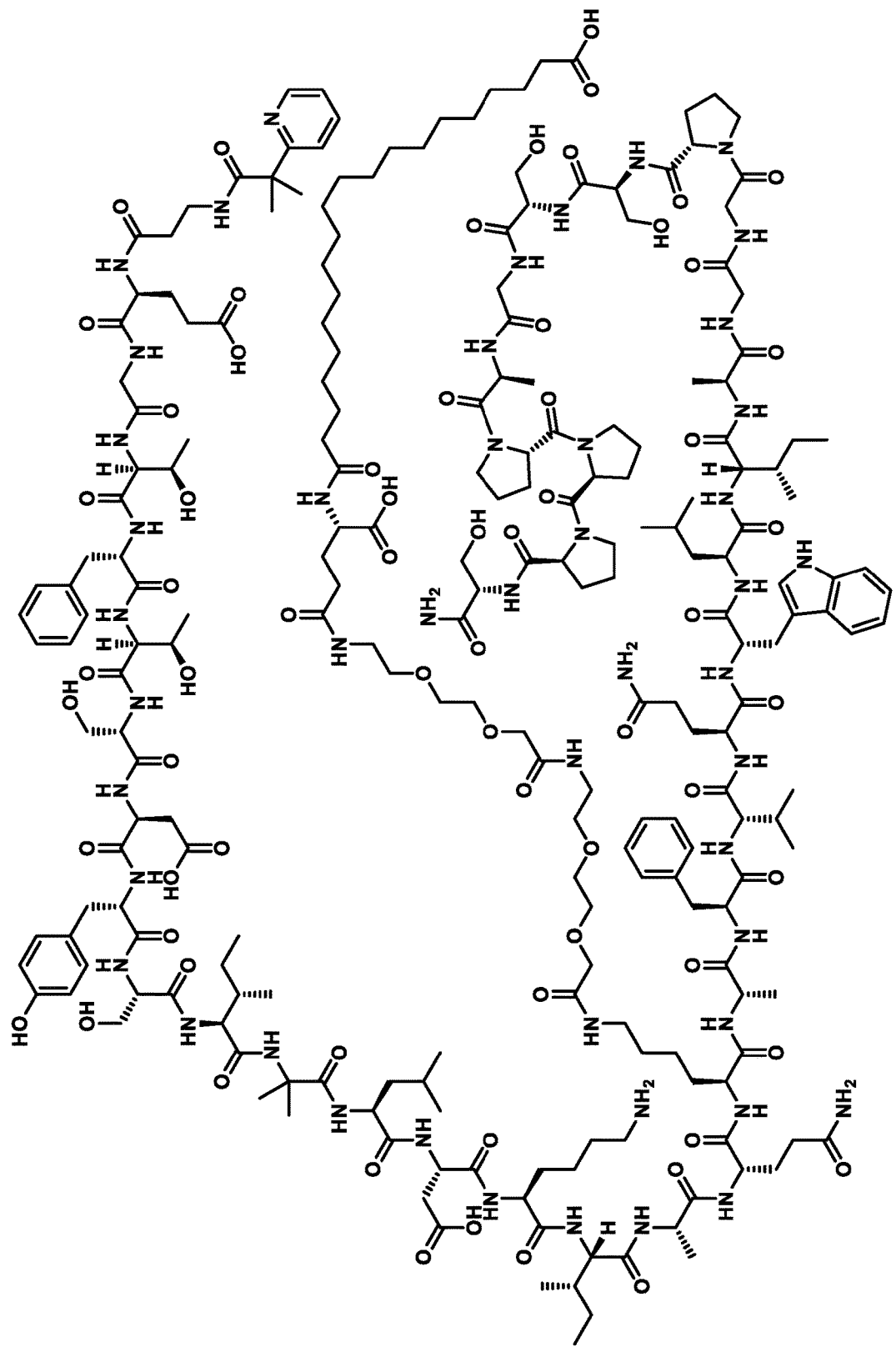
Compound 237
FIG. 1 - Cont'd

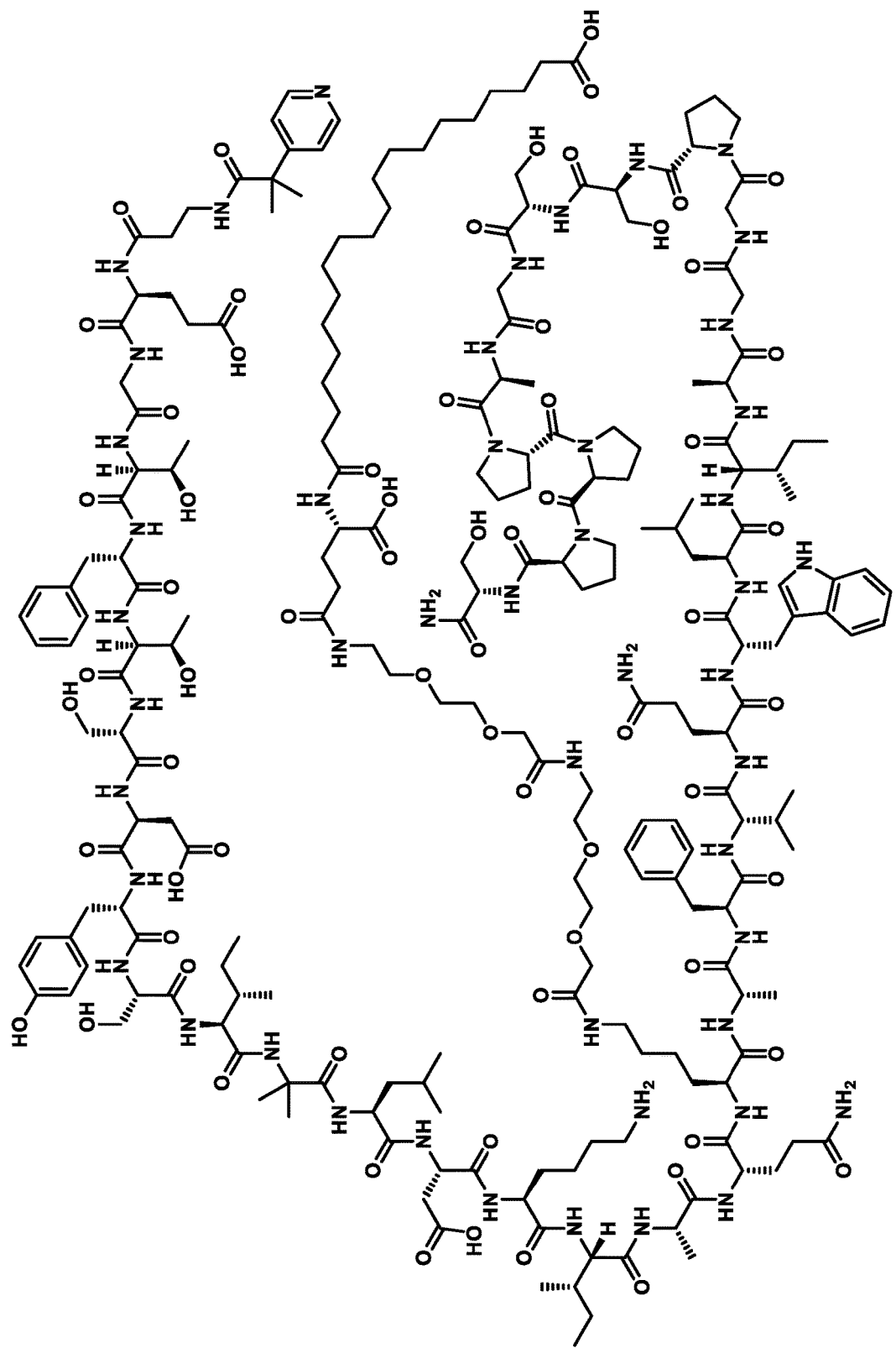
Compound 238
FIG. 1 - Cont'd

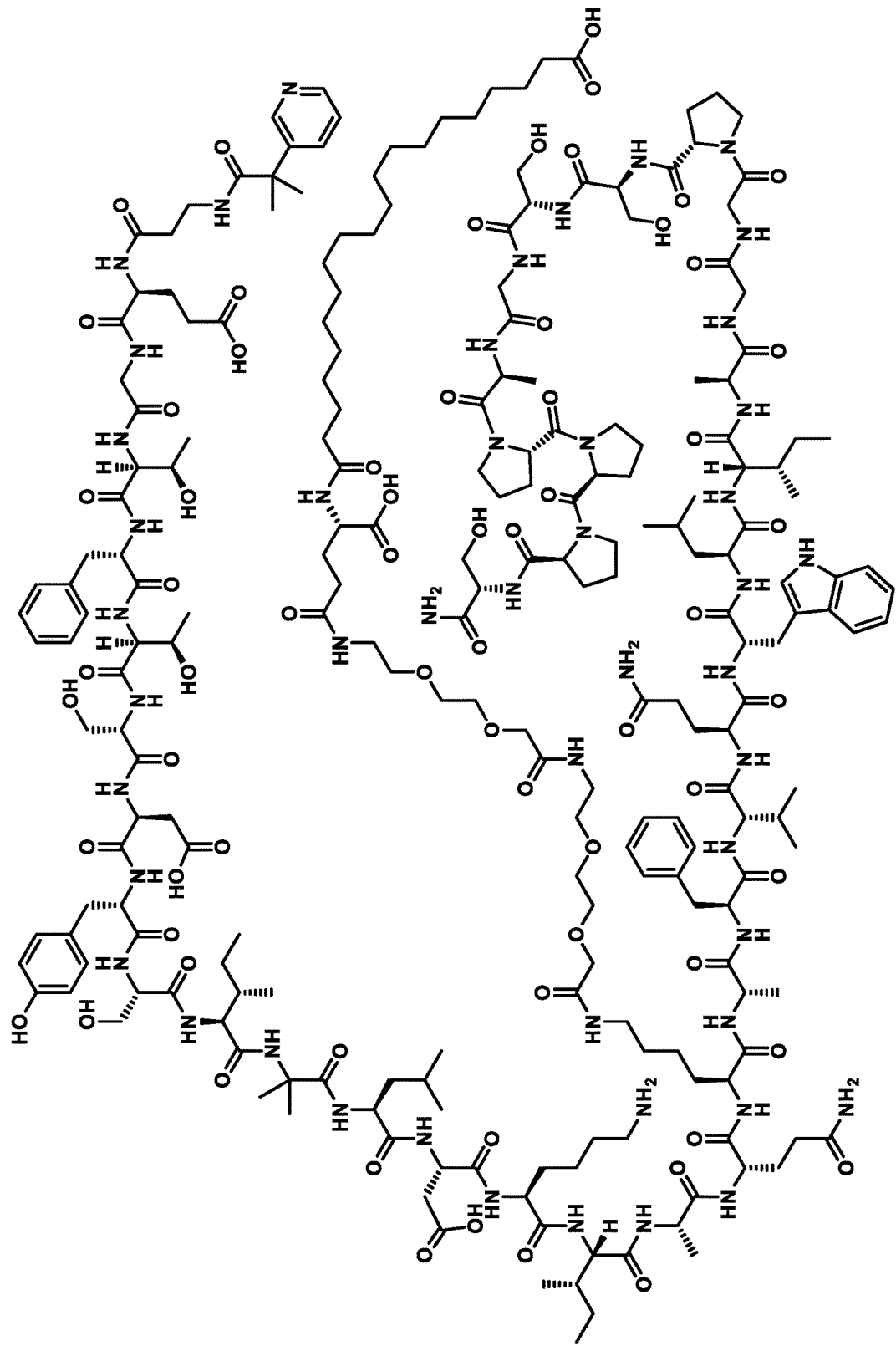
Compound 239
FIG. 1 - Cont'd

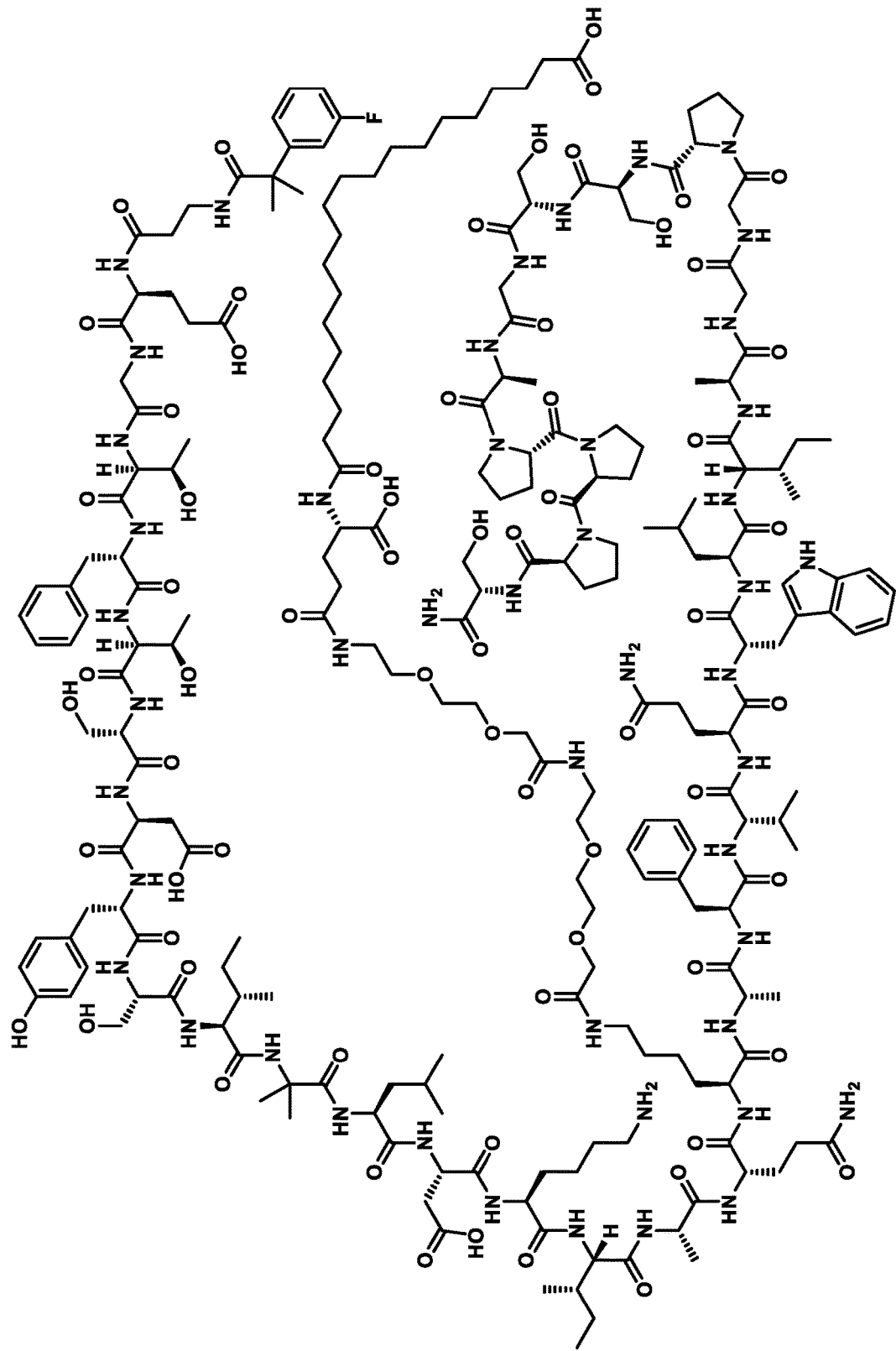
Compound 240
FIG. 1 - Cont'd

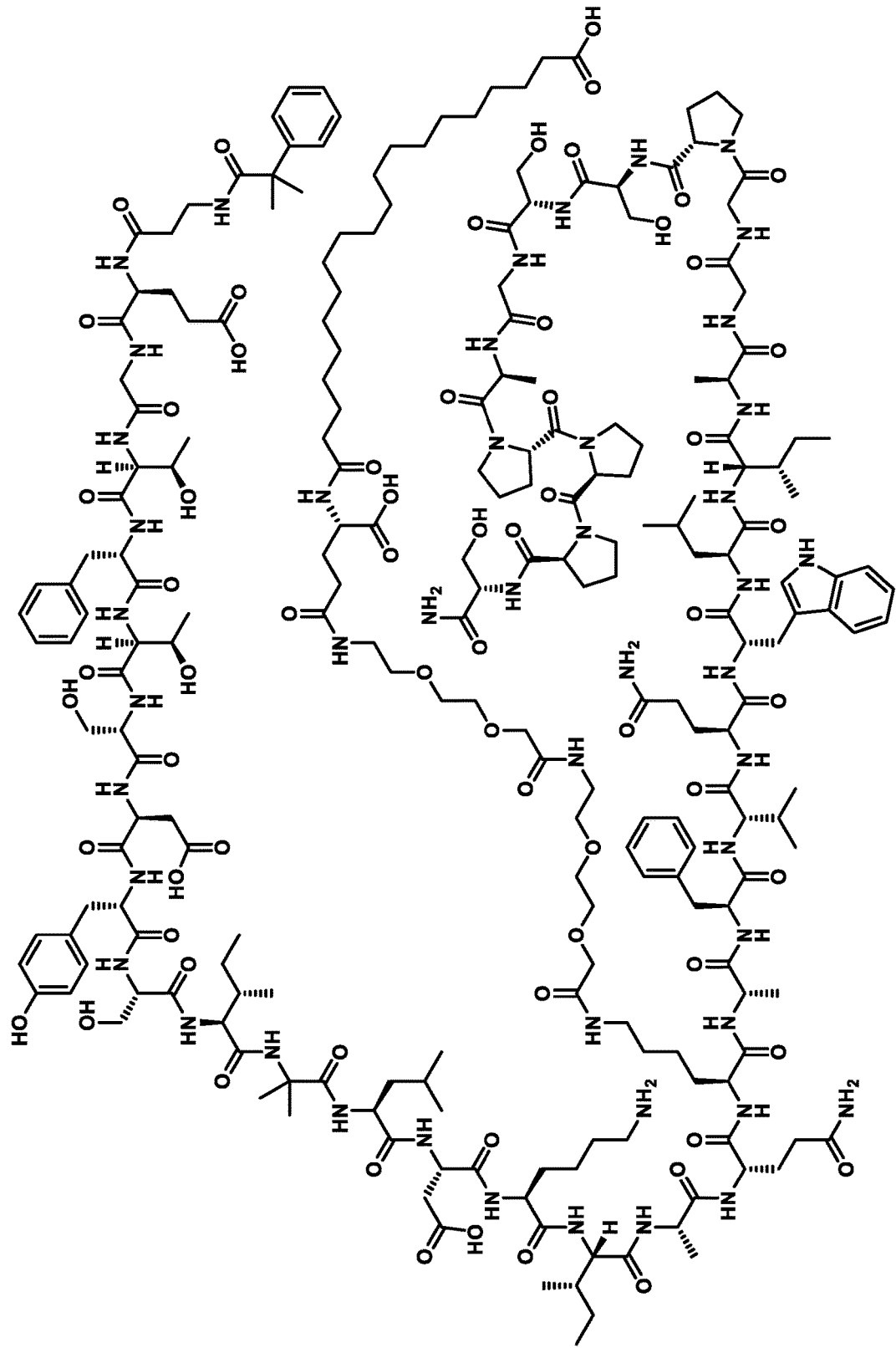
Compound 241
FIG. 1 - Cont'd

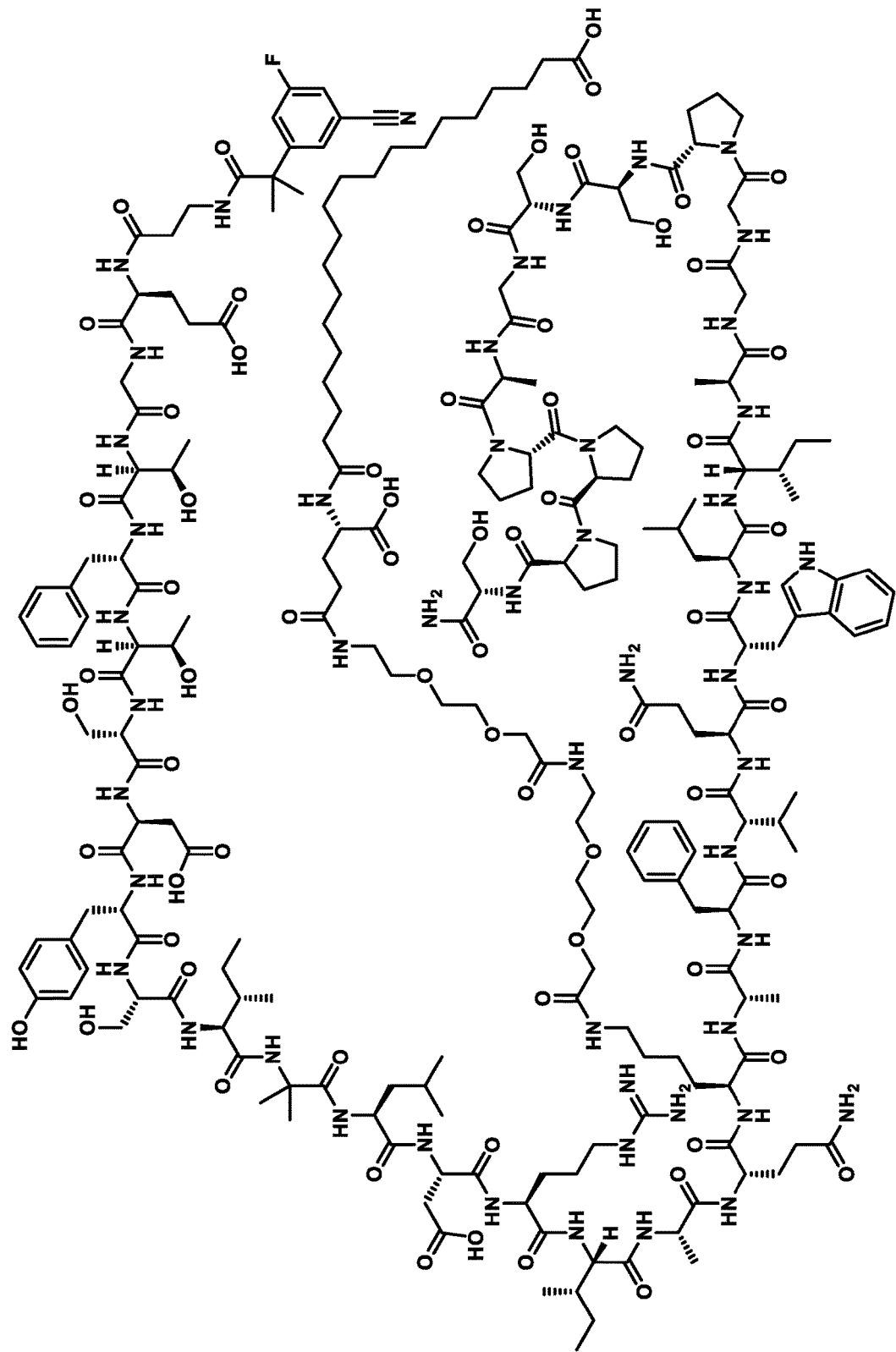
FIG. 1 - Cont'd
Compound 242

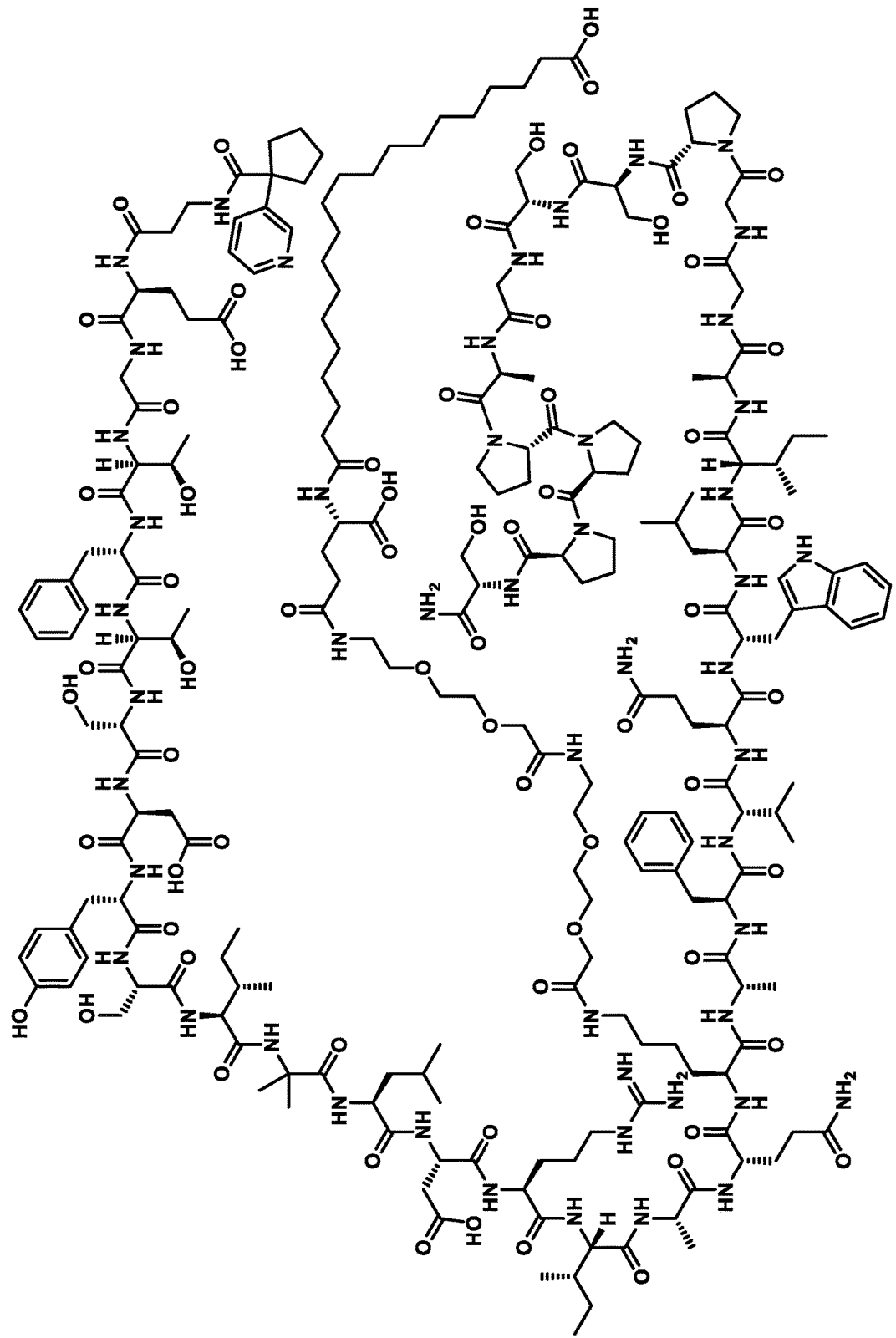
Compound 243
FIG. 1 - Cont'd

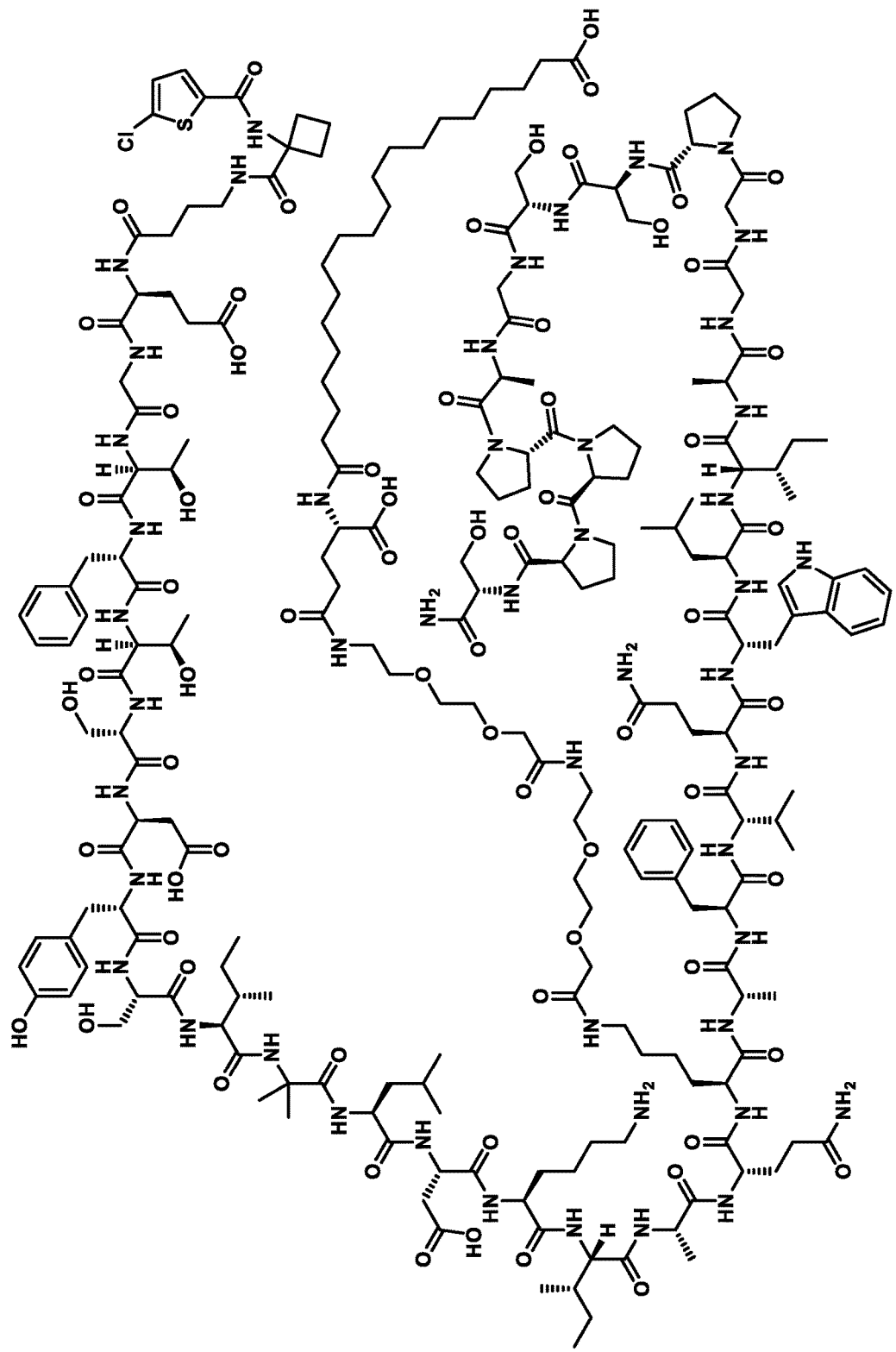
FIG. 1 - Cont'd
Compound 244

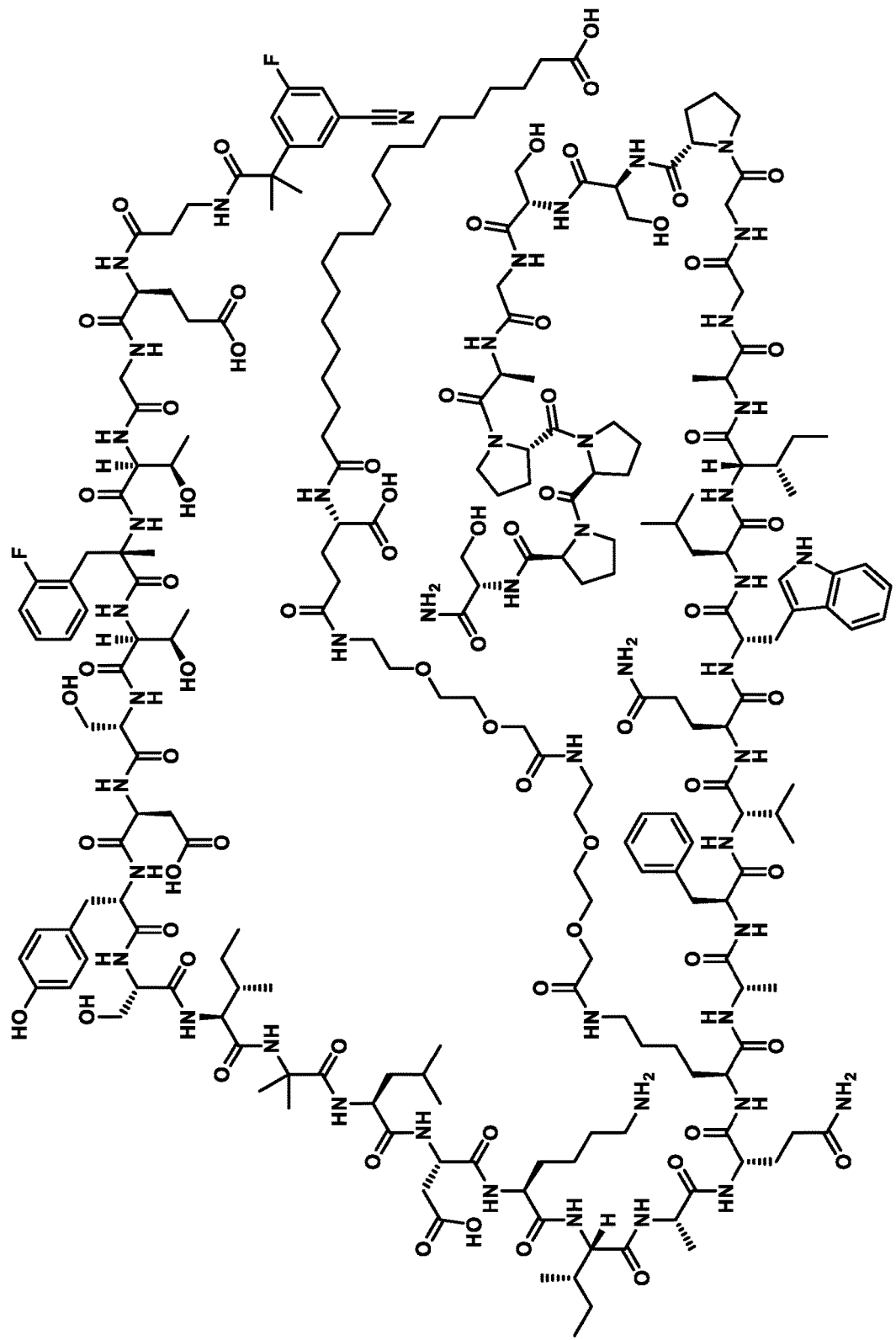
Compound 245
FIG. 1 - Cont'd

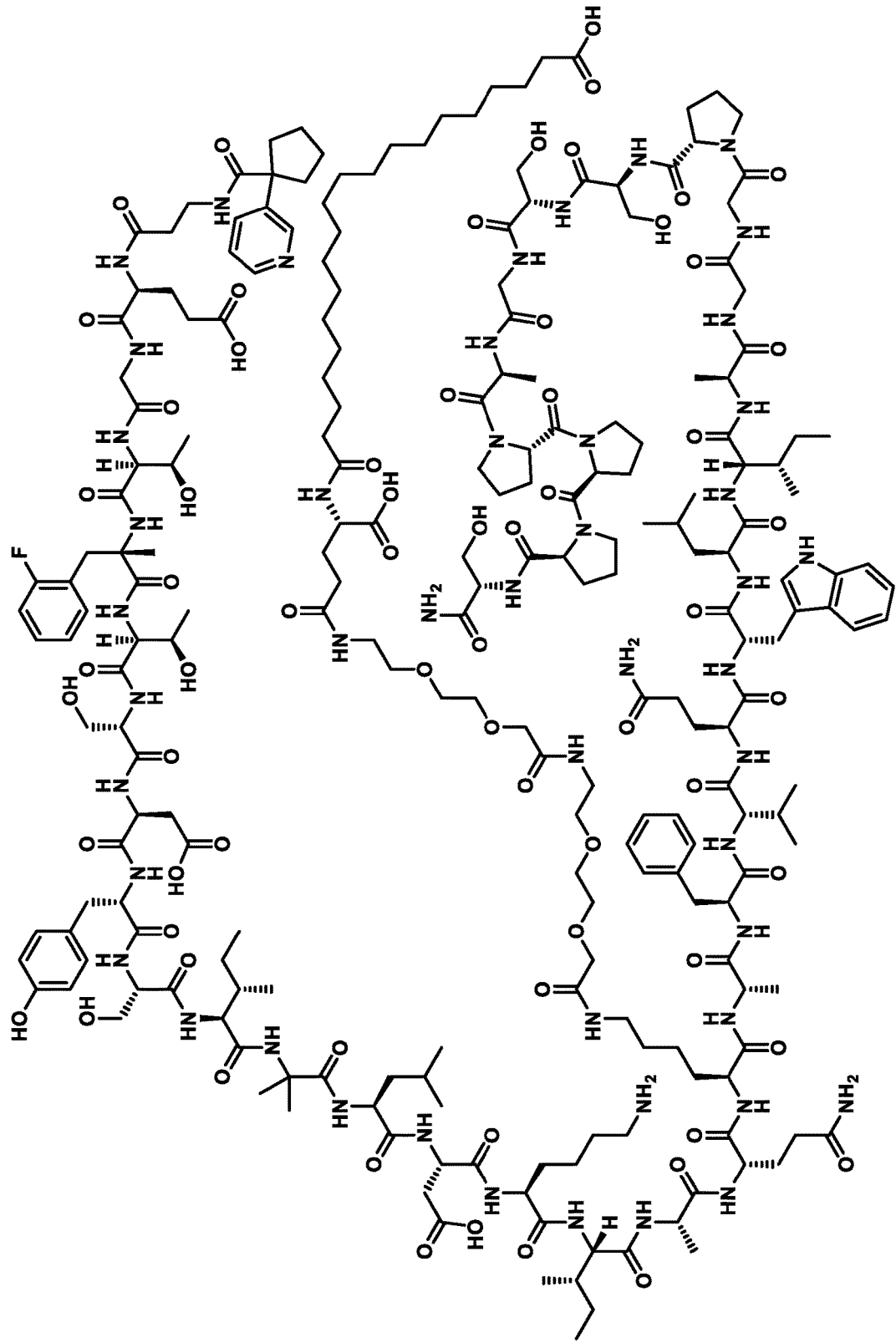
Compound 246
FIG. 1 - Cont'd

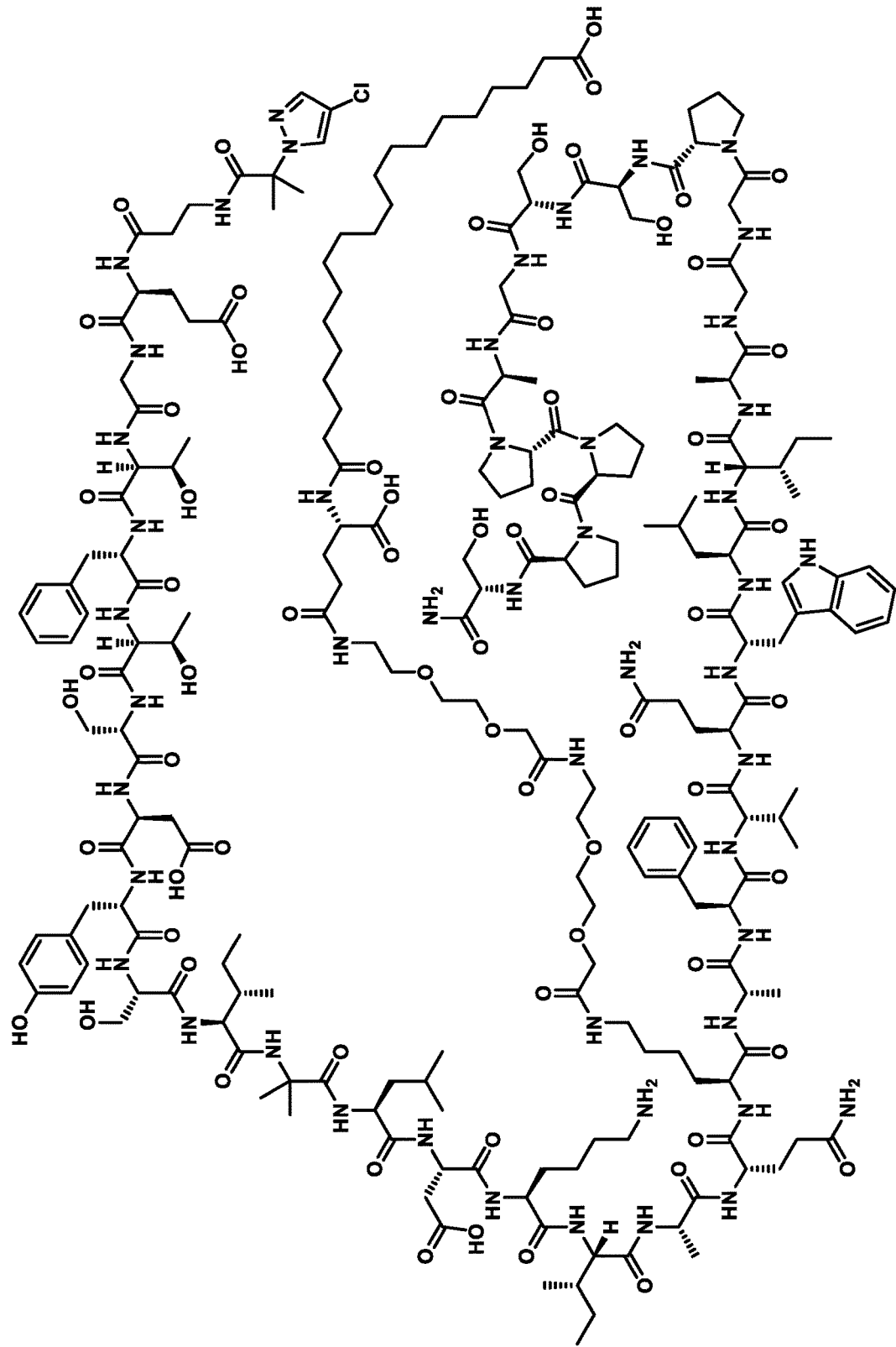
Compound 247
FIG. 1 - Cont'd

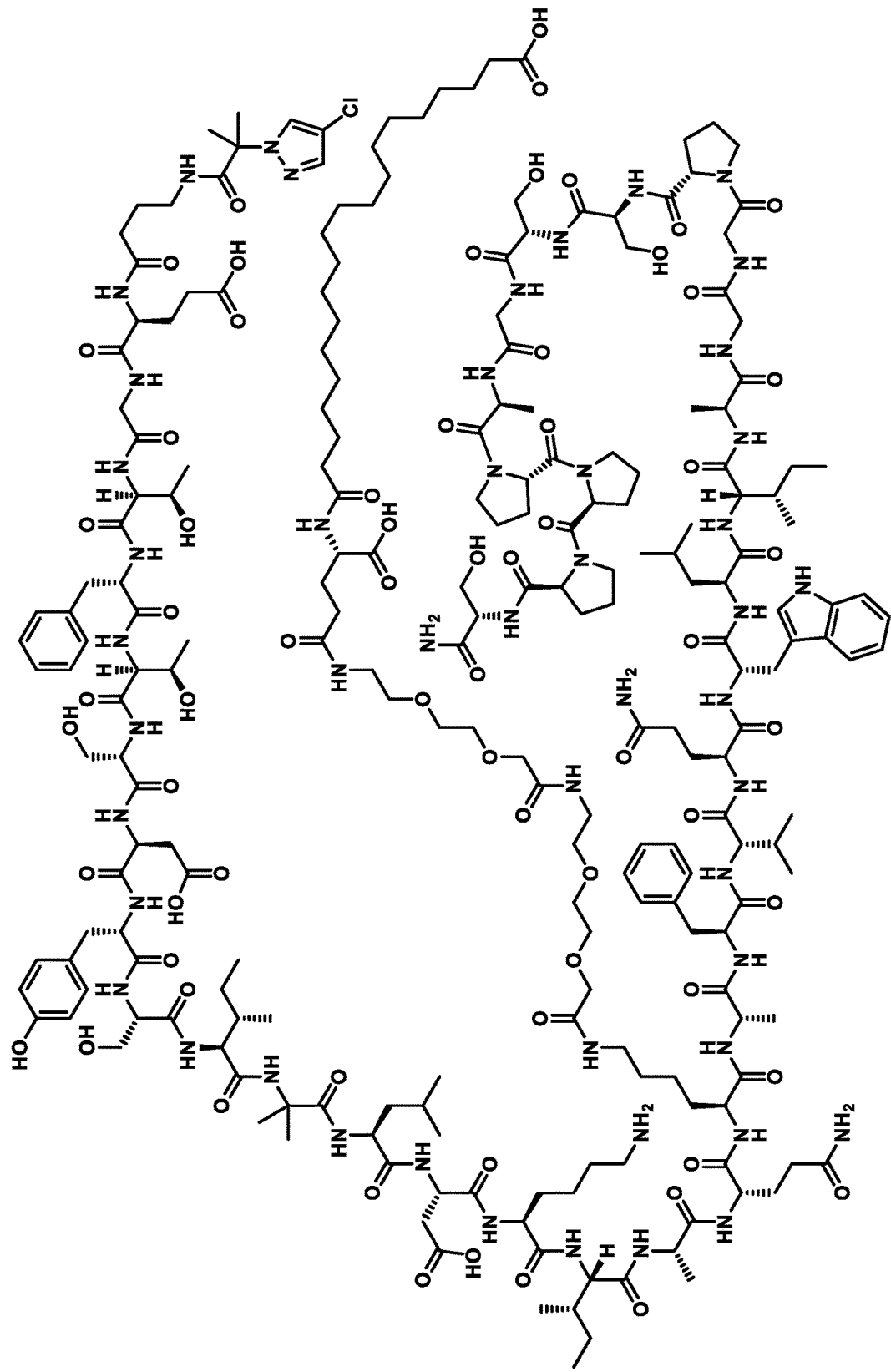
Compound 248
FIG. 1 - Cont'd

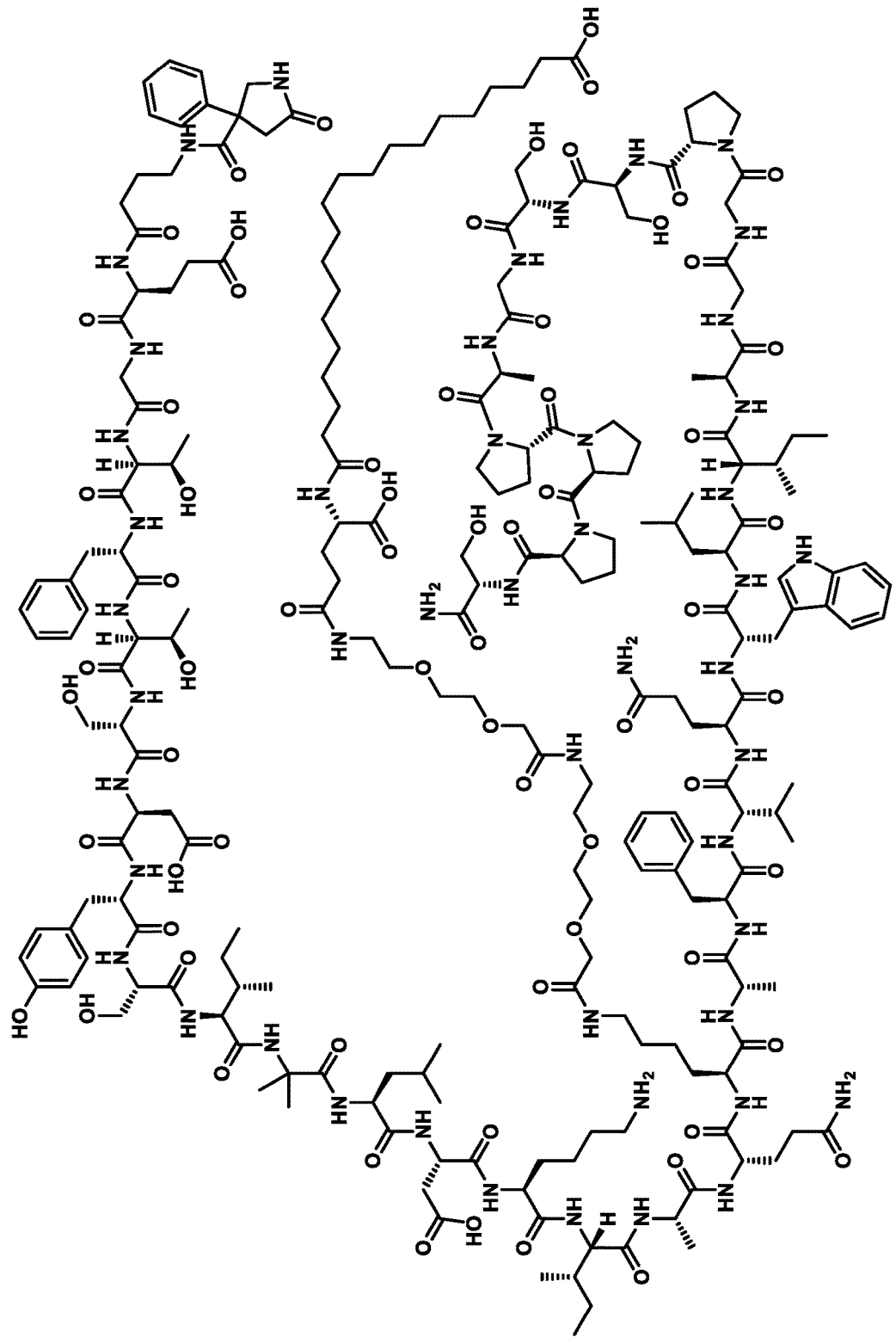
Compound 249
FIG. 1 - Cont'd

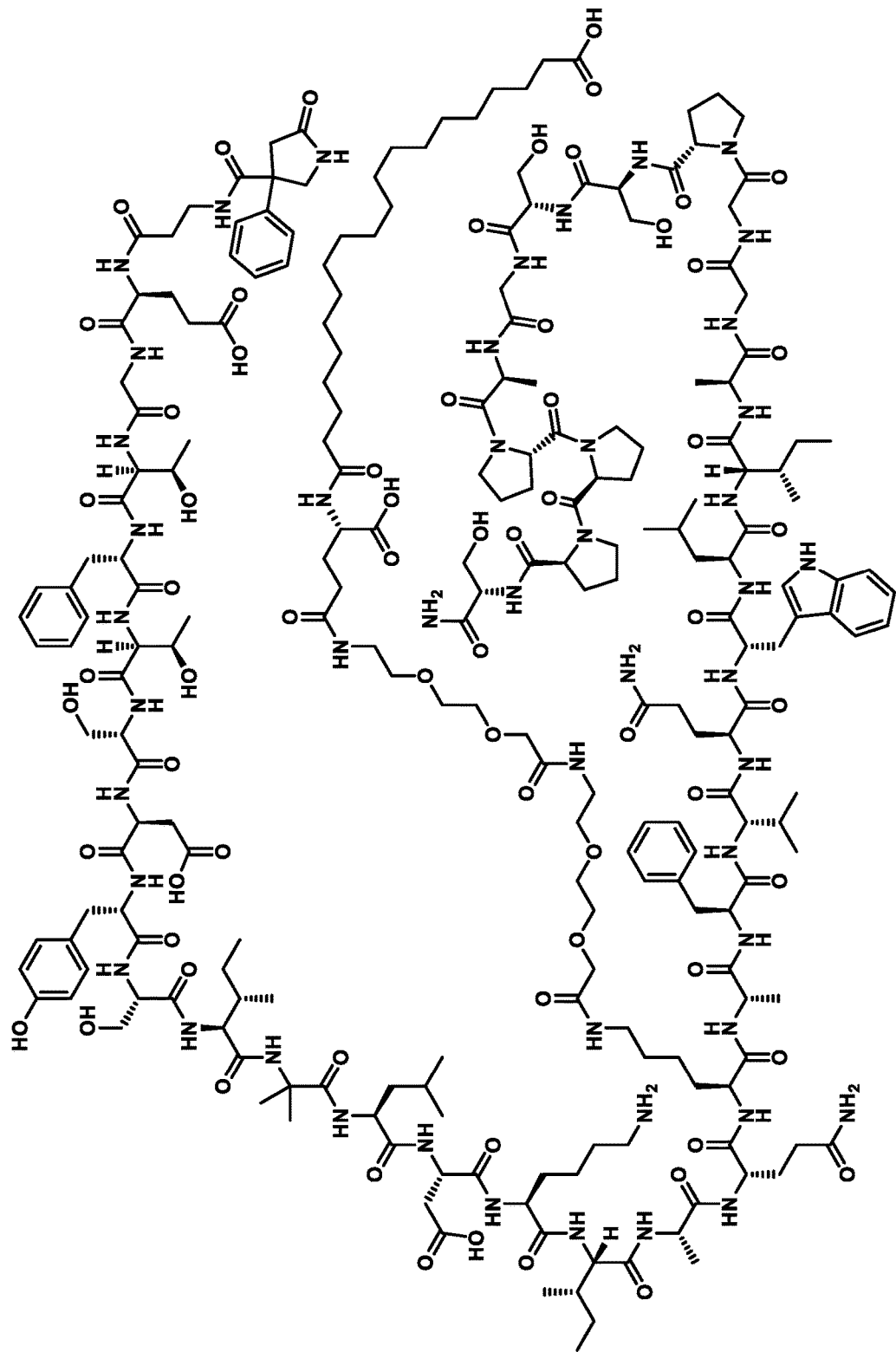
Compound 250
FIG. 1 - Cont'd

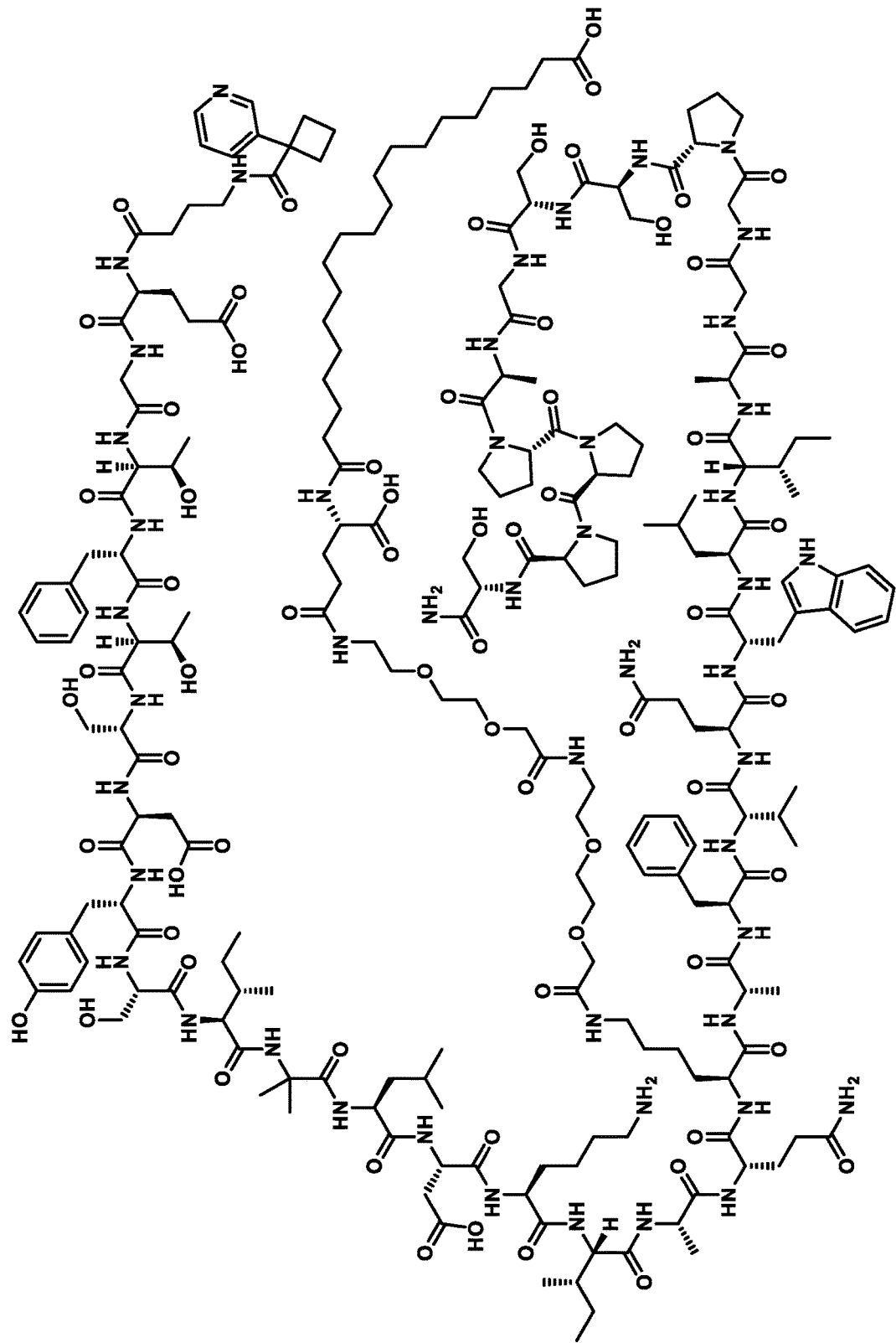
Compound 251
FIG. 1 - Cont'd

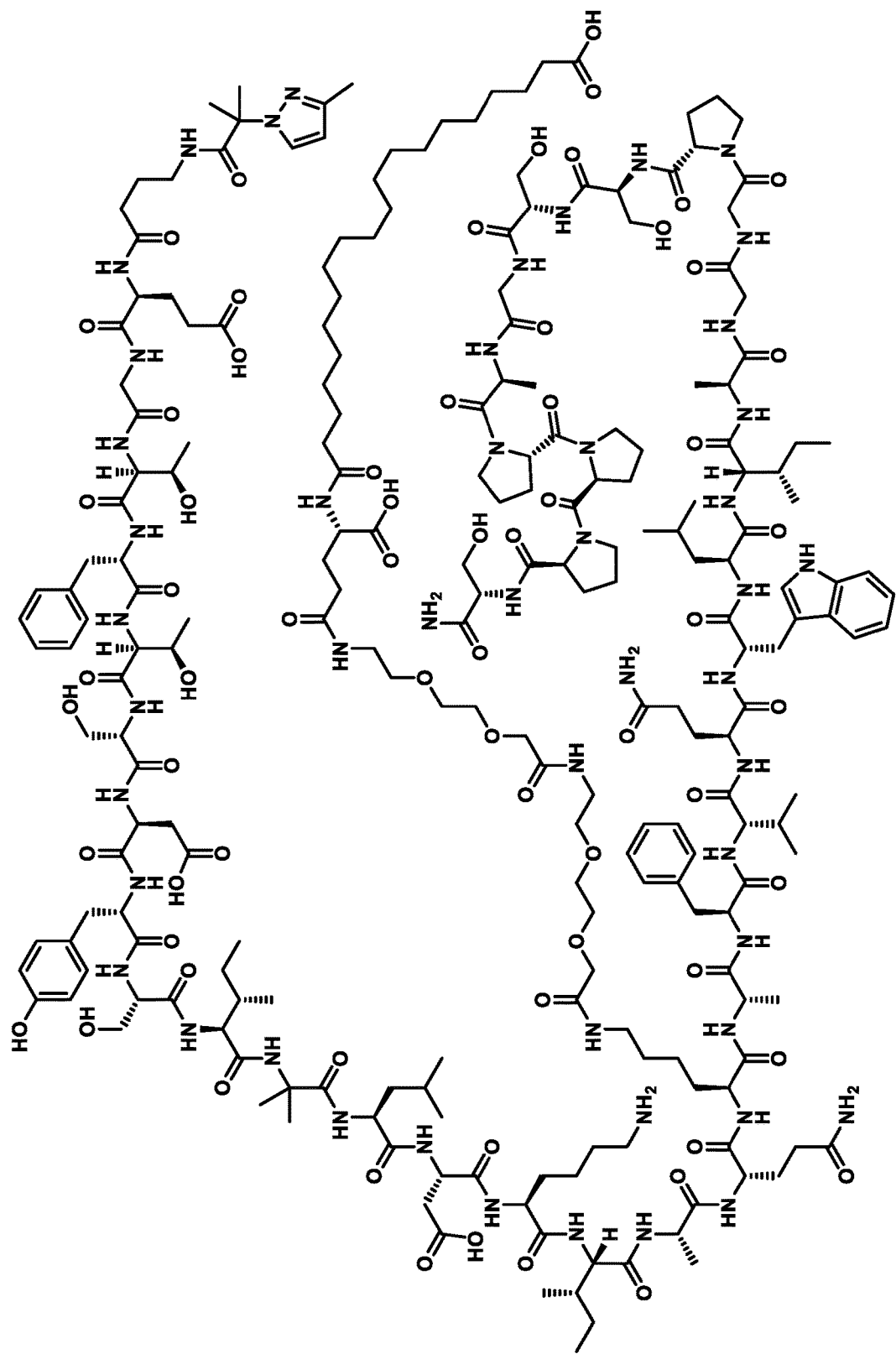
Compound 252
FIG. 1 - Cont'd

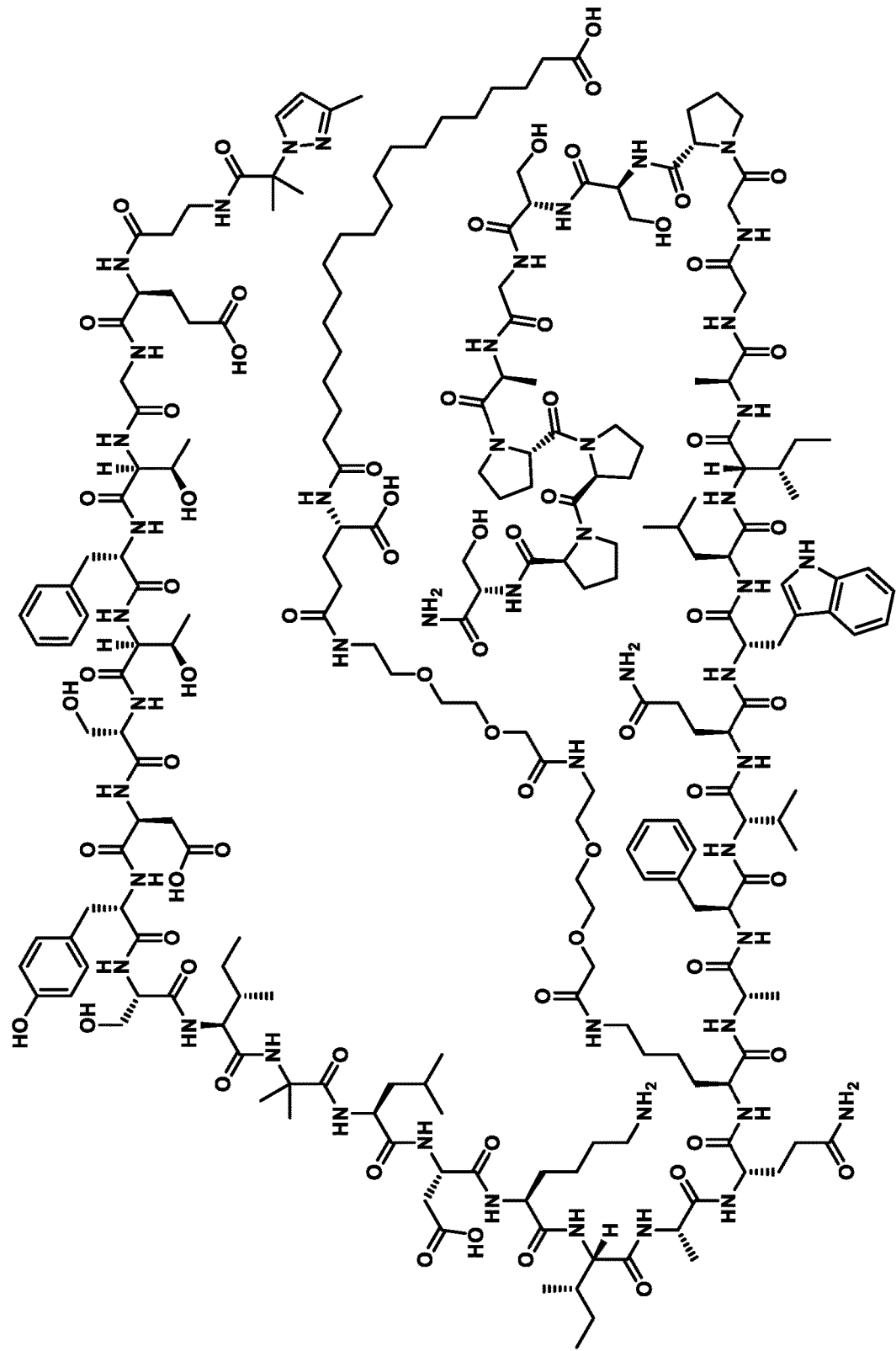
Compound 253
FIG. 1 - Cont'd

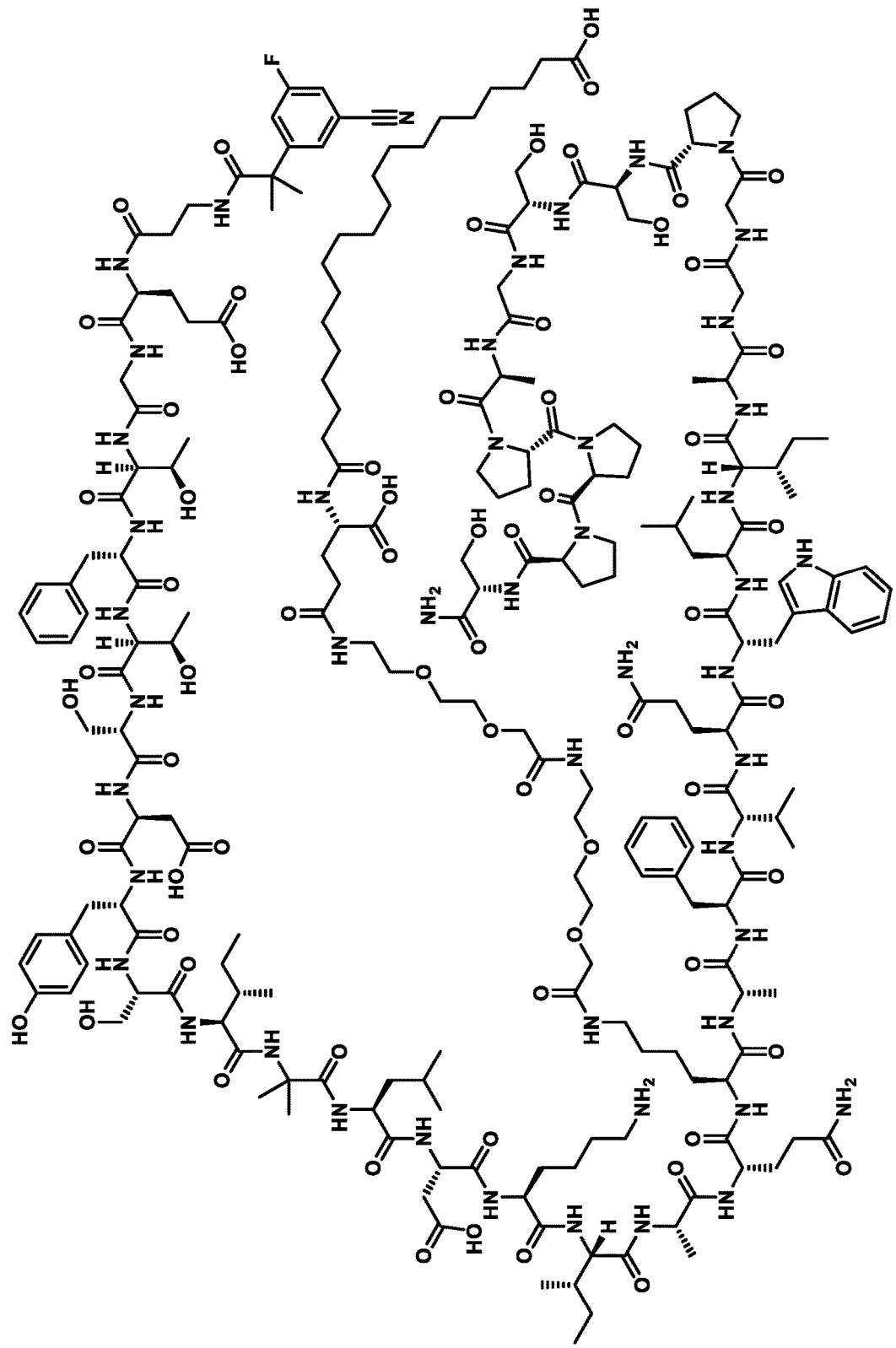
Compound 254
FIG. 1 - Cont'd

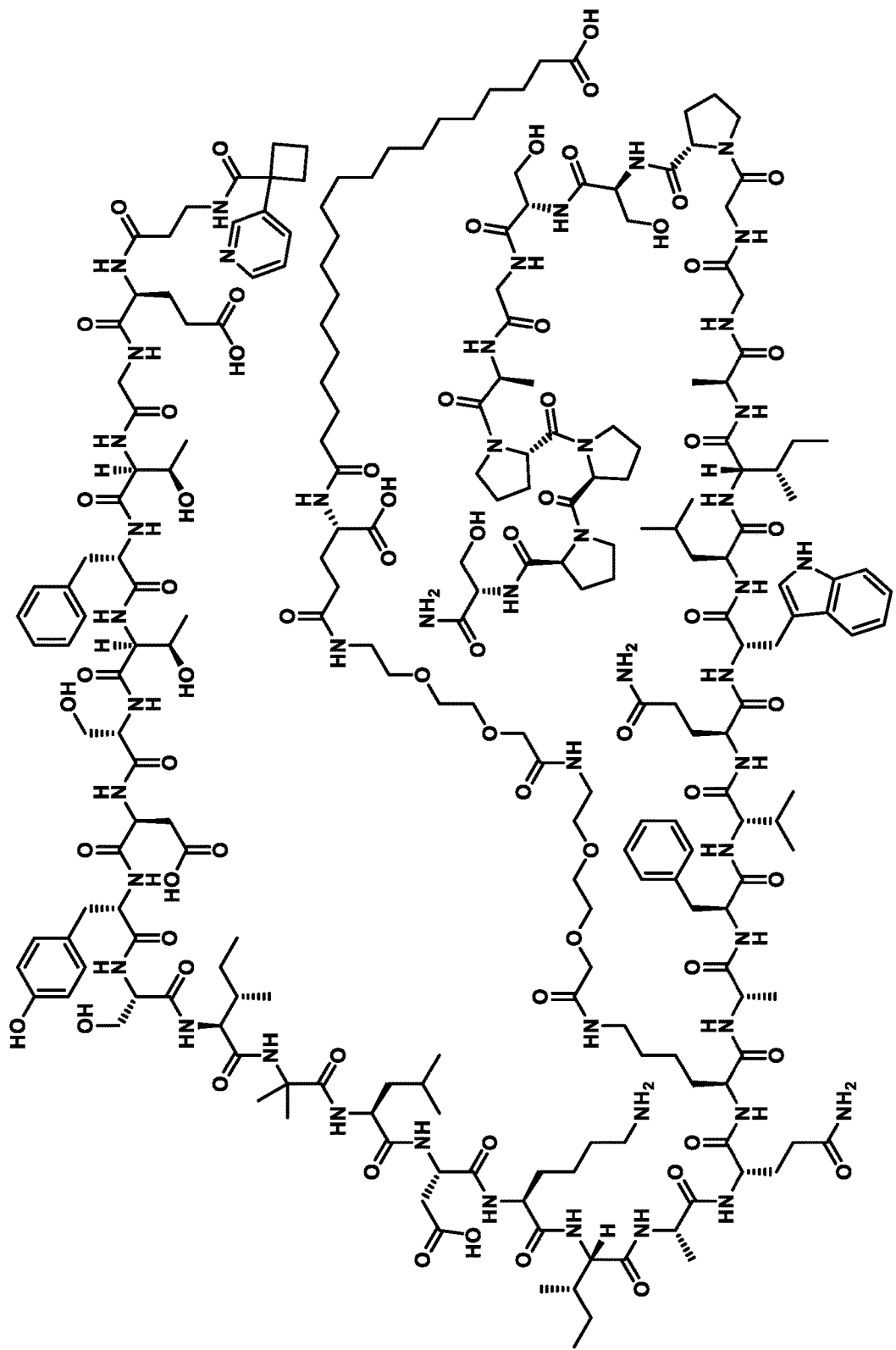
Compound 255
FIG. 1 - Cont'd

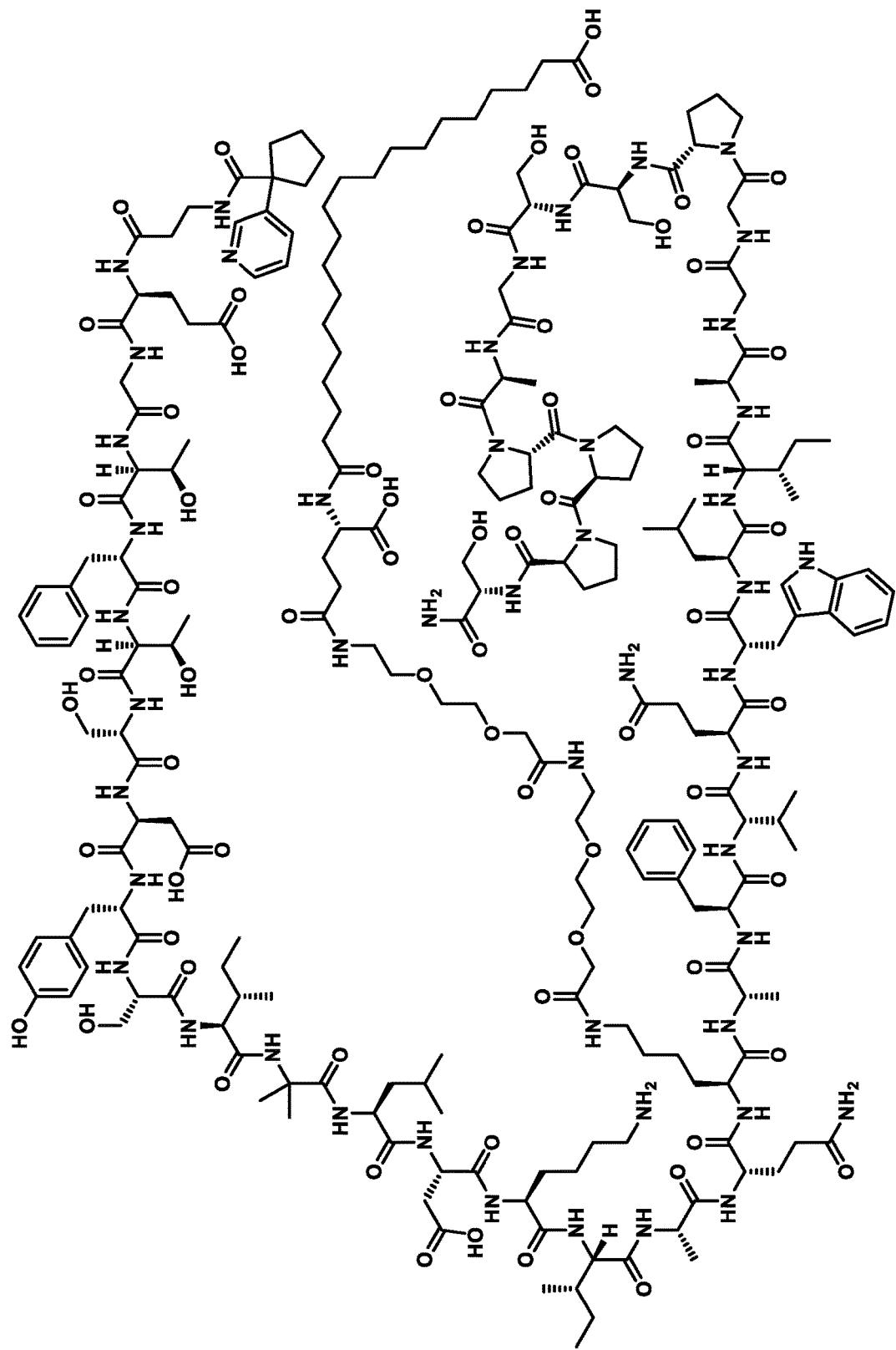
Compound 256
FIG. 1 - Cont'd

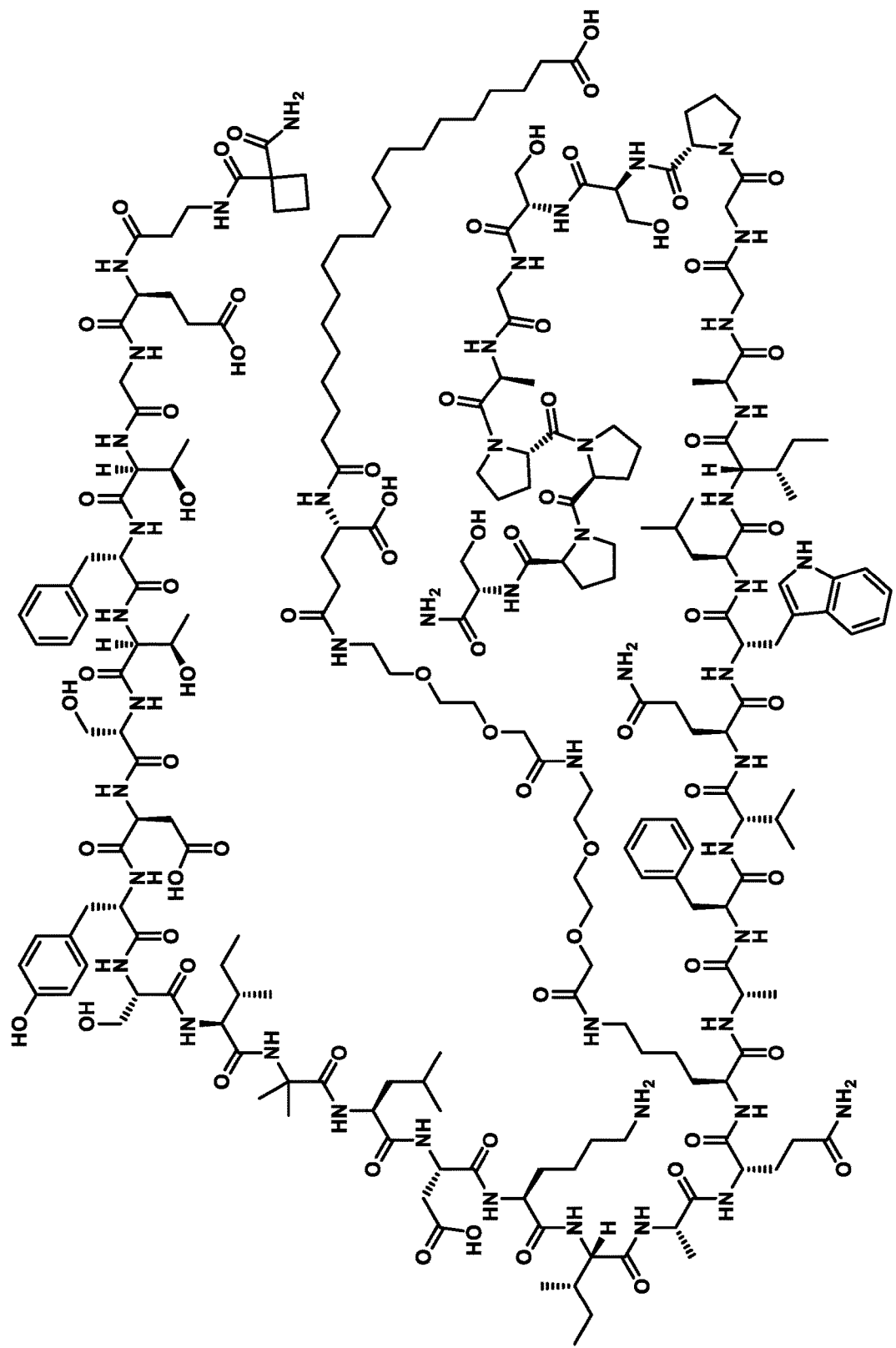
Compound 257
FIG. 1 - Cont'd

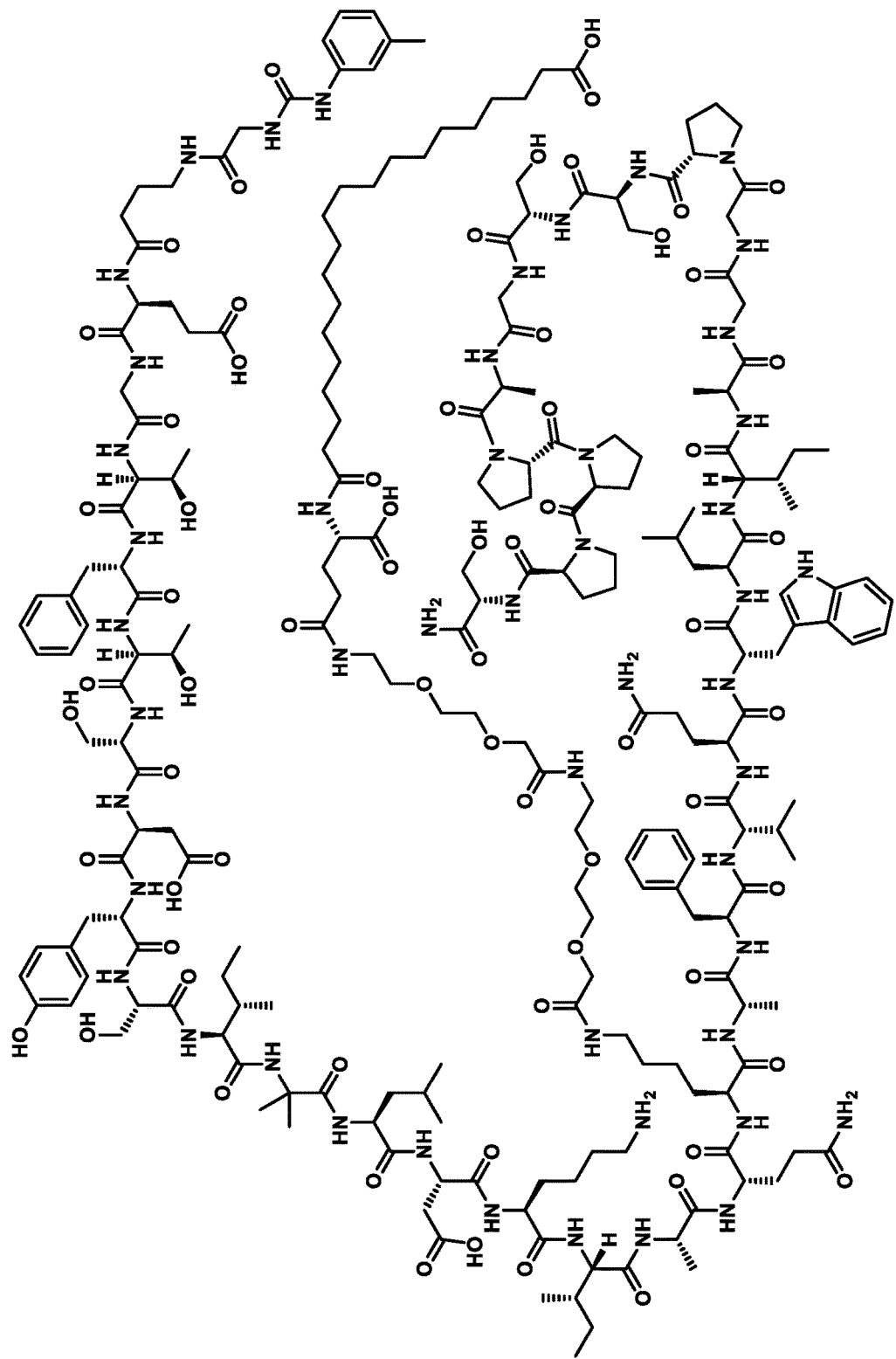
Compound 258
FIG. 1 - Cont'd

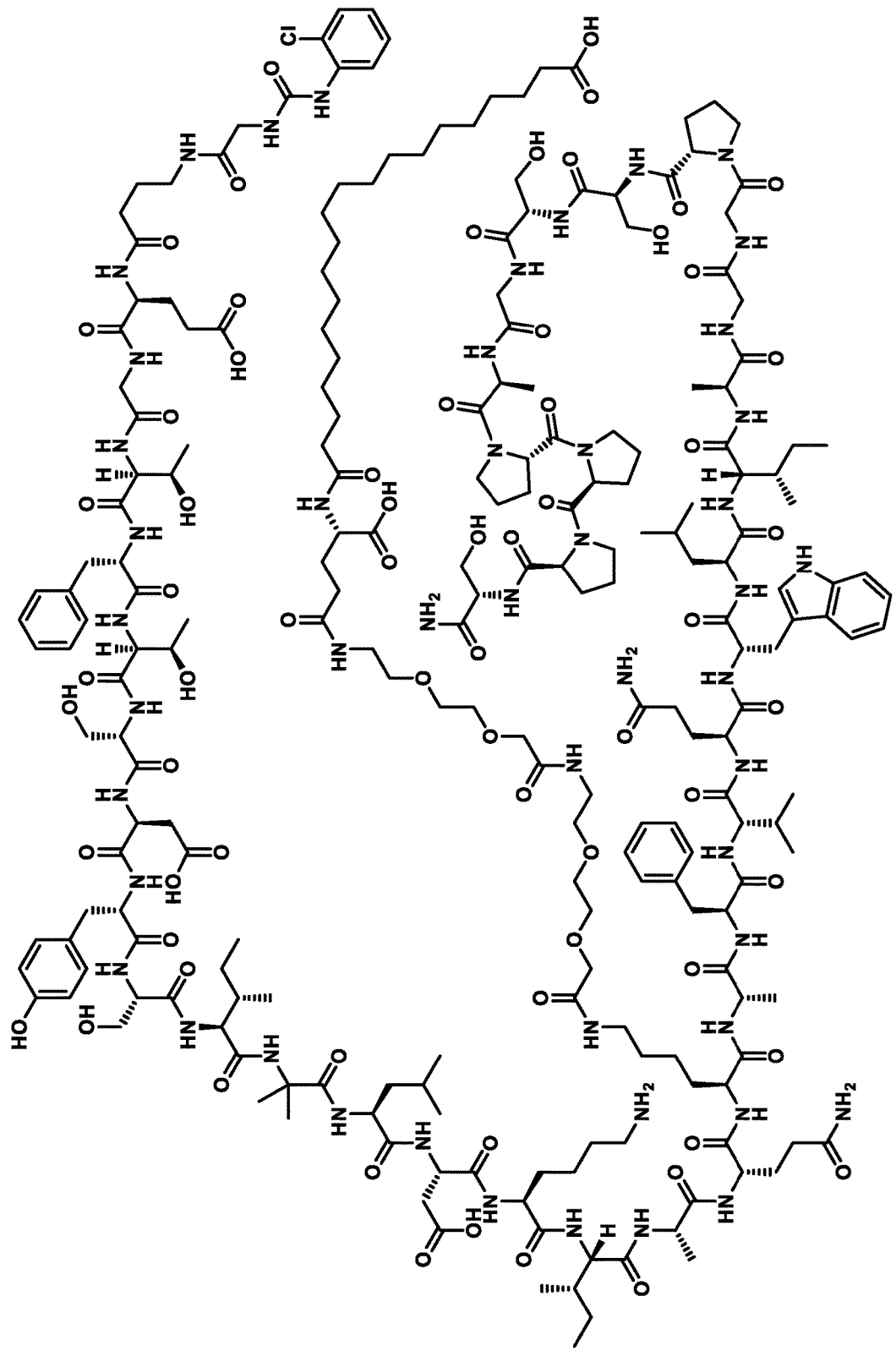
Compound 259
FIG. 1 - Cont'd

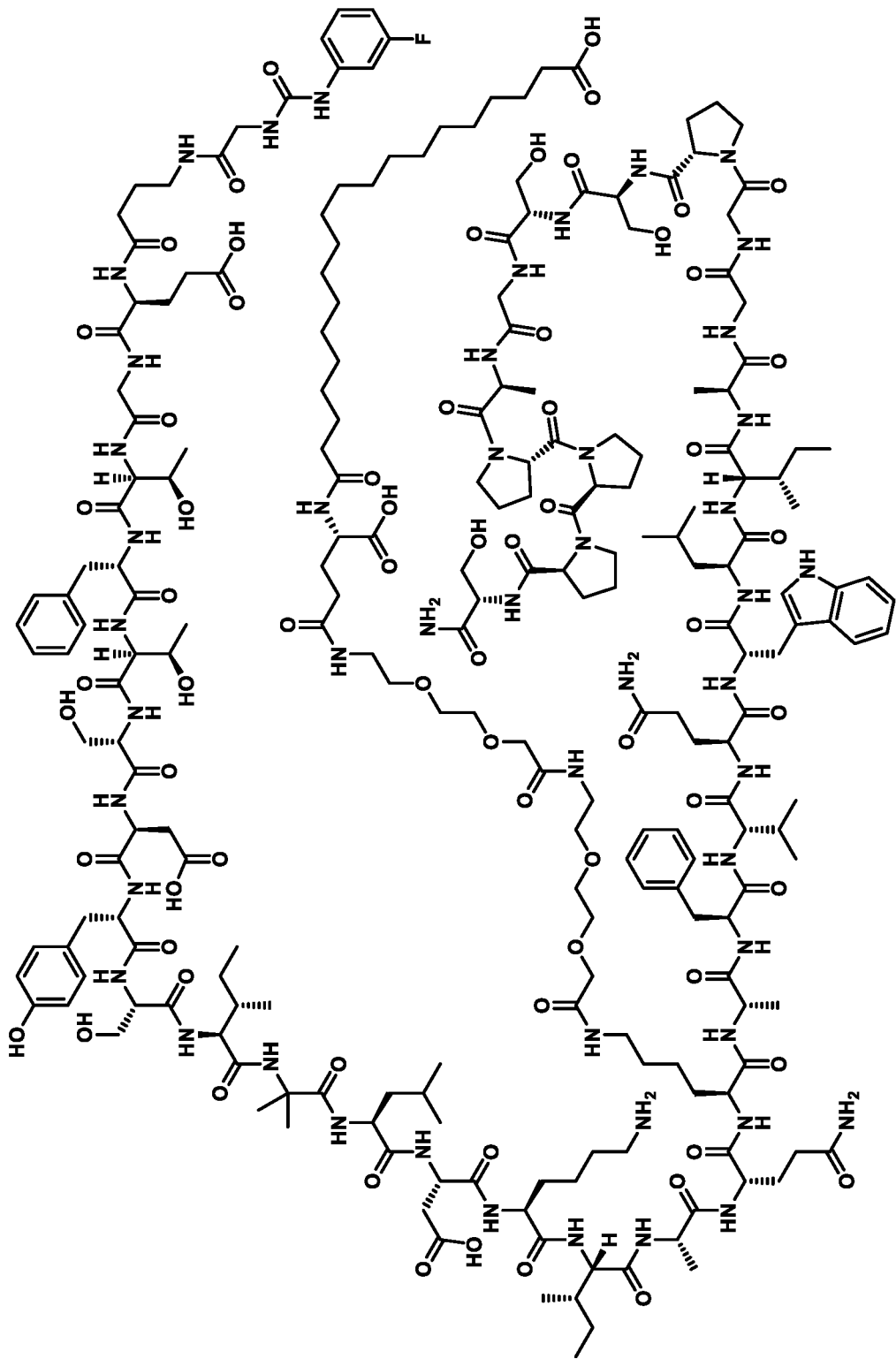
Compound 260
FIG. 1 - Cont'd

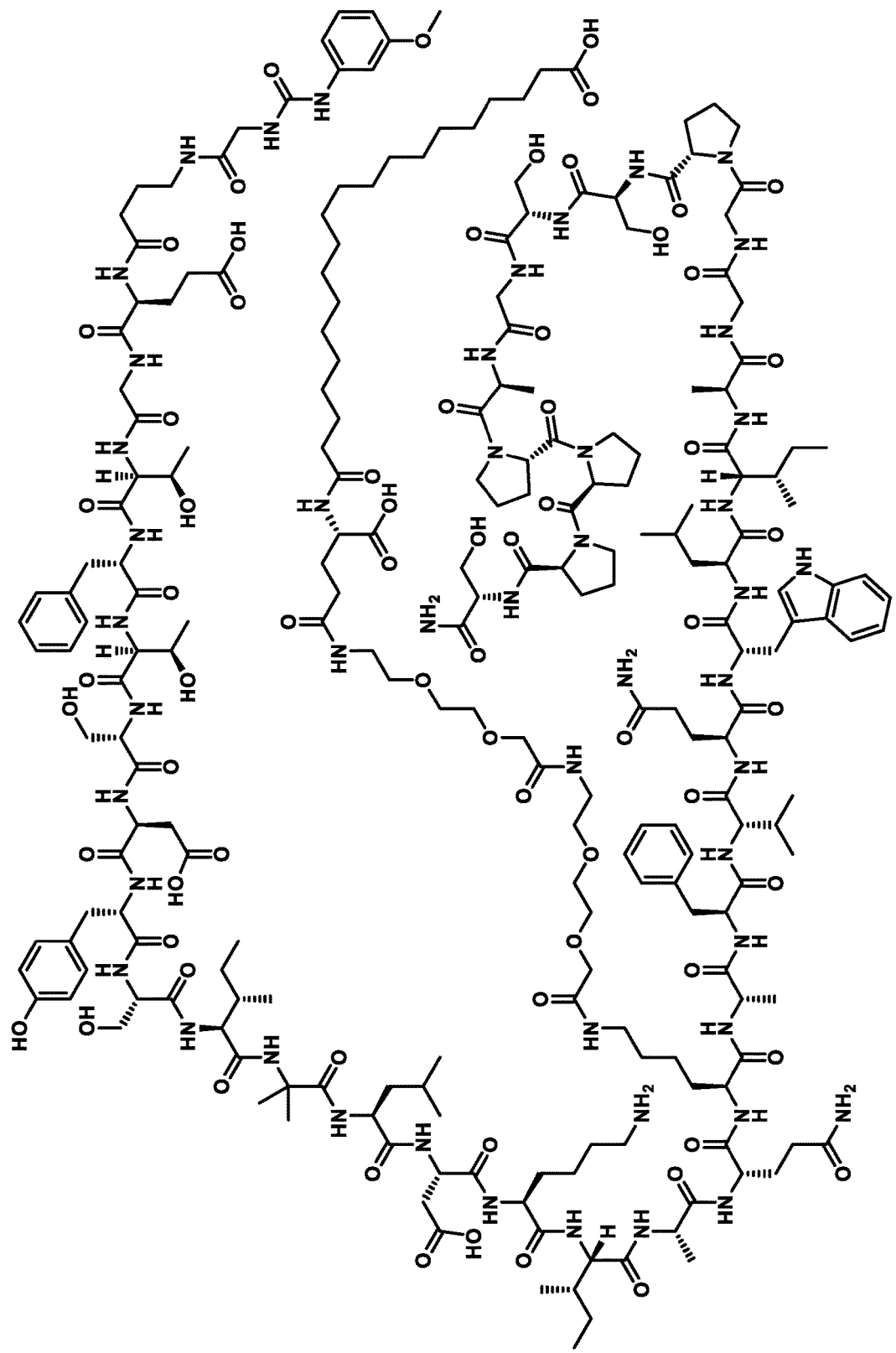
Compound 261
FIG. 1 - Cont'd

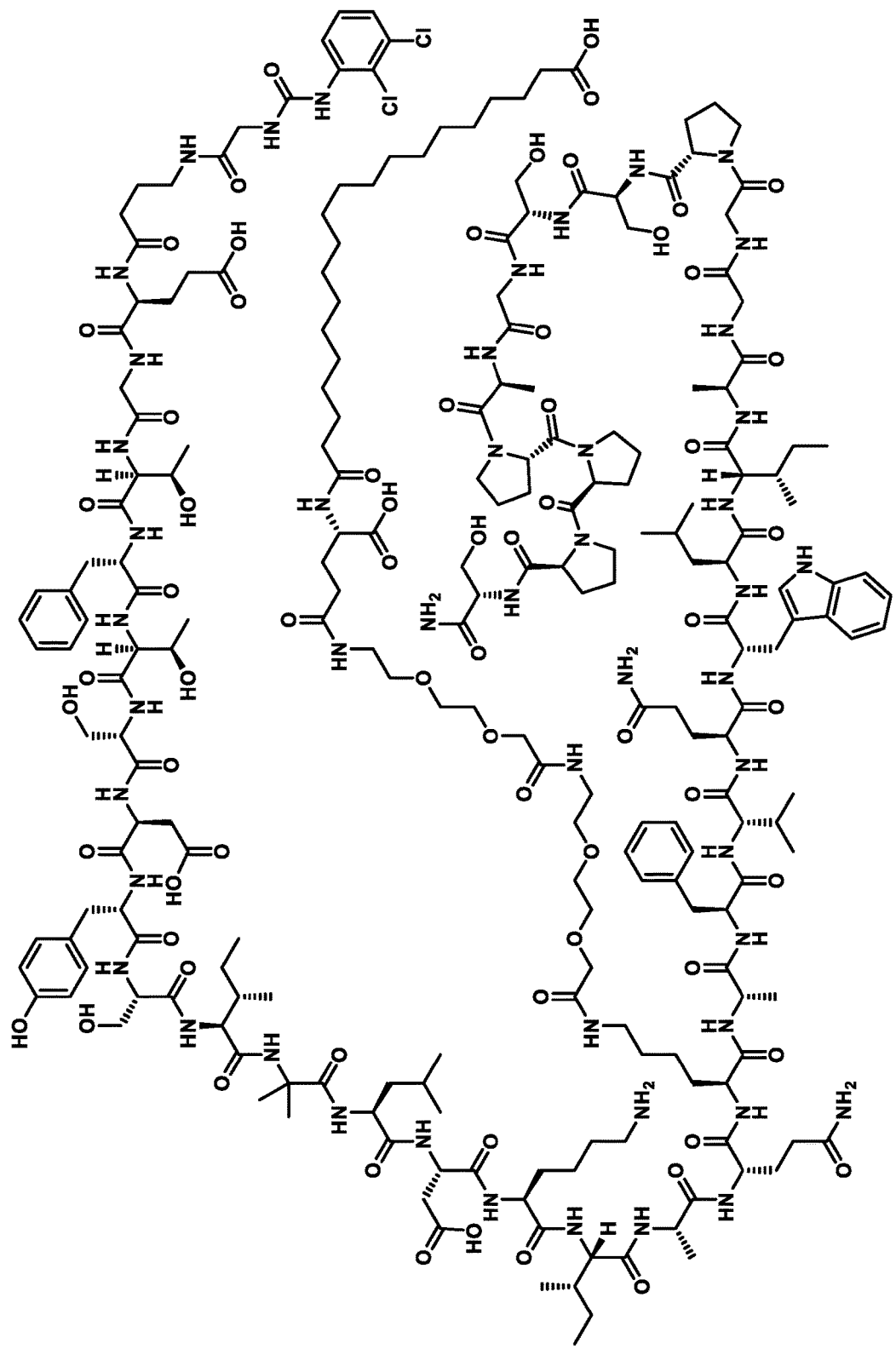
Compound 262
FIG. 1 - Cont'd

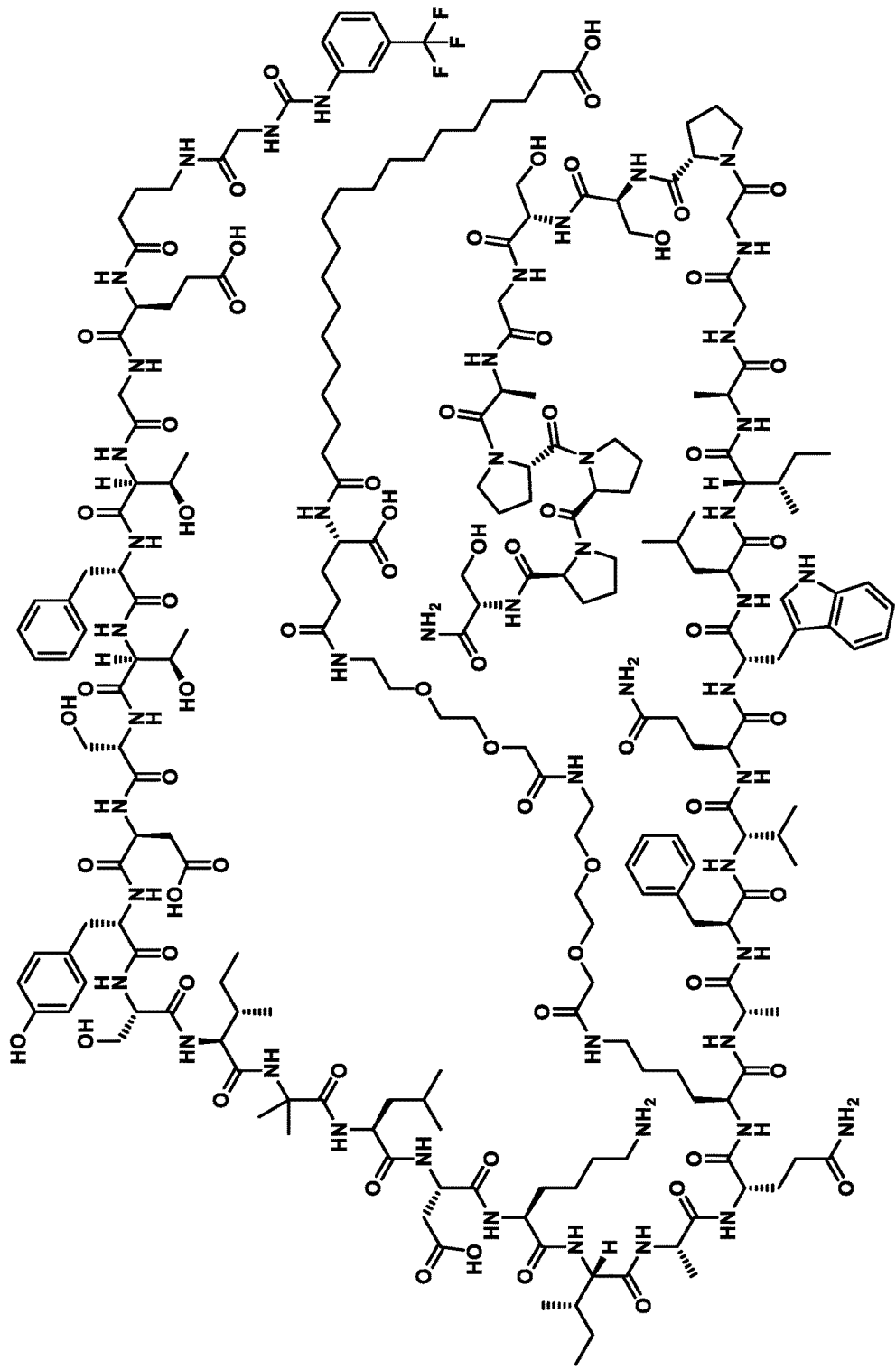
Compound 263
FIG. 1 - Cont'd

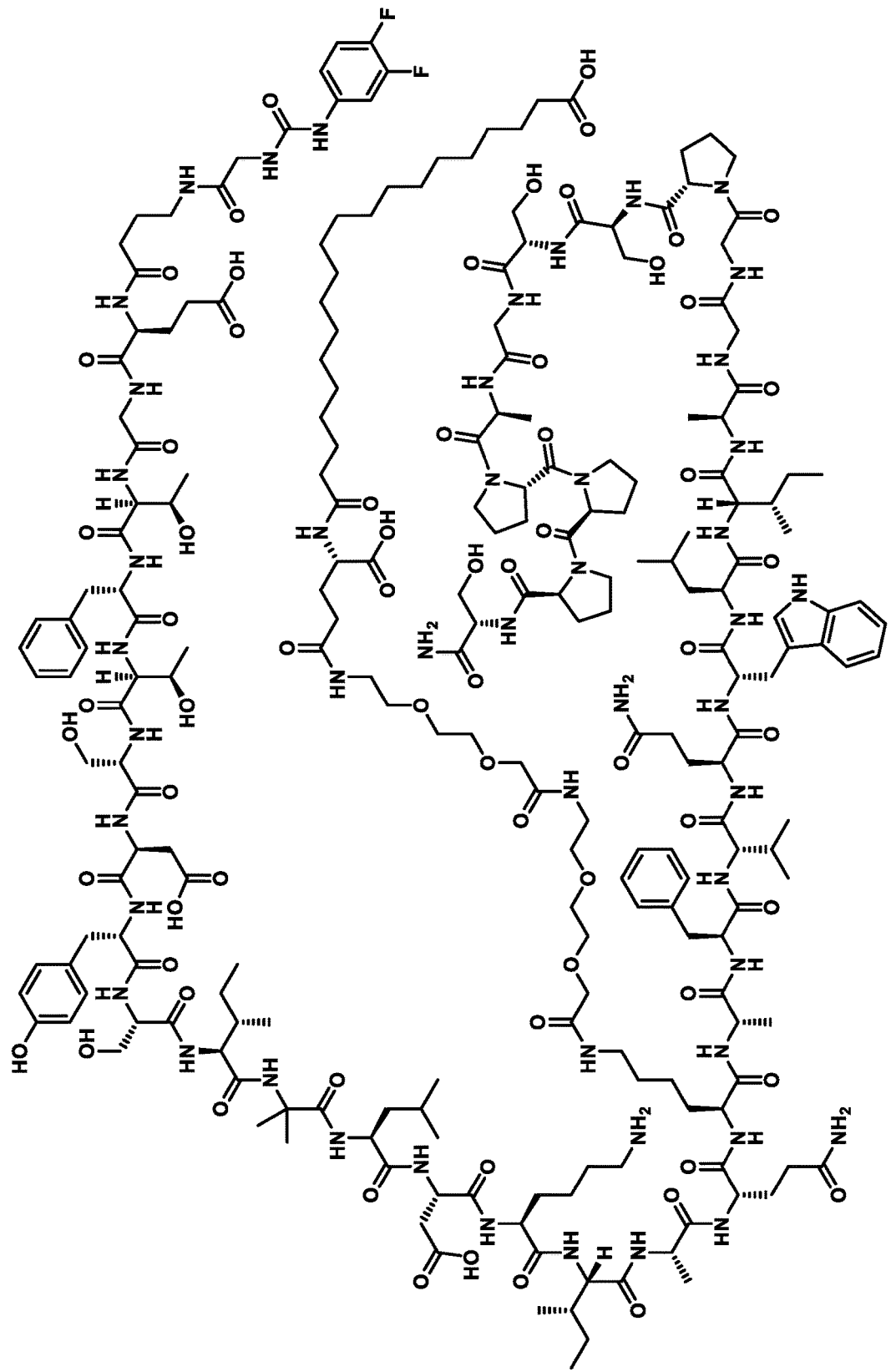
Compound 264
FIG. 1 - Cont'd

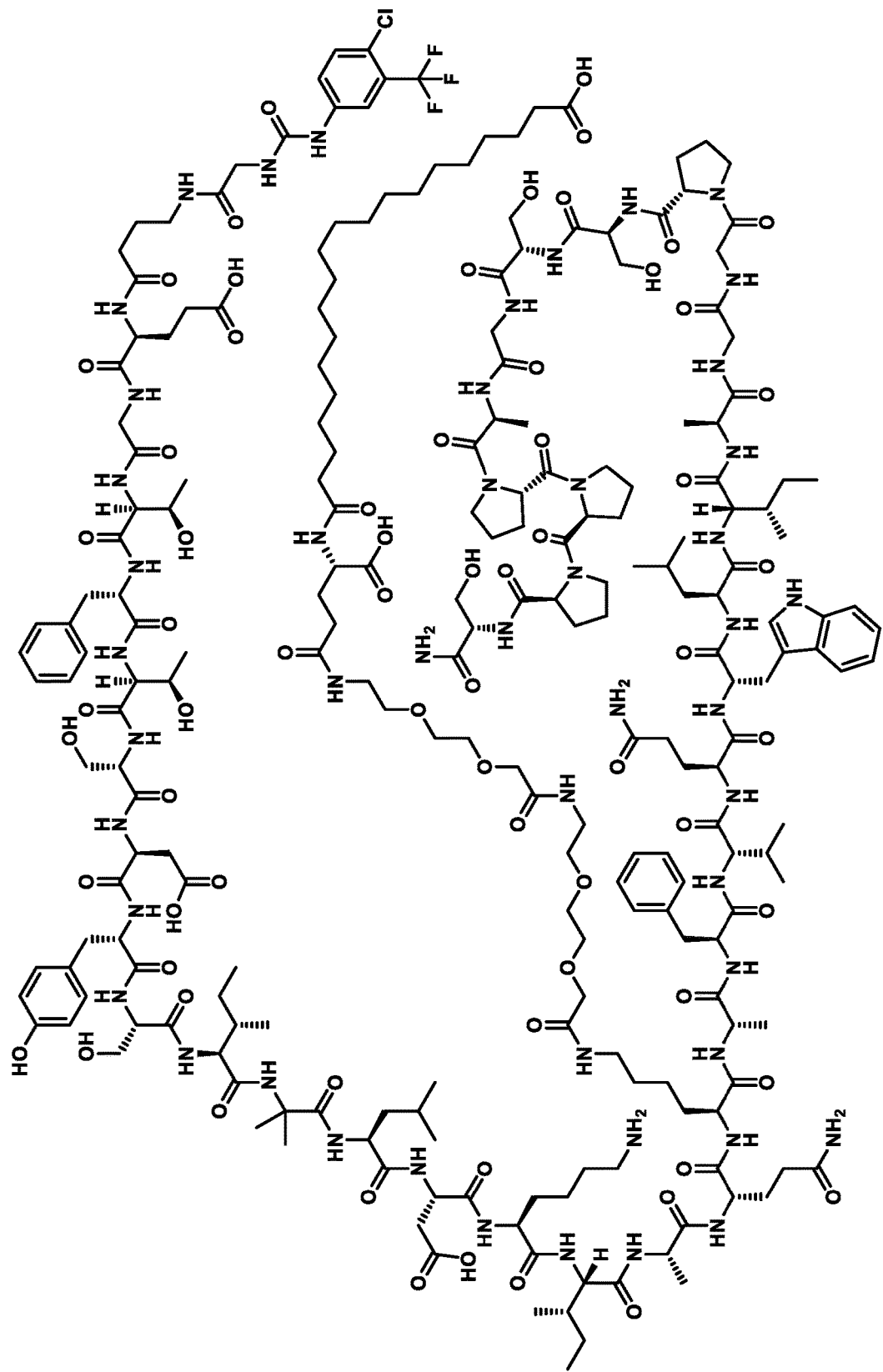
Compound 265
FIG. 1 - Cont'd

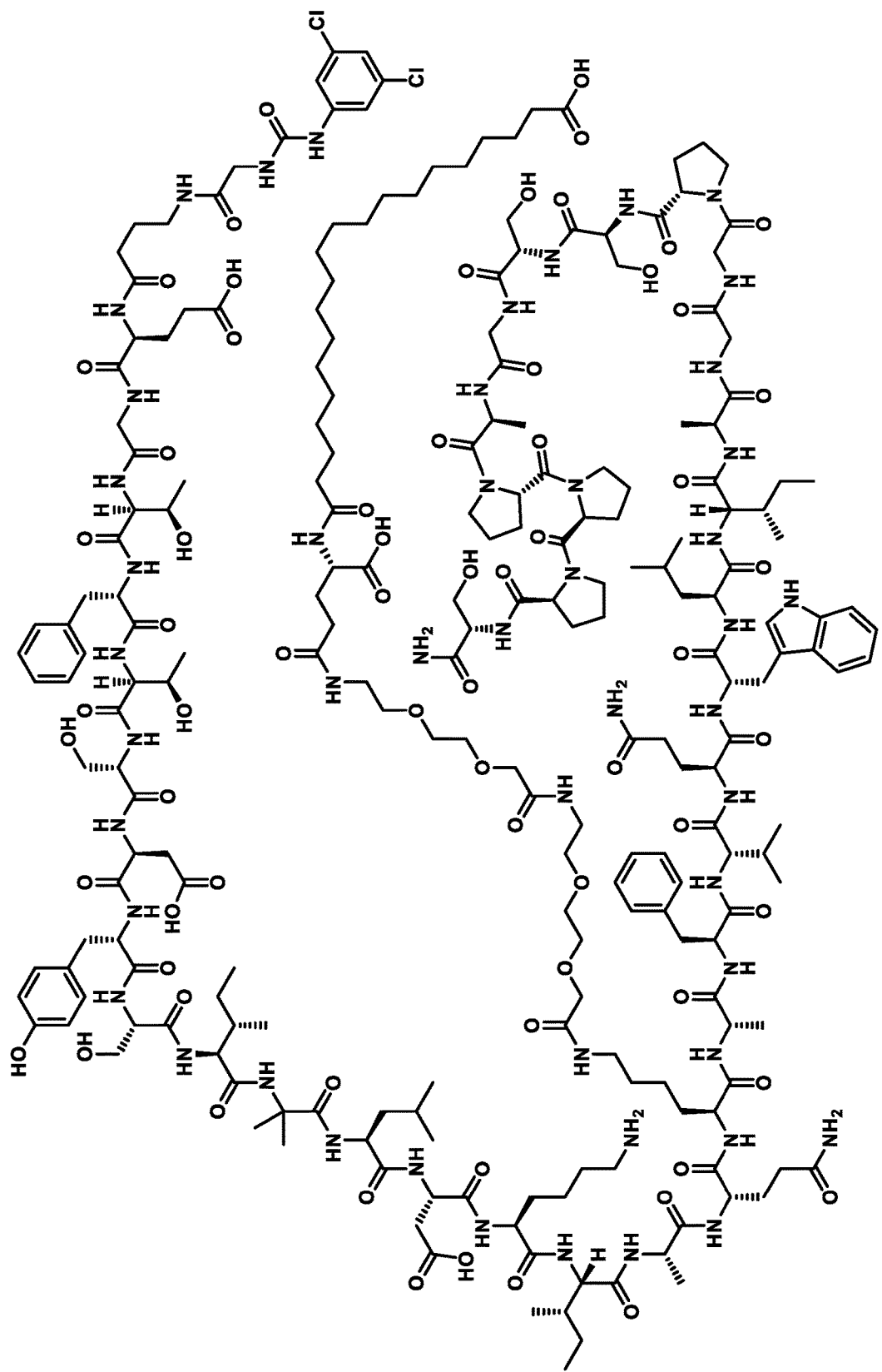
Compound 266
FIG. 1 - Cont'd

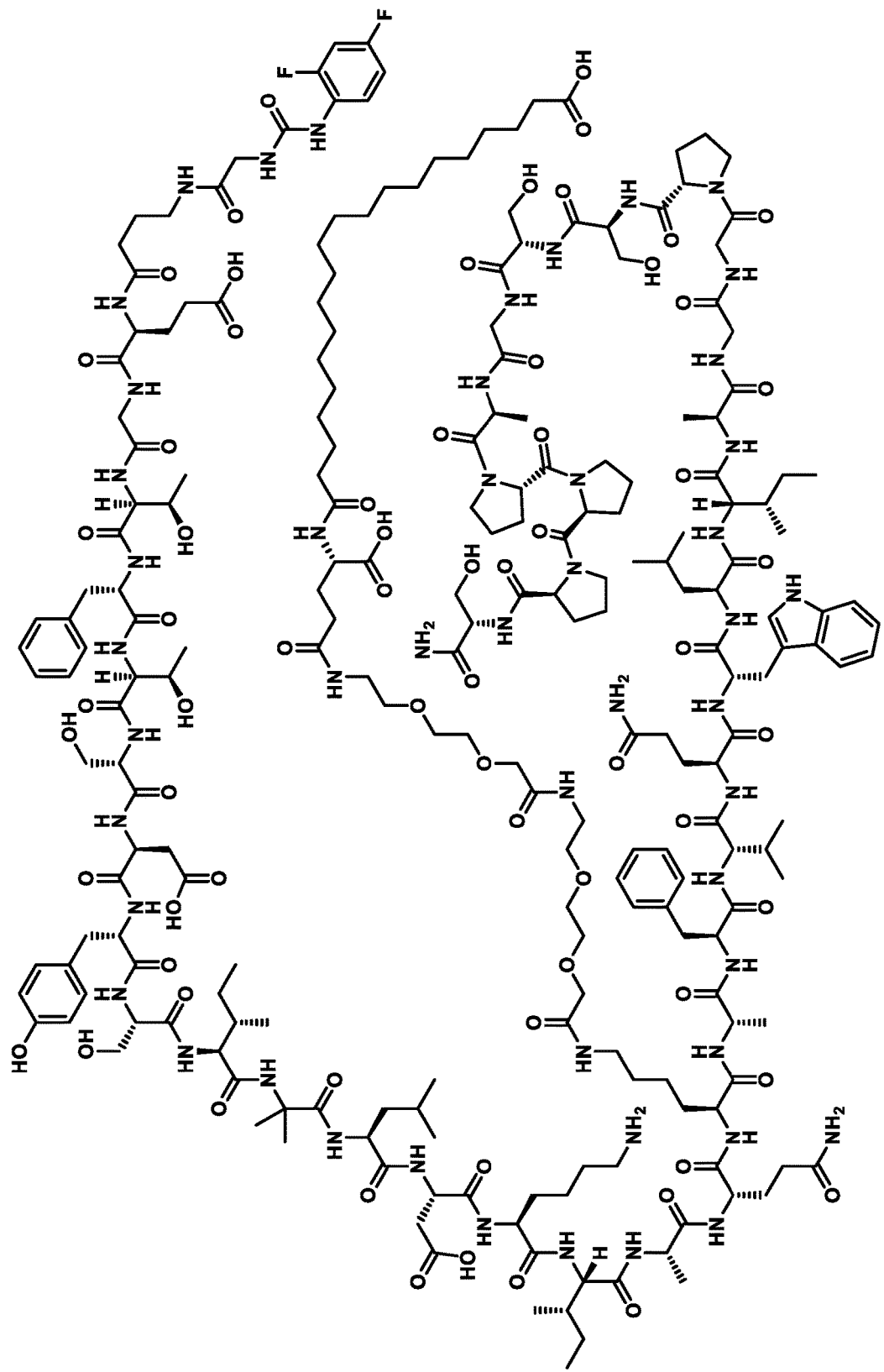
Compound 267
FIG. 1 - Cont'd

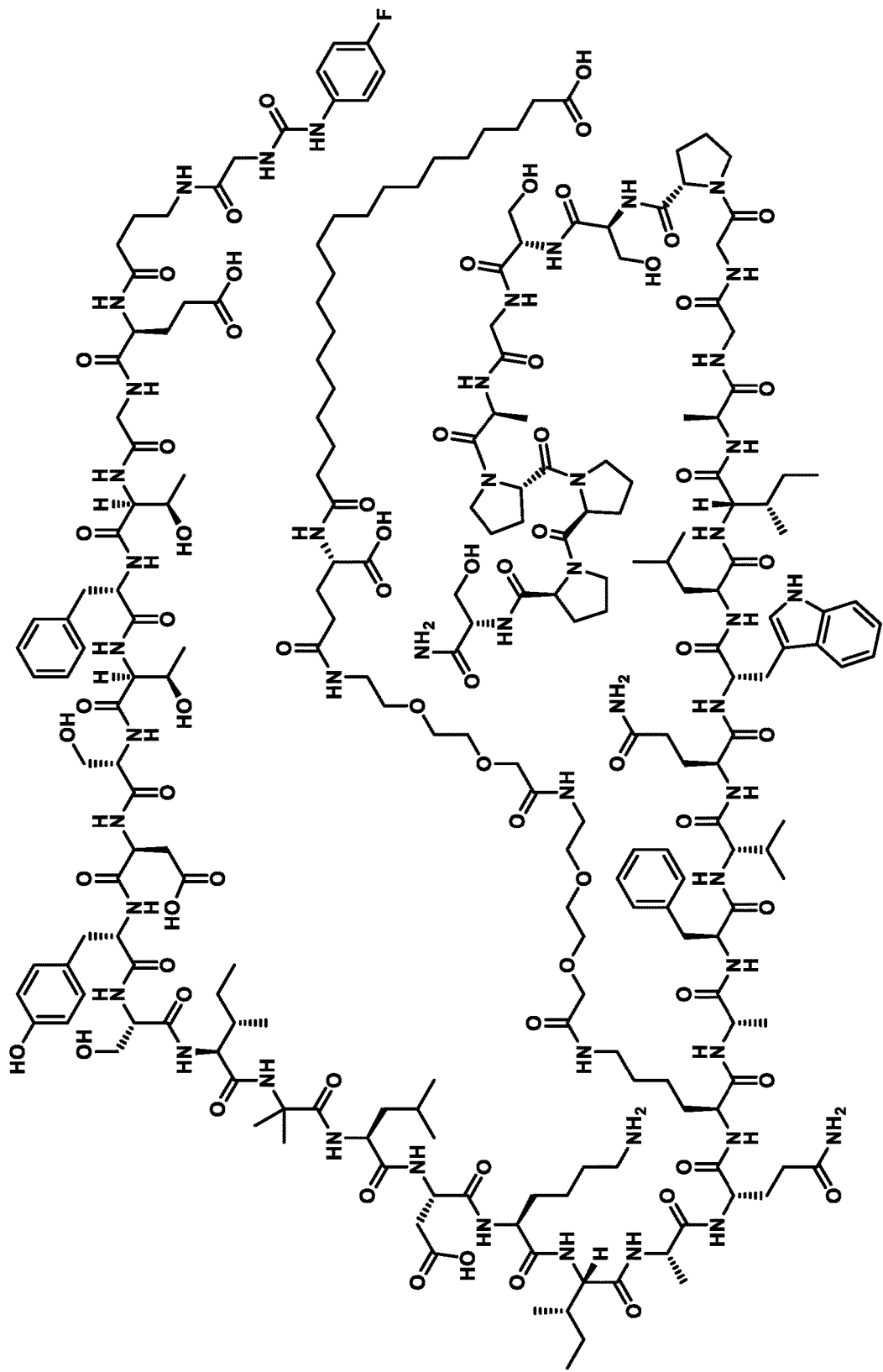
Compound 268
FIG. 1 - Cont'd

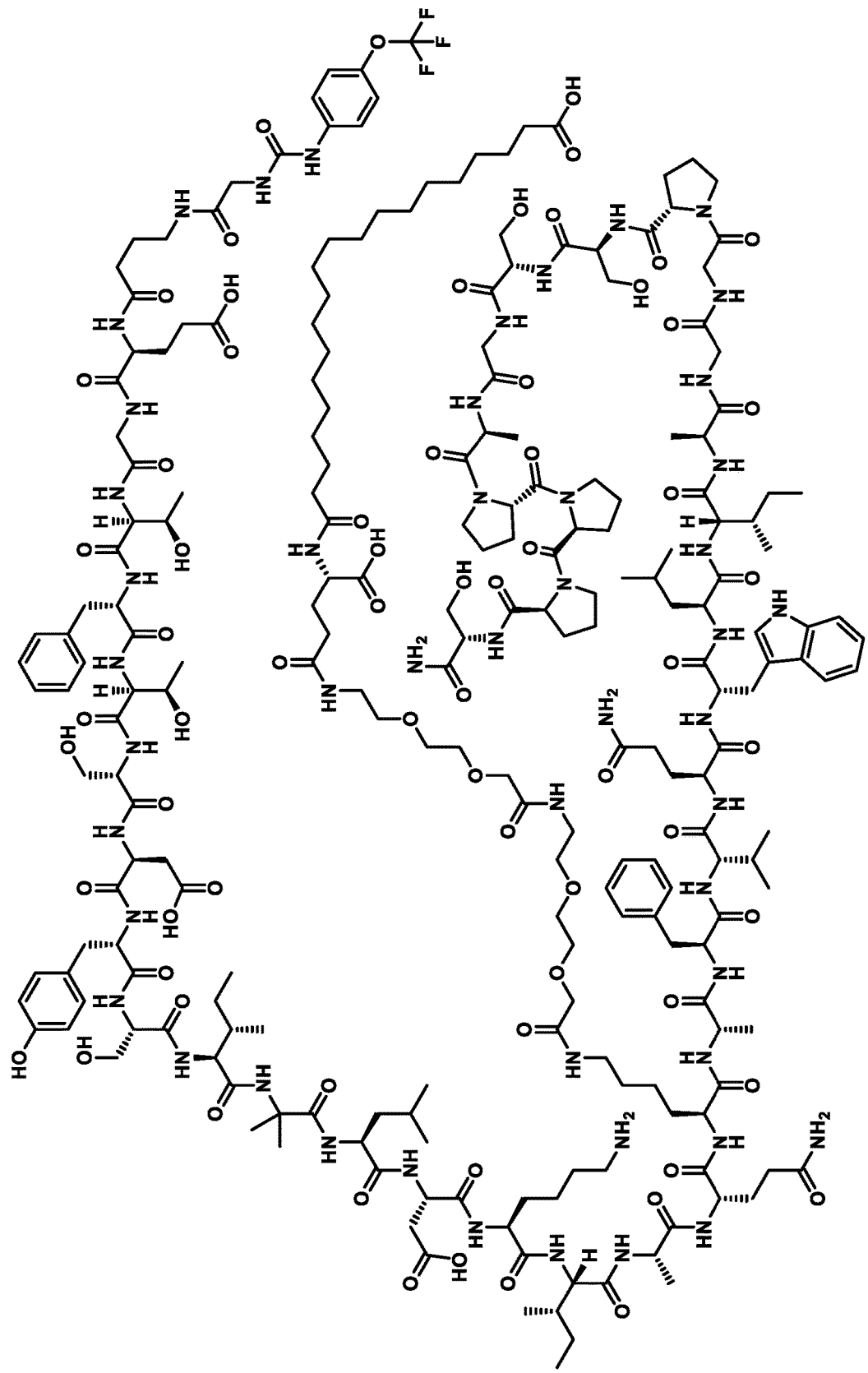
Compound 269
FIG. 1 - Cont'd

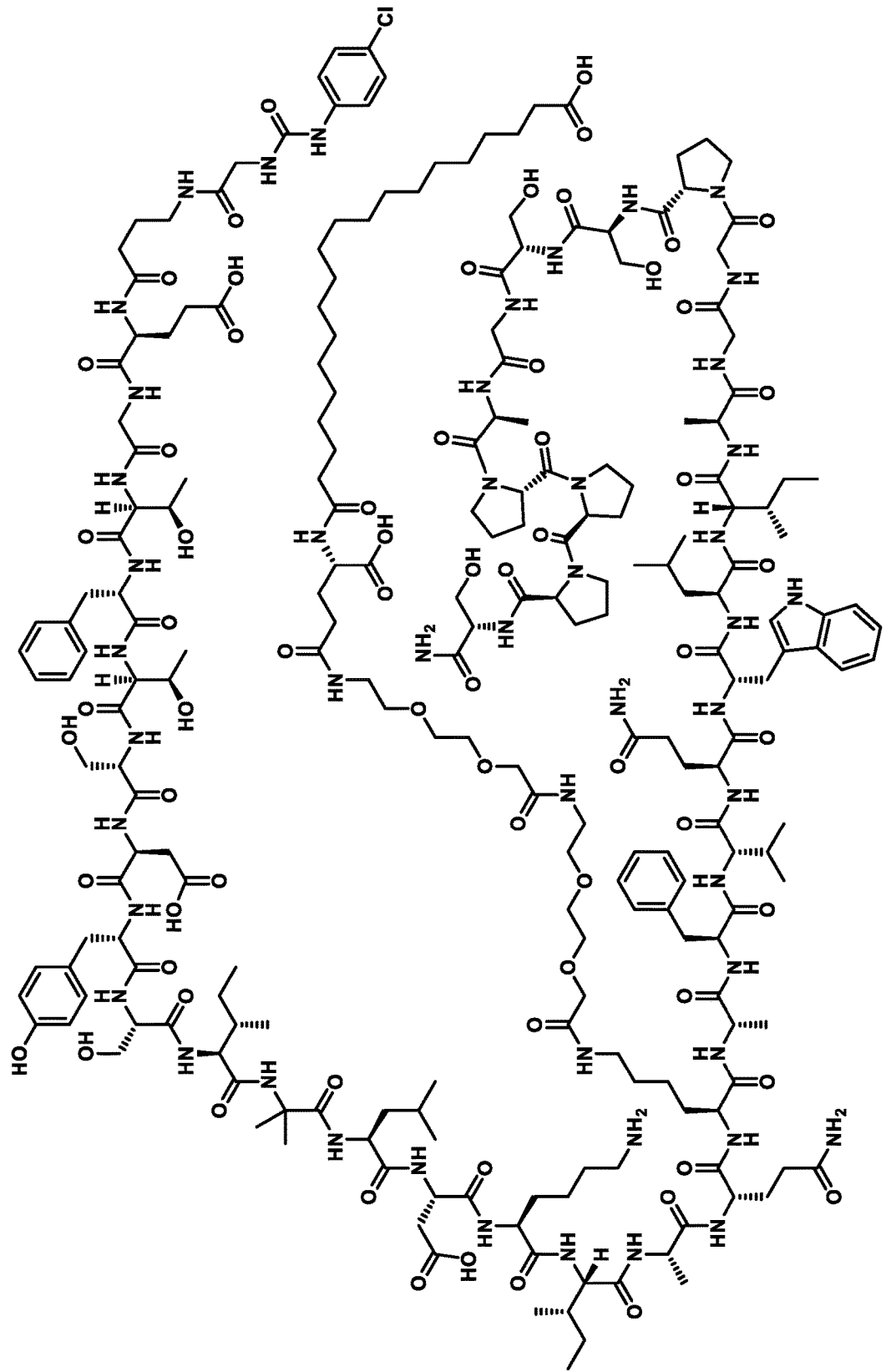
Compound 270
FIG. 1 - Cont'd

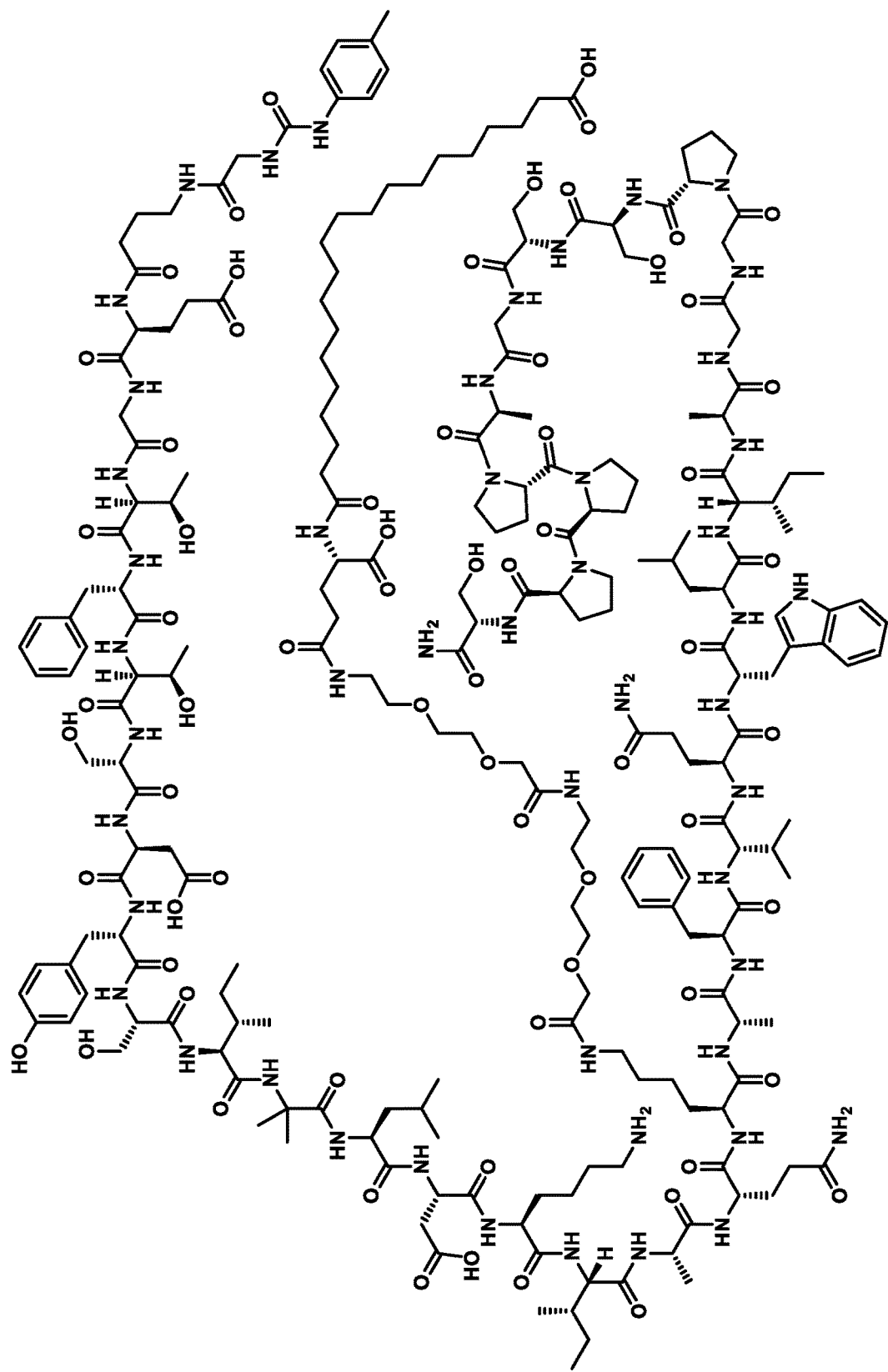
Compound 271
FIG. 1 - Cont'd

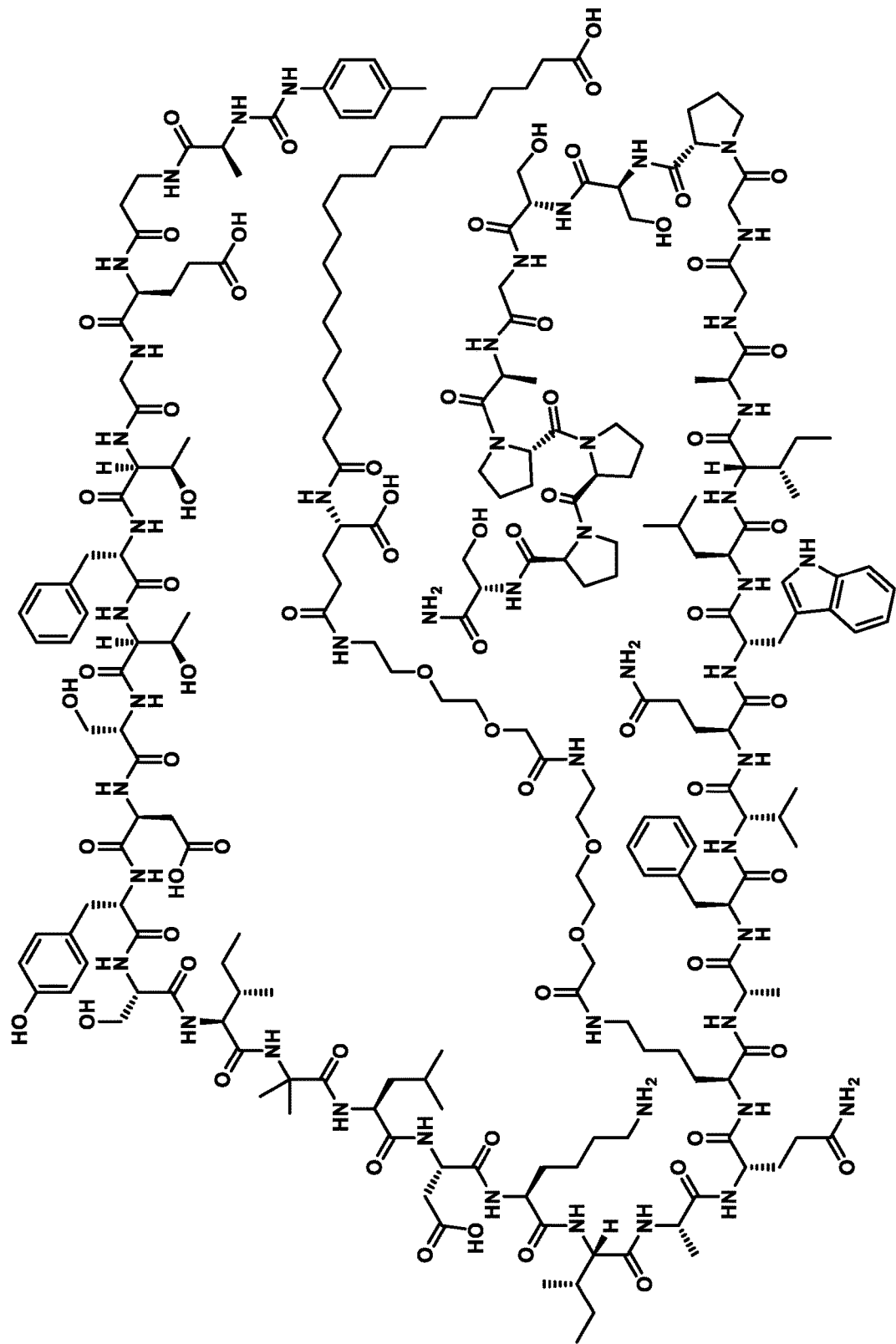
Compound 272
FIG. 1 - Cont'd

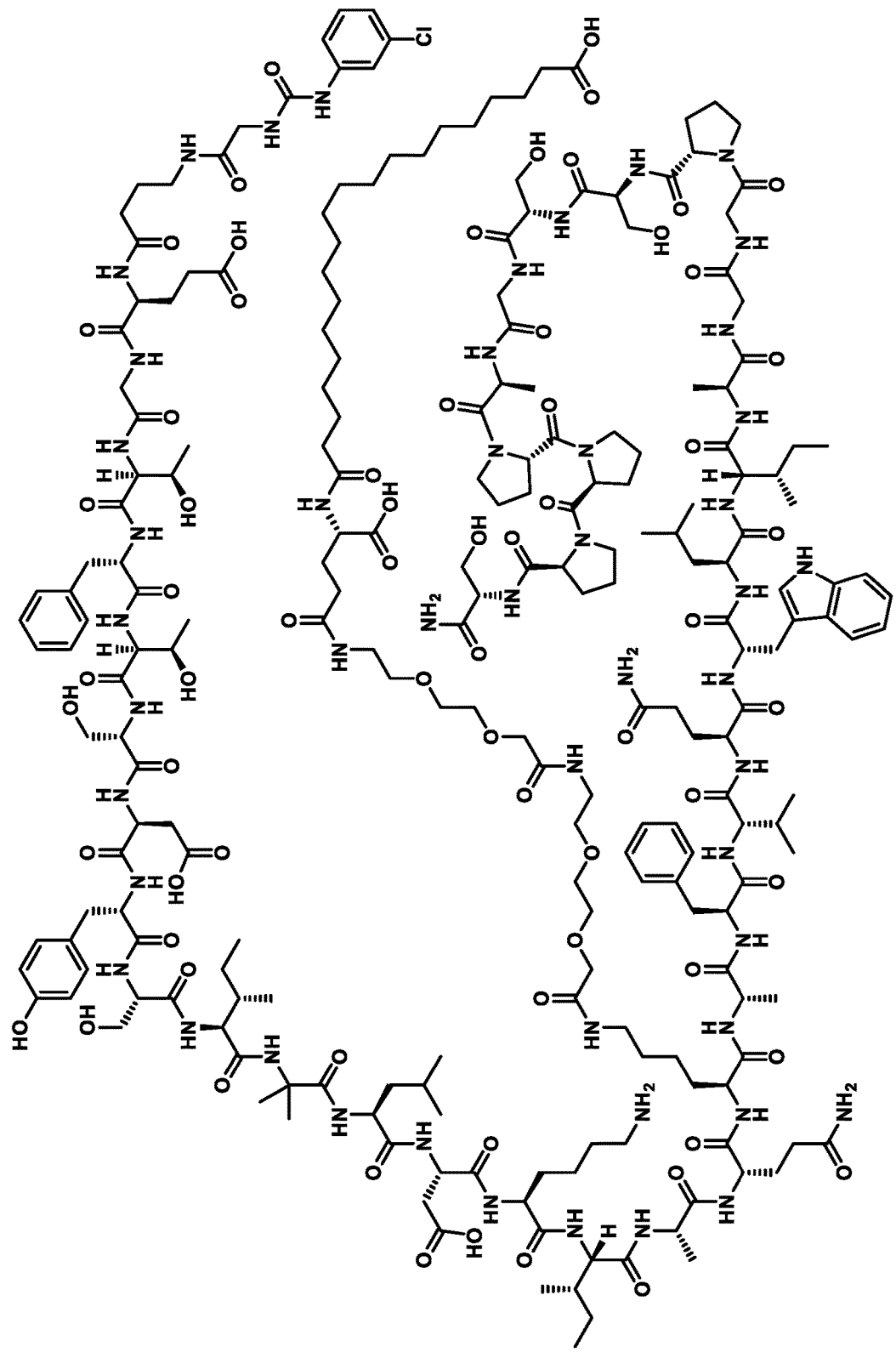
Compound 273
FIG. 1 - Cont'd

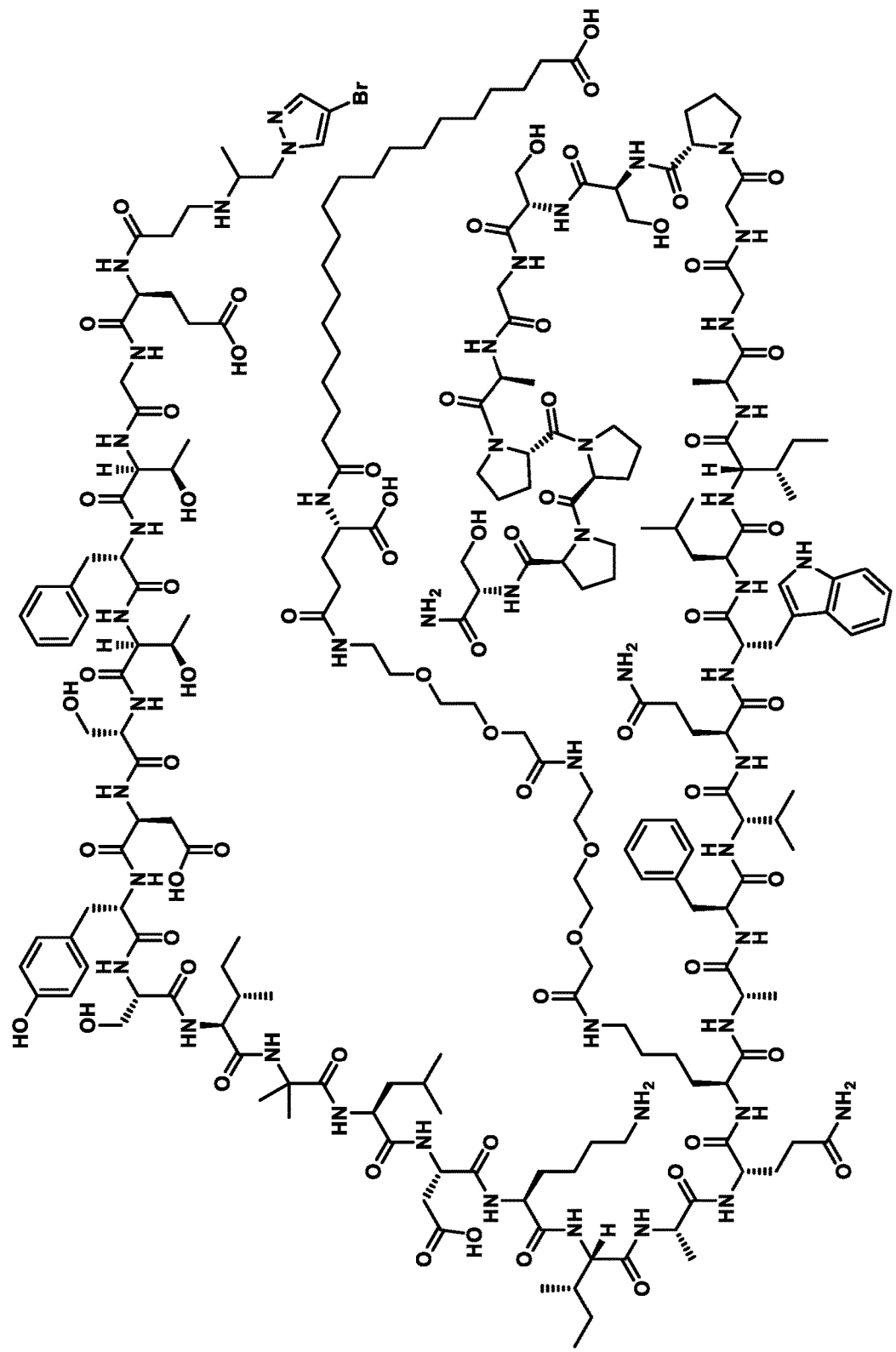
Compound 274
FIG. 1 - Cont'd

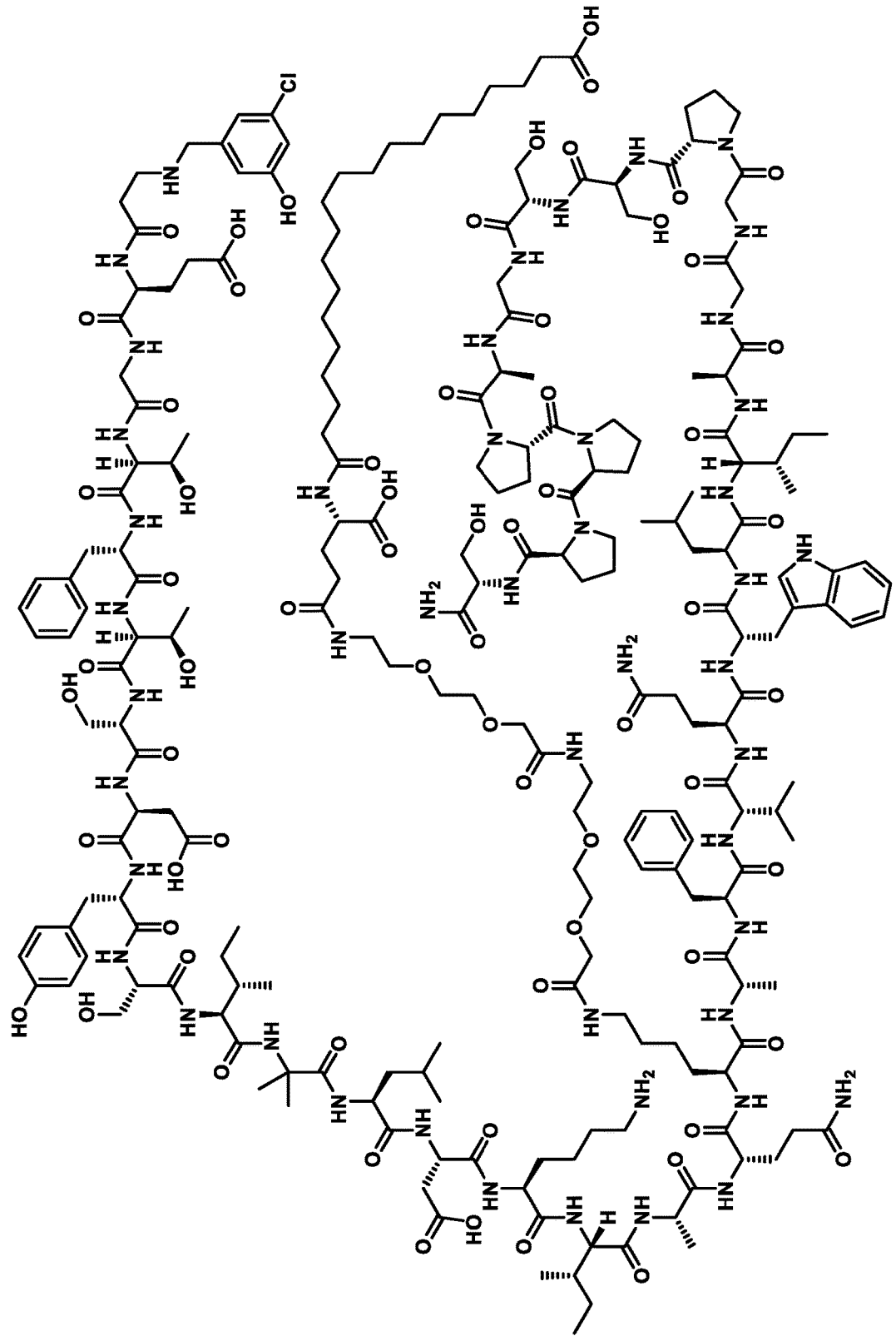
Compound 275
FIG. 1 - Cont'd

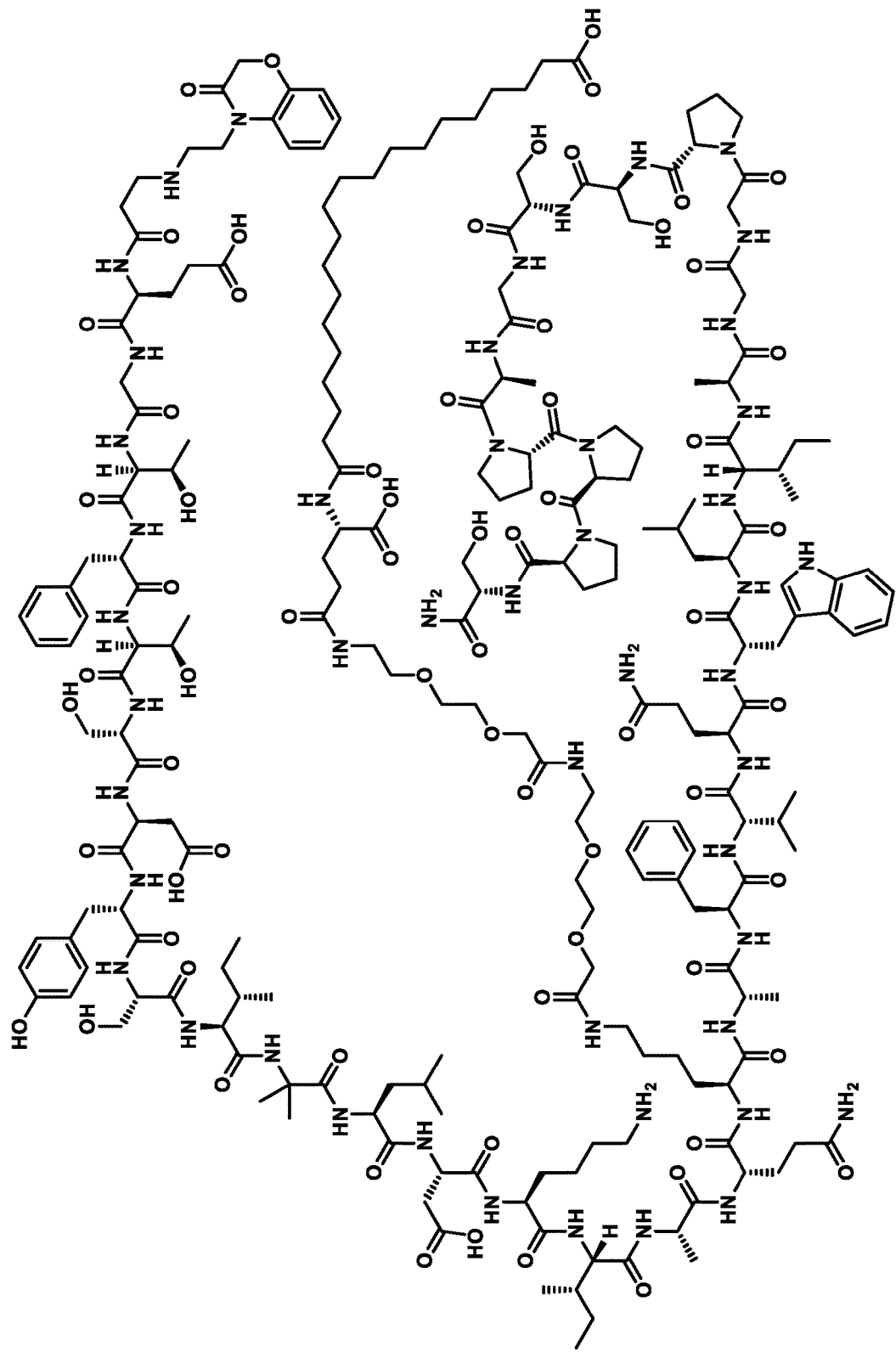
Compound 276
FIG. 1 - Cont'd

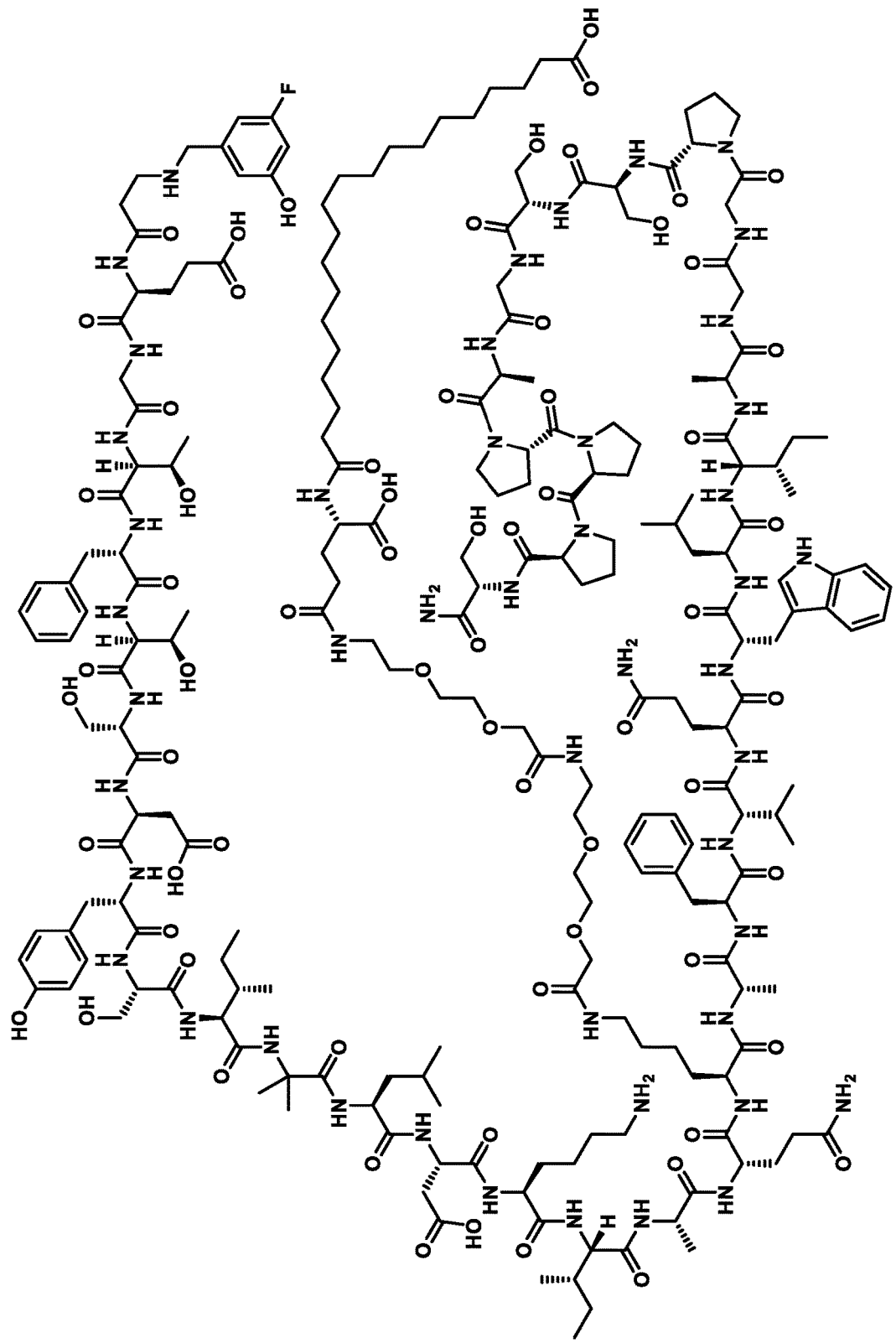
Compound 277
FIG. 1 - Cont'd

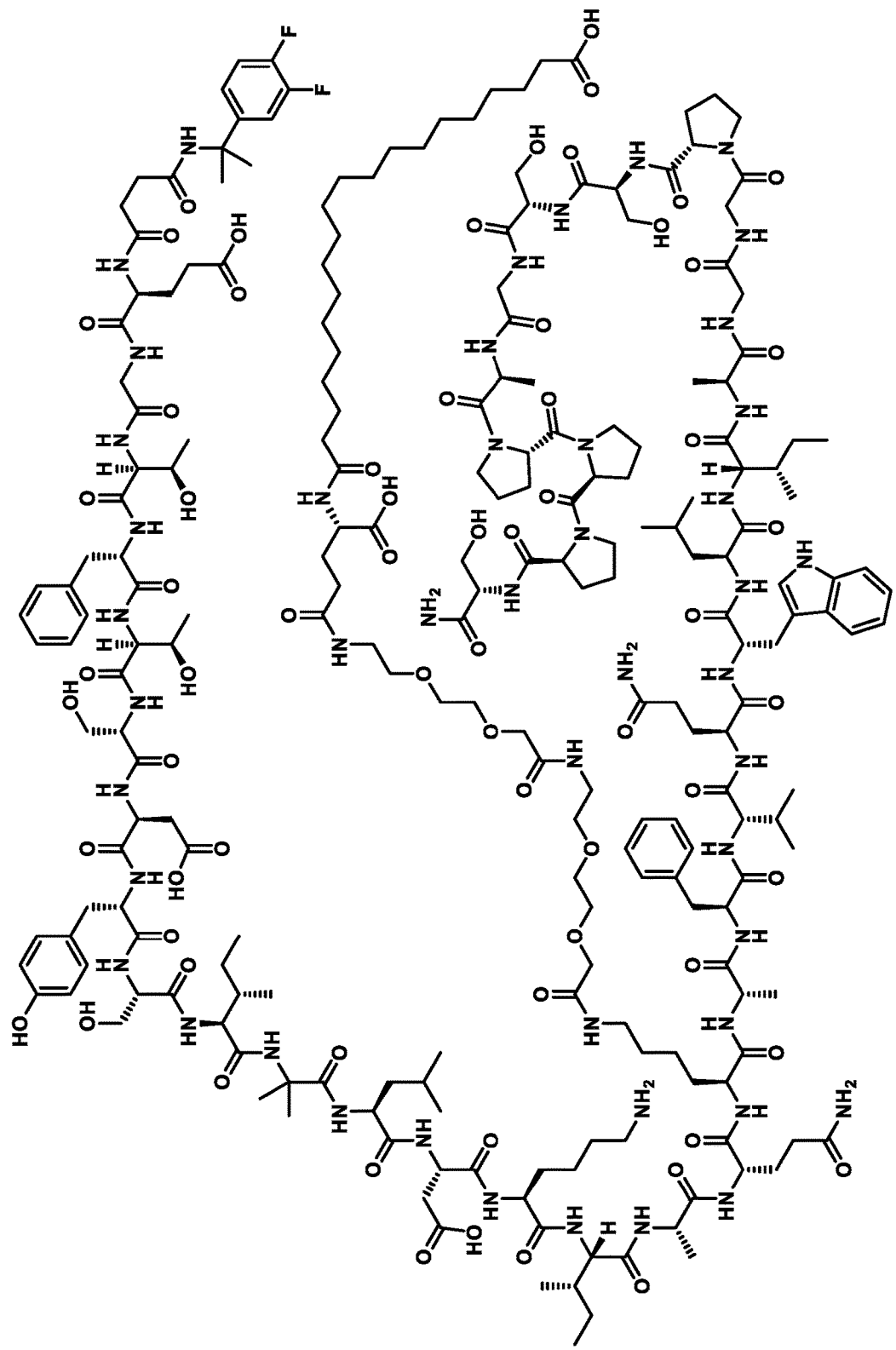
Compound 280
FIG. 1 - Cont'd

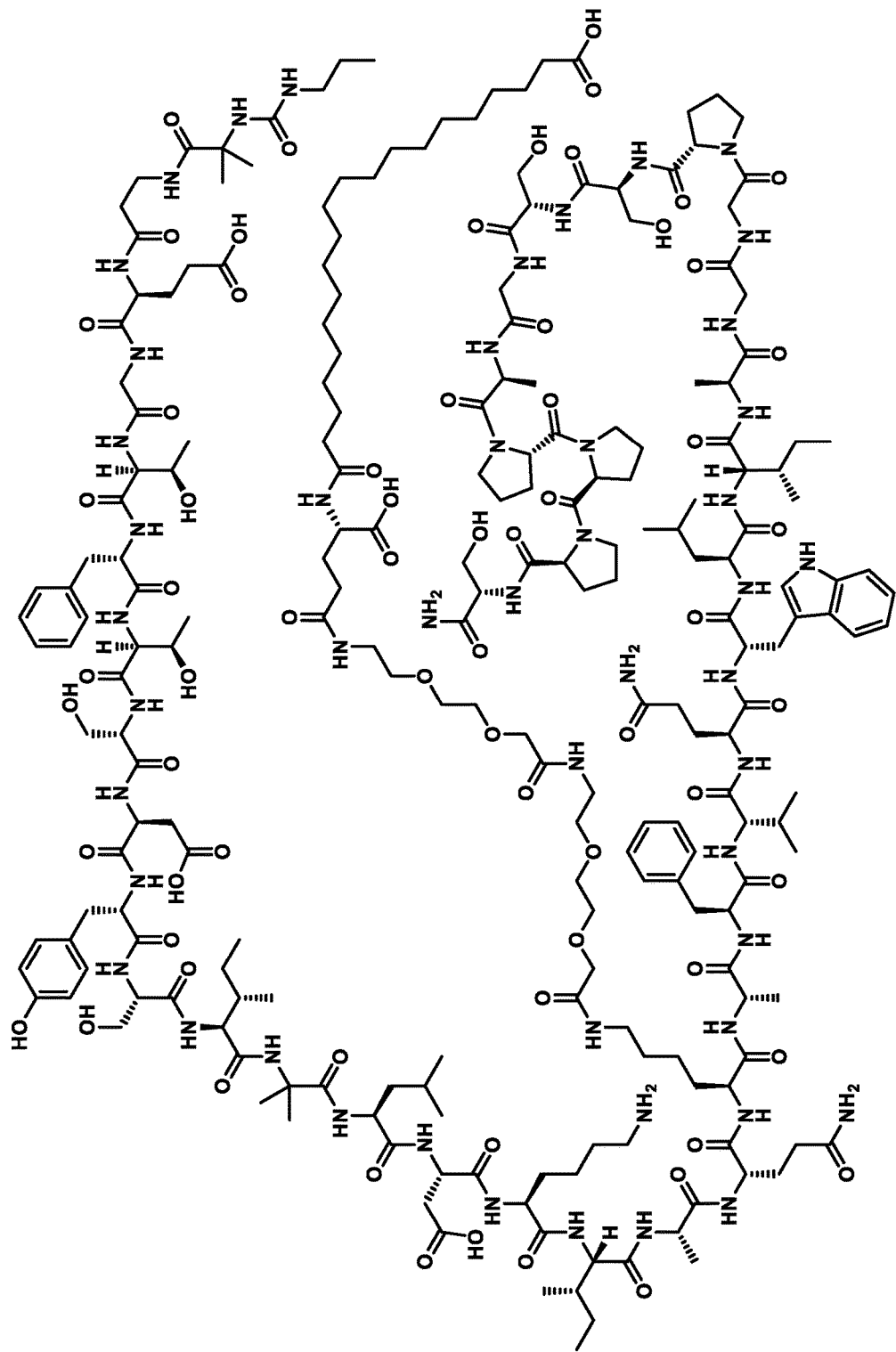
Compound 281
FIG. 1 - Cont'd

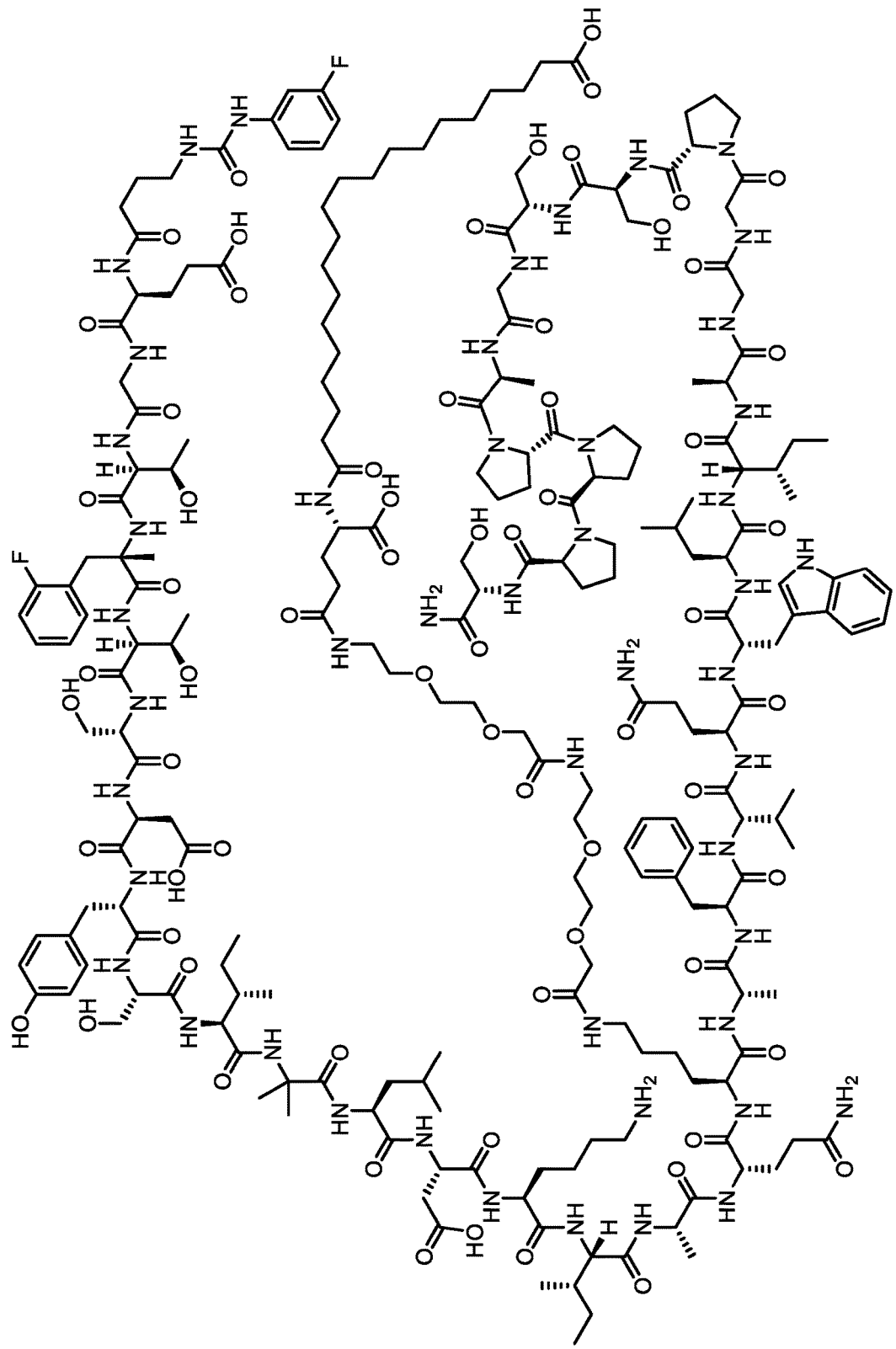
FIG. 1 - Cont'd
Compound 282

SEQUENCE LISTING

<160> NUMBER OF SEQ ID NOS: 76

<210> SEQ ID NO 1
<211> LENGTH: 44
<212> TYPE: PRT
<213> ORGANISM: Artificial Sequence
<220> FEATURE:

```
<223> OTHER INFORMATION: Description of Artificial Sequence: Synthetic
      polypeptide
<220> FEATURE:
<221> NAME/KEY: VARIANT
<222> LOCATION: (4)..(43)
<223> OTHER INFORMATION: Xaa can be any amino acid
<220> FEATURE:
<221> NAME/KEY: VARIANT
<222> LOCATION: (33)..(43)
<223> OTHER INFORMATION: Up to 10 X residues may be deleted
<220> FEATURE:
<221> NAME/KEY: VARIANT
<222> LOCATION: (44)..(44)
<223> OTHER INFORMATION: Xaa can be any amino acid, amino ester, or
      amino acid amide that is optionally substituted with from 1-2
      modifying groups
<220> FEATURE:
<221> NAME/KEY: MOD_RES
<222> LOCATION: (44)..(44)
<223> OTHER INFORMATION: Amino ester, or amino acid amide that is
      optionally substituted with from 1-2 modifying groups

<400> SEQUENCE: 1

Gly Thr Phe Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa
                20                  25                  30

Xaa Xaa Xaa Xaa Xaa Xaa Xaa Xaa Xaa Xaa Xaa Xaa
            35                  40

<210> SEQ ID NO 2

<400> SEQUENCE: 2

000

<210> SEQ ID NO 3

<400> SEQUENCE: 3

000

<210> SEQ ID NO 4
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: VARIANT
<222> LOCATION: (3)..(3)
<223> OTHER INFORMATION: Phe can be replaced by alpha-methyl-2-
      fluorophenylalaine, alpha-methyl-phenylalaine or
      2-fluorophenylalaine
<220> FEATURE:
<221> NAME/KEY: MOD_RES
<222> LOCATION: (3)..(3)
<223> OTHER INFORMATION: Alpha-methyl-2-fluorophenylalaine,
      alpha-methyl-phenylalaine or 2-fluorophenylalaine
<220> FEATURE:
<221> NAME/KEY: VARIANT
<222> LOCATION: (4)..(4)
<223> OTHER INFORMATION: Thr can be replaced by Ala or Val
<220> FEATURE:
<221> NAME/KEY: VARIANT
<222> LOCATION: (7)..(7)
<223> OTHER INFORMATION: Tyr can be replaced by a lysine residue
      substituted with a modifying group, or a C-terminal amino acid or
      an amino acid ester or amino acid amide thereof
<220> FEATURE:
<221> NAME/KEY: MOD_RES
<222> LOCATION: (7)..(7)
```

```
<223> OTHER INFORMATION: a lysine residue substituted with a modifying
      group, or a C-terminal amino acid or an amino acid ester or amino
      acid amide thereof
<220> FEATURE:
<221> NAME/KEY: VARIANT
<222> LOCATION: (10)..(10)
<223> OTHER INFORMATION: Tyr can be replaced by alpha-methyl-leucine or
      Aib
<220> FEATURE:
<221> NAME/KEY: MOD_RES
<222> LOCATION: (10)..(10)
<223> OTHER INFORMATION: Alpha-methyl-leucine or Aib
<220> FEATURE:
<221> NAME/KEY: VARIANT
<222> LOCATION: (13)..(13)
<223> OTHER INFORMATION: Lys can be replaced by Orn or Arg
<220> FEATURE:
<221> NAME/KEY: SITE
<222> LOCATION: (13)..(13)
<223> OTHER INFORMATION: Orn
<220> FEATURE:
<221> NAME/KEY: VARIANT
<222> LOCATION: (14)..(14)
<223> OTHER INFORMATION: Gln can be replaced by Ile or a lysine residue
      substituted with a modifying group, or a C-terminal amino acid or
      an amino acid ester or amino acid amide thereof
<220> FEATURE:
<221> NAME/KEY: MOD_RES
<222> LOCATION: (14)..(14)
<223> OTHER INFORMATION: a lysine residue substituted with a modifying
      group, or a C-terminal amino acid or an amino acid ester or amino
      acid amide thereof
<220> FEATURE:
<221> NAME/KEY: VARIANT
<222> LOCATION: (16)..(16)
<223> OTHER INFORMATION: Ala can be replaced by Gln
<220> FEATURE:
<221> NAME/KEY: VARIANT
<222> LOCATION: (17)..(17)
<223> OTHER INFORMATION: X can be Aib or a lysine residue substituted
      with a modifying group, or a C-terminal amino acid or an amino
      acid ester or amino acid amide thereof
<220> FEATURE:
<221> NAME/KEY: MOD_RES
<222> LOCATION: (17)..(17)
<223> OTHER INFORMATION: Aib or a lysine residue substituted with a
      modifying group, or a C-terminal amino acid or an amino acid ester
      or amino acid amide thereof
<220> FEATURE:
<221> NAME/KEY: VARIANT
<222> LOCATION: (18)..(18)
<223> OTHER INFORMATION: Ala can be replaced by Glu
<220> FEATURE:
<221> NAME/KEY: VARIANT
<222> LOCATION: (20)..(20)
<223> OTHER INFORMATION: Val can be replaced by Ile
<220> FEATURE:
<221> NAME/KEY: VARIANT
<222> LOCATION: (21)..(21)
<223> OTHER INFORMATION: Asn can be replaced by Gln, a lysine residue
      substituted with a modifying group, or a C-terminal amino acid or
      an amino acid ester or amino acid amide thereof or D-Glutamic acid
<220> FEATURE:
<221> NAME/KEY: MOD_RES
<222> LOCATION: (21)..(21)
<223> OTHER INFORMATION: a lysine residue substituted with a modifying
      group, or a C-terminal amino acid or an amino acid ester or amino
      acid amide thereof or D-Glutamic acid
<220> FEATURE:
<221> NAME/KEY: SITE
<222> LOCATION: (21)..(21)
<223> OTHER INFORMATION: D-Glutamic acid
<220> FEATURE:
<221> NAME/KEY: VARIANT
<222> LOCATION: (22)..(22)
<223> OTHER INFORMATION: Trp can be replaced by Tyr
<220> FEATURE:
<221> NAME/KEY: VARIANT
<222> LOCATION: (24)..(24)
```

```
-continued

<223> OTHER INFORMATION: Xaa can be Ile or Leu
<220> FEATURE:
<221> NAME/KEY: VARIANT
<222> LOCATION: (25)..(25)
<223> OTHER INFORMATION: Ala can be replaced by Glu
<220> FEATURE:
<221> NAME/KEY: VARIANT
<222> LOCATION: (37)..(37)
<223> OTHER INFORMATION: X can be a lysine residue substituted with a
      modifying group, or a C-terminal amino acid or an amino acid ester
      or amino acid amide thereof or absent
<220> FEATURE:
<221> NAME/KEY: MOD_RES
<222> LOCATION: (37)..(37)
<223> OTHER INFORMATION: a lysine residue substituted with a modifying
      group, or a C-terminal amino acid or an amino acid ester or amino
      acid amide thereof or absent

<400> SEQUENCE: 4

Gly Thr Phe Thr Ser Asp Tyr Ser Ile Tyr Leu Asp Lys Gln Ala Ala
 1               5                  10                  15

Xaa Ala Phe Val Asn Trp Leu Xaa Ala Gly Gly Pro Ser Ser Gly Ala
             20                  25                  30

Pro Pro Pro Ser Xaa
             35

<210> SEQ ID NO 5
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: VARIANT
<222> LOCATION: (3)..(3)
<223> OTHER INFORMATION: Phe can be replaced by alpha-methyl-2-
      fluorophenylalaine, alpha-methyl-phenylalaine or
      2-fluorophenylalaine
<220> FEATURE:
<221> NAME/KEY: MOD_RES
<222> LOCATION: (3)..(3)
<223> OTHER INFORMATION: Alpha-methyl-2-fluorophenylalaine,
      alpha-methyl-phenylalaine or 2-fluorophenylalaine
<220> FEATURE:
<221> NAME/KEY: VARIANT
<222> LOCATION: (4)..(4)
<223> OTHER INFORMATION: Thr can be replaced by Ala or Val
<220> FEATURE:
<221> NAME/KEY: VARIANT
<222> LOCATION: (7)..(7)
<223> OTHER INFORMATION: Tyr can be replaced by a lysine residue
      substituted with a modifying group, or a C-terminal amino acid or
      an amino acid ester or amino acid amide thereof
<220> FEATURE:
<221> NAME/KEY: MOD_RES
<222> LOCATION: (7)..(7)
<223> OTHER INFORMATION: a lysine residue substituted with a modifying
      group, or a C-terminal amino acid or an amino acid ester or amino
      acid amide thereof
<220> FEATURE:
<221> NAME/KEY: VARIANT
<222> LOCATION: (10)..(10)
<223> OTHER INFORMATION: Tyr can be replaced by alpha-methyl-leucine or
      Aib
<220> FEATURE:
<221> NAME/KEY: MOD_RES
<222> LOCATION: (10)..(10)
<223> OTHER INFORMATION: Alpha-methyl-leucine or Aib
<220> FEATURE:
<221> NAME/KEY: VARIANT
<222> LOCATION: (13)..(13)
<223> OTHER INFORMATION: Lys can be replaced by Orn or Arg
<220> FEATURE:
<221> NAME/KEY: SITE
```

```
<222> LOCATION: (13)..(13)
<223> OTHER INFORMATION: Orn
<220> FEATURE:
<221> NAME/KEY: VARIANT
<222> LOCATION: (14)..(14)
<223> OTHER INFORMATION: Gln can be replaced by Ile or a lysine residue
      substituted with a modifying group, or a C-terminal amino acid or
      an amino acid ester or amino acid amide thereof
<220> FEATURE:
<221> NAME/KEY: MOD_RES
<222> LOCATION: (14)..(14)
<223> OTHER INFORMATION: a lysine residue substituted with a modifying
      group, or a C-terminal amino acid or an amino acid ester or amino
      acid amide thereof
<220> FEATURE:
<221> NAME/KEY: VARIANT
<222> LOCATION: (16)..(16)
<223> OTHER INFORMATION: Ala can be replaced by Gln
<220> FEATURE:
<221> NAME/KEY: VARIANT
<222> LOCATION: (17)..(17)
<223> OTHER INFORMATION: X can be Aib or a lysine residue substituted
      with a modifying group, or a C-terminal amino acid or an amino
      acid ester or amino acid amide thereof
<220> FEATURE:
<221> NAME/KEY: MOD_RES
<222> LOCATION: (17)..(17)
<223> OTHER INFORMATION: Aib or a lysine residue substituted with a
      modifying group, or a C-terminal amino acid or an amino acid ester
      or amino acid amide thereof
<220> FEATURE:
<221> NAME/KEY: VARIANT
<222> LOCATION: (18)..(18)
<223> OTHER INFORMATION: Ala can be replaced by Glu
<220> FEATURE:
<221> NAME/KEY: VARIANT
<222> LOCATION: (20)..(20)
<223> OTHER INFORMATION: Val can be replaced by Ile
<220> FEATURE:
<221> NAME/KEY: VARIANT
<222> LOCATION: (21)..(21)
<223> OTHER INFORMATION: Asn can be replaced by Gln, a lysine residue
      substituted with a modifying group, or a C-terminal amino acid or
      an amino acid ester or amino acid amide thereof or D-Glutamic acid
<220> FEATURE:
<221> NAME/KEY: MOD_RES
<222> LOCATION: (21)..(21)
<223> OTHER INFORMATION: a lysine residue substituted with a modifying
      group, or a C-terminal amino acid or an amino acid ester or amino
      acid amide thereof or D-Glutamic acid
<220> FEATURE:
<221> NAME/KEY: SITE
<222> LOCATION: (21)..(21)
<223> OTHER INFORMATION: D-Glutamic acid
<220> FEATURE:
<221> NAME/KEY: VARIANT
<222> LOCATION: (22)..(22)
<223> OTHER INFORMATION: Trp can be replaced by Tyr
<220> FEATURE:
<221> NAME/KEY: VARIANT
<222> LOCATION: (24)..(24)
<223> OTHER INFORMATION: Xaa can be Ile or Leu
<220> FEATURE:
<221> NAME/KEY: VARIANT
<222> LOCATION: (25)..(25)
<223> OTHER INFORMATION: Ala can be replaced by Glu
<220> FEATURE:
<221> NAME/KEY: VARIANT
<222> LOCATION: (37)..(37)
<223> OTHER INFORMATION: X can be a lysine residue substituted with a
      modifying group, or a C-terminal amino acid or an amino acid ester
      or amino acid amide thereof or absent
<220> FEATURE:
<221> NAME/KEY: MOD_RES
<222> LOCATION: (37)..(37)
<223> OTHER INFORMATION: a lysine residue substituted with a modifying
      group, or a C-terminal amino acid or an amino acid ester or amino
      acid amide thereof or absent
```

```
<400> SEQUENCE: 5

Gly Thr Phe Thr Ser Asp Tyr Ser Ile Tyr Leu Asp Lys Gln Ala Ala
1               5                   10                  15

Xaa Ala Phe Val Asn Trp Leu Xaa Ala Gly Gly Pro Ser Ser Gly Ala
            20                  25                  30

Pro Pro Pro Ser Xaa
            35

<210> SEQ ID NO 6
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: VARIANT
<222> LOCATION: (3)..(3)
<223> OTHER INFORMATION: Phe can be replaced by alpha-methyl-2-
      fluorophenylalaine, alpha-methyl-phenylalaine or
      2-fluorophenylalaine
<220> FEATURE:
<221> NAME/KEY: MOD_RES
<222> LOCATION: (3)..(3)
<223> OTHER INFORMATION: Alpha-methyl-2-fluorophenylalaine,
      alpha-methyl-phenylalaine or 2-fluorophenylalaine
<220> FEATURE:
<221> NAME/KEY: VARIANT
<222> LOCATION: (4)..(4)
<223> OTHER INFORMATION: Thr can be replaced by Ala or Val
<220> FEATURE:
<221> NAME/KEY: VARIANT
<222> LOCATION: (7)..(7)
<223> OTHER INFORMATION: Tyr can be replaced by a lysine residue
      substituted with a modifying group, or a C-terminal amino acid or
      an amino acid ester or amino acid amide thereof
<220> FEATURE:
<221> NAME/KEY: MOD_RES
<222> LOCATION: (7)..(7)
<223> OTHER INFORMATION: a lysine residue substituted with a modifying
      group, or a C-terminal amino acid or an amino acid ester or amino
      acid amide thereof
<220> FEATURE:
<221> NAME/KEY: VARIANT
<222> LOCATION: (10)..(10)
<223> OTHER INFORMATION: Tyr can be replaced by alpha-methyl-leucine or
      Aib
<220> FEATURE:
<221> NAME/KEY: MOD_RES
<222> LOCATION: (10)..(10)
<223> OTHER INFORMATION: Alpha-methyl-leucine or Aib
<220> FEATURE:
<221> NAME/KEY: VARIANT
<222> LOCATION: (13)..(13)
<223> OTHER INFORMATION: Lys can be replaced by Orn or Arg
<220> FEATURE:
<221> NAME/KEY: SITE
<222> LOCATION: (13)..(13)
<223> OTHER INFORMATION: Orn
<220> FEATURE:
<221> NAME/KEY: VARIANT
<222> LOCATION: (14)..(14)
<223> OTHER INFORMATION: Gln can be replaced by Ile or a lysine residue
      substituted with a modifying group, or a C-terminal amino acid or
      an amino acid ester or amino acid amide thereof
<220> FEATURE:
<221> NAME/KEY: MOD_RES
<222> LOCATION: (14)..(14)
<223> OTHER INFORMATION: a lysine residue substituted with a modifying
      group, or a C-terminal amino acid or an amino acid ester or amino
      acid amide thereof
<220> FEATURE:
<221> NAME/KEY: VARIANT
<222> LOCATION: (16)..(16)
<223> OTHER INFORMATION: Ala can be replaced by Gln
```

```
<220> FEATURE:
<221> NAME/KEY: VARIANT
<222> LOCATION: (17)..(17)
<223> OTHER INFORMATION: X can be Aib or a lysine residue substituted
      with a modifying group, or a C-terminal amino acid or an amino
      acid ester or amino acid amide thereof
<220> FEATURE:
<221> NAME/KEY: MOD_RES
<222> LOCATION: (17)..(17)
<223> OTHER INFORMATION: Aib or a lysine residue substituted with a
      modifying group, or a C-terminal amino acid or an amino acid ester
      or amino acid amide thereof
<220> FEATURE:
<221> NAME/KEY: VARIANT
<222> LOCATION: (18)..(18)
<223> OTHER INFORMATION: Ala can be replaced by Glu
<220> FEATURE:
<221> NAME/KEY: VARIANT
<222> LOCATION: (20)..(20)
<223> OTHER INFORMATION: Val can be replaced by Ile
<220> FEATURE:
<221> NAME/KEY: VARIANT
<222> LOCATION: (21)..(21)
<223> OTHER INFORMATION: Asn can be replaced by Gln, a lysine residue
      substituted with a modifying group, or a C-terminal amino acid or
      an amino acid ester or amino acid amide thereof or D-Glutamic acid
<220> FEATURE:
<221> NAME/KEY: MOD_RES
<222> LOCATION: (21)..(21)
<223> OTHER INFORMATION: a lysine residue substituted with a modifying
      group, or a C-terminal amino acid or an amino acid ester or amino
      acid amide thereof or D-Glutamic acid
<220> FEATURE:
<221> NAME/KEY: SITE
<222> LOCATION: (21)..(21)
<223> OTHER INFORMATION: D-Glutamic acid
<220> FEATURE:
<221> NAME/KEY: VARIANT
<222> LOCATION: (22)..(22)
<223> OTHER INFORMATION: Trp can be replaced by Tyr
<220> FEATURE:
<221> NAME/KEY: VARIANT
<222> LOCATION: (24)..(24)
<223> OTHER INFORMATION: Xaa can be Ile or Leu
<220> FEATURE:
<221> NAME/KEY: VARIANT
<222> LOCATION: (25)..(25)
<223> OTHER INFORMATION: Ala can be replaced by Glu
<220> FEATURE:
<221> NAME/KEY: VARIANT
<222> LOCATION: (37)..(37)
<223> OTHER INFORMATION: X can be a lysine residue substituted with a
      modifying group, or a C-terminal amino acid or an amino acid ester
      or amino acid amide thereof or absent
<220> FEATURE:
<221> NAME/KEY: MOD_RES
<222> LOCATION: (37)..(37)
<223> OTHER INFORMATION: a lysine residue substituted with a modifying
      group, or a C-terminal amino acid or an amino acid ester or amino
      acid amide thereof or absent

<400> SEQUENCE: 6

Gly Thr Phe Thr Ser Asp Tyr Ser Ile Tyr Leu Asp Lys Gln Ala Ala
1               5                   10                  15

Xaa Ala Phe Val Asn Trp Leu Xaa Ala Gly Gly Pro Ser Ser Gly Ala
                20                  25                  30

Pro Pro Pro Ser Xaa
            35

<210> SEQ ID NO 7
<211> LENGTH: 37
<212> TYPE: PRT
<213> ORGANISM: Artificial Sequence
<220> FEATURE:
<223> OTHER INFORMATION: Description of Artificial Sequence: Synthetic
```

```
                 polypeptide
<220> FEATURE:
<221> NAME/KEY: VARIANT
<222> LOCATION: (3)..(3)
<223> OTHER INFORMATION: Phe can be replaced by alpha-methyl-2-
      fluorophenylalaine, alpha-methyl-phenylalaine or
      2-fluorophenylalaine
<220> FEATURE:
<221> NAME/KEY: MOD_RES
<222> LOCATION: (3)..(3)
<223> OTHER INFORMATION: Alpha-methyl-2-fluorophenylalaine,
      alpha-methyl-phenylalaine or 2-fluorophenylalaine
<220> FEATURE:
<221> NAME/KEY: VARIANT
<222> LOCATION: (4)..(4)
<223> OTHER INFORMATION: Thr can be replaced by Ala or Val
<220> FEATURE:
<221> NAME/KEY: VARIANT
<222> LOCATION: (7)..(7)
<223> OTHER INFORMATION: Tyr can be replaced by a lysine residue
      substituted with a modifying group, or a C-terminal amino acid or
      an amino acid ester or amino acid amide thereof
<220> FEATURE:
<221> NAME/KEY: MOD_RES
<222> LOCATION: (7)..(7)
<223> OTHER INFORMATION: a lysine residue substituted with a modifying
      group, or a C-terminal amino acid or an amino acid ester or amino
      acid amide thereof
<220> FEATURE:
<221> NAME/KEY: VARIANT
<222> LOCATION: (10)..(10)
<223> OTHER INFORMATION: Tyr can be replaced by alpha-methyl-leucine or
      Aib
<220> FEATURE:
<221> NAME/KEY: MOD_RES
<222> LOCATION: (10)..(10)
<223> OTHER INFORMATION: Alpha-methyl-leucine or Aib
<220> FEATURE:
<221> NAME/KEY: VARIANT
<222> LOCATION: (13)..(13)
<223> OTHER INFORMATION: Lys can be replaced by Orn or Arg
<220> FEATURE:
<221> NAME/KEY: SITE
<222> LOCATION: (13)..(13)
<223> OTHER INFORMATION: Orn
<220> FEATURE:
<221> NAME/KEY: VARIANT
<222> LOCATION: (14)..(14)
<223> OTHER INFORMATION: Gln can be replaced by Ile or a lysine residue
      substituted with a modifying group, or a C-terminal amino acid or
      an amino acid ester or amino acid amide thereof
<220> FEATURE:
<221> NAME/KEY: MOD_RES
<222> LOCATION: (14)..(14)
<223> OTHER INFORMATION: a lysine residue substituted with a modifying
      group, or a C-terminal amino acid or an amino acid ester or amino
      acid amide thereof
<220> FEATURE:
<221> NAME/KEY: VARIANT
<222> LOCATION: (16)..(16)
<223> OTHER INFORMATION: Ala can be replaced by Gln
<220> FEATURE:
<221> NAME/KEY: VARIANT
<222> LOCATION: (17)..(17)
<223> OTHER INFORMATION: X can be Aib or a lysine residue substituted
      with a modifying group, or a C-terminal amino acid or an amino
      acid ester or amino acid amide thereof
<220> FEATURE:
<221> NAME/KEY: MOD_RES
<222> LOCATION: (17)..(17)
<223> OTHER INFORMATION: Aib or a lysine residue substituted with a
      modifying group, or a C-terminal amino acid or an amino acid ester
      or amino acid amide thereof
<220> FEATURE:
<221> NAME/KEY: VARIANT
<222> LOCATION: (18)..(18)
<223> OTHER INFORMATION: Ala can be replaced by Glu
<220> FEATURE:
<221> NAME/KEY: VARIANT
```

```
<222> LOCATION: (20)..(20)
<223> OTHER INFORMATION: Val can be replaced by Ile
<220> FEATURE:
<221> NAME/KEY: VARIANT
<222> LOCATION: (21)..(21)
<223> OTHER INFORMATION: Asn can be replaced by Gln, a lysine residue
      substituted with a modifying group, or a C-terminal amino acid or
      an amino acid ester or amino acid amide thereof or D-Glutamic acid
<220> FEATURE:
<221> NAME/KEY: MOD_RES
<222> LOCATION: (21)..(21)
<223> OTHER INFORMATION: a lysine residue substituted with a modifying
      group, or a C-terminal amino acid or an amino acid ester or amino
      acid amide thereof or D-Glutamic acid
<220> FEATURE:
<221> NAME/KEY: SITE
<222> LOCATION: (21)..(21)
<223> OTHER INFORMATION: D-Glutamic acid
<220> FEATURE:
<221> NAME/KEY: VARIANT
<222> LOCATION: (22)..(22)
<223> OTHER INFORMATION: Trp can be replaced by Tyr
<220> FEATURE:
<221> NAME/KEY: VARIANT
<222> LOCATION: (24)..(24)
<223> OTHER INFORMATION: Xaa can be Ile or Leu
<220> FEATURE:
<221> NAME/KEY: VARIANT
<222> LOCATION: (25)..(25)
<223> OTHER INFORMATION: Ala can be replaced by Glu
<220> FEATURE:
<221> NAME/KEY: VARIANT
<222> LOCATION: (37)..(37)
<223> OTHER INFORMATION: X can be a lysine residue substituted with a
      modifying group, or a C-terminal amino acid or an amino acid ester
      or amino acid amide thereof or absent
<220> FEATURE:
<221> NAME/KEY: MOD_RES
<222> LOCATION: (37)..(37)
<223> OTHER INFORMATION: a lysine residue substituted with a modifying
      group, or a C-terminal amino acid or an amino acid ester or amino
      acid amide thereof or absent

<400> SEQUENCE: 7

Gly Thr Phe Thr Ser Asp Tyr Ser Ile Tyr Leu Asp Lys Gln Ala Ala
1               5                   10                  15

Xaa Ala Phe Val Asn Trp Leu Xaa Ala Gly Gly Pro Ser Ser Gly Ala
            20                  25                  30

Pro Pro Pro Ser Xaa
            35

<210> SEQ ID NO 8
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: VARIANT
<222> LOCATION: (3)..(3)
<223> OTHER INFORMATION: Phe can be replaced by alpha-methyl-2-
      fluorophenylalaine, alpha-methyl-phenylalaine or
      2-fluorophenylalaine
<220> FEATURE:
<221> NAME/KEY: MOD_RES
<222> LOCATION: (3)..(3)
<223> OTHER INFORMATION: Alpha-methyl-2-fluorophenylalaine,
      alpha-methyl-phenylalaine or 2-fluorophenylalaine
<220> FEATURE:
<221> NAME/KEY: VARIANT
<222> LOCATION: (4)..(4)
<223> OTHER INFORMATION: Thr can be replaced by Ala or Val
<220> FEATURE:
<221> NAME/KEY: VARIANT
```

-continued

```
<222> LOCATION: (7)..(7)
<223> OTHER INFORMATION: Tyr can be replaced by a lysine residue
      substituted with a modifying group, or a C-terminal amino acid or
      an amino acid ester or amino acid amide thereof
<220> FEATURE:
<221> NAME/KEY: MOD_RES
<222> LOCATION: (7)..(7)
<223> OTHER INFORMATION: a lysine residue substituted with a modifying
      group, or a C-terminal amino acid or an amino acid ester or amino
      acid amide thereof
<220> FEATURE:
<221> NAME/KEY: VARIANT
<222> LOCATION: (10)..(10)
<223> OTHER INFORMATION: Tyr can be replaced by alpha-methyl-leucine or
      Aib
<220> FEATURE:
<221> NAME/KEY: MOD_RES
<222> LOCATION: (10)..(10)
<223> OTHER INFORMATION: Alpha-methyl-leucine or Aib
<220> FEATURE:
<221> NAME/KEY: VARIANT
<222> LOCATION: (13)..(13)
<223> OTHER INFORMATION: Lys can be replaced by Orn or Arg
<220> FEATURE:
<221> NAME/KEY: SITE
<222> LOCATION: (13)..(13)
<223> OTHER INFORMATION: Orn
<220> FEATURE:
<221> NAME/KEY: VARIANT
<222> LOCATION: (14)..(14)
<223> OTHER INFORMATION: Gln can be replaced by Ile or a lysine residue
      substituted with a modifying group, or a C-terminal amino acid or
      an amino acid ester or amino acid amide thereof
<220> FEATURE:
<221> NAME/KEY: MOD_RES
<222> LOCATION: (14)..(14)
<223> OTHER INFORMATION: a lysine residue substituted with a modifying
      group, or a C-terminal amino acid or an amino acid ester or amino
      acid amide thereof
<220> FEATURE:
<221> NAME/KEY: VARIANT
<222> LOCATION: (16)..(16)
<223> OTHER INFORMATION: Ala can be replaced by Gln
<220> FEATURE:
<221> NAME/KEY: VARIANT
<222> LOCATION: (17)..(17)
<223> OTHER INFORMATION: X can be Aib or a lysine residue substituted
      with a modifying group, or a C-terminal amino acid or an amino
      acid ester or amino acid amide thereof
<220> FEATURE:
<221> NAME/KEY: MOD_RES
<222> LOCATION: (17)..(17)
<223> OTHER INFORMATION: Aib or a lysine residue substituted with a
      modifying group, or a C-terminal amino acid or an amino acid ester
      or amino acid amide thereof
<220> FEATURE:
<221> NAME/KEY: VARIANT
<222> LOCATION: (18)..(18)
<223> OTHER INFORMATION: Ala can be replaced by Glu
<220> FEATURE:
<221> NAME/KEY: VARIANT
<222> LOCATION: (20)..(20)
<223> OTHER INFORMATION: Val can be replaced by Ile
<220> FEATURE:
<221> NAME/KEY: VARIANT
<222> LOCATION: (21)..(21)
<223> OTHER INFORMATION: Asn can be replaced by Gln, a lysine residue
      substituted with a modifying group, or a C-terminal amino acid or
      an amino acid ester or amino acid amide thereof or D-Glutamic acid
<220> FEATURE:
<221> NAME/KEY: MOD_RES
<222> LOCATION: (21)..(21)
<223> OTHER INFORMATION: a lysine residue substituted with a modifying
      group, or a C-terminal amino acid or an amino acid ester or amino
      acid amide thereof or D-Glutamic acid
<220> FEATURE:
<221> NAME/KEY: SITE
<222> LOCATION: (21)..(21)
<223> OTHER INFORMATION: D-Glutamic acid
```

```
<220> FEATURE:
<221> NAME/KEY: VARIANT
<222> LOCATION: (22)..(22)
<223> OTHER INFORMATION: Trp can be replaced by Tyr
<220> FEATURE:
<221> NAME/KEY: VARIANT
<222> LOCATION: (24)..(24)
<223> OTHER INFORMATION: Xaa can be Ile or Leu
<220> FEATURE:
<221> NAME/KEY: VARIANT
<222> LOCATION: (25)..(25)
<223> OTHER INFORMATION: Ala can be replaced by Glu
<220> FEATURE:
<221> NAME/KEY: VARIANT
<222> LOCATION: (37)..(37)
<223> OTHER INFORMATION: X can be a lysine residue substituted with a
      modifying group, or a C-terminal amino acid or an amino acid ester
      or amino acid amide thereof or absent
<220> FEATURE:
<221> NAME/KEY: MOD_RES
<222> LOCATION: (37)..(37)
<223> OTHER INFORMATION: a lysine residue substituted with a modifying
      group, or a C-terminal amino acid or an amino acid ester or amino
      acid amide thereof or absent

<400> SEQUENCE: 8

Gly Thr Phe Thr Ser Asp Tyr Ser Ile Tyr Leu Asp Lys Gln Ala Ala
1               5                   10                  15

Xaa Ala Phe Val Asn Trp Leu Xaa Ala Gly Gly Pro Ser Ser Gly Ala
            20                  25                  30

Pro Pro Pro Ser Xaa
            35

<210> SEQ ID NO 9
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: VARIANT
<222> LOCATION: (3)..(3)
<223> OTHER INFORMATION: Phe can be replaced by alpha-methyl-2-
      fluorophenylalaine, alpha-methyl-phenylalaine or
      2-fluorophenylalaine
<220> FEATURE:
<221> NAME/KEY: MOD_RES
<222> LOCATION: (3)..(3)
<223> OTHER INFORMATION: Alpha-methyl-2-fluorophenylalaine,
      alpha-methyl-phenylalaine or 2-fluorophenylalaine
<220> FEATURE:
<221> NAME/KEY: VARIANT
<222> LOCATION: (4)..(4)
<223> OTHER INFORMATION: Thr can be replaced by Ala or Val
<220> FEATURE:
<221> NAME/KEY: VARIANT
<222> LOCATION: (7)..(7)
<223> OTHER INFORMATION: Tyr can be replaced by a lysine residue
      substituted with a modifying group, or a C-terminal amino acid or
      an amino acid ester or amino acid amide thereof
<220> FEATURE:
<221> NAME/KEY: MOD_RES
<222> LOCATION: (7)..(7)
<223> OTHER INFORMATION: a lysine residue substituted with a modifying
      group, or a C-terminal amino acid or an amino acid ester or amino
      acid amide thereof
<220> FEATURE:
<221> NAME/KEY: VARIANT
<222> LOCATION: (10)..(10)
<223> OTHER INFORMATION: Tyr can be replaced by alpha-methyl-leucine or
      Aib
<220> FEATURE:
<221> NAME/KEY: MOD_RES
<222> LOCATION: (10)..(10)
```

```
<223> OTHER INFORMATION: Alpha-methyl-leucine or Aib
<220> FEATURE:
<221> NAME/KEY: VARIANT
<222> LOCATION: (13)..(13)
<223> OTHER INFORMATION: Lys can be replaced by Orn or Arg
<220> FEATURE:
<221> NAME/KEY: SITE
<222> LOCATION: (13)..(13)
<223> OTHER INFORMATION: Orn
<220> FEATURE:
<221> NAME/KEY: VARIANT
<222> LOCATION: (14)..(14)
<223> OTHER INFORMATION: Gln can be replaced by Ile or a lysine residue
      substituted with a modifying group, or a C-terminal amino acid or
      an amino acid ester or amino acid amide thereof
<220> FEATURE:
<221> NAME/KEY: MOD_RES
<222> LOCATION: (14)..(14)
<223> OTHER INFORMATION: a lysine residue substituted with a modifying
      group, or a C-terminal amino acid or an amino acid ester or amino
      acid amide thereof
<220> FEATURE:
<221> NAME/KEY: VARIANT
<222> LOCATION: (16)..(16)
<223> OTHER INFORMATION: Ala can be replaced by Gln
<220> FEATURE:
<221> NAME/KEY: VARIANT
<222> LOCATION: (17)..(17)
<223> OTHER INFORMATION: X can be Aib or a lysine residue substituted
      with a modifying group, or a C-terminal amino acid or an amino
      acid ester or amino acid amide thereof
<220> FEATURE:
<221> NAME/KEY: MOD_RES
<222> LOCATION: (17)..(17)
<223> OTHER INFORMATION: Aib or a lysine residue substituted with a
      modifying group, or a C-terminal amino acid or an amino acid ester
      or amino acid amide thereof
<220> FEATURE:
<221> NAME/KEY: VARIANT
<222> LOCATION: (18)..(18)
<223> OTHER INFORMATION: Ala can be replaced by Glu
<220> FEATURE:
<221> NAME/KEY: VARIANT
<222> LOCATION: (20)..(20)
<223> OTHER INFORMATION: Val can be replaced by Ile
<220> FEATURE:
<221> NAME/KEY: VARIANT
<222> LOCATION: (21)..(21)
<223> OTHER INFORMATION: Asn can be replaced by Gln, a lysine residue
      substituted with a modifying group, or a C-terminal amino acid or
      an amino acid ester or amino acid amide thereof or D-Glutamic acid
<220> FEATURE:
<221> NAME/KEY: MOD_RES
<222> LOCATION: (21)..(21)
<223> OTHER INFORMATION: a lysine residue substituted with a modifying
      group, or a C-terminal amino acid or an amino acid ester or amino
      acid amide thereof or D-Glutamic acid
<220> FEATURE:
<221> NAME/KEY: SITE
<222> LOCATION: (21)..(21)
<223> OTHER INFORMATION: D-Glutamic acid
<220> FEATURE:
<221> NAME/KEY: VARIANT
<222> LOCATION: (22)..(22)
<223> OTHER INFORMATION: Trp can be replaced by Tyr
<220> FEATURE:
<221> NAME/KEY: VARIANT
<222> LOCATION: (24)..(24)
<223> OTHER INFORMATION: Xaa can be Ile or Leu
<220> FEATURE:
<221> NAME/KEY: VARIANT
<222> LOCATION: (25)..(25)
<223> OTHER INFORMATION: Ala can be replaced by Glu
<220> FEATURE:
<221> NAME/KEY: VARIANT
<222> LOCATION: (37)..(37)
<223> OTHER INFORMATION: X can be a lysine residue substituted with a
      modifying group, or a C-terminal amino acid or an amino acid ester
      or amino acid amide thereof or absent
```

```
<220> FEATURE:
<221> NAME/KEY: MOD_RES
<222> LOCATION: (37)..(37)
<223> OTHER INFORMATION: a lysine residue substituted with a modifying
      group, or a C-terminal amino acid or an amino acid ester or amino
      acid amide thereof or absent

<400> SEQUENCE: 9

Gly Thr Phe Thr Ser Asp Tyr Ser Ile Tyr Leu Asp Lys Gln Ala Ala
1               5                   10                  15

Xaa Ala Phe Val Asn Trp Leu Xaa Ala Gly Gly Pro Ser Ser Gly Ala
            20                  25                  30

Pro Pro Pro Ser Xaa
        35

<210> SEQ ID NO 10
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (10)..(10)
<223> OTHER INFORMATION: Aib
<220> FEATURE:
<221> NAME/KEY: MOD_RES
<222> LOCATION: (17)..(17)
<223> OTHER INFORMATION: (1S,28S)-1-amino-7,16,25,30-tetraoxo-
      9,12,18,21-tetraoxa-6,15,24,29-tetraazaoctatetracontane-
      1,28,48-tricarboxylic acid

<400> SEQUENCE: 10

Gly Thr Phe Thr Ser Asp Tyr Ser Ile Xaa Leu Asp Lys Ile Ala Gln
1               5                   10                  15

Xaa Ala Phe Val Gln Trp Leu Ile Ala Gly Gly Pro Ser Ser Gly Ala
            20                  25                  30

Pro Pro Pro Ser
        35

<210> SEQ ID NO 11
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Alpha-methyl-2-fluorophenylalaine
<220> FEATURE:
<221> NAME/KEY: VARIANT
<222> LOCATION: (3)..(3)
<223> OTHER INFORMATION: Phe can be replaced by alpha-methyl-2-
      fluorophenylalaine
<220> FEATURE:
<221> NAME/KEY: MOD_RES
<222> LOCATION: (10)..(10)
<223> OTHER INFORMATION: Aib
<220> FEATURE:
<221> NAME/KEY: MOD_RES
<222> LOCATION: (17)..(17)
<223> OTHER INFORMATION: (1S,28S)-1-amino-7,16,25,30-tetraoxo-
      9,12,18,21-tetraoxa-6,15,24,29-tetraazaoctatetracontane-1,28,48-
      tricarboxylic acid

<400> SEQUENCE: 11

Gly Thr Phe Thr Ser Asp Tyr Ser Ile Xaa Leu Asp Lys Ile Ala Gln
```

```
                1               5                  10                  15
Xaa Ala Phe Val Gln Trp Leu Ile Ala Gly
            20                  25

<210> SEQ ID NO 12
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (10)..(10)
<223> OTHER INFORMATION: Aib
<220> FEATURE:
<221> NAME/KEY: MOD_RES
<222> LOCATION: (17)..(17)
<223> OTHER INFORMATION: (1S,28S)-1-amino-7,16,25,30-tetraoxo-
      9,12,18,21-tetraoxa-6,15,24,29-tetraazaoctatetracontane-1,28,48-
      tricarboxylic acid

<400> SEQUENCE: 12

Gly Thr Phe Thr Ser Asp Tyr Ser Ile Xaa Leu Asp Arg Ile Ala Gln
1               5                  10                  15

Xaa Ala Phe Val Gln Trp Leu Ile Ala Gly Gly Pro Ser Ser Gly Ala
            20                  25                  30

Pro Pro Pro Ser
        35

<210> SEQ ID NO 13
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (3)..(3)
<223> OTHER INFORMATION: Alpha-methyl-2-fluorophenylalaine
<220> FEATURE:
<221> NAME/KEY: MOD_RES
<222> LOCATION: (10)..(10)
<223> OTHER INFORMATION: Aib
<220> FEATURE:
<221> NAME/KEY: MOD_RES
<222> LOCATION: (17)..(17)
<223> OTHER INFORMATION: (1S,28S)-1-amino-7,16,25,30-tetraoxo-
      9,12,18,21-tetraoxa-6,15,24,29-tetraazaoctatetracontane-1,28,48-
      tricarboxylic acid

<400> SEQUENCE: 13

Gly Thr Phe Thr Ser Asp Tyr Ser Ile Xaa Leu Asp Arg Ile Ala Gln
1               5                  10                  15

Xaa Ala Phe Val Gln Trp Leu Ile Ala Gly Gly Pro Ser Ser Gly Ala
            20                  25                  30

Pro Pro Pro Ser
        35

<210> SEQ ID NO 14
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
```

```
<222> LOCATION: (3)..(3)
<223> OTHER INFORMATION: Alpha-methyl-phenylalaine
<220> FEATURE:
<221> NAME/KEY: MOD_RES
<222> LOCATION: (10)..(10)
<223> OTHER INFORMATION: Aib
<220> FEATURE:
<221> NAME/KEY: MOD_RES
<222> LOCATION: (17)..(17)
<223> OTHER INFORMATION: (1S,28S)-1-amino-7,16,25,30-tetraoxo-
     9,12,18,21-tetraoxa-6,15,24,29-tetraazaoctatetracontane-1,28,48-
     tricarboxylic acid

<400> SEQUENCE: 14

Gly Thr Phe Thr Ser Asp Tyr Ser Ile Xaa Leu Asp Arg Ile Ala Gln
1               5                   10                  15

Xaa Ala Phe Val Gln Trp Leu Ile Ala Gly Gly Pro Ser Ser Gly Ala
            20                  25                  30

Pro Pro Pro Ser
        35

<210> SEQ ID NO 15
<211> LENGTH: 36
<212> TYPE: PRT
<213> ORGANISM: Artificial Sequence
<220> FEATURE:
<223> OTHER INFORMATION: Description of Artificial Sequence: Synthetic
     polypeptide
<220> FEATURE:
<221> NAME/KEY: MOD_RES
<222> LOCATION: (3)..(3)
<223> OTHER INFORMATION: 2-Fluorophenylalaine
<220> FEATURE:
<221> NAME/KEY: MOD_RES
<222> LOCATION: (10)..(10)
<223> OTHER INFORMATION: Aib
<220> FEATURE:
<221> NAME/KEY: MOD_RES
<222> LOCATION: (17)..(17)
<223> OTHER INFORMATION: (1S,28S)-1-amino-7,16,25,30-tetraoxo-
     9,12,18,21-tetraoxa-6,15,24,29-tetraazaoctatetracontane-1,28,48-
     tricarboxylic acid

<400> SEQUENCE: 15

Gly Thr Phe Thr Ser Asp Tyr Ser Ile Xaa Leu Asp Arg Ile Ala Gln
1               5                   10                  15

Xaa Ala Phe Val Gln Trp Leu Ile Ala Gly Gly Pro Ser Ser Gly Ala
            20                  25                  30

Pro Pro Pro Ser
        35

<210> SEQ ID NO 16
<211> LENGTH: 36
<212> TYPE: PRT
<213> ORGANISM: Artificial Sequence
<220> FEATURE:
<223> OTHER INFORMATION: Description of Artificial Sequence: Synthetic
     polypeptide
<220> FEATURE:
<221> NAME/KEY: MOD_RES
<222> LOCATION: (17)..(17)
<223> OTHER INFORMATION: (1S,28S)-1-amino-7,16,25,30-tetraoxo-
     9,12,18,21-tetraoxa-6,15,24,29-tetraazaoctatetracontane-1,28,48-
     tricarboxylic acid

<400> SEQUENCE: 16

Gly Thr Phe Thr Ser Asp Tyr Ser Ile Tyr Leu Asp Lys Ile Ala Gln
1               5                   10                  15

Xaa Ala Phe Val Gln Trp Leu Ile Ala Gly Gly Pro Ser Ser Gly Ala
```

-continued

```
                    20                  25                  30

Pro Pro Pro Ser
            35

<210> SEQ ID NO 17
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (10)..(10)
<223> OTHER INFORMATION: Aib
<220> FEATURE:
<221> NAME/KEY: MOD_RES
<222> LOCATION: (17)..(17)
<223> OTHER INFORMATION: (1S,28S)-1-amino-7,16,25,30-tetraoxo-
      9,12,18,21-tetraoxa-6,15,24,29-tetraazaoctatetracontane-1,28,48-
      tricarboxylic acid

<400> SEQUENCE: 17

Gly Thr Phe Thr Ser Asp Tyr Ser Ile Xaa Leu Asp Lys Ile Ala Gln
1               5                   10                  15

Xaa Ala Phe Val Gln Trp Leu Leu Ala Gly Gly Pro Ser Ser Gly Ala
            20                  25                  30

Pro Pro Pro Ser
            35

<210> SEQ ID NO 18
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (10)..(10)
<223> OTHER INFORMATION: Aib
<220> FEATURE:
<221> NAME/KEY: MOD_RES
<222> LOCATION: (17)..(17)
<223> OTHER INFORMATION: (1S,28S)-1-amino-7,16,25,30-tetraoxo-
      9,12,18,21-tetraoxa-6,15,24,29-tetraazaoctatetracontane-1,28,48-
      tricarboxylic acid

<400> SEQUENCE: 18

Gly Thr Phe Thr Ser Asp Tyr Ser Ile Xaa Leu Asp Lys Ile Ala Gln
1               5                   10                  15

Xaa Glu Phe Val Gln Trp Leu Ile Ala Gly Gly Pro Ser Ser Gly Ala
            20                  25                  30

Pro Pro Pro Ser
            35

<210> SEQ ID NO 19
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (10)..(10)
<223> OTHER INFORMATION: Aib
<220> FEATURE:
<221> NAME/KEY: MOD_RES
```

```
<222> LOCATION: (17)..(17)
<223> OTHER INFORMATION: (1S,28S)-1-amino-7,16,25,30-tetraoxo-
      9,12,18,21-tetraoxa-6,15,24,29-tetraazaoctatetracontane-1,28,48-
      tricarboxylic acid

<400> SEQUENCE: 19

Gly Thr Phe Thr Ser Asp Tyr Ser Ile Xaa Leu Asp Lys Gln Ala Gln
1               5                   10                  15

Xaa Ala Phe Val Gln Trp Leu Ile Ala Gly Gly Pro Ser Ser Gly Ala
            20                  25                  30

Pro Pro Pro Ser
        35

<210> SEQ ID NO 20
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (17)..(17)
<223> OTHER INFORMATION: Aib
<220> FEATURE:
<221> NAME/KEY: MOD_RES
<222> LOCATION: (37)..(37)
<223> OTHER INFORMATION: (1S,28S)-1-amino-7,16,25,30-tetraoxo-
      9,12,18,21-tetraoxa-6,15,24,29-tetraazaoctatetracontane-1,28,48-
      tricarboxylic acid

<400> SEQUENCE: 20

Gly Thr Phe Thr Ser Asp Tyr Ser Ile Tyr Leu Asp Lys Gln Ala Ala
1               5                   10                  15

Xaa Glu Phe Val Asn Trp Leu Leu Ala Gly Gly Pro Ser Ser Gly Ala
            20                  25                  30

Pro Pro Pro Ser Xaa
        35

<210> SEQ ID NO 21
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (10)..(10)
<223> OTHER INFORMATION: Aib
<220> FEATURE:
<221> NAME/KEY: MOD_RES
<222> LOCATION: (17)..(17)
<223> OTHER INFORMATION: (1S,28S)-1-amino-7,16,25,30-tetraoxo-
      9,12,18,21-tetraoxa-6,15,24,29-tetraazaoctatetracontane-1,28,48-
      tricarboxylic acid

<400> SEQUENCE: 21

Gly Thr Phe Thr Ser Asp Tyr Ser Ile Xaa Leu Asp Lys Ile Ala Ala
1               5                   10                  15

Xaa Ala Phe Val Gln Trp Leu Ile Ala Gly Gly Pro Ser Ser Gly Ala
            20                  25                  30

Pro Pro Pro Ser
        35

<210> SEQ ID NO 22
<211> LENGTH: 36
```

```
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD
<222> LOCATION: (17)..(17)
<223> OTHER INFORMATION: (1S,28S)-1-amino-7,16,25,30-tetraoxo-
      9,12,18,21-tetraoxa-6,15,24,29-tetraazaoctatetracontane-1,28,48-
      tricarboxylic acid

<400> SEQUENCE: 22

Gly Thr Phe Thr Ser Asp Tyr Ser Ile Tyr Leu Asp Lys Gln Ala Ala
1               5                   10                  15

Xaa Glu Phe Val Asn Trp Leu Leu Ala Gly Gly Pro Ser Ser Gly Ala
            20                  25                  30

Pro Pro Pro Ser
        35

<210> SEQ ID NO 23
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (10)..(10)
<223> OTHER INFORMATION: Aib
<220> FEATURE:
<221> NAME/KEY: MOD_RES
<222> LOCATION: (17)..(17)
<223> OTHER INFORMATION: (1S,28S)-1-amino-7,16,25,30-tetraoxo-
      9,12,18,21-tetraoxa-6,15,24,29-tetraazaoctatetracontane-1,28,48-
      tricarboxylic acid

<400> SEQUENCE: 23

Gly Thr Phe Thr Ser Asp Tyr Ser Ile Xaa Leu Asp Lys Ile Ala Gln
1               5                   10                  15

Xaa Ala Phe Val Asn Trp Leu Ile Ala Gly Gly Pro Ser Ser Gly Ala
            20                  25                  30

Pro Pro Pro Ser
        35

<210> SEQ ID NO 24
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (10)..(10)
<223> OTHER INFORMATION: Aib
<220> FEATURE:
<221> NAME/KEY: MOD_RES
<222> LOCATION: (17)..(17)
<223> OTHER INFORMATION: (1S,28S)-1-amino-7,16,25,30-tetraoxo-
      9,12,18,21-tetraoxa-6,15,24,29-tetraazaoctatetracontane-1,28,48-
      tricarboxylic acid

<400> SEQUENCE: 24

Gly Thr Phe Val Ser Asp Tyr Ser Ile Xaa Leu Asp Lys Ile Ala Gln
1               5                   10                  15

Xaa Ala Phe Val Gln Trp Leu Ile Ala Gly Gly Pro Ser Ser Gly Ala
            20                  25                  30
```

```
Pro Pro Pro Ser
        35

<210> SEQ ID NO 25
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (10)..(10)
<223> OTHER INFORMATION: Aib
<220> FEATURE:
<221> NAME/KEY: MOD_RES
<222> LOCATION: (17)..(17)
<223> OTHER INFORMATION: (1S,28S)-1-amino-7,16,25,30-tetraoxo-
      9,12,18,21-tetraoxa-6,15,24,29-tetraazaoctatetracontane-1,28,48-
      tricarboxylic acid

<400> SEQUENCE: 25

Gly Thr Phe Ala Ser Asp Tyr Ser Ile Xaa Leu Asp Lys Ile Ala Gln
1               5                   10                  15

Xaa Ala Phe Val Gln Trp Leu Ile Ala Gly Gly Pro Ser Ser Gly Ala
            20                  25                  30

Pro Pro Pro Ser
        35

<210> SEQ ID NO 26
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (7)..(7)
<223> OTHER INFORMATION: (1S,28S)-1-amino-7,16,25,30-tetraoxo-
      9,12,18,21-tetraoxa-6,15,24,29-tetraazaoctatetracontane-1,28,48-
      tricarboxylic acid
<220> FEATURE:
<221> NAME/KEY: MOD_RES
<222> LOCATION: (17)..(17)
<223> OTHER INFORMATION: Aib

<400> SEQUENCE: 26

Gly Thr Phe Thr Ser Asp Xaa Ser Ile Tyr Leu Asp Lys Gln Ala Ala
1               5                   10                  15

Xaa Glu Phe Val Asn Trp Leu Leu Ala Gly Gly Pro Ser Ser Gly Ala
            20                  25                  30

Pro Pro Pro Ser
        35

<210> SEQ ID NO 27
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (10)..(10)
<223> OTHER INFORMATION: Aib
<220> FEATURE:
<221> NAME/KEY: MOD_RES
<222> LOCATION: (17)..(17)
```

<223> OTHER INFORMATION: (1S,28S)-1-amino-7,16,25,30-tetraoxo-
      9,12,18,21-tetraoxa-6,15,24,29-tetraazaoctatetracontane-1,28,48-
      tricarboxylic acid

<400> SEQUENCE: 27

Gly Thr Phe Thr Ser Asp Tyr Ser Ile Xaa Leu Asp Lys Ile Ala Gln
1               5                   10                  15

Xaa Ala Phe Val Gln Trp Leu Ile Ala Gly Gly Pro Ser Ser Gly Ala
            20                  25                  30

Pro Pro Pro Ser
        35

<210> SEQ ID NO 28
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (3)..(3)
<223> OTHER INFORMATION: Alpha-methyl-2-fluorophenylalaine
<220> FEATURE:
<221> NAME/KEY: MOD_RES
<222> LOCATION: (17)..(17)
<223> OTHER INFORMATION: Aib
<220> FEATURE:
<221> NAME/KEY: MOD_RES
<222> LOCATION: (37)..(37)
<223> OTHER INFORMATION: (1S,28S)-1-amino-7,16,25,30-tetraoxo-
      9,12,18,21-tetraoxa-6,15,24,29-tetraazaoctatetracontane-1,28,48-
      tricarboxylic acid

<400> SEQUENCE: 28

Gly Thr Phe Thr Ser Asp Tyr Ser Ile Tyr Leu Asp Lys Gln Ala Ala
1               5                   10                  15

Xaa Glu Phe Val Asn Trp Leu Leu Ala Gly Gly Pro Ser Ser Gly Ala
            20                  25                  30

Pro Pro Pro Ser Xaa
        35

<210> SEQ ID NO 29
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (3)..(3)
<223> OTHER INFORMATION: Alpha-methyl-2-fluorophenylalaine
<220> FEATURE:
<221> NAME/KEY: MOD_RES
<222> LOCATION: (7)..(7)
<223> OTHER INFORMATION: (1S,28S)-1-amino-7,16,25,30-tetraoxo-
      9,12,18,21-tetraoxa-6,15,24,29-tetraazaoctatetracontane-1,28,48-
      tricarboxylic acid
<220> FEATURE:
<221> NAME/KEY: MOD_RES
<222> LOCATION: (17)..(17)
<223> OTHER INFORMATION: Aib

<400> SEQUENCE: 29

Gly Thr Phe Thr Ser Asp Xaa Ser Ile Tyr Leu Asp Lys Gln Ala Ala
1               5                   10                  15

Xaa Glu Phe Val Asn Trp Leu Leu Ala Gly Gly Pro Ser Ser Gly Ala
            20                  25                  30

Pro Pro Pro Ser
      35

<210> SEQ ID NO 30
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (10)..(10)
<223> OTHER INFORMATION: Aib
<220> FEATURE:
<221> NAME/KEY: MOD_RES
<222> LOCATION: (17)..(17)
<223> OTHER INFORMATION: (1S,28S)-1-amino-7,16,25,30-tetraoxo-
      9,12,18,21-tetraoxa-6,15,24,29-tetraazaoctatetracontane-1,28,48-
      tricarboxylic acid

<400> SEQUENCE: 30

Gly Thr Phe Thr Ser Asp Tyr Ser Ile Xaa Leu Asp Lys Ile Ala Gln
1               5                   10                  15

Xaa Ala Phe Val Gln Trp Leu Ile Ala Gly
            20                  25

<210> SEQ ID NO 31
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Alpha-methyl-2-fluorophenylalaine
<220> FEATURE:
<221> NAME/KEY: MOD_RES
<222> LOCATION: (10)..(10)
<223> OTHER INFORMATION: Aib
<220> FEATURE:
<221> NAME/KEY: MOD_RES
<222> LOCATION: (17)..(17)
<223> OTHER INFORMATION: (1S,28S)-1-amino-7,16,25,30-tetraoxo-
      9,12,18,21-tetraoxa-6,15,24,29-tetraazaoctatetracontane-1,28,48-
      tricarboxylic acid

<400> SEQUENCE: 31

Gly Thr Phe Thr Ser Asp Tyr Ser Ile Xaa Leu Asp Lys Ile Ala Gln
1               5                   10                  15

Xaa Ala Phe Val Gln Trp Leu Ile Ala Gly
            20                  25

<210> SEQ ID NO 32
<211> LENGTH: 36
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (10)..(10)
<223> OTHER INFORMATION: Alpha-methyl-leucine
<220> FEATURE:
<221> NAME/KEY: SITE
<222> LOCATION: (13)..(13)
<223> OTHER INFORMATION: Orn
<220> FEATURE:

<221> NAME/KEY: MOD_RES
<222> LOCATION: (14)..(14)
<223> OTHER INFORMATION: (1S,28S)-1-amino-7,16,25,30-tetraoxo-
9,12,18,21-tetraoxa-6,15,24,29-tetraazaoctatetracontane-1,28,48-
tricarboxylic acid
<220> FEATURE:
<221> NAME/KEY: MOD_RES
<222> LOCATION: (17)..(17)
<223> OTHER INFORMATION: Aib
<220> FEATURE:
<221> NAME/KEY: SITE
<222> LOCATION: (21)..(21)
<223> OTHER INFORMATION: D-Glutamic acid

<400> SEQUENCE: 32

Gly Thr Phe Thr Ser Asp Tyr Ser Ile Leu Leu Asp Xaa Xaa Ala Gln
1               5                   10                  15

Xaa Glu Phe Ile Glu Tyr Leu Ile Glu Gly Gly Pro Ser Ser Gly Ala
            20                  25                  30

Pro Pro Pro Ser
        35

<210> SEQ ID NO 33
<211> LENGTH: 36
<212> TYPE: PRT
<213> ORGANISM: Artificial Sequence
<220> FEATURE:
<223> OTHER INFORMATION: Description of Artificial Sequence: Synthetic
polypeptide
<220> FEATURE:
<221> NAME/KEY: MOD_RES
<222> LOCATION: (3)..(3)
<223> OTHER INFORMATION: Alpha-methyl-2-fluorophenylalaine
<220> FEATURE:
<221> NAME/KEY: MOD_RES
<222> LOCATION: (10)..(10)
<223> OTHER INFORMATION: Alpha-methyl-leucine
<220> FEATURE:
<221> NAME/KEY: SITE
<222> LOCATION: (13)..(13)
<223> OTHER INFORMATION: Orn
<220> FEATURE:
<221> NAME/KEY: MOD_RES
<222> LOCATION: (14)..(14)
<223> OTHER INFORMATION: (1S,28S)-1-amino-7,16,25,30-tetraoxo-
9,12,18,21-tetraoxa-6,15,24,29-tetraazaoctatetracontane-1,28,48-
tricarboxylic acid
<220> FEATURE:
<221> NAME/KEY: MOD_RES
<222> LOCATION: (17)..(17)
<223> OTHER INFORMATION: Aib
<220> FEATURE:
<221> NAME/KEY: SITE
<222> LOCATION: (21)..(21)
<223> OTHER INFORMATION: D-Glutamic acid

<400> SEQUENCE: 33

Gly Thr Phe Thr Ser Asp Tyr Ser Ile Leu Leu Asp Xaa Xaa Ala Gln
1               5                   10                  15

Xaa Glu Phe Ile Glu Tyr Leu Ile Glu Gly Gly Pro Ser Ser Gly Ala
            20                  25                  30

Pro Pro Pro Ser
        35

<210> SEQ ID NO 34
<211> LENGTH: 36
<212> TYPE: PRT
<213> ORGANISM: Artificial Sequence
<220> FEATURE:
<223> OTHER INFORMATION: Description of Artificial Sequence: Synthetic
polypeptide

```
<220> FEATURE:
<221> NAME/KEY: MOD_RES
<222> LOCATION: (10)..(10)
<223> OTHER INFORMATION: Aib
<220> FEATURE:
<221> NAME/KEY: MOD_RES
<222> LOCATION: (17)..(17)
<223> OTHER INFORMATION: (1S,28S)-1-amino-7,16,25,30-tetraoxo-
     9,12,18,21-tetraoxa-6,15,24,29-tetraazahexatetracontane-1,28,46-
     tricarboxylic acid

<400> SEQUENCE: 34

Gly Thr Phe Thr Ser Asp Tyr Ser Ile Xaa Leu Asp Lys Ile Ala Gln
1               5                   10                  15

Xaa Ala Phe Val Gln Trp Leu Ile Ala Gly Gly Pro Ser Ser Gly Ala
            20                  25                  30

Pro Pro Pro Ser
        35

<210> SEQ ID NO 35
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (10)..(10)
<223> OTHER INFORMATION: Aib
<220> FEATURE:
<221> NAME/KEY: MOD_RES
<222> LOCATION: (17)..(17)
<223> OTHER INFORMATION: (3S,8S,13S,22S)-22-amino-1-((1r,4S)-4-((19-
     carboxynonadecanamido)methyl)cyclohexyl)-1,6,11,16-tetraoxo-
     2,7,12,17-tetraazadocosane-3,8,13,22-tetracarboxylic acid

<400> SEQUENCE: 35

Gly Thr Phe Thr Ser Asp Tyr Ser Ile Xaa Leu Asp Lys Ile Ala Gln
1               5                   10                  15

Xaa Ala Phe Val Gln Trp Leu Ile Ala Gly Gly Pro Ser Ser Gly Ala
            20                  25                  30

Pro Pro Pro Ser
        35

<210> SEQ ID NO 36
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (14)..(14)
<223> OTHER INFORMATION: (1S,28S)-1-amino-7,16,25,30-tetraoxo-
     9,12,18,21-tetraoxa-6,15,24,29-tetraazaoctatetracontane-1,28,48-
     tricarboxylic acid
<220> FEATURE:
<221> NAME/KEY: MOD_RES
<222> LOCATION: (17)..(17)
<223> OTHER INFORMATION: Aib

<400> SEQUENCE: 36

Gly Thr Phe Thr Ser Asp Tyr Ser Ile Tyr Leu Asp Lys Xaa Ala Ala
1               5                   10                  15

Xaa Glu Phe Val Asn Trp Leu Leu Ala Gly Gly Pro Ser Ser Gly Ala
            20                  25                  30
```

```
Pro Pro Pro Ser
        35

<210> SEQ ID NO 37
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (17)..(17)
<223> OTHER INFORMATION: Aib
<220> FEATURE:
<221> NAME/KEY: MOD_RES
<222> LOCATION: (21)..(21)
<223> OTHER INFORMATION: (1S,28S)-1-amino-7,16,25,30-tetraoxo-
      9,12,18,21-tetraoxa-6,15,24,29-tetraazaoctatetracontane-1,28,48-
      tricarboxylic acid

<400> SEQUENCE: 37

Gly Thr Phe Thr Ser Asp Tyr Ser Ile Tyr Leu Asp Lys Gln Ala Ala
1               5                   10                  15

Xaa Glu Phe Val Xaa Trp Leu Leu Ala Gly Gly Pro Ser Ser Gly Ala
            20                  25                  30

Pro Pro Pro Ser
        35

<210> SEQ ID NO 38
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (11)..(11)
<223> OTHER INFORMATION: Aib
<220> FEATURE:
<221> NAME/KEY: MOD_RES
<222> LOCATION: (18)..(18)
<223> OTHER INFORMATION: (1S,28S)-1-amino-7,16,25,30-tetraoxo-
      9,12,18,21-tetraoxa-6,15,24,29-tetraazaoctatetracontane-1,28,48-
      tricarboxylic acid

<400> SEQUENCE: 38

Glu Gly Thr Phe Thr Ser Asp Tyr Ser Ile Xaa Leu Asp Lys Ile Ala
1               5                   10                  15

Gln Xaa Ala Phe Val Gln Trp Leu Ile Ala Gly Gly Pro Ser Ser Gly
            20                  25                  30

Ala Pro Pro Pro Ser
        35

<210> SEQ ID NO 39
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (11)..(11)
<223> OTHER INFORMATION: Aib
<220> FEATURE:
<221> NAME/KEY: MOD_RES
<222> LOCATION: (18)..(18)
<223> OTHER INFORMATION: (1S,28S)-1-amino-7,16,25,30-tetraoxo-
```

```
            9,12,18,21-tetraoxa-6,15,24,29-tetraazaoctatetracontane-1,28,48-
            tricarboxylic acid

<400> SEQUENCE: 39

Glu Gly Thr Phe Thr Ser Asp Tyr Ser Ile Xaa Leu Asp Arg Ile Ala
1               5                   10                  15

Gln Xaa Ala Phe Val Gln Trp Leu Ile Ala Gly Gly Pro Ser Ser Gly
            20                  25                  30

Ala Pro Pro Pro Ser
            35

<210> SEQ ID NO 40
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (4)..(4)
<223> OTHER INFORMATION: Alpha-methyl-2-fluorophenylalaine
<220> FEATURE:
<221> NAME/KEY: MOD_RES
<222> LOCATION: (11)..(11)
<223> OTHER INFORMATION: Aib
<220> FEATURE:
<221> NAME/KEY: MOD_RES
<222> LOCATION: (18)..(18)
<223> OTHER INFORMATION: (1S,28S)-1-amino-7,16,25,30-tetraoxo-
      9,12,18,21-tetraoxa-6,15,24,29-tetraazaoctatetracontane-1,28,48-
      tricarboxylic acid

<400> SEQUENCE: 40

Glu Gly Thr Phe Thr Ser Asp Tyr Ser Ile Xaa Leu Asp Arg Ile Ala
1               5                   10                  15

Gln Xaa Ala Phe Val Gln Trp Leu Ile Ala Gly Gly Pro Ser Ser Gly
            20                  25                  30

Ala Pro Pro Pro Ser
            35

<210> SEQ ID NO 41
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (4)..(4)
<223> OTHER INFORMATION: Alpha-methyl-phenylalaine
<220> FEATURE:
<221> NAME/KEY: MOD_RES
<222> LOCATION: (11)..(11)
<223> OTHER INFORMATION: Aib
<220> FEATURE:
<221> NAME/KEY: MOD_RES
<222> LOCATION: (18)..(18)
<223> OTHER INFORMATION: (1S,28S)-1-amino-7,16,25,30-tetraoxo-
      9,12,18,21-tetraoxa-6,15,24,29-tetraazaoctatetracontane-1,28,48-
      tricarboxylic acid

<400> SEQUENCE: 41

Glu Gly Thr Phe Thr Ser Asp Tyr Ser Ile Xaa Leu Asp Arg Ile Ala
1               5                   10                  15

Gln Xaa Ala Phe Val Gln Trp Leu Ile Ala Gly Gly Pro Ser Ser Gly
            20                  25                  30
```

```
-continued

Ala Pro Pro Pro Ser
        35

<210> SEQ ID NO 42
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (4)..(4)
<223> OTHER INFORMATION: 2-Fluorophenylalaine
<220> FEATURE:
<221> NAME/KEY: MOD_RES
<222> LOCATION: (11)..(11)
<223> OTHER INFORMATION: Aib
<220> FEATURE:
<221> NAME/KEY: MOD_RES
<222> LOCATION: (18)..(18)
<223> OTHER INFORMATION: (1S,28S)-1-amino-7,16,25,30-tetraoxo-
      9,12,18,21-tetraoxa-6,15,24,29-tetraazaoctatetracontane-1,28,48-
      tricarboxylic acid

<400> SEQUENCE: 42

Glu Gly Thr Phe Thr Ser Asp Tyr Ser Ile Xaa Leu Asp Arg Ile Ala
1               5                   10                  15

Gln Xaa Ala Phe Val Gln Trp Leu Ile Ala Gly Gly Pro Ser Ser Gly
            20                  25                  30

Ala Pro Pro Pro Ser
        35

<210> SEQ ID NO 43
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (18)..(18)
<223> OTHER INFORMATION: (1S,28S)-1-amino-7,16,25,30-tetraoxo-
      9,12,18,21-tetraoxa-6,15,24,29-tetraazaoctatetracontane-1,28,48-
      tricarboxylic acid

<400> SEQUENCE: 43

Glu Gly Thr Phe Thr Ser Asp Tyr Ser Ile Tyr Leu Asp Lys Ile Ala
1               5                   10                  15

Gln Xaa Ala Phe Val Gln Trp Leu Ile Ala Gly Gly Pro Ser Ser Gly
            20                  25                  30

Ala Pro Pro Pro Ser
        35

<210> SEQ ID NO 44
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (11)..(11)
<223> OTHER INFORMATION: Aib
<220> FEATURE:
<221> NAME/KEY: MOD_RES
<222> LOCATION: (18)..(18)
<223> OTHER INFORMATION: (1S,28S)-1-amino-7,16,25,30-tetraoxo-
```

```
                9,12,18,21-tetraoxa-6,15,24,29-tetraazaoctatetracontane-1,28,48-
                tricarboxylic acid

<400> SEQUENCE: 44

Glu Gly Thr Phe Thr Ser Asp Tyr Ser Ile Xaa Leu Asp Lys Ile Ala
1               5                   10                  15

Gln Xaa Ala Phe Val Gln Trp Leu Leu Ala Gly Gly Pro Ser Ser Gly
            20                  25                  30

Ala Pro Pro Pro Ser
        35

<210> SEQ ID NO 45
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (11)..(11)
<223> OTHER INFORMATION: Aib
<220> FEATURE:
<221> NAME/KEY: MOD_RES
<222> LOCATION: (18)..(18)
<223> OTHER INFORMATION: (1S,28S)-1-amino-7,16,25,30-tetraoxo-
      9,12,18,21-tetraoxa-6,15,24,29-tetraazaoctatetracontane-1,28,48-
      tricarboxylic acid

<400> SEQUENCE: 45

Glu Gly Thr Phe Thr Ser Asp Tyr Ser Ile Xaa Leu Asp Lys Ile Ala
1               5                   10                  15

Gln Xaa Glu Phe Val Gln Trp Leu Ile Ala Gly Gly Pro Ser Ser Gly
            20                  25                  30

Ala Pro Pro Pro Ser
        35

<210> SEQ ID NO 46
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (11)..(11)
<223> OTHER INFORMATION: Aib
<220> FEATURE:
<221> NAME/KEY: MOD_RES
<222> LOCATION: (18)..(18)
<223> OTHER INFORMATION: (1S,28S)-1-amino-7,16,25,30-tetraoxo-
      9,12,18,21-tetraoxa-6,15,24,29-tetraazaoctatetracontane-1,28,48-
      tricarboxylic acid

<400> SEQUENCE: 46

Glu Gly Thr Phe Thr Ser Asp Tyr Ser Ile Xaa Leu Asp Lys Gln Ala
1               5                   10                  15

Gln Xaa Ala Phe Val Gln Trp Leu Ile Ala Gly Gly Pro Ser Ser Gly
            20                  25                  30

Ala Pro Pro Pro Ser
        35

<210> SEQ ID NO 47
<211> LENGTH: 38
<212> TYPE: PRT
<213> ORGANISM: Artificial Sequence
```

```
<220> FEATURE:
<223> OTHER INFORMATION: Description of Artificial Sequence: Synthetic
      polypeptide
<220> FEATURE:
<221> NAME/KEY: MOD_RES
<222> LOCATION: (18)..(18)
<223> OTHER INFORMATION: Aib
<220> FEATURE:
<221> NAME/KEY: MOD_RES
<222> LOCATION: (38)..(38)
<223> OTHER INFORMATION: (1S,28S)-1-amino-7,16,25,30-tetraoxo-
      9,12,18,21-tetraoxa-6,15,24,29-tetraazaoctatetracontane-1,28,48-
      tricarboxylic acid

<400> SEQUENCE: 47

Glu Gly Thr Phe Thr Ser Asp Tyr Ser Ile Tyr Leu Asp Lys Gln Ala
1               5                   10                  15

Ala Xaa Glu Phe Val Asn Trp Leu Leu Ala Gly Gly Pro Ser Ser Gly
            20                  25                  30

Ala Pro Pro Pro Ser Xaa
        35

<210> SEQ ID NO 48
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (11)..(11)
<223> OTHER INFORMATION: Aib
<220> FEATURE:
<221> NAME/KEY: MOD_RES
<222> LOCATION: (18)..(18)
<223> OTHER INFORMATION: (1S,28S)-1-amino-7,16,25,30-tetraoxo-
      9,12,18,21-tetraoxa-6,15,24,29-tetraazaoctatetracontane-1,28,48-
      tricarboxylic acid

<400> SEQUENCE: 48

Glu Gly Thr Phe Thr Ser Asp Tyr Ser Ile Xaa Leu Asp Lys Ile Ala
1               5                   10                  15

Ala Xaa Ala Phe Val Gln Trp Leu Ile Ala Gly Gly Pro Ser Ser Gly
            20                  25                  30

Ala Pro Pro Pro Ser
        35

<210> SEQ ID NO 49
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (18)..(18)
<223> OTHER INFORMATION: (1S,28S)-1-amino-7,16,25,30-tetraoxo-
      9,12,18,21-tetraoxa-6,15,24,29-tetraazaoctatetracontane-1,28,48-
      tricarboxylic acid

<400> SEQUENCE: 49

Glu Gly Thr Phe Thr Ser Asp Tyr Ser Ile Tyr Leu Asp Lys Gln Ala
1               5                   10                  15

Ala Xaa Glu Phe Val Asn Trp Leu Leu Ala Gly Gly Pro Ser Ser Gly
            20                  25                  30

Ala Pro Pro Pro Ser
```

```
<210> SEQ ID NO 50
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (11)..(11)
<223> OTHER INFORMATION: Aib
<220> FEATURE:
<221> NAME/KEY: MOD_RES
<222> LOCATION: (18)..(18)
<223> OTHER INFORMATION: (1S,28S)-1-amino-7,16,25,30-tetraoxo-
      9,12,18,21-tetraoxa-6,15,24,29-tetraazaoctatetracontane-1,28,48-
      tricarboxylic acid

<400> SEQUENCE: 50

Glu Gly Thr Phe Thr Ser Asp Tyr Ser Ile Xaa Leu Asp Lys Ile Ala
1               5                   10                  15

Gln Xaa Ala Phe Val Asn Trp Leu Ile Ala Gly Gly Pro Ser Ser Gly
            20                  25                  30

Ala Pro Pro Pro Ser
        35

<210> SEQ ID NO 51
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (11)..(11)
<223> OTHER INFORMATION: Aib
<220> FEATURE:
<221> NAME/KEY: MOD_RES
<222> LOCATION: (18)..(18)
<223> OTHER INFORMATION: (1S,28S)-1-amino-7,16,25,30-tetraoxo-
      9,12,18,21-tetraoxa-6,15,24,29-tetraazaoctatetracontane-1,28,48-
      tricarboxylic acid

<400> SEQUENCE: 51

Glu Gly Thr Phe Val Ser Asp Tyr Ser Ile Xaa Leu Asp Lys Ile Ala
1               5                   10                  15

Gln Xaa Ala Phe Val Gln Trp Leu Ile Ala Gly Gly Pro Ser Ser Gly
            20                  25                  30

Ala Pro Pro Pro Ser
        35

<210> SEQ ID NO 52
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (11)..(11)
<223> OTHER INFORMATION: Aib
<220> FEATURE:
<221> NAME/KEY: MOD_RES
<222> LOCATION: (18)..(18)
<223> OTHER INFORMATION: (1S,28S)-1-amino-7,16,25,30-tetraoxo-
      9,12,18,21-tetraoxa-6,15,24,29-tetraazaoctatetracontane-1,28,48-
``` tricarboxylic acid

<400> SEQUENCE: 52

Glu Gly Thr Phe Ala Ser Asp Tyr Ser Ile Xaa Leu Asp Lys Ile Ala
1               5                   10                  15

Gln Xaa Ala Phe Val Gln Trp Leu Ile Ala Gly Gly Pro Ser Ser Gly
            20                  25                  30

Ala Pro Pro Pro Ser
        35

<210> SEQ ID NO 53
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (8)..(8)
<223> OTHER INFORMATION: (1S,28S)-1-amino-7,16,25,30-tetraoxo-
      9,12,18,21-tetraoxa-6,15,24,29-tetraazaoctatetracontane-1,28,48-
      tricarboxylic acid
<220> FEATURE:
<221> NAME/KEY: MOD_RES
<222> LOCATION: (18)..(18)
<223> OTHER INFORMATION: Aib

<400> SEQUENCE: 53

Glu Gly Thr Phe Thr Ser Asp Xaa Ser Ile Tyr Leu Asp Lys Gln Ala
1               5                   10                  15

Ala Xaa Glu Phe Val Asn Trp Leu Leu Ala Gly Gly Pro Ser Ser Gly
            20                  25                  30

Ala Pro Pro Pro Ser
        35

<210> SEQ ID NO 54
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (11)..(11)
<223> OTHER INFORMATION: Aib
<220> FEATURE:
<221> NAME/KEY: MOD_RES
<222> LOCATION: (18)..(18)
<223> OTHER INFORMATION: (1S,28S)-1-amino-7,16,25,30-tetraoxo-
      9,12,18,21-tetraoxa-6,15,24,29-tetraazaoctatetracontane-1,28,48-
      tricarboxylic acid

<400> SEQUENCE: 54

Glu Gly Thr Phe Thr Ser Asp Tyr Ser Ile Xaa Leu Asp Lys Ile Ala
1               5                   10                  15

Gln Xaa Ala Phe Val Gln Trp Leu Ile Ala Gly Gly Pro Ser Ser Gly
            20                  25                  30

Ala Pro Pro Pro Ser
        35

<210> SEQ ID NO 55
<211> LENGTH: 37
<212> TYPE: PRT
<213> ORGANISM: Artificial Sequence
<220> FEATURE:

```
<223> OTHER INFORMATION: Description of Artificial Sequence: Synthetic
      polypeptide
<220> FEATURE:
<221> NAME/KEY: MOD_RES
<222> LOCATION: (4)..(4)
<223> OTHER INFORMATION: Alpha-methyl-2-fluorophenylalaine
<220> FEATURE:
<221> NAME/KEY: MOD_RES
<222> LOCATION: (11)..(11)
<223> OTHER INFORMATION: Aib
<220> FEATURE:
<221> NAME/KEY: MOD_RES
<222> LOCATION: (18)..(18)
<223> OTHER INFORMATION: (1S,28S)-1-amino-7,16,25,30-tetraoxo-
      9,12,18,21-tetraoxa-6,15,24,29-tetraazaoctatetracontane-1,28,48-
      tricarboxylic acid

<400> SEQUENCE: 55

Glu Gly Thr Phe Thr Ser Asp Tyr Ser Ile Xaa Leu Asp Lys Ile Ala
1               5                   10                  15

Gln Xaa Ala Phe Val Gln Trp Leu Ile Ala Gly Gly Pro Ser Ser Gly
            20                  25                  30

Ala Pro Pro Pro Ser
            35

<210> SEQ ID NO 56
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (4)..(4)
<223> OTHER INFORMATION: Alpha-methyl-2-fluorophenylalaine
<220> FEATURE:
<221> NAME/KEY: MOD_RES
<222> LOCATION: (18)..(18)
<223> OTHER INFORMATION: Aib
<220> FEATURE:
<221> NAME/KEY: MOD_RES
<222> LOCATION: (38)..(38)
<223> OTHER INFORMATION: (1S,28S)-1-amino-7,16,25,30-tetraoxo-
      9,12,18,21-tetraoxa-6,15,24,29-tetraazaoctatetracontane-1,28,48-
      tricarboxylic acid

<400> SEQUENCE: 56

Glu Gly Thr Phe Thr Ser Asp Tyr Ser Ile Tyr Leu Asp Lys Gln Ala
1               5                   10                  15

Ala Xaa Glu Phe Val Asn Trp Leu Leu Ala Gly Gly Pro Ser Ser Gly
            20                  25                  30

Ala Pro Pro Pro Ser Xaa
            35

<210> SEQ ID NO 57
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (4)..(4)
<223> OTHER INFORMATION: Alpha-methyl-2-fluorophenylalaine
<220> FEATURE:
<221> NAME/KEY: MOD_RES
<222> LOCATION: (8)..(8)
<223> OTHER INFORMATION: (1S,28S)-1-amino-7,16,25,30-tetraoxo-
      9,12,18,21-tetraoxa-6,15,24,29-tetraazaoctatetracontane-1,28,48-
```

```
        tricarboxylic acid
<220> FEATURE:
<221> NAME/KEY: MOD_RES
<222> LOCATION: (18)..(18)
<223> OTHER INFORMATION: Aib

<400> SEQUENCE: 57

Glu Gly Thr Phe Thr Ser Asp Xaa Ser Ile Tyr Leu Asp Lys Gln Ala
1               5                   10                  15

Ala Xaa Glu Phe Val Asn Trp Leu Leu Ala Gly Gly Pro Ser Ser Gly
            20                  25                  30

Ala Pro Pro Pro Ser
        35

<210> SEQ ID NO 58
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (11)..(11)
<223> OTHER INFORMATION: Aib
<220> FEATURE:
<221> NAME/KEY: MOD_RES
<222> LOCATION: (18)..(18)
<223> OTHER INFORMATION: (1S,28S)-1-amino-7,16,25,30-tetraoxo-
      9,12,18,21-tetraoxa-6,15,24,29-tetraazaoctatetracontane-1,28,48-
      tricarboxylic acid

<400> SEQUENCE: 58

Glu Gly Thr Phe Thr Ser Asp Tyr Ser Ile Xaa Leu Asp Lys Ile Ala
1               5                   10                  15

Gln Xaa Ala Phe Val Gln Trp Leu Ile Ala Gly
            20                  25

<210> SEQ ID NO 59
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Alpha-methyl-2-fluorophenylalaine
<220> FEATURE:
<221> NAME/KEY: MOD_RES
<222> LOCATION: (11)..(11)
<223> OTHER INFORMATION: Aib
<220> FEATURE:
<221> NAME/KEY: MOD_RES
<222> LOCATION: (18)..(18)
<223> OTHER INFORMATION: (1S,28S)-1-amino-7,16,25,30-tetraoxo-
      9,12,18,21-tetraoxa-6,15,24,29-tetraazaoctatetracontane-1,28,48-
      tricarboxylic acid

<400> SEQUENCE: 59

Glu Gly Thr Phe Thr Ser Asp Tyr Ser Ile Xaa Leu Asp Lys Ile Ala
1               5                   10                  15

Gln Xaa Ala Phe Val Gln Trp Leu Ile Ala Gly
            20                  25

<210> SEQ ID NO 60
<211> LENGTH: 37
<212> TYPE: PRT
```

```
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (11)..(11)
<223> OTHER INFORMATION: Alpha-methyl-leucine
<220> FEATURE:
<221> NAME/KEY: SITE
<222> LOCATION: (14)..(14)
<223> OTHER INFORMATION: Orn
<220> FEATURE:
<221> NAME/KEY: MOD_RES
<222> LOCATION: (15)..(15)
<223> OTHER INFORMATION: (1S,28S)-1-amino-7,16,25,30-tetraoxo-
      9,12,18,21-tetraoxa-6,15,24,29-tetraazaoctatetracontane-1,28,48-
      tricarboxylic acid
<220> FEATURE:
<221> NAME/KEY: MOD_RES
<222> LOCATION: (18)..(18)
<223> OTHER INFORMATION: Aib
<220> FEATURE:
<221> NAME/KEY: SITE
<222> LOCATION: (22)..(22)
<223> OTHER INFORMATION: D-Glutamic acid

<400> SEQUENCE: 60

Glu Gly Thr Phe Thr Ser Asp Tyr Ser Ile Leu Leu Asp Xaa Xaa Ala
1               5                   10                  15

Gln Xaa Glu Phe Ile Glu Tyr Leu Ile Glu Gly Gly Pro Ser Ser Gly
            20                  25                  30

Ala Pro Pro Pro Ser
            35

<210> SEQ ID NO 61
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (4)..(4)
<223> OTHER INFORMATION: Alpha-methyl-2-fluorophenylalaine
<220> FEATURE:
<221> NAME/KEY: MOD_RES
<222> LOCATION: (11)..(11)
<223> OTHER INFORMATION: Alpha-methyl-leucine
<220> FEATURE:
<221> NAME/KEY: SITE
<222> LOCATION: (14)..(14)
<223> OTHER INFORMATION: Orn
<220> FEATURE:
<221> NAME/KEY: MOD_RES
<222> LOCATION: (15)..(15)
<223> OTHER INFORMATION: (1S,28S)-1-amino-7,16,25,30-tetraoxo-
      9,12,18,21-tetraoxa-6,15,24,29-tetraazaoctatetracontane-1,28,48-
      tricarboxylic acid
<220> FEATURE:
<221> NAME/KEY: MOD_RES
<222> LOCATION: (18)..(18)
<223> OTHER INFORMATION: Aib
<220> FEATURE:
<221> NAME/KEY: SITE
<222> LOCATION: (22)..(22)
<223> OTHER INFORMATION: D-Glutamic acid

<400> SEQUENCE: 61

Glu Gly Thr Phe Thr Ser Asp Tyr Ser Ile Leu Leu Asp Xaa Xaa Ala
1               5                   10                  15

Gln Xaa Glu Phe Ile Glu Tyr Leu Ile Glu Gly Gly Pro Ser Ser Gly
```

Ala Pro Pro Pro Ser
        35

<210> SEQ ID NO 62
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (11)..(11)
<223> OTHER INFORMATION: Aib
<220> FEATURE:
<221> NAME/KEY: MOD_RES
<222> LOCATION: (18)..(18)
<223> OTHER INFORMATION: (1S,28S)-1-amino-7,16,25,30-tetraoxo-
      9,12,18,21-tetraoxa-6,15,24,29-tetraazahexatetracontane-1,28,46-
      tricarboxylic acid

<400> SEQUENCE: 62

Glu Gly Thr Phe Thr Ser Asp Tyr Ser Ile Xaa Leu Asp Lys Ile Ala
1               5                   10                  15

Gln Xaa Ala Phe Val Gln Trp Leu Ile Ala Gly Gly Pro Ser Ser Gly
            20                  25                  30

Ala Pro Pro Pro Ser
        35

<210> SEQ ID NO 63
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (11)..(11)
<223> OTHER INFORMATION: Aib
<220> FEATURE:
<221> NAME/KEY: MOD_RES
<222> LOCATION: (18)..(18)
<223> OTHER INFORMATION: (3S,8S,13S,22S)-22-amino-1-((1r,4S)-4-((19-
      carboxynonadecanamido)methyl)cyclohexyl)-1,6,11,16-tetraoxo-
      2,7,12,17-tetraazadocosane-3,8,13,22-tetracarboxylic acid

<400> SEQUENCE: 63

Glu Gly Thr Phe Thr Ser Asp Tyr Ser Ile Xaa Leu Asp Lys Ile Ala
1               5                   10                  15

Gln Xaa Ala Phe Val Gln Trp Leu Ile Ala Gly Gly Pro Ser Ser Gly
            20                  25                  30

Ala Pro Pro Pro Ser
        35

<210> SEQ ID NO 64
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: SITE
<222> LOCATION: (1)..(1)
<223> OTHER INFORMATION: D-Aspartic acid
<220> FEATURE:
<221> NAME/KEY: MOD_RES

```
<222> LOCATION: (11)..(11)
<223> OTHER INFORMATION: Aib
<220> FEATURE:
<221> NAME/KEY: MOD_RES
<222> LOCATION: (18)..(18)
<223> OTHER INFORMATION: (1S,28S)-1-amino-7,16,25,30-tetraoxo-
      9,12,18,21-tetraoxa-6,15,24,29-tetraazaoctatetracontane-1,28,48-
      tricarboxylic acid

<400> SEQUENCE: 64

Asp Gly Thr Phe Thr Ser Asp Tyr Ser Ile Xaa Leu Asp Lys Ile Ala
1               5                   10                  15

Gln Xaa Ala Phe Val Gln Trp Leu Ile Ala Gly Gly Pro Ser Ser Gly
            20                  25                  30

Ala Pro Pro Pro Ser
        35

<210> SEQ ID NO 65
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (11)..(11)
<223> OTHER INFORMATION: Aib
<220> FEATURE:
<221> NAME/KEY: MOD_RES
<222> LOCATION: (18)..(18)
<223> OTHER INFORMATION: (1S,28S)-1-amino-7,16,25,30-tetraoxo-
      9,12,18,21-tetraoxa-6,15,24,29-tetraazahexatetracontane-1,28,46-
      tricarboxylic acid

<400> SEQUENCE: 65

Asp Gly Thr Phe Thr Ser Asp Tyr Ser Ile Xaa Leu Asp Lys Ile Ala
1               5                   10                  15

Gln Xaa Ala Phe Val Gln Trp Leu Ile Ala Gly Gly Pro Ser Ser Gly
            20                  25                  30

Ala Pro Pro Pro Ser
        35

<210> SEQ ID NO 66
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: SITE
<222> LOCATION: (1)..(1)
<223> OTHER INFORMATION: D-Glutamic acid
<220> FEATURE:
<221> NAME/KEY: MOD_RES
<222> LOCATION: (11)..(11)
<223> OTHER INFORMATION: Aib
<220> FEATURE:
<221> NAME/KEY: MOD_RES
<222> LOCATION: (18)..(18)
<223> OTHER INFORMATION: (1S,28S)-1-amino-7,16,25,30-tetraoxo-
      9,12,18,21-tetraoxa-6,15,24,29-tetraazahexatetracontane-1,28,46-
      tricarboxylic acid

<400> SEQUENCE: 66

Glu Gly Thr Phe Thr Ser Asp Tyr Ser Ile Xaa Leu Asp Lys Ile Ala
1               5                   10                  15

Gln Xaa Ala Phe Val Gln Trp Leu Ile Ala Gly Gly Pro Ser Ser Gly
```

<210> SEQ ID NO 67
<211> LENGTH: 37
<212> TYPE: PRT
<213> ORGANISM: Artificial Sequence
<220> FEATURE:
<223> OTHER INFORMATION: Description of Artificial Sequence: Synthetic
     polypeptide
<220> FEATURE:
<221> NAME/KEY: MOD_RES
<222> LOCATION: (15)..(15)
<223> OTHER INFORMATION: (1S,28S)-1-amino-7,16,25,30-tetraoxo-
     9,12,18,21-tetraoxa-6,15,24,29-tetraazaoctatetracontane-1,28,48-
     tricarboxylic acid
<220> FEATURE:
<221> NAME/KEY: MOD_RES
<222> LOCATION: (18)..(18)
<223> OTHER INFORMATION: Aib

<400> SEQUENCE: 67

Glu Gly Thr Phe Thr Ser Asp Tyr Ser Ile Tyr Leu Asp Lys Xaa Ala
1               5                   10                  15

Ala Xaa Glu Phe Val Asn Trp Leu Leu Ala Gly Gly Pro Ser Ser Gly
            20                  25                  30

Ala Pro Pro Pro Ser
        35

<210> SEQ ID NO 68
<211> LENGTH: 37
<212> TYPE: PRT
<213> ORGANISM: Artificial Sequence
<220> FEATURE:
<223> OTHER INFORMATION: Description of Artificial Sequence: Synthetic
     polypeptide
<220> FEATURE:
<221> NAME/KEY: MOD_RES
<222> LOCATION: (18)..(18)
<223> OTHER INFORMATION: Aib
<220> FEATURE:
<221> NAME/KEY: MOD_RES
<222> LOCATION: (22)..(22)
<223> OTHER INFORMATION: (1S,28S)-1-amino-7,16,25,30-tetraoxo-
     9,12,18,21-tetraoxa-6,15,24,29-tetraazaoctatetracontane-1,28,48-
     tricarboxylic acid

<400> SEQUENCE: 68

Glu Gly Thr Phe Thr Ser Asp Tyr Ser Ile Tyr Leu Asp Lys Gln Ala
1               5                   10                  15

Ala Xaa Glu Phe Val Xaa Trp Leu Leu Ala Gly Gly Pro Ser Ser Gly
            20                  25                  30

Ala Pro Pro Pro Ser
        35

<210> SEQ ID NO 69
<211> LENGTH: 37
<212> TYPE: PRT
<213> ORGANISM: Artificial Sequence
<220> FEATURE:
<223> OTHER INFORMATION: Description of Artificial Sequence: Synthetic
     polypeptide
<220> FEATURE:
<221> NAME/KEY: MOD_RES
<222> LOCATION: (11)..(11)
<223> OTHER INFORMATION: Aib
<220> FEATURE:
<221> NAME/KEY: MOD_RES

```
<222> LOCATION: (18)..(18)
<223> OTHER INFORMATION: (1S,28S)-1-amino-7,16,25,30-tetraoxo-
      9,12,18,21-tetraoxa-6,15,24,29-tetraazaoctatetracontane-1,28,48-
      tricarboxylic acid

<400> SEQUENCE: 69

Glu Gly Thr Phe Thr Ser Asp Tyr Ser Ile Xaa Leu Asp Lys Ile Ala
1               5                   10                  15

Gln Xaa Ala Phe Val Gln Trp Leu Ile Ala Gly Gly Pro Ser Ser Gly
            20                  25                  30

Ala Pro Pro Pro Ser
            35

<210> SEQ ID NO 70
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (11)..(11)
<223> OTHER INFORMATION: Aib
<220> FEATURE:
<221> NAME/KEY: MOD_RES
<222> LOCATION: (18)..(18)
<223> OTHER INFORMATION: (1S,28S)-1-amino-7,16,25,30-tetraoxo-
      9,12,18,21-tetraoxa-6,15,24,29-tetraazaoctatetracontane-1,28,48-
      tricarboxylic acid

<400> SEQUENCE: 70

Glu Gly Thr Phe Thr Ser Asp Tyr Ser Ile Xaa Leu Asp Lys Ile Ala
1               5                   10                  15

Gln Xaa Ala Phe Val Gln Trp Leu Ile Ala Gly Gly Pro Ser Ser Gly
            20                  25                  30

Ala Pro Pro Pro Ser
            35

<210> SEQ ID NO 71
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (11)..(11)
<223> OTHER INFORMATION: Aib
<220> FEATURE:
<221> NAME/KEY: MOD_RES
<222> LOCATION: (18)..(18)
<223> OTHER INFORMATION: (1S,28S)-1-amino-7,16,25,30-tetraoxo-
      9,12,18,21-tetraoxa-6,15,24,29-tetraazaoctatetracontane-1,28,48-
      tricarboxylic acid

<400> SEQUENCE: 71

Glu Gly Thr Phe Thr Ser Asp Tyr Ser Ile Xaa Leu Asp Lys Ile Ala
1               5                   10                  15

Gln Xaa Ala Phe Val Gln Trp Leu Ile Ala Gly Gly Pro Ser Ser Gly
            20                  25                  30

Ala Pro Pro Pro Ser
            35

<210> SEQ ID NO 72
<211> LENGTH: 37
```

```
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (4)..(4)
<223> OTHER INFORMATION: Alpha-Methyl-L-2-fluorophenylalanine
<220> FEATURE:
<221> NAME/KEY: MOD_RES
<222> LOCATION: (11)..(11)
<223> OTHER INFORMATION: 2-Methyl-L-leucine
<220> FEATURE:
<221> NAME/KEY: SITE
<222> LOCATION: (14)..(14)
<223> OTHER INFORMATION: Orn
<220> FEATURE:
<221> NAME/KEY: MOD_RES
<222> LOCATION: (15)..(15)
<223> OTHER INFORMATION: (1S,28S)-1-amino-7,16,25,30-tetraoxo-
      9,12,18,21-tetraoxa-6,15,24,29-tetraazaoctatetracontane-1,28,48-
      tricarboxylic acid
<220> FEATURE:
<221> NAME/KEY: MOD_RES
<222> LOCATION: (18)..(18)
<223> OTHER INFORMATION: Aib

<400> SEQUENCE: 72

Glu Gly Thr Phe Thr Ser Asp Tyr Ser Ile Leu Leu Asp Xaa Xaa Ala
1               5                   10                  15

Gln Xaa Glu Phe Ile Glu Tyr Leu Ile Glu Gly Gly Pro Ser Ser Gly
            20                  25                  30

Ala Pro Pro Pro Ser
            35

<210> SEQ ID NO 73
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (11)..(11)
<223> OTHER INFORMATION: Aib
<220> FEATURE:
<221> NAME/KEY: MOD_RES
<222> LOCATION: (18)..(18)
<223> OTHER INFORMATION: (1S,28S)-1-amino-7,16,25,30-tetraoxo-
      9,12,18,21-tetraoxa-6,15,24,29-tetraazaoctatetracontane-1,28,48-
      tricarboxylic acid

<400> SEQUENCE: 73

Glu Gly Thr Phe Thr Ser Asp Tyr Ser Ile Xaa Leu Asp Lys Ile Ala
1               5                   10                  15

Gln Xaa Ala Phe Val Gln Trp Leu Ile Ala Gly Gly Pro Ser Ser Gly
            20                  25                  30

Ala Pro Pro Pro Ser
            35

<210> SEQ ID NO 74
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
```

<222> LOCATION: (4)..(4)
<223> OTHER INFORMATION: 2-Fluoro-L-phenylalanine
<220> FEATURE:
<221> NAME/KEY: MOD_RES
<222> LOCATION: (11)..(11)
<223> OTHER INFORMATION: Aib
<220> FEATURE:
<221> NAME/KEY: MOD_RES
<222> LOCATION: (18)..(18)
<223> OTHER INFORMATION: (1S,28S)-1-amino-7,16,25,30-tetraoxo-
     9,12,18,21-tetraoxa-6,15,24,29-tetraazaoctatetracontane-1,28,48-
     tricarboxylic acid

<400> SEQUENCE: 74

Glu Gly Thr Phe Thr Ser Asp Tyr Ser Ile Xaa Leu Asp Lys Ile Ala
1               5                   10                  15

Gln Xaa Ala Phe Val Gln Trp Leu Ile Ala Gly Gly Pro Ser Ser Gly
            20                  25                  30

Ala Pro Pro Pro Ser
        35

<210> SEQ ID NO 75
<211> LENGTH: 37
<212> TYPE: PRT
<213> ORGANISM: Artificial Sequence
<220> FEATURE:
<223> OTHER INFORMATION: Description of Artificial Sequence: Synthetic
     polypeptide
<220> FEATURE:
<221> NAME/KEY: MOD_RES
<222> LOCATION: (11)..(11)
<223> OTHER INFORMATION: Aib
<220> FEATURE:
<221> NAME/KEY: MOD_RES
<222> LOCATION: (18)..(18)
<223> OTHER INFORMATION: (1S,28S)-1-amino-7,16,25,30-tetraoxo-
     9,12,18,21-tetraoxa-6,15,24,29-tetraazaoctatetracontane-1,28,48-
     tricarboxylic acid

<400> SEQUENCE: 75

Glu Gly Thr Phe Thr Ser Asp Tyr Ser Ile Xaa Leu Asp Lys Ile Ala
1               5                   10                  15

Gln Xaa Ala Phe Val Gln Trp Leu Ile Ala Gly Gly Pro Ser Ser Gly
            20                  25                  30

Ala Pro Pro Pro Ser
        35

<210> SEQ ID NO 76
<211> LENGTH: 37
<212> TYPE: PRT
<213> ORGANISM: Artificial Sequence
<220> FEATURE:
<223> OTHER INFORMATION: Description of Artificial Sequence: Synthetic
     polypeptide
<220> FEATURE:
<221> NAME/KEY: MOD_RES
<222> LOCATION: (11)..(11)
<223> OTHER INFORMATION: Aib
<220> FEATURE:
<221> NAME/KEY: MOD_RES
<222> LOCATION: (18)..(18)
<223> OTHER INFORMATION: (1S,28S)-1-amino-7,16,25,30-tetraoxo-
     9,12,18,21-tetraoxa-6,15,24,29-tetraazaoctatetracontane-1,28,48-
     tricarboxylic acid

<400> SEQUENCE: 76

Glu Gly Thr Phe Thr Ser Asp Tyr Ser Ile Xaa Leu Asp Lys Ile Ala
1               5                   10                  15

Gln Xaa Ala Phe Val Gln Trp Leu Ile Ala Gly Gly Pro Ser Ser Gly

-continued
```
                20                  25                  30
Ala Pro Pro Pro Ser
                35
```

MODULATORS OF G-PROTEIN COUPLED RECEPTORS

CROSS REFERENCE TO RELATED APPLICATIONS

This application claims the benefit of U.S. Provisional Application No. 63/188,342, filed on May 13, 2021, which is incorporated herein by reference in its entirety.

SEQUENCE LISTING

The instant application contains a Sequence Listing which has been submitted electronically in ASCII format and is hereby incorporated by reference in its entirety. Said ASCII copy, created on Jul. 18, 2024, is named 124921_US003_SL_rev2.txt and is 74,254 bytes in size.

TECHNICAL FIELD

This disclosure features chemical entities (e.g., a compound or a pharmaceutically acceptable salt and/or hydrate and/or prodrug of the compound) that modulate (e.g., agonize or partially agonize or antagonize) glucagon-like peptide-1 receptor ("GLP-1R") and/or the gastric inhibitory polypeptide receptor ("GIPR"). The chemical entities are useful, e.g., for treating a subject (e.g., a human) having a disease, disorder, or condition in which modulation (e.g., agonism, partial agonism or antagonism) of GLP-1R and/or GIPR activities is beneficial for the treatment or prevention of the underlying pathology and/or symptoms and/or progression of the disease, disorder, or condition. In some embodiments, the modulation results in an enhancement of (e.g., an increase in) existing levels (e.g., normal, or below normal levels) of GLP-1R and/or GIPR activity (e.g., signaling). In some embodiments, the chemical entities described herein further modulate (e.g., attenuate, uncouple) β-arrestin signaling relative to what is observed with the native ligand. This disclosure also features compositions as well as other methods of using and making the said chemical entities.

BACKGROUND

Diabetes mellitus type 2 (type-2 diabetes) is characterized by high blood glucose and insulin resistance. Type 2 diabetes as well as conditions that are co-morbid or sequela with type-2 diabetes affect tens of millions of people in the United States alone. Type-2 diabetes is frequently associated with obesity.

Nonalcoholic steatohepatitis (NASH) is liver inflammation and damage caused by a buildup of fat in the liver. It is part of a group of conditions called nonalcoholic fatty liver disease (NAFLD). NASH and NAFLD tend to develop in patients having one of the following risk factors: obesity, dyslipidemia, and glucose intolerance and appears to be linked to insulin resistance (e.g., as in obesity or metabolic syndrome).

Incretin hormones are hormones that provide glycemic control in response to food intake. Gastric inhibitory polypeptide ("GIP") and glucagon-like peptide-1 ("GLP-1") are primary incretin hormones secreted from small intestinal L cells and K cells, respectively, on ingestion of glucose or nutrients to stimulate insulin secretion from pancreatic β cells. GIP and GLP-1 undergo degradation by dipeptidyl peptidase-4 (DPP-4), and rapidly lose their biological activities (see, e.g., Y. Sieno, et. al, *Journal of Diabetes Investigation* 2013, 4, 108-130).

The actions of GIP and GLP-1 are believed to be mediated by their specific receptors, the GIP receptor (GIPR) and the GLP-1 receptor (GLP-1R), respectively, which both belong to the G-protein coupled receptor family and are expressed in pancreatic β-cells, as well as in various tissues and organs. GLP-1 activities include, without limitation, stimulation of insulin synthesis and secretion, inhibition of glucagon secretion, and inhibition of food intake. GIP activities include, without limitation, stimulation of glucose-dependent insulin secretion, an increase in β-cell mass, stimulation of glucagon secretion, and a decrease in gastric acid secretion. See, e.g., WO 2016/131893.

GLP-1 and GLP-1 analogues, acting as agonists at the GLP-1 receptor, have been shown to be effective in glycemic control, e.g., type-2 diabetes. See, e.g., WO 2016/131893. In addition to their insulinotropic effects, GIP and GLP-1 are believed to be involved in various biological processes in different tissues and organs that express GIPR and GLP-1R, including, e.g., the pancreas, fat, bone, brain, heart, kidney, eye, nerves, and liver. By way of example, investigations using mice lacking GIPR and/or GLP-1R, as well as mice lacking DPP-4, showed involvement of GIP and GLP-1 in divergent biological activities. The results of these investigations point to involvement of GIP and GLP-1 in treating and/or preventing diabetes-related microvascular complications (e.g., retinopathy, nephropathy and neuropathy) and macrovascular complications (e.g., coronary artery disease, peripheral artery disease and cerebrovascular disease), as well as diabetes-related comorbidity (e.g., obesity, nonalcoholic fatty liver disease, bone fracture and cognitive dysfunction). See, e.g., Sieno at page 108.

SUMMARY

This disclosure features chemical entities (e.g., a compound or a pharmaceutically acceptable salt and/or hydrate and/or prodrug of the compound) that modulate (e.g., agonize or partially agonize or antagonize) glucagon-like peptide-1 receptor ("GLP-1R") and/or the gastric inhibitory polypeptide receptor ("GIPR"). The chemical entities are useful, e.g., for treating a subject (e.g., a human) having a disease, disorder, or condition in which modulation (e.g., agonism, partial agonism or antagonism) of GLP-1R and/or GIPR activities is beneficial for the treatment or prevention of the underlying pathology and/or symptoms and/or progression of the disease, disorder, or condition. In some embodiments, the modulation results in an enhancement of (e.g., an increase in) existing levels (e.g., normal, or below normal levels) of GLP-1R and/or GIPR activity (e.g., signaling). In some embodiments, the chemical entities described herein further modulate (e.g., attenuate, uncouple) β-arrestin signaling relative to what is observed with the native ligand. This disclosure also features compositions as well as other methods of using and making the said chemical entities.

An "agonist" of GLP-1R includes compounds that, at the protein level, directly bind or modify GLP-1R such that an activity of GLP-1R is increased, e.g., by activation, stabilization, altered distribution, or otherwise relative to GLP-1R activity in absence of ligand.

Certain compounds described herein that agonize GLP-1R to a lesser extent (partial agonists) than a GLP-1R full agonist (e.g., native GLP-1) can function in assays as antagonists as well as agonists. These compounds antagonize activation of GLP-1R by a GLP-1R full agonist because they prevent the full effect of GLP-1R interaction. However, the compounds also, on their own, activate some GLP-1R activity, typically less than a corresponding amount of the GLP-1R full agonist. Such compounds are sometimes referred to herein as "partial agonists of GLP-1R".

An "antagonist" of GLP-1R includes compounds that, at the protein level, directly bind or modify GLP-1R such that an activity of GLP-1R is decreased, e.g., by inhibition, blocking or dampening agonist-mediated responses, altered distribution, or otherwise relative to GLP-1R activity in absence of ligand.

In some embodiments, the compounds described herein are agonists (e.g., full agonists) of GLP-1R. In other embodiments, the compounds described herein are partial agonists or antagonists of GLP-1R.

An "agonist" of GIPR includes compounds that, at the protein level, directly bind or modify GIPR such that an activity of GIPR is increased, e.g., by activation, stabilization, altered distribution, or otherwise relative to GIPR activity in absence of ligand.

Certain compounds described herein that agonize GIPR to a lesser extent than native GIP (s full agonist) can function as antagonists as well as agonists. These compounds are partial antagonists as they reduce activation of GIPR by native GIP because they reduce the full effect of native GIP. However, the compounds also, on their own, activate some GIPR activity, typically less than a corresponding amount of native GIP. Such compounds are sometimes referred to herein as "partial agonists of GIPR".

An "antagonist" of GIPR includes compounds that, at the protein level, directly bind or modify GIPR such that an activity of GIPR is decreased, e.g., by inhibition, blocking or dampening agonist-mediated responses, altered distribution, or otherwise relative to GIPR activity in absence of ligand.

In some embodiments, the compounds described herein are agonists (e.g., full agonists) of GIPR. In other embodiments, the compounds described herein are partial agonists of GIPR. In still other embodiments, the compounds described herein are or antagonists of GIPR.

In some embodiments, the compounds described herein are full agonists of both GLP-1R and GIPR. In some embodiments, the compounds described herein are partial agonists of both GLP-1R and GIPR. This disclosure also contemplates chemical entities that (i) agonize one of GLP-1R and GIPR (e.g., GLP-1R); and antagonize the other of GLP-1R and GIPR (e.g., GIPR). For example, this disclosure contemplates chemical entities that (i) fully agonize one of GLP-1R and GIPR (e.g., GLP-1R); and partially agonize or antagonize the other of GLP-1R and GIPR (e.g., GIPR). In certain embodiments, the chemical entities that are full agonists of GLP-1R and partial agonists or antagonists of GIPR; or that are partial agonists or antagonists of GLP-1R and full agonists of GIPR.

Generally, a receptor exists in an active (Ra) and an inactive (Ri) conformation. Certain compounds that affect the receptor can alter the ratio of Ra to Ri (Ra/Ri). For example, a full agonist increases the ratio of Ra/Ri and can cause a "maximal", saturating effect. A partial agonist, when bound to the receptor, gives a response that is lower than that elicited by a full agonist (e.g., an endogenous agonist). Thus, the Ra/Ri for a partial agonist is less than for a full agonist. However, the potency of a partial agonist may be greater or less than that of the full agonist.

In some embodiments, the chemical entities described herein further modulate (e.g., reduce, e.g., attenuate, disrupt, inhibit) β-arrestin coupling and/or b-arrestin signaling, and GLP-1R and/or GIPR internalization. In certain embodiments, the chemical entities described herein modulate (e.g., reduce, e.g., attenuate, disrupt, inhibit) recruitment of β-arrestin to a G-protein coupled receptor (e.g., GLP-1R). In certain embodiments, the chemical entities described herein modulate (e.g., reduce, e.g., attenuate, disrupt, inhibit) formation of a complex ("coupling") (e.g., a signaling complex) between β-arrestin and a G-protein coupled receptor (e.g., GLP-1R or GIPR). The effects of the chemical entities described herein on β-arrestin signaling and associated downstream processes (e.g., those delineated above) can be assessed using conventional methods, e.g., PathHunter β-arrestin Assay for determining β-arresting coupling (see Examples section). By way of example, a value of β-arrestin (GLP-1R) EC50<1 µM in the aforementioned assay indicates a compound that induces β-arrestin recruitment to GLP-1R. GLP-1, the native ligand for GLP-1R, and therapeutic analogs thereof, such a liraglutide, are potent recruiters of β-arrestin. As another example, a value of β-arrestin (GLP1R) $EC_{50}$>1 µM (e.g., >10 µM) indicates a compound that does not substantially induce β-arrestin recruitment to GLP-1R. Therapeutic agents that modulate G-protein coupled receptors (e.g., GLP-1R and/or GIPR) can produce a variety of effects depending on the degree of cAMP activation versus β-arrestin-based signaling. It has been shown that b-arrestin coupling is a key step in receptor internalization and subsequent de-sensitization and attenuation of signaling. Both GLP-1 (and the liraglutide analog) and GIP have been shown to produce rapid receptor internalization. Thus, compounds that activate GLP-1R and/or GIPR cAMP signaling but do not substantially couple to β-arrestin have the potential to prolong receptor signaling and extend pharmacological benefits. In some embodiments, the chemical entities described herein exhibit relatively strong GLP-1R and/or GIPR mediated cAMP activation with minimal or no detectable β-arrestin coupling. In some embodiments, the chemical entities described herein exhibit relatively strong GLP-1R mediated cAMP activation and no or little GIPR mediated cAMP activation with minimal or no detectable β-arrestin coupling.

In some embodiments, the compounds described herein show reduced activity in a rodent aversion model, while maintaining a relatively high potency in glucose clearance assay. Aversion models, such as conditioned taste aversion, are commonly used to identify compounds with adverse effects such as nausea. Nausea causing agents, such a Exendin-4 and liraglutide, are known to have a strong signal in conditioned taste aversion models. Advantageously, some of the chemical entities described herein are therefore expected to have a reduced likelihood of producing unwanted side effects, such as nausea, when administered to a patient, while maintaining full pharmacological benefit.

Accordingly, in one aspect, this disclosure features peptide-based chemical entities (e.g., N-protected peptide-based chemical entities; e.g., peptide-based chemical entities having from 30-50 amino acids, 30-45 amino acids, 30-40 amino acids, 35-40 amino acids; e.g., an N-protected peptide-based chemical entities having from 30-50 amino acids, 30-45 amino acids, 30-40 amino acids, 35-40 amino acids). The peptide-based chemical entities modulate (e.g., agonize or partially agonize or antagonize) glucagon-like peptide-1 receptor ("GLP-1R") and/or the gastric inhibitory polypeptide receptor ("GIPR") and optionally further modulate (e.g., uncouple, attenuate) β-arrestin signaling and/or aversion as described herein.

In some embodiments, the peptide-based chemical entities agonize or partially agonize GLP-1R.

In some embodiments, the peptide-based chemical entities agonize or partially agonize or antagonize GIPR.

In some embodiments, said peptide-based chemical entities reduce (e.g., uncouple, attenuate, inhibit) β-arrestin signaling; e.g., reduce (e.g., uncouple, attenuate, inhibit) the recruitment of β-arrestin to a G-protein coupled receptor (e.g., GLP-1R); e.g., reduce (e.g., attenuate, disrupt, inhibit) the formation of a complex (e.g., a signaling complex) between β-arrestin and a G-protein coupled receptor (e.g., GLP-1R).

In certain embodiments, the peptide-based chemical entities:

agonize or partially agonize GLP-1R;

agonize or partially agonize or antagonize GIPR;

reduce (e.g., uncouple, attenuate, inhibit) β-arrestin signaling; e.g., reduce (e.g., attenuate, disrupt, inhibit) the recruitment of β-arrestin to a G-protein coupled receptor (e.g., GLP-1R and/or GIPR); e.g., reduce (e.g., attenuate, disrupt, inhibit) the formation of a complex (e.g., a signaling complex) between β-arrestin and a G-protein coupled receptor (e.g., GLP-1R and/or GIPR); and stimulate glucose clearance in vivo (GTT test) without causing aversion.

In some embodiments, the peptide-based chemical entities exhibit a value of cAMP (GLP1R) EC50 of less than about 10 nM, 5 nM, or 1 nM (e.g., less than about 1 nM).

In some embodiments, the peptide-based chemical entities exhibit a value of cAMP (GIPR) EC50 of less than about 100 nm, 50 nM, or 10 nM (e.g., less than about 10 nM).

In some embodiments, the peptide-based chemical entities inhibit GIP induced CAMP production (GIPR antagonism).

In some embodiments, the compounds described herein exhibit a value of β-arrestin (GLP1R) EC50>1 μM.

In some embodiments, the peptide-based chemical entities:

exhibit a value of cAMP (GLPIR) EC50 of less than about 10 nM, 5 nM, or 1 nM (e.g., less than about 1 nM);

exhibit a value of cAMP (GIPR) EC50 of less than about 100 nm, 50 nM, or 10 nM (e.g., less than about 10 nM) or are GIPR antagonists;

exhibit a value of β-arrestin (GLPIR) EC50>1 μM; and stimulate glucose clearance in vivo (GTT test) without causing aversion (nausea)

In one aspect, the featured peptide-based chemical entities include compounds of Formula (I), or a pharmaceutically acceptable salt thereof:

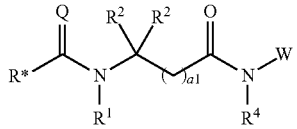

(Formula I)

in which R*, $R^1$, $R^2$, $R^{2'}$, a1, $R^4$, and W can be as defined anywhere herein.

In one aspect, pharmaceutical compositions are featured that include a chemical entity described herein (e.g., a compound described generically or specifically herein or a pharmaceutically acceptable salt thereof or compositions containing the same) and one or more pharmaceutically acceptable excipients.

In one aspect, methods for modulating (e.g., agonizing, partially agonizing, or antagonizing) GLP-1R and/or GIPR activities are featured that include contacting GLP-1R and/or GIPR with a chemical entity described herein (e.g., a compound described generically or specifically herein or a pharmaceutically acceptable salt thereof or compositions containing the same). Methods include in vitro methods, e.g., contacting a sample that includes one or more cells, each independently comprising one or more of GLP-1R and/or GIPR with the chemical entity. Methods can also include in vivo methods; e.g., administering the chemical entity to a subject (e.g., a human) having a disease, disorder, or condition in which modulation of GLP-1R and/or GIPR signaling is beneficial for the treatment of the underlying pathology and/or symptoms and/or progression of the disease, disorder, or condition (e.g., diabetes; e.g., NASH; e.g., obesity). In vivo methods include, but are not limited to modulating (e.g., increasing) insulin levels and modulating (e.g., decreasing) glucose levels in a subject (e.g., a human).

In some of the foregoing embodiments, said methods of modulating are achieved without substantially stimulating β-arrestin signaling; e.g., without stimulating the recruitment of β-arrestin to a G-protein coupled receptor (e.g., GLP-1R); e.g., without stimulating the formation of a complex (e.g., a signaling complex) between β-arrestin and a G-protein coupled receptor (e.g., GLP-1R). In some of the foregoing embodiments, said methods of modulating are achieved without causing aversion or nausea.

In a further aspect, methods of treatment of a disease, disorder, or condition are featured, in which modulation of GLP-1R and/or GIPR signaling is beneficial for the treatment of the underlying pathology and/or symptoms and/or progression of the disease, disorder, or condition. The methods include administering to a subject in need of such treatment an effective amount of a chemical entity described herein (e.g., a compound described generically or specifically herein, a pharmaceutically acceptable salt thereof, or compositions containing the same).

In another aspect, this disclosure features methods of treating a subject having a disease, disorder, or condition in which modulation of GLP-1R and/or GIPR signaling is beneficial for the treatment of the underlying pathology and/or symptoms and/or progression of the disease, disorder, or condition. The methods include administering a chemical entity described herein (e.g., a compound described generically or specifically herein, a pharmaceutically acceptable salt thereof or compositions containing the same) in an amount effective to treat the disease, disorder, or condition.

In a further aspect, methods of treatment are featured that include administering to a subject chemical entity described herein (e.g., a compound described generically or specifically herein, a pharmaceutically acceptable salt thereof, or compositions containing the same). The methods include administering the chemical entity in an amount effective to treat a disease, disorder, or condition, wherein modulation of GLP-1R and/or GIPR is beneficial for the treatment of the underlying pathology and/or symptoms and/or progression of the disease, disorder, or condition, thereby treating the disease, disorder, or condition.

In another aspect, methods of treatment can further include:

(i) administering a first therapeutic agent that modulates (e.g., agonizes, partially agonizes, or antagonizes) GLP-1R and/or GIPR to a subject as defined anywhere herein;

(ii) determining that the subject is suffering from one or more side effects (e.g., aversion, nausea or vomiting); and (iii) ceasing administration of the first therapeutic agent and administering a chemical entity as described herein (e.g., a compound having Formula (I)).

Non-limiting examples of such diseases, disorders, and conditions include metabolic syndrome; diabetes (e.g., type 2 diabetes); obesity; obesity-related disorders; impaired glucose tolerance; insulin resistance; non-alcoholic steatohepatitis (NASH); fatty liver disease; steatohepatitis; and other forms of inflammation in metabolically important tissues including, liver, fat, pancreas, kidney, and gut.

Other non-limiting examples of such diseases, disorders, and conditions include neurological disorders include brain insulin resistance, mild cognitive impairment (MCI), Alzheimer's disease (AD), Parkinson's disease (PD), anxiety, dementia (e.g., senile dementia), traumatic brain injury, Huntington's chores, tardive dyskinesia, hyperkinesia, mania, Morbus Parkinson, steel-Richard syndrome, Down's syndrome, myasthenia gravis, nerve trauma, brain trauma, vascular amyloidosis, cerebral hemorrhage I with amyloidosis, brain inflammation, Friedrich's ataxia, acute confusion disorder, amyotrophic lateral sclerosis (ALS), glaucoma, and apoptosis-mediated degenerative diseases of the central nervous system (e.g., Creutzfeldt-Jakob Disease, bovine spongiform encephalopathy (mad cow disease), and chronic wasting syndrome).

Still other non-limiting examples of such diseases, disorders, and conditions include bone disorder characterized by altered bone metabolism, such as osteoporosis, including post-menopausal osteoporosis, poor bone strength, osteopenia, Paget's disease, osteolytic metastasis in cancer patients, osteodystrophy in liver disease and the altered bone metabolism caused by renal failure or hemodialysis, bone fracture, bone surgery, aging, pregnancy, protection against bone fractures, and malnutrition.

In certain embodiments, the disease, disorder, or condition is diabetes.

In other embodiments, the disease, disorder, or condition is NASH.

In still other embodiments, the disease, disorder, or condition is obesity.

In other embodiments, the disease, disorder, or condition is Alzheimer's disease (AD) or Parkinson's disease (PD).

In still other embodiments, the disease, disorder, or condition is a bone disorder characterized by altered bone metabolism, such as osteoporosis, including post-menopausal osteoporosis, poor bone strength, osteopenia, Paget's disease, osteolytic metastasis in cancer patients, osteodystrophy in liver disease and the altered bone metabolism caused by renal failure or hemodialysis, bone fracture, bone surgery, aging, or pregnancy.

In certain embodiments, the chemical entities described herein are useful for protection against bone fractures.

The methods described herein can further include treating one or more conditions associated, co-morbid or sequela with any one or more of the conditions described herein. By way of non-limiting example, the methods can further include treating one or more conditions that are co-morbid or sequela with diabetes (e.g., type 2 diabetes), such as obesity, obesity-related disorders, metabolic syndrome, impaired glucose tolerance; insulin resistance; cardiovascular risk factors. (e.g., coronary artery disease, peripheral artery disease, cerebrovascular disease, hypertension, and risk factors related to unmanaged cholesterol and/or lipid levels, and/or inflammation), retinopathy, nephropathy, neuropathy, NASH, bone fracture and cognitive dysfunction.

In another aspect, this disclosure features methods for screening a candidate compound for treatment of a disease, disorder, or condition, in which modulation of GLP-1R and/or GIPR is beneficial for the treatment of the underlying pathology and/or symptoms and/or progression of the disease, disorder, or condition; the method comprising:

(a) contacting the candidate compound with (i) a β-Arrestin-coupled GPCR receptor signaling complex or (ii) one or more GPCR receptor signaling complexes that are not complexed with β-arrestin (e.g., uncoupled GLP-1R and/or uncoupled GIPR); and (b) detecting (i) the disruption of the b-arrestin coupled complex; or (ii) detecting the formation of the signaling complex in the absence of b-arrestin coupling; wherein the candidate compound modulates (e.g., agonizes, partially agonizes) GLP-1R and/or GIPR.

In certain embodiments, the methods further include selecting a candidate compound that exhibits a value of β-arrestin (GLP-1R) $EC_{50>1}$ μM.

The methods can further include identifying the subject.

The methods can further include administering one or more other therapeutic agents (e.g., in combination with a chemical entity described herein).

Embodiments can include one of more of the following advantageous properties.

In some embodiments, the compounds described herein exhibit a value of AUC Score of 0-25% of vehicle, which corresponds to a finding of maximal decrease in glucose excursion compared to control.

In some embodiments, the compounds described herein exhibit a value of cAMP (GLP-1R) $EC_{50}$ of less than about 1 nM, which is indicative that the compound is a relatively potent GLP-1R agonist.

In some embodiments, the compounds described herein exhibit a value of cAMP (GLP-1R) Emax of greater than about 80%, which is indicative that the compound is an agonist that can fully activate GLP-1R.

In some embodiments, the compounds described herein exhibit a value of cAMP (GIPR) $EC_{50}$ of less than about 10 nM, which is indicative that the compound is a relatively potent GIPR agonist.

In some embodiments, the compounds described herein exhibit a value of cAMP (GIPR) $EC_{50}$ of less than about 10 nM, which is indicative that the compound is a relatively potent GIPR antagonist.

GLP-1 and GIP are susceptible to rapid degradation by dipeptidyl peptidase-IV (DPP-IV) (see, e.g., Deacon, et al. Journal of Clinical Endocrinology & Metabolism, 1995, 80, 952-957). As such, GLP-1 and GIP have been shown to exhibit relatively short half-life times in human due to DPP-IV degradation. Advantageously, the compounds described herein exhibit relatively long half-life times in the presence of DPP-IV when compared to those of GLP-1 and GIP.

In some embodiments, the compounds described herein exhibit a value of β-arrestin coupling (GLP-1R) EC50>1 μM in a β-arrestin (GLPIR) assay that measures the formation of a complex between GLP-1R and β-arrestin in cells. A value of β-arrestin (GLP1R) EC50>1 μM indicates a compound that does not substantially induce β-arrestin recruitment to GLP-1R.

In some embodiments, the compounds described herein exhibit a value of conditioned taste aversion ("CTA")=0.6-1.0, which indicates no measurable aversion to a compound, which is desired. A value of CTA=0.0-0.6 indicates significant aversion to a compound. The conditioned taste aversion assay measures the preference for a dilute saccharin solution that is associated with compound administration.

In some embodiments, the compounds described herein have a reduced likelihood of producing unwanted side effects when administered to a patient. A non-limiting example of such a side effect is nausea.

Other embodiments include those described in the Detailed Description, drawings, and/or in the claims.

ADDITIONAL DEFINITIONS

Figure 1:
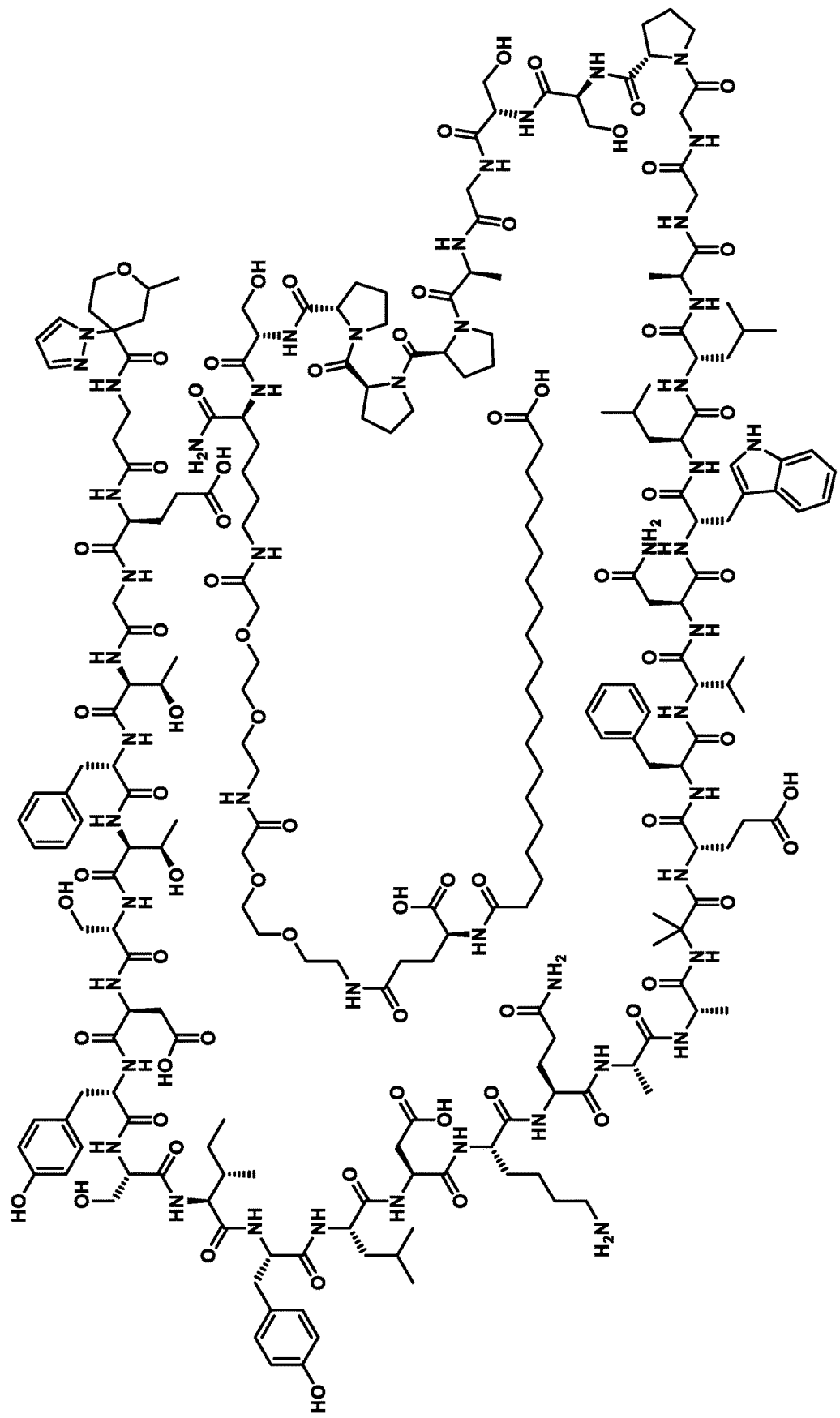
FIG. 1 depicts representative compounds of Formula (I). For the avoidance of doubt, in FIG. 1 when a stereogenic carbon is denoted with "*", it is intended to mean that said stereogenic center has been resolved (e.g., by chromatography).

To facilitate understanding of the disclosure set forth herein, a number of additional terms are defined below. Generally, the nomenclature used herein and the laboratory procedures in organic chemistry, medicinal chemistry, and pharmacology described herein are those well-known and commonly employed in the art. Unless defined otherwise, all technical and scientific terms used herein generally have the same meaning as commonly understood by one of ordinary skill in the art to which this disclosure belongs. Each of the patents, applications, published applications, and other publications that are mentioned throughout the specification and the attached appendices are incorporated herein by reference in their entireties.

As used herein, the term "GLP-1R" is meant to include, without limitation, nucleic acids, polynucleotides, oligonucleotides, sense and antisense polynucleotide strands, complementary sequences, peptides, polypeptides, proteins, homologous and/or orthologous GLP-1R molecules, isoforms, precursors, mutants, variants, derivatives, splice variants, alleles, different species, and active fragments thereof.

As used herein, the term "GIPR" is meant to include, without limitation, nucleic acids, polynucleotides, oligonucleotides, sense and antisense polynucleotide strands, complementary sequences, peptides, polypeptides, proteins, homologous and/or orthologous GIPR molecules, isoforms, precursors, mutants, variants, derivatives, splice variants, alleles, different species, and active fragments thereof.

The term "acceptable" with respect to a formulation, composition or ingredient, as used herein, means having no persistent detrimental effect on the general health of the subject being treated.

"API" refers to an active pharmaceutical ingredient.

The term "IC50" or "EC50" refers an amount, concentration, or dosage of a compound that is required for 50% inhibition or activation of a maximal response observed for such compound (or that of a reference compound as the case may be) in an assay that measures such response.

The terms "effective amount" or "therapeutically effective amount," as used herein, refer to a sufficient amount of a chemical entity (e.g., a compound described generically or specifically herein, a pharmaceutically acceptable salt thereof, or compositions containing the same) being administered which will relieve to some extent one or more of the symptoms of the disease or condition being treated. The result includes reduction and/or alleviation of the signs, symptoms, or causes of a disease, or any other desired alteration of a biological system. For example, an "effective amount" for therapeutic uses is the amount of the composition comprising a compound as disclosed herein required to provide a clinically significant decrease in disease symptoms. An appropriate "effective" amount in any individual case is determined using any suitable technique, such as a dose escalation study.

The term "excipient" or "pharmaceutically acceptable excipient" means a pharmaceutically-acceptable material, composition, or vehicle, such as a liquid or solid filler, diluent, carrier, solvent, or encapsulating material. In one embodiment, each component is "pharmaceutically acceptable" in the sense of being compatible with the other ingredients of a pharmaceutical formulation, and suitable for use in contact with the tissue or organ of humans and animals without excessive toxicity, irritation, allergic response, immunogenicity, or other problems or complications, commensurate with a reasonable benefit/risk ratio. See, e.g., *Remington: The Science and Practice of Pharmacy*, 21*st ed.*; Lippincott Williams & Wilkins: Philadelphia, P A, 2005; *Handbook of Pharmaceutical Excipients*, 6*th ed.*; Rowe et al., Eds.; The Pharmaceutical Press and the American Pharmaceutical Association: 2009; *Handbook of Pharmaceutical Additives*, 3*rd ed.*; Ash and Ash Eds.; Gower Publishing Company: 2007; *Pharmaceutical Preformulation and Formulation*, 2*nd ed.*; Gibson Ed.; CRC Press LLC: Boca Raton, F L, 2009.

The term "pharmaceutically acceptable salt" refers to a formulation of a compound that does not cause significant irritation to an organism to which it is administered and does not abrogate the biological activity and properties of the compound. In certain instances, pharmaceutically acceptable salts are obtained by reacting a compound described herein, with acids such as hydrochloric acid, hydrobromic acid, sulfuric acid, nitric acid, phosphoric acid, methanesulfonic acid, ethanesulfonic acid, p-toluenesulfonic acid, salicylic acid and the like. In some instances, pharmaceutically acceptable salts are obtained by reacting a compound having acidic group described herein with a base to form a salt such as an ammonium salt, an alkali metal salt, such as a sodium or a potassium salt, an alkaline earth metal salt, such as a calcium or a magnesium salt, a salt of organic bases such as dicyclohexylamine, N-methyl-D-glutamine, tris(hydroxymethyl)methylamine, and salts with amino acids such as arginine, lysine, and the like, or by other methods previously determined. The pharmacologically acceptable salt s not specifically limited as far as it can be used in medicaments. Examples of a salt that the compounds described herein form with a base include the following: salts thereof with inorganic bases such as sodium, potassium, magnesium, calcium, and aluminum; salts thereof with organic bases such as methylamine, ethylamine and ethanolamine; salts thereof with basic amino acids such as lysine and ornithine; and ammonium salt. The salts may be acid addition salts, which are specifically exemplified by acid addition salts with the following: mineral acids such as hydrochloric acid, hydrobromic acid, hydroiodic acid, sulfuric acid, nitric acid, and phosphoric acid; organic acids such as formic acid, acetic acid, propionic acid, oxalic acid, malonic acid, succinic acid, fumaric acid, maleic acid, lactic acid, malic acid, tartaric acid, citric acid, methanesulfonic acid, and ethanesulfonic acid; acidic amino acids such as aspartic acid and glutamic acid.

The term "pharmaceutical composition" refers to a mixture of a compound described herein with other chemical components (referred to collectively herein as "excipients"), such as carriers, stabilizers, diluents, dispersing agents, suspending agents, and/or thickening agents. The pharmaceutical composition facilitates administration of the compound to an organism. Multiple techniques of administering a compound exist in the art including, but not limited to rectal, oral, intravenous, aerosol, parenteral, ophthalmic, pulmonary, and topical administration.

The term "subject" refers to an animal, including, but not limited to, a primate (e.g., human), monkey, cow, pig, sheep, goat, horse, dog, cat, rabbit, rat, or mouse. The terms "subject" and "patient" are used interchangeably herein in reference, for example, to a mammalian subject, such as a human.

The terms "treat," "treating," and "treatment," in the context of treating a disease, disorder, or condition, are meant to include alleviating or abrogating a disorder, disease, or condition, or one or more of the symptoms associated with the disorder, disease, or condition; or to slowing the progression, spread or worsening of a disease, disorder or condition or of one or more symptoms thereof.

The term "halo" refers to fluoro (F), chloro (Cl), bromo (Br), or iodo (I).

The term "alkyl" refers to a hydrocarbon chain that may be a straight chain or branched chain, containing the indicated number of carbon atoms. For example, $C_{1-10}$ indicates that the group may have from 1 to 10 (inclusive) carbon atoms in it. Non-limiting examples include methyl, ethyl, iso-propyl, tert-butyl, n-hexyl.

The term "haloalkyl" refers to an alkyl, in which one or more hydrogen atoms is/are replaced with an independently selected halo.

The term "alkoxy" refers to an —O-alkyl radical (e.g., —OCH$_3$).

The term "haloalkoxy" refers to an —O-haloalkyl radical (e.g., —OCF$_3$).

The term "alkylene" refers to a branched or unbranched divalent alkyl (e.g., —CH$_2$—).

The term "arylene" and the like refer to divalent forms of the ring system, here divalent aryl.

The term "alkenyl" refers to a hydrocarbon chain that may be a straight chain or branched chain having one or more carbon-carbon double bonds. The alkenyl moiety contains the indicated number of carbon atoms. For example, $C_{2-6}$ indicates that the group may have from 2 to 6 (inclusive) carbon atoms in it.

The term "alkynyl" refers to a hydrocarbon chain that may be a straight chain or branched chain having one or more carbon-carbon triple bonds. The alkynyl moiety contains the indicated number of carbon atoms. For example, $C_{2-6}$ indicates that the group may have from 2 to 6 (inclusive) carbon atoms in it.

The term "aryl" refers to a 6-carbon monocyclic, 10-carbon bicyclic, or 14-carbon tricyclic aromatic ring system wherein 0, 1, 2, 3, or 4 atoms of each ring may be substituted by a substituent, and wherein the ring comprising a monocyclic radical is aromatic and wherein at least one of the fused rings comprising a bicyclic or tricyclic radical is aromatic e.g. tetrahydronaphthyl. Examples of aryl groups also include phenyl, naphthyl and the like.

The term "cycloalkyl" as used herein includes saturated cyclic hydrocarbon groups having 3 to 10 carbons, preferably 3 to 8 carbons, and more preferably 3 to 6 carbons, wherein the cycloalkyl group may be optionally substituted. Preferred cycloalkyl groups include, without limitation, cyclopropyl, cyclobutyl, cyclopentyl, cyclopentenyl, cyclohexyl, cyclohexenyl, cycloheptyl, and cyclooctyl.

The term "heteroaryl" refers to an aromatic 5-8 membered monocyclic, 8-12 membered bicyclic, or 11-14 membered tricyclic ring system having 1-3 heteroatoms if monocyclic, 1-6 heteroatoms if bicyclic, or 1-9 heteroatoms if tricyclic, said heteroatoms selected from O, N, or S (e.g., carbon atoms and 1-3, 1-6, or 1-9 heteroatoms of N, O, or S if monocyclic, bicyclic, or tricyclic, respectively), wherein 0, 1, 2, 3, or 4 atoms of each ring may be substituted by a substituent, and wherein the ring comprising a monocyclic radical is aromatic and wherein at least one of the fused rings comprising a bicyclic or tricyclic radical is aromatic (but does not have to be a ring which contains a heteroatom, e.g. tetrahydroisoquinolinyl. Examples of heteroaryl groups also include pyridyl, furyl or furanyl, imidazolyl, benzimidazolyl, pyrimidinyl, thiophenyl or thienyl, quinolinyl, indolyl, thiazolyl, and the like.

The term "heterocyclyl" refers to a nonaromatic 5-8 membered monocyclic, 8-12 membered bicyclic, or 11-14 membered tricyclic ring system having 1-3 heteroatoms if monocyclic, 1-6 heteroatoms if bicyclic, or 1-9 heteroatoms if tricyclic, said heteroatoms selected from O, N, or S (e.g., carbon atoms and 1-3, 1-6, or 1-9 heteroatoms of N, O, or S if monocyclic, bicyclic, or tricyclic, respectively), wherein 0, 1, 2 or 3 atoms of each ring may be substituted by a substituent. Examples of heterocyclyl groups include piperazinyl, pyrrolidinyl, dioxanyl, morpholinyl, tetrahydrofuranyl, and the like.

In addition, atoms making up the compounds of the present embodiments are intended to include all isotopic forms of such atoms. Isotopes, as used herein, include those atoms having the same atomic number but different mass numbers. By way of general example and without limitation, isotopes of hydrogen include tritium and deuterium, and isotopes of carbon include $^{13}$C and $^{14}$C.

The details of one or more embodiments of the invention are set forth in the description below and in the drawings. Other features and advantages will also be apparent from the claims.

DETAILED DESCRIPTION

This disclosure features chemical entities (e.g., a compound or a pharmaceutically acceptable salt and/or hydrate and/or prodrug of the compound) that modulate (e.g., agonize or partially agonize or antagonize) glucagon-like peptide-1 receptor ("GLP-1R") and/or the gastric inhibitory polypeptide receptor ("GIPR"). The chemical entities are useful, e.g., for treating a subject (e.g., a human) having a disease, disorder, or condition in which modulation (e.g., agonism, partial agonism or antagonism) of GLP-1R and/or GIPR activities is beneficial for the treatment or prevention of the underlying pathology and/or symptoms and/or progression of the disease, disorder, or condition. In some embodiments, the modulation results in an enhancement of (e.g., an increase in) existing levels (e.g., normal, or below normal levels) of GLP-1R and/or GIPR activity (e.g., signaling). In some embodiments, the chemical entities described herein further modulate (e.g., attenuate, uncouple) β-arrestin signaling relative to what is observed with the native ligand. This disclosure also features compositions as well as other methods of using and making the said chemical entities.

In one aspect, the disclosure provides a compound having Formula (I), or a pharmaceutically acceptable salt thereof:

Formula (I)

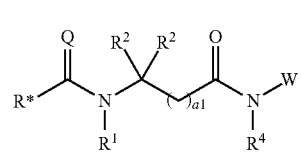

wherein:

Q is O or S;

R* is as defined in (i), (ii), or (iii) below:

(i)

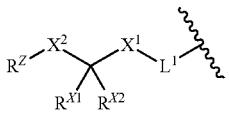

Formula (A)

wherein:

L$^1$ is selected from the group consisting of:

C$_{1-10}$ alkylene optionally substituted with from 1-3 substituents each independently selected from the group consisting of: halo; C$_{1-4}$ alkoxy; —OH; phenyl; and NR'R"; and

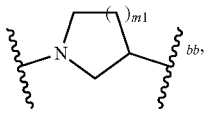

wherein m1 is 0, 1, 2, 3, or 4;

X$^1$ is selected from the group consisting of: C(=O); C(=S); S(O)$_{1-2}$; C(=O)N(R')*; C(=S)N(R')*; S(O)$_{1-2}$N(R')*; (R')NC(=O)*; (R')NC(=S)*; and (R')NS(O)$_2$*, wherein * represents the point of attachment to L$^1$;

R$^{X1}$ and R$^{X2}$ are each defined according to (AA) or (AB):

(AA)

R$^{X1}$ and R$^{X2}$ are each independently selected from the group consisting of:

—H, —F;

C$_{1-8}$ alkyl, C$_{2-6}$ alkenyl, and C$_{2-6}$ alkynyl, each of which is optionally substituted with from 1-3 R$^a$; and C$_{3-8}$ cycloalkyl which is optionally substituted with from 1-3 R$^b$, (AB)

R$^{X1}$ and R$^{X2}$ taken together with the carbon atom to which each is attached form a saturated or partially unsaturated ring having from 3-10 ring atoms, wherein from 0-2 ring atoms are heteroatoms each independently selected from the group consisting of: O, N, N(H), N(R$^c$), and S(O)$_{0-2}$, wherein the ring is optionally substituted at one or more ring carbon atoms with from 1-3 R$^b$, X$^2$ is selected from the group consisting of: a bond; CH$_2$; —N(R')—; —O—; C(=O); C(=S); S(O)$_{1-2}$; C(=O)N(R')*; C(=S)N(R')*; S(O)$_{1-2}$N(R')*; N(R')C(=O)*; N(R')C(=S)*; and N(R')S(O)$_{1-2}$*, wherein * represents the point of attachment to C(R$^{X1}$R$^{X2}$); and R$^Z$ is selected from the group consisting of:

H;

C$_{1-6}$ alkyl optionally substituted with from 1-6 R$^a$;

—R$^{ZA}$; and

-L$^{ZA}$-R$^{ZA}$;

L$^{ZA}$ is C$_{1-6}$ alkylene optionally substituted with from 1-3 independently selected R$^a$;

R$^{ZA}$ is R$^e$;

or (ii)

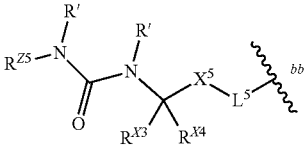

Formula (B)

wherein:

L$^5$ is C$_{1-10}$ alkylene optionally substituted with from 1-3 substituents each independently selected from the group consisting of: halo; C$_{1-4}$ alkoxy; —OH; phenyl; and NR'R";

X$^5$ is selected from the group consisting of: a bond; C(=O); C(=S); S(O)$_{1-2}$; C(=O)N(R')*; C(=S)N(R')*; and S(O)$_{1-2}$N(R')*, wherein * represents the point of attachment to L$^5$;

R$^{X3}$ and R$^{X4}$ are each defined according to (BA) or (BB):

(BA)

R$^{X3}$ and R$^{X4}$ are each independently selected from the group consisting of:

—H, —F;

C$_{1-8}$ alkyl, C$_{2-6}$ alkenyl, and C$_{2-6}$ alkynyl, each of which is optionally substituted with from 1-3 R$^a$; and C$_{3-6}$ cycloalkyl which is optionally substituted with from 1-3 R$^b$;

(BB)

R$^{X3}$ and R$^{X4}$ taken together with the carbon atom to which each is attached form a saturated or partially unsaturated ring having from 3-10 ring atoms, wherein from 0-2 ring atoms are heteroatoms each independently selected from the group consisting of: O, N, N(H), N(R$^c$), and S(O)$_{0-2}$, wherein the ring is optionally substituted at one or more ring carbon atoms with from 1-3 R$^b$, and R$^{Z5}$ is selected from the group consisting of: —R$^{ZE}$; -L$^{ZE}$-R$^{ZE}$; and C$_{1-6}$ alkyl optionally substituted with from 1-6 R$^a$;

L$^{ZE}$ is C$_{1-6}$ alkylene optionally substituted with from 1-3 independently selected R$^a$;

R$^{ZE}$ is R$^e$;

or (iii)

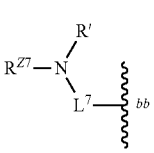

Formula (C)

L$^7$ is C$_{1-10}$ alkylene optionally substituted with from 1-3 substituents each independently selected from the group consisting of: halo; C$_{1-4}$ alkoxy; —OH; phenyl; and NR'R"; and R$^{Z7}$ is -L$^{ZG}$-R$^{ZG}$.

L$^{ZG}$ is C$_{1-6}$ alkylene optionally substituted with from 1-3 independently selected R$^a$;

R$^{ZG}$ is R$^e$;

each of R$^1$ and R$^2$ is independently selected from the group consisting of H and C$_1$-3 alkyl;

a1 is 0, 1, 2, 3, or 4;

$R^{2'}$ is

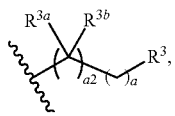

wherein:
$R^3$ is —C(O)OH, —C(O)OR$^{4a}$, —CH(C(O)OH)$_2$, or a carboxylic acid isostere;
a is 0, 1, 2, 3, 4, or 5; a2 is 0 or 1;
each of $R^{3a}$ and $R^{3b}$ is independently H or $C_{1-3}$ alkyl; and
$R^{4a}$ is —(C$_{0-3}$ alkylene)-R$^e$ or C$_{1-6}$ alkyl optionally substituted with from 1-6 R$^a$
N(R$^4$)—W is a peptide having formula N(R$^4$)—W$^1$—R$^5$, wherein:
N(R$^4$)—W$^1$ is a sequence of from 5-60 amino acids;
$R^5$ is a C-terminal amino acid, amino ester, or amino acid amide that is optionally substituted with from 1-2 modifying groups;
N(R$^4$) is the amino group of the N-terminal amino acid in W$^1$ (e.g., if the N-terminal amino acid of is glycyl residue, it is intended to have the following structure:

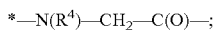

*—N(R$^4$)—CH$_2$—C(O)—;

wherein the * represent the point of connection to the carbonyl group in formula (I)); and
$R^4$ is H or C$_1$-C$_3$ alkyl;
each occurrence of R$^a$ is independently selected from the group consisting of: halo; —OH; —N(R$^f$)(R'); C$_{1-4}$ alkoxy; C$_{1-4}$ haloalkoxy; —OC(=O)(C$_{1-6}$ alkyl); —C(=O)O(C$_{1-6}$ alkyl); —C(=O)OH, —C(=O)N(R')(R''), —S(O)$_{1-2}$(C$_{1-6}$ alkyl); and cyano;
each occurrence of R$^b$ is independently selected from the group consisting of: C$_{1-6}$ alkyl optionally substituted with from 1-6 R$^a$; C$_{2-6}$ alkenyl; C$_{2-6}$ alkynyl; —OH; oxo; -halo; —N(R$^f$)(R'); C$_{1-4}$ alkoxy; C$_{1-4}$ haloalkoxy; —C(=O)(C$_{1-4}$ alkyl); —C(=O)O(C$_{1-6}$ alkyl); —C(=O)OH; —C(=O)N(R')(R''); —S(O)$_{1-2}$N(R') (R''); —S(O)$_{1-2}$(C$_{1-6}$ alkyl); —SF$_5$; —NO$_2$; and cyano;
each occurrence of R$^c$ is independently selected from the group consisting of: C$_{1-6}$ alkyl; C$_{1-6}$ haloalkyl; —C(=O)(C$_{1-6}$ alkyl); —C(=O)O(C$_{1-6}$ alkyl); —C(=O)N(R')(R''); and —S(O)$_{1-2}$(C$_{1-6}$ alkyl);
each occurrence of R$^d$ is independently selected from the group consisting of: —R$^e$, —(C$_{1-3}$ alkylene)-R$^e$, —O—(C$_{0-3}$ alkylene)-R$^e$, —C(=O)(C$_{0-3}$ alkylene)-R$^e$, and —C(=O)(C$_{0-3}$ alkylene)O—R$^e$;
each occurrence of R$^e$ is independently selected from the group consisting of:
(i) C$_{3-10}$ cycloalkyl, wherein the cycloalkyl is optionally substituted with from 1-4 independently selected R$^b$;
(ii) heterocyclyl including from 3-10 ring atoms, wherein from 1-3 ring atoms are each independently selected from the group consisting of N, N(H), N(R$^c$), O, and S(O)$_{0-2}$, wherein the heterocyclyl is optionally substituted with from 1-4 independently selected R$^b$ at one or more ring carbon atoms;
(iii) C$_{6-10}$ aryl, wherein the aryl is optionally substituted with from 1-5 independently selected R$^b$; and
(iv) heteroaryl including from 5-10 ring atoms, wherein from 1-4 ring atoms are each independently selected from the group consisting of N, N(H), N(R$^c$), O, and S(O)$_{0-2}$, wherein the heteroaryl is optionally substituted with from 1-3 independently selected R$^b$ at one or more ring carbon atoms;
each occurrence of R$^f$ is independently selected from the group consisting of: H; C$_{1-4}$ alkyl; C$_{3-6}$ cycloalkyl; —C(=O)(C$_{1-6}$ alkyl); —C(=O)O(C$_{1-6}$ alkyl); and —S(O)$_{1-2}$(C$_{1-6}$ alkyl); and
each occurrence of R' and R" is independently selected from the group consisting of: H and C$_{1-6}$ alkyl.

In another aspect, this disclosure features a compound of Formula (I), or a pharmaceutically acceptable salt thereof:

Formula (I)

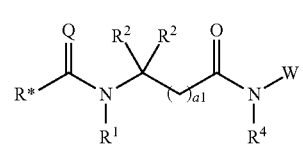

wherein:
Q is O or S;
R* is as defined in (i), (ii), or (iii), below:

(i)

Formula (A)

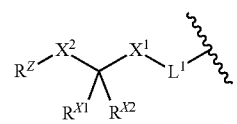

wherein:
L$^1$ is selected from the group consisting of:
C$_{1-10}$ alkylene optionally substituted with from 1-3 substituents each independently selected from the group consisting of: halo; C$_{1-4}$ alkoxy; —OH; phenyl; and NR'R''; and

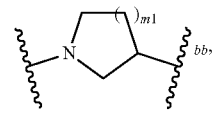

wherein m1 is 0, 1, 2, 3, or 4;
X$^1$ is selected from the group consisting of: C(=O); C(=S); S(O)$_{1-2}$; C(=O)N(R')*; C(=S)N(R')*; S(O)$_{1-2}$N(R')*; N(R')C(=O)*; N(R')C(=S)*; and N(R')S(O)$_{1-2}$*, wherein * represents the point of attachment to L$^1$;
R$^{X1}$ and R$^{X2}$ are each defined according to (AA) or (AB):
(AA)
R$^{X1}$ and R$^{X2}$ are each independently selected from the group consisting of:
—H, —F;
C$_{1-8}$ alkyl, C$_{2-6}$ alkenyl, and C$_{2-6}$ alkynyl, each of which is optionally substituted with from 1-3 R$^a$; and
C$_{3-8}$ cycloalkyl which is optionally substituted with from 1-3 R$^b$;
(AB)
R$^{X1}$ and R$^{X2}$ taken together with the carbon atom to which each is attached form a saturated or partially unsaturated ring having from 3-10 ring atoms, wherein from 0-2 ring atoms are heteroatoms each independently selected from the group consisting of: O, N, N(H), N(R$^c$), and S(O)$_{0-2}$, wherein the ring is optionally substituted at one or more ring carbon atoms with from 1-3 R$^b$;

$X^2$ is selected from the group consisting of: a bond; CH$_2$; —N(R')—; —O—; C(=O); C(=S); S(O)$_{1-2}$; C(=O)N(R')*; C(=S)N(R')*; S(O)$_{1-2}$N(R')*; N(R')C(=O)*; N(R')C(=S)*; and N(R')S(O)$_{1-2}$*, wherein * represents the point of attachment to C(R$^{X1}$R$^{X2}$); and R$^Z$ is selected from the group consisting of:
H;
C$_{1-6}$ alkyl optionally substituted with from 1-6 R$^a$;
—R$^{ZA}$; and
-L$^{ZA}$-R$^{ZA}$;
L$^{ZA}$ is C$_{1-6}$ alkylene optionally substituted with from 1-3 independently selected R$^a$; and
R$^{ZA}$ is R$^e$;

(ii)

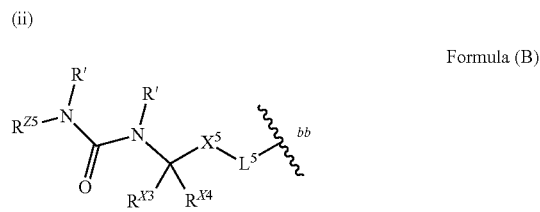

Formula (B)

wherein:
L$^5$ is C$_{1-10}$ alkylene optionally substituted with from 1-3 substituents each independently selected from the group consisting of: halo; C$_{1-4}$ alkoxy; —OH; phenyl; and NR'R";
X$^5$ is selected from the group consisting of: a bond; C(=O); C(=S); S(O)$_{1-2}$; C(=O)N(R')*; C(=S)N(R')*; and S(O)$_{1-2}$N(R')*, wherein * represents the point of attachment to L$^5$;
R$^{X3}$ and R$^{X4}$ are each defined according to (BA) or (BB):
(BA)
R$^{X3}$ and R$^{X4}$ are each independently selected from the group consisting of:
—H, —F;
C$_{1-8}$ alkyl, C$_{2-6}$ alkenyl, and C$_{2-6}$ alkynyl, each of which is optionally substituted with from 1-3 R$^a$; and
C$_{3-6}$ cycloalkyl which is optionally substituted with from 1-3 R$^b$;
(BB)
R$^{X3}$ and R$^{X4}$ taken together with the carbon atom to which each is attached form a saturated or partially unsaturated ring having from 3-10 ring atoms, wherein from 0-2 ring atoms are heteroatoms each independently selected from the group consisting of: O, N, N(H), N(R$^c$), and S(O)$_{0-2}$, wherein the ring is optionally substituted at one or more ring carbon atoms with from 1-3 R$^b$; and
R$^{Z5}$ is selected from the group consisting of: —R$^{ZE}$; -L$^{ZE}$-R$^{ZE}$; and C$_{1-6}$ alkyl optionally substituted with from 1-6 R$^a$;
L$^{ZE}$ is C$_{1-6}$ alkylene optionally substituted with from 1-3 independently selected R$^a$; and
R$^{ZE}$ is R$^e$;

(iii)

Formula (C)

L$^7$ is C$_{1-10}$ alkylene optionally substituted with from 1-3 substituents each independently selected from the group consisting of: halo; C$_{1-4}$ alkoxy; —OH; phenyl; and NR'R"; and
R$^{Z7}$ is -L$^{ZG}$-R$^{ZG}$.
L$^{ZG}$ is C$_{1-6}$ alkylene optionally substituted with from 1-3 independently selected R$^a$;
R$^{ZG}$ is R$^e$;
each of R$^1$ and R$^2$ is independently selected from the group consisting of H and C$_{1-3}$ alkyl;
a1 is 0, 1, 2, 3, or 4;
R$^{2t}$ is

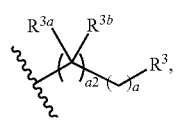

wherein:
R$^3$ is —C(O)OH, —C(O)OR$^{4a}$, —CH(C(O)OH)$_2$, or a carboxylic acid isostere;
a is 0, 1, 2, 3, 4, or 5; a2 is 0 or 1;
each of R$^{3a}$ and R$^{3b}$ is independently H or C$_{1-3}$ alkyl; and
R$^{4a}$ is —(C$_{0-3}$ alkylene)-R$^e$ or C$_{1-6}$ alkyl optionally substituted with from 1-6 R$^a$
—N(R$^4$)—W has Formula WD:
*GT(Xaa3)(Xaa4)SD(Xaa7)SI(Xaa10)LD(Xaa13)(Xaa14)A(Xaa16)(Xaa17)(X aa18)F(Xaa20)(Xaa21)(Xaa22)L(Xaa24)(Xaa25)GGPSSGAPPPS(Xaa37)-R$^6$ (SEQ ID NO: 4),
wherein:
Xaa3 is F, F*, F†, or F$\backslash$;
Xaa4 is T, A or V;
Xaa7 is Y, or K*;
Xaa10 is Y, L*, or Aib;
Xaa13 is K, Orn, or R;
Xaa14 is Q, I, or K*;
Xaa16 is A, or Q;
Xaa17 is Aib, or K*;
Xaa18 is A, or E;
Xaa20 is V or I;
Xaa21 is N, Q, K*, or dE;
Xaa22 is W or Y;
Xaa24 is I or L;
Xaa25 is A or E;
Xaa37 is K* or absent;
R$^6$ is —NH$_2$ or —OH;
wherein —N(R$^4$)—W is attached to the remainder of Formula (I) by the amino group of N-terminal amino acid *G;
each occurrence of R$^a$ is independently selected from the group consisting of: halo; —OH; —N(R')(R'); C$_{1-4}$ alkoxy; C$_{1-4}$ haloalkoxy; —OC(=O)(C$_{1-6}$ alkyl); —C(=O)O(C$_{1-6}$ alkyl); —C(=O)OH, —C(=O)N(R')(R'''), —S(O)$_{1-2}$(C$_{1-6}$ alkyl); and cyano;
each occurrence of R$^b$ is independently selected from the group consisting of: C$_{1-6}$ alkyl optionally substituted with from 1-6 R$^a$; C$_{2-6}$ alkenyl; C$_{2-6}$ alkynyl; —OH; oxo; -halo; —N(R$^f$)(R'); C$_{1-4}$ alkoxy; C$_{1-4}$ haloalkoxy; —C(=O)(C$_{1-4}$ alkyl); —C(=O)O(C$_{1-6}$ alkyl); —C(=O)OH; —C(=O)N(R')(R"); —S(O)$_{1-2}$N(R')(R"); —S(O)$_{1-2}$(C$_{1-6}$ alkyl); —SF$_5$; —NO$_2$; and cyano;
each occurrence of R$^e$ is independently selected from the group consisting of: C$_{1-6}$ alkyl; C$_{1-6}$ haloalkyl;

—C(=O)(C$_{1-6}$ alkyl); —C(=O)O(C$_{1-6}$ alkyl); —C(=O)N(R')(R''); and —S(O)$_{1-2}$(C$_{1-6}$ alkyl);

each occurrence of R$^d$ is independently selected from the group consisting of: —R$^e$, —(C$_{1-3}$ alkylene)-R$^e$, —O—(C$_{0-3}$ alkylene)-R$^e$, —C(=O)(C$_{0-3}$ alkylene)-R$^e$, and —C(=O)(C$_{0-3}$ alkylene)O—R$^e$;

each occurrence of R$^e$ is independently selected from the group consisting of:
(i) C$_{3-10}$ cycloalkyl, wherein the cycloalkyl is optionally substituted with from 1-4 independently selected R$^b$;
(ii) heterocyclyl including from 3-10 ring atoms, wherein from 1-3 ring atoms are each independently selected from the group consisting of N, N(H), N(R$^c$), O, and S(O)$_{0-2}$, wherein the heterocyclyl is optionally substituted with from 1-4 independently selected R$^b$ at one or more ring carbon atoms;
(iii) C$_{6-10}$ aryl, wherein the aryl is optionally substituted with from 1-5 independently selected R$^b$; and
(iv) heteroaryl including from 5-10 ring atoms, wherein from 1-4 ring atoms are each independently selected from the group consisting of N, N(H), N(R$^c$), O, and S(O)$_{0-2}$, wherein the heteroaryl is optionally substituted with from 1-3 independently selected R$^b$ at one or more ring carbon atoms;

each occurrence of R' is independently selected from the group consisting of: H; C$_{1-4}$ alkyl; C$_{3-6}$ cycloalkyl; —C(=O)(C$_{1-6}$ alkyl); —C(=O)O(C$_{1-6}$ alkyl); and —S(O)$_{1-2}$(C$_{1-6}$ alkyl); and each occurrence of R' and R'' is independently selected from the group consisting of: H and C$_{1-6}$ alkyl.

In a further aspect, the disclosure provides a compound having Formula (I), or a pharmaceutically acceptable salt thereof:

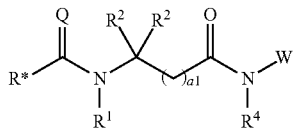

Formula (I)

Q is O or S;
R* is as defined in (i), (ii), or (iii), below:
(i)

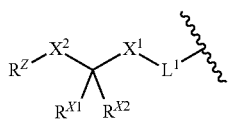

Formula (A)

wherein:
L$^1$ is selected from the group consisting of:
C$_{1-10}$ alkylene optionally substituted with from 1-3 substituents each independently selected from the group consisting of: halo; C$_{1-4}$ alkoxy; —OH; phenyl; and NR'R''; and

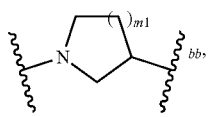

wherein m1 is 0, 1, 2, 3, or 4;

X$^1$ is selected from the group consisting of: C(=O); C(=S); S(O)$_{1-2}$; C(=O)N(R')*; C(=S)N(R')*; S(O)$_{1-2}$N(R')*; N(R')C(=O)*; N(R')C(=S)*; and N(R')S(O)$_{1-2}$*, wherein * represents the point of attachment to L$^1$;

R$^{X1}$ and R$^{X2}$ are each defined according to (AA) or (AB):
(AA)
R$^{X1}$ and R$^{X2}$ are each independently selected from the group consisting of:
—H, —F;
C$_{1-8}$ alkyl, C$_{2-6}$ alkenyl, and C$_{2-6}$ alkynyl, each of which is optionally substituted with from 1-3 R$^a$; and
C$_{3-8}$ cycloalkyl which is optionally substituted with from 1-3 R$^b$;
(AB)
R$^{X1}$ and R$^{X2}$ taken together with the carbon atom to which each is attached form a saturated or partially unsaturated ring having from 3-10 ring atoms, wherein from 0-2 ring atoms are heteroatoms each independently selected from the group consisting of: O, N, N(H), N(R$^c$), and S(O)$_{0-2}$, wherein the ring is optionally substituted at one or more ring carbon atoms with from 1-3 R$^b$;

X$^2$ is a bond; and
R$^Z$ is selected from the group consisting of:
H;
C$_{1-6}$ alkyl optionally substituted with from 1-6 R$^a$;
—R$^{ZA}$; and
-L$^{ZA}$-R$^{ZA}$;
L$^{ZA}$ is C$_{1-6}$ alkylene optionally substituted with from 1-3 independently selected R$^a$; and
R$^{ZA}$ is R$^e$;

(ii)

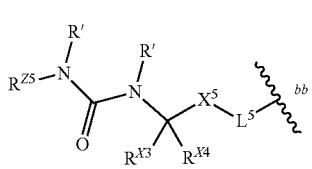

Formula (B)

wherein:
L$^5$ is C$_{1-10}$ alkylene optionally substituted with from 1-3 substituents each independently selected from the group consisting of: halo; C$_{1-4}$ alkoxy; —OH; phenyl; and NR'R'';

X$^5$ is selected from the group consisting of: a bond; C(=O); C(=S); S(O)$_{1-2}$; C(=O)N(R')*; C(=S)N(R')*; and S(O)$_{1-2}$N(R')*, wherein * represents the point of attachment to L$^5$, R$^{X3}$ and R$^{X4}$ are each defined according to (BA) or (BB):
(BA)
R$^{X3}$ and R$^{X4}$ are each independently selected from the group consisting of:
—H, —F;
C$_{1-8}$ alkyl, C$_{2-6}$ alkenyl, and C$_{2-6}$ alkynyl, each of which is optionally substituted with from 1-3 R$^a$; and
C$_{3-6}$ cycloalkyl which is optionally substituted with from 1-3 R$^b$;
(BB)
R$^{X3}$ and R$^{X4}$ taken together with the carbon atom to which each is attached form a saturated or partially unsaturated ring having from 3-10 ring atoms, wherein from 0-2 ring atoms are heteroatoms each independently selected from the group consisting of: O, N, N(H), N(R$^c$), and S(O)$_{0-2}$, wherein the ring is optionally substituted at one or more ring carbon atoms with from 1-3 R$^b$; and R$^{Z5}$ is selected from the group consisting of: —R$^{ZE}$; -L$^{ZE}$-R$^{ZE}$; and C$_{1-6}$ alkyl optionally substituted with from 1-6 R$^a$;

L$^{ZE}$ is C$_{1-6}$ alkylene optionally substituted with from 1-3 independently selected R$^a$; and R$^{ZE}$ is R$^e$;

(iii)

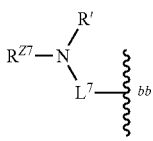

Formula (C)

L$^7$ is C$_{1-10}$ alkylene optionally substituted with from 1-3 substituents each independently selected from the group consisting of: halo; C$_{1-4}$ alkoxy; —OH; phenyl; and NR'R''; and R$^{Z7}$ is -L$^{ZG}$-R$^{ZG}$;

L$^{ZG}$ is C$_{1-6}$ alkylene optionally substituted with from 1-3 independently selected R$^a$;

R$^{ZG}$ is R$^e$;

each of R$^1$ and R$^2$ is independently selected from the group consisting of H and C$_{1-3}$ alkyl;

a1 is 0, 1, 2, 3, or 4;

R$^{2'}$ is

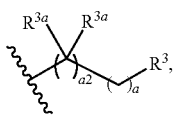

wherein:

R$^3$ is —C(O)OH, —C(O)OR$^{4a}$, —CH(C(O)OH)$_2$, or a carboxylic acid isostere;

a is 0, 1, 2, 3, 4, or 5; a2 is 0 or 1;

each of R$^{3a}$ and R$^{3b}$ is independently H or C$_{1-3}$ alkyl; and

R$^{4a}$ is —(C$_{0-3}$ alkylene)-R$^e$ or C$_{1-6}$ alkyl optionally substituted with from 1-6 R$^a$ —N(R$^4$)—W has Formula WD:

*GT(Xaa3)(Xaa4)SD(Xaa7)SI(Xaa10)LD(Xaa13)(Xaa14)A(Xaa16)(Xaa17)(Xaa18)F(Xaa20)(Xaa21)(Xaa22)L(Xaa24)(Xaa25)GGPSSGAPPPS(Xaa37)-R$^6$ (SEQ ID NO: 4), wherein:

Xaa3 is F, F*, F†, or F†$^†$;
Xaa4 is T, A or V;
Xaa7 is Y, or K*;
Xaa10 is Y, L*, or Aib;
Xaa13 is K, Orn, or R;
Xaa14 is Q, I, or K*;
Xaa16 is A, or Q;
Xaa17 is Aib, or K*;
Xaa18 is A, or E;
Xaa20 is V or I;
Xaa21 is N, Q, K*, or dE;
Xaa22 is W or Y;
Xaa24 is I or L;
Xaa25 is A or E;
Xaa37 is K* or absent;
R$^6$ is —NH$_2$ or —OH;

wherein —N(R$^4$)—W is attached to the remainder of Formula (I) by the amino group of N-terminal amino acid *G;

each occurrence of R$^a$ is independently selected from the group consisting of: halo; —OH; —N(R$^f$)(R'); C$_{1-4}$ alkoxy; C$_{1-4}$ haloalkoxy; —OC(=O)(C$_{1-6}$ alkyl); —C(=O)O(C$_{1-6}$ alkyl); —C(=O)OH, —C(=O)N(R')(R'''), —S(O)$_{1-2}$(C$_{1-6}$ alkyl); and cyano;

each occurrence of R$^b$ is independently selected from the group consisting of: C$_{1-6}$ alkyl optionally substituted with from 1-6 R$^a$; C$_{2-6}$ alkenyl; C$_{2-6}$ alkynyl; —OH; oxo; -halo; —N(R$^f$)(R'); C$_{1-4}$ alkoxy; C$_{1-4}$ haloalkoxy; —C(=O)(C$_{1-4}$ alkyl); —C(=O)O(C$_{1-6}$ alkyl); —C(=O)OH; —C(=O)N(R')(R''); —S(O)$_{1-2}$N(R')(R''); —S(O)$_{1-2}$(C$_{1-6}$ alkyl); —SF$_5$; —NO$_2$; and cyano;

each occurrence of R$^e$ is independently selected from the group consisting of: C$_{1-6}$ alkyl; C$_{1-6}$ haloalkyl; —C(=O)(C$_{1-6}$ alkyl); —C(=O)O(C$_{1-6}$ alkyl); —C(=O)N(R')(R''); and —S(O)$_{1-2}$(C$_{1-6}$ alkyl);

each occurrence of R$^d$ is independently selected from the group consisting of: —R$^e$, —(C$_{1-3}$ alkylene)-R$^e$, —O—(C$_{0-3}$ alkylene)-R$^e$, —C(=O)(C$_{0-3}$ alkylene)-R$^e$, and —C(=O)(C$_{0-3}$ alkylene)O—R$^e$;

each occurrence of R$^e$ is independently selected from the group consisting of:

(i) C$_{3-10}$ cycloalkyl, wherein the cycloalkyl is optionally substituted with from 1-4 independently selected R$^b$;

(ii) heterocyclyl including from 3-10 ring atoms, wherein from 1-3 ring atoms are each independently selected from the group consisting of N, N(H), N(R$^c$), O, and S(O)$_{0-2}$, wherein the heterocyclyl is optionally substituted with from 1-4 independently selected R$^b$ at one or more ring carbon atoms;

(iii) C$_{6-10}$ aryl, wherein the aryl is optionally substituted with from 1-5 independently selected R$^b$; and (iv) heteroaryl including from 5-10 ring atoms, wherein from 1-4 ring atoms are each independently selected from the group consisting of N, N(H), N(R$^c$), O, and S(O)$_{0-2}$, wherein the heteroaryl is optionally substituted with from 1-3 independently selected R$^b$ at one or more ring carbon atoms;

each occurrence of R$^f$ is independently selected from the group consisting of: H; C$_{1-4}$ alkyl; C$_{3-6}$ cycloalkyl; —C(=O)(C$_{1-6}$ alkyl); —C(=O)O(C$_{1-6}$ alkyl); and —S(O)$_{1-2}$(C$_{1-6}$ alkyl); and each occurrence of R' and R'' is independently selected from the group consisting of: H and C$_{1-6}$ alkyl.

Variable R*
Formula (A)
In some embodiments, R* is (i)

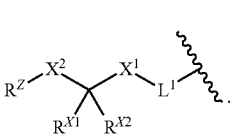

(Formula A)

In some embodiments, $R^{X1}$ and $R^{X2}$ are defined according to (AA), i.e., $R^{X1}$ and $R^{X2}$ are each independently selected from the group consisting of:

—F;

$C_{1-8}$ alkyl, $C_{2-6}$ alkenyl, and $C_{2-6}$ alkynyl, each of which is optionally substituted with from 1-3 $R^a$; and $C_{3-6}$ cycloalkyl which is optionally substituted with from 1-3 $R^b$.

In certain of the foregoing embodiments, $R^{X1}$ and $R^{X2}$ are the same. In certain other embodiments, $R^{X1}$ and $R^{X2}$ are the different.

In certain embodiments, $R^{X1}$ and $R^{X2}$ are each an independently selected $C_{1-8}$ alkyl, which is optionally substituted with from 1-3 $R^a$. In certain of these embodiments, $R^{X1}$ and $R^{X2}$ are each an independently selected unsubstituted $C_{1-6}$ alkyl. In certain embodiments, $R^{X1}$ and $R^{X2}$ are independently selected unsubstituted $C_{1-3}$ alkyl. As a non-limiting example, $R^{X1}$ and $R^{X2}$ can both be methyl. As another non-limiting example, $R^{X1}$ and $R^{X2}$ can both be ethyl.

In certain embodiments, $R^{X1}$ and $R^{X2}$ are both —F.

In some embodiments, $R^{X1}$ and $R^{X2}$ are defined according to (AB), i.e., $R^{X1}$ and $R^{X2}$ taken together with the carbon atom to which each is attached form a saturated or partially unsaturated ring having from 3-10 ring atoms, wherein from 0-2 ring atoms are heteroatoms each independently selected from the group consisting of: O, N, N(H), N($R^c$), and S(O)$_{0-2}$, wherein the ring is optionally substituted at one or more ring carbon atoms with from 1-3 $R^b$.

In certain of these embodiments, $R^{X1}$ and $R^{X2}$ taken together with the carbon atom to which each is attached form a $C_{3-8}$ cycloalkyl ring which is optionally substituted with from 1-3 $R^b$. In certain of the foregoing embodiments, $R^{X1}$ and $R^{X2}$ taken together with the carbon atom to which each is attached form a $C_{3-6}$ cycloalkyl ring which is optionally substituted with from 1-3 independently selected $C_{1-3}$ alkyl.

As non-limiting examples, $R^{X1}$ and $R^{X2}$ taken together with the carbon atom to which each is attached can form an optionally substituted cyclopropyl ring, cyclobutyl ring, cyclopentyl ring, or cyclohexyl ring. In certain embodiments, said cyclopropyl ring, cyclobutyl ring, cyclopentyl ring, or cyclohexyl ring is unsubstituted.

In certain embodiments, $R^{X1}$ and $R^{X2}$ taken together with the carbon atom to which each is attached form a saturated or partially unsaturated ring having from 4-10 ring atoms, wherein from 1-2 ring atoms are heteroatoms each independently selected from the group consisting of: O, N, N(H), N($R^c$), and S(O)$_{0-2}$, wherein the ring is optionally substituted at one or more ring carbon atoms with from 1-3 $R^b$.

In certain of these embodiments, $R^{X1}$ and $R^{X2}$ taken together with the carbon atom to which each is attached form a saturated ring having from 4-6 ring atoms, wherein one ring atom is a heteroatom selected from the group consisting of: O, N, N(H), N($R^c$), and S(O)$_{0-2}$, wherein the ring is optionally substituted at one or more ring carbon atoms with from 1-3 $R^b$.

As non-limiting examples, $R^{X1}$ and $R^{X2}$ taken together with the carbon atom to which each is attached can form

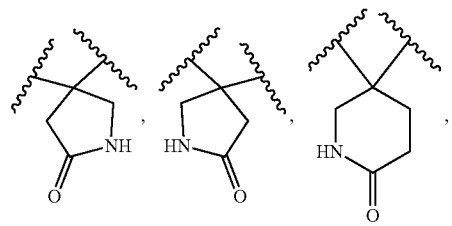

-continued

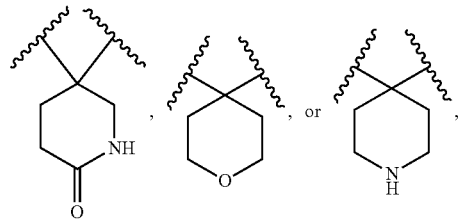

each of which is optionally substituted with from 1-2 independently selected $C_{1-3}$ alkyl.

In certain embodiments, $X^2$ is other than C(=O)N(R')*; C(=S)N(R')*; S(O)$_{1-2}$N(R')*; N(R')C(=O)*; N(R')C(=S)*; and N(R')S(O)$_{1-2}$*, wherein * represents the point of attachment to C($R^{X1}R^{X2}$);

In certain embodiments, $X^2$ is a bond.

In certain embodiments, $R^Z$ is -$L^{ZA}$-$R^{ZA}$. In certain of these embodiments, $L^{ZA}$ is $C_{1-6}$ alkylene optionally substituted with from 1-3 independently selected $R^a$. In certain embodiments, $L^{ZA}$ is unsubstituted $C_{1-6}$ alkylene. In certain of the foregoing embodiments, $L^{ZA}$ is unsubstituted $C_{2-4}$ alkylene. In certain embodiments, $L^{ZA}$ is unsubstituted $C_{1-3}$ alkylene. As a non-limiting example, $L^{ZA}$ can be —CH$_2$CH$_2$CH$_2$—. In certain embodiments, $L^{ZA}$ is unsubstituted $C_2$ alkylene. As a non-limiting example, $L^{ZA}$ can be —CH$_2$CH$_2$—. As still another non-limiting example, $L^{ZA}$ can be —CH$_2$—.

In certain embodiments (when $R^Z$ is -$L^{ZA}$-$R^{ZA}$), $R^{ZA}$ is selected from the group consisting of:

(iii) $C_{6-10}$ aryl, wherein the aryl is optionally substituted with from 1-5 independently selected $R^b$; and (iv) heteroaryl including from 5-10 ring atoms, wherein from 1-4 ring atoms are each independently selected from the group consisting of N, N(H), N($R^c$), O, and S(O)$_{0-2}$, wherein the heteroaryl is optionally substituted with from 1-3 independently selected $R^b$ at one or more ring carbon atoms.

In certain of these embodiments, $R^{ZA}$ is $C_{6-10}$ aryl, wherein the aryl is optionally substituted with from 1-5 independently selected $R^b$. For example, $R^{ZA}$ can be phenyl which is optionally substituted with from 1-3 independently selected $R^b$.

In certain embodiments, embodiments, $R^Z$ is —$R^{ZA}$.

In certain of these embodiments, $R^Z$ is selected from the group consisting of:

(iii) $C_{6-10}$ aryl, wherein the aryl is optionally substituted with from 1-5 independently selected $R^b$; and (iv) heteroaryl including from 5-10 ring atoms, wherein from 1-4 ring atoms are each independently selected from the group consisting of N, N(H), N($R^c$), O, and S(O)$_{0-2}$, wherein the heteroaryl is optionally substituted with from 1-3 independently selected $R^b$ at one or more ring carbon atoms.

In certain embodiments, $R^Z$ is $C_{6-10}$ aryl, wherein the aryl is optionally substituted with from 1-5 independently selected $R^b$.

In certain embodiments, $R^Z$ is phenyl which is optionally substituted with from 1-3 independently selected $R^b$.

As non-limiting examples, $R^Z$ can be selected from the group consisting of:

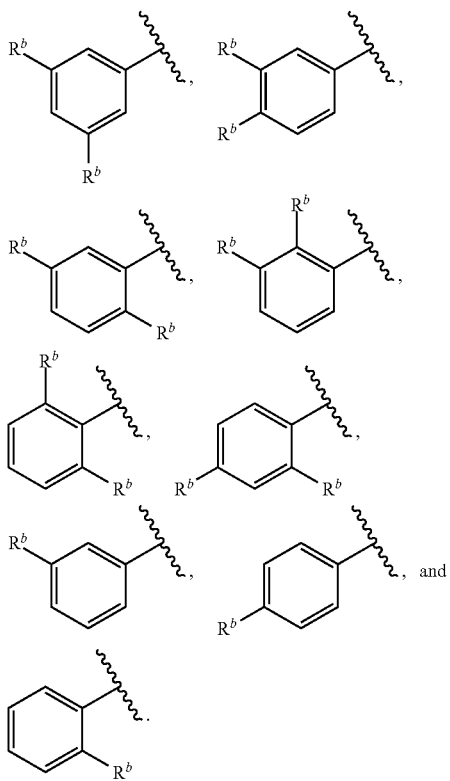

For example, $R^Z$ can be

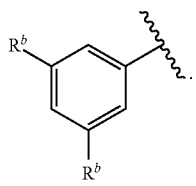

In certain embodiments, $R^Z$ is heteroaryl including from 5-10 ring atoms, wherein from 1-4 ring atoms are each independently selected from the group consisting of N, N(H), N($R^c$), O, and S(O)$_{0-2}$, wherein the heteroaryl is optionally substituted with from 1-3 independently selected $R^b$ at one or more ring carbon atoms.

In certain embodiments, $R^Z$ is monocyclic heteroaryl including from 5-6 ring atoms, wherein from 1-4 ring atoms are each independently selected from the group consisting of N, N(H), N($R^c$), O, and S, wherein the heteroaryl is optionally substituted with from 1-3 independently selected $R^b$ at one or more ring carbon atoms.

In certain embodiments, $R^Z$ is monocyclic heteroaryl including 6 ring atoms, wherein from 1-2 ring atoms are ring nitrogen atoms, wherein the heteroaryl is optionally substituted with from 1-3 independently selected $R^b$ at one or more ring carbon atoms.

As non-limiting examples, $R^Z$ can be selected from the group consisting of:

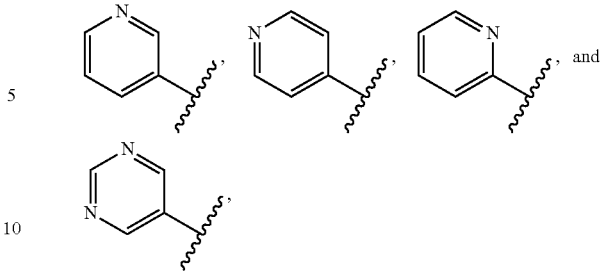

each optionally substituted with $R^b$.

In certain embodiments, $R^Z$ is monocyclic heteroaryl including 5 ring atoms, wherein from 1-4 ring atoms are each independently selected from the group consisting of N, N(H), N($R^c$), O, and S, wherein the heteroaryl is optionally substituted with from 1-2 independently selected $R^b$ at one or more ring carbon atoms.

As non-limiting examples, $R^Z$ can be selected from the group consisting of:

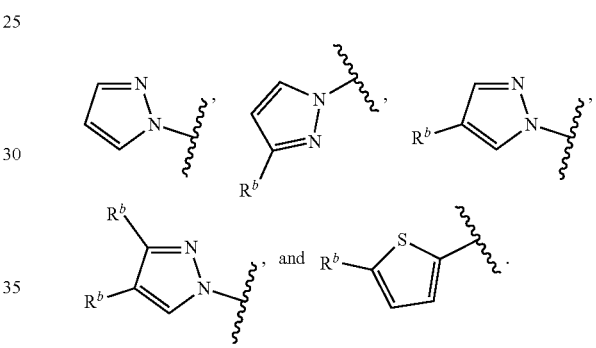

In some embodiments, each $R^b$ present in $R^Z$ is independently selected from the group consisting of: $C_{1-3}$ alkyl optionally substituted with from 1-3 independently selected halo; —F; —Cl; —N($R^f$)(R'); $C_{1-4}$ alkoxy; $C_{1-4}$ haloalkoxy; —C(=O)OH; —C(=O)N(R')(R''); and cyano.

In certain embodiments, $R^Z$ is selected from the group consisting of:

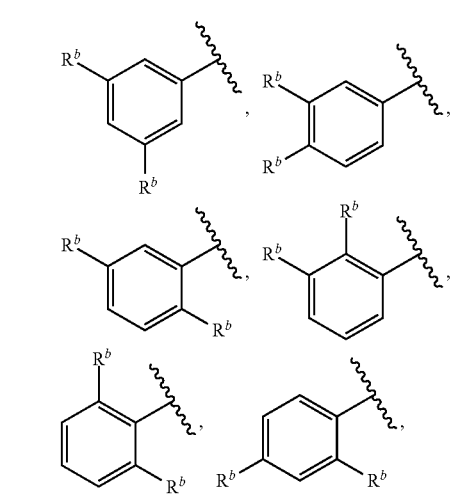

-continued

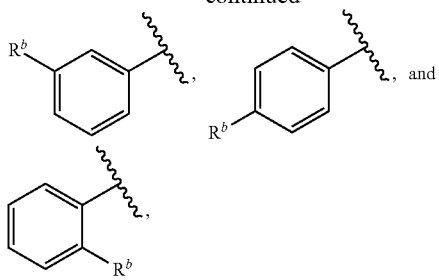

wherein each $R^b$ present in $R^Z$ is independently selected from the group consisting of: $C_{1-3}$ alkyl optionally substituted with from 1-3 independently selected halo; —F; —Cl; —N(R')(R'); $C_{1-4}$ alkoxy; $C_{1-4}$ haloalkoxy; —C(=O)OH; —C(=O)N(R')(R"); and cyano.

In certain of the foregoing embodiments, $R^Z$ is

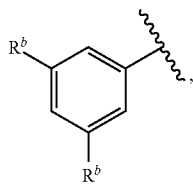

wherein each $R^b$ present in $R^Z$ is independently selected from the group consisting of: $C_{1-3}$ alkyl optionally substituted with from 1-3 independently selected halo; —F; —Cl; —N(R')(R'); $C_{1-4}$ alkoxy; $C_1$-4 haloalkoxy; —C(=O)OH; —C(=O)N(R')(R"); and cyano.

In some embodiments, $L^1$ is $C_{1-10}$ alkylene optionally substituted with from 1-3 substituents each independently selected from the group consisting of: halo; $C_{1-4}$ alkoxy; —OH; phenyl; and NR'R".

In certain embodiments, $L^1$ is unsubstituted $C_{1-10}$ alkylene. In certain of these embodiments, $L^1$ is unsubstituted $C_{1-6}$ alkylene. In certain embodiments, $L^1$ is unsubstituted $C_{2-4}$ alkylene. In certain embodiments, $L^1$ is unsubstituted $C_3$ alkylene. As a non-limiting example, $L^1$ can be —CH$_2$CH$_2$CH$_2$—. In certain embodiments, $L^1$ is unsubstituted $C_2$ alkylene. As a non-limiting example, $L^1$ can be —CH$_2$CH$_2$—.

In certain embodiments, $X^1$ is selected from the group consisting of: C(=O)N(R')*; C(=S)N(R')*; and S(O)$_{1-2}$N(R')*, wherein * represents the point of attachment to $L^1$.

In certain of these embodiments, $X^1$ can be C(=O)N(R')*. As a non-limiting example, $X^1$ can be C(=O)N(H)*.

In certain embodiments, $X^1$ is C(=S)N(R')*. As a non-limiting example, $X^1$ can be C(=S)N(H)*.

In certain embodiments, $L^1$ is unsubstituted $C_{2-4}$ alkylene; and $X^1$ is C(=O)N(R')*.

In certain of these embodiments, $L^1$ is —CH$_2$CH$_2$—, or —CH$_2$CH$_2$CH$_2$—; and $X^1$ is C(=O)N(H)*.

In certain embodiments, $L^1$ is unsubstituted $C_{2-4}$ alkylene; and $X^1$ is C(=S)N(R')*.

In certain of these embodiments, $L^1$ is —CH$_2$CH$_2$—, or —CH$_2$CH$_2$CH$_2$—; and $X^1$ is C(=S)N(H)*.

In certain embodiments, R* is a group of Formula (A), wherein:

$L^1$ is unsubstituted $C_{2-4}$ alkylene (e.g., linear $C_{2-4}$ alkylene, such as —CH$_2$CH$_2$— or —CH$_2$CH$_2$CH$_2$, e.g., —CH$_2$CH$_2$—)—;

$X^1$ is C(=O)N(R')* (e.g., C(=O)N(H)*) or C(=S)N(R')* (e.g., C(=S)N(H)*);

$R^Z$ is phenyl optionally substituted with from 1-3 $R^b$; and $R^{X1}$ and $R^{X2}$ are each independently selected unsubstituted $C_{1-3}$ alkyl; or $R^{X1}$ and $R^{X2}$ taken together with the carbon atom to which each is attached form a $C_{3-6}$ cycloalkyl ring which is optionally substituted with from 1-3 independently selected $C_{1-3}$ alkyl.

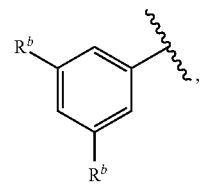

In certain of the foregoing embodiments, $R^Z$ is wherein each $R^b$ present in $R^Z$ is independently selected from the group consisting of: $C_{1-3}$ alkyl optionally substituted with from 1-3 independently selected halo; —F; —Cl; —N(R$^f$)(R'); $C_{1-4}$ alkoxy; $C_{1-4}$ haloalkoxy; —C(=O)OH; —C(=O)N(R')(R"); and cyano; and/or $X^1$ is C(=O)N(H) or C(=S)N(H);

$X^2$ is a bond;

$R^{X1}$ and $R^{42}$ are each independently methyl or ethyl; or $R^{X1}$ and $R^{X2}$ taken together with the carbon atom to which each is attached form a cyclopropyl ring, cyclobutyl ring, or cyclopentyl ring.

Formula (B)

In some embodiments, R* is (ii)

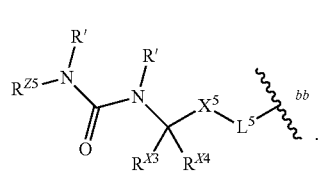

(Formula (B))

In certain embodiments, $R^{X3}$ and $R^{X4}$ are each defined according to (BA).

In certain embodiments, $R^{X3}$ and $R^{X4}$ are the same.

In certain embodiments, $R^{X3}$ and $R^{X4}$ are the different.

In certain of these embodiments, $R^{X3}$ and $R^{X4}$ are each H.

In certain embodiments, $R^{X3}$ and $R^{X4}$ are each independently selected from the group consisting of:

—F;

$C_{1-8}$ alkyl, $C_{2-6}$ alkenyl, and $C_{2-6}$ alkynyl, each of which is optionally substituted with from 1-3 $R^a$; and $C_{3-6}$ cycloalkyl which is optionally substituted with from 1-3 $R^b$.

In certain embodiments, $R^{X3}$ and $R^{X4}$ are independently selected $C_{1-8}$ alkyl, which is optionally substituted with from 1-3 $R^a$. In certain of these embodiments, $R^{X3}$ and $R^{X4}$ are independently selected unsubstituted $C_{1-6}$ alkyl. In certain embodiments, $R^{X3}$ and $R^{X4}$ are independently selected unsubstituted $C_{1-3}$ alkyl. As a non-limiting example, $R^{X3}$ and $R^{X4}$ can both be methyl. As another non-limiting example, $R^{X3}$ and $R^{X4}$ can both be ethyl.

In certain embodiments, $R^{X3}$ and $R^{X4}$ are each —F.

In certain embodiments, $R^{X3}$ and $R^{X4}$ are each defined according to (BB).

In certain of these embodiments, $R^{X3}$ and $R^{X4}$ taken together with the carbon atom to which each is attached form a saturated or partially unsaturated ring having from 3-10 ring atoms, wherein from 0-2 ring atoms are heteroatoms each independently selected from the group consisting of: O, N, N(H), N($R^c$), and S(O)$_{0-2}$, wherein the ring is optionally substituted at one or more ring carbon atoms with from 1-3 $R^b$.

In certain embodiments, $R^{X3}$ and $R^{X4}$ taken together with the carbon atom to which each is attached form a $C_{3-8}$ cycloalkyl ring which is optionally substituted with from 1-3 $R^b$.

In certain embodiments, $R^{X3}$ and $R^{X4}$ taken together with the carbon atom to which each is attached form a $C_{3-6}$ cycloalkyl ring which is optionally substituted with from 1-3 independently selected $C_{1-3}$ alkyl.

As non-limiting examples, $R^{X3}$ and $R^{X4}$ taken together with the carbon atom to which each is attached can form a cyclopropyl ring, cyclobutyl ring, cyclopentyl ring, or cyclohexyl ring.

In certain embodiments, $R^{X3}$ and $R^{X4}$ taken together with the carbon atom to which each is attached form a saturated or partially unsaturated ring having from 4-10 ring atoms, wherein from 1-2 ring atoms are heteroatoms each independently selected from the group consisting of: O, N, N(H), N($R^c$), and S(O)$_{0-2}$, wherein the ring is optionally substituted at one or more ring carbon atoms with from 1-3 $R^b$.

In certain embodiments, $R^{X3}$ and $R^{X4}$ taken together with the carbon atom to which each is attached form a saturated ring having from 4-6 ring atoms, wherein one ring atom is a heteroatom selected from the group consisting of: O, N, N(H), N($R^c$), and S(O)$_{0-2}$, wherein the ring is optionally substituted at one or more ring carbon atoms with from 1-3 $R^b$.

As non-limiting examples, $R^{X3}$ and $R^{X4}$ taken together with the carbon atom to which each is attached can form

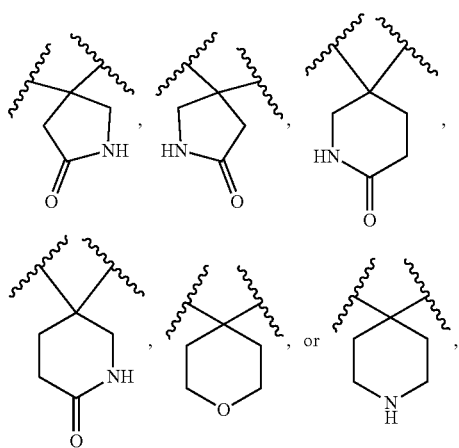

each of which is optionally substituted with from 1-2 independently selected $C_{1-3}$ alkyl.

In certain embodiments, $R^{Z5}$ is —$R^{ZE}$.

In certain embodiments, $R^{Z5}$ is -$L^{ZE}$-$R^{ZE}$. In certain of these embodiments, $L^{ZE}$ is $C_{1-6}$ alkylene optionally substituted with from 1-3 independently selected $R^a$; In certain embodiments, $L^{ZE}$ is unsubstituted $C_{1-6}$ alkylene. In certain embodiments, $L^{ZE}$ is unsubstituted $C_{2-4}$ alkylene. In certain embodiments, $L^{ZE}$ is unsubstituted $C_{1-3}$ alkylene. As a non-limiting example, $L^{ZE}$ can be —CH$_2$CH$_2$CH$_2$—. As another non-limiting example, $L^{ZE}$ can be —CH$_2$CH$_2$—. As still another non-limiting example, $L^{ZE}$ can be —CH$_2$—.

In certain embodiments (when $R^{Z5}$ is —$R^{ZE}$; or when $R^{Z5}$ is -$L^{ZE}$-$R^{ZE}$), $R^{ZE}$ is selected from the group consisting of:
(iii) $C_{6-10}$ aryl, wherein the aryl is optionally substituted with from 1-5 independently selected $R^b$; and
(iv) heteroaryl including from 5-10 ring atoms, wherein from 1-4 ring atoms are each independently selected from the group consisting of N, N(H), N($R^c$), O, and S(O)$_{0-2}$, wherein the heteroaryl is optionally substituted with from 1-3 independently selected $R^b$ at one or more ring carbon atoms.

In certain of these embodiments, $R^{ZE}$ is $C_{6-10}$ aryl, wherein the aryl is optionally substituted with from 1-5 independently selected $R^b$.

In certain of the foregoing embodiments, $R^{ZE}$ is phenyl which is optionally substituted with from 1-3 independently selected $R^b$.

As non-limiting examples, $R^{ZE}$ can be selected from the group consisting of:

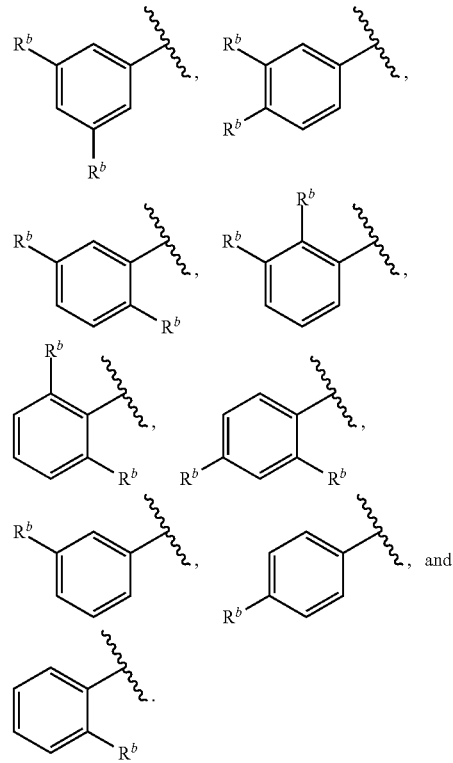

In certain embodiments, $R^{ZE}$ is heteroaryl including from 5-10 ring atoms, wherein from 1-4 ring atoms are each independently selected from the group consisting of N, N(H), N($R^c$), O, and S(O)$_{0-2}$, wherein the heteroaryl is optionally substituted with from 1-3 independently selected $R^b$ at one or more ring carbon atoms.

In certain embodiments, $R^{ZE}$ is monocyclic heteroaryl including from 5-6 ring atoms, wherein from 1-4 ring atoms are each independently selected from the group consisting of N, N(H), N($R^c$), O, and S, wherein the heteroaryl is optionally substituted with from 1-3 independently selected $R^b$ at one or more ring carbon atoms.

In certain embodiments, $R^{ZE}$ is monocyclic heteroaryl including 6 ring atoms, wherein from 1-2 ring atoms are ring nitrogen atoms, wherein the heteroaryl is optionally substituted with from 1-3 independently selected $R^b$ at one or more ring carbon atoms.

In certain embodiments, each $R^b$ present in $R^{ZE}$ is independently selected from the group consisting of: $C_{1-3}$ alkyl optionally substituted with from 1-3 independently selected halo; —F; —Cl; —N(R$^f$)(R'); $C_{1-4}$ alkoxy; $C_{1-4}$ haloalkoxy; —C(=O)OH; —C(=O)N(R')(R"); and cyano.

In certain embodiments, $R^{ZE}$ is selected from the group consisting of:

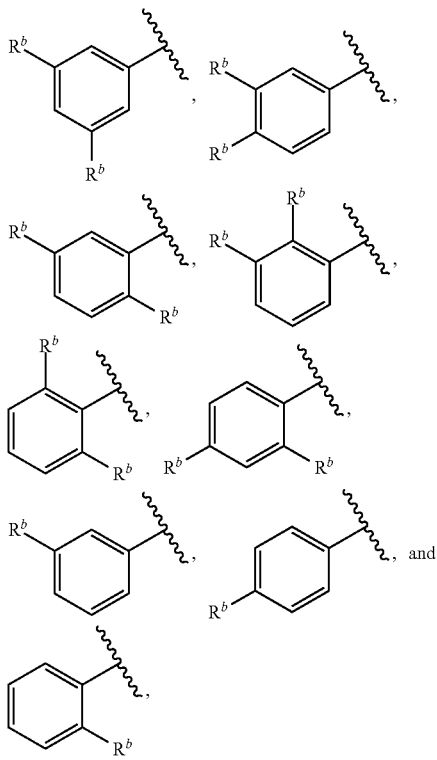

wherein each $R^b$ present in $R^Z$ is independently selected from the group consisting of: $C_{1-3}$ alkyl optionally substituted with from 1-3 independently selected halo; —F; —Cl; —N(R$^f$)(R'); $C_{1-4}$ alkoxy; $C_{1-4}$ haloalkoxy; —C(=O)OH; —C(=O)N(R')(R"); and cyano.

In certain embodiments, $L^5$ is unsubstituted $C_{1-10}$ alkylene. In certain of these embodiments, $L^5$ is unsubstituted $C_{1-6}$ alkylene. In certain embodiments, $L^5$ is unsubstituted $C_{2-4}$ alkylene. In certain embodiments, $L^5$ is unsubstituted $C_3$ alkylene. As a non-limiting example, $L^5$ can be —CH$_2$CH$_2$CH$_2$—. In certain embodiments, $L^5$ is unsubstituted $C_2$ alkylene. As a non-limiting example, $L^5$ can be —CH$_2$CH$_2$—.

In certain embodiments, $X^5$ is selected from the group consisting of: C(=O)N(R')*; C(=S)N(R')*; and S(O)$_{1-2}$N(R')*, wherein * represents the point of attachment to $L^1$.

In certain of these embodiments, $X^5$ can be C(=O)N(R')*. As a non-limiting example, $X^5$ can be C(=O)N(H)*.

In certain embodiments, $X^5$ is C(=S)N(R')*. As a non-limiting example, $X^5$ can be C(=S)N(H)*.

In certain embodiments, $L^5$ is unsubstituted $C_{2-4}$ alkylene; and $X^5$ is C(=O)N(R')*.

In certain of these embodiments, $L^5$ is —CH$_2$CH$_2$—, or —CH$_2$CH$_2$CH$_2$—; and $X^5$ is C(=O)N(H)*.

In certain embodiments, $L^5$ is unsubstituted $C_{2-4}$ alkylene; and $X^5$ is C(=S)N(R')*.

In certain of these embodiments, $L^5$ is —CH$_2$CH$_2$—, or —CH$_2$CH$_2$CH$_2$—; and $X^5$ is C(=S)N(H)*.

In certain embodiments, the group of Formula (B) has Formula (B-1):

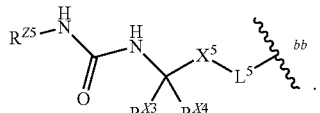

In certain embodiments, R* is a group of Formula (B), wherein:
$R^{X3}$ and $R^{X4}$ are each independently H or unsubstituted $C_{1-3}$ alkyl (e.g., H or methyl);
$L^5$ is unsubstituted $C_{2-4}$ alkylene (e.g., linear $C_{2-4}$ alkylene (e.g., —CH$_2$CH$_2$— or —CH$_2$CH$_2$CH$_2$—);
$X^5$ is C(=O)N(R')* (e.g., C(=O)N(H)*); and
$R^{Z5}$ is phenyl optionally substituted with from 1-3 $R^b$.

In certain of these embodiments, the group of Formula (B) has Formula (B-1); and/or each $R^b$ present in $R^{Z5}$ is independently selected from the group consisting of: $C_{1-3}$ alkyl optionally substituted with from 1-3 independently selected halo; —F; —Cl; —N(R$^f$)(R'); $C_{1-4}$ alkoxy; $C_{1-4}$ haloalkoxy; —C(=O)OH; —C(=O)N(R')(R"); and cyano.

Formula (C)

In some embodiments, R* is (iii)

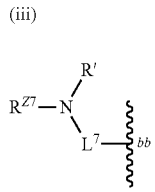

(Formula (C))

In certain embodiments, $R^{Z7}$ is -$L^{ZG}$-$R^{ZG}$, wherein $L^{ZG}$ is as defined anywhere infra.

In certain embodiments, $L^{ZG}$ is unsubstituted $C_{1-6}$ alkylene. In certain embodiments, $L^{ZG}$ is unsubstituted $C_{2-4}$ alkylene. In certain of these embodiments, $L^{ZG}$ is unsubstituted $C_3$ alkylene. As a non-limiting example, $L^{ZG}$ can be —CH$_2$CH$_2$CH$_2$—. In certain embodiments, $L^{ZG}$ is unsubstituted $C_2$ alkylene. As a non-limiting example, $L^{ZG}$ can be —CH$_2$CH$_2$—. In certain embodiments, $L^{ZG}$ is —CH$_2$—.

In certain embodiments, $R^{ZG}$ is selected from the group consisting of:
(iii) $C_{6-10}$ aryl, wherein the aryl is optionally substituted with from 1-5 independently selected $R^b$; and
(iv) heteroaryl including from 5-10 ring atoms, wherein from 1-4 ring atoms are each independently selected from the group consisting of N, N(H), N(R$^c$), O, and S(O)$_{0-2}$, wherein the heteroaryl is optionally substituted with from 1-3 independently selected $R^b$ at one or more ring carbon atoms.

In certain embodiments, $R^{ZG}$ is $C_{6-10}$ aryl, wherein the aryl is optionally substituted with from 1-5 independently selected $R^b$.

In certain embodiments, $R^{ZG}$ is phenyl which is optionally substituted with from 1-3 independently selected $R^b$.

As non-limiting examples, $R^{ZG}$ can be selected from the group consisting of:

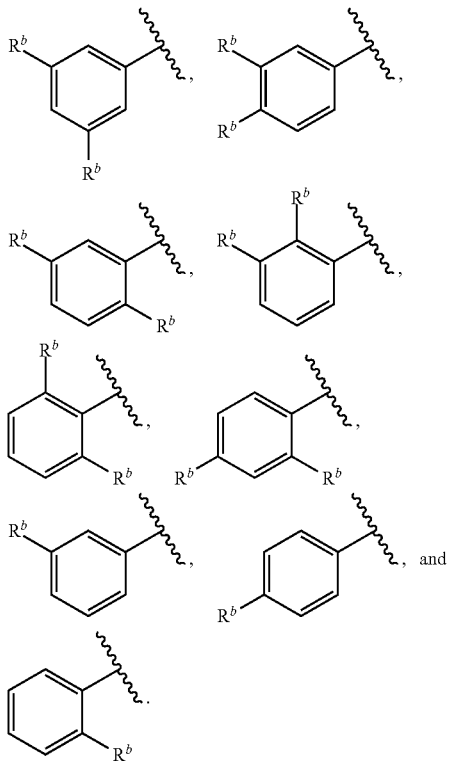

For example, $R^{ZG}$ can be

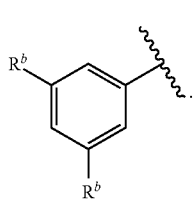

In certain embodiments, $R^{ZG}$ is heteroaryl including from 5-10 ring atoms, wherein from 1-4 ring atoms are each independently selected from the group consisting of N, N(H), N(R$^c$), O, and S(O)$_{0-2}$, wherein the heteroaryl is optionally substituted with from 1-3 independently selected R$^b$ at one or more ring carbon atoms.

In certain embodiments, $R^{ZG}$ is monocyclic heteroaryl including from 5-6 ring atoms, wherein from 1-4 ring atoms are each independently selected from the group consisting of N, N(H), N(R$^c$), O, and S, wherein the heteroaryl is optionally substituted with from 1-3 independently selected R$^b$ at one or more ring carbon atoms.

In certain embodiments, $R^{ZG}$ is monocyclic heteroaryl including 6 ring atoms, wherein from 1-2 ring atoms are ring nitrogen atoms, wherein the heteroaryl is optionally substituted with from 1-3 independently selected R$^b$ at one or more ring carbon atoms.

In certain embodiments, $R^{ZG}$ is monocyclic heteroaryl including 5 ring atoms, wherein from 1-4 ring atoms are each independently selected from the group consisting of N, N(H), N(R$^c$), O, and S, wherein the heteroaryl is optionally substituted with from 1-2 independently selected R$^b$ at one or more ring carbon atoms.

As non-limiting examples, $R^{ZG}$ can be selected from the group consisting of:

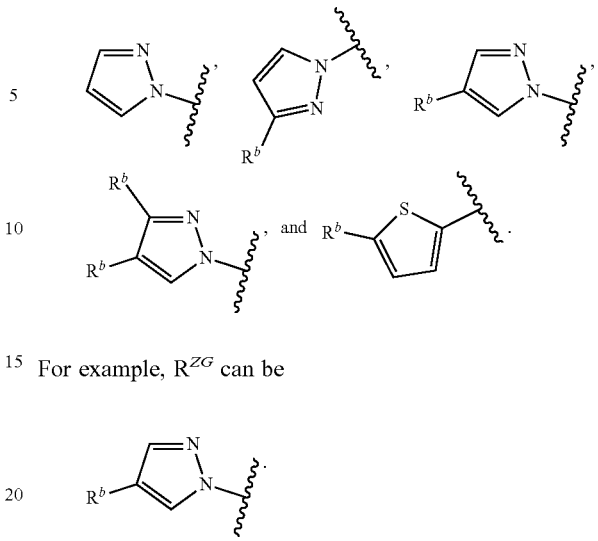

For example, $R^{ZG}$ can be

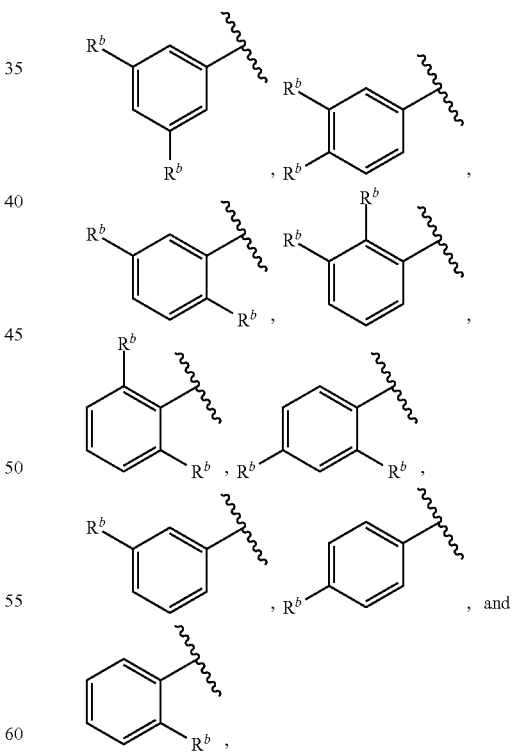

In some embodiments, each R$^b$ present in $R^{ZG}$ is independently selected from the group consisting of: C$_{1-3}$ alkyl optionally substituted with from 1-3 independently selected halo; —F; —Cl; —N(R$^f$)(R'); C$_{1-4}$ alkoxy; C$_{1-4}$ haloalkoxy; —C(=O)OH; —C(=O)N(R')(R''); and cyano.

As non-limiting examples, $R^{ZG}$ can be selected from the group consisting of:

wherein each R$^b$ present in $R^Z$ is independently selected from the group consisting of: C$_{1-3}$ alkyl optionally substituted with from 1-3 independently selected halo; —F; —Cl; —N(R')(R'); C$_{1-4}$ alkoxy; C$_{1-4}$ haloalkoxy; —C(=O)OH; —C(=O)N(R')(R''); and cyano.

In certain embodiments, $L^7$ is $C_{1-10}$ alkylene optionally substituted with from 1-3 substituents each independently selected from the group consisting of: halo; $C_{1-4}$ alkoxy; —OH; phenyl; and NR'R".

In certain embodiments, $L^7$ is unsubstituted $C_{1-10}$ alkylene. In certain embodiments, $L'$ is unsubstituted $C_{1-6}$ alkylene. In certain embodiments, $L^7$ is unsubstituted $C_{2-4}$ alkylene. In certain embodiments, $L^7$ is unsubstituted $C_3$ alkylene. As a non-limiting example, $L^7$ can be —CH$_2$CH$_2$CH$_2$—. In certain embodiments, $L^7$ is unsubstituted $C_2$ alkylene. As a non-limiting example, $L^7$ can be —CH$_2$CH$_2$—.

Variable Q, $R^1$, a1, $R^2$

In some embodiments, Q is O.

In some embodiments, $R^1$ is —H.

In some embodiments, a1 is 0. In some embodiments, a1 is 1, 2, or 3. For example, a1 can be 1. As another non-limiting example, a1 can be 2. As yet another non-limiting example, a1 can be 3.

In some embodiments, $R^2$ is —H.

In some embodiments, $R^2$ is $C_{1-3}$ alkyl. For example, $R^2$ can be methyl.

Variable $R^{2'}$

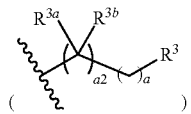

In certain embodiments, a2 is 1. In certain embodiments, a2 is 0.

In certain embodiments (when a2 is 1), $R^{3a}$ and $R^{3b}$ are both H.

In certain embodiments, a is 1. In certain embodiments, a is 0.

In certain embodiments, $R^{2'}$ is —CH$_2$CH$_2$R$^3$. In certain embodiments, $R^{2'}$ is —CH$_2$R$^3$. In some embodiments, $R^{2'}$ is —R$^3$.

In certain embodiments, $R^3$ is —C(O)OH. In certain embodiments, $R^3$ is —CH(C(O)OH)$_2$.

In certain embodiments, $R^3$ is a carboxylic acid bioisostere. As a non-limiting example, $R^3$ can be tetrazolyl.

In certain embodiments, a1 is 0; $R^1$ and $R^2$ are each H; and $R^{2'}$ is —CH$_2$CH$_2$R$^3$, wherein $R^3$ is —C(O)OH.

Variables $N(R^4)$—W, $N(R^4)$—W$^1$, $N(R^4)$—W$^{1'}$, W$^{1''}$, W'', and $R^5$ In some embodiments, $N(R^4)$—W is a peptide having formula $N(R^4)$—W$^1$—R$^5$, wherein: $N(R^4)$—W$^1$ is a sequence of from 5-60 amino acids; and $R^5$ is a C-terminal amino acid, amino ester, or amino acid amide that is optionally substituted with from 1-2 modifying groups. $R^4$ is H or $C_1$-$C_3$ alkyl For purposes of clarification, $N(R^4)$ represents the amino group of the N-terminal amino acid in formulas reciting W and/or W$^1$ (e.g., if the N-terminal amino acid of W and/or W$^1$ is a glycyl residue, then the following structure is intended for said N-terminal amino acid:

\*—N(R$^4$)—CH$_2$—C(O)— . . . ;

wherein the * represent the point of connection of the N-terminal amino acid amino group to the remainder of formula (I)). As a further illustration, if the N-terminal amino acid of W and W$^1$ is glycine itself (e.g., as represented by G; e.g., as shown in embodiments of $N(R^4)$—W and $N(R^4)$—W$^1$—R$^5$ described herein; e.g., formulas WD, WD-1, WD-2, WD-3, WD-4, WD-5, WE, WF, and the sequences delineated in Table 1), then it is understood that $R^4$ is H in the illustrative formula above.

In certain embodiments, $N(R^4)$—W$^1$ is a sequence of from 25-45 amino acids; optionally 30-45 amino acids; optionally 30-40 amino acids.

In certain embodiments, $N(R^4)$—W$^1$ is a sequence of from 36-38 (e.g., 36) amino acids.

In certain embodiments, W$^1$ has the formula $N(R^4)$—W$^{1'}$-(AA)-W$^{1'''}$, wherein: $N(R^4)$—W$^{1'}$ is a sequence of 10-20 amino acids (optionally 15-20 amino acids; optionally 16 amino acids); W$^{1'''}$ is a sequence of 15-25 amino acids (optionally 17-21 amino acids; optionally 19 amino acids; or optionally 18 amino acids); and AA is a modified amino acid (e.g., a modified lysine, sometimes referred to herein as "K*").

In certain of these embodiments, AA is a lysyl residue that is optionally substituted with from 1-2 modifying groups (e.g., 1-2 groups selected from an acyl group and a PEG group; and combinations thereof).

In certain embodiments, AA is an L-lysyl residue that is optionally substituted with from 1-2 modifying groups (e.g., 1-2 groups selected from an acyl group and a PEG group; and combinations thereof).

In certain embodiments, AA has the formula:

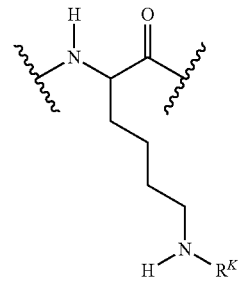

wherein, $R^K$ is a modifying group selected from an acyl group, a PEG group, and combinations thereof.

In certain embodiments, $R^K$ is a group of Formula (KA):

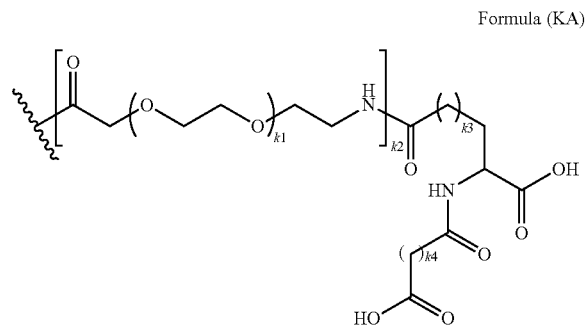

Formula (KA)

wherein:

k1 is 1, 2, 3, or 4;

k2 is 1, 2, 3, or 4;

k3 is 0, 1, 2, 3, or 4; and k4 is an integer from 5 to 25.

In certain embodiments of Formula (KA), k1 is 1.

In certain embodiments of Formula (KA), k2 is 2.

In certain embodiments of Formula (KA), k3 is 1.

In certain embodiments of Formula (KA), k4 is an integer from 10 to 20.

In certain embodiments of Formula (KA), k4 is an integer from 15 to 20. As non-limiting examples, k4 can be 16 or 18. For example, k4 can be 16. As another non-limiting example, k4 can be 16.

In certain embodiments of Formula (KA), k1 is 1; k2 is 2; k3 is 1; and k4 is an integer from 15 to 20 (e.g., 16 or 18).

As a non-limiting example, $R^K$ can be

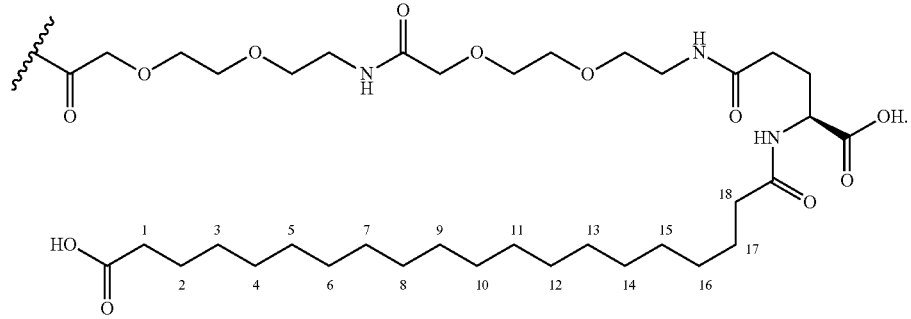

(K18)

As another non-limiting example, $R^K$ can be

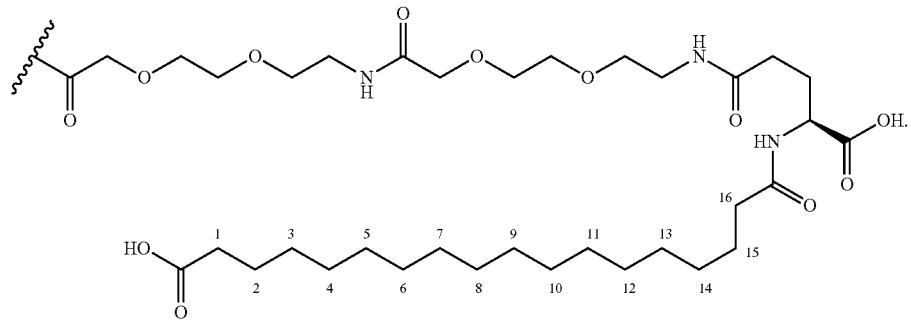

(K16)

In certain embodiments, $R^K$ is:

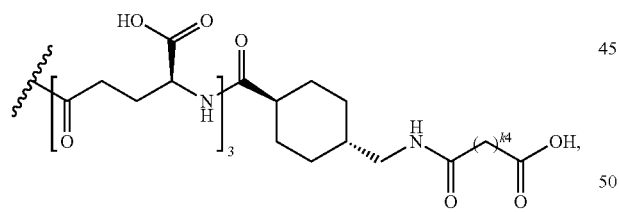

wherein k4 is an integer from 5-25. For example, k4 can be 18.

For example, $R^K$ can be

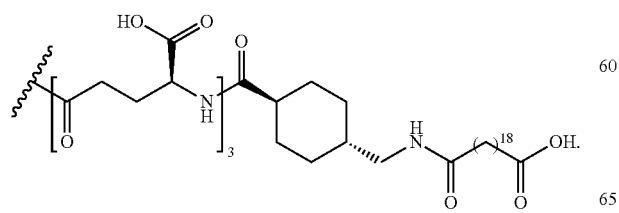

As a non-limiting example, (AA) can be an internal amino acid having the formula:

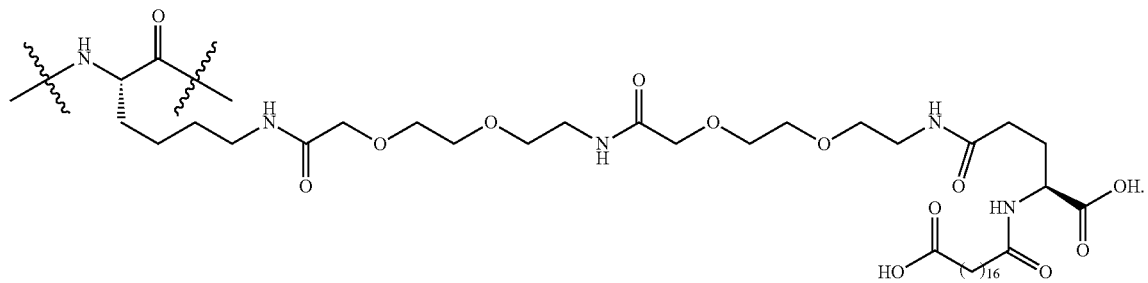

As another non-limiting example, (AA) can be an internal amino acid having the formula:

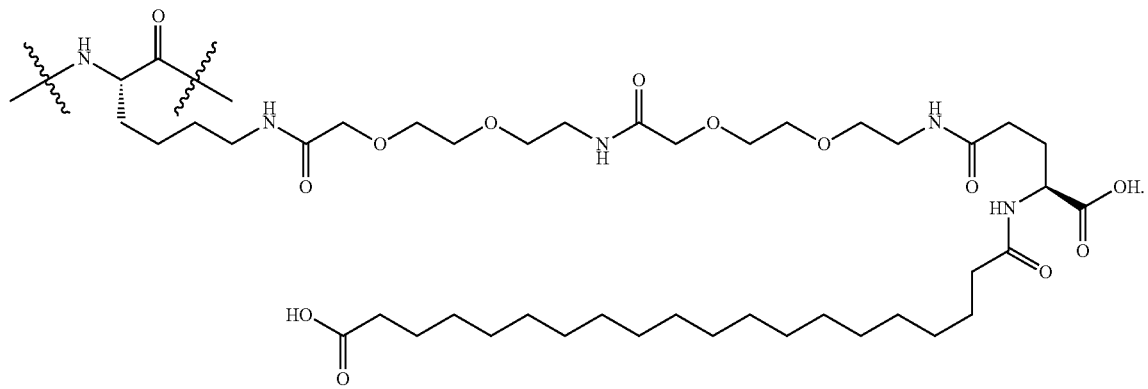 [SMILES: *N[C@@H](CCCCNC(=O)COCCOCCNC(=O)COCCOCCNC(=O)CC[C@H](NC(=O)CCCCCCCCCCCCCCCCCCC(=O)O)C(=O)O)C(*)=O]

As still another non-limiting example, (AA) can be an internal amino acid having the formula:

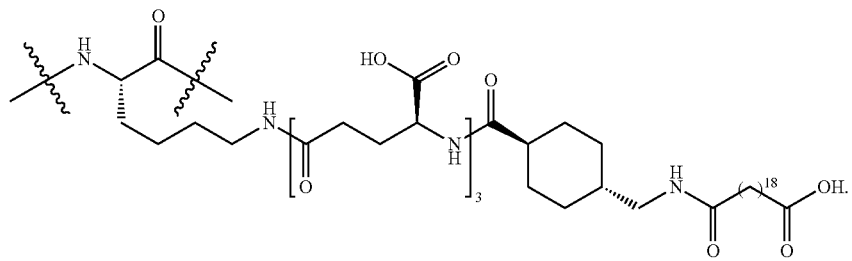

In certain embodiments, $R^5$ is a C-terminal amino acid that is optionally substituted with from 1-2 modifying groups.

In certain embodiments, $R^5$ is a C-terminal amino acid amide that is optionally substituted with from 1-2 modifying groups. In certain of these embodiments, $R^5$ is a C-terminal amino acid amide. For example, $R^5$ can be serine amide (e.g., 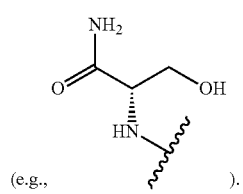 [SMILES: *N[C@@H](CO)C(N)=O] ).

In certain embodiments, —N($R^4$)—W has formula: -GTF-W"—$R^5$, wherein W" is a sequence of 30-40 (e.g., 31-36, 33) amino acids, wherein W" comprises a modified amino acid (AA) as defined anywhere herein; optionally wherein (AA) is an internal amino acid; and $R^5$ is a C-terminal amino acid, amino ester, or amino acid amide that is optionally substituted with from 1-2 modifying groups. In certain embodiments, $R^5$ is a C-terminal amino acid, which is not substituted with any modifying groups. $R^5$ is a C-terminal amino acid amide, which is not substituted with any modifying groups.

In certain of these embodiments, AA is a lysyl residue that is optionally substituted with from 1-2 modifying groups (e.g., 1-2 groups selected from an acyl group and a PEG group; and combinations thereof). In certain embodiments, lysyl residues modified in this manner, including as exampled below and throughout the description and claims, are also referred to herein as "K*"

In certain of the foregoing embodiments, AA has the formula:

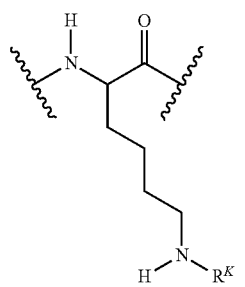
wherein R" is a group of Formula (KA):
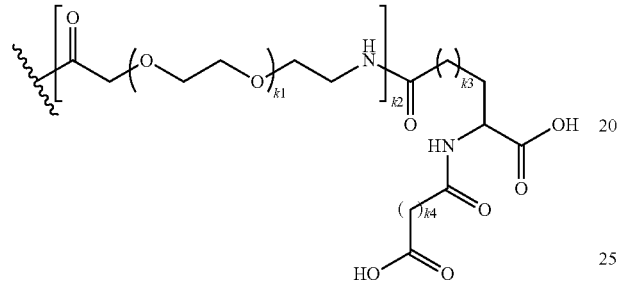
Formula (KA)
wherein:
k1 is 1, 2, 3, or 4;
k2 is 1, 2, 3, or 4;
k3 is 0, 1, 2, 3, or 4; and
k4 is an integer from 5 to 25.
As a non-limiting example, (AA) can be an internal amino acid having the formula:
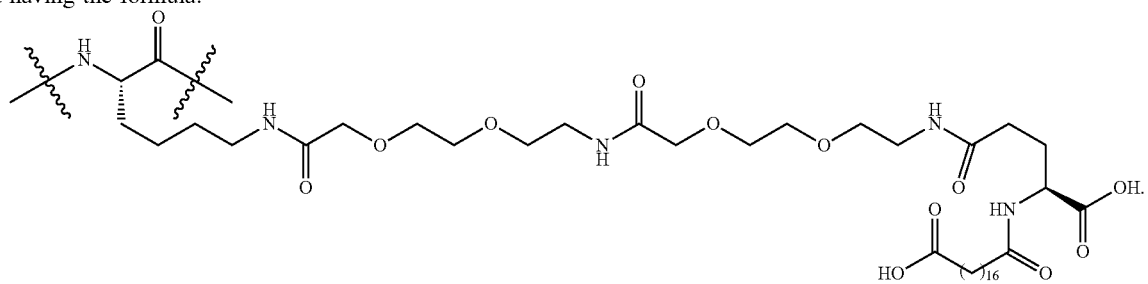
As another non-limiting example, (AA) can be an internal amino acid having the formula:
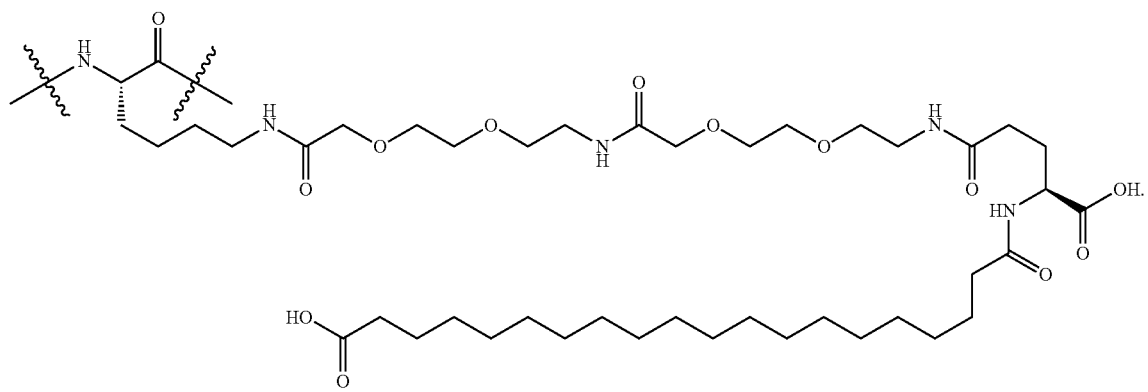 [SMILES: *N[C@@H](CCCCNC(=O)COCCOCCNC(=O)COCCOCCNC(=O)CC[C@H](NC(=O)CCCCCCCCCCCCCCCCCCC(=O)O)C(=O)O)C(*)=O]

As still another non-limiting example, (AA) can be an internal amino acid having the formula:

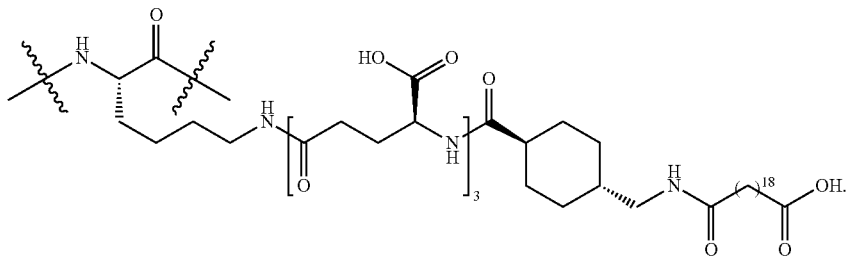

In certain embodiments, $R^5$ is a C-terminal amino acid that is optionally substituted with from 1-2 modifying groups.

In certain embodiments, $R^5$ is a C-terminal amino acid amide that is optionally substituted with from 1-2 modifying groups. In certain of these embodiments, $R^5$ is a C-terminal amino acid amide. For example, $R^5$ can be serine amide (e.g., 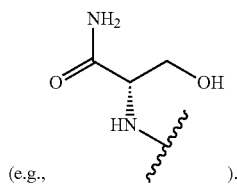).

Constituent Amino Acids and Modifications Thereof

In some embodiments, variables $N(R^4)$—W, $N(R^4)$—$W^1$, $N(R^4)$—$W^{1'}$, $W^{1''}$, and/or W'' herein include one or more naturally occurring amino acids found, e.g., in polypeptides and/or proteins produced by living organisms, such as Ala (A), Val (V), Leu (L), Ile (I), Pro (P), Phe (F), Trp (W), Met (M), Gly (G), Ser (S), Thr (T), Cys (C), Tyr (Y), Asn (N), Gln (Q), Asp (D), Glu (E), Lys (K), Arg (R), and His (H). Unless otherwise indicated, conventional one and three letter amino acid abbreviations are adhered to herein throughout the description and claims.

In some embodiments, $N(R^4)$—W, $N(R^4)$—$W^1$, $N(R^4)$—$W^{1'}$, $W^{1''}$, and/or W'' include one or more independently selected modifications that occur present in so-called modified peptides. Such modifications include, but not limited to: (i) the incorporation of lactam-bridge; (ii) head-to-tail cyclization; (iii) one or more alternative or non-naturally occurring (D or L) amino acids, such as synthetic non-native amino acids, substituted amino acids, and D-amino acids; (iv) peptide bond replacements; (v) targeting groups; and the like. In certain embodiments, $N(R^4)$—W includes one modification in either the $N(R^4)$—$W^1$ (e.g., $N(R^4)$—$W^{1'}$ or $W^{1''}$) or $R^5$ component. In other embodiments, W includes more than one independently selected modification (e.g., 2 independently selected modifications, 3 independently selected modifications, 4 independently selected modifications, 5 independently selected modifications, 6 independently selected modifications, 7 independently selected modifications, 8 independently selected modifications, 9 independently selected modifications, or 10 independently selected modifications that occur in the $N(R^4)$—$W^1$ (e.g., $N(R^4)$—$W^{1'}$ or $W^{1''}$) and/or $R^5$ component (e.g., in the $N(R^4)$—$W^1$ component only; or in the $R^5$ component only; or in both the $N(R^4)$—$W^1$ and $R^5$ components).

Non-limiting examples of alternative or non-naturally amino acids include, D-amino acids; beta-amino acids; homocysteine, phosphoserine, phosphothreonine, phosphotyrosine, hydroxyproline, gamma-carboxyglutamate; hippuric acid, octahydroindole-2-carboxylic acid, statine, 1,2,3,4,-tetrahydroisoquinoline-3-carboxylic acid, penicillamine (3-mercapto-D-valine), ornithine, citruline, alpha-methyl-alanine, alpha-methyl-phenylalanine, para-benzoylphenyl-alanine, para-amino phenylalanine, p-fluorophenylalanine, o-fluorophenylalanine, o-chlorophenylalanine, alpha-methyl-o-fluorophenylalanine, alpha-methyl-tyrosine, phenylglycine, propargylglycine, sarcosine, and tert-butylglycine), diaminobutyric acid, 7-hydroxy-tetrahydroisoquinoline carboxylic acid, naphthylalanine, biphenylalanine, cyclohexylalanine, amino-isobutyric acid, norvaline, norleucine, tert-leucine, alpha-methyl-leucine, tetrahydroisoquinoline carboxylic acid, pipecolic acid, phenylglycine, homophenylalanine, cyclohexylglycine, dehydroleucine, 2,2-diethylglycine, 1-amino-1-cyclopentanecarboxylic acid, 1-amino-1-cyclohexanecarboxylic acid, amino-benzoic acid, amino-naphthoic acid, gamma-aminobutyric acid, difluorophenylalanine, nipecotic acid, alpha-amino butyric acid, thienyl-alanine, t-butylglycine, trifluorovaline; hexafluoroleucine; fluorinated analogs; azide-modified amino acids; alkyne-modified amino acids; cyano-modified amino acids; tetrazole-modified amino acids, and derivatives thereof (each which can be, where appropriate can each independently be D or L amino acids).

Non-limiting examples of peptide bond replacements include urea, thiourea, carbamate, sulfonyl urea, trifluoroethylamine, ortho-(aminoalkyl)-phenylacetic acid, para-(aminoalkyl)-phenylacetic acid, meta-(aminoalkyl)-phenylacetic acid, thioamide, tetrazole, boronic ester, olefinic group, and derivatives thereof.

Other non-limiting examples of modifications and/or moieties include PEGylation; glycosylation; HESylation; ELPylation; lipidation; acetylation; amidation; end-capping modifications (e.g., amidation at the C-terminus, introduction of C-terminal alcohol, aldehyde, ester, and thioester moieties); cyano groups; phosphorylation; cyclization, conjugation with targeting moieties and/or agents that increase retention in the body (e.g., agents such as cellulose, fatty acids, polyethylene glycol (PEG) or combinations thereof); incorporation of retro-inverso peptide motif (ie., a peptide with a reversal of the direction of the peptide bond on at least one position);

In certain embodiments, $N(R^4)$—W, $N(R^4)$—$W^1$, $N(R^4)$—$W^{1'}$, $W^{1''}$, and/or W'' include only naturally occurring amino acids. In other embodiments, W, $W^{1'}$, $W^{1''}$, and/or W'' include only alternative or non-naturally occurring amino acids. In still other embodiments, $N(R^4)$—W, $N(R^4)$—$W^{1'}$, $W^{1''}$, and/or W'' include one or more naturally occurring amino acids and one or more alternative or non-naturally occurring amino acids. In certain of the foregoing embodiments, $N(R^4)$—W, $N(R^4)$—$W^{1\prime}$, $W^{1\prime\prime}$, and/or $W''$ include only L amino acids; or $N(R^4)$—W, $N(R^4)$—$W^{1\prime}$, $W^{1\prime\prime}$, and/or $W''$ include both D and L amino acids; or $N(R^4)$—W, $N(R^4)$—$W^{1\prime}$, $W^{1\prime\prime}$, and/or $W''$ include only D amino acids. While not wishing to be bound by theory, it is believed that the incorporation of D amino acids can confer enhanced in vivo or intracellular stability to the compounds described herein.

In some embodiments, $N(R^4)$—W, $N(R^4)$—$W^{1\prime}$, $W^{1\prime\prime}$, and/or $W''$ include amino acid residues each of Formula XAA:

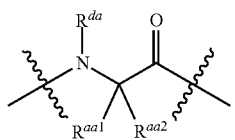

XAA wherein each of $R^{aa1}$ and $R^{aa2}$ is independently selected from:
- (a) H;
- (b) $C_{1-6}$ alkyl, which is optionally substituted with from 1-3 $R^{ba}$,
- (c) $(C_{0-3}$ alkylene)-$C_{3-10}$ cycloalkyl, which is optionally substituted with from 1-4 $R^{ba}$;
- (d) $(C_{0-3}$ alkylene)-heterocyclyl, wherein the heterocyclyl includes from 3-10 ring atoms, wherein from 1-3 ring atoms are heteroatoms, each independently selected from the group consisting of $N(R^{da})$, O, and S, and wherein one or more of the heterocyclyl ring carbon atoms are optionally substituted with from 1-4 independently selected $R^{ba}$
- (e) $(C_{0-3}$ alkylene)-$C_6$-$C_{10}$ aryl, which is optionally substituted with from 1-4 $R^{ca}$;
- (f) $(C_{0-3}$ alkylene)-heteroaryl, wherein the heteroaryl includes from 5-10 ring atoms, wherein from 1-4 ring atoms are heteroatoms, each independently selected from the group consisting of N, $N(R^{da})$, O, and S, and wherein one or more of the heteroaryl ring carbon atoms are optionally substituted with from 1-4 independently selected $R^{ca}$;

OR
- (g) $R^{aa1}$ and $R^{da}$, in the —C(=O)$CR^{aa1}(R^{aa2})N(R^{da})$— group, combine to form a ring including from 5-8 ring atoms, wherein the ring includes: (a) from 1-6 ring carbon atoms (in addition to $CR^{aa1}(R^{aa2})$), each of which is substituted with from 1-2 substituents independently selected from H and $C_{1-3}$ alkyl; and (b) from 0-3 ring heteroatoms (in addition to the nitrogen atom attached to $R^{da}$), which are each independently selected from the group consisting of $N(R^{da})$, O, and S;

each occurrence of $R^{ba}$ is selected from the group consisting of —C(=O)(OH); —C(=O)($C_{2-20}$ alkyl); —C(=O)NR'R''; —NHC(=NR')NR'R''; —C(=O)O ($C_{2-20}$ alkyl); —S(O)$_{0-2}$ ($C_{1-6}$ alkyl); oxo; F; $C_{1-10}$ alkoxy; $C_{1-10}$ haloalkoxy; azido; —N($R^{ga}$)($R^{ha}$);

each occurrence of $R^{ca}$ is independently selected from the group consisting of: —OH; —SH; —F; —Cl; —Br; —NR'R''; $C_{1-4}$ alkyl; $C_{1-4}$ haloalkyl; $C_{1-4}$ alkoxy; $C_{1-4}$ haloalkoxy; —C(=O)O($C_{1-4}$ alkyl); —C(=O)($C_{1-4}$ alkyl); —C(=O)OH; —CON(R')(R''); —S(O)$_{1-2}$ (NR'R''); —S(O)$_{0-2}$($C_{1-4}$ alkyl); cyano; —NR'C (=NR')NR'R''; $C_{6-10}$ aryl optionally substituted with 1-4 substituents independently selected from halo, $C_{1-4}$ alkyl, and $C_{1-4}$ haloalkyl; and $C_{3-6}$ cycloalkyl optionally substituted with from 1-4 independently selected $C_{1-4}$ alkyl;

each occurrence of $R^{da}$ is independently selected from the group consisting of: H, $C_{1-6}$ alkyl; $C_{3-6}$ cycloalkyl; —C(O)($C_{1-4}$ alkyl); —C(O)O($C_{1-4}$ alkyl); —CON(R')

each occurrence of $R^{da}$ is independently selected from the group consisting of: H, $C_{1-6}$ alkyl; $C_{3-6}$ cycloalkyl; —C(O)($C_{1-4}$ alkyl); —C(O)O($C_{1-4}$ alkyl); —CON(R') (R''); —S(O)$_{1-2}$(NR'R''); —S(O)$_{1-2}$($C_{1-4}$ alkyl); —OH; and $C_{1-4}$ alkoxy; or $R^{aa1}$ and $R^{da}$, in the —C(=O) $CR^{aa1}(R^{aa2}) N(R^{da})$— group, combine to form a ring including from 5-8 ring atoms as defined above;

each occurrence of $R^{ga}$ and $R^{ha}$ is independently selected from the group consisting of H; $C_{1-4}$ alkyl; —C(=O) O($C_{2-20}$ alkyl); and —S(O)$_{1-2}$($C_{1-6}$ alkyl); and each occurrence of R' and R'' is independently selected from the group consisting of: H and $C_{1-4}$ alkyl; or R' and R'' together with the nitrogen atom to which each is attached forms a ring including from 3-8 ring atoms, wherein the ring includes: (a) from 1-7 ring carbon atoms, each of which is substituted with from 1-2 substituents independently selected from H and $C_{1-3}$ alkyl; and (b) from 0-3 ring heteroatoms (in addition to the nitrogen atom attached to R' and R''), which are each independently selected from the group consisting of N(H), O, and S;

or a C-terminal amino acid or an amino acid ester or an amino acid amide thereof.

In some embodiments, $N(R^4)$—W includes 25-45 (e.g., 30-40 (e.g., 35-37)) amino acid residues of Formula XAA, wherein $R^{aa2}$ is H; or a C-terminal amino acid or an amino acid ester or an amino acid amide thereof.

In certain of these embodiments, $R^{aa1}$ is selected from the group consisting of:
H;
$C_1$-$C_6$ alkyl optionally substituted with 1-2 substituents selected from —$NH_2$, —OH, —SH, —SMe, —NH (C=NH)$NH_2$, $CO_2H$, and $CO_2NH_2$;
($C_1$-$C_6$ alkylene)-phenyl, optionally substituted with 1-2—OH;
($C_1$-$C_6$ alkylene)-indolyl; and
($C_1$-$C_6$ alkylene)-imidazolyl; or
$R^{aa1}$ and $R^{da}$, in the —CH($R^{aa1}$)N($R^{da}$)— group, combine to form a pyrrolidine ring.

As non-limiting examples of the foregoing, $N(R^4)$—W can include from 25-45 naturally occurring amino acids found, e.g., in polypeptides and/or proteins produced by living organisms, such as Ala (A), Val (V), Leu (L), Ile (I), Pro (P), Phe (F), Trp (W), Met (M), Gly (G), Ser (S), Thr (T), Cys (C), Tyr (Y), Asn (N), Gln (Q), Asp (D), Glu (E), Lys (K), Arg (R), and His (H); or amino acid ester or amino acid amide thereof.

In certain embodiments, $N(R^4)$—W includes from 1-2 (e.g., 1) amino acid residue of Formula XAA, wherein $R^{aa2}$ is H; $R^{aa1}$ is: $C_{1-6}$ alkyl, which is substituted with from 1-2 (e.g., 1) $R^{ba}$; and each occurrence of $R^{ba}$ is independently selected from:
—N($R^{ga}$)($R^{ha}$);

or a C-terminal amino acid or an amino acid ester or an amino acid amide thereof.

In certain embodiments, $N(R^4)$—W includes an amino acid residue AA which is a lysyl residue that is substituted with from 1-2 modifying groups (e.g., 1-2 groups selected from an acyl group and a PEG group; and combinations thereof).

In certain of the foregoing embodiments, AA has the formula:

wherein $R^K$ is a group of Formula (KA):
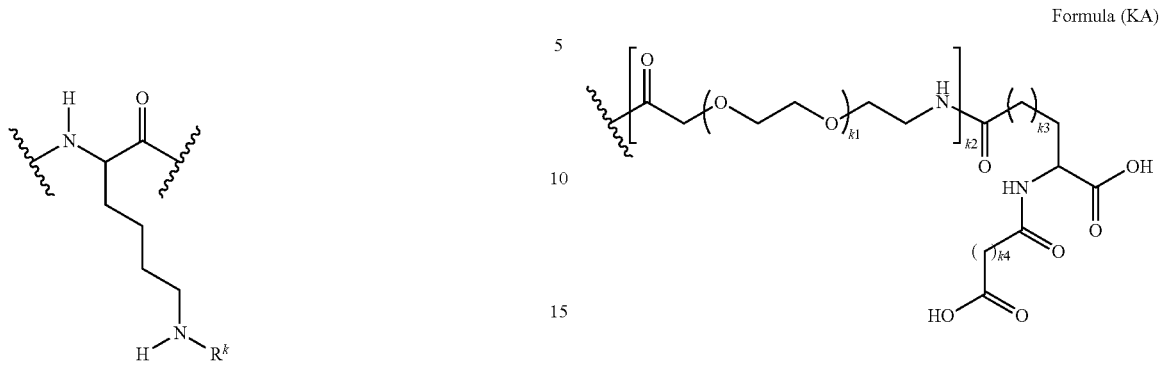
Formula (KA)
wherein:
k1 is 1, 2, 3, or 4;
k2 is 1, 2, 3, or 4;
k3 is 0, 1, 2, 3, or 4; and
k4 is an integer from 5 to 25.
As a non-limiting example, (AA) can be an internal amino acid having the formula:
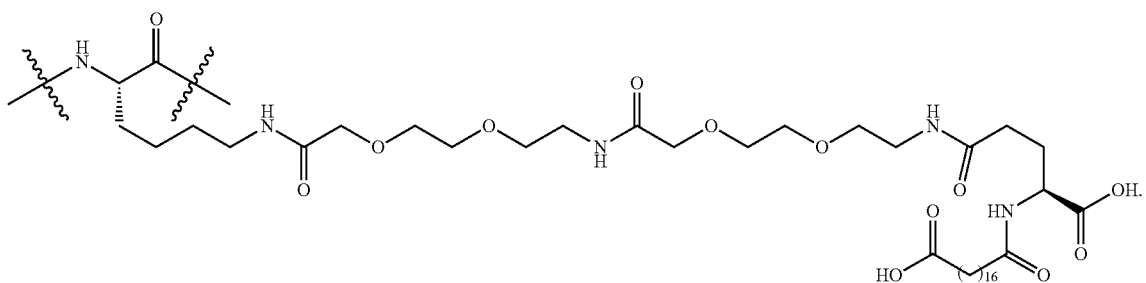
As another non-limiting example, (AA) can be an internal amino acid having the formula:
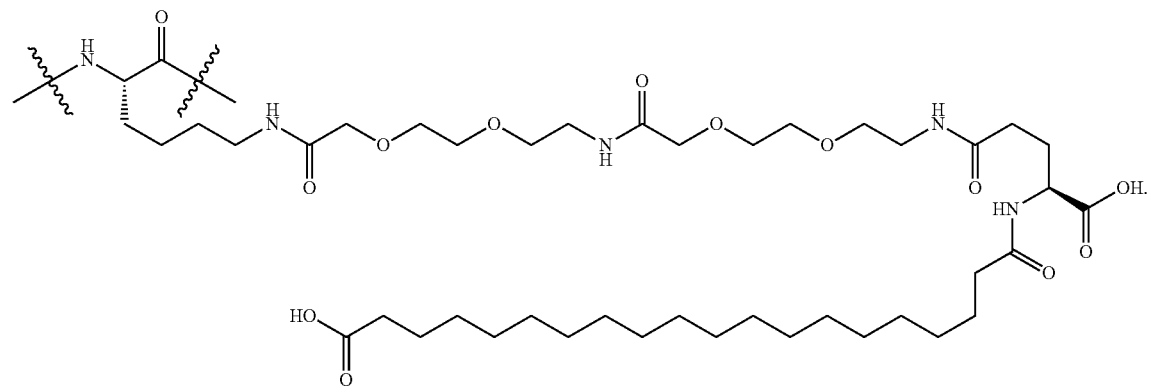 [SMILES: *N[C@@H](CCCCNC(=O)COCCOCCNC(=O)COCCOCCNC(=O)CC[C@H](NC(=O)CCCCCCCCCCCCCCCCCCC(=O)O)C(=O)O)C(*)=O]

As still another non-limiting example, (AA) can be an internal amino acid having the formula:

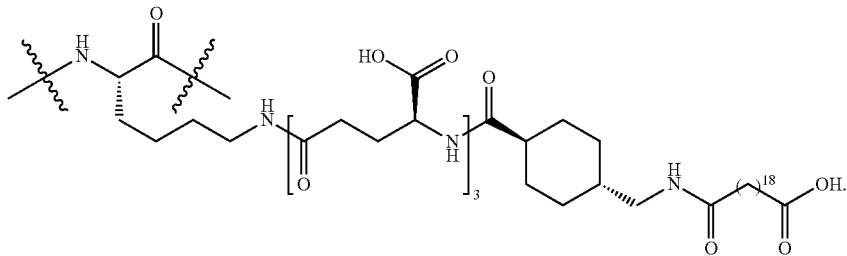

In certain embodiments, $N(R^4)$—W includes from 1-2 (e.g., 1) amino acid residue of Formula XAA, wherein $R^{aa2}$ is $C_{1-3}$ alkyl (e.g., methyl); and $R^{aa1}$ is other than H;

or a C-terminal amino acid or an amino acid ester or an amino acid amide thereof.

Non-limiting examples include:

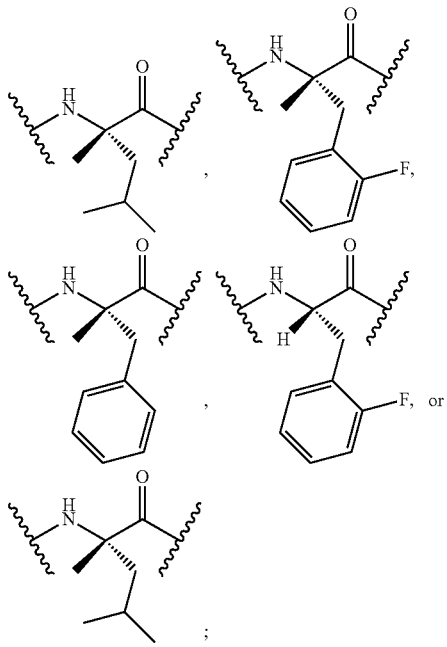

or a C-terminal amino acid or an amino acid ester or an amino acid amide thereof.

Non-Limiting Examples of W

In some embodiments, the amino acid sequence present in $N(R^4)$—W is, or includes, the sequence that is present in native GLP-1-OH or GLP-1-NH$_2$. In other embodiments, the amino acid sequence present in $N(R^4)$—W is, or includes, the sequence that is present in native GIP. In still other embodiments, the amino acid sequence present in $N(R^4)$—W is, or includes, a hybrid sequence having one or more fragments (e.g., functional fragments) present in native GLP-1-OH or GLP-1-NH$_2$ and one or more fragments (e.g., functional fragments) present in native GIP. This disclosure further contemplates variations of the foregoing embodiments, e.g., $N(R^4)$—W is, or includes, a conservatively substituted variation of the foregoing, meaning that one or more amino acid residues of an original peptide are replaced by different residues, and that the conservatively substituted peptide retains a desired biological activity. Examples of conservative substitutions include substitution of amino acids that tend not alter the secondary and/or tertiary structure of the compounds described herein, substitutions that do not change the overall or local hydrophobic character, substitutions that do not change the overall or local charge, substitutions by residues of equivalent side chain size, or substitutions by side chains with similar reactive groups.

A given amino acid can be replaced by a residue having similar physiochemical characteristics, e.g., substituting one aliphatic residue for another (such as Ile, Val, Leu, or Ala for one another), or substitution of one polar residue for another (such as between Lys and Arg; Glu and Asp; or Gln and Asn). Other such conservative substitutions, e.g., substitutions of entire regions having similar hydrophobicity characteristics or substitutions of residues with similar side chain volume are also within the scope of this disclosure.

Amino acids can be grouped according to similarities in the properties of their side chains (in A. L. Lehninger, in Biochemistry, second ed., pp. 73-75, Worth Publishers, New York (1975)): (1) non-polar: Ala (A), Val (V), Leu (L), Ile (I), Pro (P), Phe (F), Trp (W), Met (M); (2) uncharged polar: Gly (G), Ser (S), Thr (T), Cys (C), Tyr (Y), Asn (N), Gln (Q); (3) acidic: Asp (D), Glu (E); (4) basic: Lys (K), Arg (R), His (H). Alternatively, naturally occurring residues can be divided into groups based on common side-chain properties: (1) hydrophobic: Norleucine, Met, Ala, Val, Leu, Ile, Phe, Trp; (2) neutral hydrophilic: Cys, Ser, Thr, Asn, Gln, Ala, Tyr, His, Pro, Gly; (3) acidic: Asp, Glu; (4) basic: His, Lys, Arg; (5) residues that influence chain orientation: Gly, Pro; (6) aromatic: Trp, Tyr, Phe, Pro, His, or hydroxyproline. Non-conservative substitutions will entail exchanging a member of one of these classes for another class.

In certain embodiments, conservative substitutions for use in the variants described herein are as follows: Ala into Gly or into Ser; Arg into Lys; Asn into Gln or into His; Asp into Glu or into Asn; Cys into Ser; Gln into Asn; Glu into Asp; Gly into Ala or into Pro; His into Asn or into Gln; Ile into Leu or into Val; Leu into Ile or into Val; Lys into Arg, into Gln or into Glu; Met into Leu, into Tyr or into Ile; Phe into Met, into Leu or into Tyr; Ser into Thr; Thr into Ser; Trp into Tyr or into Phe; Tyr into Phe or into Trp; and/or Phe into Val, into Tyr, into Ile or into Leu. In general, conservative substitutions encompass residue exchanges with those of similar physicochemical properties (i.e. substitution of a hydrophobic residue for another hydrophobic amino acid).

In still other embodiments, the amino acid sequence present in $N(R^4)$—W is, or includes, or is based upon a sequence that is present in a peptide having at least 0.01% of the GLP-1 receptor activation activity of the native GLP-1, such as at least 0.1%, 0.2%, 0.5%, 0.8%, 1%, 3%, 5%, 10%, 20%, 30%, 40%, 50%, 60%, 70%, 80%, 90%, 95%, 99% of the GLP-1 receptor activation activity of the native GLP-1-OH or GLP-1-NH$_2$ and/or at least 0.01% of the GIP receptor activation activity of GIP, such as at least 0.1%, 0.2%, 0.5%, 0.8%, 1%, 3%, 5%, 10%, 20%, 30%, 40%, 50%, 60%, 70%, 80%, 90%, 95%, 99% of the GIP receptor activation activity of the native GIP.

In still other embodiments, the amino acid sequence present in N(R$^4$)—W is, or includes, or is based upon a sequence that is present in a peptide having at least 0.1%, 0.2%, 0.5%, 0.8%, 1%, 3%, 5%, 10%, 20%, 30%, 40%, 50%, 60%, 70%, 80%, 90%, 95%, 99% sequence identity to the native GLP-1-OH or GLP-1-NH$_2$ and/or at least 0.1%, 0.2%, 0.5%, 0.8%, 1%, 3%, 5%, 10%, 20%, 30%, 40%, 50%, 60%, 70%, 80%, 90%, 95%, 99% sequence identity to the native GIP.

As used herein the term "native GLP-1" refers to a peptide comprising the sequence of human GLP-1 (7-36, or 7-37), and term "native GIP" refers to a peptide comprising the sequence of human GIP (1-42). As used herein, a general reference to "GLP-1" or "GIP" in the absence of any further designation is intended to mean native GLP-1 or native GIP, respectively.

In some embodiments, N(R$^4$)—W has formula WA: -GTF-W"—R$^5$ (SEQ ID NO: 1), wherein W" is a sequence of 30-40 (e.g., 31-36, 33, or 32) amino acids and comprises a modified amino acid (AA) as defined anywhere herein; optionally wherein (AA) is an internal amino acid; and R$^5$ is a C-terminal amino acid, amino ester, or amino acid amide that is optionally substituted with from 1-2 modifying groups.

In certain of these embodiments, AA formula

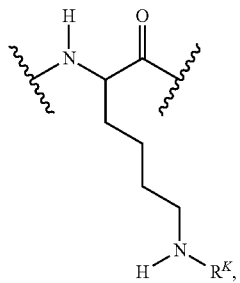

wherein R$^K$ can be as defined anywhere herein.

In some embodiments, N(R$^4$)—W has the formula WB: —N(R$^4$)—W$^{1'}$-(AA)-W$^{1'''}$—R$^5$ (SEQ ID NO: 2), wherein: N(R$^4$)—W$^{1'}$ is a sequence of 10-20 amino acids (optionally 15-20 amino acids; optionally 16 amino acids); W$^{1'''}$ is a sequence of 15-25 amino acids (optionally 17-21 amino acids; optionally 19 amino acids; or optionally 18 amino acids); and AA is a modified amino acid.

In certain of these embodiments, N(R$^4$)—W has the Formula WC:

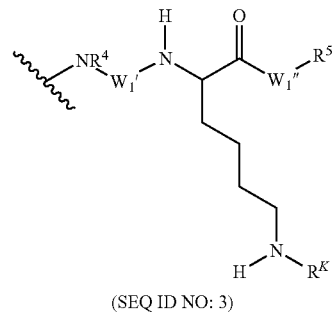

(SEQ ID NO: 3)

wherein:
N(R$^4$)—W$^{1'}$ is a sequence of 10-20 amino acids (optionally 15-20 amino acids; optionally 16 amino acids);
W$^{1'''}$ is a sequence of 15-25 amino acids (optionally 17-21 amino acids; optionally 19 amino acids; or optionally 18 amino acids); and
R$^K$ is a modifying group selected from an acyl group and a PEG group and combinations thereof.

In certain embodiments of Formula (WC), R$^K$ is a group of Formula (KA):

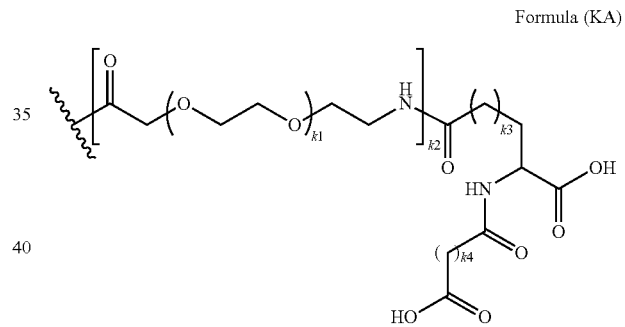

Formula (KA)

wherein:
k1 is 1, 2, 3, or 4;
k2 is 1, 2, 3, or 4;
k3 is 0, 1, 2, 3, or 4; and
k4 is an integer from 5 to 25.
For example, R$^K$ can be:

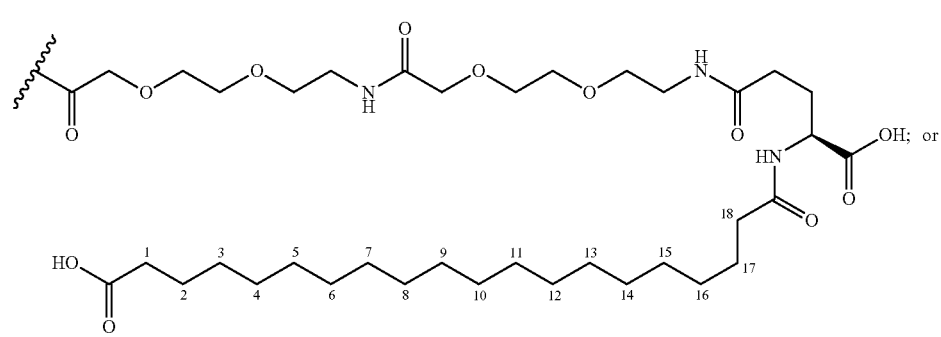

(K18)

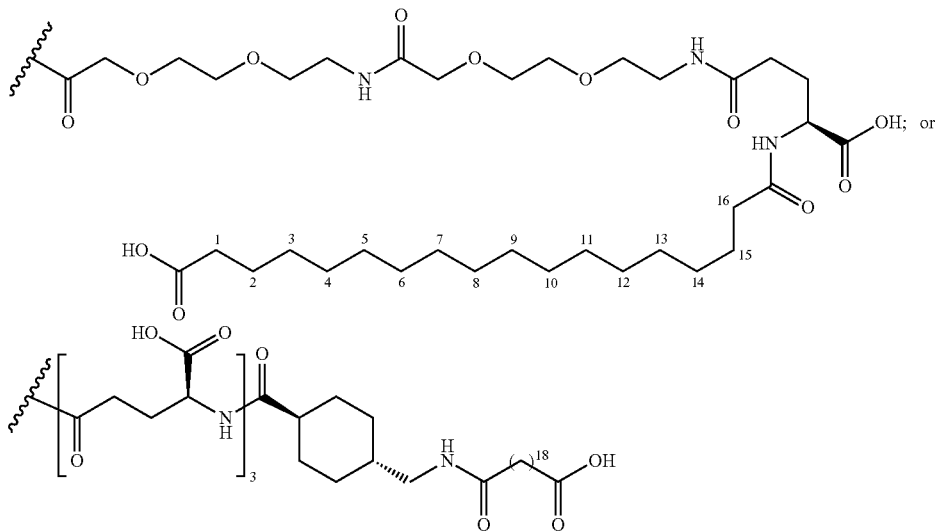

In some embodiments, N(R⁴)—W has Formula WD:

```
                                                        (SEQ ID NO: 4)
GT(Xaa3)(Xaa4)SD(Xaa7)SI(Xaa10)LD(Xaa13)(Xaa14)A (Xaa16)(Xaa17)(Xaa18)F(Xaa20)(Xaa21)(Xaa22)L (Xaa24)(Xaa25)GGPSSGAPPPS(Xaa37)-R⁶,
``` wherein:
Xaa3 is F, F*, F†, or F+† (e.g., F);
Xaa4 is T, A or V (e.g., T);
Xaa7 is Y, or K* (e.g., Y);
Xaa10 is Y, L*, or Aib (e.g., Aib);
Xaa13 is K, Orn, or R (e.g., K);
Xaa14 is Q, I, or K*(e.g., Q);
Xaa16 is A, or Q (e.g., A);
Xaa17 is Aib, or K* (e.g., K*);
Xaa18 is A, or E (e.g., A);
Xaa20 is V or I (e.g., V);
Xaa21 is N, Q, K*, or dE (e.g., Q);
Xaa22 is W or Y (e.g., W);
Xaa24 is I or L (e.g., I);
Xaa25 is A or E (e.g., A);
Xaa37 is K* or absent (e.g., absent);
R⁶ is —NH₂ or —OH.

In certain embodiments of Formula WD, N(R⁴)—W has Formula WD-1:

```
                                                        (SEQ ID NO: 5)
GT(Xaa3)(Xaa4)SD(K*)SI(Xaa10)LD(Xaa13)(Xaa14)A (Xaa16)(Xaa17)(Xaa18)F(Xaa20)(Xaa21)(Xaa22)L (Xaa24)(Xaa25)GGPSSGAPPPS(Xaa37)-R⁶.
```

In certain embodiments of Formula WD, N(R⁴)—W has Formula WD-2:

```
                                                        (SEQ ID NO: 6)
GT(Xaa3)(Xaa4)SD(Xaa7)SI(Xaa10)LD(Xaa13)(K*)A (Xaa16)(Xaa17)(Xaa18)F(Xaa20)(Xaa21)(Xaa22)L (Xaa24)(Xaa25)GGPSSGAPPPS(Xaa37)-R⁶.
```

In certain embodiments of Formula WD, N(R⁴)—W has Formula WD-3:

```
                                                        (SEQ ID NO: 7)
GT(Xaa3)(Xaa4)SD(Xaa7)SI(Xaa10)LD(Xaa13)(Xaa14)A (Xaa16)(K*)(Xaa18)F(Xaa20)(Xaa21)(Xaa22)L(Xaa24)

(Xaa25)GGPSSGAPPPS(Xaa37)-R⁶.
```

In certain embodiments of Formula WD, N(R⁴)—W has Formula WD-4:

```
                                                        (SEQ ID NO: 8)
GT(Xaa3)(Xaa4)SD(Xaa7)SI(Xaa10)LD(Xaa13)(Xaa14)A (Xaa16)(Xaa17)(Xaa18)F(Xaa20)(K*)(Xaa22)L(Xaa24)

(Xaa25)GGPSSGAPPPS(Xaa37)-R⁶.
```

In certain embodiments of Formula WD, N(R⁴)—W has formula WD-5:

```
                                                        (SEQ ID NO: 9)
GT(Xaa3)(Xaa4)SD(Xaa7)SI(Xaa10)LD(Xaa13)(Xaa14)A (Xaa16)(Xaa17)(Xaa18)F(Xaa20)(Xaa21)(Xaa22)L (Xaa24)(Xaa25)GGPSSGAPPPS(K*)-R⁶.
```

In certain embodiments of Formula WD (e.g., when the group of Formula (WD) has Formula (WD-1), (WD-2), (WD-3), (WD-4), or (WD-5)), Xaa3 is F. In certain embodiments, Xaa3 is F*. In certain embodiments, Xaa3 is F†. In certain embodiments, Xaa3 is F+†.

In certain embodiments of Formula WD (e.g., when the group of Formula (WD) has Formula (WD-1), (WD-2), (WD-3), (WD-4), or (WD-5)), Xaa4 is T. I In certain embodiments, Xaa4 is A. In certain embodiments, Xaa4 is V.

In certain embodiments of Formula WD (e.g., when the group of Formula (WD) has Formula (WD-2), (WD-3), (WD-4), or (WD-5)), Xaa7 is Y. In certain embodiments, Xaa7 is K*.

In certain embodiments of Formula WD (e.g., when the group of Formula (WD) has Formula (WD-1), (WD-2), (WD-3), (WD-4), or (WD-5)), Xaa10 is Y. In certain embodiments, Xaa10 is L*.

In certain embodiments of Formula WD (e.g., when the group of Formula (WD) has Formula (WD-1), (WD-2), (WD-3), (WD-4), or (WD-5)), Xaa13 is K. In certain embodiments, Xaa13 is Orn. In certain embodiments, Xaa13 is R.

In certain embodiments of Formula WD (e.g., when the group of Formula (WD) has Formula (WD-1), (WD-3), (WD-4), or (WD-5)), Xaa14 is Q. In certain embodiments, Xaa14 is I. In certain embodiments, Xaa14 is K*.

In certain embodiments of Formula WD (e.g., when the group of Formula (WD) has Formula (WD-1), (WD-2), (WD-3), (WD-4), or (WD-5)), Xaa16 is A. In certain embodiments, Xaa16 is Q.

In certain embodiments of Formula WD (e.g., when the group of Formula (WD) has Formula (WD-1), (WD-2), (WD-4), or (WD-5)), Xaa17 is K*. In certain embodiments, Xaa17 is Aib.

In certain embodiments of Formula WD (e.g., when the group of Formula (WD) has Formula (WD-1), (WD-2), (WD-3), (WD-4), or (WD-5)), Xaa18 is A. In certain embodiments, Xaa18 is E.

In certain embodiments of Formula WD (e.g., when the group of Formula (WD) has Formula (WD-1), (WD-2), (WD-3), (WD-4), or (WD-5)), Xaa20 is V. In certain embodiments, Xaa20 is V.

In certain embodiments of Formula WD (e.g., when the group of Formula (WD) has Formula (WD-1), (WD-2), (WD-3), or (WD-5)), Xaa21 is N. In certain embodiments, Xaa21 is Q. In certain, Xaa21 is K*. In certain of the foregoing embodiments, Xaa21 is dE.

In certain embodiments of Formula WD (e.g., when the group of Formula (WD) has Formula (WD-1), (WD-2), (WD-3), (WD-4), or (WD-5)), Xaa22 is W. In certain embodiments, Xaa22 is L.

In certain embodiments of Formula WD (e.g., when the group of Formula (WD) has Formula (WD-1), (WD-2), (WD-3), (WD-4), or (WD-5)), Xaa24 is I. In certain embodiments, Xaa24 is L.

In certain embodiments of Formula WD (e.g., when the group of Formula (WD) has Formula (WD-1), (WD-2), (WD-3), (WD-4), or (WD-5)), Xaa25 is A. In certain embodiments, Xaa25 is E.

In certain embodiments of Formula WD (e.g., when the group of Formula (WD) has Formula (WD-1), (WD-2), (WD-3), or (WD-4), Xaa37 is absent. In certain embodiments, Xaa37 is K*.

In certain of the foregoing embodiments, $R^6$ is —$NH_2$. In certain of the foregoing embodiments, $R^6$ is —OH.

In certain embodiments of Formula WD, Xaa4 is T; Xaa7 is Y; and Xaa13 is K. In certain of these embodiments, Xaa 20 is V; and/or Xaa22 is W; and/or Xaa25 is A; and/or Xaa37 is absent. In certain of the foregoing embodiments, $R^6$ is $NH_2$.

In certain embodiments of Formula WD, Xaa4 is T; Xaa7 is Y; Xaa13 is K; Xaa 20 is V.

In certain embodiments of Formula WD, Xaa4 is T; Xaa7 is Y; Xaa13 is K; Xaa 20 is V; and Xaa22 is W.

In certain embodiments of Formula WD, Xaa4 is T; Xaa7 is Y; Xaa13 is K; Xaa 20 is V; Xaa22 is W; and Xaa25 is A.

In certain embodiments of Formula WD, Xaa4 is T; Xaa7 is Y; Xaa13 is K; Xaa 20 is V; Xaa22 is W; Xaa25 is A; and Xaa37 is absent.

In certain of the foregoing embodiments, Xaa4 is T; Xaa7 is Y; Xaa13 is K; Xaa 20 is V; Xaa22 is W; Xaa25 is A; Xaa37 is absent; $R^6$ is $NH_2$. In certain of these embodiments, Xaa14 is I. In certain of these embodiments, Xaa14 is K*.

In certain of the foregoing embodiments, Xaa14 is I.

In certain of the foregoing embodiments, Xaa21 is Q.

In certain of the foregoing embodiments, Xaa24 is I.

In certain of the foregoing embodiments, Xaa3 is F, Xaa16 is Q, and Xaa18 is A.

In certain of the foregoing embodiments, Xaa17 is K*.

In certain of the foregoing embodiments, Xaa14 and Xaa24 are I; and, Xaa21 is Q.

In certain of the foregoing embodiments, Xaa14 and Xaa24 are I; Xaa21 is Q; Xaa3 is F, Xaa16 is Q, and Xaa18 is A.

In certain of the foregoing embodiments, Xaa14 and Xaa24 are I; Xaa21 is Q; Xaa3 is F, Xaa16 is Q, Xaa18 is A; and Xaa17 is K*.

In certain embodiments, $N(R^4)$—W has formula WE:
-GTFTSDYSI(Aib)LDKIAQK*AFVQWLIAGGPSSGAPPPS-$NH_2$ (SEQ ID NO: 10).

In some embodiments, $N(R^4)$—W has formula WF:
GT(Xaa3)TSDYSI(Aib)LDKIAQK*AFVQWLIAG-$NH_2$ (SEQ ID NO: 11),
wherein Xaa3 is F or F*.

As used herein "Aib" refers to

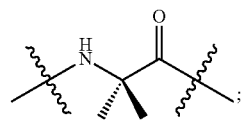

"F*" refers to

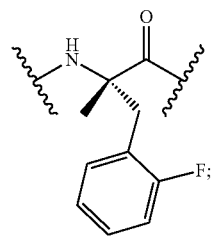 [SMILES: *N[C@@](C)(Cc1ccccc1F)C(*)=O]

"F†" refers to

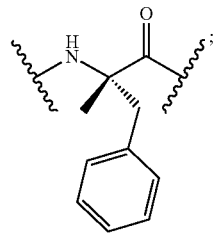 [SMILES: *N[C@@](C)(Cc1ccccc1)C(*)=O]

"F†+" refers to

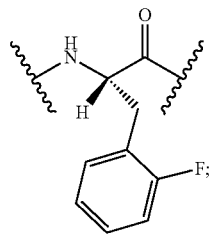 [SMILES: *N[C@@H](Cc1ccccc1F)C(*)=O]

"L*" refers to

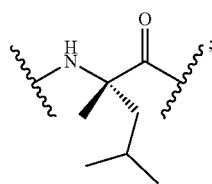 [SMILES: *N[C@@](C)(CC(C)C)C(*)=O]

"Orn" refers to

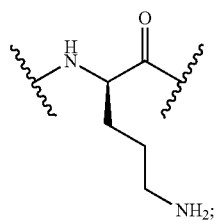 [SMILES: *N[C@H](CCCN)C(*)=O]

"dE" refers to

"dD" refers to

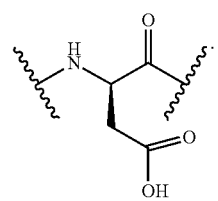 [SMILES: *N[C@H](CC(=O)O)C(*)=O]

or a C-terminal amino acid or an amino acid ester or an amino acid amide thereof.

As used herein K* is a lysine residue substituted with a modifying group, or a C-terminal amino acid or an amino acid ester or amino acid amide thereof.

Non-limiting examples of K* can include an amino acid residue selected from:

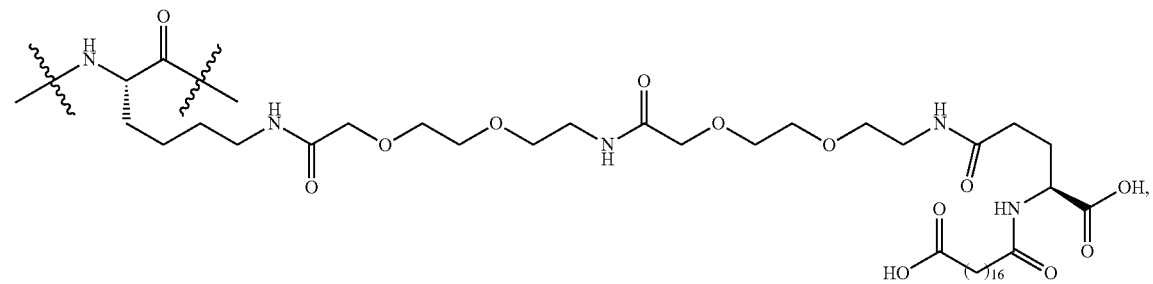

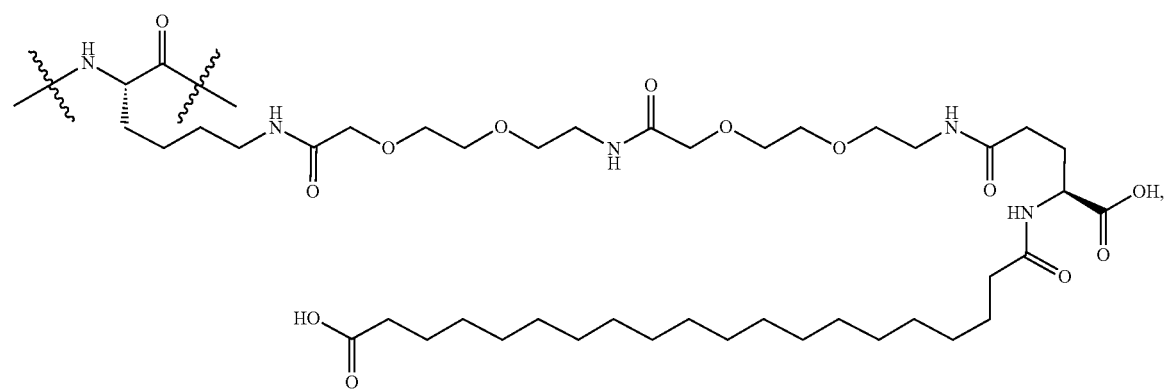

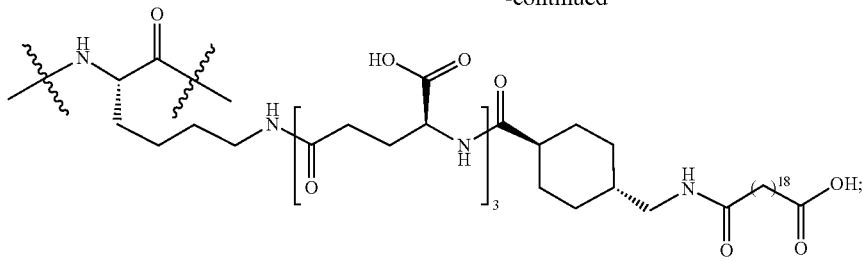

or a C-terminal amino acid or an amino acid ester or an amino acid amide thereof.

In some embodiments, N(R$^4$)—W is represented by formula (WA), (WB), (WC), (WD), (WD-1), (WD-2), (WD-3), (WD-4), (WD-5), (WE), (WF), or any of SEQ ID Nos. 1-37.

For example, N(R$^4$)—W can have any of the sequences delineated in Table 1.

TABLE 1

| SEQ ID NO: | CT SEQ. ID | Sequence |
|---|---|---|
| 10 | A | GTFTSDYSI(Aib)LDKIAQK*AFVQWLIAGGPSSGAPPPS—NH$_2$ |
| 12 | B | GTFTSDYSI(Aib)LDKIAQK*AFVQWLIAGGPSSGAPPPS—NH$_2$ |
| 13 | C | GTF*TSDYSI(Aib)LDRIAQK*AFVQWLIAGGPSSGAPPPS—NH$_2$ |
| 14 | D | GTF$^J$TSDYSI(Aib)LDRIAQK*AFVQWLIAGGPSSGAPPPS—NH$_2$ |
| 15 | E | GTF$^+$TSDYSI(Aib)LDRIAQK*AFVQWLIAGGPSSGAPPPS—NH$_2$ |
| 16 | I | GTFTSDYSIYLDKIAQK*AFVQWLIAGGPSSGAPPPS—NH$_2$ |
| 17 | J | GTFTSDYSI(Aib)LDKIAQK*AFVQWLLAGGPSSGAPPPS—NH$_2$ |
| 18 | K | GTFTSDYSI(Aib)LDKIAQK*EFVQWLIAGGPSSGAPPS—NH$_2$ |
| 19 | L | GTFTSDYSI(Aib)LDKQAQK*AFVQWLIAGGPSSGAPPPS—NH$_2$ |
| 20 | M | GTFTSDYSIYLDKQAA(Aib)EFVNWLLAGGPSSGAPPPSK*—NH$_2$ |
| 21 | N | GTFTSDYSI(AiB)LDKIAAK*AFVQWLIAGGPSSGAPPPS—NH$_2$ |
| 22 | O | GTFTSDYSIYLDKQAAK*EFVNWLLAGGPSSGAPPPS—NH$_2$ |
| 23 | P | GTFTSDYSI(Aib)LDKIAQK*AFVNWLIAGGPSSGAPPPSNH$_2$ |
| 24 | Q | GTFVSDYSI(Aib)LDKIAQK*AFVQWLIAGGPSSGAPPPS—NH$_2$ |
| 25 | R | GTFASDYSI(Aib)LDKIAQK*AFVQWLIAGGPSSGAPPPS—NH$_2$ |
| 26 | S | GTFTSDK*SIYLDKQAA(Aib)EFVNWLLAGGPSSGAPPPS—NH$_2$ |
| 27 | T | GTF*TSDYSIYLDKQAA(Aib)EFVNWLLAGGPSSGAPPPSK*—NH$_2$ |
| 28 | V | GTF*TSDK*SIYLDKQAA(Aib)EFVNWLLAGGPSSGAPPPS—NH$_2$ |

TABLE 1-continued

| SEQ ID NO: | CT SEQ. ID | Sequence |
|---|---|---|
| 29 | W | GTFTSDYSI(Aib)LDKIAQK*AFVQWLIAGGPSSGAPPPS—OH |
| 30 | X | GTFTSDYSI(Aib)LDKIAQK*AFVQWLIAG—NH$_2$ |
| 31 | Y | GTF*TSDYSI(Aib)LDKIAQK*AFVQWLIAG—NH$_2$ |
| 32 | Z | GTFTSDYSIL*LD(Orn)K*AQ(Aib)EFI(dE)YLIEGGPSSGAPPPS—NH$_2$ |
| 33 | AA | GTF*TSDYSIL*LD(Orn)K*AQ(Aib)EFI(dE)YLIEGGPSSGAPPPS—NH$_2$ |
| 34 | AB | GTFTSDYSI(Aib)LDKIAQK*AFVQWLIAGGPSSGAPPPS—NH$_2$ |

K* = [structure shown]

| 35 | AC | GTFTSDYSI(Aib)LDKIAQK*AFVQWLIAGGPSSGAPPPS—NH$_2$ |

K* = [structure shown]

| 36 | AG | GTFTSDYSIYLDKK*AA(Aib)EFVNWLLAGGPSSGAPPPS—NH$_2$ |
| 37 | AH | GTFTSDYSILDKQAA(Aib)EFVK*WLLAGGPSSGAPPPS—NH$_2$ |

Unless otherwise specified, modified amino acid residues in TABLE 1 have the definitions below:

F* = [structure shown: 2-fluorophenylalanine with α-methyl]

Orn = [structure shown: ornithine]

L* = [structure shown: α-methyl leucine]

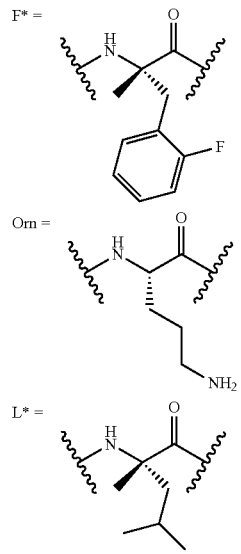

TABLE 1-continued
| SEQ ID NO: | CT SEQ. ID | Sequence |
|---|---|---|
dE = 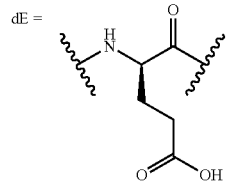 [SMILES: *N[C@H](CCC(=O)O)C(*)=O]
Aib = 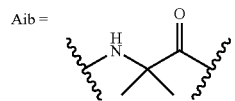 [SMILES: *NC(C)(C)C(*)=O]
F† = 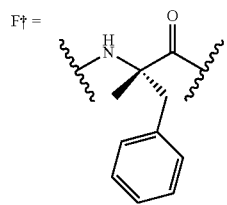 [SMILES: *N[C@@](C)(Cc1ccccc1)C(*)=O]
F‡ = 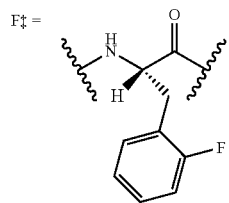 [SMILES: *N[C@@H](Cc1ccccc1F)C(*)=O]
dD = 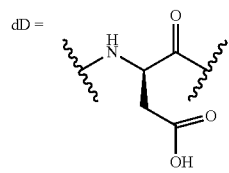 [SMILES: *N[C@H](CC(=O)O)C(*)=O]
K* = 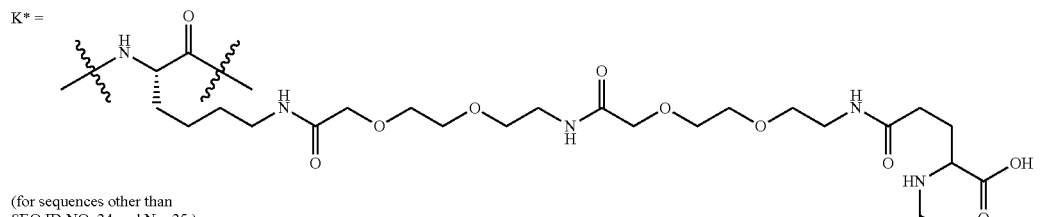
(for sequences other than SEQ ID NO. 34 and No. 35.)
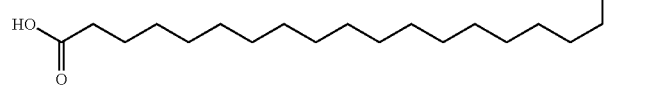
K* = 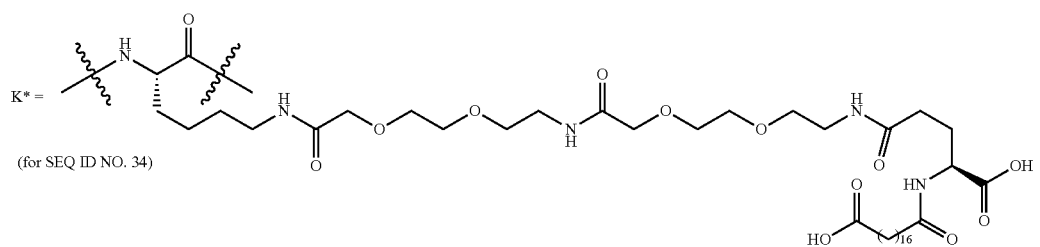
(for SEQ ID NO. 34)

TABLE 1-continued

| SEQ ID NO: | CT SEQ. ID | Sequence |
|---|---|---|
| | | K* = 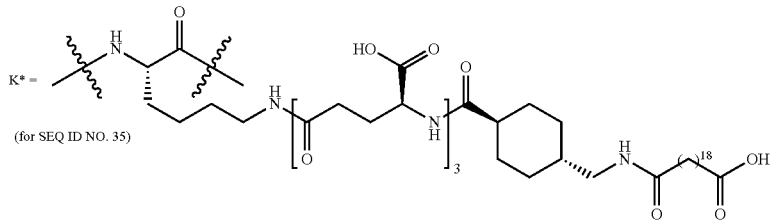

(for SEQ ID NO. 35) |

Non-Limiting Combinations

[1]

In certain embodiments of the compound of Formula (I), R* is a group of Formula (A), wherein:

$L^1$ is unsubstituted $C_{2-4}$ alkylene (e.g., linear $C_{2-4}$ alkylene, optionally —$CH_2CH_2$— or —$CH_2CH_2CH_2$);

$X^1$ is C(=O)N(R')* (e.g., C(=O)N(H)*) or C(=S)N(R')* (e.g., C(=S)N(H)*);

$R^Z$ is selected from the group consisting of:
  phenyl optionally substituted with from 1-3 $R^b$; and
  heteroaryl including 6 ring atoms, wherein from 1-3 ring atoms are ring nitrogen atoms, and wherein the heteroaryl is optionally substituted with from 1-3 independently selected $R^b$ at one or more ring carbon atoms;

$R^{X1}$ and $R^{X2}$ are each independently selected unsubstituted $C_{1-3}$ alkyl; or $R^{X1}$ and $R^{X2}$ taken together with the carbon atom to which each is attached form a $C_{3-6}$ cycloalkyl ring which is optionally substituted with from 1-3 independently selected $C_{1-3}$ alkyl;

$N(R^4)$—W has the formula WC:

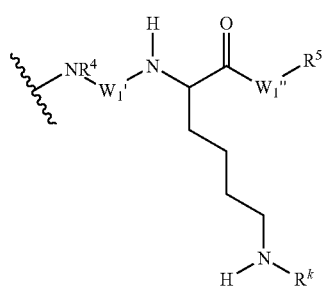

Formula WC (SEQ ID NO: 3)

wherein:

$N(R^4)$—$W^{1'}$ is a sequence of 10-20 amino acids (optionally 15-20 amino acids; optionally 16 amino acids);

$W^{1'''}$ is a sequence of 15-25 amino acids (optionally 17-21 amino acids; optionally 19 amino acids; or optionally 18 amino acids); and $R^K$ is a group of Formula (KA):

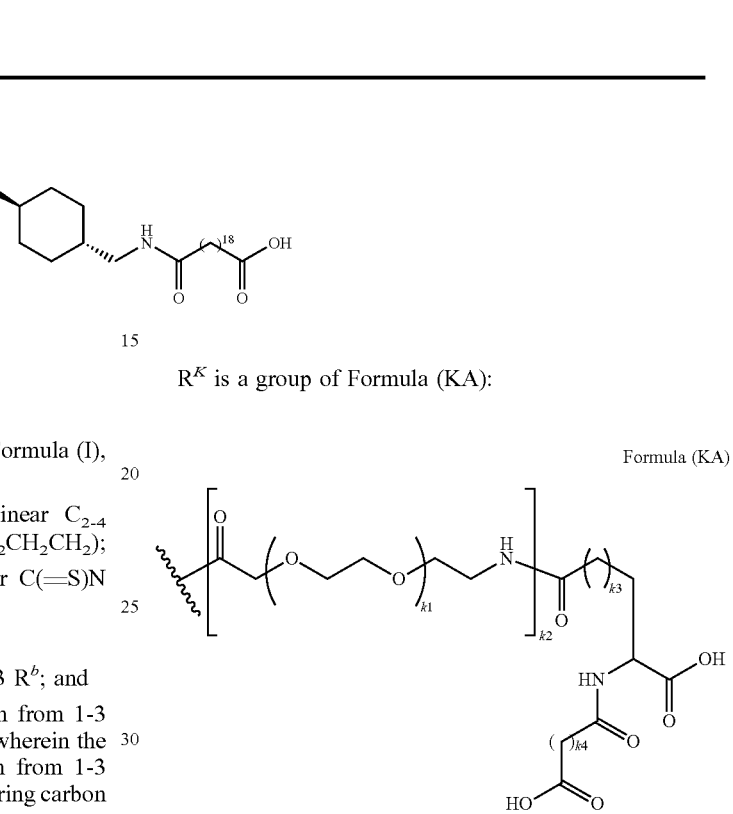

Formula (KA)

wherein:
k1 is 1, 2, 3, or 4;
k2 is 1, 2, 3, or 4;
k3 is 0, 1, 2, 3, or 4; and
k4 is an integer from 5 to 25.

In certain embodiments of non-limiting combination [1], —$N(R^4)$—W has Formula WD:

In certain embodiments of non-limiting combination [1], —$N(R^4)$—W has Formula WD-1:

In certain embodiments of non-limiting combination [1], —$N(R^4)$—W has Formula WD-2:

In certain embodiments of non-limiting combination [1], —$N(R^4)$—W has Formula WD-3:

In certain embodiments of non-limiting combination [1], —$N(R^4)$—W has Formula WD-4:

In certain embodiments of non-limiting combination [1], —$N(R^4)$—W has Formula WD-5:

In certain embodiments of non-limiting combination [1], $X^2$ is a bond.

In certain embodiments of non-limiting combination [1], Q is O.

In certain embodiments of non-limiting combination [1], $R^1$ is H.

In certain embodiments of non-limiting combination [1], $R^4$ is H.

In certain embodiments of non-limiting combination [1], a2 is 1; and a1 is 1.

In certain embodiments of non-limiting combination [1], $R^{2'}$ is —$CH_2CH_2R^3$.

In certain embodiments of non-limiting combination [1], $R^3$ is —C(O)OH.

In certain embodiments of non-limiting combination [1], Q is O; $R^1$ is H; $R^4$ is H; $R^{2'}$ is —$CH_2CH_2R^3$; and $R^3$ is —C(O)OH.

In certain embodiments of non-limiting combination [1], $R^Z$ is phenyl or pyridyl each optionally substituted with from 1-3 $R^b$. In certain of these embodiments, $R^Z$ is phenyl or pyridyl, each of which is substituted with from 1-3 $R^b$.

In certain embodiments of non-limiting combination [1], each $R^b$ present in $R^Z$ is independently selected from the group consisting of: $C_{1-3}$ alkyl optionally substituted with from 1-3 independently selected halo; —F; —Cl; —N(R$^f$)(R'); $C_{1-4}$ alkoxy; $C_{1-4}$ haloalkoxy; —C(=O)OH; —C(=O)N(R')(R"); and cyano.

In certain embodiments of non-limiting combination [1], $X^2$ is a bond.

In certain embodiments of non-limiting combination [1], each of $R^{X1}$ and $R^{X2}$ is independently selected $C_{1-3}$ alkyl. For example, each of $R^{X1}$ and $R^{X2}$ can be methyl.

In certain embodiments of non-limiting combination [1], $R^{X1}$ and $R^{X2}$ taken together with the carbon atom to which each is attached form a $C_{3-6}$ cycloalkyl ring. In certain of these embodiments, $R^{X1}$ and $R^{X2}$ taken together with the carbon to which each is attached form cyclopropyl ring, cyclobutyl ring, or cyclopentyl ring. For example, $R^{X1}$ and $R^{X2}$ taken together with the carbon to which each is attached can form cyclopentyl ring.

In certain embodiments of non-limiting combination [1], $R^K$ is

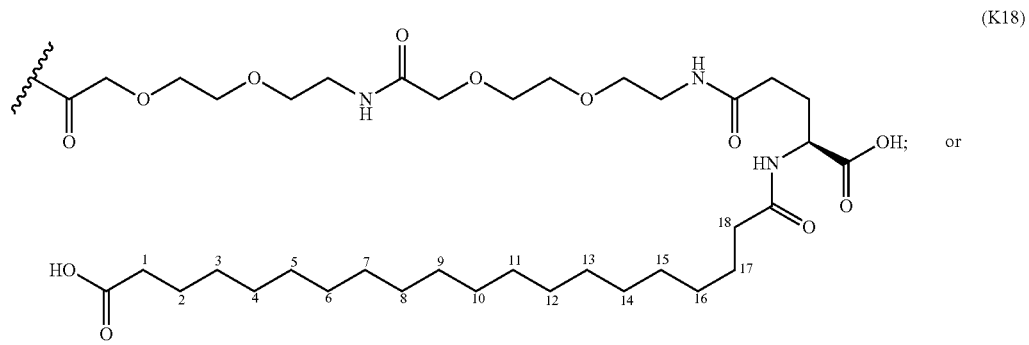

(K18)

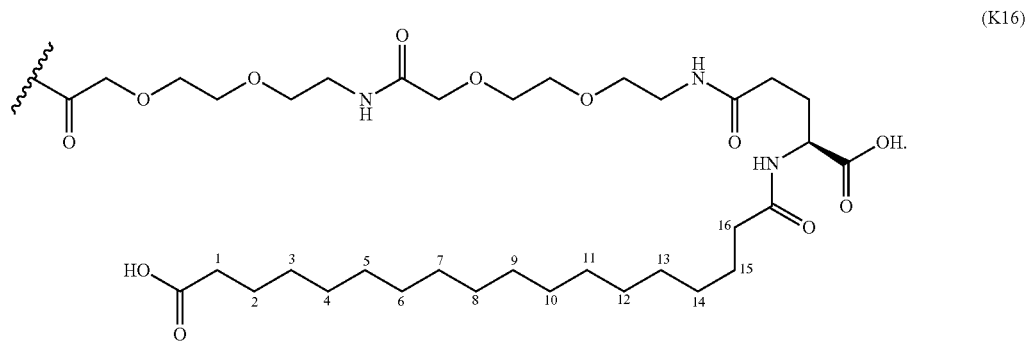

(K16)

In certain embodiments of non-limiting combination [1], $R^5$ is a C-terminal amino acid amide that is optionally substituted. For example, $R^5$ can be serine amide.

In certain embodiments of non-limiting combination [1], N(R)—W is:

-GTFTSDYSI(Aib)LDKIAQK*AFVQWLIAGGPSSGAPPPS-NH$_2$ (SEQ ID NO: 10), wherein K* is:

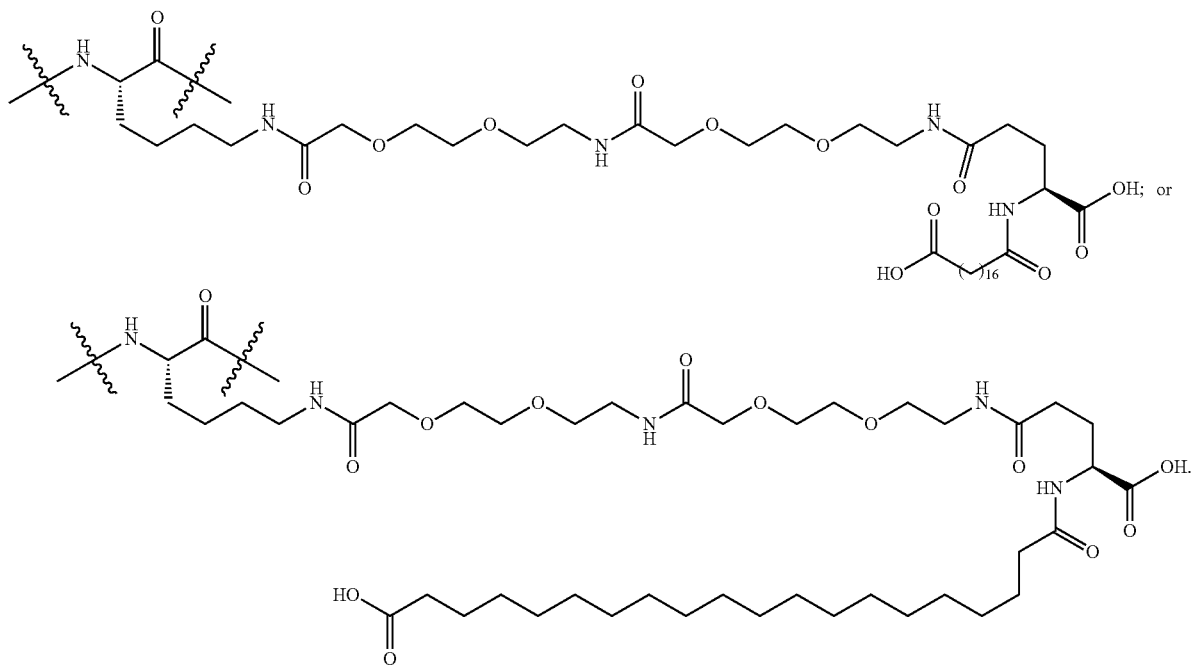

[2]

In certain embodiments of the compound of Formula (I), R* is a group of Formula (A), wherein:
$L^1$ is —$CH_2CH_2$— or —$CH_2CH_2CH_2$—;
$X^1$ is C(=O)N(H)* or C(=S)N(H)*;
$X^2$ is a bond
$R^Z$ is phenyl or pyridyl, each substituted with from 1-3 $R^b$; and
$R^{X1}$ and $R^{X2}$ are each independently selected unsubstituted $C_{1-3}$ alkyl; or
$R^{X1}$ and $R^{X2}$ taken together with the carbon atom to which each is attached form a $C_{3-6}$ cycloalkyl ring;
Q is O;
$R^1$ is H; $R^4$ is H;
$R^{2'}$ is —$CH_2CH_2R^3$;
$R^3$ is —C(O)OH.
W has the formula WC:

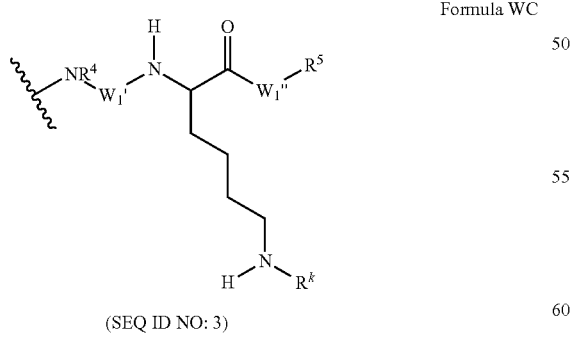

Formula WC (SEQ ID NO: 3)

wherein:
$W^{1'}$ is a sequence of 10-20 amino acids (optionally 15-20 amino acids; optionally 16 amino acids);
$W^{1'''}$ is a sequence of 15-25 amino acids (optionally 17-21 amino acids; optionally 19 amino acids); and $R^K$ is:

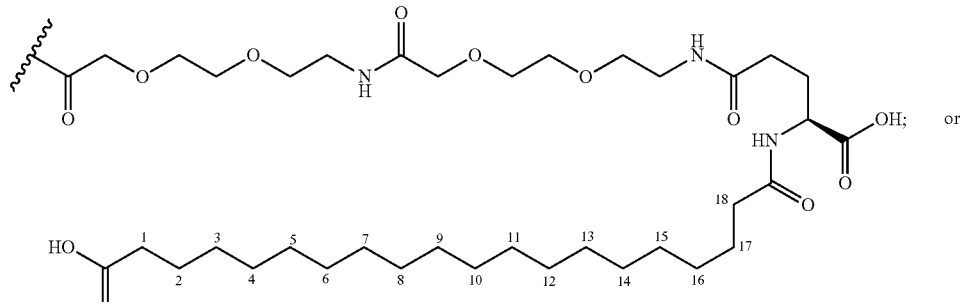

(K18)

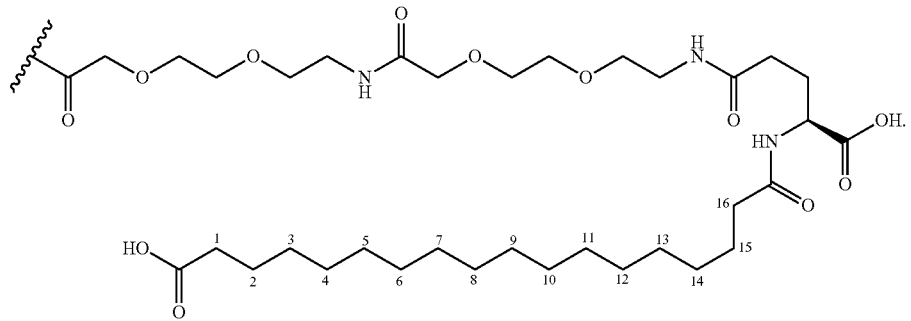

(K16)

In certain embodiments of non-limiting combination [1], —N(R⁴)—W has Formula WD:

In certain embodiments of non-limiting combination [2], —N(R⁴)—W has Formula WD-1:

In certain embodiments of non-limiting combination [2], —N(R⁴)—W has Formula WD-2:

In certain embodiments of non-limiting combination [2], —N(R⁴)—W has Formula WD-3:

In certain embodiments of non-limiting combination [2], —N(R⁴)—W has Formula WD-4:

In certain embodiments of non-limiting combination [2], —N(R⁴)—W has Formula WD-5:

In certain embodiments of non-limiting combination [2], each $R^b$ present in $R^Z$ is independently selected from the group consisting of: $C_{1-3}$ alkyl optionally substituted with from 1-3 independently selected halo; —F; —Cl; —N(R$^f$)(R'); $C_{1-4}$ alkoxy; $C_{1-4}$ haloalkoxy; —C(=O)OH; —C(=O)N(R')(R"); and cyano.

In certain embodiments of non-limiting combination [2], each of $R^{X1}$ and $R^{X2}$ is independently selected $C_{1-3}$ alkyl. For example, each $R^{X1}$ and $R^{X2}$ can be methyl.

In certain embodiments of non-limiting combination [2], $R^{X1}$ and $R^{X2}$ taken together with the carbon atom to which each is attached form a $C_{3-6}$ cycloalkyl ring. In certain of these embodiments, $R^{X1}$ and $R^{X2}$ taken together with the carbon to which each is attached form cyclopropyl ring, cyclobutyl ring, or cyclopentyl ring. For example, $R^{X1}$ and $R^{X2}$ taken together with the carbon to which each is attached can form cyclopentyl.

In certain embodiments of non-limiting combination [2], W is:

-GTFTSDYSI(Aib)LDKIAQK*AFVQWLIAGGPSSGAPPPS-NH₂ (SEQ ID NO: 10), wherein K* is:

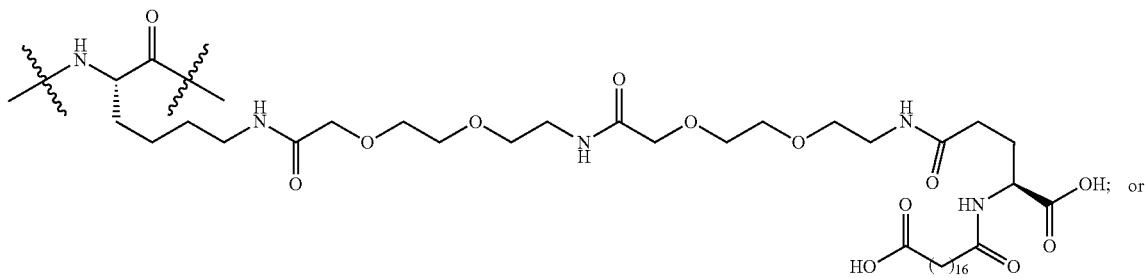

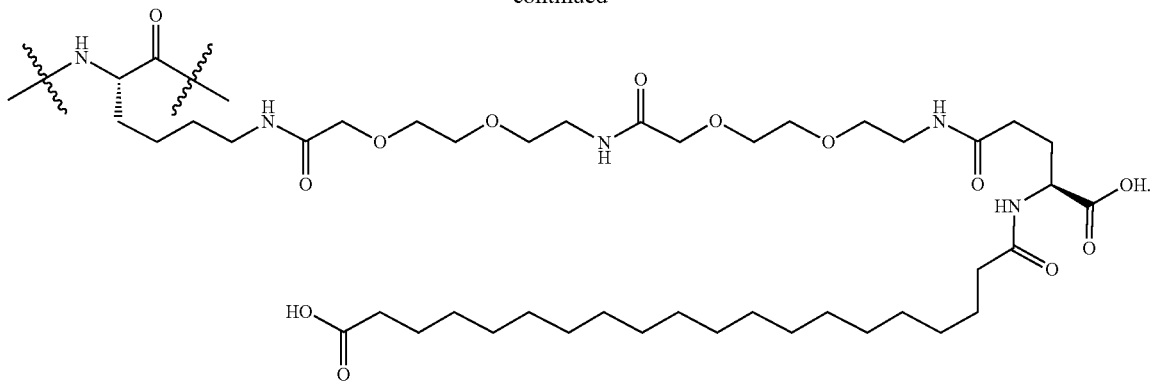

In certain embodiments of non-limiting combination [2], $R^5$ is a C-terminal amino acid amide that is optionally substituted. For example, $R^5$ can be serine amide.

[3] In certain embodiments of the compound of Formula (I), R* is a group of Formula (A), wherein:
- $L^1$ is unsubstituted $C_{2-4}$ alkylene (e.g., linear $C_{2-4}$ alkylene, optionally —$CH_2CH_2$— or —$CH_2CH_2CH_2$);
- $X^1$ is C(=O)N(R')*(e.g., C(=O)N(H)*) or C(=S)N(R')* (e.g., C(=S)N(H)*);
- $R^Z$ is $R^{ZA}$ and is selected from the group consisting of: phenyl optionally substituted with from 1-3 $R^b$, and heteroaryl including 6 ring atoms, wherein from 1-3 ring atoms are ring nitrogen atoms, and wherein the heteroaryl is optionally substituted with from 1-3 independently selected $R^b$ at one or more ring carbon atoms;
- $R^{X1}$ and $R^{X2}$ are each independently selected unsubstituted $C_{1-3}$ alkyl; or
- $R^{X1}$ and $R^{X2}$ taken together with the carbon atom to which each is attached form a $C_{3-6}$ cycloalkyl ring which is optionally substituted with from 1-3 independently selected $C_{1-3}$ alkyl;
- $X^2$ is a bond; and
- $N(R^4)$—W has Formula WD.

In certain embodiments of non-limiting combination [3], Q is O.

In certain embodiments of non-limiting combination [3], $R^1$ is H.

In certain embodiments of non-limiting combination [3], a2 is 1; and a1 is 1.

In certain embodiments of non-limiting combination [3], $R^{2'}$ is —$CH_2CH_2R^3$.

In certain embodiments of non-limiting combination [3], $R^3$ is —C(O)OH.

In certain embodiments of non-limiting combination [3], Q is O; $R^1$ is H; $R^4$ is H; $R^{2'}$ is —$CH_2CH_2R^3$; and $R^3$ is —C(O)OH.

In certain embodiments of non-limiting combination [3], $R^Z$ is phenyl or pyridyl each optionally substituted with from 1-3 $R^b$. In certain of these embodiments, $R^Z$ is phenyl or pyridyl, each of which is substituted with from 1-3 $R^b$.

In certain embodiments of non-limiting combination [3], $R^Z$ is phenyl optionally substituted with from 1-3 $R^b$. In certain of these embodiments, $R^Z$ is phenyl substituted with from 1-3 $R^b$.

In certain embodiments of non-limiting combination [3], each $R^b$ present in $R^Z$ is independently selected from the group consisting of: $C_{1-3}$ alkyl optionally substituted with from 1-3 independently selected halo; —F; —Cl; —N(R$^f$)(R'); $C_{1-4}$ alkoxy; $C_{1-4}$ haloalkoxy; —C(=O)OH; —C(=O)N(R')(R''); and cyano.

In certain embodiments of non-limiting combination [3], $X^1$ is C(=O)N(R'). For example, $X^1$ is C(=O)N(H)*).

In certain embodiments of non-limiting combination [3], each of $R^{X1}$ and $R^{X2}$ is independently selected $C_{1-3}$ alkyl. For example, each of $R^{X1}$ and $R^{X2}$ can be methyl.

In certain embodiments of non-limiting combination [3], $R^{X1}$ and $R^{X2}$ taken together with the carbon atom to which each is attached form a $C_{3-6}$ cycloalkyl ring. In certain of these embodiments, $R^{X1}$ and $R^{X2}$ taken together with the carbon to which each is attached form cyclopropyl ring, cyclobutyl ring, or cyclopentyl ring. For example, $R^{X1}$ and $R^{X2}$ taken together with the carbon to which each is attached can form cyclopentyl ring.

In certain embodiments of non-limiting combination [3], K* is present and $R^K$ is:

(K18)

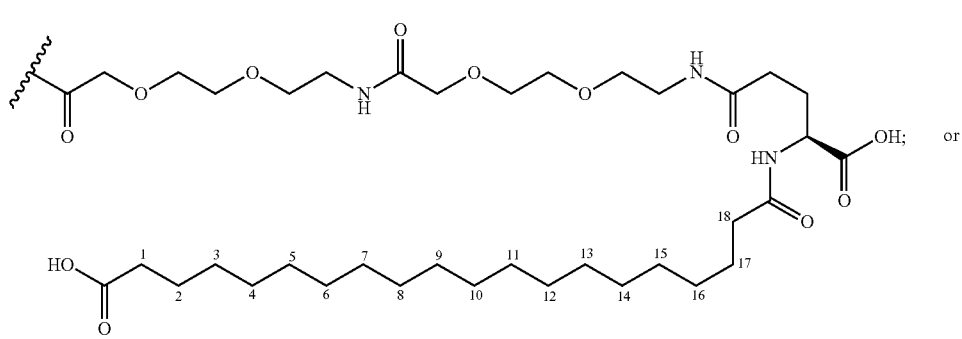

or

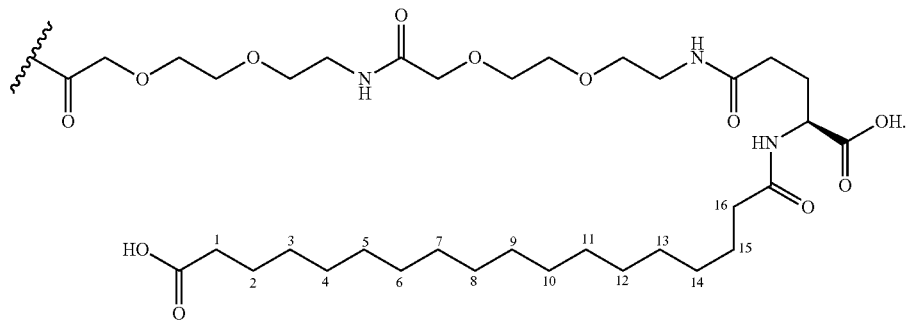

(K16)

In certain embodiments of non-limiting combination [3], —N(R⁴)—W has Formula WD-1:

In certain embodiments of non-limiting combination [3], —N(R⁴)—W has Formula WD-2:

In certain embodiments of non-limiting combination [3], —N(R⁴)—W has Formula WD-3:

In certain embodiments of non-limiting combination [3], —N(R⁴)—W has Formula WD-4:

In certain embodiments of non-limiting combination [3], —N(R⁴)—W has Formula WD-5.

In certain embodiments of non-limiting combination [3], one or more of the following apply.

In certain embodiments of Formula WD (e.g., when the group of Formula (WD) has Formula (WD-1), (WD-2), (WD-3), (WD-4), or (WD-5)), Xaa4 is T; Xaa7 is Y; and Xaa13 is K. In certain of these embodiments, Xaa 20 is V; and/or Xaa22 is W; and/or Xaa25 is A; and/or Xaa37 is absent. In certain of the foregoing embodiments, $R^6$ is $NH_2$.

In certain embodiments of Formula WD (e.g., when the group of Formula (WD) has Formula (WD-1), (WD-2), (WD-3), (WD-4), or (WD-5)), Xaa4 is T; Xaa7 is Y; Xaa13 is K; Xaa 20 is V.

In certain embodiments of Formula WD (e.g., when the group of Formula (WD) has Formula (WD-1), (WD-2), (WD-3), (WD-4), or (WD-5)), Xaa4 is T; Xaa7 is Y; Xaa13 is K; Xaa 20 is V; and Xaa22 is W.

In certain embodiments of Formula WD (e.g., when the group of Formula (WD) has Formula (WD-1), (WD-2), (WD-3), (WD-4), or (WD-5)), Xaa4 is T; Xaa7 is Y; Xaa13 is K; Xaa 20 is V; Xaa22 is W; and Xaa25 is A.

In certain embodiments of Formula WD (e.g., when the group of Formula (WD) has Formula (WD-1), (WD-2), (WD-3), (WD-4), or (WD-5)), Xaa4 is T; Xaa7 is Y; Xaa13 is K; Xaa 20 is V; Xaa22 is W; Xaa25 is A; and Xaa37 is absent.

In certain embodiments of Formula WD (e.g., when the group of Formula (WD) has Formula (WD-1), (WD-2), (WD-3), (WD-4), or (WD-5)), Xaa4 is T; Xaa7 is Y; Xaa13 is K; Xaa 20 is V; Xaa22 is W; Xaa25 is A; Xaa37 is absent; $R^6$ is $NH_2$.

In certain of the foregoing embodiments, Xaa14 is I.
In certain of the foregoing embodiments, Xaa21 is Q.
In certain of the foregoing embodiments, Xaa24 is I.
In certain of the foregoing embodiments, Xaa3 is F, Xaa16 is Q, and Xaa18 is A.
In certain of the foregoing embodiments, Xaa17 is K*.
In certain of the foregoing embodiments, Xaa14 and Xaa24 are I; and, Xaa21 is Q.
In certain of the foregoing embodiments, Xaa14 and Xaa24 are I; Xaa21 is Q; Xaa3 is F, Xaa16 is Q, and Xaa18 is A.
In certain of the foregoing embodiments, Xaa14 and Xaa24 are I; Xaa21 is Q; Xaa3 is F, Xaa16 is Q, Xaa18 is A; and Xaa17 is K*.

In certain embodiments of non-limiting combination [3], $R^5$ is a C-terminal amino acid amide that is optionally substituted. For example, $R^5$ can be serine amide.

In certain embodiments of non-limiting combination [3], N(R⁴)—W is:
-GTFTSDYSI(Aib)LDKIAQK*AFVQWLIAGGPSSGAPPPS-NH₂ (SEQ ID NO: 10), optionally wherein K* is:

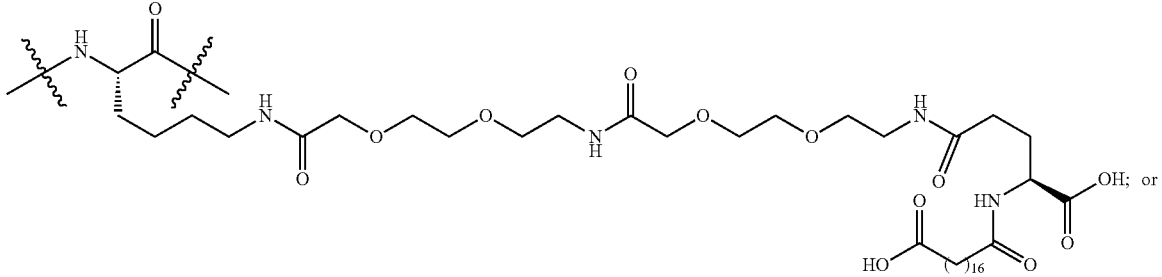

-continued

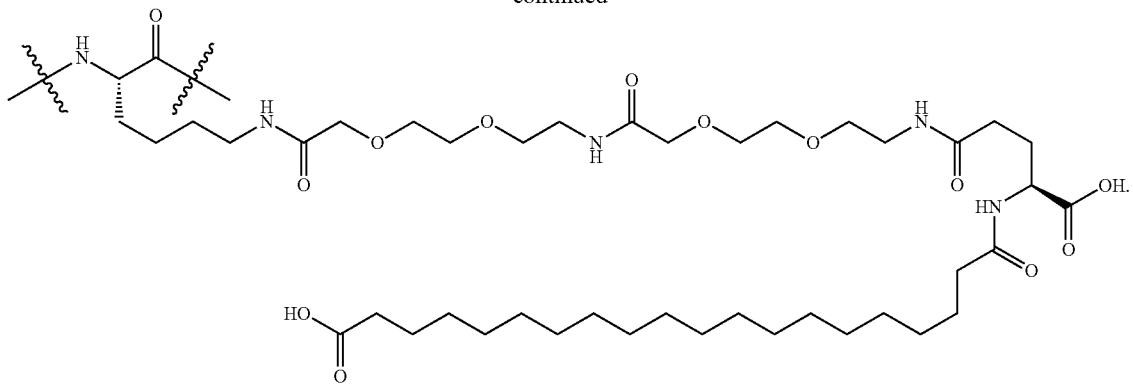

[4] In certain embodiments of the compound of Formula (I), R* is a group of Formula (A), wherein:
- $L^1$ is unsubstituted $C_{2-4}$ alkylene (e.g., linear $C_{2-4}$ alkylene, optionally —$CH_2CH_2$— or —$CH_2CH_2CH_2$);
- $X^1$ is C(=O)N(R')* (e.g., C(=O)N(H)*) or C(=S)N(R')* (e.g., C(=S)N(H)*);
- $R^Z$ is $R^{ZA}$ and is selected from the group consisting of: phenyl optionally substituted with from 1-3 $R^b$; and heteroaryl including 6 ring atoms, wherein from 1-3 ring atoms are ring nitrogen atoms, and wherein the heteroaryl is optionally substituted with from 1-3 independently selected $R^b$ at one or more ring carbon atoms;
- $R^{X1}$ and $R^{X2}$ are each independently selected unsubstituted $C_{1-3}$ alkyl;
- $X^2$ is a bond; and
- $N(R^4)$—W has Formula WD.

In certain embodiments of non-limiting combination [4], Q is O.

In certain embodiments of non-limiting combination [4], $R^1$ is H.

In certain embodiments of non-limiting combination [4], a2 is 1; and a1 is 1.

In certain embodiments of non-limiting combination [4], $R^{2'}$ is —$CH_2CH_2R^3$.

In certain embodiments of non-limiting combination [4], $R^3$ is —C(O)OH.

In certain embodiments of non-limiting combination [4], Q is O; $R^1$ is H; $R^4$ is H; $R^{2'}$ is —$CH_2CH_2R^3$; and $R^3$ is —C(O)OH.

In certain embodiments of non-limiting combination [4], $R^Z$ is phenyl or pyridyl each optionally substituted with from 1-3 $R^b$. In certain of these embodiments, $R^Z$ is phenyl or pyridyl, each of which is substituted with from 1-3 $R^b$.

In certain embodiments of non-limiting combination [4], $R^Z$ is phenyl optionally substituted with from 1-3 $R^b$. In certain of these embodiments, $R^Z$ is phenyl substituted with from 1-3 $R^b$.

In certain embodiments of non-limiting combination [4], each $R^b$ present in $R^Z$ is independently selected from the group consisting of: $C_{1-3}$ alkyl optionally substituted with from 1-3 independently selected halo; —F; —Cl; —N(R')(R'); $C_{1-4}$ alkoxy; $C_{1-4}$ haloalkoxy; —C(=O)OH; —C(=O)N(R')(R''); and cyano.

In certain embodiments of non-limiting combination [4], $X^1$ is C(=O)N(R'). For example, $X^1$ is C(=O)N(H)*.

In certain embodiments of non-limiting combination [4], each of $R^{X1}$ and $R^{X2}$ is independently selected $C_{1-3}$ alkyl. For example, each of $R^{X1}$ and $R^{X2}$ can be methyl.

In certain embodiments of non-limiting combination [4], K* is present and $R^K$ is:

(K18)

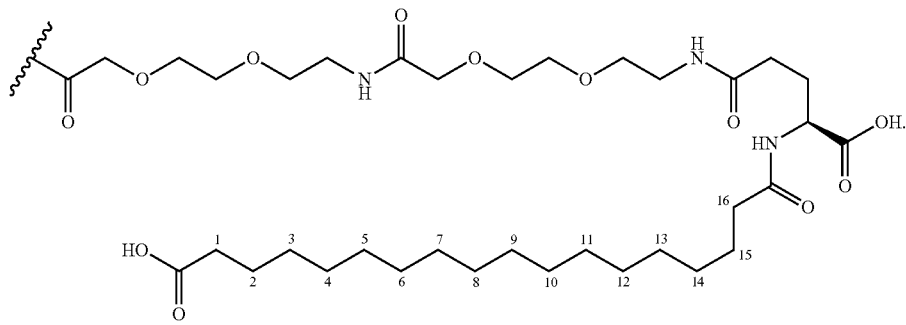
(K16)

In certain embodiments of non-limiting combination [4], —N(R⁴)—W has Formula WD-1:

In certain embodiments of non-limiting combination [4], —N(R⁴)—W has Formula WD-2:

In certain embodiments of non-limiting combination [4], —N(R⁴)—W has Formula WD-3:

In certain embodiments of non-limiting combination [4], —N(R⁴)—W has Formula WD-4:

In certain embodiments of non-limiting combination [4], —N(R⁴)—W has Formula WD-5.

In certain embodiments of non-limiting combination [4], one or more of the following apply.

In certain embodiments of Formula WD (e.g., when the group of Formula (WD) has Formula (WD-1), (WD-2), (WD-3), (WD-4), or (WD-5)), Xaa4 is T; Xaa7 is Y; and Xaa13 is K. In certain of these embodiments, Xaa 20 is V; and/or Xaa22 is W; and/or Xaa25 is A; and/or Xaa37 is absent. In certain of the foregoing embodiments, R⁶ is NH₂.

In certain embodiments of Formula WD (e.g., when the group of Formula (WD) has Formula (WD-1), (WD-2), (WD-3), (WD-4), or (WD-5)), Xaa4 is T; Xaa7 is Y; Xaa13 is K; Xaa 20 is V.

In certain embodiments of Formula WD (e.g., when the group of Formula (WD) has Formula (WD-1), (WD-2), (WD-3), (WD-4), or (WD-5)), Xaa4 is T; Xaa7 is Y; Xaa13 is K; Xaa 20 is V; and Xaa22 is W.

In certain embodiments of Formula WD (e.g., when the group of Formula (WD) has Formula (WD-1), (WD-2), (WD-3), (WD-4), or (WD-5)), Xaa4 is T; Xaa7 is Y; Xaa13 is K; Xaa 20 is V; Xaa22 is W; and Xaa25 is A.

In certain embodiments of Formula WD (e.g., when the group of Formula (WD) has Formula (WD-1), (WD-2), (WD-3), (WD-4), or (WD-5)), Xaa4 is T; Xaa7 is Y; Xaa13 is K; Xaa 20 is V; Xaa22 is W; Xaa25 is A; and Xaa37 is absent.

In certain embodiments of Formula WD (e.g., when the group of Formula (WD) has Formula (WD-1), (WD-2), (WD-3), (WD-4), or (WD-5)), Xaa4 is T; Xaa7 is Y; Xaa13 is K; Xaa 20 is V; Xaa22 is W; Xaa25 is A; Xaa37 is absent; R⁶ is NH₂.

In certain of the foregoing embodiments, Xaa14 is I.
In certain of the foregoing embodiments, Xaa21 is Q.
In certain of the foregoing embodiments, Xaa24 is I.
In certain of the foregoing embodiments, Xaa3 is F, Xaa16 is Q, and Xaa18 is A.
In certain of the foregoing embodiments, Xaa17 is K*.
In certain of the foregoing embodiments, Xaa14 and Xaa24 are I; and, Xaa21 is Q.
In certain of the foregoing embodiments, Xaa14 and Xaa24 are I; Xaa21 is Q; Xaa3 is F, Xaa16 is Q, and Xaa18 is A.
In certain of the foregoing embodiments, Xaa14 and Xaa24 are I; Xaa21 is Q; Xaa3 is F, Xaa16 is Q, Xaa18 is A; and Xaa17 is K*.

In certain embodiments of non-limiting combination [4], R⁵ is a ('-terminal amino acid amide that is optionally substituted. For example, R⁵ can be serine amide.

In certain embodiments of non-limiting combination [4], N(R⁴)—W is:
-GTFTSDYSI(Aib)LDKIAQK*AFVQWLIAGGPSSGAPPPS-NH₂ (SEQ ID NO: 10), optionally wherein K* is:

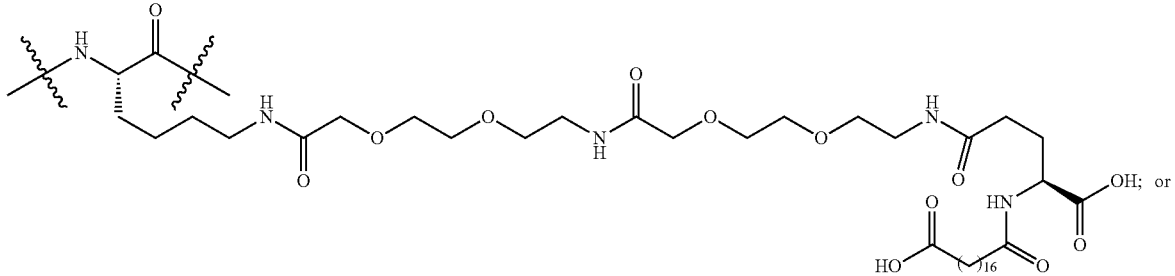

-continued

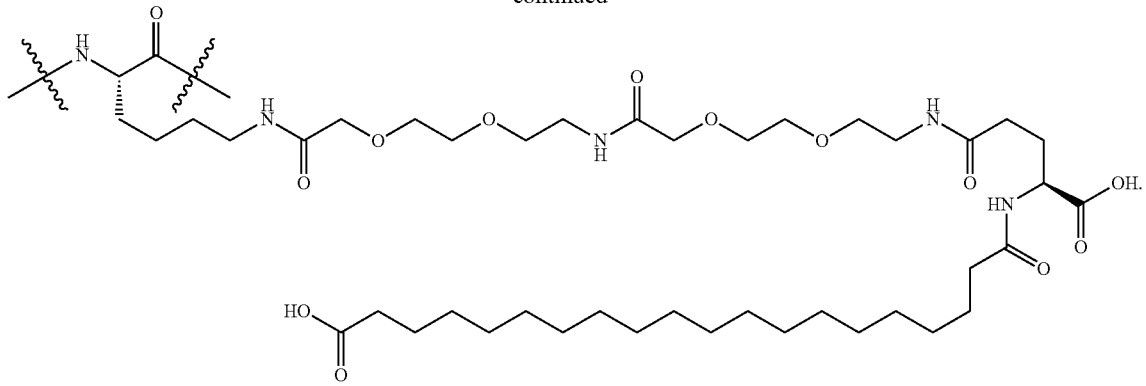

The skilled artisan will recognize that some chemical structures described herein may be represented on paper by one or more other resonance forms; or may exist in one or more other tautomeric forms, even when kinetically, the artisan recognizes that such tautomeric forms represent only a very small portion of a sample of such compound(s). Such compounds are contemplated within the scope of this disclosure, though such resonance forms or tautomers are not explicitly represented herein.

Pharmaceutical Compositions and Administration
General

In some embodiments, a chemical entity (e.g., a compound or a pharmaceutically acceptable salt and/or hydrate and/or prodrug of the compound) that modulates (e.g., agonizes or partially agonizes or antagonizes) glucagon-like peptide-1 receptor ("GLP-1R") and/or the gastric inhibitory polypeptide receptor ("GIPR"), is administered as a pharmaceutical composition that includes the chemical entity and one or more pharmaceutically acceptable excipients, and optionally one or more additional therapeutic agents as described herein.

In some embodiments, the chemical entities can be administered in combination with one or more conventional pharmaceutical excipients. Pharmaceutically acceptable excipients include, but are not limited to, ion exchangers, alumina, aluminum stearate, lecithin, self-emulsifying drug delivery systems (SEDDS) such as d-α-tocopherol polyethylene glycol 1000 succinate, surfactants used in pharmaceutical dosage forms such as Tweens, poloxamers or other similar polymeric delivery matrices, serum proteins, such as human serum albumin, buffer substances such as phosphates, tris, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium-chloride, zinc salts, colloidal silica, magnesium trisilicate, polyvinyl pyrrolidone, cellulose-based substances, polyethylene glycol, sodium carboxymethyl cellulose, polyacrylates, waxes, polyethylene-polyoxypropylene-block polymers, and wool fat. Cyclodextrins such as α-, β, and γ-cyclodextrin, or chemically modified derivatives such as hydroxyalkylcyclodextrins, including 2- and 3-hydroxypropyl-β-cyclodextrins, or other solubilized derivatives can also be used to enhance delivery of compounds described herein. Dosage forms or compositions containing a chemical entity as described herein in the range of 0.005% to 100% with the balance made up from non-toxic excipient may be prepared. The contemplated compositions may contain 0.001%-100% of a chemical entity provided herein, in one embodiment 0.1-95%, in another embodiment 75-85%, in a further embodiment 20-80%. Actual methods of preparing such dosage forms are known, or will be apparent, to those skilled in this art; for example, see Remington: The Science and Practice of Pharmacy, $22^{nd}$ Edition (Pharmaceutical Press, London, U K. 2012).

Routes of Administration and Composition Components

In some embodiments, the chemical entities described herein or a pharmaceutical composition thereof can be administered to subject in need thereof by any accepted route of administration. Acceptable routes of administration include, but are not limited to, buccal, cutaneous, endocervical, endosinusial, endotracheal, enteral, epidural, interstitial, intra-abdominal, intra-arterial, intrabronchial, intrabursal, intracerebral, intracisternal, intracoronary, intradermal, intraductal, intraduodenal, intradural, intraepidermal, intraesophageal, intragastric, intragingival, intraileal, intralymphatic, intramedullary, intrameningeal, intramuscular, intraovarian, intraperitoneal, intraprostatic, intrapulmonary, intrasinal, intraspinal, intrasynovial, intratesticular, intrathecal, intratubular, intratumoral, intrauterine, intravascular, intravenous, nasal, nasogastric, oral, parenteral, percutaneous, peridural, rectal, respiratory (inhalation), subcutaneous, sublingual, submucosal, topical, transdermal, transmucosal, transtracheal, ureteral, urethral and vaginal. In certain embodiments, a preferred route of administration is parenteral (e.g., intratumoral).

Compositions can be formulated for parenteral administration, e.g., formulated for injection via the intravenous, intramuscular, sub-cutaneous, or even intraperitoneal routes. Typically, such compositions can be prepared as injectables, either as liquid solutions or suspensions; solid forms suitable for use to prepare solutions or suspensions upon the addition of a liquid prior to injection can also be prepared; and the preparations can also be emulsified. The preparation of such formulations will be known to those of skill in the art in light of the present disclosure.

The pharmaceutical forms suitable for injectable use include sterile aqueous solutions or dispersions; formulations including sesame oil, peanut oil, or aqueous propylene glycol; and sterile powders for the extemporaneous preparation of sterile injectable solutions or dispersions. In general, the form must be sterile and must be fluid to the extent that it may be easily injected. It also should be stable under the conditions of manufacture and storage and must be preserved against the contaminating action of microorganisms, such as bacteria and fungi.

The carrier also can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion, and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques, which yield a powder of the active ingredient, plus any additional desired ingredient from a previously sterile-filtered solution thereof.

Pharmacologically acceptable excipients usable in the rectal composition as a gel, cream, enema, or rectal suppository, include, without limitation, any one or more of cocoa butter glycerides, synthetic polymers such as polyvinylpyrrolidone, PEG (like PEG ointments), glycerine, glycerinated gelatin, hydrogenated vegetable oils, poloxamers, mixtures of polyethylene glycols of various molecular weights and fatty acid esters of polyethylene glycol Vaseline, anhydrous lanolin, shark liver oil, sodium saccharinate, menthol, sweet almond oil, sorbitol, sodium benzoate, anoxid SBN, vanilla essential oil, aerosol, parabens in phenoxyethanol, sodium methyl p-oxybenzoate, sodium propyl p-oxybenzoate, diethylamine, carbomers, carbopol, methyloxybenzoate, macrogol cetostearyl ether, cocoyl caprylocaprate, isopropyl alcohol, propylene glycol, liquid paraffin, xanthan gum, carboxy-metabisulfite, sodium edetate, sodium benzoate, potassium metabisulfite, grapefruit seed extract, methyl sulfonyl methane (MSM), lactic acid, glycine, vitamins, such as vitamin A and E and potassium acetate.

In certain embodiments, suppositories can be prepared by mixing the chemical entities described herein with suitable non-irritating excipients or carriers such as cocoa butter, polyethylene glycol or a suppository wax which are solid at ambient temperature but liquid at body temperature and therefore melt in the rectum and release the active compound. In other embodiments, compositions for rectal administration are in the form of an enema.

In other embodiments, the compounds described herein or a pharmaceutical composition thereof are suitable for local delivery to the digestive or GI tract by way of oral administration (e.g., solid or liquid dosage forms).

Solid dosage forms for oral administration include capsules, tablets, pills, powders, and granules. In such solid dosage forms, the chemical entity is mixed with one or more pharmaceutically acceptable excipients, such as sodium citrate or dicalcium phosphate and/or: a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents. Solid compositions of a similar type may also be employed as fillers in soft and hard-filled gelatin capsules using such excipients as lactose or milk sugar as well as high molecular weight polyethylene glycols and the like.

In one embodiment, the compositions will take the form of a unit dosage form such as a pill or tablet and thus the composition may contain, along with a chemical entity provided herein, a diluent such as lactose, sucrose, dicalcium phosphate, or the like; a lubricant such as magnesium stearate or the like; and a binder such as starch, gum acacia, polyvinylpyrrolidine, gelatin, cellulose, cellulose derivatives or the like. In another solid dosage form, a powder, marume, solution or suspension (e.g., in propylene carbonate, vegetable oils, PEG's, poloxamer 124 or triglycerides) is encapsulated in a capsule (gelatin or cellulose base capsule). Unit dosage forms in which one or more chemical entities provided herein or additional active agents are physically separated are also contemplated; e.g., capsules with granules (or tablets in a capsule) of each drug; two-layer tablets; two-compartment gel caps, etc. Enteric coated or delayed release oral dosage forms are also contemplated.

Other physiologically acceptable compounds include wetting agents, emulsifying agents, dispersing agents or preservatives that are particularly useful for preventing the growth or action of microorganisms. Various preservatives are well known and include, for example, phenol and ascorbic acid.

In certain embodiments the excipients are sterile and generally free of undesirable matter. These compositions can be sterilized by conventional, well-known sterilization techniques. For various oral dosage form excipients such as tablets and capsules, sterility is not required. The USP/NF standard is usually sufficient.

Ocular compositions can include, without limitation, one or more of any of the following: viscogens (e.g., Carboxymethylcellulose, Glycerin, Polyvinylpyrrolidone, Polyethylene glycol); Stabilizers (e.g., Pluronic (triblock copolymers), Cyclodextrins); Preservatives (e.g., Benzalkonium chloride, ETDA, SofZia (boric acid, propylene glycol, sorbitol, and zinc chloride; Alcon Laboratories, Inc.), Purite (stabilized oxychloro complex; Allergan, Inc.)).

Topical compositions can include ointments and creams. Ointments are semisolid preparations that are typically based on petrolatum or other petroleum derivatives. Creams containing the selected active agent are typically viscous liquid or semisolid emulsions, often either oil-in-water or water-in-oil. Cream bases are typically water-washable, and contain an oil phase, an emulsifier and an aqueous phase. The oil phase, also sometimes called the "internal" phase, is generally comprised of petrolatum and a fatty alcohol such as cetyl or stearyl alcohol; the aqueous phase usually, although not necessarily, exceeds the oil phase in volume, and generally contains a humectant. The emulsifier in a cream formulation is generally a nonionic, anionic, cationic or amphoteric surfactant. As with other carriers or vehicles, an ointment base should be inert, stable, nonirritating and non-sensitizing.

In any of the foregoing embodiments, pharmaceutical compositions described herein can include one or more one or more of the following: lipids, interbilayer crosslinked multilamellar vesicles, biodegradeable poly(D,L-lactic-co-glycolic acid) [PLGA]-based or poly anhydride-based nanoparticles or microparticles, and nanoporous particle-supported lipid bilayers.

Dosages

The dosages may be varied depending on the requirement of the patient, the severity of the condition being treating and the particular compound being employed. Proper dosage for a particular situation can be determined by one skilled in the medical arts. In some cases, the total daily dosage may be divided and administered in portions throughout the day or by means providing continuous delivery.

In some embodiments, the compounds described herein are administered at a dosage of from about 0.0002 mg/Kg to about 100 mg/Kg (e.g., from about 0.0002 mg/Kg to about 50 mg/Kg; from about 0.0002 mg/Kg to about 25 mg/Kg; from about 0.0002 mg/Kg to about 10 mg/Kg; from about 0.0002 mg/Kg to about 5 mg/Kg; from about 0.0002 mg/Kg to about 1 mg/Kg; from about 0.0002 mg/Kg to about 0.5 mg/Kg; from about 0.0002 mg/Kg to about 0.1 mg/Kg; from about 0.001 mg/Kg to about 50 mg/Kg; from about 0.001 mg/Kg to about 25 mg/Kg; from about 0.001 mg/Kg to about 10 mg/Kg; from about 0.001 mg/Kg to about 5 mg/Kg; from about 0.001 mg/Kg to about 1 mg/Kg; from about 0.001 mg/Kg to about 0.5 mg/Kg; from about 0.001 mg/Kg to about 0.1 mg/Kg; from about 0.01 mg/Kg to about 50 mg/Kg; from about 0.01 mg/Kg to about 25 mg/Kg; from about 0.01 mg/Kg to about 10 mg/Kg; from about 0.01 mg/Kg to about 5 mg/Kg; from about 0.01 mg/Kg to about 1 mg/Kg; from about 0.01 mg/Kg to about 0.5 mg/Kg; from about 0.01 mg/Kg to about 0.1 mg/Kg; from about 0.1 mg/Kg to about 50 mg/Kg; from about 0.1 mg/Kg to about 25 mg/Kg; from about 0.1 mg/Kg to about 10 mg/Kg; from about 0.1 mg/Kg to about 5 mg/Kg; from about 0.1 mg/Kg to about 1 mg/Kg; from about 0.1 mg/Kg to about 0.5 mg/Kg).

Regimens

The foregoing dosages can be administered on a daily basis (e.g., as a single dose or as two or more divided doses) or non-daily basis (e.g., every other day, every two days, every three days, once weekly, twice weeks, once every two weeks, once a month).

In some embodiments, the period of administration of a compound described herein is for 1 day, 2 days, 3 days, 4 days, 5 days, 6 days, 7 days, 8 days, 9 days, 10 days, 11 days, 12 days, 13 days, 14 days, 3 weeks, 4 weeks, 5 weeks, 6 weeks, 7 weeks, 8 weeks, 9 weeks, 10 weeks, 11 weeks, 12 weeks, 4 months, 5 months, 6 months, 7 months, 8 months, 9 months, 10 months, 11 months, 12 months, or more. In a further embodiment, a period of during which administration is stopped is for 1 day, 2 days, 3 days, 4 days, 5 days, 6 days, 7 days, 8 days, 9 days, 10 days, 11 days, 12 days, 13 days, 14 days, 3 weeks, 4 weeks, 5 weeks, 6 weeks, 7 weeks, 8 weeks, 9 weeks, 10 weeks, 11 weeks, 12 weeks, 4 months, 5 months, 6 months, 7 months, 8 months, 9 months, 10 months, 11 months, 12 months, or more. In an embodiment, a therapeutic compound is administered to an individual for a period of time followed by a separate period of time. In another embodiment, a therapeutic compound is administered for a first period and a second period following the first period, with administration stopped during the second period, followed by a third period where administration of the therapeutic compound is started and then a fourth period following the third period where administration is stopped. In an aspect of this embodiment, the period of administration of a therapeutic compound followed by a period where administration is stopped is repeated for a determined or undetermined period of time. In a further embodiment, a period of administration is for 1 day, 2 days, 3 days, 4 days, 5 days, 6 days, 7 days, 8 days, 9 days, 10 days, 11 days, 12 days, 13 days, 14 days, 3 weeks, 4 weeks, 5 weeks, 6 weeks, 7 weeks, 8 weeks, 9 weeks, 10 weeks, 11 weeks, 12 weeks, 4 months, 5 months, 6 months, 7 months, 8 months, 9 months, 10 months, 11 months, 12 months, or more. In a further embodiment, a period of during which administration is stopped is for 1 day, 2 days, 3 days, 4 days, 5 days, 6 days, 7 days, 8 days, 9 days, 10 days, 11 days, 12 days, 13 days, 14 days, 3 weeks, 4 weeks, 5 weeks, 6 weeks, 7 weeks, 8 weeks, 9 weeks, 10 weeks, 11 weeks, 12 weeks, 4 months, 5 months, 6 months, 7 months, 8 months, 9 months, 10 months, 11 months, 12 months, or more.

Methods of Treatment

This disclosure features methods for treating a subject (e.g., a human) having a disease, disorder, or condition in which modulation of GLP-1R and/or GIPR activities (e.g., repressed or impaired and/or elevated or unwanted GLP-1R and/or GIPR signaling) is beneficial for the treatment of the underlying pathology and/or symptoms and/or progression of the disease, disorder, or condition. In certain embodiments, the methods described herein can include or further include treating one or more conditions associated, co-morbid or sequela with any one or more of the conditions described herein.

In certain embodiments, the chemical entities described herein induce blood glucose reduction (e.g., reduce blood glucose levels), promote insulin synthesis, stimulate insulin secretion, increase the mass of B-cells, modulate gastric acid secretion, modulate gastric emptying, and/or decrease glucagon production. In certain embodiments, the chemical entities described herein stabilize serum glucose and serum insulin levels.

Indications

Obesity

In some embodiments, the condition, disease or disorder is obesity and conditions, diseases or disorders that are associated with obesity. Non-limiting examples of obesity and obesity related conditions include symptomatic obesity, simple obesity, childhood obesity, morbid obesity and abdominal obesity (central obesity characterized by abdominal adiposity). Non-limiting examples of symptomatic obesity include endocrine obesity (e.g., Cushing syndrome, hypothyroidism, insulinoma, obese type II diabetes, pseudo-hypoparathyroidism, hypogonadism), hypothalamic obesity, hereditary obesity (e.g., Prader-Willi syndrome, Laurence-Moon-Biedl syndrome), and drug-induced obesity (e.g., steroid, phenothiazine, insulin, sulfonylurea agent, or β-blocker-induced obesity).

In some embodiments, the condition, disease or disorder is associated with obesity. Examples of such conditions, disease or disorders include, without limitation, glucose tolerance disorders, diabetes (e.g., type 2 diabetes, obese diabetes), lipid metabolism abnormality, hyperlipidemia, hypertension, cardiac failure, hyperuricemia, gout, fatty liver (including non-alcoholic steatohepatitis (NASH)), coronary heart disease (e.g., myocardial infarction, angina pectoris), cerebral infarction (e.g., brain thrombosis, transient cerebral ischemic attack), bone or articular disease (e.g., knee osteoarthritis, hip osteoarthritis, spondylitis deformans, lumbago), sleep apnea syndrome, obesity hypoventilation syndrome (Pickwickian syndrome), menstrual disorder (e.g., abnormal menstrual cycle, abnormality of menstrual flow and cycle, amenorrhea, abnormal catamenial symptom), visceral obesity syndrome, and metabolic syndrome. In certain embodiments, the chemical entities described herein can be used to treat subjects exhibiting symptoms of both obesity and insulin deficiency.

Diabetes

In some embodiments, the condition, disease or disorder is diabetes. Non-limiting examples of diabetes include type 1 diabetes, type 2 diabetes (e.g., diet-treated type 2-diabetes, sulfonylurea-treated type 2-diabetes, a far-advanced stage type 2-diabetes, long-term insulin-treated type 2-diabetes), diabetes mellitus (e.g., non-insulin-dependent diabetes mellitus, insulin-dependent diabetes mellitus), gestational diabetes, obese diabetes, autoimmune diabetes, and borderline type diabetes.

In some embodiments, the condition, disease or disorder is associated with diabetes (e.g., a complication of diabetes). Non-limiting examples of disorders associated with diabetes include obesity, obesity-related disorders, metabolic syndrome, neuropathy, nephropathy (e.g., diabetic nephropathy), retinopathy, diabetic cardiomyopathy, cataract, macroangiopathy, osteopenia, hyperosmolar diabetic coma, infectious disease (e.g., respiratory infection, urinary tract infection, gastrointestinal infection, dermal soft tissue infections, inferior limb infection), diabetic gangrene, xerostomia, hypacusis, cerebrovascular disorder, diabetic cachexia, delayed wound healing, diabetic dyslipidemia peripheral blood circulation disorder, cardiovascular risk factors. (e.g., coronary artery disease, peripheral artery disease, cerebrovascular disease, hypertension, and risk factors related to unmanaged cholesterol and/or lipid levels, and/or inflammation), NASH, bone fracture and cognitive dysfunction Other non-limiting examples of disorders related to diabetes include pre-diabetes, hyperlipidemia (e.g., hypertriglyceridemia, hypercholesterolemia, high LDL-cholesterolemia, low HDL-cholesterolemia, postprandial hyperlipemia), metabolic syndrome (e.g., metabolic disorder where activation of GLP-1R is beneficial, metabolic syndrome X), hypertension, impaired glucose tolerance (IGT), insulin resistance, and sarcopenia.

In some embodiments, the condition, disease or disorder is diabetes and obesity (diabesity). In certain embodiments, the compounds described herein are also useful in improving the therapeutic effectiveness of metformin.

Disorders of Metabolically Important Tissues

In some embodiments, the condition, disease or disorder is a disorder of a metabolically important tissue.

In some embodiments, the condition, disease or disorder is a fatty liver disease. Fatty liver diseases include, but are not limited to, non-alcoholic fatty acid liver disease (NAFLD), steatohepatitis, non-alcoholic steatohepatitis (NASH), fatty liver disease resulting from hepatitis, fatty liver disease resulting from obesity, fatty liver disease resulting from diabetes, fatty liver disease resulting from insulin resistance, fatty liver disease resulting from hypertriglyceridemia, Abetalipoproteinemia, glycogen storage diseases, Weber-Christian disease, Wolmans disease, acute fatty liver of pregnancy, and lipodystrophy.

Non-alcoholic fatty liver disease (NAFLD) represents a spectrum of disease occurring in the absence of alcohol abuse and is typically characterized by the presence of steatosis (fat in the liver). NAFLD is believed to be linked to a variety of conditions, e.g., metabolic syndrome (including obesity, diabetes and hypertriglyceridemia) and insulin resistance. It can cause liver disease in adults and children and may ultimately lead to cirrhosis (Skelly et al., J Hepatol 2001; 35: 195-9; Chitturi et al., Hepatology 2002; 35(2): 373-9). The severity of NAFLD ranges from the relatively benign isolated predominantly macrovesicular steatosis (i.e., nonalcoholic fatty liver or NAFL) to non-alcoholic steatohepatitis (NASH) (Angulo et al., J Gastroenterol Hepatol 2002; 17 Suppl:S186-90). In certain embodiments, the subject is a pediatric subject (e.g., 6-16 years old; or 6-12 years old; or 6-10 years old). In certain embodiments, the subject is an adult subject.

Other non-limiting examples of disorders in metabolically important tissues include joint disorders (e.g., osteoarthritis, secondary osteoarthritis), steatosis (e.g. in the liver); gall stones; gallbladder disorders; gastroesophageal reflux; sleep apnea; hepatitis; fatty liver; bone disorder characterized by altered bone metabolism, such as osteoporosis, including post-menopausal osteoporosis, poor bone strength, osteopenia, Paget's disease, osteolytic metastasis in cancer patients, osteodystrophy in liver disease and the altered bone metabolism caused by renal failure or hemodialysis, bone fracture, bone surgery, aging, pregnancy, protection against bone fractures, and malnutrition polycystic ovary syndrome; renal disease (e.g., chronic renal failure, glomerulonephritis, glomerulosclerosis, nephrotic syndrome, hypertensive nephrosclerosis, end-stage renal disease); muscular dystrophy, angina pectoris, acute or chronic diarrhea, testicular dysfunction, respiratory dysfunction, frailty, sexual dysfunction (e.g., erectile dysfunction) and geriatric syndrome. In certain embodiments, the chemical entities described herein can be used for treating surgical trauma by improving recovery after surgery and/or by preventing the catabolic reaction caused by surgical trauma.

Cardiovascular Diseases

In some embodiments, the condition, disease or disorder is a cardiovascular disease. Non-limiting examples of cardiovascular disease include congestive heart failure, atherosclerosis, arteriosclerosis, coronary heart disease, or peripheral artery disease, stroke, coronary artery disease, congestive heart failure, coronary heart disease, hypertension, cardiac failure, cerebrovascular disorder (e.g., cerebral infarction), vascular dysfunction, myocardial infarction, elevated blood pressure (e.g., 130/85 mm Hg or higher), and prothrombotic state (exemplified by high fibrinogen or plasminogen activator inhibitor in the blood).

Neurological Diseases

In some embodiments, the condition, disease or disorder is a neurological disorder (e.g., neurodegenerative disorder) or a psychiatric disorder. Non-limiting examples of neurological disorders include brain insulin resistance, mild cognitive impairment (MCI), Alzheimer's disease (AD), Parkinson's disease (PD), anxiety, dementia (e.g., senile dementia), traumatic brain injury, Huntington's chores, tardive dyskinesia, hyperkinesia, mania, Morbus Parkinson, steel-Richard syndrome, Down's syndrome, myasthenia gravis, nerve trauma, brain trauma, vascular amyloidosis, cerebral hemorrhage I with amyloidosis, brain inflammation, Friedrich's ataxia, acute confusion disorder, amyotrophic lateral sclerosis (ALS), glaucoma, and apoptosis-mediated degenerative diseases of the central nervous system (e.g., Creutzfeldt-Jakob Disease, bovine spongiform encephalopathy (mad cow disease), chronic wasting syndrome). See, e.g., US20060275288A1.

Non-limiting examples of psychiatric disorders include drug dependence/addiction (narcotics and amphetamines and attention deficit/hyperactivity disorder (ADHD). The chemical entities described herein can be useful in improving behavioral response to addictive drugs, decreasing drug dependence, prevention drug abuse relapse, and relieving anxiety caused by the absence of a given addictive substance. See, e.g., US20120021979A1.

In certain embodiments, the chemical entities described herein are useful in improving learning and memory by enhancing neuronal plasticity and facilitation of cellular differentiation, and also in preserving dopamine neurons and motor function in Morbus Parkinson.

Insulin-Related

In some embodiments, the condition, disease or disorder is impaired fasting glucose (IFG), impaired fasting glycemia (IFG), hyperglycemia, insulin resistance (impaired glucose homeostasis), hyperinsulinemia, elevated blood levels of fatty acids or glycerol, a hypoglycemic condition, insulin resistant syndrome, paresthesia caused by hyperinsulinemia, hyperlipidemia, hypercholesteremia, impaired wound healing, leptin resistance, glucose intolerance, increased fasting glucose, dyslipidemia (e.g., hyperlipidemia, atherogenic dyslipidemia characterized by high triglycerides and low HDL cholesterol), glucagonoma, hyperuricacidemia, hypoglycemia (e.g., nighttime hypoglycemia), and concomitant comatose endpoint associated with insulin.

In certain embodiments, the chemical entities described herein can reduce or slow down the progression of borderline type, impaired fasting glucose or impaired fasting glycemia into diabetes.

Autoimmune Disorders

In some embodiments, the condition, disease or disorder is an autoimmune disorder. Non-limiting examples of autoimmune disorders include multiple sclerosis, experimental autoimmune encephalomyelitis, autoimmune disorder is associated with immune rejection, graft versus host disease, uveitis, optic neuropathies, optic neuritis, transverse myelitis, inflammatory bowel disease, rheumatoid arthritis, ankylosing spondylitis, systemic lupus erythematosus, myasthenia gravis, and Graves' disease. See, e.g., US20120148586A1.

Stomach and Intestine-Related Disorders

In some embodiments, the condition, disease or disorder is a stomach or intestine related disorder. Non-limiting examples of these disorders include ulcers of any etiology (e.g. peptic ulcers, Zollinger-Ellison syndrome, drug-induced ulcers, ulcers related to infections or other pathogens), digestion disorders, malabsorption, short bowel syndrome, cul-de-sac syndrome, inflammatory bowel diseases (Crohn's disease and ulcerative colitis), celiac sprue, hypogammaglobulinemic sprue, chemotherapy and/or radiation therapy-induced mucositis and diarrhea, gastrointestinal inflammation, short bowel syndrome, colitis ulcerosa, gastric mucosal injury (e.g., gastric mucosal injury caused by aspirin), small intestinal mucosal injury, and cachexia (e.g., cancerous cachexia, tuberculous cachexia, cachexia associated with blood disease, cachexia associated with endocrine disease, cachexia associated with infectious disease, cachexia caused by acquired immunodeficiency syndrome).

Body Weight

In some embodiments, the chemical entities described herein can be used to reduce body weight (e.g., excess body weight), prevent body weight gain, induce weight loss, decrease body fat, or reduce food intake in a subject (e.g., a subject in need thereof). In certain embodiments, the weight increase in a subject may be attributed to excessive ingestion of food or unbalanced diets, or may be weight increase derived from a concomitant drug (e.g., insulin sensitizers having a PPARγ agonist-like action, such as troglitazone, rosiglitazone, englitazone, ciglitazone, pioglitazone and the like). Alternatively, the weight increase may be weight increase before reaching obesity, or may be weight increase in an obese subject. The weight increase may also be medication-induced weight gain or weight gain subsequent to cessation of smoking.

In some embodiments, the condition, disease or disorder is an eating disorder, such as hyperphagia, binge eating, bulimia, or compulsive eating.

Inflammatory Diseases

In some embodiments, the condition, disease or disorder is an inflammatory disorder. Non-limiting examples of inflammatory disorders include chronic rheumatoid arthritis, spondylitis deformans, arthritis deformans, lumbago, gout, post-operational or post-traumatic inflammation, bloating, neuralgia, laryngopharyngitis, cystitis, pneumonia, pancreatitis, enteritis, inflammatory bowel disease (including inflammatory large bowel disease), inflammation in metabolically important tissues including liver, fat, pancreas, kidney and gut, and a proinflammatory state (e.g., elevated levels of proinflammatory cytokines or markers of inflammation-like C-reactive protein in the blood).

Cancer

In some embodiments, the condition, disease or disorder is cancer. Suitable examples of cancer include breast cancer (e.g., invasive ductal breast cancer, noninvasive ductal breast cancer, inflammatory breast cancer), prostate cancer (e.g., hormone-dependent prostate cancer, hormone-independent prostate cancer), pancreatic cancer (e.g., ductal pancreatic cancer), gastric cancer (e.g., papillary adenocarcinoma, mucous adenocarcinoma, adenosquamous carcinoma), lung cancer (e.g., non-small cell lung cancer, small-cell lung cancer, malignant mesothelioma), colon cancer (e.g., gastrointestinal stromal tumor), rectal cancer (e.g., gastrointestinal stromal tumor), colorectal cancer (e.g., familial colorectal cancer, hereditary non-polyposis colorectal cancer, gastrointestinal stromal tumor), small intestinal cancer (e.g., non-Hodgkin's lymphoma, gastrointestinal stromal tumor), esophageal cancer, duodenal cancer, tongue cancer, pharyngeal cancer (e.g., nasopharyngeal cancer, oropharynx cancer, hypopharyngeal cancer), salivary gland cancer, brain tumor (e.g., pineal astrocytoma, pilocytic astrocytoma, diffuse astrocytoma, anaplastic astrocytoma), neurilemmoma, liver cancer (e.g., primary liver cancer, extrahepatic bile duct cancer), renal cancer (e.g., renal cell cancer, transitional cell cancer of the renal pelvis and ureter), bile duct cancer, endometrial cancer, uterine cervical cancer, ovarian cancer (e.g., epithelial ovarian cancer, extragonadal germ cell tumor, ovarian germ cell tumor, ovarian tumor of low malignant potential), bladder cancer, urethral cancer, skin cancer (e.g., intraocular (ocular) melanoma, Merkel cell carcinoma), hemangioma, malignant lymphoma, malignant melanoma, thyroid cancer (e.g., medullary thyroid cancer), parathyroid cancer, nasal cavity cancer, sinus cancer, bone tumor (e.g., osteosarcoma, Ewing tumor, uterine sarcoma, soft tissue sarcoma), angiofibroma, sarcoma of the retina, penis cancer, testicular tumor, pediatric solid tumor (e.g., Wilms' tumor, childhood kidney tumor), Kaposi's sarcoma, Kaposi's sarcoma caused by AIDS, tumor of maxillary sinus, fibrous histiocytoma, leiomyosarcoma, rhabdomyosarcoma, and leukemia (e.g., acute myeloid leukemia, acute lymphoblastic leukemia).

Combination Therapy

This disclosure contemplates both monotherapy regimens as well as combination therapy regimens.

In some embodiments, the methods described herein can further include administering one or more additional therapies (e.g., one or more additional therapeutic agents and/or one or more therapeutic regimens) in combination with administration of the compounds described herein.

In some embodiments, the methods described herein include administering a compound described herein in combination with one or more of a diet therapy (e.g., diet therapy for diabetes), an exercise therapy, blood sugar monitoring, and diet modifications.

In some embodiments, the compound described herein can be administered in combination with one or more of additional therapeutic agents.

Representative additional therapeutic agents include, but are not limited to, anti-obesity agents, therapeutic agents for diabetes, therapeutic agents for diabetic complications, therapeutic agents for hyperlipidemia, antihypertensive agents, diuretics, chemotherapeutics, immunotherapeutics, anti-inflammatory drugs, antithrombotic agents, anti-oxidants, therapeutic agents for osteoporosis, vitamins, antidementia drugs, erectile dysfunction drugs, therapeutic drugs for urinary frequency or urinary incontinence, therapeutic agents for NAFLD, and therapeutic agents for dysuria.

In some embodiments, the one or more additional therapeutic agents include those useful, e.g., as anti-obesity agents. Non-limiting examples include:
  monoamine uptake inhibitors (e.g., tramadol, phentermine, sibutramine, mazindol, fluoxetine, tesofensine);
  serotonin 2C receptor agonists (e.g., lorcaserin);
  serotonin 6 receptor antagonists;
  histamine H3 receptor modulator;
  GABA modulator (e.g., topiramate), including GABA receptor agonists (e.g., gabapentin, pregabalin);
  neuropeptide Y antagonists (e.g., velneperit);
  cannabinoid receptor antagonists (e.g., rimonabant, taranabant);
  ghrelin antagonists;
  ghrelin receptor antagonists;
  ghrelin acylation enzyme inhibitors;
  opioid receptor antagonists (e.g., GSK-1521498);
  orexin receptor antagonists;
  melanocortin 4 receptor agonists;
  11β-hydroxysteroid dehydrogenase inhibitors (e.g., AZD-4017, BVT-3498, INCB-13739);
  pancreatic lipase inhibitors (e.g., orlistat, cetilistat);
  β3 agonists (e.g., N-5984);
  diacylglycerol acyltransferase 1 (DGAT1) inhibitors;
  acetylCoA carboxylase (ACC) inhibitors;
  stearoyl-CoA desaturated enzyme inhibitors;
  microsomal triglyceride transfer protein inhibitors (e.g., R-256918);
  Na-glucose cotransporter 2 (SGLT-2) inhibitors (e.g., JNJ-28431754, dapagliflozin, AVE2268, TS-033, YM543, TA-7284, ASP1941, remogliflozin);
  NFK inhibitors (e.g., HE-3286);
  PPAR agonists (e.g., GFT-505, DRF-11605, gemfibrozil and fenofibrate);
  phosphotyrosine phosphatase inhibitors (e.g., sodium vanadate, trodusquemin);
  GPR119 agonists (e.g., PSN-821, MBX-2982, APD597);
  glucokinase activators (e.g., piragliatin, AZD-1656, AZD6370, TTP-355, compounds described in W0006/112549, W0007/028135, W0008/047821, W0008/050821, W0008/136428 and W0008/156757);
  leptin, leptin derivatives (e.g., metreleptin), leptin resistance improving drugs;
  CNTF (ciliary neurotrophic factor);
  BDNF (brain-derived neurotrophic factor);
  cholecystokinin agonists, amylin preparations (e.g., pramlintide, AC-2307);
  neuropeptide Y agonists (e.g., PYY3-36, derivatives of PYY3-36, obineptide, TM-30339, TM-30335);
  oxyntomodulin (OXM) preparations;
  appetite suppressants (e.g. ephedrine);
  FGF21 preparations (e.g., animal FGF21 preparations extracted from the pancreas of bovine or swine; human FGF21 preparations genetically synthesized using *Escherichia coli* or yeast; fragments or derivatives of FGF21); and
  anorexigenic agents (e.g., P-57).

In some embodiments, the one or more additional therapeutic agents include those useful, e.g., as anti-diabetic agents. Non-limiting examples include:
  insulin and insulin preparations (e.g., animal insulin preparations extracted from the pancreas of bovine or swine; human insulin preparations genetically synthesized using *Escherichia coli* or yeast; zinc insulin; protamine zinc insulin; fragment or derivative of insulin (e.g., INS-1), oral insulin preparation, synthetic human insulin);
  insulin sensitizers (e.g., pioglitazone or a salt thereof);
  biguanides (e.g., metformin, buformin or a salt thereof (e.g., hydrochloride, fumarate, succinate));
  glucagon analogs (e.g., any of glucagon analogs described, e.g., in WO 2010/011439);
  agents which antagonize the actions of or reduce secretion of glucagon;
  sulfonylurea agents (e.g., chlorpropamide, tolazamide, gliclazide, glimepiride, tolbutamide, glibenclamide, gliclazide, acetohexamide, glyclopyamide, glybuzole, glyburide);
  thiazolidinedione agents (e.g. rosiglitazone or pioglitazone);
  α-glucosidase inhibitors (e.g., voglibose, acarbose, miglitol, emiglitate);
  insulin secretagogues, such as prandial glucose regulators (sometimes called "short-acting secretagogues"), e.g., meglitinides (e.g. repaglinide and nateglinide);
  cholinesterase inhibitors (e.g., donepezil, galantamine, rivastigmine, tacrine);
  NMDA receptor antagonists;
  dual GLP-1/GIP receptor agonists (e.g., LBT-2000, ZPD1-70);
  GLP-1R agonists (e.g., exenatide, liraglutide, albiglutide, dulaglutide, AVE-0010, S4P and Boc5); and
  dipeptidyl peptidase IV (DPP-4) inhibitors (e.g., vildagliptin, dutogliptin, gemigliptin, alogliptin, saxagliptin, sitagliptin, linagliptin, berberine, alogliptin, BI1356, GRC8200, MP-513, PF-00734200, PHX1149, SK-0403, ALS2-0426, TA-6666, TS-021, KRP-104, trelagliptin).

In some embodiments, the one or more additional therapeutic agents include those useful, e.g., for treating NAFL and NASH. Non-limiting examples include glycyrrhizin, schisandra extract, ascorbic acid, glutathione, silymarin, lipoic acid, and d-alpha-tocopherol, ascorbic acid, glutathione, vitamin B-complex, glitazones/thiazolidinediones (e.g., troglitazone, rosiglitazone, pioglitazone), metformin, cystamine, sulfonylureas, alpha-glucosidase inhibitors, meglitinides, vitamin E, tetrahydrolipstatin, milk thistle protein, anti-virals, and anti-oxidants.

In some embodiments, the one or more additional therapeutic agents include those useful, e.g., for treating diabetic complications. Non-limiting examples include:
  aldose reductase inhibitors (e.g., tolrestat, epalrestat, zopolrestat, fidarestat, CT-112, ranirestat, lidorestat);

neurotrophic factor and increasing agents thereof (e.g., NGF, NT-3, BDNF, neurotrophic production/secretion promoting agents described in WO01/14372 (e.g., 4-(4-chlorophenyl)-2-(2-methyl-1-imidazolyl)-5-[3-(2-methylphenoxyl)propyl]oxazole), compounds described in WO2004/039365);

PKC inhibitors (e.g., ruboxistaurin mesylate);

AGE inhibitors (e.g., ALT946, N-phenacylthiazolium bromide (ALT766), EXO-226, pyridorin, pyridoxamine);

serotonin and noradrenalin reuptake inhibitors (e.g., duloxetine);

sodium channel inhibitors (e.g., lacosamide);

active oxygen scavengers (e.g., thioctic acid);

cerebral vasodilators (e.g., tiapuride, mexiletine);

somatostatin receptor agonists (e.g., BIM23190); and apoptosis signal regulating kinase-1 (ASK-1) inhibitors.

In some embodiments, the one or more additional therapeutic agents include those useful, e.g., for treating hyperlipidemia. Non-limiting examples include:

HMG-COA reductase inhibitors (e.g., pravastatin, simvastatin, lovastatin, atorvastatin, fluvastatin, rosuvastatin, pitavastatin or a salt thereof (e.g., sodium salt, calcium salt));

squalene synthase inhibitors (e.g., compounds described in WO97/10224, e.g., N-[[(3R,5S)-1-(3-acetoxy-2,2-dimethylpropyl)-7-chloro-5-(2,3-dimethoxyphenyl)-2-oxo-1,2,3,5-tetrahydro-4, 1-benzoxazepin-3-yl]acetyl]piperidin-4-acetic acid);

fibrate compounds (e.g., bezafibrate, clofibrate, simfibrate, clinofibrate);

anion exchange resin (e.g., cholestyramine);

nicotinic acid drugs (e.g., nicomol, niceritrol, niaspan);

phytosterols (e.g., soysterol, gamma oryzanol (γ-oryzanol));

cholesterol absorption inhibitors (e.g., zechia);

CETP inhibitors (e.g., dalcetrapib, anacetrapib); and

ω-3 fatty acid preparations (e.g., ω-3-fatty acid ethyl esters 90).

In some embodiments, the one or more additional therapeutic agents include those useful, e.g., as anti-hypertensive agents. Non-limiting examples include:

angiotensin converting enzyme inhibitors (e.g., captopril, enalapril, delapril);

angiotensin II antagonists (e.g., candesartan cilexetil, candesartan, losartan, losartan potassium, eprosartan, valsartan, telmisartan, irbesartan, tasosartan, olmesartan, olmesartan medoxomil, azilsartan, azilsartan medoxomil);

calcium antagonists (e.g., manidipine, nifedipine, amlodipine, efonidipine, nicardipine, cilnidipine); and β-blockers (e.g., metoprolol, atenolol, propranolol, carvedilol, pindolol).

In some embodiments, the one or more additional therapeutic agents include those useful, e.g., as diuretics. Non-limiting examples include:

xanthine derivatives (e.g., theobromine sodium salicylate, theobromine calcium salicylate);

thiazide preparations (e.g., ethiazide, cyclopenthiazide, trichloromethiazide, hydrochlorothiazide, hydroflumethiazide, benzylhydrochlorothiazide, penfluthiazide, polythiazide, methyclothiazide);

antialdosterone preparations (e.g., spironolactone, triamterene);

carbonic anhydrase inhibitors (e.g., acetazolamide); and chlorobenzenesulfonamide agents (e.g., chlortalidone, mefruside, indapamide).

In some embodiments, the one or more additional therapeutic agents include those useful, e.g., as immunotherapeutic agents. Non-limiting examples include: microbial or bacterial compounds (e.g., muramyl dipeptide derivative, picibanil); polysaccharides having immunoenhancing activity (e.g., lentinan, sizofiran, krestin); cytokines obtained by genetic engineering approaches (e.g., interferon, interleukin (IL) such as IL-1, IL-2, IL-12); and colony-stimulating factors (e.g., granulocyte colony-stimulating factor, erythropoietin).

In some embodiments, the one or more additional therapeutic agents include those useful, e.g., as anti-thrombotic agents. Non-limiting examples include: heparins (e.g., heparin sodium, heparin calcium, enoxaparin sodium, dalteparin sodium); warfarin (e.g., warfarin potassium); anti-thrombin drugs (e.g., aragatroban, dabigatran); FXa inhibitors (e.g., rivaroxaban, apixaban, edoxaban, YM150, compounds described in WO02/06234, WO2004/048363, WO2005/030740, WO2005/058823, and WO2005/113504); thrombolytic agents (e.g., urokinase, tisokinase, alteplase, nateplase, monteplase, pamiteplase); and platelet aggregation inhibitors (e.g., ticlopidine hydrochloride, clopidogrel, prasugrel, E5555, SHC530348, cilostazol, ethyl icosapentaene, beraprost sodium, sarpogrelate hydrochloride).

In some embodiments, the one or more additional therapeutic agents include those useful, e.g., for treating osteoporosis. Non-limiting examples include: alfacalcidol, calcitriol, elcatonin, calcitonin salmon, estriol, ipriflavone, pamidronate disodium, alendronate sodium hydrate, incadronate disodium, and risedronate disodium. Suitable examples of vitamins include vitamin B1 and vitamin B12. Suitable examples of erectile dysfunction drugs include apomorphine and sildenafil citrate. Suitable examples of therapeutic agents for urinary frequency or urinary incontinence include flavoxate hydrochloride, oxybutynin hydrochloride and propiverine hydrochloride. Suitable examples of therapeutic agents for dysuria include acetylcholine esterase inhibitors (e.g., distamine). Suitable examples of anti-inflammatory agents include nonsteroidal anti-inflammatory drugs such as aspirin, acetaminophen, indomethacin.

Other additional therapeutic agents include:

agents that modulate hepatic glucose balance (e.g., fructose 1,6-bisphosphatase inhibitors, glycogen phosphorylase inhibitors, glycogen synthase kinase inhibitors, glucokinase activators);

agents designed to treat the complications of prolonged hyperglycemia, such as aldose reductase inhibitors (e.g. epalrestat and ranirestat);

agents used to treat complications related to micro-angiopathies;

anti-dyslipidemia agents, such as HMG-COA reductase inhibitors (statins, e.g. rosuvastatin);

cholesterol-lowering agents;

bile acid sequestrants (e.g., cholestyramine);

cholesterol absorption inhibitors (e.g. plant sterols such as phytosterols);

cholesteryl ester transfer protein (CETP) inhibitors;

inhibitors of the ileal bile acid transport system (IBAT inhibitors);

bile acid binding resins;

nicotinic acid (niacin) and analogues thereof;

anti-oxidants, such as probucol;

omega-3 fatty acids;

antihypertensive agents, including adrenergic receptor antagonists, such as beta blockers (e.g. atenolol), alpha blockers (e.g. doxazosin), and mixed alpha/beta blockers (e.g. labetalol);

adrenergic receptor agonists, including alpha-2 agonists (e.g. clonidine);

angiotensin converting enzyme (ACE) inhibitors (e.g. lisinopril);

calcium channel blockers, such as dihydropridines (e.g. nifedipine), phenylalkylamines (e.g. verapamil), and benzothiazepines (e.g. diltiazem);

angiotensin II receptor antagonists (e.g. candesartan);

aldosterone receptor antagonists (e.g. eplerenone);

centrally acting adrenergic drugs, such as central alpha agonists (e.g. clonidine);

diuretic agents (e.g. furosemide);

haemostasis modulators, including antithrombotics (e.g., activators of fibrinolysis), thrombin antagonists, factor VIIa inhibitors, anticoagulants (e.g., vitamin K antagonists such as warfarin), heparin and low molecular weight analogues thereof, factor Xa inhibitors, and direct thrombin inhibitors (e.g. argatroban);

antiplatelet agents (e.g., cyclooxygenase inhibitors (e.g. aspirin));

adenosine diphosphate (ADP) receptor inhibitors (e.g. clopidogrel);

phosphodiesterase inhibitors (e.g. cilostazol);

glycoprotein IIB/IIA inhibitors (e.g. tirofiban);

adenosine reuptake inhibitors (e.g. dipyridamole);

noradrenergic agents (e.g. phentermine);

serotonergic agents (e.g. sibutramine);

diacyl glycerolacyltransferase (DGAT) inhibitors;

feeding behavior modifying agents;

pyruvate dehydrogenase kinase (PDK) modulators;

serotonin receptor modulators;

monoamine transmission-modulating agents, such as selective serotonin reuptake inhibitors (SSRI) (e.g. fluoxetine), noradrenaline reuptake inhibitors (NARI), noradrenaline-serotonin reuptake inhibitors (SNRI), and monoamine oxidase inhibitors (MAOI) (e.g. toloxatone and amiflamine);

compounds described in W0007/013694, WO2007/018314, WO2008/093639 and WO2008/099794;

GPR40 agonists (e.g., fasiglifam or a hydrate thereof, compounds described in WO2004/041266, WO2004/106276, WO2005/063729, WO2005/063725, WO2005/087710, WO2005/095338, WO2007/013689 and WO2008/001931);

SGLT1 inhibitors;

adiponectin or agonist thereof;

IKK inhibitors (e.g., AS-2868);

somatostatin receptor agonists;

ACC2 inhibitors;

cachexia-ameliorating agents, such as a cyclooxygenase inhibitors (e.g., indomethacin), progesterone derivatives (e.g., megestrol acetate), glucocorticoids (e.g., dexamethasone), metoclopramide agents, tetrahydrocannabinol agents, agents for improving fat metabolism (e.g., eicosapentaenoic acid), growth hormones, IGF-1, antibodies against a cachexia-inducing factor TNF-α, LIF, IL-6, and oncostatin M;

metabolism-modifying proteins or peptides such as glucokinase (GK), glucokinase regulatory protein (GKRP), uncoupling proteins 2 and 3 (UCP2 and UCP3), peroxisome proliferator-activated receptor a (PPARα);

MC4r agonists;

insulin receptor agonist;

PDE 5 inhibitors;

glycation inhibitors (e.g., ALT-711);

nerve regeneration-promoting drugs (e.g., Y-128, VX853, prosaptide);

antidepressants (e.g., desipramine, amitriptyline, imipramine);

antiepileptic drugs (e.g., lamotrigine, trileptal, keppra, zonegran, pregabalin, harkoseride, carbamazepine);

antiarrhythmic drugs (e.g., mexiletine);

acetylcholine receptor ligands (e.g., ABT-594);

endothelin receptor antagonists (e.g., ABT-627);

narcotic analgesics (e.g., morphine);

a2 receptor agonists (e.g., clonidine);

local analgesics (e.g., capsaicin);

antianxiety drugs (e.g., benzothiazepine);

phosphodiesterase inhibitors (e.g., sildenafil);

dopamine receptor agonists (e.g., apomorphine);

cytotoxic antibodies (e.g., T-cell receptor and IL-2 receptor-specific antibodies);

B cell depleting therapies (e.g., anti-CD20 antibody (e.g., rituxan), i-BLyS antibody);

drugs affecting T cell migration (e.g., anti-integrin alpha 4/beta 1 antibody (e.g., tysabri);

drugs that act on immunophilins (e.g., cyclosporine, tacrolimus, sirolimus, rapamycin);

interferons (e.g., IFN-β);

immunomodulators (e.g., glatiramer);

TNF-binding proteins (e.g., circulating receptors);

immunosuppressants (e.g., mycophenolate); and metaglidasen, AMG-131, balaglitazone, MBX-2044, rivoglitazone, aleglitazar, chiglitazar, lobeglitazone, PLX-204, PN-2034, GFT-505, THR-0921, exenatide, exendin-4, memantine, midazolam, ketoconazole, ethyl icosapentate, clonidine, azosemide, isosorbide, ethacrynic acid, piretanide, bumetanide, etoposide.

In certain embodiments, the second therapeutic agent or regimen is administered to the subject prior to contacting with or administering the chemical entity (e.g., about one hour prior, or about 6 hours prior, or about 12 hours prior, or about 24 hours prior, or about 48 hours prior, or about 1 week prior, or about 1 month prior).

In other embodiments, the second therapeutic agent or regimen is administered to the subject at about the same time as contacting with or administering the chemical entity. By way of example, the second therapeutic agent or regimen and the chemical entity are provided to the subject simultaneously in the same dosage form. As another example, the second therapeutic agent or regimen and the chemical entity are provided to the subject concurrently in separate dosage forms.

In still other embodiments, the second therapeutic agent or regimen is administered to the subject after contacting with or administering the chemical entity (e.g., about one hour after, or about 6 hours after, or about 12 hours after, or about 24 hours after, or about 48 hours after, or about 1 week after, or about 1 month after).

Patient Selection

In some embodiments, the methods described herein further include the step of identifying a subject (e.g., a patient) in need of such treatment (e.g., by way of biopsy, endoscopy, or other conventional method known in the art).

Compound Preparation and Biological Assays

As can be appreciated by the skilled artisan, methods of synthesizing the compounds of the formulae herein will be evident to those of ordinary skill in the art. Synthetic chemistry transformations and protecting group methodologies (protection and deprotection) useful in synthesizing the compounds described herein are known in the art and include, for example, those such as described in R. Larock, Comprehensive Organic Transformations, VCH Publishers (1989); T. W. Greene and RGM. Wuts, Protective Groups in Organic Synthesis, 2d. Ed., John Wiley and Sons (1991); L. Fieser and M. Fieser, Fieser and Fieser's Reagents for Organic Synthesis, John Wiley and Sons (1994); and L. Paquette, ed., Encyclopedia of Reagents for Organic Synthesis, John Wiley and Sons (1995), and subsequent editions thereof.

In some embodiments, intermediates useful for preparing the compounds described herein can be prepared using the chemistries delineated in any one or more of the following schemes and non-limiting examples.

A. Abbreviations:
AcOH=Acetic acid
DCM=Dichloromethane
DIC=Diisopropylcarbodiimide
DMF=N,N-dimethylformamide
DMSO=Dimethylsulfoxide
ESI-MS=Electrospray ionization mass spectrometry
Et$_2$O=Diethyl ether
EtOAc=Ethyl acetate
EtOH=Ethanol
HATU=1-[Bis(dimethylamino)methylene]-1H-1,2,3-triazolo[4,5-b]pyridinium 3-oxide hexafluorophosphate
HCl=Hydrochloric acid
HPLC=High performance liquid chromatography
LC-MS=Liquid chromatography-mass spectrometry
MeCN=Acetonitrile
MeOH=Methanol
NMR=Nuclear magnetic resonance
Oxyma=Ethyl (hydroxyamino)cyanoacetate
SFC=Supercritical fluid chromatography
TEA=Triethylamine
TFA=Trifluoroacetic acid
THF=Tetrahydrofuran
TIS=Triisopropylsilane
TLC=Thin layer chromatography B. Peptide Sequences Corresponding to Compounds in Table 2:

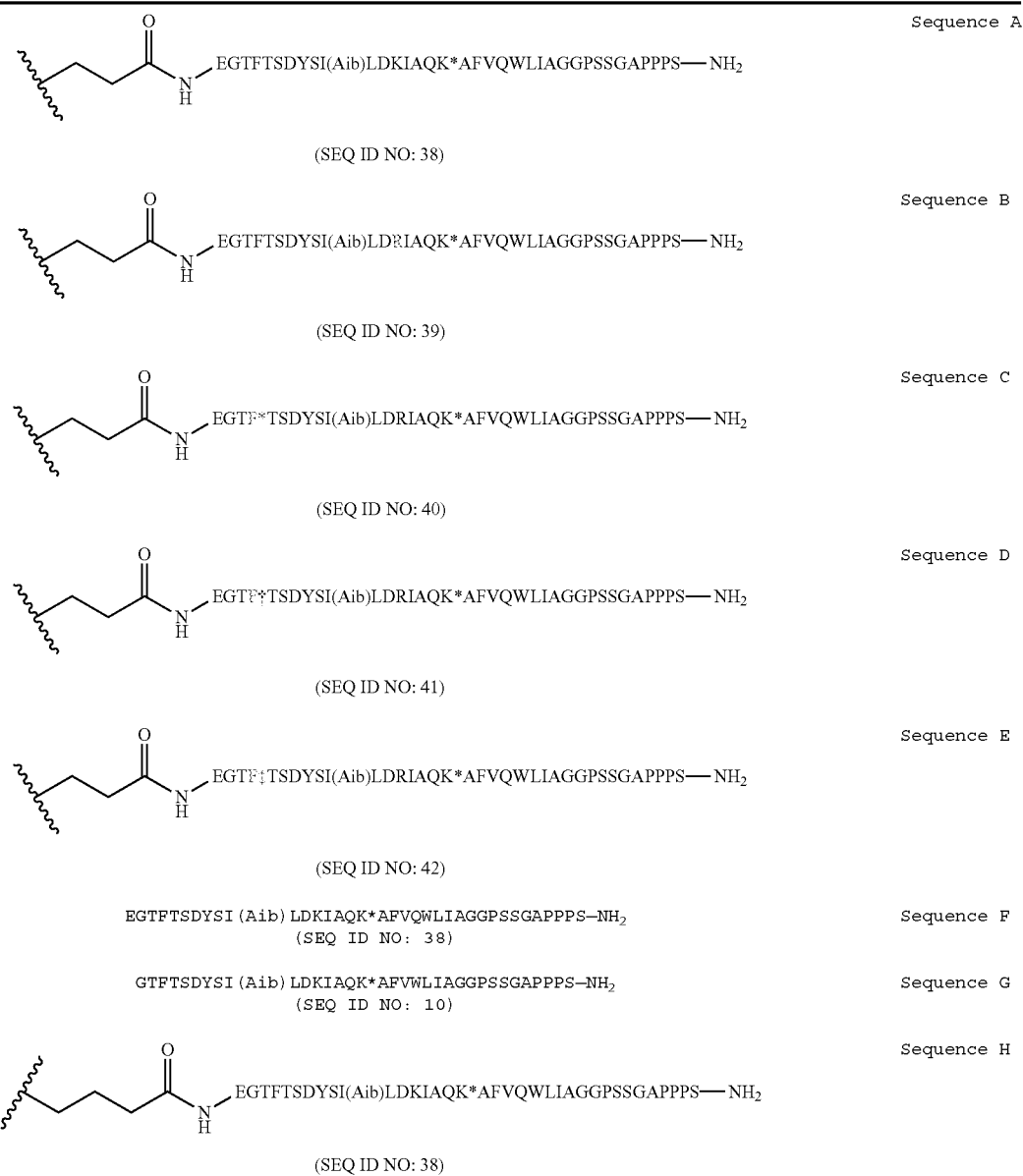

Sequence I
EGTFTSDYSIYLDKIAQK*AFVQWLIAGGPSSGAPPS—NH₂
(SEQ ID NO: 43)
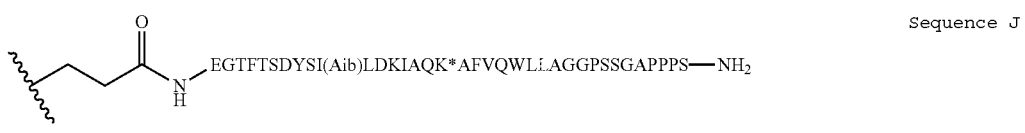
Sequence J
EGTFTSDYSI(Aib)LDKIAQK*AFVQWLIAGGPSSGAPPPS—NH₂
(SEQ ID NO: 44)
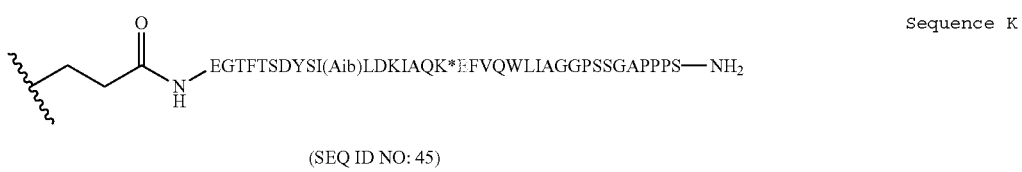
Sequence K
EGTFTSDYSI(Aib)LDKIAQK*ƗFVQWLIAGGPSSGAPPPS—NH₂
(SEQ ID NO: 45)
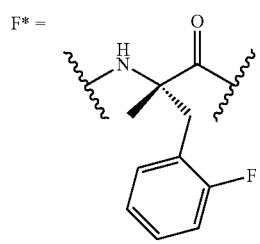
F* =
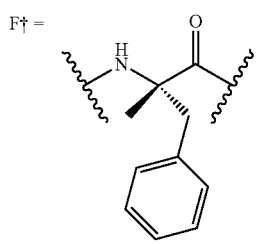 [SMILES: *N[C@@](C)(Cc1ccccc1)C(*)=O]
FƗ =
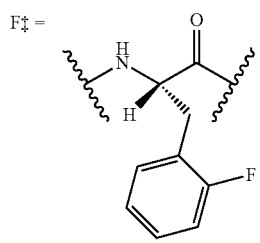 [SMILES: *N[C@@H](Cc1ccccc1F)C(*)=O]
FƗ =
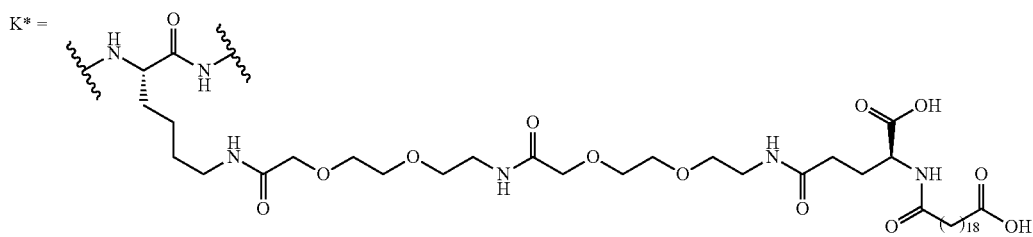
K* =
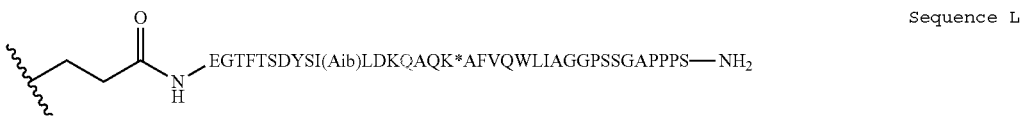
Sequence L
EGTFTSDYSI(Aib)LDKQAQK*AFVQWLIAGGPSSGAPPPS—NH₂
(SEQ ID NO: 46)
Sequence M
EGTFTSDYSIYLDKQAA(Aib)ƗFVNWLIAGGPSSGAPPPSK*—NH₂
(SEQ ID NO: 47)

-continued
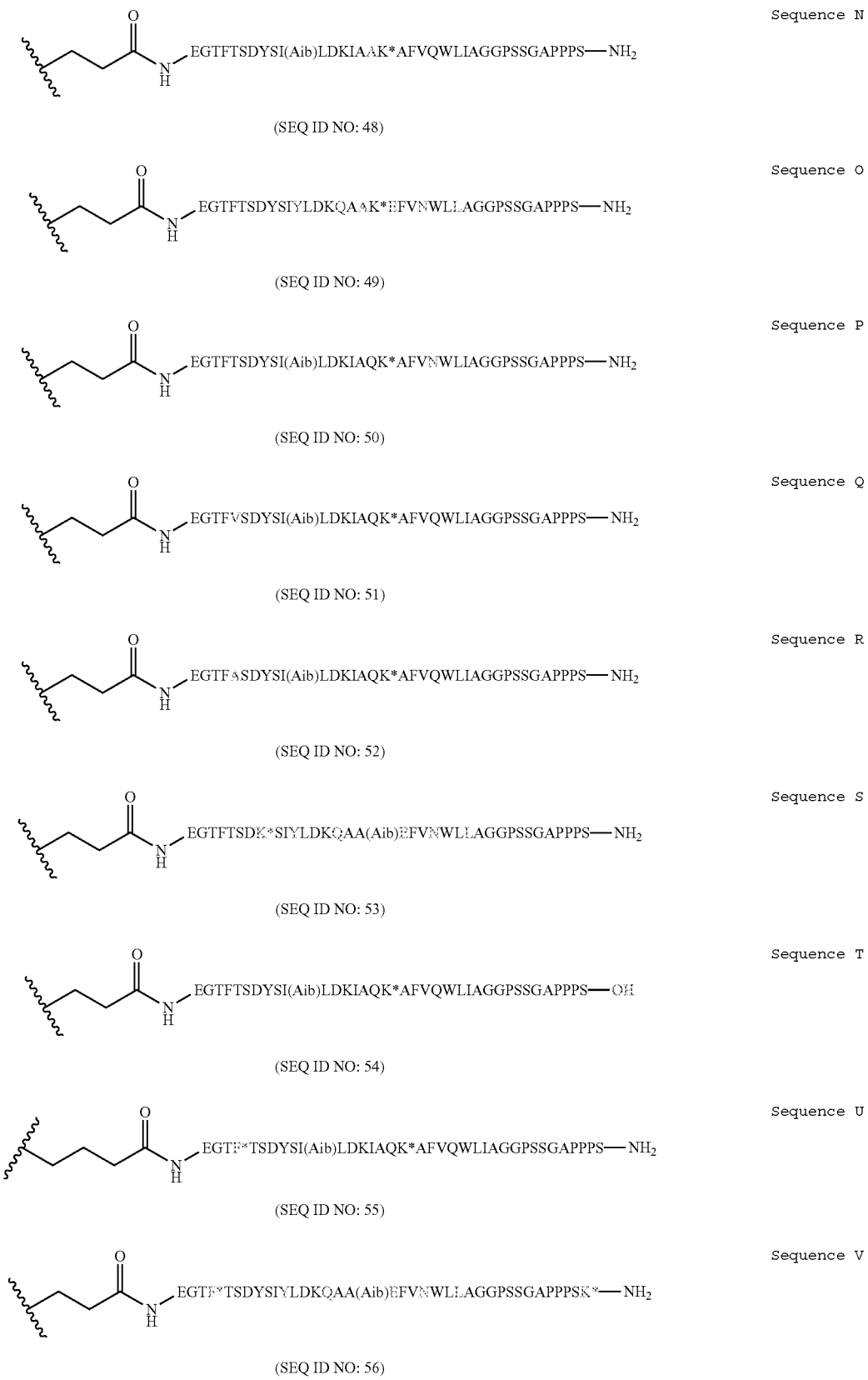

-continued
Sequence W
(SEQ ID NO: 57)
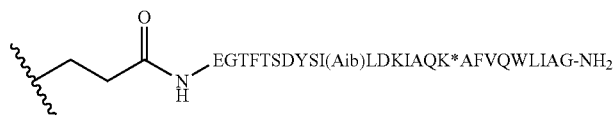
Sequence X
(SEQ ID NO: 58)
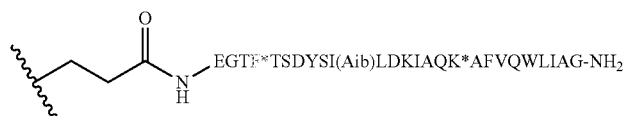
Sequence Y
(SEQ ID NO: 59)
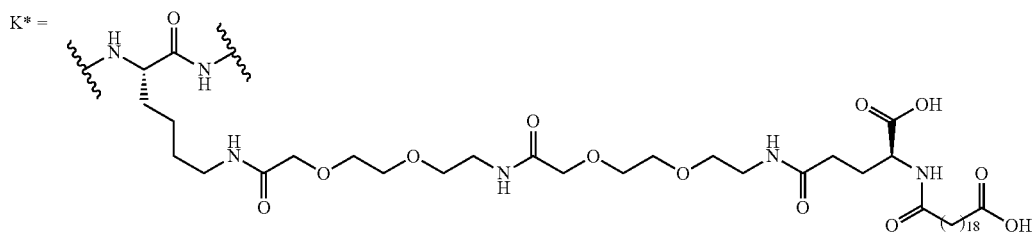
K* =
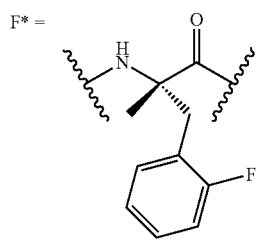 [SMILES: *N[C@@](C)(Cc1ccccc1F)C(*)=O]
F* =
Sequence Z
(SEQ ID NO: 60)
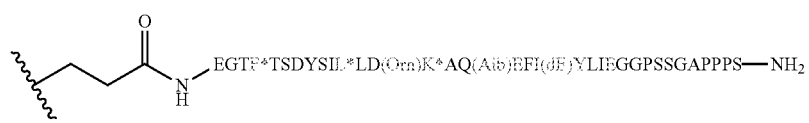
Sequence AA
(SEQ ID NO: 61)
Sequence AB
(SEQ ID NO: 62)

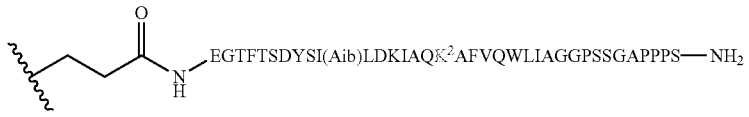

Sequence AC

EGTFTSDYSI(Aib)LDKIAQK²AFVQWLIAGGPSSGAPPPS—NH₂

(SEQ ID NO: 63)

(dP)GTFTSDYSI(Aib)LDKIAQK*AFVQWLIAGGPSSGAPPPS-NH₂  
(SEQ ID NO: 64)

Sequence AD

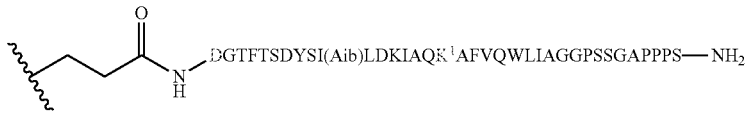

Sequence AE

DGTFTSDYSI(Aib)LDKIAQK¹AFVQWLIAGGPSSGAPPPS—NH₂

(SEQ ID NO: 65)

Sequence AF (dE)GTFTSDYSI(Aib)LDKIAQK¹AFVQWLIAGGPSSGAPPPS—NH₂

(SEQ ID NO: 66)

Sequence AG

EGTFTSDYSIYLDKK*AA(Aib)EFVNWLLAGGPSSGAPPPS—NH₂

(SEQ ID NO: 67)

Sequence AH

EGTFTSKYSIYLDKQAA(Aib)EFVK*WLLAGGPSSGAPPPS—NH₂

(SEQ ID NO: 68)

F* = 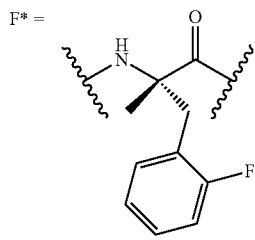 [SMILES: *N[C@@](C)(Cc1ccccc1F)C(*)=O]

Orn = 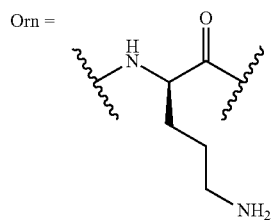 [SMILES: *N[C@H](CCCN)C(*)=O]

L* = 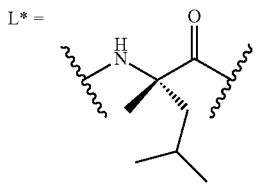 [SMILES: *N[C@@](C)(CC(C)C)C(*)=O]

dE = 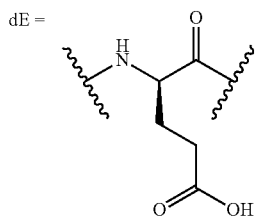 [SMILES: *N[C@H](CCC(=O)O)C(*)=O]

dD = 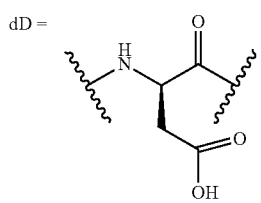 [SMILES: *N[C@H](CC(=O)O)C(*)=O]

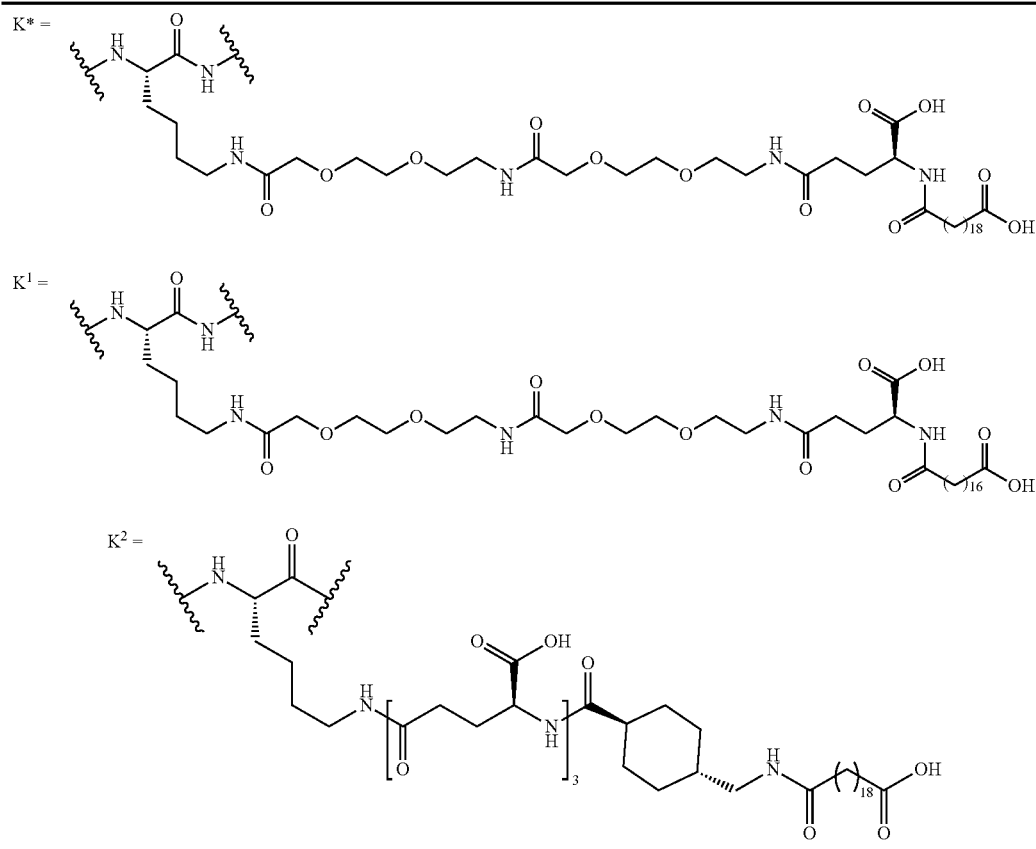

C. General Procedures and Protocols

Peptide Synthesis

All peptide sequences were synthesized conventionally with microwave synthesis conditions using a CEM Liberty Blue system on 0.025-0.1 mmol scale using a 5-fold excess of reagents. Fmoc-amino acids (0.2 M solution in DMF), DIC (0.5 or 1.0 M solution in DMF) and Oxyma (1.0 M solution in DMF) were employed on Rink amide resin (estimated loading 0.2 mmol/g) and Fmoc-Gly-Wang resin (estimated loading 0.27 mmol/g).

Cleavage of Compound from Resin

Cleavage of compound was performed with TFA/TIS/H$_2$O/PhOH (88:2:5:5 v/v/v/v), 5 mL/100 mg of resin for 1-3 hours. The cleavage mixture was filtered and the resin was washed with TFA (2×), and the filtrate and washes were combined and concentrated. Diethyl ether (5 mL/100 mg of resin) was added to the residue afforded to precipitate the peptide, which was isolated by centrifugation.

Purification of Compounds by Preparative HPLC

Crude peptides were dissolved in glacial AcOH or DMSO and purified by HPLC using the following conditions:
Column: Phenomenex Jupiter 10 um Proteo 90 A 250×21.2 mm AXIA packed Solvent A=25 mM ammonium acetate, Solvent B=MeCN

| Gradient | | |
|---|---|---|
| Time (min) | % A | % B |
| 0 | 100 | 0 |
| 3 | 100 | 0 |
| 4 | 70 | 30 |
| 33 | 40 | 60 |
| 34 | 0 | 100 |
| 43 | 0 | 100 |
| 43.1 | 100 | 0 |
| 48 | 100 | 0 |

Synthesis of Intermediates to Compounds Described in this Invention

Synthesis of I-2

Scheme 1

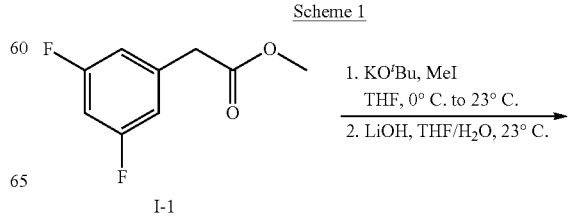

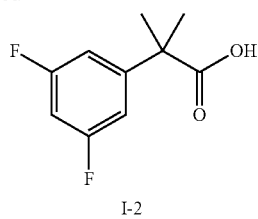

I-2

The synthesis of acid I-2 is depicted in Scheme 1. A solution of methyl ester I-1 (254.3 mg, 1.37 mmol) in THF (10 mL) in the presence of methyl iodide (0.85 mL, 10.0 equiv.) was cooled in an ice-water bath. A solution of potassium tert-butoxide (1.6 M in THF, 5.1 mL, 6.0 equiv.) was added over 2 minutes. The reaction mixture was then allowed to warm to ambient temperature. After 19 hours, 1M HCl (30 mL) was added to quench the reaction. The aqueous phase was extracted with EtOAc (2×50 mL). The organic extracts were combined and washed with brine (30 mL), dried (MgSO$_4$) and concentrated to afford the crude methylation product as a brown oil. The brown oil was redissolved in THF (6 mL) and lithium hydroxide (98.1 mg, 3.0 equiv.) was added as a solution in H$_2$O (2 mL). The reaction mixture was stirred at ambient temperature for 20 hours. The reaction mixture was acidified with 1M HCl (20 mL). The aqueous phase was extracted with EtOAc (2×30 mL). The organic extracts were combined and washed with brine (30 mL), dried (MgSO$_4$) and concentrated to afford the crude product, which was purified by preparative HPLC solvent A=0.1% TFA in H$_2$O, solvent B=0.1% TFA in MeCN, gradient of 0-100% B over 30 minutes) to afford carboxylic acid I-2 (63.6 mg, 23% yield over 2 steps) as a colorless oil, m/z (ESI): 201.1, (M+1).

Synthesis of I-8

The synthesis of I-8 involved 5 steps as shown in scheme 2.

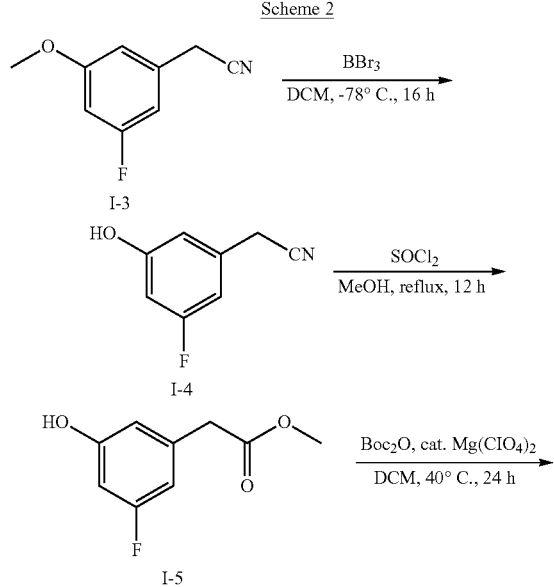

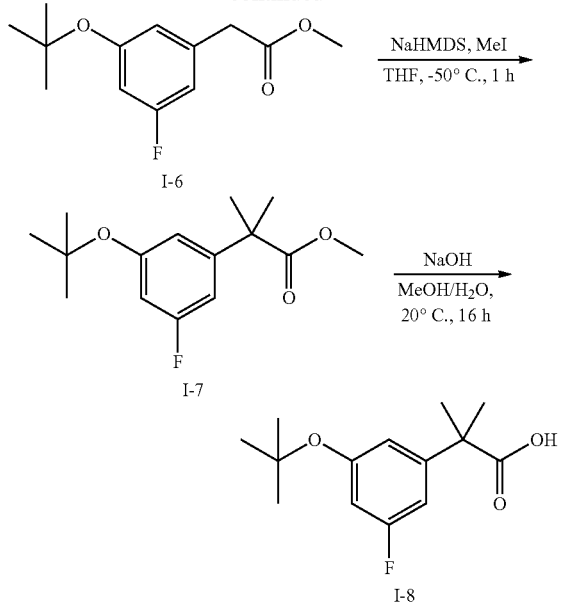

2-(3-fluoro-5-hydroxyphenyl)acetonitrile (I-4)
To a solution of 2-(3-fluoro-5-methoxyphenyl)acetonitrile (3 g, 18.2 mmol, 1 equiv, cas:914637-31-3) in DCM (30 mL) stirred at −78° C. was added BBr$_3$ (9.1 g, 36.4 mmol, 2 equiv.). The reaction mixture was allowed to warm to 25° C. and stirred for 16 hours. On completion, the reaction mixture was diluted with H$_2$O (30 mL) and extracted with EtOAc (3×20 mL). The combined organic extracts were dried and concentrated to afford 2.2 g of the crude phenol I-4 (84% yield, 90% purity) as a yellow solid. MS (ESI, pos. ion) m/z:152.1, (M+1).
Methyl 2-(3-fluoro-5-hydroxyphenyl)acetate (1-5)
To a solution of 2-(3-fluoro-5-hydroxyphenyl)acetonitrile (2.3 g, 15 mmol, 1 equiv.) in MeOH (20 mL) stirred at ambient temperature was added 5 mL of thionyl chloride. After completion of the addition, the reaction mixture was refluxed for 16 hours. The reaction mixture was then diluted with H$_2$O (15 mL) and extracted with EtOAc (3×20 mL). The combined organic extracts were dried and concentrated to afford 2.0 g of the crude methyl ester I-5 (77% yield, 95% purity) as a colourless oil. MS (ESI, pos. ion) m/z: 185.1, (M+1).
Methyl 2-(3-(tert-butoxy)-5-fluorophenyl)acetate (I-6)
To a solution of methyl 2-(3-fluoro-5-hydroxyphenyl)acetate (2.0 g, 13 mmol, 1 equiv.), and Boc$_2$O (8.5 g, 39 mmol, 3 equiv.) in DCM (30 mL) stirred at 40° C. was added Mg(ClO$_4$)$_2$ (0.29 g, 1.3 mmol, 0.1 equiv.). The reaction mixture was stirred at 40° C. for 20 hours. When the reaction was deemed complete, the reaction mixture was diluted with H$_2$O (15 mL) and extracted with EtOAc (3×20 mL). The combined organic extracts were dried and concentrated to a residue, which was purified by silica gel chromatography (Petroleum ether:EtOAc=1:15) to afford 1.8 g of ester I-6 (67% yield, 95% purity) as a white solid. 1H NMR (400 MHZ, CD$_3$OD) δ 6.97 (d, J=9.2 Hz, 1H), 6.94-6.87 (m, 2H), 3.70 (s, 5H), 1.53 (s, 9H).
Methyl 2-(3-(tert-butoxy)-5-fluorophenyl)-2-methylpropanoate (I-7)
Methyl 2-[3-(tert-butoxy)-5-fluorophenyl]acetate (1.2 g, 0.005 mol, 1 equiv.) was dissolved in THF (20 mL) in the presence of NaHMDS (2.3 g, 0.013 mol, 2.5 equiv.). The solution was cooled to −50° C. and stirred under nitrogen for 30 minutes. Methyl iodide (3.55 g, 0.025 mol, 5 equiv.) was then added and the reaction mixture was stirred at −50° C. for 30 minutes. Once the reaction was deemed complete, the reaction mixture was diluted with $H_2O$ (15 mL) and extracted with EtOAc (3×20 mL). The combined organic extracts were dried and concentrated to a residue, which was purified by silica gel chromatography (Petroleum ether: EtOAc=1:20) to afford 1.0 g of ester I-7 (70% yield, 95% purity) as colourless oil. 1H NMR (400 MHZ, $CD_3OD$) δ 6.80 (d, J=10.2 Hz, 1H), 6.72 (s, 1H), 6.62 (dd, J=10.2, 2.1 Hz, 1H), 3.65 (s, 3H), 1.52 (s, 6H), 1.34 (s, 9H).

2-(3-(tert-butoxy)-5-fluorophenyl)-2-methylpropanoic acid (I-8)

To a solution of ester, I-7 (200 mg, 0.8 mmol, 1 equiv.) in MeOH (10 mL) stirred at 25° C. was added a solution of sodium hydroxide (160 mg, 4 mmol, 5 equiv.) in $H_2O$ (5 mL). The reaction mixture was stirred at 25° C. for 5 hours. On completion, the reaction was cooled in an ice bath and acidified to pH 5 by addition of 1N HCl (2.0 mL). The reaction mixture was extracted with EtOAc (3×20 mL) and the combined organic extracts were dried and concentrated to afford 150 mg (70% yield, 95% purity) of the carboxylic acid I-8 as a white solid, which was taken on to the next step without further purification. 1H NMR (400 MHZ, $CD_3OD$) δ 6.84 (dd, J=10.2, 2.0 Hz, 1H), 6.80 (d, J=1.6 Hz, 1H), 6.61 (d, J=10.2 Hz, 1H), 1.51 (s, 6H), 1.34 (s, 9H).

The synthesis of compound I-12 involved 3 steps as depicted in scheme 3.

Methyl 2-(3-fluoro-5-(trifluoromethoxy)phenyl)acetate (I-10)

To a solution of 2-(3-fluoro-5-(trifluoromethoxy)phenyl) acetic acid I-9 (CAS: 1352999-94-0, 1.0 g, 4.2 mmol, 1.0 equiv) in MeOH (15 mL) was added thionyl chloride (511 mg, 4.2 mmol, 1.0 equiv) and DMF (30 mg, 0.2 mmol, 0.05 equiv). The reaction mixture was stirred at 5° C. for 2 hours. On completion, the reaction mixture was concentrated to afford crude methyl 2-(3-fluoro-5-(trifluoromethoxy)phenyl)acetate I-10 (1.1 g, 90% yield, 90% purity) as a yellow oil, which was taken forward to the next step without further purification.

Methyl 2-(3-fluoro-5-(trifluoromethoxy)phenyl)-2-methylpropanoate (I-11)

To a solution of methyl 2-(3-fluoro-5-(trifluoromethoxy)phenyl)acetate I-10 (1.0 g, 3.9 mmol, 1.0 equiv) in DMF (20 mL) was added NaH (60% dispersion, 780 mg, 19.5 mmol, 5.0 equiv). The reaction mixture was stirred at 0-5° C. for 1 hour and iodomethane (1.1 g, 7.8 mmol, 2.0 equiv) was added. The reaction mixture was then stirred at 0-5° C. for 30 minutes. After completion, the reaction mixture was quenched with ice water (15 mL) and extracted with EtOAc (3×20 mL). The combined organic extracts were dried and concentrated to afford a residue, which was purified by silica gel chromatography (Petroleum ether/EtOAc=5:1) to afford methyl 2-(3-fluoro-5-(trifluoromethoxy)phenyl)-2-methylpropanoate I-11 (500 mg, 55% yield, 90% purity) as a yellow oil. 1H NMR (400 MHz, DMSO-$d_6$) δ 7.28 (dd, J=9.7, 8.0 Hz, 2H), 7.13 (s, 1H), 3.63 (s, 3H), 1.53 (s, 6H).

2-[(3-fluoro-5-(trifluoromethoxy)phenyl)-2-methylpropanoic acid (I-12)

To a solution of methyl 2-(3-fluoro-5-(trifluoromethoxy) phenyl)-2-methylpropanoate I-11 (200 mg, 0.7 mmol, 1.0 equiv) in 5 mL of MeOH/Water (1:1 v/v) was added NaOH (140 mg, 3.5 mmol, 5 equiv), and the reaction mixture was stirred at 20° C. for 16 hours. On completion, the reaction mixture was quenched with water (20 mL) and acidified to pH 4 using 2N HCl. The aqueous phase was extracted with EtOAc (3×20 mL). The combined organic extracts were dried and concentrated to afford a residue, which was purified by preparative TLC (Petroleum ether/EtOAc/AcOH=1:1:0.01) to afford 2-(3-fluoro-5-(trifluoromethoxy) phenyl)-2-methylpropanoic acid I-12 (110 mg, 58% yield, 90% purity) as white solid. MS (ESI) m/z: 267.1 (M+1). 1H NMR (400 MHZ, $CD_3OD$) δ 7.23-7.07 (m, 2H), 6.97 (d, J=8.7 Hz, 1H), 1.54 (s, 6H).

Synthesis of I-15

The synthesis of I-15 involved 3 steps as depicted in scheme 4.

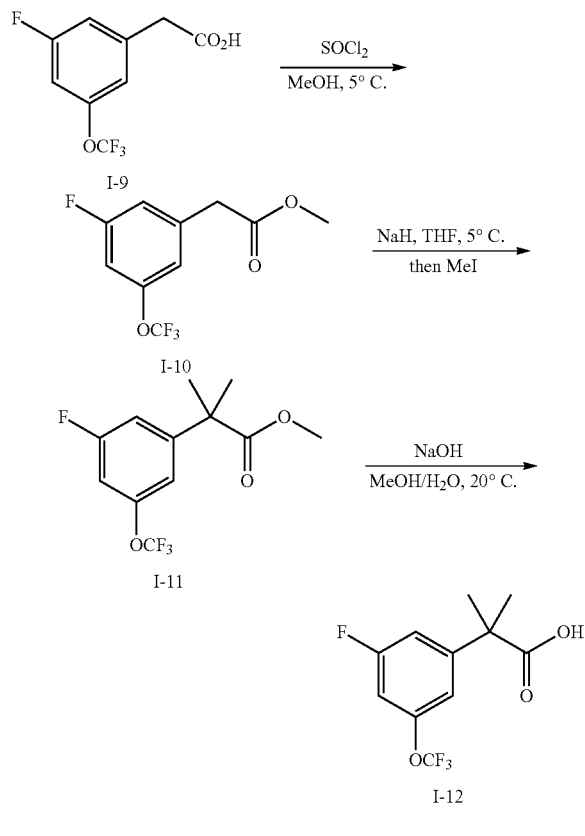

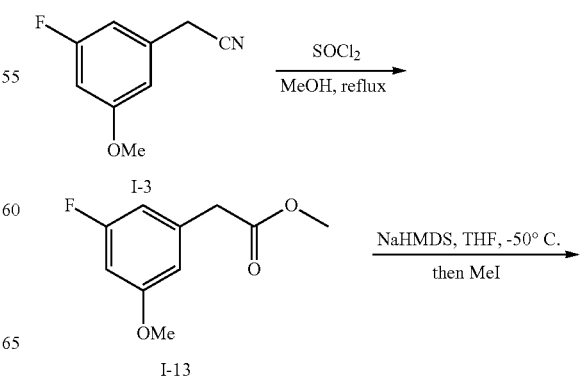

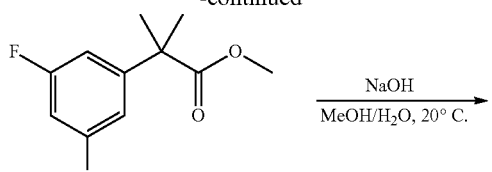

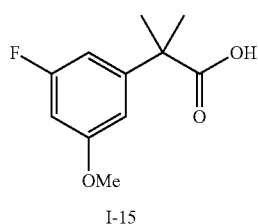

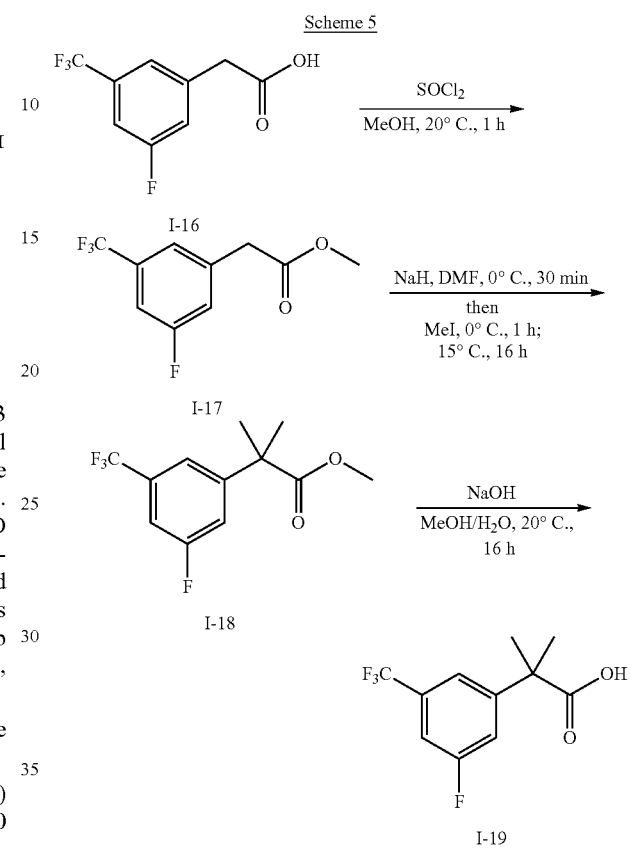

Synthesis of I-19

The synthesis of I-19 involved 3 steps as shown in scheme 5.

Methyl 2-(3-fluoro-5-methoxyphenyl)acetate (I-13)

To a solution of 2-(3-fluoro-5-methoxyphenyl)acetonitrile (3 g, 0.018 mol, 1 equiv.) in MeOH (35 mL) was added Thionyl chloride (5 mL). Once the addition was complete, the reaction mixture was stirred heated to reflux for 20 hours. On completion, the reaction mixture was diluted with H$_2$O (10 mL) and extracted with EtOAc (3×30 mL). The combined organic extracts were dried and concentrated to afford 3.1 g (82% yield, 95% purity) of the methyl ester I-13 as colourless oil, which was taken forward to the next step without further purification. MS (ESI, pos. ion) m/z: 199.1, (M+1).

Methyl 2-(3-fluoro-5-methoxyphenyl)-2-methylpropanoate (I-14)

A solution of methyl ester I-13 (2 g, 0.0101 mol, 1 equiv.) and NaHMDS (4.6 g, 0.0252 mol, 2.5 equiv.) in THF (20 mL) was stirred under nitrogen at −50° C. for 30 minutes. Iodomethane (7.2 g, 0.0505 mol, 5 equiv.) was then added and the reaction mixture was stirred at −50° ° C. for 1 hour. After completion, the reaction mixture was diluted with H$_2$O (15 mL) and extracted with EtOAc (3×20 mL). The combined organic extracts were dried and concentrated to a residue, which was purified by silica gel chromatography (Petroleum ether:EtOAc=1:10) to afford 1.9 g (75% yield, 90% purity) of ester I-14 as colorless oil. 1H NMR (400 MHZ, CDCl$_3$) δ 6.67-6.61 (m, 2H), 6.49 (dt, J=10.4, 2.2 Hz, 1H), 3.77 (s, 3H), 3.65 (s, 3H), 1.53 (s, 6H).

2-(3-fluoro-5-methoxyphenyl)-2-methylpropanoic acid (I-15)

To a solution of methyl 2-(3-fluoro-5-methoxyphenyl)-2-methylpropanoate (1 g, 4.4 mmol, 1 equiv.) in THF (25 mL) stirred at 25° C. was added a solution of sodium hydroxide (1.8 g, 44 mol, 10 equiv.) in H$_2$O (10 mL). The reaction mixture was stirred at 25° C. for 16 hours. On completion, the reaction mixture was cooled in an ice-water bath and acidified to pH 5 by addition of 1N HCl (3 mL). The reaction mixture was then extracted with EtOAc (3×15 mL). The combined organic extracts were dried and concentrated to a residue, which was purified by silica gel chromatography (EtOAc in Petroleum ether 20-30%) to afford 0.7 g (71% yield, 95% purity) of carboxylic acid I-15 as a white solid. MS (ESI, pos. ion) m/z:213.1, (M+1). 1H NMR (400 MHZ, CD$_3$OD) δ 6.72 (d, J=1.6 Hz, 1H), 6.71-6.65 (m, 1H), 6.57 (dt, J=10.7, 2.2 Hz, 1H), 3.78 (s, 3H), 1.51 (s, 6H).

Methyl 2-(3-fluoro-5-(trifluoromethyl) phenyl) acetate (I-17)

Thionyl chloride (0.1 mL) was added to a solution of 2-(3-fluoro-5-(trifluoromethyl) phenyl) acetic acid I-16 (cas: 195447-79-1, 50 mg, 0.22 mmol, 1.0 equiv.) in methanol (1 mL) at 20° C. The reaction mixture was stirred for 1 hour at 20° C. and then concentrated to afford methyl 2-(3-fluoro-5-(trifluoromethyl) phenyl) acetate I-17 (50 mg, 86% yield, 90% purity) as a colorless solid, which was taken forward to the next step without further purification. 1H NMR (400 MHZ, CD$_3$OD) δ 7.45 (s, 1H), 7.36 (s, 1H), 7.34 (s, 1H), 3.80 (s, 2H), 3.71 (s, 3H).

Methyl 2-(3-fluoro-5-(trifluoromethyl) phenyl)-2-methylpropanoate (I-18)

To a suspension of NaH (60% dispersion in mineral oil, 42 mg, 1.05 mmol, 5.0 equiv.) in DMF (2 mL) that had been cooled to 0° C. was added methyl 2-(3-fluoro-5-(trifluoromethyl) phenyl) acetate I-17 (50 mg, 0.21 mmol, 1.0 equiv.). The reaction mixture was stirred for 30 minutes at 0° C., at which point iodomethane (119 mg, 0.84 mmol, 4.0 equiv.) was added. The reaction mixture was stirred at 0° C. for 1 hour and allowed to warm to 15° C. and then maintained at that temperature for 16 hours. The reaction mixture was then cooled in an ice-water bath and water (5 mL) was added to quench the reaction. The reaction mixture was extracted with EtOAc (3×5 mL) and the combined organic extracts were washed with water (5 mL) and brine (5 mL), dried and concentrated to a residue, which was purified by silica gel chromatography (0-10% EtOAc in Petroleum ether) to afford methyl 2-(3-fluoro-5-(trifluoromethyl) phenyl)-2-methylpropanoate I-18 (20 mg, 32% yield, 90% purity) as a colorless oil. 1H NMR (400 MHZ, CD$_3$OD) δ 7.44 (s, 1H), 7.40 (dd, J=10.2, 1.9 Hz, 1H), 7.35 (d, J=8.4 Hz, 1H), 3.67 (s, 3H), 1.60 (s, 6H).

2-(3-fluoro-5-(trifluoromethyl) phenyl)-2-methylpropanoic acid (I-19)

To a solution of methyl 2-(3-fluoro-5-(trifluoromethyl) phenyl)-2-methylpropanoate I-18 (250 mg, 0.94 mmol, 1.0 equiv.) in THF (5 mL) was added an aqueous solution of Lithium hydroxide (45 mg, 1.88 mmol, 2.0 equiv. in 2.5 mL H$_2$O) at 20° C. The reaction mixture was stirred for 16 hours and then concentrated to remove THF. The pH was adjusted to 4 using 1N hydrochloric acid, and the aqueous phase was extracted with DCM (5 mL). The organic extract was washed with water (2 mL) and brine (2 mL), dried over magnesium sulfate, and concentrated to a residue, which was purified by reversed phase column chromatography (Mobile Phase: Solvent A=0.1% formic acid in H2O, Solvent B=0.1% formic acid in MeCN; Gradient: 0-60% B) to afford carboxylic acid I-19 (154 mg, 65% yield, >99% purity) as a white solid. 1H NMR (400 MHZ, DMSO-d$_6$) δ 12.71 (s, 1H), 7.59 (d, J=8.5 Hz, 1H), 7.54 (d, J=10.3 Hz, 1H), 7.47 (s, 1H), 1.52 (s, 6H).

Synthesis of I-25R* and I-25S*

The synthesis of I-25R* and I-25S* involved 5 steps as described in scheme 6.

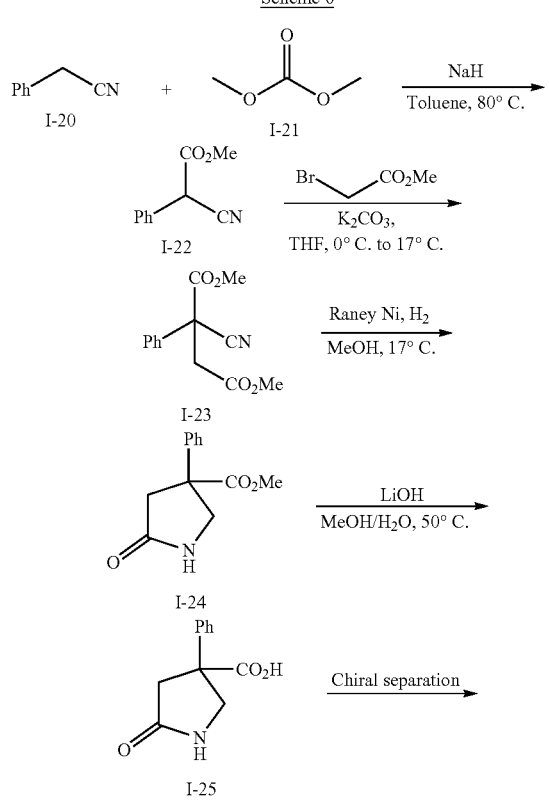

Scheme 6

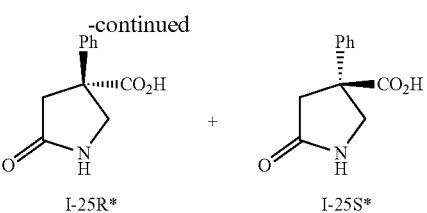

Methyl 2-cyano-2-phenylacetate. (I-22)

To a suspension of sodium hydride (6.82 g, 0.171 mol, 60% dispersion in mineral oil) in toluene (200 mL) was added phenylacetonitrile (cas: 140-29-4, 10.0 g, 0.0854 mol, 1.0 equiv.) and dimethyl carbonate (cas: 616-38-6, 61.5 g, 0.6832 mol, 8.0 equiv.) at 17° C. The reaction mixture was heated to 80° ° C. for 2 hours, then cooled to 17° C. and 1 N HCl (160 mL) was added. The reaction mixture was extracted with EtOAc (2×150 mL). The combined organic extracts were dried (Na$_2$SO$_4$), and concentrated to afford a yellow oil, which was purified by silica gel chromatography (EtOAc/Petroleum ether=1:10) to afford methyl 2-cyano-2-phenylacetate I-22 (13 g, 83% yield) as a yellow oil. MS (ESI) m/z: 176.1, (M+1). 1H NMR (400 MHZ, CDCl$_3$) d 7.49-7.37 (m, 5H), 4.74 (s, 1H), 3.80 (s, 3H).

Dimethyl 2-cyano-2-phenylsuccinate (I-23)

To a solution of ester, I-22 (2.5 g, 14.3 mmol, 1.0 equiv.) in THF (50 mL) that had been cooled to 0° ° C. was added K$_2$CO$_3$ (5.92 g, 42.9 mmol, 3.0 equiv.), followed by methyl 2-bromoacetate (3.28 g, 21.4 mmol, 1.5 equiv.). The reaction mixture was allowed to warm to ambient temperature (17° C.) and stirred for 18 hours, then quenched with water (15 mL) and extracted with EtOAc (3×35 mL). The combined organic extracts were washed with brine (15 mL), dried (Na$_2$SO$_4$), and concentrated to afford a residue, which was purified by silica gel chromatography (EtOAc/Petroleum ether=1:10) to afford ester I-23 (3.5 g, 88% yield) as a colorless oil. MS (ESI, pos. ion) m/z: 270.1, (M+23). 1H NMR (400 MHZ, CDCl$_3$) d 7.65-7.56 (m, 2H), 7.50-7.40 (m, 3H), 3.88 (s, 3H), 3.80 (s, 3H), 3.59 (d, J=17.3 Hz, 1H), 3.09 (d, J=17.3 Hz, 1H).

Methyl 5-oxo-3-phenylpyrrolidine-3-carboxylate (I-24)

To a solution of 1,4-dimethyl 2-cyano-2-phenylbutanedioate (3.5 g, 0.01 mol, 1.0 equiv.) in MeOH (20 mL) was added Raney-Ni (1.5 g). The reaction mixture was then stirred at ambient temperature in the presence of hydrogen gas (1 atm) for 5 hours, then filtered to remove Raney-Ni. The filtrate was concentrated to a residue, which was purified by silica gel chromatography (DCM/MeOH=20:1) to afford methyl 5-oxo-3-phenylpyrrolidine-3-carboxylate I-24 (2.2 g, 90% yield) as a white solid. MS (ESI, pos. ion) m/z: 220.1, (M+1).

Methyl 5-oxo-3-phenylpyrrolidine-3-carboxylate (I-25)

To a solution of methyl 5-oxo-3-phenylpyrrolidine-3-carboxylate I-24 (1.0 g, 4.6 mmol, 1.0 equiv.) in MeOH (16 mL) was added a solution of Lithium hydroxide (550 mg, 23 mmol, 5.0 equiv.) in H$_2$O (3 mL). The reaction mixture was stirred at 30° C. for 2 hours and then acidified to pH 6 by addition of 1N HCl. The reaction mixture was concentrated to afford a residue, which was purified by reverse phase chromatography (C18 stationary phase, Water/MeCN with 0.5% TFA as a modifier) to afford 5-oxo-3-phenylpyrrolidine-3-carboxylic acid I-25 (0.8 g, yield:76%) as a white solid. The racemic carboxylic acid was then purified by SFC using a chiral stationary phase to afford the enantiomers I-25R* (318.9 mg, 34% yield) as a white solid and I-25S* (474.9 mg, 51% yield) as a white solid. I-25R*: MS (ESI, pos. ion) m/z: 206.1, (M+1). 1H NMR (400 MHZ, DMSO-d$_6$) 12.93 (s, 1H), 7.78 (s, 1H), 7.38-7.23 (m, 5H), 4.08 (d, J=9.7 Hz, 1H), 3.47 (d, J=9.7 Hz, 1H), 2.99 (d, J=16.0 Hz, 1H), 2.56 (d, J=16.0 Hz, 1H). I-25S*: MS (ESI, pos. ion) m/z: 206.1, (M+1). 1H NMR (400 MHZ, DMSO-d$_6$) 12.94 (s, 1H), 7.79 (s, 1H), 7.40-7.25 (m, 5H), 4.09 (d, J=9.7 Hz, 1H), 3.48 (d, J=9.8 Hz, 1H), 3.00 (d, J=16.0 Hz, 1H), 2.57 (d, J=16.0 Hz, 1H). The absolute configuration of each enantiomer was not determined.

Synthesis of I-29

The synthesis of I-29 involved 2 steps as described in scheme 7.

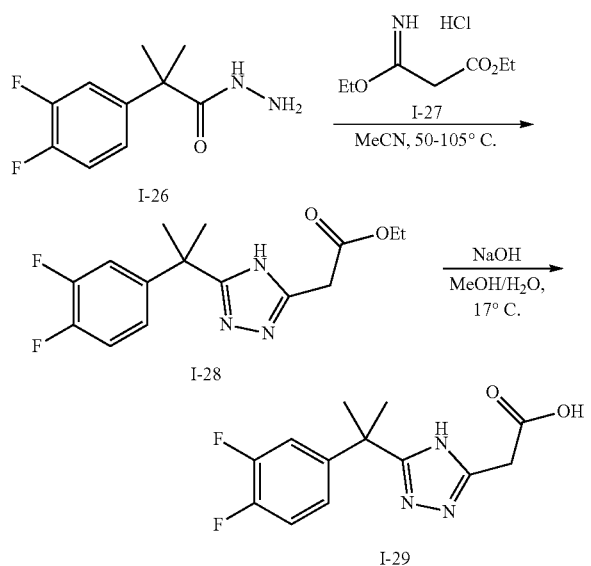

Ethyl 2-(5-(2-(3,4-difluorophenyl)propan-2-yl)-4H-1,2,4-triazol-3-yl)acetate. (I-28)
Ethyl 3-ethoxy-3-iminopropanoate hydrochloride (1.56 g, 8.0 mmol, 5.0 equiv.) was dissolved in water (8 mL) and the pH of the solution was adjusted to 7 by addition of NaHCO$_3$. The reaction mixture was extracted with DCM (2×15 mL). The combined organic extracts were dried (Na$_2$SO$_4$) and concentrated to afford ethyl 3-ethoxy-3-iminopropanoate, which was redissolved in MeCN (15 mL) in the presence of 2-(3,5-difluorophenyl)-2-methylpropanehydrazide I-26 (0.35 g, 1.6 mmol, 1.0 equiv.). The reaction mixture was stirred at 50° C. for 18 hours, then heated to reflux for a further 18 hours. The reaction mixture was then cooled and concentrated to a residue, which was purified by preparative TLC on silica gel (EtOAc/Petroleum ether=1:2) to afford ethyl 2-{5-[2-(3,5-difluorophenyl)propan-2-yl]-4H-1,2,4-triazol-3-yl}acetate I-28 (0.4 g, 38% yield, 50%) as a yellow oil. MS (ESI, pos. ion) m/z: 310.1. (M+1).
2-(5-(2-(3,4-difluorophenyl)propan-2-yl)-4H-1,2,4-triazol-3-yl)acetic acid. (I-29)
Ester I-28 (400 mg, 1.29 mmol, 1.0 equiv.) was dissolved in MeOH (4 mL) and a solution of NaOH (256 mg, 6.45 mmol, 5.0 equiv.) in H$_2$O (4 mL) was added. The reaction mixture was stirred at ambient temperature (17° C.) for 4 hours, then concentrated to afford a residue. The residue was redissolved in H$_2$O (3 mL) and extracted with EtOAc (2×3 mL). The combined organic extracts were discarded. The aqueous layer was acidified to pH 4 by addition of 1N HCl. This reaction mixture was concentrated to afford a residue, which was purified by reverse phase chromatography (C18 stationary phase with the mobile phase comprising MeCN/H$_2$O with 0.05% NH$_4$HCO$_3$ as a modifier) to afford {5-[2-(3,4-difluorophenyl)propan-2-yl]-4H-1,2,4-triazol-3-yl}acetic acid I-29 (49.7 mg, 13% yield) as a white solid. MS (ESI, pos. ion) m/z: 282.1, (M+1). 1H NMR (400 MHZ, CD$_3$OD) d 7.22-7.10 (m, 2H), 7.05 (s, 1H), 3.65 (s, 2H), 1.72 (s, 6H).

Synthesis of I-37

The synthesis of I-37 involved 7 steps as shown in scheme 8.

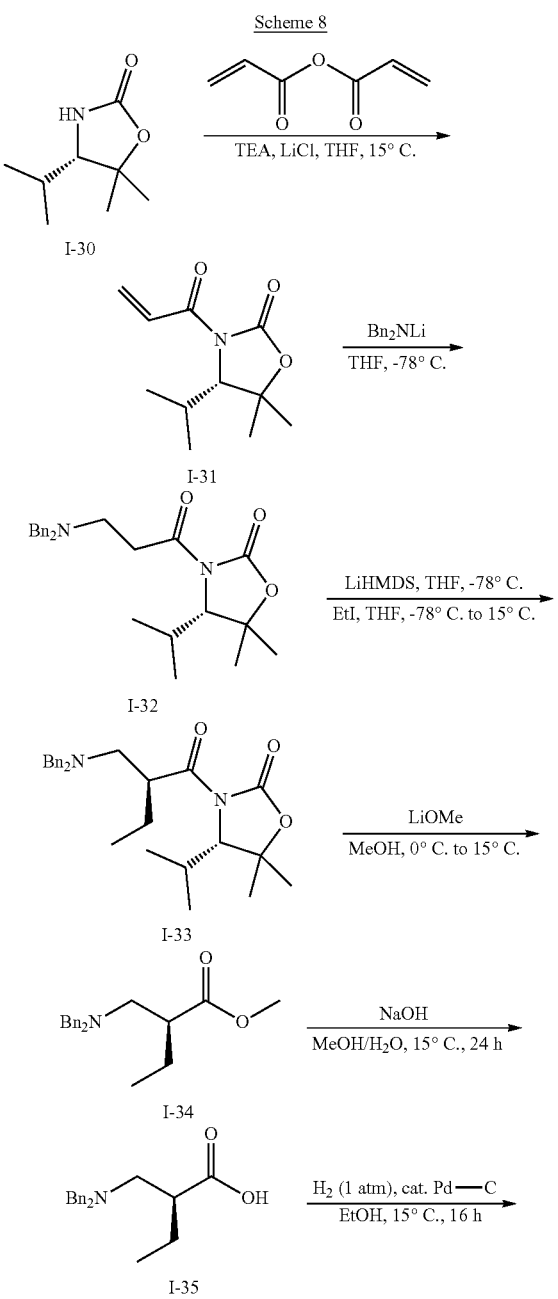

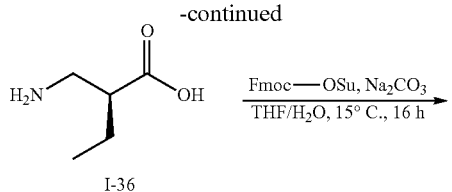

I-36

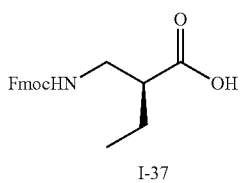

I-37

(S)-3-acryloyl-4-isopropyl-5,5-dimethyloxazolidin-2-one (1-31: To a solution of (4S)-4-isopropyl-5,5-dimethyl-1,3-oxazolidin-2-one (2 g, 12.74 mmol) in anhydrous THF (20 mL) was added LiCl (668 mg, 15.92 mmol, 1.25 equiv.) and TEA (1.6 g, 15.92 mmol, 1.25 equiv.) followed by acrylic anhydride (2.0 g, 15.92 mmol, 1.25 equiv.). The reaction mixture was stirred at 15° C. for 16 hours, then diluted with EtOAc (50 mL) and the organic phase was washed with brine (50 mL), dried and concentrated to a residue, which was purified by silica gel chromatography (20% EtOAc in petroleum ether) to afford oxazolidinone I-31 (1.4 g, 50% yield) as a white solid. MS (ESI, pos. ion) m/z: 212.1 (M+1); 1H NMR (400 MHZ, CDCl$_3$): δ7.53-7.60 (m, 1H), 6.53 (d, J=12.0 Hz, 1H), 5.89 (d, J=8.0 Hz, 1H), 4.22 (d, J=4.0 Hz, 1H), 2.16-2.20 (m, 1H), 1.53 (s, 3H), 1.40 (s, 3H), 1.04 (d, J=8.0 Hz, 3H). 0.96 (d, J=8.0 Hz, 3H).

(S)-3-(3-(dibenzylamino)propanoyl)-4-isopropyl-5,5-dimethyloxazolidin-2-one (I-32)
To a solution of dibenzylamine (3.9 g, 19.72 mmol, 1.6 equiv.) in THF (30 mL) that had been cooled to −78° C. was added n-BuLi (8.2 mL, 19.72 mmol, 1.6 equiv.). The reaction mixture was stirred for 30 minutes at −78° C. and a solution of (S)-3-acryloyl-4-isopropyl-5,5-dimethyloxazolidin-2-one I-31 (2.6 g, 12.32 mmol, 1.0 equiv.) in THF (5 mL) that had been cooled to −78° C., was transferred via cannula. The reaction mixture was stirred for 2 hours and quenched by the addition of saturated aqueous NH$_4$Cl (50 mL), then extracted with ethyl acetate (3×100 mL). The combined organic extracts were washed with aqueous citric acid solution (10% w/v), saturated aqueous NaHCO$_3$ and brine. The organic layer was dried and concentrated to a residue, which was purified by silica gel chromatography (10% EtOAc in Petroleum ether) to afford the desired oxazolidinone I-32 (3.3 g, 62% yield) as a white solid. MS (ESI, pos. ion) m/z: 409.3, (M+1).

(S)-3-((S)-2-((dibenzylamino)methyl)butanoyl)-4-isopropyl-5,5-dimethyloxazolidin-2-one (1-33)
To a solution of (4S)-3-{3-[bis(1-methylphenyl)amino]propanoyl}-4-isopropyl-5,5-dimethyl-1,3-oxazolidin-2-one I-32 (1.5 g, 3.68 mmol, 1.0 equiv.) in THF (15 mL) that had been cooled to −78° C. was added a solution of LiHMDS (1M in THF, 18.4 mL, 18.40 mmol, 5.0 equiv.). The reaction mixture was stirred at −78° C. for 1 hour. Iodoethane (2.87 g, 18.38 mmol, 5.0 equiv.) was then added and the reaction mixture was stirred at −78° C. for an additional 1 hour, then allowed to warm to 15° C. and stirred at that temperature for 14 hours. The reaction mixture was then quenched with saturated aqueous NH$_4$Cl and extracted with EtOAc (2×50 mL). The combined organic extracts were dried and concentrated to a residue, which was purified by reverse phase chromatography (C18 stationary phase, mobile phase comprising 9:1 v/v MeCN/H$_2$O with 0.05% by volume formic acid as a modifier) to afford the desired oxazolidinone I-33 (750 mg, 39% yield) as a white solid. MS (ESI, pos. ion) m/z: 437.3, (M+1)

Methyl (S)-2-((dibenzylamino)methyl)butanoate (I-34)
To anhydrous MeOH (20 mL) that had been cooled to 0° C. was added n-BuLi (2.4 M in hexanes, 5.7 mL, 13.8 mmol, 5.0 equiv.). The reaction mixture was stirred at 0° C. for 30 minutes and(S)-3-((S)-2-((dibenzylamino)methyl)butanoyl)-4-isopropyl-5,5-dimethyloxazolidin-2-one I-33 (1.2 g, 2.75 mmol, 1.0 equiv.) was added. The reaction mixture was allowed to warm to 15° C. and stirred for 16 hours. At this point, the reaction mixture was concentrated to a residue, which was purified by reversed phase chromatography (C18 stationary phase, mobile phase comprising 9:1 v/v MeCN/H$_2$O with 0.05% by volume formic acid as a modifier) to afford the desired ester I-34 (620 mg, 65% yield) as a white solid. MS (ESI, pos. ion) m/z: 312.1, (M+1).

(S)-2-((dibenzylamino)methyl)butanoic acid (I-35)
To a solution of methyl (S)-2-((dibenzylamino)methyl)butanoate (600 mg, 1.93 mmol, 1.0 equiv.) in 1:1 v/v MeOH/H$_2$O (10 mL) was added NaOH (154 mg, 3.86 mmol, 2.0 equiv.). The reaction mixture was stirred at 15 °C for 24 hours when the reaction was deemed complete. The reaction mixture was then acidified to pH 5 by the addition of 1N HCl and extracted with EtOAc (3×20 mL). The combined organic extracts were dried and concentrated to afford the desired carboxylic acid 1-35 (570 mg, 98% yield) as a white solid. MS (ESI, pos. ion) m/z: 298.1, (M+1).

(S)-2-(aminomethyl)butanoic acid (1-36)
To a solution of (S)-2-((dibenzylamino)methyl)butanoic acid (800 mg, 2.67 mmol) in EtOH (10 mL) was added Pd/C (200 mg). The mixture was stirred under H$_2$ (1 atm) at 15 °C for 16 hours. The reaction mixture was filtered, and the filtrate was concentrated to afford the desired amino acid I-36 (305 mg, 97% yield) as a white solid. MS (ESI, pos. ion) m/z: 118.2, (M+1).

(S)-2-(((((9H-fluoren-9-yl)methoxy)carbonyl)amino)methyl)butanoic acid (1-37)
To a solution of (2S)-2-(aminomethyl)butanoic acid (250 mg, 2.14 mmol, 1.0 equiv.) in 1:1 v/v THF/H$_2$O (5 mL) was added Na$_2$CO$_3$ (453 mg, 4.28 mmol, 2.0 equiv.), followed by FmocOSu (793 mg, 2.35 mmol, 1.1 equiv.). The reaction mixture was stirred at 15° C. for 16 hours, and then acidified to pH 3 by addition of 1N HCl. The reaction mixture was extracted with ethyl acetate (10 mL). The ethyl acetate extract was washed with brine (15 mL), dried (Na$_2$SO$_4$) and concentrated to a residue, which was purified by reversed phase chromatography using a C18 stationary phase (70% MeCN/H$_2$O with 0.05% Formic acid as a modifier) to afford the desired amino acid I-37 as a white solid (200 mg, 28% yield) as a white solid. MS (ESI, pos. ion) m/z: 340.1, (M+1) 1H NMR (400 MHZ, DMSO-d$_6$) δ 7.86 (d, J=8.0 Hz, 2H), 7.63 (d, J=8.0 Hz, 2H), 7.39 (t, J=8.0 Hz, 2H), 7.30 (t, J=8.0 Hz, 2H), 7.15-7.18 (m, 1H), 4.16-4.24 (m, 3H), 3.02 (t, J=8.0 Hz, 2H), 1.93-1.97 (m, 1H), 1.42-1.49 (m, 1H), 1.25-1.32 (m, 1H), 0.79 (t, J=8.0 Hz, 3H).

Synthesis of I-41

The synthesis of I-41 involved 4 steps as depicted in scheme 9.

Scheme 9

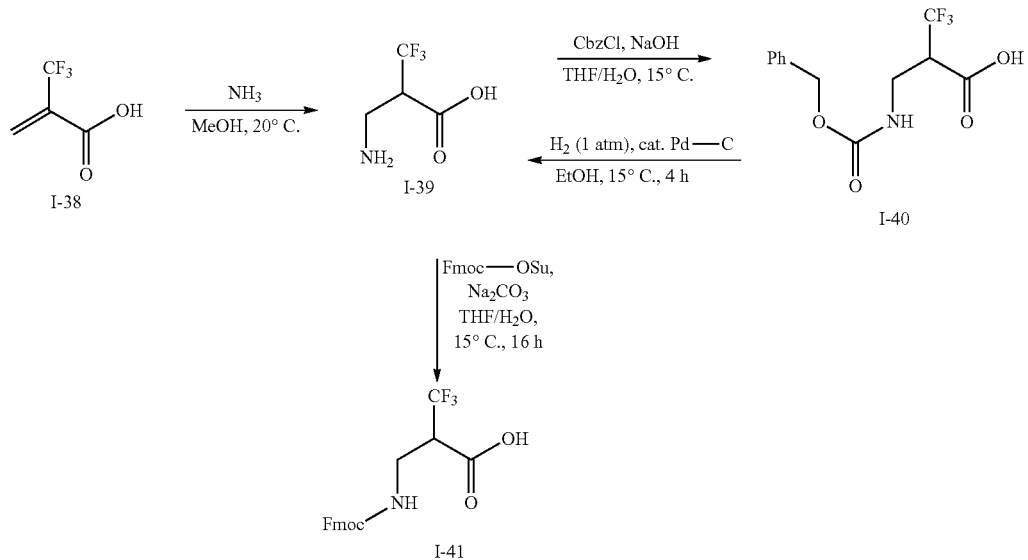

2-(aminomethyl)-3,3,3-trifluoropropanoic acid (I-39)
To 2-(trifluoromethyl)acrylic acid (10 g, 71.43 mmol, CAS: 381-98-6) was added 7 N $NH_3$ in MeOH (400 mL). The reaction mixture was stirred at 20° C. for 2 hours, then concentrated to afford the crude amino acid I-39 (10.5 g), which was taken forward to the next step without further purification. MS (ESI, pos. ion) m/z: 158.1, (M+21)
2-((((benzyloxy)carbonyl)amino)methyl)-3,3,3-trifluoropropanoic acid (I-40)
To a solution of 2-(aminomethyl)-3,3,3-trifluoropropanoic acid (10.5 g, 66.9 mmol, 1.0 equiv.) and NaOH (8.0 g, 200.6 mmol, 3.0 equiv.) in 1:1 v/v $THF/H_2O$ (150 mL) was added CbzCl (17.1 g, 100.3 mmol, 1.5 equiv.). The reaction mixture was stirred at 15° C. for 16 hours, and then acidified to pH 3 by addition of 1N HCl and extracted with EtOAc (2×40 mL). The combined EtOAc extracts were dried and concentrated to a residue, which was purified by reversed phase chromatography (65% $MeCN/H_2O$, using 0.05% Formic acid as a modifier) to afford the desired carboxylic acid I-40 as a white solid. (5.3 g, 27% yield) as a white solid. MS (ESI, pos. ion) m/z: 314.0, (M+1)
2-(aminomethyl)-3,3,3-trifluoropropanoic acid (I-39)
To a solution of carboxylic acid, I-40 (400 mg, 1.37 mmol) in EtOH (10 mL) was added Pd/C (100 mg). The reaction mixture was stirred at 15° C. under $H_2$ (1 atm) for 4 hours, then filtered. The filtrate was concentrated to afford the desired amino acid I-39 (215 mg, quantitative yield) as a white solid. MS (ESI, pos. ion) m/z: 158.1, (M+1)
2-(((((9H-fluoren-9-yl)methoxy)carbonyl)amino)methyl)-3,3,3-trifluoropropanoic acid (1-41)
To a solution of amino acid, I-39 (215 mg, 1.37 mmol, 1.0 equiv.) and $Na_2CO_3$ (350 mg, 3.30 mmol, 2.4 equiv.) in 50% v/v $THF/H_2O$ (10 mL) was added FmocOSu (556 mg, 1.65 mmol, 1.2 equiv.). The reaction mixture was stirred at 15° C. for 16 hours and acidified to pH 3 by addition of 1N HCl. The aqueous phase was extracted with EtOAc (2×20 mL). The combined organic extracts were dried and concentrated to a residue, which was purified by reverse phase chromatography (60% $MeCN/H_2O$ with 0.05% Formic acid as a modifier) to afford the desired Fmoc-protected amino acid I-41 (230 mg, 42% yield) as a white solid. MS (ESI, pos. ion) m/z: 402.1, (M+23)
$^1$H NMR (400 MHZ, DMSO-d6) δ13.39 (brs, 1H), 7.87 (d, J=8.0 Hz, 2H), 7.66-7.70 (m, 3H), 7.40 (t, J=8.0 Hz, 2H), 7.31 (t, J=8.0 Hz, 2H), 4.28-4.30 (m, 2H), 4.19-4.22 (m, 1H), 3.44-3.46 (m, 3H).

Synthesis of I-43

Scheme 10

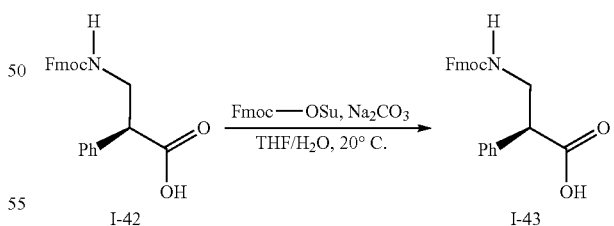

(S)-3-((((9H-fluoren-9-yl)methoxy)carbonyl)amino)-2-phenylpropanoic acid (I-43)
To a solution of (2S)-3-amino-2-phenylpropanoic acid (400 mg, 1.2 mmol, CAS: 1076-51-3, 1.0 equiv.) and $Na_2CO_3$ (636 mg, 6 mmol, 5 equiv.) in 1:1 v/v $THF/H_2O$ (10 mL) was added FmocOSu (900 mg, 2.67 mmol, 2.2 equiv.). The reaction mixture was stirred at 20° C. for 2 hours, then acidified to pH 3 by addition of 1N HCl and extracted with EtOAc (2×10 mL). The combined EtOAc extracts were dried and concentrated to a residue, which was purified by silica gel chromatography (5% MeOH in DCM) to afford the desired protected amino acid I-43 (810 mg, 83% yield) as a white solid. MS (ESI, pos. ion) m/z: 410.1 (M+Na⁺). 1H NMR (400 MHz, DMSO-$d_6$) δ12.57 (brs, 1H), 7.87 (d, J=8.0 Hz, 2H), 7.63 (d, J=4.0 Hz, 2H), 7.45-7.46 (m, 1H), 7.40 (t, J=8.0 Hz, 2H), 7.24-7.34 (m, 6H), 4.16-4.26 (m, 3H), 3.74-3.77 (m, 1H), 3.52-3.56 (m, 1H), 3.24-3.29 (m, 1H).

The synthesis of compound I-48 involved 4 steps as depicted in scheme 11.

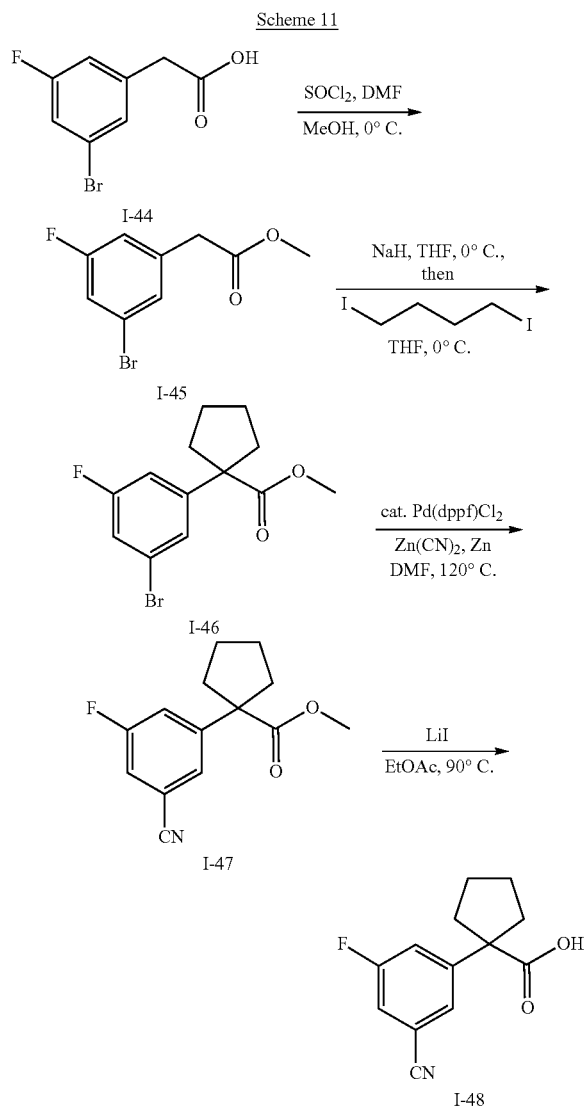

Methyl 2-(3-bromo-5-fluorophenyl)acetate (I-45)
To a solution of 2-(3-bromo-5-fluorophenyl)acetic acid I-44 (CAS: 202000-99-5, 1.0 g, 4.3 mmol, 1.0 equiv) in MeOH (15 mL) was added thionyl chloride (511 mg, 4.3 mmol, 1.0 equiv) and DMF (30 mg, 0.2 mmol, 0.05 equiv). The reaction mixture was stirred at 20° C. for 1 hour, at which point the reaction was deemed complete. The reaction mixture was then concentrated to afford methyl 2-(3-bromo-5-fluorophenyl)acetate I-45 (1.1 g, 90% yield, 90% purity) as a yellow oil. which was taken on to the next step without further purification. MS (ESI, pos. ion) m/z: 247.0 (M+1).
Methyl 1-(3-bromo-5-fluorophenyl)cyclopentane-1-carboxylate (1-46)

To a solution of methyl 2-(3-bromo-5-fluorophenyl)acetate (1.0 g, 4.0 mmol, 1.0 equiv) in THF (20 mL) was added NaH (60% dispersion in mineral oil, 480 mg, 12 mmol, 3.0 equiv). The reaction mixture was stirred at 0° C. for 30 minutes, then 1,4-diiodobutane (CAS: 628-21-7, 2.5 g, 8.0 mmol, 2.0 equiv) was added. The reaction mixture was stirred at 0° C. for an additional 30 minutes, at which point the reaction was deemed complete. The reaction mixture was quenched with ice water (15 mL) and extracted with EtOAc (3×20 mL). The combined organic extracts were dried and concentrated to a residue, which was purified by silica gel chromatography (Petroleum/EtOAc=5:1) to afford methyl 1-(3-bromo-5-fluorophenyl)cyclopentane-1-carboxylate I-46 (700 mg, 68% yield, 90% purity) as a yellow oil. MS (ESI, pos. ion) m/z: 301.0 (M+1).

Methyl 1-(3-cyano-5-fluorophenyl)cyclopentane-1-carboxylate (I-47)

To a solution of ester, I-46 (250 mg, 0.83 mmol, 1.0 equiv) in DMF (5 mL) was added Zn(CN)₂ (68 mg, 0.58 mmol, 0.7 equiv), Zn dust (5 mg, 0.08 mmol, 0.1 equiv) and Pd(dppf)Cl₂.DCM (128 mg, 0.16 mmol, 0.2 equiv). The reaction mixture was stirred at 120° C. for 2 hours under N₂. On completion, the reaction mixture was quenched with water (20 mL) and extracted with EtOAc (3×20 mL). The combined organic extracts were dried and concentrated to afford a residue, which was purified by silica gel chromatography (Petroleum ether/EtOAc=1:1) to afford ester I-47 (164 mg, 80% yield, 90% purity) as a yellow oil. MS (ESI, pos. ion) m/z: 248.1 (M+1).

1-(3-cyano-5-fluorophenyl)cyclopentane-1-carboxylic acid (I-48)

To a solution of ester, I-47 (250 mg, 1.0 mmol, 1.0 equiv) in EtOAc (5 mL) was added LiI (1.35 g, 10 mmol, 10 equiv). The reaction mixture was stirred at 90° C. for 16 hours. On completion, the reaction mixture was quenched with water (20 mL). The reaction mixture was acidified to pH 4 by addition of 2N HCl, then extracted with EtOAc (3×20 mL). The combined organic extracts were dried and concentrated to afford a residue, which was purified by preparative TLC (Petroleum ether/EtOAc/AcOH=1:1:0.01) to afford carboxylic acid I-48 (127 mg, 55% yield, 90% purity) as a white solid. MS (ESI, pos. ion) m/z: 234.1 (M+1). 1H NMR (400 MHZ, CD₃OD) δ 7.56 (s, 1H), 7.48-7.44 (m, 1H), 7.41 (ddd, J=8.1, 2.3, 1.2 Hz, 1H), 2.64 (dd, J=11.8, 5.9 Hz, 2H), 1.87 (dd, J=12.5, 7.8 Hz, 2H), 1.76 (dd, J=7.5, 6.3 Hz, 4H).

The synthesis of compound I-52 involved 3 steps as shown in scheme 12.

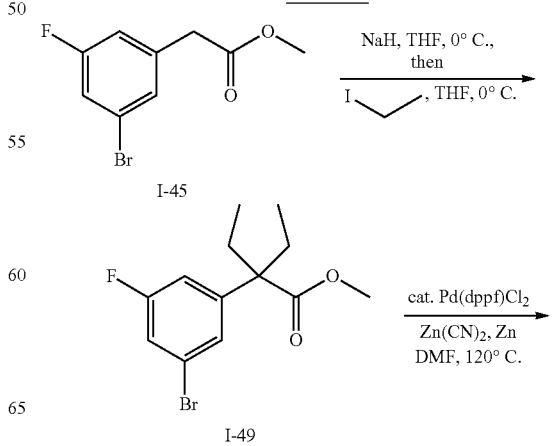

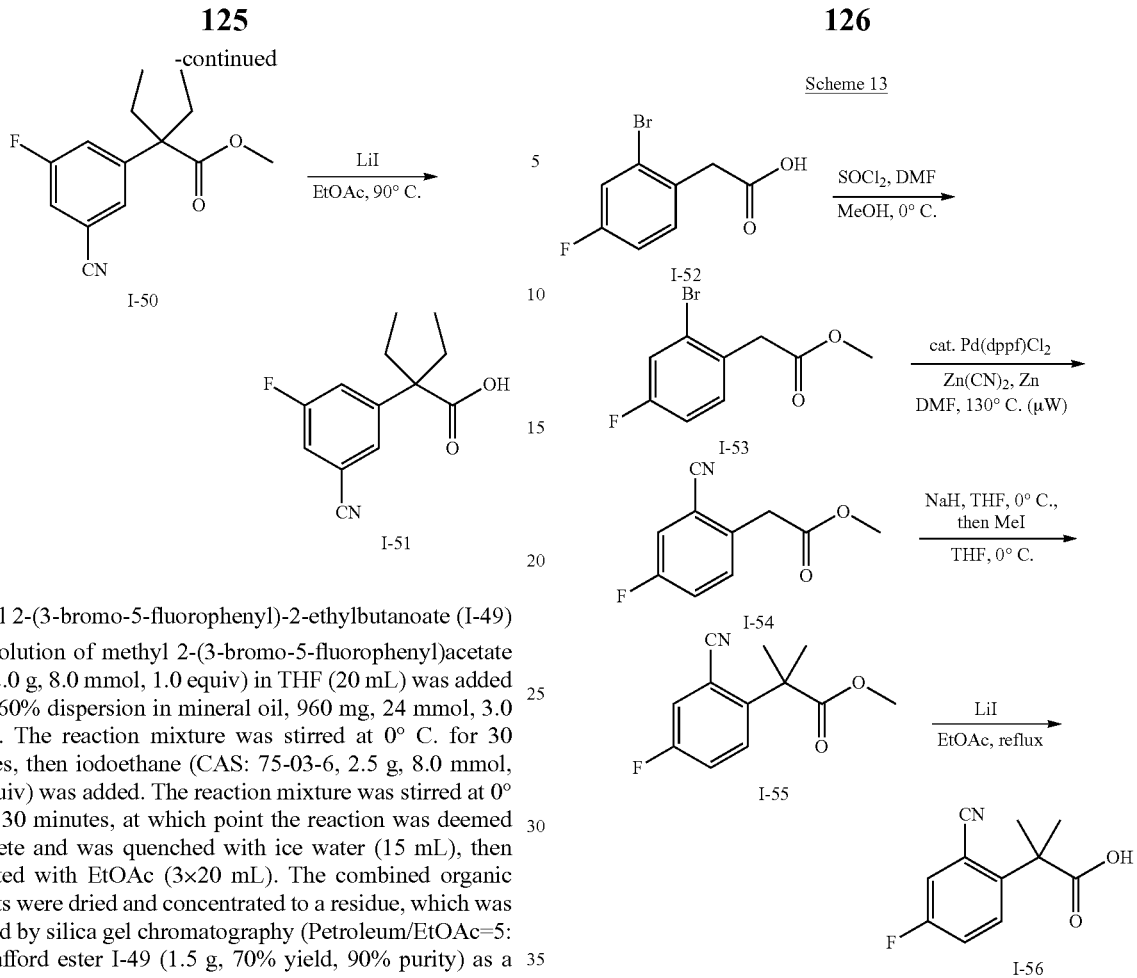

Methyl 2-(3-bromo-5-fluorophenyl)-2-ethylbutanoate (I-49)

To a solution of methyl 2-(3-bromo-5-fluorophenyl)acetate I-45 (2.0 g, 8.0 mmol, 1.0 equiv) in THF (20 mL) was added NaH (60% dispersion in mineral oil, 960 mg, 24 mmol, 3.0 equiv). The reaction mixture was stirred at 0° C. for 30 minutes, then iodoethane (CAS: 75-03-6, 2.5 g, 8.0 mmol, 2.0 equiv) was added. The reaction mixture was stirred at 0° C. for 30 minutes, at which point the reaction was deemed complete and was quenched with ice water (15 mL), then extracted with EtOAc (3×20 mL). The combined organic extracts were dried and concentrated to a residue, which was purified by silica gel chromatography (Petroleum/EtOAc=5: 1) to afford ester I-49 (1.5 g, 70% yield, 90% purity) as a yellow oil. MS (ESI, pos. ion) m/z: 303.0 (M+1).

Methyl 2-(3-cyano-5-fluorophenyl)-2-ethylbutanoate (I-50)

To a solution of ester, I-49 (1.5 g, 5 mmol, 1.0 equiv) in DMF (20 mL) was added Zn(CN)$_2$ (413 mg, 3.5 mmol, 0.7 equiv), Zn dust (33 mg, 0.5 mmol, 0.1 equiv) and Pd(dppf)Cl$_2$.DCM (802 mg, 1.0 mmol, 0.2 equiv). The reaction mixture was stirred at 120° C. for 2 hours under N$_2$. On completion, the reaction mixture was quenched with water (200 mL), and extracted with EtOAc (3×50 mL). The combined organic extracts were dried and concentrated to afford a residue, which was purified by silica gel chromatography (petroleum ether/EtOAc=1:1) to afford ester I-50 (1.2 g, 96% yield, 90% purity) as a yellow oil. MS (ESI, pos. ion) m/z: 250.2 (M+1).

2-(3-cyano-5-fluorophenyl)-2-ethylbutanoic acid (I-51)

To a solution of ester, I-50 (250 mg, 1.0 mmol, 1.0 equiv) in EtOAc (5 mL) was added LiI (1.35 g, 10 mmol, 10 equiv). The reaction mixture was stirred at 90° C. in a sealed tube for 16 hours. On completion, the reaction mixture was quenched with water (20 mL) and acidified with 2N HCl to pH 4, then extracted with EtOAc (3×20 mL). The combined organic extracts were dried and concentrated to afford a residue, which was purified by preparative TLC (Petroleum/EtOAc/AcOH=1:1:0.01) to afford carboxylic acid I-51 (127 mg, 55% yield, 90% purity) as a white solid. MS (ESI, pos. ion) m/z: 236.1 (M+1). 1H NMR (400 MHZ, CD$_3$OD) δ 7.51 (t, J=1.4 Hz, 1H), 7.44 (t, J=1.5 Hz, 1H), 7.43-7.40 (m, 1H), 2.03 (dd, J=13.9, 7.1 Hz, 4H), 0.76 (t, J=7.4 Hz, 6H).

The synthesis of carboxylic acid I-57 involved 4 steps as shown in scheme 13.

2-(2-bromo-4-fluorophenyl)acetate (I-53)

To a solution of carboxylic acid, I-52 (CAS: 61150-59-2, 1.0 g, 4.3 mmol, 1.0 equiv) in MeOH (15 mL) was added thionyl chloride (511 mg, 4.3 mmol, 1.0 equiv) and DMF (30 mg, 0.2 mmol, 0.05 equiv). The reaction mixture was stirred at 0° C. for 2 hours, then concentrated to afford the crude methyl ester I-53 (1.1 g, 90% yield, 90% purity) as a yellow oil, which was taken forward to the next step without further purification. MS (ESI, pos. ion) m/z: 247.0 (M+1).

Methyl 2-(2-cyano-4-fluorophenyl)acetate (I-54)

To a solution of ester, I-53 (250 mg, 1.0 mmol, 1.0 equiv) in DMF (5 mL) was added Zn(CN)$_2$ (83 mg, 0.7 mmol, 0.7 equiv), Zn dust (7 mg, 0.1 mmol, 0.1 equiv) and Pd(dppf)Cl$_2$.DCM (162 mg, 0.2 mmol, 0.2 equiv). The reaction mixture was stirred at 130 °C for 4 hours under microwave irradiation, at which point the reaction was deemed complete. The reaction mixture was quenched with water (20 mL) and extracted with EtOAc (3×20 mL). The combined organic extracts were dried and concentrated to afford a residue, which was purified by silica gel chromatography (Petroleum ether/EtOAc=1:1) to afford ester I-54 (100 mg, 52% yield, 90% purity) as a yellow oil. MS (ESI, pos. ion) m/z: 194.1 (M+1).

Methyl 2-(2-cyano-4-fluorophenyl)-2-methylpropanoate (I-55)

To a solution of ester, I-54 (1.0 g, 5.2 mmol, 1.0 equiv) in THF (20 mL) was added NaH (60% dispersion in mineral oil, 620 mg, 15.6 mmol, 3.0 equiv). The reaction mixture was stirred at 0° C. for 30 minutes and iodomethane (2.5 g, 8.0 mmol, 2.0 equiv) was added. The reaction mixture was stirred at 0° C. for 30 minutes and quenched with ice water (15 mL), then extracted with EtOAc (3×20 mL). The combined organic extracts were dried and concentrated to afford a residue, which was purified by silica gel chromatography (Petroleum ether/EtOAc=5:1) to afford ester I-55 (700 mg, 61% yield, 90% purity) as a yellow oil. MS (ESI, pos. ion) m/z: 222.1 (M+1).

2-(2-cyano-4-fluorophenyl)-2-methylpropanoic acid (I-56)

To a solution of ester, I-55 (500 mg, 2.3 mmol, 1.0 equiv) in EtOAc (5 mL) was added LiI (3.0 g, 23 mmol, 10 equiv). The reaction mixture was heated at reflux for 16 hours. On completion, the reaction mixture was quenched with water (20 mL) and acidified with 2N HCl to pH 4, then extracted with EtOAc (3×20 mL). The combined organic extracts were dried and concentrated to afford a residue, which was purified by preparative TLC (Petroleum/EtOAc/Acetic acid=1:1:0.01) to afford carboxylic acid I-57 (250 mg, 52% yield, 90% purity) as a white solid. MS (ESI, pos. ion) m/z: 208.1 (M+1). 1H NMR (400 MHz, CD$_3$OD) δ 7.62 (dd, J=8.9, 5.2 Hz, 1H), 7.54 (dd, J=8.2, 2.8 Hz, 1H), 7.40 (td, J=8.6, 2.9 Hz, 1H), 1.66 (s, 6H).

Synthesis of I-62

The synthesis of I-62 involved 4 steps as shown in scheme 14.

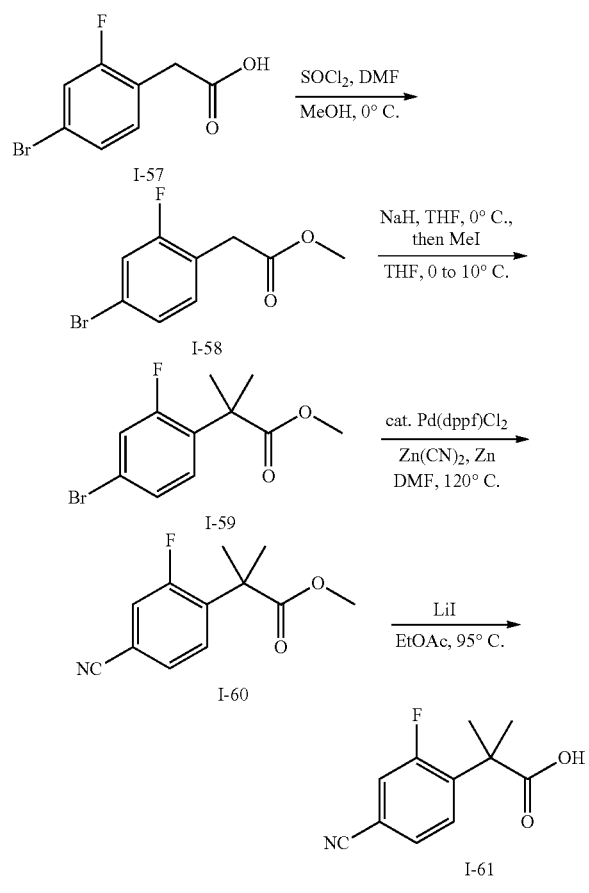

Scheme 14

Methyl 2-(4-bromo-2-fluorophenyl)acetate. (I-58)

To a solution of (4-bromo-2-fluorophenyl)acetic acid I-57 (2.0 g, 8.6 mmol, 1.0 equiv.) in MeOH (30 mL) that had been cooled in an ice-water bath was added thionyl chloride (1.53 g, 12.9 mmol, 1.5 equiv.) and DMF (0.06 mL). The reaction mixture was stirred at 0-5° C. for 2 hours, then concentrated to afford methyl 2-(4-bromo-2-fluorophenyl)acetate I-58 (1.99 g, 84% yield) as a colorless oil, which was taken forward to the next step without further purification. MS (ESI, pos. ion) m/z: 247.0, 249.0, (M+1, M+3).

Methyl 2-(4-bromo-2-fluorophenyl)-2-methylpropanoate. (I-59)

To a solution of ester, I-58 (1.8 g, 7.3 mmol, 1.0 equiv.) in DMF (30 mL) that had been cooled to 0-5° C. was added NaH (2.4 g, 58.4 mmol, 8.0 equiv, 60% dispersion in mineral oil). The reaction mixture was stirred at 0-5° C. for 30 minutes. Methyl iodide (2.3 mL) was then added, and the reaction mixture was allowed to warm to 12° C. and stirred for a further 4 hours. The reaction mixture was quenched with saturated aqueous NH$_4$Cl and diluted with EtOAc (120 mL). The phases were separated, and the organic phase was washed with water (100 mL) and brine (100 mL), dried (Na$_2$SO$_4$), and concentrated to afford a residue, which was purified by silica gel chromatography (EtOAc/Petroleum ether=1:12) to afford ester I-59 (1.6 g, 75% yield) as a colorless oil. MS (ESI, pos. ion) m/z: 275.0, 277.0. (M+1, M+3). 1H NMR (400 MHZ, CDCl$_3$) d 7.30-7.26 (m, 1H), 7.22-7.20 (m, 1H), 7.20-7.16 (m, 1H), 3.67 (s, 3H), 1.54 (s, 6H).

Methyl 2-(4-cyano-2-fluorophenyl)-2-methylpropanoate. (I-60)

To a solution of ester, I-59 (1.6 g, 5.8 mmol, 1.0 equiv.) in DMF (16 mL) was added Zn (379 mg, 5.8 mmol, 1.0 equiv.), 1,1'-Bis(diphenylphosphino)ferrocene-palladium(II)dichloride (366 mg, 0.5 mmol, 0.1 equiv.) and Zn(CN)$_2$ (684 mg, 5.8 mmol, 1.0 equiv.). The reaction mixture was stirred under nitrogen at 120° C. for 10 hours and then cooled to 12° ° C. The reaction was quenched with water (30 mL) and extracted with EtOAc (3×50 mL). The combined organic extracts were dried (Na$_2$SO$_4$) and concentrated to a residue, which was purified by silica gel chromatography (Petroleum/EtOAc=1:17) to afford methyl 2-(4-cyano-2-fluorophenyl)-2-methylpropanoate I-60 (1.06 g, 74% yield) as a light-yellow solid. MS (ESI, pos. ion) m/z: 222.1. (M+1).

2-(4-cyano-2-fluorophenyl)-2-methylpropanoic acid. (I-61)

Lithium iodide (2.12 g, 15.8 mmol, 10.0 equiv.) was added to a solution of ester I-60 (350 mg, 1.58 mmol, 1.0 equiv.) in EtOAc (6 mL). The reaction mixture was heated to 95° C. in a sealed tube for 18 hours. The reaction mixture was then poured into water (15 mL) and acidified to pH 5 with concentrated HCl. The reaction mixture was extracted with EtOAc (3×50 mL). The combined organic extracts were dried (Na$_2$SO$_4$) and concentrated to afford a residue, which was purified by preparative TLC (EtOAc/Petroleum ether=1:1) to afford 2-(4-cyano-2-fluorophenyl)-2-methylpropanoic acid I-61 (150 mg, 44% yield) as a white solid. MS (ESI, pos. ion) m/z: 208.1. (M+1). 1H NMR (400 MHZ, CDCl$_3$) d 7.47 (d, J=5.8 Hz, 2H), 7.38-7.33 (m, 1H), 1.62 (s, 6H).

Synthesis of I-65

The synthesis of I-65 involved 2 steps as shown in scheme 15.

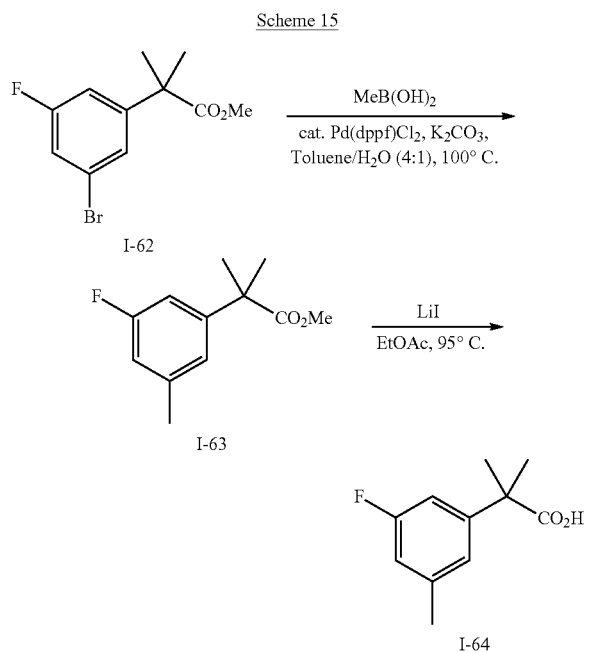

Scheme 15

Methyl 2-(3-fluoro-5-methylphenyl)-2-methylpropanoate (I-64)

To a solution of methyl 2-(3-bromo-5-fluorophenyl)-2-methylpropanoate I-62 (1.1 g, 4 mmol, 1.0 equiv.), methylboronic acid (1.25 g, 20.9 mmol, 5.2 equiv.) and Pd(dppf)Cl$_2$ (293 mg, 0.4 mmol, 0.1 equiv.) in 80:20 v/v toluene/H$_2$O (15 ml) was added K$_2$CO$_3$ (1.65 g, 12 mmol, 3.0 equiv.). The reaction mixture was stirred under N$_2$ at 100° C. for 16 hours. The reaction mixture was cooled to ambient temperature and the phases were separated. The organic phase was washed with brine (15 mL), dried over Na$_2$SO$_4$ and concentrated to a residue, which was purified by silica gel chromatography (5% EtOAc in petroleum ether) to afford ester I-63 (560 mg, 63%) as a yellow oil. MS (ESI, pos. ion) m/z: 211.1, (M+1).

2-(3-fluoro-5-methylphenyl)-2-methylpropanoic acid (I-64)

To a solution of ester, I-63 (600 mg, 2.85 mmol, 1.0 equiv.) in EtOAc (10 mL) was added LiI (3.8 g, 28.6 mmol, 10.0 equiv.). The reaction mixture was stirred at 90° C. in a sealed tube for 24 hours, then cooled and acidified to pH 3 with 1N HCl. The phases were separated, and the organic phase was washed with brine (2×15 mL), dried, and concentrated to a residue, which was purified by reversed phase chromatography (60% MeCN/H$_2$O with 0.05% Formic acid as a modifier) to afford the carboxylic acid I-64 as a yellow solid (280 mg, 49% yield).

$^1$H NMR (400 MHZ, DMSO-d$_6$) δ 12.42 (brs, 1H), 6.98 (s, 1H), 6.89-6.93 (m, 2H), 2.31 (s, 3H), 1.46 (s, 6H).

General Procedure for N-Terminus Derivatization

The appropriate peptide sequence with deprotected N-terminal amino group was treated with the carboxylic acid (5.5 equiv.) and HATU (5.0 equiv.) in 20% Collidine/DMF (1 mL per 40 mg of resin of estimated loading 0.19 mmol/g). The reaction mixture was agitated at ambient temperature for 12 hours and the resin was filtered, then washed with DMF (5×2 mL) and DCM (5×2 mL) and dried in vacuo. The compound was isolated after cleavage from the resin, followed by purification by preparative HPLC. Characterization for the compounds is presented in Table 2.

TABLE 2

Non-Limiting Exemplary Compounds

| Example | Compound # | Formula | Mass observed | Mass calculated |
|---|---|---|---|---|
| 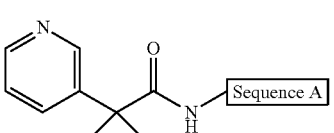<br>1 | 255 | $C_{225}H_{346}N_{48}O_{67}$ | 1199.6 | 1199.1 (M + 4H$^+$) |
| 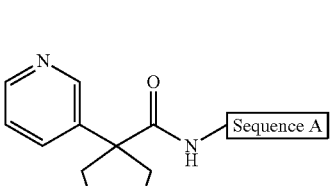<br>2 | 256 | $C_{226}H_{348}N_{48}O_{67}$ | 1203.1 | 1202.6 (M + 4H$^+$) |

TABLE 2-continued
Non-Limiting Exemplary Compounds
| Example | Compound # | Formula | Mass observed | Mass calculated |
|---|---|---|---|---|
| 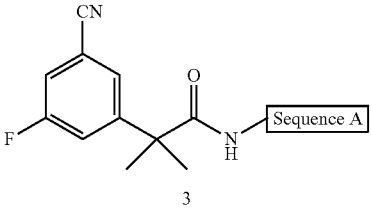<br>3 | 254 | $C_{226}H_{345}FN_{48}O_{67}$ | 1207.2 | 1206.6 (M + 4H$^+$) |
| 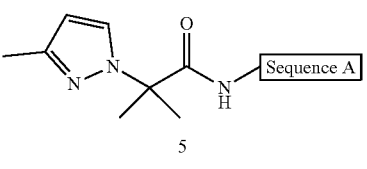<br>5 | 253 | $C_{223}H_{347}N_{49}O_{67}$ | 1197.3 | 1196.9 (M + 4H$^+$) |
| 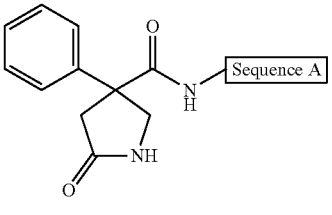<br>6 | 250 | $C_{226}H_{346}N_{48}O_{68}$ | 1206.7 | 1206.1 (M + 4H$^+$) |
| 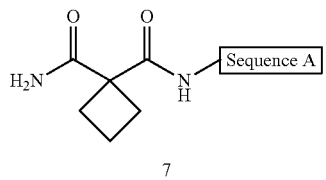<br>7 | 257 | $C_{221}H_{344}N_{48}O_{68}$ | 1191.2 (M + 4H$^+$) | 1190.6 (M + 4H$^+$) |
| 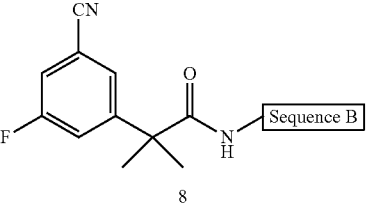<br>8 | 242 | $C_{226}H_{345}FN_{50}O_{67}$ | 1214.0 | 1213.6 (M + 4H$^+$) |
| 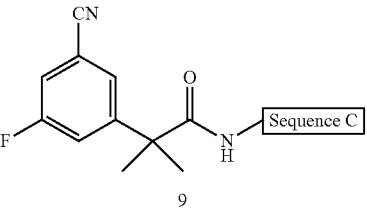<br>9 | 245 | $C_{227}H_{346}F_2N_{48}O_{67}$ | 1215.1 | 1214.6 (M + 4H$^+$) |
| 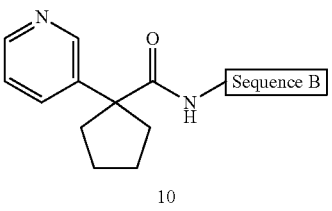<br>10 | 243 | $C_{226}H_{348}N_{50}O_{67}$ | 1210.1 | 1209.6 (M + 4H$^+$) |

TABLE 2-continued
Non-Limiting Exemplary Compounds
| Example | Compound # | Formula | Mass observed | Mass calculated |
|---|---|---|---|---|
| 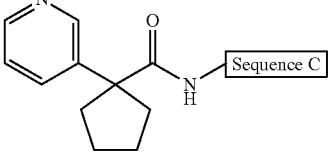<br>11 | 246 | $C_{227}H_{349}FN_{48}O_{67}$ | 1211.2 | 1210.6 (M + 4H$^+$) |
| 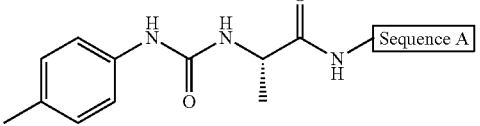<br>12 | 272 | $C_{226}H_{349}N_{49}O_{68}$ | 1210.9 | 1210.4 (M + 4H$^+$) |
| 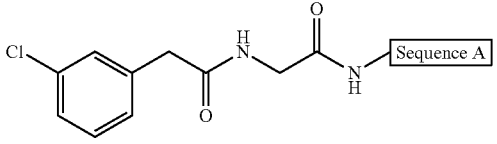<br>13 | 230 | $C_{225}H_{345}ClN_{48}O_{68}$ | 1212.3 | 1211.6 (M + 4H$^+$) |
| 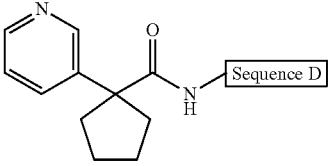<br>14 | 234 | $C_{227}H_{350}N_{48}O_{67}$ | 1206.8 | 1206.1 (M + 4H$^+$) |
| 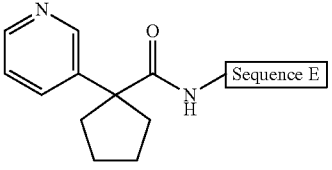<br>15 | 231 | $C_{226}H_{347}FN_{48}O_{67}$ | 1207.6 | 1207.1 (M + 4H$^+$) |
| 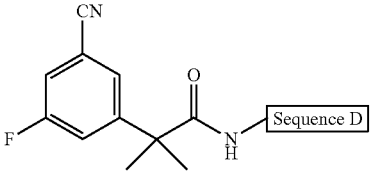<br>16 | 235 | $C_{227}H_{347}FN_{48}O_{67}$ | 1210.5 | 1210.1 (M + 4H$^+$) |
| 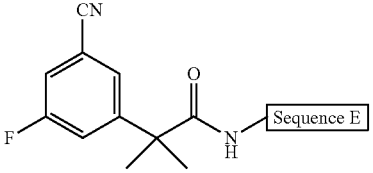<br>17 | 233 | $C_{226}H_{344}F_2N_{48}O_{67}$ | 1211.5 | 1211.1 (M + 4H$^+$) |

TABLE 2-continued
Non-Limiting Exemplary Compounds
| Example | Compound # | Formula | Mass observed | Mass calculated |
|---|---|---|---|---|
| 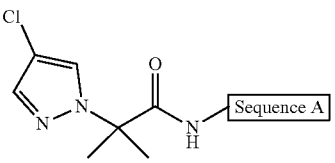 18 | 247 | $C_{222}H_{344}ClN_{49}O_{67}$ | 1202.3 | 1201.9 (M + 4H$^+$) |
| 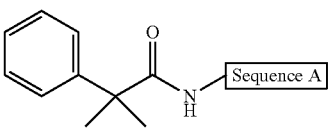 19 | 241 | $C_{225}H_{347}N_{47}O_{67}$ | 1196.3 | 1195.9 (M + 4H$^+$) |
| 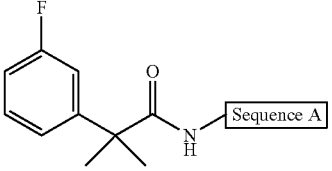 20 | 240 | $C_{225}H_{346}FN_{47}O_{67}$ | 1200.8 | 1200.4 (M + 4H$^+$) |
| 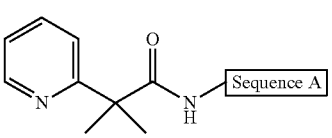 21 | 237 | $C_{224}H_{346}N_{48}O_{67}$ | 1196.6 | 1196.1 (M + 4H$^+$) |
| 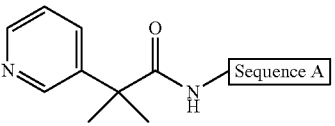 22 | 239 | $C_{224}H_{346}N_{48}O_{67}$ | 1196.6 | 1196.1 (M + 4H$^+$) |
| 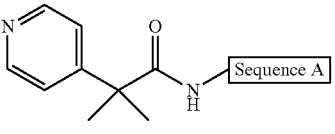 23 | 238 | $C_{224}H_{346}N_{48}O_{67}$ | 1196.6 | 1196.1 (M + 4H$^+$) |
| 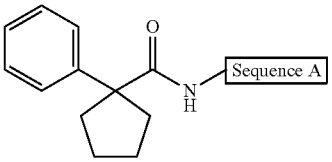 24 | 236 | $C_{227}H_{349}N_{47}O_{67}$ | 1202.8 | 1202.4 (M + 4H$^+$) |

TABLE 2-continued
Non-Limiting Exemplary Compounds
| Example | Compound # | Formula | Mass observed | Mass calculated |
|---|---|---|---|---|
| 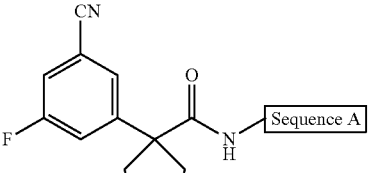<br>25 | 162 | $C_{228}H_{349}FN_{48}O_{67}$ | 1214.3 | 1213.6 (M + 4H$^+$) |
| 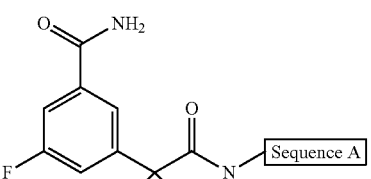<br>26 | 159 | $C_{226}H_{347}FN_{48}O_{68}$ | 1613.3 | 1612.5 (M − 3H$^+$) |
| 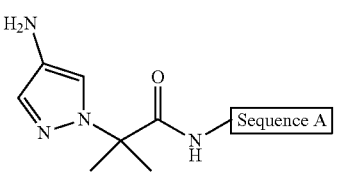<br>27 | 157 | $C_{222}H_{346}N_{50}O_{67}$ | 1594.6 | 1593.8 (M − 3H$^+$) |
| 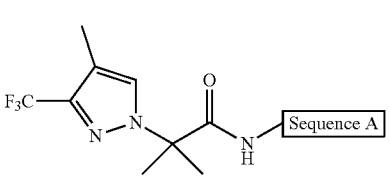<br>28 | 158 | $C_{224}H_{346}F_3N_{49}O_{67}$ | 1617.0 | 1616.2 (M − 3H$^+$) |
| 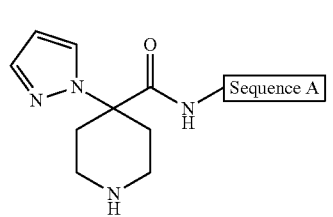<br>29 | 160 | $C_{224}H_{348}N_{50}O_{67}$ | 1204.2 | 1203.6 (M + 4H$^+$) |
| 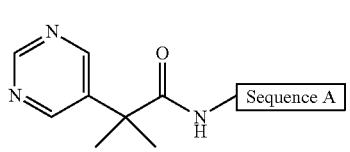<br>30 | 161 | $C_{223}H_{345}N_{49}O_{67}$ | 1196.9 | 1196.4 (M + 4H$^+$) |

TABLE 2-continued
Non-Limiting Exemplary Compounds
| Example | Compound # | Formula | Mass observed | Mass calculated |
|---|---|---|---|---|
| 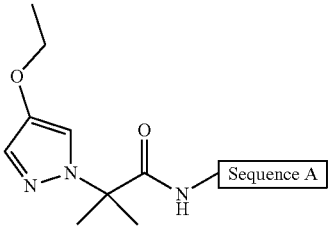<br>31 | 152 | $C_{224}H_{349}N_{49}O_{68}$ | 1604.3 | 1603.5<br>(M − 3H$^+$) |
| 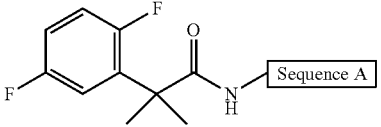<br>32 | 146 | $C_{225}H_{345}F_2N_{47}O_{67}$ | 1606.8 | 1606.2<br>(M + 3H$^+$) |
| 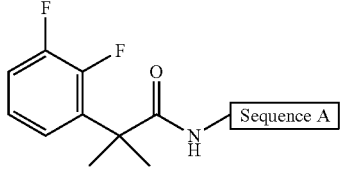<br>33 | 147 | $C_{225}H_{345}F_2N_{47}O_{67}$ | 1606.7 | 1606.2<br>(M + 3H$^+$) |
| 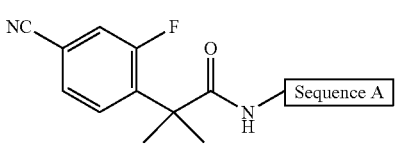<br>34 | 149 | $C_{226}H_{345}FN_{48}O_{67}$ | 1609.3 | 1608.5<br>(M + 3H$^+$) |
| 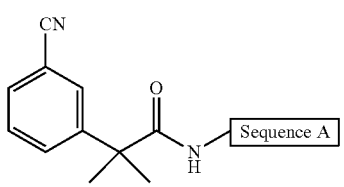<br>35 | 150 | $C_{226}H_{346}N_{48}O_{67}$ | 1603.2 | 1602.5<br>(M + 3H$^+$) |
| 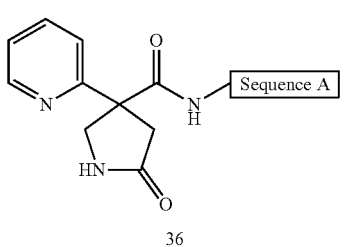<br>36 | 151 | $C_{225}H_{345}N_{49}O_{68}$ | 1609.0 | 1608.2<br>(M + 3H$^+$) |

TABLE 2-continued
Non-Limiting Exemplary Compounds
| Example | Compound # | Formula | Mass observed | Mass calculated |
|---|---|---|---|---|
| 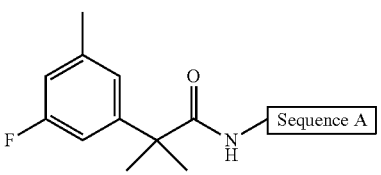 37 | 144 | $C_{226}H_{348}FN_{47}O_{67}$ | 1603.8 | 1602.8 (M − 3H$^+$) |
| 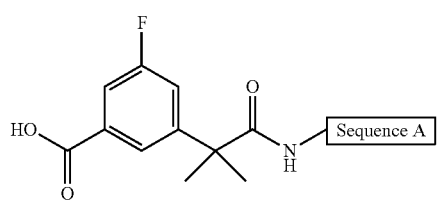 38 | 139 | $C_{226}H_{346}FN_{47}O_{69}$ | 1613.6 | 1612.8 (M − 3H$^+$) |
| 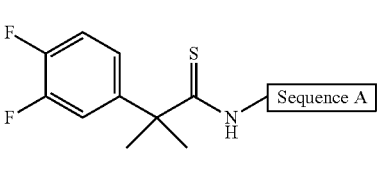 39 | 137 | $C_{225}H_{345}F_2N_{47}O_{66}S$ | 1209.4 | 1208.9 (M + 4H$^+$) |
| 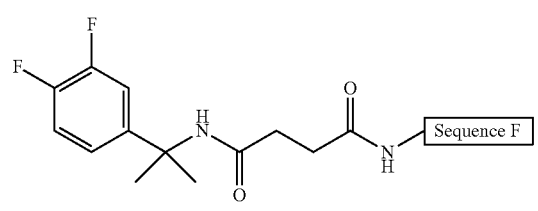 40 | 280 | $C_{225}H_{345}F_2N_{47}O_{67}$ | 1605.0 | 1604.2 (M − 3H$^+$) |
| 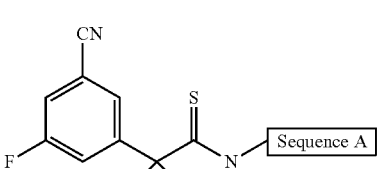 41 | 135 | $C_{226}H_{345}FN_{48}O_{66}S$ | 1612.7 | 1611.8 (M − 3H$^+$) |
| 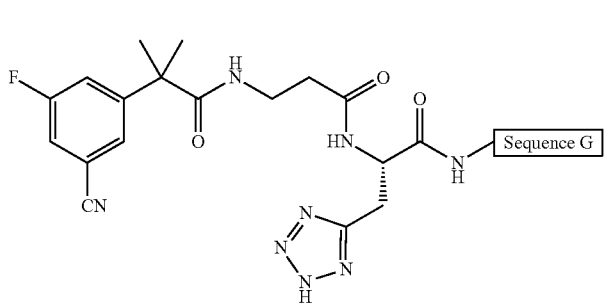 42 | 136 | $C_{225}H_{343}FN_{52}O_{65}$ | 1610.6 | 1609.8 (M − 3H$^+$) |

TABLE 2-continued
Non-Limiting Exemplary Compounds
| Example | Compound # | Formula | Mass observed | Mass calculated |
|---|---|---|---|---|
| 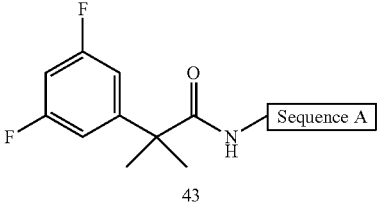<br>43 | 173 | $C_{225}H_{345}F_2N_{47}O_{67}$ | 1205.3 | 1204.9 $(M + 4H^+)$ |
| 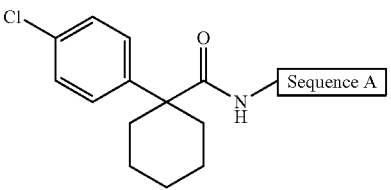<br>44 | 174 | $C_{228}H_{350}ClN_{47}O_{67}$ | 1215.2 | 1214.4 $(M + 4H^+)$ |
| 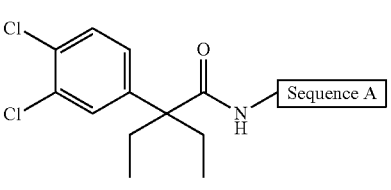<br>45 | 175 | $C_{227}H_{349}Cl_2N_{47}O_{67}$ | 1220.7 | 1219.9 $(M + 4H^+)$ |
| 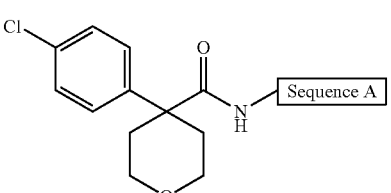<br>46 | 172 | $C_{227}H_{348}ClN_{47}O_{68}$ | 1215.7 | 1214.9 $(M + 4H^+)$ |
| 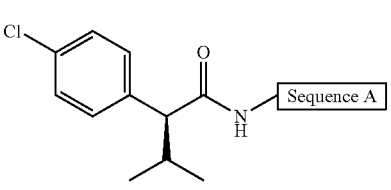<br>47 | 177 | $C_{226}H_{348}ClN_{47}O_{67}$ | 1208.4 | 1207.9 $(M + 4H^+)$ |
| 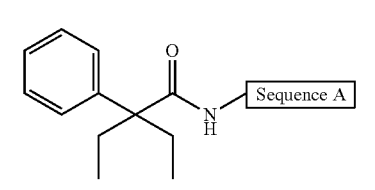<br>48 | 218 | $C_{227}H_{351}N_{47}O_{67}$ | 1203.4 | 1202.9 $(M + 4H^+)$ |

TABLE 2-continued

Non-Limiting Exemplary Compounds

| Example | Compound # | Formula | Mass observed | Mass calculated |
|---|---|---|---|---|
| 49 | 217 | $C_{227}H_{348}ClN_{47}O_{67}$ | 1211.5 | 1210.9 (M + 4H$^+$) |
| 50 | 214 | $C_{227}H_{348}FN_{47}O_{67}$ | 1207.6 | 1206.9 (M + 4H$^+$) |
| 51 | 220 | $C_{227}H_{347}F_2N_{47}O_{67}$ | 1211.9 | 1211.4 (M + 4H$^+$) |
| 52 | 215 | $C_{225}H_{345}F_2N_{47}O_{67}$ | 1205.6 | 1204.9 (M + 4H$^+$) |
| 53 | 185 | $C_{225}H_{346}ClN_{47}O_{67}$ | 1204.9 | 1204.4 (M + 4H$^+$) |
| 54 | 176 | $C_{227}H_{350}ClN_{47}O_{67}$ | 1212.0 | 1211.4 (M + 4H$^+$) |
| 55 | 163 | $C_{225}H_{345}F_2N_{47}O_{67}$ | 1205.4 | 1204.8 (M + 4H$^+$) |

TABLE 2-continued
| Example | Compound # | Formula | Mass observed | Mass calculated |
|---|---|---|---|---|
| 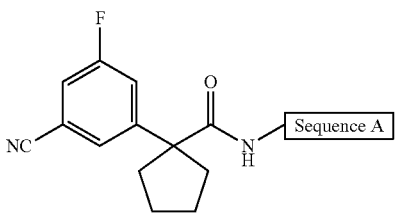 56 | 164 | $C_{228}H_{347}FN_{48}O_{67}$ | 1213.8 | 1213.1 (M + 4H$^+$) |
| 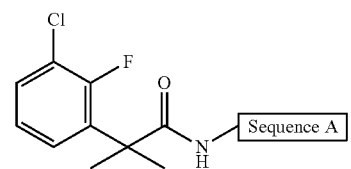 57 | 219 | $C_{225}H_{345}ClFN_{47}O_{67}$ | 1209.5 | 1208.9 (M + 4H$^+$) |
| 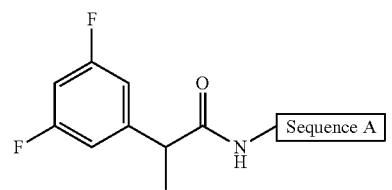 58 | 216 | $C_{224}H_{343}F_2N_{47}O_{67}$ | 1201.8 | 1201.4 (M + 4H$^+$) |
| 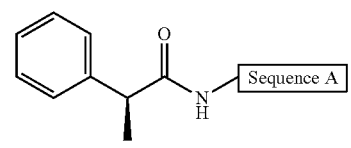 59 | 211 | $C_{224}H_{345}N_{47}O_{67}$ | 1192.8 | 1192.4 (M + 4H$^+$) |
| 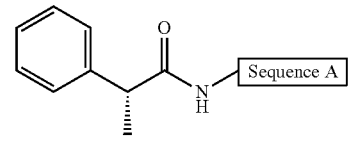 60 | 204 | $C_{224}H_{345}N_{47}O_{67}$ | 1192.8 | 1192.4 (M + 4H$^+$) |
| 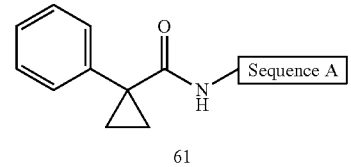 61 | 199 | $C_{225}H_{345}N_{47}O_{67}$ | 1195.8 | 1195.4 (M + 4H$^+$) |
| 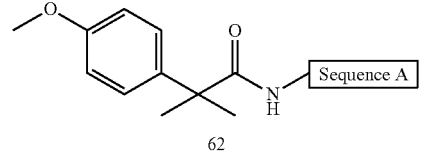 62 | 203 | $C_{226}H_{349}N_{47}O_{68}$ | 1203.8 | 1203.4 (M + 4H$^+$) |

TABLE 2-continued
Non-Limiting Exemplary Compounds
| Example | Compound # | Formula | Mass observed | Mass calculated |
|---|---|---|---|---|
| 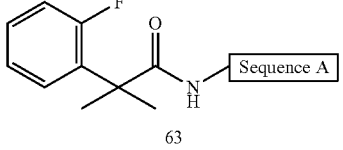<br>63 | 198 | $C_{225}H_{346}FN_{47}O_{67}$ | 1200.8 | 1200.4 (M + 4H$^+$) |
| 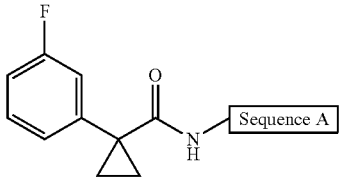<br>64 | 206 | $C_{225}H_{344}FN_{47}O_{67}$ | 1200.4 | 1199.9 (M + 4H$^+$) |
| 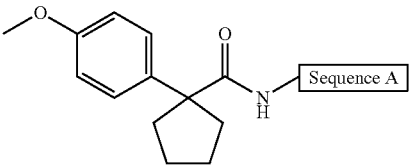<br>65 | 208 | $C_{228}H_{351}N_{47}O_{68}$ | 1210.3 | 1209.9 (M + 4H$^+$) |
| 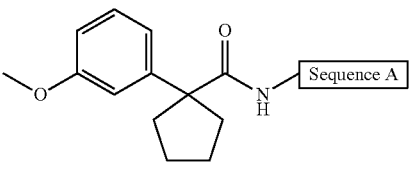<br>66 | 207 | $C_{228}H_{351}N_{47}O_{68}$ | 1210.4 | 1209.9 (M + 4H$^+$) |
| 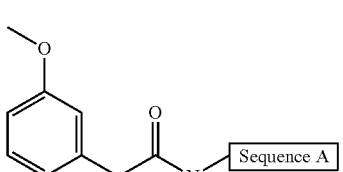<br>67 | 209 | $C_{226}H_{349}N_{47}O_{68}$ | 1203.9 | 1203.4 (M + 4H$^+$) |
| 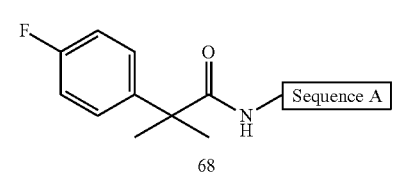<br>68 | 210 | $C_{225}H_{346}FN_{47}O_{67}$ | 1200.9 | 1200.4 (M + 4H$^+$) |
| 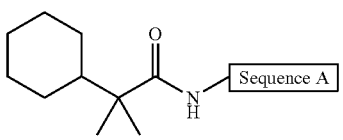<br>69 | 205 | $C_{225}H_{353}N_{47}O_{67}$ | 1197.9 | 1197.4 (M + 4H$^+$) |

TABLE 2-continued
Non-Limiting Exemplary Compounds
| Example | Compound # | Formula | Mass observed | Mass calculated |
|---|---|---|---|---|
| 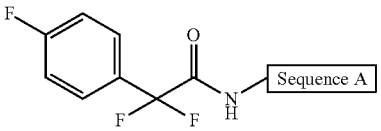<br>70 | 188 | $C_{223}H_{340}F_3N_{47}O_{67}$ | 1202.8 | 1202.4 (M + 4H$^+$) |
| 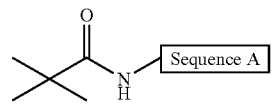<br>71 | 197 | $C_{220}H_{345}N_{47}O_{67}$ | 1180.9 | 1180.4 (M + 4H$^+$) |
| 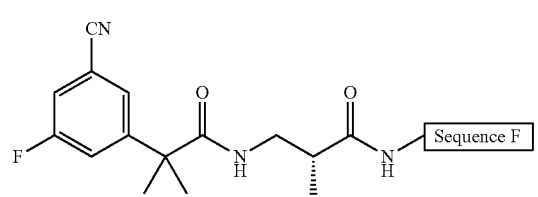<br>72 | 225 | $C_{227}H_{347}FN_{48}O_{67}$ | 1210.7 | 1210.1 (M + 4H$^+$) |
| 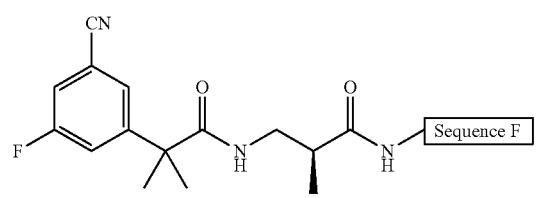<br>73 | 224 | $C_{227}H_{347}FN_{48}O_{67}$ | 1210.6 | 1210.1 (M + 4H$^+$) |
| 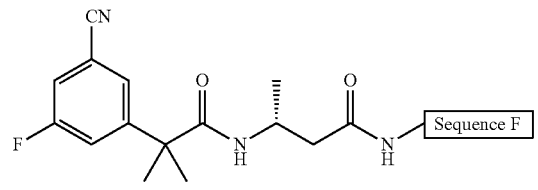<br>74 | 223 | $C_{227}H_{347}FN_{48}O_{67}$ | 1210.6 | 1210.1 (M + 4H$^+$) |
| 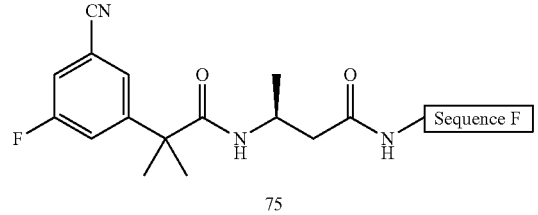<br>75 | 222 | $C_{227}H_{347}FN_{48}O_{67}$ | 1210.7 | 1210.1 (M + 4H$^+$) |
| 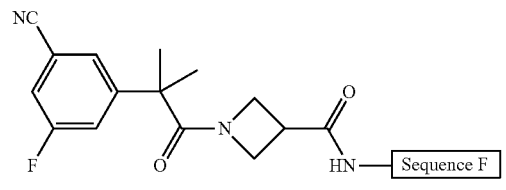<br>76 | 213 | $C_{227}H_{345}FN_{48}O_{67}$ | 1210.1 | 1209.6 (M + 4H$^+$) |

TABLE 2-continued
Non-Limiting Exemplary Compounds
| Example | Compound # | Formula | Mass observed | Mass calculated |
|---|---|---|---|---|
| 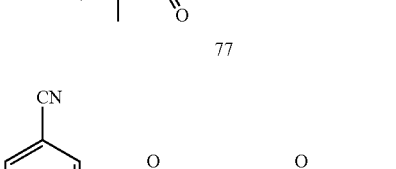 77 | 212 | $C_{229}H_{349}FN_{48}O_{67}$ | 1217.2 | 1216.6 (M + 4H$^+$) |
| 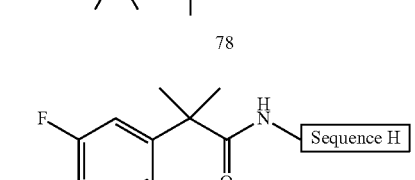 78 | 201 | $C_{227}H_{347}FN_{48}O_{67}$ | 1210.6 | 1210.1 (M + 4H$^+$) |
| 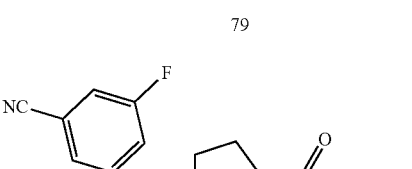 79 | 200 | $C_{227}H_{347}FN_{48}O_{67}$ | 1210.6 | 1210.1 (M + 4H$^+$) |
| 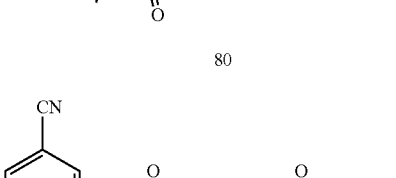 80 | 195 | $C_{228}H_{347}FN_{48}O_{67}$ | 1213.8 | 1213.1 (M + 4H$^+$) |
| 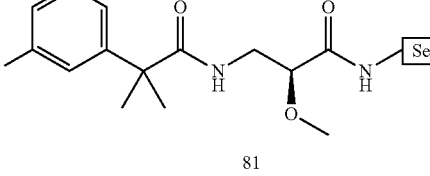 81 | 194 | $C_{227}H_{347}FN_{48}O_{68}$ | 1214.7 | 1214.1 (M + 4H$^+$) |
| 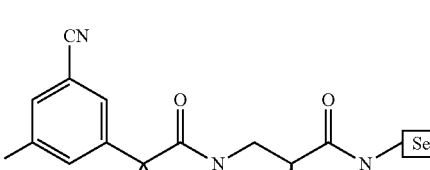 82 | 191 | $C_{226}H_{346}FN_{49}O_{67}$ | 1210.8 | 1210.4 (M + 4H$^+$) |

TABLE 2-continued
Non-Limiting Exemplary Compounds
| Example | Compound # | Formula | Mass observed | Mass calculated |
|---|---|---|---|---|
| 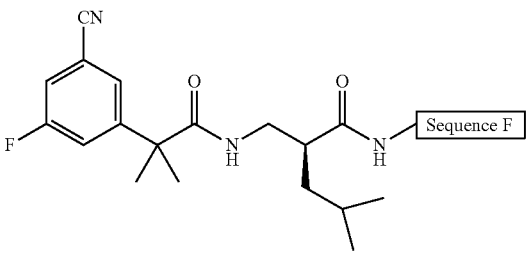 83 | 193 | $C_{230}H_{353}FN_{48}O_{67}$ | 1221.2 | 1220.7 (M + 4H$^+$) |
| 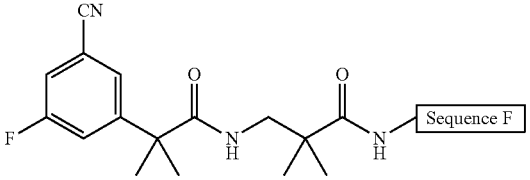 84 | 192 | $C_{228}H_{349}FN_{48}O_{67}$ | 1214.2 | 1213.6 (M + 4H$^+$) |
| 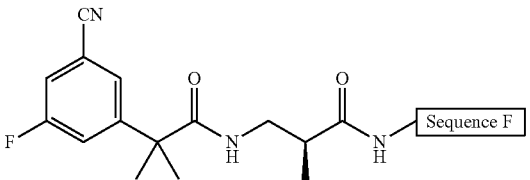 85 | 171 | $C_{229}H_{351}FN_{48}O_{67}$ | 1217.8 | 1217.2 (M + 4H$^+$) |
| 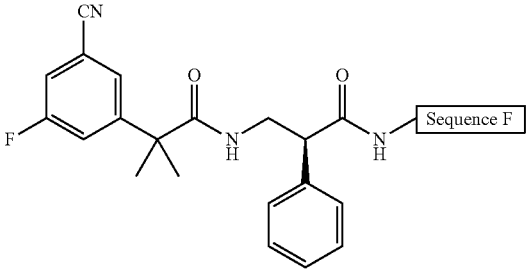 86 | 170 | $C_{232}H_{349}FN_{48}O_{67}$ | 1226.2 | 1225.6 (M + 4H$^+$) |
| 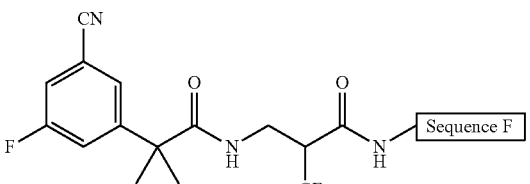 87 | 165 | $C_{227}H_{344}F_4N_{48}O_{67}$ | 1224.2 | 1223.6 (M + 4H$^+$) |

TABLE 2-continued

Non-Limiting Exemplary Compounds

| Example | Compound # | Formula | Mass observed | Mass calculated |
|---|---|---|---|---|
| 88 | 148 | $C_{228}H_{349}FN_{48}O_{67}$ | 1618.6 | 1617.9 (M + 3H$^+$) |
| 89 | 189 | $C_{231}H_{347}FN_{48}O_{68}$ | 1226.8 | 1226.1 (M + 4H$^+$) |
| 90 | 190 | $C_{226}H_{345}FN_{48}O_{67}$ | 1207.1 | 1206.6 (M + 4H$^+$) |
| 91 | 196 | $C_{228}H_{347}FN_{48}O_{69}$ | 1221.7 | 1221.1 (M + 4H$^+$) |
| 92 | 186 | $C_{225}H_{342}FN_{49}O_{68}$ | 1614.2 | 1613.5 (M + 3H$^+$) |
| 93 | 187 | $C_{233}H_{348}FN_{49}O_{71}$ | 1664.2 | 1663.5 (M + 3H$^+$) |

TABLE 2-continued
| Example | Compound # | Formula | Mass observed | Mass calculated |
|---|---|---|---|---|
| 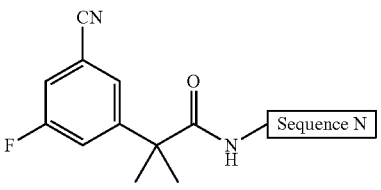 94 | 183 | $C_{224}H_{342}FN_{47}O_{66}$ | 1590.5 | 1589.5 (M + 3H$^+$) |
| 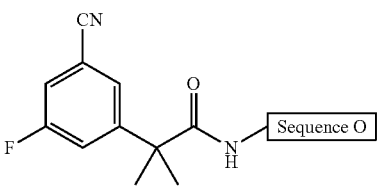 95 | 184 | $C_{229}H_{341}FN_{48}O_{70}$ | 1636.2 | 1635.2 (M + 4H$^+$) |
| 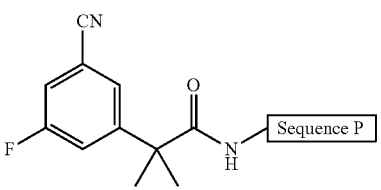 96 | 182 | $C_{225}H_{343}FN_{48}O_{67}$ | 1604.8 | 1603.8 (M + 4H$^+$) |
| 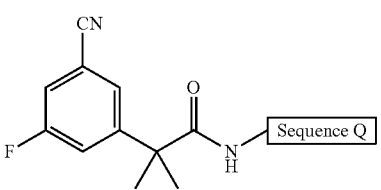 97 | 166 | $C_{227}H_{347}FN_{48}O_{66}$ | 1206.6 | 1206.1 (M + 4H$^+$) |
| 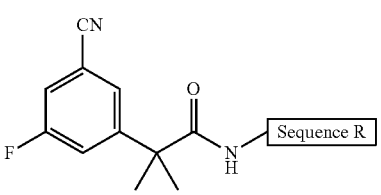 98 | 168 | $C_{225}H_{343}FN_{48}O_{66}$ | 1199.8 | 1199.1 (M + 4H$^+$) |
| 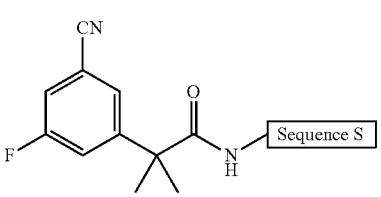 99 | 167 | $C_{224}H_{339}FN_{48}O_{69}$ | 1207.7 | 1207.1 (M + 4H$^+$) |

TABLE 2-continued
Non-Limiting Exemplary Compounds
| Example | Compound # | Formula | Mass observed | Mass calculated |
|---|---|---|---|---|
| 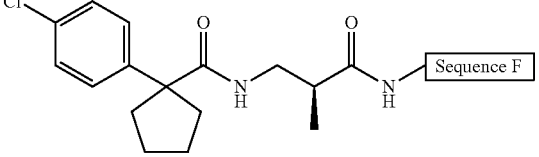 100 | 181 | $C_{228}H_{350}ClN_{47}O_{67}$ | 1215.0 | 1214.4 (M + 4H$^+$) |
| 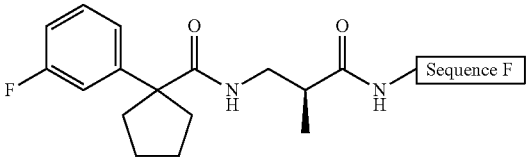 101 | 180 | $C_{228}H_{350}FN_{47}O_{67}$ | 1210.9 | 1210.4 (M + 4H$^+$) |
| 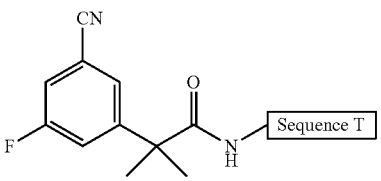 102 | 169 | $C_{226}H_{344}FN_{47}O_{68}$ | 1207.4 | 1206.9 (M + 4H$^+$) |
| 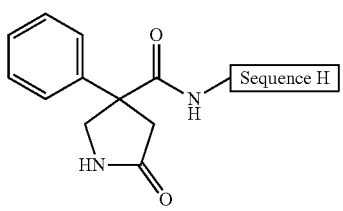 103 | 249 | $C_{227}H_{348}N_{48}O_{68}$ | 1210.1 | 1209.6 (M + 4H$^+$) |
| 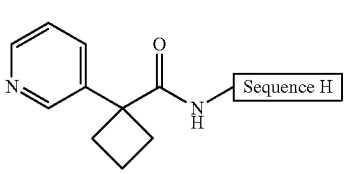 105 | 251 | $C_{226}H_{348}N_{48}O_{67}$ | 1203.0 | 1202.6 (M + 4H$^+$) |
| 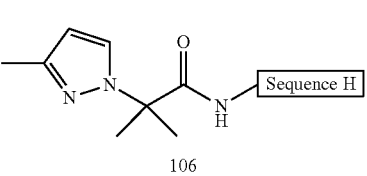 106 | 252 | $C_{224}H_{349}N_{49}O_{67}$ | 1200.9 | 1200.4 (M + 4H$^+$) |
| 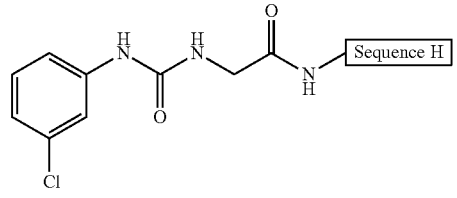 107 | 273 | $C_{225}H_{346}ClN_{49}O_{68}$ | 1215.8 | 1215.4 (M + 4H$^+$) |

TABLE 2-continued
Non-Limiting Exemplary Compounds
| Example | Compound # | Formula | Mass observed | Mass calculated |
|---|---|---|---|---|
| 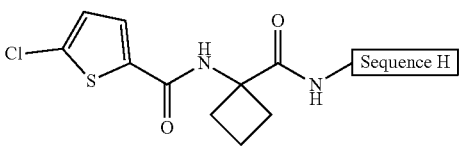 109 | 244 | $C_{226}H_{347}ClN_{48}O_{68}S$ | 1223.8 | 1223.1 (M + 4H$^+$) |
| 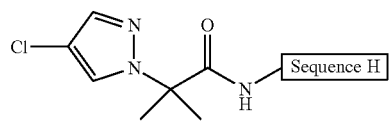 110 | 248 | $C_{223}H_{346}ClN_{49}O_{67}$ | 1206.0 | 1205.4 (M + 4H$^+$) |
| 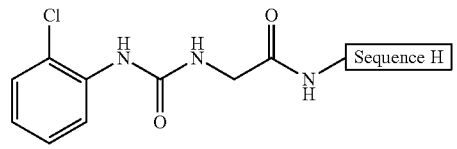 111 | 259 | $C_{225}H_{346}ClN_{49}O_{68}$ | 1215.9 | 1215.4 (M + 4H$^+$) |
| 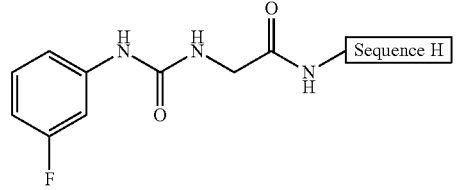 112 | 260 | $C_{225}H_{346}FN_{49}O_{68}$ | 1211.9 | 1211.4 (M + 4H$^+$) |
| 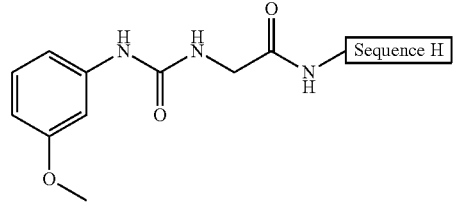 113 | 261 | $C_{226}H_{349}N_{49}O_{69}$ | 1214.9 | 1214.4 (M + 4H$^+$) |
| 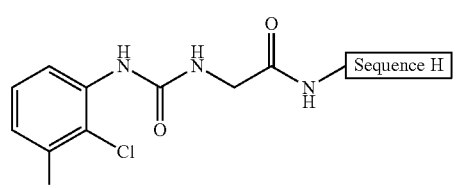 114 | 262 | $C_{225}H_{345}Cl_2N_{49}O_{68}$ | 1224.6 | 1223.9 (M + 4H$^+$) |

TABLE 2-continued
Non-Limiting Exemplary Compounds
| Example | Compound # | Formula | Mass observed | Mass calculated |
|---|---|---|---|---|
| 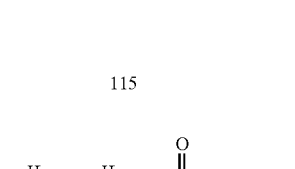 115 | 263 | $C_{226}H_{346}F_3N_{49}O_{68}$ | 1224.4 | 1223.9 (M + 4H$^+$) |
| 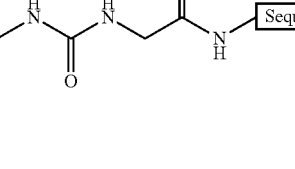 116 | 264 | $C_{225}H_{345}F_2N_{49}O_{68}$ | 1216.2 | 1215.9 (M + 4H$^+$) |
| 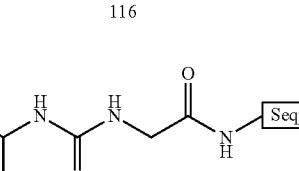 117 | 265 | $C_{226}H_{345}ClF_3N_{49}O_{68}$ | 1232.9 | 1232.4 (M + 4H$^+$) |
| 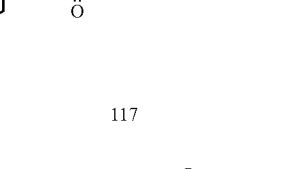 118 | 266 | $C_{225}H_{345}Cl_2N_{49}O_{68}$ | 1224.6 | 1223.9 (M + 4H$^+$) |
| 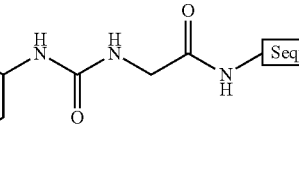 119 | 267 | $C_{225}H_{345}F_2N_{49}O_{68}$ | 1216.4 | 1215.9 (M + 4H$^+$) |
| 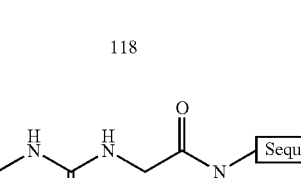 120 | 268 | $C_{225}H_{346}FN_{49}O_{68}$ | 1211.9 | 1211.4 (M + 4H$^+$) |

TABLE 2-continued
Non-Limiting Exemplary Compounds
| Example | Compound # | Formula | Mass observed | Mass calculated |
|---|---|---|---|---|
| 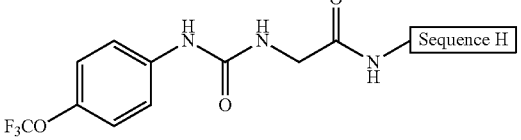<br>121 | 269 | $C_{226}H_{346}F_3N_{49}O_{69}$ | 1228.4 | 1227.9 (M + 4H$^+$) |
| 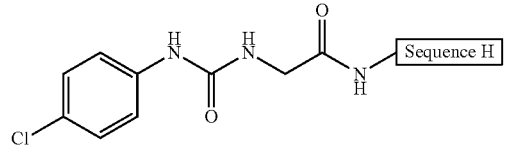<br>122 | 270 | $C_{225}H_{346}ClN_{49}O_{68}$ | 1215.9 | 1215.4 (M + 4H$^+$) |
| 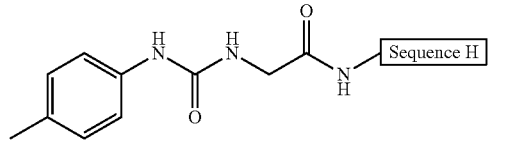<br>123 | 271 | $C_{226}H_{349}N_{49}O_{68}$ | 1210.8 | 1210.4 (M + 4H$^+$) |
| 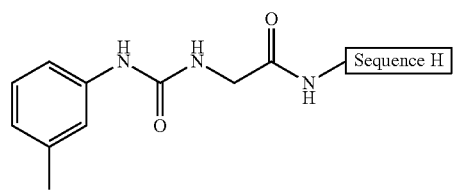<br>124 | 258 | $C_{226}H_{349}N_{49}O_{68}$ | 1210.9 | 1210.4 (M + 4H$^+$) |
| 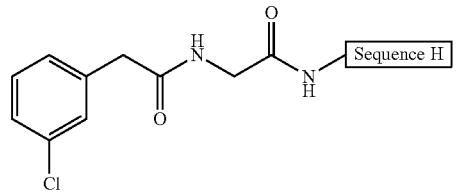<br>125 | 221 | $C_{226}H_{347}ClN_{48}O_{68}$ | 1215.8 | 1215.1 (M + 4H$^+$) |
| 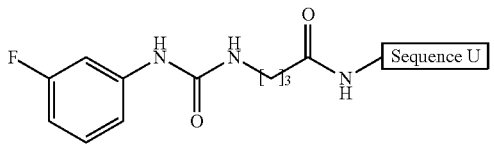<br>126 | 282 | $C_{224}H_{344}F_2N_{48}O_{67}$ | 1205.9 | 1205.1 (M + 4H$^+$) |
| 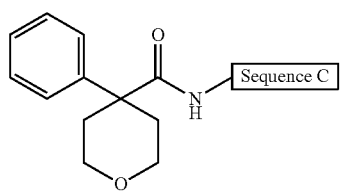<br>127 | 178 | $C_{228}H_{350}FN_{47}O_{68}$ | 1214.9 | 1214.4 (M + 4H$^+$) |

TABLE 2-continued

| Non-Limiting Exemplary Compounds | | | | |
|---|---|---|---|---|
| Example | Compound # | Formula | Mass observed | Mass calculated |
| 128 | 179 | $C_{228}H_{349}ClFN_{47}O_{67}$ | 1219.4 | 1218.9 (M + 4H$^+$) |
| 129 | 154 | $C_{234}H_{352}N_{48}O_{72}$ | 1661.8 | 1661.2 (M − 3H$^+$) |
| 130 | 155 | $C_{234}H_{351}ClN_{48}O_{71}$ | 1668.2 | 1667.2 (M − 3H$^+$) |
| 131 | 156 | $C_{234}H_{351}N_{49}O_{72}$ | 1666.2 | 1665.5 (M − 3H$^+$) |
| 132 | 145 | $C_{234}H_{350}F_2N_{48}O_{71}$ | 1668.9 | 1667.8 (M − 3H$^+$) |
| 134 | 101 | $C_{232}H_{352}N_{50}O_{72}$ | 1663.3 | 1662.5 (M − 3H$^+$) |

TABLE 2-continued
Non-Limiting Exemplary Compounds
| Example | Compound # | Formula | Mass observed | Mass calculated |
|---|---|---|---|---|
| 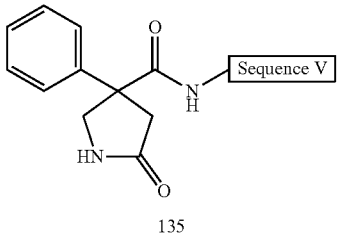<br>135 | 142 | $C_{234}H_{350}FN_{49}O_{72}$ | 1672.2 | 1671.5 $(M - 3H^+)$ |
| 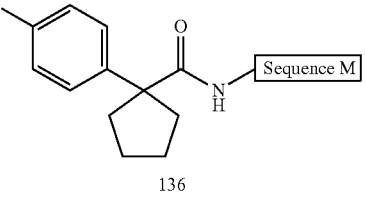<br>136 | 141 | $C_{235}H_{352}ClFN_{48}O_{71}$ | 1678.8 | 1677.8 $(M - 3H^+)$ |
| 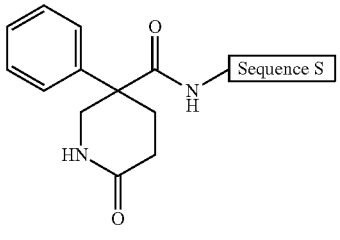<br>137 | 153 | $C_{225}H_{342}N_{48}O_{70}$ | 1611.9 | 1611.2 $(M - 3H^+)$ |
| 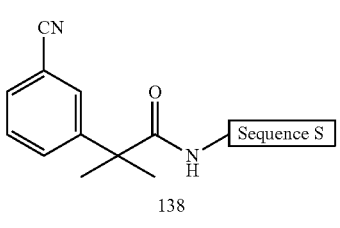<br>138 | 143 | $C_{224}H_{340}N_{48}O_{69}$ | 1602.1 | 1601.1 $(M - 3H^+)$ |
| 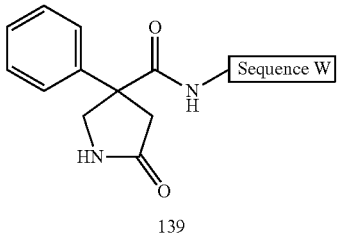<br>139 | 138 | $C_{225}H_{341}FN_{48}O_{70}$ | 1618.3 | 1617.2 $(M - 3H^+)$ |
| 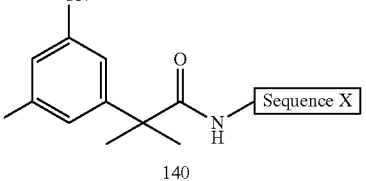<br>140 | 229 | $C_{190}H_{291}FN_{38}O_{54}$ | 1330.8 | 1330.4 $(M + 3H^+)$ |

TABLE 2-continued

Non-Limiting Exemplary Compounds

| Example | Compound # | Formula | Mass observed | Mass calculated |
|---|---|---|---|---|
| 141 | 228 | $C_{191}H_{292}F_2N_{38}O_{54}$ | 1341.5 | 1341.0 (M + 3H$^+$) |
| 142 | 227 | $C_{190}H_{294}N_{38}O_{54}$ | 1325.6 | 1325.1 (M + 3H$^+$) |
| 143 | 226 | $C_{191}H_{295}FN_{38}O_{54}$ | 1336.2 | 1335.7 (M + 3H$^+$) |
| 144 | 140 | $C_{230}H_{350}F_2N_{46}O_{73}$ | 1654.1 | 1653.2 (M − 3H$^+$) |
| 145 | 134 | $C_{229}H_{349}FN_{46}O_{73}$ | 1643.3 | 1642.5 (M − 3H$^+$) |
| 146 | 277 | $C_{222}H_{342}FN_{47}O_{67}$ | 1585.4 | 1584.8 (M − 3H$^+$) |

TABLE 2-continued
Non-Limiting Exemplary Compounds
| Example | Compound # | Formula | Mass observed | Mass calculated |
|---|---|---|---|---|
| 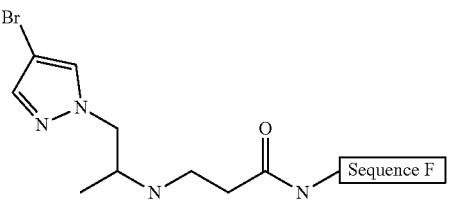 147 | 274 | $C_{221}H_{344}BrN_{49}O_{66}$ | 1606.7 | 1605.5 (M − 3H$^+$) |
| 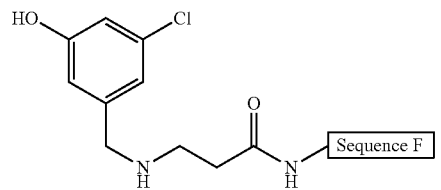 148 | 275 | $C_{222}H_{342}ClN_{47}O_{67}$ | 1591.1 | 1590.1 (M − 3H$^+$) |
| 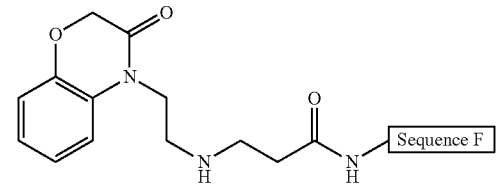 149 | 276 | $C_{225}H_{346}N_{48}O_{68}$ | 1203.7 | 1203.1 (M + 4H$^+$) |
| 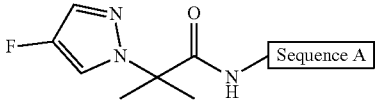 150 | 132 | $C_{222}H_{344}FN_{49}O_{67}$ | 1595.5 | 1594.8 (M − 3H$^+$) |
| 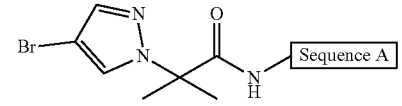 151 | 131 | $C_{222}H_{344}BrN_{49}O_{67}$ | 1615.8 | 1614.8 (M − 3H$^+$) |
| 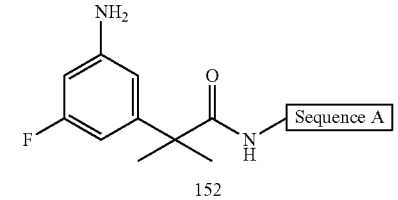 152 | 133 | $C_{225}H_{347}FN_{48}O_{67}$ | 1204.7 | 1204.1 (M + 4H$^+$) |
| 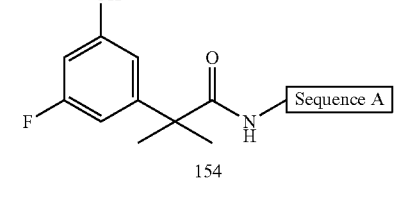 154 | 117 | $C_{225}H_{346}FN_{47}O_{68}$ | 1606.2 | 1605.5 (M + 3H$^+$) |

TABLE 2-continued
Non-Limiting Exemplary Compounds
| Example | Compound # | Formula | Mass observed | Mass calculated |
|---|---|---|---|---|
| 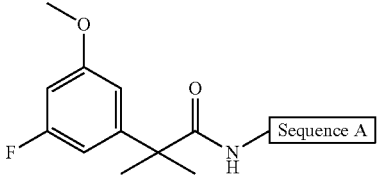 155 | 118 | $C_{226}H_{348}FN_{47}O_{68}$ | 1609 | 1608.2 (M − 3H$^+$) |
| 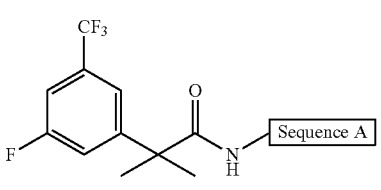 156 | 119 | $C_{226}H_{345}F_4N_{47}O_{67}$ | 1621.6 | 1620.8 (M − 3H$^+$) |
| 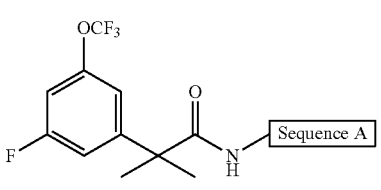 157 | 112 | $C_{226}H_{345}F_4N_{47}O_{68}$ | 1627 | 1626.2 (M − 3H$^+$) |
| 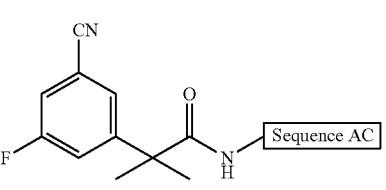 158 | 107 | $C_{232}H_{350}FN_{49}O_{68}$ | 1645.1 | 1644.2 (M + 3H$^+$) |
| 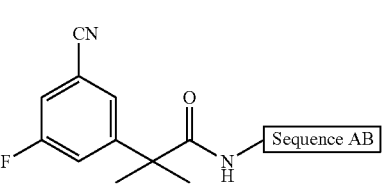 159 | 106 | $C_{224}H_{341}FN_{48}O_{67}$ | 1600.0 | 1599.2 (M + 3H$^+$) |
| 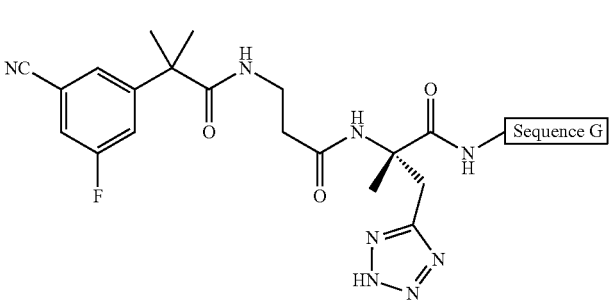 160 | 126 | $C_{226}H_{345}FN_{52}O_{65}$ | 1615.2 | 1614.5 (M − 3H$^+$) |

TABLE 2-continued

Non-Limiting Exemplary Compounds

| Example | Compound # | Formula | Mass observed | Mass calculated |
|---|---|---|---|---|
| 161 | 127 | $C_{225}H_{343}FN_{48}O_{67}$ | 1602.7 | 1601.8 (M − 3H⁺) |
| 162 | 120 | $C_{226}H_{345}FN_{48}O_{67}$ | 1607.3 | 1606.5 (M − 3H⁺) |
| 164 | 122 | $C_{225}H_{344}N_{48}O_{68}$ | 1602 | 1601.2 (M − 3H⁺) |
| 165 | 121 | $C_{226}H_{346}N_{48}O_{68}$ | 1606.7 | 1605.8 (M − 3H⁺) |
| 166 | 115 | $C_{226}H_{345}FN_{48}O_{67}$ | 1609.2 | 1608.5 (M + 3H⁺) |

TABLE 2-continued

Non-Limiting Exemplary Compounds

| Example | Compound # | Formula | Mass observed | Mass calculated |
|---|---|---|---|---|
| 167 | 104 | $C_{226}H_{345}FN_{48}O_{67}$ | 1207.2 | 1206.6 (M + 4H⁺) |
| 168 | 116 | $C_{227}H_{347}FN_{48}O_{67}$ | 1613.9 | 1613.2 (M + 3H⁺) |
| 169 | 110 | $C_{226}H_{345}FN_{48}O_{67}$ | 1609.3 | 1608.5 (M + 3H⁺) |
| 170 | 111 | $C_{227}H_{345}FN_{48}O_{69}$ | 1624.2 | 1623.2 (M + 3H⁺) |
| 171 | 108 | $C_{225}H_{343}FN_{48}O_{67}$ | 1604.6 | 1603.8 (M + 3H⁺) |

TABLE 2-continued
Non-Limiting Exemplary Compounds
| Example | Compound # | Formula | Mass observed | Mass calculated |
|---|---|---|---|---|
| 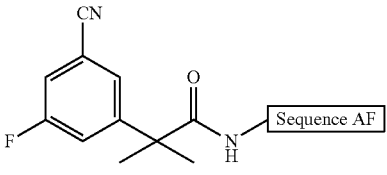<br>172 | 109 | $C_{226}H_{345}FN_{48}O_{67}$ | 1609.2 | 1608.5<br>$(M + 3H^+)$ |
| 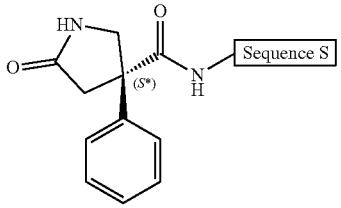<br>173 | 123 | $C_{224}H_{340}N_{48}O_{70}$ | 1205.3 | 1204.6<br>$(M - 4H^+)$ |
| 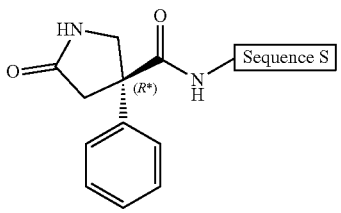<br>174 | 129 | $C_{224}H_{340}N_{48}O_{70}$ | 1607.2 | 1606.5<br>$(M - 3H^+)$ |
| 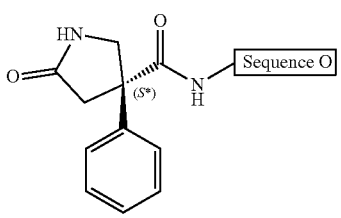<br>175 | 124 | $C_{229}H_{342}N_{48}O_{71}$ | 1224.7 | 1224.1<br>$(M - 4H^+)$ |
| 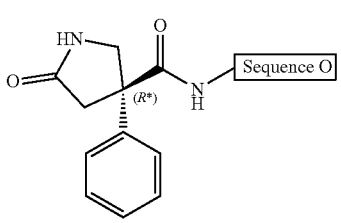<br>176 | 128 | $C_{229}H_{342}N_{48}O_{71}$ | 1633.2 | 1632.5<br>$(M - 3H^+)$ |
| 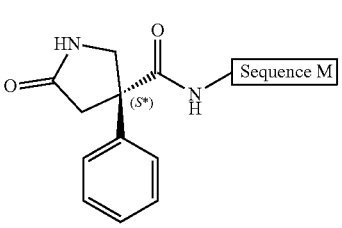<br>177 | 125 | $C_{233}H_{349}N_{49}O_{72}$ | 1246.1 | 1245.4<br>$(M - 4H^+)$ |

185
186
TABLE 2-continued
Non-Limiting Exemplary Compounds
| Example | Compound # | Formula | Mass observed | Mass calculated |
|---|---|---|---|---|
| 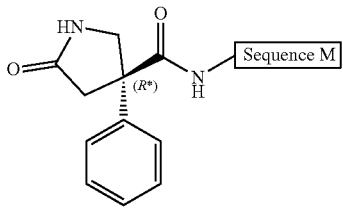 178 | 130 | $C_{233}H_{349}N_{49}O_{72}$ | 1661.8 | 1660.8 (M − 3H$^+$) |
| 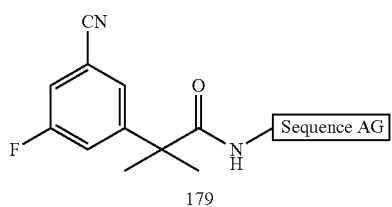 179 | 114 | $C_{228}H_{340}FN_{47}O_{69}$ | 1619.6 | 1618.8 (M − 3H$^+$) |
| 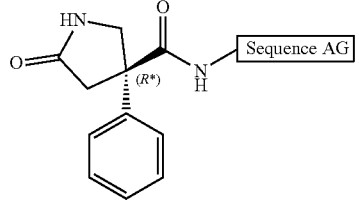 180 | 113 | $C_{228}H_{341}N_{47}O_{70}$ | 1618.9 | 1618.1 (M − 3H$^+$) |
| 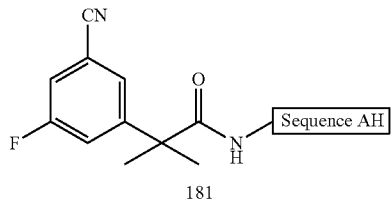 181 | 103 | $C_{229}H_{341}FN_{46}O_{70}$ | 1624.2 | 1623.8 (M − 3H$^+$) |
| 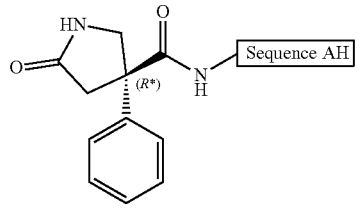 182 | 102 | $C_{229}H_{342}N_{46}O_{71}$ | 1623.6 | 1623.1 (M − 3H$^+$) |
| 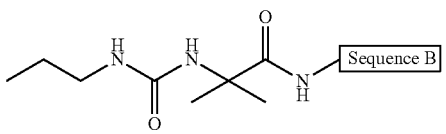 183 | 281 | $C_{223}H_{351}N_{49}O_{68}$ | 1600.9 | 1600.2 (M − 3H$^+$) |

TABLE 2-continued

Non-Limiting Exemplary Compounds

| Example | Compound # | Formula | Mass observed | Mass calculated |
|---|---|---|---|---|
| 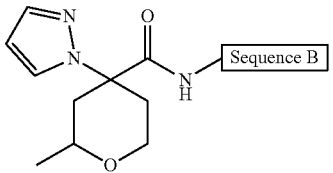  184 | 105 | $C_{225}H_{349}N_{49}O_{68}$ | 1608.3 | 1607.5 (M − 3H⁺) |

D. Biological Assays a) HitHunter cAMP Assay

CAMP accumulation was measured in Chinese hamster ovary (CHO) cells stably expressing the human GLP-1 receptor or GIP receptor using the HitHunter CAMP Assay for Small Molecules Kit (Eurofins). Briefly, cells were grown in Ham's F12 Nutrient Mix with 10% FBS and lifted with Cell dissociation buffer, Enzyme free, PBS based (ThermoFisher). Cells were pelleted and resuspended in Hank's buffered saline solution with 10 mM Hepes and 625 µM 3-isobutyl-1-methylxanthine. The antibody reagent was then added to cells at a 1:2 ratio and 5 µL of mixture was seeded in 384-well small volume white assay plates, at 10,000 cells/well. Cells were then treated with 50 nl compound in DMSO using an ECHO 550 acoustic dispenser (Labcyte) in a 20-point dose response format in triplicate for 30 min. Cells were the lysed and detection reagents added according to the manufacturer's protocol. After overnight incubation, luminescence was measured using a Perkin Elmer Envision plate reader. Raw data was normalized to the maximum signal from GLP-1 or GIP (high) and DMSO (low). Dose response curves were analyzed using GraphPad Prism 9.0.

Results of the HitHunter CAMP assay are presented in Table 3.

TABLE 3

| Compound # | $EC_{50}(E_{max})$ GLP-1R/nM | $EC_{50}(E_{max})$ GIP-1R/nM |
|---|---|---|
| 101 | +++ (93) | ++ (96) |
| 102 | ++++ (91) | +++ (101) |
| 103 | ++++ (89) | ++ (96) |
| 104 | + (60) | + (66) |
| 105 | ++++ (95) | +++ (112) |
| 106 | ++++ (97) | ++ (98) |
| 107 | ++++ (95) | +++ (106) |
| 108 | +++++ (93) | +++ (95) |
| 109 | ++ (82) | ++ (96) |
| 110 | + (31) | + (32) |
| 111 | +++ (95) | ++ (105) |
| 112 | +++ (115) | + (99) |
| 113 | ++++ (112) | +++ (98) |
| 114 | ++++ (114) | ++ (95) |
| 115 | +++ (120) | + (111) |
| 116 | ++ (94) | + (66) |
| 117 | ++++ (96) | +++ (100) |
| 118 | +++ (103) | ++ (105) |
| 119 | +++ (102) | ++ (99) |
| 120 | ++ (104) | + (40) |
| 121 | ++ (72) | − (76) |
| 122 | +++ (100) | ++ (92) |
| 123 | ++ (95) | ++ (103) |
| 124 | ++ (97) | ++ (102) |

TABLE 3-continued

| Compound # | $EC_{50}(E_{max})$ GLP-1R/nM | $EC_{50}(E_{max})$ GIP-1R/nM |
|---|---|---|
| 125 | ++ (101) | ++ (105) |
| 126 | + (59) | + (97) |
| 127 | +++ (93) | + (82) |
| 128 | +++ (99) | ++ (101) |
| 129 | +++ (108) | ++ (106) |
| 130 | +++ (107) | +++ (106) |
| 131 | ++++ (102) | ++ (96) |
| 132 | +++++ (98) | ++ (104) |
| 133 | ++++ (104) | + (107) |
| 134 | ++++ (102) | +++ (109) |
| 135 | ++++ (99) | ++ (87) |
| 136 | +++++ (101) | +++ (99) |
| 137 | ++++ (99) | ++ (87) |
| 138 | +++++ (100) | ++++ (100) |
| 139 | +++ (102) | ++ (109) |
| 140 | +++++ (104) | +++++ (108) |
| 141 | ++++ (97) | ++++ (108) |
| 142 | ++++ (99) | +++++ (99) |
| 143 | +++++ (101) | ++ (100) |
| 144 | +++++ (99) | +++ (103) |
| 145 | +++ (97) | +++ (102) |
| 146 | ++++ (102) | +++ (104) |
| 147 | ++++ (99) | ++++ (102) |
| 148 | +++ (99) | ++ (101) |
| 149 | ++++ (98) | +++ (96) |
| 150 | ++++ (103) | ++++ (91) |
| 151 | +++ (101) | +++ (105) |
| 152 | ++++ (98) | ++ (104) |
| 153 | ++++ (101) | +++ (105) |
| 154 | +++ (99) | ++ (106) |
| 155 | +++ (101) | ++ (104) |
| 156 | +++ (95) | +++ (95) |
| 157 | ++++ (100) | ++ (106) |
| 158 | ++++ (97) | ++ (118) |
| 159 | +++ (100) | ++ (104) |
| 160 | ++ (97) | + (94) |
| 161 | ++++ (113) | ++ (94) |
| 162 | +++ (127) | +++ (113) |
| 163 | ++++ (104) | ++ (105) |
| 164 | +++ (112) | +++ (106) |
| 165 | ++ (111) | + (92) |
| 166 | ++ (77) | +++ (108) |
| 167 | ++++ (108) | ++ (91) |
| 168 | ++ (87) | +++ (112) |
| 169 | ++++ (108) | +++ (110) |
| 170 | + (57) | + (37) |
| 171 | ++ (109) | + (94) |
| 172 | +++ (89) | +++ (109) |
| 173 | +++++ (98) | +++ (103) |
| 174 | ++ (93) | ++ (104) |
| 175 | +++ (94) | +++ (110) |
| 176 | +++ (110) | +++ (110) |
| 177 | +++ (95) | ++ (94) |
| 178 | ++++ (98) | ++++ (105) |
| 179 | ++++ (100) | ++++ (106) |
| 180 | ++++ (101) | ++++ (105) |

TABLE 3-continued

| Compound # | EC$_{50}$(E$_{max}$) GLP-1R/nM | EC$_{50}$(E$_{max}$) GIP-1R/nM |
|---|---|---|
| 181 | ++++ (97) | +++ (106) |
| 182 | ++++ (96) | ++ (98) |
| 183 | ++++ (96) | ++ (95) |
| 184 | +++ (99) | + (90) |
| 185 | ++++ (101) | ++ (95) |
| 186 | ++++ (99) | ++ (100) |
| 187 | +++ (95) | ++ (95) |
| 188 | ++++ (91) | ++ (79) |
| 189 | ++++ (95) | ++ (93) |
| 190 | +++ (98) | +++ (100) |
| 191 | +++ (92) | ++ (98) |
| 192 | ++++ (101) | +++ (104) |
| 193 | ++ (77) | + (70) |
| 194 | ++ (80) | ++ (78) |
| 195 | + (51) | + (72) |
| 196 | ++++ (95) | +++ (100) |
| 197 | ++++ (96) | ++ (97) |
| 198 | ++++ (99) | +++ (102) |
| 199 | +++ (100) | ++ (102) |
| 200 | ++++ (104) | ++ (102) |
| 201 | ++ (108) | + (107) |
| 203 | ++++ (103) | +++ (103) |
| 204 | +++ (106) | ++ (105) |
| 205 | +++ (99) | ++ (99) |
| 206 | +++ (98) | ++ (106) |
| 207 | +++ (97) | +++ (109) |
| 208 | +++ (111) | +++ (109) |
| 209 | ++++ (101) | ++ (105) |
| 210 | ++++ (104) | +++ (101) |
| 211 | ++++ (107) | ++ (103) |
| 212 | ++ (89) | − |
| 213 | + (78) | + (92) |
| 214 | ++++ (97) | ++++ (101) |
| 215 | ++++ (98) | ++++ (99) |
| 216 | ++++ (102) | ++ (93) |
| 217 | ++++ (101) | ++++ (108) |
| 218 | ++++ (103) | ++++ (100) |
| 219 | +++++ (104) | ++++ (106) |
| 220 | ++++ (102) | ++++ (108) |
| 221 | ++ (95) | ++ (95) |
| 222 | ++++ (108) | ++ (101) |
| 223 | ++ (96) | + (42) |
| 224 | ++++ (102) | +++ (103) |
| 225 | ++++ (102) | ++ (98) |
| 226 | ++++ (104) | ++++ (102) |
| 227 | +++ (102) | +++ (112) |
| 228 | ++++ (100) | ++++ (105) |
| 229 | ++++ (102) | +++ (107) |
| 230 | +++ (99) | ++ (96) |
| 231 | ++++ (111) | ++++ (110) |
| 233 | ++++ (121) | ++++ (109) |
| 234 | ++++ (105) | ++++ (112) |
| 235 | ++++ (122) | ++++ (108) |
| 236 | ++++ (127) | +++ (114) |
| 237 | +++++ (93) | +++ (91) |
| 238 | ++++ (91) | ++ (100) |
| 239 | +++++ (91) | +++ (99) |
| 240 | +++++ (93) | +++ (95) |
| 241 | ++++ (95) | +++ (100) |
| 242 | ++++ (99) | ++ (115) |
| 243 | ++++ (109) | +++ (110) |
| 244 | +++ (109) | +++ (120) |
| 245 | ++++ (122) | ++++ (90) |
| 246 | ++++ (130) | ++++ (100) |
| 247 | ++++ (101) | +++ (105) |
| 248 | ++++ (90) | +++ (104) |
| 249 | ++++ (97) | ++ (104) |
| 250 | ++++ (90) | ++++ (89) |
| 251 | ++++ (91) | ++ (92) |
| 252 | ++++ (90) | ++ (100) |
| 253 | +++++ (94) | +++ (105) |
| 254 | ++++ (93) | +++ (102) |
| 255 | ++++ (90) | +++ (99) |
| 256 | ++++ (98) | +++ (104) |
| 257 | +++++ (89) | +++ (92) |
| 258 | +++ (100) | ++ (101) |
| 259 | +++ (103) | +++ (103) |
| 260 | ++++ (124) | +++ (107) |
| 261 | +++ (106) | +++ (107) |
| 262 | ++ (90) | +++ (106) |
| 263 | +++ (98) | +++ (104) |
| 264 | +++ (97) | +++ (106) |
| 265 | ++ (94) | +++ (107) |
| 266 | +++ (105) | +++ (105) |
| 267 | +++ (105) | +++ (106) |
| 268 | +++ (95) | +++ (103) |
| 269 | +++ (96) | +++ (103) |
| 270 | ++ (91) | +++ (104) |
| 271 | +++ (94) | +++ (105) |
| 272 | ++ (75) | ++ (91) |
| 273 | +++ (106) | +++ (99) |
| 274 | ++ (88) | + (36) |
| 275 | +++ (99) | ++ (17) |
| 276 | ++ (95) | + (35) |
| 277 | +++ (89) | + (6) |
| 280 | +++ (90) | +++ (114) |
| 281 | ++++ (95) | +++ (108) |
| 282 | ++++ (92) | ++ (90) |

Note:
In table 3 "+++++" denotes EC$_{50}$ < 0.1 nM; "++++" denotes 0.1 nM ≤ EC$_{50}$ < 1 nM; "+++" denotes 1 nM ≤ EC$_{50}$ < 10 nM; "++" denotes 10 nM ≤ EC$_{50}$ < 100 nM; "+" denotes 100 nM ≤ EC$_{50}$ ≤ 1000 nM; and "−" denotes EC$_{50}$ > 1000 nM.

b) PathHunter β-Arrestin Assay

β-arrestin-2 recruitment for GLP-1 receptor or GIP receptor was measured using the DiscoverX PathHunter Detection Kit and PathHunter® CHO-K1 GLPIR β-Arrestin Cell Line or PathHunter® CHO-K1 GIPR β-Arrestin Cell Line, respectively). Briefly, cells were grown in Ham's F12 Nutrient Mix with 10% FBS and lifted with Cell dissociation buffer, Enzyme free, PBS based (ThermoFisher). Harvested cells were pelleted and resuspended in Assay Complete Cell Plating Reagent 2 and 5000 cells per well were plated in tissue culture treated 384-well small volume white assay plates. Plates were then incubated at 37° C. and 5% CO$_2$ overnight. The media was then replaced with fresh Assay Complete Cell Plating Reagent 2. Cells were then treated with 10 nl compound in DMSO using an ECHO 550 acoustic dispenser (Labcyte) in a 20-point dose response format in duplicate for 90 min at 37° C. The assay was then completed according to the manufacturer's instructions. Luminescence was measured using a Perkin Elmer Envision plate reader. Raw data was normalized to the maximum signal from GLP-1 or GIP (high) and DMSO (low). Dose response curves were analyzed using GraphPad Prism 9.0. EC$_{50}$ values were only assigned to compounds with an E$_{max}$ greater than 10% of high controls. NA means the EC$_{50}$ data are not available. The results are summarized in Table 5, below.

TABLE 5

| | β-arrestin activity | |
|---|---|---|
| Compound # | GLP-1R β Arrestin EC$_{50}$ | GIPR β Arrestin EC$_{50}$ |
| 101 | >1 μM | >1 μM |
| 102 | >1 μM | >1 μM |
| 103 | >1 μM | >1 μM |
| 104 | >1 μM | >1 μM |
| 105 | >1 μM | >1 μM |
| 106 | >1 μM | >1 μM |
| 107 | >1 μM | <1 μM |
| 108 | >1 μM | <1 μM |
| 109 | >1 μM | >1 μM |
| 110 | >1 μM | >1 μM |
| 111 | >1 μM | >1 μM |
| 112 | >1 μM | >1 μM |

TABLE 5-continued

β-arrestin activity

| Compound # | GLP-1R β Arrestin EC$_{50}$ | GIPR β Arrestin EC$_{50}$ |
|---|---|---|
| 113 | >1 μM | >1 μM |
| 114 | >1 μM | >1 μM |
| 115 | >1 μM | >1 μM |
| 116 | >1 μM | >1 μM |
| 117 | >1 μM | >1 μM |
| 118 | >1 μM | >1 μM |
| 119 | >1 μM | >1 μM |
| 120 | >1 μM | >1 μM |
| 121 | >1 μM | <1 μM |
| 122 | >1 μM | <1 μM |
| 123 | >1 μM | >1 μM |
| 124 | >1 μM | >1 μM |
| 125 | >1 μM | >1 μM |
| 126 | >1 μM | >1 μM |
| 127 | >1 μM | >1 μM |
| 128 | >1 μM | >1 μM |
| 129 | >1 μM | >1 μM |
| 130 | >1 μM | >1 μM |
| 131 | >1 μM | >1 μM |
| 132 | <1 μM | >1 μM |
| 133 | >1 μM | >1 μM |
| 134 | >1 μM | >1 μM |
| 135 | >1 μM | >1 μM |
| 136 | >1 μM | <1 μM |
| 137 | >1 μM | >1 μM |
| 138 | <1 μM | <1 μM |
| 139 | >1 μM | >1 μM |
| 140 | >1 μM | <1 μM |
| 141 | >1 μM | <1 μM |
| 142 | <1 μM | <1 μM |
| 143 | <1 μM | >1 μM |
| 144 | >1 μM | >1 μM |
| 145 | >1 μM | >1 μM |
| 146 | >1 μM | <1 μM |
| 147 | >1 μM | >1 μM |
| 148 | >1 μM | >1 μM |
| 149 | >1 μM | <1 μM |
| 150 | >1 μM | <1 μM |
| 151 | >1 μM | >1 μM |
| 152 | >1 μM | >1 μM |
| 153 | >1 μM | >1 μM |
| 154 | >1 μM | >1 μM |
| 155 | >1 μM | >1 μM |
| 156 | >1 μM | >1 μM |
| 157 | >1 μM | >1 μM |
| 158 | >1 μM | >1 μM |
| 159 | >1 μM | >1 μM |
| 160 | >1 μM | >1 μM |
| 161 | >1 μM | >1 μM |
| 162 | >1 μM | <1 μM |
| 163 | >1 μM | <1 μM |
| 164 | >1 μM | >1 μM |
| 165 | >1 μM | >1 μM |
| 166 | >1 μM | <1 μM |
| 167 | >1 μM | >1 μM |
| 168 | >1 μM | <1 μM |
| 169 | >1 μM | <1 μM |
| 170 | >1 μM | >1 μM |
| 171 | >1 μM | >1 μM |
| 172 | >1 μM | >1 μM |
| 173 | >1 μM | >1 μM |
| 174 | >1 μM | >1 μM |
| 175 | >1 μM | <1 μM |
| 176 | >1 μM | <1 μM |
| 177 | >1 μM | >1 μM |
| 178 | >1 μM | <1 μM |
| 179 | >1 μM | >1 μM |
| 180 | >1 μM | <1 μM |
| 181 | >1 μM | <1 μM |
| 182 | >1 μM | <1 μM |
| 183 | >1 μM | <1 μM |
| 184 | >1 μM | >1 μM |
| 185 | <1 μM | >1 μM |
| 186 | >1 μM | <1 μM |
| 187 | >1 μM | >1 μM |
| 188 | >1 μM | >1 μM |
| 189 | >1 μM | >1 μM |
| 190 | >1 μM | >1 μM |
| 191 | >1 μM | >1 μM |
| 192 | >1 μM | >1 μM |
| 193 | >1 μM | >1 μM |
| 194 | >1 μM | >1 μM |
| 195 | >1 μM | >1 μM |
| 196 | >1 μM | >1 μM |
| 197 | >1 μM | >1 μM |
| 198 | >1 μM | <1 μM |
| 199 | >1 μM | >1 μM |
| 200 | >1 μM | >1 μM |
| 201 | >1 μM | >1 μM |
| 203 | >1 μM | >1 μM |
| 204 | >1 μM | >1 μM |
| 205 | >1 μM | >1 μM |
| 206 | >1 μM | >1 μM |
| 207 | >1 μM | >1 μM |
| 208 | >1 μM | <1 μM |
| 209 | >1 μM | >1 μM |
| 210 | >1 μM | >1 μM |
| 211 | >1 μM | >1 μM |
| 212 | >1 μM | >1 μM |
| 213 | >1 μM | >1 μM |
| 214 | >1 μM | >1 μM |
| 215 | >1 μM | <1 μM |
| 216 | >1 μM | >1 μM |
| 217 | >1 μM | >1 μM |
| 218 | >1 μM | <1 μM |
| 219 | >1 μM | <1 μM |
| 220 | >1 μM | <1 μM |
| 221 | >1 μM | >1 μM |
| 222 | >1 μM | >1 μM |
| 223 | >1 μM | >1 μM |
| 224 | >1 μM | <1 μM |
| 225 | >1 μM | >1 μM |
| 226 | >1 μM | <1 μM |
| 227 | >1 μM | >1 μM |
| 228 | >1 μM | <1 μM |
| 229 | >1 μM | <1 μM |
| 230 | >1 μM | >1 μM |
| 231 | >1 μM | >1 μM |
| 233 | >1 μM | <1 μM |
| 234 | >1 μM | <1 μM |
| 235 | >1 μM | <1 μM |
| 236 | >1 μM | >1 μM |
| 237 | >1 μM | <1 μM |
| 238 | >1 μM | >1 μM |
| 239 | <1 μM | >1 μM |
| 240 | <1 μM | <1 μM |
| 241 | <1 μM | <1 μM |
| 242 | >1 μM | NA |
| 243 | >1 μM | NA |
| 244 | >1 μM | NA |
| 245 | >1 μM | <1 μM |
| 246 | <1 μM | <1 μM |
| 247 | >1 μM | >1 μM |
| 248 | >1 μM | NA |
| 249 | >1 μM | NA |
| 250 | >1 μM | NA |
| 252 | <1 μM | NA |
| 253 | <1 μM | NA |
| 254 | >1 μM | >1 μM |
| 255 | >1 μM | >1 μM |
| 256 | >1 μM | <1 μM |
| 257 | >1 μM | >1 μM |
| 258 | >1 μM | >1 μM |
| 259 | >1 μM | >1 μM |
| 260 | >1 μM | >1 μM |
| 261 | >1 μM | >1 μM |
| 262 | >1 μM | >1 μM |
| 263 | >1 μM | >1 μM |
| 264 | >1 μM | <1 μM |
| 265 | >1 μM | <1 μM |

TABLE 5-continued

| | β-arrestin activity | |
|---|---|---|
| Compound # | GLP-1R β Arrestin $EC_{50}$ | GIPR β Arrestin $EC_{50}$ |
| 266 | >1 μM | <1 μM |
| 267 | >1 μM | >1 μM |
| 268 | >1 μM | >1 μM |
| 269 | >1 μM | <1 μM |
| 270 | >1 μM | <1 μM |
| 271 | >1 μM | <1 μM |
| 272 | >1 μM | >1 μM |
| 273 | >1 μM | >1 μM |
| 274 | >1 μM | >1 μM |
| 275 | >1 μM | >1 μM |
| 276 | >1 μM | >1 μM |
| 277 | >1 μM | >1 μM |
| 280 | >1 μM | >1 μM |
| 281 | >1 μM | >1 μM |
| 282 | >1 μM | >1 μM |

OTHER EMBODIMENTS

Clauses

1. A compound of Formula (I):

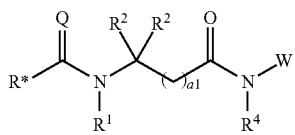

Formula (I)

or a pharmaceutically acceptable salt thereof, wherein:
Q is O or S;
R* is as defined in (i), (ii), or (iii), below:

(i)

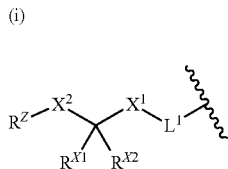

(Formula A)

wherein:
$L^1$ is selected from the group consisting of:
  $C_{1-10}$ alkylene optionally substituted with from 1-3 substituents each independently selected from the group consisting of: halo; $C_{1-4}$ alkoxy; —OH; phenyl; and NR'R''; and

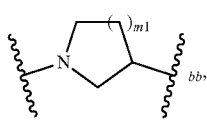

wherein m1 is 0, 1, 2, 3, or 4;
$X^1$ is selected from the group consisting of: C(=O); C(=S); S(O)$_{1-2}$; C(=O)N(R')*; C(=S)N(R')*; S(O)$_{1-2}$N(R')*; N(R')C(=O)*; N(R')C(=S)*; and N(R')S(O)$_{1-2}$*, wherein * represents the point of attachment to $L^1$;
$R^{X1}$ and $R^{X2}$ are each defined according to (AA) or (AB):

(AA)
$R^{X1}$ and $R^{X2}$ are each independently selected from the group consisting of:
  —H, —F;
  $C_{1-8}$ alkyl, $C_{2-6}$ alkenyl, and $C_{2-6}$ alkynyl, each of which is optionally substituted with from 1-3 $R^a$; and
  $C_{3-8}$ cycloalkyl which is optionally substituted with from 1-3 $R^b$;

(AB)
$R^{X1}$ and $R^{X2}$ taken together with the carbon atom to which each is attached form a saturated or partially unsaturated ring having from 3-10 ring atoms, wherein from 0-2 ring atoms are heteroatoms each independently selected from the group consisting of: O, N, N(H), N($R^c$), and S(O)$_{0-2}$, wherein the ring is optionally substituted at one or more ring carbon atoms with from 1-3 $R^b$;

$X^2$ is selected from the group consisting of: a bond; $CH_2$; —N(R')—; —O—; C(=O); C(=S); S(O)$_{1-2}$; C(=O)N(R')*; C(=S)N(R')*; S(O)$_{1-2}$N(R')*; N(R')C(=O)*; N(R')C(=S)*; and N(R')S(O)$_{1-2}$*, wherein * represents the point of attachment to C($R^{X1}R^{X2}$); and $R^Z$ is selected from the group consisting of:
  H;
  $C_{1-6}$ alkyl optionally substituted with from 1-6 $R^a$;
  —$R^{ZA}$; and
  -$L^{ZA}$-$R^{ZA}$;
$L^{ZA}$ is $C_{1-6}$ alkylene optionally substituted with from 1-3 independently selected $R^a$;
$R^{ZA}$ is $R^e$;

or (ii)

Formula (B)

wherein:
$L^5$ is $C_{1-10}$ alkylene optionally substituted with from 1-3 substituents each independently selected from the group consisting of: halo; $C_{1-4}$ alkoxy; —OH; phenyl; and NR'R'';
$X^5$ is selected from the group consisting of: a bond; C(=O); C(=S); S(O)$_{1-2}$; C(=O)N(R')*; C(=S)N(R')*; and S(O)$_{1-2}$N(R')*, wherein * represents the point of attachment to $L^5$;
$R^{X3}$ and $R^{X4}$ are each defined according to (BA) or (BB):

(BA)
$R^{X3}$ and $R^{X4}$ are each independently selected from the group consisting of:
  —H, —F;
  $C_{1-8}$ alkyl, $C_{2-6}$ alkenyl, and $C_{2-6}$ alkynyl, each of which is optionally substituted with from 1-3 $R^a$; and
  $C_{3-6}$ cycloalkyl which is optionally substituted with from 1-3 $R^b$;

(BB)
$R^{X3}$ and $R^{X4}$ taken together with the carbon atom to which each is attached form a saturated or partially unsaturated ring having from 3-10 ring atoms, wherein from 0-2 ring atoms are heteroatoms each independently selected from the group consisting of: O, N, N(H), N($R^c$), and S(O)$_{0-2}$, wherein the ring is optionally substituted at one or more ring carbon atoms with from 1-3 $R^b$; and $R^{Z5}$ is selected from the group consisting of: —$R^{ZE}$; -$L^{ZE}$-$R^{ZE}$; and $C_{1-6}$ alkyl optionally substituted with from 1-6 $R^a$;

$L^{ZE}$ is $C_{1-6}$ alkylene optionally substituted with from 1-3 independently selected $R^a$;

$R^{ZE}$ is $R^e$;

or (iii)

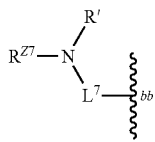

Formula (C)

L' is $C_{1-10}$ alkylene optionally substituted with from 1-3 substituents each independently selected from the group consisting of: halo; $C_{1-4}$ alkoxy; —OH; phenyl; and NR'R"; and $R^{Z7}$ is -$L^{ZG}$-$R^{ZG}$; $L^{ZG}$ is $C_{1-6}$ alkylene optionally substituted with from 1-3 independently selected $R^a$;

$R^{ZG}$ is $R^e$;

each of $R^1$ and $R^2$ is independently selected from the group consisting of H and $C_{1-3}$ alkyl;

a1 is 0, 1, 2, 3, or 4;

$R^{2'}$ is

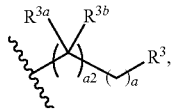

wherein:

$R^3$ is —C(O)OH, —C(O)OR$^4$, —CH(C(O)OH)$_2$, or a carboxylic acid isostere;

a is 0, 1, 2, 3, 4, or 5; a2 is 0 or 1;

each of $R^{3a}$ and $R^{3b}$ is independently H or $C_{1-3}$ alkyl; and $R^4$ is —(C$_{0-3}$ alkylene)-R$^e$ or $C_{1-6}$ alkyl optionally substituted with from 1-6 $R^a$ W is a peptide having formula —W$^1$—R$^5$, wherein:

$W^1$ is a sequence of from 5-60 amino acids; and $R^5$ is a C-terminal amino acid, amino ester, or amino acid amide that is optionally substituted with from 1-2 modifying groups;

each occurrence of $R^a$ is independently selected from the group consisting of: halo; —OH; —N(R$^f$)(R'); $C_{1-4}$ alkoxy; $C_{1-4}$ haloalkoxy; —OC(=O)(C$_{1-6}$ alkyl); —C(=O)O(C$_{1-6}$ alkyl); —C(=O)OH, —C(=O)N(R')(R'''), —S(O)$_{1-2}$(C$_{1-6}$ alkyl); and cyano;

each occurrence of $R^b$ is independently selected from the group consisting of: $C_{1-6}$ alkyl optionally substituted with from 1-6 $R^a$; $C_{2-6}$ alkenyl; $C_{2-6}$ alkynyl; —OH; oxo; -halo; —N(R$^f$)(R'); $C_{1-4}$ alkoxy; $C_{1-4}$ haloalkoxy; —C(=O)(C$_{1-4}$ alkyl); —C(=O)O(C$_{1-6}$ alkyl); —C(=O)OH; —C(=O)N(R')(R"); —S(O)$_{1-2}$N(R') (R"); —S(O)$_{1-2}$(C$_{1-6}$ alkyl); —SF$_5$; —NO$_2$; and cyano;

each occurrence of $R^e$ is independently selected from the group consisting of: $C_{1-6}$ alkyl; $C_{1-6}$ haloalkyl; —C(=O)(C$_{1-6}$ alkyl); —C(=O)O(C$_{1-6}$ alkyl); —C(=O)N(R')(R"); and —S(O)$_{1-2}$(C$_{1-6}$ alkyl);

each occurrence of $R^d$ is independently selected from the group consisting of: —R$^e$, —(C$_{1-3}$ alkylene)-R$^e$, —O—(C$_{0-3}$ alkylene)-R$^e$, —C(=O)(C$_{0-3}$ alkylene)-R$^e$, and —C(=O)(C$_{0-3}$ alkylene)O—R$^e$;

each occurrence of $R^e$ is independently selected from the group consisting of:

(i) $C_{3-10}$ cycloalkyl, wherein the cycloalkyl is optionally substituted with from 1-4 independently selected $R^b$;

(ii) heterocyclyl including from 3-10 ring atoms, wherein from 1-3 ring atoms are each independently selected from the group consisting of N, N(H), N(R$^c$), O, and S(O)$_{0-2}$, wherein the heterocyclyl is optionally substituted with from 1-4 independently selected $R^b$ at one or more ring carbon atoms;

(iii) $C_{6-10}$ aryl, wherein the aryl is optionally substituted with from 1-5 independently selected $R^b$; and (iv) heteroaryl including from 5-10 ring atoms, wherein from 1-4 ring atoms are each independently selected from the group consisting of N, N(H), N(R$^c$), O, and S(O)$_{0-2}$, wherein the heteroaryl is optionally substituted with from 1-3 independently selected $R^b$ at one or more ring carbon atoms;

each occurrence of $R^f$ is independently selected from the group consisting of: H; $C_{1-4}$ alkyl; $C_{3-6}$ cycloalkyl; —C(=O)(C$_{1-6}$ alkyl); —C(=O)O(C$_{1-6}$ alkyl); and —S(O)$_{1-2}$(C$_{1-6}$ alkyl); and each occurrence of R' and R" is independently selected from the group consisting of: H and $C_{1-6}$ alkyl.

2. The compound of clause 1, wherein R* is (i)

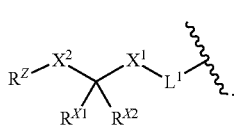

(Formula A)

3. The compound of clauses 1 or 2, wherein $R^{X1}$ and $R^{X2}$ are each defined according to (AA) or (AB):

(AA)

$R^{X1}$ and $R^{X2}$ are each independently selected from the group consisting of:

—F;

$C_{1-8}$ alkyl, $C_{2-6}$ alkenyl, and $C_{2-6}$ alkynyl, each of which is optionally substituted with from 1-3 $R^a$; and $C_{3-6}$ cycloalkyl which is optionally substituted with from 1-3 $R^b$, or (AB)

$R^{X1}$ and $R^{X2}$ taken together with the carbon atom to which each is attached form a saturated or partially unsaturated ring having from 3-10 ring atoms, wherein from 0-2 ring atoms are heteroatoms each independently selected from the group consisting of: O, N, N(H), N(R$^c$), and S(O)$_{0-2}$, wherein the ring is optionally substituted at one or more ring carbon atoms with from 1-3 $R^b$.

4. The compound of any one of clauses 1-3, wherein $R^{X1}$ and $R^{X2}$ are each independently selected from the group consisting of:

—F;

$C_{1-8}$ alkyl, $C_{2-6}$ alkenyl, and $C_{2-6}$ alkynyl, each of which is optionally substituted with from 1-3 $R^a$; and $C_{3-6}$ cycloalkyl which is optionally substituted with from 1-3 $R^b$.

5. The compound of any one of clauses 1-4, wherein $R^{X1}$ and $R^{X2}$ are the same.

6. The compound of any one of clauses 1-4, wherein $R^{X1}$ and $R^{X2}$ are different.

7. The compound of any one of clauses 1-6, wherein $R^{X1}$ and $R^{X2}$ are independently selected $C_{1-8}$ alkyl, which is optionally substituted with from 1-3 $R^a$.

8. The compound of any one of clauses 1-7, wherein $R^{X1}$ and $R^{X2}$ are independently selected unsubstituted $C_{1-6}$ alkyl.

9. The compound of any one of clauses 1-8, wherein $R^{X1}$ and $R^{X2}$ are independently selected unsubstituted $C_{1-3}$ alkyl.

10. The compound of any one of clauses 1-5 or 7-9, wherein $R^{X1}$ and $R^{X2}$ are both methyl.

11. The compound of any one of clauses 1-5 or 7-9, wherein $R^{X1}$ and $R^{X2}$ are both ethyl.

12. The compound of any one of clauses 1-5, wherein $R^{X1}$ and $R^{X2}$ are both —F.

13. The compound of any one of clauses 1-3, wherein $R^{X1}$ and $R^{X2}$ taken together with the carbon atom to which each is attached form a saturated or partially unsaturated ring having from 3-10 ring atoms, wherein from 0-2 ring atoms are heteroatoms each independently selected from the group consisting of: O, N, N(H), N($R^e$), and S(O)$_{0-2}$, wherein the ring is optionally substituted at one or more ring carbon atoms with from 1-3 $R^b$.

14. The compound of any one of clauses 1-3 or 13, wherein $R^{X1}$ and $R^{X2}$ taken together with the carbon atom to which each is attached form a $C_{3-8}$ cycloalkyl ring which is optionally substituted with from 1-3 $R^b$.

15. The compound of any one of clauses 1-3 or 13-14, wherein $R^{X1}$ and $R^{X2}$ taken together with the carbon atom to which each is attached form a $C_{3-6}$ cycloalkyl ring which is optionally substituted with from 1-3 independently selected $C_{1-3}$ alkyl.

16. The compound of any one of clauses 1-3 or 13-15, wherein $R^{X1}$ and $R^{X2}$ taken together with the carbon atom to which each is attached form a cyclopropyl ring, cyclobutyl ring, cyclopentyl ring, or cyclohexyl ring.

17. The compound of any one of clauses 1-3 or 13, wherein $R^{X1}$ and $R^{X2}$ taken together with the carbon atom to which each is attached form a saturated or partially unsaturated ring having from 4-10 ring atoms, wherein from 1-2 ring atoms are heteroatoms each independently selected from the group consisting of: O, N, N(H), N($R^c$), and S(O)$_{0-2}$, wherein the ring is optionally substituted at one or more ring carbon atoms with from 1-3 $R^b$.

18. The compound of any one of clauses 1-3, 13, or 17, wherein $R^{X1}$ and $R^{X2}$ taken together with the carbon atom to which each is attached form a saturated ring having from 4-6 ring atoms, wherein one ring atom is a heteroatom selected from the group consisting of: O, N, N(H), N($R^c$), and S(O)$_{0-2}$, wherein the ring is optionally substituted at one or more ring carbon atoms with from 1-3 $R^b$.

19. The compound of any one of clauses 1-3, 13, or 17-18, wherein $R^{X1}$ and $R^{X2}$ taken together with the carbon atom to which each is attached form

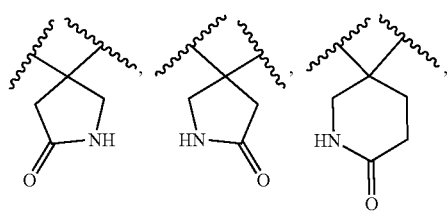

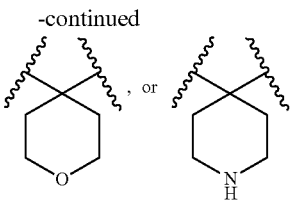

each of which is optionally substituted with from 1-2 independently selected $C_{1-3}$ alkyl.

20. The compound of any one of clauses 1-19, wherein $X^2$ is a bond.

21. The compound of any one of clauses 1-20, wherein $R^Z$ is —$R^{ZA}$.

22. The compound of any one of clauses 1-21, wherein $R^Z$ is selected from the group consisting of:
  (iii) $C_{6-10}$ aryl, wherein the aryl is optionally substituted with from 1-5 independently selected $R^b$; and
  (iv) heteroaryl including from 5-10 ring atoms, wherein from 1-4 ring atoms are each independently selected from the group consisting of N, N(H), N($R^c$), O, and S(O)$_{0-2}$, wherein the heteroaryl is optionally substituted with from 1-3 independently selected $R^b$ at one or more ring carbon atoms.

23. The compound of any one of clauses 1-22, wherein $R^Z$ is $C_{6-10}$ aryl, wherein the aryl is optionally substituted with from 1-5 independently selected $R^b$.

24. The compound of any one of clauses 1-23, wherein $R^Z$ is phenyl which is optionally substituted with from 1-3 independently selected $R^b$.

25. The compound of any one of clauses 1-24, wherein $R^Z$ is selected from the group consisting of:

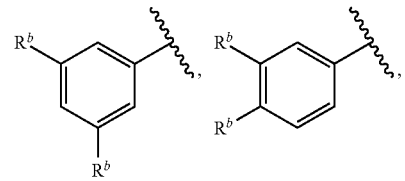

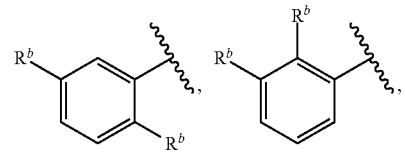

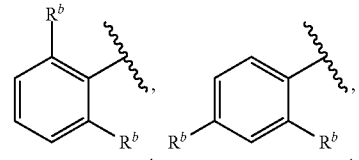

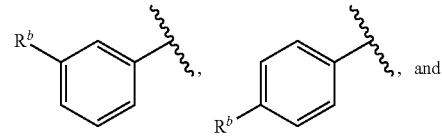

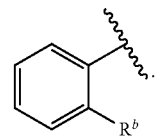

26. The compound of any one of clauses 1-25, wherein $R^Z$ is

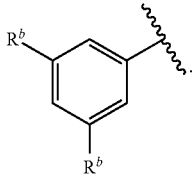

27. The compound of any one of clauses 1-22, wherein $R^Z$ is heteroaryl including from 5-10 ring atoms, wherein from 1-4 ring atoms are each independently selected from the group consisting of N, N(H), N($R^c$), O, and S(O)$_{0-2}$, wherein the heteroaryl is optionally substituted with from 1-3 independently selected $R^b$ at one or more ring carbon atoms.

28. The compound of any one of clauses 1-22 or 27, wherein $R^Z$ is monocyclic heteroaryl including from 5-6 ring atoms, wherein from 1-4 ring atoms are each independently selected from the group consisting of N, N(H), N($R^c$), O, and S, wherein the heteroaryl is optionally substituted with from 1-3 independently selected $R^b$ at one or more ring carbon atoms.

29. The compound of any one of clauses 1-22 or 27-28, wherein $R^Z$ is monocyclic heteroaryl including 6 ring atoms, wherein from 1-2 ring atoms are ring nitrogen atoms, wherein the heteroaryl is optionally substituted with from 1-3 independently selected $R^b$ at one or more ring carbon atoms.

30. The compound of any one of clauses 1-22 or 27-29, wherein $R^Z$ is selected from the group consisting of:

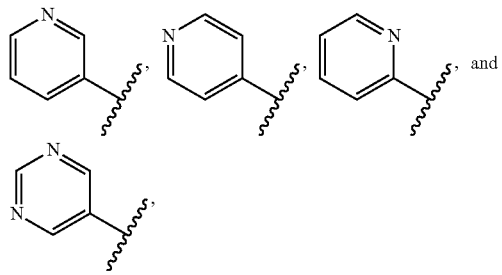

each optionally substituted with $R^b$.

31. The compound of any one of clauses 1-22 or 27, wherein $R^Z$ is monocyclic heteroaryl including 5 ring atoms, wherein from 1-4 ring atoms are each independently selected from the group consisting of N, N(H), N($R^c$), O, and S, wherein the heteroaryl is optionally substituted with from 1-2 independently selected $R^b$ at one or more ring carbon atoms.

32. The compound of any one of clauses 1-22, 27, or 31, wherein $R^Z$ is selected from the group consisting of:

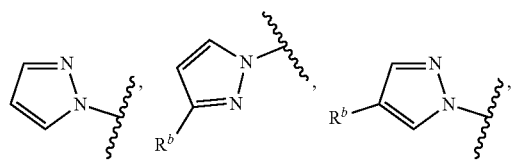

-continued

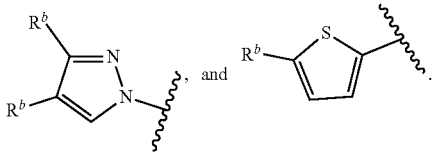

33. The compound of any one of clauses 22-32, wherein each $R^b$ present in $R^Z$ is independently selected from the group consisting of: $C_{1-3}$ alkyl optionally substituted with from 1-3 independently selected halo; —F; —Cl; —N($R^f$)(R'); $C_{1-4}$ alkoxy; $C_{1-4}$ haloalkoxy; —C(=O)OH; —C(=O)N(R')(R''); and cyano.

34. The compound of any one of clauses 1-22, wherein $R^Z$ is selected from the group consisting of:

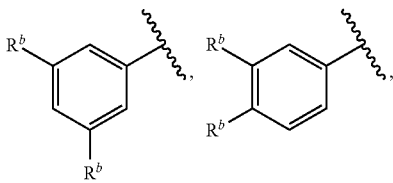

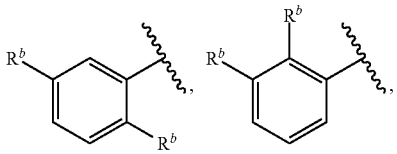

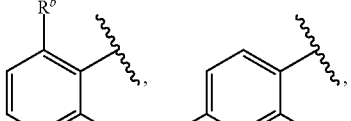

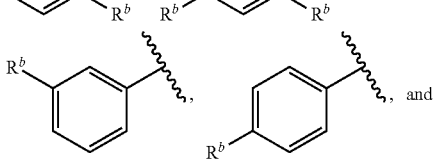

wherein each $R^b$ present in $R^Z$ is independently selected from the group consisting of: $C_{1-3}$ alkyl optionally substituted with from 1-3 independently selected halo; —F; —Cl; —N($R^f$)(R'); $C_{1-4}$ alkoxy; $C_{1-4}$ haloalkoxy; —C(=O)OH; —C(=O)N(R')(R''); and cyano.

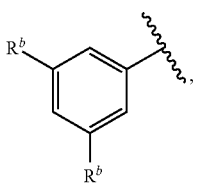

35. The compound of any one of clauses 1-22, wherein $R^Z$ is wherein each $R^b$ present in $R^Z$ is independently selected from the group consisting of: $C_1$-3 alkyl optionally substituted with from 1-3 independently selected halo; —F; —Cl; —N(R$^f$)(R'); C$_{1-4}$ alkoxy; C$_{1-4}$ haloalkoxy; —C(=O)OH; —C(=O)N(R')(R"); and cyano.

36. The compound of any one of clauses 1-35, wherein L$^1$ is C$_{1-10}$ alkylene optionally substituted with from 1-3 substituents each independently selected from the group consisting of: halo; C$_{1-4}$ alkoxy; —OH; phenyl; and NR'R".

37. The compound of any one of clauses 1-36, wherein L$^1$ is unsubstituted C$_{1-10}$ alkylene.

38. The compound of any one of clauses 1-37, wherein L$^1$ is unsubstituted C$_{1-6}$ alkylene.

39. The compound of any one of clauses 1-38, wherein L$^1$ is unsubstituted C$_{2-4}$ alkylene.

40. The compound of any one of clauses 1-39, wherein L$^1$ is unsubstituted C$_3$ alkylene.

41. The compound of any one of clauses 1-40, wherein L$^1$ is —CH$_2$CH$_2$CH$_2$—.

42. The compound of any one of clauses 1-39, wherein L$^1$ is —CH$_2$CH$_2$—.

43. The compound of any one of clauses 1-42, wherein X$^1$ is selected from the group consisting of: C(=O)N(R')*; C(=S)N(R')*; and S(O)$_{1-2}$N(R')*, wherein * represents the point of attachment to L$^1$.

44. The compound of any one of clauses 1-43, wherein X$^1$ is C(=O)N(R')*.

45. The compound of any one of clauses 1-44, wherein X$^1$ is C(=O)N(H)*.

46. The compound of any one of clauses 1-43, wherein X$^1$ is C(=S)N(R')*.

47. The compound of any one of clauses 1-43 or 46, wherein X$^1$ is C(=S)N(H)*.

48. The compound of any one of clauses 1-36, wherein L$^1$ is unsubstituted C$_{2-4}$ alkylene; and X$^1$ is C(=O)N(R')*.

49. The compound of any one of clauses 1-36 or 48, wherein L$^1$ is —CH$_2$CH$_2$—, or —CH$_2$CH$_2$CH$_2$—; and X$^1$ is C(=O)N(H)*.

50. The compound of any one of clauses 1-36, wherein L$^1$ is unsubstituted C$_{2-4}$ alkylene; and X$^1$ is C(=S)N(R')*.

51. The compound of any one of clauses 1-36 or 50, wherein L$^1$ is —CH$_2$CH$_2$—, or —CH$_2$CH$_2$CH$_2$—; and X$^1$ is C(=S)N(H)*.

52. The compound of any one of clauses 1-51, wherein Q is O.

53. The compound of any one of clauses 1-52, wherein R$^1$ is —H.

54. The compound of any one of clauses 1-53, wherein a1 is 0.

55. The compound of any one of clauses 1-53, wherein a1 is 1, 2, or 3.

56. The compound of any one of clauses 1-55, wherein R$^2$ is —H.

57. The compound of any one of clauses 1-55, wherein R$^2$ is C$_{1-3}$ alkyl, optionally methyl.

58. The compound of any one of clauses 1-57, wherein a2 is 1.

59. The compound of clause 58, wherein R$^{3a}$ and R$^{3b}$ are both H.

60. The compound of any one of clauses 1-57, wherein a2 is 0.

61. The compound of any one of clauses 1-60, wherein a is 1.

62. The compound of any one of clauses 1-60, wherein a is 0.

63. The compound of any one of clauses 1-62, wherein R$^{2'}$ is —CH$_2$CH$_2$R$^3$.

64. The compound of any one of clauses 1-62, wherein R$^{2'}$ is —CH$_2$R$^3$.

65. The compound of any one of clauses 1-62, wherein R$^{2'}$ is —R$^3$.

66. The compound of any one of clauses 63-65, wherein R$^3$ is —C(O)OH.

67. The compound of any one of clauses 63-65, wherein R$^3$ is —CH(C(O)OH)$_2$.

68. The compound of any one of clauses 63-65, wherein R$^3$ is a carboxylic acid bioisostere.

69. The compound of any one of clause 63-65 or 68, wherein R$^3$ is tetrazolyl.

70. The compound of any one of clauses 1-53, wherein a1 is 0; R$^1$ and R$^2$ are each H; and R$^{2'}$ is —CH$_2$CH$_2$R$^3$, wherein R$^3$ is —C(O)OH.

71. The compound of any one of clauses 1-70, wherein W$^1$ is a sequence of from 25-45 amino acids; optionally 30-45 amino acids; optionally 30-40 amino acids.

72. The compound of any one of clauses 1-71, wherein W$^1$ is a sequence of 36 amino acids.

73. The compound of any one of clauses 1-72, wherein W$^1$ has the formula —W$^{1'}$-(AA)-W$^{1'''}$, wherein: W$^{1'}$ is a sequence of 10-20 amino acids (optionally 15-20 amino acids; optionally 16 amino acids); W$^{1'''}$ is a sequence of 15-25 amino acids (optionally 17-21 amino acids; optionally 19 amino acids); and AA is a modified amino acid.

74. The compound of clause 73, wherein AA is a lysyl residue that is optionally substituted with from 1-2 modifying groups (e.g., 1-2 groups selected from an acyl group and a PEG group; and combinations thereof).

75. The compound of clause 73 or 74, wherein AA is an L-lysyl residue that is optionally substituted with from 1-2 modifying groups (e.g., 1-2 groups selected from an acyl group and a PEG group; and combinations thereof).

76. The compound of any one of clauses 73-75, wherein AA has the formula:

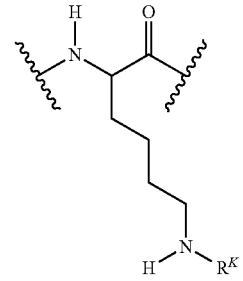

wherein, R$^K$ is a modifying group selected from an acyl group and a PEG group and combinations thereof.

77. The compound of clause 76, wherein R$^K$ is a group of Formula (KA):

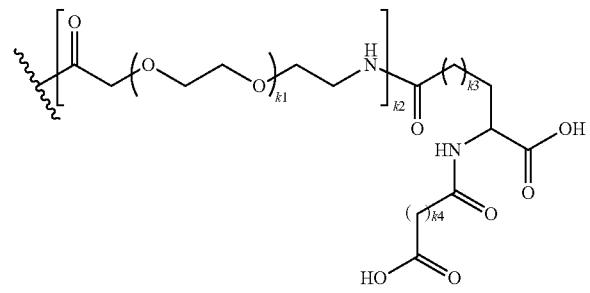

Formula (KA)

wherein:

k1 is 1, 2, 3, or 4;
k2 is 1, 2, 3, or 4;
k3 is 0, 1, 2, 3, or 4; and
k4 is an integer from 5 to 25.

78. The compound of clause 77, wherein k1 is 1.
79. The compound of clauses 77 or 78, wherein k2 is 2.
80. The compound of any one of clauses 77-79, wherein k3 is 1.
81. The compound of any one of clauses 77-80, wherein k4 is an integer from 10 to 20.
82. The compound of any one of clauses 77-81, wherein k4 is an integer from 15 to 20.
83. The compound of any one of clauses 77-82, wherein k4 is 16 or 18.
84. The compound of clause 142, wherein k1 is 1; k2 is 2; k3 is 1; and k4 is an integer from 15 to 20.
85. The compound of any one of clauses 76-84, wherein $R^K$ is

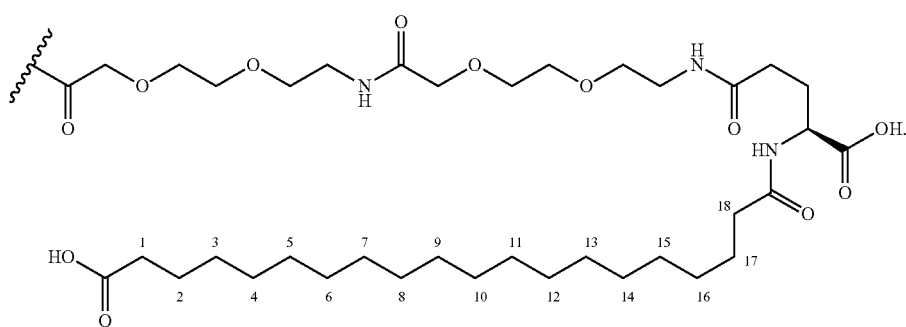

(K18)

86. The compound of any one of clauses 76-84, wherein $R^K$ is

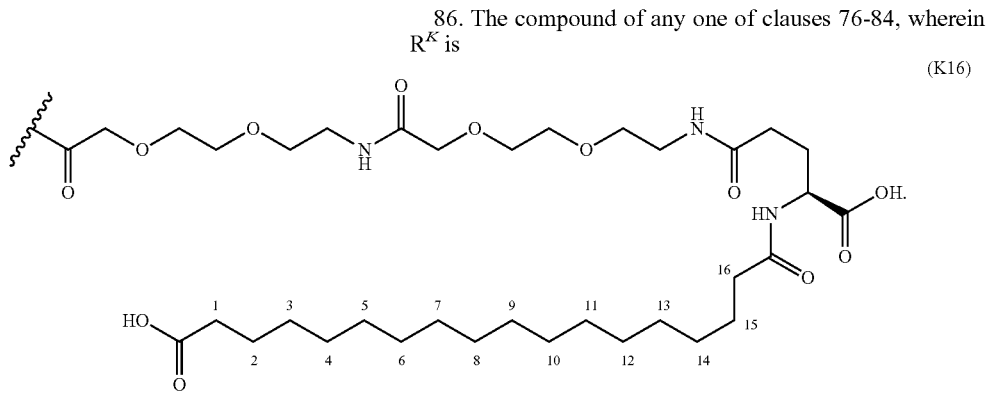

(K16)

87. The compound of any one of clauses 1-86, wherein W has formula: -GTF-W'''—$R^5$, wherein W''' is a sequence of 30-40 (e.g., 31-36, 33) amino acids and comprises a modified amino acid (AA) as defined in any one of clauses 138-151; optionally wherein (AA) is an internal amino acid; and $R^5$ is a C-terminal amino acid, amino ester, or amino acid amide that is optionally substituted with from 1-2 modifying groups.

88. The compound of any one of clauses 73-87, wherein (AA) is an internal amino acid having the formula:

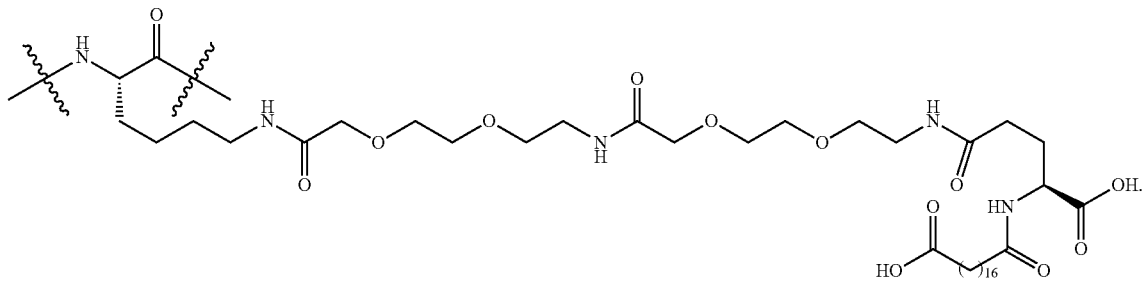

89. The compound of any one of clauses 73-87, wherein (AA) is an internal amino acid having the formula:

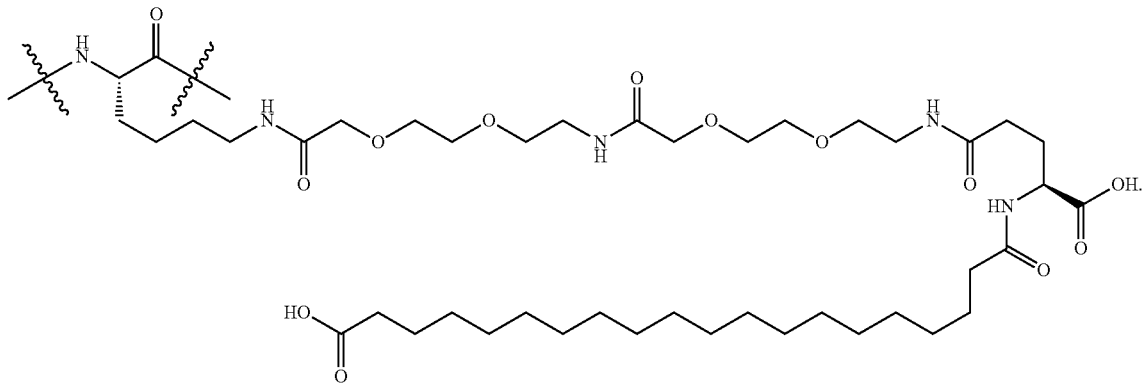 [SMILES: *N[C@@H](CCCCNC(=O)COCCOCCNC(=O)COCCOCCNC(=O)CC[C@H](NC(=O)CCCCCCCCCCCCCCCCCCC(=O)O)C(=O)O)C(*)=O]

90. The compound of any one of clauses 1-89, wherein $R^5$ is a C-terminal amino acid that is optionally substituted; or wherein $R^5$ is a C-terminal amino acid amide that is optionally substituted, optionally $R^5$ is serine amide.

91. The compound of clause 1, wherein the compound is selected from the group consisting of the compounds delineated in FIG. 1, or a pharmaceutically acceptable salt thereof.

92. A pharmaceutical composition comprising a compound or salt as clauseed in any one of clauses 1-91 and one or more pharmaceutically acceptable excipients.

93. A method for modulating GLP-1R and/or GIPR activity, the method comprising contacting GLP-1R and/or GIPR with a compound as clauseed in any one of clauses 1-156.

94. The method of clause 93, wherein the modulating comprises agonizing GLP-1R and/or GIPR.

95. The method of clause 94, wherein the modulating comprises partially agonizing or antagonizing GLP-1R and/or GIPR.

96. The method of any one of clauses 93-95, which is carried out in vitro.

97. The method of any one of clauses 93-95, which is carried out in vivo.

98. A method for modulating GLP-1R and/or GIPR induced aversion, nausea and/or vomiting, the method comprising contacting GLP-1R and/or GIPR with a compound as clauseed in any one of clauses 1-91 or a pharmaceutical composition as clauseed in clause 92.

99. A method for modulating (e.g., increasing) insulin levels in a subject in need of such modulating, the method comprising administering to the subject an effective amount of a compound as clauseed in any one of clauses 1-91 or a pharmaceutical composition as clauseed in clause 92.

100. A method for modulating (e.g., decreasing) glucose levels in a subject in need of such modulating, the method comprising administering to the subject an effective amount of a compound as clauseed in any one of clauses 1-91 or a pharmaceutical composition as clauseed in clause 92.

101. A method for treating a disease, disorder, or condition, in which modulating GLP-1R and/or GIPR signaling can alter the pathology and/or symptoms and/or progression of the disease, disorder, or condition, the method comprising administering to the subject in need thereof an effective amount of a compound as clauseed in any one of clauses 1-91 or a pharmaceutical composition as clauseed in clause 92.

102. The method of clause 101, wherein the disease, disorder, or condition or disorder is diabetes.

103. The method of clause 101, wherein the disease, disorder, or condition or disorder is NASH.

104. The method of clause 101, wherein the disease, disorder, or condition or disorder is obesity.

105. The method of clause 101, wherein the disease, disorder, or condition or disorder is fatty liver disease.

106. The method of clause 101, wherein the disease, disorder, or condition or disorder is steatohepatitis.

107. The method of any one of clauses 101-106, wherein the method further comprises identifying the subject.

108. The method of any one of clauses 99-107, wherein the subject is a human.

109. A method for treating a disease, disorder, or condition, in which modulating GLP-1R and/or GIPR signaling causes aversion, nausea or vomiting, the method comprising administering to the subject in need thereof an effective amount of a compound as clauseed in any one of clauses 1-91 or a pharmaceutical composition as clauseed in clause 92.

A number of embodiments of this disclosure have been described. Nevertheless, it will be understood that various modifications may be made without departing from the spirit and scope of this disclosure. Accordingly, other embodiments are within the scope of the following claims.

What is claimed is:
1. A compound, or pharmaceutically acceptable salt thereof, wherein the compound is selected from the group consisting of:
Compound 101
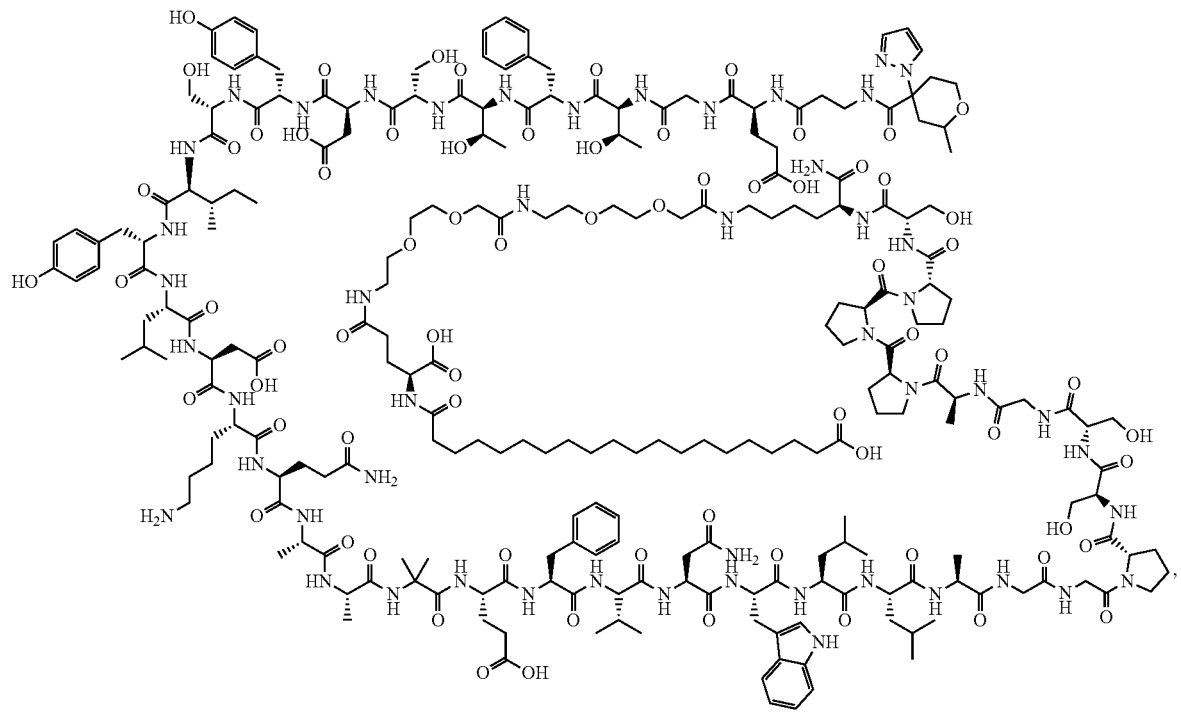
Compound 102
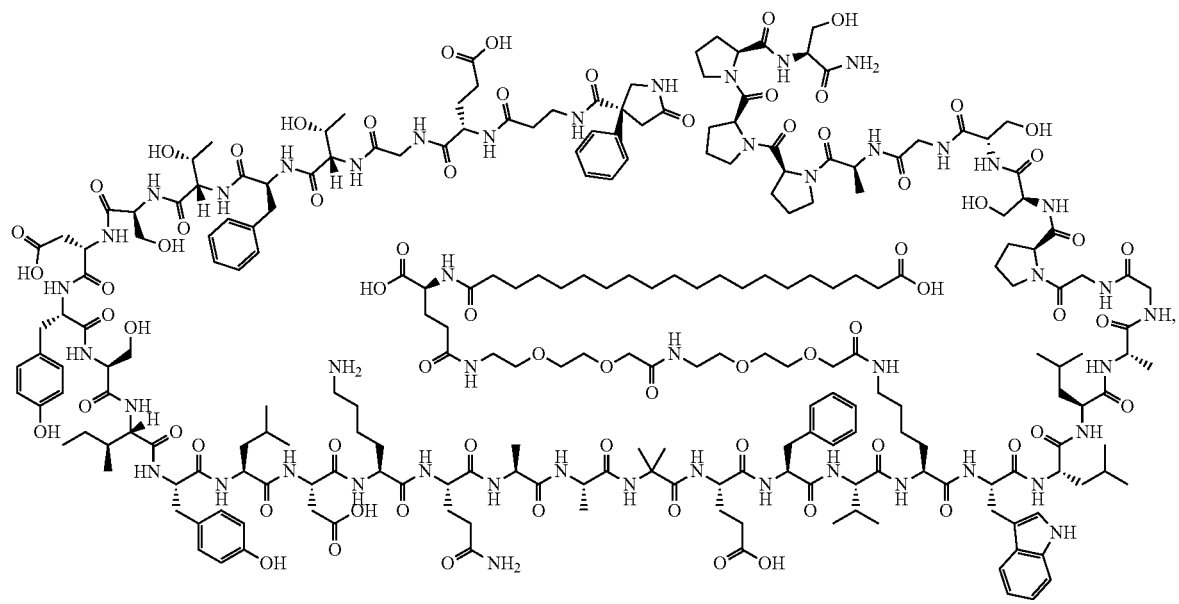

Compound 103
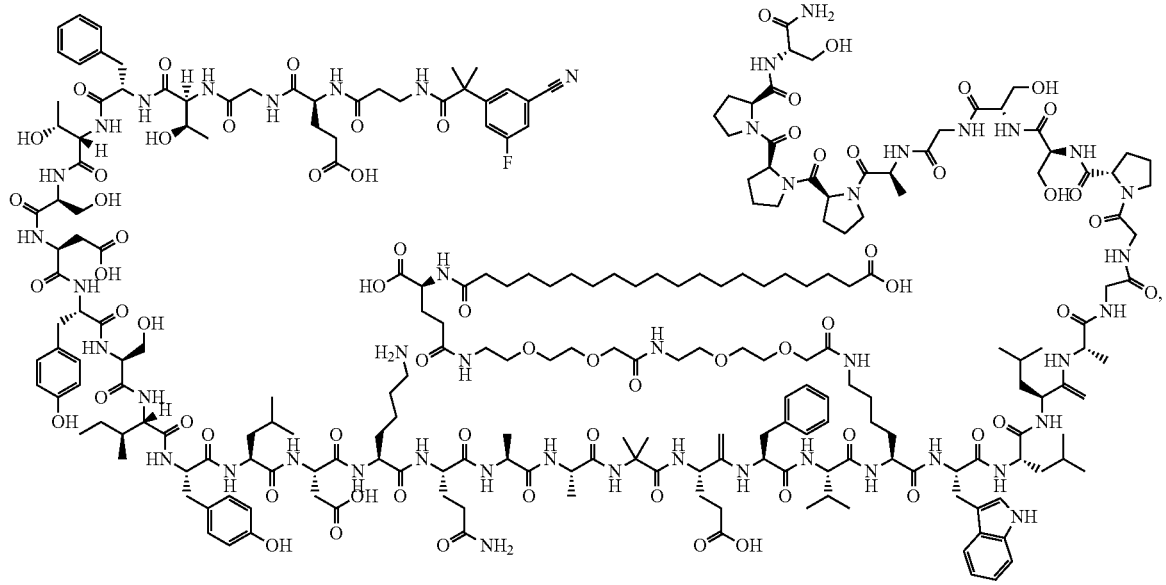
Compound 104
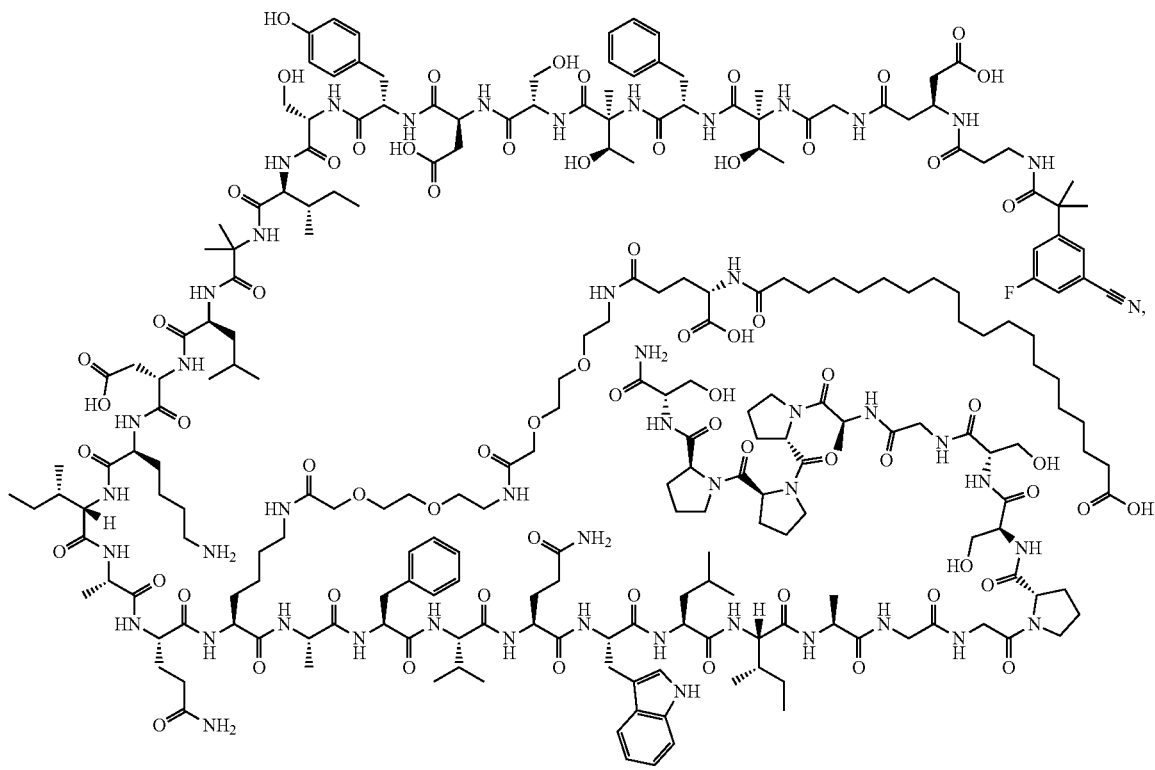

Compound 105
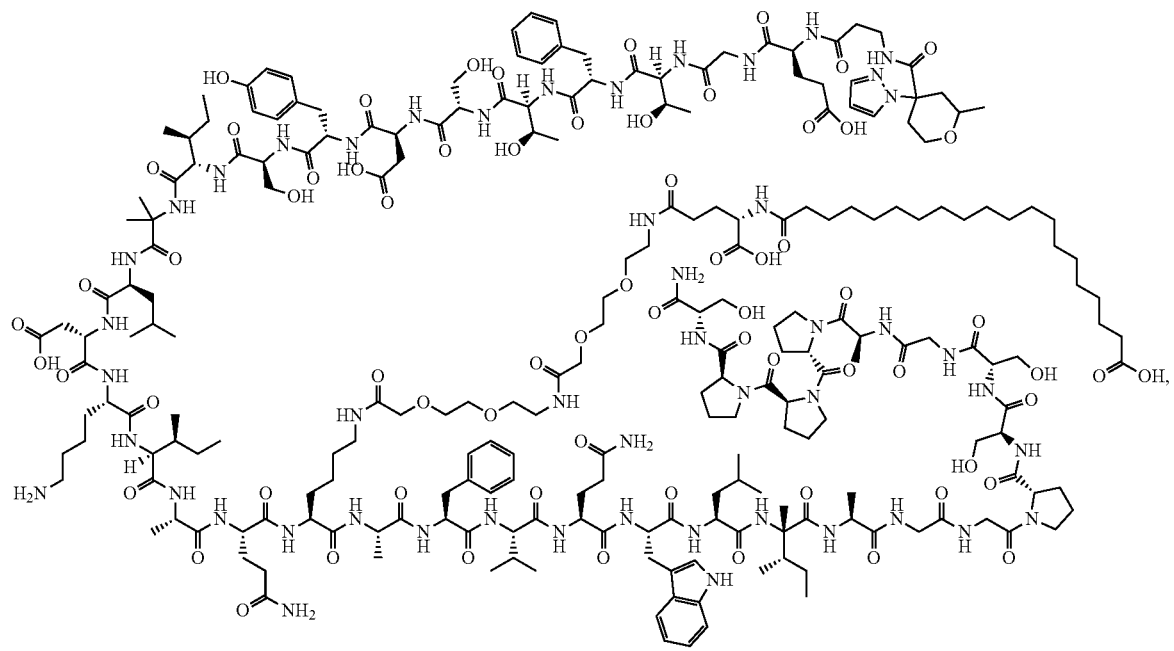
Compound 106
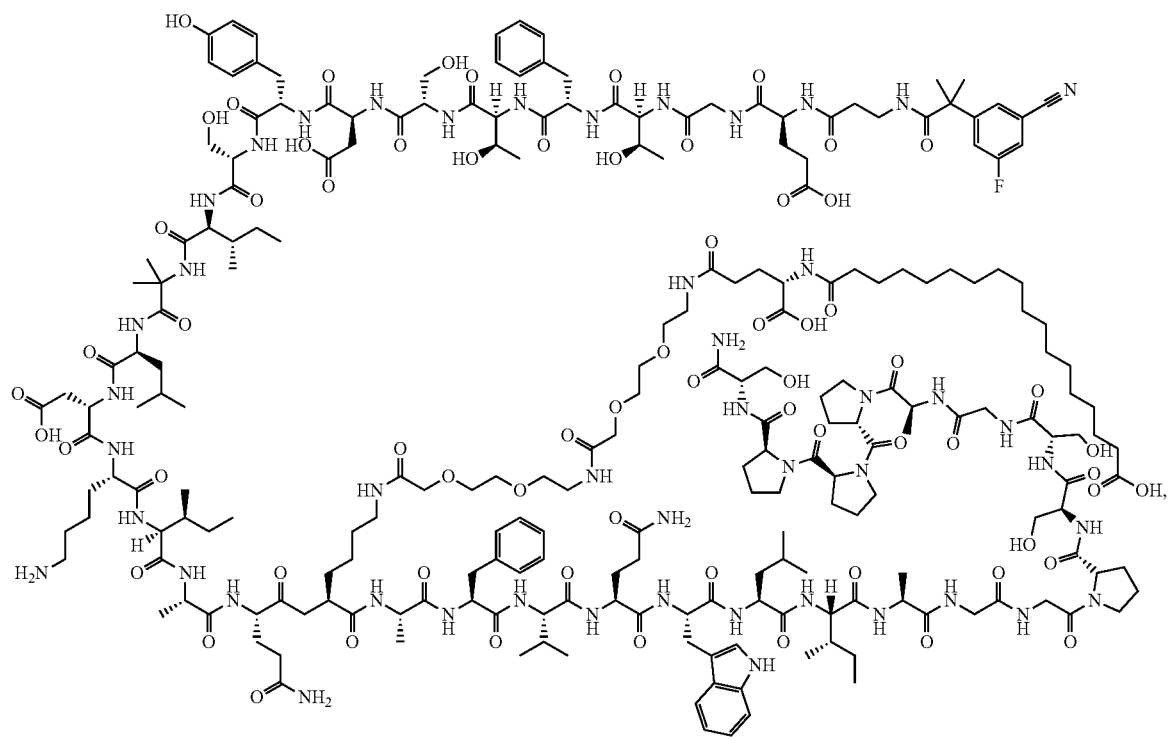

Compound 107
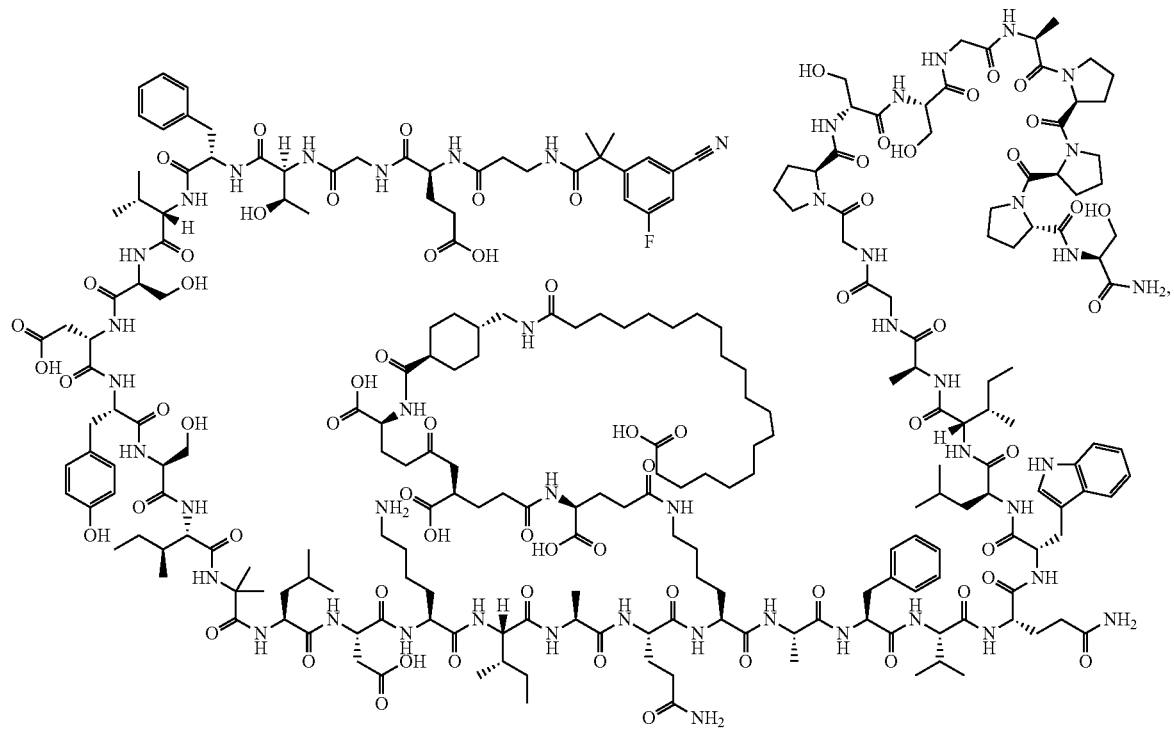
Compound 108
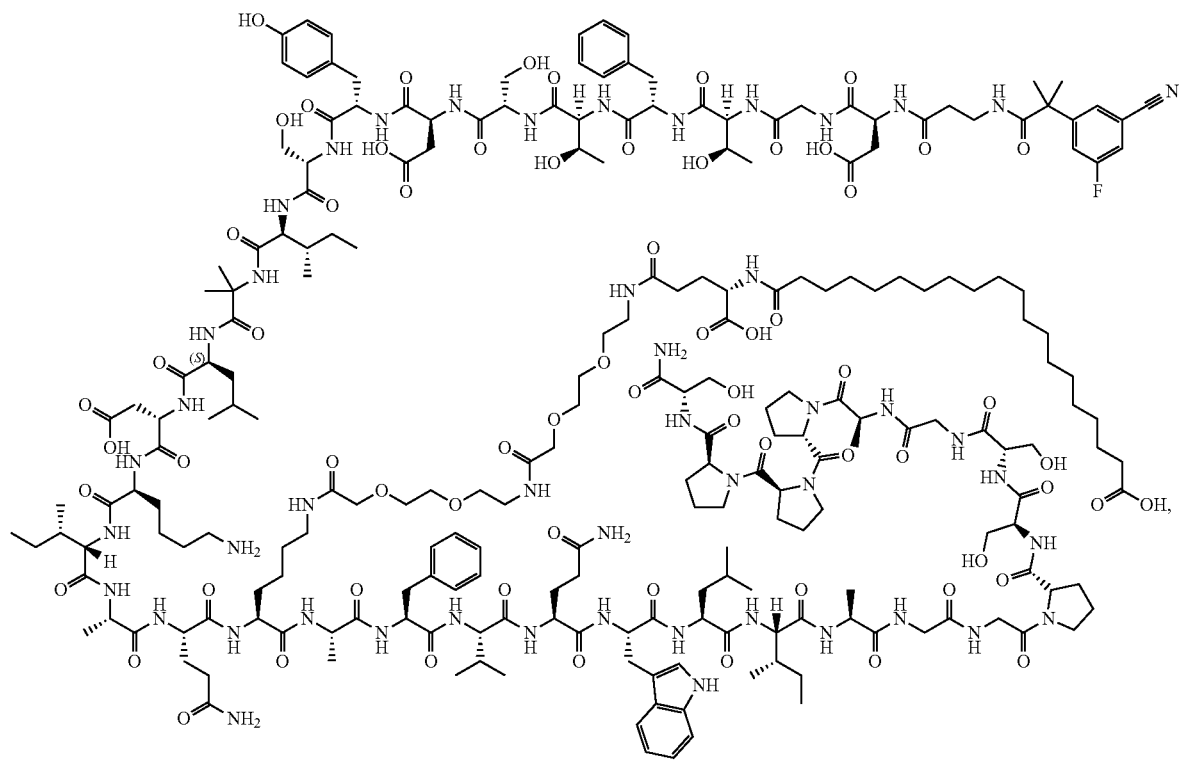

Compound 109
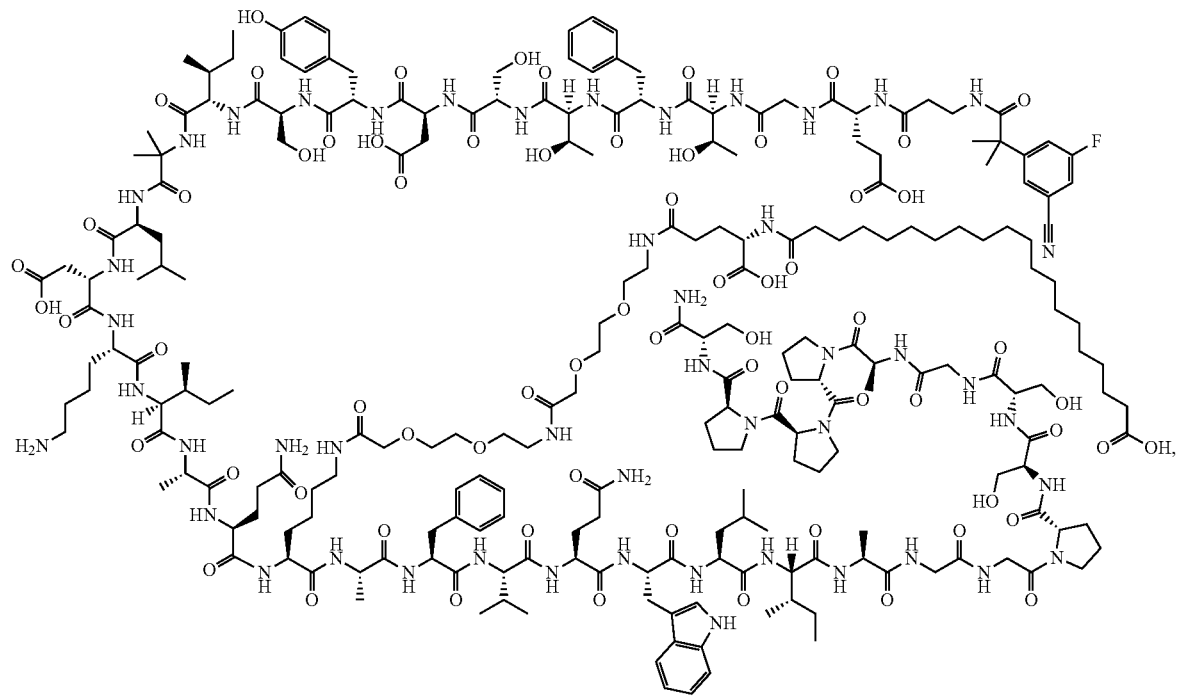
Compound 110
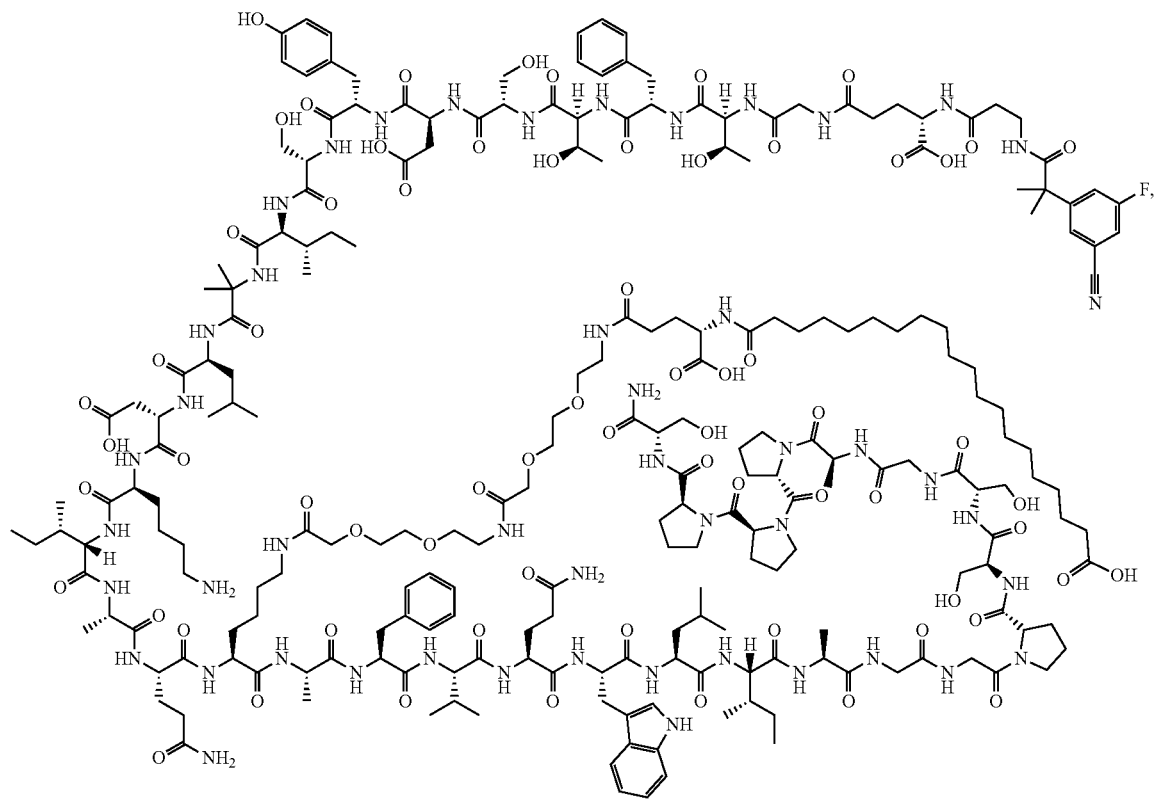

Compound 111
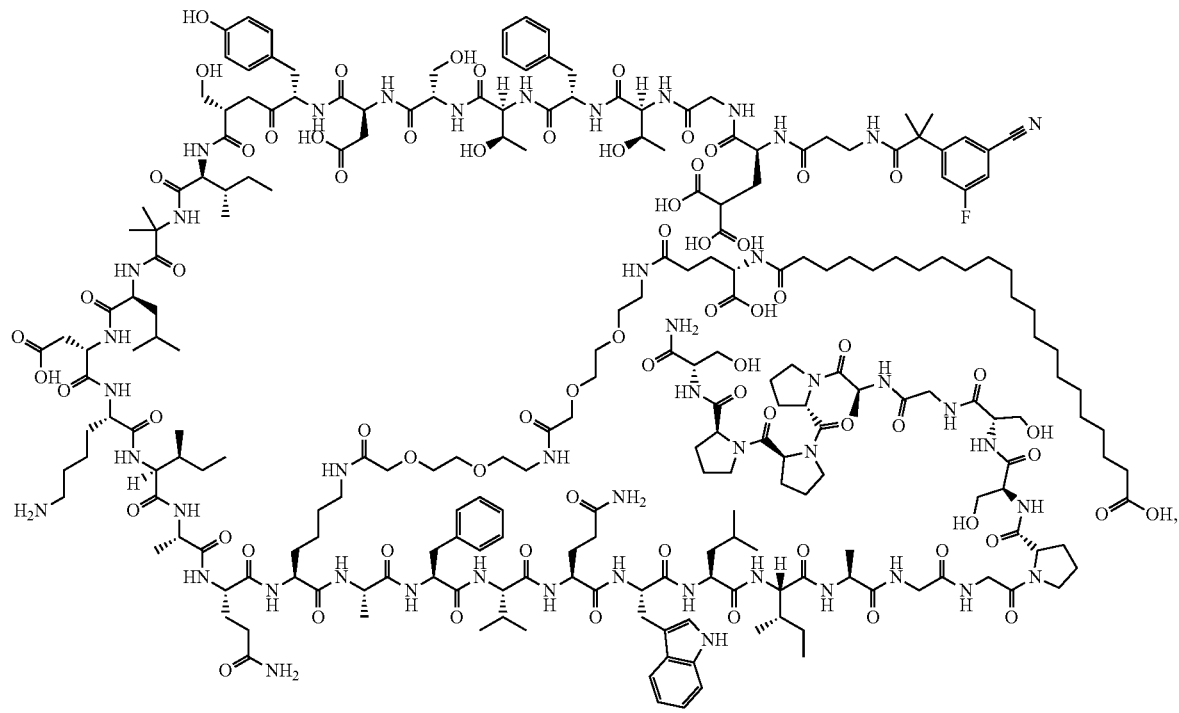
Compound 112
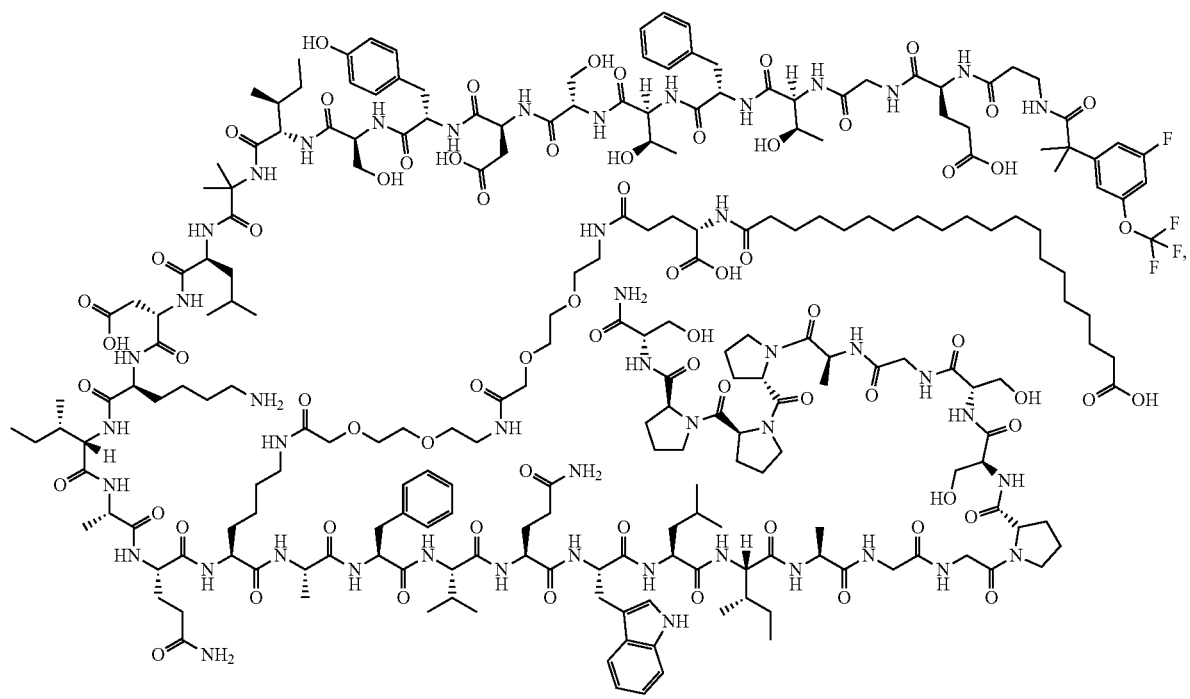

Compound 113
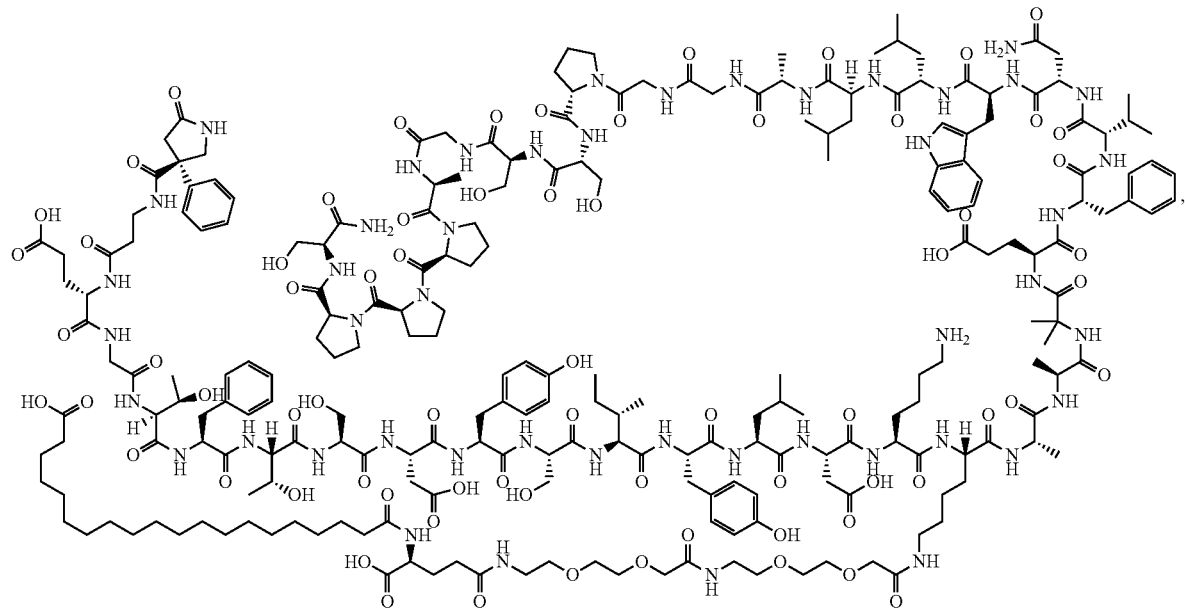
Compound 114
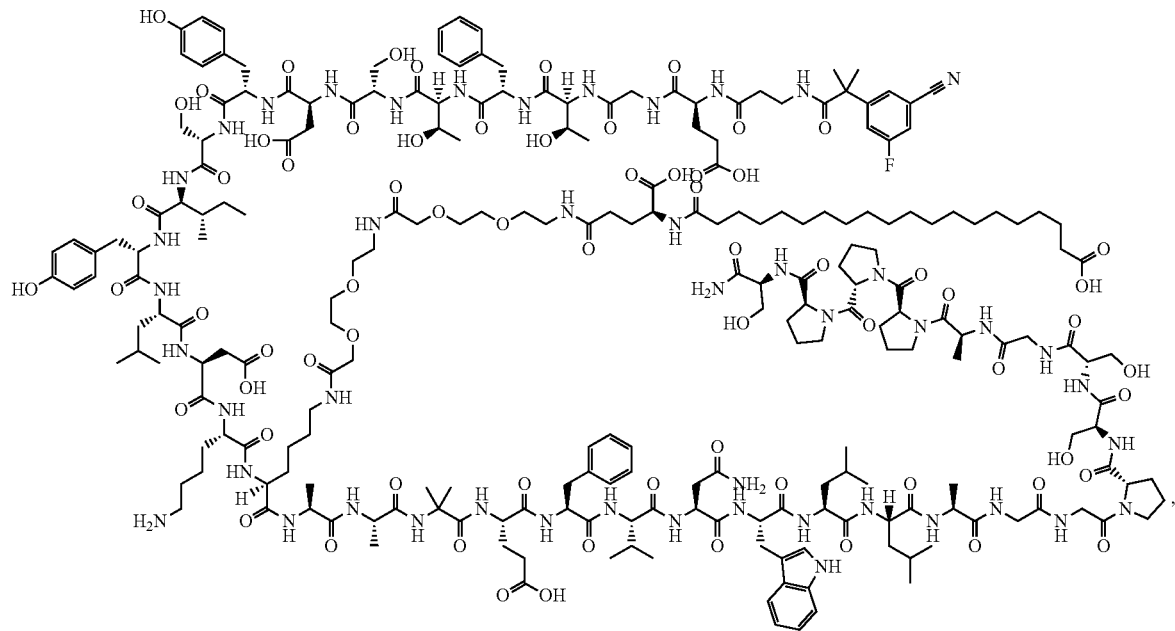

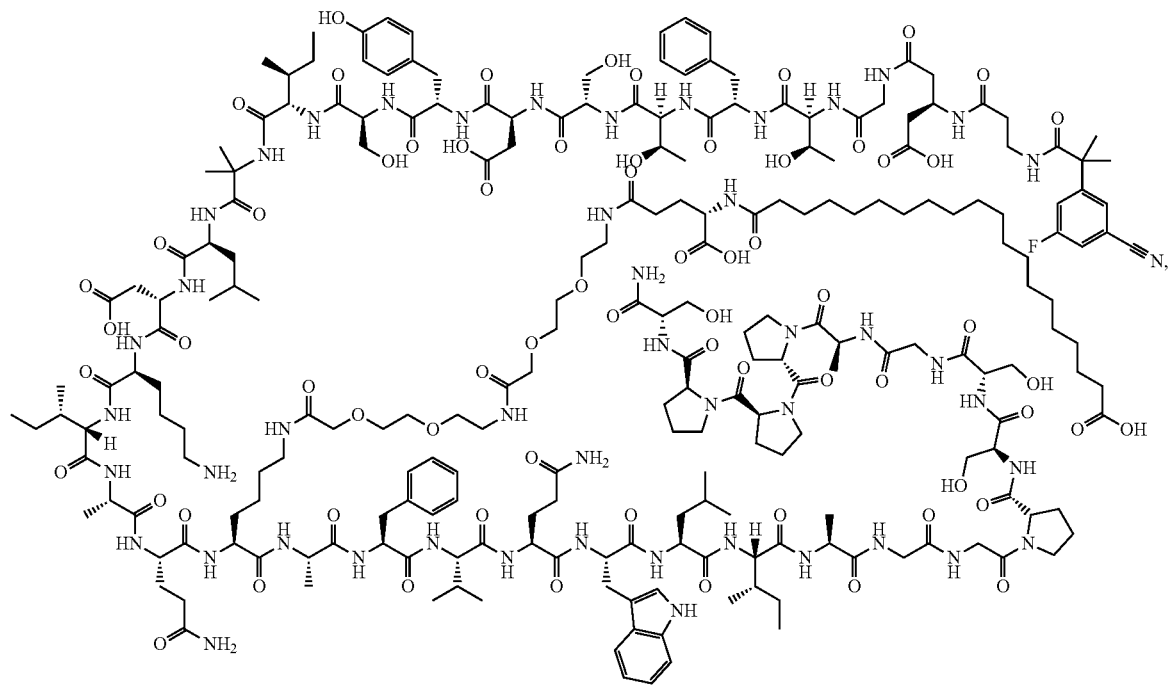
Compound 115
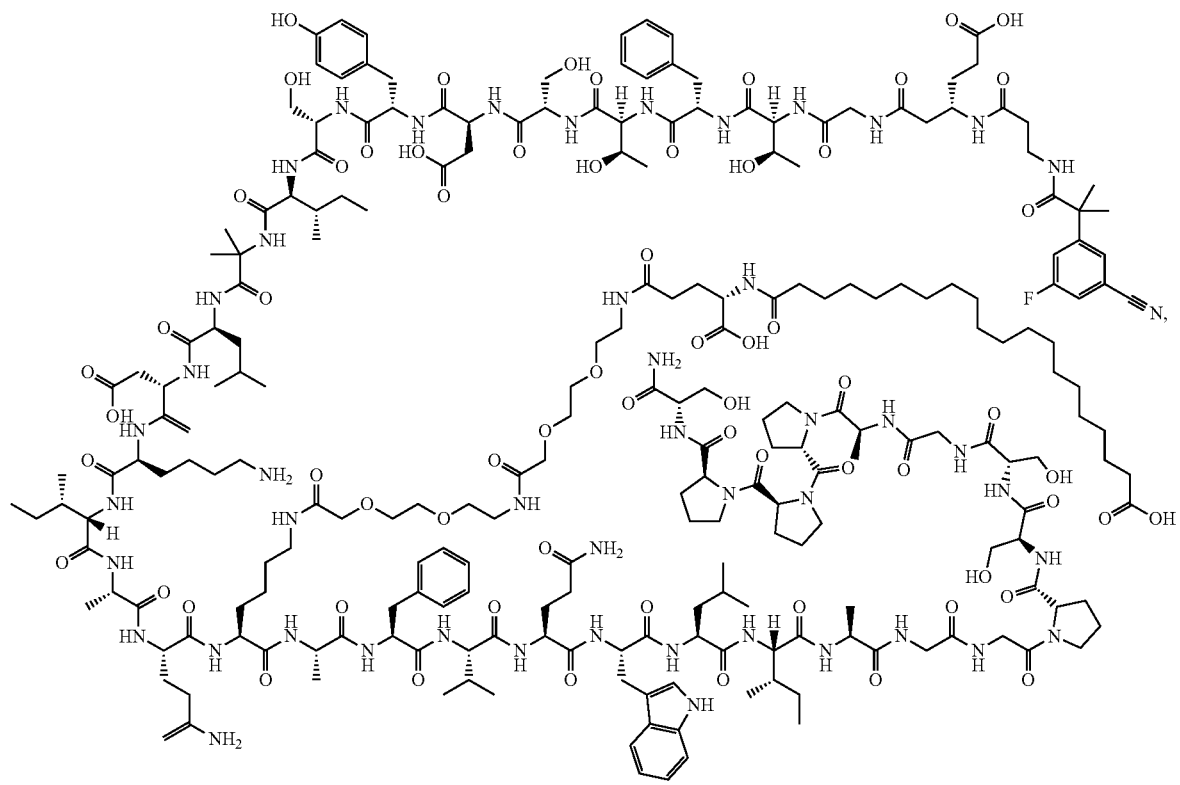
Compound 116

Compound 117
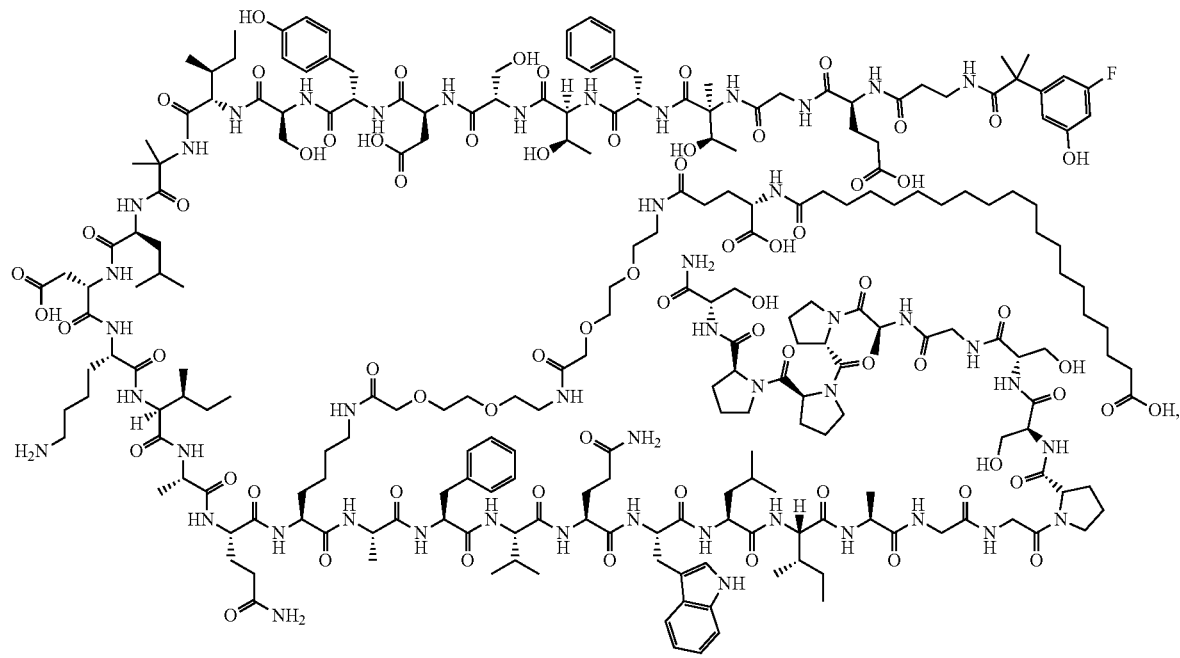
Compound 118
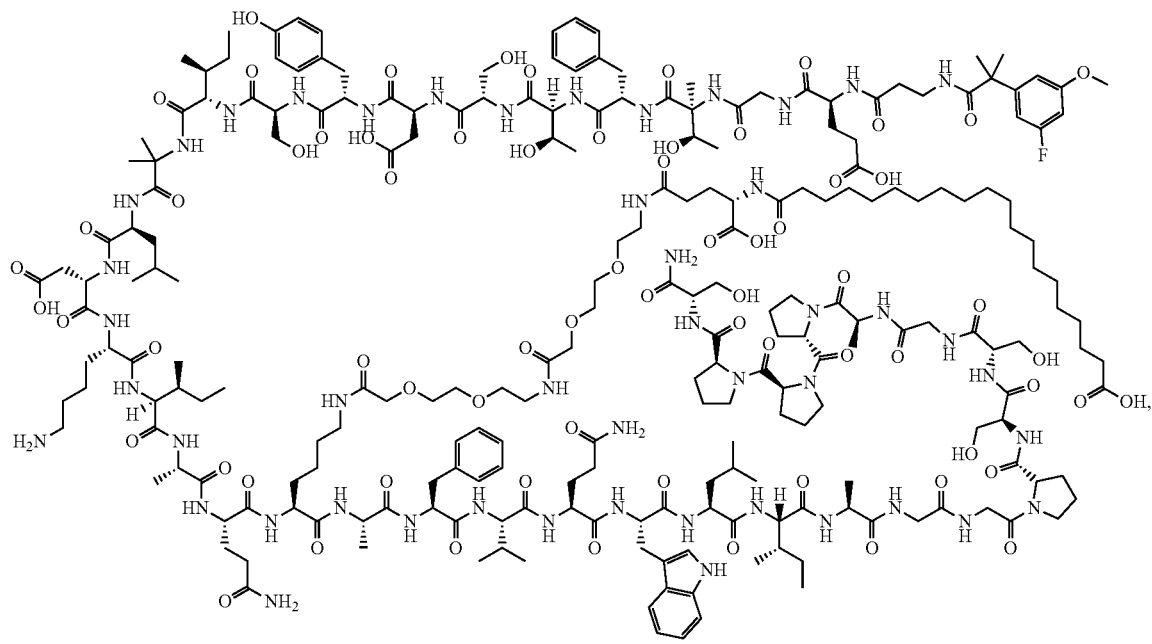

-continued
Compound 119
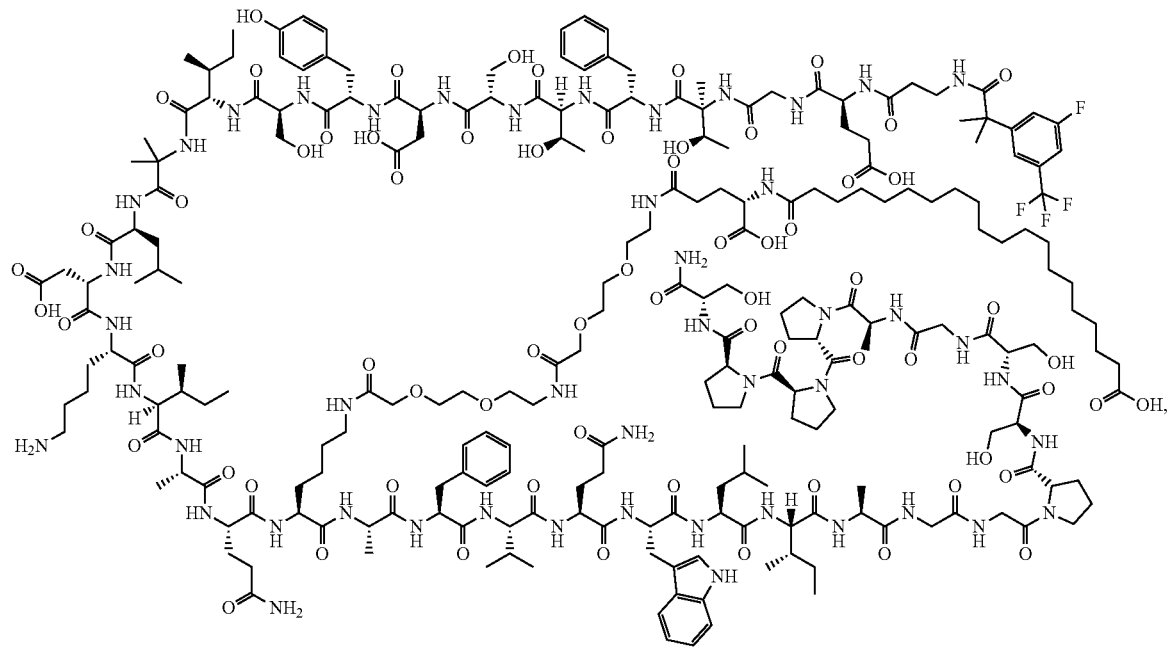
Compound 120
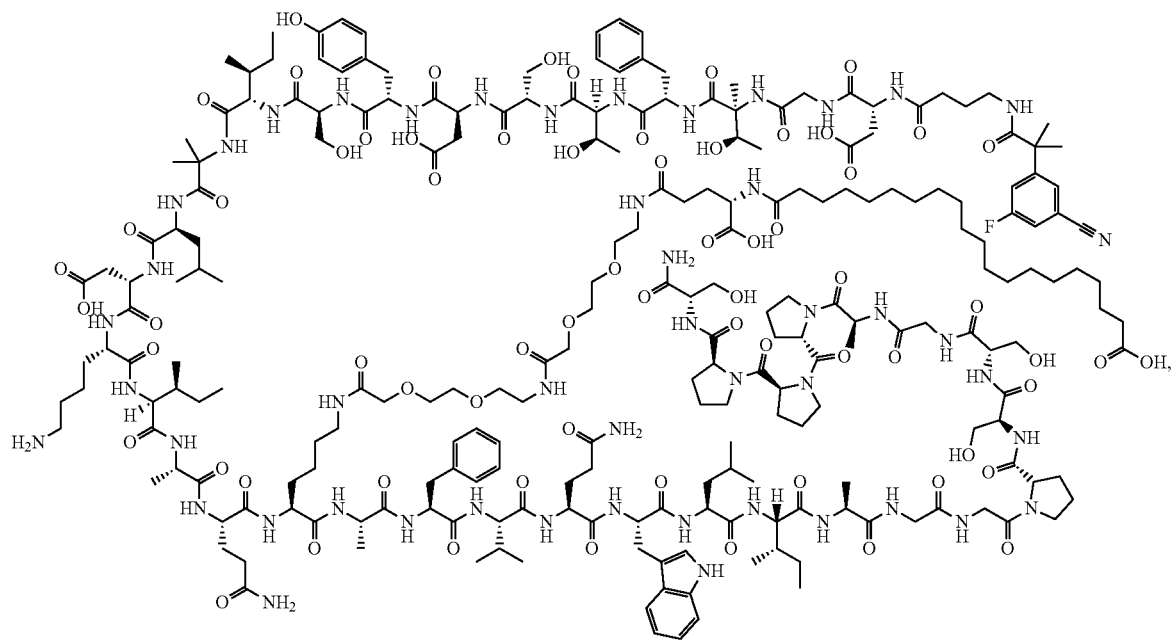

Compound 121
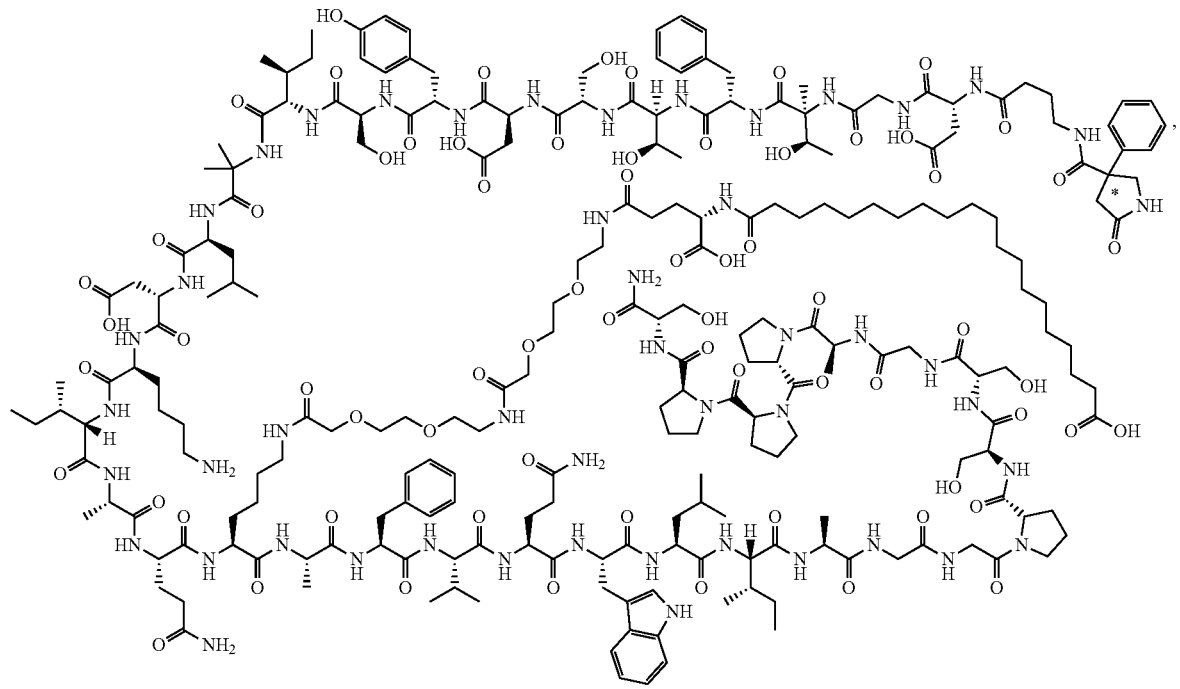
Compound 122
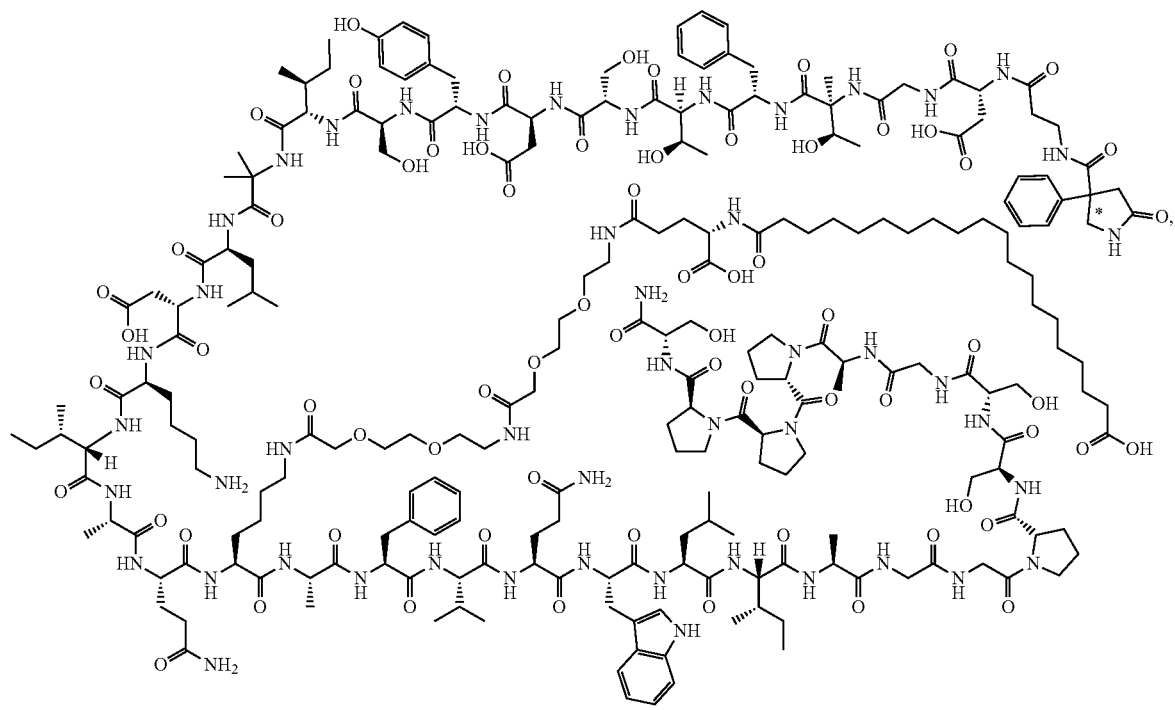

Compound 123
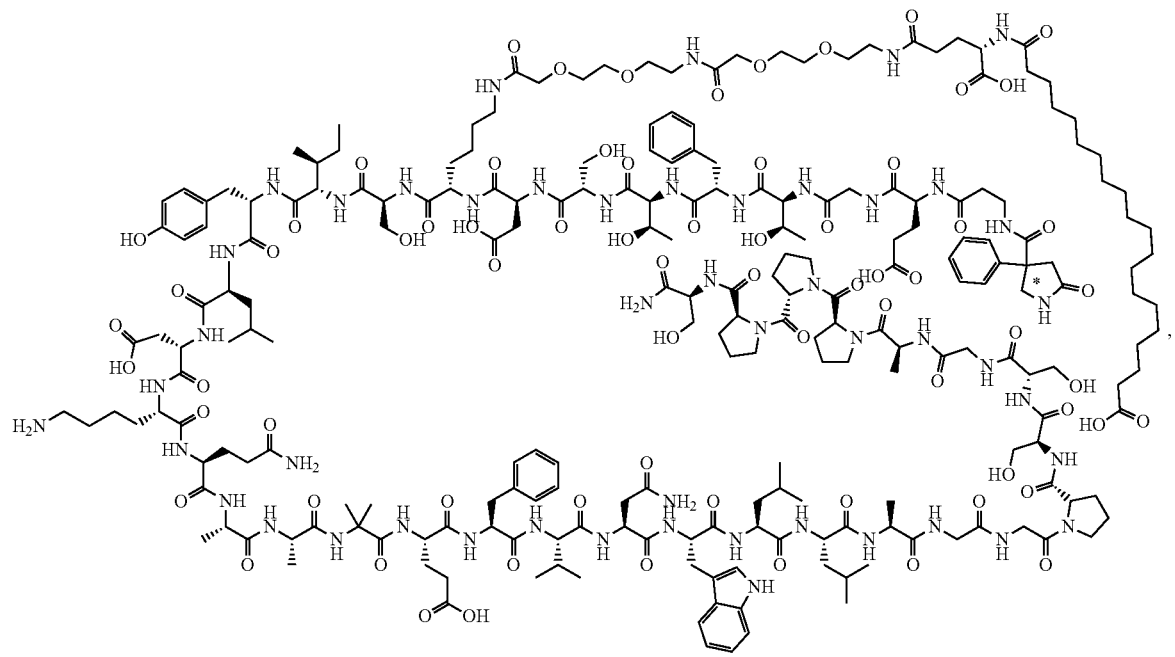
Compound 124
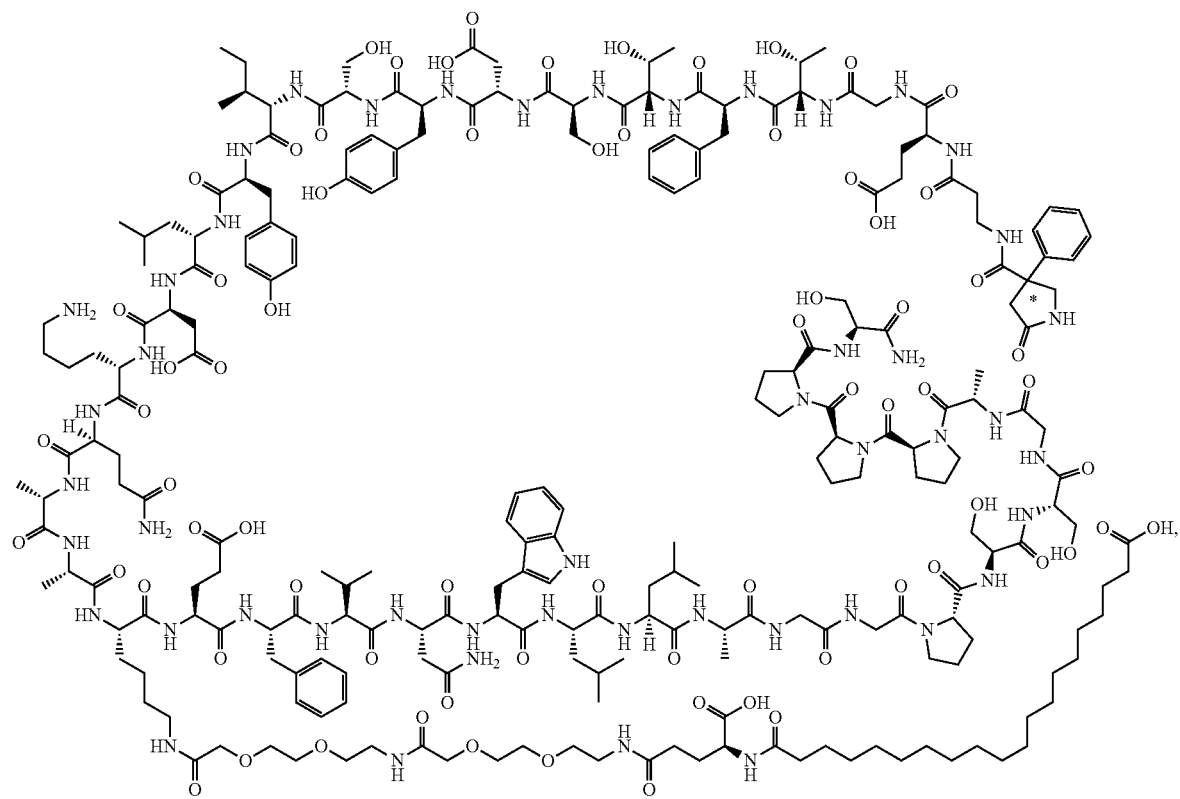

Compound 125
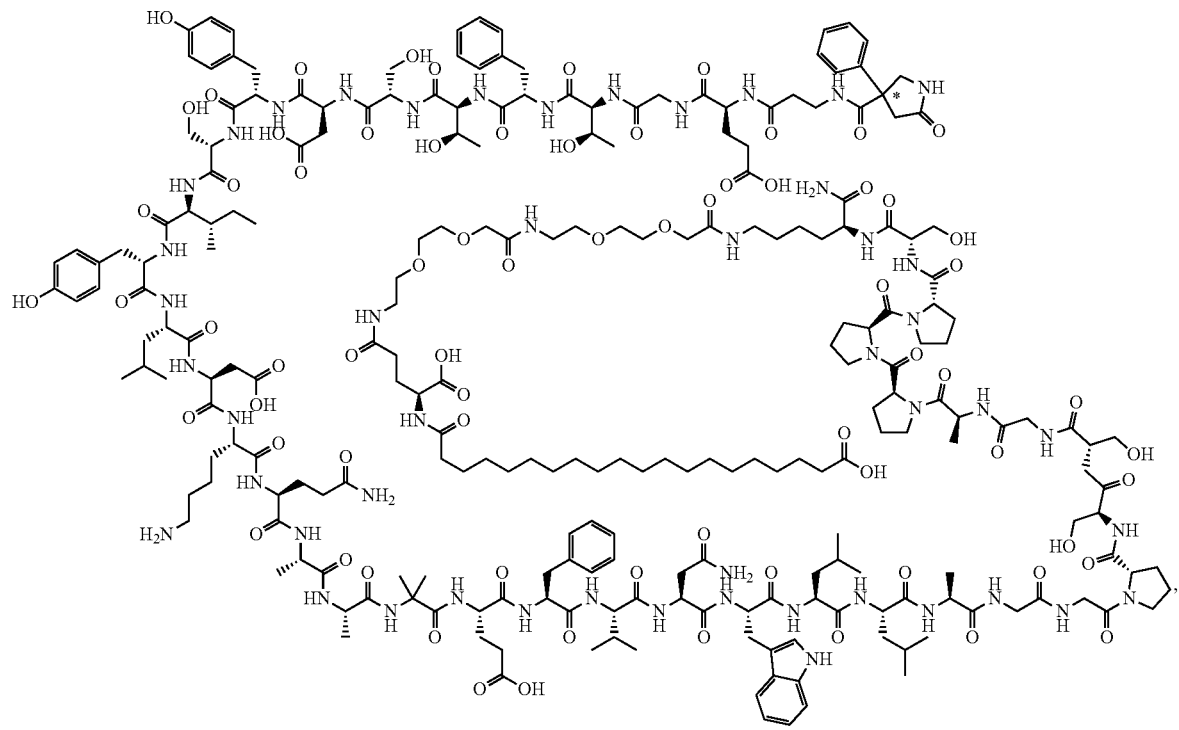
Compound 126
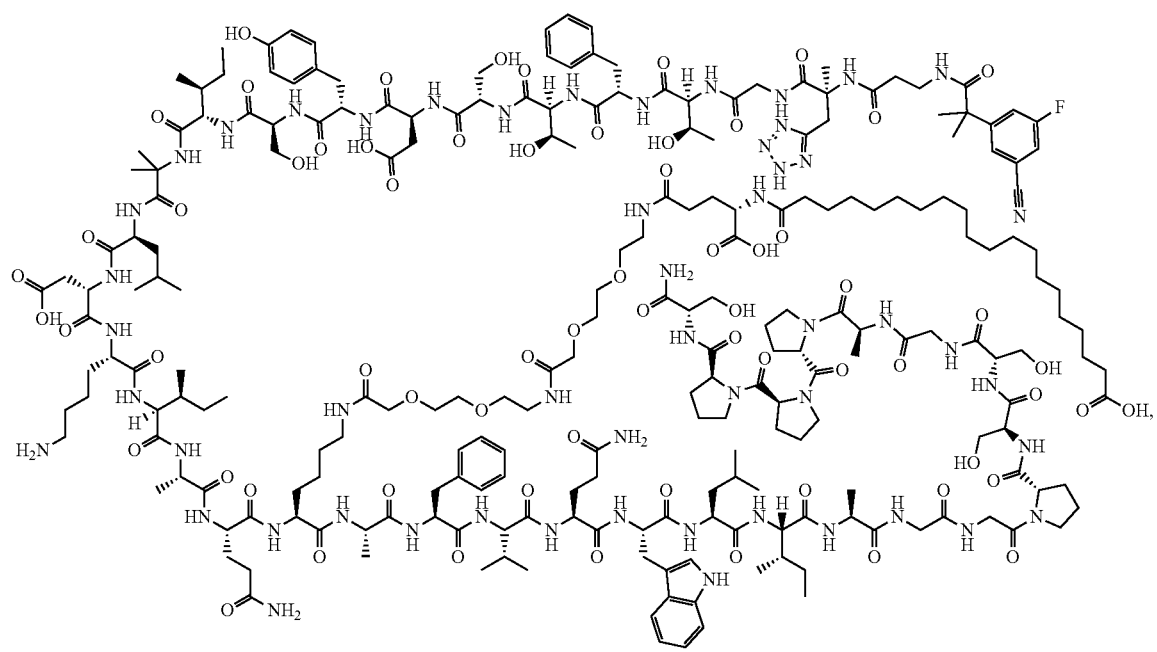

Compound 127
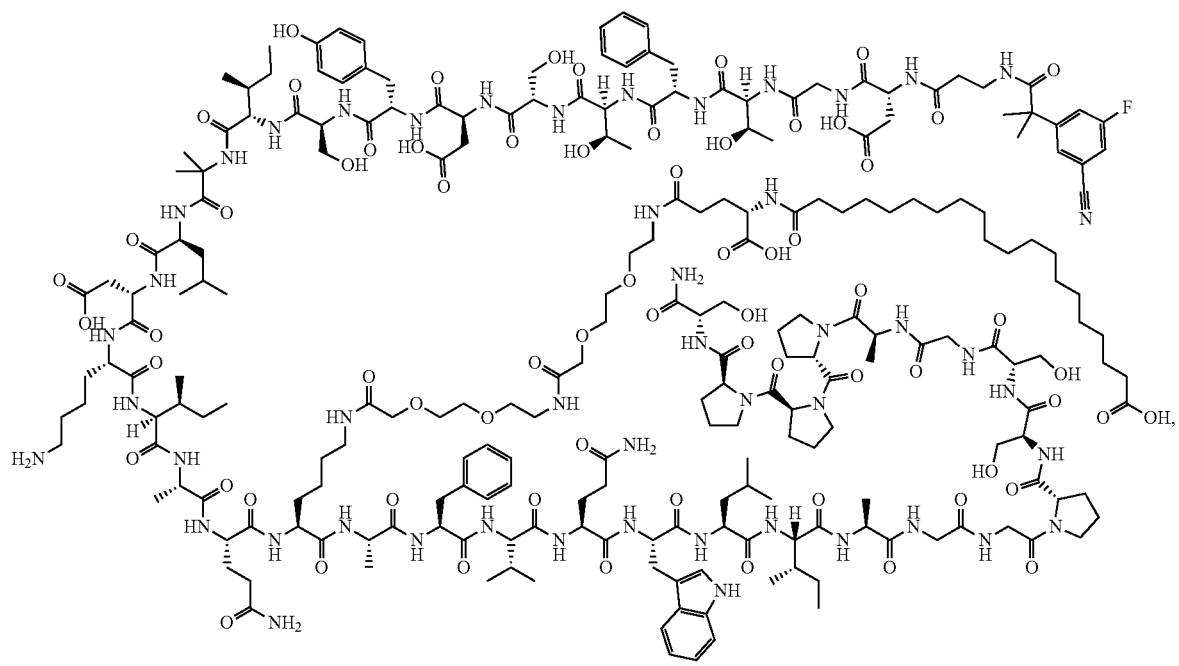
Compound 128
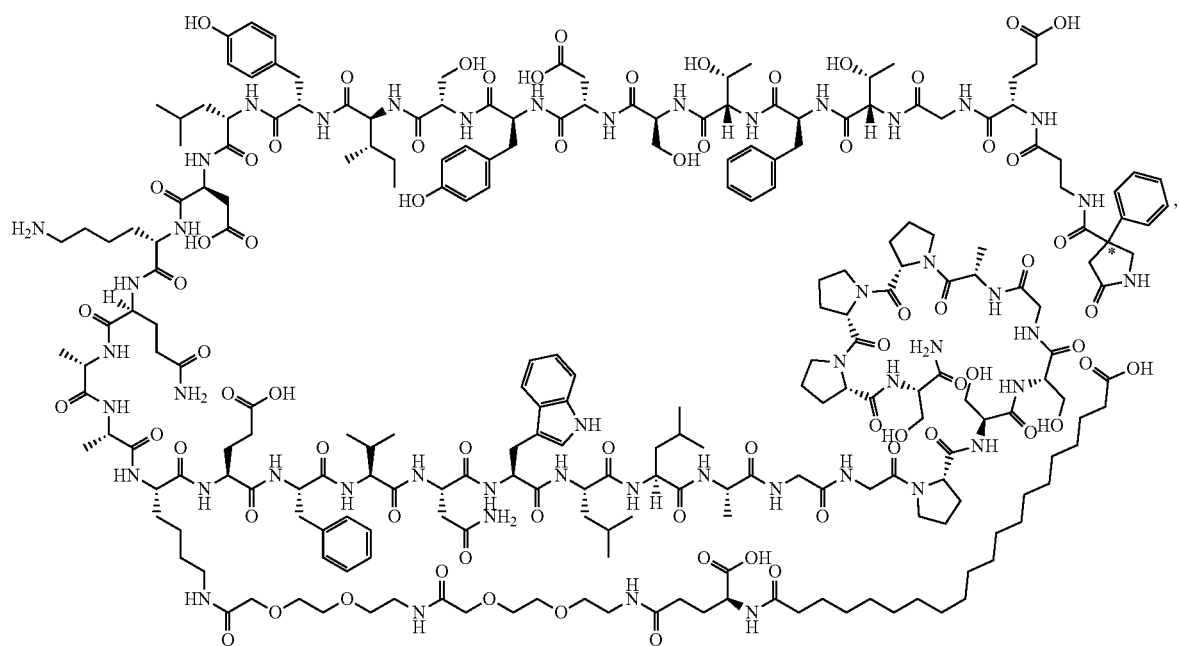

Compound 129
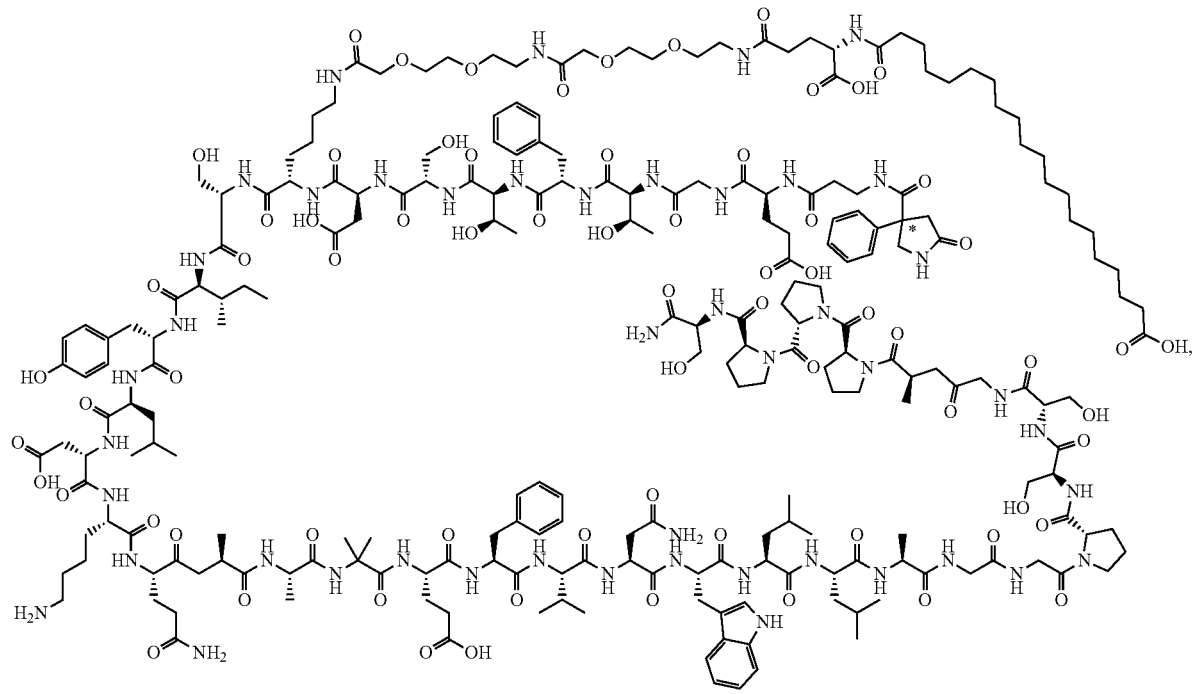
Compound 130
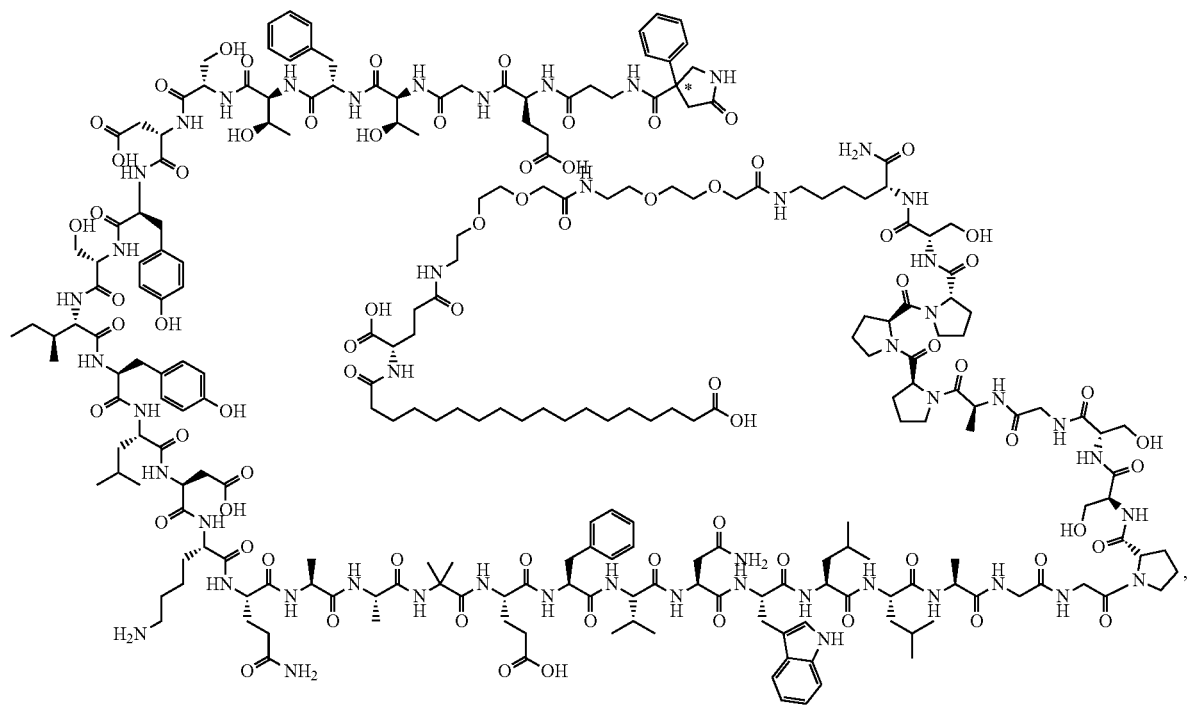

Compound 131
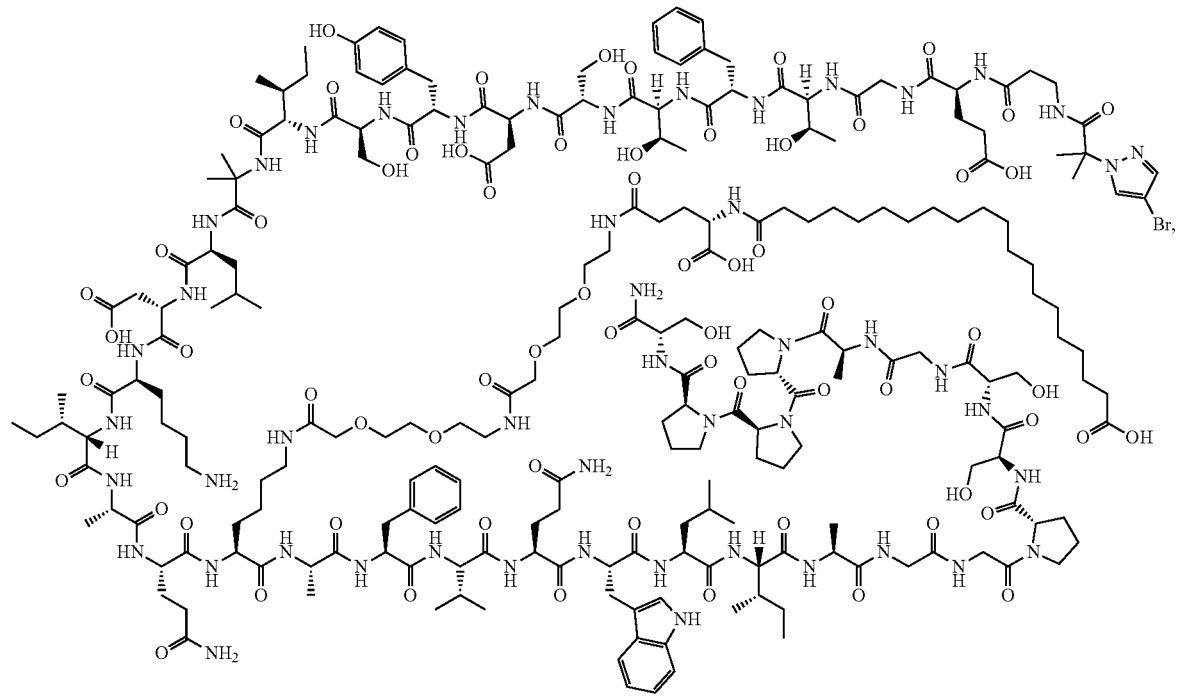
Compound 132
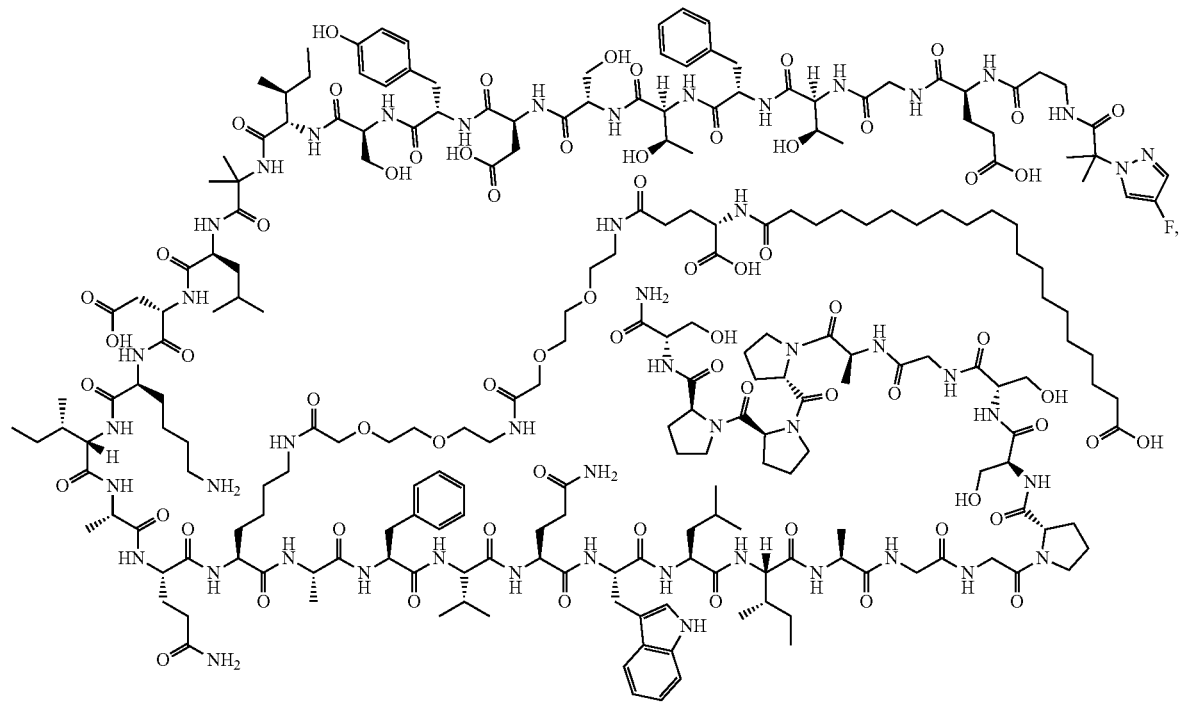

Compound 133
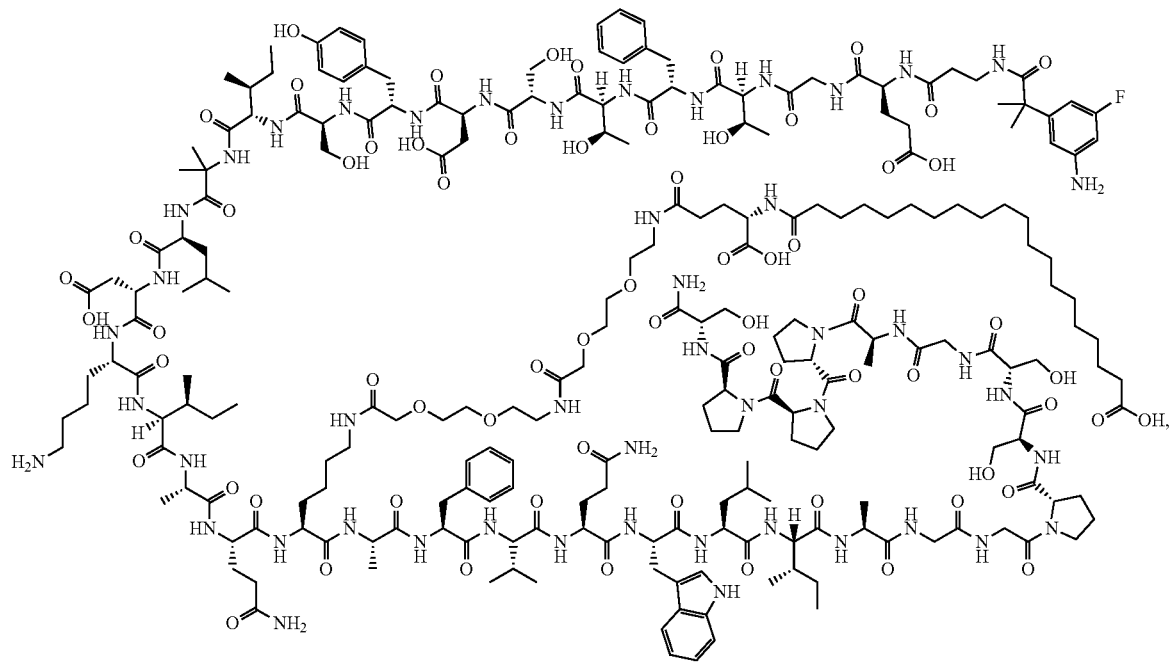
Compound 134
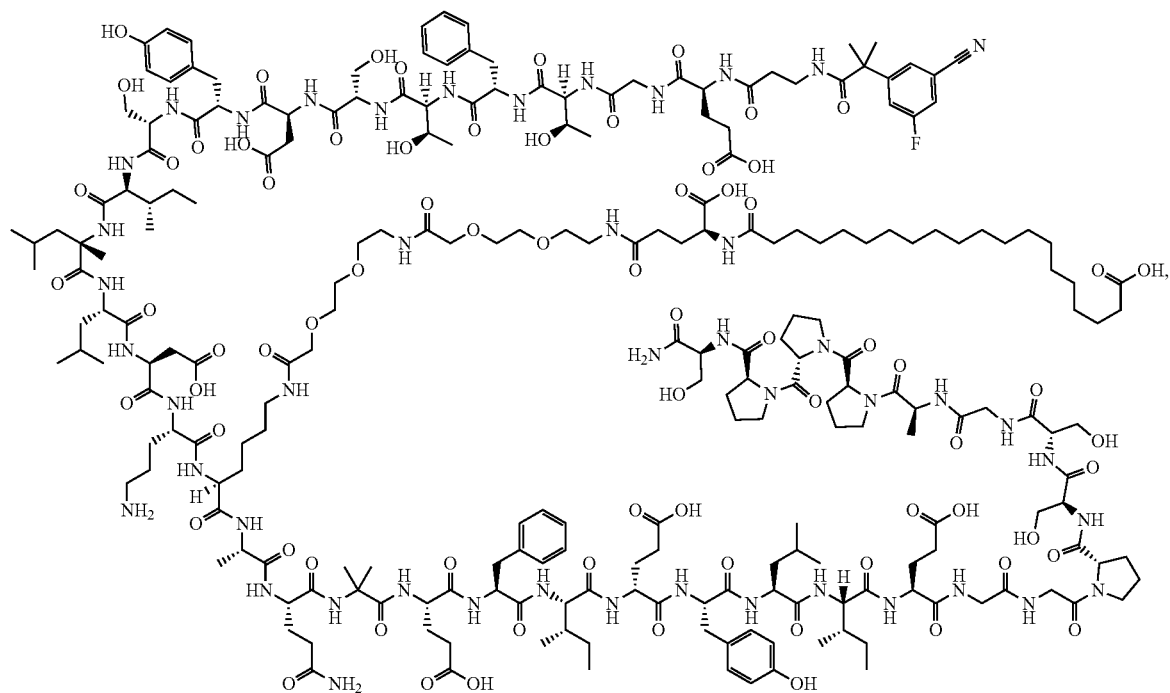

Compound 135
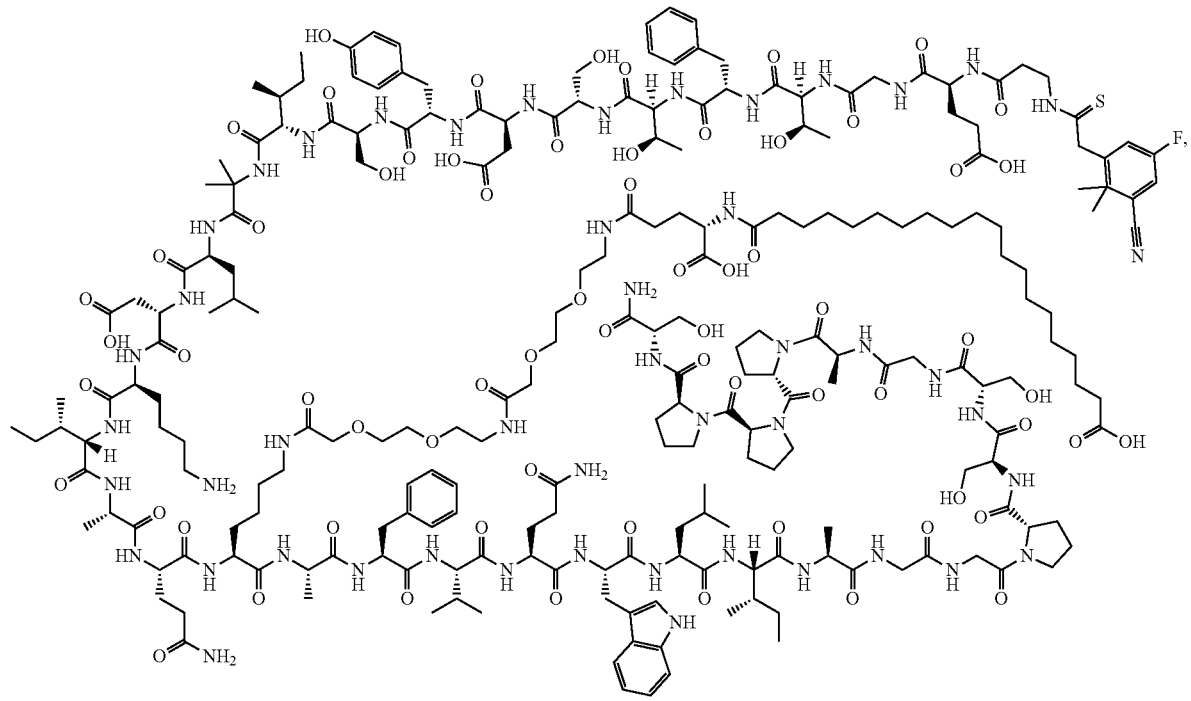
Compound 136
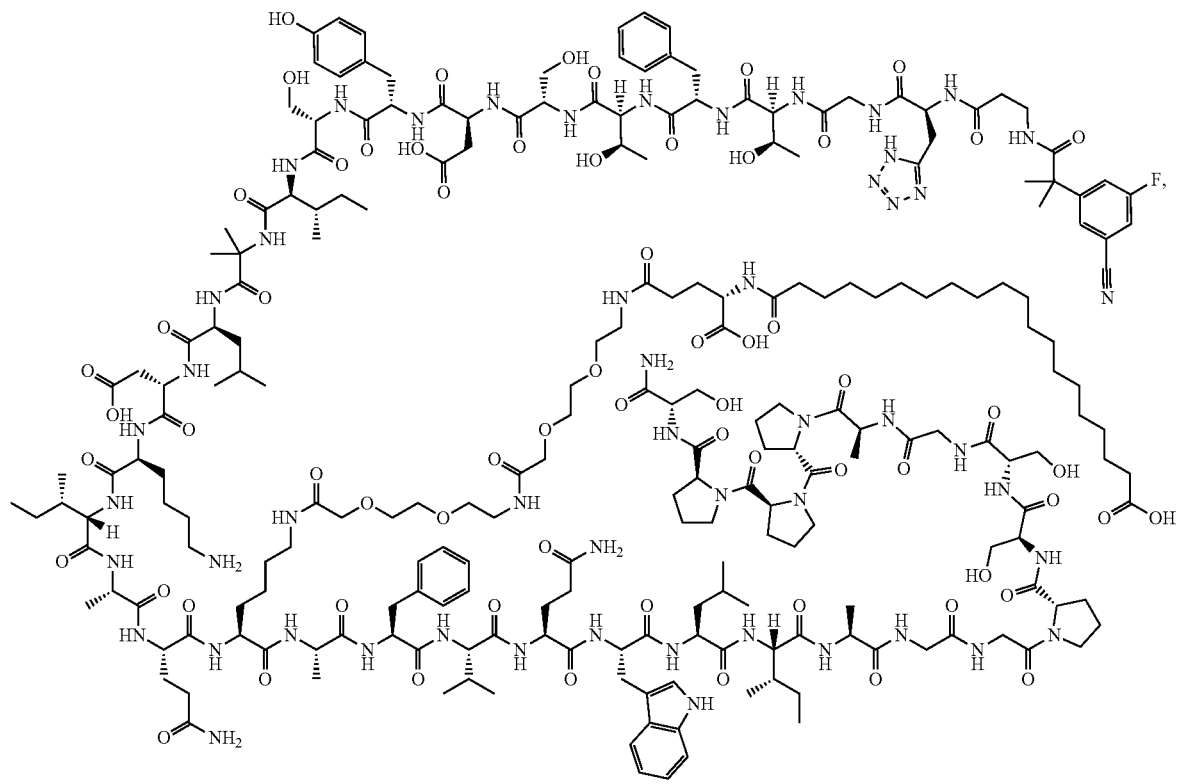

Compound 137
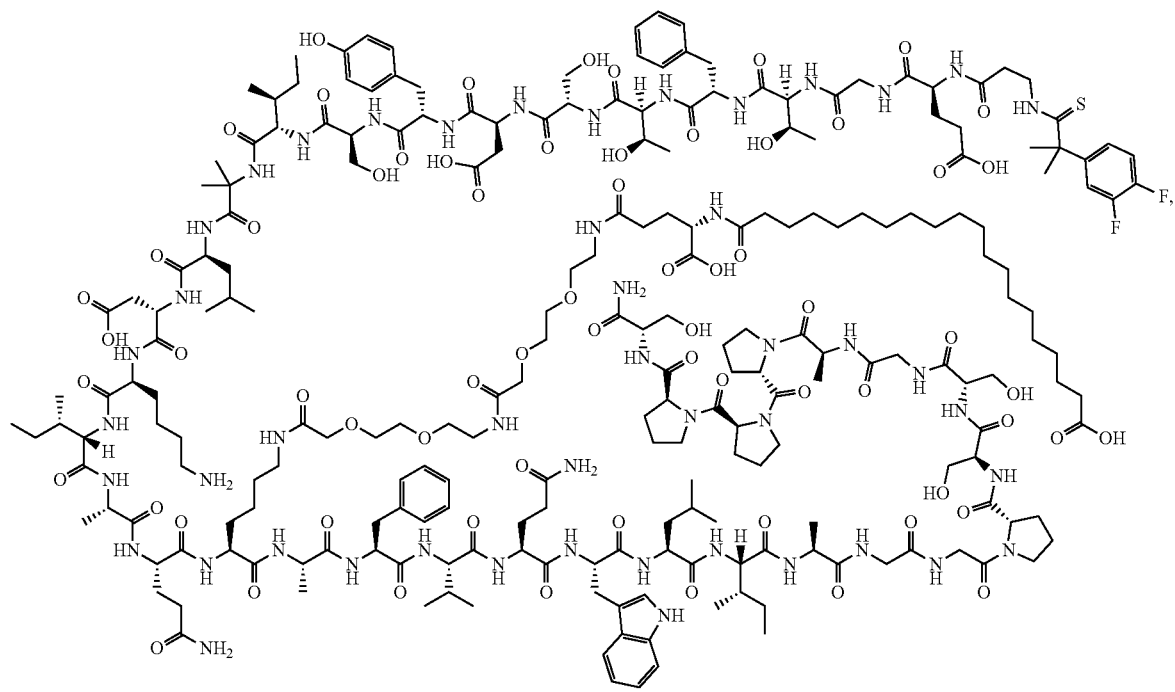
Compound 138
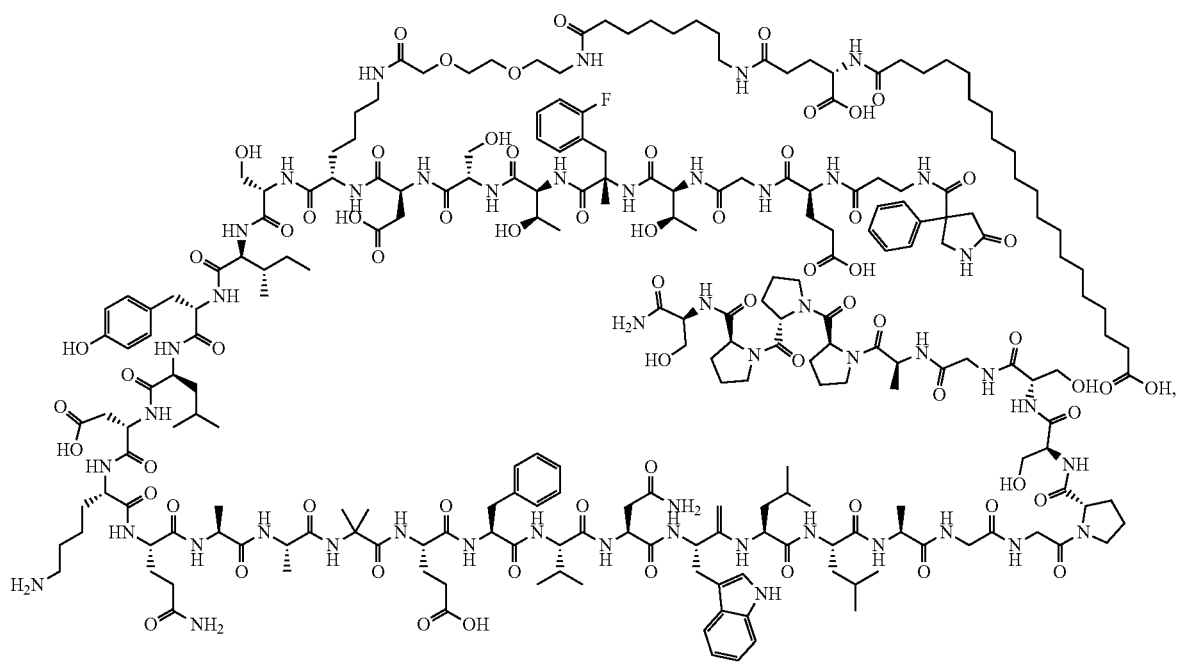

Compound 139
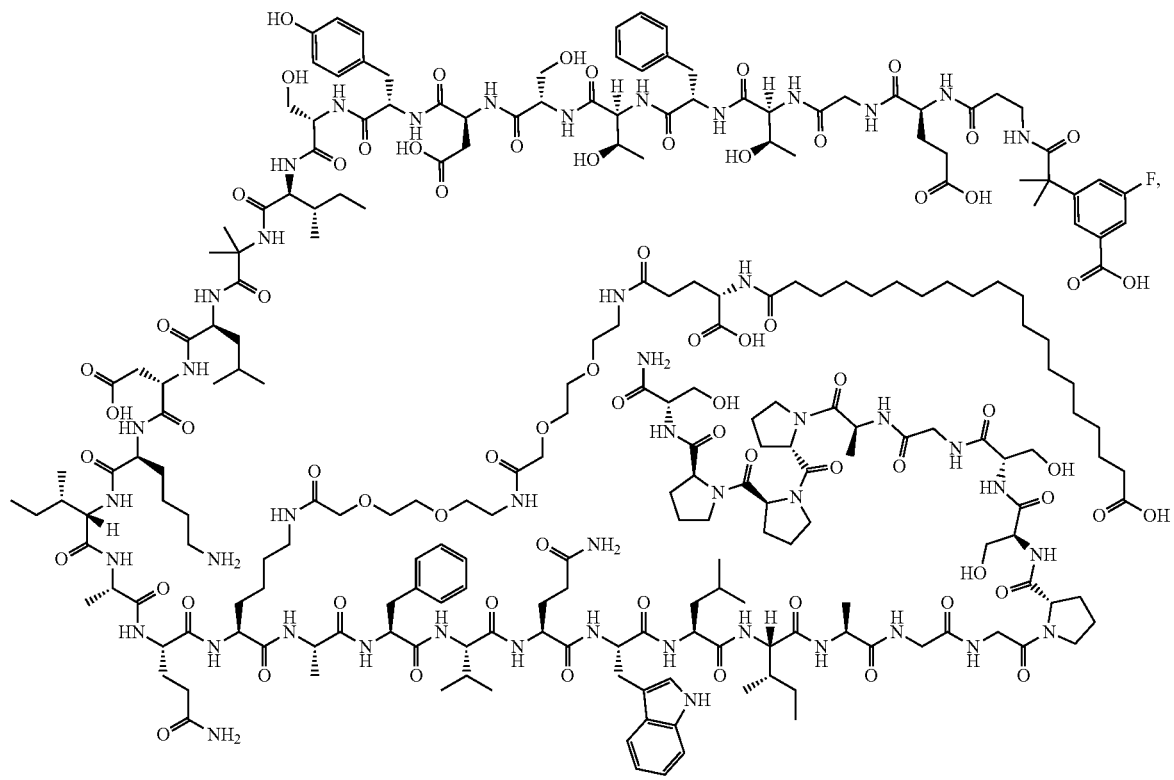
Compound 140
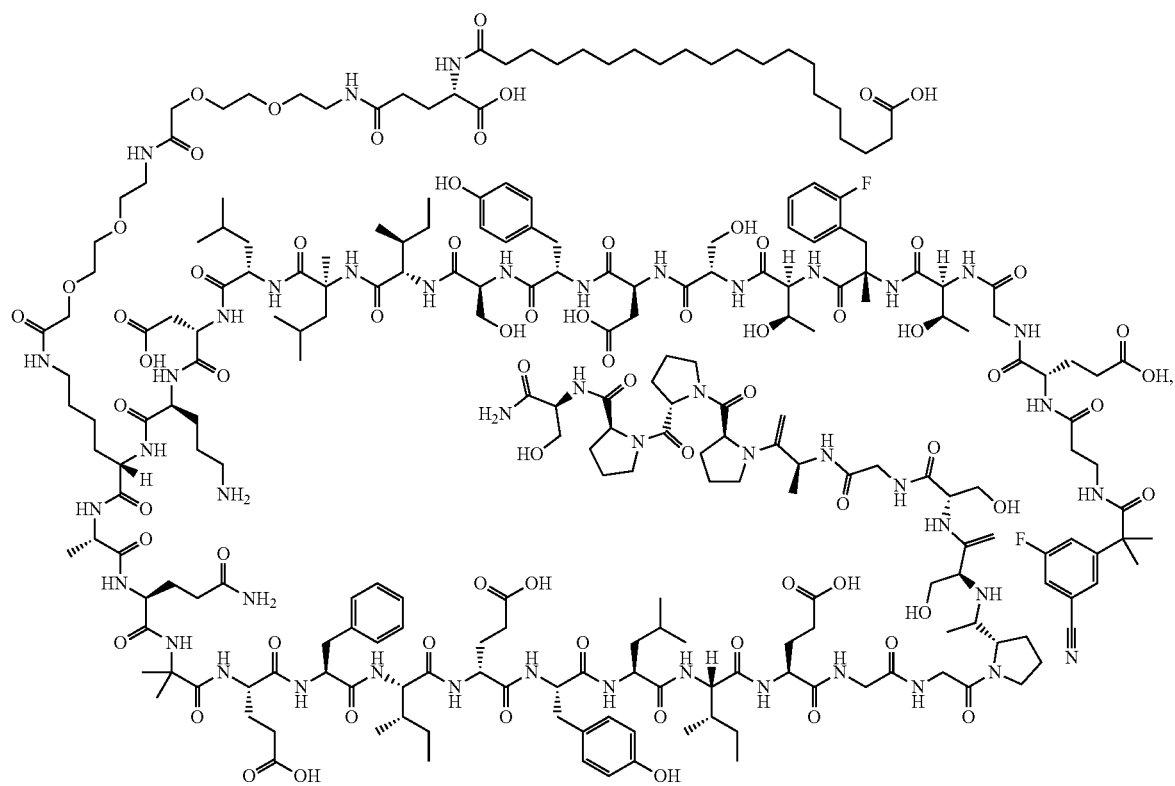

-continued
Compound 141
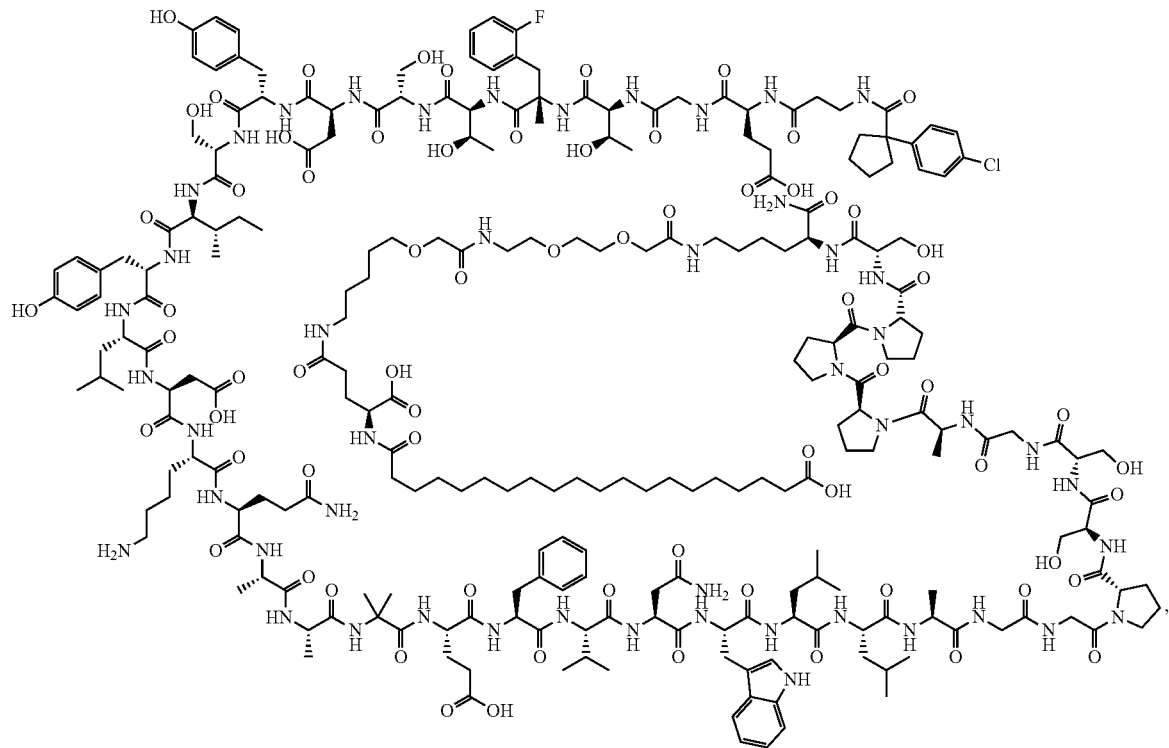
Compound 142
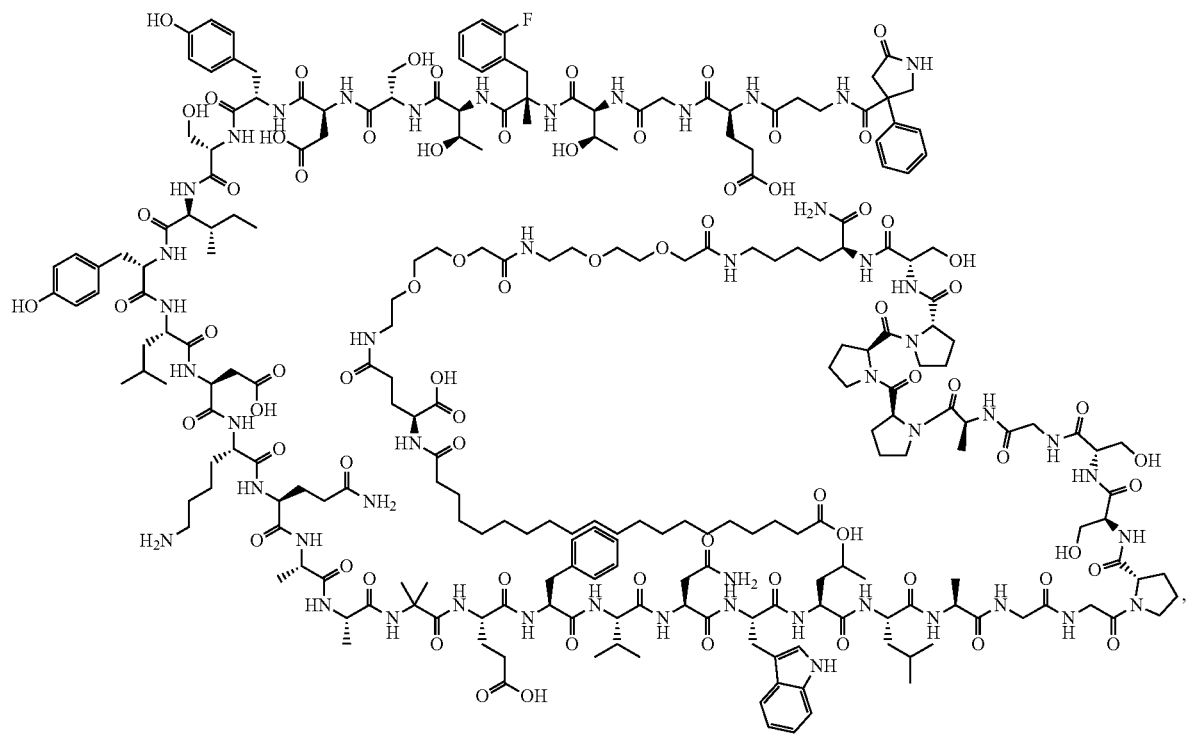

Compound 143
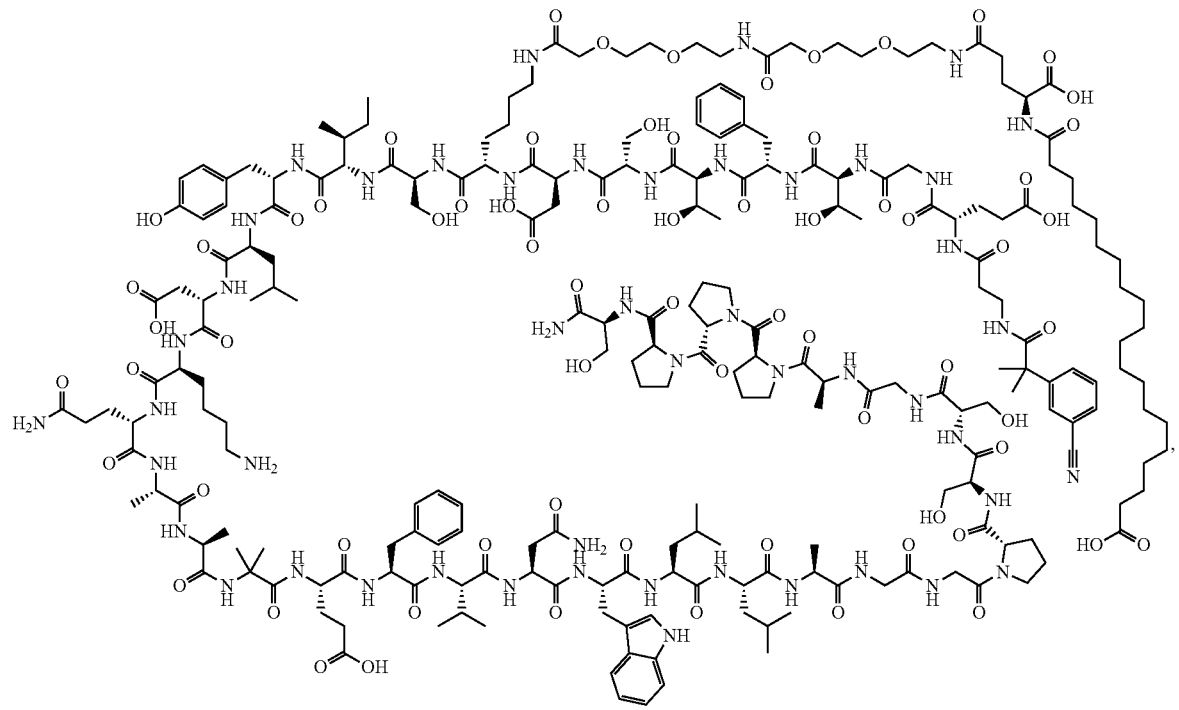
Compound 144
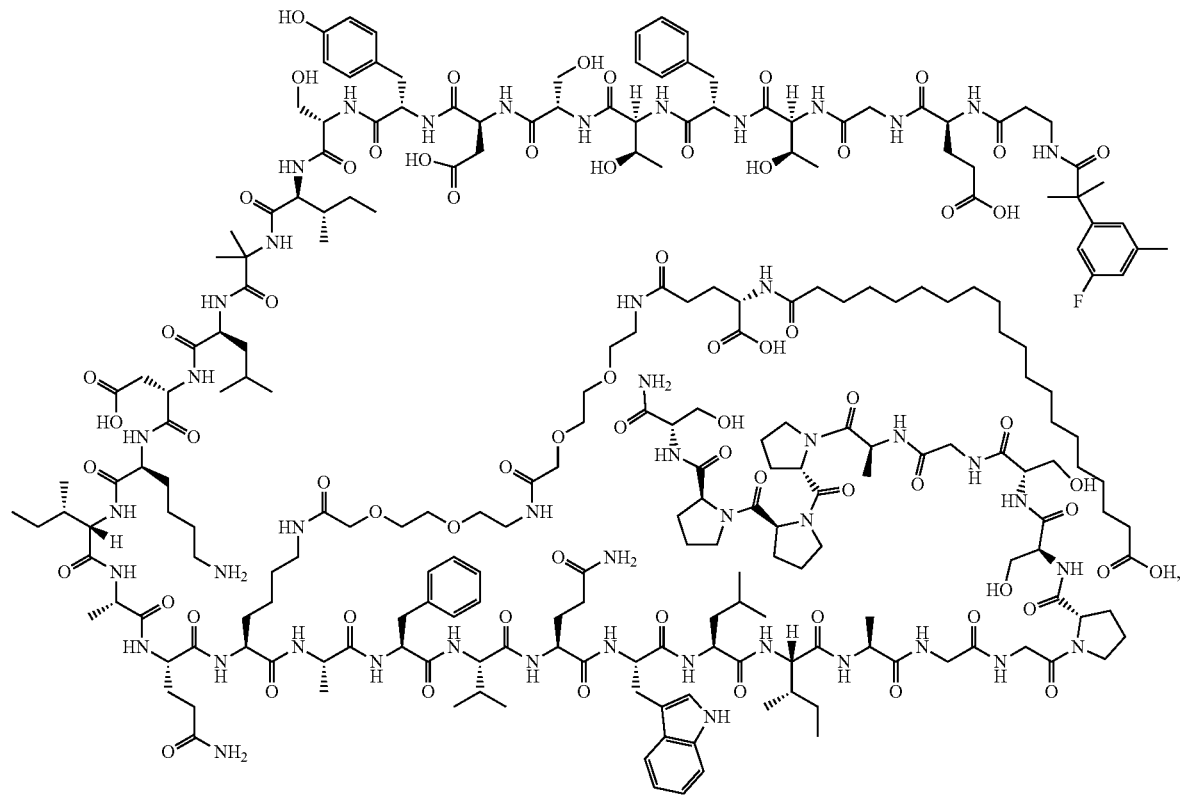

Compound 145
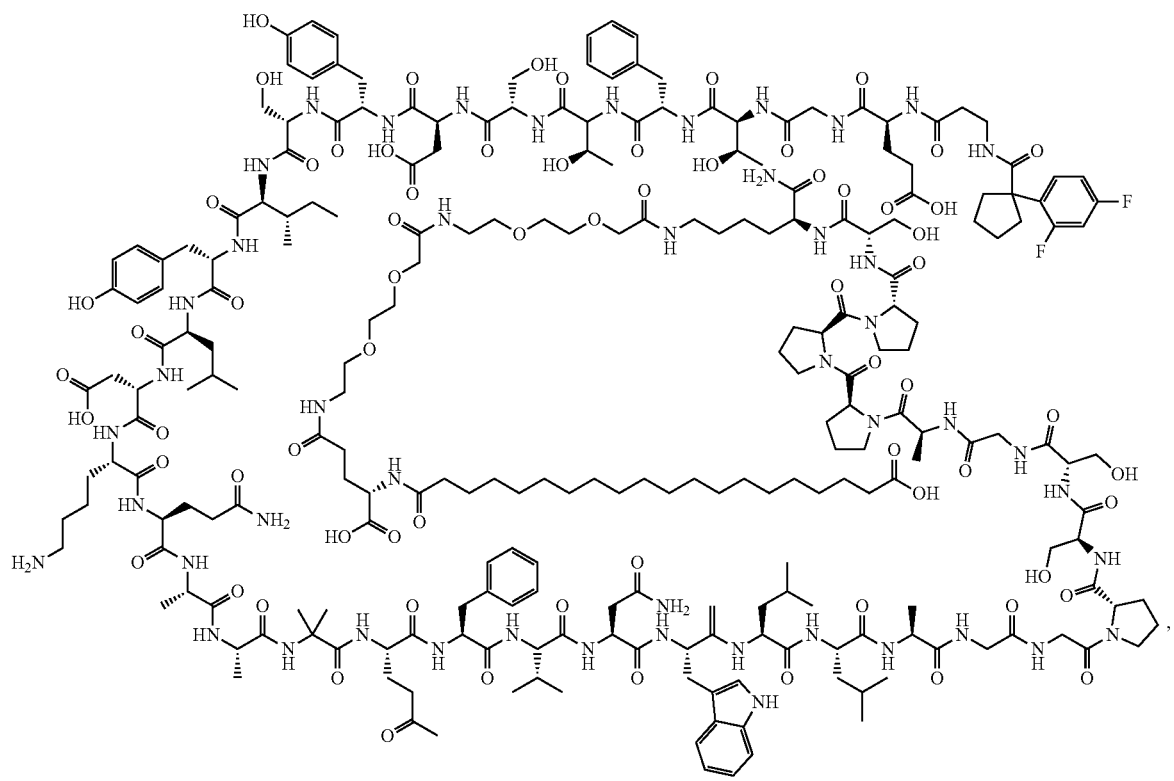
Compound 146
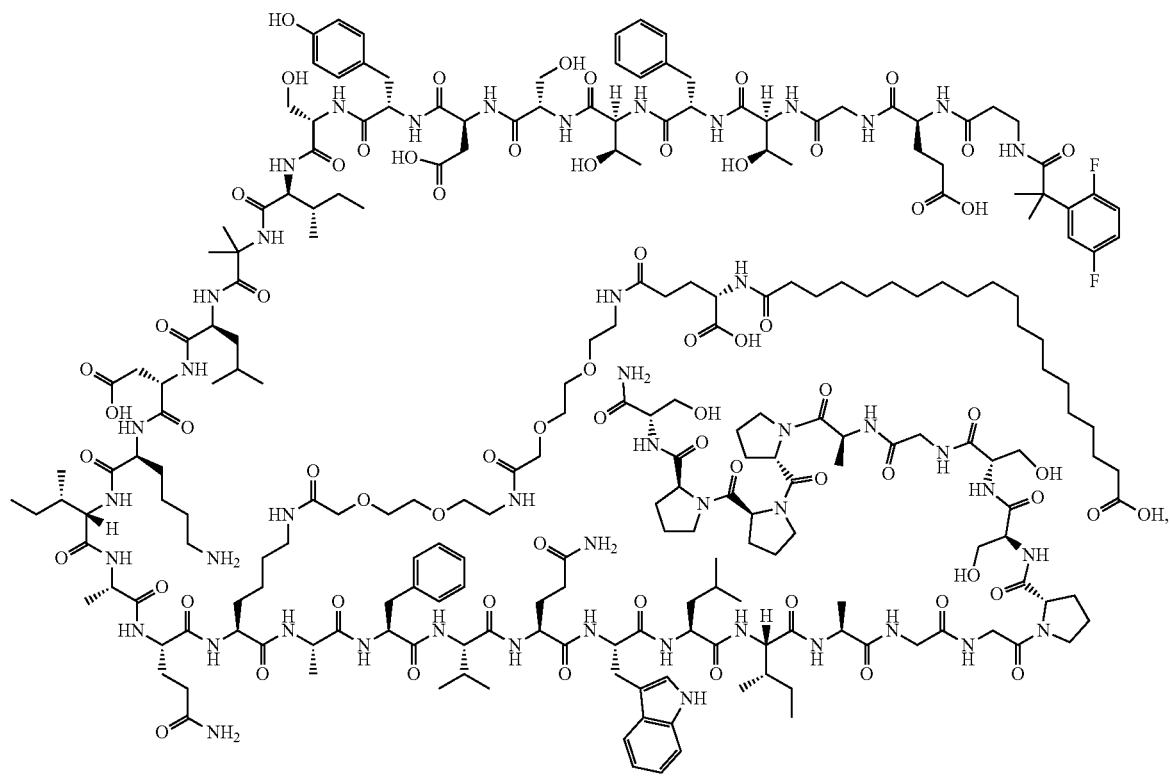

Compound 147
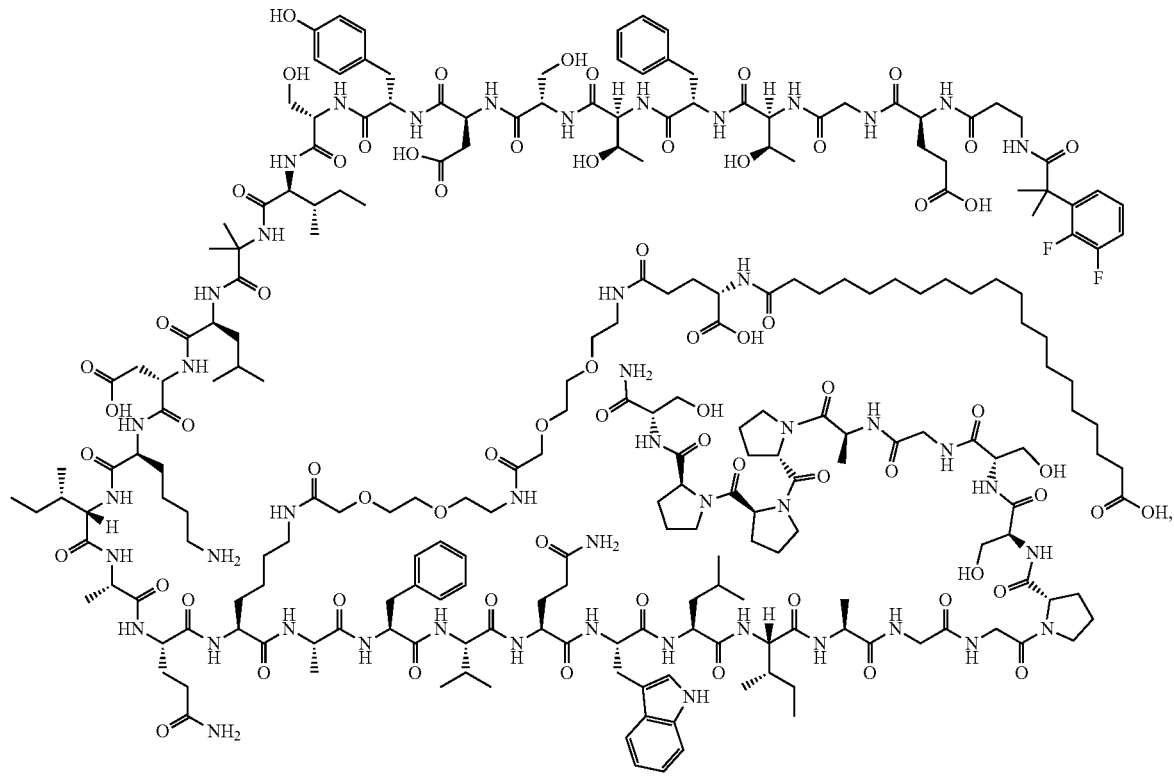
Compound 148
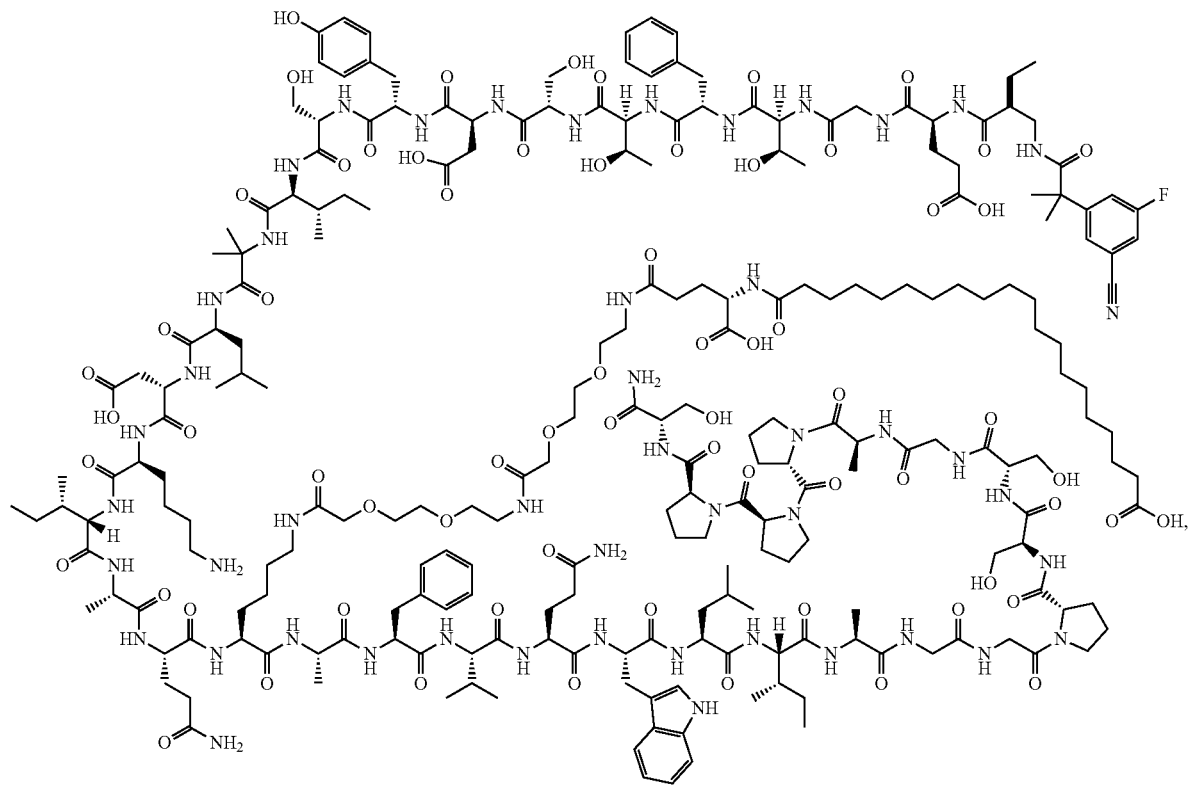

-continued
Compound 149
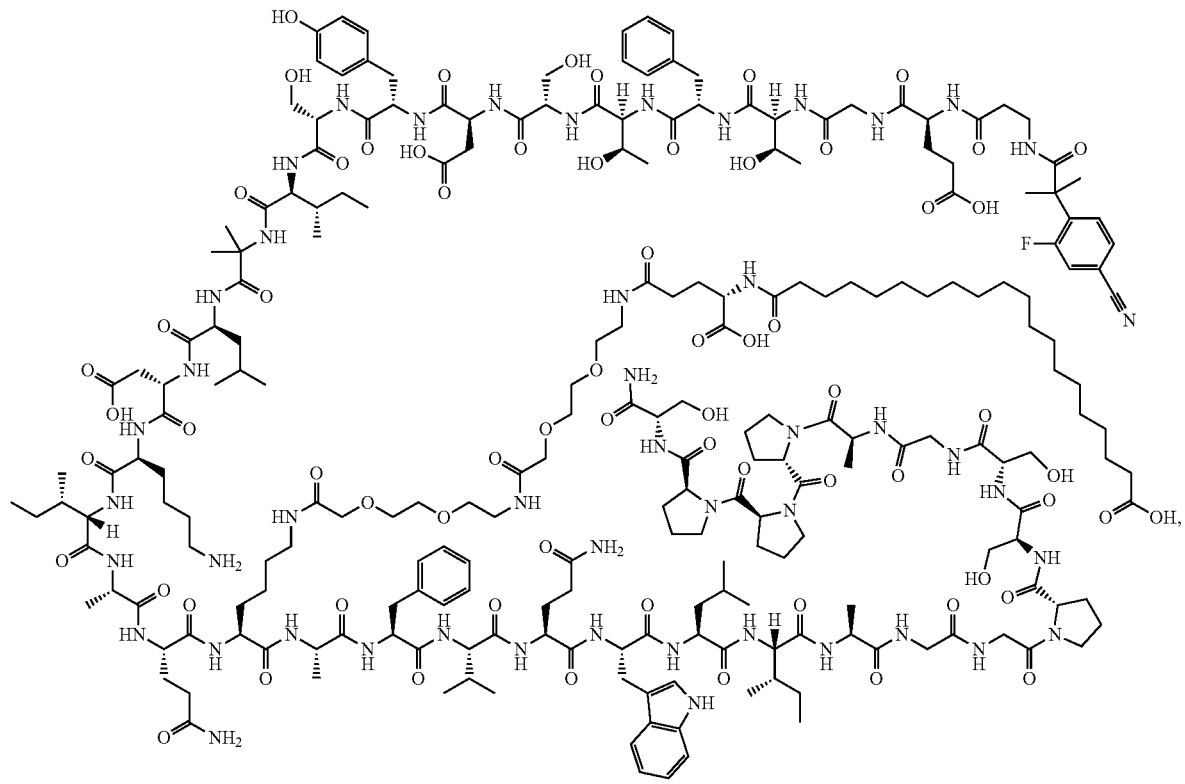
Compound 150
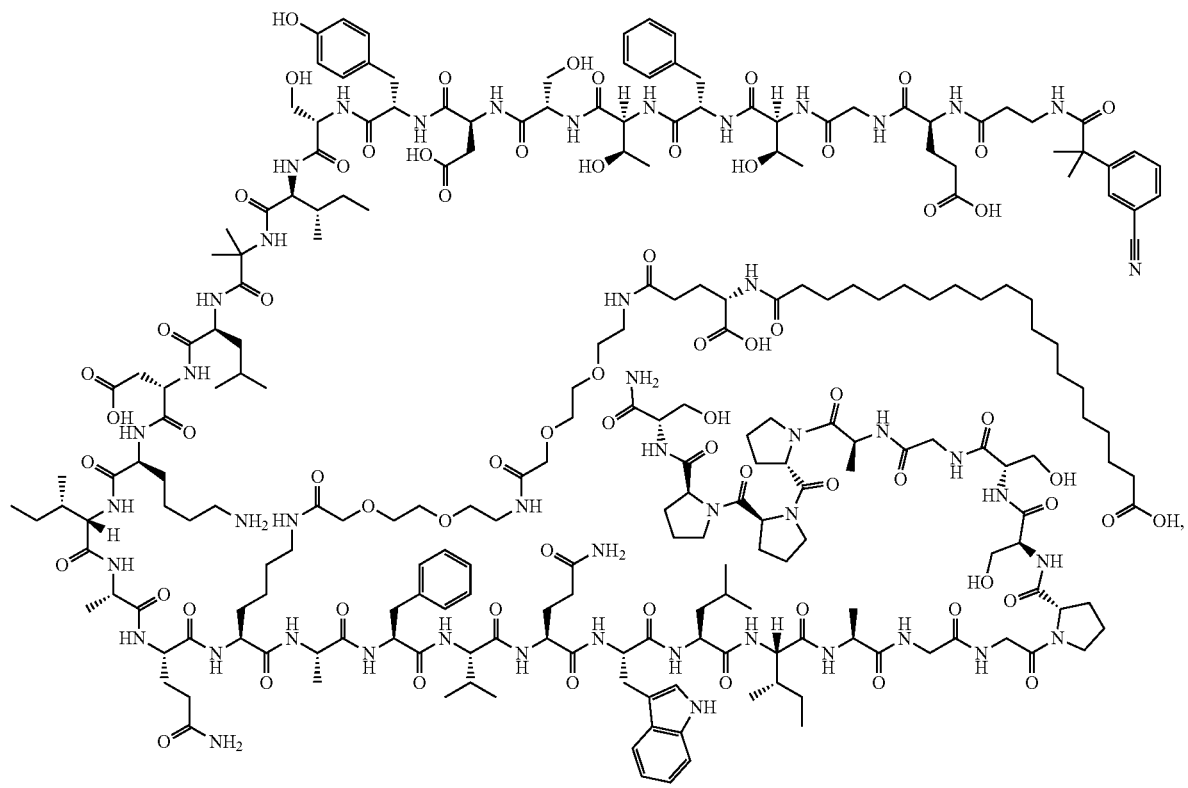

Compound 151
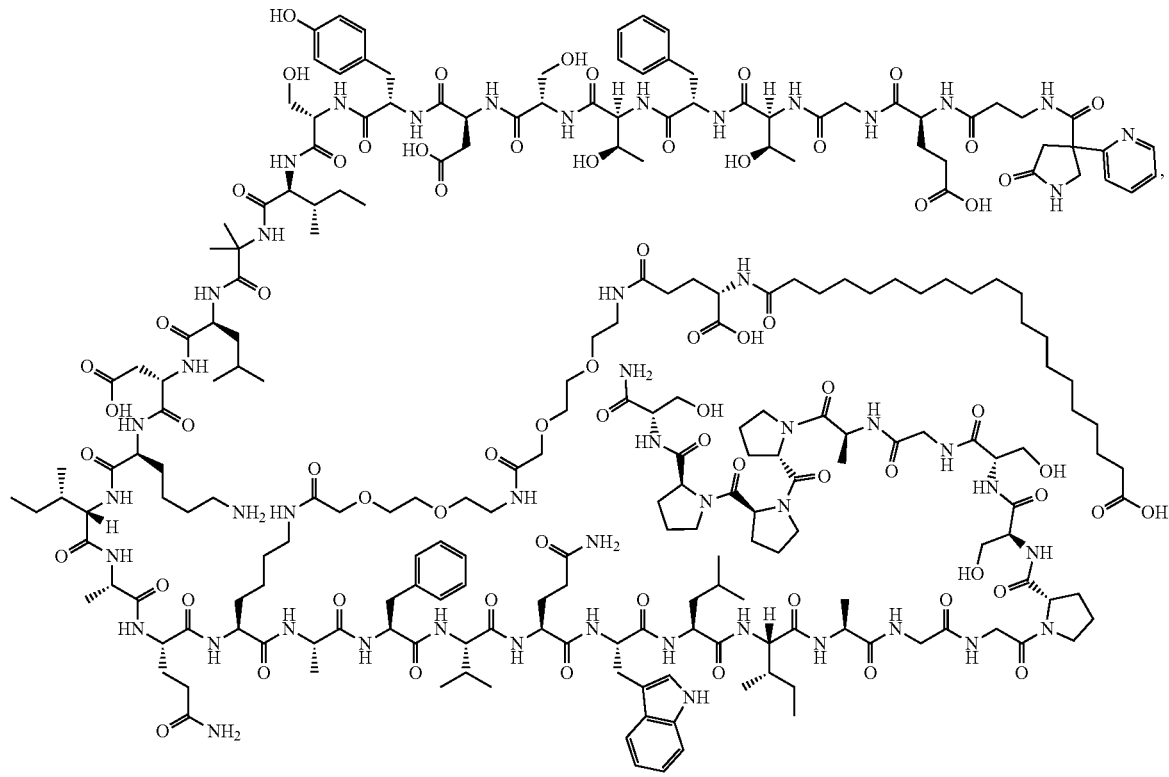
Compound 152
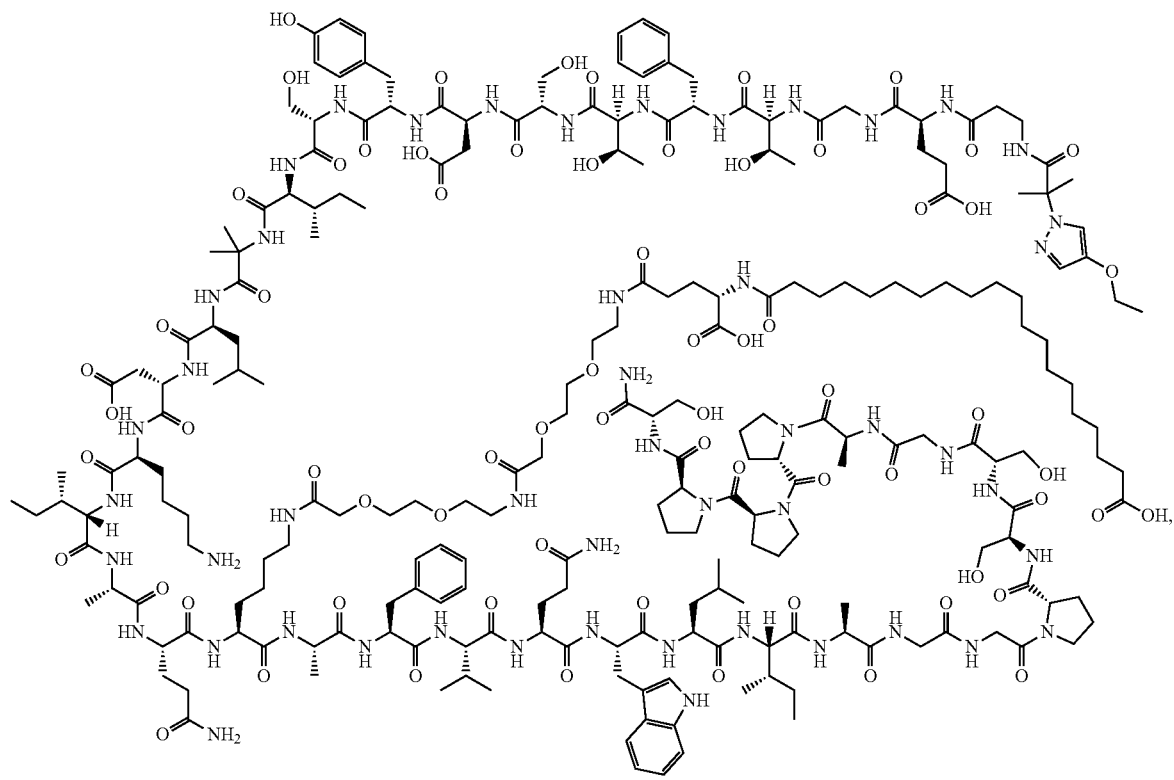

-continued
Compound 153
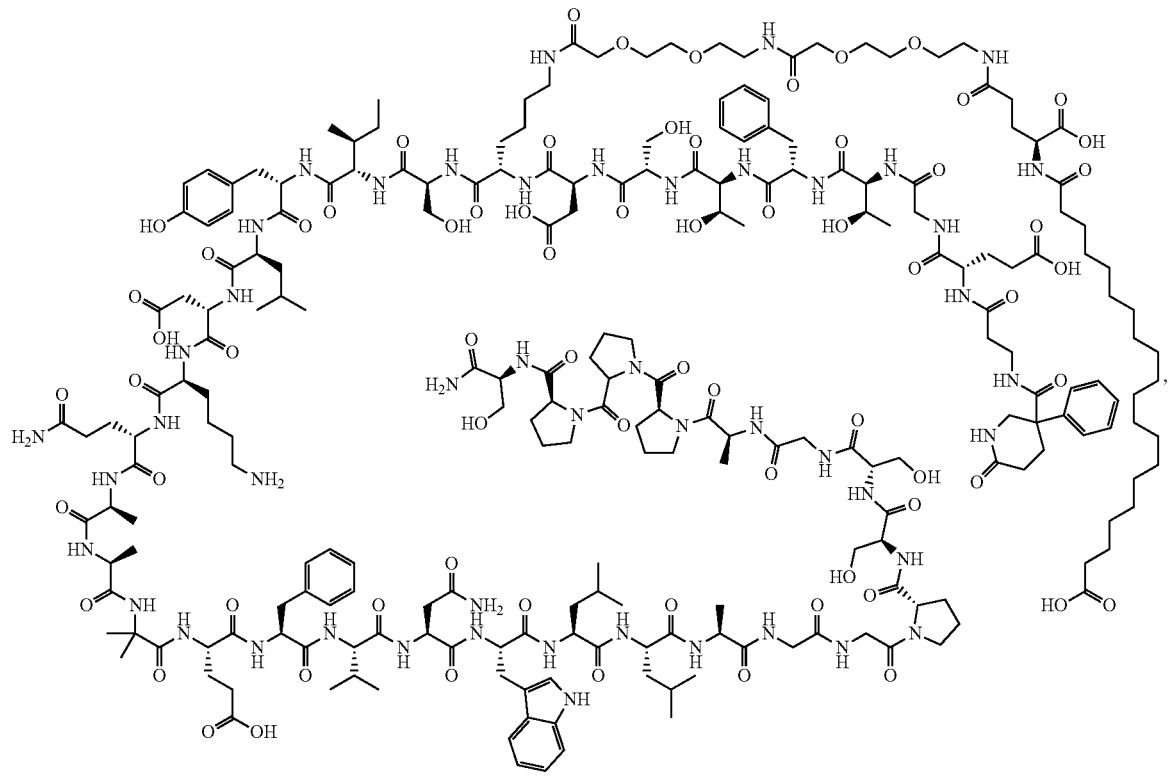
Compound 154
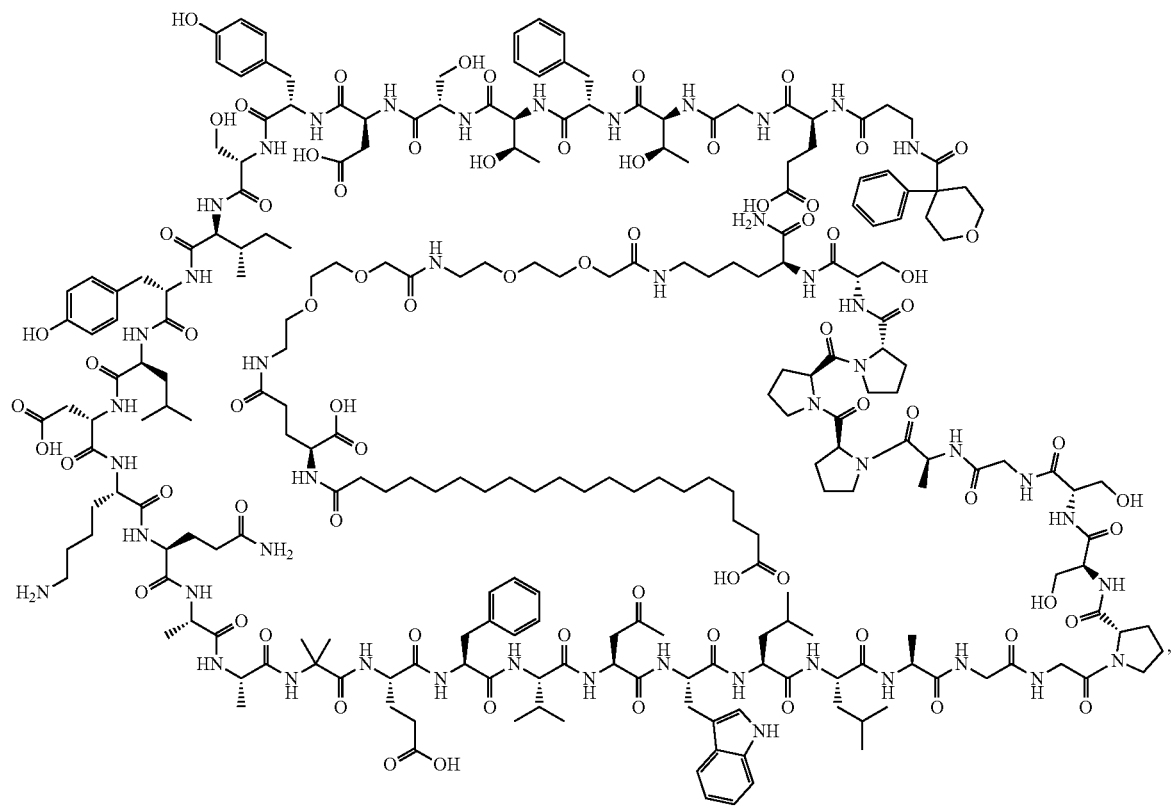

Compound 155
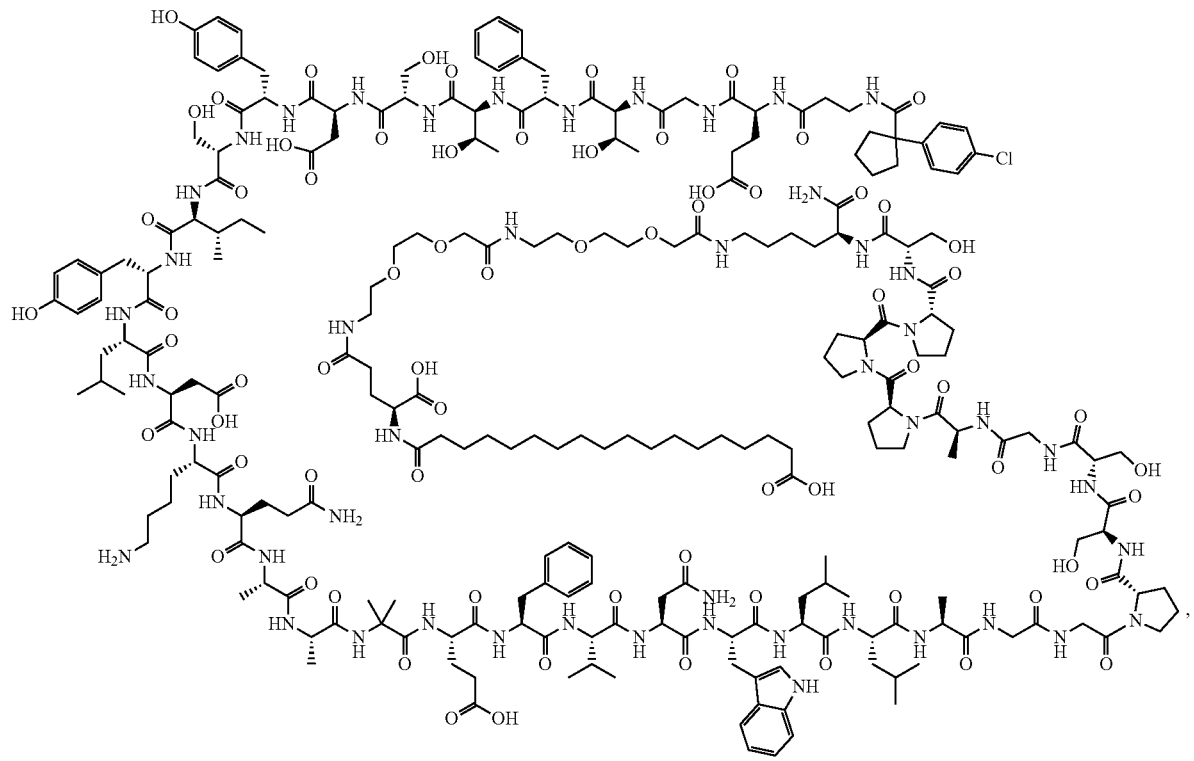
Compound 156
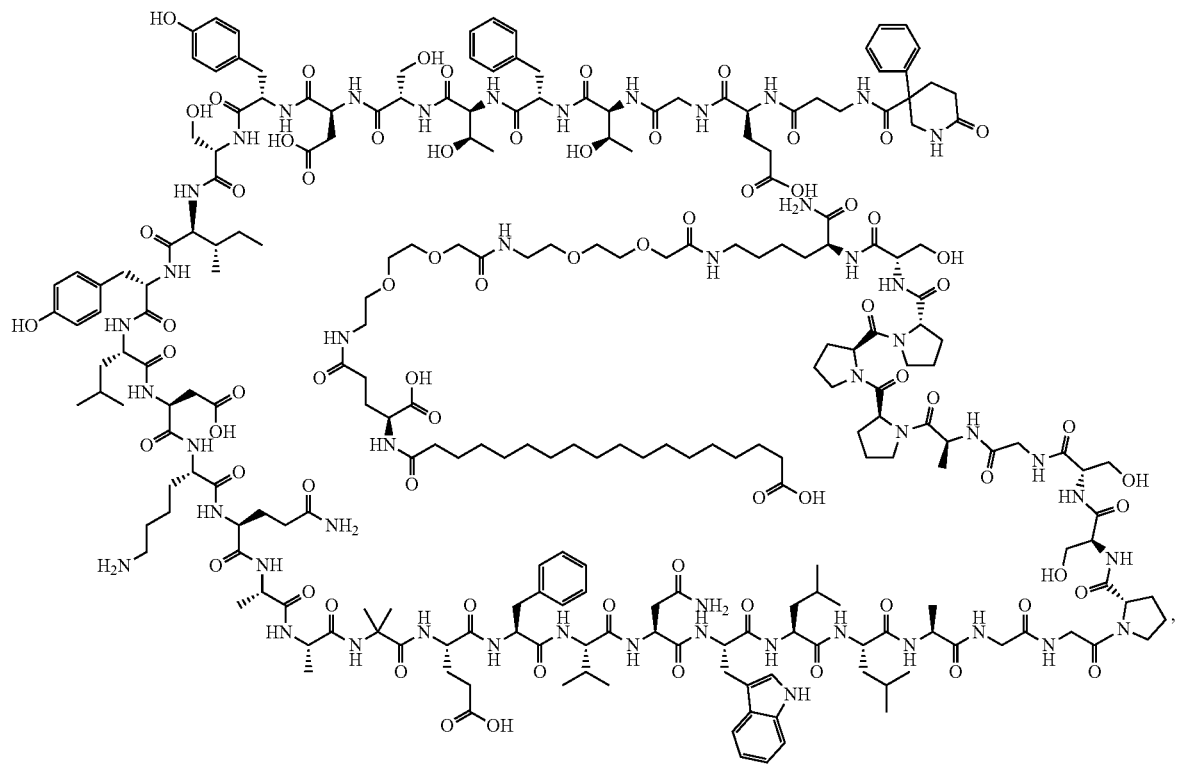

-continued
Compound 157
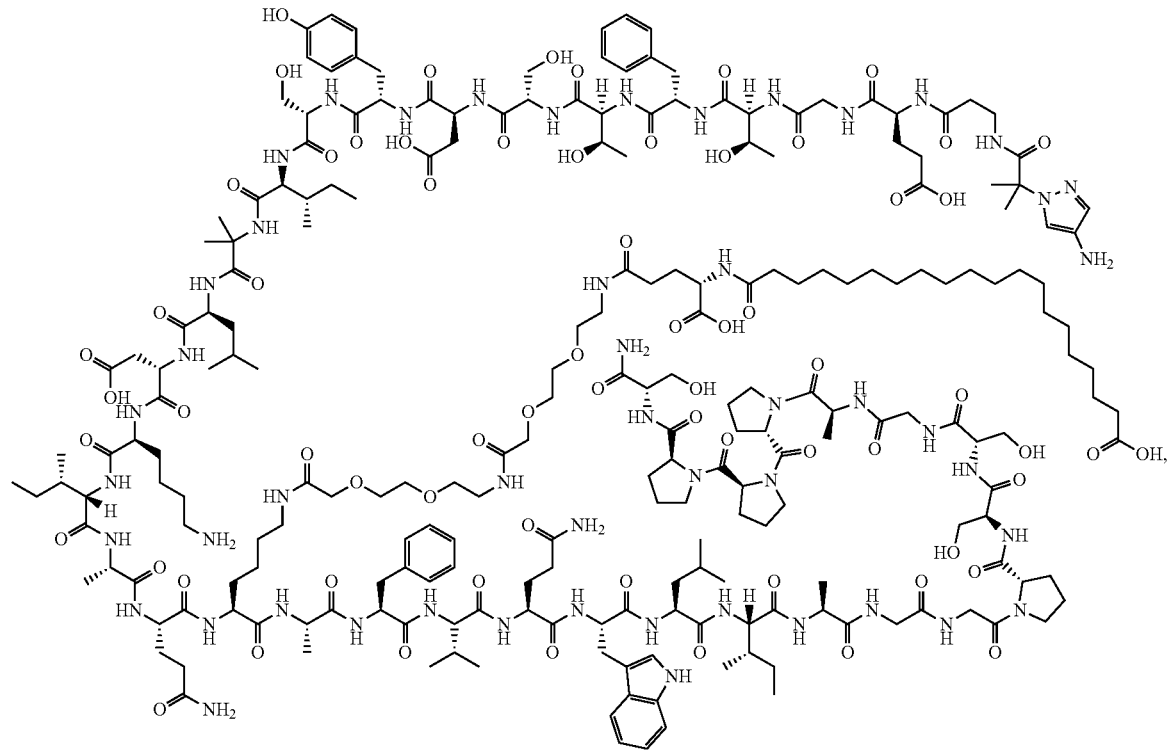
Compound 158
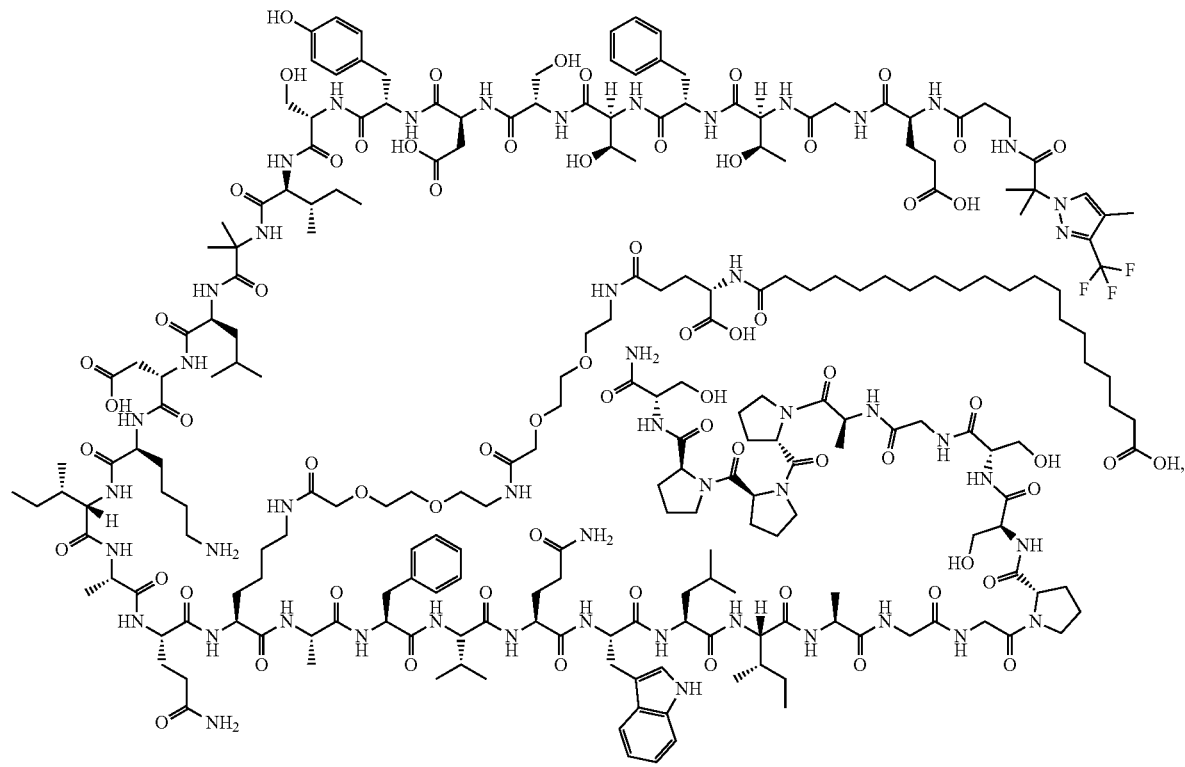

Compound 159
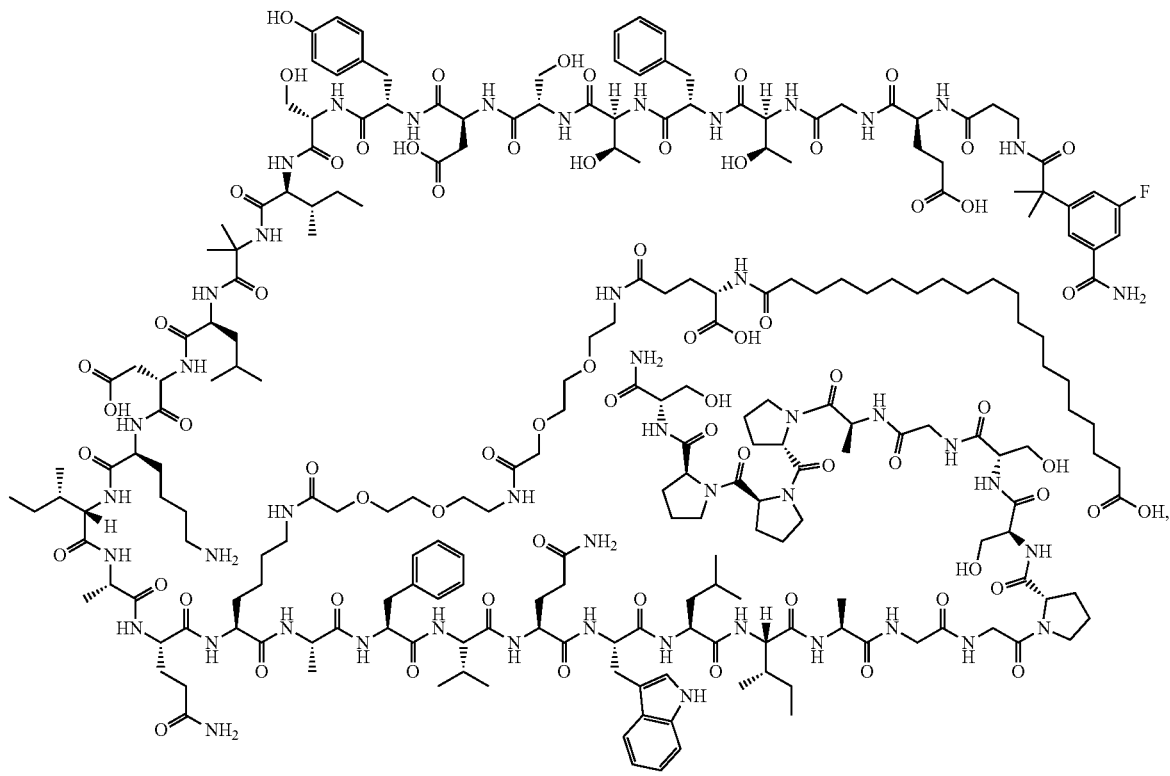
Compound 160
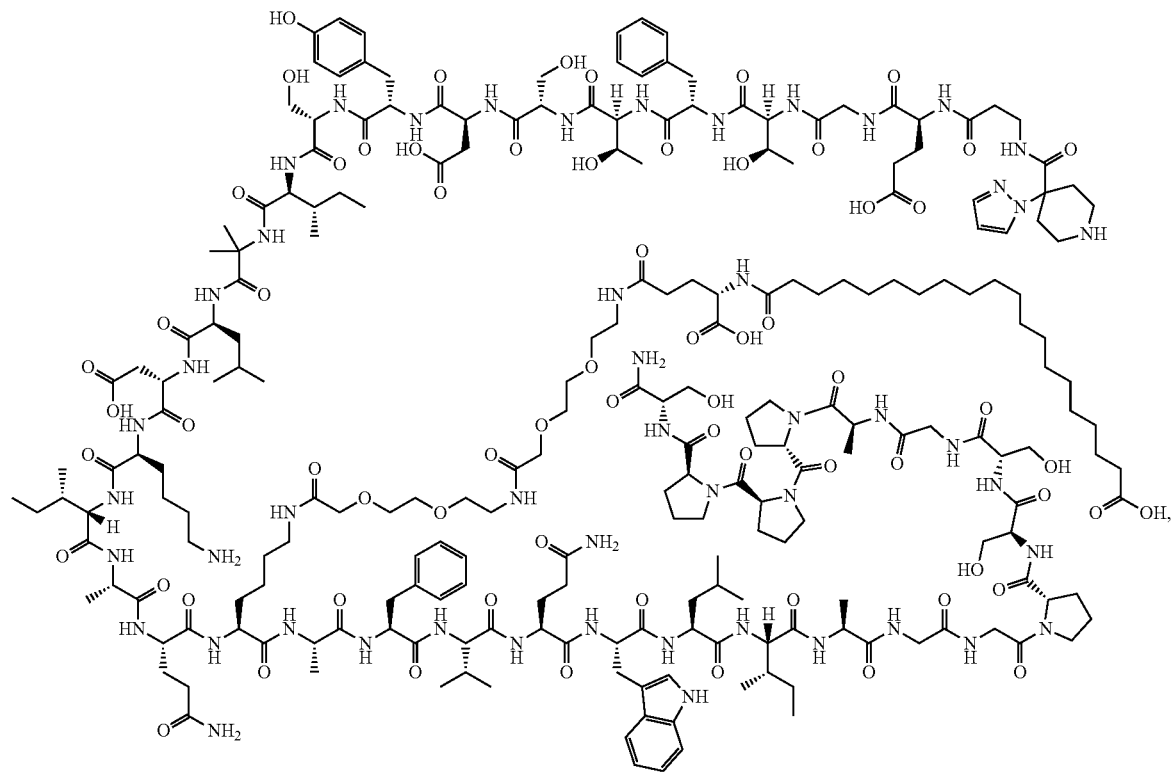

-continued
Compound 161
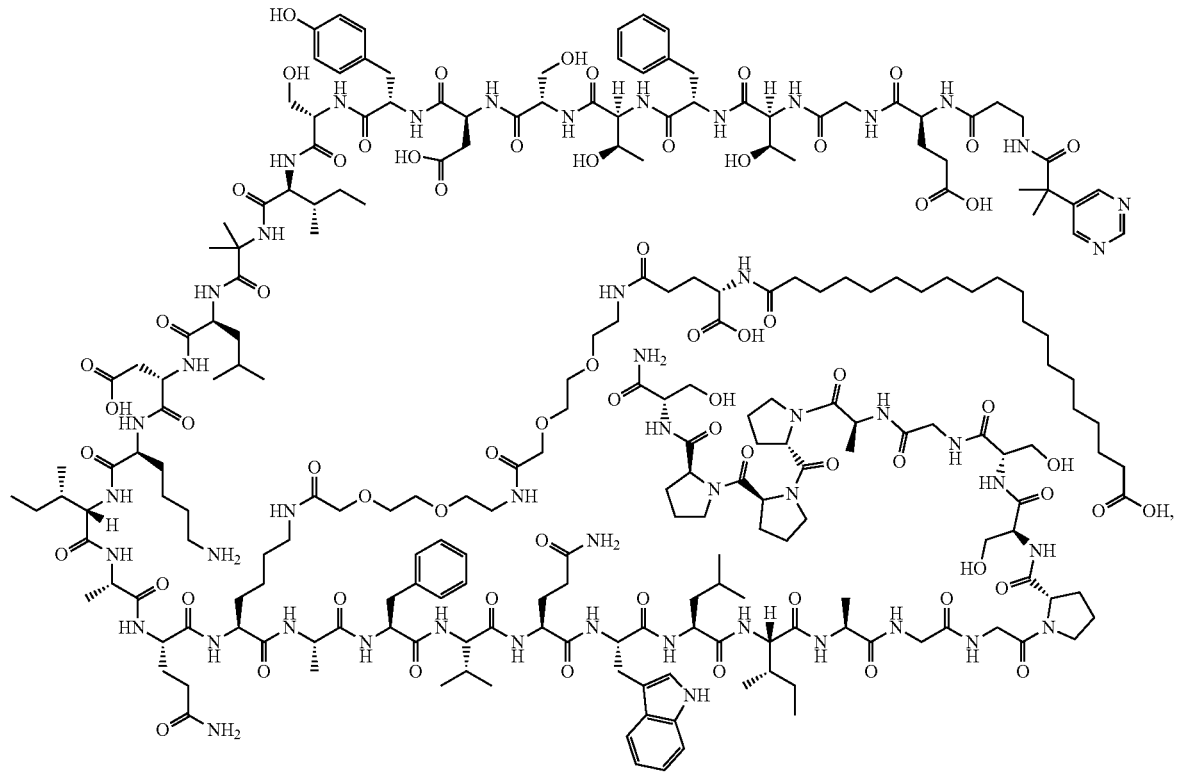
Compound 162
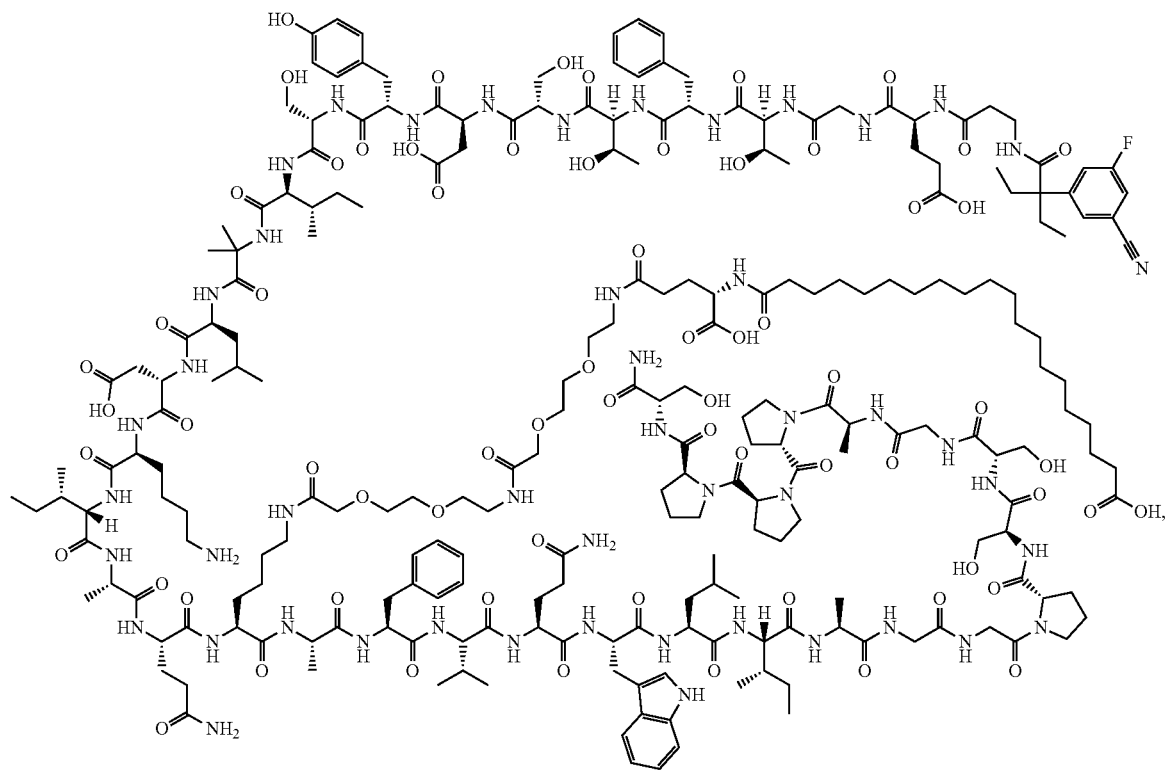

Compound 163
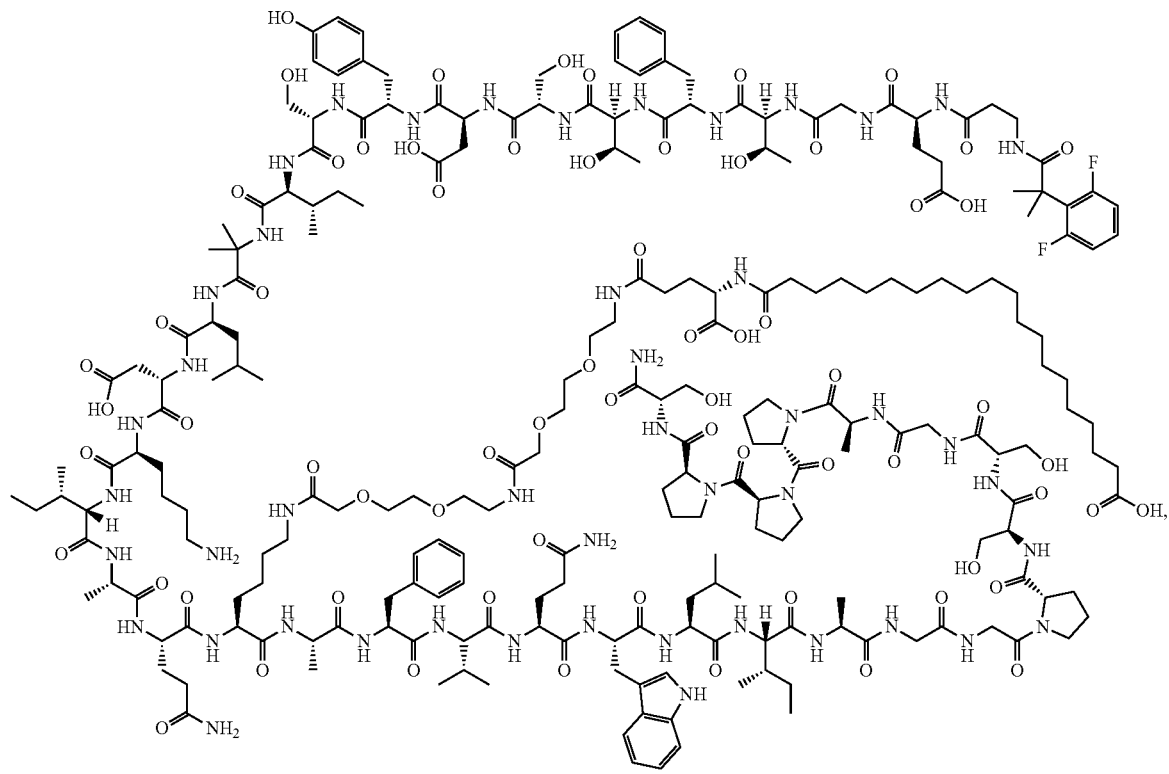
Compound 164
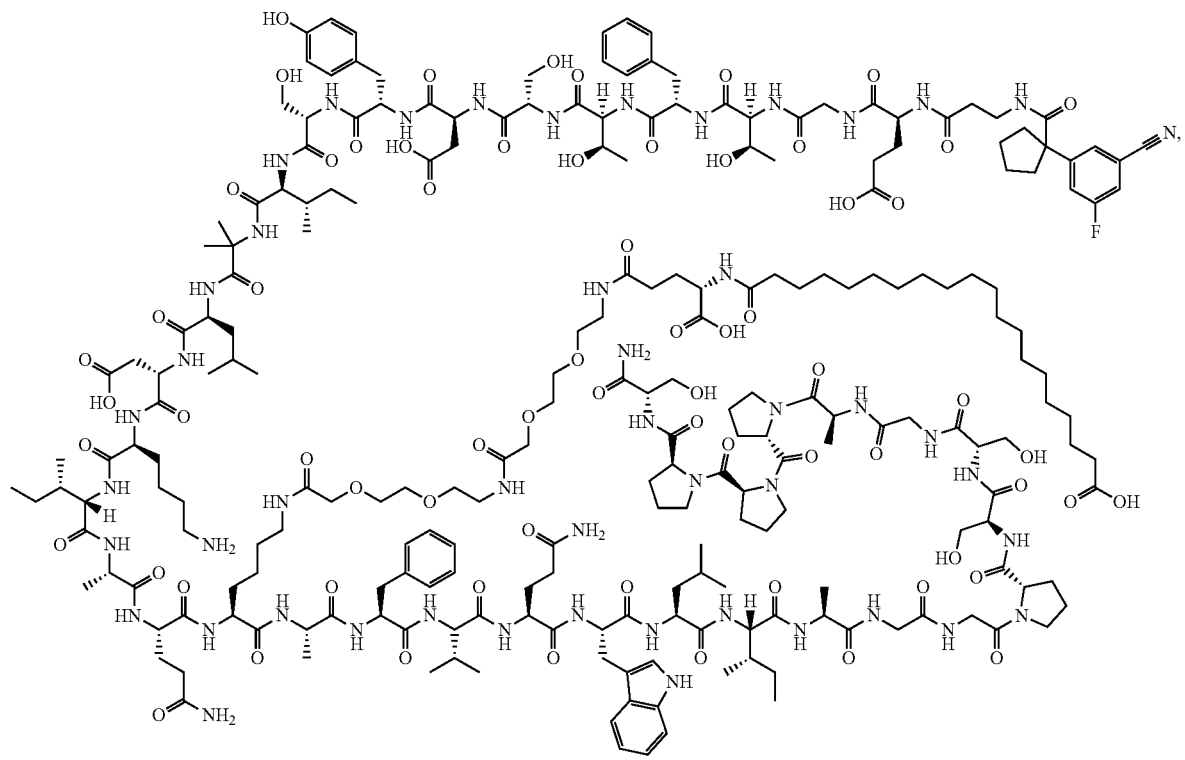

Compound 165
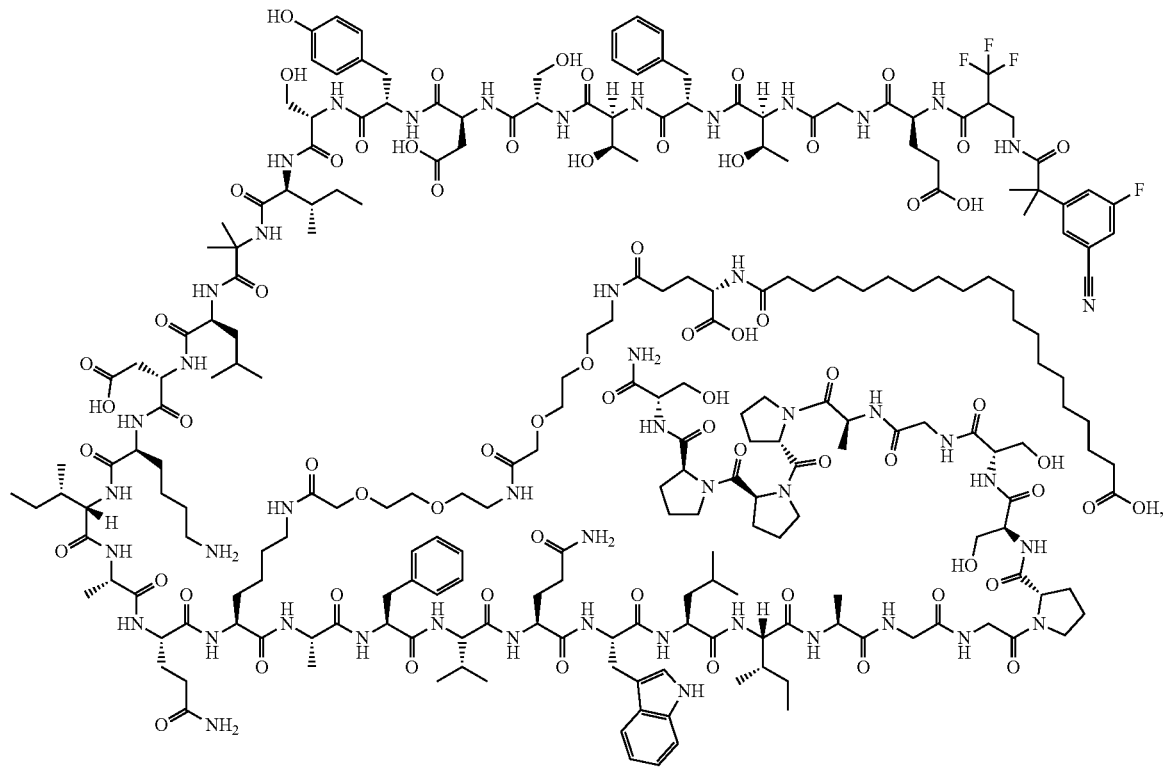
Compound 166
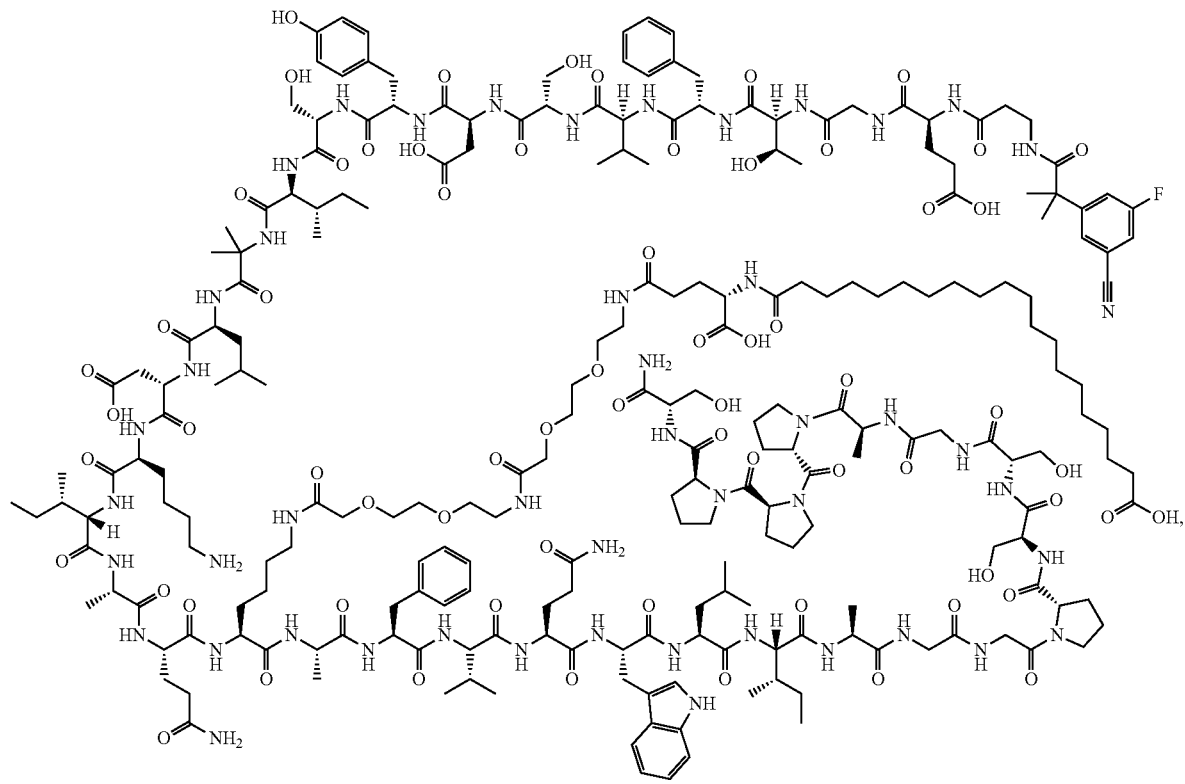

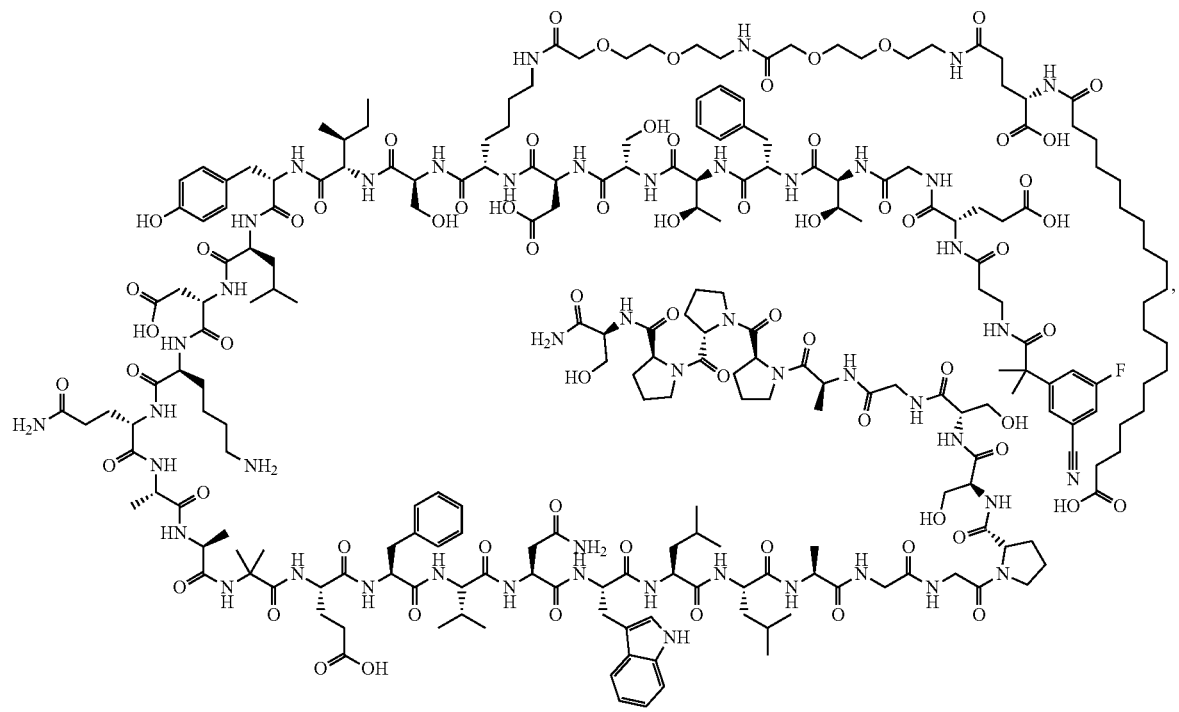
Compound 167
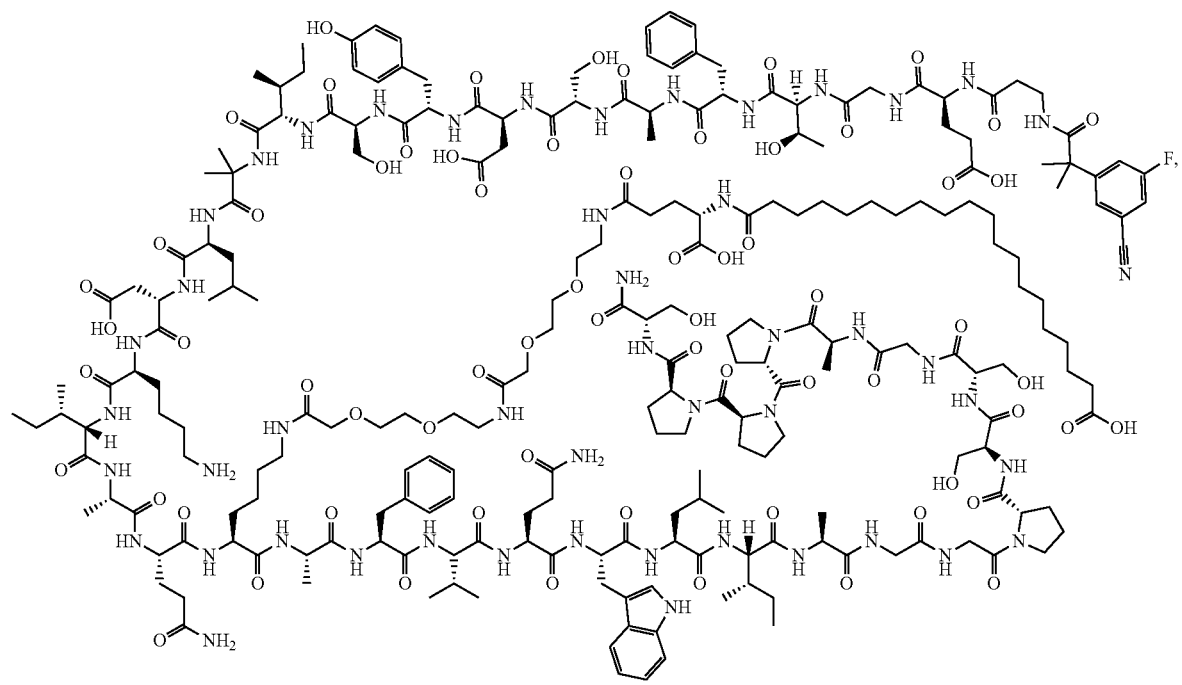
Compound 168

Compound 169
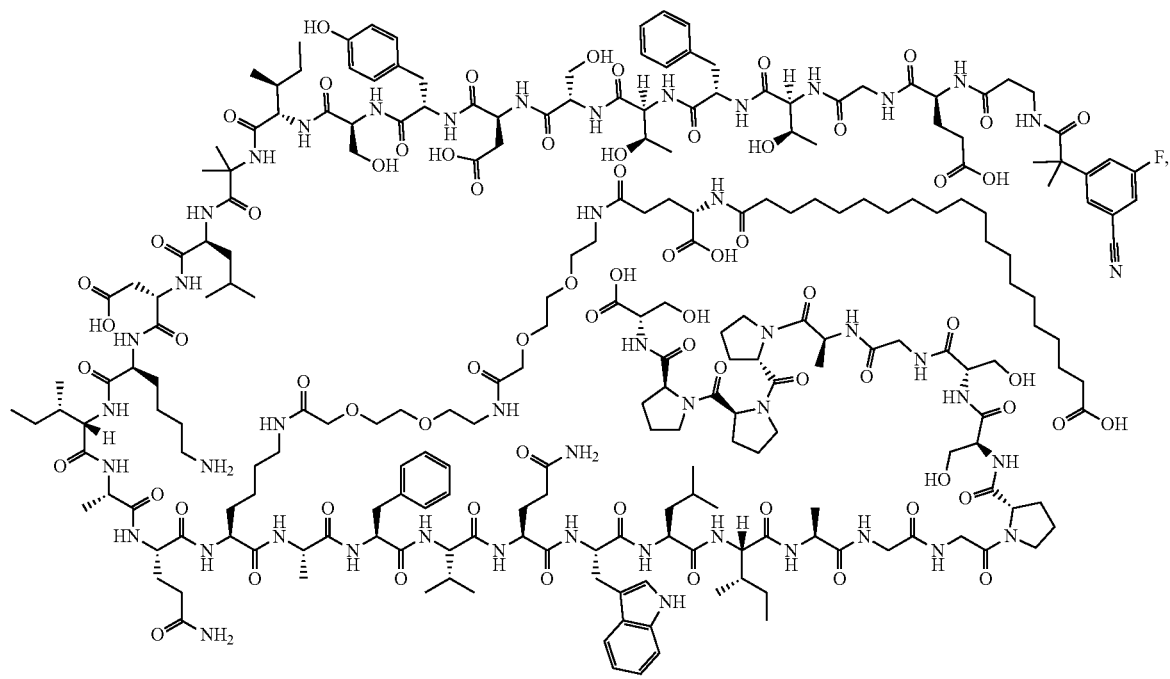
Compound 170
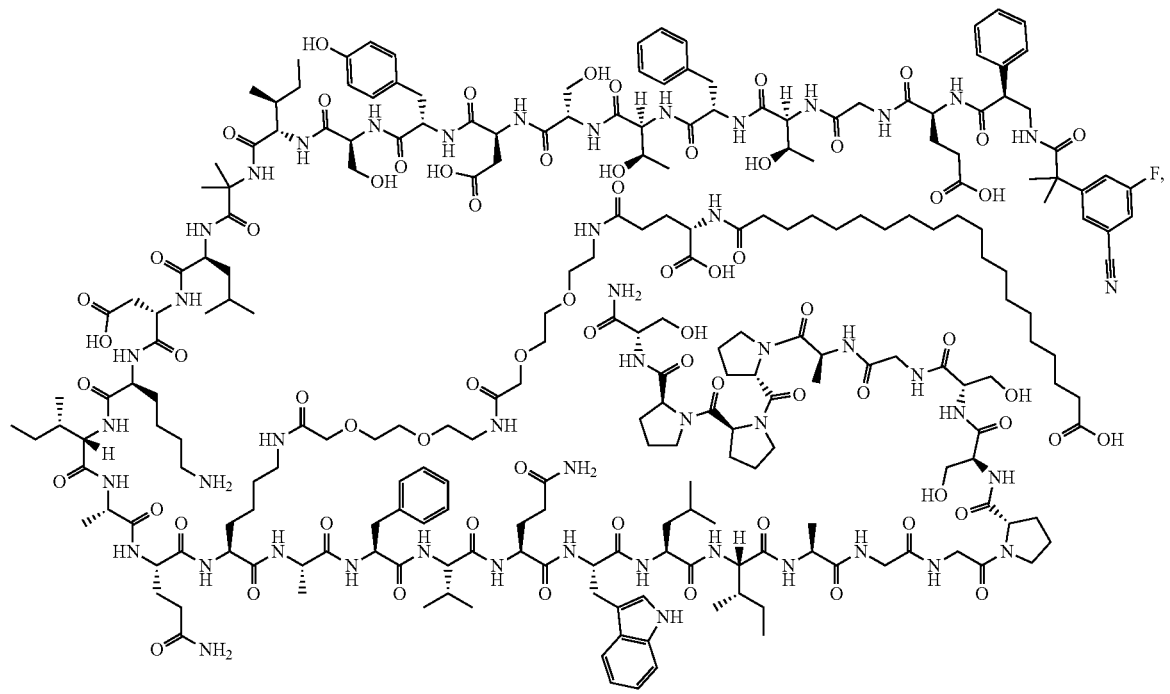

-continued
Compound 171
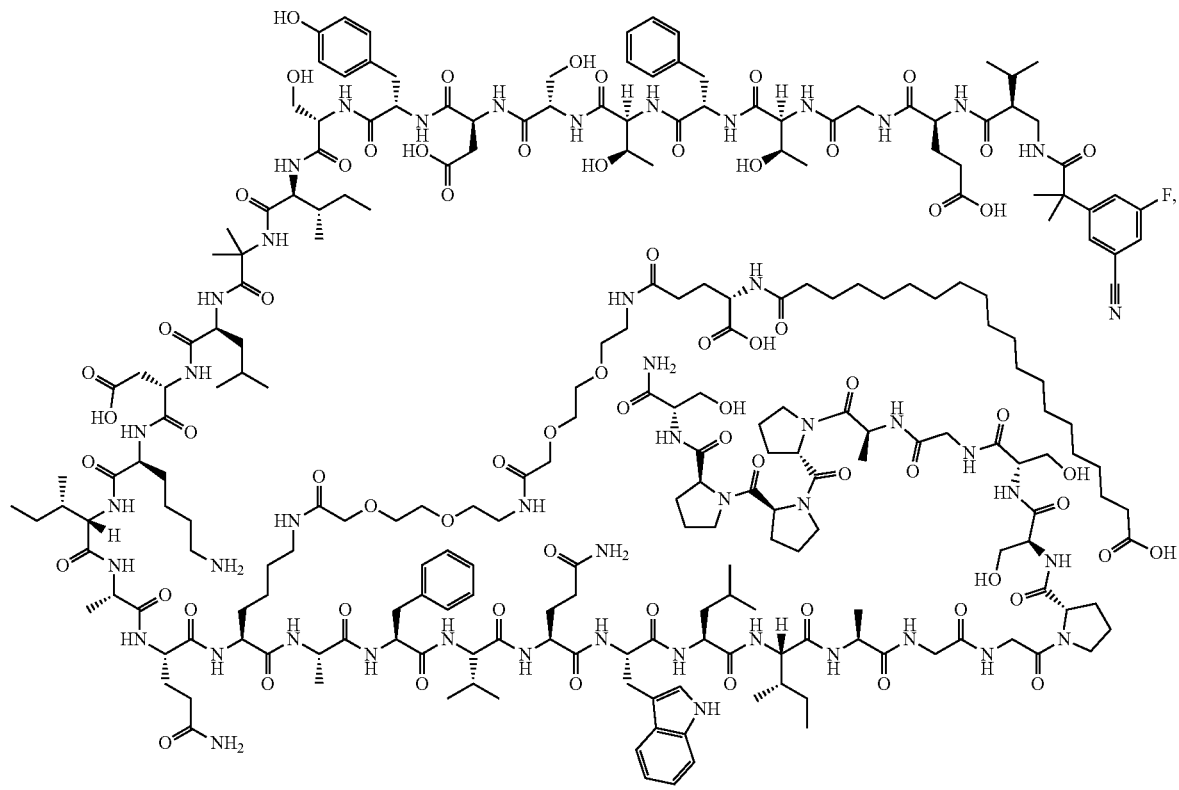
Compound 172
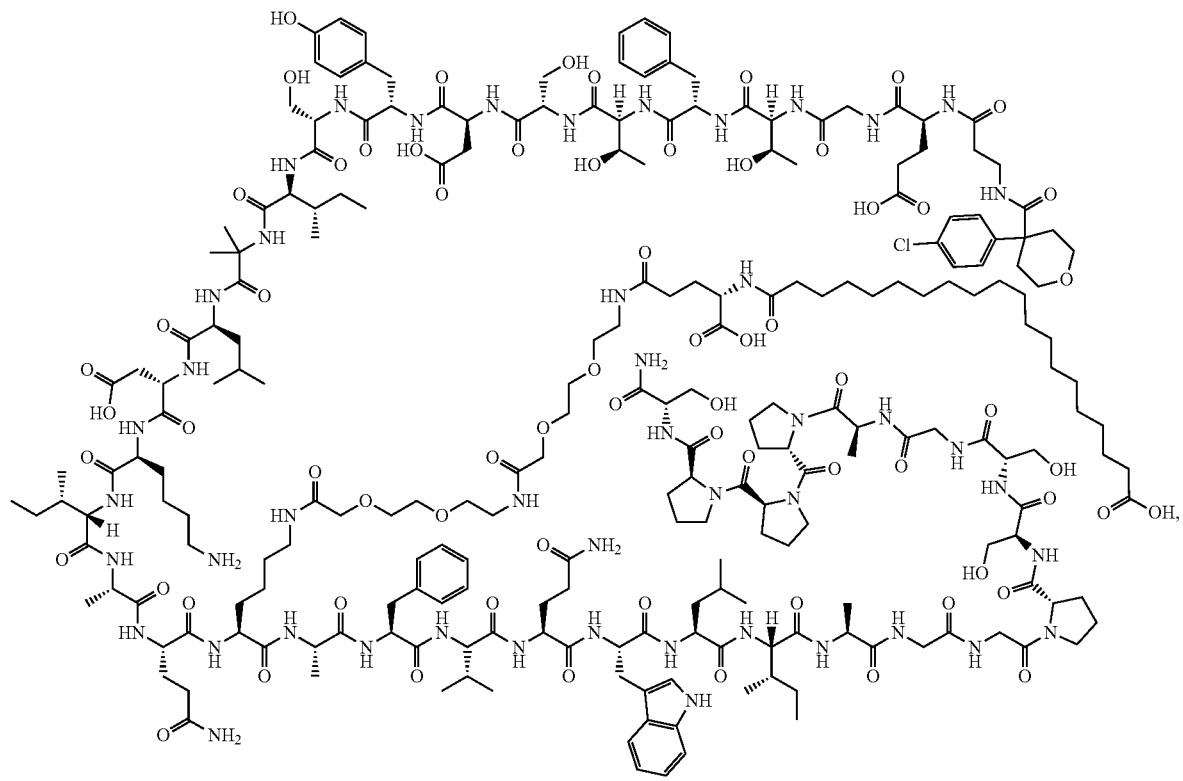

-continued
Compound 173
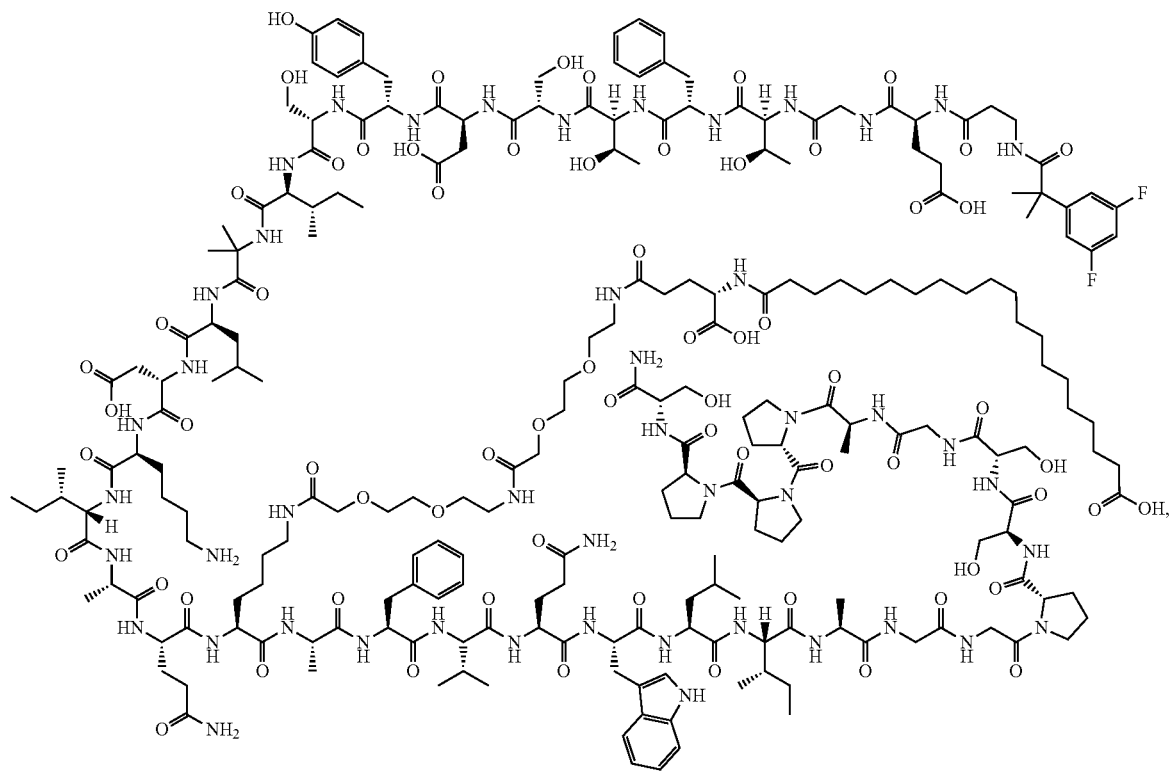
Compound 174
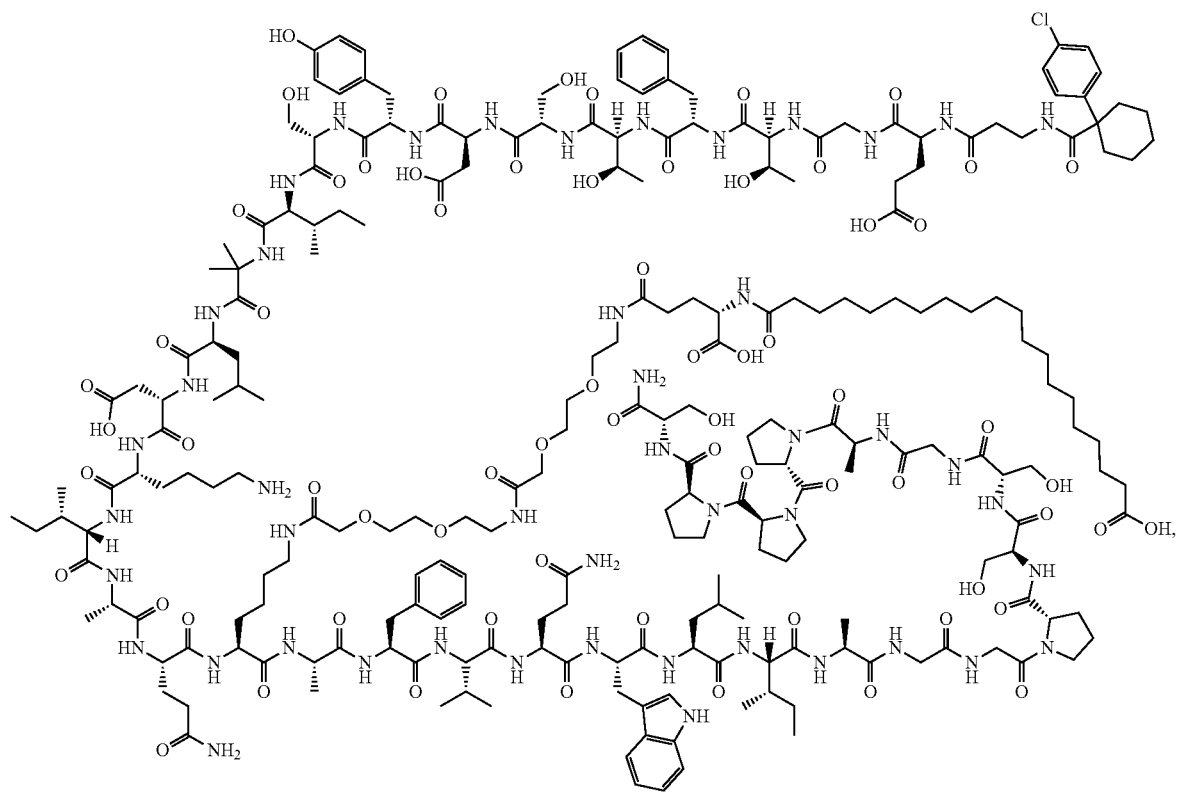

-continued
Compound 175
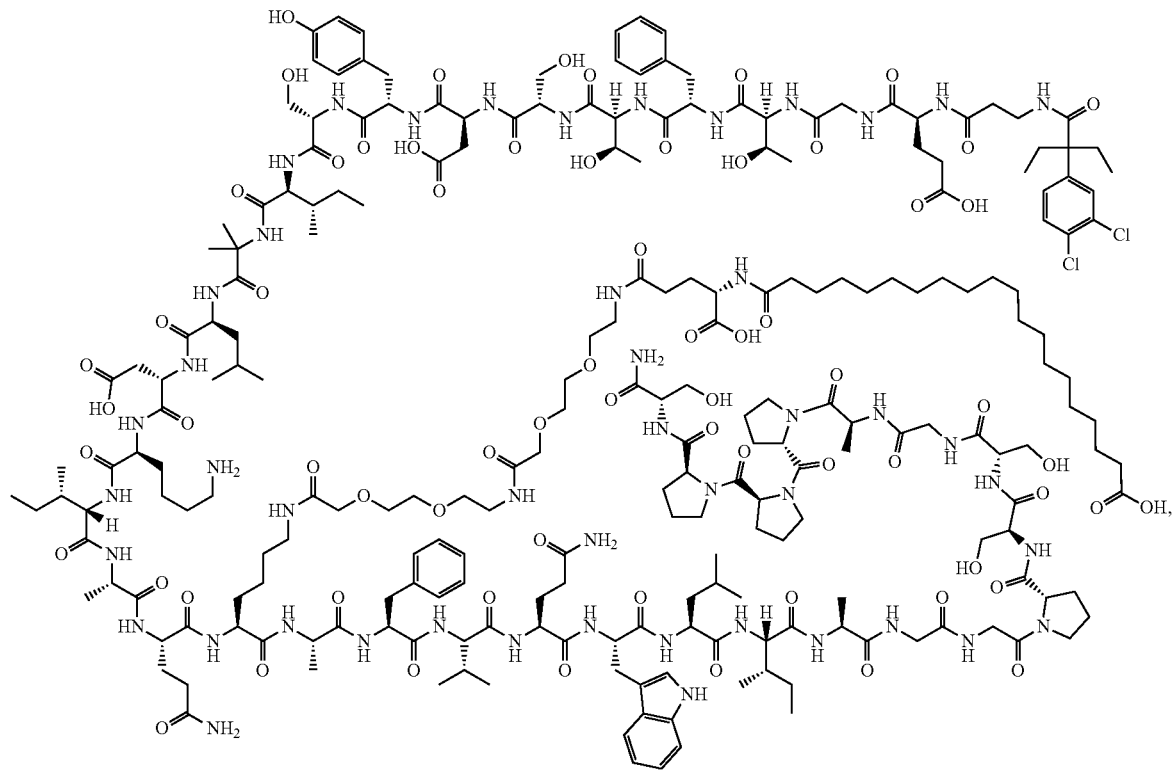
Compound 176
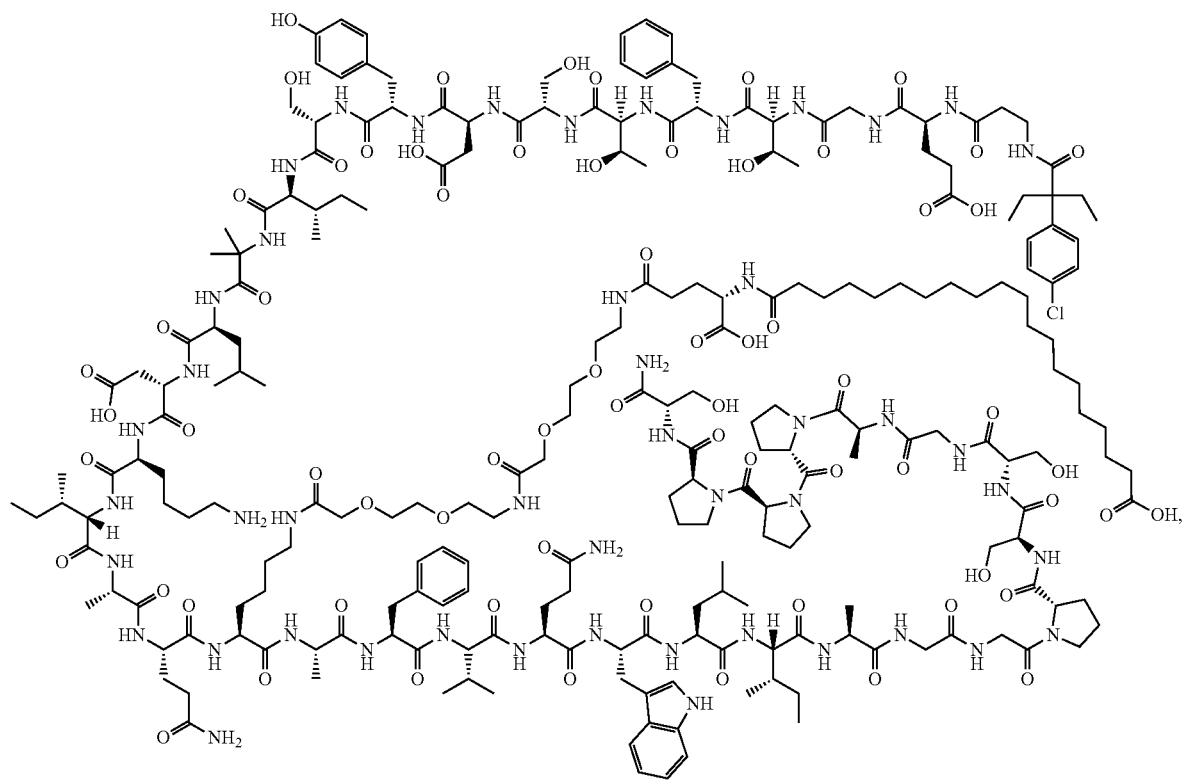

Compound 177
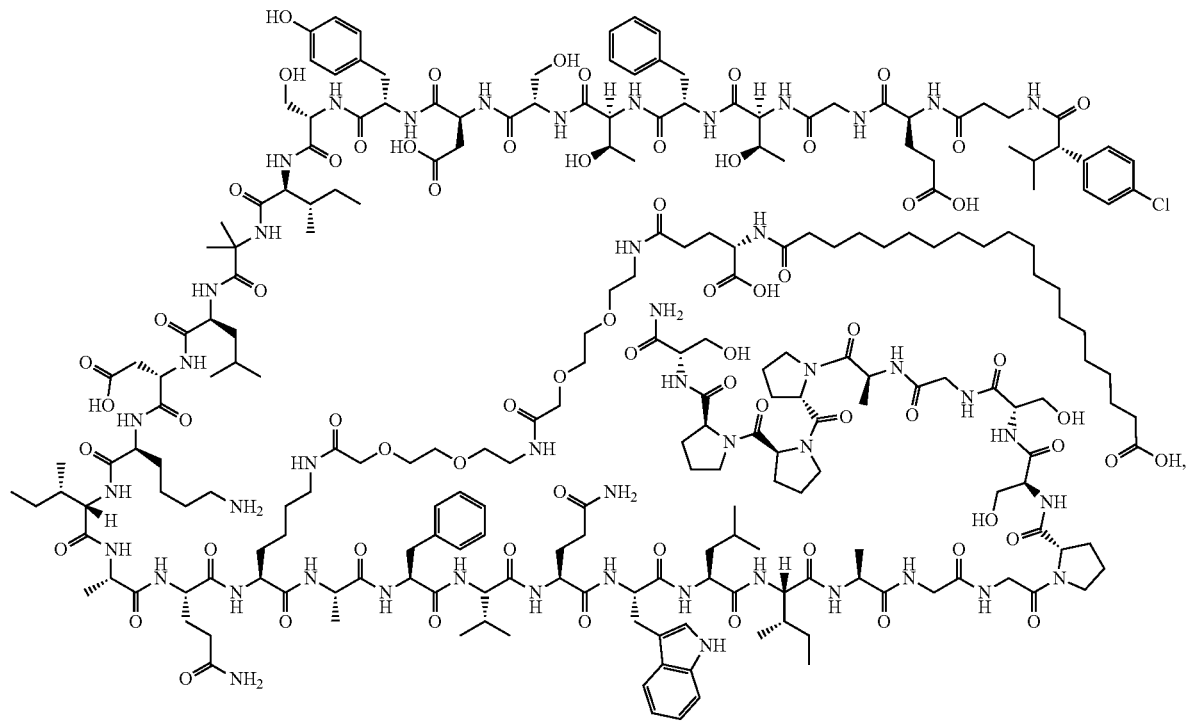
Compound 178
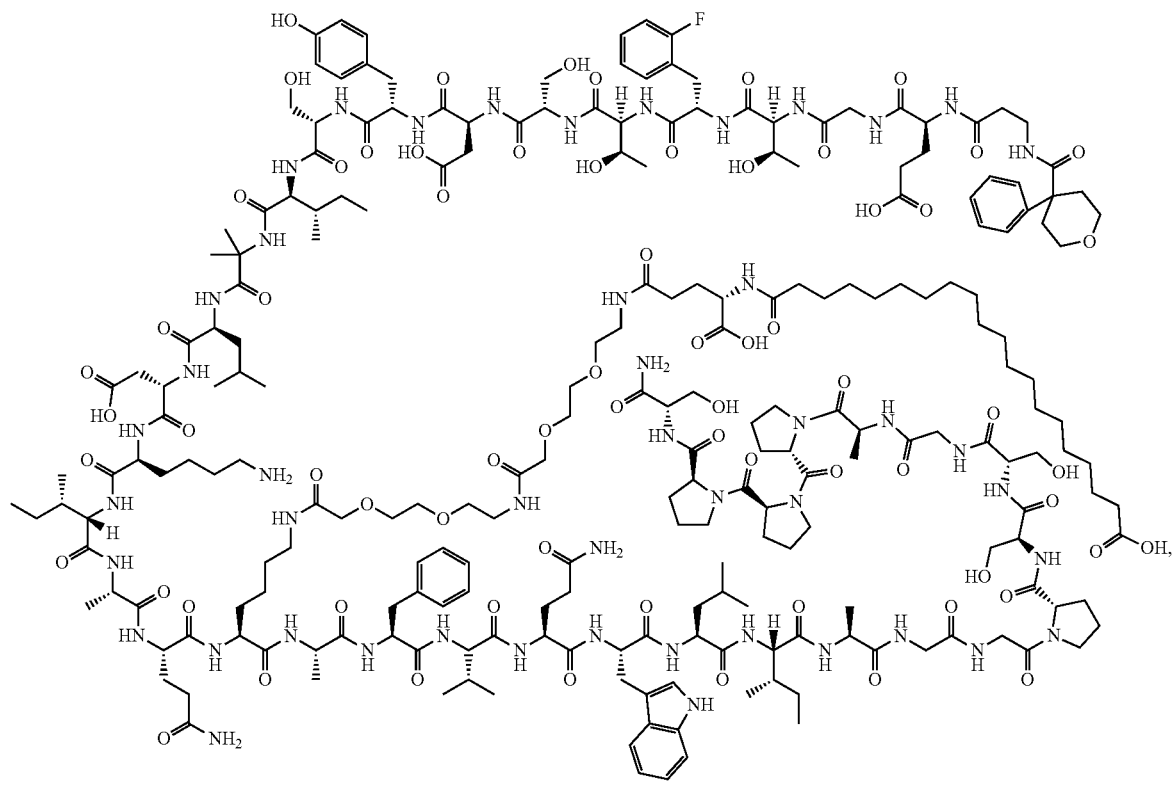

-continued
Compound 179
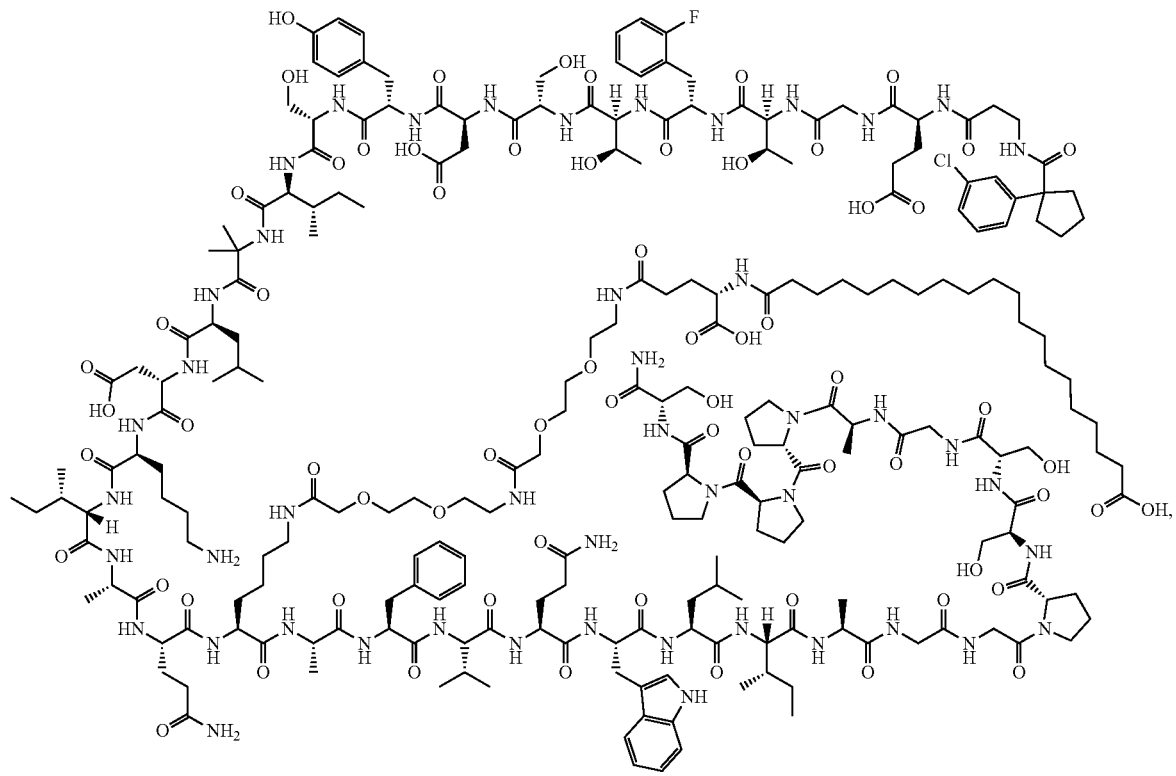
Compound 180
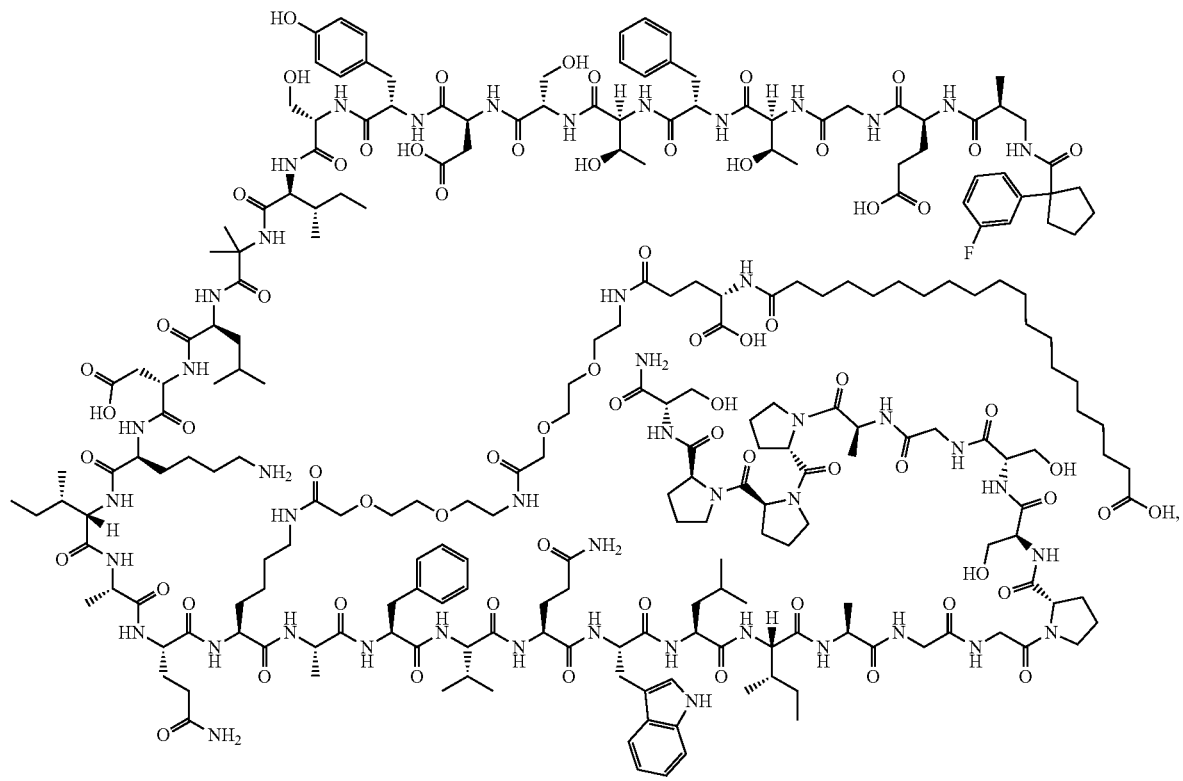

Compound 181
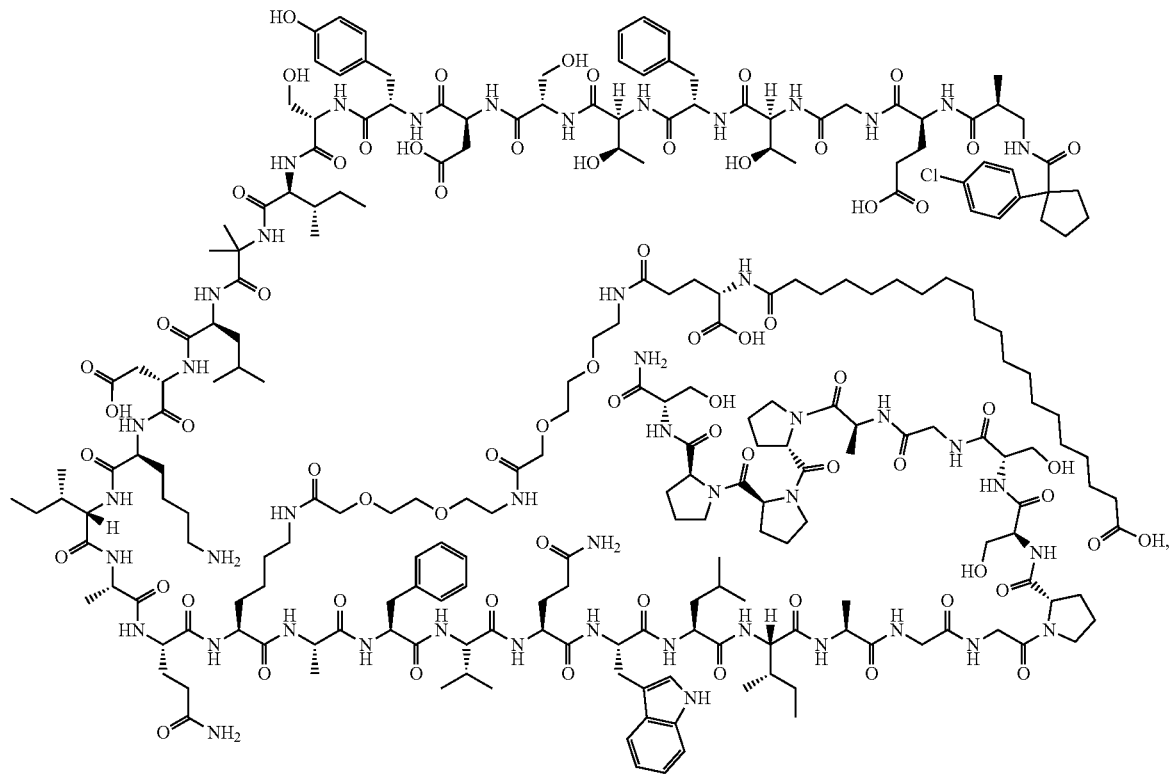
Compound 182
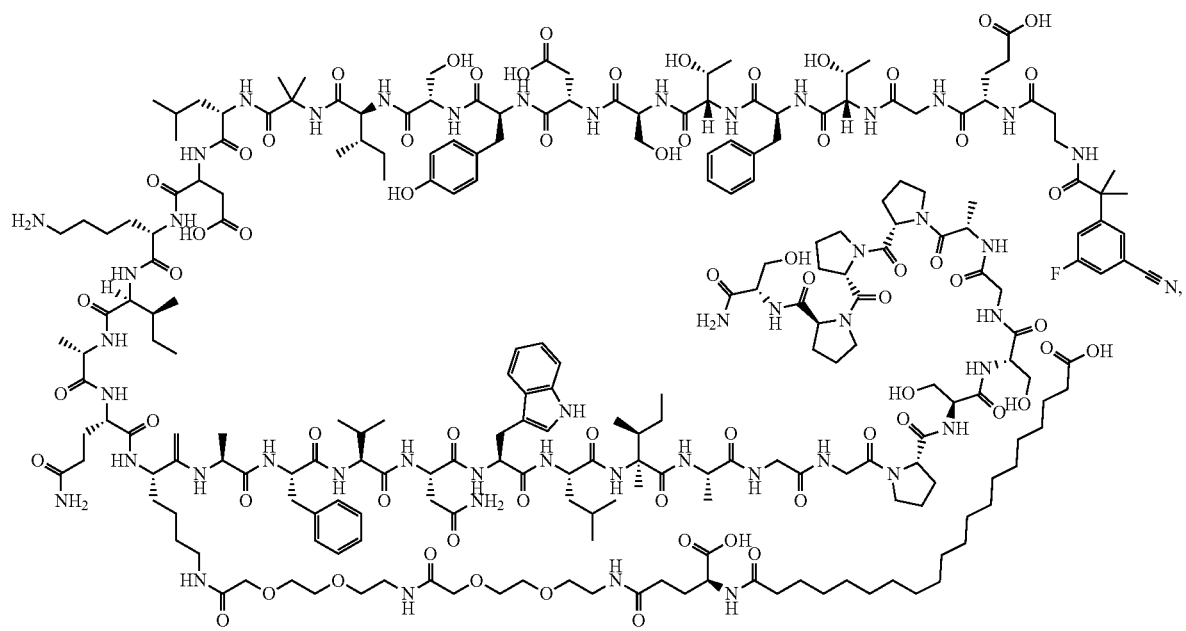

Compound 183
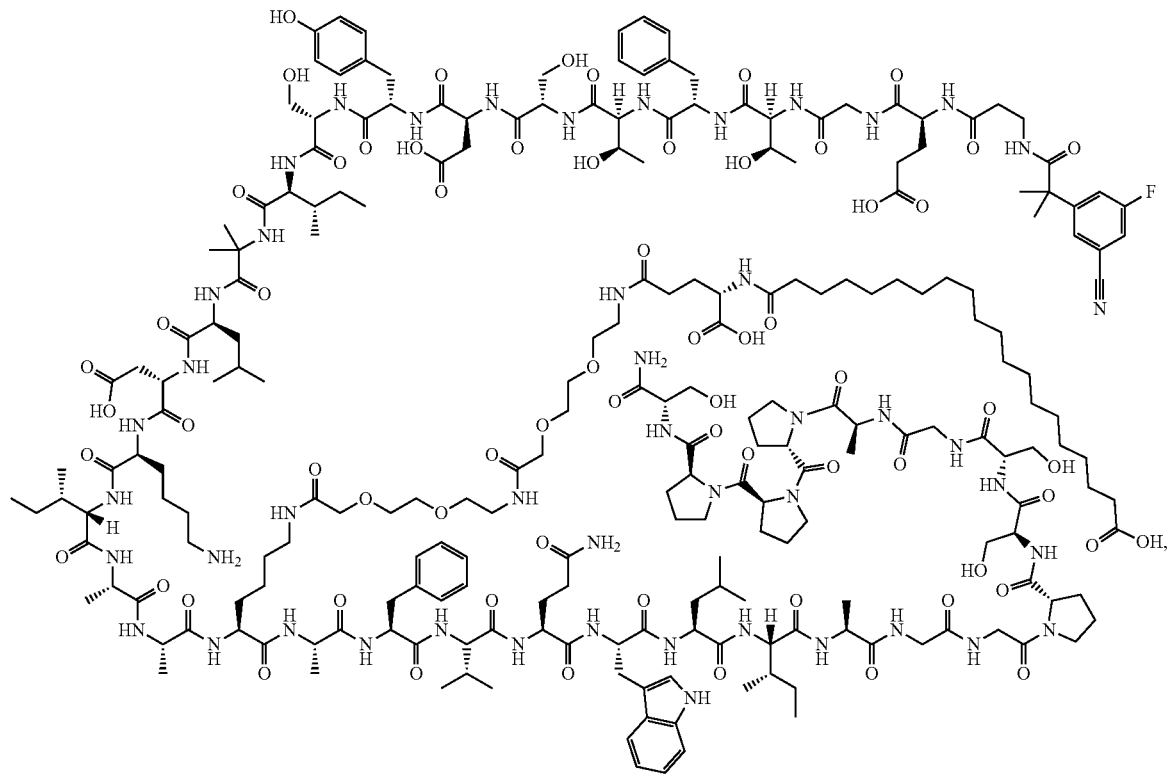
Compound 184
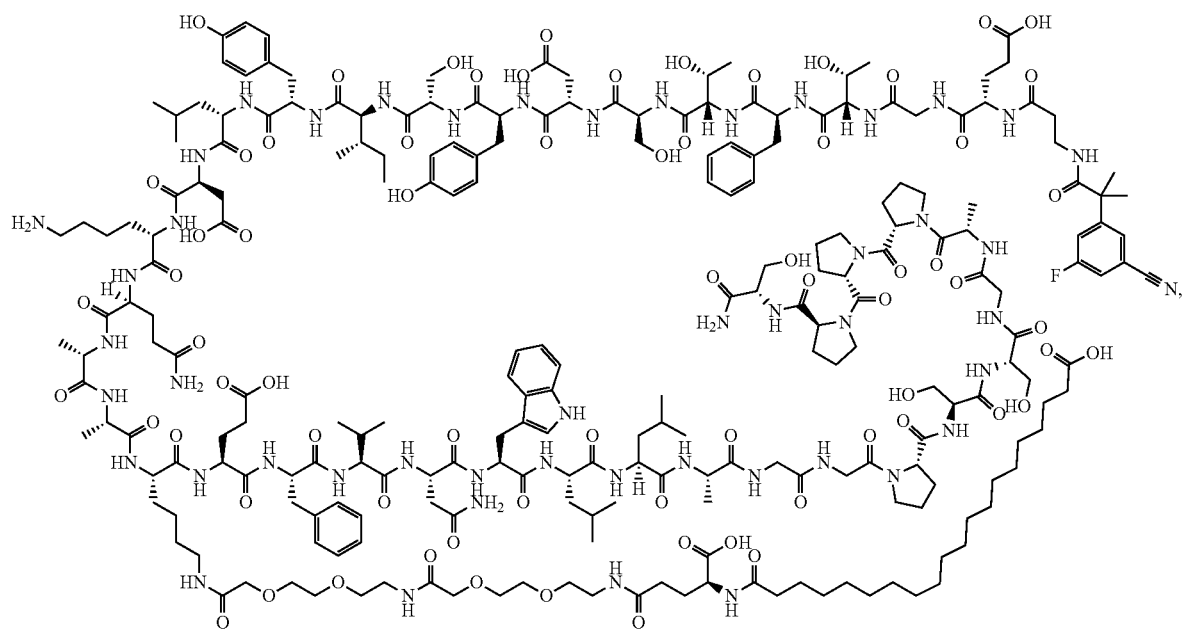

-continued
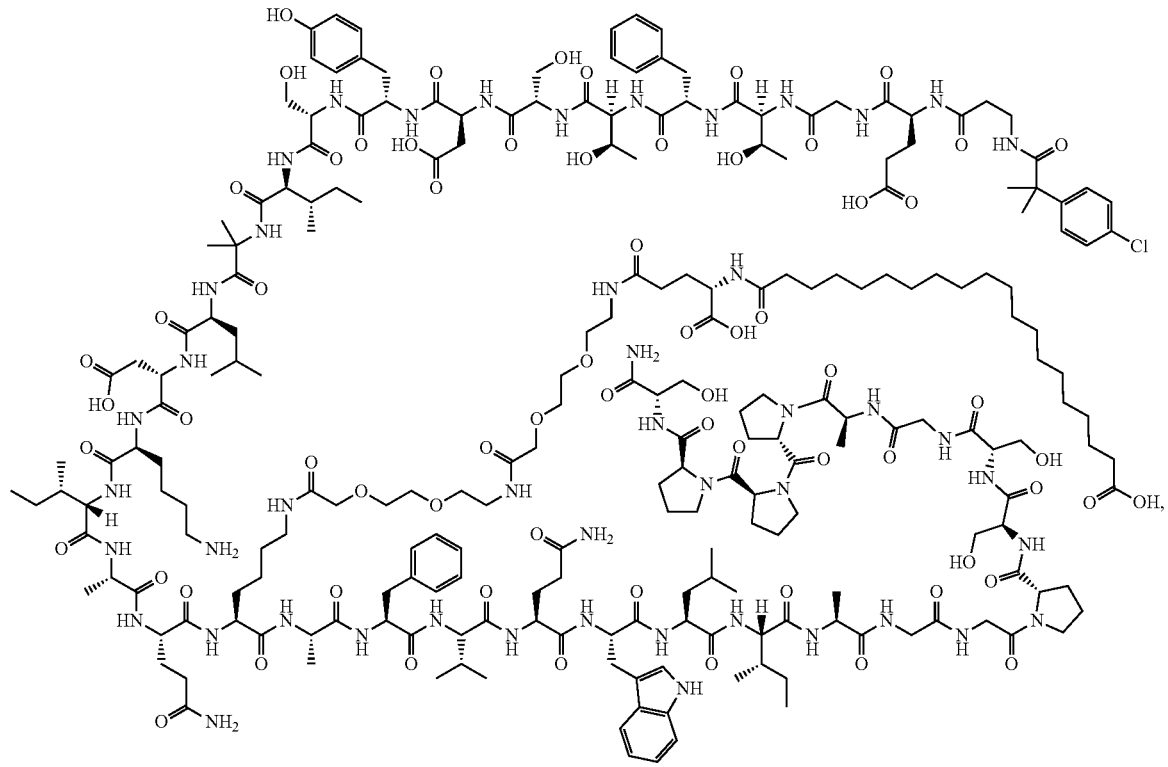
Compound 185
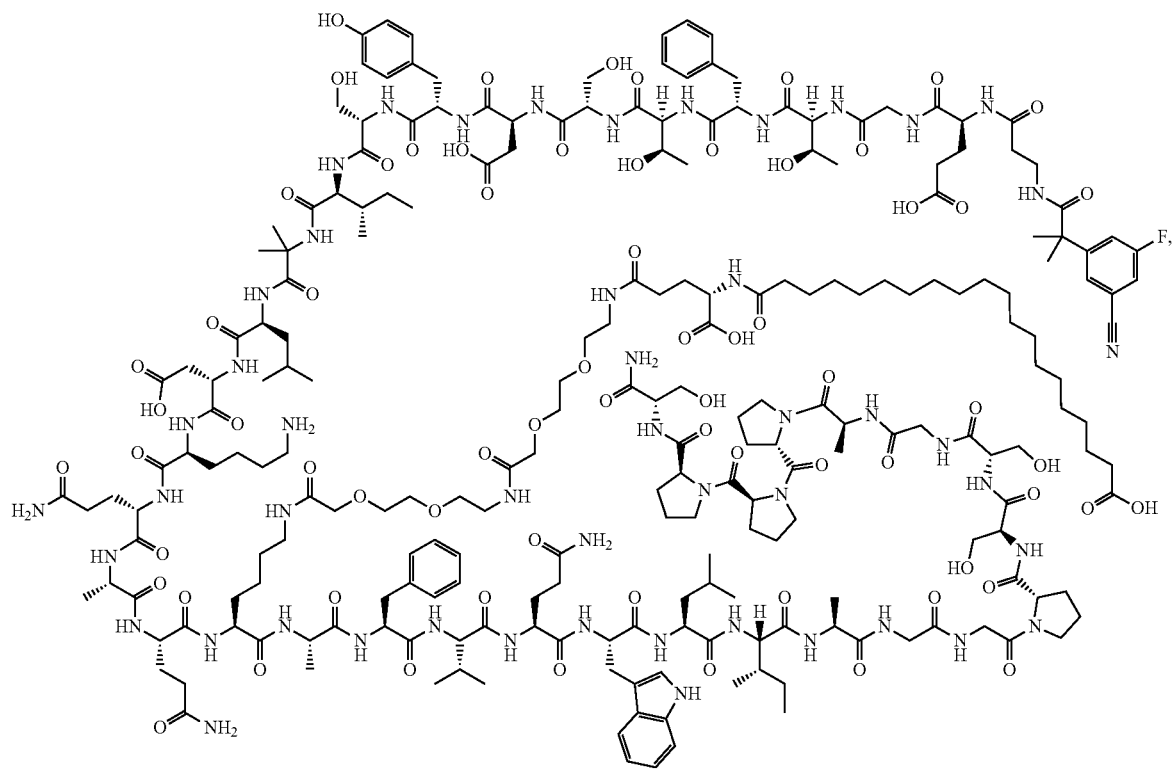
Compound 186

Compound 187
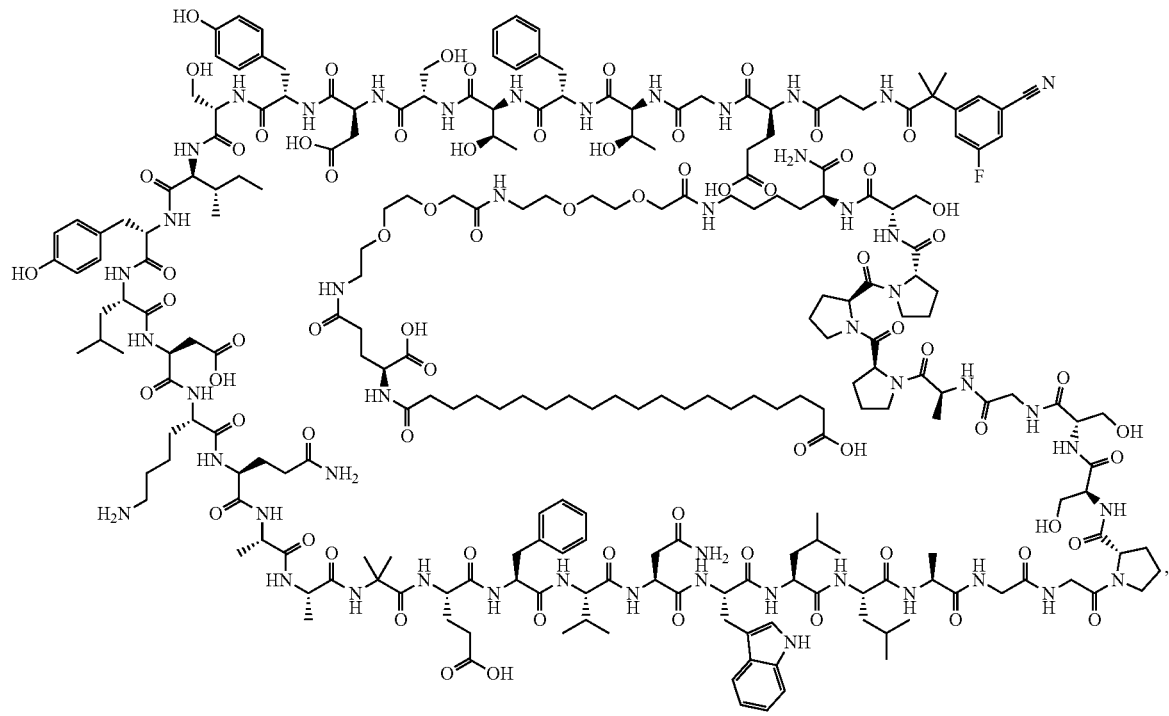
Compound 188
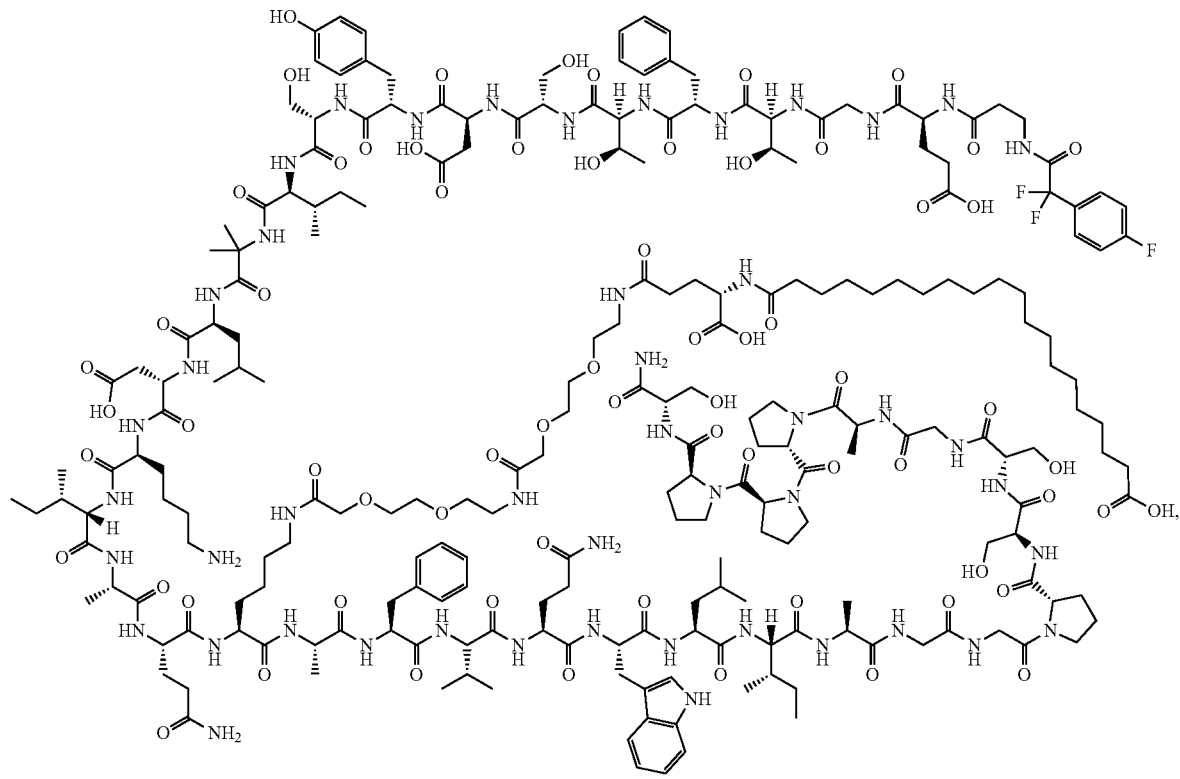

Compound 189
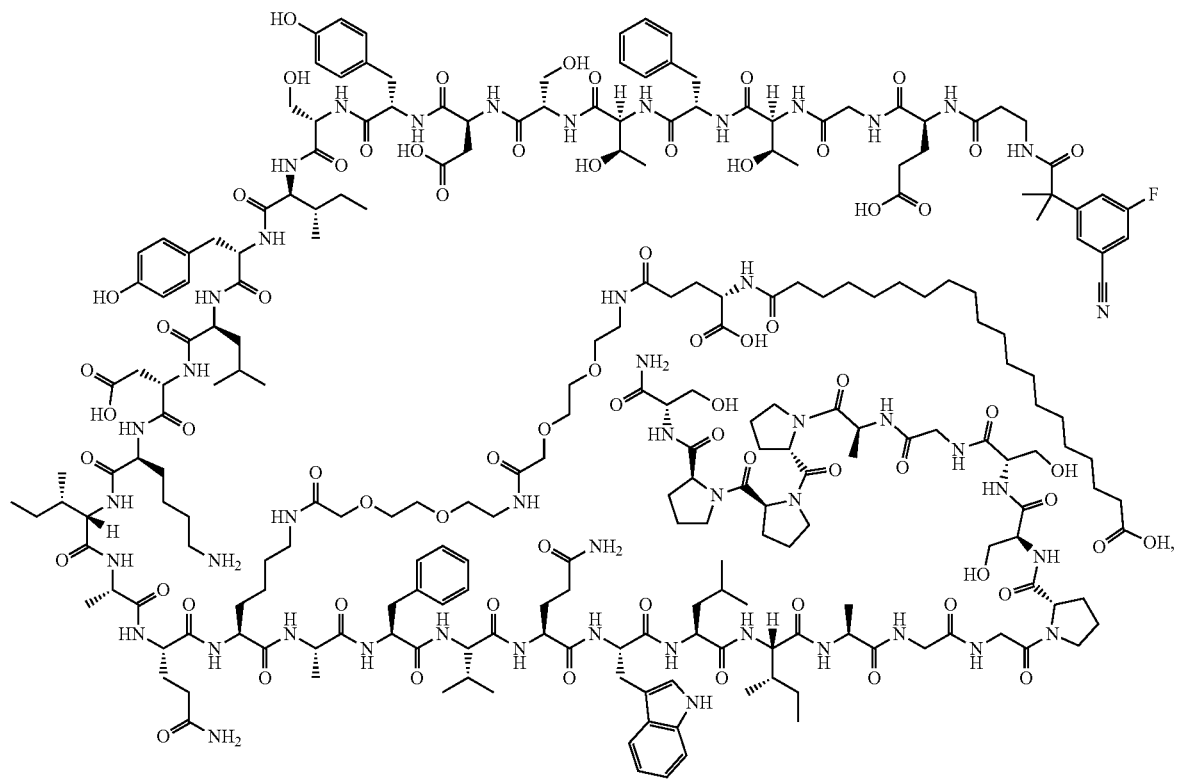
Compound 190
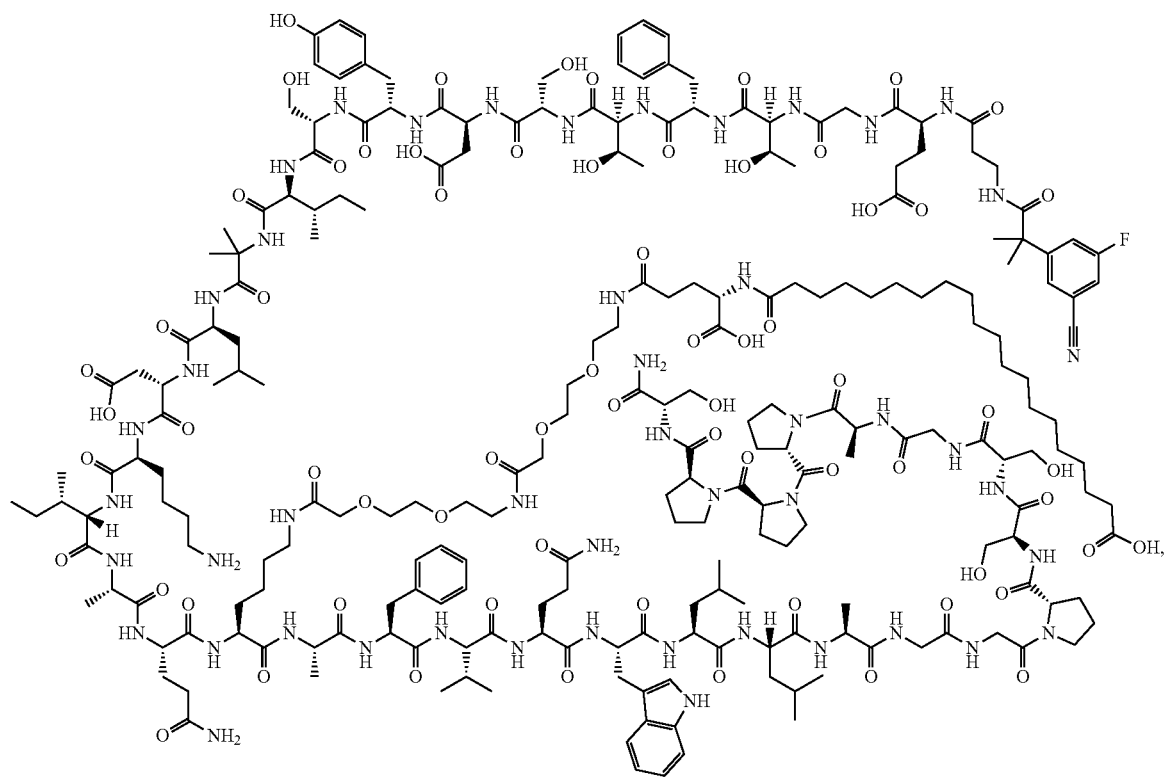

-continued
Compound 191
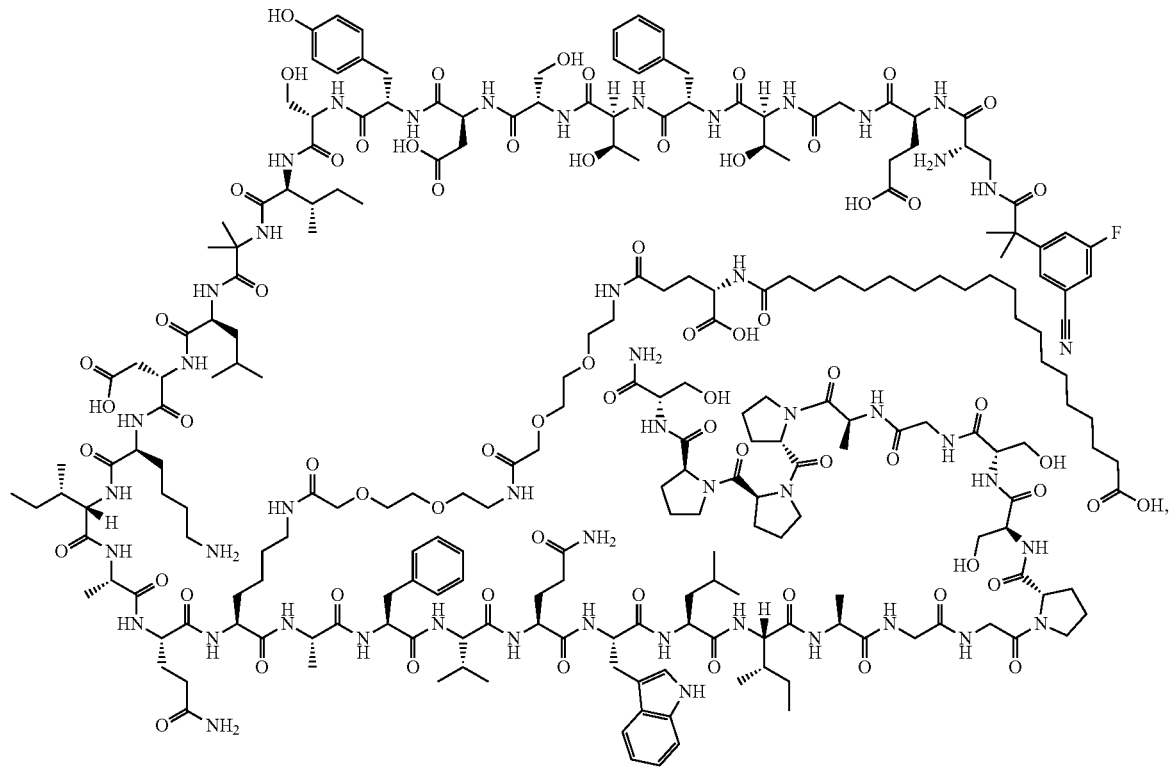
Compound 192
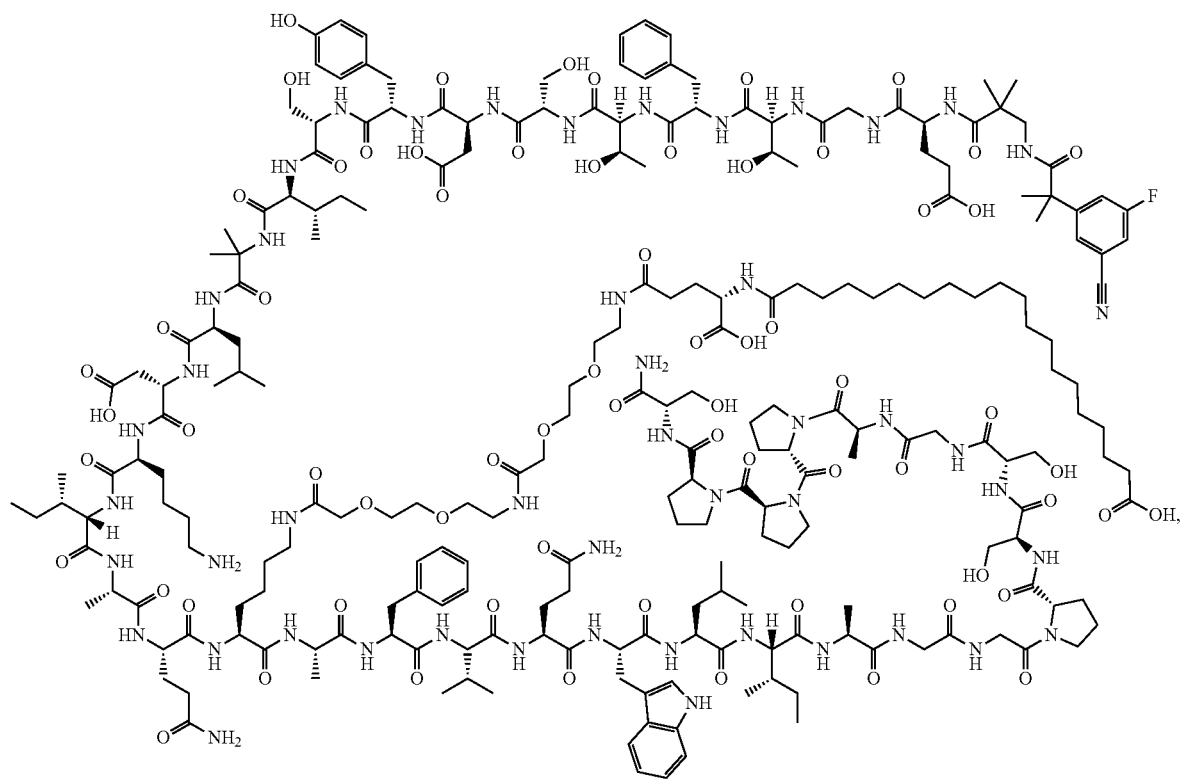

Compound 193
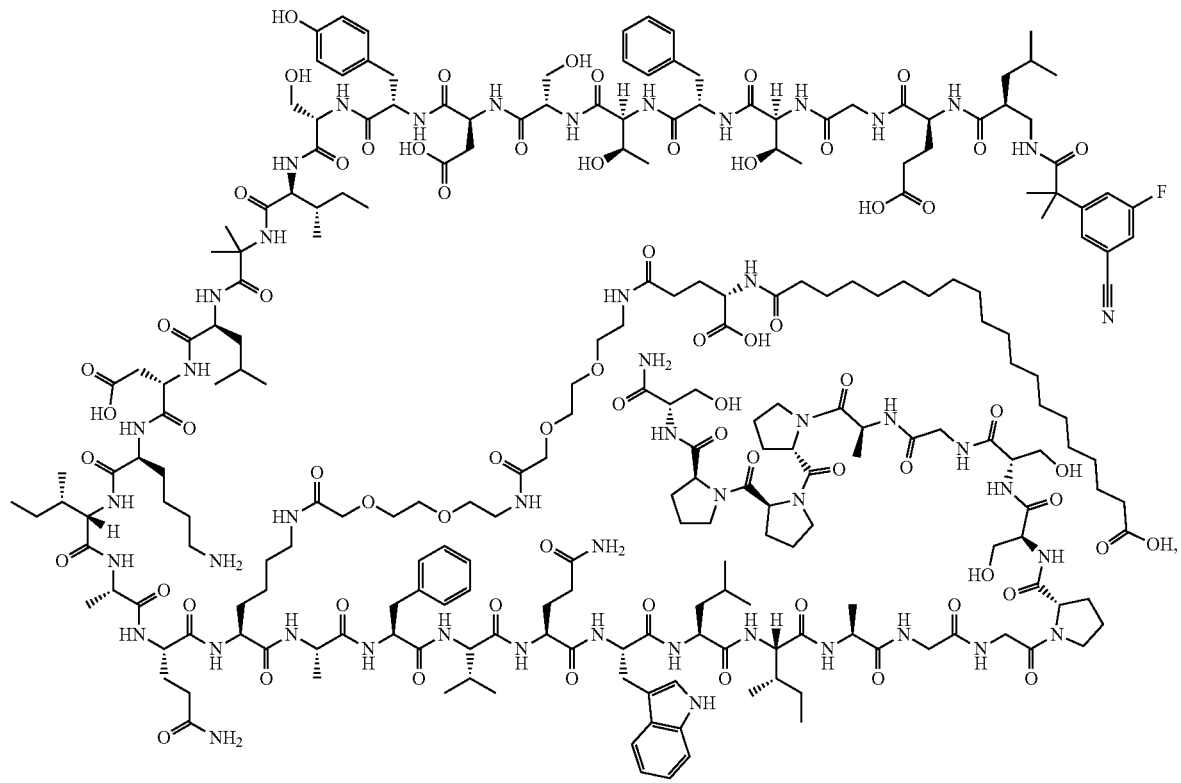
Compound 194
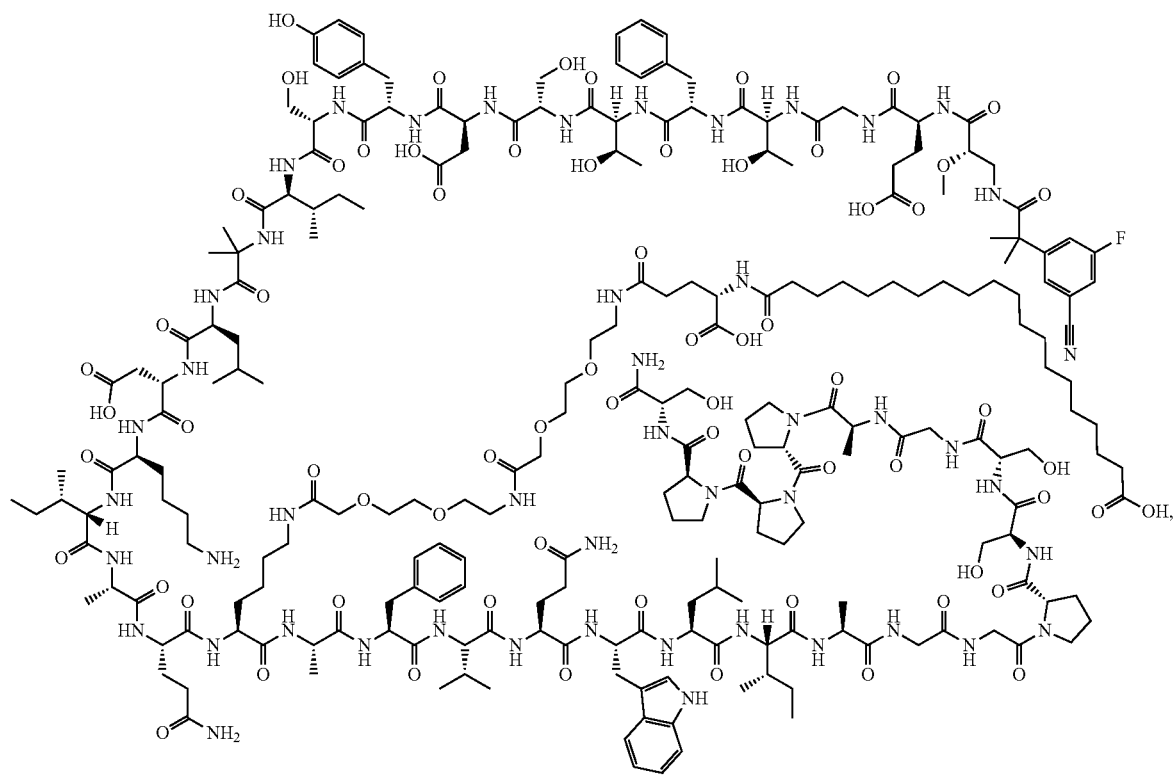

Compound 195
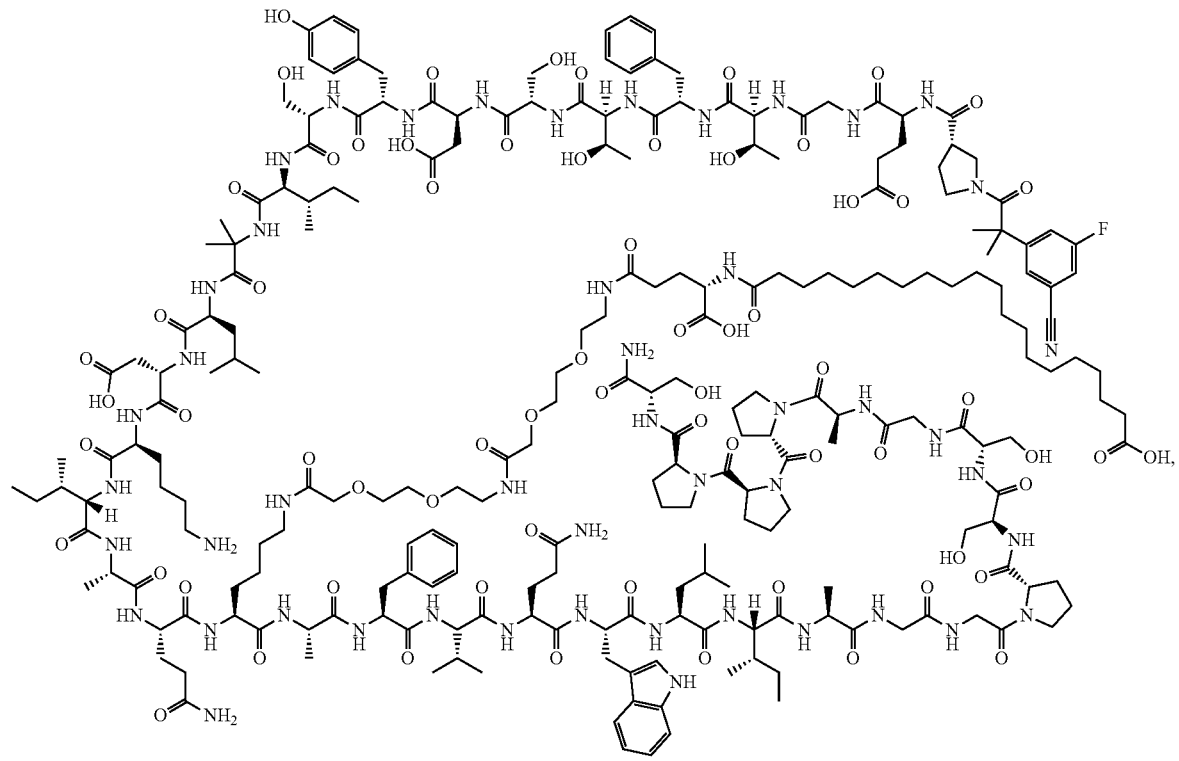
Compound 196
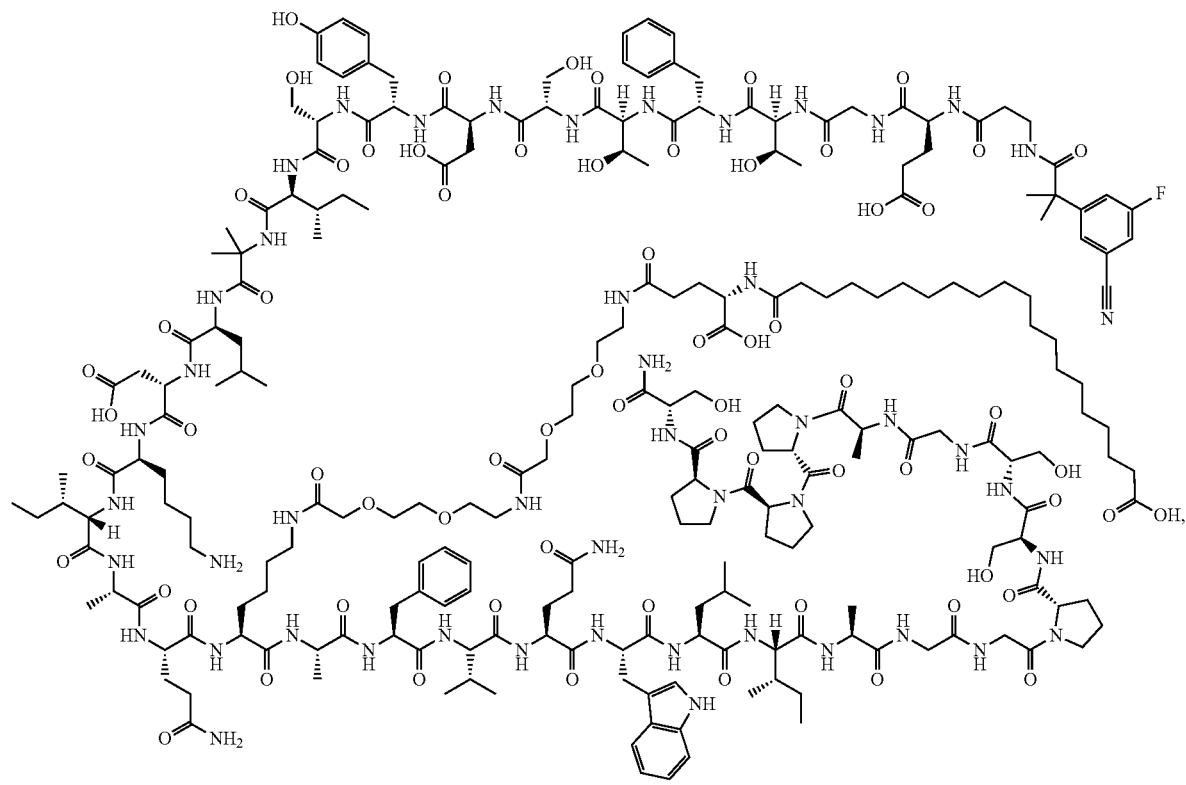

-continued
Compound 197
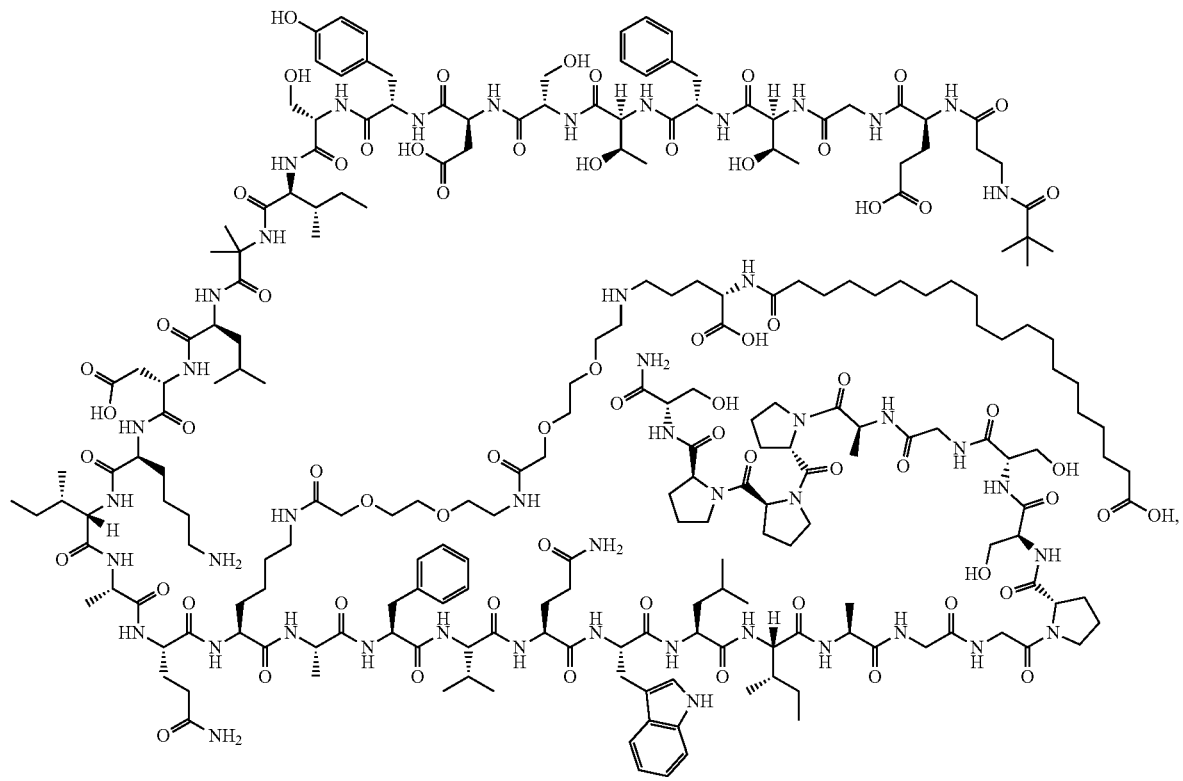
Compound 198
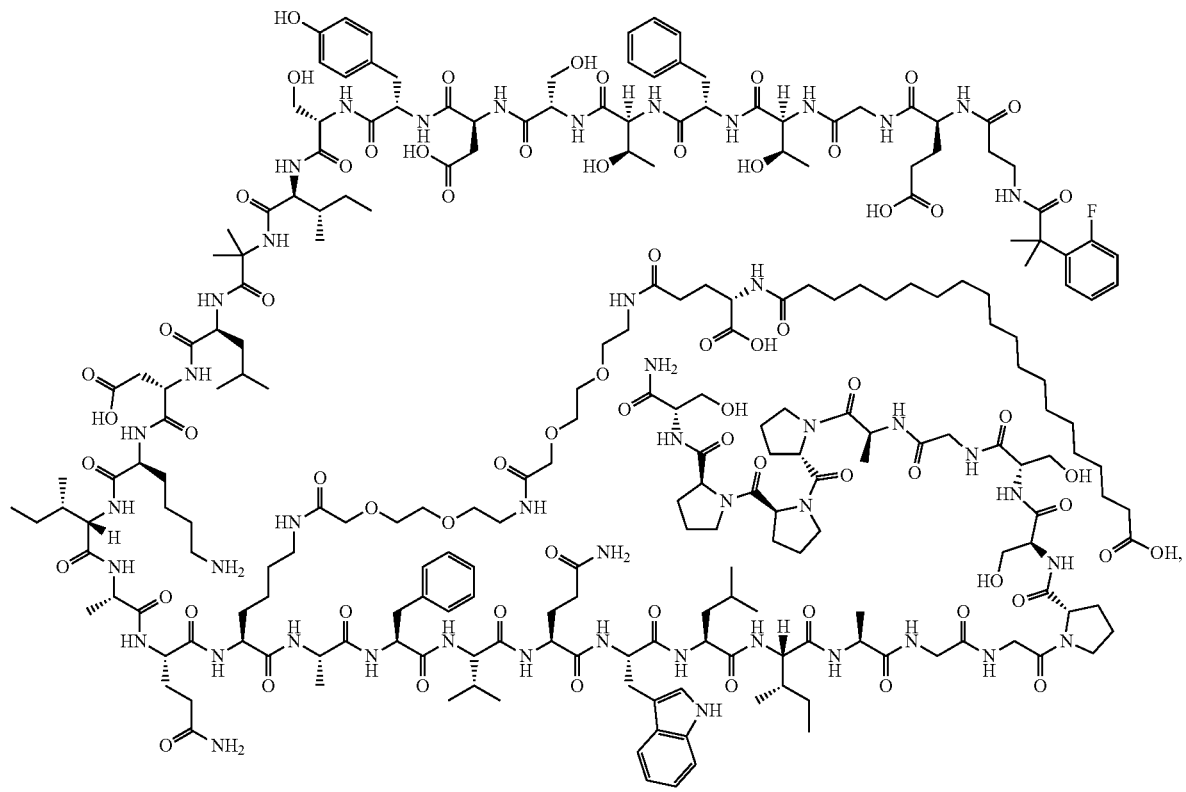

-continued
Compound 199
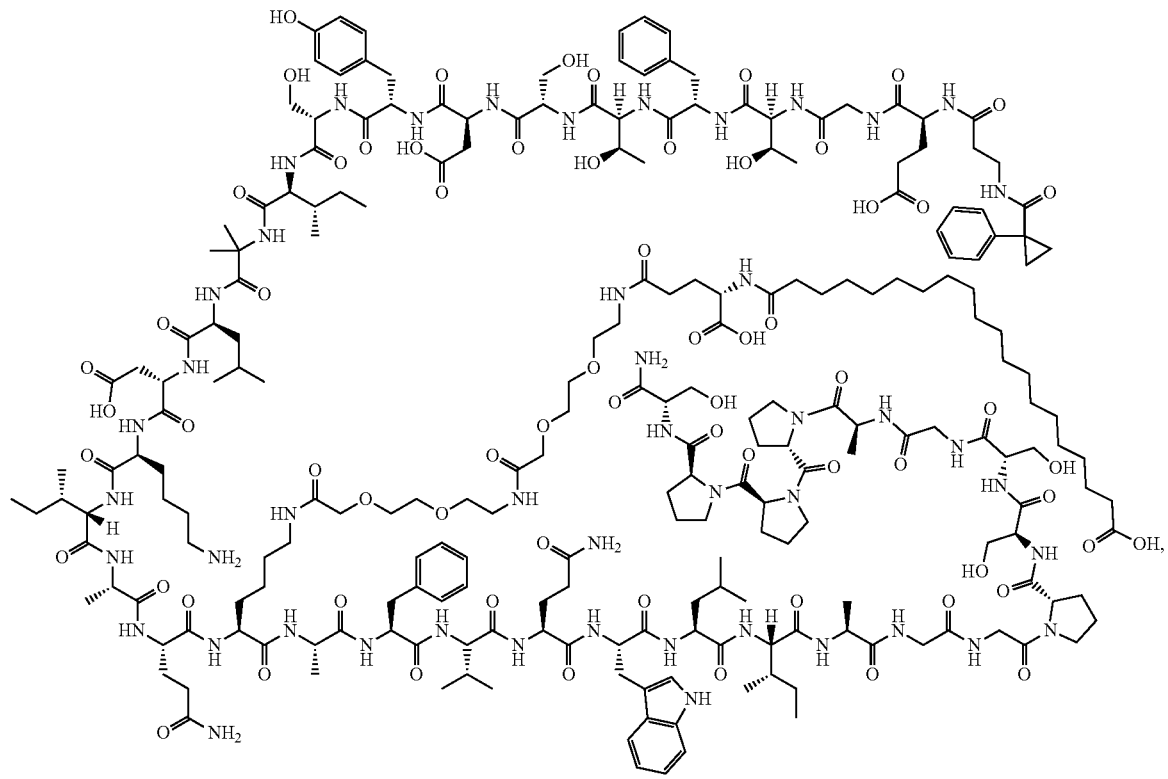
Compound 200
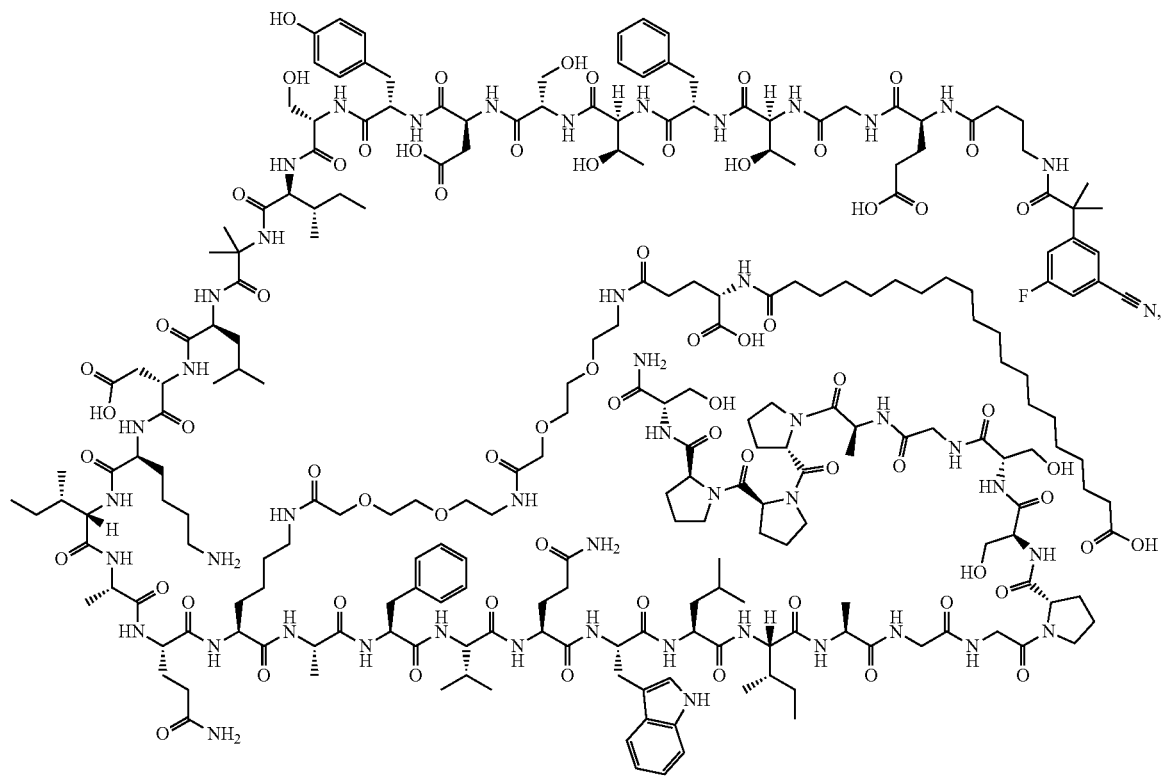

Compound 201
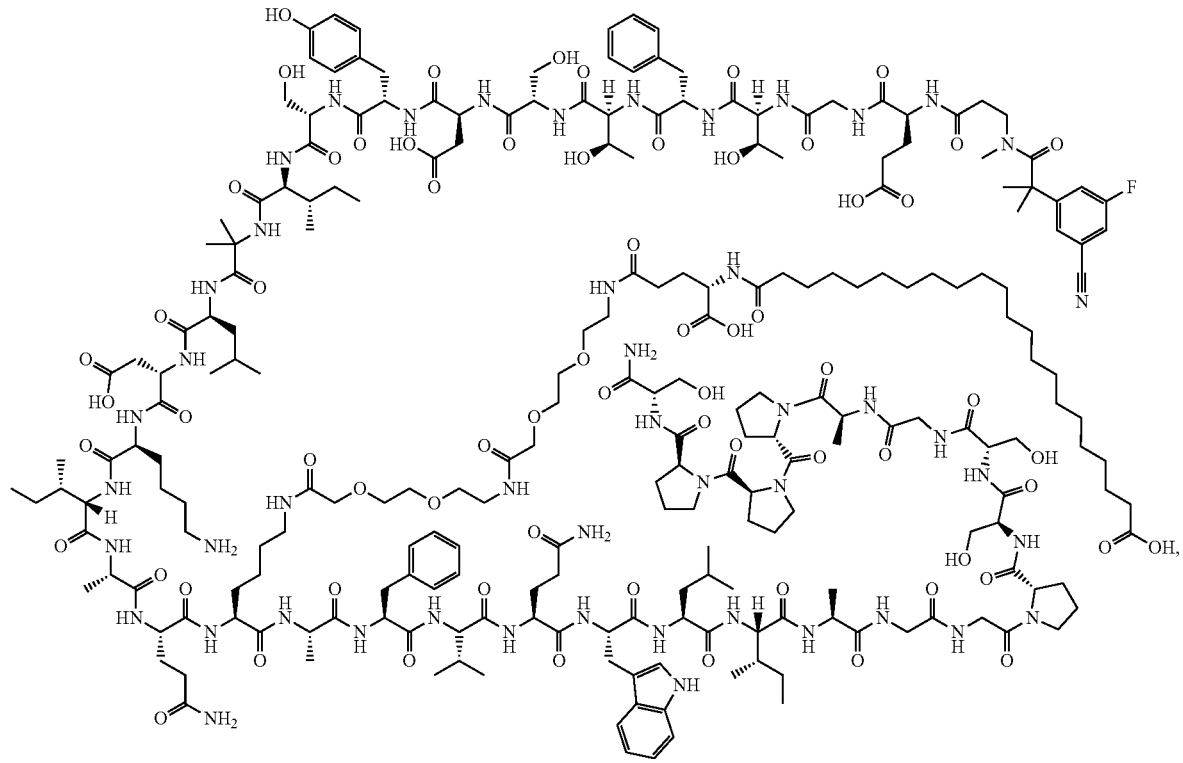
Compound 203
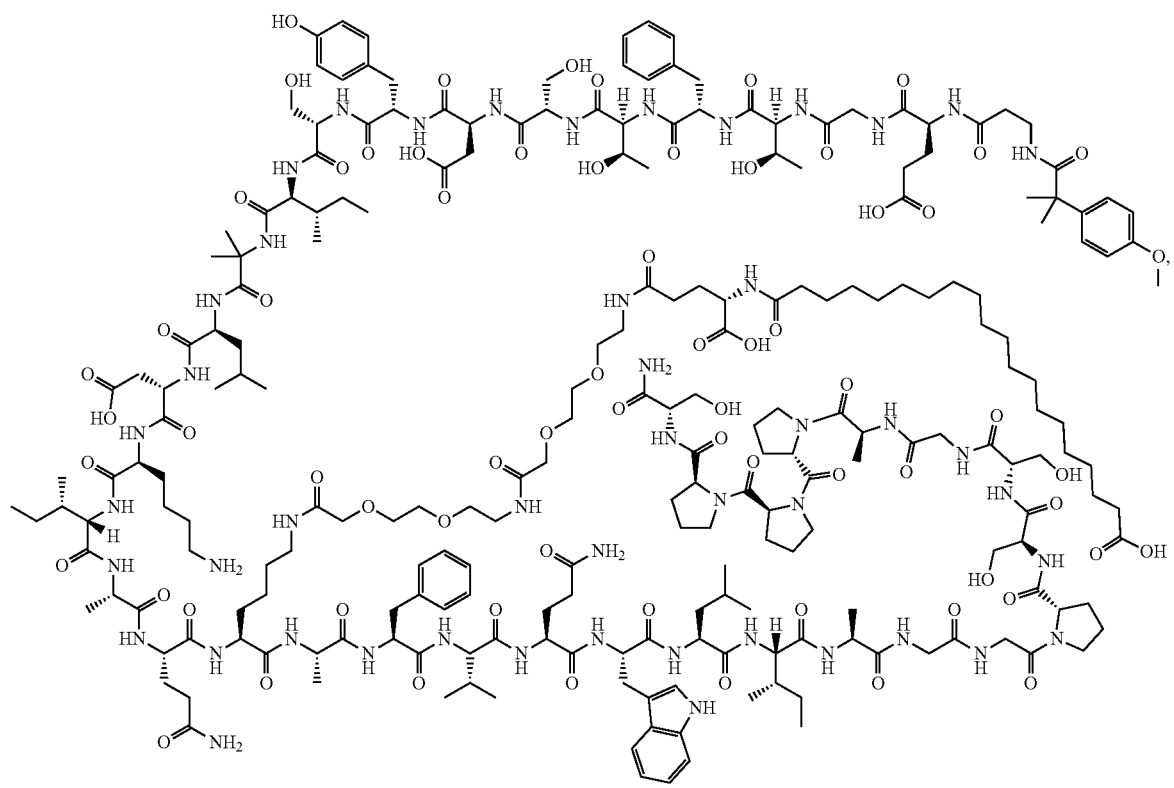

Compound 204
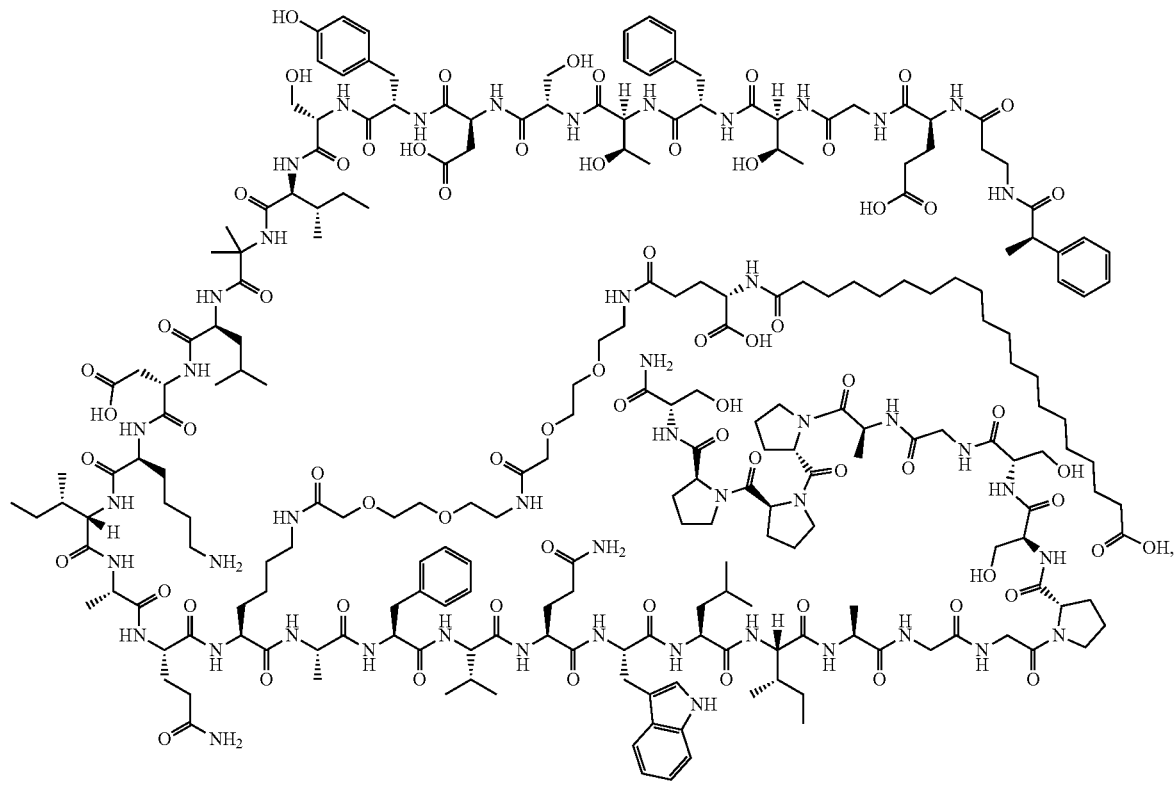
Compound 205
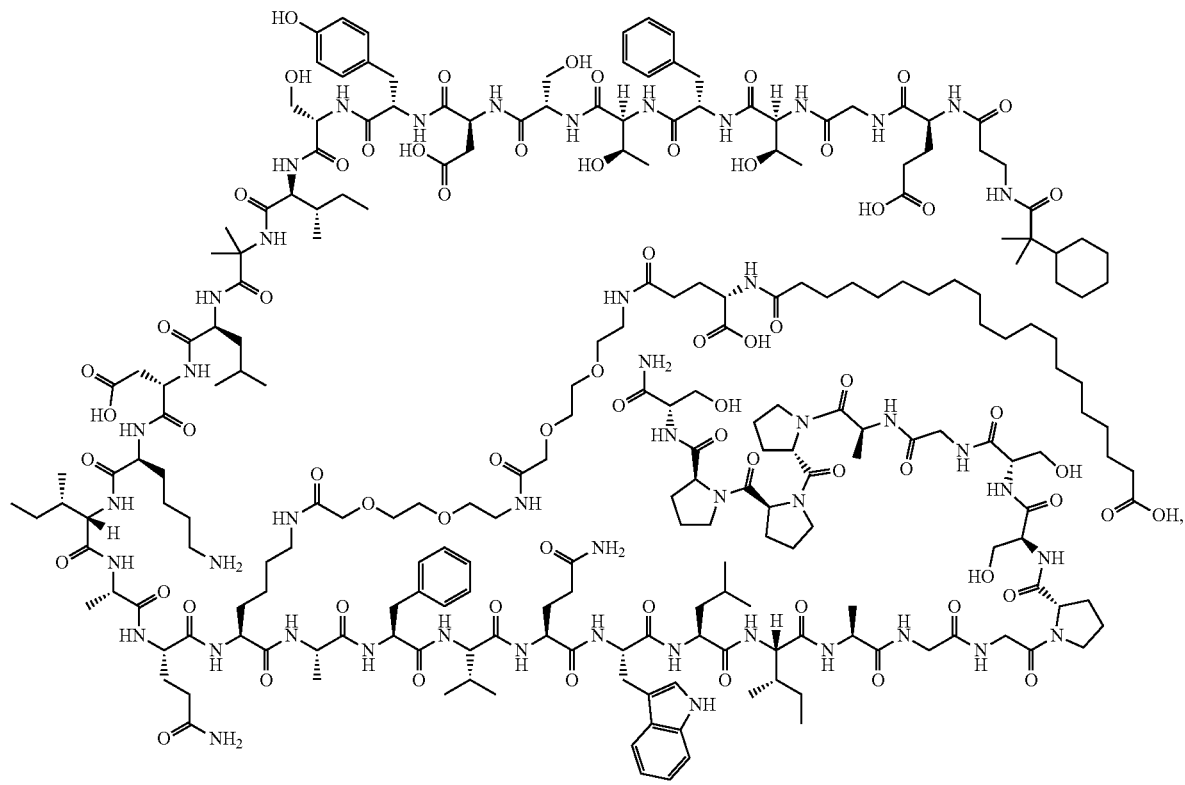

-continued
Compound 206
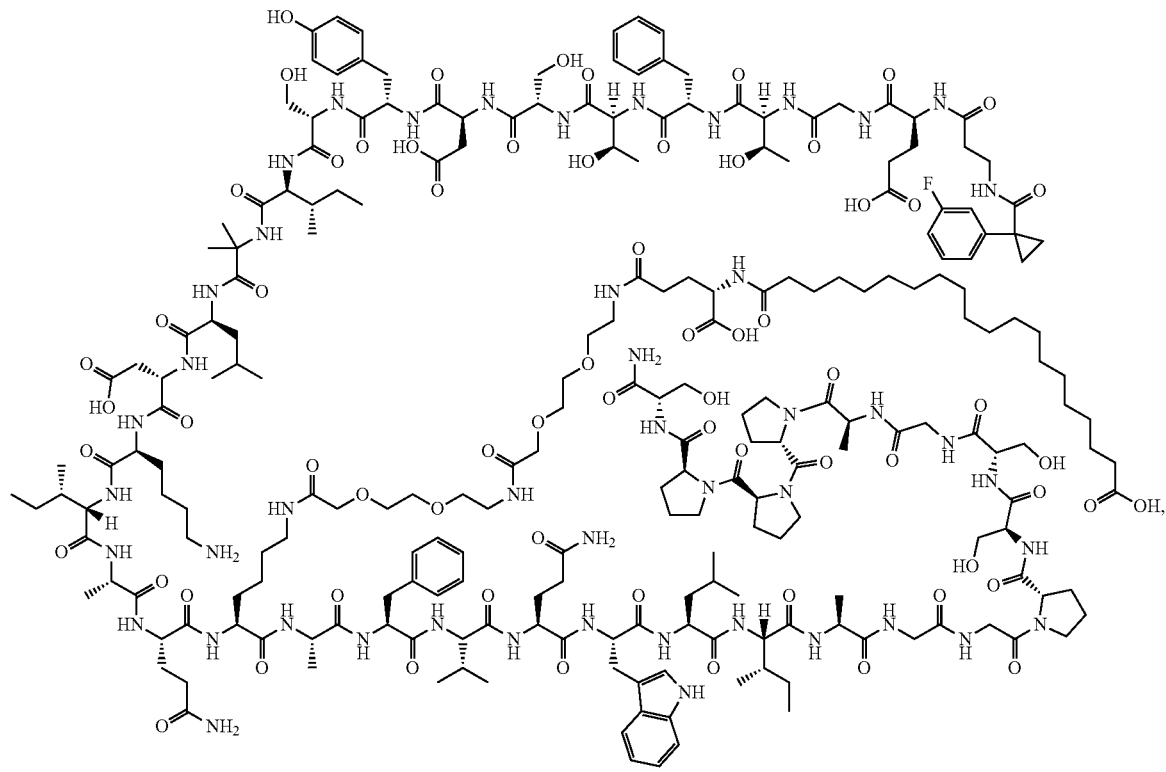
Compound 207
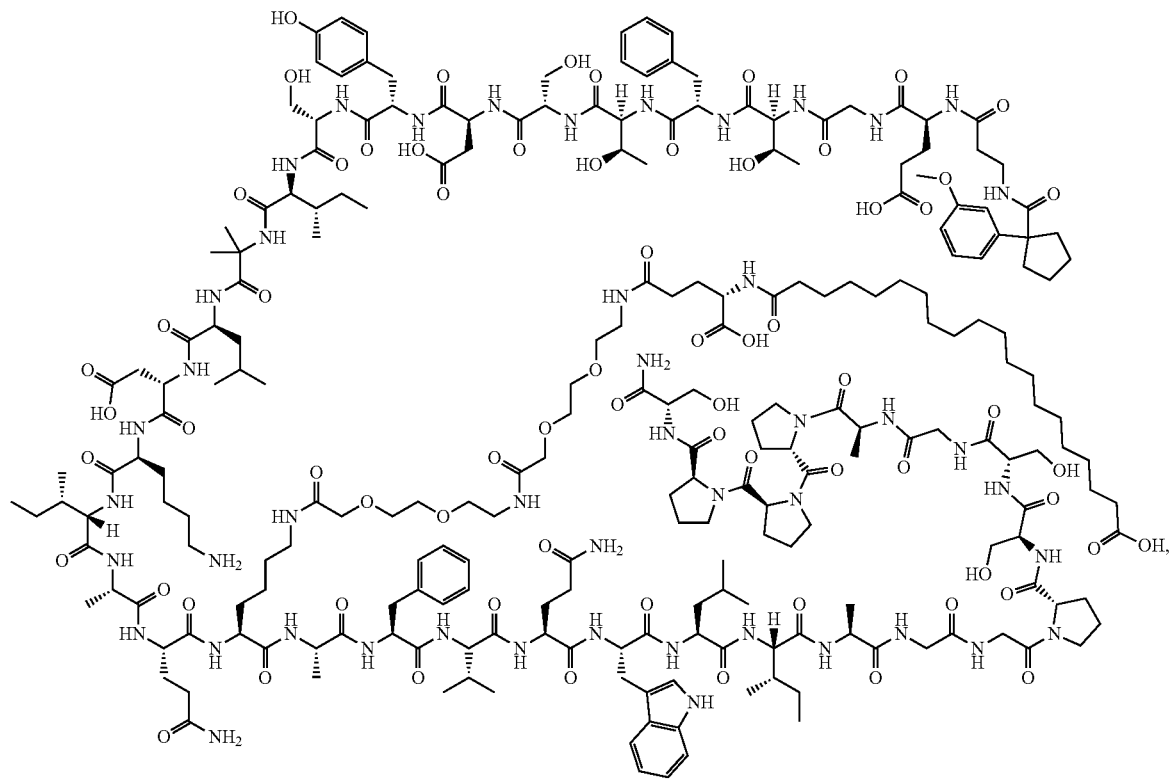

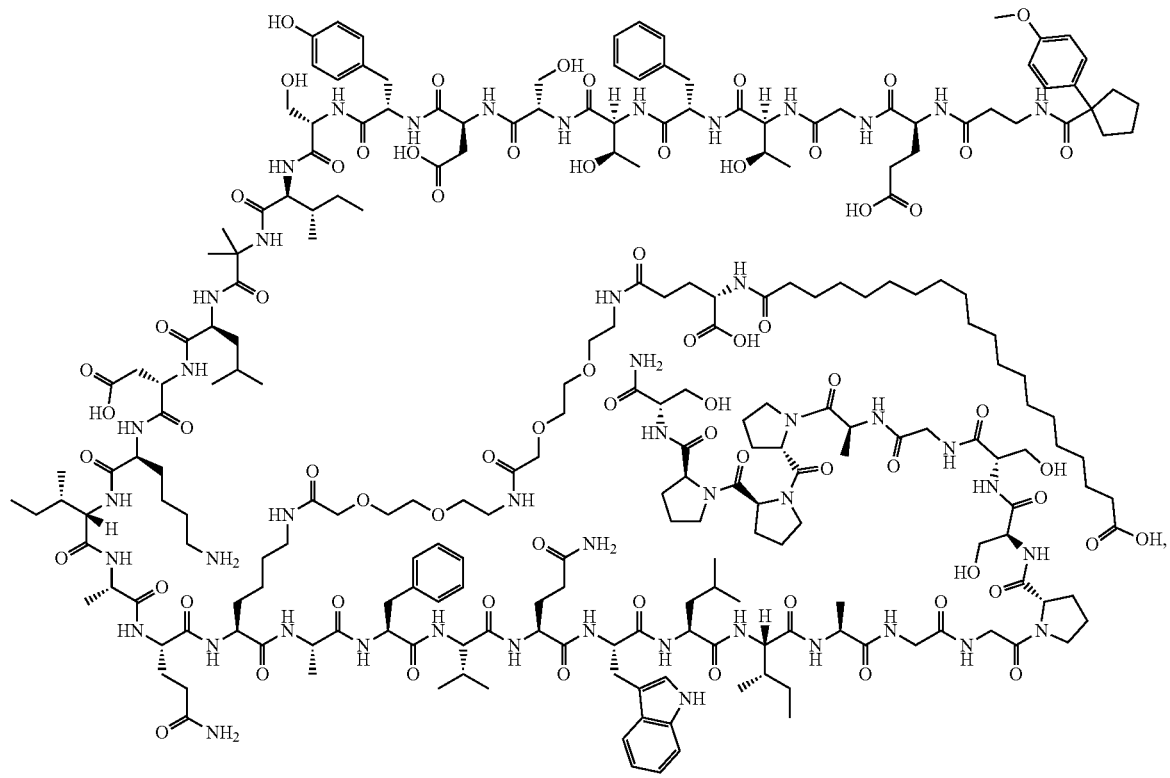
Compound 208
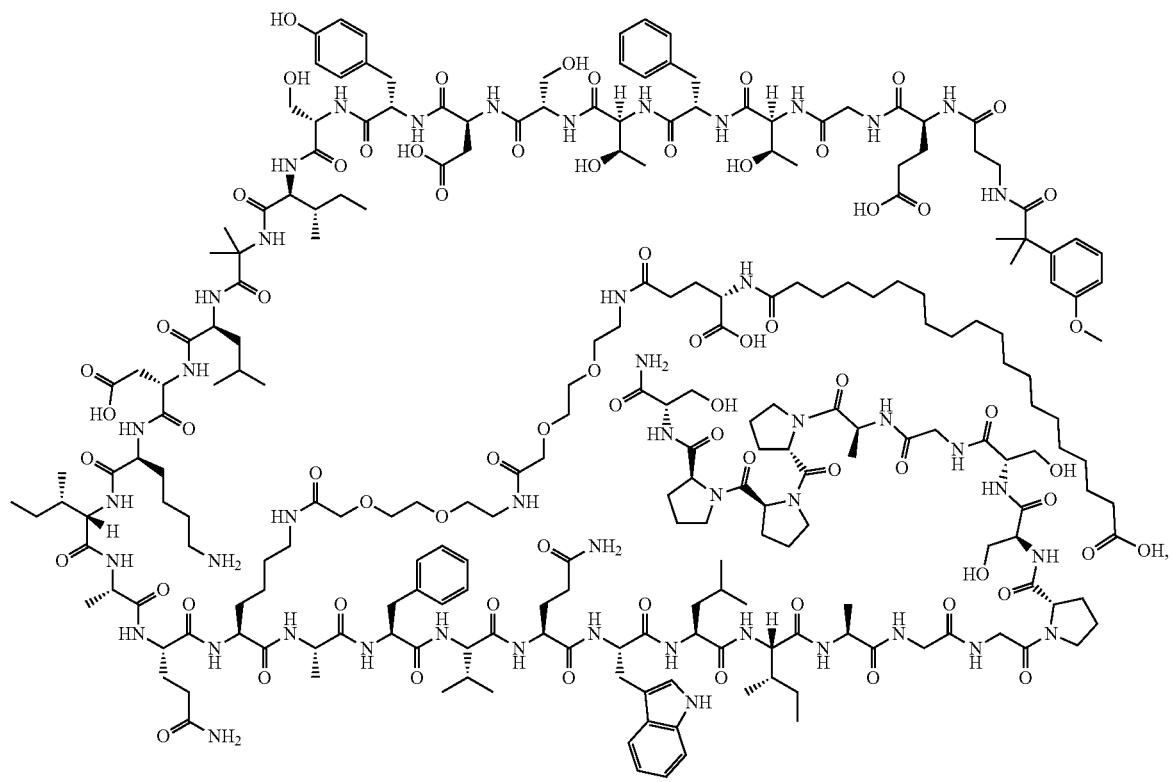
Compound 209

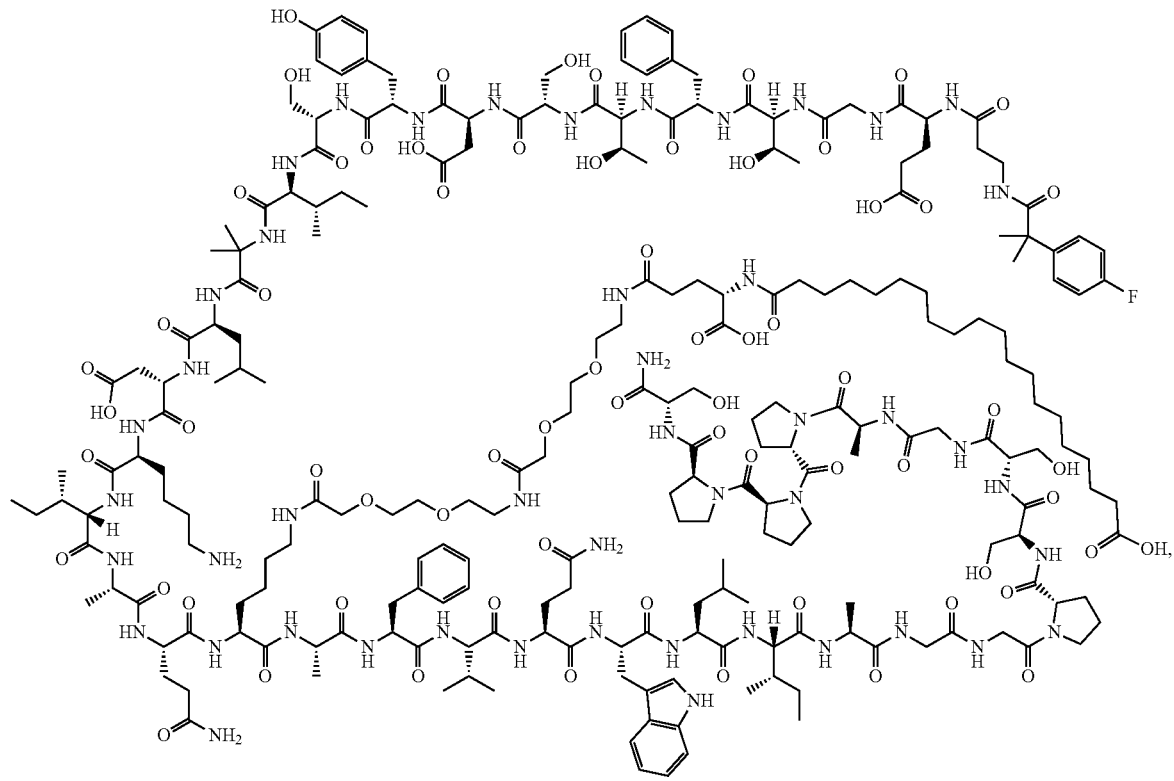
Compound 210
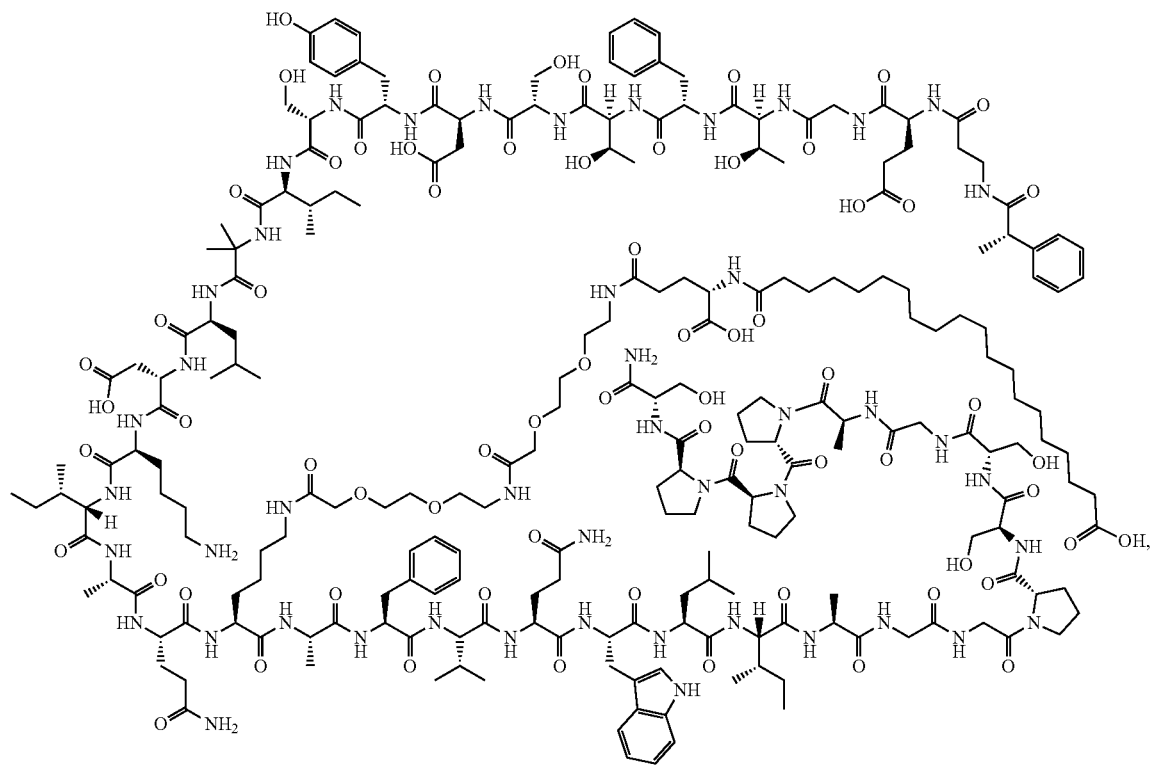
Compound 211

-continued
Compound 212
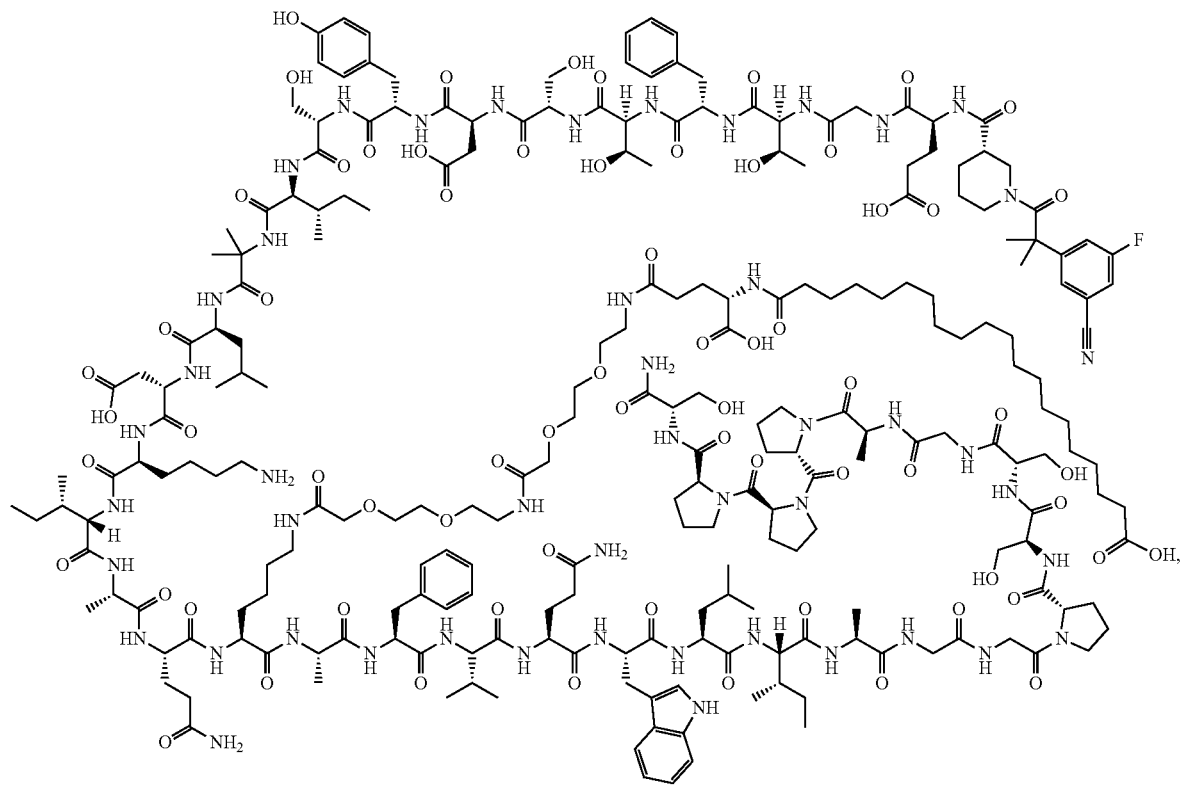
Compound 213
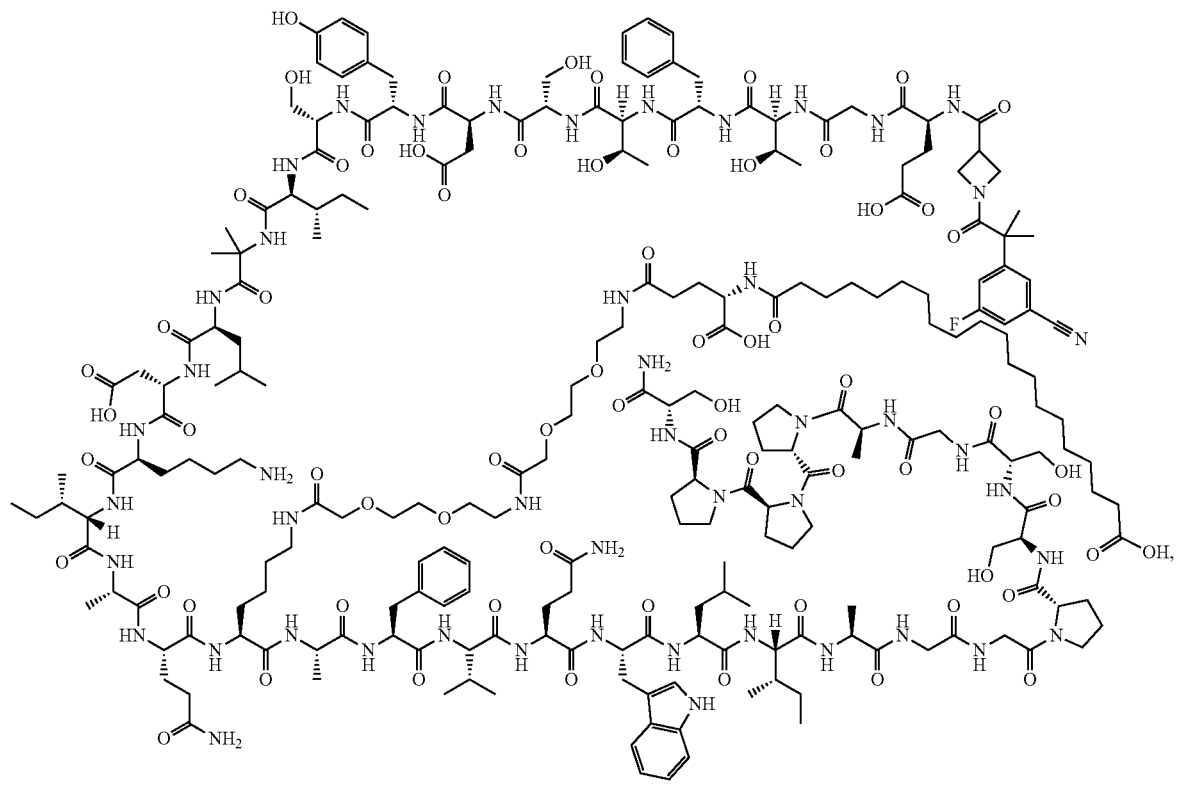

Compound 214
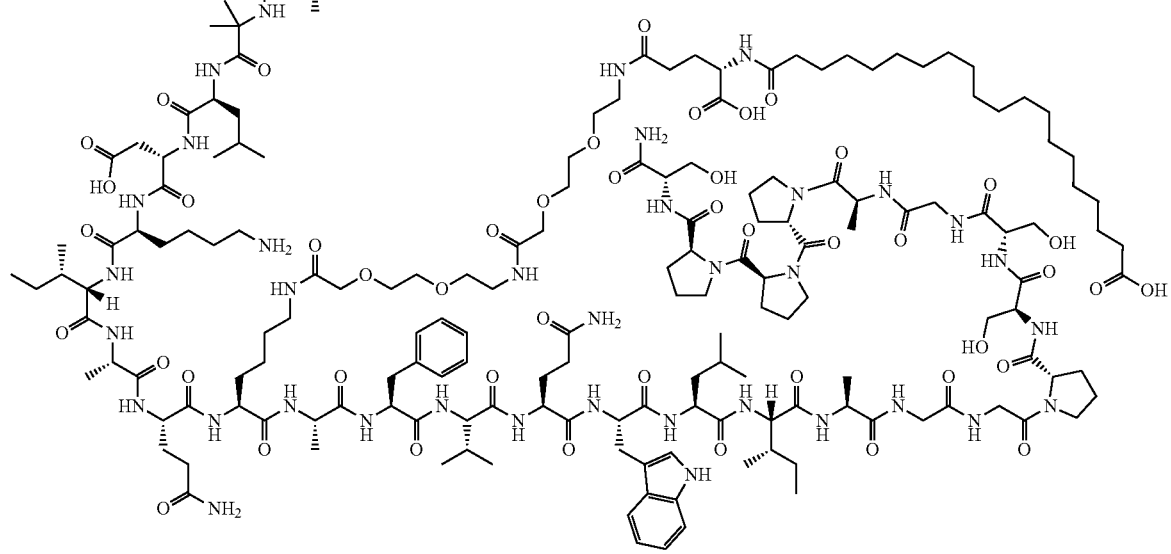
Compound 215
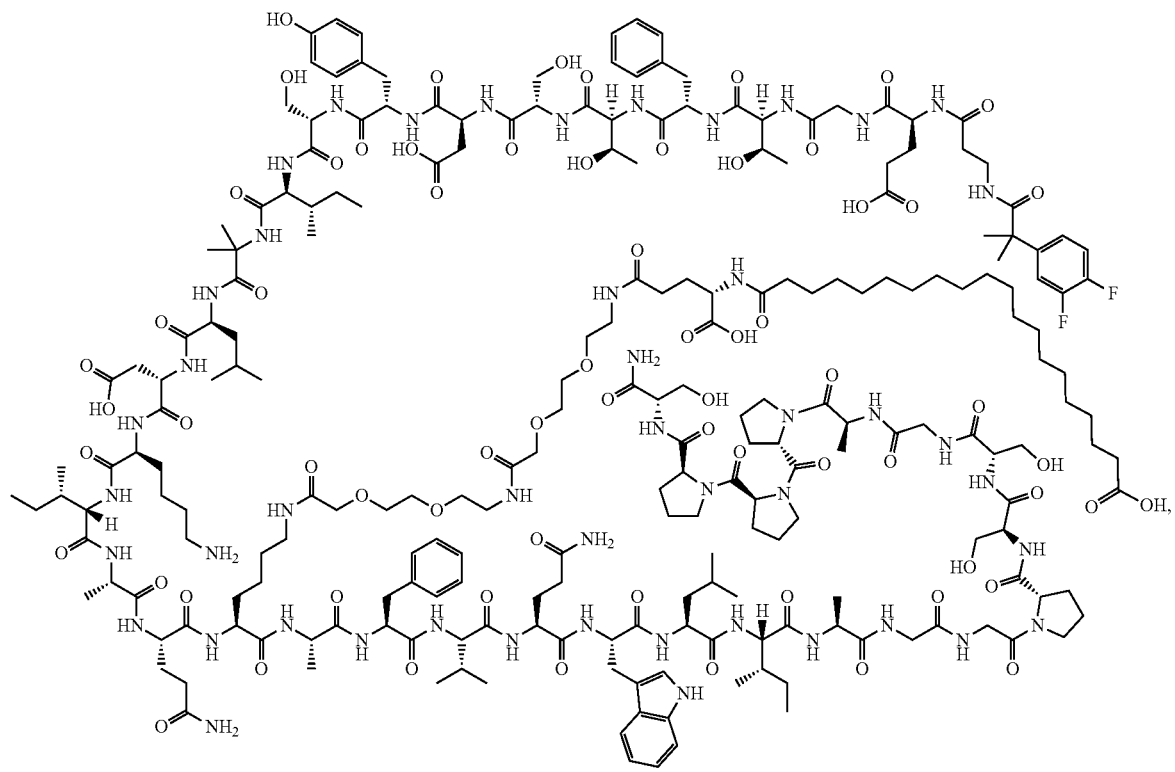

Compound 216
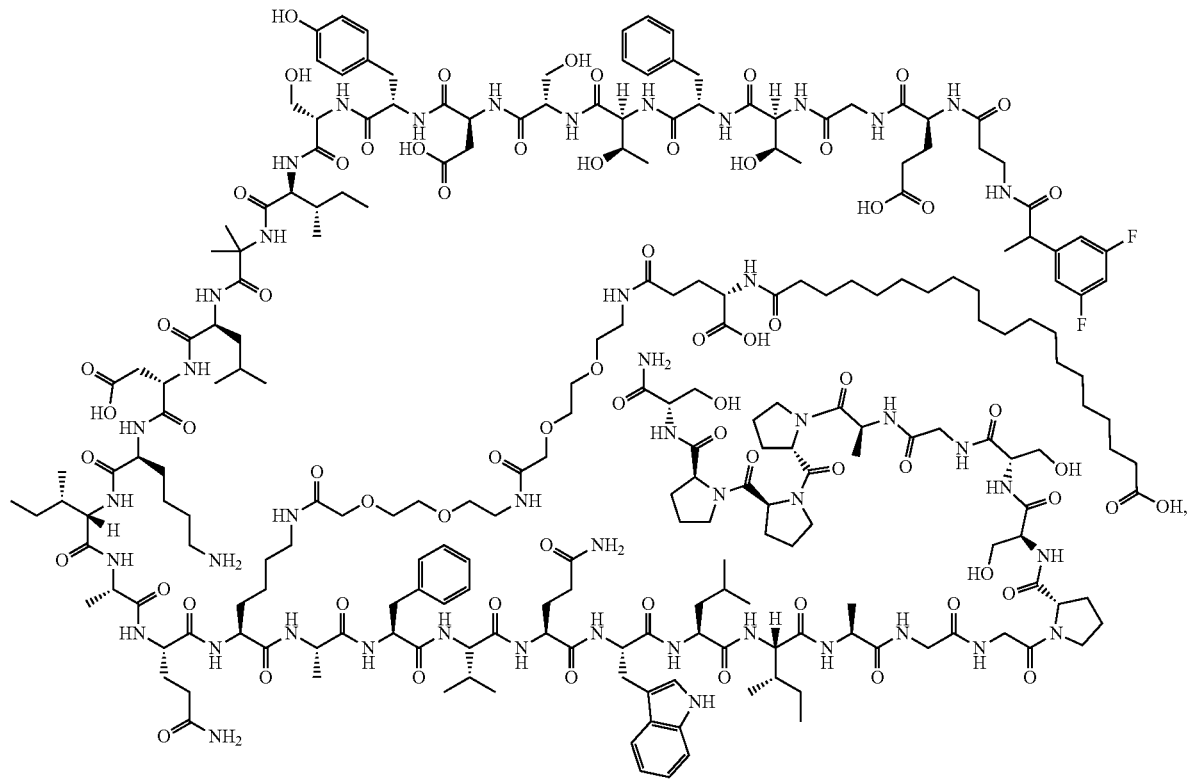
Compound 217
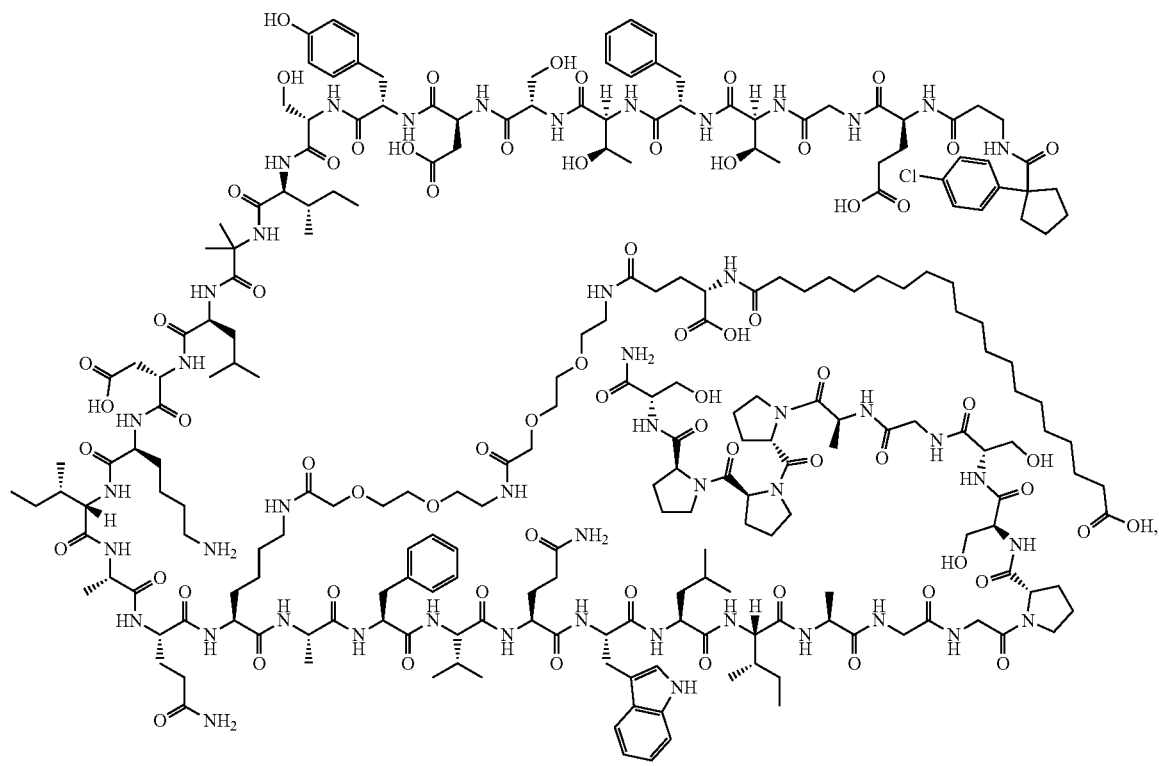

-continued
Compound 218
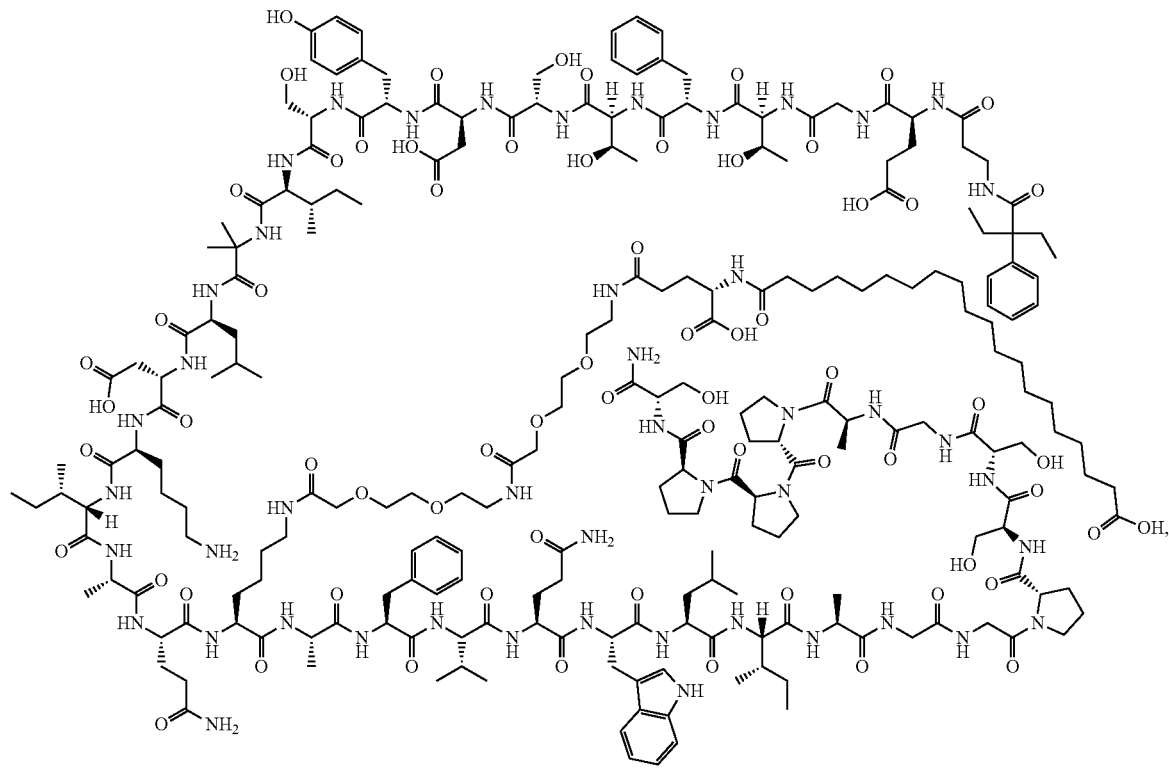
Compound 219
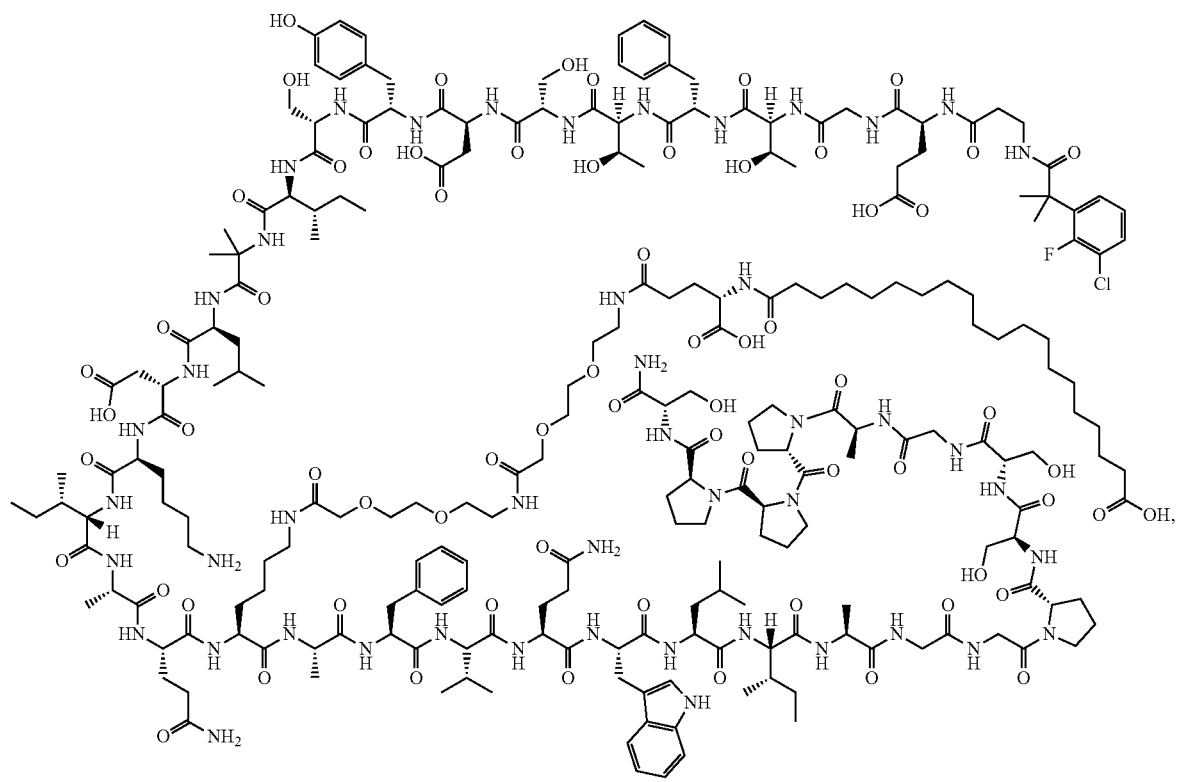

-continued
Compound 220
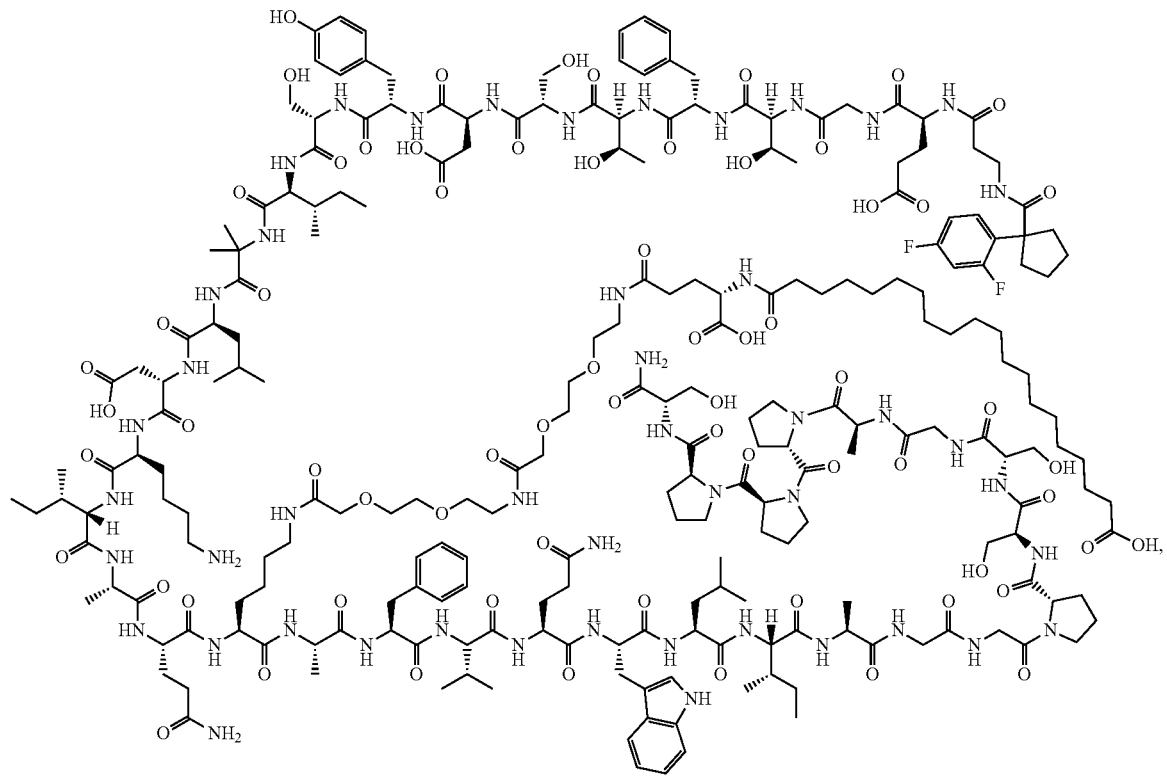
Compound 221
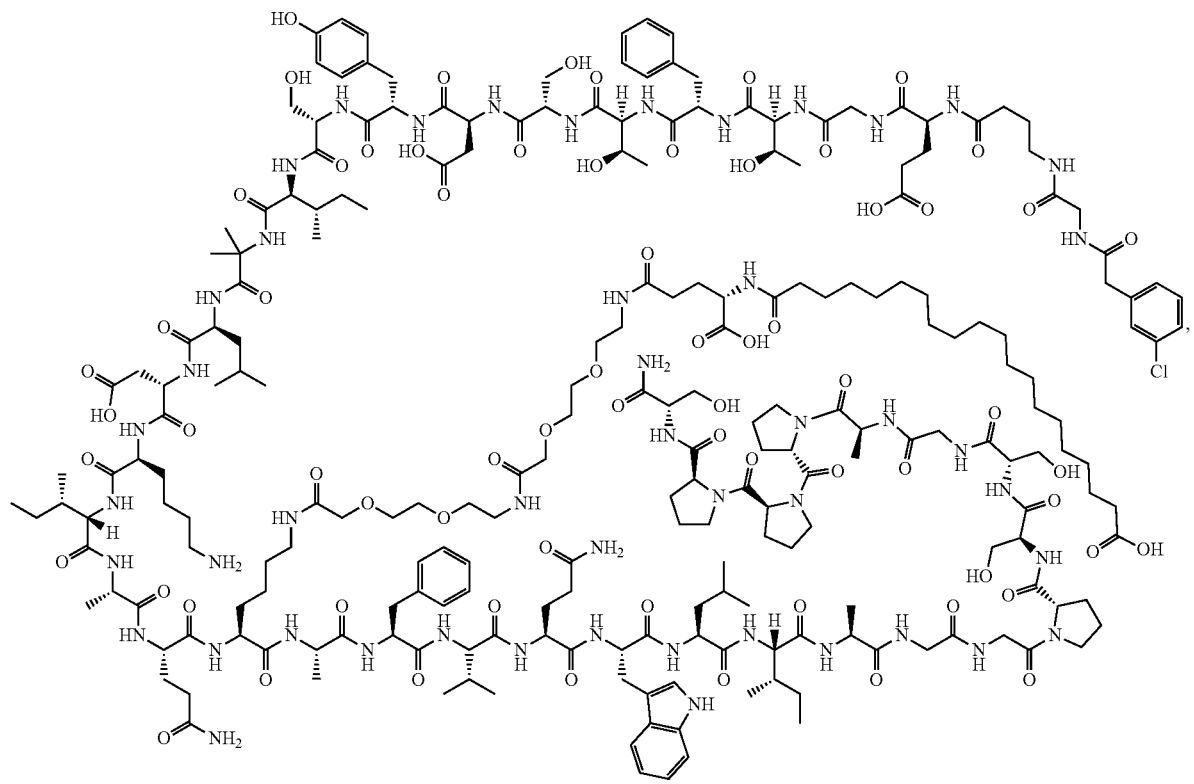

Compound 222
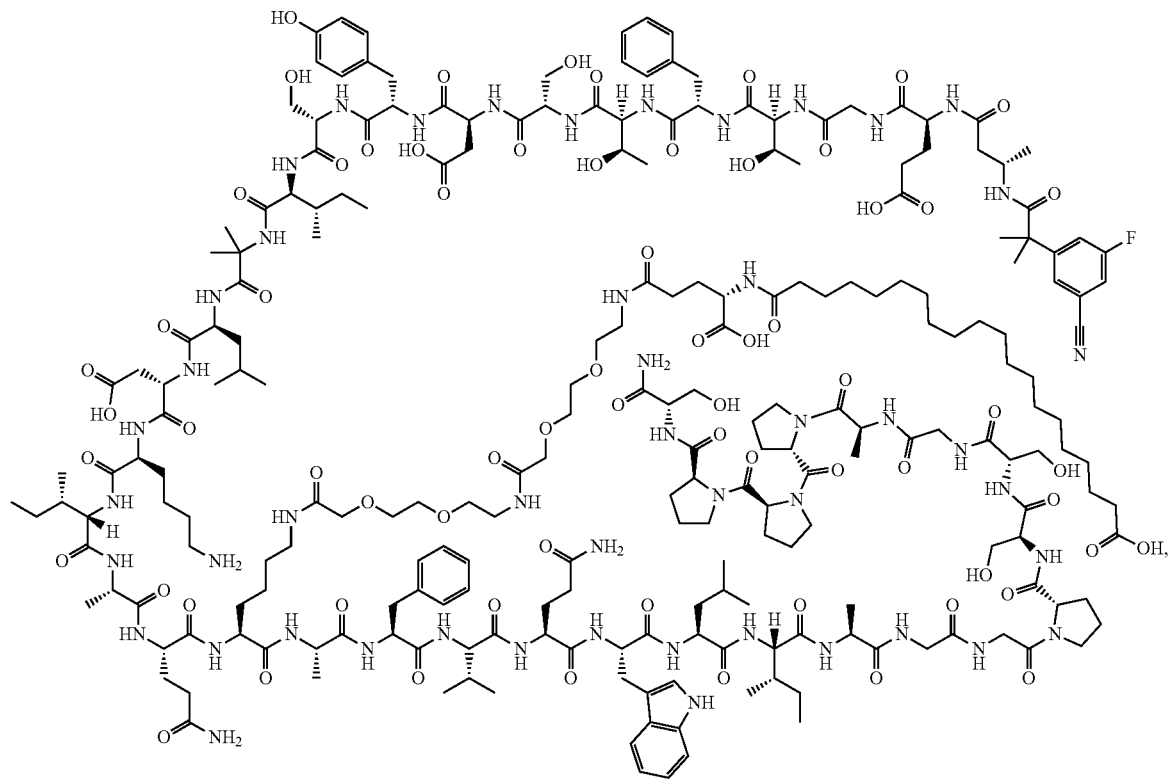
Compound 223
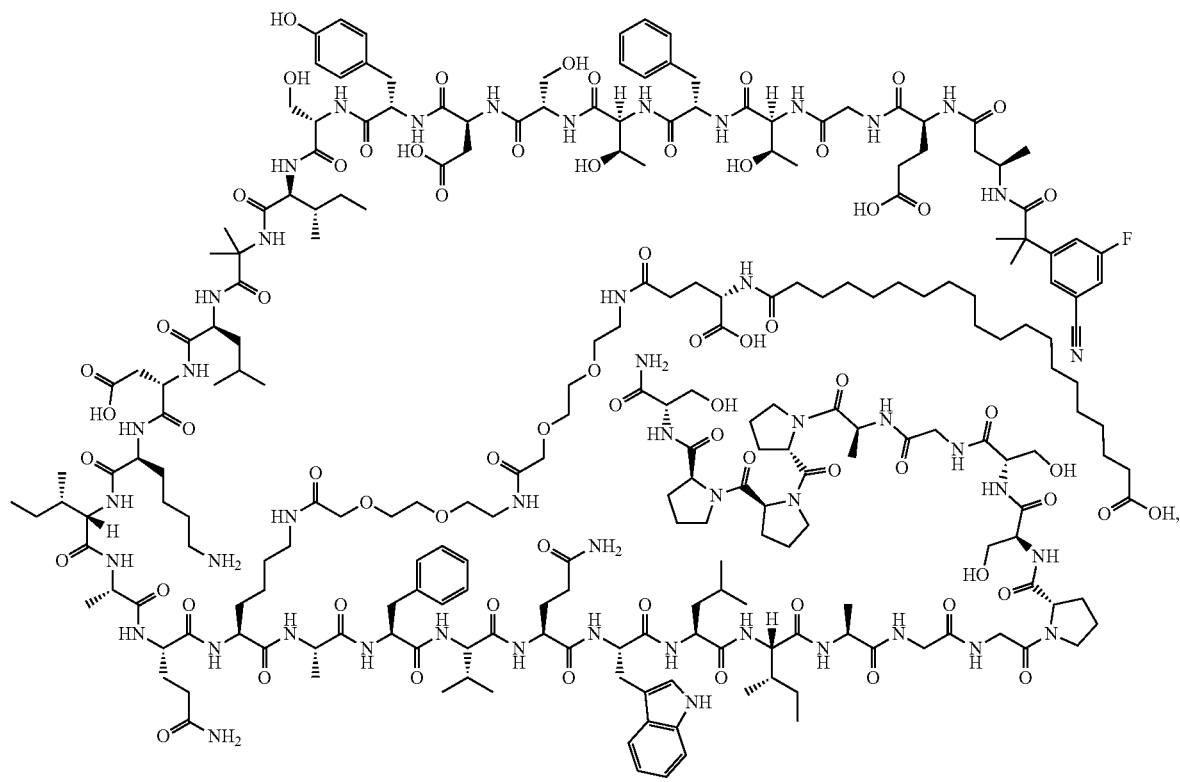

Compound 224
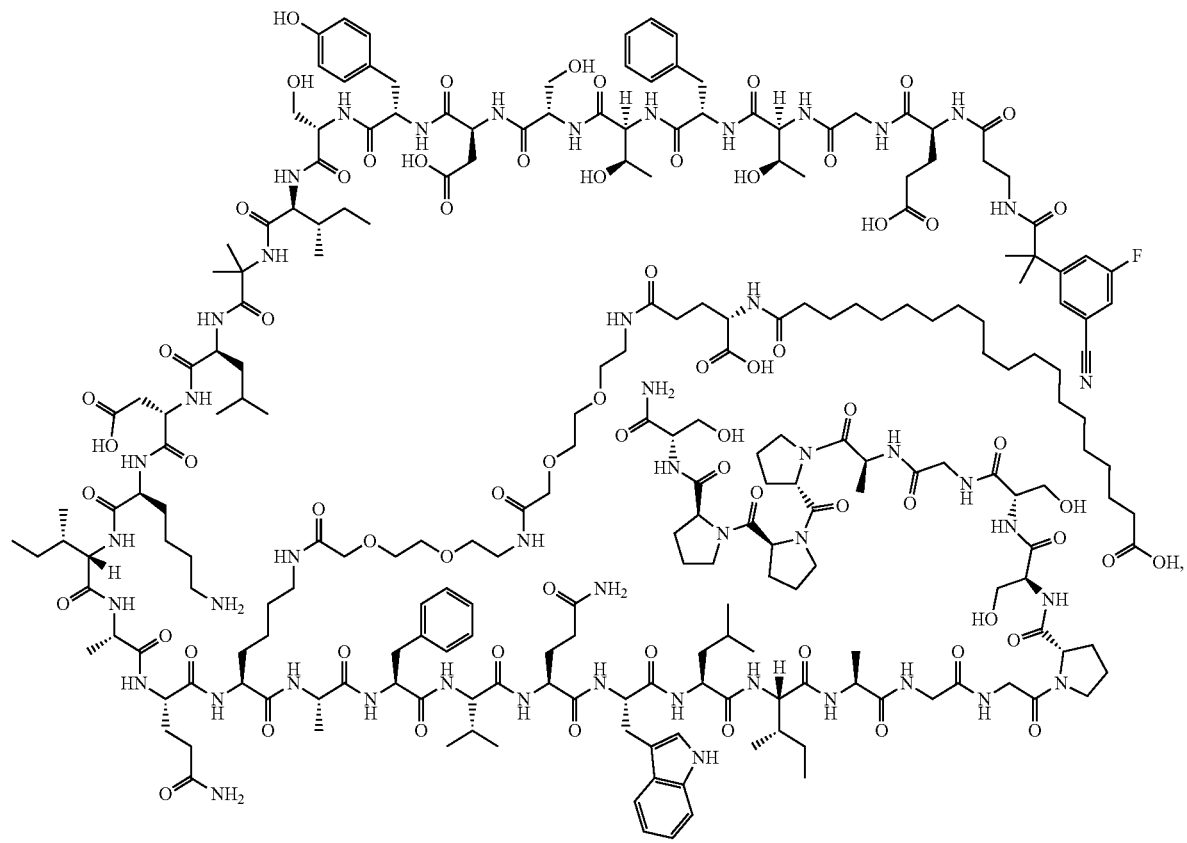
Compound 225
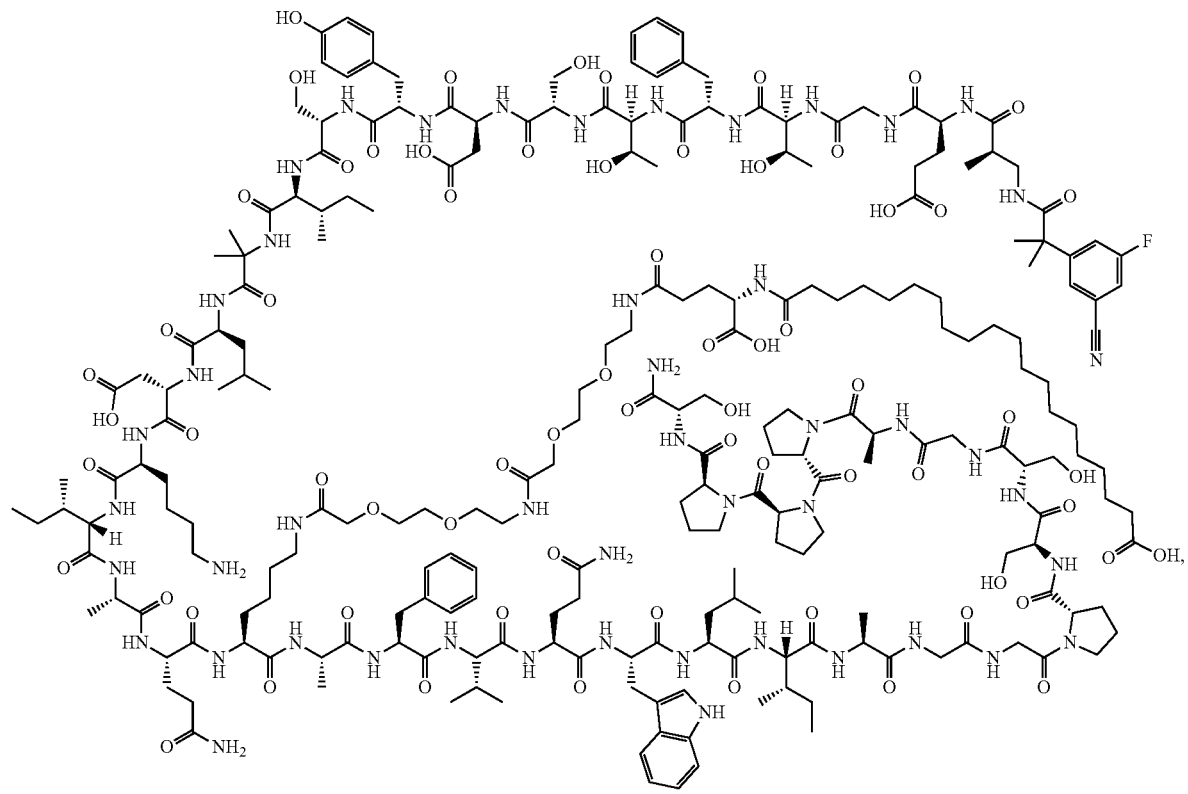

Compound 226
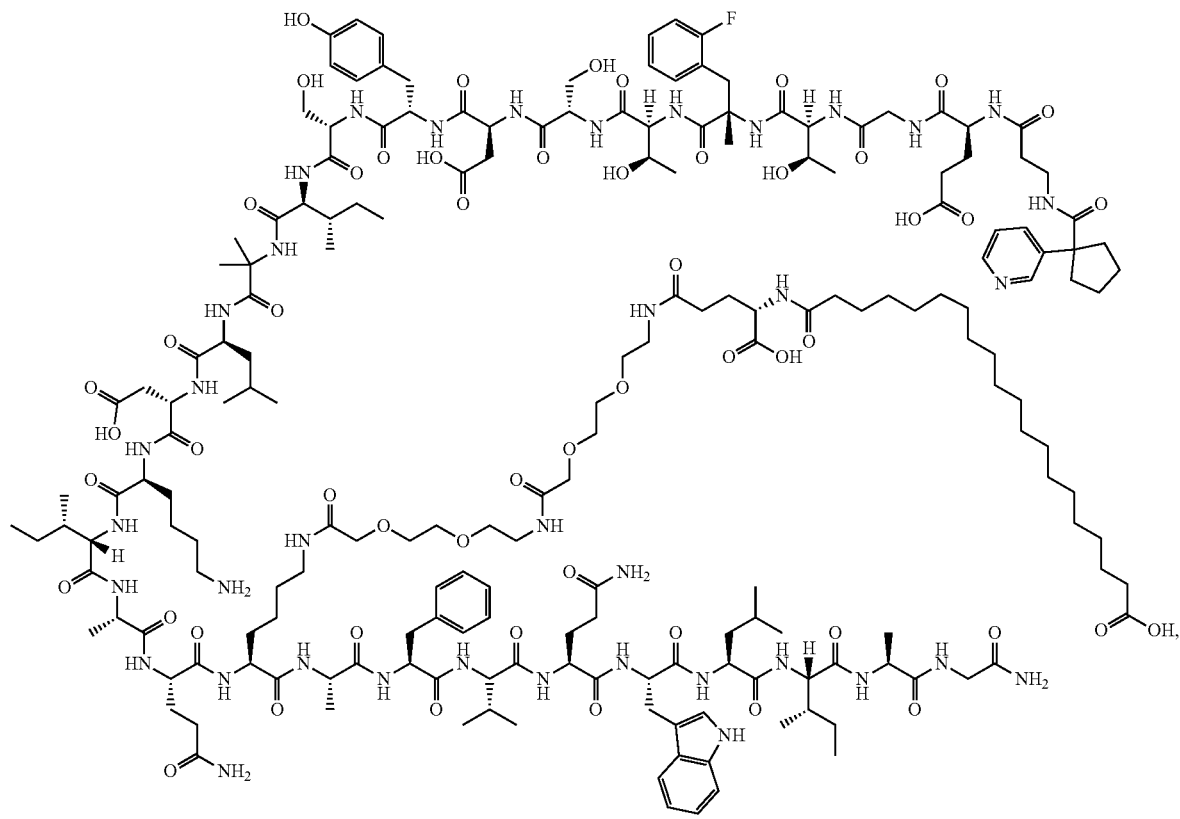
Compound 227
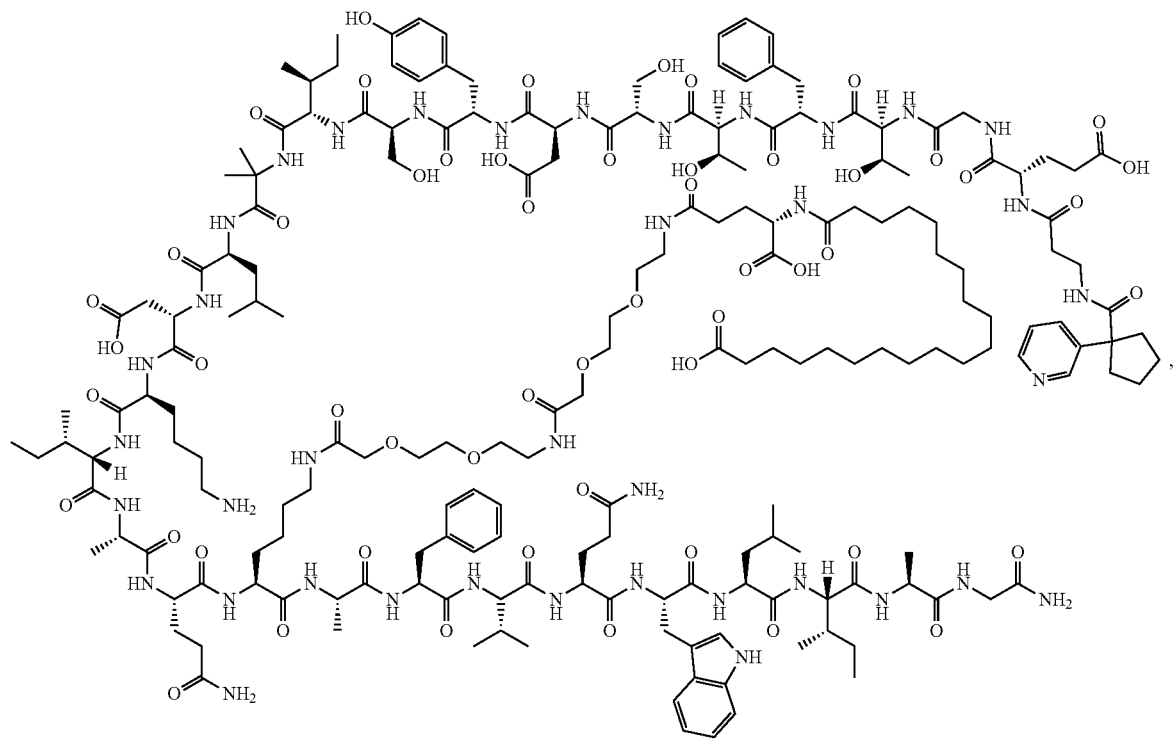

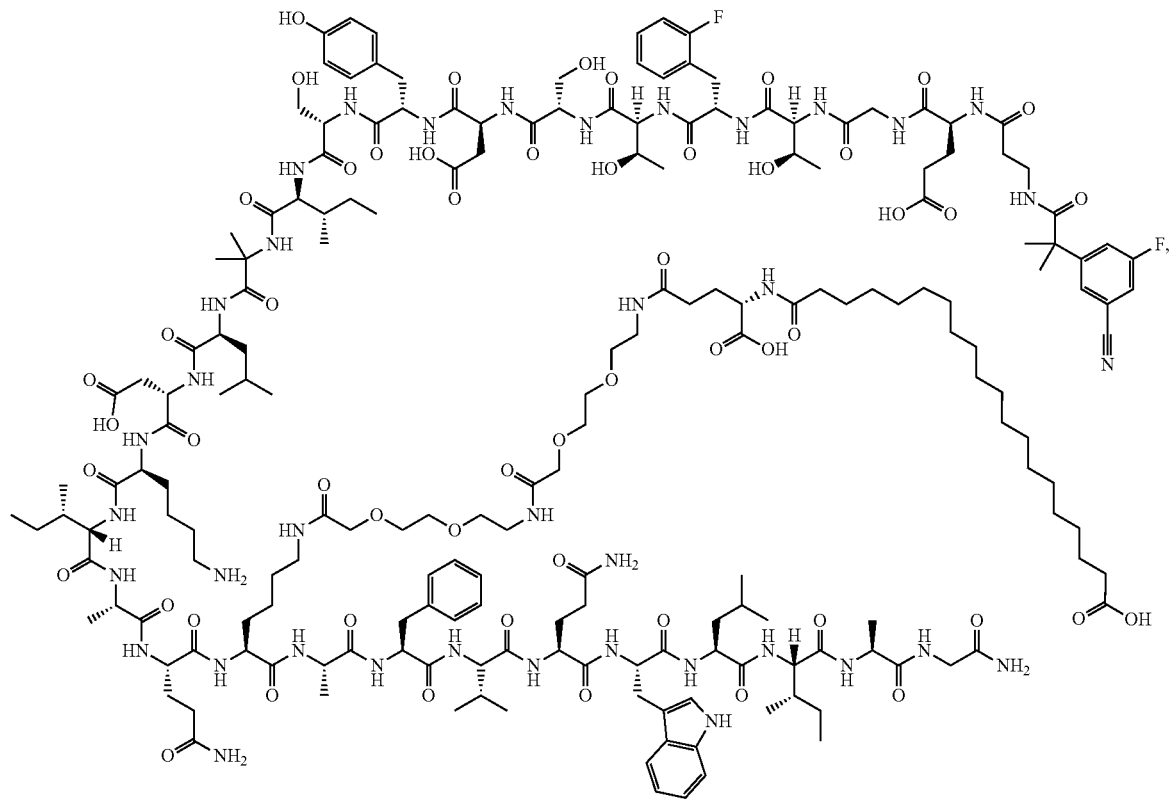
Compound 228
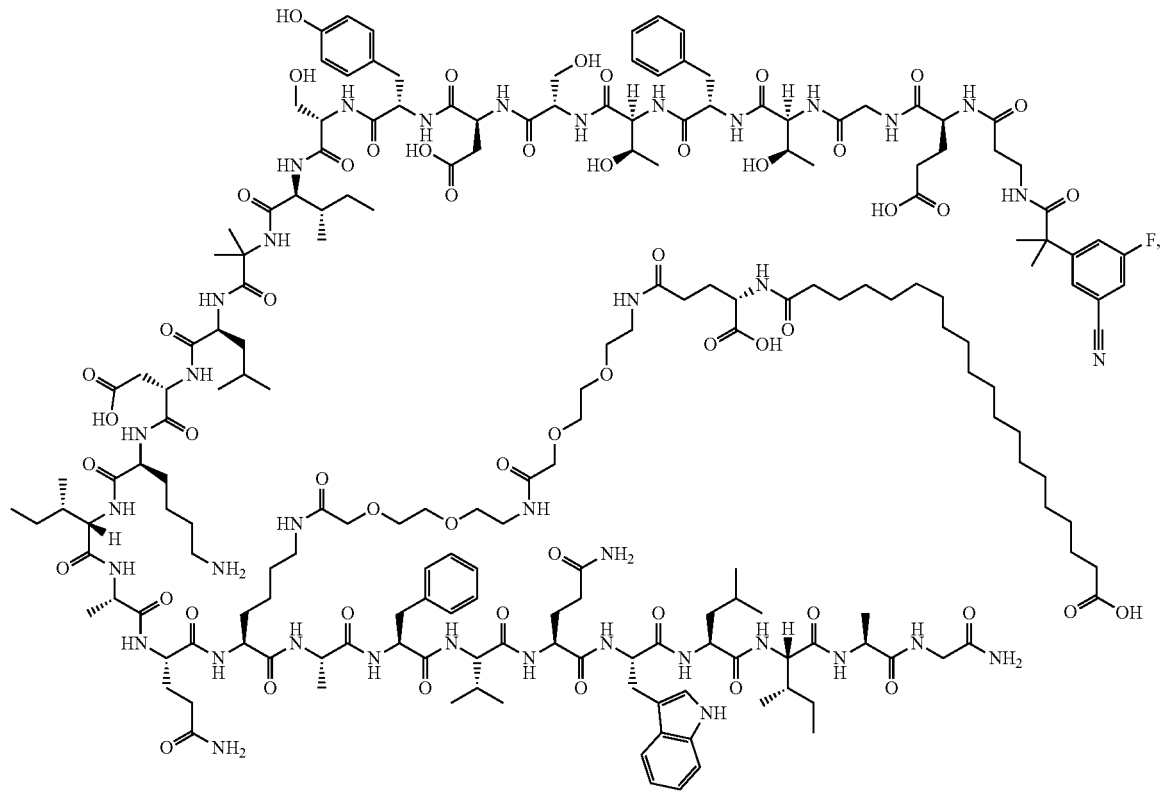
Compound 229

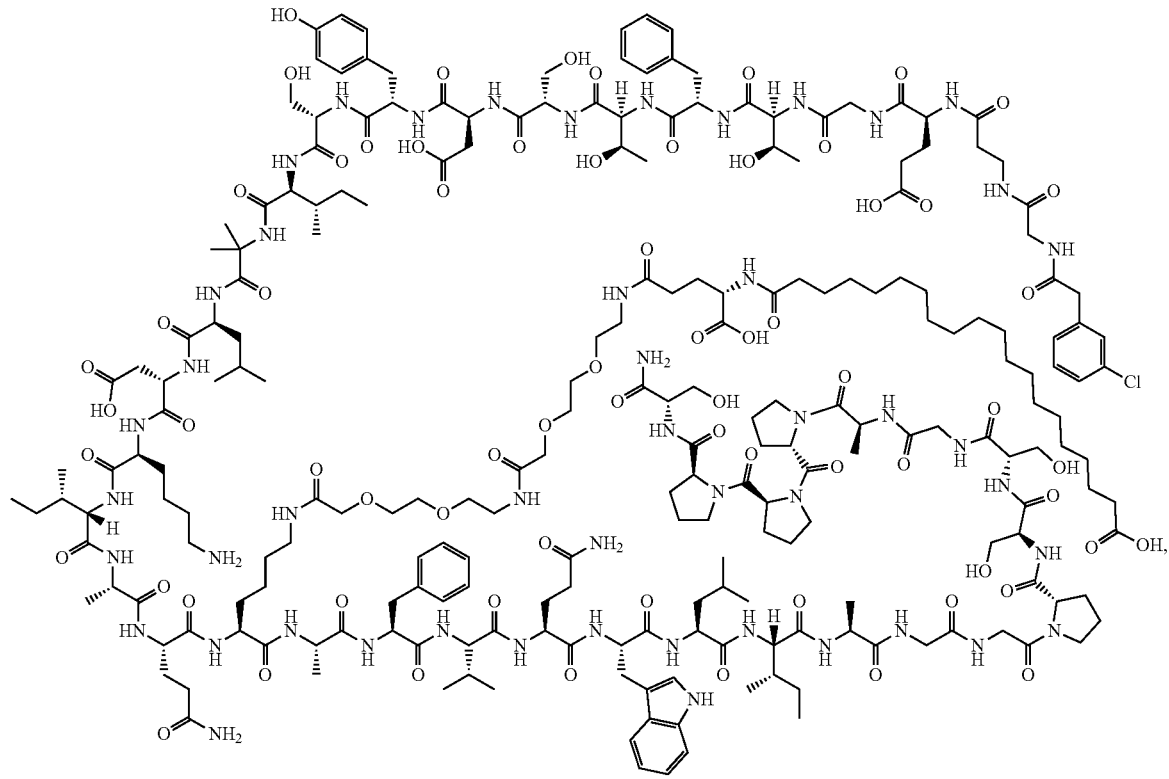
Compound 230
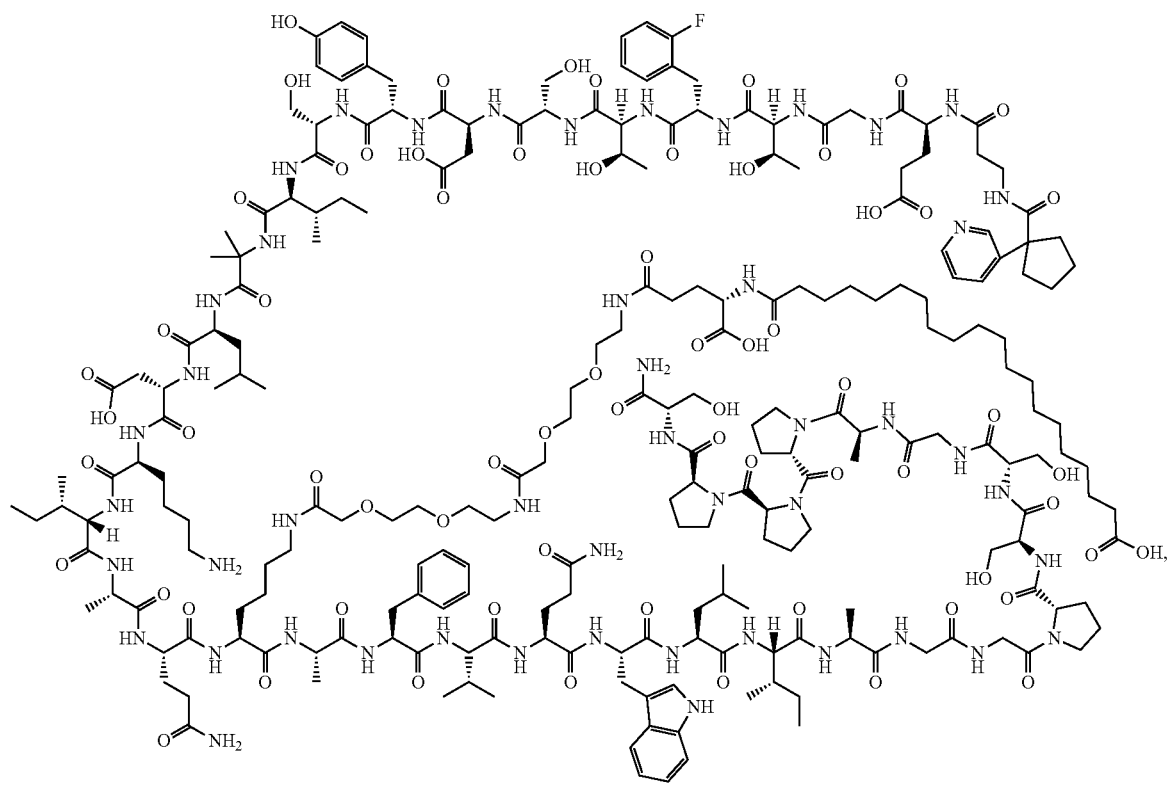
Compound 231

Compound 233
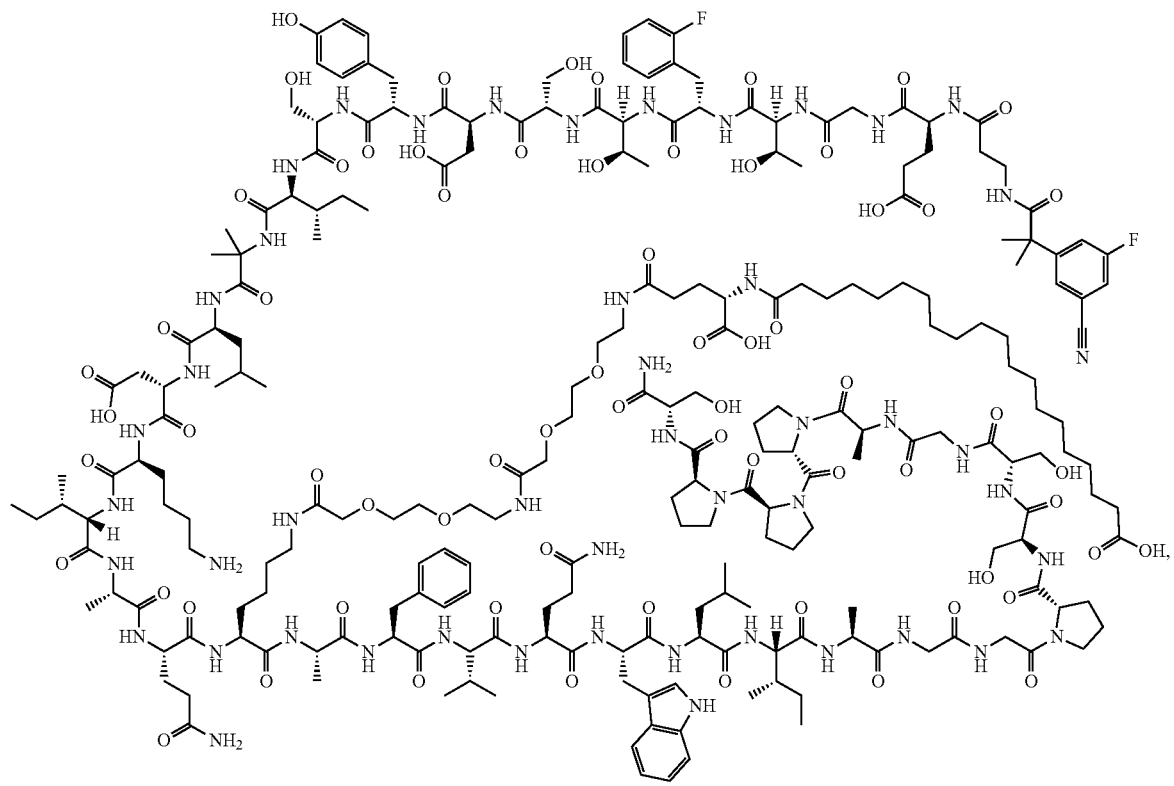
Compound 234
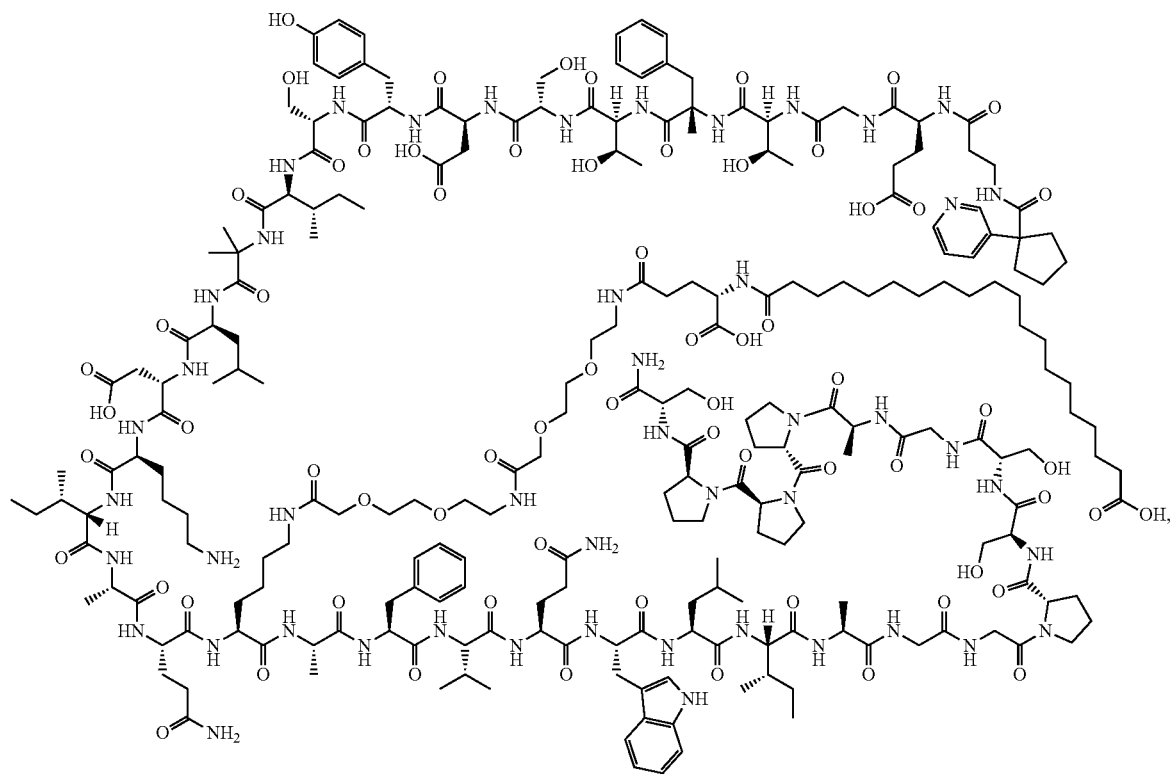

Compound 235
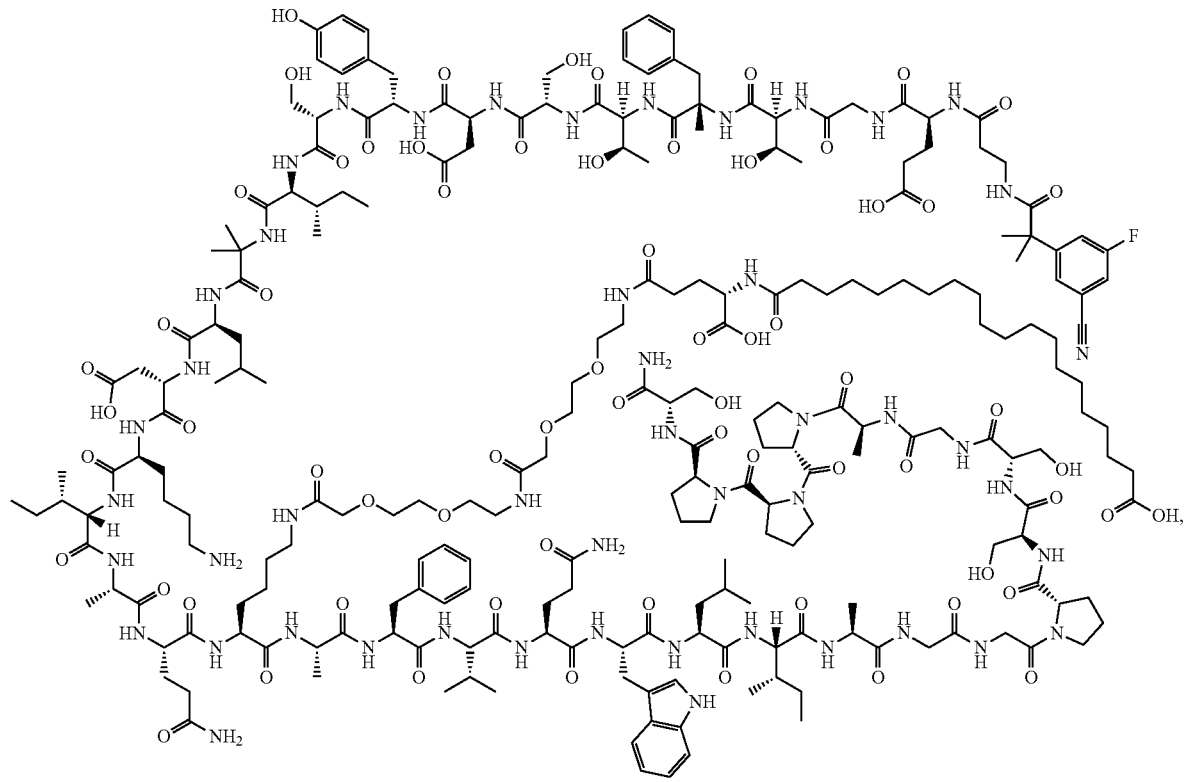
Compound 236
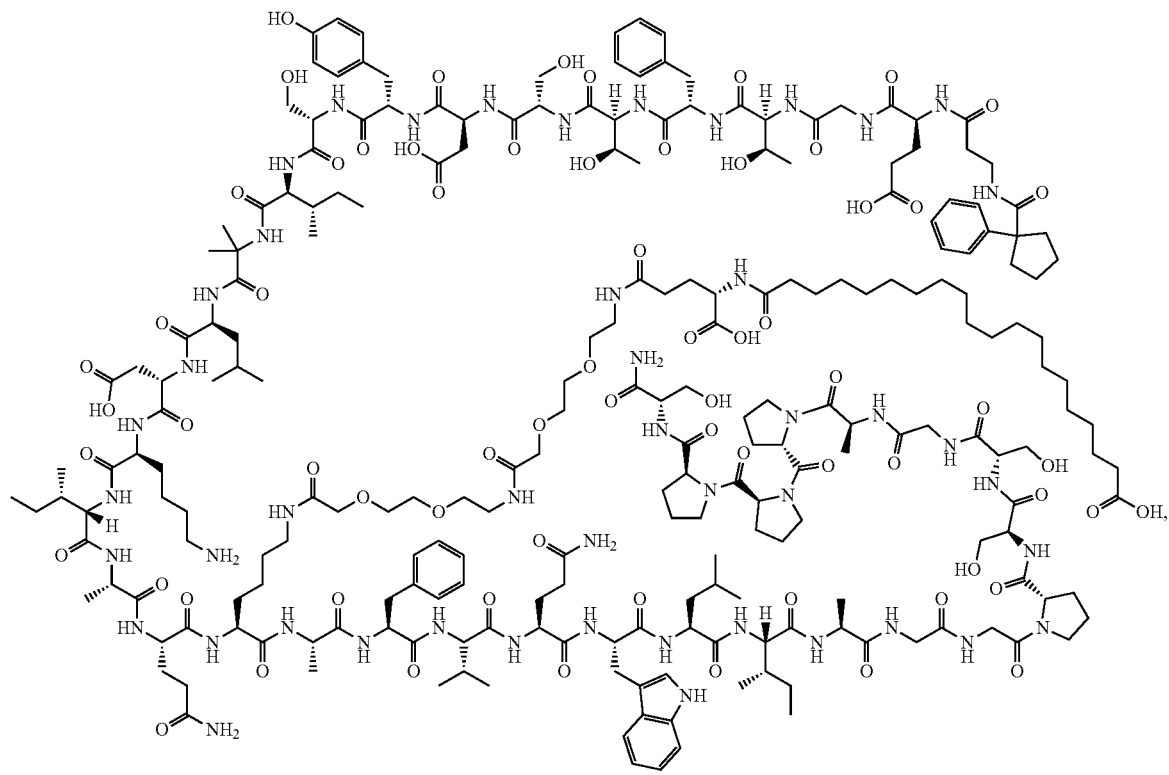

-continued
Compound 237
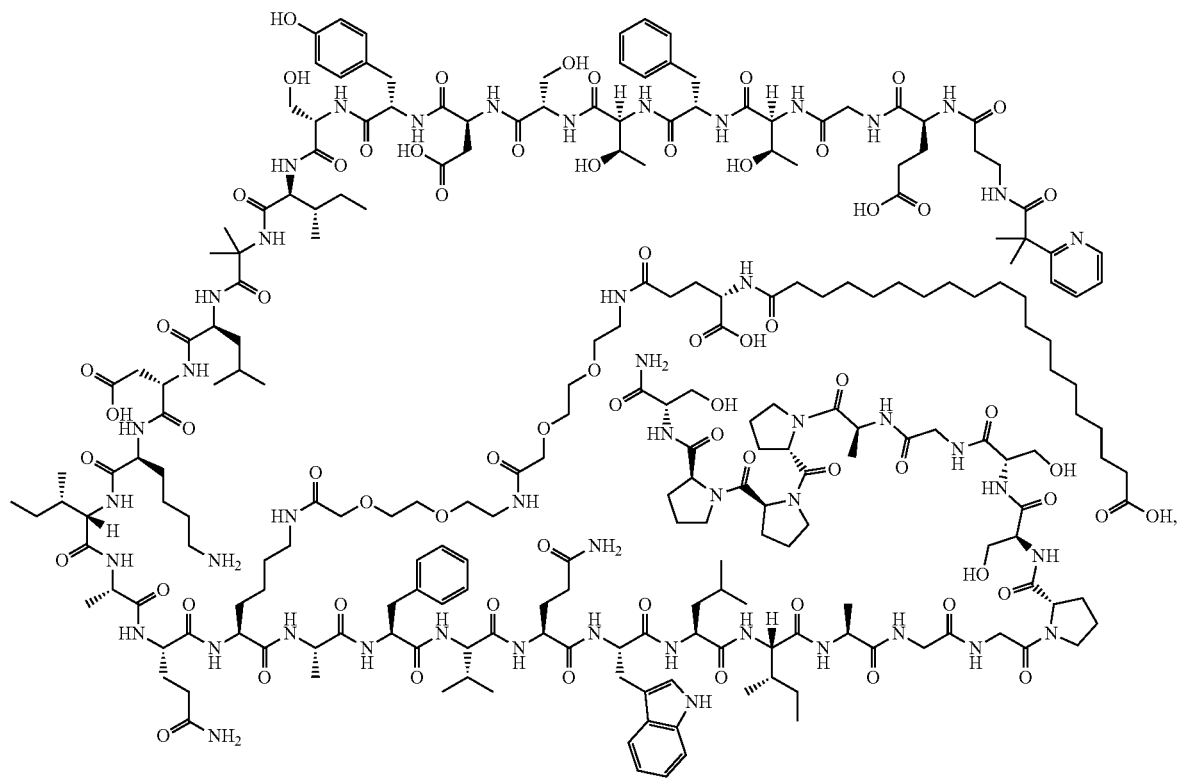
Compound 238
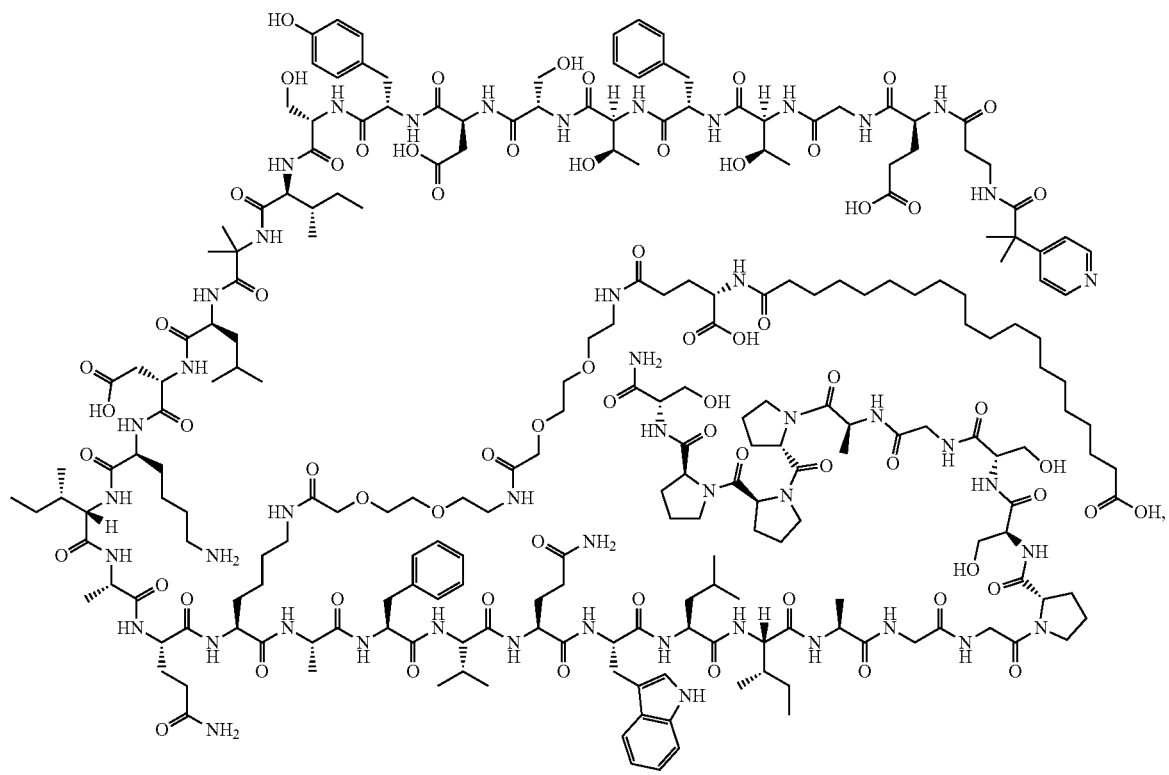

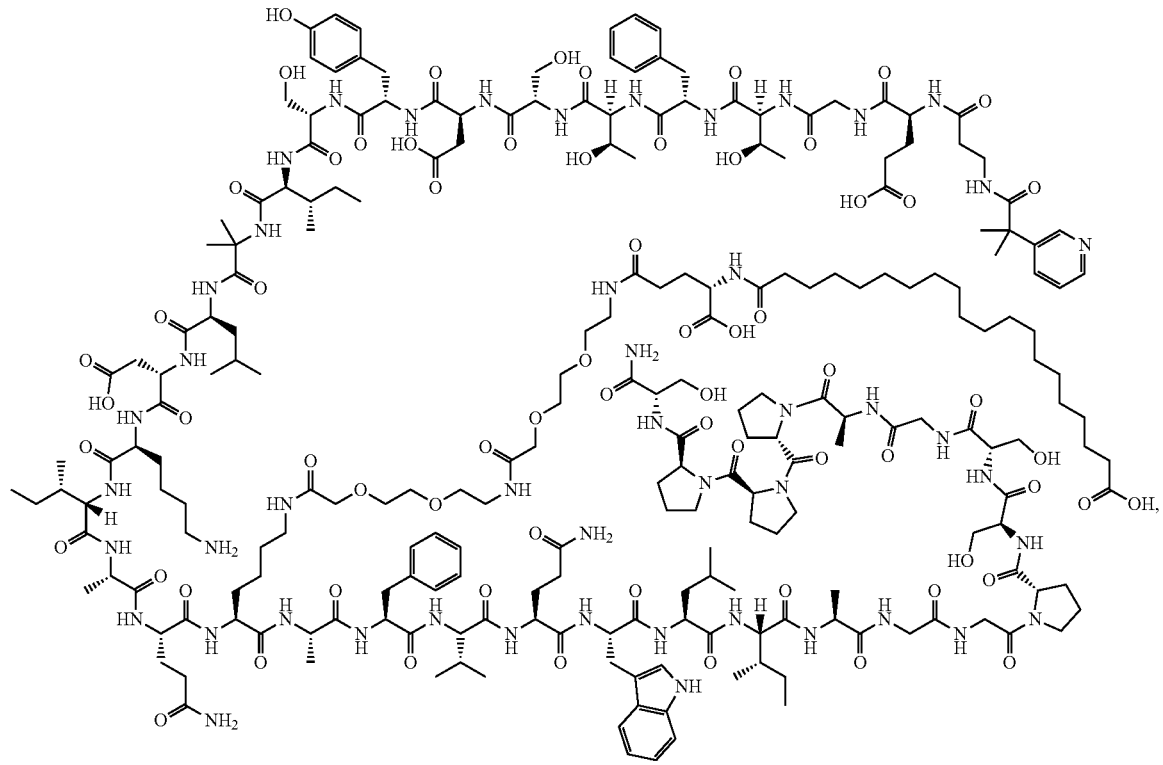
Compound 239
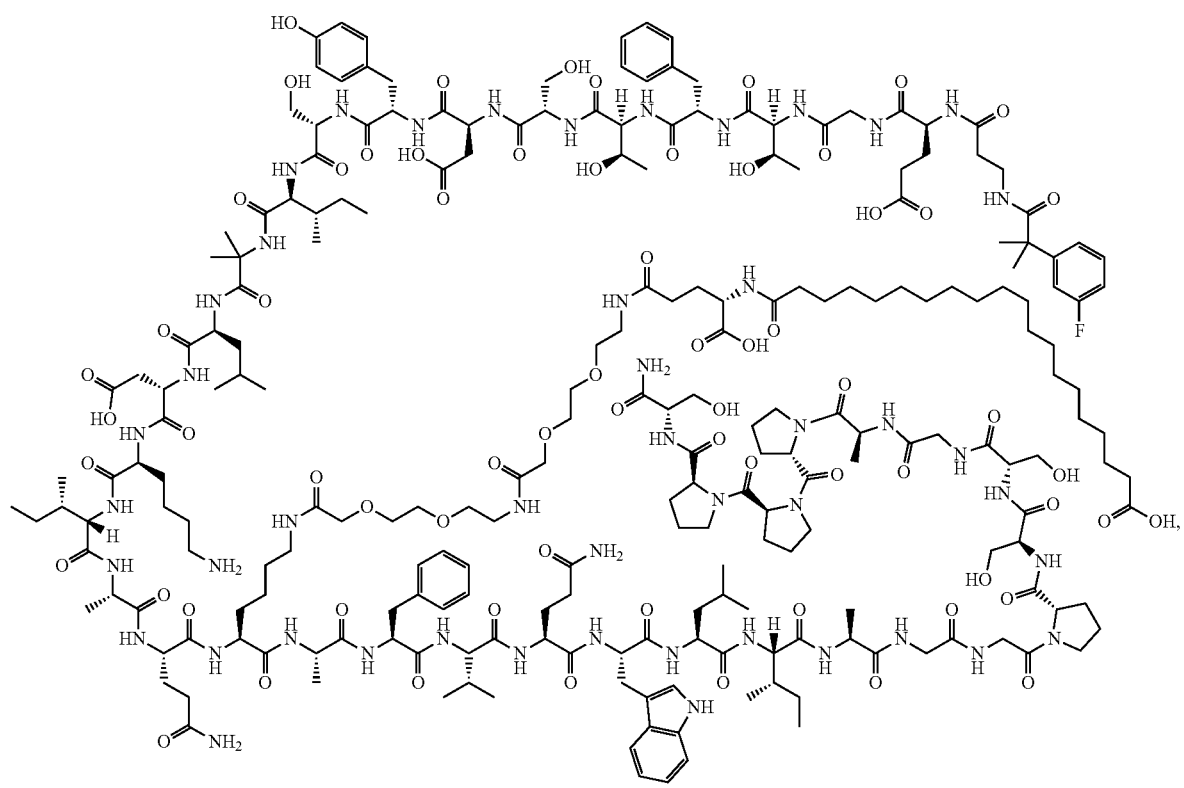
Compound 240

Compound 241
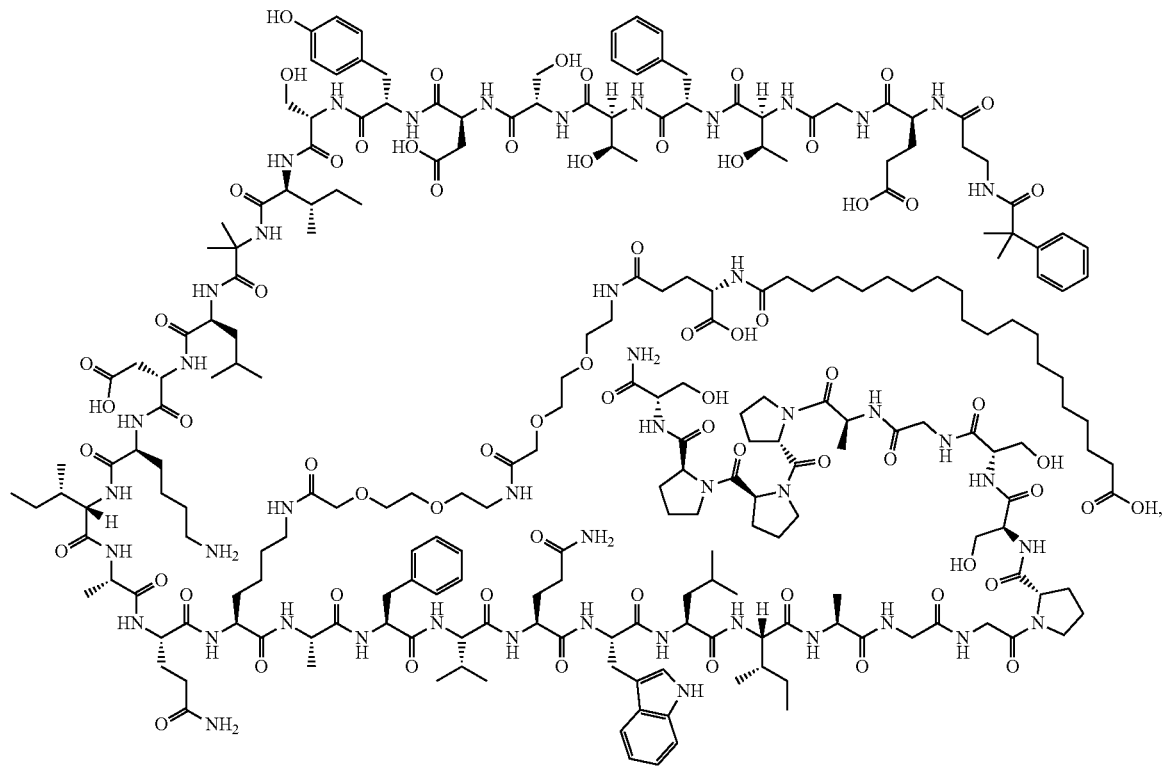
Compound 242
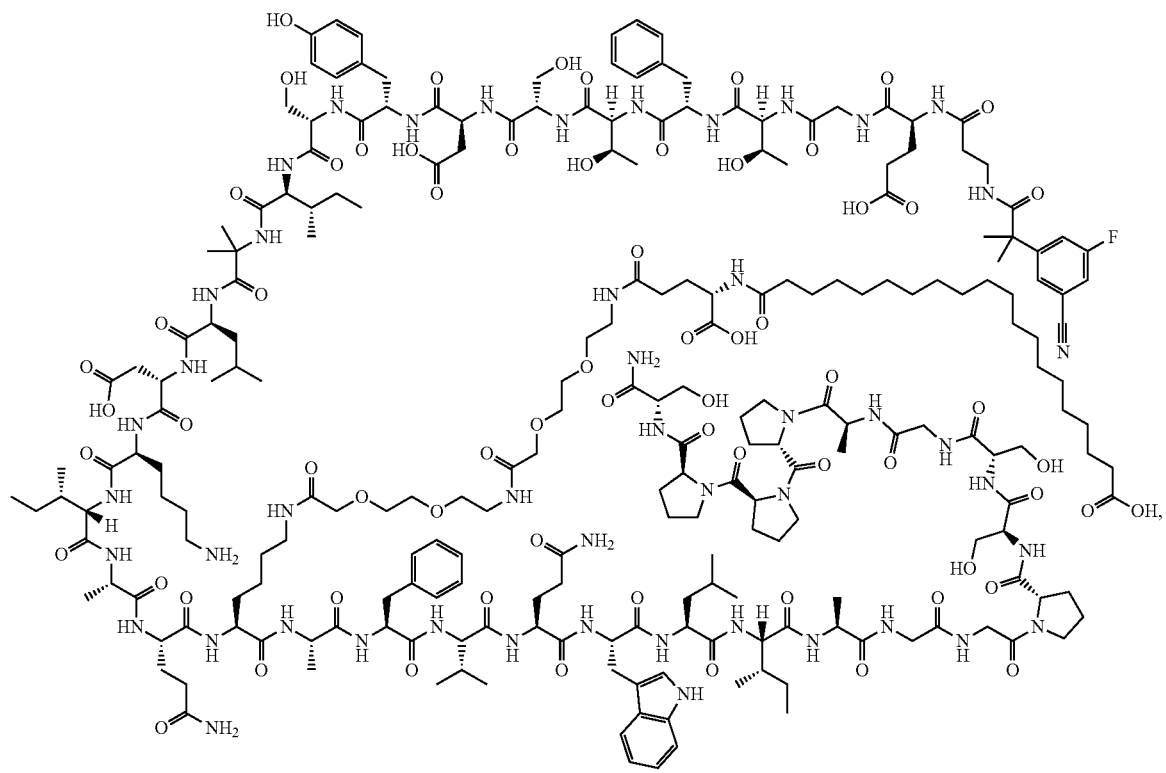

-continued
Compound 243
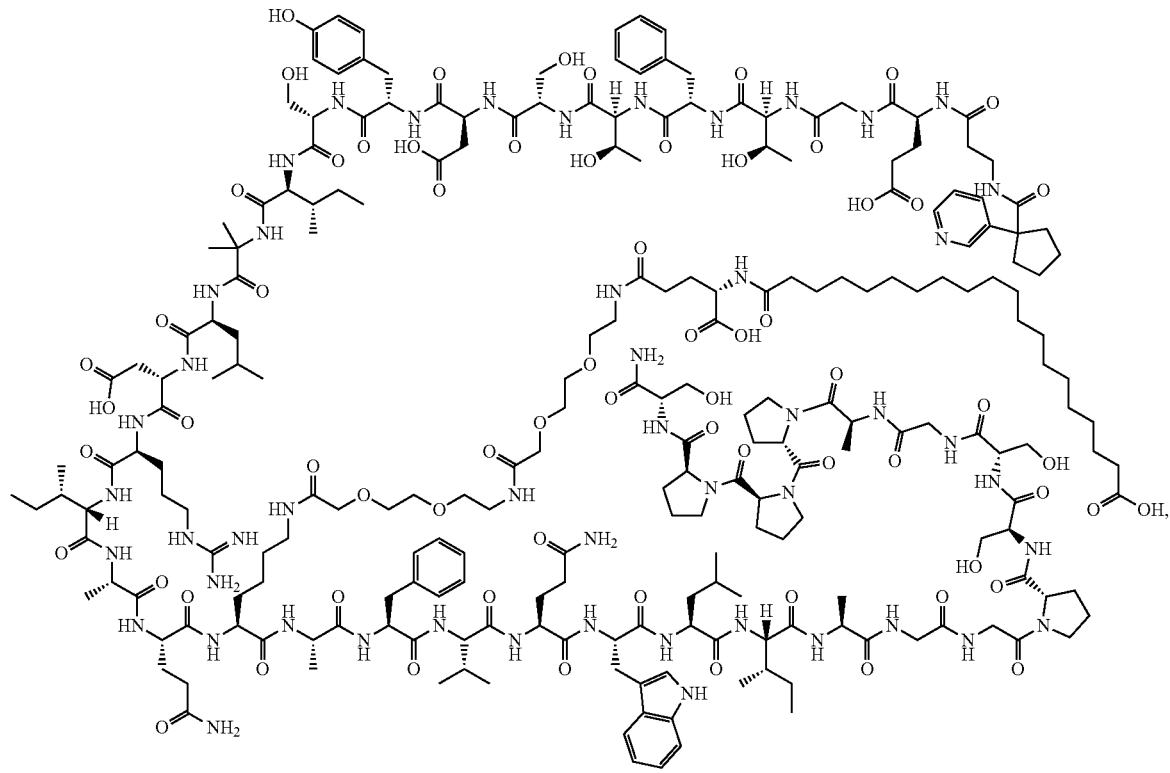
Compound 244
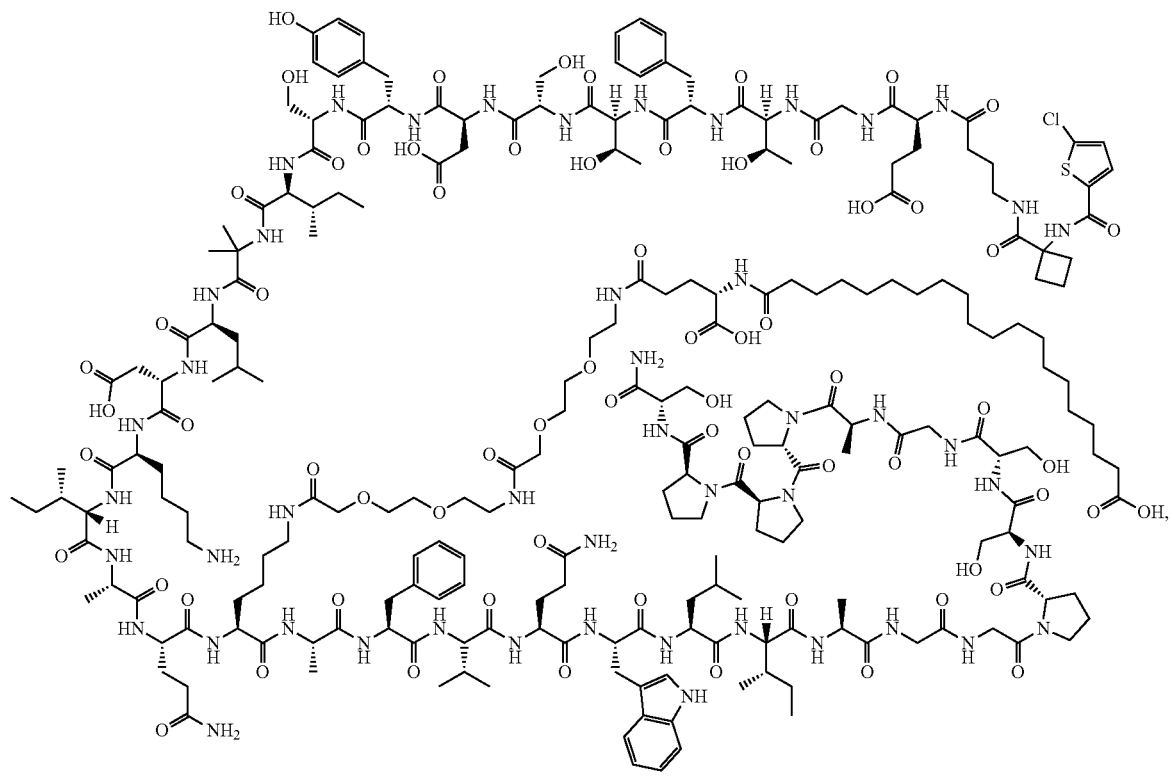

Compound 245
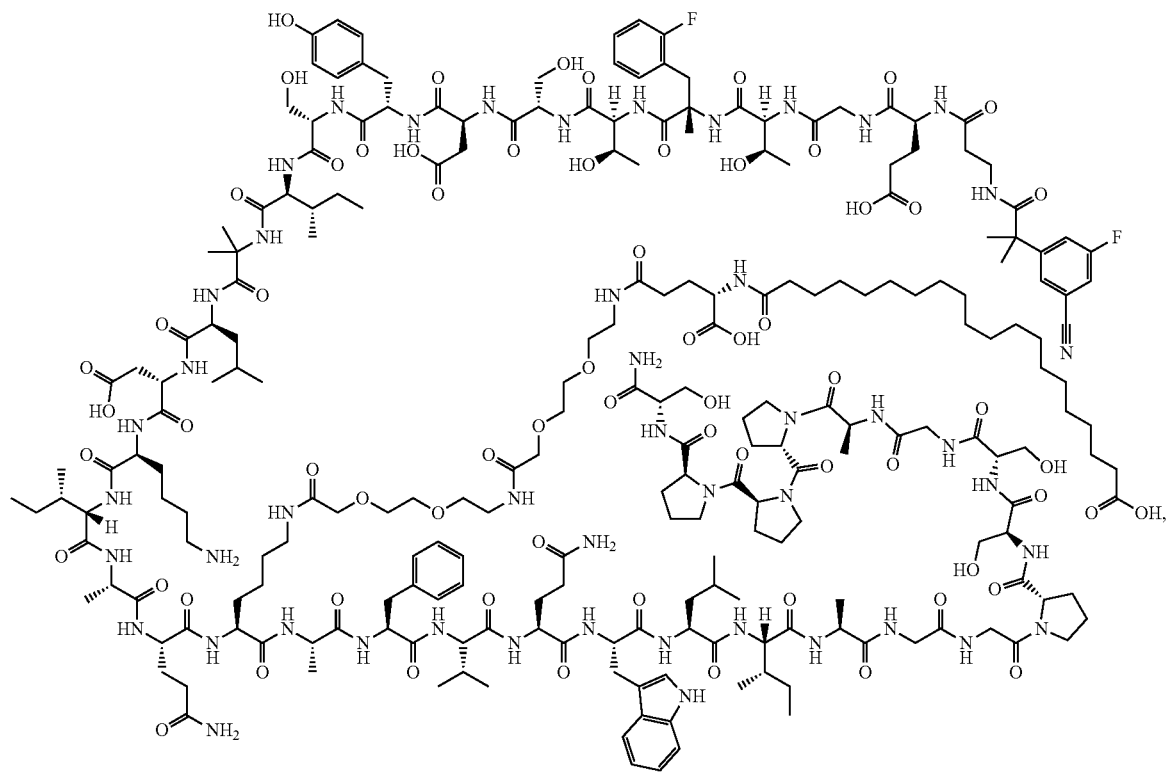
Compound 246
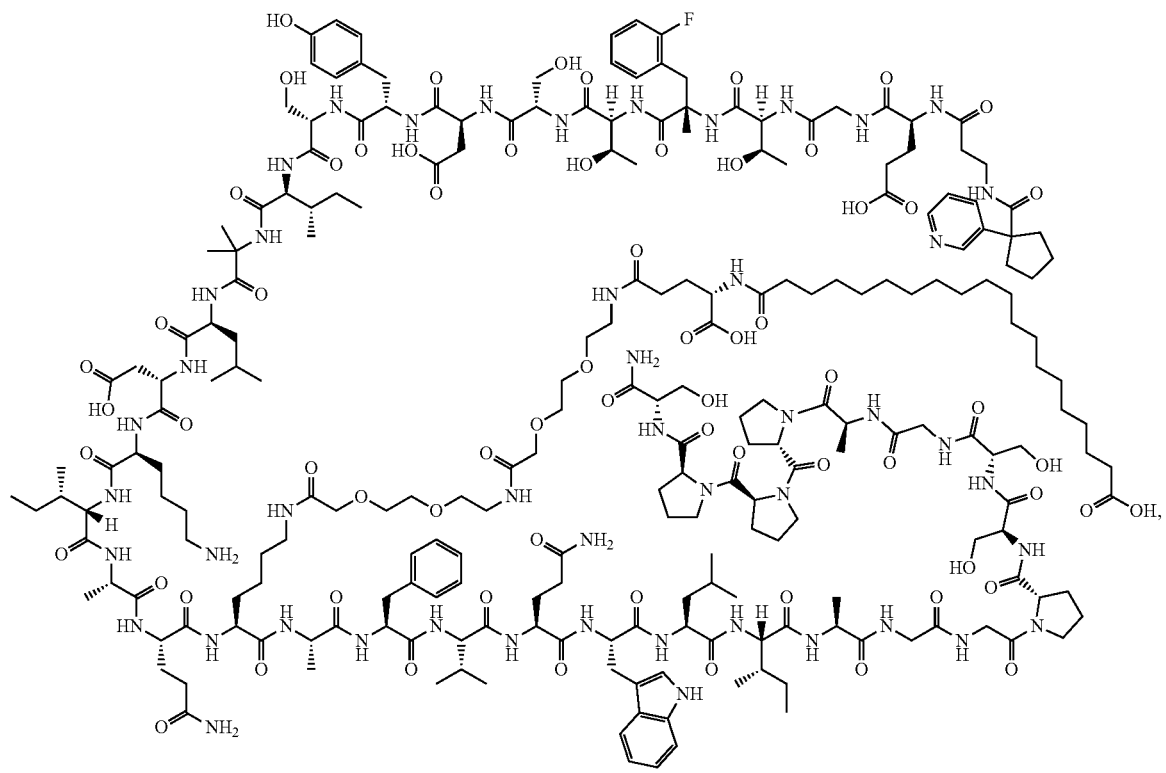

Compound 247
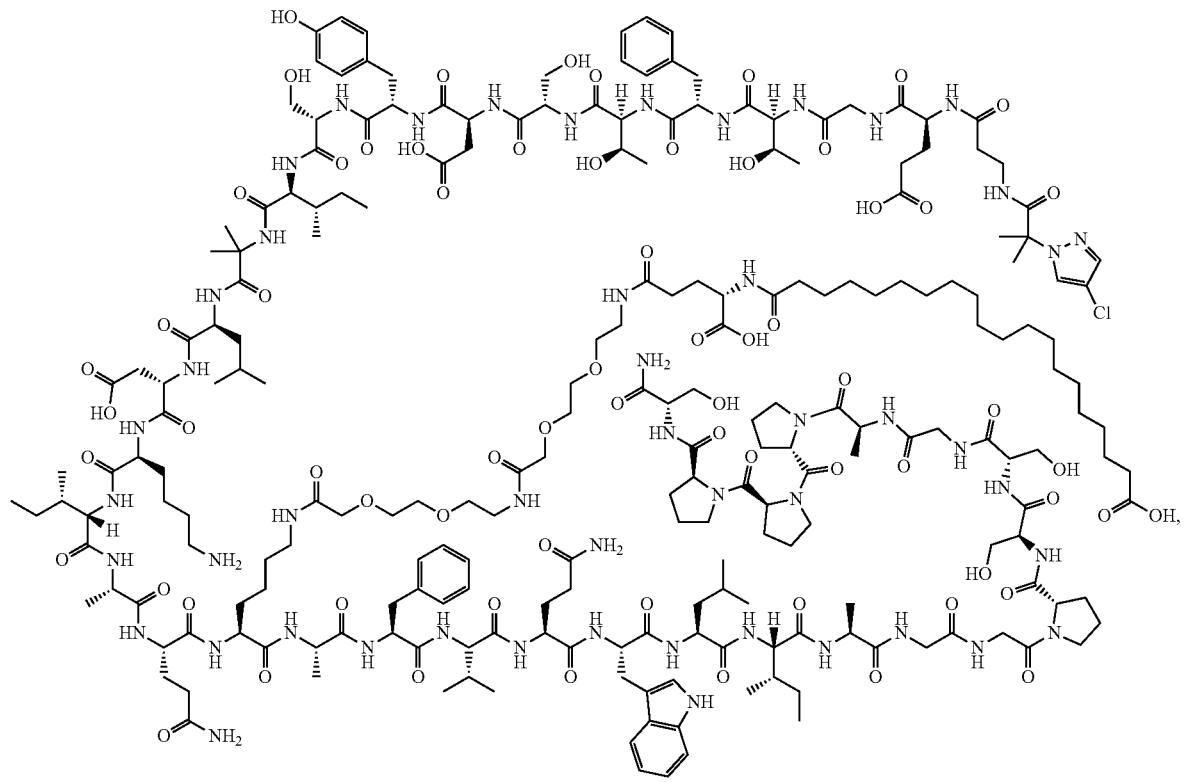
Compound 248
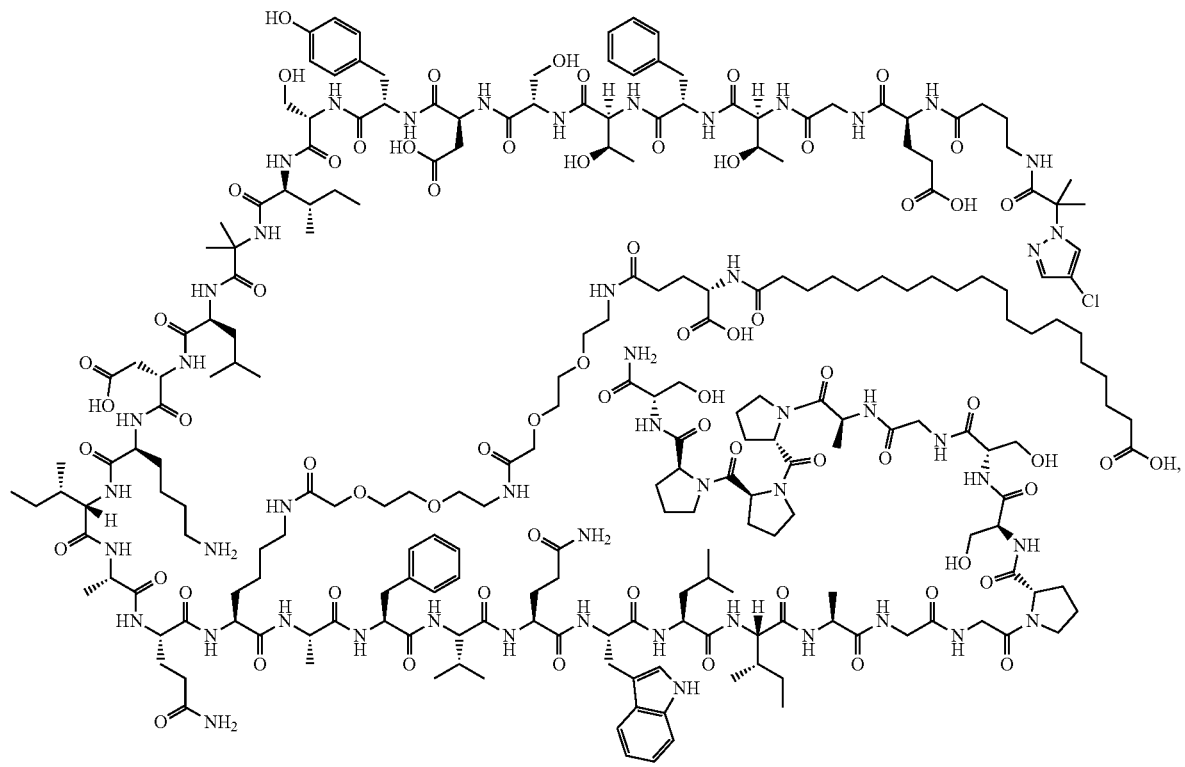

Compound 249
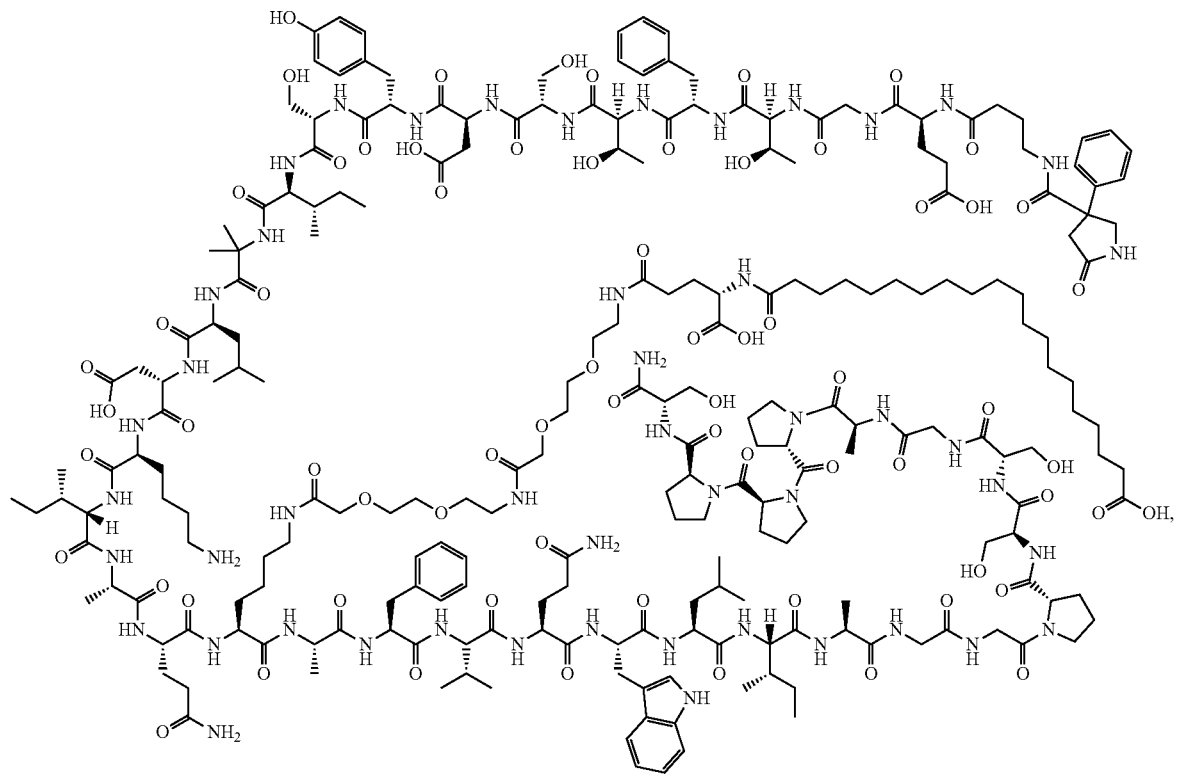
Compound 250
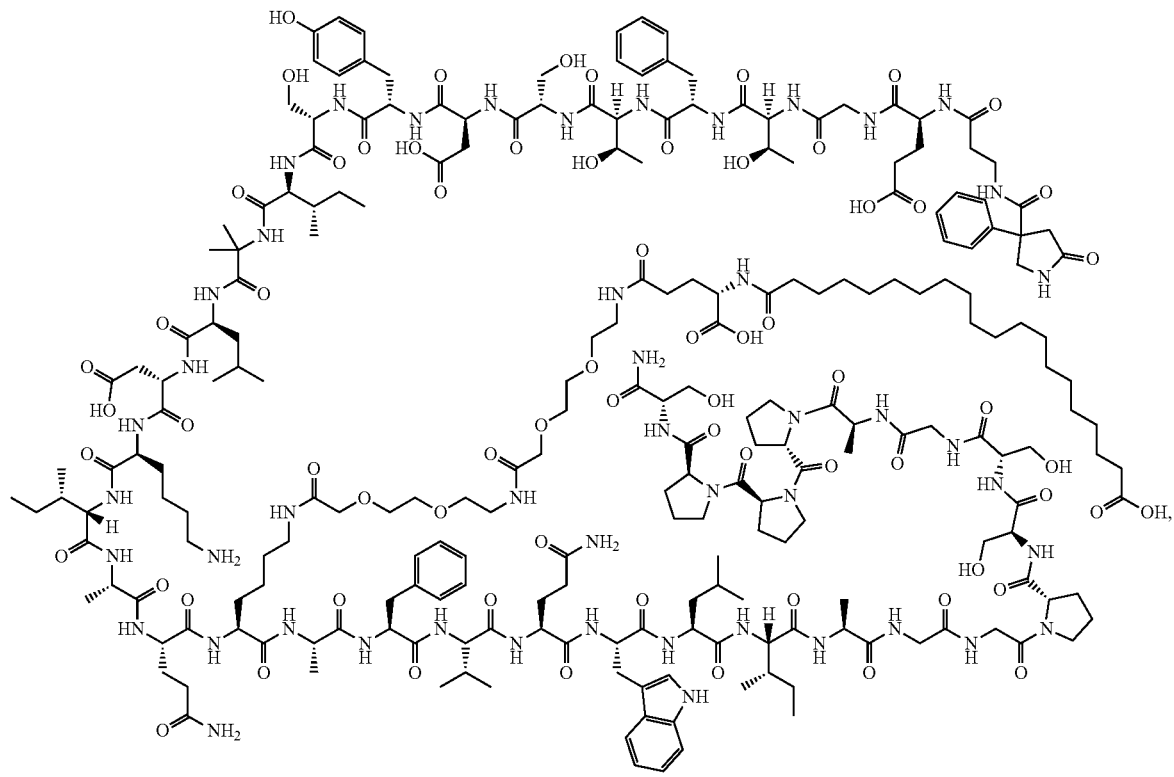

-continued
Compound 251
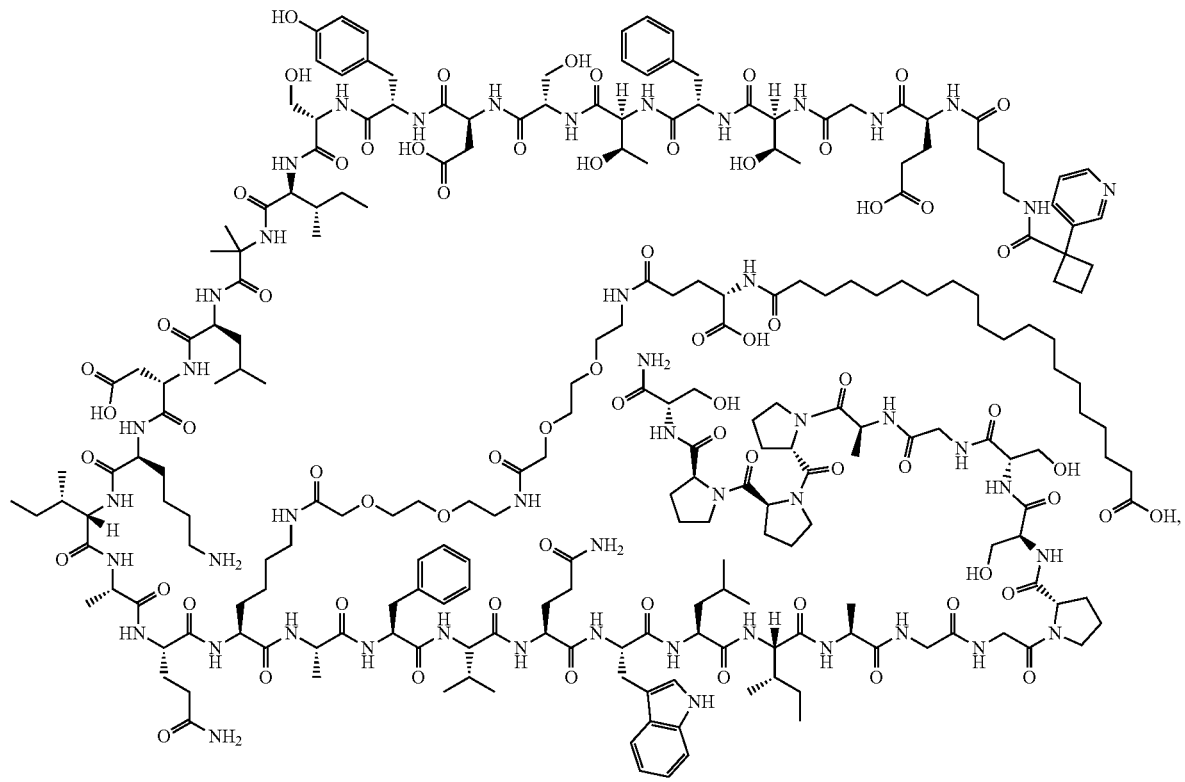
Compound 252
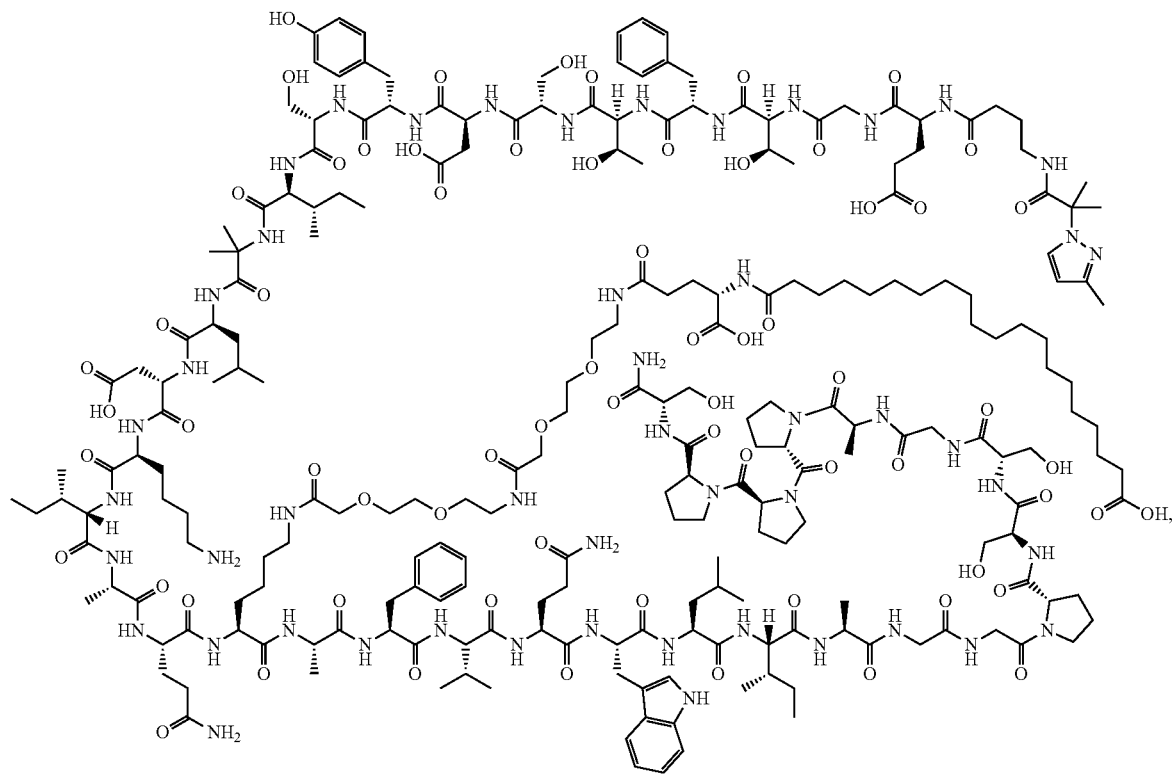

Compound 253
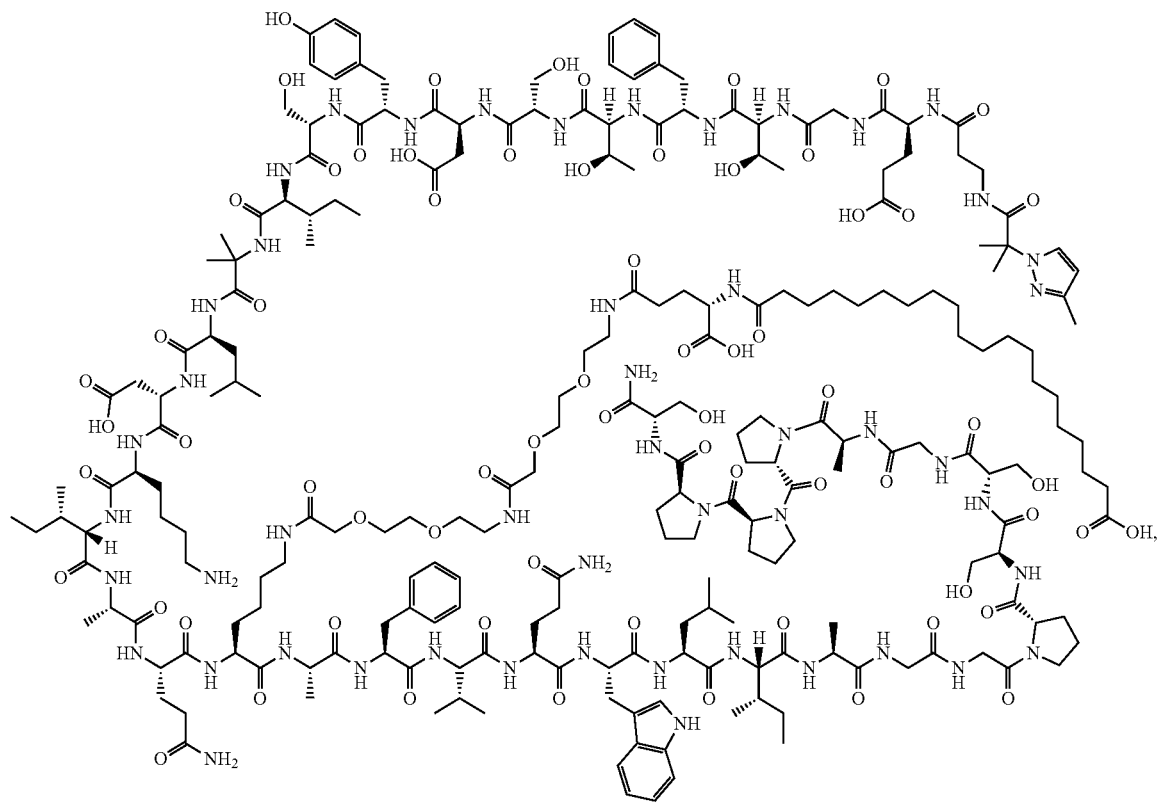
Compound 254
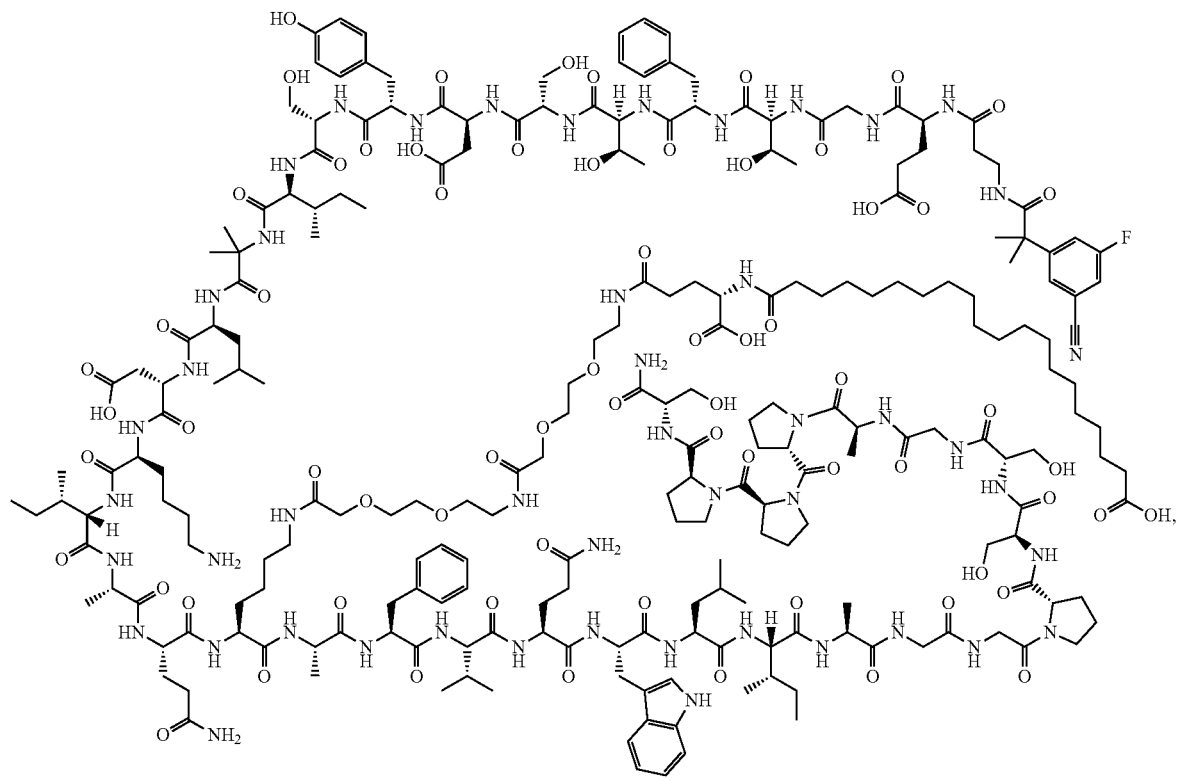

-continued
Compound 255
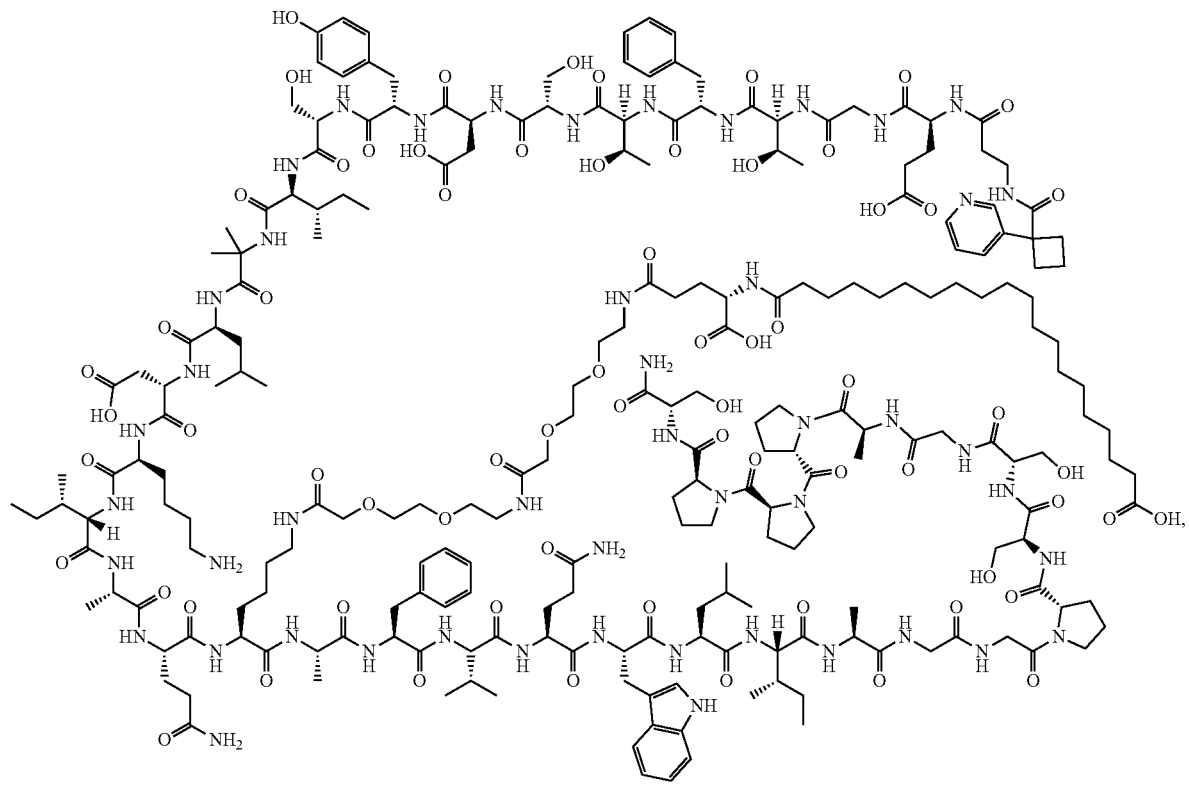
Compound 256
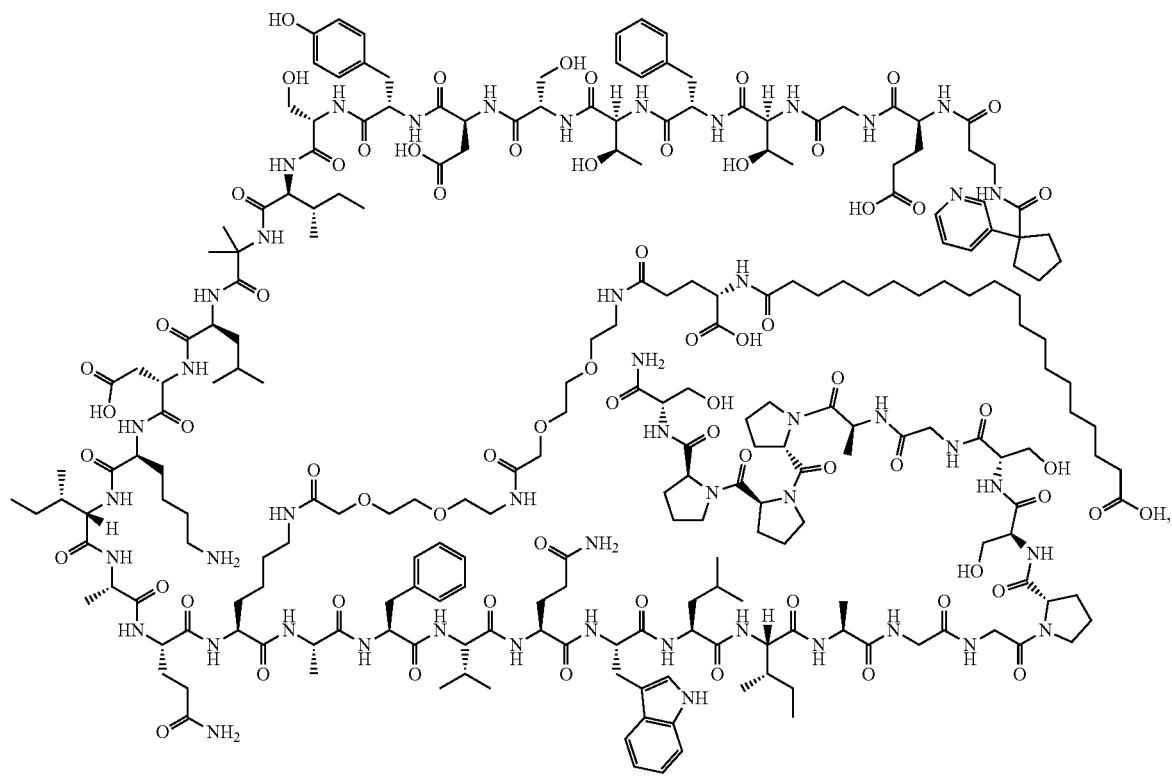

-continued
Compound 257
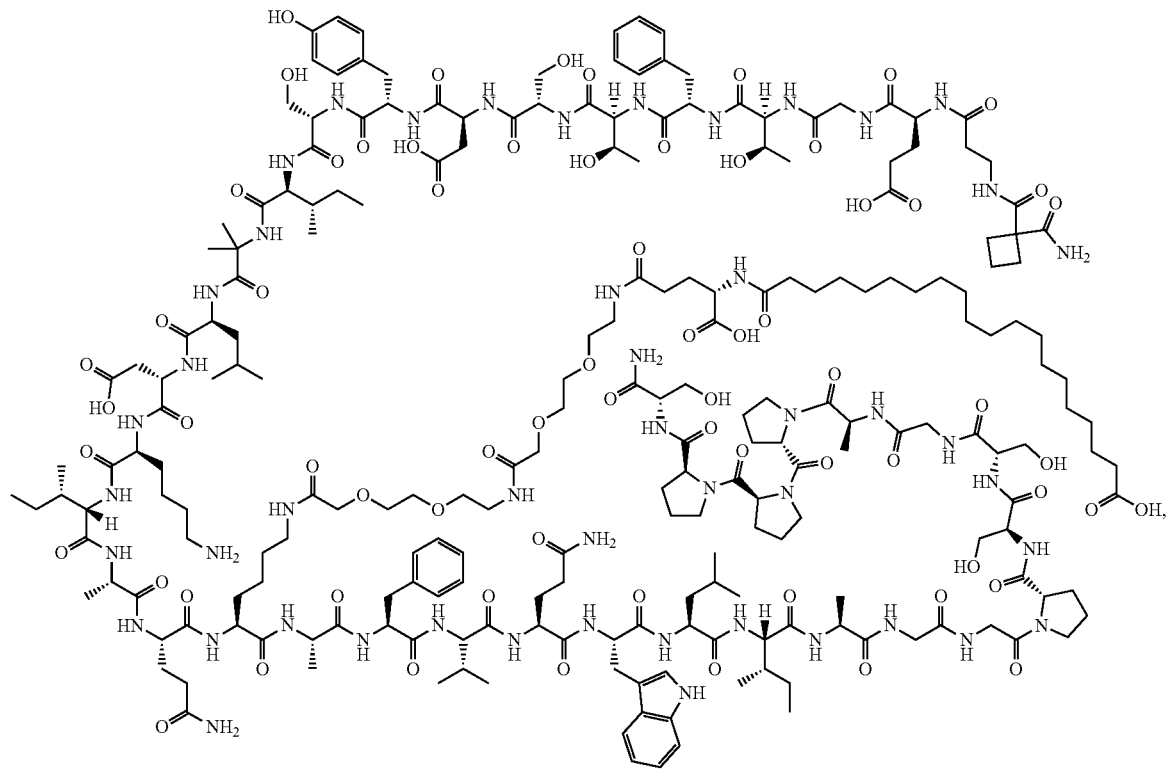
Compound 258
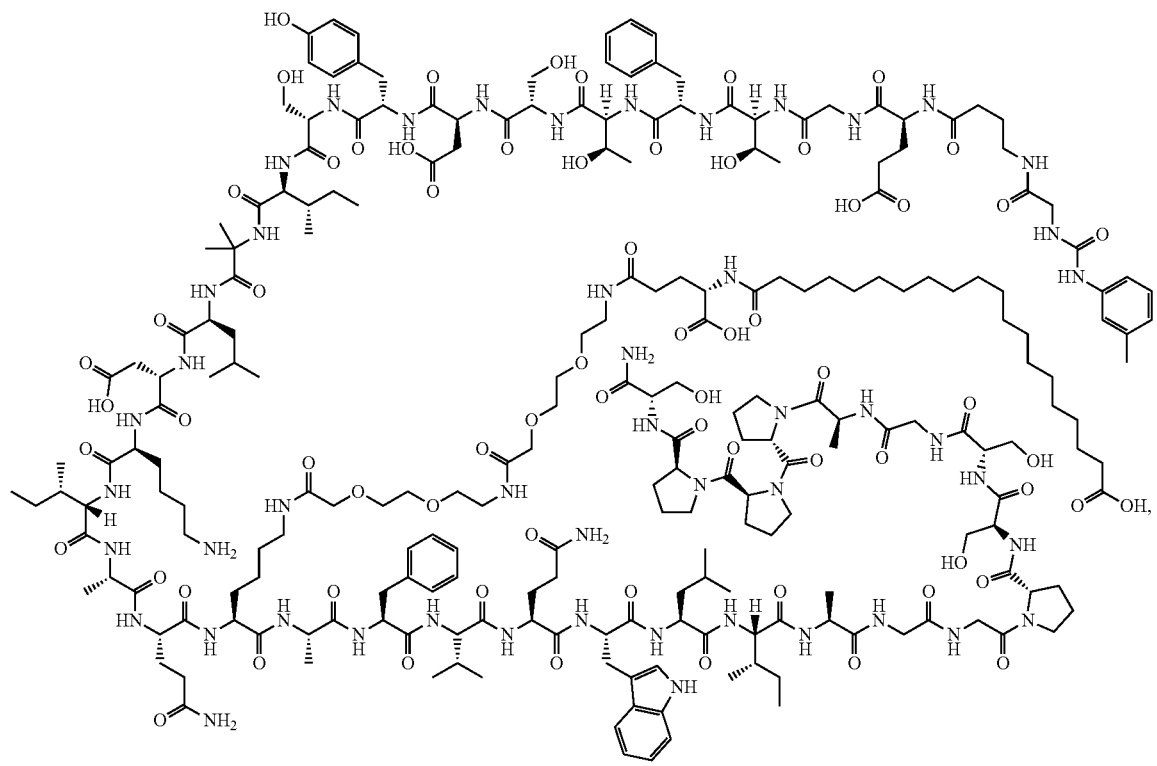

Compound 259
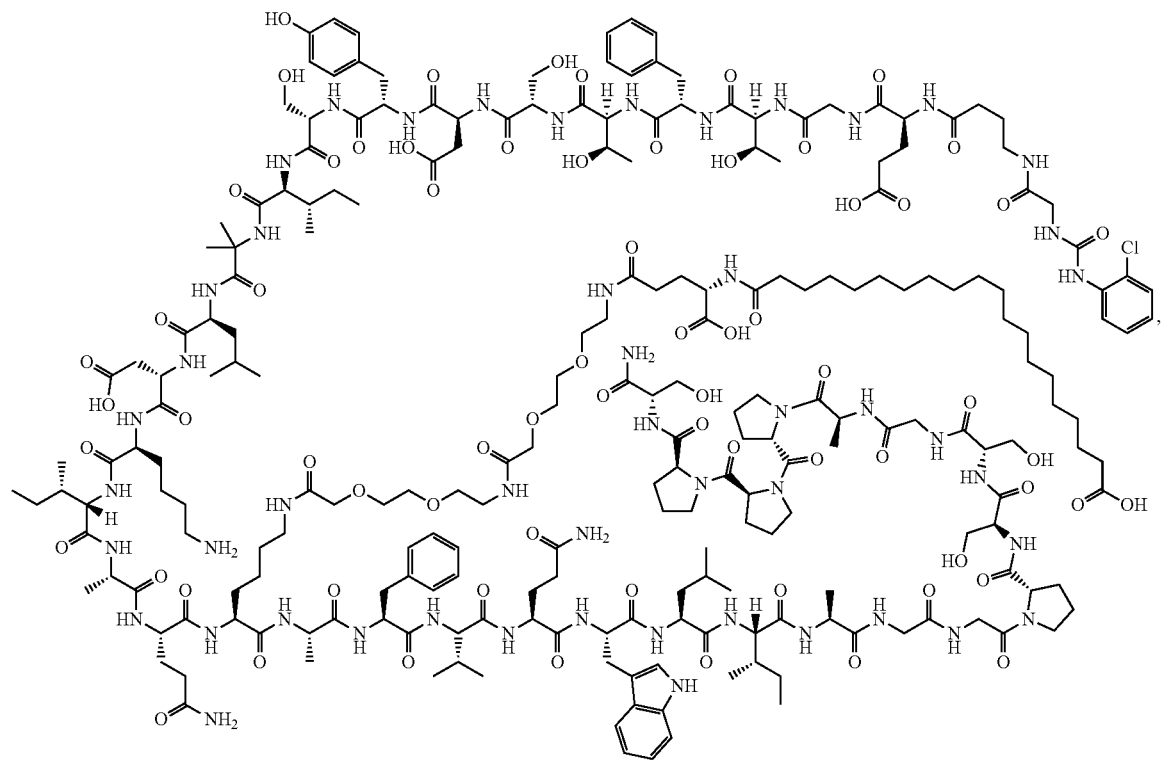
Compound 260
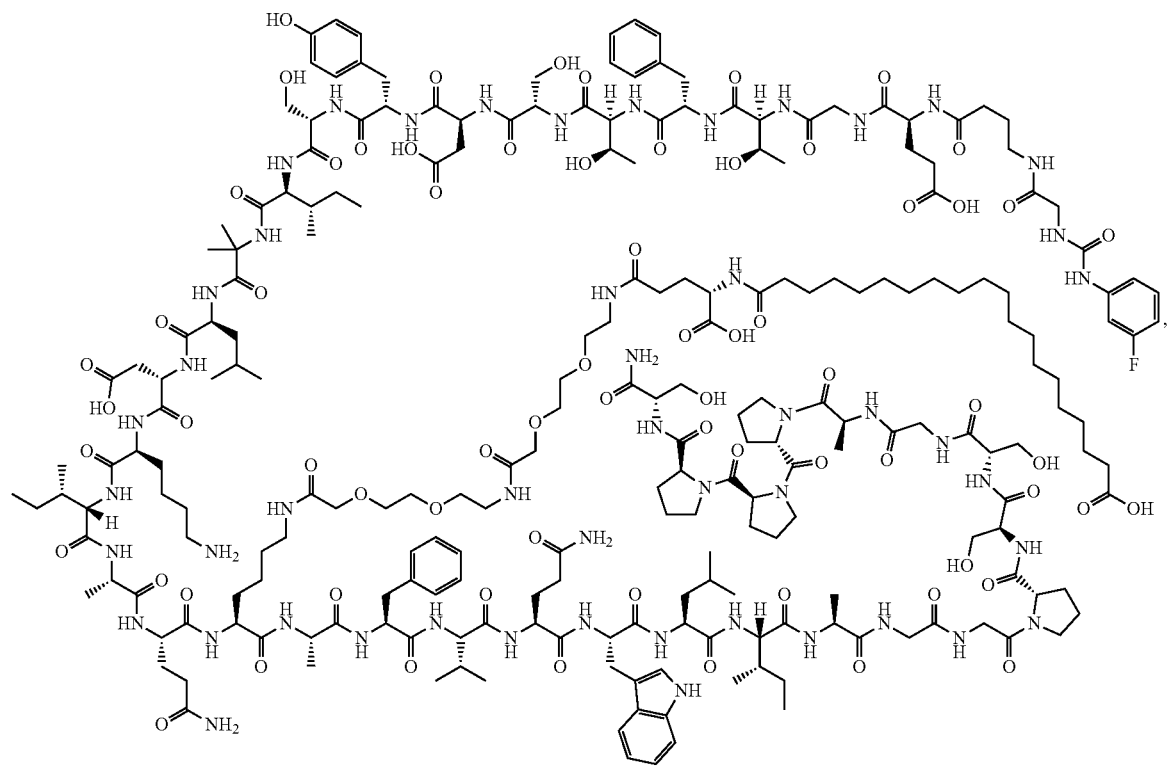

Compound 261
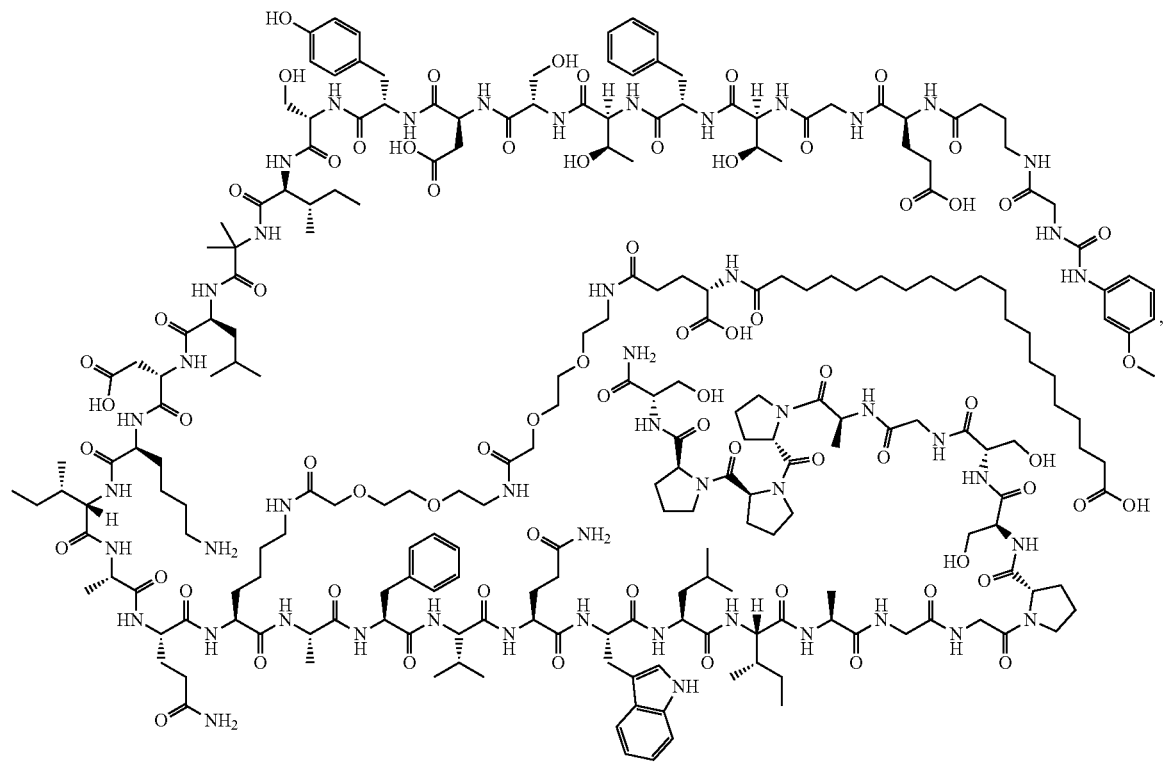
Compound 262
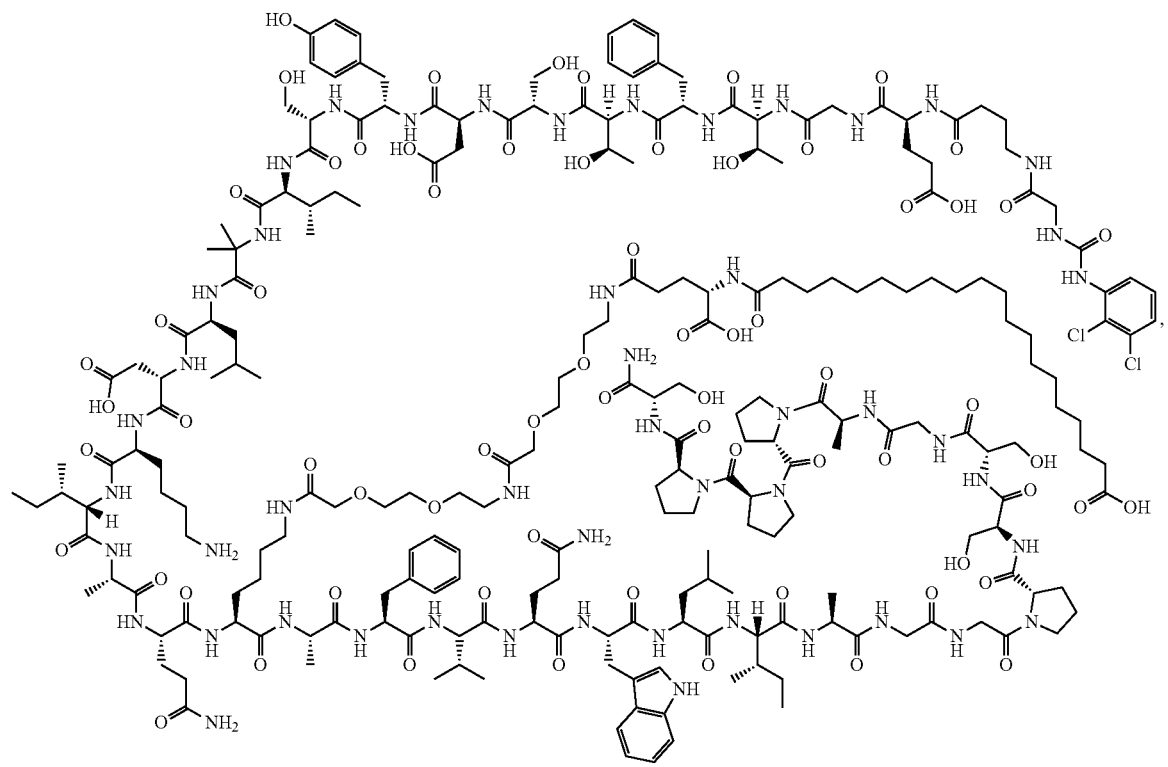

Compound 263
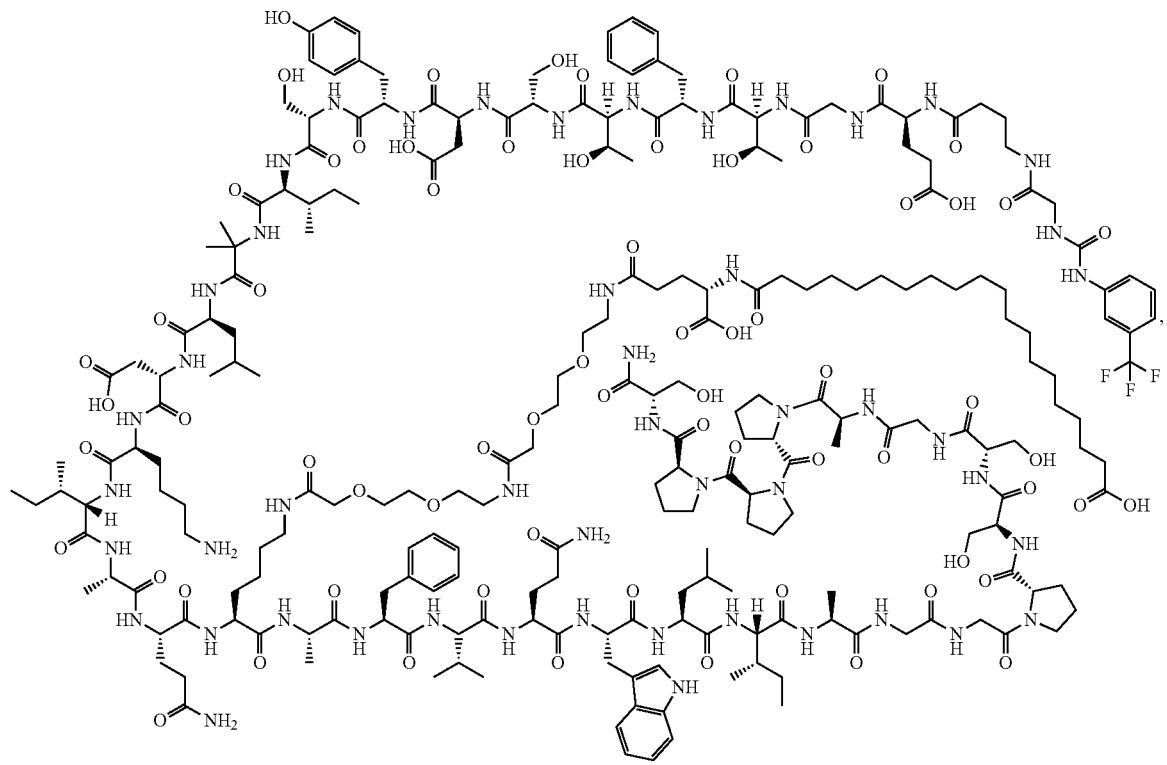
Compound 264
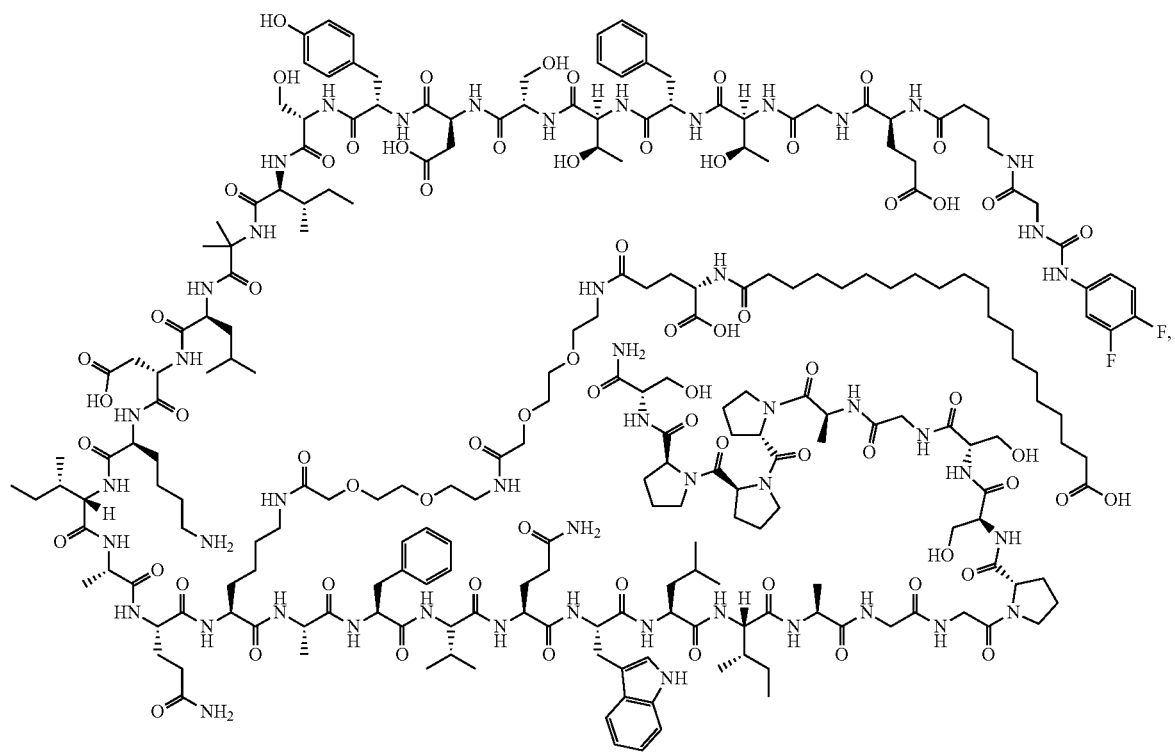

-continued
Compound 265
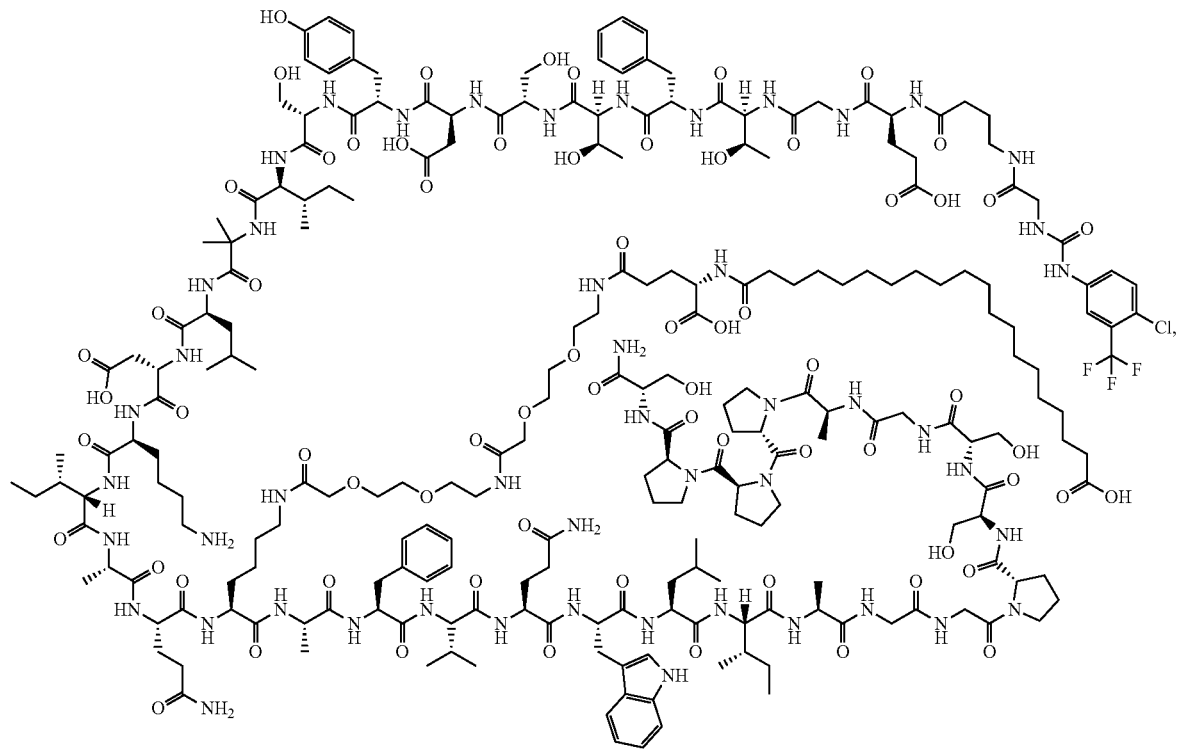
Compound 266
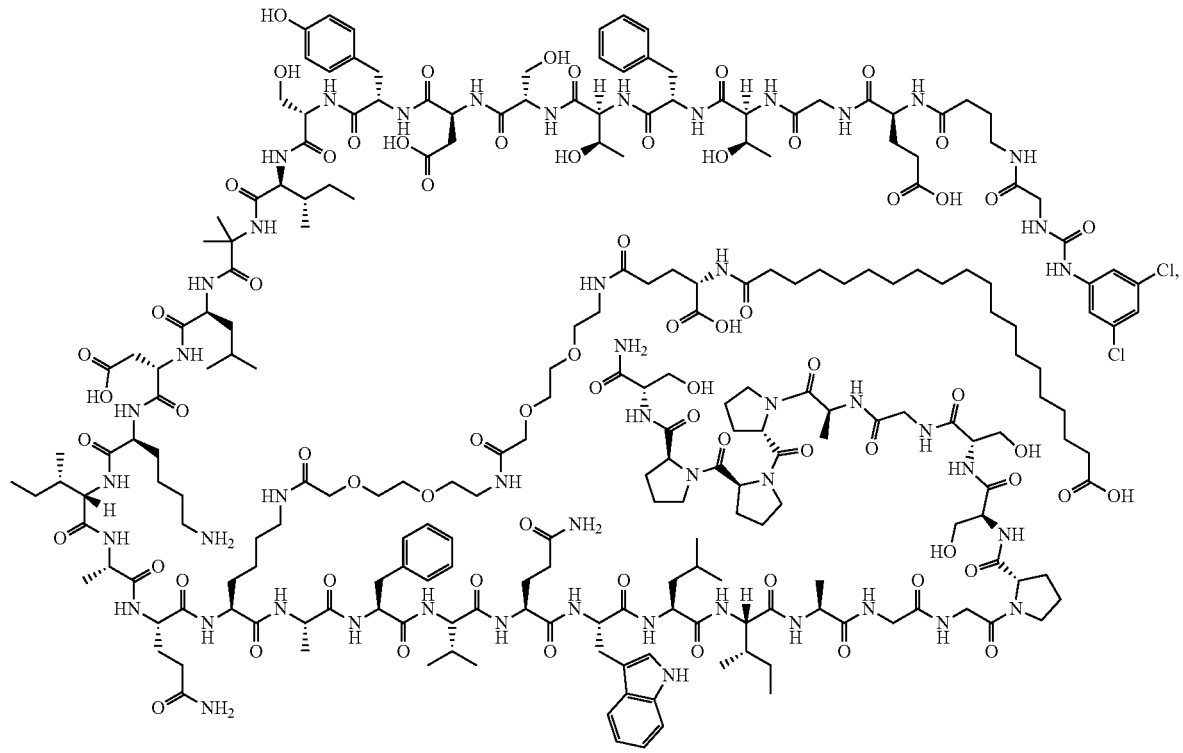

-continued
Compound 267
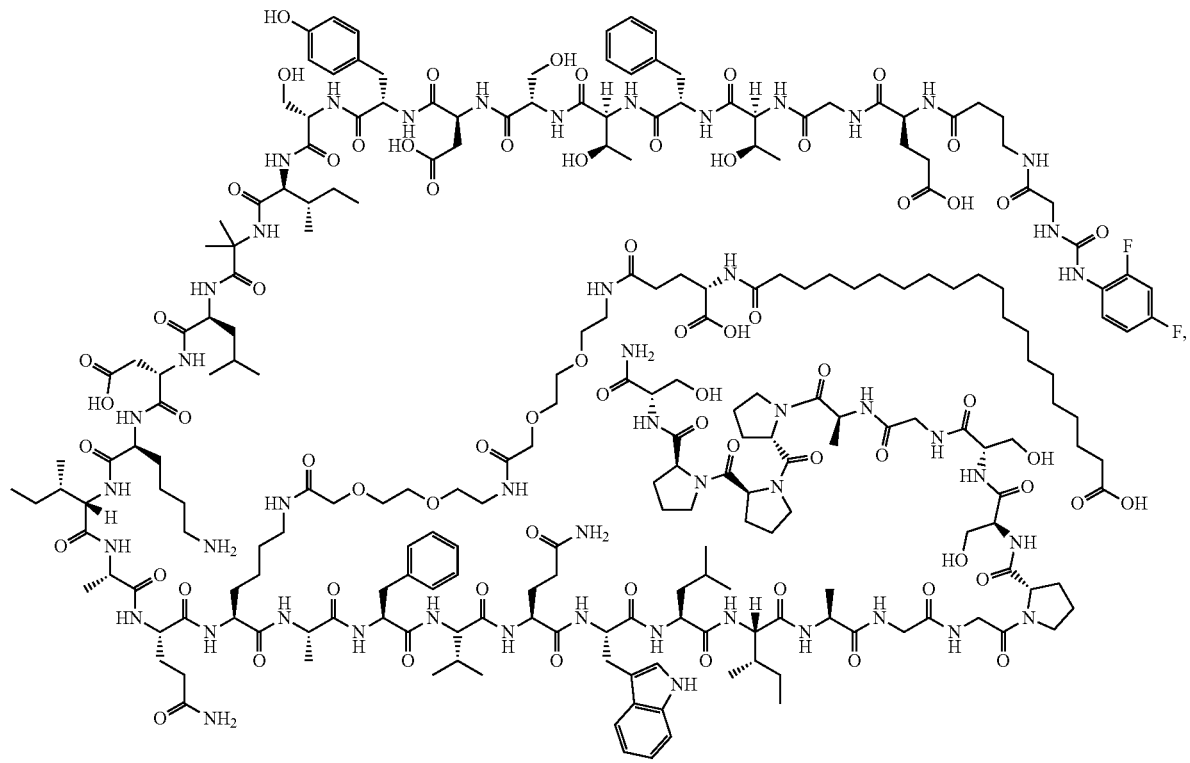
Compound 268
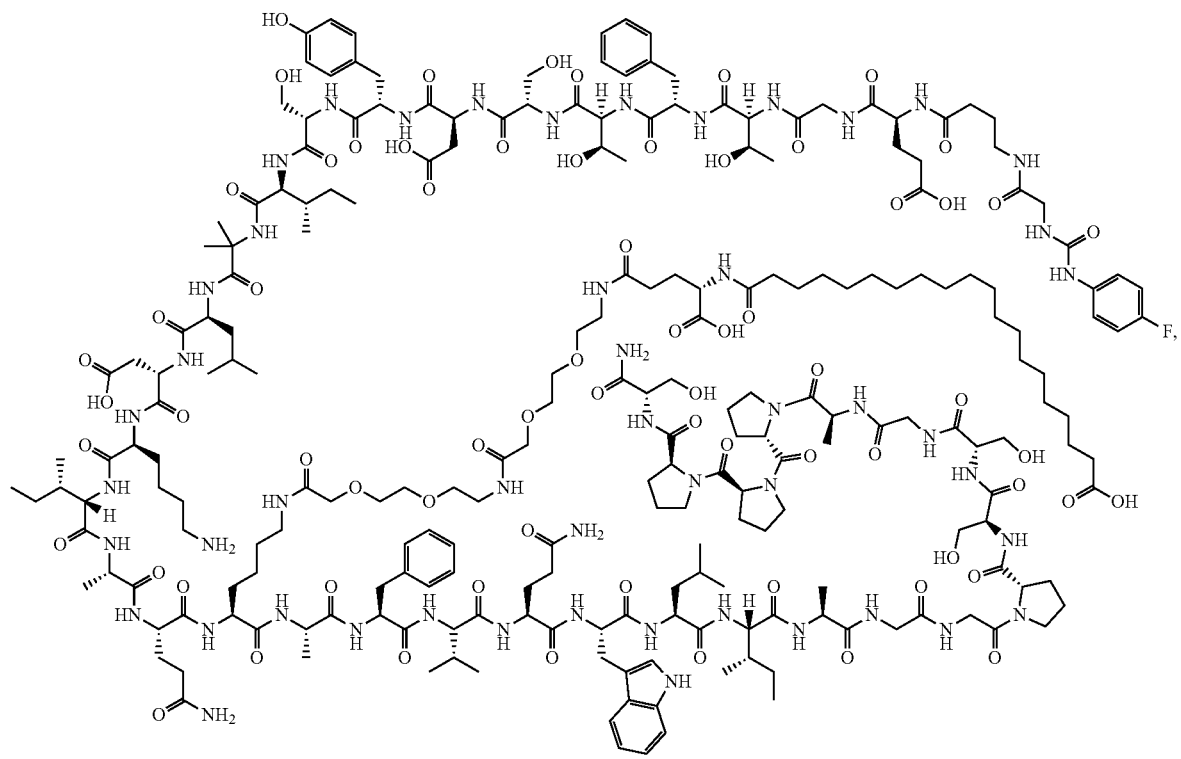

Compound 269
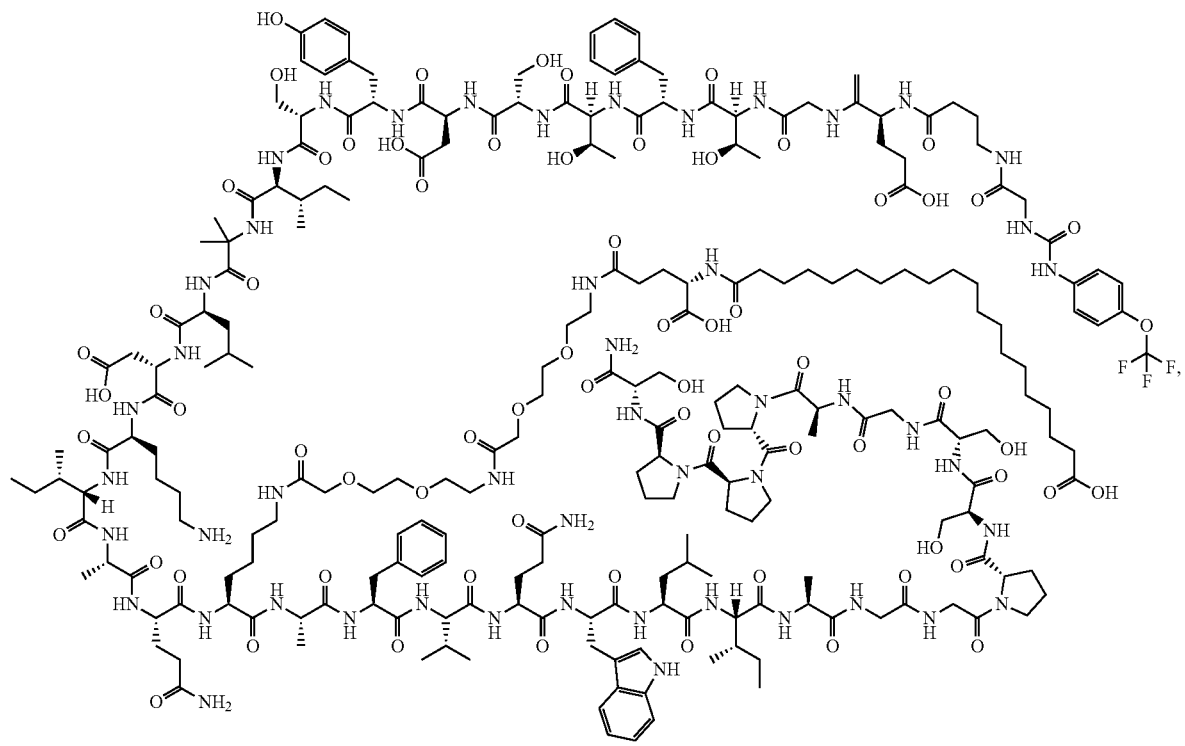
Compound 270
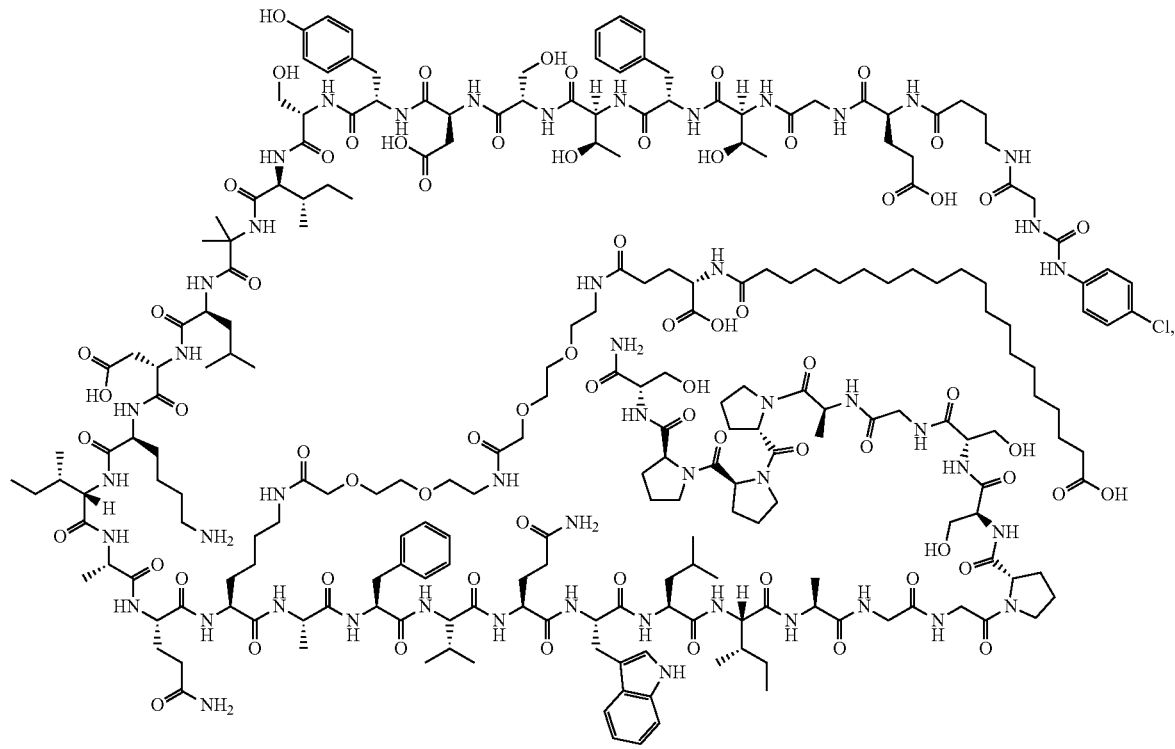

Compound 271
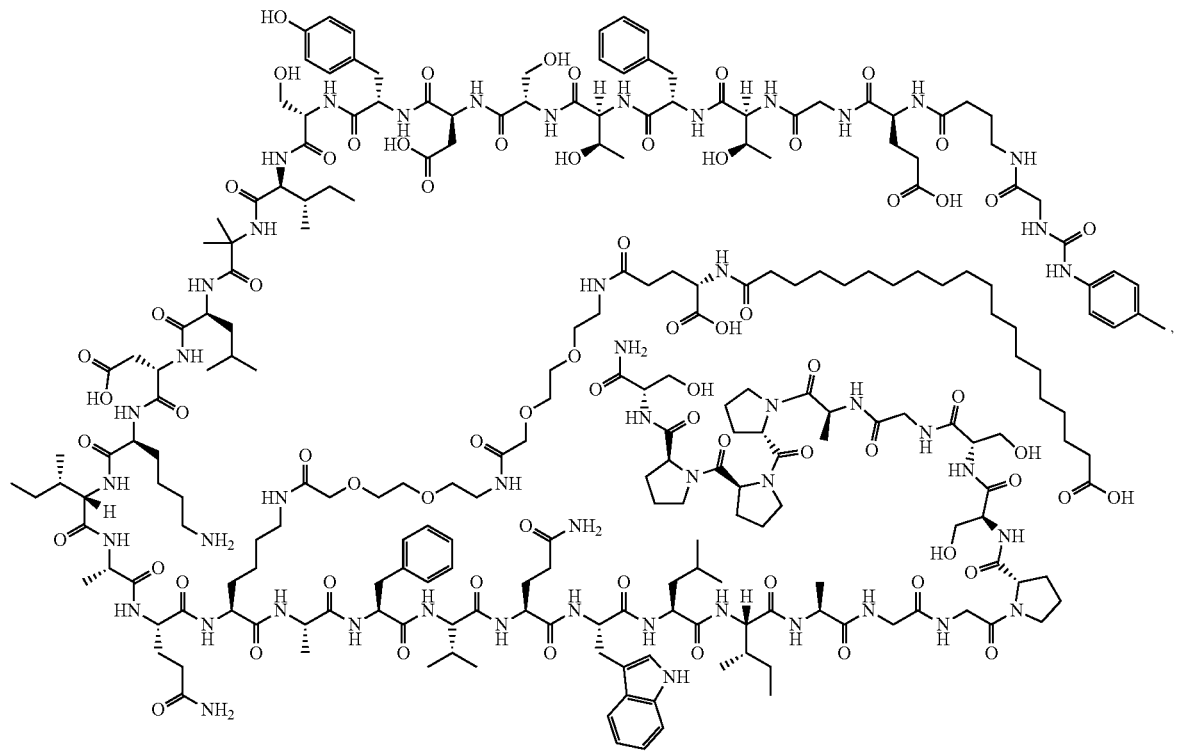
Compound 272
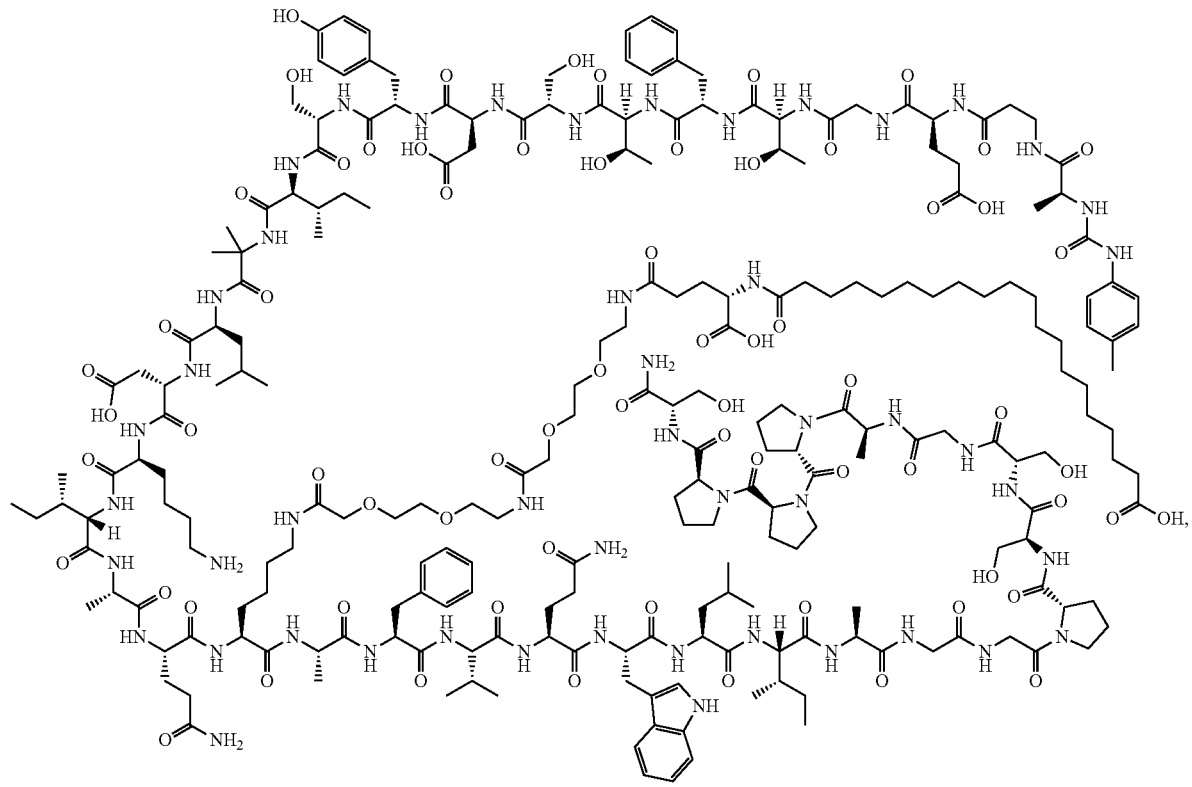

Compound 273
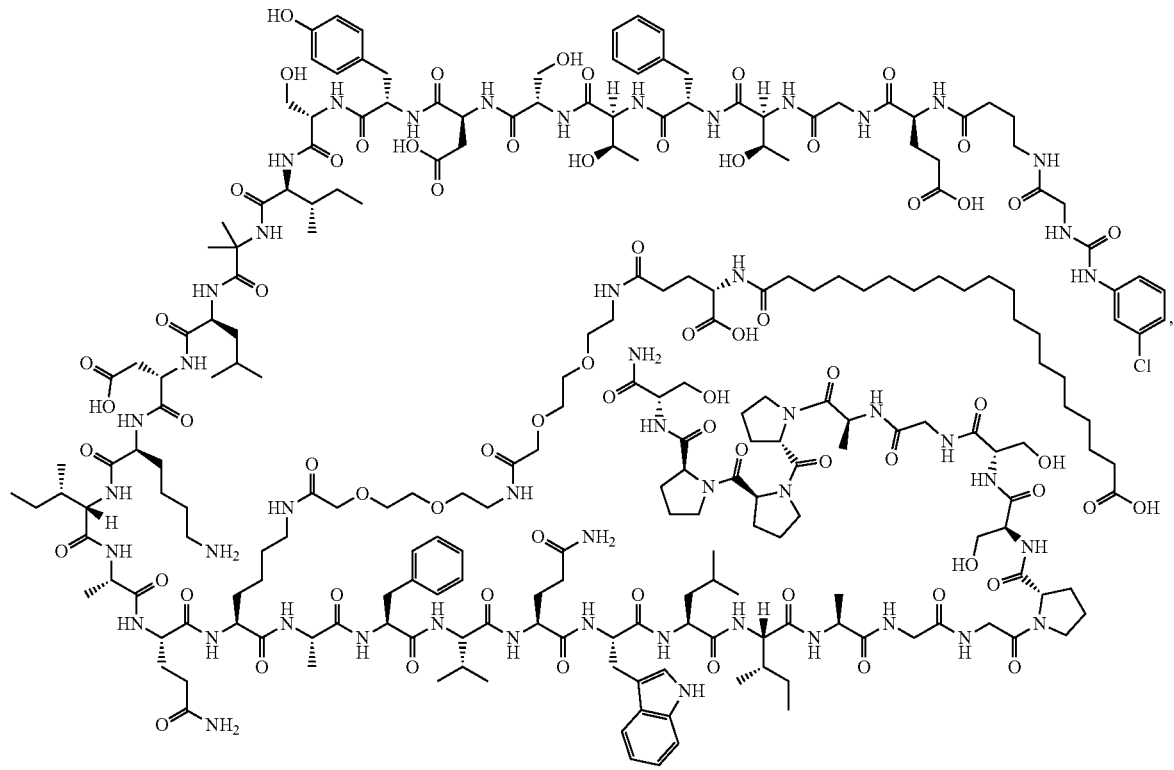
Compound 274
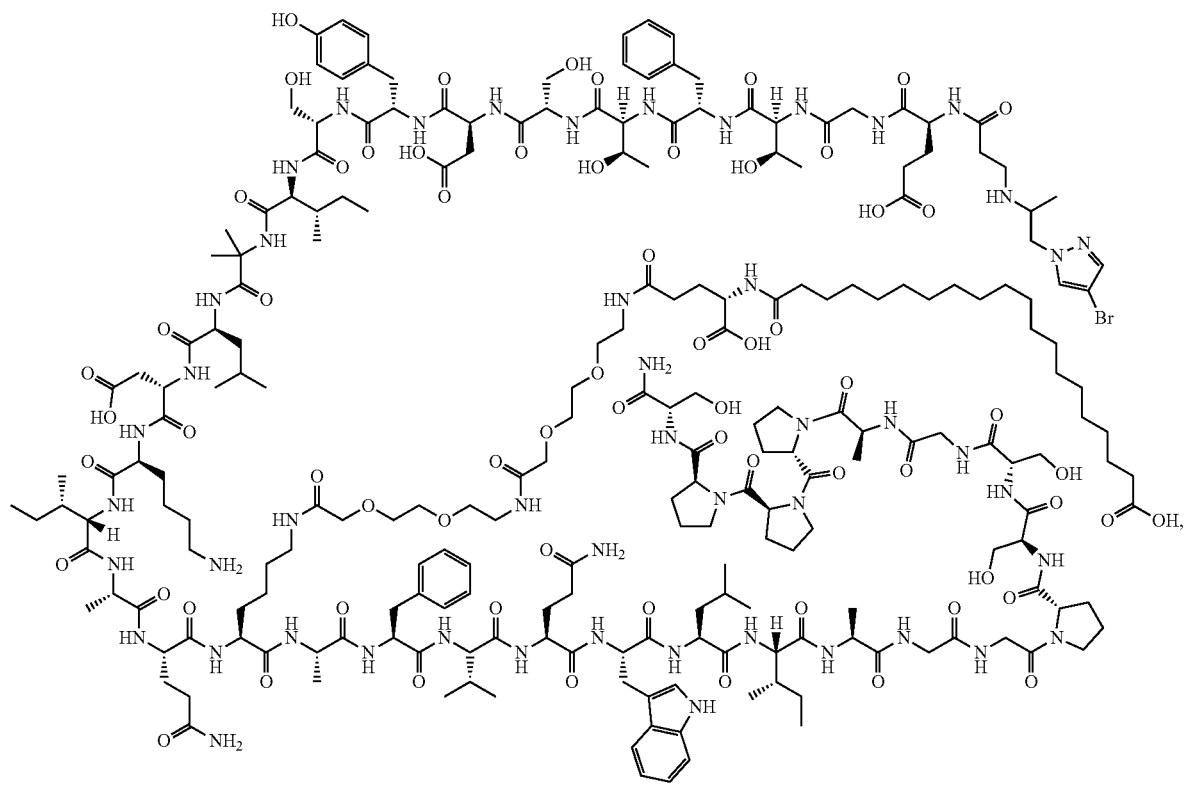

Compound 275
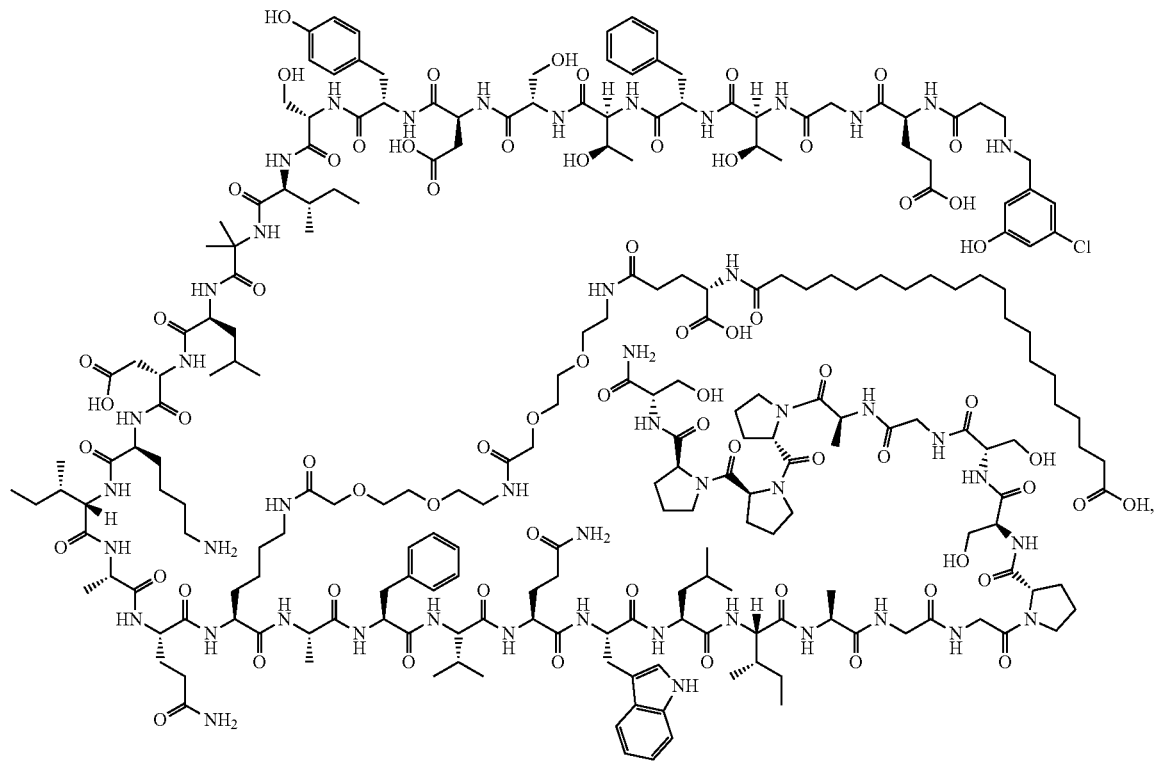
Compound 276
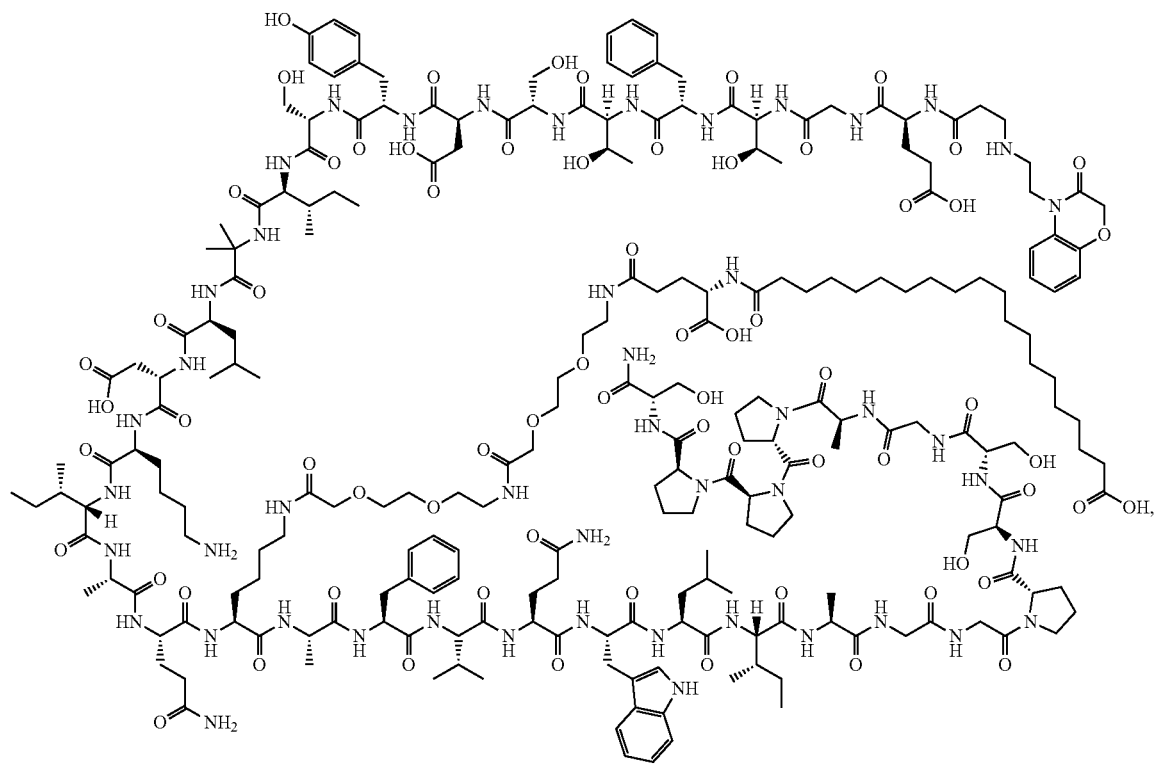

-continued
Compound 277
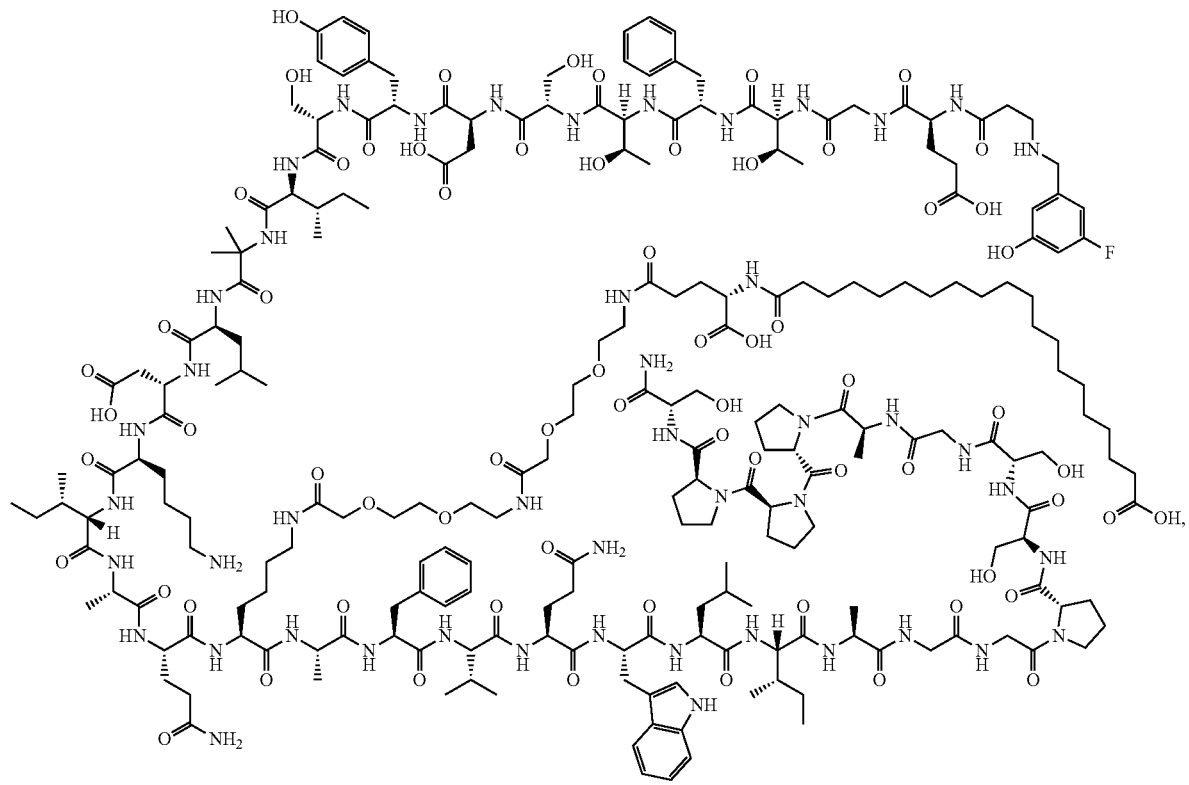
Compound 280
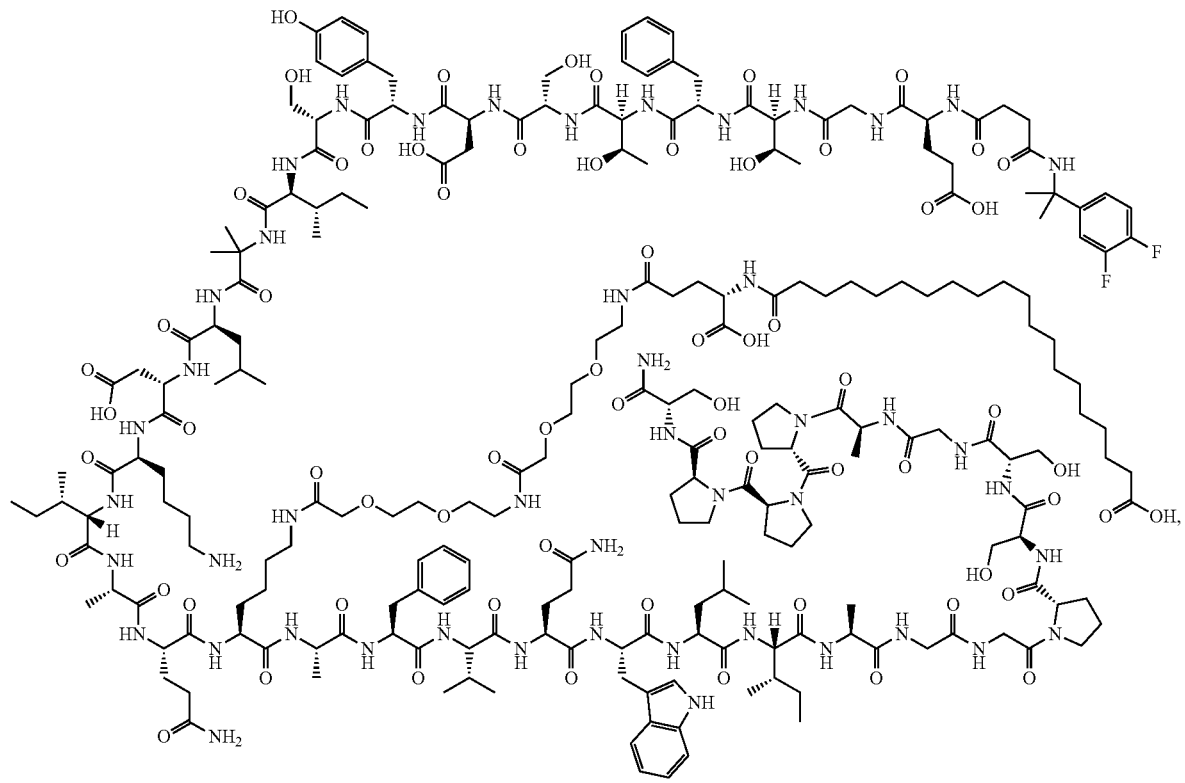

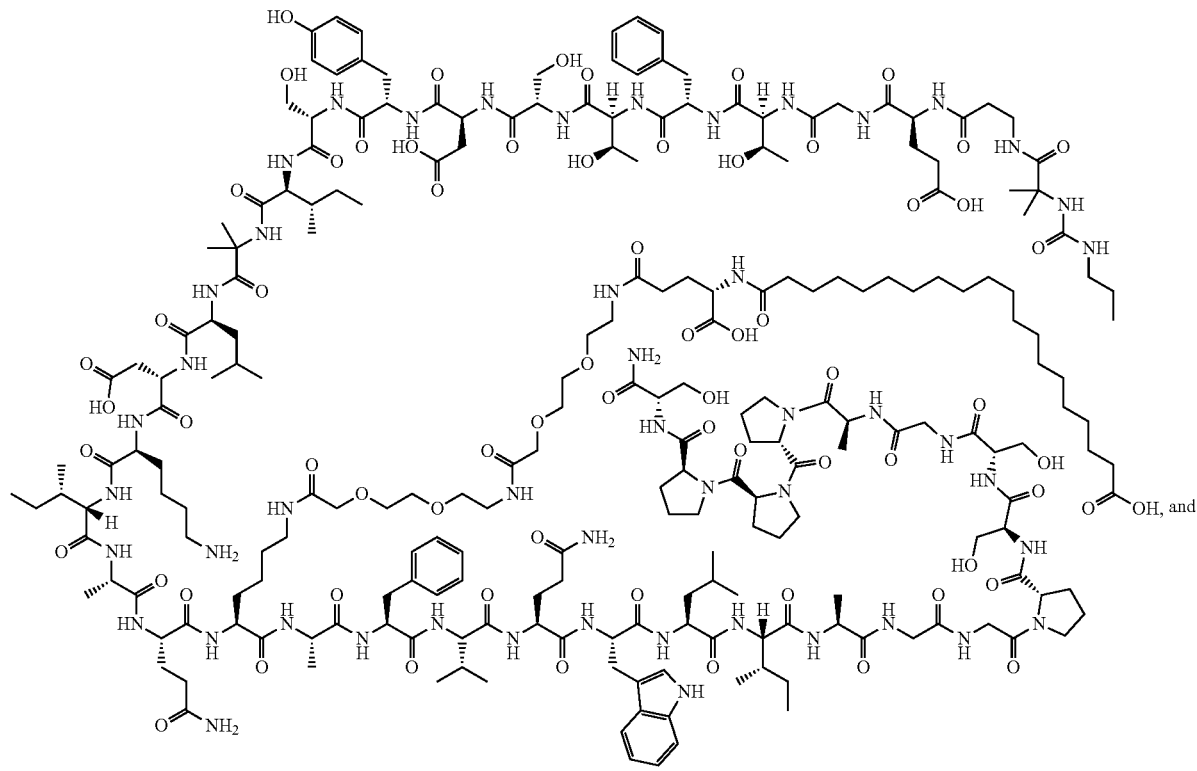
Compound 281
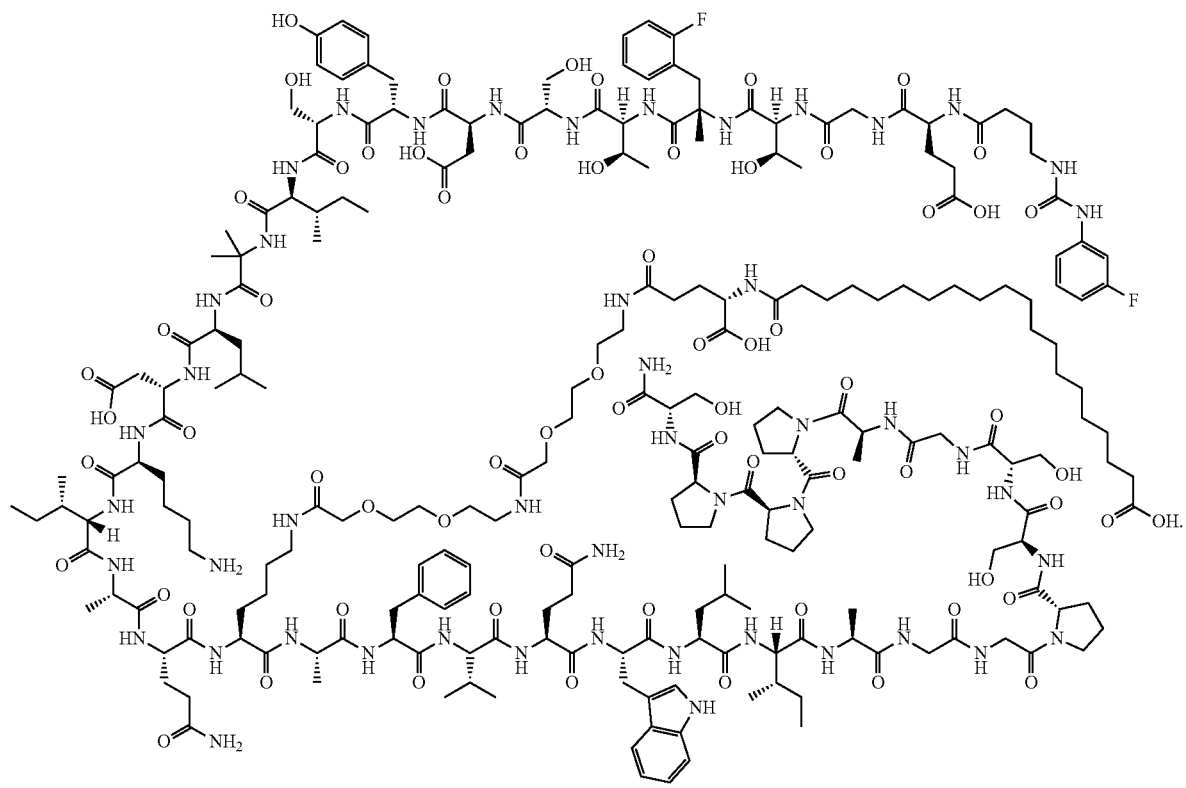
Compound 282

2. A compound, or pharmaceutically acceptable salt thereof, wherein the compound is selected form the group consisting of:
(SEQ ID NO: 69)
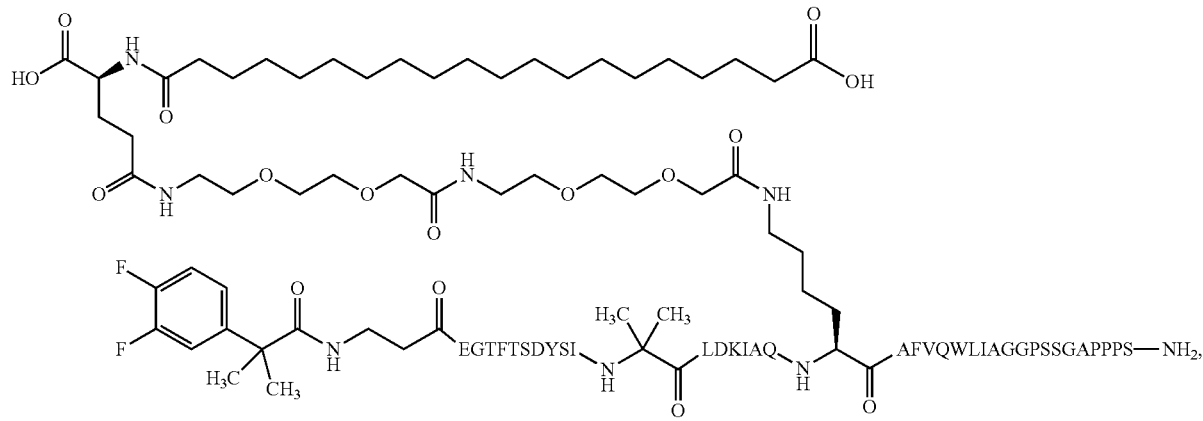
(SEQ ID NO: 70)
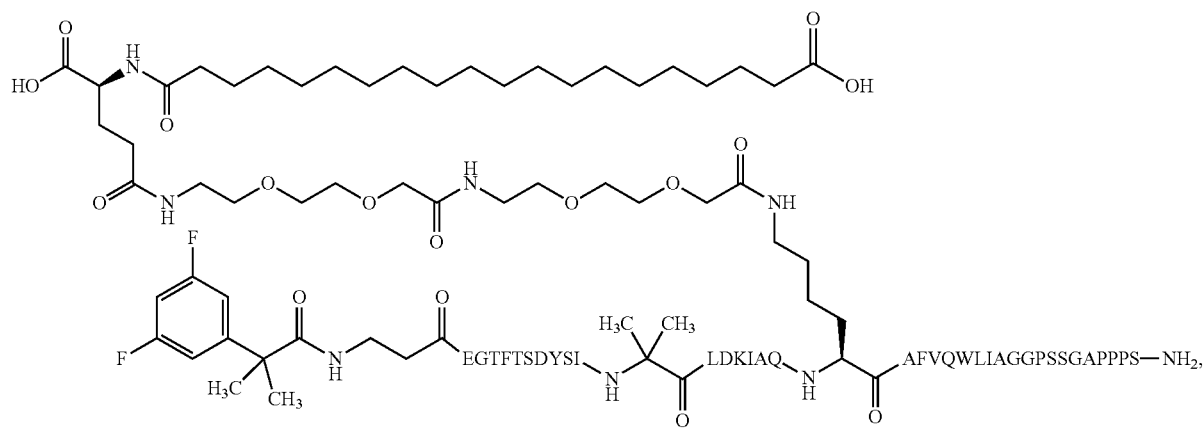
(SEQ ID NO: 71)
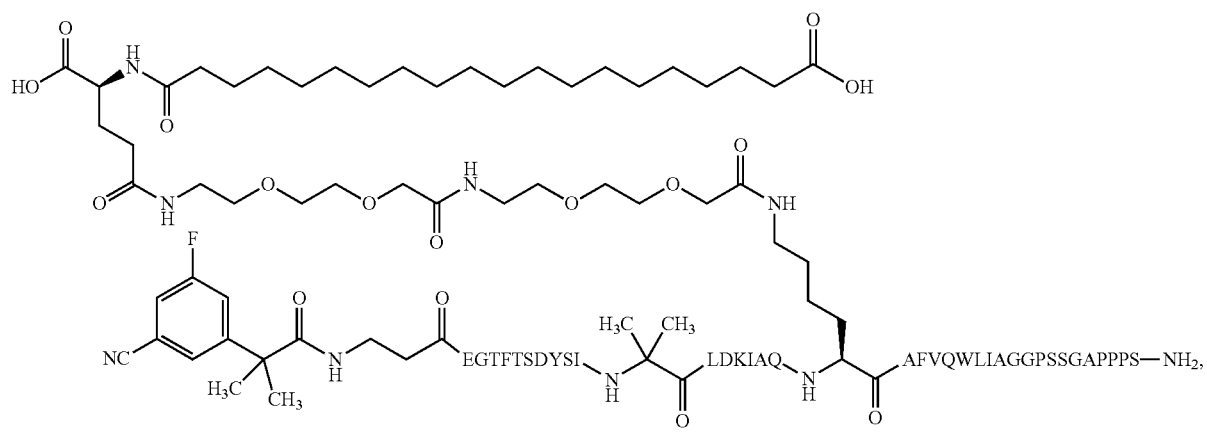

(SEQ ID NO: 72)
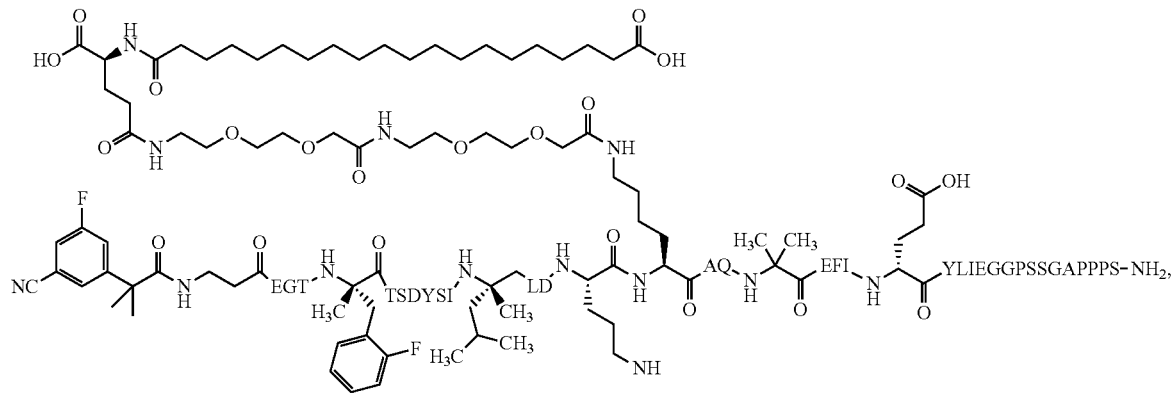
(SEQ ID NO: 73)
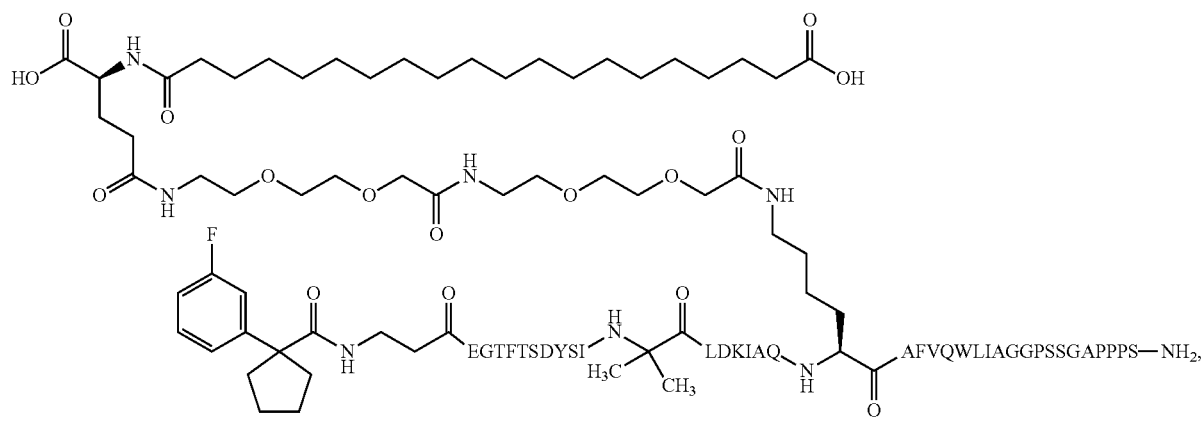
(SEQ ID NO: 74)
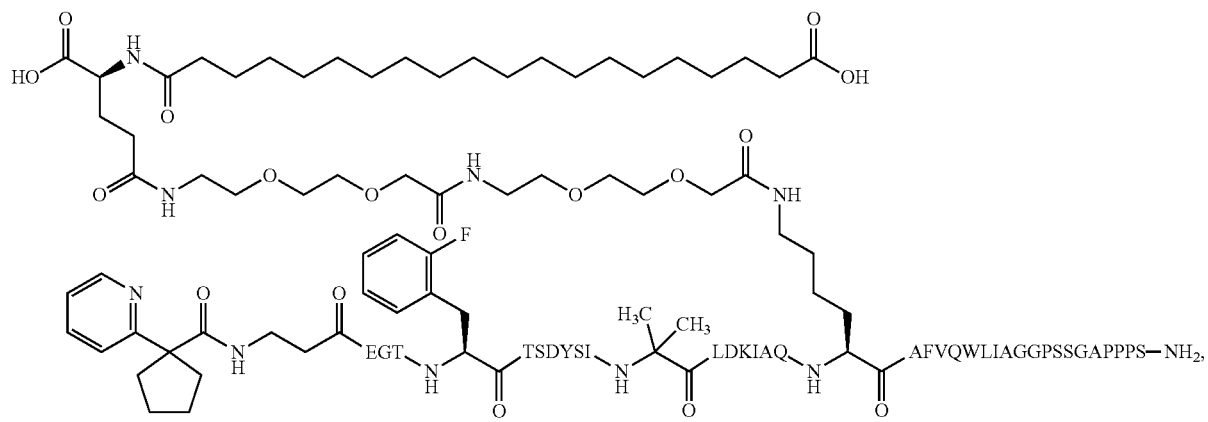

-continued
(SEQ ID NO: 75)
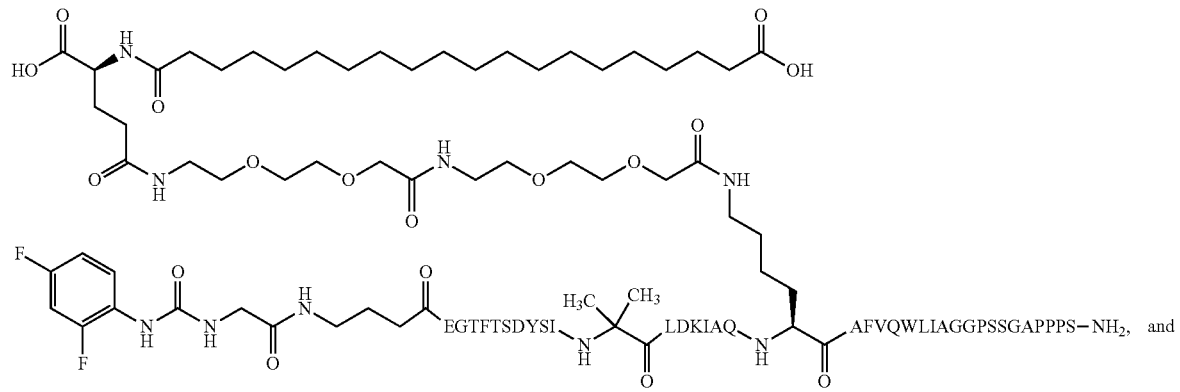
, and
(SEQ ID NO: 76)
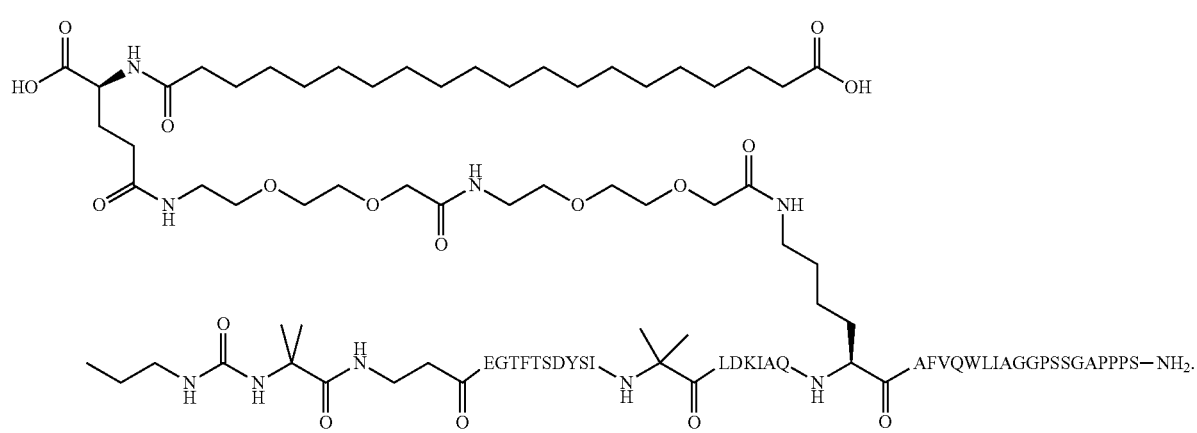
3. The compound of claim 2, wherein the compound is:
(SEQ ID NO: 69)
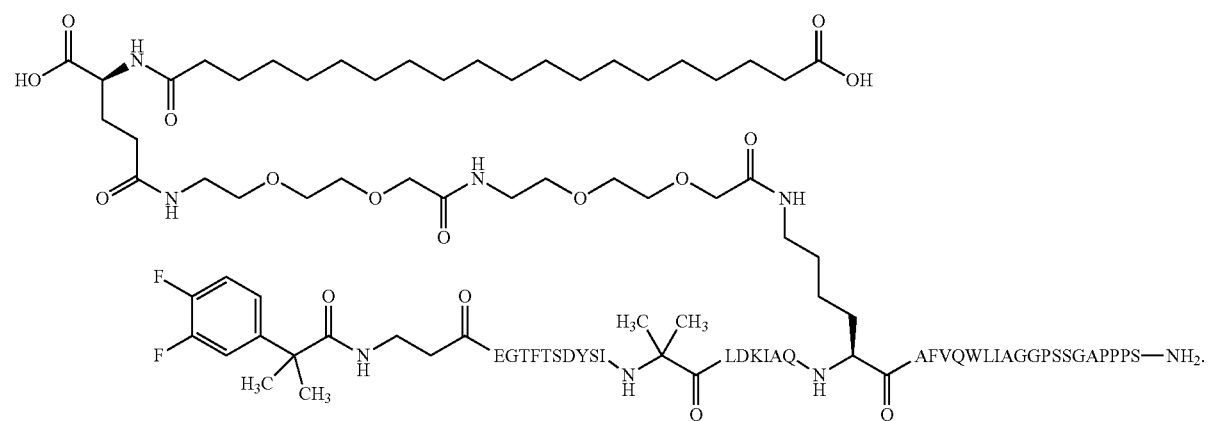

4. The compound of claim 2, wherein the compound is:
(SEQ ID NO: 70)
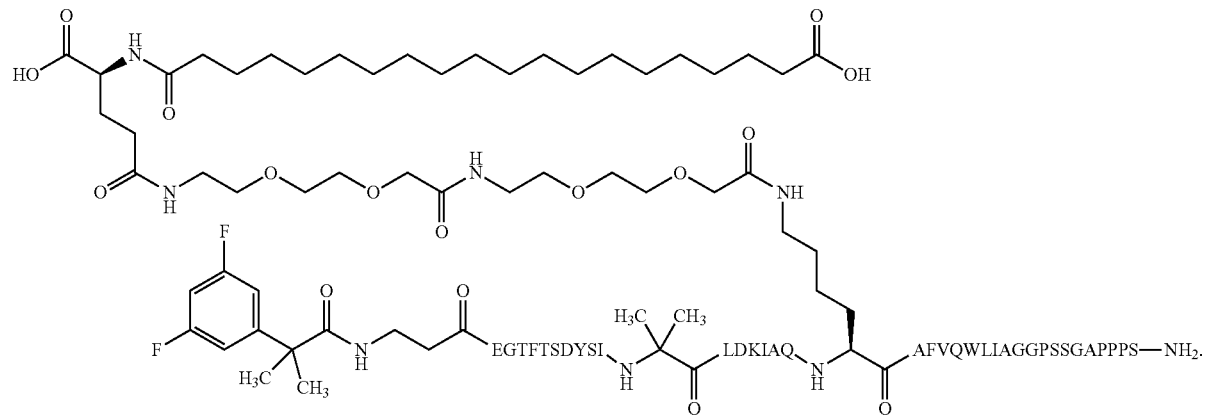
5. The compound of claim 2, wherein the compound is:
(SEQ ID NO: 71)
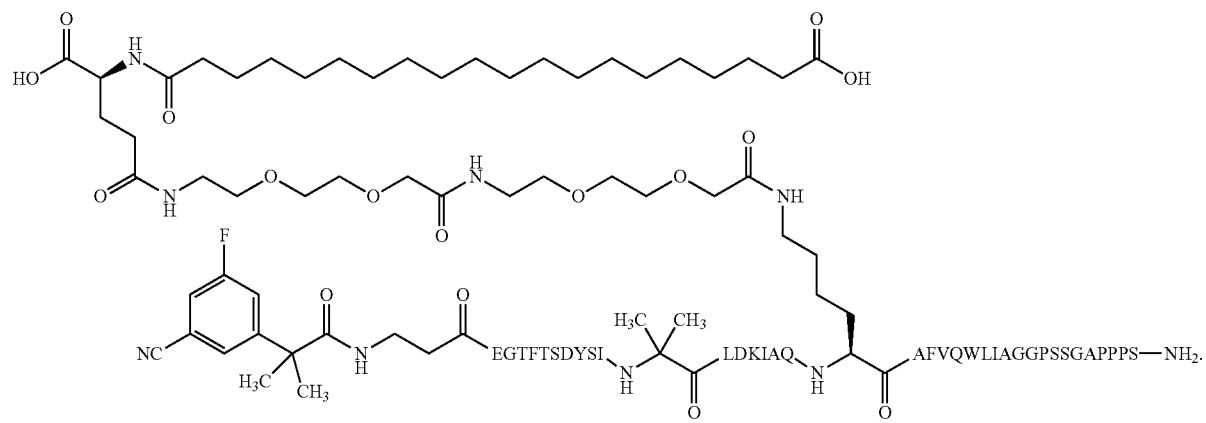
6. The compound of claim 2, wherein the compound is:
(SEQ ID NO: 72)
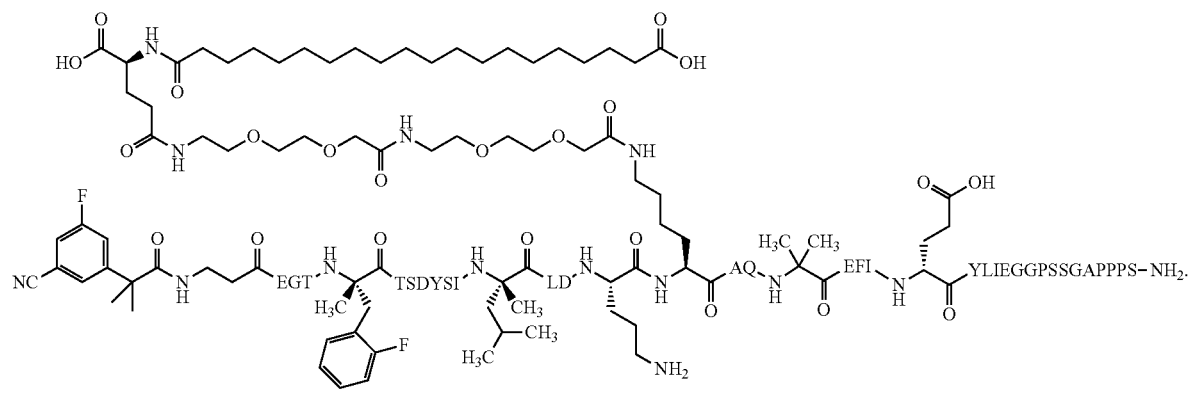

7. The compound of claim 2, wherein the compound is:
(SEQ ID NO: 73)
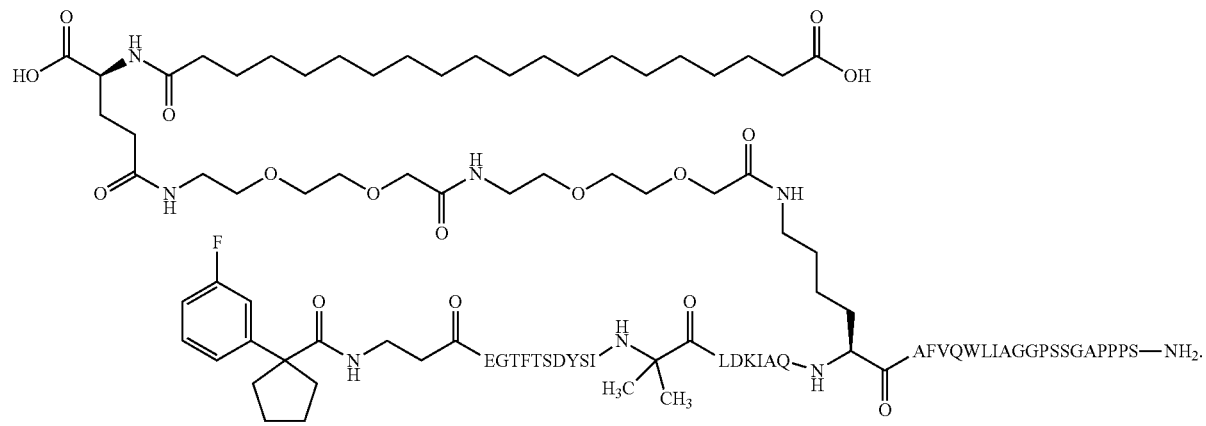
8. The compound of claim 2, wherein the compound is:
(SEQ ID NO: 74)
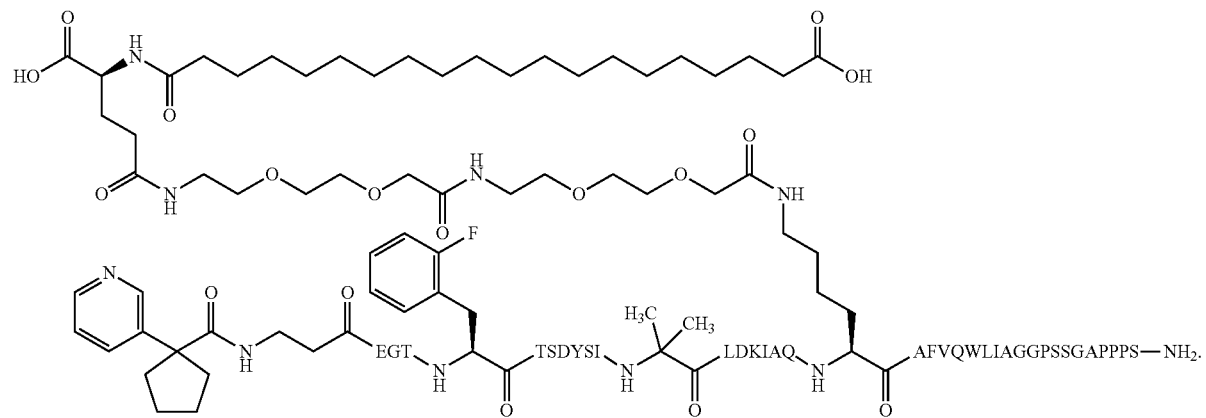
9. The compound of claim 2, wherein the compound is:
(SEQ ID NO: 75)
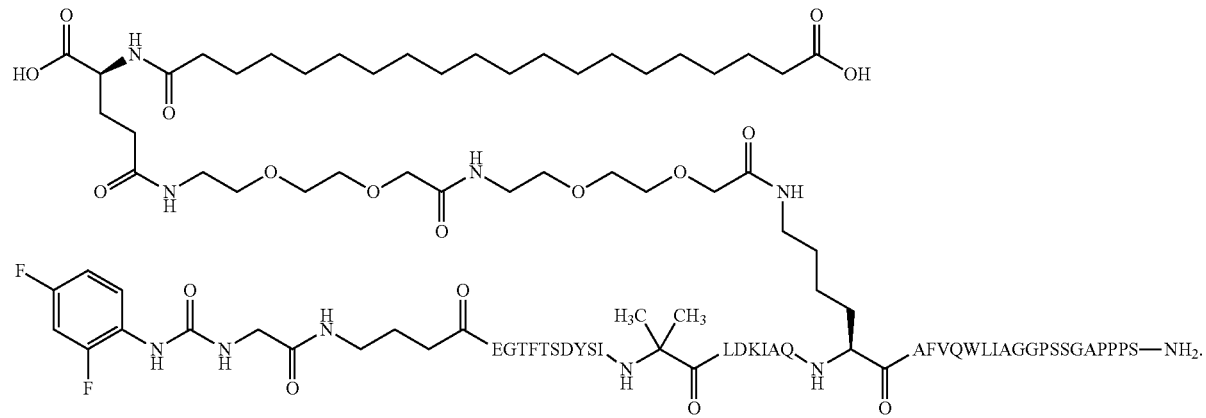

10. The compound of claim 2, wherein the compound is:
(SEQ ID NO: 76)
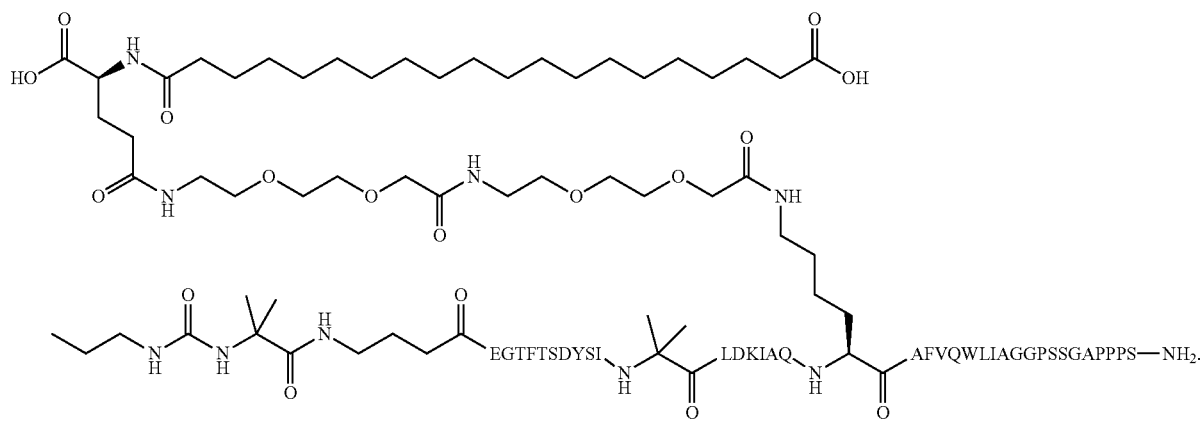
11. A pharmaceutical composition comprising the compound, or pharmaceutically acceptable salt thereof, of claim 1 or 2 and one or more pharmaceutically acceptable excipients.
* * * * *